US012579768B2

(12) United States Patent
Wetmore

(10) Patent No.: US 12,579,768 B2
(45) Date of Patent: Mar. 17, 2026

(54) WEARABLE ELECTRONIC DEVICES, EXTENDED REALITY SYSTEMS INCLUDING NEUROMUSCULAR SENSORS, AND METHODS FOR GENERATING TEXT FROM SPEECH INPUT AND MODIFYING THE GENERATED TEXT BASED ON NEUROMUSCULAR DATA

(71) Applicant: Meta Platforms Technologies, LLC, Menlo Park, CA (US)

(72) Inventor: Daniel Wetmore, Brooklyn, CA (US)

(73) Assignee: Meta Platforms Technologies, LLC, Menlo Park, CA (US)

( * ) Notice: Subject to any disclaimer, the term of this patent is extended or adjusted under 35 U.S.C. 154(b) by 0 days.

(21) Appl. No.: 18/890,622

(22) Filed: Sep. 19, 2024

(65) Prior Publication Data

US 2025/0095302 A1 Mar. 20, 2025

Related U.S. Application Data

(63) Continuation of application No. 17/722,128, filed on Apr. 15, 2022, now abandoned, which is a (Continued)

(51) Int. Cl.
*G06F 3/01* (2006.01)
*A61B 5/00* (2006.01)
(Continued)

(52) U.S. Cl.
CPC .......... *G06T 19/006* (2013.01); *A61B 5/1107* (2013.01); *A61B 5/22* (2013.01);
(Continued)

(58) Field of Classification Search
CPC ........ G16H 20/30; G16H 80/00; G16H 40/40; G06F 3/016; G06F 3/015; G06F 3/013;
(Continued)

(56) References Cited

U.S. PATENT DOCUMENTS 1,411,995 A 4/1922 Dull
3,408,133 A 10/1968 Lee
(Continued)

FOREIGN PATENT DOCUMENTS

CA 2902045 A1 8/2014
CA 2921954 A1 2/2015
(Continued)

OTHER PUBLICATIONS

Final Office Action mailed Jul. 23, 2021 for U.S. Appl. No. 14/461,044, filed Aug. 15, 2014, 15 Pages.
(Continued)

*Primary Examiner* — Olga V Merkoulova
(74) *Attorney, Agent, or Firm* — Morgan, Lewis & Bockius LLP

(57) ABSTRACT

The disclosed system for interacting with objects in an extended reality (XR) environment generated by an XR system may include (1) neuromuscular sensors configured to sense neuromuscular signals from a wrist of a user and (2) at least one computer processor programmed to (a) determine, based at least in part on the sensed neuromuscular signals, information relating to an interaction of the user with an object in the XR environment and (b) instruct the XR system to, based on the determined information relating to the interaction of the user with the object, augment the interaction of the user with the object in the XR environment. Other embodiments of this aspect include corresponding apparatus, and computer programs recorded on one or more computer storage devices, each configured to perform the actions of the methods.

20 Claims, 224 Drawing Sheets

Related U.S. Application Data continuation-in-part of application No. 17/667,442, filed on Feb. 8, 2022, now abandoned, which is a continuation-in-part of application No. 17/569,836, filed on Jan. 6, 2022, now abandoned, and a continuation-in-part of application No. 17/487,695, filed on Sep. 28, 2021, now abandoned, and a continuation-in-part of application No. 17/469,537, filed on Sep. 8, 2021, now Pat. No. 11,481,031, and a continuation-in-part of application No. 17/389,899, filed on Jul. 30, 2021, now abandoned, and a continuation-in-part of application No. 17/293,472, filed as application No. PCT/US2019/006175 on Nov. 15, 2019, now abandoned, and a continuation-in-part of application No. 17/213,686, filed on Mar. 26, 2021, now abandoned, and a continuation-in-part of application No. 17/173, 996, filed on Feb. 11, 2021, now abandoned, and a continuation-in-part of application No. 17/094,712, filed on Nov. 10, 2020, now Pat. No. 11,907,423, and a continuation-in-part of application No. 17/010,689, filed on Sep. 2, 2020, now Pat. No. 11,493,993, and a continuation-in-part of application No. 16/995,859, filed on Aug. 18, 2020, now abandoned, and a continuation-in-part of application No. 16/994,380, filed on Aug. 14, 2020, now abandoned, said application No. 17/469,537 is a continuation of application No. 16/863,098, filed on Apr. 30, 2020, now Pat. No. 11,150,730, said application No. 17/722,128 is a continuation-in-part of application No. 16/862,050, filed on Apr. 29, 2020, now Pat. No. 11,331,045, said application No. 17/667,442 is a continuation of application No. 16/854,668, filed on Apr. 21, 2020, now Pat. No. 11,281,293, said application No. 17/722,128 is a continuation-in-part of application No. 16/833, 626, filed on Mar. 29, 2020, now abandoned, and a continuation-in-part of application No. 16/833,309, filed on Mar. 27, 2020, now Pat. No. 11,327,566, and a continuation-in-part of application No. 16/832,978, filed on Mar. 27, 2020, now Pat. No. 11,961,494, and a continuation-in-part of application No. 16/833,307, filed on Mar. 27, 2020, now Pat. No. 11,481,030, said application No. 17/213,686 is a continuation of application No. 16/593,446, filed on Oct. 4, 2019, now Pat. No. 10,970,936, said application No. 17/722,128 is a continuation-in-part of application No. 16/577, 352, filed on Sep. 20, 2019, now Pat. No. 11,567,573, said application No. 17/569,836 is a continuation of application No. 16/577,207, filed on Sep. 20, 2019, now abandoned, said application No. 17/487,695 is a continuation of application No. 16/557,342, filed on Aug. 30, 2019, now abandoned, said application No. 17/389,899 is a continuation of application No. 16/539,755, filed on Aug. 13, 2019, now Pat. No. 11,179,066, said application No. 16/995,859 is a continuation of application No. 16/389,419, filed on Apr. 19, 2019, now Pat. No. 10,772,519, said application No. 16/862,050 is a continuation-in-part of application No. 16/258,279, filed on Jan. 25, 2019, now abandoned, said application No. 17/173,996 is a continuation of application No. 15/974,454, filed on May 8, 2018, now Pat. No. 10,937,414.

(60) Provisional application No. 62/968,495, filed on Jan. 31, 2020, provisional application No. 62/940,121, filed on Nov. 25, 2019, provisional application No. 62/931,082, filed on Nov. 5, 2019, provisional application No. 62/898,417, filed on Sep. 10, 2019, provisional application No. 62/897,592, filed on Sep. 9, 2019, provisional application No. 62/897,483, filed on Sep. 9, 2019, provisional application No. 62/895,888, filed on Sep. 4, 2019, provisional application No. 62/895,782, filed on Sep. 4, 2019, provisional application No. 62/895,894, filed on Sep. 4, 2019, provisional application No. 62/887,521, filed on Aug. 15, 2019, provisional application No. 62/887,528, filed on Aug. 15, 2019, provisional application No. 62/887,496, filed on Aug. 15, 2019, provisional application No. 62/887,515, filed on Aug. 15, 2019, provisional application No. 62/887,485, filed on Aug. 15, 2019, provisional application No. 62/887,507, filed on Aug. 15, 2019, provisional application No. 62/887,502, filed on Aug. 15, 2019, provisional application No. 62/841,156, filed on Apr. 30, 2019, provisional application No. 62/841,069, filed on Apr. 30, 2019, provisional application No. 62/840,966, filed on Apr. 30, 2019, provisional application No. 62/841,054, filed on Apr. 30, 2019, provisional application No. 62/841,107, filed on Apr. 30, 2019, provisional application No. 62/840,803, filed on Apr. 30, 2019, provisional application No. 62/841,061, filed on Apr. 30, 2019, provisional application No. 62/841,147, filed on Apr. 30, 2019, provisional application No. 62/841,100, filed on Apr. 30, 2019, provisional application No. 62/840,947, filed on Apr. 30, 2019, provisional application No. 62/840,980, filed on Apr. 30, 2019, provisional application No. 62/826,516, filed on Mar. 29, 2019, provisional application No. 62/826,574, filed on Mar. 29, 2019, provisional application No. 62/826,478, filed on Mar. 29, 2019, provisional application No. 62/826,493, filed on Mar. 29, 2019, provisional application No. 62/768,741, filed on Nov. 16, 2018, provisional application No. 62/741,781, filed on Oct. 5, 2018, provisional application No. 62/734,145, filed on Sep. 20, 2018, provisional application No. 62/734,138, filed on Sep. 20, 2018, provisional application No. 62/726,159, filed on Aug. 31, 2018, provisional application No. 62/718,337, filed on Aug. 13, 2018, provisional application No. 62/676,567, filed on May 25, 2018, provisional application No. 62/621,829, filed on Jan. 25, 2018.

(51) Int. Cl.
| | |
|---|---|
| *A61B 5/11* | (2006.01) |
| *A61B 5/22* | (2006.01) |
| *G06T 19/00* | (2011.01) |
| *G16H 20/30* | (2018.01) |
| *G16H 80/00* | (2018.01) |

(52) U.S. Cl.
CPC ............ *A61B 5/4519* (2013.01); *G06F 3/015* (2013.01); *G16H 20/30* (2018.01); *G16H 80/00* (2018.01)

(58) Field of Classification Search
CPC .......... G06F 3/011; G06F 3/017; G06F 3/014; G06T 19/006; A61B 5/389; A61B 5/24; A61B 5/22
See application file for complete search history.

(56) References Cited

U.S. PATENT DOCUMENTS

| | | | |
|---|---|---|---|
| 3,580,243 A | 5/1971 | Johnson | |
| 3,620,208 A | 11/1971 | Wayne et al. | |
| 3,712,716 A | 1/1973 | Cornsweet et al. | |
| 3,735,425 A | 5/1973 | Hoshall et al. | |
| 3,880,146 A | 4/1975 | Everett et al. | |
| 4,055,168 A | 10/1977 | Miller et al. | |
| 4,602,639 A | 7/1986 | Hoogendoorn et al. | |
| 4,705,408 A | 11/1987 | Jordi | |
| 4,817,064 A | 3/1989 | Milles | |
| 4,896,120 A | 1/1990 | Kamil | |
| 4,978,213 A | 12/1990 | El Hage | |
| 5,003,978 A | 4/1991 | Dunseath, Jr. | |
| D322,227 S | 12/1991 | Warhol | |
| 5,081,852 A | 1/1992 | Cox | |
| 5,103,323 A | 4/1992 | Magarinos et al. | |
| 5,231,674 A | 7/1993 | Cleveland et al. | |
| 5,251,189 A | 10/1993 | Thorp | |
| D348,660 S | 7/1994 | Parsons | |
| 5,445,869 A | 8/1995 | Ishikawa et al. | |
| 5,462,065 A | 10/1995 | Cusimano | |
| 5,467,104 A | 11/1995 | Furness, III et al. | |
| 5,482,051 A | 1/1996 | Reddy et al. | |
| 5,589,956 A | 12/1996 | Morishima et al. | |
| 5,596,339 A | 1/1997 | Furness, III et al. | |
| 5,605,059 A | 2/1997 | Woodward | |
| 5,625,577 A | 4/1997 | Kunii et al. | |
| 5,683,404 A | 11/1997 | Johnson | |
| 5,742,421 A | 4/1998 | Wells et al. | |
| 6,005,548 A | 12/1999 | Latypov et al. | |
| 6,008,781 A | 12/1999 | Furness, III et al. | |
| 6,009,210 A | 12/1999 | Kang | |
| 6,027,216 A | 2/2000 | Guyton et al. | |
| 6,032,530 A | 3/2000 | Hock | |
| D422,617 S | 4/2000 | Simioni | |
| 6,066,794 A | 5/2000 | Longo | |
| 6,184,847 B1 | 2/2001 | Fateh et al. | |
| 6,236,476 B1 | 5/2001 | Son et al. | |
| 6,238,338 B1 | 5/2001 | DeLuca et al. | |
| 6,244,873 B1 | 6/2001 | Hill et al. | |
| 6,317,103 B1 | 11/2001 | Furness, III et al. | |
| 6,377,277 B1 | 4/2002 | Yamamoto | |
| D459,352 S | 6/2002 | Giovanniello | |
| 6,411,843 B1 | 6/2002 | Zarychta | |
| 6,487,906 B1 | 12/2002 | Hock | |
| 6,510,333 B1 | 1/2003 | Licata et al. | |
| 6,527,711 B1 | 3/2003 | Stivoric et al. | |
| 6,619,836 B1 | 9/2003 | Silvant et al. | |
| 6,639,570 B2 | 10/2003 | Furness, III et al. | |
| 6,658,287 B1 | 12/2003 | Litt et al. | |
| 6,720,984 B1 | 4/2004 | Jorgensen et al. | |
| 6,743,982 B2 | 6/2004 | Biegelsen et al. | |
| 6,771,294 B1 | 8/2004 | Pulli et al. | |
| 6,774,885 B1 | 8/2004 | Even-Zohar | |
| 6,807,438 B1 | 10/2004 | Brun Del Re et al. | |
| D502,661 S | 3/2005 | Rapport | |
| D502,662 S | 3/2005 | Rapport | |
| 6,865,409 B2 | 3/2005 | Getsla et al. | |
| D503,646 S | 4/2005 | Rapport | |
| 6,880,364 B1 | 4/2005 | Vidolin et al. | |
| 6,901,286 B1 | 5/2005 | Sinderby et al. | |
| 6,927,343 B2 | 8/2005 | Watanabe et al. | |
| 6,942,621 B2 | 9/2005 | Avinash et al. | |
| 6,965,842 B2 | 11/2005 | Rekimoto | |
| 6,972,734 B1 | 12/2005 | Ohshima et al. | |
| 6,984,208 B2 | 1/2006 | Zheng | |
| 7,022,919 B2 | 4/2006 | Brist et al. | |
| 7,028,507 B2 | 4/2006 | Rapport | |
| 7,086,218 B1 | 8/2006 | Pasach | |
| 7,089,148 B1 | 8/2006 | Bachmann et al. | |
| D535,401 S | 1/2007 | Travis et al. | |
| 7,173,437 B2 | 2/2007 | Hervieux et al. | |
| 7,209,114 B2 | 4/2007 | Radley-Smith | |
| D543,212 S | 5/2007 | Marks | |
| 7,265,298 B2 | 9/2007 | Maghribi et al. | |
| 7,271,774 B2 | 9/2007 | Puuri | |
| 7,333,090 B2 | 2/2008 | Tanaka et al. | |
| 7,351,975 B2 | 4/2008 | Brady et al. | |
| 7,450,107 B2 | 11/2008 | Radley-Smith | |
| 7,473,888 B2 | 1/2009 | Wine et al. | |
| 7,491,892 B2 | 2/2009 | Wagner et al. | |
| 7,517,725 B2 | 4/2009 | Reis | |
| 7,558,622 B2 | 7/2009 | Tran | |
| 7,574,253 B2 | 8/2009 | Edney et al. | |
| 7,580,742 B2 | 8/2009 | Tan et al. | |
| 7,596,393 B2 | 9/2009 | Jung et al. | |
| 7,618,260 B2 | 11/2009 | Daniel et al. | |
| 7,636,549 B2 | 12/2009 | Ma et al. | |
| 7,640,007 B2 | 12/2009 | Chen et al. | |
| 7,660,126 B2 | 2/2010 | Cho et al. | |
| 7,684,105 B2 | 3/2010 | Lamontagne et al. | |
| 7,747,113 B2 | 6/2010 | Mukawa et al. | |
| 7,761,390 B2 | 7/2010 | Ford | |
| 7,773,111 B2 | 8/2010 | Cleveland et al. | |
| 7,787,946 B2 | 8/2010 | Stahmann et al. | |
| 7,805,386 B2 | 9/2010 | Greer | |
| 7,809,435 B1 | 10/2010 | Ettare et al. | |
| 7,844,310 B2 | 11/2010 | Anderson | |
| D628,616 S | 12/2010 | Yuan | |
| 7,850,306 B2 | 12/2010 | Uusitalo et al. | |
| 7,870,211 B2 | 1/2011 | Pascal et al. | |
| D633,939 S | 3/2011 | Puentes et al. | |
| D634,771 S | 3/2011 | Fuchs | |
| 7,901,368 B2 | 3/2011 | Flaherty et al. | |
| 7,925,100 B2 | 4/2011 | Howell et al. | |
| 7,948,763 B2 | 5/2011 | Chuang | |
| D640,314 S | 6/2011 | Yang | |
| D643,428 S | 8/2011 | Janky et al. | |
| D646,192 S | 10/2011 | Woode | |
| D649,177 S | 11/2011 | Cho et al. | |
| 8,054,061 B2 | 11/2011 | Prance et al. | |
| D654,622 S | 2/2012 | Hsu | |
| 8,120,828 B2 | 2/2012 | Schwerdtner | |
| 8,170,656 B2 | 5/2012 | Tan et al. | |
| 8,179,604 B1 | 5/2012 | Prada Gomez et al. | |
| 8,188,937 B1 | 5/2012 | Amafuji et al. | |
| 8,190,249 B1 | 5/2012 | Gharieb et al. | |
| D661,613 S | 6/2012 | Demeglio | |
| 8,203,502 B1 | 6/2012 | Chi et al. | |
| 8,207,473 B2 | 6/2012 | Axisa et al. | |
| 8,212,859 B2 | 7/2012 | Tang et al. | |
| D667,482 S | 9/2012 | Healy et al. | |
| D669,522 S | 10/2012 | Klinar et al. | |
| D669,523 S | 10/2012 | Wakata et al. | |
| D671,590 S | 11/2012 | Klinar et al. | |
| 8,311,623 B2 | 11/2012 | Sanger | |
| 8,348,538 B2 | 1/2013 | Van Loenen et al. | |
| 8,351,651 B2 | 1/2013 | Lee | |
| 8,355,671 B2 | 1/2013 | Kramer et al. | |
| 8,384,683 B2 | 2/2013 | Luo | |
| 8,386,025 B2 | 2/2013 | Hoppe | |
| 8,389,862 B2 | 3/2013 | Arora et al. | |
| 8,421,634 B2 | 4/2013 | Tan et al. | |
| 8,427,977 B2 | 4/2013 | Workman et al. | |
| D682,343 S | 5/2013 | Waters | |
| D682,727 S | 5/2013 | Bulgari | |
| 8,435,191 B2 | 5/2013 | Barboutis et al. | |
| 8,437,844 B2 | 5/2013 | Syed Momen et al. | |
| 8,447,704 B2 * | 5/2013 | Tan | G06F 3/017 |
| | | | 706/62 |
| D685,019 S | 6/2013 | Li | |
| 8,467,270 B2 | 6/2013 | Gossweiler, III et al. | |
| 8,469,741 B2 | 6/2013 | Oster et al. | |
| D687,087 S | 7/2013 | Iurilli | |
| 8,484,022 B1 | 7/2013 | Vanhoucke | |
| D689,862 S | 9/2013 | Liu | |
| D692,941 S | 11/2013 | Klinar et al. | |
| 8,591,411 B2 | 11/2013 | Banet et al. | |
| D695,333 S | 12/2013 | Farnam et al. | |
| D695,454 S | 12/2013 | Moore | |
| 8,620,361 B2 | 12/2013 | Bailey et al. | |
| 8,624,124 B2 | 1/2014 | Koo et al. | |
| 8,634,119 B2 | 1/2014 | Bablumyan et al. | |
| D701,555 S | 3/2014 | Markovitz et al. | |
| 8,666,212 B1 | 3/2014 | Amirparviz | |

(56) References Cited

U.S. PATENT DOCUMENTS

| | | | |
|---|---|---|---|
| 8,702,629 B2 | 4/2014 | Giuffrida et al. |
| 8,704,882 B2 | 4/2014 | Turner |
| D704,248 S | 5/2014 | DiChiara |
| 8,718,980 B2 | 5/2014 | Garudadri et al. |
| 8,743,052 B1 | 6/2014 | Keller et al. |
| 8,744,543 B2 | 6/2014 | Li et al. |
| 8,754,862 B2 | 6/2014 | Zaliva |
| 8,777,668 B2 | 7/2014 | Ikeda et al. |
| D716,457 S | 10/2014 | Brefka et al. |
| D717,685 S | 11/2014 | Bailey et al. |
| 8,879,276 B2 | 11/2014 | Wang |
| 8,880,163 B2 | 11/2014 | Barachant et al. |
| 8,883,287 B2 | 11/2014 | Boyce et al. |
| 8,890,875 B2 | 11/2014 | Jammes et al. |
| 8,892,479 B2 | 11/2014 | Tan et al. |
| 8,895,865 B2 | 11/2014 | Lenahan et al. |
| D719,568 S | 12/2014 | Heinrich et al. |
| D719,570 S | 12/2014 | Heinrich et al. |
| 8,912,094 B2 | 12/2014 | Koo et al. |
| 8,914,472 B1 | 12/2014 | Lee et al. |
| 8,922,481 B1 | 12/2014 | Kauffmann et al. |
| D723,093 S | 2/2015 | Li |
| 8,954,135 B2 | 2/2015 | Yuen et al. |
| D724,647 S | 3/2015 | Rohrbach |
| 8,970,571 B1 | 3/2015 | Wong et al. |
| 8,971,023 B2 | 3/2015 | Olsson et al. |
| 9,018,532 B2 | 4/2015 | Wesselmann et al. |
| 9,037,530 B2 | 5/2015 | Tan et al. |
| 9,086,687 B2 | 7/2015 | Park et al. |
| 9,092,664 B2 | 7/2015 | Forutanpour et al. |
| D736,664 S | 8/2015 | Paradise et al. |
| 9,107,586 B2 | 8/2015 | Tran |
| D738,373 S | 9/2015 | Davies et al. |
| 9,135,708 B2 | 9/2015 | Ebisawa |
| 9,146,730 B2 | 9/2015 | Lazar |
| D741,855 S | 10/2015 | Park et al. |
| 9,170,674 B2 | 10/2015 | Forutanpour et al. |
| D742,272 S | 11/2015 | Bailey et al. |
| D742,874 S | 11/2015 | Cheng et al. |
| D743,963 S | 11/2015 | Osterhout |
| 9,182,826 B2 | 11/2015 | Powledge et al. |
| 9,211,417 B2 | 12/2015 | Heldman et al. |
| 9,218,574 B2 | 12/2015 | Phillipps et al. |
| D747,714 S | 1/2016 | Erbeus |
| D747,759 S | 1/2016 | Ho |
| 9,235,934 B2 | 1/2016 | Mandella et al. |
| 9,240,069 B1 | 1/2016 | Li |
| D750,623 S | 3/2016 | Park et al. |
| D751,065 S | 3/2016 | Magi |
| 9,278,453 B2 | 3/2016 | Assad |
| 9,299,248 B2 | 3/2016 | Lake et al. |
| D756,359 S | 5/2016 | Bailey et al. |
| 9,329,694 B2 | 5/2016 | Slonneger |
| 9,341,659 B2 | 5/2016 | Poupyrev et al. |
| 9,349,280 B2 | 5/2016 | Baldwin et al. |
| 9,351,653 B1 | 5/2016 | Harrison |
| D758,476 S | 6/2016 | Ho |
| D760,313 S | 6/2016 | Ho et al. |
| 9,367,139 B2 | 6/2016 | Ataee et al. |
| 9,372,535 B2 | 6/2016 | Bailey et al. |
| 9,389,694 B2 | 7/2016 | Ataee et al. |
| 9,393,418 B2 | 7/2016 | Giuffrida et al. |
| 9,402,582 B1 | 8/2016 | Parviz et al. |
| 9,408,316 B2 | 8/2016 | Bailey et al. |
| 9,418,927 B2 | 8/2016 | Axisa et al. |
| D766,895 S | 9/2016 | Choi |
| 9,439,566 B2 | 9/2016 | Arne et al. |
| D768,627 S | 10/2016 | Rochat et al. |
| 9,459,697 B2 | 10/2016 | Bedikian et al. |
| 9,472,956 B2 | 10/2016 | Michaelis et al. |
| 9,477,313 B2 | 10/2016 | Mistry et al. |
| D771,735 S | 11/2016 | Lee et al. |
| 9,483,123 B2 | 11/2016 | Aleem et al. |
| 9,529,434 B2 | 12/2016 | Choi et al. |
| D780,828 S | 3/2017 | Bonaventura et al. |
| D780,829 S | 3/2017 | Bonaventura et al. |
| 9,597,015 B2 | 3/2017 | McNames et al. |
| 9,600,030 B2 | 3/2017 | Bailey et al. |
| 9,612,661 B2 | 4/2017 | Wagner et al. |
| 9,613,262 B2 | 4/2017 | Holz |
| 9,652,047 B2 | 5/2017 | Mullins et al. |
| 9,654,477 B1 | 5/2017 | Kotamraju |
| 9,659,403 B1 | 5/2017 | Horowitz |
| 9,687,168 B2 | 6/2017 | John |
| 9,696,795 B2 | 7/2017 | Marcolina et al. |
| 9,720,515 B2 | 8/2017 | Wagner et al. |
| 9,741,169 B1 | 8/2017 | Holz |
| 9,766,709 B2 | 9/2017 | Holz |
| 9,785,247 B1 | 10/2017 | Horowitz et al. |
| 9,788,789 B2 | 10/2017 | Bailey |
| 9,807,221 B2 | 10/2017 | Bailey et al. |
| 9,864,431 B2 | 1/2018 | Keskin et al. |
| 9,867,548 B2 | 1/2018 | Le et al. |
| 9,880,632 B2 | 1/2018 | Ataee et al. |
| 9,891,718 B2 | 2/2018 | Connor |
| 9,921,641 B1 | 3/2018 | Worley, III et al. |
| 9,996,983 B2 | 6/2018 | Mullins |
| 10,024,678 B2* | 7/2018 | Moore ............... G01C 21/1656 |
| 10,042,422 B2 | 8/2018 | Morun et al. |
| 10,070,799 B2 | 9/2018 | Ang et al. |
| 10,078,435 B2 | 9/2018 | Noel |
| 10,101,809 B2 | 10/2018 | Morun et al. |
| 10,152,082 B2 | 12/2018 | Bailey |
| 10,185,416 B2 | 1/2019 | Mistry et al. |
| 10,188,309 B2 | 1/2019 | Morun et al. |
| 10,198,871 B1 | 2/2019 | Hariton |
| 10,199,008 B2 | 2/2019 | Aleem et al. |
| 10,203,751 B2 | 2/2019 | Keskin et al. |
| 10,216,274 B2 | 2/2019 | Chapeskie et al. |
| 10,251,577 B2 | 4/2019 | Morun et al. |
| 10,310,601 B2 | 6/2019 | Morun et al. |
| 10,331,210 B2 | 6/2019 | Morun et al. |
| 10,362,958 B2 | 7/2019 | Morun et al. |
| 10,409,371 B2 | 9/2019 | Kaifosh et al. |
| 10,429,928 B2 | 10/2019 | Morun et al. |
| 10,437,335 B2 | 10/2019 | Daniels |
| 10,460,455 B2 | 10/2019 | Giurgica-Tiron et al. |
| 10,489,986 B2 | 11/2019 | Kaifosh et al. |
| 10,496,168 B2 | 12/2019 | Kaifosh et al. |
| 10,504,286 B2 | 12/2019 | Kaifosh et al. |
| 10,520,378 B1 | 12/2019 | Brown et al. |
| 10,528,135 B2 | 1/2020 | Bailey et al. |
| 10,558,273 B2 | 2/2020 | Park et al. |
| 10,592,001 B2 | 3/2020 | Berenzweig et al. |
| 10,610,737 B1 | 4/2020 | Crawford |
| 10,676,083 B1 | 6/2020 | De Sapio et al. |
| 10,687,759 B2 | 6/2020 | Guo et al. |
| 10,905,350 B2 | 2/2021 | Berenzweig et al. |
| 10,905,383 B2 | 2/2021 | Barachant |
| 10,937,414 B2 | 3/2021 | Berenzweig et al. |
| 10,990,174 B2 | 4/2021 | Kaifosh et al. |
| 11,009,951 B2 | 5/2021 | Bailey et al. |
| 11,106,273 B2* | 8/2021 | Hazra .................... G06F 3/017 |
| 11,150,730 B1 | 10/2021 | Anderson et al. |
| 11,314,399 B2* | 4/2022 | Davis ................. G02B 27/0093 |
| 11,327,566 B2 | 5/2022 | Hussami et al. |
| 11,635,736 B2 | 4/2023 | Kaifosh et al. |
| 11,644,799 B2 | 5/2023 | Lake et al. |
| 12,299,196 B2 | 5/2025 | Edelson et al. |
| 2001/0033402 A1 | 10/2001 | Popovich |
| 2002/0003627 A1 | 1/2002 | Rieder |
| 2002/0009972 A1 | 1/2002 | Amento et al. |
| 2002/0030636 A1 | 3/2002 | Richards |
| 2002/0032386 A1 | 3/2002 | Sackner et al. |
| 2002/0077534 A1 | 6/2002 | DuRousseau |
| 2002/0094701 A1 | 7/2002 | Biegelsen et al. |
| 2002/0120415 A1 | 8/2002 | Millott et al. |
| 2002/0120916 A1 | 8/2002 | Snider, Jr. |
| 2002/0198472 A1 | 12/2002 | Kramer |
| 2003/0030595 A1 | 2/2003 | Radley-Smith |
| 2003/0036691 A1 | 2/2003 | Stanaland et al. |
| 2003/0051505 A1 | 3/2003 | Robertson et al. |
| 2003/0144586 A1 | 7/2003 | Tsubata |
| 2003/0144829 A1 | 7/2003 | Geatz et al. |

(56) References Cited

U.S. PATENT DOCUMENTS

| | | |
|---|---|---|
| 2003/0171921 A1 | 9/2003 | Manabe et al. |
| 2003/0182630 A1 | 9/2003 | Saund et al. |
| 2003/0184544 A1 | 10/2003 | Prudent |
| 2004/0010210 A1 | 1/2004 | Avinash et al. |
| 2004/0024312 A1 | 2/2004 | Zheng |
| 2004/0054273 A1 | 3/2004 | Finneran et al. |
| 2004/0068409 A1 | 4/2004 | Tanaka et al. |
| 2004/0073104 A1 | 4/2004 | Brun del Re et al. |
| 2004/0073414 A1 | 4/2004 | Bienenstock et al. |
| 2004/0080499 A1 | 4/2004 | Lui |
| 2004/0092839 A1 | 5/2004 | Shin et al. |
| 2004/0138580 A1 | 7/2004 | Frei et al. |
| 2004/0194500 A1 | 10/2004 | Rapport |
| 2004/0210165 A1 | 10/2004 | Marmaropoulos et al. |
| 2004/0243342 A1 | 12/2004 | Rekimoto |
| 2004/0254617 A1 | 12/2004 | Hemmerling et al. |
| 2005/0005637 A1 | 1/2005 | Rapport |
| 2005/0012715 A1 | 1/2005 | Ford |
| 2005/0070227 A1 | 3/2005 | Shen et al. |
| 2005/0070791 A1 | 3/2005 | Edney et al. |
| 2005/0115561 A1 | 6/2005 | Stahmann et al. |
| 2005/0119701 A1 | 6/2005 | Lauter et al. |
| 2005/0177038 A1 | 8/2005 | Kolpin et al. |
| 2005/0179644 A1 | 8/2005 | Alsio et al. |
| 2006/0018833 A1 | 1/2006 | Murphy et al. |
| 2006/0037359 A1 | 2/2006 | Stinespring |
| 2006/0058699 A1 | 3/2006 | Vitiello et al. |
| 2006/0061544 A1 | 3/2006 | Min et al. |
| 2006/0121958 A1 | 6/2006 | Jung et al. |
| 2006/0129057 A1 | 6/2006 | Maekawa et al. |
| 2006/0132705 A1 | 6/2006 | Li |
| 2006/0149338 A1 | 7/2006 | Flaherty et al. |
| 2006/0211956 A1 | 9/2006 | Sankai |
| 2006/0238707 A1 | 10/2006 | Elvesjo et al. |
| 2007/0009151 A1 | 1/2007 | Pittman et al. |
| 2007/0016265 A1 | 1/2007 | Davoodi et al. |
| 2007/0023662 A1 | 2/2007 | Brady et al. |
| 2007/0078308 A1 | 4/2007 | Daly |
| 2007/0132785 A1 | 6/2007 | Ebersole, Jr. et al. |
| 2007/0148624 A1 | 6/2007 | Nativ |
| 2007/0172797 A1 | 7/2007 | Hada et al. |
| 2007/0177770 A1 | 8/2007 | Derchak et al. |
| 2007/0185697 A1 | 8/2007 | Tan et al. |
| 2007/0196033 A1 | 8/2007 | Russo |
| 2007/0256494 A1 | 11/2007 | Nakamura et al. |
| 2007/0276270 A1 | 11/2007 | Tran |
| 2007/0279852 A1 | 12/2007 | Daniel et al. |
| 2007/0285399 A1 | 12/2007 | Lund |
| 2008/0001735 A1 | 1/2008 | Tran |
| 2008/0032638 A1 | 2/2008 | Anderson |
| 2008/0051673 A1 | 2/2008 | Kong et al. |
| 2008/0052643 A1 | 2/2008 | Ike et al. |
| 2008/0058668 A1 | 3/2008 | Seyed Momen et al. |
| 2008/0103639 A1 | 5/2008 | Troy et al. |
| 2008/0103769 A1 | 5/2008 | Schultz et al. |
| 2008/0136775 A1 | 6/2008 | Conant |
| 2008/0152217 A1 | 6/2008 | Greer |
| 2008/0163130 A1 | 7/2008 | Westerman |
| 2008/0214360 A1 | 9/2008 | Stirling et al. |
| 2008/0221487 A1 | 9/2008 | Zohar et al. |
| 2008/0262772 A1 | 10/2008 | Luinge et al. |
| 2008/0278497 A1 | 11/2008 | Jammes et al. |
| 2008/0285805 A1 | 11/2008 | Luinge et al. |
| 2009/0005700 A1* | 1/2009 | Joshi .................... A61B 5/389 |
| | | 600/546 |
| 2009/0007597 A1 | 1/2009 | Hanevold |
| 2009/0027337 A1 | 1/2009 | Hildreth |
| 2009/0031757 A1 | 2/2009 | Harding |
| 2009/0040016 A1 | 2/2009 | Ikeda |
| 2009/0051544 A1 | 2/2009 | Niknejad |
| 2009/0079607 A1 | 3/2009 | Denison et al. |
| 2009/0079813 A1 | 3/2009 | Hildreth |
| 2009/0082692 A1 | 3/2009 | Hale et al. |
| 2009/0082701 A1 | 3/2009 | Zohar et al. |
| 2009/0085864 A1 | 4/2009 | Kutliroff et al. |
| 2009/0102580 A1 | 4/2009 | Uchaykin |
| 2009/0109241 A1 | 4/2009 | Tsujimoto |
| 2009/0112080 A1 | 4/2009 | Matthews |
| 2009/0124881 A1 | 5/2009 | Rytky |
| 2009/0147004 A1 | 6/2009 | Ramon et al. |
| 2009/0179824 A1 | 7/2009 | Tsujimoto et al. |
| 2009/0189864 A1 | 7/2009 | Walker et al. |
| 2009/0189867 A1 | 7/2009 | Krah et al. |
| 2009/0195497 A1 | 8/2009 | Fitzgerald et al. |
| 2009/0204031 A1 | 8/2009 | McNames et al. |
| 2009/0207464 A1 | 8/2009 | Wiltshire et al. |
| 2009/0209878 A1 | 8/2009 | Sanger |
| 2009/0251407 A1 | 10/2009 | Flake et al. |
| 2009/0258669 A1 | 10/2009 | Nie et al. |
| 2009/0265671 A1 | 10/2009 | Sachs et al. |
| 2009/0318785 A1 | 12/2009 | Ishikawa et al. |
| 2009/0319230 A1 | 12/2009 | Case, Jr. et al. |
| 2009/0322653 A1 | 12/2009 | Putilin et al. |
| 2009/0326406 A1 | 12/2009 | Tan et al. |
| 2009/0327171 A1* | 12/2009 | Tan ........................ G06F 3/015 |
| | | 706/12 |
| 2010/0030532 A1 | 2/2010 | Arora et al. |
| 2010/0041974 A1 | 2/2010 | Ting et al. |
| 2010/0045619 A1 | 2/2010 | Birnbaum et al. |
| 2010/0063794 A1 | 3/2010 | Hernandez-Rebollar |
| 2010/0066664 A1 | 3/2010 | Son et al. |
| 2010/0106044 A1 | 4/2010 | Linderman |
| 2010/0113910 A1 | 5/2010 | Brauers et al. |
| 2010/0142015 A1 | 6/2010 | Kuwahara et al. |
| 2010/0149073 A1 | 6/2010 | Chaum et al. |
| 2010/0150415 A1 | 6/2010 | Atkinson et al. |
| 2010/0228487 A1 | 9/2010 | Leuthardt et al. |
| 2010/0234696 A1 | 9/2010 | Li et al. |
| 2010/0240981 A1 | 9/2010 | Barboutis et al. |
| 2010/0249635 A1 | 9/2010 | Van Der Reijden |
| 2010/0280628 A1 | 11/2010 | Sankai |
| 2010/0292595 A1 | 11/2010 | Paul |
| 2010/0292606 A1 | 11/2010 | Prakash et al. |
| 2010/0292617 A1 | 11/2010 | Lei et al. |
| 2010/0293115 A1 | 11/2010 | Seyed Momen |
| 2010/0306713 A1 | 12/2010 | Geisner et al. |
| 2010/0315266 A1 | 12/2010 | Gunawardana et al. |
| 2010/0317958 A1 | 12/2010 | Beck et al. |
| 2011/0007035 A1 | 1/2011 | Shai |
| 2011/0018754 A1 | 1/2011 | Tojima et al. |
| 2011/0025982 A1 | 2/2011 | Takahashi |
| 2011/0054360 A1 | 3/2011 | Son et al. |
| 2011/0065319 A1 | 3/2011 | Oster et al. |
| 2011/0066381 A1 | 3/2011 | Garudadri et al. |
| 2011/0072510 A1 | 3/2011 | Cheswick |
| 2011/0077484 A1 | 3/2011 | Van Slyke et al. |
| 2011/0082838 A1 | 4/2011 | Niemela |
| 2011/0092826 A1 | 4/2011 | Lee et al. |
| 2011/0105859 A1 | 5/2011 | Popovic et al. |
| 2011/0119216 A1 | 5/2011 | Wigdor |
| 2011/0133934 A1 | 6/2011 | Tan et al. |
| 2011/0134026 A1 | 6/2011 | Kang et al. |
| 2011/0151974 A1 | 6/2011 | Deaguero |
| 2011/0166434 A1 | 7/2011 | Gargiulo |
| 2011/0172503 A1 | 7/2011 | Knepper et al. |
| 2011/0173204 A1 | 7/2011 | Murillo et al. |
| 2011/0173574 A1 | 7/2011 | Clavin et al. |
| 2011/0181527 A1 | 7/2011 | Capela et al. |
| 2011/0202493 A1 | 8/2011 | Li |
| 2011/0205242 A1 | 8/2011 | Friesen |
| 2011/0213278 A1 | 9/2011 | Horak et al. |
| 2011/0221656 A1* | 9/2011 | Haddick .................. H04N 5/44 |
| | | 345/156 |
| 2011/0221672 A1 | 9/2011 | Osterhout et al. |
| 2011/0224507 A1 | 9/2011 | Banet et al. |
| 2011/0224556 A1 | 9/2011 | Moon et al. |
| 2011/0224564 A1 | 9/2011 | Moon et al. |
| 2011/0230782 A1 | 9/2011 | Bartol et al. |
| 2011/0248914 A1 | 10/2011 | Sherr |
| 2011/0262002 A1 | 10/2011 | Lee |
| 2011/0270135 A1 | 11/2011 | Dooley et al. |
| 2011/0295100 A1 | 12/2011 | Hegde et al. |
| 2011/0313762 A1 | 12/2011 | Ben-David et al. |
| 2012/0002256 A1 | 1/2012 | Lacoste et al. |

(56)                 References Cited

U.S. PATENT DOCUMENTS

| | | |
|---|---|---|
| 2012/0007821 A1 | 1/2012 | Zaliva |
| 2012/0029322 A1 | 2/2012 | Wartena et al. |
| 2012/0051005 A1 | 3/2012 | Vanfleteren et al. |
| 2012/0052268 A1 | 3/2012 | Axisa et al. |
| 2012/0053439 A1 | 3/2012 | Ylostalo et al. |
| 2012/0066163 A1 | 3/2012 | Balls et al. |
| 2012/0071092 A1 | 3/2012 | Pasquero et al. |
| 2012/0071780 A1 | 3/2012 | Barachant et al. |
| 2012/0101357 A1 | 4/2012 | Hoskuldsson et al. |
| 2012/0117514 A1 | 5/2012 | Kim et al. |
| 2012/0139817 A1 | 6/2012 | Freeman |
| 2012/0157789 A1 | 6/2012 | Kangas et al. |
| 2012/0157886 A1 | 6/2012 | Tenn et al. |
| 2012/0165695 A1 | 6/2012 | Kidmose et al. |
| 2012/0182309 A1 | 7/2012 | Griffin et al. |
| 2012/0184838 A1 | 7/2012 | John |
| 2012/0188158 A1 | 7/2012 | Tan et al. |
| 2012/0203076 A1 | 8/2012 | Fatta et al. |
| 2012/0209134 A1 | 8/2012 | Morita et al. |
| 2012/0226130 A1 | 9/2012 | De Graff et al. |
| 2012/0249797 A1 | 10/2012 | Haddick et al. |
| 2012/0265090 A1 | 10/2012 | Fink et al. |
| 2012/0265480 A1 | 10/2012 | Oshima |
| 2012/0275621 A1 | 11/2012 | Elko |
| 2012/0283526 A1 | 11/2012 | Gommesen et al. |
| 2012/0283896 A1 | 11/2012 | Persaud et al. |
| 2012/0293548 A1 | 11/2012 | Perez et al. |
| 2012/0302858 A1 | 11/2012 | Kidmose et al. |
| 2012/0320532 A1 | 12/2012 | Wang |
| 2012/0323521 A1 | 12/2012 | De Foras et al. |
| 2013/0004033 A1 | 1/2013 | Trugenberger |
| 2013/0005303 A1 | 1/2013 | Song et al. |
| 2013/0016292 A1 | 1/2013 | Miao et al. |
| 2013/0016413 A1 | 1/2013 | Saeedi et al. |
| 2013/0020948 A1 | 1/2013 | Han et al. |
| 2013/0027341 A1 | 1/2013 | Mastandrea |
| 2013/0038707 A1 | 2/2013 | Cunningham et al. |
| 2013/0077820 A1 | 3/2013 | Marais et al. |
| 2013/0080794 A1 | 3/2013 | Hsieh |
| 2013/0106686 A1 | 5/2013 | Bennett |
| 2013/0123656 A1* | 5/2013 | Heck ........... A63F 13/235 463/36 |
| 2013/0123666 A1 | 5/2013 | Giuffrida et al. |
| 2013/0127708 A1 | 5/2013 | Jung et al. |
| 2013/0131538 A1 | 5/2013 | Gaw et al. |
| 2013/0135223 A1 | 5/2013 | Shai |
| 2013/0135722 A1 | 5/2013 | Yokoyama |
| 2013/0141375 A1 | 6/2013 | Ludwig et al. |
| 2013/0144629 A1 | 6/2013 | Johnston et al. |
| 2013/0165813 A1 | 6/2013 | Chang et al. |
| 2013/0191741 A1 | 7/2013 | Dickinson et al. |
| 2013/0198694 A1 | 8/2013 | Rahman et al. |
| 2013/0207889 A1 | 8/2013 | Chang et al. |
| 2013/0207963 A1 | 8/2013 | Stirbu et al. |
| 2013/0215235 A1 | 8/2013 | Russell |
| 2013/0217998 A1 | 8/2013 | Mahfouz et al. |
| 2013/0221996 A1 | 8/2013 | Poupyrev et al. |
| 2013/0222384 A1 | 8/2013 | Futterer |
| 2013/0232095 A1 | 9/2013 | Tan et al. |
| 2013/0259238 A1 | 10/2013 | Xiang et al. |
| 2013/0265229 A1 | 10/2013 | Forutanpour et al. |
| 2013/0265437 A1 | 10/2013 | Thorn et al. |
| 2013/0271292 A1 | 10/2013 | McDermott |
| 2013/0285901 A1 | 10/2013 | Lee et al. |
| 2013/0285913 A1 | 10/2013 | Griffin et al. |
| 2013/0293580 A1 | 11/2013 | Spivack |
| 2013/0310979 A1 | 11/2013 | Herr et al. |
| 2013/0312256 A1 | 11/2013 | Wesselmann et al. |
| 2013/0317382 A1 | 11/2013 | Le |
| 2013/0317648 A1 | 11/2013 | Assad |
| 2013/0332196 A1 | 12/2013 | Pinsker |
| 2013/0335302 A1 | 12/2013 | Crane et al. |
| 2014/0005743 A1 | 1/2014 | Giuffrida et al. |
| 2014/0020945 A1 | 1/2014 | Hurwitz et al. |
| 2014/0028539 A1 | 1/2014 | Newham et al. |
| 2014/0028546 A1 | 1/2014 | Jeon et al. |
| 2014/0045547 A1 | 2/2014 | Singamsetty et al. |
| 2014/0049417 A1 | 2/2014 | Abdurrahman et al. |
| 2014/0051946 A1 | 2/2014 | Arne et al. |
| 2014/0052150 A1 | 2/2014 | Taylor et al. |
| 2014/0074179 A1 | 3/2014 | Heldman et al. |
| 2014/0092009 A1 | 4/2014 | Yen et al. |
| 2014/0094675 A1 | 4/2014 | Luna et al. |
| 2014/0098018 A1 | 4/2014 | Kim et al. |
| 2014/0100432 A1 | 4/2014 | Golda et al. |
| 2014/0107493 A1 | 4/2014 | Yuen et al. |
| 2014/0121471 A1 | 5/2014 | Walker |
| 2014/0122958 A1 | 5/2014 | Greenebrg et al. |
| 2014/0132512 A1 | 5/2014 | Gomez Sainz-Garcia |
| 2014/0139422 A1 | 5/2014 | Mistry et al. |
| 2014/0142937 A1 | 5/2014 | Powledge et al. |
| 2014/0143064 A1 | 5/2014 | Tran |
| 2014/0147820 A1 | 5/2014 | Snow et al. |
| 2014/0157168 A1 | 6/2014 | Albouyeh et al. |
| 2014/0194062 A1 | 7/2014 | Palin et al. |
| 2014/0196131 A1 | 7/2014 | Lee |
| 2014/0198034 A1 | 7/2014 | Bailey et al. |
| 2014/0198035 A1 | 7/2014 | Bailey et al. |
| 2014/0198944 A1 | 7/2014 | Forutanpour et al. |
| 2014/0200432 A1 | 7/2014 | Banerji et al. |
| 2014/0201666 A1 | 7/2014 | Bedikian et al. |
| 2014/0202643 A1 | 7/2014 | Hikmet et al. |
| 2014/0204455 A1 | 7/2014 | Popovich et al. |
| 2014/0207017 A1 | 7/2014 | Gilmore et al. |
| 2014/0223462 A1 | 8/2014 | Aimone et al. |
| 2014/0226193 A1 | 8/2014 | Sun |
| 2014/0232651 A1 | 8/2014 | Kress et al. |
| 2014/0236031 A1 | 8/2014 | Banet et al. |
| 2014/0240103 A1 | 8/2014 | Lake et al. |
| 2014/0240223 A1 | 8/2014 | Lake et al. |
| 2014/0245200 A1 | 8/2014 | Holz |
| 2014/0249397 A1 | 9/2014 | Lake et al. |
| 2014/0257141 A1 | 9/2014 | Giuffrida et al. |
| 2014/0258864 A1 | 9/2014 | Shenoy et al. |
| 2014/0277622 A1 | 9/2014 | Raniere |
| 2014/0278139 A1 | 9/2014 | Hong et al. |
| 2014/0278441 A1 | 9/2014 | Ton et al. |
| 2014/0279860 A1 | 9/2014 | Pan et al. |
| 2014/0282282 A1 | 9/2014 | Holz |
| 2014/0285326 A1 | 9/2014 | Luna et al. |
| 2014/0285429 A1 | 9/2014 | Simmons |
| 2014/0297528 A1 | 10/2014 | Agrawal et al. |
| 2014/0299362 A1 | 10/2014 | Park et al. |
| 2014/0304665 A1 | 10/2014 | Holz |
| 2014/0310595 A1 | 10/2014 | Acharya et al. |
| 2014/0330404 A1 | 11/2014 | Abdelghani et al. |
| 2014/0334083 A1 | 11/2014 | Bailey |
| 2014/0334653 A1 | 11/2014 | Luna et al. |
| 2014/0337861 A1 | 11/2014 | Chang et al. |
| 2014/0340857 A1 | 11/2014 | Hsu et al. |
| 2014/0344731 A1 | 11/2014 | Holz |
| 2014/0349257 A1 | 11/2014 | Connor |
| 2014/0354528 A1 | 12/2014 | Laughlin et al. |
| 2014/0354529 A1 | 12/2014 | Laughlin et al. |
| 2014/0355825 A1 | 12/2014 | Kim et al. |
| 2014/0358024 A1 | 12/2014 | Nelson et al. |
| 2014/0358825 A1 | 12/2014 | Phillipps et al. |
| 2014/0359540 A1 | 12/2014 | Kelsey et al. |
| 2014/0361988 A1 | 12/2014 | Katz et al. |
| 2014/0364703 A1 | 12/2014 | Kim et al. |
| 2014/0365163 A1 | 12/2014 | Jallon |
| 2014/0368424 A1 | 12/2014 | Choi et al. |
| 2014/0368428 A1 | 12/2014 | Pinault |
| 2014/0368474 A1 | 12/2014 | Kim et al. |
| 2014/0368896 A1 | 12/2014 | Nakazono et al. |
| 2014/0375465 A1 | 12/2014 | Fenuccio et al. |
| 2014/0376773 A1 | 12/2014 | Holz |
| 2015/0006120 A1 | 1/2015 | Sett et al. |
| 2015/0010203 A1 | 1/2015 | Muninder et al. |
| 2015/0011857 A1 | 1/2015 | Henson et al. |
| 2015/0019135 A1 | 1/2015 | Kacyvenski et al. |
| 2015/0025355 A1 | 1/2015 | Bailey et al. |
| 2015/0029092 A1 | 1/2015 | Holz et al. |
| 2015/0035827 A1 | 2/2015 | Yamaoka et al. |

(56) References Cited

U.S. PATENT DOCUMENTS

| | | |
|---|---|---|
| 2015/0036221 A1 | 2/2015 | Stephenson |
| 2015/0045689 A1 | 2/2015 | Barone |
| 2015/0045699 A1 | 2/2015 | Mokaya et al. |
| 2015/0051470 A1 | 2/2015 | Bailey et al. |
| 2015/0057506 A1 | 2/2015 | Luna et al. |
| 2015/0057770 A1 | 2/2015 | Bailey et al. |
| 2015/0065840 A1 | 3/2015 | Bailey |
| 2015/0070270 A1 | 3/2015 | Bailey et al. |
| 2015/0070274 A1 | 3/2015 | Morozov |
| 2015/0072326 A1 | 3/2015 | Mauri et al. |
| 2015/0084860 A1 | 3/2015 | Aleem et al. |
| 2015/0091790 A1 | 4/2015 | Forutanpour et al. |
| 2015/0094564 A1 | 4/2015 | Tashman et al. |
| 2015/0099946 A1 | 4/2015 | Sahin |
| 2015/0106052 A1 | 4/2015 | Balakrishnan et al. |
| 2015/0109202 A1 | 4/2015 | Ataee et al. |
| 2015/0124566 A1 | 5/2015 | Lake et al. |
| 2015/0128094 A1 | 5/2015 | Baldwin et al. |
| 2015/0141784 A1 | 5/2015 | Morun et al. |
| 2015/0148641 A1 | 5/2015 | Morun et al. |
| 2015/0148728 A1 | 5/2015 | Sallum et al. |
| 2015/0157944 A1 | 6/2015 | Gottlieb |
| 2015/0160621 A1 | 6/2015 | Yilmaz |
| 2015/0169074 A1 | 6/2015 | Ataee et al. |
| 2015/0170421 A1 | 6/2015 | Mandella et al. |
| 2015/0177841 A1 | 6/2015 | Vanblon et al. |
| 2015/0182113 A1 | 7/2015 | Utter, II |
| 2015/0182130 A1 | 7/2015 | Utter, II |
| 2015/0182160 A1 | 7/2015 | Kim et al. |
| 2015/0182163 A1 | 7/2015 | Utter |
| 2015/0182164 A1 | 7/2015 | Utter, II |
| 2015/0182165 A1 | 7/2015 | Miller et al. |
| 2015/0185838 A1 | 7/2015 | Camacho-Perez et al. |
| 2015/0185853 A1 | 7/2015 | Clausen et al. |
| 2015/0186609 A1 | 7/2015 | Utter, II |
| 2015/0187355 A1 | 7/2015 | Parkinson et al. |
| 2015/0193949 A1 | 7/2015 | Katz et al. |
| 2015/0199025 A1 | 7/2015 | Holz |
| 2015/0205126 A1 | 7/2015 | Schowengerdt |
| 2015/0205134 A1 | 7/2015 | Bailey et al. |
| 2015/0213191 A1 | 7/2015 | Abdelghani et al. |
| 2015/0216475 A1 | 8/2015 | Luna et al. |
| 2015/0220152 A1 | 8/2015 | Tait et al. |
| 2015/0223716 A1 | 8/2015 | Korkala et al. |
| 2015/0230756 A1 | 8/2015 | Luna et al. |
| 2015/0234426 A1 | 8/2015 | Bailey et al. |
| 2015/0234477 A1 | 8/2015 | Abovitz et al. |
| 2015/0237716 A1 | 8/2015 | Su et al. |
| 2015/0242009 A1 | 8/2015 | Xiao et al. |
| 2015/0242120 A1 | 8/2015 | Rodriguez |
| 2015/0242575 A1 | 8/2015 | Abovitz et al. |
| 2015/0261306 A1 | 9/2015 | Lake |
| 2015/0261318 A1 | 9/2015 | Scavezze et al. |
| 2015/0272483 A1 | 10/2015 | Etemad et al. |
| 2015/0277575 A1 | 10/2015 | Ataee et al. |
| 2015/0288944 A1 | 10/2015 | Nistico et al. |
| 2015/0289995 A1 | 10/2015 | Wilkinson et al. |
| 2015/0293592 A1 | 10/2015 | Cheong et al. |
| 2015/0296553 A1 | 10/2015 | DiFranco et al. |
| 2015/0302168 A1 | 10/2015 | De Sapio et al. |
| 2015/0305672 A1 | 10/2015 | Grey et al. |
| 2015/0309563 A1 | 10/2015 | Connor |
| 2015/0309582 A1 | 10/2015 | Gupta |
| 2015/0310766 A1 | 10/2015 | Alshehri et al. |
| 2015/0312175 A1 | 10/2015 | Langholz |
| 2015/0313496 A1 | 11/2015 | Connor |
| 2015/0323998 A1 | 11/2015 | Kudekar et al. |
| 2015/0325202 A1 | 11/2015 | Lake et al. |
| 2015/0332013 A1 | 11/2015 | Lee et al. |
| 2015/0346701 A1 | 12/2015 | Gordon et al. |
| 2015/0351690 A1 | 12/2015 | Toth et al. |
| 2015/0355716 A1 | 12/2015 | Balasubramanian et al. |
| 2015/0355718 A1 | 12/2015 | Slonneger |
| 2015/0362734 A1 | 12/2015 | Moser et al. |
| 2015/0366504 A1 | 12/2015 | Connor |
| 2015/0370326 A1 | 12/2015 | Chapeskie et al. |
| 2015/0370333 A1 | 12/2015 | Ataee et al. |
| 2015/0378161 A1 | 12/2015 | Bailey et al. |
| 2015/0378162 A1 | 12/2015 | Bailey et al. |
| 2015/0378164 A1 | 12/2015 | Bailey et al. |
| 2015/0379770 A1 | 12/2015 | Haley, Jr. et al. |
| 2016/0011668 A1 | 1/2016 | Gilad-Bachrach et al. |
| 2016/0020500 A1 | 1/2016 | Matsuda |
| 2016/0026853 A1 | 1/2016 | Wexler et al. |
| 2016/0033771 A1 | 2/2016 | Tremblay et al. |
| 2016/0049073 A1 | 2/2016 | Lee |
| 2016/0050037 A1 | 2/2016 | Webb |
| 2016/0071319 A1 | 3/2016 | Fallon et al. |
| 2016/0080897 A1 | 3/2016 | Moore et al. |
| 2016/0092504 A1 | 3/2016 | Mitri et al. |
| 2016/0093106 A1 | 3/2016 | Black |
| 2016/0099010 A1 | 4/2016 | Sainath et al. |
| 2016/0107309 A1 | 4/2016 | Walsh et al. |
| 2016/0113587 A1 | 4/2016 | Kothe et al. |
| 2016/0144172 A1 | 5/2016 | Hsueh et al. |
| 2016/0150636 A1 | 5/2016 | Otsubo |
| 2016/0156762 A1 | 6/2016 | Bailey et al. |
| 2016/0162604 A1 | 6/2016 | Xiaoli et al. |
| 2016/0170710 A1 | 6/2016 | Kim et al. |
| 2016/0187992 A1 | 6/2016 | Yamamoto et al. |
| 2016/0195928 A1 | 7/2016 | Wagner et al. |
| 2016/0199699 A1 | 7/2016 | Klassen |
| 2016/0202081 A1 | 7/2016 | Debieuvre et al. |
| 2016/0206206 A1 | 7/2016 | Avila et al. |
| 2016/0207201 A1 | 7/2016 | Herr et al. |
| 2016/0217614 A1 | 7/2016 | Kraver et al. |
| 2016/0235323 A1 | 8/2016 | Tadi et al. |
| 2016/0238845 A1 | 8/2016 | Alexander et al. |
| 2016/0239080 A1 | 8/2016 | Marcolina et al. |
| 2016/0242646 A1 | 8/2016 | Obma |
| 2016/0259407 A1 | 9/2016 | Schick |
| 2016/0262687 A1 | 9/2016 | Vaidyanathan et al. |
| 2016/0263458 A1 | 9/2016 | Mather et al. |
| 2016/0274365 A1 | 9/2016 | Bailey et al. |
| 2016/0274732 A1 | 9/2016 | Bang et al. |
| 2016/0274758 A1 | 9/2016 | Bailey |
| 2016/0282947 A1 | 9/2016 | Schwarz et al. |
| 2016/0291768 A1 | 10/2016 | Cho et al. |
| 2016/0292497 A1 | 10/2016 | Kehtarnavaz et al. |
| 2016/0309249 A1 | 10/2016 | Wu et al. |
| 2016/0313798 A1 | 10/2016 | Connor |
| 2016/0313801 A1 | 10/2016 | Wagner et al. |
| 2016/0313890 A1 | 10/2016 | Walline et al. |
| 2016/0313899 A1 | 10/2016 | Noel |
| 2016/0314623 A1 | 10/2016 | Coleman et al. |
| 2016/0327796 A1 | 11/2016 | Bailey et al. |
| 2016/0327797 A1 | 11/2016 | Bailey et al. |
| 2016/0342227 A1 | 11/2016 | Natzke et al. |
| 2016/0349514 A1 | 12/2016 | Alexander et al. |
| 2016/0349515 A1 | 12/2016 | Alexander et al. |
| 2016/0349516 A1 | 12/2016 | Alexander et al. |
| 2016/0350973 A1 | 12/2016 | Shapira et al. |
| 2016/0377865 A1 | 12/2016 | Alexander et al. |
| 2016/0377866 A1 | 12/2016 | Alexander et al. |
| 2017/0025026 A1 | 1/2017 | Ortiz Catalan |
| 2017/0031502 A1 | 2/2017 | Rosenberg et al. |
| 2017/0035313 A1 | 2/2017 | Hong et al. |
| 2017/0061817 A1 | 3/2017 | Mettler May |
| 2017/0068095 A1 | 3/2017 | Holland et al. |
| 2017/0068445 A1 | 3/2017 | Lee et al. |
| 2017/0075426 A1 | 3/2017 | Camacho Perez et al. |
| 2017/0079828 A1 | 3/2017 | Pedtke et al. |
| 2017/0080346 A1 | 3/2017 | Abbas |
| 2017/0090604 A1 | 3/2017 | Barbier |
| 2017/0091567 A1 | 3/2017 | Wang et al. |
| 2017/0095178 A1 | 4/2017 | Schoen et al. |
| 2017/0097753 A1 | 4/2017 | Bailey et al. |
| 2017/0115483 A1 | 4/2017 | Aleem et al. |
| 2017/0119472 A1 | 5/2017 | Herrmann et al. |
| 2017/0123487 A1* | 5/2017 | Hazra ................... G06F 3/0482 |
| 2017/0124474 A1 | 5/2017 | Kashyap |
| 2017/0124816 A1 | 5/2017 | Yang et al. |
| 2017/0127354 A1 | 5/2017 | Garland et al. |
| 2017/0147077 A1 | 5/2017 | Park et al. |

(56)                References Cited

U.S. PATENT DOCUMENTS

| | | |
|---|---|---|
| 2017/0153701 A1 | 6/2017 | Mahon et al. |
| 2017/0161635 A1 | 6/2017 | Oono et al. |
| 2017/0188878 A1 | 7/2017 | Lee |
| 2017/0188980 A1 | 7/2017 | Ash |
| 2017/0197142 A1 | 7/2017 | Stafford et al. |
| 2017/0205876 A1 | 7/2017 | Vidal et al. |
| 2017/0209055 A1 | 7/2017 | Pantelopoulos et al. |
| 2017/0212290 A1 | 7/2017 | Alexander et al. |
| 2017/0212349 A1 | 7/2017 | Bailey et al. |
| 2017/0219829 A1 | 8/2017 | Bailey |
| 2017/0220923 A1 | 8/2017 | Bae et al. |
| 2017/0237789 A1 | 8/2017 | Harner et al. |
| 2017/0237901 A1 | 8/2017 | Lee et al. |
| 2017/0259167 A1 | 9/2017 | Cook et al. |
| 2017/0262064 A1 | 9/2017 | Ofir et al. |
| 2017/0277282 A1 | 9/2017 | Go |
| 2017/0285744 A1 | 10/2017 | Juliato |
| 2017/0285756 A1 | 10/2017 | Wang et al. |
| 2017/0285757 A1 | 10/2017 | Robertson et al. |
| 2017/0285848 A1 | 10/2017 | Rosenberg et al. |
| 2017/0296363 A1 | 10/2017 | Yetkin et al. |
| 2017/0299956 A1 | 10/2017 | Holland et al. |
| 2017/0301630 A1 | 10/2017 | Nguyen et al. |
| 2017/0308118 A1 | 10/2017 | Ito |
| 2017/0312614 A1 | 11/2017 | Tran et al. |
| 2017/0329392 A1 | 11/2017 | Keskin et al. |
| 2017/0329404 A1 | 11/2017 | Keskin et al. |
| 2017/0340506 A1 | 11/2017 | Zhang et al. |
| 2017/0344706 A1 | 11/2017 | Torres et al. |
| 2017/0347908 A1 | 12/2017 | Watanabe et al. |
| 2017/0371403 A1 | 12/2017 | Wetzler et al. |
| 2018/0000367 A1 | 1/2018 | Longinotti-Buitoni |
| 2018/0018825 A1 | 1/2018 | Kim et al. |
| 2018/0020285 A1 | 1/2018 | Zass |
| 2018/0020951 A1 | 1/2018 | Kaifosh et al. |
| 2018/0020978 A1 | 1/2018 | Kaifosh et al. |
| 2018/0020990 A1 | 1/2018 | Park et al. |
| 2018/0024634 A1 | 1/2018 | Kaifosh et al. |
| 2018/0024635 A1 | 1/2018 | Kaifosh et al. |
| 2018/0024641 A1 | 1/2018 | Mao et al. |
| 2018/0064363 A1 | 3/2018 | Morun et al. |
| 2018/0067553 A1 | 3/2018 | Morun et al. |
| 2018/0068489 A1 | 3/2018 | Kim et al. |
| 2018/0074332 A1 | 3/2018 | Li et al. |
| 2018/0081439 A1 | 3/2018 | Daniels |
| 2018/0088675 A1 | 3/2018 | Vogel et al. |
| 2018/0088765 A1 | 3/2018 | Bailey |
| 2018/0092599 A1 | 4/2018 | Kerth et al. |
| 2018/0093181 A1 | 4/2018 | Goslin et al. |
| 2018/0095542 A1 | 4/2018 | Mallinson |
| 2018/0095630 A1 | 4/2018 | Bailey |
| 2018/0101235 A1 | 4/2018 | Bodensteiner et al. |
| 2018/0101289 A1 | 4/2018 | Bailey |
| 2018/0101599 A1 | 4/2018 | Arnold et al. |
| 2018/0107275 A1 | 4/2018 | Chen et al. |
| 2018/0120948 A1 | 5/2018 | Aleem et al. |
| 2018/0133551 A1 | 5/2018 | Chang et al. |
| 2018/0140441 A1 | 5/2018 | Poirters |
| 2018/0150033 A1 | 5/2018 | Lake et al. |
| 2018/0153430 A1 | 6/2018 | Ang et al. |
| 2018/0153444 A1 | 6/2018 | Yang et al. |
| 2018/0154140 A1 | 6/2018 | Bouton et al. |
| 2018/0168905 A1 | 6/2018 | Goodall et al. |
| 2018/0178008 A1 | 6/2018 | Bouton et al. |
| 2018/0217249 A1 | 8/2018 | La Salla et al. |
| 2018/0239430 A1 | 8/2018 | Tadi et al. |
| 2018/0240459 A1 | 8/2018 | Weng et al. |
| 2018/0247443 A1 | 8/2018 | Briggs et al. |
| 2018/0279919 A1 | 10/2018 | Bansbach et al. |
| 2018/0301057 A1 | 10/2018 | Hargrove et al. |
| 2018/0307303 A1 | 10/2018 | Powderly et al. |
| 2018/0307314 A1 | 10/2018 | Connor |
| 2018/0314879 A1 | 11/2018 | Khwaja et al. |
| 2018/0321745 A1 | 11/2018 | Morun et al. |
| 2018/0321746 A1 | 11/2018 | Morun et al. |
| 2018/0330549 A1 | 11/2018 | Brenton |
| 2018/0333575 A1 | 11/2018 | Bouton |
| 2018/0344195 A1 | 12/2018 | Morun et al. |
| 2018/0356890 A1 | 12/2018 | Zhang et al. |
| 2018/0360379 A1 | 12/2018 | Harrison et al. |
| 2019/0008453 A1 | 1/2019 | Spoof |
| 2019/0025919 A1 | 1/2019 | Tadi et al. |
| 2019/0027141 A1 | 1/2019 | Strong et al. |
| 2019/0033967 A1 | 1/2019 | Morun et al. |
| 2019/0033974 A1 | 1/2019 | Mu et al. |
| 2019/0038166 A1 | 2/2019 | Tavabi et al. |
| 2019/0056422 A1 | 2/2019 | Park et al. |
| 2019/0076716 A1 | 3/2019 | Chiou et al. |
| 2019/0089898 A1 | 3/2019 | Kim et al. |
| 2019/0113973 A1 | 4/2019 | Coleman et al. |
| 2019/0121305 A1 | 4/2019 | Kaifosh et al. |
| 2019/0121306 A1 | 4/2019 | Kaifosh et al. |
| 2019/0121522 A1 | 4/2019 | Davis et al. |
| 2019/0146809 A1 | 5/2019 | Lee et al. |
| 2019/0150777 A1 | 5/2019 | Guo et al. |
| 2019/0192037 A1 | 6/2019 | Morun et al. |
| 2019/0196585 A1 | 6/2019 | Laszlo et al. |
| 2019/0196586 A1 | 6/2019 | Laszlo et al. |
| 2019/0197778 A1 | 6/2019 | Sachdeva et al. |
| 2019/0209034 A1 | 7/2019 | Deno et al. |
| 2019/0212817 A1 | 7/2019 | Kaifosh et al. |
| 2019/0216619 A1 | 7/2019 | McDonnall et al. |
| 2019/0223748 A1 | 7/2019 | Al-Natsheh et al. |
| 2019/0227627 A1 | 7/2019 | Kaifosh et al. |
| 2019/0228330 A1 | 7/2019 | Kaifosh et al. |
| 2019/0228533 A1* | 7/2019 | Giurgica-Tiron ....... G06F 3/015 |
| 2019/0228579 A1 | 7/2019 | Kaifosh et al. |
| 2019/0228590 A1 | 7/2019 | Kaifosh et al. |
| 2019/0228591 A1 | 7/2019 | Giurgica-Tiron et al. |
| 2019/0247650 A1 | 8/2019 | Tran |
| 2019/0279407 A1 | 9/2019 | McHugh et al. |
| 2019/0294243 A1 | 9/2019 | Laszlo et al. |
| 2019/0324549 A1 | 10/2019 | Araki et al. |
| 2019/0332140 A1 | 10/2019 | Wang et al. |
| 2019/0348026 A1 | 11/2019 | Berenzweig et al. |
| 2019/0348027 A1 | 11/2019 | Berenzweig et al. |
| 2019/0357787 A1 | 11/2019 | Barachant et al. |
| 2019/0362557 A1 | 11/2019 | Lacey et al. |
| 2020/0042089 A1 | 2/2020 | Ang et al. |
| 2020/0057661 A1 | 2/2020 | Bendfeldt |
| 2020/0065569 A1 | 2/2020 | Nduka et al. |
| 2020/0069210 A1 | 3/2020 | Berenzweig et al. |
| 2020/0069211 A1 | 3/2020 | Berenzweig et al. |
| 2020/0073483 A1 | 3/2020 | Berenzweig et al. |
| 2020/0077955 A1 | 3/2020 | Shui et al. |
| 2020/0097081 A1 | 3/2020 | Stone et al. |
| 2020/0097083 A1 | 3/2020 | Mao et al. |
| 2020/0111260 A1 | 4/2020 | Osborn et al. |
| 2020/0125171 A1 | 4/2020 | Morun et al. |
| 2020/0142490 A1 | 5/2020 | Xiong et al. |
| 2020/0143795 A1 | 5/2020 | Park et al. |
| 2020/0159322 A1 | 5/2020 | Morun et al. |
| 2020/0163562 A1 | 5/2020 | Neaves |
| 2020/0205932 A1 | 7/2020 | Zar et al. |
| 2020/0225320 A1 | 7/2020 | Belskikh et al. |
| 2020/0245873 A1 | 8/2020 | Frank et al. |
| 2020/0249752 A1 | 8/2020 | Parshionikar |
| 2020/0275895 A1 | 9/2020 | Barachant |
| 2020/0301509 A1 | 9/2020 | Liu et al. |
| 2020/0305795 A1 | 10/2020 | Floyd et al. |
| 2020/0310540 A1 | 10/2020 | Hussami et al. |
| 2020/0320335 A1 | 10/2020 | Shamun et al. |
| 2021/0109598 A1 | 4/2021 | Zhang et al. |
| 2021/0117523 A1 | 4/2021 | Kim et al. |
| 2021/0290159 A1 | 9/2021 | Bruinsma et al. |
| 2021/0311546 A1 | 10/2021 | Kodama et al. |
| 2022/0019284 A1 | 1/2022 | Kaifosh et al. |
| 2022/0134219 A1 | 5/2022 | Stafford et al. |
| 2022/0256706 A1 | 8/2022 | Xiong et al. |

(56)  References Cited

U.S. PATENT DOCUMENTS

| | | | |
|---|---|---|---|
| 2024/0302899 | A1 | 9/2024 | Edelson et al. |
| 2025/0095302 | A1* | 3/2025 | Wetmore ............... G06F 3/013 |

FOREIGN PATENT DOCUMENTS

| | | | |
|---|---|---|---|
| CA | 2939644 | A1 | 8/2015 |
| CN | 1838933 | A | 9/2006 |
| CN | 101310242 | A | 11/2008 |
| CN | 102129343 | A | 7/2011 |
| CN | 102246125 | A | 11/2011 |
| CN | 102349037 | A | 2/2012 |
| CN | 102566756 | A | 7/2012 |
| CN | 103501694 | A | 1/2014 |
| CN | 103720470 | A | 4/2014 |
| CN | 103764021 | A | 4/2014 |
| CN | 103777752 | A | 5/2014 |
| CN | 103858073 | A | 6/2014 |
| CN | 103886215 | A | 6/2014 |
| CN | 104107134 | A | 10/2014 |
| CN | 104205015 | A | 12/2014 |
| CN | 104951069 | A | 9/2015 |
| CN | 105009031 | A | 10/2015 |
| CN | 105190477 | A | 12/2015 |
| CN | 105190578 | A | 12/2015 |
| CN | 105511615 | A | 4/2016 |
| CN | 106061369 | A | 10/2016 |
| CN | 106067178 | A | 11/2016 |
| CN | 106102504 | A | 11/2016 |
| CN | 106108898 | A | 11/2016 |
| CN | 107203272 | A | 9/2017 |
| CN | 107209566 | A | 9/2017 |
| CN | 107589782 | A | 1/2018 |
| CN | 107864440 | A | 3/2018 |
| CN | 107928980 | A | 4/2018 |
| CN | 108431736 | A | 8/2018 |
| CN | 108463271 | A | 8/2018 |
| CN | 108665956 | A | 10/2018 |
| CN | 109243572 | A | 1/2019 |
| CN | 109620651 | A | 4/2019 |
| CN | 110300542 | A | 10/2019 |
| CN | 111616847 | A | 9/2020 |
| CN | 112074225 | A | 12/2020 |
| CN | 112469469 | A | 3/2021 |
| CN | 112789577 | A | 5/2021 |
| CN | 112822992 | A | 5/2021 |
| CN | 113632176 | A | 11/2021 |
| CN | ZL2019800218996 | | 8/2023 |
| DE | 4412278 | A1 | 10/1995 |
| EP | 0301790 | A2 | 2/1989 |
| EP | 1345210 | A2 | 9/2003 |
| EP | 1408443 | B1 | 10/2006 |
| EP | 2198521 | B1 | 6/2012 |
| EP | 2541763 | A1 | 1/2013 |
| EP | 2733578 | A2 | 5/2014 |
| EP | 2959394 | A1 | 12/2015 |
| EP | 3104737 | A1 | 12/2016 |
| EP | 3200051 | A1 | 8/2017 |
| EP | 3487395 | A1 | 5/2019 |
| EP | 3697297 | A4 | 12/2020 |
| EP | 2959394 | B1 | 5/2021 |
| EP | 3948881 | A1 | 2/2022 |
| JP | S61198892 | A | 9/1986 |
| JP | H05277080 | A | 10/1993 |
| JP | H0639754 | A | 2/1994 |
| JP | H07248873 | A | 9/1995 |
| JP | 3103427 | B2 | 10/2000 |
| JP | 2001051726 | A | 2/2001 |
| JP | 2001054507 | A | 2/2001 |
| JP | 2002287869 | A | 10/2002 |
| JP | 2003303047 | A | 10/2003 |
| JP | 2005095561 | A | 4/2005 |
| JP | 2005352739 | A | 12/2005 |
| JP | 2008192004 | A | 8/2008 |
| JP | 2009050679 | A | 3/2009 |
| JP | 2010520561 | A | 6/2010 |
| JP | 2013160905 | A | 8/2013 |
| JP | 2015512550 | A | 4/2015 |
| JP | 2015514467 | A | 5/2015 |
| JP | 2016507098 | A | 3/2016 |
| JP | 2016507851 | A | 3/2016 |
| JP | 2016150118 | A | 8/2016 |
| JP | 2016540276 | A | 12/2016 |
| JP | 2017509386 | A | 4/2017 |
| JP | 2018511122 | A | 4/2018 |
| JP | 2018190127 | A | 11/2018 |
| JP | 2019023941 | A | 2/2019 |
| JP | 2019185531 | A | 10/2019 |
| JP | 2021072136 | A | 5/2021 |
| KR | 20110040165 | A | 4/2011 |
| KR | 20120094870 | A | 8/2012 |
| KR | 20120097997 | A | 9/2012 |
| KR | 20150123254 | A | 11/2015 |
| KR | 20160121552 | A | 10/2016 |
| KR | 20170067873 | A | 6/2017 |
| KR | 20170107283 | A | 9/2017 |
| KR | 101790147 | B1 | 10/2017 |
| KR | 20190022329 | A | 3/2019 |
| WO | 9527341 | A1 | 10/1995 |
| WO | 2006086504 | A2 | 8/2006 |
| WO | 2008109248 | A2 | 9/2008 |
| WO | 2009042313 | A1 | 4/2009 |
| WO | 2010095636 | A1 | 8/2010 |
| WO | 2010104879 | A2 | 9/2010 |
| WO | 2011011750 | A1 | 1/2011 |
| WO | 2011070554 | A2 | 6/2011 |
| WO | 2012155157 | A1 | 11/2012 |
| WO | 2013154864 | A1 | 10/2013 |
| WO | 2014130871 | A1 | 8/2014 |
| WO | 2014155288 | A2 | 10/2014 |
| WO | 2014186370 | A1 | 11/2014 |
| WO | 2014194257 | A1 | 12/2014 |
| WO | 2014197443 | A1 | 12/2014 |
| WO | 2015027089 | A1 | 2/2015 |
| WO | 2015063520 | A1 | 5/2015 |
| WO | 2015073713 | A1 | 5/2015 |
| WO | 2015081113 | A1 | 6/2015 |
| WO | 2015100172 | A1 | 7/2015 |
| WO | 2015123445 | A1 | 8/2015 |
| WO | 2015123775 | A1 | 8/2015 |
| WO | 2015184760 | A1 | 12/2015 |
| WO | 2015192117 | A1 | 12/2015 |
| WO | 2015199747 | A1 | 12/2015 |
| WO | 2016041088 | A1 | 3/2016 |
| WO | 2017062544 | A1 | 4/2017 |
| WO | 2017075611 | A1 | 5/2017 |
| WO | 2017092225 | A1 | 6/2017 |
| WO | 2017120669 | A1 | 7/2017 |
| WO | 2017172185 | A1 | 10/2017 |
| WO | 2017208167 | A1 | 12/2017 |
| WO | 2018022602 | A1 | 2/2018 |
| WO | 2018098046 | A2 | 5/2018 |
| WO | 2018175257 | A1 | 9/2018 |
| WO | 2019099758 | A1 | 5/2019 |
| WO | 2019147953 | A1 | 8/2019 |
| WO | 2019147958 | A1 | 8/2019 |
| WO | 2019147996 | A1 | 8/2019 |
| WO | 2019217419 | A2 | 11/2019 |
| WO | 2019226259 | A1 | 11/2019 |
| WO | 2019231911 | A1 | 12/2019 |
| WO | 2020047429 | A1 | 3/2020 |
| WO | 2020061440 | A1 | 3/2020 |
| WO | 2020061451 | A1 | 3/2020 |
| WO | 2020072915 | A1 | 4/2020 |

OTHER PUBLICATIONS

Final Office Action mailed Sep. 23, 2020 for U.S. Appl. No. 15/816,435, filed Nov. 17, 2017, 70 Pages.
Final Office Action mailed Jan. 28, 2020 for U.S. Appl. No. 16/557,342, filed Aug. 30, 2019, 15 Pages.
Final Office Action mailed Jul. 28, 2017 for U.S. Appl. No. 14/505,836, filed Oct. 3, 2014, 52 Pages.

(56) References Cited

OTHER PUBLICATIONS

Final Office Action mailed Jun. 28, 2021 for U.S. Appl. No. 16/557,342, filed Aug. 30, 2019, 11 Pages.
Final Office Action mailed Nov. 29, 2019 for U.S. Appl. No. 15/659,072, filed Jul. 25, 2017, 36 Pages.
Final Office Action mailed Nov. 29, 2019 for U.S. Appl. No. 16/353,998, filed Mar. 14, 2019, 33 Pages.
Final Office Action received for U.S. Appl. No. 14/155,087 dated Dec. 16, 2016, 32 pages.
Final Office Action received for U.S. Appl. No. 14/155,087 dated Jul. 20, 2015, 27 pages.
Final Office Action received for U.S. Appl. No. 14/155,087 dated Jul. 8, 2016, 27 pages.
Final Office Action received for U.S. Appl. No. 14/155,087 dated Nov. 27, 2017, 40 pages.
Final Office Action received for U.S. Appl. No. 14/155,107 dated Dec. 19, 2016, 35 pages.
Final Office Action received for U.S. Appl. No. 14/155,107 dated Jan. 17, 2019, 46 pages.
Final Office Action received for U.S. Appl. No. 14/155,107 dated Jul. 16, 2015, 28 pages.
Final Office Action received for U.S. Appl. No. 14/155,107 dated Jul. 8, 2016, 31 pages.
Final Office Action received for U.S. Appl. No. 14/155,107 dated Nov. 27, 2017, 44 pages.
First Office Action mailed Nov. 25, 2020, for Canadian Application No. 2921954, filed Aug. 21, 2014, 4 pages.
Fong H.C., et al., "PepperGram With Interactive Control," 22nd International Conference Onvirtual System Multimedia (VSMM), Oct. 17, 2016, 5 pages.
Gallina A., et al., "Surface EMG Biofeedback," Surface Electromyography: Physiology, Engineering, and Applications, 2016, pp. 485-500.
Gargiulo G., et al., "Giga-Ohm High-Impedance FET Input Amplifiers for Dry Electrode Biosensor Circuits and Systems," Integrated Microsystems: Electronics, Photonics, and Biotechnolgy, Dec. 19, 2017, 41 Pages.
Gargiulo G., et al., "Giga-Ohm High-Impedance FET Input Amplifiers for Dry Electrode Biosensor Circuits and Systems," Integrated Microsystems: Electronics, Photonics, and Biotechnology, Jan. 2011, 41 pages.
Ghasemzadeh H., et al., "A Body Sensor Network With Electromyogram and Inertial Sensors: Multimodal Interpretation of Muscular Activities," IEEE Transactions on Information Technology in Biomedicine, Mar. 2010, vol. 14 (2), pp. 198-206.
Gopura R.A.R.C., et al., "A Human Forearm and Wrist Motion Assist Exoskeleton Robot With EMG-Based Fuzzy-Neuro Control," Proceedings of the 2nd Biennial IEEE/RAS-EMBS International Conference on Biomedical Robotics and Biomechatronics, Oct. 19-22, 2008, 6 pages.
Gourmelon L., et al., "Contactless Sensors for Surface Electromyography," Proceedings of the 28th IEEE EMBS Annual International Conference, New York City, NY, Aug. 30-Sep. 3, 2006, pp. 2514-2517.
Hainich R.R., et al., "Chapter 10: Near-Eye Displays," Displays: Fundamentals Applications, AK Peters/CRC Press, 2011, 65 pages.
Hauschild M., et al., "A Virtual Reality Environment for Designing and Fitting Neural Prosthetic Limbs," IEEE Transactions on Neural Systems and Rehabilitation Engineering, Mar. 2007, vol. 15 (1), pp. 9-15.
Hornstein S., et al., "Maradin's Micro-Mirror—System Level Synchronization Notes," SID Digest, 2012, pp. 981-984.
"IEEE 100 The Authoritative Dictionary of IEEE Standards Terms," Seventh Edition, Standards Information Network IEEE Press, Dec. 2000, 3 pages.
International Search Report and Written Opinion for International Application No. PCT/US2014/017799, mailed May 16, 2014, 9 pages.

International Search Report and Written Opinion for International Application No. PCT/US2014/037863, mailed Aug. 21, 2014, 10 pages.
International Preliminary Report on Patentability for International Application No. PCT/US2014/017799, mailed Sep. 3, 2015, 8 Pages.
International Preliminary Report on Patentability for International Application No. PCT/US2014/037863, mailed Nov. 26, 2015, 8 pages.
International Preliminary Report on Patentability for International Application No. PCT/US2014/052143, mailed Mar. 3, 2016, 7 pages.
International Preliminary Report on Patentability for International Application No. PCT/US2014/067443, mailed Jun. 9, 2016, 7 pages.
International Preliminary Report on Patentability for International Application No. PCT/US2015/015675, mailed Aug. 25, 2016, 8 Pages.
International Preliminary Report on Patentability for International Application No. PCT/US2017/043686, mailed Feb. 7, 2019, 8 pages.
International Preliminary Report on Patentability for International Application No. PCT/US2017/043693, mailed Feb. 7, 2019, 7 Pages.
International Preliminary Report on Patentability for International Application No. PCT/US2017/043791, mailed Feb. 7, 2019, 9 Pages.
International Preliminary Report on Patentability for International Application No. PCT/US2017/043792, mailed Feb. 7, 2019, 8 Pages.
International Preliminary Report on Patentability for International Application No. PCT/US2018/056768, mailed Apr. 30, 2020, 7 pages.
International Preliminary Report on Patentability for International Application No. PCT/US2018/061409, mailed May 28, 2020, 10 pages.
International Preliminary Report on Patentability for International Application No. PCT/US2019/015174, mailed Aug. 6, 2020, 7 pages.
International Preliminary Report on Patentability for International Application No. PCT/US2019/015183, mailed Aug. 6, 2020, 7 pages.
International Preliminary Report on Patentability for International Application No. PCT/US2019/015238, mailed Aug. 6, 2020, 7 pages.
International Preliminary Report on Patentability for International Application No. PCT/US2019/028299, mailed Dec. 10, 2020, 11 pages.
International Preliminary Report on Patentability for International Application No. PCT/US2019/031114, mailed Nov. 19, 2020, 16 pages.
International Preliminary Report on Patentability for International Application No. PCT/US2019/034173, mailed Dec. 10, 2020, 9 pages.
International Preliminary Report on Patentability for International Application No. PCT/US2019/046351, mailed Feb. 25, 2021, 8 pages.
International Preliminary Report on Patentability for International Application No. PCT/US2019/049094, mailed Mar. 11, 2021, 24 Pages.
International Preliminary Report on Patentability for International Application No. PCT/US2019/052131, mailed on Apr. 1, 2021, 8 pages.
Kainz et al., "Approach to Hand Tracking and Gesture Recognition Based on Depth-Sensing Cameras and EMG Monitoring," Acta Informatica Pragensia, vol. 3, Jan. 1, 2014, pp. 104-112, Retrieved from the Internet: URL: https://aip.vse.cz/pdfs/aip/2014/01/08.pdf.
Kawaguchi J., et al., "Estimation of Finger Joint Angles Based on Electromechanical Sensing of Wrist Shape," IEEE Transactions on Neural Systems and Rehabilitation Engineering, Sep. 2017, vol. 25 (9), pp. 1409-1418.
Kessler D., "Optics of Near to Eye Displays (NEDs)," Presentation—Oasis, Tel Aviv, Feb. 19, 2013, 37 pages.

(56) References Cited

OTHER PUBLICATIONS

Khezri M. et al., "A Novel Approach to Recognize Hand Movements Via SEMG Patterns," 2007 Annual International Conference of the IEEE Engineering in Medicine and Biology Society. Aug. 22, 2007, pp. 4907-4910.

Kim H., et al., "Real-Time Human Pose Estimation and Gesture Recognition from Depth Images Using Superpixels and SVM Classifier," Sensors, 2015, vol. 15, pp. 12410-12427.

Koerner M.D., "Design and Characterization of the Exo-Skin Haptic Device: A Novel Tendon Actuated Textile Hand Exoskeleton," Abstract of thesis for Drexel University Masters Degree [online], Nov. 2, 2017, 5 pages, Retrieved from the Internet: URL: https://dialog.proquest.com/professional/docview/1931047627?accountid=153692.

Krees B.C., et al., "Diffractive and Holographic Optics as Optical Combiners in Head Mounted Displays," UbiComp, Zurich, Switzerland, Sep. 8-12, 2013, pp. 1479-1482.

Kress B., et al., "A Review of Head-Mounted Displays (HMD) Technologies and Applications for Consumer Electronics," Proceedings of SPIE, 2013, vol. 8720, pp. 87200A-1-87200A-13.

Kress B., "Optical Architectures for See-Through Wearable Displays," Presentation, Bay Area SID Seminar, Apr. 30, 2014, 156 pages.

Lake et al., "Method and Apparatus for Analyzing Capacitive EMG and IMU Sensor Signals for Gesture Control," Amendment filed Aug. 21, 2015, for U.S. Appl. No. 14/186,878, 13 pages.

Lake et al., "Method and Apparatus for Analyzing Capacitive EMG and IMU Sensor Signals for Gesture Control," Office Action dated Jun. 17, 2015, for U.S. Appl. No. 14/186,878, 13 pages.

Lake et al.' "Method and Apparatus for Analyzing Capacitive EMG and IMU Sensor Signals for Gesture Control," Preliminary Amendment filed May 9, 2014, for U.S. Appl. No. 14/186,878, 9 pages.

Lake et al., "Method and Apparatus for Analyzing Capacitive EMG and IMU Sensor Signals for Gesture Control," U.S. Appl. No. 14/186,878, filed Feb. 21, 2014, 29 pages.

Lake et al., "Methods and Devices for Combining Muscle Activity Sensor Signals and Inertial Sensor Signals for Gesture-Based Control," Amendment filed Jan. 8, 2016, for U.S. Appl. No. 14/186,889, 16 pages.

Lake et al., "Methods and Devices for Combining Muscle Activity Sensor Signals and Inertial Sensor Signals for Gesture-Based Control," Amendment filed Jul. 13, 2016, for U.S. Appl. No. 14/186,889, 12 pages.

Lake et al., "Methods and Devices for Combining Muscle Activity Sensor Signals and Inertial Sensor Signals for Gesture-Based Control," Office Action dated Jun. 16, 2016, for U.S. Appl. No. 14/186,889, 13 pages.

Lake et al., "Methods and Devices for Combining Muscle Activity Sensor Signals and Inertial Sensor Signals for Gesture-Based Control," Office Action dated Nov. 5, 2015, for U.S. Appl. No. 14/186,889, 11 pages.

Lake et al., "Methods and Devices That Combine Muscle Activity Sensor Signals and Inertial Sensor Signals for Gesture-Based Control," U.S. Appl. No. 14/186,889, filed Feb. 21, 2014, 58 pages.

Lee D.C., et al., "Motion and Force Estimation System of Human Fingers," Journal of Institute of Control, Robotics and Systems, 2011, vol. 17 (10), pp. 1014-1020.

Levola T., "7.1: Invited Paper: Novel Diffractive Optical Components for Near to Eye Displays," SID Symposium Digest of Technical Papers, 2006, vol. 37 (1), pp. 64-67.

Li Y., et al., "Motor Function Evaluation of Hemiplegic Upper-Extremities Using Data Fusion from Wearable Inertial and Surface EMG Sensors," Sensors, MDPI, 2017, vol. 17 (582), pp. 1-17.

Liao C.D., et al., "The Evolution of MEMS Displays," IEEE Transactions on Industrial Electronics, Apr. 2009, vol. 56 (4), pp. 1057-1065.

Lippert T.M., "Chapter 6: Display Devices: RSD™ (Retinal Scanning Display)," The Avionics Handbook, CRC Press, 2001, 8 pages.

Lopes J., et al., "Hand/Arm Gesture Segmentation by Motion Using IMU and EMG Sensing," ScienceDirect, Jun. 27-30, 2017, vol. 11, pp. 107-113.

Machine Translation of CN102238282A, 2011, 42 pages.

Majaranta P., et al., "Chapter 3: Eye Tracking and Eye-Based Human-Computer Interaction," Advances in Physiological Computing, Springer-Verlag London, 2014, pp. 39-65.

Marcard T.V., et al., "Sparse Inertial Poser: Automatic 3D Human Pose Estimation from Sparse IMUs," arxiv.org, Computer Graphics Forum, 2017, vol. 36 (2), 12 pages, XP080759137.

Martin H., et al., "A Novel Approach of Prosthetic Arm Control using Computer Vision, Biosignals, and Motion Capture," IEEE Symposium on Computational Intelligence in Robotic Rehabilitation and Assistive Technologies (CIR2AT), 2014, 5 pages.

Mcintee S.S., "A Task Model of Free-Space Movement-Based Geastures," Dissertation, Graduate Faculty of North Carolina State University, Computer Science, 2016, 129 pages.

Mendes Jr.J.J.A., et al., "Sensor Fusion and Smart Sensor in Sports and Biomedical Applications," Sensors, 2016, vol. 16 (1569), pp. 1-31.

Merriam-Webster, "Radio Frequencies," download date Jul. 12, 2017, 2 pages, Retrieved from the Internet: URL: https://www.merriam-webster.com/table/collegiate/radiofre.htm.

Mohamed O.H., "Homogeneous Cognitive Based Biometrics for Static Authentication," Dissertation submitted to University of Victoria, Canada, 2010, [last accessed Oct. 11, 2019], 149 pages, Retrieved from the Internet: URL: http://hdl.handle.net/1828/321.

Morris D., et al., "Emerging Input Technologies for Always-Available Mobile Interaction," Foundations and Trends in Human-Computer Interaction, 2010, vol. 4 (4), pp. 245-316.

Morun C., et al., "Systems, Articles, and Methods for Capacitive Electromyography Sensors," U.S. Appl. No. 16/437,351, filed Jun. 11, 2019, 51 pages.

Naik. G.R., et al., "SEMG for Identifying Hand Gestures using ICA," In Proceedings of the 2nd International Workshop on Biosignal Processing and Classification, Jan. 31, 2006, pp. 61-67.

Naik G.R., et al., "Source Separation and Identification issues in Bio Signals: A Solution using Blind Source Separation," Chapter 4 of Recent Advances in Biomedical Engineering, Intech, 2009, 23 pages.

Naik G.R., et al., "Real-Time Hand Gesture Identification for Human Computer Interaction Based on ICA of Surface Electromyogram," IADIS International Conference Interfaces and Human Computer Interaction, 2007, pp. 83-90.

Naik G.R., et al., "Subtle Hand Gesture Identification for HCI Using Temporal Decorrelation Source Separation BSS of Surface EMG," Digital Image Computing Techniques and Applications, IEEE Computer Society, 2007, pp. 30-37.

Negro F., et al., "Multi-Channel Intramuscular and Surface EMG Decomposition by Convolutive Blind Source Separation," Journal of Neural Engineering, Feb. 29, 2016, vol. 13, 18 Pages.

Non-Final Office Action mailed Mar. 1, 2018 for U.S. Appl. No. 14/553,657, filed Nov. 25, 2014, 29 Pages.

Non-Final Office Action mailed Mar. 2, 2021 for U.S. Appl. No. 15/974,430, filed May 8, 2018, 32 Pages.

Non-Final Office Action mailed May 2, 2018 for U.S. Appl. No. 15/799,628, filed Oct. 31, 2017, 25 Pages.

Non-Final Office Action mailed Sep. 2, 2020 for U.S. Appl. No. 15/882,858, filed Jan. 29, 2018, 66 Pages.

Non-Final Office Action mailed Aug. 3, 2020 for U.S. Appl. No. 16/593,446, filed Oct. 4, 2019, 44 pages.

Non-Final Office Action mailed Jun. 3, 2021 for U.S. Appl. No. 15/816,435, filed Nov. 17, 2017, 32 Pages.

Non-Final Office Action mailed Jun. 5, 2020 for U.S. Appl. No. 15/659,072, filed Jul. 25, 2017, 59 Pages.

Non-Final Office Action mailed Oct. 5, 2022 for U.S. Appl. No. 17/576,815, filed Jan. 14, 2022, 14 pages.

Non-Final Office Action mailed Nov. 6, 2018 for U.S. Appl. No. 16/057,573, filed Aug. 7, 2018, 14 Pages.

Non-Final Office Action mailed Sep. 6, 2019 for U.S. Appl. No. 16/424,144, filed May 28, 2019, 11 Pages.

Office Action mailed Jan. 20, 2023 for Chinese Application No. 201780059093.7, filed Jul. 25, 2017,16 pages.

(56)          References Cited

OTHER PUBLICATIONS

Office Action mailed Jun. 22, 2023 for European Patent Application No. 19863248.1, filed on Sep. 20, 2019, 5 pages.

Office Action mailed Nov. 28, 2023 for Japanese Patent Application No. 2021-534144, filed on Jun. 14, 2021, 5 pages.

Office Action mailed Sep. 28, 2022 for Chinese Application No. 201780059093.7, filed Jul. 25, 2017, 16 pages.

Office Action mailed Sep. 28, 2023 for Chinese Application No. 201980022051.5, filed Jan. 25, 2019, 18 pages.

Office Action mailed Aug. 29, 2023 for Japanese Application No. 2021-506985, filed Feb. 9, 2021,6 pages.

Office Action mailed Feb. 7, 2023 for European Application No. 19810524.9, filed May 28, 2019, 7 pages.

Partial Supplementary European Search Report for European Application No. 18879156.0, mailed Dec. 7, 2020, 9 pages.

Picard R.W., et al., "Affective Wearables," Proceedings of the IEEE 1st International Symposium on Wearable Computers, ISWC, Cambridge, MA, USA, Oct. 13-14, 1997, pp. 90-97.

Preinterview First Office Action mailed Jun. 24, 2020 for U.S. Appl. No. 16/785,680, filed Feb. 10, 2020, 90 Pages.

Rekimoto J., "GestureWrist and GesturePad: Unobtrusive Wearable Interaction Devices," ISWC Proceedings of the 5th IEEE International Symposium on Wearable Computers, 2001, 7 pages.

Restriction Requirement mailed Aug. 8, 2017 for U.S. Appl. No. 14/553,657, filed Nov. 25, 2014, 7 Pages.

Saponas T.S., et al., "Demonstrating the Feasibility of Using Forearm Electromyography for Muscle-Computer Interfaces," CHI Proceedings, Physiological Sensing for Input, Apr. 5-10, 2008, pp. 515-524.

Saponas T.S., et al., "Enabling Always-Available Input with Muscle-Computer Interfaces," Conference: Proceedings of the 22nd Annual ACM Symposium on User Interface Software and Technology, Oct. 7, 2009, pp. 167-176.

Saponas T.S., et al., "Making Muscle-Computer Interfaces More Practical," CHI, Atlanta, Georgia, USA, Apr. 10-15, 2010, 4 pages.

Sartori M., et al., "Neural Data-Driven Musculoskeletal Modeling for Personalized Neurorehabilitation Technologies," IEEE Transactions on Biomedical Engineering, May 5, 2016, vol. 63 (5), pp. 879-893.

Sato M., et al., "Touche: Enhancing Touch Interaction on Humans, Screens, Liquids, and Everyday Objects," CHI, Austin, Texas, May 5-10, 2012, 10 pages.

Sauras-Perez P., et al., "A Voice and Pointing Gesture Interaction System for Supporting Human Spontaneous Decisions in Autonomous Cars," Clemson University, All Dissertations, May 2017, 174 pages.

Schowengerdt B.T., et al., "Stereoscopic Retinal Scanning Laser Display With Integrated Focus Cues for Ocular Accommodation," Proceedings of SPIE-IS&T Electronic Imaging, 2004, vol. 5291, pp. 366-376.

Shen S., et al., "I Am a Smartwatch and I Can Track My User's Arm," University of Illinois at Urbana-Champaign, MobiSys, Jun. 25-30, 2016, 12 pages.

Silverman N.L., et al., "58.5L: Late-News Paper: Engineering a Retinal Scanning Laser Display with Integrated Accommodative Depth Cues," SID 03 Digest, 2003, pp. 1538-1541.

Son M., et al., "Evaluating the Utility of Two Gestural Discomfort Evaluation Methods," PLOS One, Apr. 19, 2017, 21 pages.

Strbac M., et al., "Microsoft Kinect-Based Artificial Perception System for Control of Functional Electrical Stimulation Assisted Grasping," Hindawi Publishing Corporation, BioMed Research International [online], 2014, Article No. 740469, 13 pages, Retrieved from the Internet: URL: https://dx.doi.org/10.1155/2014/740469.

Takatsuka Y., et al., "Retinal Projection Display Using Diffractive Optical Element," Tenth International Conference on Intelligent Information Hiding and Multimedia Signal Processing, IEEE, 2014, pp. 403-406.

Tibold R., et al., "Prediction of Muscle Activity during Loaded Movements of The Upper Limb," Journal of NeuroEngineering Rehabilitation, 2015 vol. 12, No. 6, DOI: https://doi.org/10.1186/1743-0003-12-6, 12 pages.

Torres T., "Myo Gesture Control Armband," PCMag, Jun. 8, 2015, 9 pages, Retrieved from the Internet: URL: https://www.pcmag.com/article2/0,2817,2485462,00.asp.

Ueno A., et al., "A Capacitive Sensor System for Measuring Laplacian Electromyogram through Cloth: A Pilot Study," Proceedings of the 29th Annual International Conference of the IEEE EMBS, Cite Internationale, Lyon, France, Aug. 23-26, 2007, pp. 5731-5734.

Ueno A., et al., "Feasibility of Capacitive Sensing of Surface Electromyographic Potential through Cloth," Sensors and Materials, 2012, vol. 24 (6), pp. 335-346.

Urey H., "Diffractive Exit-Pupil Expander for Display Applications," Applied Optics, Nov. 10, 2001, vol. 40 (32), pp. 5840-5851.

Urey H., et al., "Optical Performance Requirements for MEMS-Scanner Based Microdisplays," Conferences on MOEMS and Miniaturized Systems, SPIE, 2000, vol. 4178, pp. 176-185.

Valero-Cuevas F. J., et al. "Computational Models for Neuromuscular Function," IEEE reviews in Biomedical Engineering. Dec. 31, 2009, vol. 2, pp. 110-135.

Valero-Cuevas F.J., et al., "Computational Models for Neuromuscular Function," IEEE Reviews in Biomedical Engineering, 2009, vol. 2, NIH Public Access Author Manuscript [online], Jun. 16, 2011 [Retrieved on Jul. 29, 2019], 52 pages, Retrieved from the Internet: URL: https://www.ncbi.nlm.nih.gov/pmc/articles/PMC3116649/.

Virre E., et al., "The Virtual Retinal Display: A New Technology for Virtual Reality and Augmented Vision in Medicine," Proceedings of Medicine Meets Virtual Reality, IOS Press and Ohmsha, 1998, pp. 252-257.

Wijk U., et al., "Forearm Amputee's Views of Prosthesis Use and Sensory Feedback," Journal of Hand Therapy, Jul. 2015, vol. 28 (3), pp. 269-278.

Wittevrongel B., et al., "Spatiotemporal Beamforming: A Transparent and Unified Decoding Approach to Synchronous Visual Brain-Computer Interfacing," Frontiers in Neuroscience, Nov. 15, 2017, vol. 11, Article No. 630, 13 Pages.

Wodzinski M., et al., "Sequential Classification of Palm Gestures Based on A* Algorithm and MLP Neural Network for Quadrocopter Control," Metrology and Measurement Systems, 2017, vol. 24 (2), pp. 265-276.

Written Opinion for International Application No. PCT/US2014/057029, mailed Feb. 24, 2015, 9 Pages.

Xiong A., et al., "A Novel HCI based on EMG and IMU," Proceedings of the 2011 IEEE International Conference on Robotics and Biomimetics, Phuket, Thailand, Dec. 7-11, 2011, pp. 2653-2657.

Xu Z., et al., "Hand Gesture Recognition and Virtual Game Control Based on 3D Accelerometer and EMG Sensors," Proceedings of the 14th International Conference on Intelligent User Interfaces, D211 Sanibel Island, Florida, Feb. 8-11, 2009, pp. 401-406.

Xue Y., et al., "Multiple Sensors Based Hand Motion Recognition Using Adaptive Directed Acyclic Graph," Applied Sciences, MDPI, 2017, vol. 7 (358), pp. 1-14.

Yang Z., et al., "Surface EMG Based Handgrip Force Predictions Using Gene Expression Programming," Neurocomputing, 2016, vol. 207, pp. 568-579.

Zacharaki E.I., et al., "Spike Pattern Recognition by Supervised Classification in Low Dimensional Embedding Space," Brain Informatics, 2016, vol. 3, pp. 73-83.

Zhang X., et al., "A Framework for Hand Gesture Recognition Based on Accelerometer and EMG Sensors," IEEE Transactions on Systems, Man, and Cybernetics—Part A: Systems and Humans, Nov. 2011, vol. 41 (6), pp. 1064-1076.

Al-Jumaily A., et al., "Electromyogram(EMG) Driven System based Virtual Reality for Prosthetic and Rehabilitation Devices," Proceedings of the 11th InternationalConference on Information Integration andweb-Based Applications & Services, Jan. 1, 2009, pp. 582-586.

Al-Mashhadany Y.I., "Inverse Kinematics Problem (IKP) of 6-DOF Manipulator By Locally Recurrent Neural Networks (LRNNs),"

(56) References Cited

OTHER PUBLICATIONS

Management and Service Science (MASS), International Conference on Management and Service Science., IEEE, Aug. 24, 2010, 5 pages.

Ai-Timemy A.H., et al., "Improving the Performance Against Force Variation of EMG Controlled Multifunctional Upper- Limb Prostheses for Transradial Amputees," IEEE Transactions on Neural Systems and Rehabilitation Engineering, Jun. 2016, vol. 24 (6), 12 Pages.

Amitai Y., "P-27: A Two-Dimensional Aperture Expander for Ultra-Compact, High-Performance Head-Worn Displays," SID Symposium Digest of Technical Papers, 2005, vol. 36 (1), pp. 360-363.

Arkenbout E.A., et al., "Robust Hand Motion Tracking through Data Fusion of 5DT Data Glove and Nimble VR Kinect Camera Measurements," Sensors, 2015, vol. 15, pp. 31644-31671.

Ayras P., et al., "Exit Pupil Expander With a Large Field of View Based on Diffractive Optics," Journal of the SID, 2009, vol. 17 (8), pp. 659-664.

Bailey ct al., Wearable Muscle Interface Systems, Devices and Methods That Interact With Content Displayed on an Electronic Display, Office Action mailed Mar. 31, 2015, for U.S. Appl. No. 14/155,107, 17 pages.

Bailey et al., "Muscle Interface Device and Method for Interacting With Content Displayed on Wearable Head Mounted Displays," Amendment filed Aug. 25, 2015, for U.S. Appl. No. 14/155,087, 10 pages.

Bailey et al., "Muscle Interface Device and Method for Interacting With Content Displayed on Wearable Head Mounted Displays," Amendment filed Aug. 9, 2016, for U.S. Appl. No. 14/155,087, 8 pages.

Bailey et al., "Muscle Interface Device and Method for Interacting With Content Displayed on Wearable Head Mounted Displays," Amendment filed May 17, 2016, for U.S. Appl. No. 14/155,087, 13 pages.

Bailey et al., "Muscle Interface Device and Method for Interacting With Content Displayed on Wearable Head Mounted Displays," Office Action dated Feb. 17, 2016, for U.S. Appl. No. 14/155,087, 16 pages.

Bailey et al., "Muscle Interface Device and Method for Interacting With Content Displayed on Wearable Head Mounted Displays," Office Action dated Jul. 20, 2015, for U.S. Appl. No. 14/155,087, 14 pages.

Bailey et al., "Muscle Interface Device and Method for Interacting With Content Displayed on Wearable Head Mounted Displays," Office Action dated Jul. 8, 2016, for U.S. Appl. No. 14/155,087, 16 pages.

Bailey et al., "Muscle Interface Device and Method for Interacting With Content Displayed on Wearable Head Mounted Displays," Office Action dated Mar. 31, 2015, for U.S. Appl. No. 14/155,087, 15 pages.

Bailey et al., "Muscle Interface Device and Method for Interacting With Content Displayed on Wearable Head Mounted Displays," Preliminary Amendment filed Jan. 28, 2014, for U.S. Appl. No. 14/155,087, 8 pages.

Bailey et al., "Wearable Muscle Interface Systems, Devices and Methods That Interact With. Content Displayed on an Electronic Display," Amendment filed Aug. 9, 2016, for U.S. Appl. No. 14/155,107, 8 pages.

Bailey et al., "Wearable Muscle Interface Systems, Devices and Methods That Interact With Content Displayed on an Electronic Display," Amendment filed May 11, 2016, for U.S. Appl. No. 14/155,107, 15 pages.

Bailey et al., Wearable Muscle Interface Systems, Devices and Methods That Interact With Content Displayed on an Electronic Display/ Office Action mailed Feb. 11, 2016, for U.S. Appl. No. 14/155,107, 20 pages.

Bailey et al., Wearable Muscle Interface Systems, Devices and Methods That Interact With Content Displayed on an Electronic Display, Office Action mailed Jul. 16, 2015, forU.S. Appl. No. 14/155,107, 20 pages.

Bailey et al., Wearable Muscle Interface Systems. Devices and Methods That Interact With Content Displayed on an Electronic Display/ Office Action mailed Jul. 8, 2016, for U.S. Appl. No. 14/155,107, 21 pages.

Bailey., et al., "Wearable Muscle Interface Systems, Devices And Methods That Interact With Content Displayed on an Electronic Display," Office Action mailed Mar. 31, 2015, for U.S. Appl. No. 14/155,107, 17 pages.

Benko H., et al., "Enhancing Input On and Above the Interactive Surface with Muscle Sensing," The ACM International Conference on Interactive Tabletops and Surfaces (ITS), Nov. 23-25, 2009, pp. 93-100.

Berenzweig A., et al., "Wearable Devices and Methods for Improved Speech Recognition," U.S. Appl. No. 16/785,680, filed Feb. 10, 2020, 67 pages.

Boyali A., et al., "Spectral Collaborative Representation based Classification for Hand Gestures Recognition on Electromyography Signals," Biomedical Signal Processing and Control, 2016, vol. 24, pp. 11-18.

Brownlee J., "Finite State Machines (FSM): Finite State Machines as a Control Technique in Artificial Intelligence (AI)," FSM, Jun. 2002, 12 pages.

Cannan J., et al., "A Wearable Sensor Fusion Armband for Simple Motion Control and Selection for Disabled and Non-Disabled Users," Computer Science and Electronic Engineering Conference, IEEE, Sep. 12, 2012, pp. 216-219, XP032276745.

Chellappan K.V., et al., "Laser-Based Displays: A Review," Applied Optics, Sep. 1, 2010, vol. 49 (25), pp. F79-F98.

Cheng J., et al., "A Novel Phonology—and Radical-Coded Chinese Sign Language Recognition Framework Using Accelerometer and Surface Electromyography Sensors," Sensors, 2015, vol. 15, pp. 23303-23324.

Communication Pursuant to Article 94(3) for European Patent Application No. 17835112.8, dated Dec. 14, 2020, 6 Pages.

Communication Pursuant to Rule 164(1) EPC, Partial Supplementary European Search Report for European Application No. 14753949.8, mailed Sep. 30, 2016, 7 pages.

Co-pending U.S. Appl. No. 15/659,072, inventors Patrick; Kaifosh et al., filed Jul. 25, 2017.

Co-pending U.S. Appl. No. 15/816,435, inventors Ning; Guo et al., filed Nov. 17, 2017.

Co-pending U.S. Appl. No. 15/882,858, inventors Stephen; Lake et al., filed Jan. 29, 2018.

Co-pending U.S. Appl. No. 15/974,430, inventors Adam; Berenzweig et al., filed May 8, 2018.

Co-pending U.S. Appl. No. 16/353,998, inventors Patrick; Kaifosh et al., filed Mar. 14, 2019.

Co-pending U.S. Appl. No. 16/557,383, inventors Adam; Berenzweig et al., filed Aug. 30, 2019.

Co-pending U.S. Appl. No. 16/557,427, inventors Adam; Berenzweig et al., filed Aug. 30, 2019.

Co-Pending U.S. Appl. No. 15/974,430, filed May 8, 2018, 44 Pages.

Co-Pending U.S. Appl. No. 16/353,998, filed Mar. 14, 2019, 43 pages.

Co-Pending U.S. Appl. No. 16/557,383, filed Aug. 30, 2019, 94 Pages.

Co-Pending U.S. Appl. No. 16/557,427, filed Aug. 30, 2019, 93 Pages.

Co-Pending U.S. Appl. No. 16/577,207, filed Sep. 20, 2019, 67 Pages.

Co-Pending U.S. Appl. No. 14/505,836, filed Oct. 3, 2014, 59 Pages.

Co-Pending U.S. Appl. No. 15/816,435, filed Nov. 17, 2017, 24 Pages.

Co-Pending U.S. Appl. No. 15/882,858, filed Jan. 29, 2018, 54 Pages.

Co-Pending U.S. Appl. No. 15/974,384, filed May 8, 2018, 44 Pages.

Co-Pending U.S. Appl. No. 15/974,454, filed May 8, 2018, 45 Pages.

Co-Pending U.S. Appl. No. 16/557,342, filed Aug. 30, 2019, 93 Pages.

(56) References Cited

OTHER PUBLICATIONS

Co-Pending U.S. Appl. No. 16/430,299, filed Jun. 3, 2019, 42 Pages.
Corazza S., et al.,"A Markerless Motion Capture System to Study Musculoskeletal Biomechanics: Visual Hull and Simulated Annealing Approach," Annals of Biomedical Engineering, Jul. 2006, vol. 34 (6), pp. 1019-1029, [Retrieved on Dec. 11, 2019], 11 pages, Retrieved from the Internet: URL: https://www.researchgate.net/publication/6999610_A_Markerless_Motion_Capture_System_to_Study_Musculoskeletal_Biomechanics_Visual_Hull_and_Simulated_Annealing_Approach.
Non-Final Office Action mailed May 7, 2021 for U.S. Appl. No. 16/899,843, filed Jun. 12, 2020, 24 Pages.
Non-Final Office Action mailed Oct. 7, 2022 for U.S. Appl. No. 17/141,646, filed Jan. 5, 2021, 6 pages.
Non-Final Office Action mailed Feb. 8, 2021 for U.S. Appl. No. 16/557,342, filed Aug. 30, 2019, 11 Pages.
Non-Final Office Action mailed Oct. 8, 2020 for U.S. Appl. No. 16/577,207, filed Sep. 20, 2019, 51 Pages.
Non-Final Office Action mailed Apr. 9, 2019 for U.S. Appl. No. 16/258,409, filed Jan. 25, 2019, 71 Pages.
Non-Final Office Action mailed Aug. 11, 2021 for U.S. Appl. No. 16/577,207, filed Sep. 20, 2019, 35 Pages.
Non-Final Office Action mailed Sep. 11, 2019 for U.S. Appl. No. 14/465,194, filed Aug. 21, 2014, 72 Pages.
Non-Final Office Action mailed Sep. 11, 2024 for U.S. Appl. No. 17/741,263, filed May 10, 2022, 7 pages.
Non-Final Office Action mailed May 12, 2022 for U.S. Appl. No. 16/899,843, filed Jun. 12, 2020, 34 Pages.
Non-Final Office Action mailed Jun. 13, 2019 for U.S. Appl. No. 16/258,279, filed Jan. 25, 2019, 38 Pages.
Non-Final Office Action mailed Sep. 14, 2017 for U.S. Appl. No. 14/539,773, filed Nov. 12, 2014, 28 pages.
Non-Final Office Action mailed Aug. 15, 2018 for U.S. Appl. No. 14/465,194, filed Aug. 21, 2014, 64 Pages.
Non-Final Office Action mailed Jun. 15, 2020 for U.S. Appl. No. 16/292,609, filed Mar. 5, 2019, 26 Pages.
Non-Final Office Action mailed Jun. 15, 2020 for U.S. Appl. No. 16/557,342, filed Aug. 30, 2019, 46 Pages.
Non-Final Office Action mailed Jan. 16, 2020 for U.S. Appl. No. 16/389,419, filed Apr. 19, 2019, 26 Pages.
Non-Final Office Action mailed May 16, 2019 for U.S. Appl. No. 15/974,384, filed May 8, 2018, 13 Pages.
Non-Final Office Action mailed May 16, 2019 for U.S. Appl. No. 15/974,430, filed May 8, 2018, 12 Pages.
Non-Final Office Action mailed Aug. 17, 2017 for U.S. Appl. No. 14/465,194, filed Aug. 21, 2014, 81 Pages.
Non-Final Office Action mailed Dec. 17, 2018 for U.S. Appl. No. 16/137,960, filed Sep. 21, 2018, 10 pages.
Non-Final Office Action mailed Jan. 18, 2018 for U.S. Appl. No. 15/799,621, filed Oct. 31, 2017, 10 pages.
Non-Final Office Action mailed Nov. 19, 2019 for U.S. Appl. No. 16/577,207, filed Sep. 20, 2019, 32 Pages.
Non-Final Office Action mailed Aug. 20, 2020 for U.S. Appl. No. 15/974,454, filed May 8, 2018, 59 Pages.
Non-Final Office Action mailed Dec. 20, 2019 for U.S. Appl. No. 15/974,454, filed May 8, 2018, 41 Pages.
Non-Final Office Action mailed Jan. 22, 2020 for U.S. Appl. No. 15/816,435, filed Nov. 17, 2017, 35 Pages.
Non-Final Office Action mailed Jun. 22, 2017 for U.S. Appl. No. 14/461,044, filed Aug. 15, 2014, 21 Pages.
Non-Final Office Action mailed Oct. 22, 2019 for U.S. Appl. No. 16/557,342, filed Aug. 30, 2019, 16 Pages.
Non-Final Office Action mailed Dec. 23, 2019 for U.S. Appl. No. 16/557,383, filed Aug. 30, 2019, 53 Pages.
Non-Final Office Action mailed Dec. 23, 2019 for U.S. Appl. No. 16/557,427, filed Aug. 30, 2019, 52 Pages.
Non-Final Office Action mailed Feb. 23, 2017 for U.S. Appl. No. 14/505,836, filed Oct. 3, 2014, 54 Pages.
Non-Final Office Action mailed Jul. 23, 2020 for U.S. Appl. No. 16/593,446, filed Oct. 4, 2019, 28 pages.

Non-Final Office Action mailed May 24, 2019 for U.S. Appl. No. 16/353,998, filed Mar. 14, 2019, 20 Pages.
Non-Final Office Action mailed Feb. 25, 2021 for U.S. Appl. No. 14/461,044, filed Aug. 15, 2014, 17 Pages.
Non-Final Office Action mailed May 26, 2020 for U.S. Appl. No. 16/353,998, filed Mar. 14, 2019, 60 Pages.
Non-Final Office Action mailed Nov. 27, 2020 for U.S. Appl. No. 16/258,279, filed Jan. 25, 2019, 44 Pages.
Non-Final Office Action mailed Aug. 28, 2018 for U.S. Appl. No. 16/023,276, filed Jun. 29, 2018, 10 pages.
Non-Final Office Action mailed Aug. 28, 2018 for U.S. Appl. No. 16/023,300, filed Jun. 29, 2018, 11 pages.
Non-Final Office Action mailed Jun. 28, 2021 for U.S. Appl. No. 16/550,905, filed Aug. 26, 2019, 5 Pages.
Non-Final Office Action mailed Apr. 29, 2019 for U.S. Appl. No. 16/257,979, filed Jan. 25, 2019, 63 Pages.
Non-Final Office Action mailed Apr. 30, 2019 for U.S. Appl. No. 15/659,072, filed Jul. 25, 2017, 99 Pages.
Non-Final Office Action mailed Apr. 30, 2020 for U.S. Appl. No. 15/974,430, filed May 8, 2018, 57 Pages.
Non-Final Office Action mailed Dec. 30, 2019 for U.S. Appl. No. 16/593,446, filed Oct. 4, 2019, 43 pages.
Non-Final Office Action mailed Jun. 30, 2016 for U.S. Appl. No. 14/505,836, filed Oct. 3, 2014, 37 Pages.
Non-Final Office Action mailed Oct. 30, 2019 for U.S. Appl. No. 15/882,858, filed Jan. 29, 2018, 22 Pages.
Non-Final Office Action received for U.S. Appl. No. 14/155,087 dated Aug. 16, 2016, 28 pages.
Non-Final Office Action received for U.S. Appl. No. 14/155,087 dated Aug. 7, 2017, 28 pages.
Non-Final Office Action received for U.S. Appl. No. 14/155,087 dated Feb. 17, 2016, 26 pages.
Non-Final Office Action received for U.S. Appl. No. 14/155,087 dated Mar. 31, 2015, 22 pages.
Non-Final Office Action received for U.S. Appl. No. 14/155,107 dated Aug. 17, 2016, 37 pages.
Non-Final Office Action received for U.S. Appl. No. 14/155,107 dated Aug. 7, 2017, 34 pages.
Non-Final Office Action received for U.S. Appl. No. 14/155,107 dated Feb. 11, 2016, 42 pages.
Non-Final Office Action received for U.S. Appl. No. 14/155,107 dated Jul. 13, 2018, 45 pages.
Non-Final Office Action received for U.S. Appl. No. 14/155,107 dated Mar. 31, 2015, 26 pages.
Notice of Allowance mailed May 1, 2019 for U.S. Appl. No. 16/137,960, filed Sep. 21, 2018, 14 pages.
Notice of Allowance mailed Nov. 2, 2020 for U.S. Appl. No. 15/974,454, filed May 8, 2018, 24 Pages.
Notice of Allowance mailed Nov. 4, 2019 for U.S. Appl. No. 15/974,384, filed May 8, 2018, 39 Pages.
Notice of Allowance mailed Mar. 5, 2019 for U.S. Appl. No. 16/057,573, filed Aug. 7, 2018, 31 Pages.
Notice of Allowance mailed Feb. 6, 2020 for U.S. Appl. No. 16/424,144, filed May 28, 2019, 28 Pages.
Notice of Allowance mailed Feb. 8, 2019 for U.S. Appl. No. 16/023,276, filed Jun. 29, 2018, 15 pages.
Notice of Allowance mailed Feb. 9, 2022 for U.S. Appl. No. 15/882,858, filed Jan. 29, 2018, 9 pages.
Notice of Allowance mailed Nov. 10, 2021 for U.S. Appl. No. 15/882,858, filed Jan. 29, 2018, 6 pages.
Notice of Allowance mailed Mar. 11, 2020 for U.S. Appl. No. 14/465,194, filed Aug. 21, 2014, 29 Pages.
Notice of Allowance mailed Dec. 14, 2022 for U.S. Appl. No. 15/882,858, filed Jan. 29, 2018, 10pages.
Notice of Allowance mailed Jul. 15, 2021 for U.S. Appl. No. 15/882,858, filed Jan. 29, 2018, 2 pages.
Notice of Allowance mailed Jun. 15, 2018 for U.S. Appl. No. 15/799,621, filed Oct. 31, 2017, 27 pages.
Notice of Allowance mailed Dec. 16, 2020 for U.S. Appl. No. 16/593,446, filed Oct. 4, 2019, 44 pages.
Notice of Allowance mailed Jul. 18, 2022 for U.S. Appl. No. 16/550,905, filed Aug. 26, 2019, 7 pages.

(56)        References Cited

OTHER PUBLICATIONS

Notice of Allowance mailed May 18, 2020 for U.S. Appl. No. 16/258,279, filed Jan. 25, 2019, 42 Pages.
Notice of Allowance mailed May 18, 2022 for U.S. Appl. No. 15/882,858, filed Jan. 29, 2018, 10 pages.
Notice of Allowance mailed Aug. 19, 2020 for U.S. Appl. No. 16/557,427, filed Aug. 30, 2019, 22 Pages.
Notice of Allowance mailed Jul. 19, 2019 for U.S. Appl. No. 16/258,409, filed Jan. 25, 2019, 36 Pages.
Notice of Allowance mailed Apr. 20, 2022 for U.S. Appl. No. 14/461,044, filed Aug. 15, 2014, 08 pages.
Notice of Allowance mailed May 20, 2020 for U.S. Appl. No. 16/389,419, filed Apr. 19, 2019, 28 Pages.
Notice of Allowance mailed Aug. 22, 2022 for U.S. Appl. No. 15/882,858, filed Jan. 29, 2018, 9 pages.
Notice of Allowance mailed Oct. 22, 2021 for U.S. Appl. No. 15/882,858, filed Jan. 29, 2018 , 8 pages.
Notice of Allowance mailed Aug. 23, 2021 for U.S. Appl. No. 15/974,430, filed May 8, 2018, 12 pages.
Notice of Allowance mailed Dec. 23, 2020 for U.S. Appl. No. 15/659,072, filed Jul. 25, 2017, 26 Pages.
Notice of Allowance mailed Sep. 24, 2020 for U.S. Appl. No. 16/292,609, filed Mar. 5, 2019, 20 Pages.
Notice of Allowance mailed Mar. 25, 2022 for U.S. Appl. No. 16/550,905, filed Aug. 26, 2019, 7 pages.
Notice of Allowance mailed Sep. 25, 2018 for U.S. Appl. No. 14/553,657, filed Nov. 25, 2014, 25 Pages.
Notice of Allowance mailed Jan. 28, 2019 for U.S. Appl. No. 16/023,300, filed Jun. 29, 2018, 31 pages.
Notice of Allowance mailed Jun. 28, 2021 for U.S. Appl. No. 15/882,858, filed Jan. 29, 2018, 18 pages.
Notice of Allowance mailed Nov. 3, 2022 for U.S. Appl. No. 16/899,843, filed Jun. 12, 2020, 10 pages.
Notice of Allowance mailed Mar. 30, 2018 for U.S. Appl. No. 14/539,773, filed Nov. 12, 2014, 17 pages.
Notice of Allowance mailed Nov. 30, 2018 for U.S. Appl. No. 15/799,628, filed Oct. 31, 2017, 19 Pages.
Notice of Allowance mailed Jul. 31, 2019 for U.S. Appl. No. 16/257,979, filed Jan. 25, 2019, 22 Pages.
Notice of Allowance received for U.S. Appl. No. 14/155,107 dated Aug. 30, 2019, 16 pages.
Office action for European Application No. 17835112.8, dated Feb. 11, 2022, 11 Pages.
Office Action for European Application No. 19806723.3, mailed Oct. 27, 2022, 8 pages.
Office Action for European Patent Application No. 19743717.1, mailed Apr. 11, 2022, 10 pages.
Office Action mailed May 7, 2024 for European Patent Application No. 19743717.1, filed on Jan. 25, 2019, 9 pages.
Office Action mailed Jan. 12, 2024 for Chinese Application No. 201980072093.X, filed Aug. 30, 2019, 13 pages.
Office Action mailed Sep. 14, 2023 for Chinese Application No. 201980035465.1, filed May 28, 2019, 9 pages.
Office Action mailed Aug. 15, 2023 for Japanese Patent Application No. 2021-507757, filed on Feb. 15, 2021,9 pages.
Office Action mailed Aug. 16, 2023 for Chinese Application No. 201880082887.X, filed Oct. 19, 2018, 17 pages.
Office Action mailed Aug. 16, 2023 for Chinese Application No. 202080062417.4, filed Sep. 3, 2020, 11 pages.
Costanza E., et al., "EMG as a Subtle Input Interface for Mobile Computing," Mobile HCI, LNCS 3160, 2004, pp. 426-430.
Costanza E., et al., "Toward Subtle Intimate Interfaces for Mobile Devices Using an EMG Controller," CHI, Proceedings of the SIGCHI Conference on Human Factors in Computing Systems, Apr. 2-7, 2005, pp. 481-489.
Cote-Allard U., et al., "Deep Learning for Electromyographic Hand Gesture Signal Classification Using Transfer Learning," IEEE Transactions on Neural Systems and Rehabilitation Engineering, Jan. 26, 2019, vol. 27 (4), 11 Pages.

Csapo A.B., et al., "Evaluation of Human-Myo Gesture Control Capabilities in Continuous Search and Select Operations," 7th IEEE International Conference on Cognitive Infocommunications, Oct. 16-18, 2016, pp. 000415-000420.
Cui L., et al., "Diffraction From Angular Multiplexing Slanted Volume Hologram Gratings," Optik, 2005, vol. 116, pp. 118-122.
Curatu C., et al., "Dual Purpose Lens for an Eye-Tracked Projection Head-Mounted Display," International Optical Design Conference SPIE-OSA, 2006, vol. 6342, pp. 63420X-1-63420X-7.
Curatu C., et al., "Projection-Based Head-Mounted Display With Eye-Tracking Capabilities," Proceedings of SPIE, 2005, vol. 5875, pp. 58750J-1-58750J-9.
Davoodi R., et al., "Development of a Physics-Based Target Shooting Game to Train Amputee Users of Multi joint Upper Limb Prostheses," Presence, Massachusetts Institute of Technology, 2012, vol. 21 (1), pp. 85-95.
Delis A.L., et al., "Development of a Myoelectric Controller Based on Knee Angle Estimation," Biodevices, International Conference on Biomedical Electronics and Devices, Jan. 17, 2009, 7 pages.
Diener L., et al., "Direct Conversion From Facial Myoelectric Signals to Speech Using Deep Neural Networks," International Joint Conference on Neural Networks (IJCNN), Oct. 1, 2015, 7 pages.
Ding I-J., et al., "HMM with Improved Feature Extraction-Based Feature Parameters for Identity Recognition of Gesture Command Operators by Using a Sensed Kinect-Data Stream," Neurocomputing, 2017, vol. 262, pp. 108-119.
Essex D., "Tutorial on Optomechanical Beam Steering Mechanisms," OPTI 521 Tutorial, College of Optical Sciences, University of Arizona, 2006, 8 pages.
European Search Report for European Application No. 19861903.3, dated Oct. 12, 2021, 2 pages.
European Search Report for European Application No. 19863248.1, dated Oct. 19, 2021, 2 pages.
European Search Report for European Application No. 19868789.9, mailed May 9, 2022, 9 pages.
European Search Report for European Application No. 19890394.0, mailed Apr. 29, 2022, 9 pages.
European Search Report for European Patent Application No., 23186202.0. dated Aug. 2, 2023, 7 pages.
Extended European Search Report for European Application No. 17835111.0, mailed Nov. 21, 2019, 6 pages.
Extended European Search Report for European Application No. 17835112.8, mailed Feb. 5, 2020, 17 pages.
Extended European Search Report for European Application No. 17835140.9, mailed Nov. 26, 2019, 10 Pages.
Extended European Search Report for European Application No. 18869441.8, mailed Nov. 17, 2020, 20 Pages.
Extended European Search Report for European Application No. 18879156.0, mailed Mar. 12, 2021, 11 pages.
Extended European Search Report for European Application No. 19743717.1, mailed Mar. 3, 2021, 12 pages.
Extended European Search Report for European Application No. 19744404.5, mailed Mar. 29, 2021, 11 pages.
Extended European Search Report for European Application No. 19799947.7, mailed May 26, 2021, 10 pages.
Extended European Search Report for European Application No. 19806723.3, mailed Jul. 7, 2021, 13 pages.
Extended European Search Report for European Application No. 19810524.9, mailed Mar. 17, 2021, 11 pages.
Extended European Search Report for European Application No. 19850130.6, mailed Sep. 1, 2021, 14 Pages.
Extended European Search Report for European Application No. 19855191.3, dated Dec. 6, 2021, 11 pages.
Extended European Search Report for European Application No. 19883839.3, mailed Dec. 15, 2021, 7 pages.
Farina D., et al., "Man/Machine Interface Based on the Discharge Timings of Spinal Motor Neurons After Targeted Muscle Reinnervation," Nature Biomedical Engineering, Feb. 6, 2017, vol. 1, Article No. 0025, pp. 1-12.
Farina D., et al., "The Extraction of Neural Information from the Surface EMG for the Control of Upper-Limb Prostheses: Emerging

(56) References Cited

OTHER PUBLICATIONS

Avenues and Challenges," IEEE Transactions on Neural Systems andRehabilitation Engineering, vol. 22, No. 4, Jul. 1, 2014, pp. 797-809.

Favorskaya M., et al., "Localization and Recognition of Dynamic Hand Gestures Based on Hierarchy of Manifold Classifiers," International Archives of the Photogrammetry, Remote Sensing and Spatial Information Sciences, May 25-27, 2015, vol. XL-5/W6, pp. 1-8.

Fernandez E., et al., "Optimization of a Thick Polyvinyl Alcohol-Acrylamide Photopolymer for Data Storage Using a Combination of Angular and Peristrophic Holographic Multiplexing," Applied Optics, Oct. 10, 2009, vol. 45 (29), pp. 7661-7666.

Final Office Action mailed Jun. 2, 2020 for U.S. Appl. No. 15/882,858, filed Jan. 29, 2018, 127 Pages.

Final Office Action mailed Jun. 2, 2020 for U.S. Appl. No. 16/557,383, filed Aug. 30, 2019, 66 Pages.

Final Office Action mailed Jan. 3, 2019 for U.S. Appl. No. 14/465,194, filed Aug. 21, 2014, 61 Pages.

Final Office Action mailed Nov. 3, 2020 for U.S. Appl. No. 15/974,430, filed May 8, 2018, 27 Pages.

Final Office Action mailed Feb. 4, 2020 for U.S. Appl. No. 16/577,207, filed Sep. 20, 2019, 76 Pages.

Final Office Action mailed Feb. 4, 2021 for U.S. Appl. No. 15/882,858, filed Jan. 29, 2018, 42 Pages.

Final Office Action mailed Jun. 5, 2020 for U.S. Appl. No. 16/557,427, filed Aug. 30, 2019, 95 Pages.

Final Office Action mailed Oct. 8, 2020 for U.S. Appl. No. 16/557,342, filed Aug. 30, 2019, 73 Pages.

Final Office Action mailed Apr. 9, 2020 for U.S. Appl. No. 15/974,454, filed May 8, 2018, 19 Pages.

Final Office Action mailed Jan. 10, 2018 for U.S. Appl. No. 14/465,194, filed Aug. 21, 2014, 50 Pages.

Final Office Action mailed Dec. 11, 2019 for U.S. Appl. No. 15/974,430, filed May 8, 2018, 30 Pages.

Final Office Action mailed Jan. 13, 2021 for U.S. Appl. No. 16/577,207, filed Sep. 20, 2019, 91 Pages.

Final Office Action mailed Dec. 18, 2019 for U.S. Appl. No. 16/258,279, filed Jan. 25, 2019, 45 Pages.

Final Office Action mailed Nov. 18, 2020 for U.S. Appl. No. 14/461,044, filed Aug. 15, 2014, 14 Pages.

Final Office Action mailed Feb. 19, 2021 for U.S. Appl. No. 16/258,279, filed Jan. 25, 2019, 58 Pages.

Final Office Action mailed Oct. 21, 2021 for U.S. Appl. No. 16/899,843, filed Jun. 12, 2020, 29 Pages.

International Preliminary Report on Patentability for International Application No. PCT/US2019/052151, mailed Apr. 1, 2021, 9 pages.

International Preliminary Report on Patentability for International Application No. PCT/US2019/054716, mailed on Apr. 15, 2021, 10 pages.

International Preliminary Report on Patentability for International Application No. PCT/US2019/061759, mailed May 27, 2021, 12 pages.

International Preliminary Report on Patentability for International Application No. PCT/US2019/063587, mailed Jun. 10, 2021, 13 pages.

International Preliminary Report on Patentability for International Application No. PCT/US2020/049274, mailed Mar. 17, 2022, 14 pages.

International Preliminary Report on Patentability for International Application No. PCT/US2020/061392, mailed Jun. 9, 2022, 11 pages.

International Search Report and Written Opinion for International Application No. PCT/US2014/052143, mailed Nov. 21, 2014, 8 Pages.

International Search Report and Written Opinion for International Application No. PCT/US2014/067443, mailed Feb. 27, 2015, 8 pages.

International Search Report and Written Opinion for International Application No. PCT/US2015/015675, mailed May 27, 2015, 9 Pages.

International Search Report and Written Opinion for International Application No. PCT/US2016/018293, mailed Jun. 8, 2016, 17 Pages.

International Search Report and Written Opinion for International Application No. PCT/US2016/018298, mailed Jun. 8, 2016, 14 Pages.

International Search Report and Written Opinion for International Application No. PCT/US2016/018299, mailed Jun. 8, 2016, 12 Pages.

International Search Report and Written Opinion for International Application No. PCT/US2016/067246, mailed Apr. 25, 2017, 10 Pages.

International Search Report and Written Opinion for International Application No. PCT/US2017/043686, mailed Oct. 6, 2017, 9 Pages.

International Search Report and Written Opinion for International Application No. PCT/US2017/043693, mailed Oct. 6, 2017, 7 Pages.

International Search Report and Written Opinion for International Application No. PCT/US2017/043791, mailed Oct. 5, 2017, 10 Pages.

International Search Report and Written Opinion for International Application No. PCT/US2018/056768, mailed Jan. 15, 2019, 8 pages.

International Search Report and Written Opinion for International Application No. PCT/US2018/061409, mailed Mar. 12, 2019, 11 pages.

International Search Report and Written Opinion for International Application No. PCT/US2018/063215, mailed Mar. 21, 2019, 17 Pages.

International Search Report and Written Opinion for International Application No. PCT/US2019/015167, mailed May 21, 2019, 7 Pages.

International Search Report and Written Opinion for International Application No. PCT/US2019/015174, mailed May 21, 2019, 8 pages.

International Search Report and Written Opinion for International Application No. PCT/US2019/015244, mailed May 16, 2019, 8 Pages.

International Search Report and Written Opinion for International Application No. PCT/US2019/020065, mailed May 16, 2019, 10 Pages.

International Search Report and Written Opinion for International Application No. PCT/US2019/028299, mailed Aug. 9, 2019, 12 pages.

International Search Report and Written Opinion for International Application No. PCT/US2019/031114, mailed Dec. 20, 2019, 18 Pages.

International Search Report and Written Opinion for International Application No. PCT/US2019/034173, mailed Sep. 18, 2019, 10 Pages.

International Search Report and Written Opinion for International Application No. PCT/US2019/037302, mailed Oct. 11, 2019, 13 Pages.

International Search Report and Written Opinion for International Application No. PCT/US2019/042579, mailed Oct. 31, 2019, 8 Pages.

International Search Report and Written Opinion for International Application No. PCT/US2019/046351, mailed Nov. 7, 2019, 9 pages.

International Search Report and Written Opinion for International Application No. PCT/US2019/049094, mailed Jan. 9, 2020, 27 Pages.

International Search Report and Written Opinion for International Application No. PCT/US2019/052131, mailed on Dec. 6, 2019, 8 pages.

International Search Report and Written Opinion for International Application No. PCT/US2019/052151, mailed Jan. 15, 2020, 10 pages.

(56) References Cited

OTHER PUBLICATIONS

International Search Report and Written Opinion for International Application No. PCT/US2019/054716, mailed Dec. 20, 2019, 11 Pages.
International Search Report and Written Opinion for International Application No. PCT/US2019/061759, mailed Jan. 29, 2020, 12 pages.
International Search Report and Written Opinion for International Application No. PCT/US2019/063587, mailed Mar. 25, 2020, 16 pages.
International Search Report and Written Opinion for International Application No. PCT/US2020/025735, mailed Jun. 22, 2020, 10 pages.
International Search Report and Written Opinion for International Application No. PCT/US2020/025772, mailed Aug. 3, 2020, 11 pages.
International Search Report and Written Opinion for International Application No. PCT/US2020/025797, mailed Jul. 9, 2020, 10 pages.
International Search Report and Written Opinion for International Application No. PCT/US2020/049274, mailed Feb. 1, 2021, 17 pages.
International Search Report and Written Opinion for International Application No. PCT/US2020/061392, mailed Mar. 12, 2021, 12 pages.
International Search Report and Written Opinion for International Application No. PCT/US2017/043792, mailed Oct. 5, 2017, 9 Pages.
International Search Report and Written Opinion for International Application No. PCT/US2019/015134, mailed May 15, 2019, 11 Pages.
International Search Report and Written Opinion for International Application No. PCT/US2019/015180, mailed May 28, 2019, 10 Pages.
International Search Report and Written Opinion for International Application No. PCT/US2019/015183, mailed May 3, 2019, 8 Pages.
International Search Report and Written Opinion for International Application No. PCT/US2019/015238, mailed May 16, 2019, 8 Pages.
Invitation to Pay Additional Fees for International Application No. PCT/US2019/031114, mailed Aug. 6, 2019, 7 pages.
Invitation to Pay Additional Fees for International Application No. PCT/US2019/049094, mailed Oct. 24, 2019, 2 Pages.
Itoh Y., et al., "Interaction-Free Calibration for Optical See-Through Head-Mounted Displays based on 3D Eye Localization," IEEE Symposium on 3D User Interfaces (3DUI), 2014, pp. 75-82.
Janssen C., "Radio Frequency (RF)," 2013, [Retrieved on Jul. 12, 2017], 2 pages, Retrieved from the Internet: URL: https://web.

archive.org/web/20130726153946/https://www.techopedia.com/definition/5083/radio-frequency-rf.
Jiang H., "Effective and Interactive Interpretation of Gestures by Individuals with Mobility Impairments," Thesis/Dissertation Acceptance, Purdue University Graduate School, Graduate School Form 30, Updated on Jan. 15, 2015, 24 pages.
Final Office Action mailed Feb. 24, 2025 for U.S. Appl. No. 17/741,263, filed May 10, 2022, 9 pages.
Office Action mailed Feb. 4, 2025 for European Patent Application No. 20824840.1, filed on Nov. 19, 2020, 7 pages.
Office Action mailed Jan. 16, 2025 for Chinese Application No. 202080082075.2, filed Nov. 19, 2020, 24 pages.
Amma C., et al., "Airwriting: A Wearable Handwriting Recognition System," Personal and Ubiquitous Computing, Springer Verlag, Jan. 1, 2014, vol. 18, No. 1, pp. 191-203.
European Search Report for European Patent Application No. 24203369.4, dated Mar. 20, 2025, 10 pages.
Non-Final Office Action mailed Apr. 18, 2025 for U.S. Appl. No. 18/415,563, filed Jan. 17, 2024, 20 pages.
Notice of Allowance mailed Jul. 1, 2025 for U.S. Appl. No. 17/741,263, filed May 10, 2022, 5 pages.
Notice of Allowance mailed Jul. 15, 2025 for U.S. Appl. No. 17/741,263, filed May 10, 2022, 2 pages.
Office Action mailed May 1, 2025 for Chinese Application No. 202080026319.5, filed Mar. 30, 2020, 1 page.
Office Action mailed Jul. 8, 2025 for Chinese Application No. 202080082075.2, filed Nov. 19, 2020, 1 pages.
Kipke D.R., et al., "Silicon-Substrate Intracortical Microelectrode Arrays for Long-Term Recording of Neuronal Spike Activity in Cerebral Cortex," IEEE Transactions on Neural Systems and Rehabilitation Engineering, Jun. 2003, vol. 1 (2), 5 pages, Retrieved on Oct. 7, 2019 [Jul. 10, 2019] Retrieved from the Internet: URL: <https://www.ece.uvic.cal-bctill/papers/neurimp/Kipke_etal_2003_01214707.pdf>.
Naik G R., et al., "Hand Gestures for HCI Using ICA of EMG," ACM International Conference Proceeding Series, 2006, 6 Pages.
Non-Final Office Action mailed Oct. 21, 2025 for U.S. Appl. No. 19/031,332, filed Jan. 17, 2025, 17 pages.
Non-Final Office Action mailed Oct. 23, 2025 for U.S. Appl. No. 18/187,183, filed Mar. 21, 2023, 16 pages.
Notice of Allowance mailed Nov. 5, 2025 for U.S. Appl. No. 17/741,263, filed May 10, 2022, 2 pages.
Notice of Allowance mailed Oct. 15, 2025 for U.S. Appl. No. 18/415,563, filed Jan. 17, 2024, 7 pages.
Notice of Allowance mailed Oct. 24, 2025 for U.S. Appl. No. 17/741,263, filed May 10, 2022, 5 pages.
Office Action mailed Dec. 11, 2025 for European Patent Application No. 19890394.0, filed on Nov. 27, 2019, 8 pages.
Office Action mailed Nov. 24, 2025 for European Patent Application No. 19861903.3, filed on Sep. 20, 2019, 4 pages.

* cited by examiner

*500*                                                    *510*

Identify Physical Objects in
AR Environment Using Camera(s)

*512*

Identify User Interaction
with Physical Object in AR Environment

*514*

Activate Set of Control Actions
Associated with Physical Object

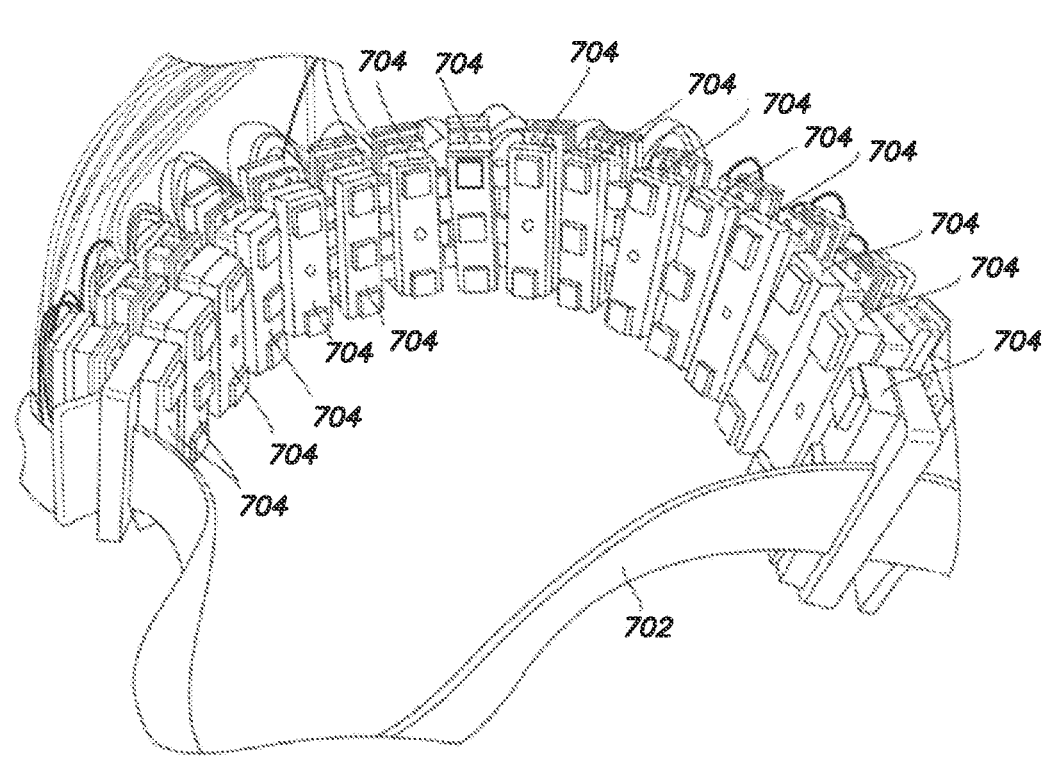
FIG. 7A

1202

1204

1206(B)

1206(A)

System
1200

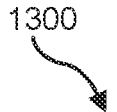
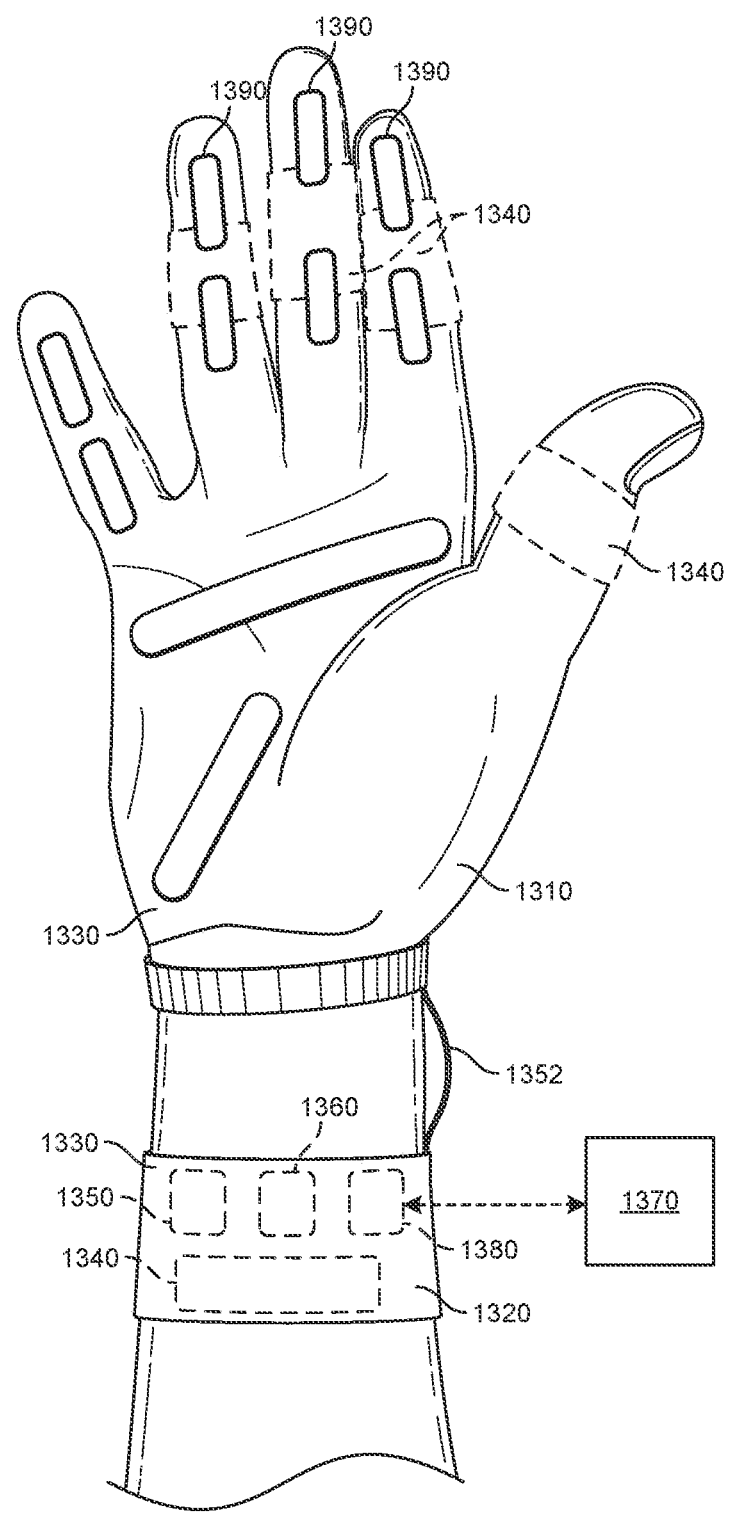
*FIG. 13*

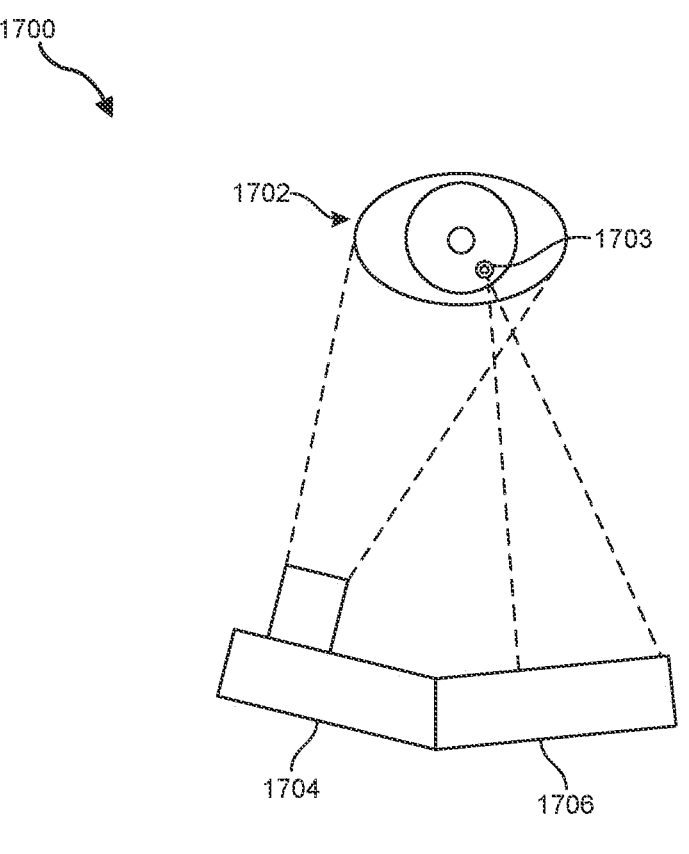
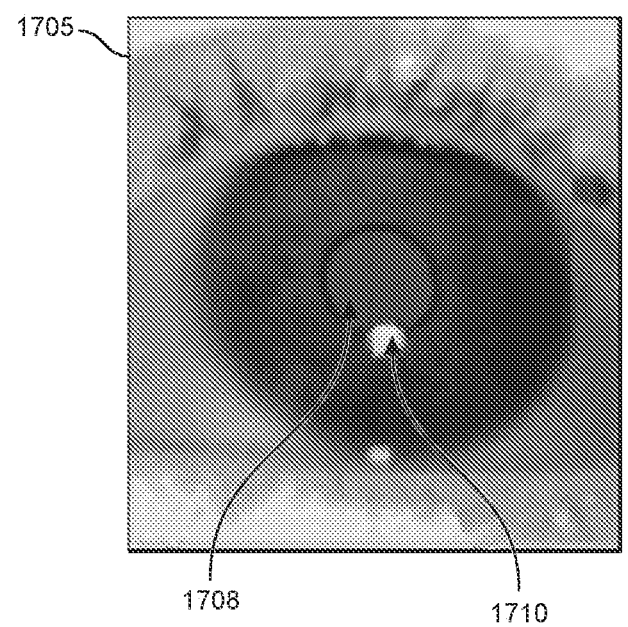
*FIG. 17*

19100

19102 SENSORS

19104 STATISTICAL MODEL(S)

19106 MUSCULO-SKELETAL REPRESENTATION

19108 VISUAL REPRESENTATION

19502 — OBTAIN SENSOR SIGNALS

19504 — OBTAIN POSITION INFORMATION

19506 — PROCESS SENSOR SIGNALS AND/OR POSITION INFORMATION

19508 — DETERMINE MUSCULO-SKELETAL POSITION CHARACTERISTICS BASED ON POSITION INFORMATION

19510 — GENERATE TRAINING DATA

19512 — TRAIN STATISTICAL MODEL BASED ON SENSOR SIGNALS AND MUSCULO-SKELETAL POSITION CHARACTERISTICS

19514 — STORE TRAINED STATISTICAL MODEL

191000

191002

191004

191006

20300

RECORD NEUROMUSCULAR SIGNALS — 20310

PROVIDE FEEDBACK BASED ON RECORDED NEUROMUSCULAR SIGNALS — 20320

STORE INFORMATION ABOUT SUB-MUSCULAR ACTIVATION — 20330

21400

DETERMINE SPIKE
EVENT(S) ASSOCIATED
WITH MOTOR UNIT(S) — 21410

DETERMINE MUSCLE(S)
TO WHICH MOTOR
UNIT(S) BELONGS — 21412

GENERATE OUTPUT
BASED ON DETERMINED
MUSCLE — 21414

21500

DETECT A PLURALITY OF SPIKE
EVENTS IN RECORDED
NEUROMUSCULAR SIGNALS — 21510

CLUSTER THE DETECTED PLURALITY OF
SPIKE EVENTS BASED ON
SPATIOTEMPORAL PATTERNS — 21512

GENERATE FILTERS BASED ON ONE OR
MORE CLUSTERS OF SPIKE EVENTS — 21514

Time (s)

*22600*

22610

Receive and Process Camera Input

22620

Determine Position Information
from Captured Image

22630

Update Parameter of Inference
Model Based on Position Information

*22700*

22710

Receive and Process Camera Input

22720

Determine Geometry Information
from Captured Image

22730

Update Parameter of Inference
Model Based on Determined Geometry

23904

910

251710

251708

251704

251708

251704

251702

251706

26200

26220

26210

26310

26350

System
26400

26410

26430

26420

26900

26950

26940

AC Magnetic Field

Magnetic Shield

Amplifier

Filter

ADC

26910

26920

26930

261000

Amplifier

ADC

Micro Processor

261010

261020

261030

Method
261100

Start

PROVIDE ANALOG CIRCUIT INCLUDING FULLY DIFFERENTIAL
AMPLIFIER AND DIFFERENTIAL ADC
261110

USE FULLY-DIFFERENTIAL AMPLIFIER TO REDUCE
ELECTROMAGNETIC NOISE SIGNALS
261120

FURTHER REDUCE NOISE SIGNALS USING DIFFERENTIAL
ADC
261130

End

Method
261200

Start

PROVIDE ANALOG CIRCUIT INCLUDING AMPLIFIER AND ADC
261210

REDUCE ELECTROMAGNETIC NOISE BY INTRODUCING ANTI-
ALIASING FILTER BETWEEN AMPLIFIER AND ADC,
PROXIMATE THE ADC
261220

PROVIDE ELECTROMAGNETIC SHIELDING FOR ANALOG
CIRCUIT
261230

End

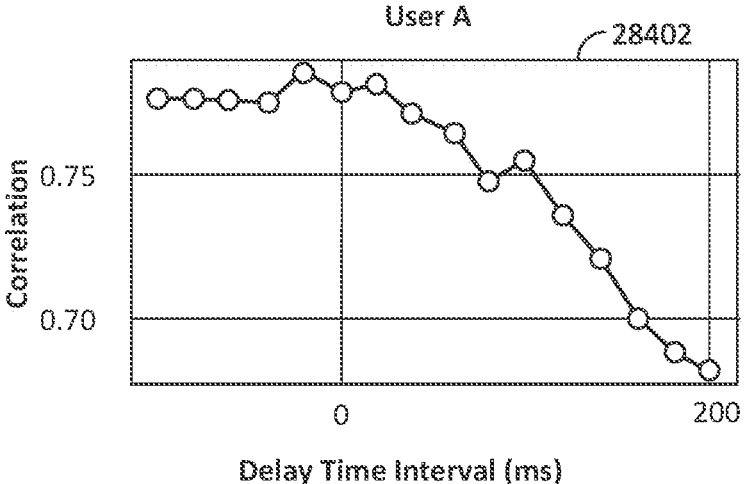
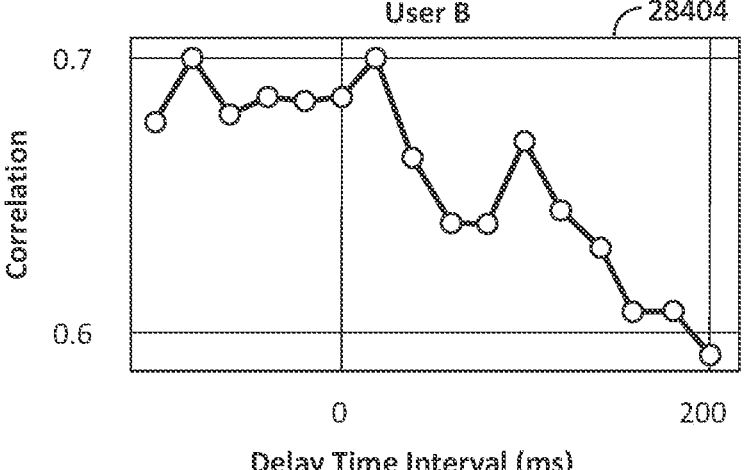
*FIG. 28E*

28500

28600

Input sensor data to inferential
model(s)
28602

Determine derived sensor data
28604

Determine handstate information
28606

Update musculoskeletal
representation
28608

28700

28720

28710

28900

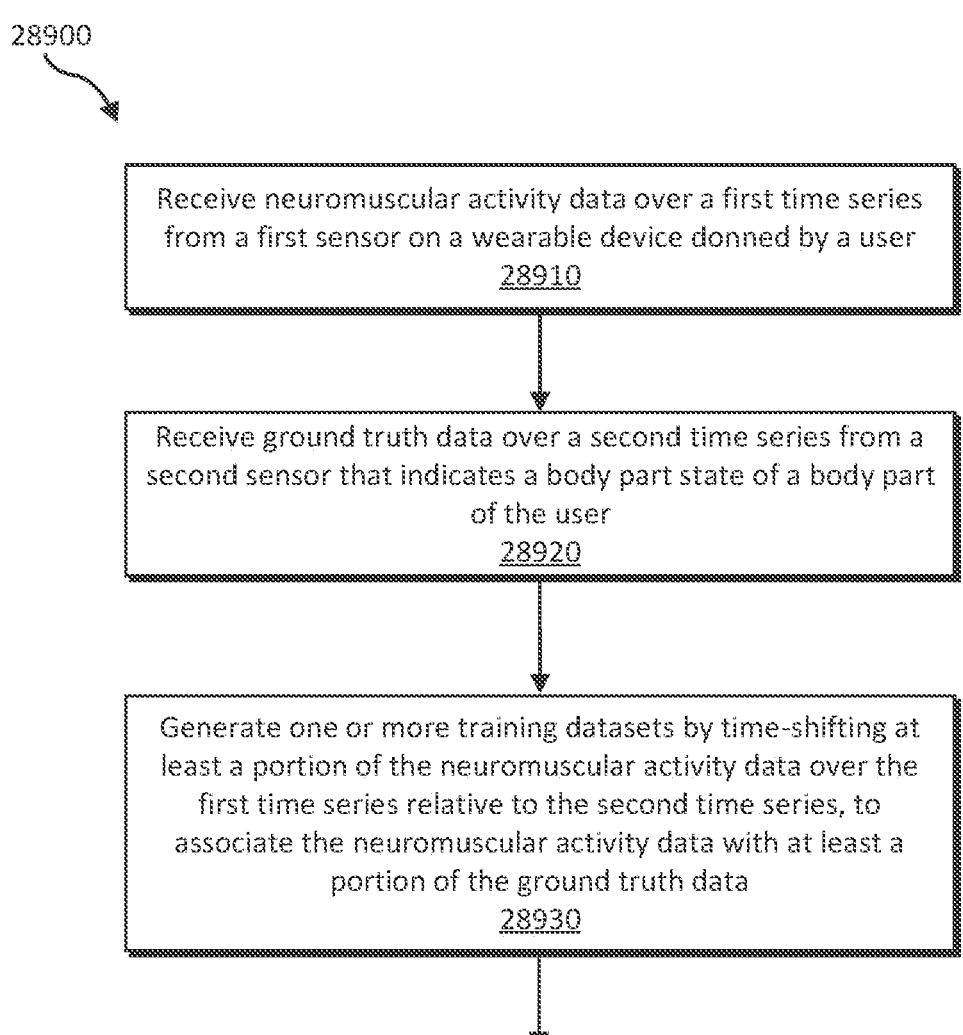

Receive neuromuscular activity data over a first time series from a first sensor on a wearable device donned by a user
28910

Receive ground truth data over a second time series from a second sensor that indicates a body part state of a body part of the user
28920

Generate one or more training datasets by time-shifting at least a portion of the neuromuscular activity data over the first time series relative to the second time series, to associate the neuromuscular activity data with at least a portion of the ground truth data
28930

Train one or more inferential models based on the one or more training datasets
28940

*FIG. 28J*

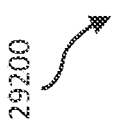
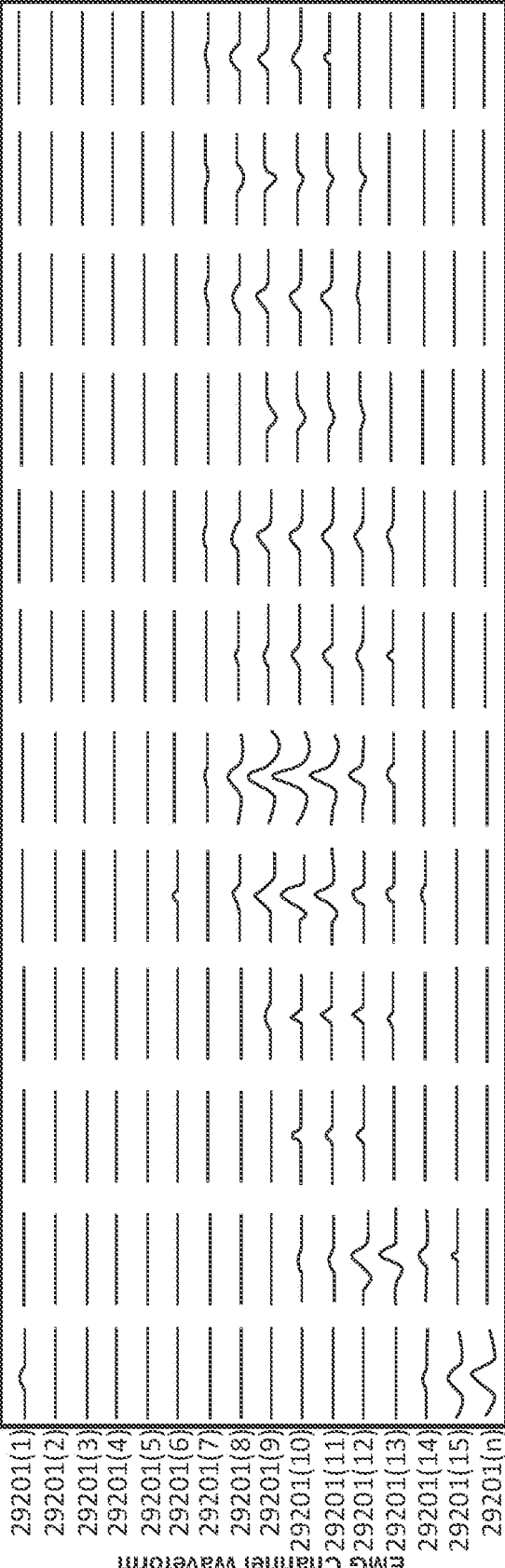
Biological Source
*FIG. 29B*

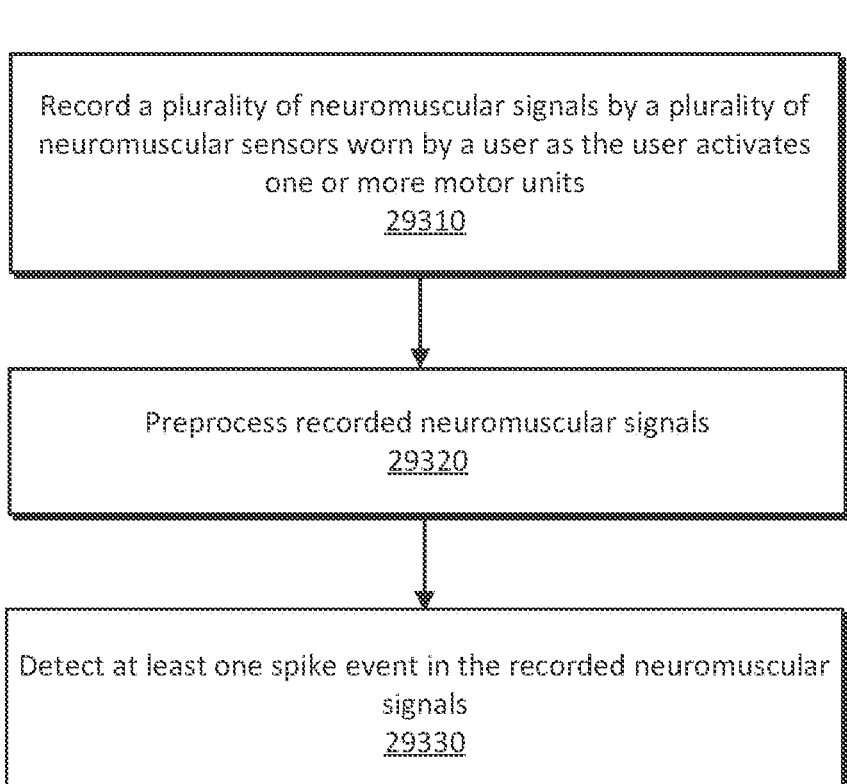
FIG. 29C

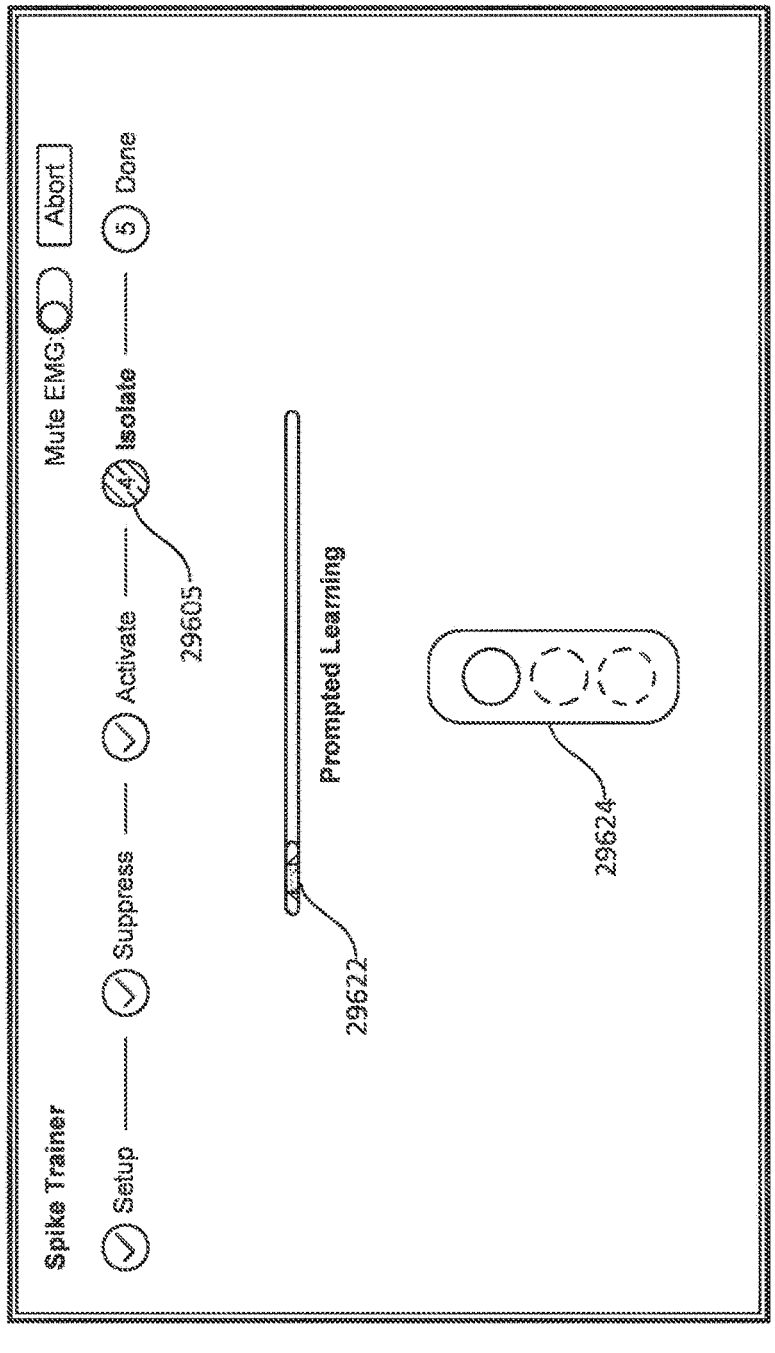
*FIG. 29F*

29700

Configure a plurality of neuromuscular sensors to record a plurality of neuromuscular signals from a user, wherein the plurality of neuromuscular sensors are arranged on one or more wearable devices
29710

Train, using the plurality of neuromuscular signals, an inference model to determine at least one spatiotemporal waveform and a corresponding weight to be applied to the at least one spatiotemporal waveform, wherein the at least one spatiotemporal waveform is related to firing of an action potential in at least one motor unit of the user and training the inference model comprises determining one or more parameters for a biophysical model simulating the at least one motor unit of the user
29720

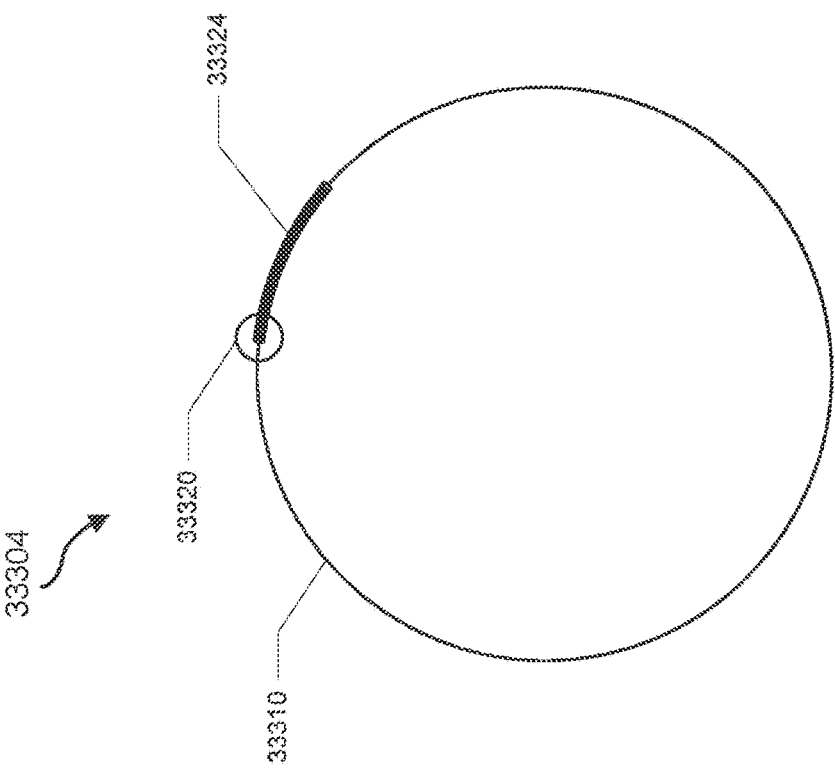
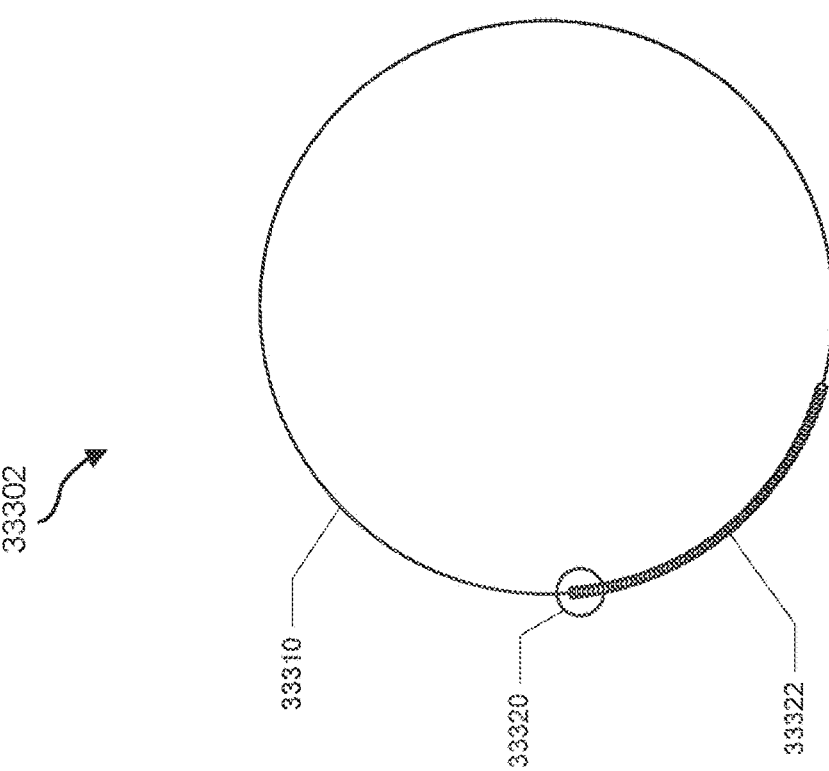
FIG. 33C

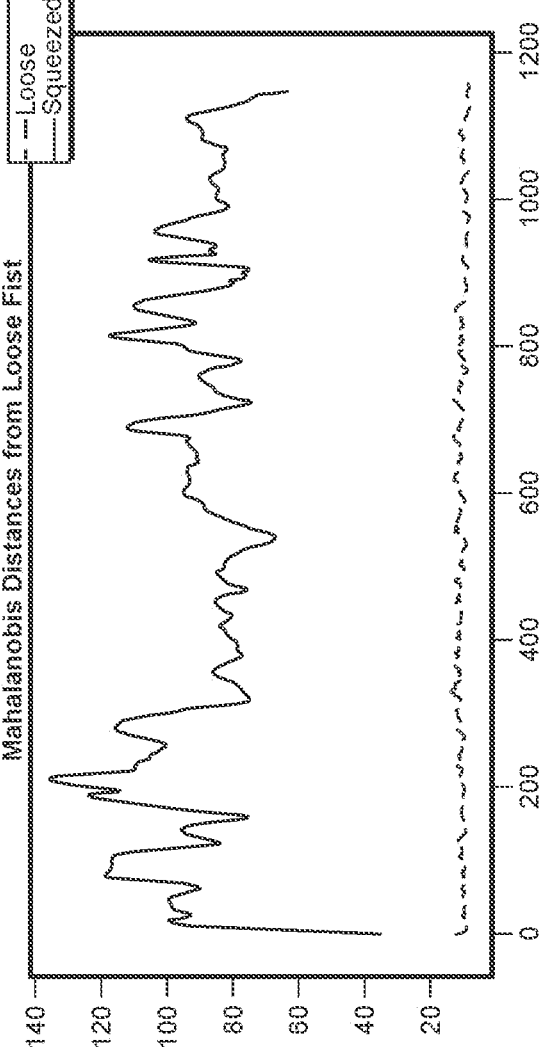
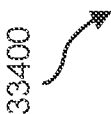
*FIG. 33D*

331106

331104

331102

Straight Lines

Curvy Lines
(Bezier)

Circles and
Ellipses

Polygons

Spokes

Numbers and
Letters

180 Degrees
Turns

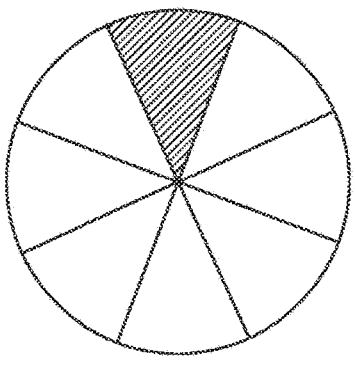
*FIG. 33Q*
Tier 3: >= 4 Discretized Angles        Tier 2: >= 8 Discretized Angles        Tier 1: >= 16 Discretized Angles
Hold for 2 Sec                                    Hold for 2 Sec                                    Hold for 2 Sec
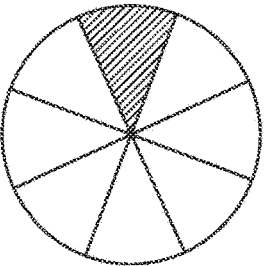
Navigate
+ Hold 2 Seconds
+ Click'
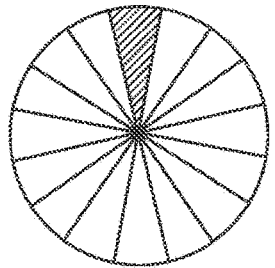
Consistency: (Subjective) 3 Trails        Consistency: (Subjective) 3 Trails        Consistency: (Subjective) 3 Trails
Combinatorics: In Region. 1 'Click'        Combinatorics: In Region. 1 'Click'        Combinatorics: In Region. 2 'Click's
*FIG. 33R*

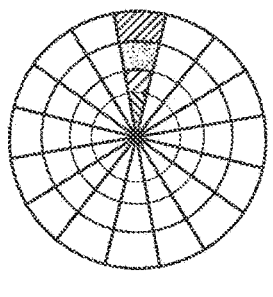
*FIG. 33S*
Tier 3: 2 Magnitudes, >= 4
Discretized Angles Hold for 2 Sec
Tier 2: 3 Magnitudes, >= 8
Discretized Angles Hold for 2 Sec
Tier 1: 4 Magnitudes, >= 16
Discretized Angles Hold For 2 Sec
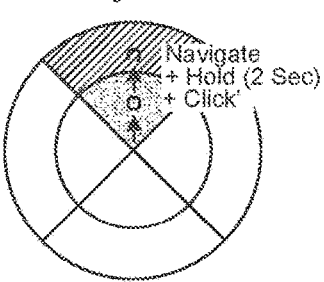
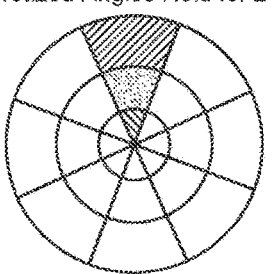
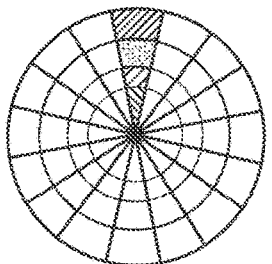
Consistency: (Subjective) 3 Trails
Combinatorics: In Region, 1 'Click'
Consistency: (Subjective) 3 Trails
Combinatorics: In Region, 1 'Click'
Consistency: (Subjective) 3 Trails
Combinatorics: In Region, 2 'Click's
*FIG. 33T*

Tier 3 (5x Typical Mouse)
- - Reachability:     Can Trace Entire Area
- - Stability:     Hold for 2 sec. at > 3 Points
- - Consistency:     Same Action 3 Trails
- - Path Efficiency:     Within + /- 50 of Mouse
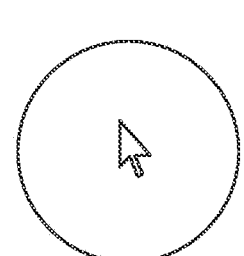
Tier 2 (2x Typical Mouse)
- - Path Efficiency:     Within + / - 30% of Mouse
Tier 1 (Typical Mouse)
- - Path Efficiency:     With + / - 10 of Mouse
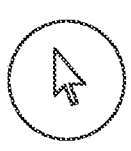
*FIG. 33V*

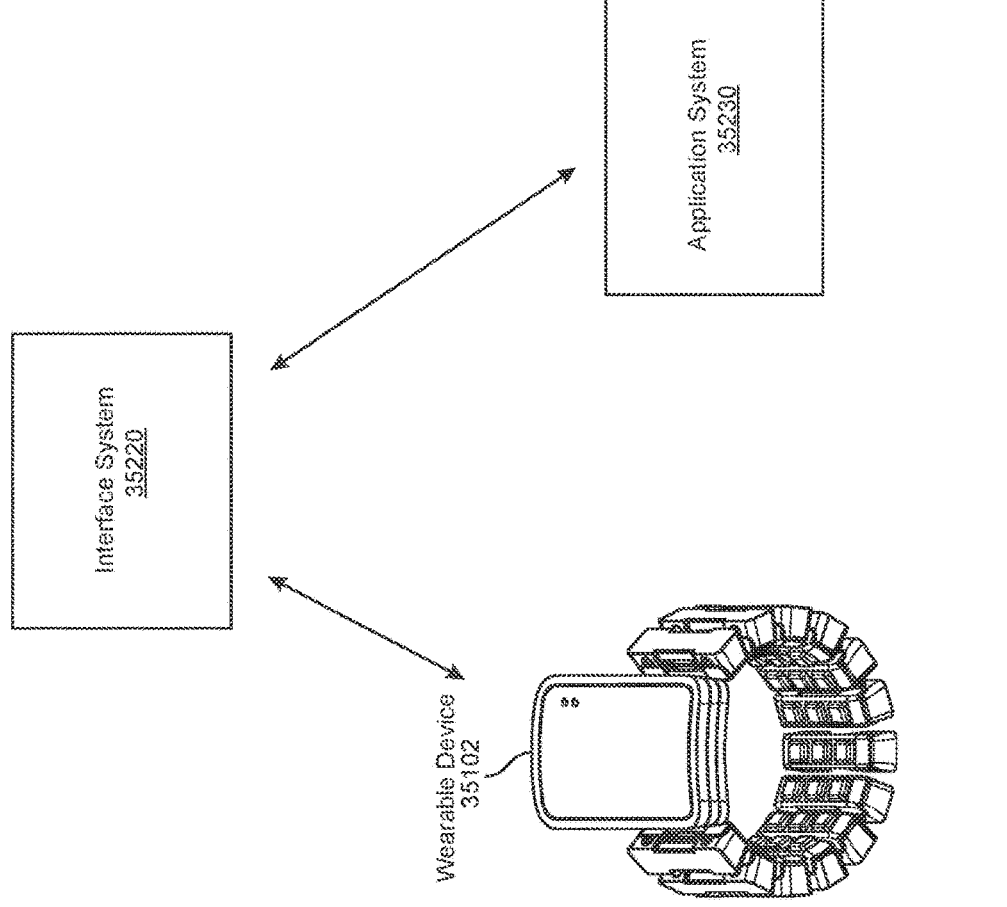
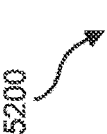
FIG. 35B

35102

35420

35430

35410

35420

35430

35410

35102
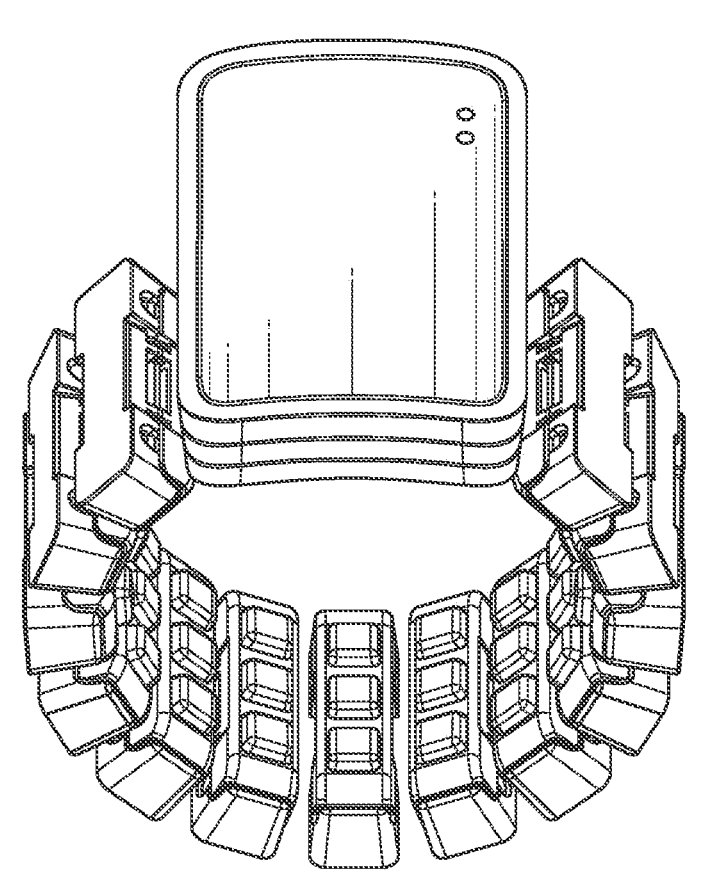
FIG. 35H

35700

35804

35802

35800

351008

351006

351004

351002

State Indicator 351012

Idle

351000

351052 Action

351000

State Indicator 351010

Menu

Action 351040

Selection Indicator 351020

Action 351050

351000

Selection Indicator 351020

351000

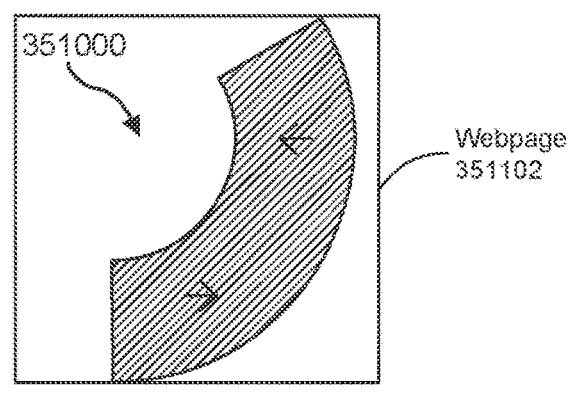
FIG. 36A
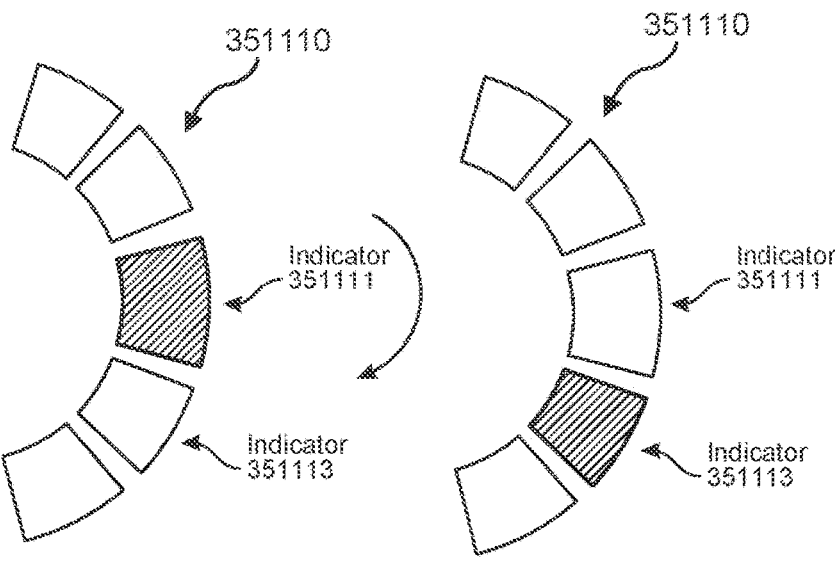
FIG. 36B        FIG. 36C
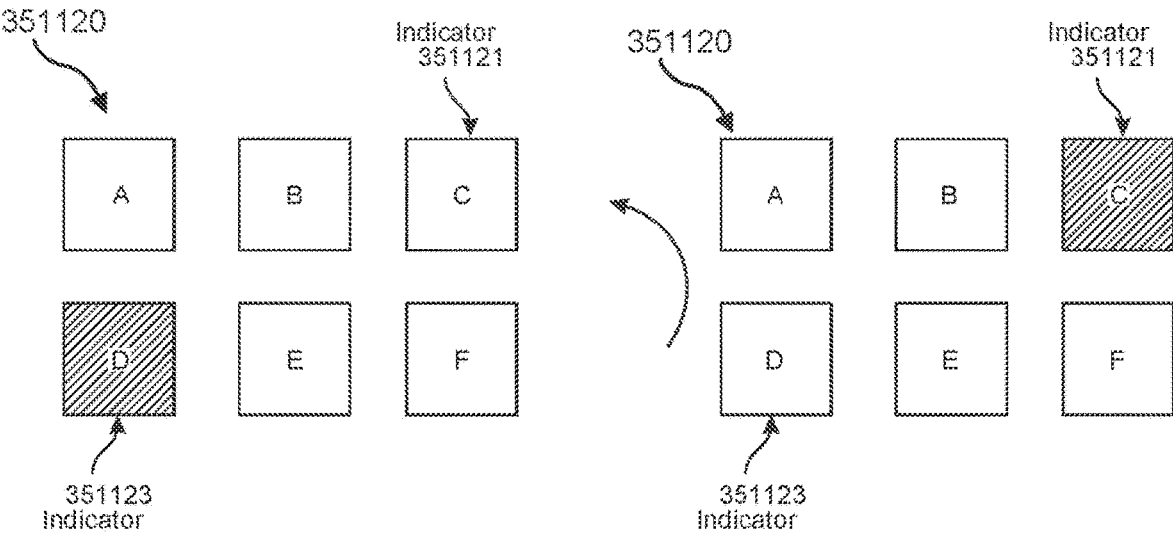
FIG. 36D            FIG. 36E

351200

351300

351300

351300

Enabled     API     Data

▽ Control Options

▽ scroll:options downPose

| ring_pinch       ▽ | upPose

| pinky_pinch       ▽ | rate

────────────○──────────────

▷ linksActivate:options

▷ linksDeactivate:options

▷ click:options

▷ buttons:options

▷ menuActivate:options

▷ menuDeactivate:options

▷ burstSelect:options

| VIEW GRAPH |    | RESET SETTINGS |

351300

Enabled ✔ API Data

▽ Control Options

▷ scroll:options

▽ linksActivate:options
     duration

━━━━━◯━━━━━━━━━ pose
     | middle_pinch ▽ |

▷ linksDeactivate:options

▷ click:options

▷ buttons:options

▷ menuActivate:options

▷ menuDeactivate:options

▷ burstSelect:options

| VIEW GRAPH |    | RESET SETTINGS |

351700

Enabled        API   ◎    Data   ◎

▽ Control Options

▷ scroll:options

▷ linksActivate:options

▷ linksDeactivate:options

▽ click:options duration pose

| index_pinch | ▽ |
|---|---|

▷ buttons:options

▷ menuActivate:options

▷ menuDeactivate:options

▷ burstSelect:options

| VIEW GRAPH | | RESET SETTINGS |
|---|---|---|

351800

351802

Update cursor position

351804

Associate element

351806

Indicate association

351808

Perform activation action

351900

Element
351906

Cursor
351902

Connector
351904

352000

352200

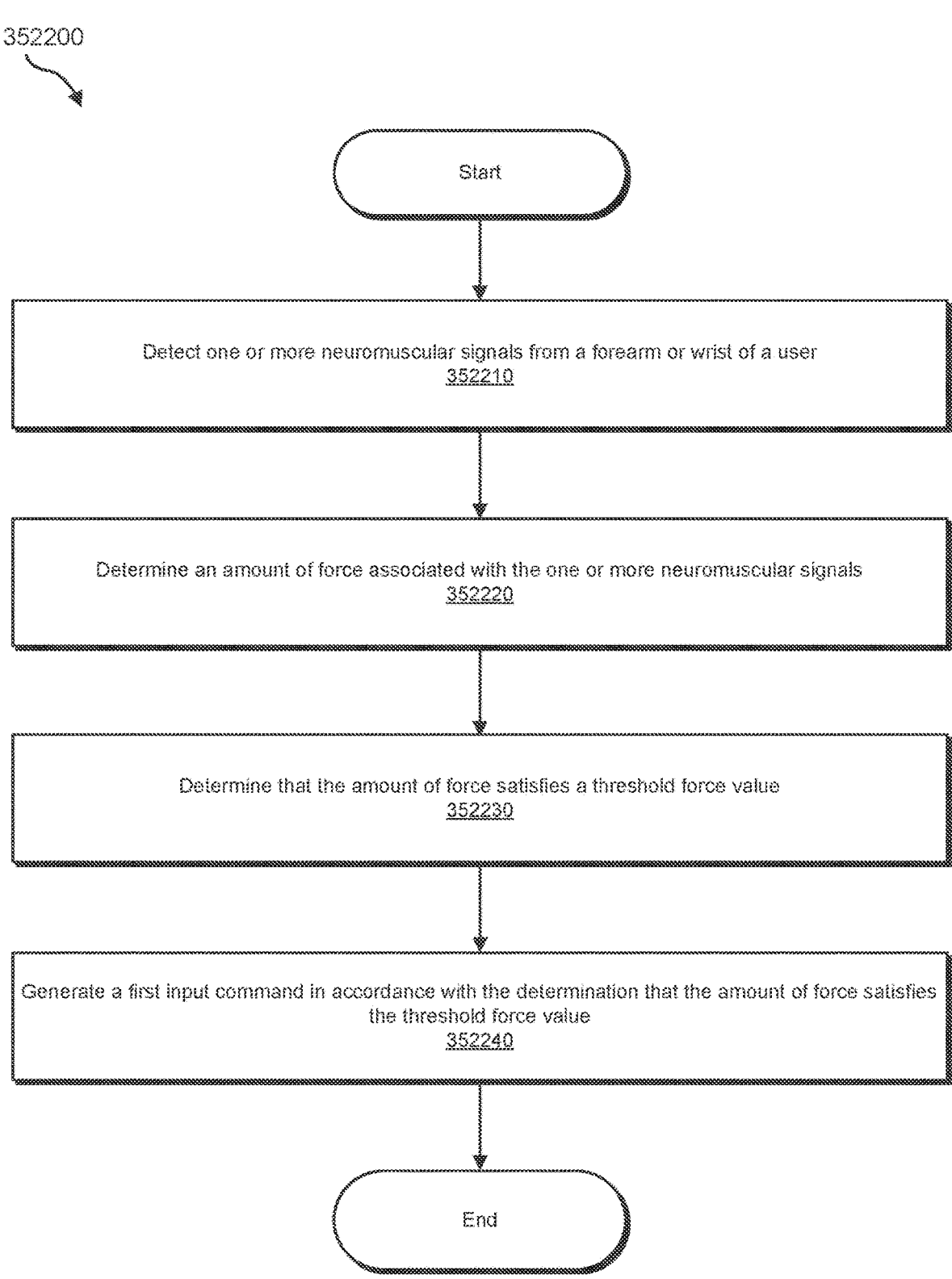

```
                    ┌──────────────┐
                    │    Start     │
                    └──────────────┘
                           │
                           ▼
 ┌──────────────────────────────────────────────────────────────┐
 │  Detect one or more neuromuscular signals from a forearm       │
 │  or wrist of a user                                            │
 │                        352210                                  │
 └──────────────────────────────────────────────────────────────┘
                           │
                           ▼
 ┌──────────────────────────────────────────────────────────────┐
 │  Determine an amount of force associated with the one or more  │
 │  neuromuscular signals                                         │
 │                        352220                                  │
 └──────────────────────────────────────────────────────────────┘
                           │
                           ▼
 ┌──────────────────────────────────────────────────────────────┐
 │  Determine that the amount of force satisfies a threshold       │
 │  force value                                                   │
 │                        352230                                  │
 └──────────────────────────────────────────────────────────────┘
                           │
                           ▼
 ┌──────────────────────────────────────────────────────────────┐
 │  Generate a first input command in accordance with the         │
 │  determination that the amount of force satisfies              │
 │  the threshold force value                                     │
 │                        352240                                  │
 └──────────────────────────────────────────────────────────────┘
                           │
                           ▼
                    ┌──────────────┐
                    │     End      │
                    └──────────────┘
```

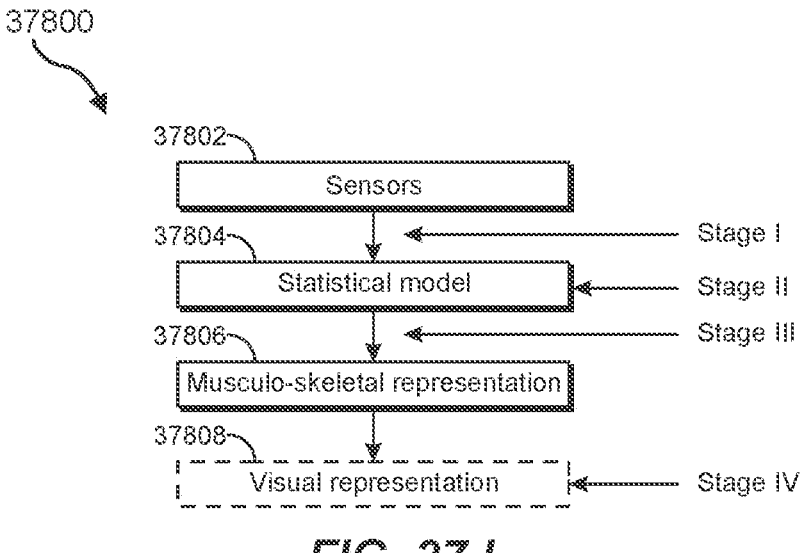

37802 — Sensors

37804 — Statistical model ← Stage I
← Stage II
37806 — ← Stage III
Musculo-skeletal representation 37808 — Visual representation ← Stage IV

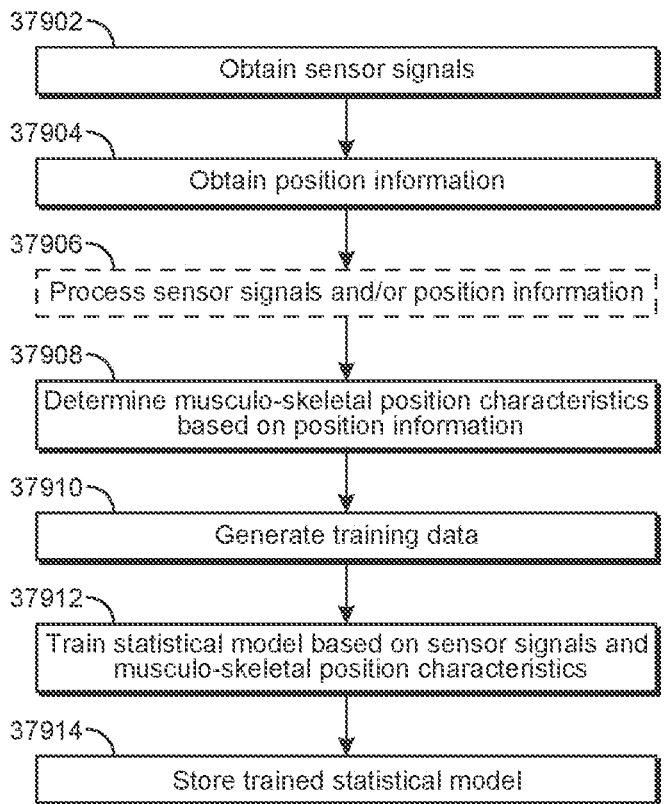

37902 — Obtain sensor signals

37904 — Obtain position information

37906 — Process sensor signals and/or position information

37908 — Determine musculo-skeletal position characteristics based on position information 37910 — Generate training data 37912 — Train statistical model based on sensor signals and musculo-skeletal position characteristics 37914 — Store trained statistical model

FIG. 37K

Method
371000

371010 — Present sensory cue via user interface

371020 — Receive neuromuscular signals from wearable device

371030 — Interpret neuromuscular signals as input commands

371040 — Perform specified tasks based on input commands

371120 —

Interface System

Wearable Device
371110

371130 —

Application System

371210 — Record Neuromuscular Signals

371212 — Modeling

371214 — Constrain Output

371216 — Produce Text

371300

371312 — Processor(s)

371314 — Inference Model(s)

371310 — Sensors

371316 — Controller

371318 — User Interface

371410 — Capture on-keyboard "labeled" data

371412 — Generated generalized model based on labeled data

371414 — Collect off-keyboard "unlabeled" data

371416 — Use unlabeled data to personalize model for user

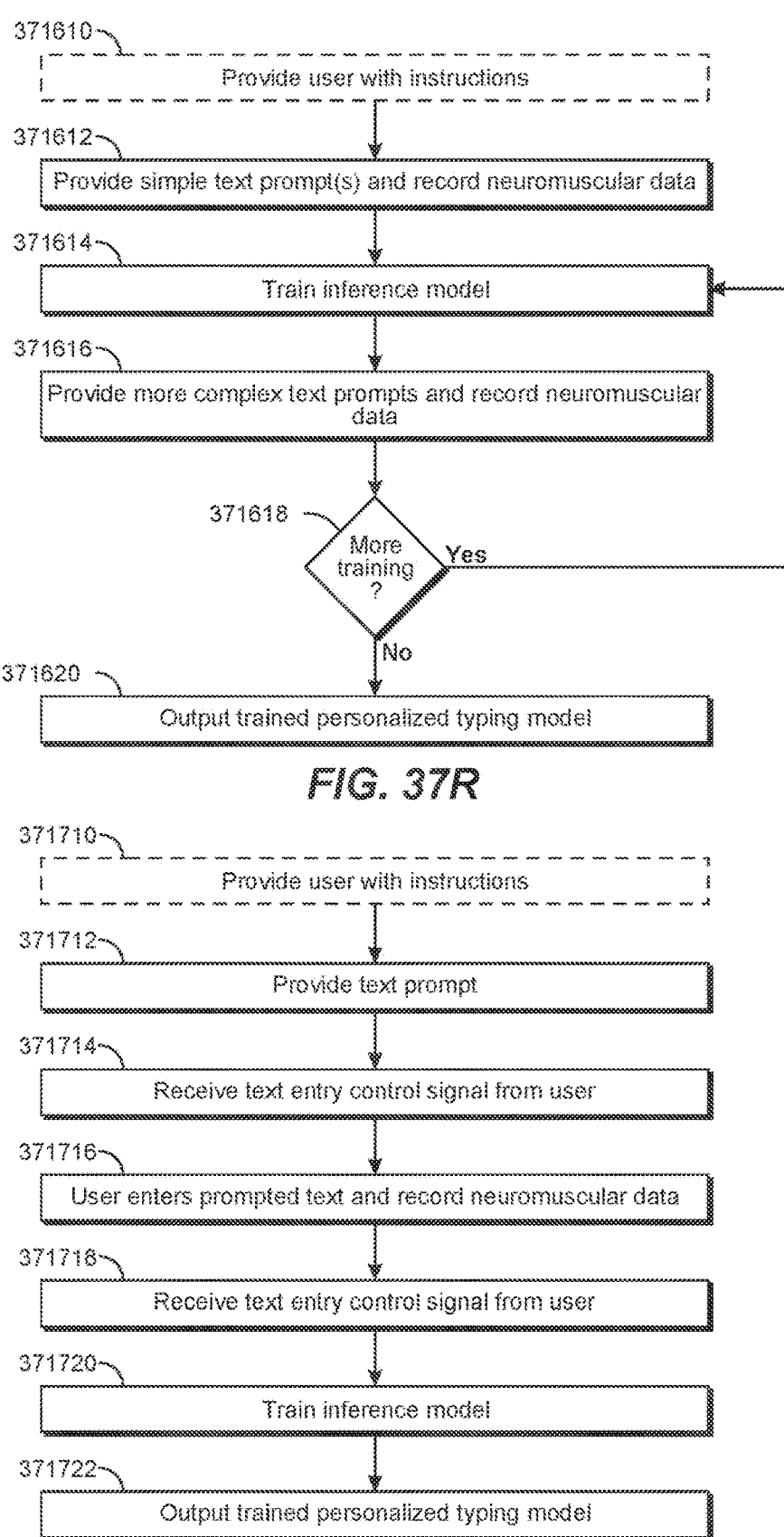

371610 — Provide user with instructions

371612 — Provide simple text prompt(s) and record neuromuscular data

371614 — Train inference model

371616 — Provide more complex text prompts and record neuromuscular data

371618 — More training ?   Yes

No

371620 — Output trained personalized typing model

*FIG. 37R*

371710 — Provide user with instructions

371712 — Provide text prompt

371714 — Receive text entry control signal from user

371716 — User enters prompted text and record neuromuscular data

371718 — Receive text entry control signal from user

371720 — Train inference model

371722 — Output trained personalized typing model

*FIG. 37S*

372210 — Process neuromuscular signals using dimensional reduction technique

372212 — Apply peak detection to identify when a discrete event occurs

372214 — Identify epochs of neuromuscular data including discrete event

372216 — Apply clustering to identified epochs

372218 — Temporally align clustered events

372220 — Generate labels for training data

39100

39400

39420

39430

39410

39420

39430

39210

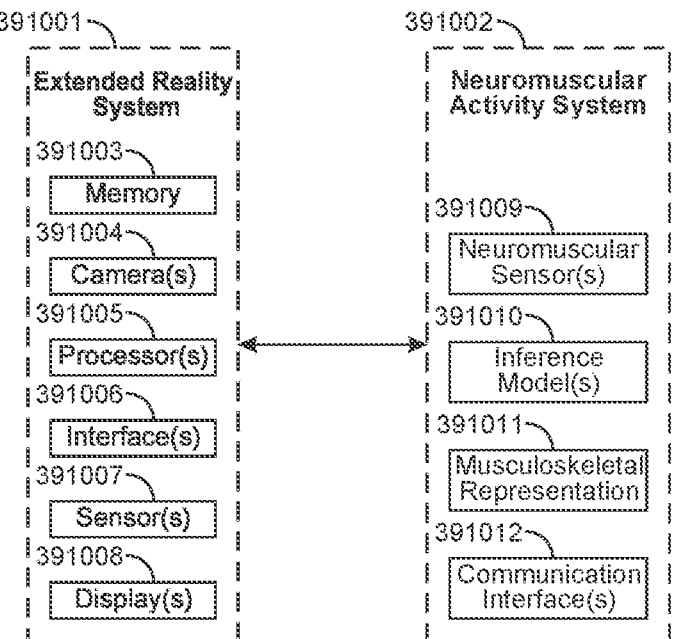
FIG. 39P

391100

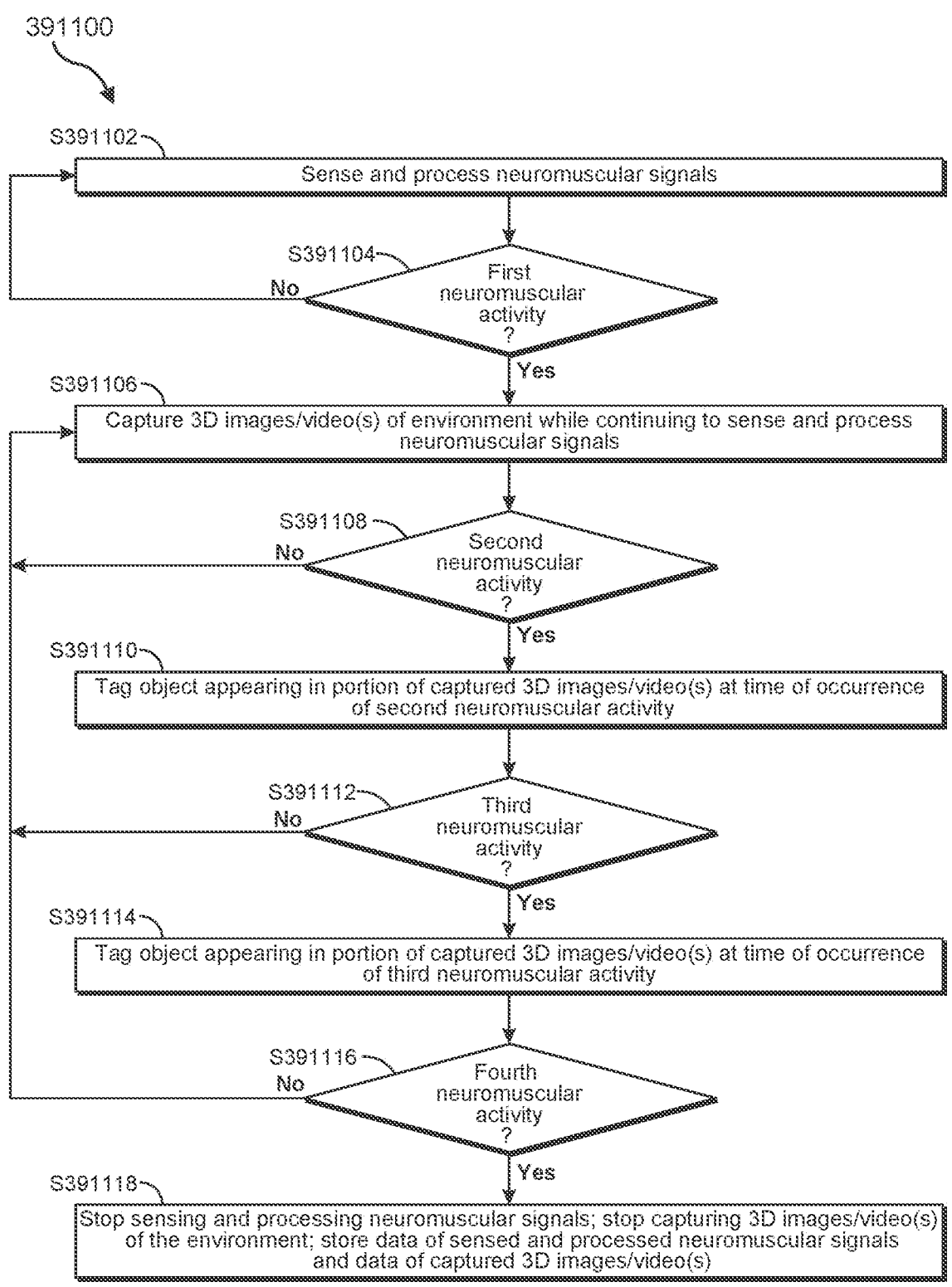

S391102 — Sense and process neuromuscular signals

S391104 — First neuromuscular activity ?
No

Yes

S391106 — Capture 3D images/video(s) of environment while continuing to sense and process neuromuscular signals S391108 — Second neuromuscular activity ?
No Yes S391110 — Tag object appearing in portion of captured 3D images/video(s) at time of occurrence of second neuromuscular activity S391112 — Third neuromuscular activity ?
No Yes S391114 — Tag object appearing in portion of captured 3D images/video(s) at time of occurrence of third neuromuscular activity S391116 — Fourth neuromuscular activity ?
No Yes S391118 — Stop sensing and processing neuromuscular signals; stop capturing 3D images/video(s) of the environment; store data of sensed and processed neuromuscular signals and data of captured 3D images/video(s)

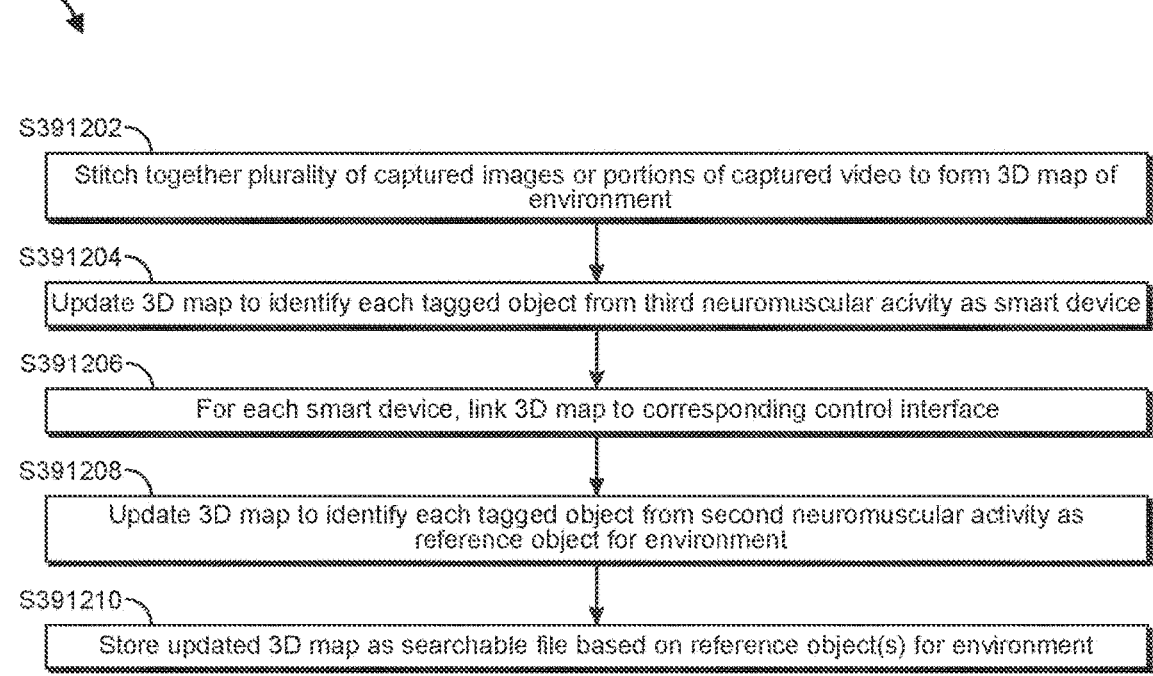

S391202
Stitch together plurality of captured images or portions of captured video to form 3D map of environment S391204
Update 3D map to identify each tagged object from third neuromuscular acivity as smart device S391206
For each smart device, link 3D map to corresponding control interface S391208
Update 3D map to identify each tagged object from second neuromuscular activity as reference object for environment S391210
Store updated 3D map as searchable file based on reference object(s) for environment

*FIG. 39R*

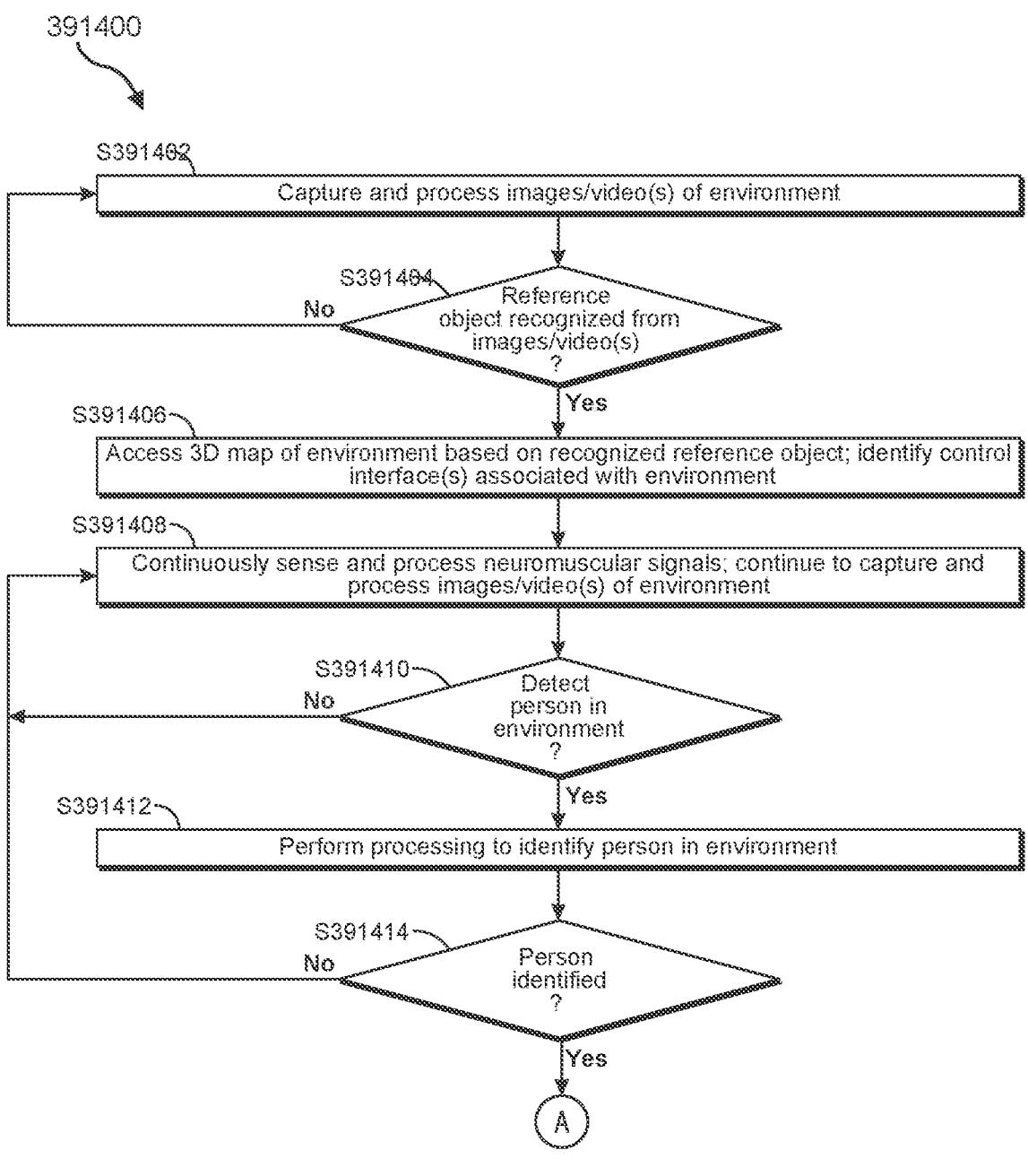

391400

S391402  Capture and process images/video(s) of environment

S391404  Reference object recognized from images/video(s) ?

No

Yes

S391406  Access 3D map of environment based on recognized reference object; identify control interface(s) associated with environment S391408  Continuously sense and process neuromuscular signals; continue to capture and process images/video(s) of environment S391410  Detect person in environment ?

No

Yes

S391412  Perform processing to identify person in environment

S391414  Person identified ?

No

Yes

WEARABLE ELECTRONIC DEVICES, EXTENDED REALITY SYSTEMS INCLUDING NEUROMUSCULAR SENSORS, AND METHODS FOR GENERATING TEXT FROM SPEECH INPUT AND MODIFYING THE GENERATED TEXT BASED ON NEUROMUSCULAR DATA

PRIORITY AND RELATED APPLICATIONS

This application is a continuation of U.S. application Ser. No. 17/722,128, filed Apr. 15, 2022, which is a continuation-in-part of U.S. application Ser. No. 17/213,686, filed Mar. 26, 2021, which is a continuation of U.S. application Ser. No. 16/593,446, filed Oct. 4, 2019, which claims the benefit of U.S. Provisional Application No. 62/741,781, filed Oct. 5, 2018, the disclosures of each of which are incorporated, in their entirety, by this reference. U.S. application Ser. No. 17/722,128 is also a continuation-in-part of U.S. application Ser. No. 16/862,050, filed Apr. 29, 2020, which is a continuation-in-part of U.S. application Ser. No. 16/258,279, filed Jan. 25, 2019, which claims the benefit of U.S. Provisional Application No. 62/621,829, filed Jan. 25, 2018, and which claims the benefit of U.S. Provisional Application No. 62/841,061, filed Apr. 30, 2019, the disclosures of each of which are incorporated, in their entirety, by this reference. U.S. application Ser. No. 17/722,128 is also a continuation-in-part of U.S. application Ser. No. 16/995,859, filed Aug. 18, 2020, which is a continuation of U.S. application Ser. No. 16/389,419, filed Apr. 19, 2019, which claims the benefit of U.S. Provisional Application No. 62/676,567, filed May 25, 2018, the disclosures of each of which are incorporated, in their entirety, by this reference. U.S. application Ser. No. 17/722,128 is also a continuation-in-part of U.S. application Ser. No. 17/389,899, filed Jul. 30, 2021, which is a continuation of U.S. application Ser. No. 16/539,755, filed Aug. 13, 2019, which claims the benefit of U.S. Provisional Application No. 62/718,337, filed Aug. 13, 2018, the disclosures of each of which are incorporated, in their entirety, by this reference. U.S. application Ser. No. 17/722,128 is also a continuation-in-part of U.S. application Ser. No. 17/487,695, filed Sep. 28, 2021, which is a continuation of U.S. application Ser. No. 16/557,342, filed Aug. 30, 2019, which claims the benefit of U.S. Provisional Application No. 62/726,159, filed Aug. 31, 2018, the disclosures of each of which are incorporated, in their entirety, by this reference. U.S. application Ser. No. 17/722,128 is also a continuation-in-part of U.S. application Ser. No. 16/577,352, filed Sep. 20, 2019, which claims the benefit of U.S. Provisional Application No. 62/734,138, filed Sep. 20, 2018, the disclosures of each of which are incorporated, in their entirety, by this reference. U.S. application Ser. No. 17/722,128 is also a continuation-in-part of U.S. application Ser. No. 17/569,836, filed Jan. 6, 2022, which is a continuation of U.S. application Ser. No. 16/577,207, filed Sep. 20, 2019, which claims the benefit of U.S. Provisional Application No. 62/734,145, filed Sep. 20, 2018, the disclosures of each of which are incorporated, in their entirety, by this reference. U.S. application Ser. No. 17/722,128 is also a continuation-in-part of U.S. application Ser. No. 17/293, 472, filed May 12, 2021, which is a National Stage of International Application no. PCT/US2019/061759, filed Nov. 15, 2019, which claims the benefit of U.S. Provisional Application No. 62/768,741, filed Nov. 16, 2018, the disclosures of each of which are incorporated, in their entirety, by this reference. U.S. application Ser. No. 17/722,128 is also a continuation-in-part of U.S. application Ser. No.

16/832,978, filed Mar. 27, 2020, which claims the benefit of U.S. Provisional Application No. 62/826,574, filed Mar. 29, 2019, the disclosures of each of which are incorporated, in their entirety, by this reference. U.S. application Ser. No. 17/722,128 is also a continuation-in-part of U.S. application Ser. No. 16/833,307, filed Mar. 27, 2020, which claims the benefit of U.S. Provisional Application No. 62/826,478, filed Mar. 29, 2019, the disclosures of each of which are incorporated, in their entirety, by this reference. U.S. application Ser. No. 17/722,128 is also a continuation-in-part of U.S. application Ser. No. 16/833,309, filed Mar. 27, 2020, which claims the benefit of U.S. Provisional Application No. 62/826,516, filed Mar. 29, 2019, which claims the benefit of U.S. Provisional Application No. 62/841,054, filed Apr. 30, 2019, the disclosures of each of which are incorporated, in their entirety, by this reference. U.S. application Ser. No. 17/722,128 is also a continuation-in-part of U.S. application Ser. No. 16/833,626, filed Mar. 29, 2020, which claims the benefit of U.S. Provisional Application No. 62/826,493, filed Mar. 29, 2019, U.S. Provisional Application No. 62/840, 803, filed Apr. 30, 2019, and U.S. Provisional Application No. 62/968,495, filed Jan. 31, 2020, the disclosures of each of which are incorporated, in their entirety, by this reference. U.S. application Ser. No. 17/722,128 is also a continuation-in-part of U.S. application Ser. No. 17/469,537, filed Sep. 8, 2021, which is a continuation of U.S. application Ser. No. 16/863,098, filed Apr. 30, 2020, which claims the benefit of U.S. Provisional Application No. 62/841,107, filed Apr. 30, 2019, U.S. Provisional Application No. 62/841,100, filed Apr. 30, 2019, U.S. Provisional Application No. 62/840,966, filed Apr. 30, 2019, U.S. Provisional Application No. 62/840,947, filed Apr. 30, 2019, U.S. Provisional Application No. 62/841,069, filed Apr. 30, 2019, and U.S. Provisional Application No. 62/840,980, filed Apr. 30, 2019, the disclosures of each of which are incorporated, in their entirety, by this reference. U.S. application Ser. No. 17/722, 128 is also a continuation-in-part of U.S. application Ser. No. 17/667,442, filed Feb. 8, 2022, which is a continuation of U.S. application Ser. No. 16/854,668, filed Apr. 21, 2020, which claims the benefit of U.S. Provisional Application No. 62/841,156, filed Apr. 30, 2019, and U.S. Provisional Application No. 62/841,147, filed Apr. 30, 2019, the disclosures of each of which are incorporated, in their entirety, by this reference. U.S. application Ser. No. 17/722,128 is also a continuation-in-part of U.S. application Ser. No. 16/994, 380, filed Aug. 14, 2020, which claims the benefit of U.S. Provisional Application No. 62/931,082, filed Nov. 5, 2019, U.S. Provisional Application No. 62/895,894, filed Sep. 4, 2019, U.S. Provisional Application No. 62/898,417, filed Sep. 10, 2019, U.S. Provisional Application No. 62/887,528, filed Aug. 15, 2019, U.S. Provisional Application No. 62/887,521, filed Aug. 15, 2019, U.S. Provisional Application No. 62/887,515, filed Aug. 15, 2019, U.S. Provisional Application No. 62/887,507, filed Aug. 15, 2019, U.S. Provisional Application No. 62/887,502, filed Aug. 15, 2019, U.S. Provisional Application No. 62/887,496, filed Aug. 15, 2019, and U.S. Provisional Application No. 62/887,485, filed Aug. 15, 2019, the disclosures of each of which are incorporated, in their entirety, by this reference. U.S. application Ser. No. 17/722,128 is also a continuation-in-part of U.S. application Ser. No. 17/010,689, filed Sep. 2, 2020, which claims the benefit of U.S. Provisional Application No. 62/897,483, filed Sep. 9, 2019, U.S. Provisional Application No. 62/897,592, filed Sep. 9, 2019, U.S. Provisional Application No. 62/895,888, filed Sep. 4, 2019, and U.S. Provisional Application No. 62/895,782, filed Sep. 4, 2019., the disclosures of each of which are incorporated, in their entirety, by this reference. U.S. application Ser. No. 17/722,128 is also a continuation-in-part of U.S. application Ser. No. 17/094,712, filed Nov. 10, 2020, which claims the benefit of U.S. Provisional Application No. 62/940,121, filed Nov. 25, 2019, the disclosures of each of which are incorporated, in their entirety, by this reference. U.S. application Ser. No. 17/722,128 is also a continuation-in-part of U.S. application Ser. No. 17/173,996, filed Feb. 11, 2021, which is a continuation of U.S. application Ser. No. 15/974,454, filed May 8, 2018, the disclosures of each of which are incorporated, in their entirety, by this reference.

BRIEF DESCRIPTION OF THE DRAWINGS

The accompanying drawings illustrate a number of exemplary embodiments and are a part of the specification. Together with the following description, these drawings demonstrate and explain various principles of the present disclosure.

FIG. 7A illustrates a wristband having EMG sensors arranged circumferentially thereon, in accordance with some embodiments of the technology described herein.

FIG. 9A illustrates a wearable portion of the computer-based system, and FIG. 9B illustrates a dongle portion connected to a computer, wherein the dongle portion is configured to communicate with the wearable portion.

FIG. 13 is an illustration of exemplary haptic devices that may be used in connection with embodiments of this disclosure.

FIG. 17 is a more detailed illustration of various aspects of the eye-tracking subsystem illustrated in FIG. 16.

FIG. 26F illustrates a schematic of a control device of the computer-based system and FIG. 26G illustrates an example dongle portion that may be connected to a computer, where the dongle portion is configured to communicate with the control device (and a similar configuration may be used within a head-mounted device in communication with the control device).

FIG. 26J illustrates a first configuration in which an anti-aliasing filter is positioned away from an analog-to-digital converter, and FIG. 26K illustrates a second configuration in which the anti-aliasing filter is located proximate to the analog-to-digital converter.

FIG. 26O shows a power spectrum of a first channel and FIG. 26P shows a power spectrum of a second channel of a 16-channel EMG control interface.

FIG. 26Q shows a power spectrum of the same channel as FIG. 26O, and FIG. 26R shows a power spectrum of the same channel as FIG. 26P.

FIG. 28E illustrates two charts depicting user dependence in a relationship between delay time interval and body state prediction accuracy, in accordance with embodiments of the present disclosure.

FIG. 28J is an illustration of a flowchart of an example method for predicting a body state based on neuromuscular data, in accordance with embodiments of the present disclosure.

FIG. 29B is a chart representing neuromuscular signal data acquired by neuromuscular sensors arranged on a wearable device, according to at least one embodiment of the present disclosure.

FIG. 29C is a flowchart of an example method for detecting spike event information from neuromuscular signals, according to at least one embodiment of the present disclosure.

FIG. 29F illustrates the user interface in a third state for prompting a user to volitionally control a single motor unit, according to at least one embodiment of the present disclosure.

FIG. 29G is a flowchart of an example method for training an inference model to determine at least one spatiotemporal waveform and a corresponding weight to be applied to the at least one spatiotemporal waveform, according to at least one embodiment of the present disclosure.

FIGS. 31A-31Q show example distributions of two classes of gestures.

FIGS. 32A-32B show examples of separated clusters using UMAP and PCA.

FIG. 32C shows an example of accuracy levels achieved using a self-supervised model.

FIG. 32D shows an example of accuracy levels achieved using a supervised user specific models and a self-supervised user specific model, versus the number of training events.

FIG. 32E shows an example of window size determination for user specific and self-supervised models.

FIGS. 32F-32I show example models of each event class associated with a first user.

FIGS. 32J-32K show an example of aligned models of each event class associated with a first user and a second user.

FIGS. 32L-32M show example data before and after transformation, respectively.

FIG. 32N shows an example transfer matrix across users from all users in a group of users.

FIG. 32O shows determination of data size for a supervised domain adaptation based on a transfer function.

FIG. 32P illustrates a wearable system with EMG sensors arranged circumferentially around an elastic band configured to be worn around a user's lower arm or wrist, in accordance with some embodiments.

FIG. 32Q is a cross-sectional view through one of the EMG sensors illustrated in FIG. 32P.

Figures 32A, 32B:
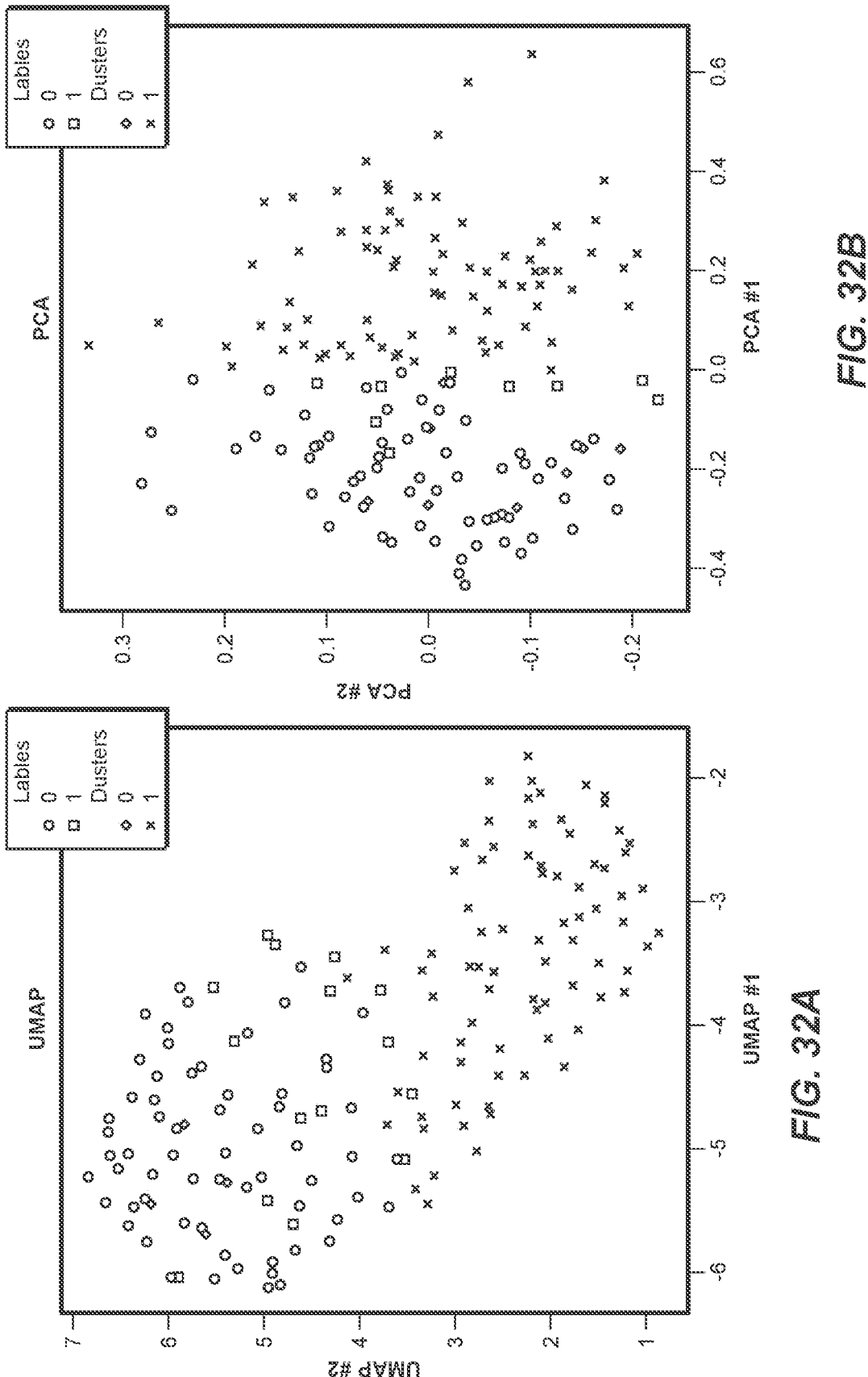
Figure 32C:
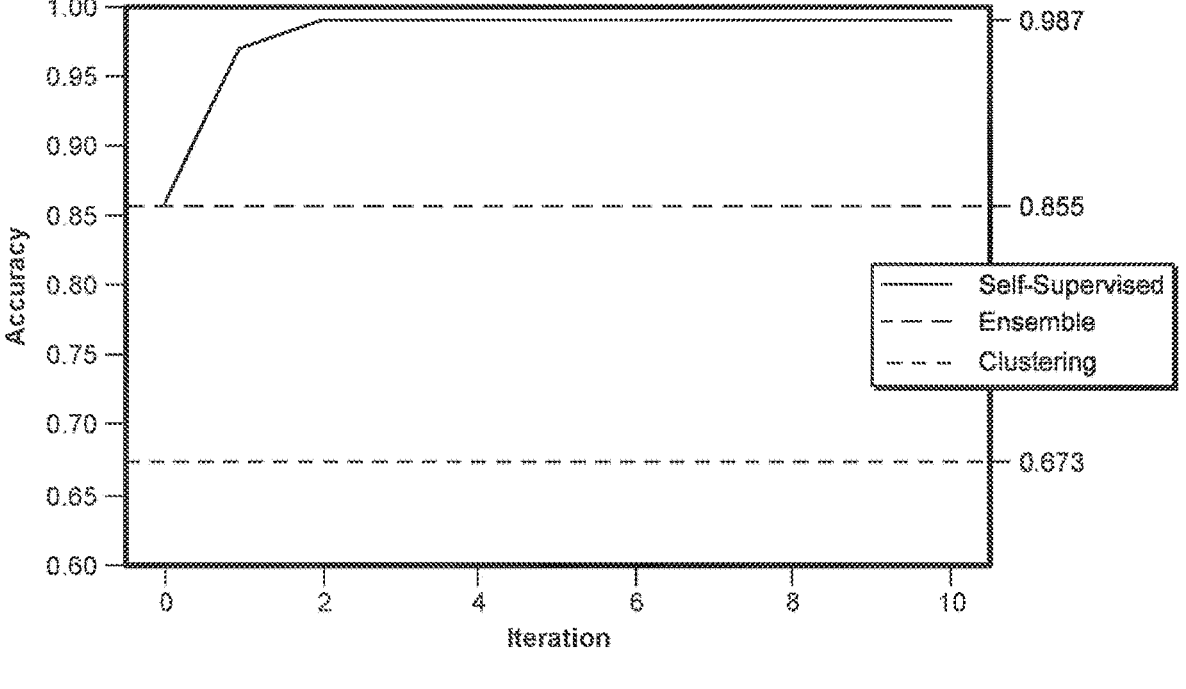
Figure 32D:
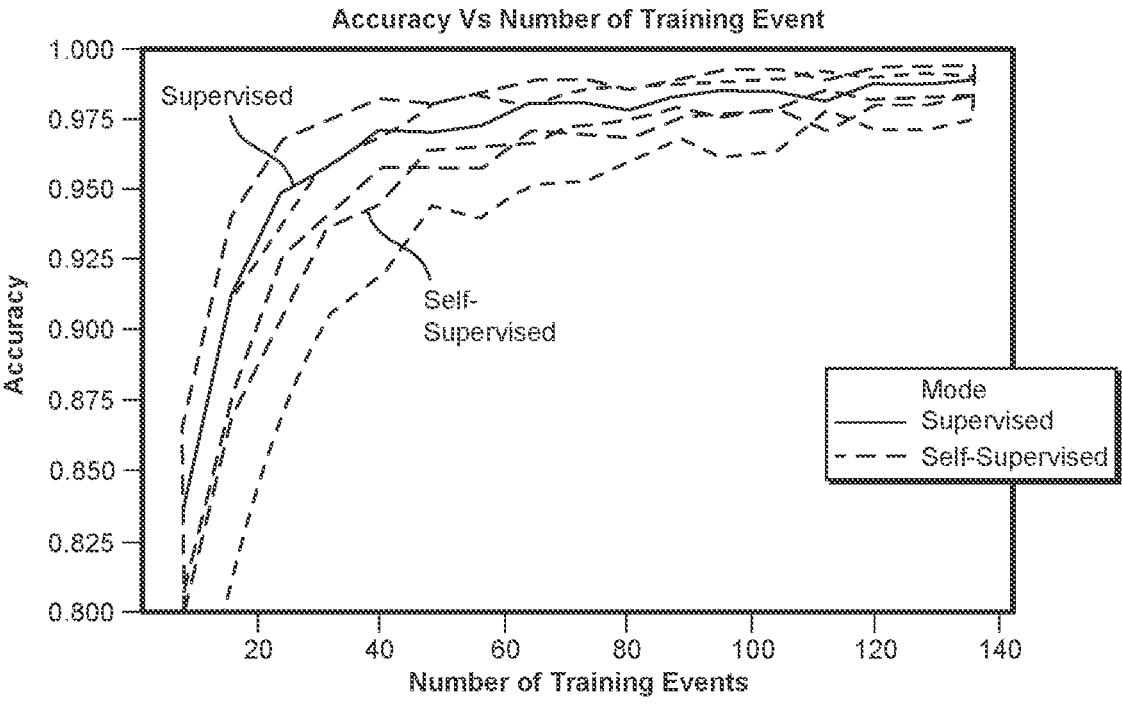
Figure 32E:
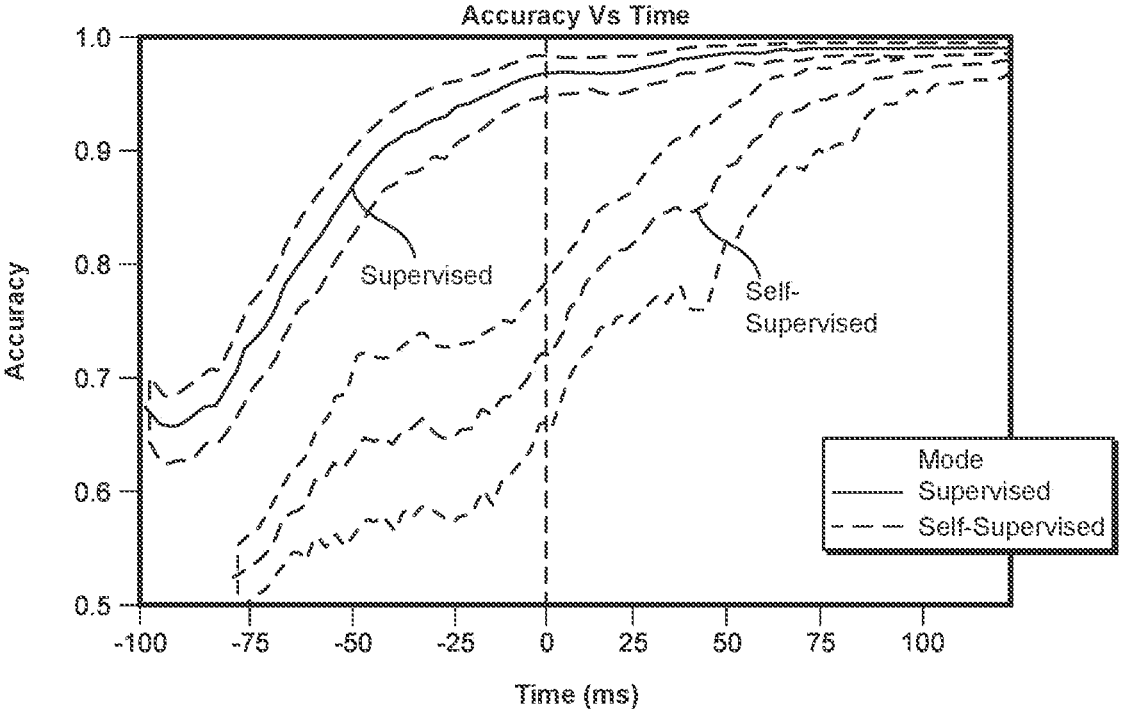
Figure 32F:
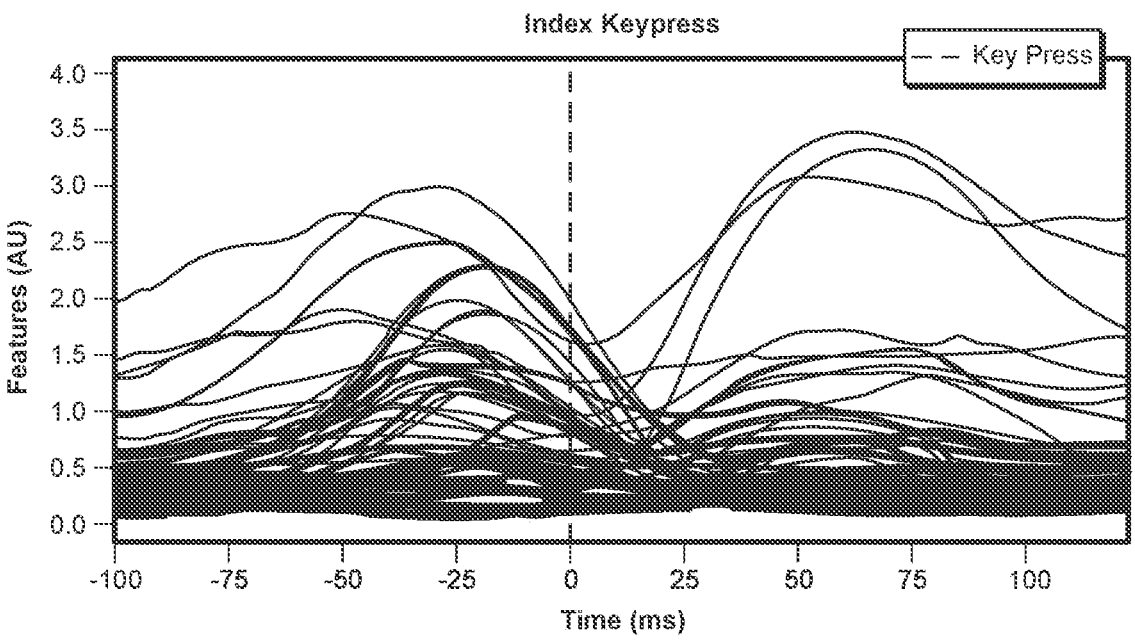
Figure 32G:
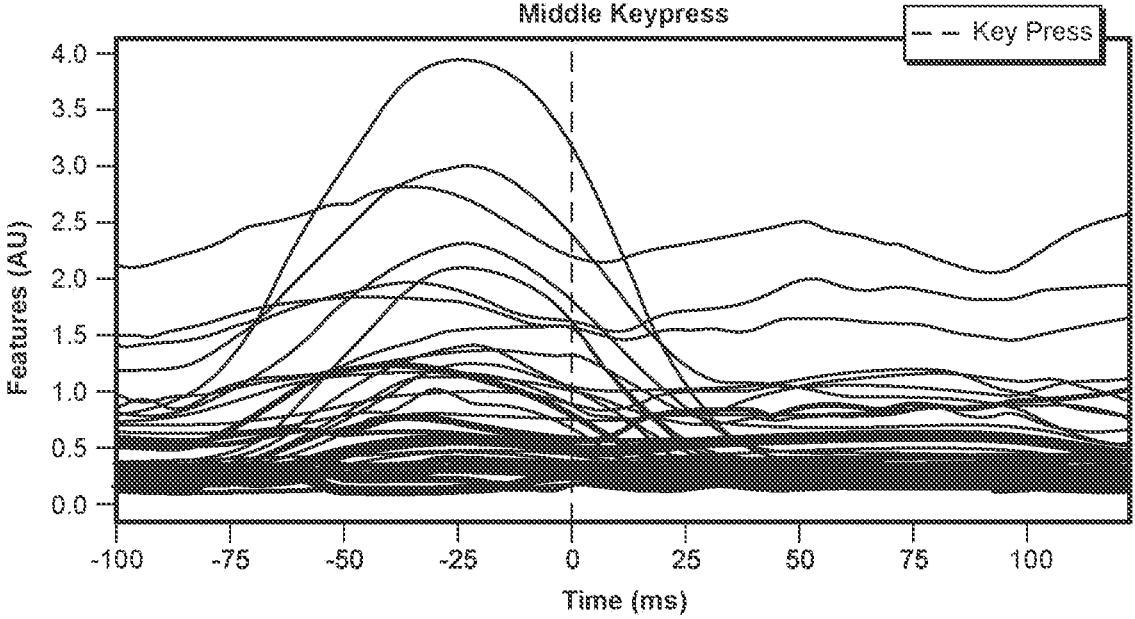
Figure 32H:
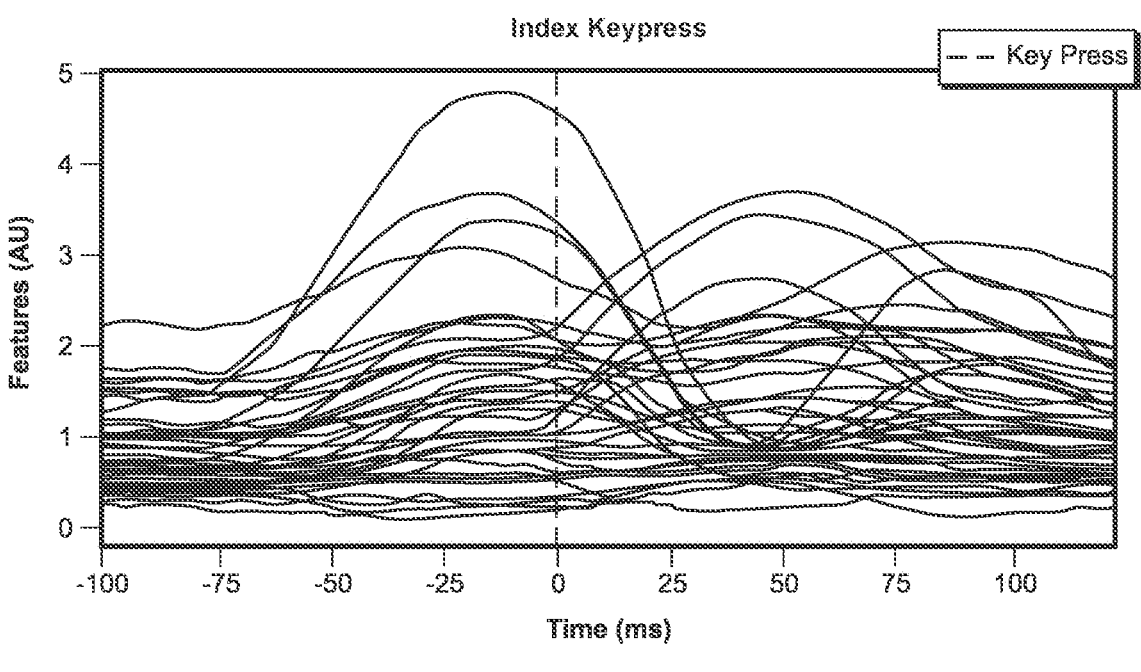
Figure 32I:
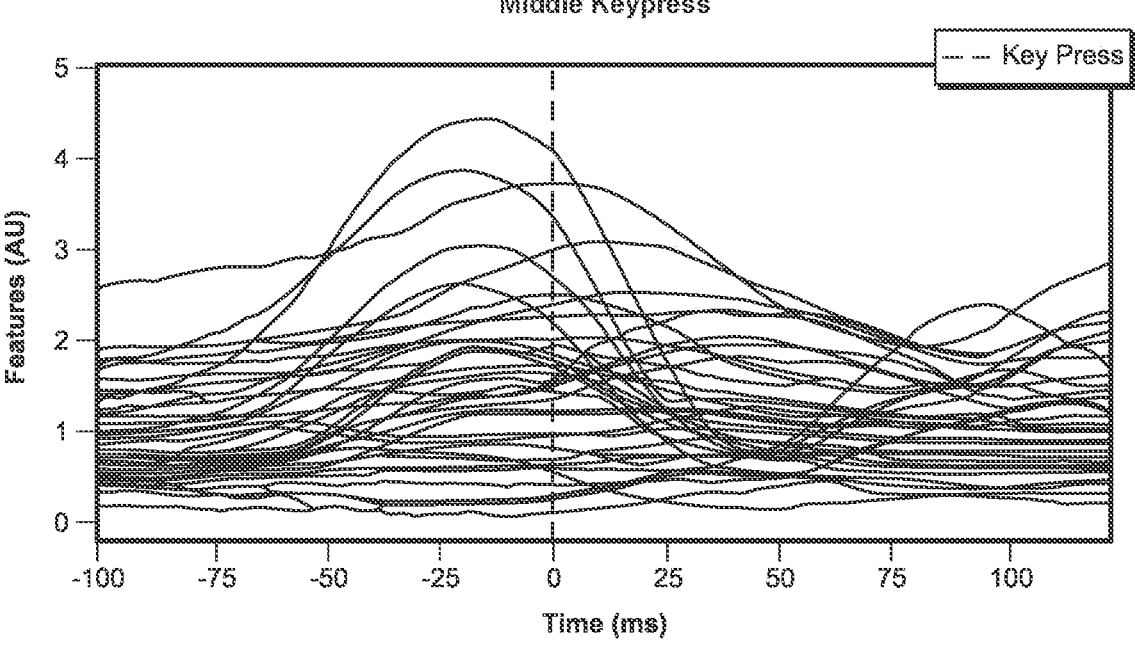
Figure 32J:
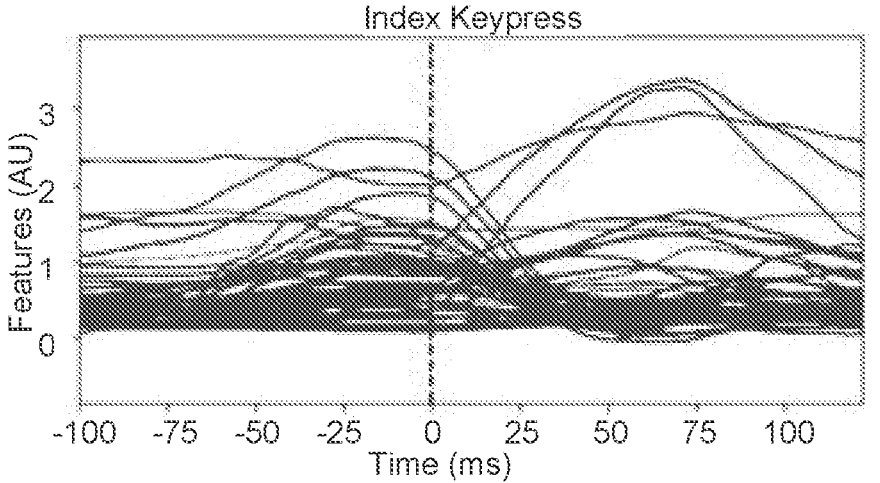
Figure 32K:
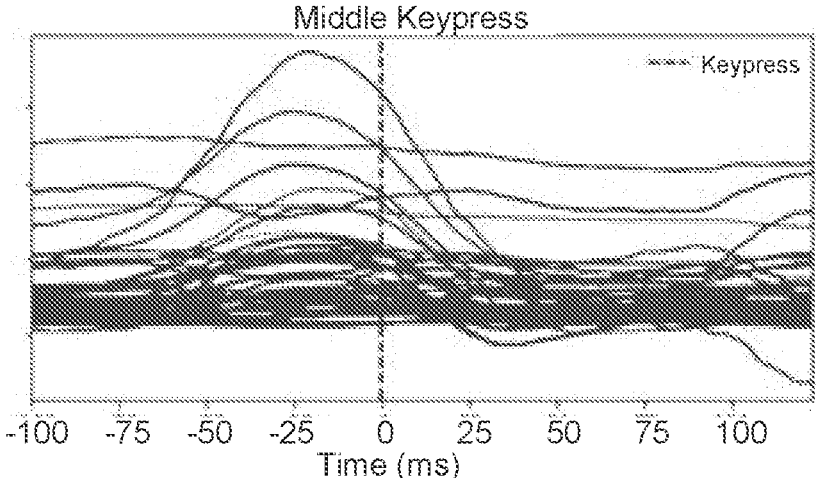
Figures 32L, 32M:
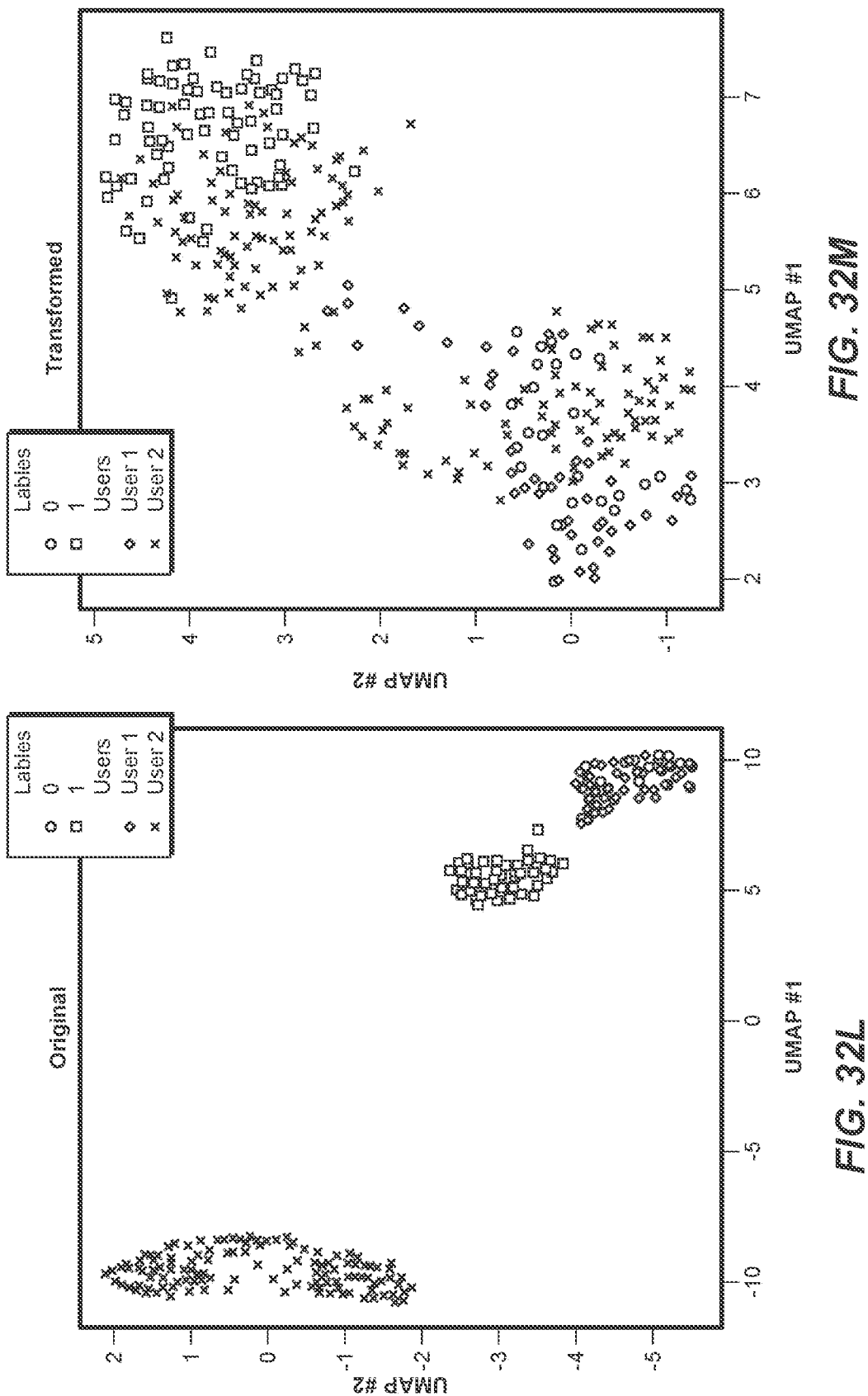
Figure 32N:
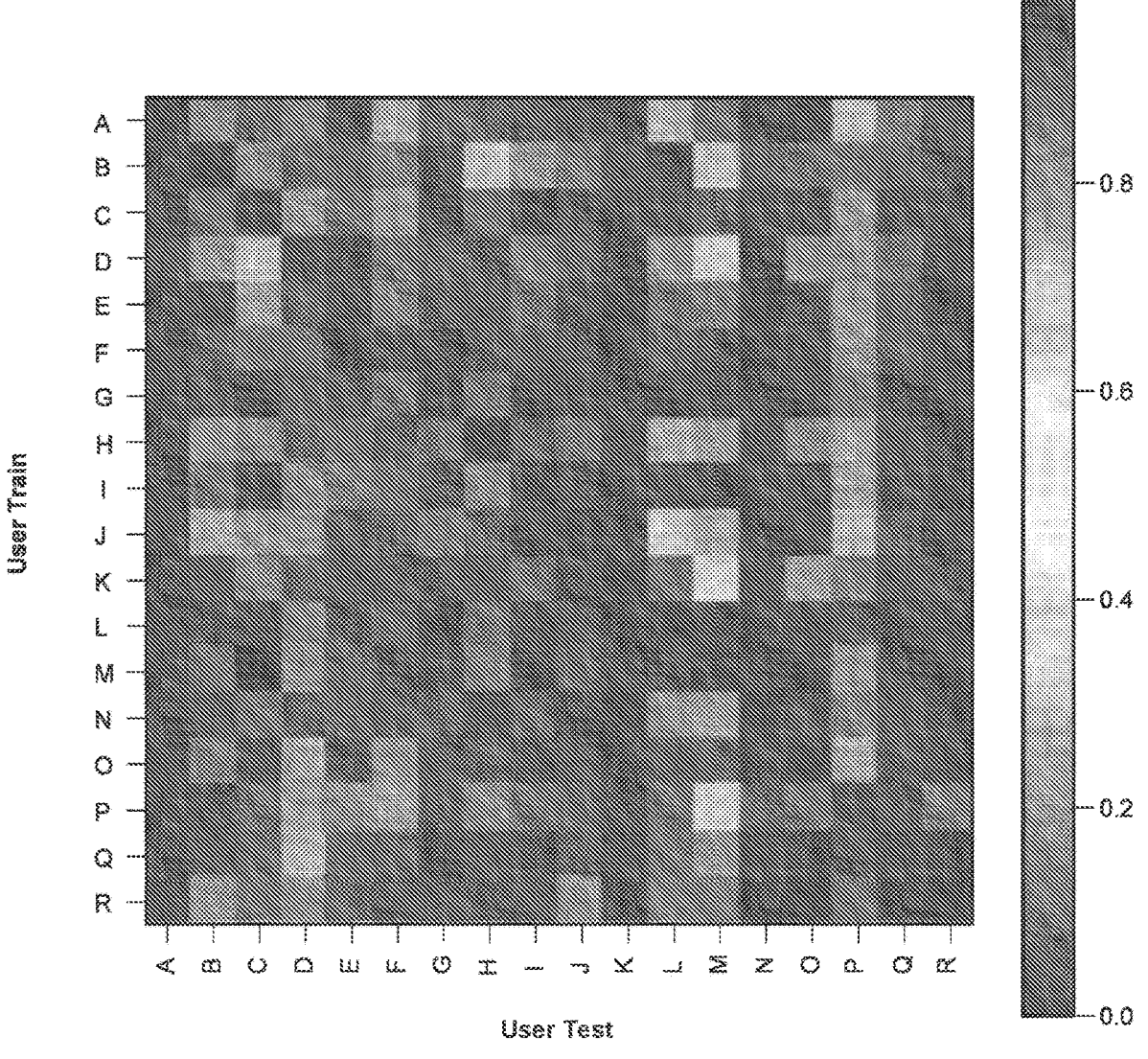
Figure 32O:
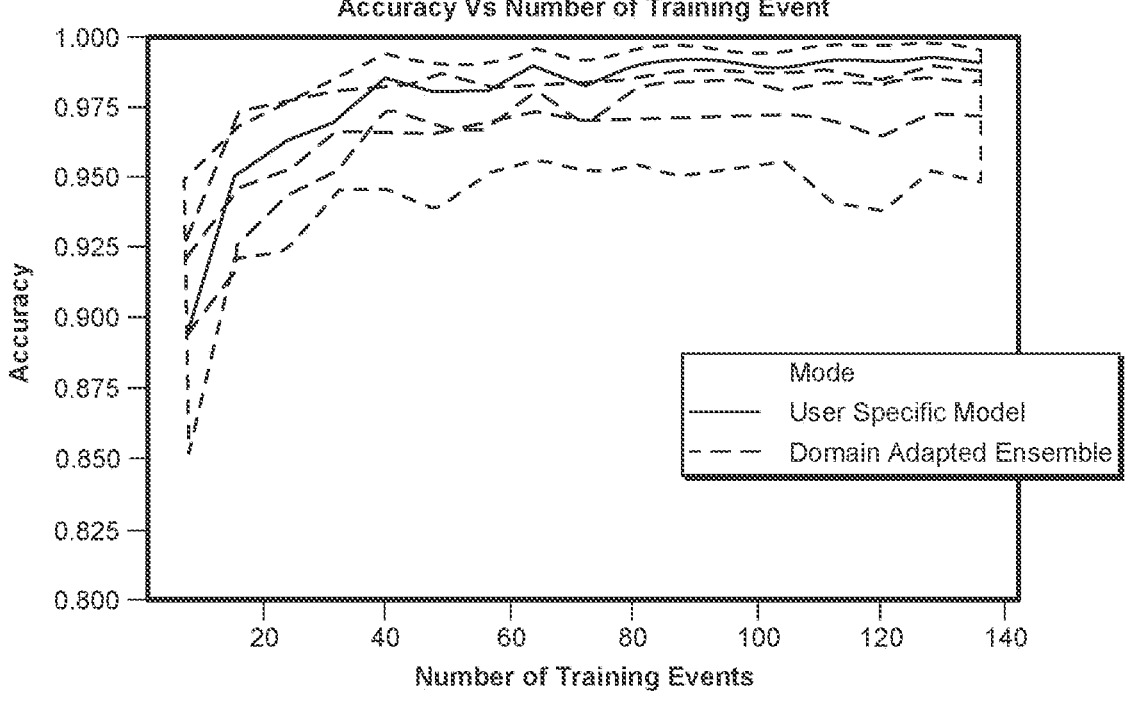
Figure 32P:
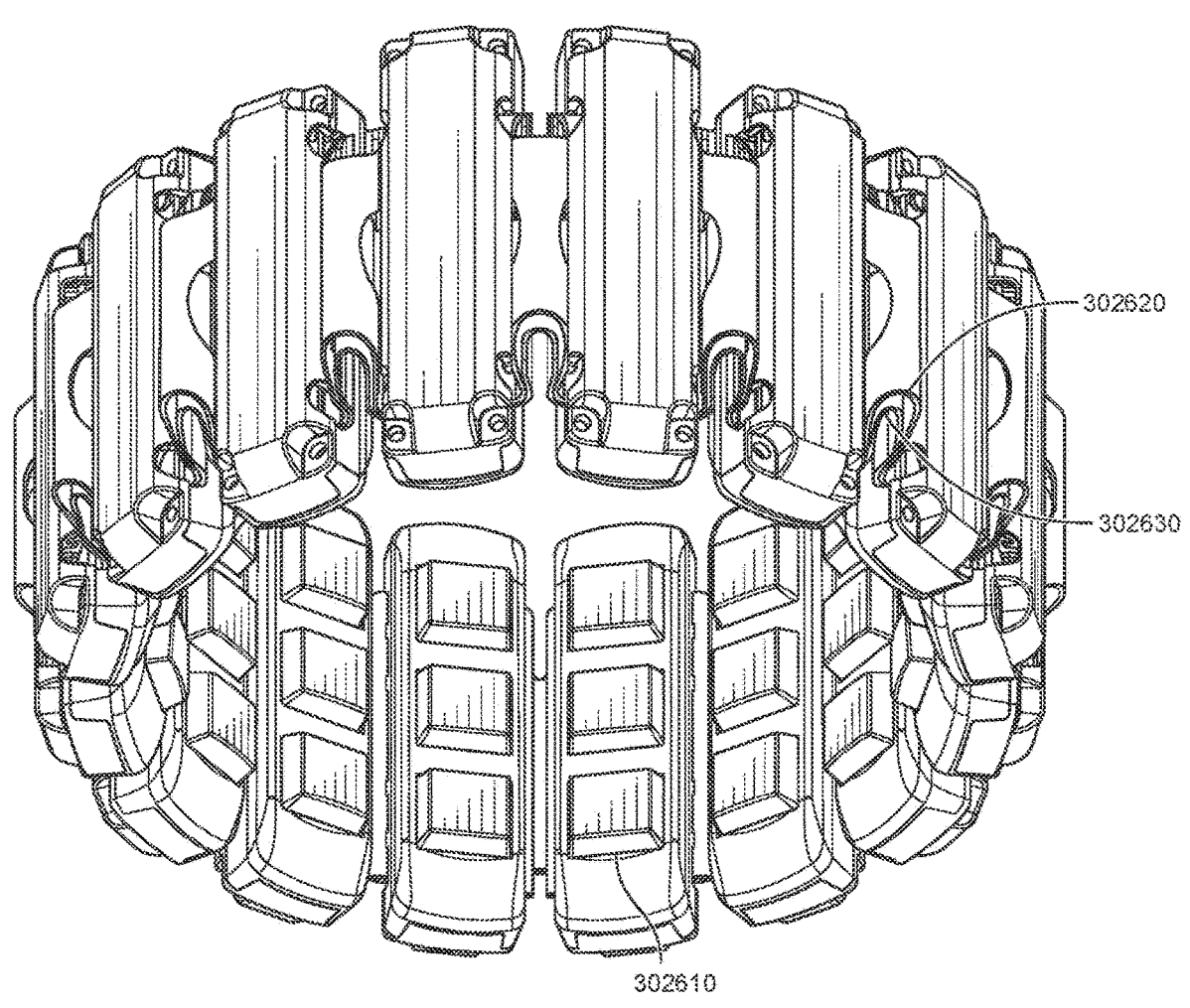
Figure 32Q:
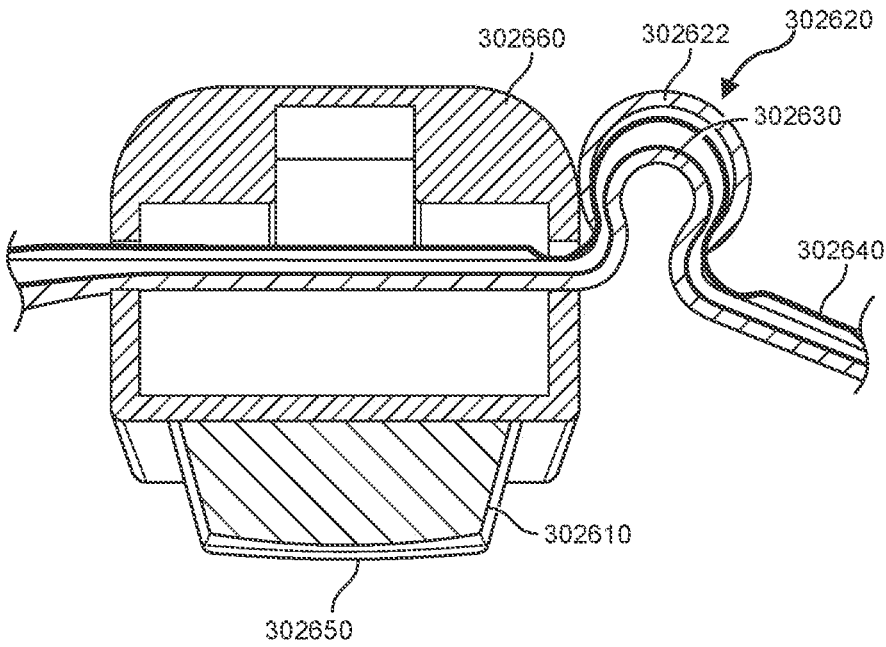
Figure 32R:
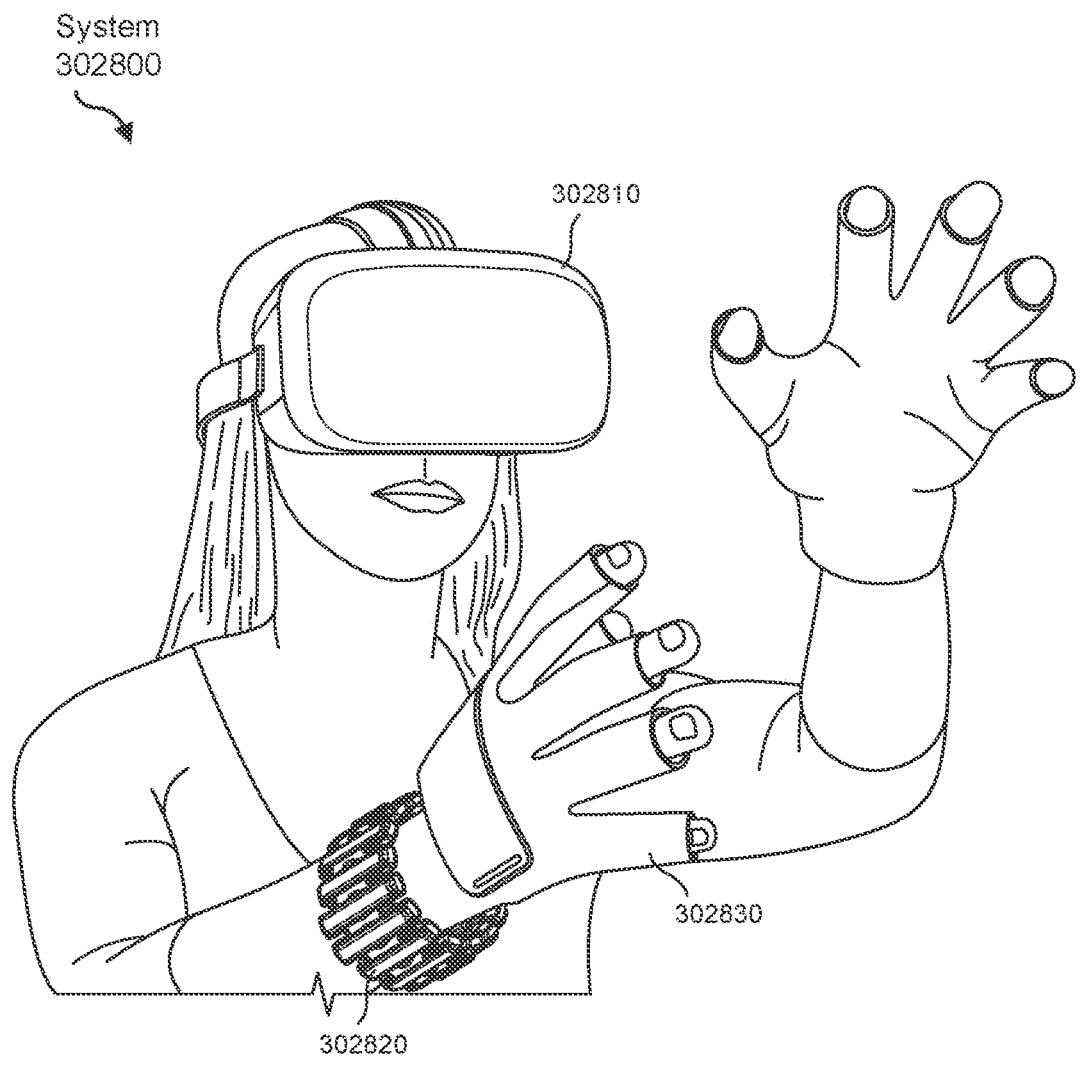

FIG. 32R shows an example implementation wherein a wearable device interfaces with a head-mounted wearable display.

Figure 32S:
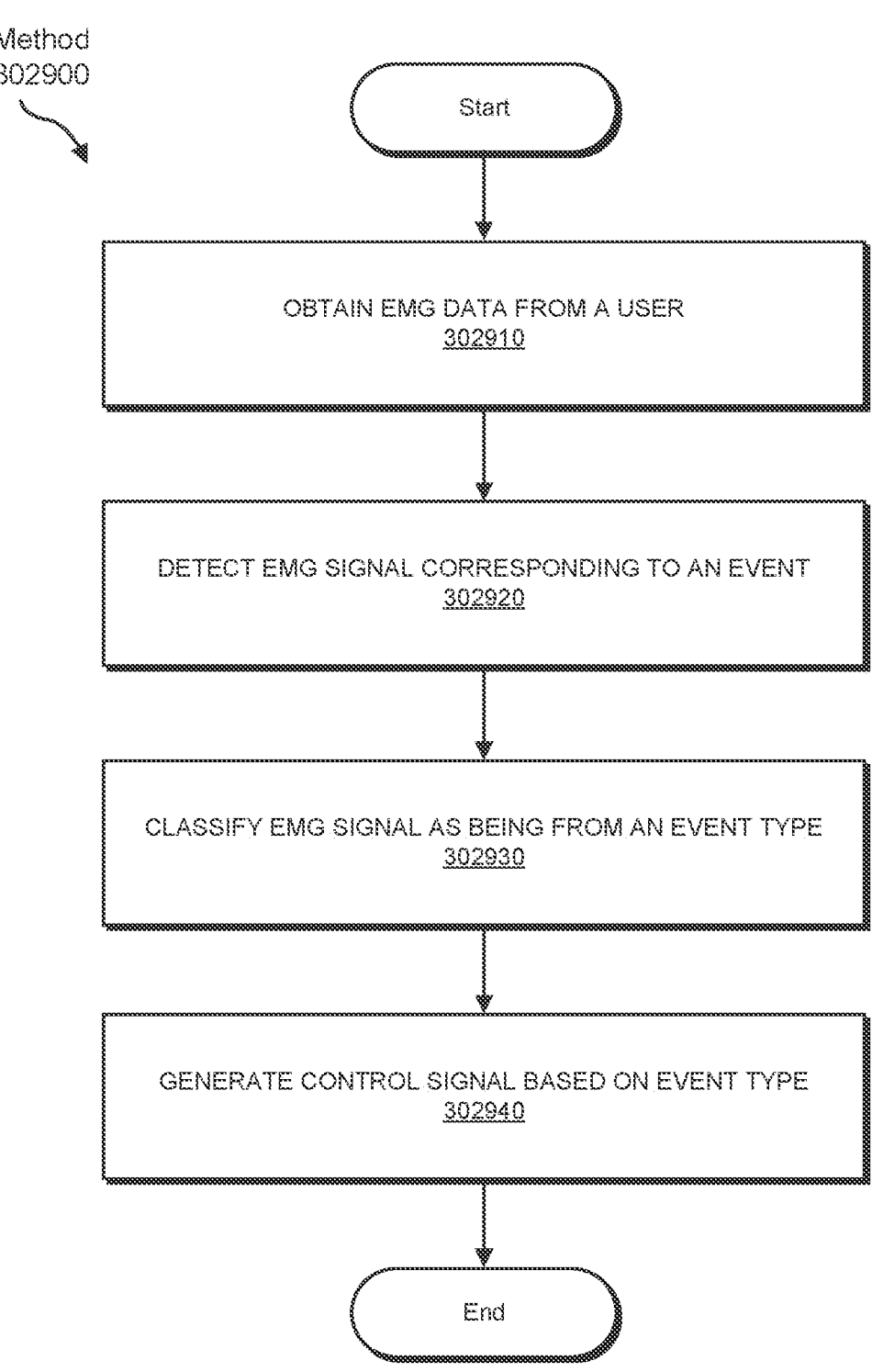
Figure 32T:
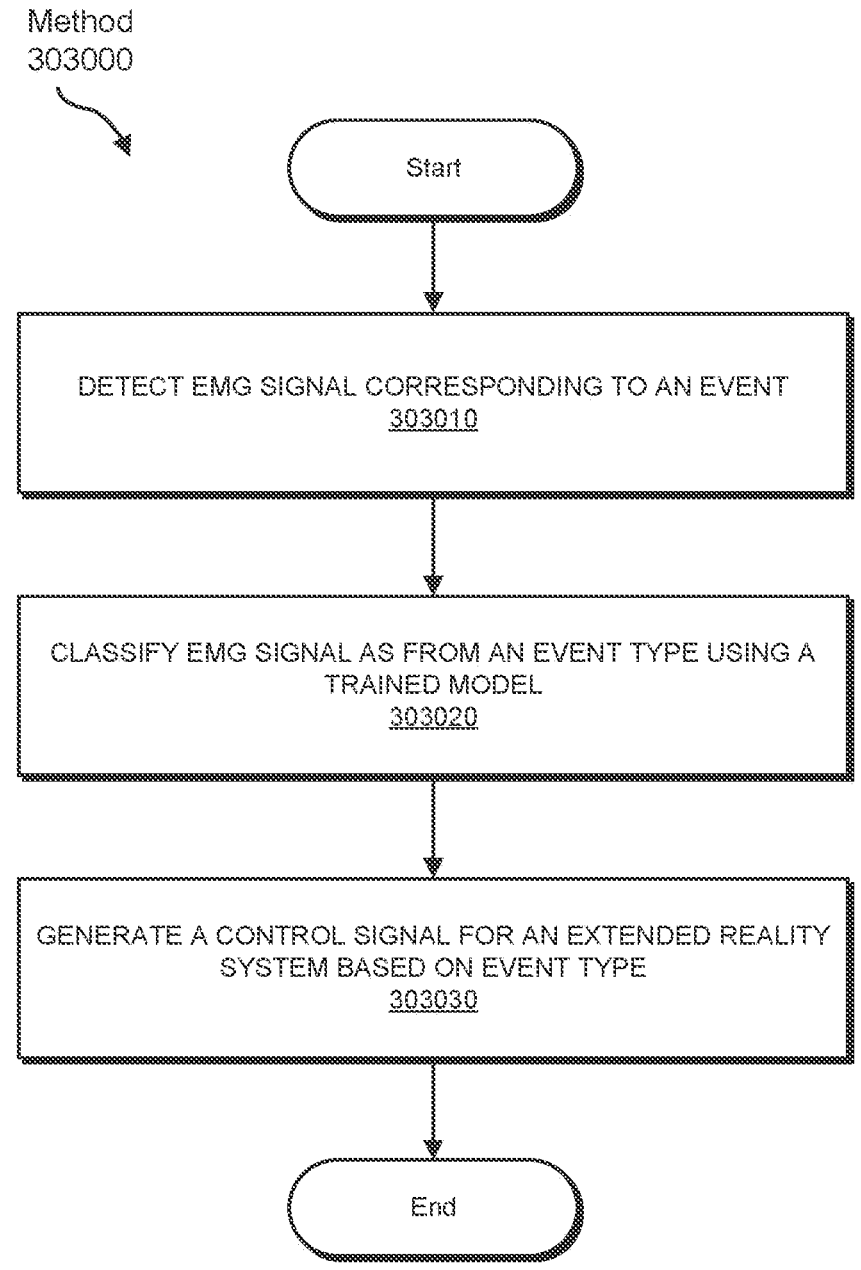

FIG. 32S and FIG. 32T illustrate example methods.

Figure 33A:
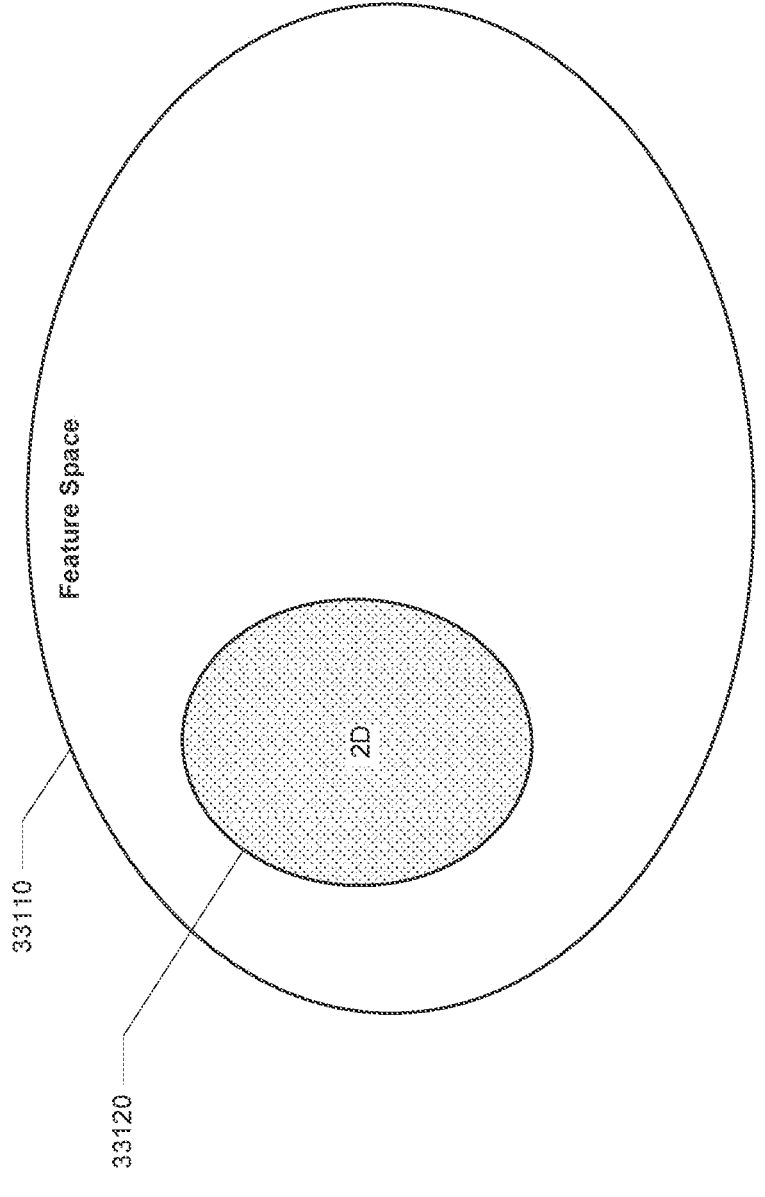

FIG. 33A is an illustration of an example feature space for neuromuscular data.

Figure 33B:
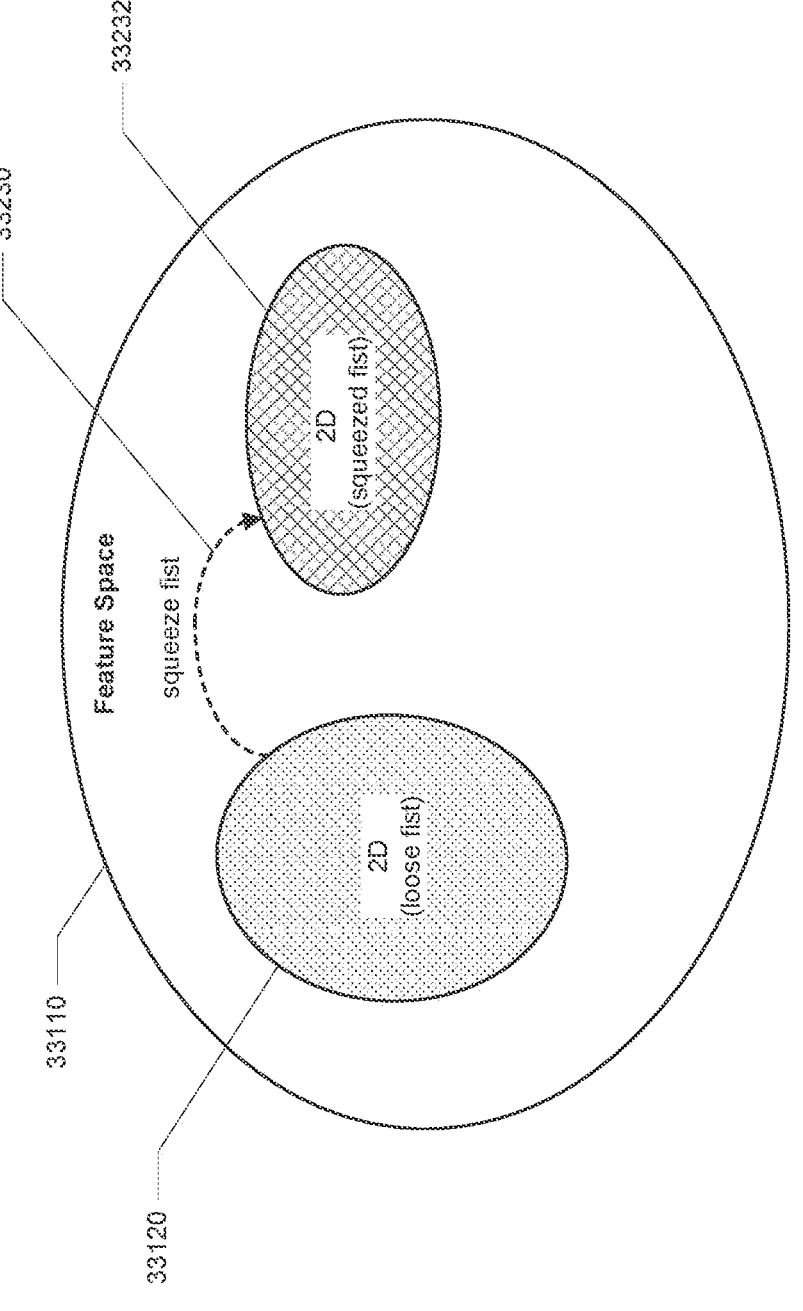

FIG. 33B is an illustration of the example feature space of FIG. 33A and a transition within the feature space.

FIG. 33C is an illustration of an example graphical user interface for online training of an inference model for 2D movement via wrist rotation.

FIG. 33D is an illustration of a plot comparing distributions of data points for training different inference models.

Figure 33E:
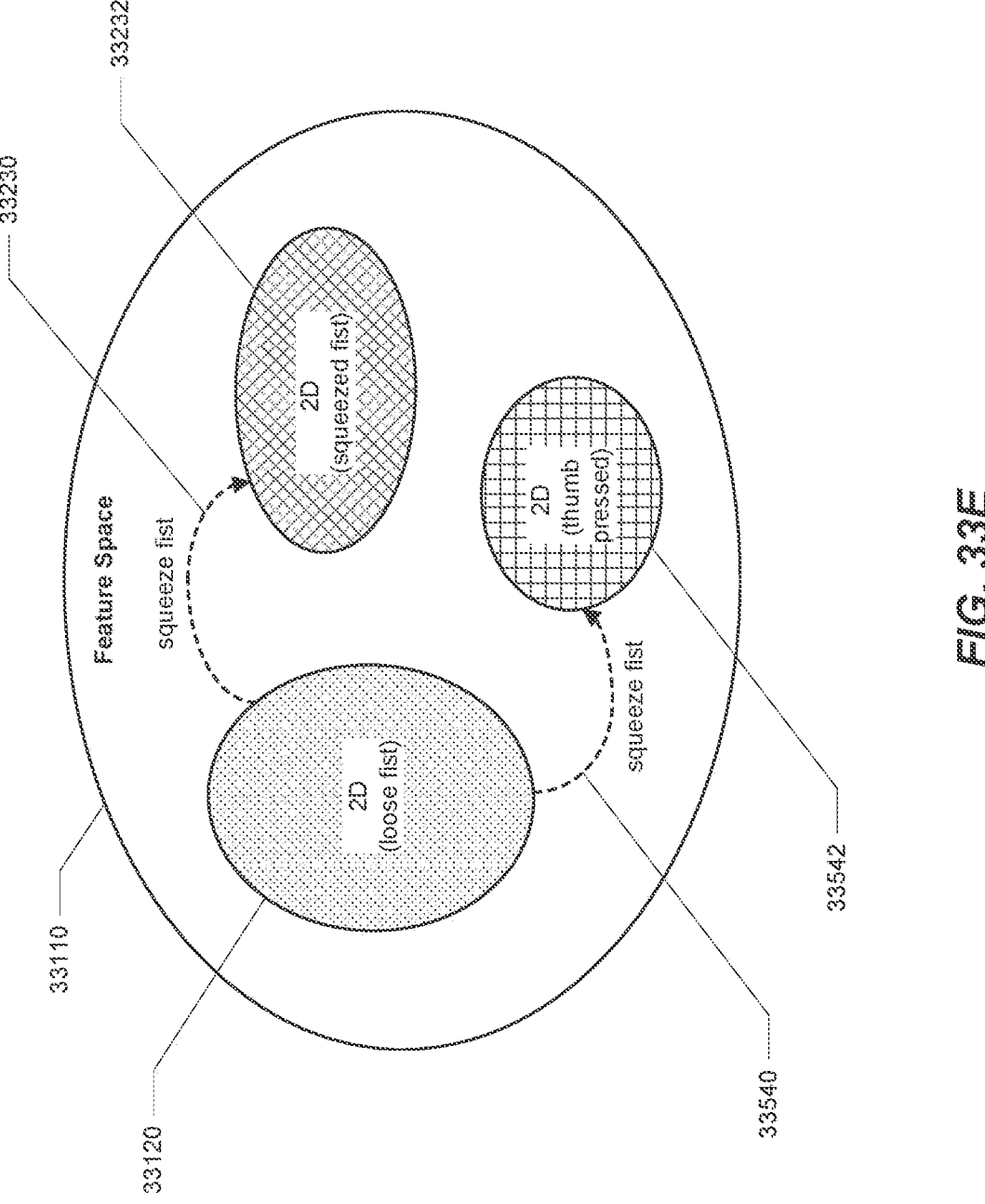

FIG. 33E is an illustration of the example feature space of FIG. 33A and another transition within the feature space.

Figure 33F:
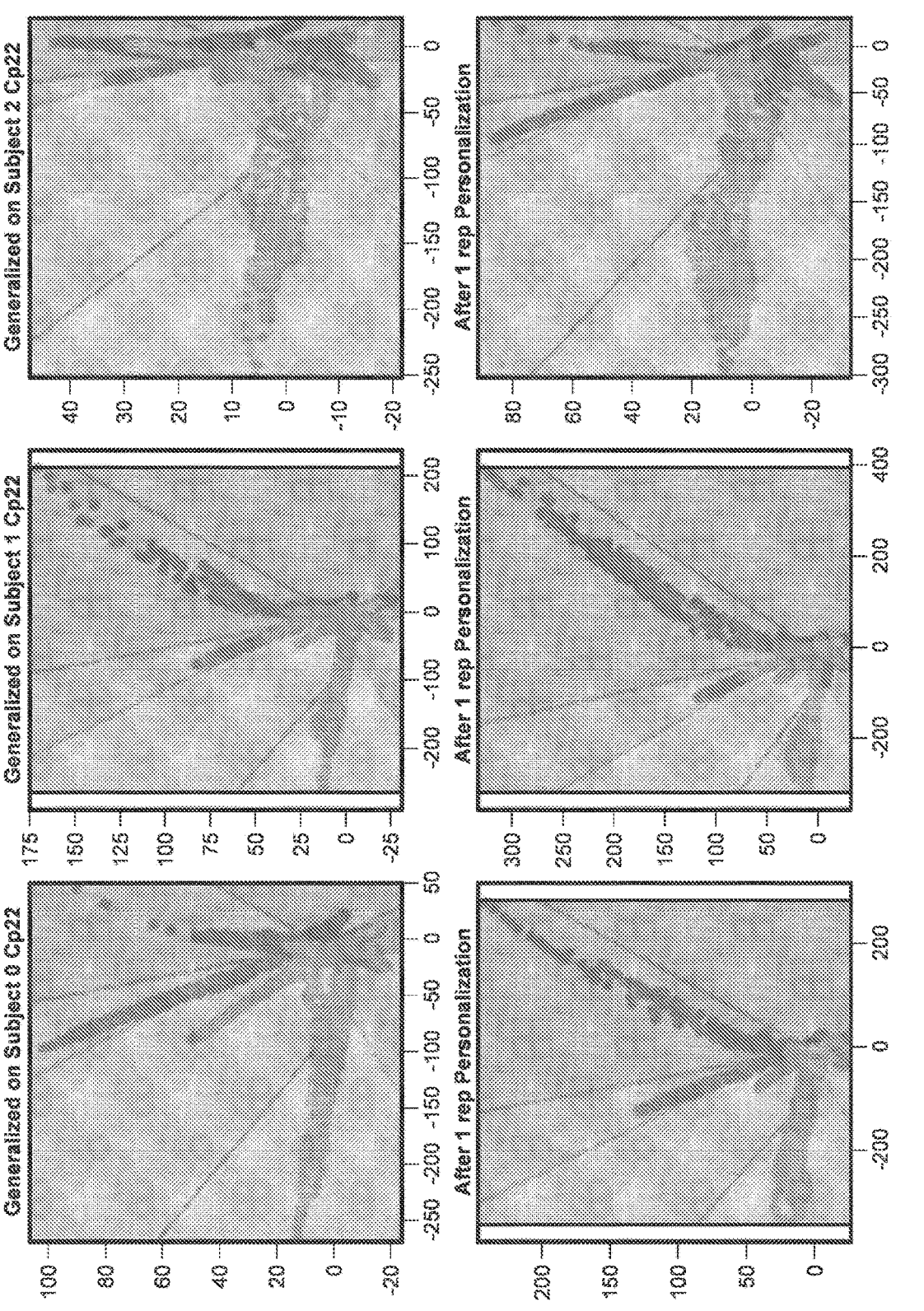

FIG. 33F is an illustration of example plots of processed neuromuscular data that represent 2D visualizations of latent vectors representing user hand poses.

Figure 33G:
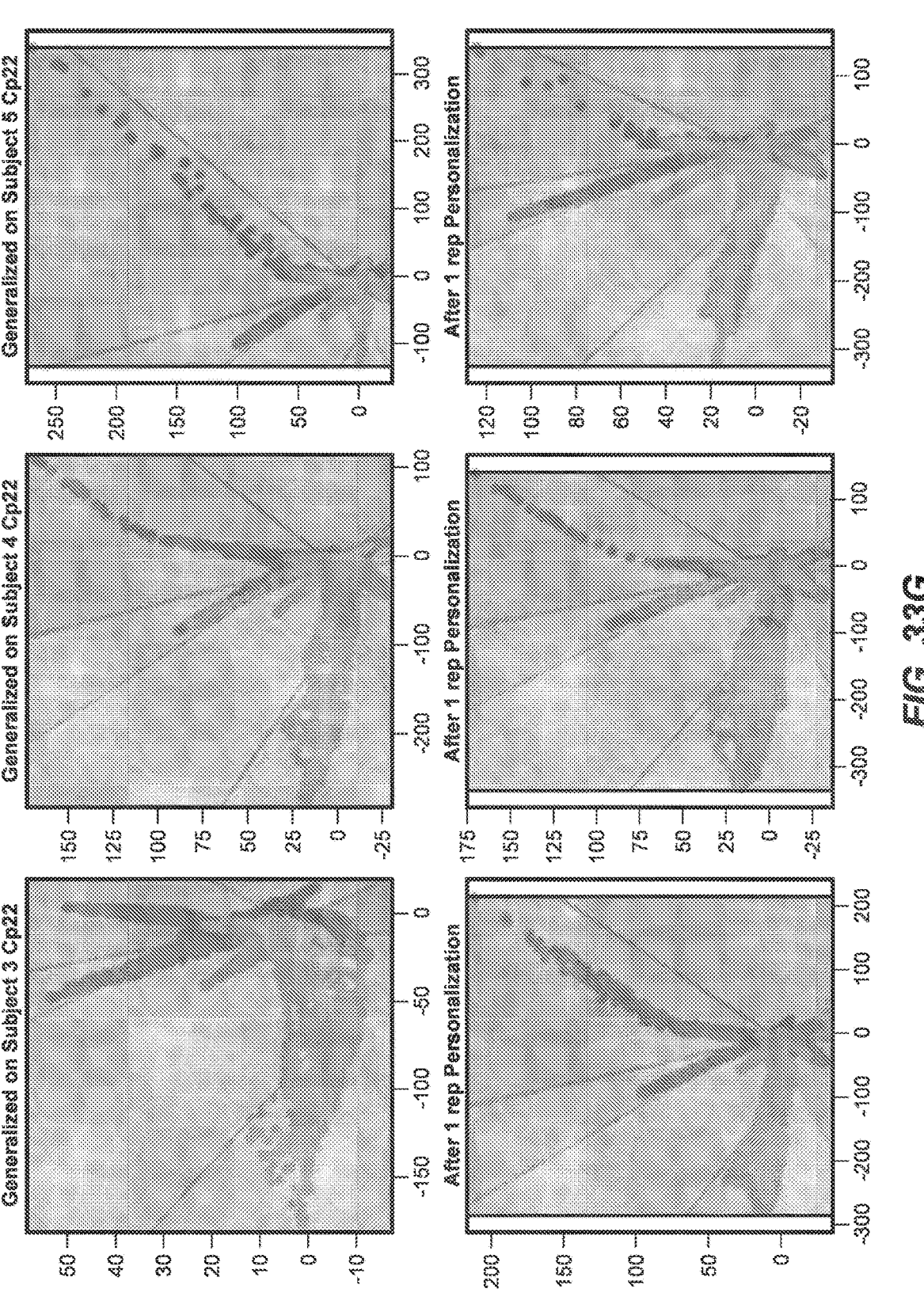

FIG. 33G is an additional illustration of example plots of processed neuromuscular data that represent 2D visualizations of latent vectors representing user hand poses.

Figure 33H:
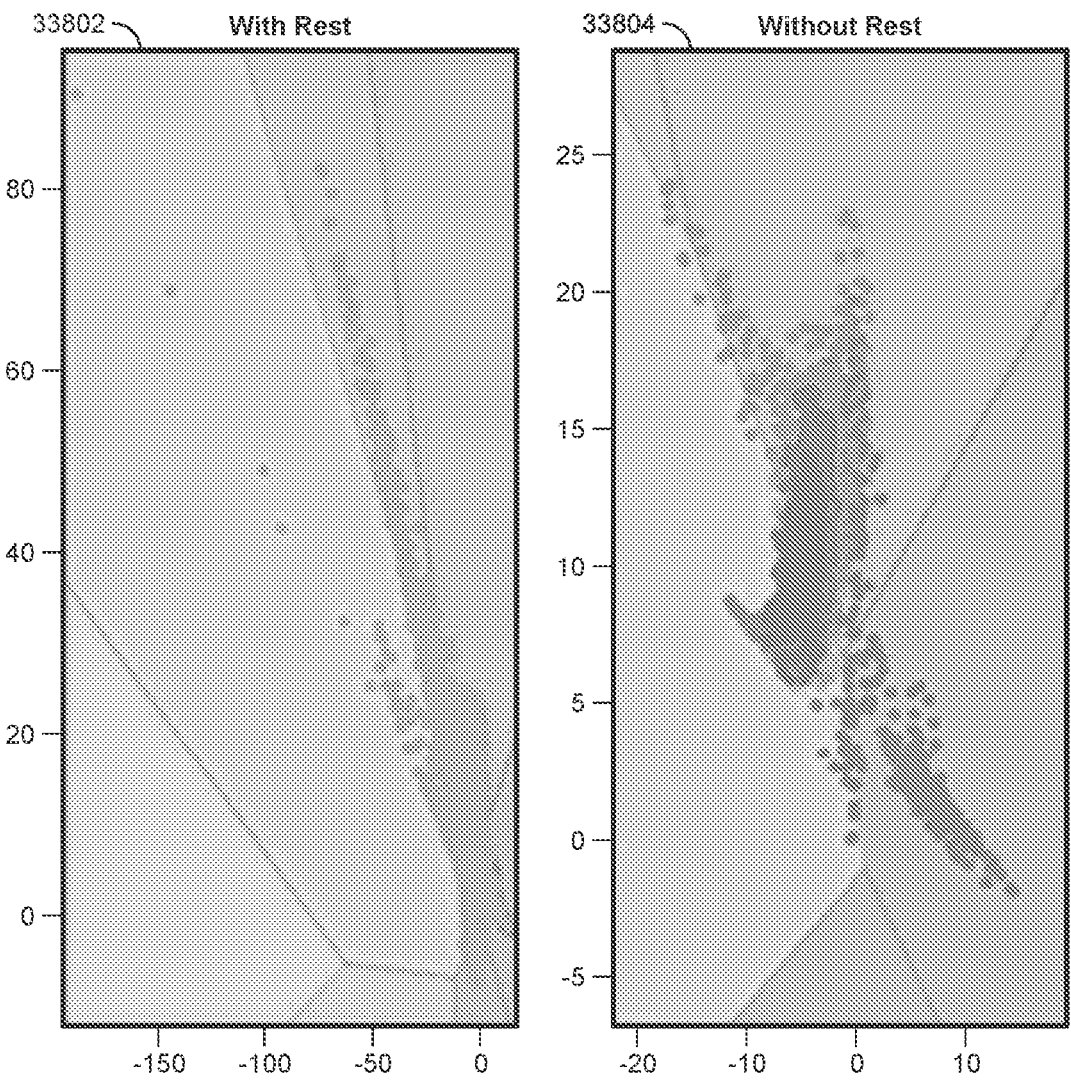

FIG. 33H is an additional illustration of example plots of processed neuromuscular data that represent 2D visualizations of latent vectors representing user hand poses.

Figure 33I:
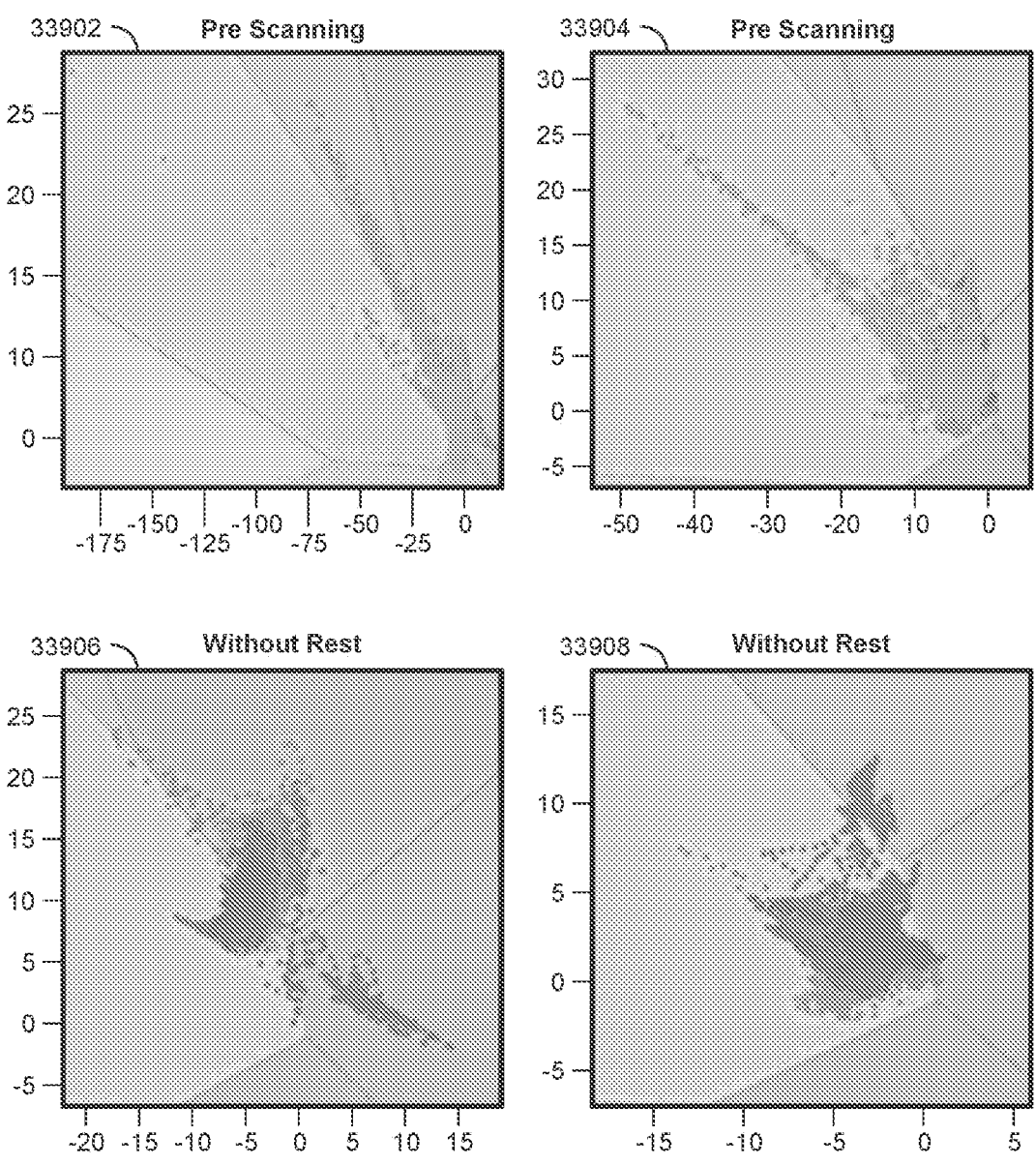

FIG. 33I is an additional illustration of example plots of processed neuromuscular data that represent 2D visualizations of latent vectors representing user hand poses.

Figure 33J:
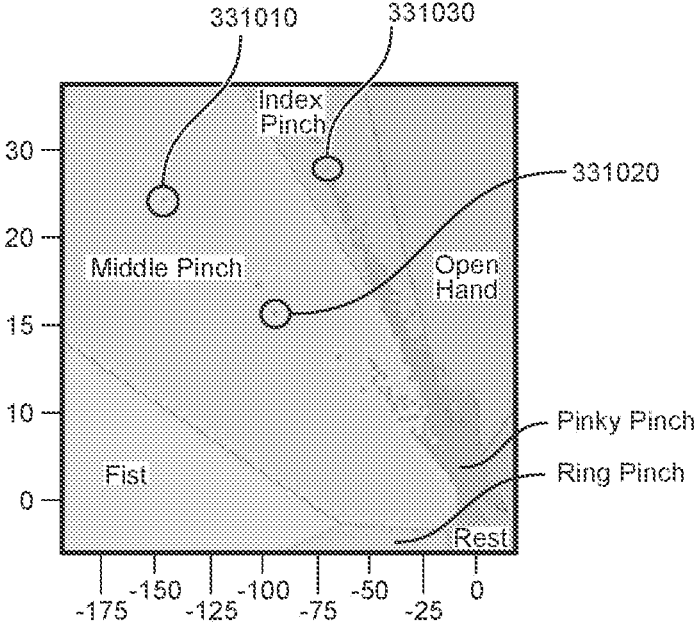

FIG. 33J is an illustration of an example interface for visualizing processed neuromuscular data with 2D visualizations of latent vectors representing user hand poses.

Figure 33K:
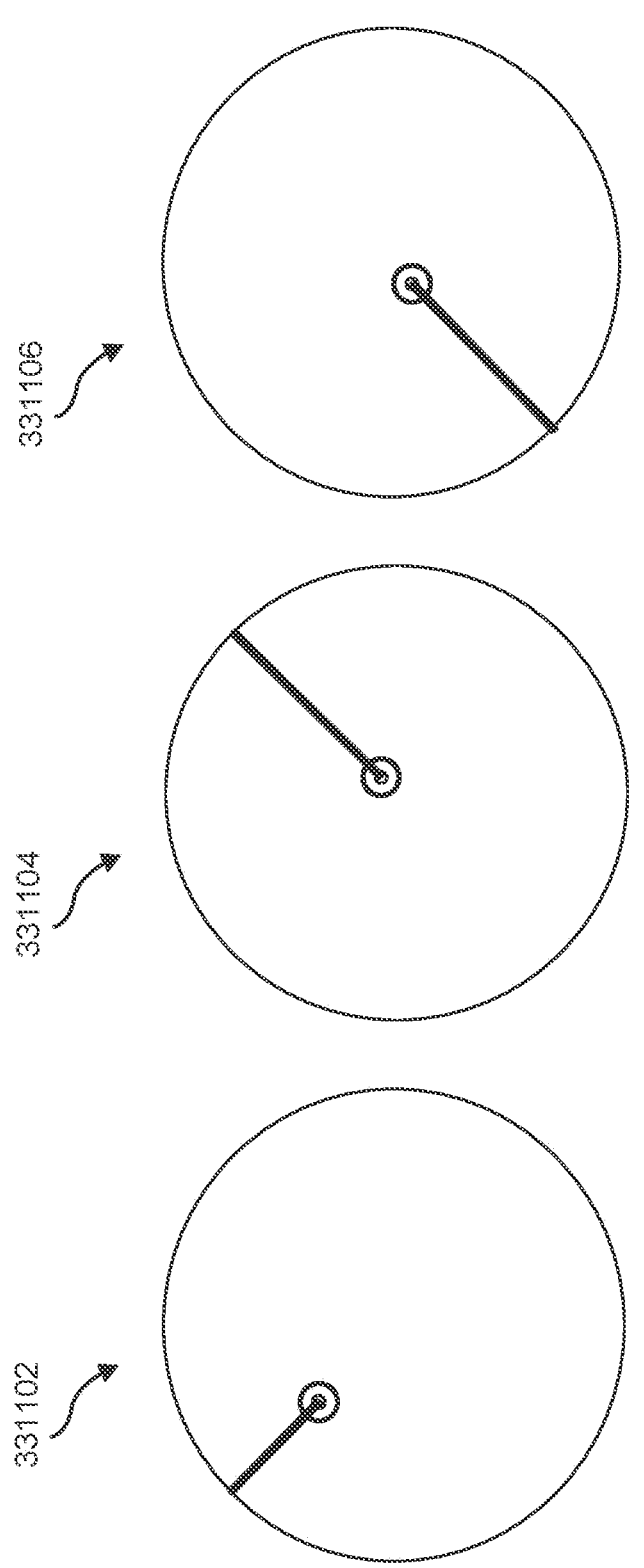

FIG. 33K is an illustration of an example training task for an inferential model.

Figures 33L, 33M, 33N:
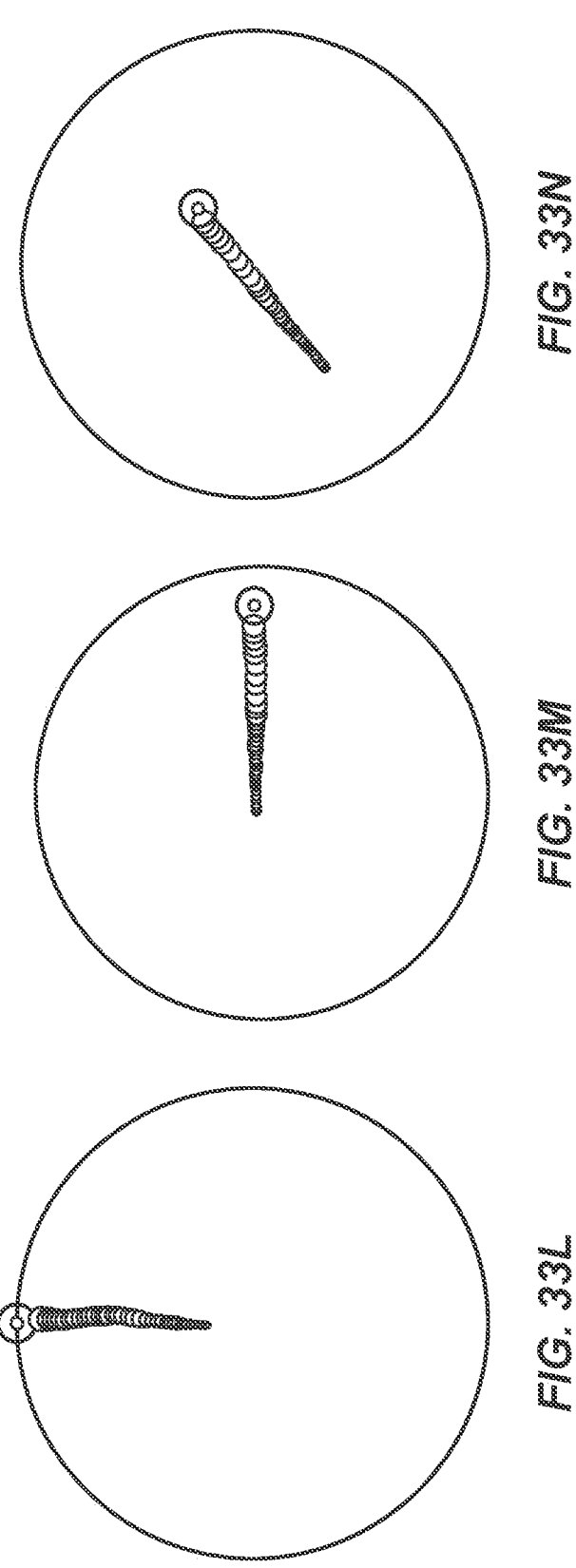

FIGS. 33L-N are illustrations of an example interface for cursor control based on the application of inferential models to neuromuscular data.

Figure 33O:
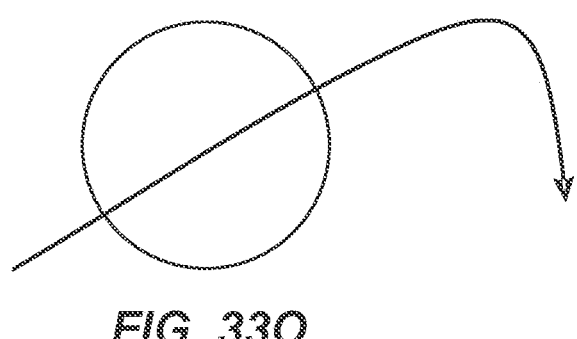
Figure 33P:
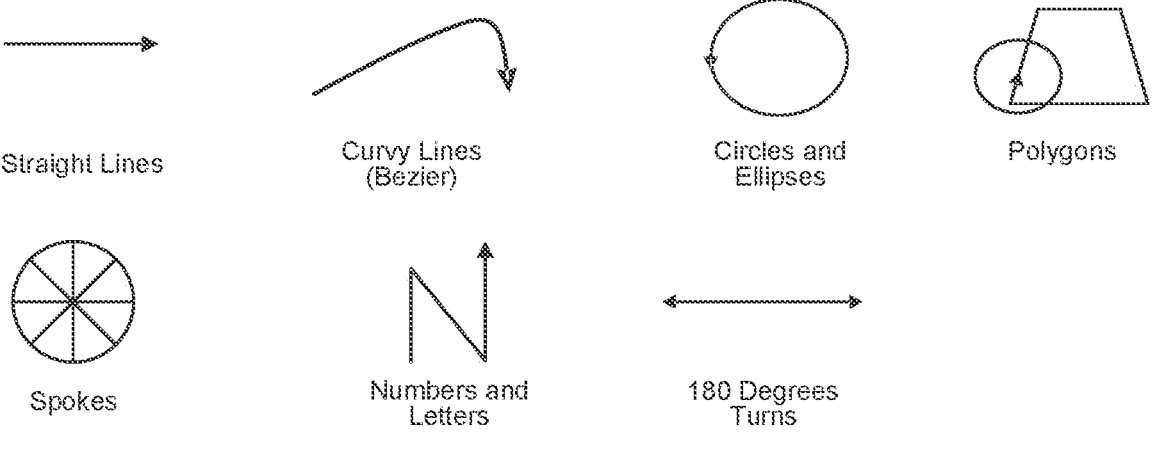

FIGS. 33O-P are illustrations of representations of path efficiency metrics.

FIGS. 33Q-R are illustrations of representations of stability metrics.

FIGS. 33S-T are illustrations of representations of reachability metrics.

Figure 33U:
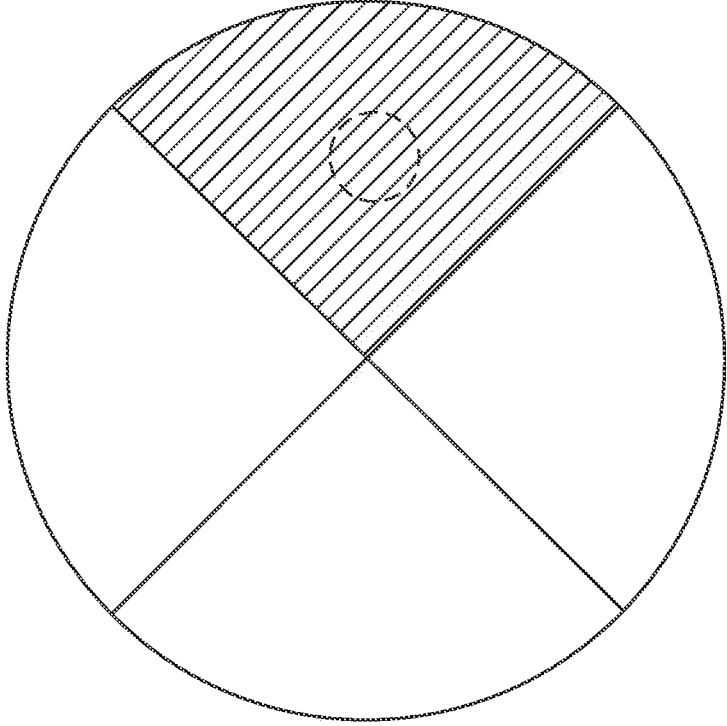

FIG. 33U is an illustration of a representation of combinatorics metrics.

FIG. 33V is an illustration of example cursor indicators.

Figure 34A:
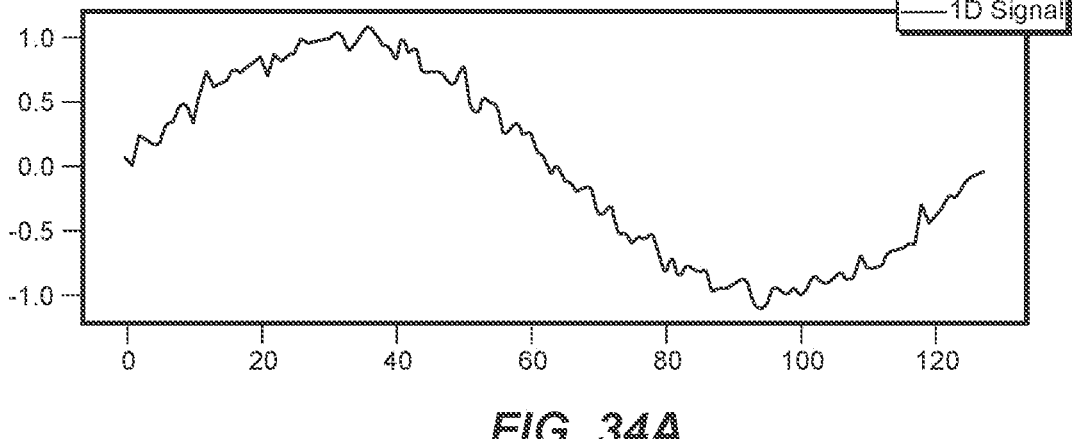
Figure 34B:
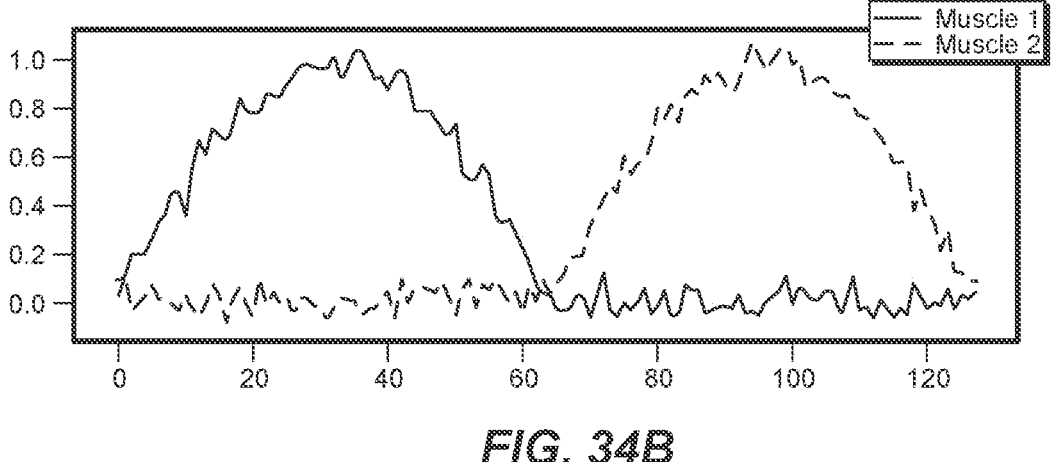

FIGS. 34A-B are illustrations of example plots of continuous 1D output of the neuromuscular data produced by sensing a pair of muscles.

Figure 34C:
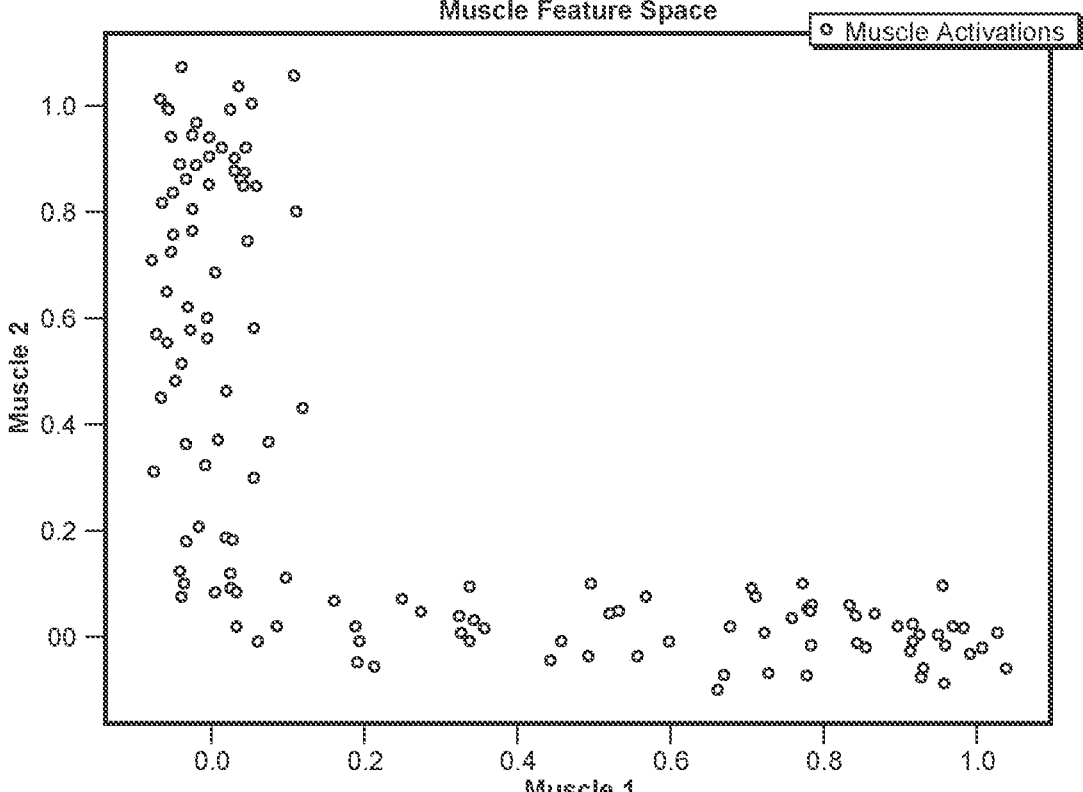

FIG. 34C is an illustration of a 1D neuromuscular signal mapped to a feature space.

Figure 34D:
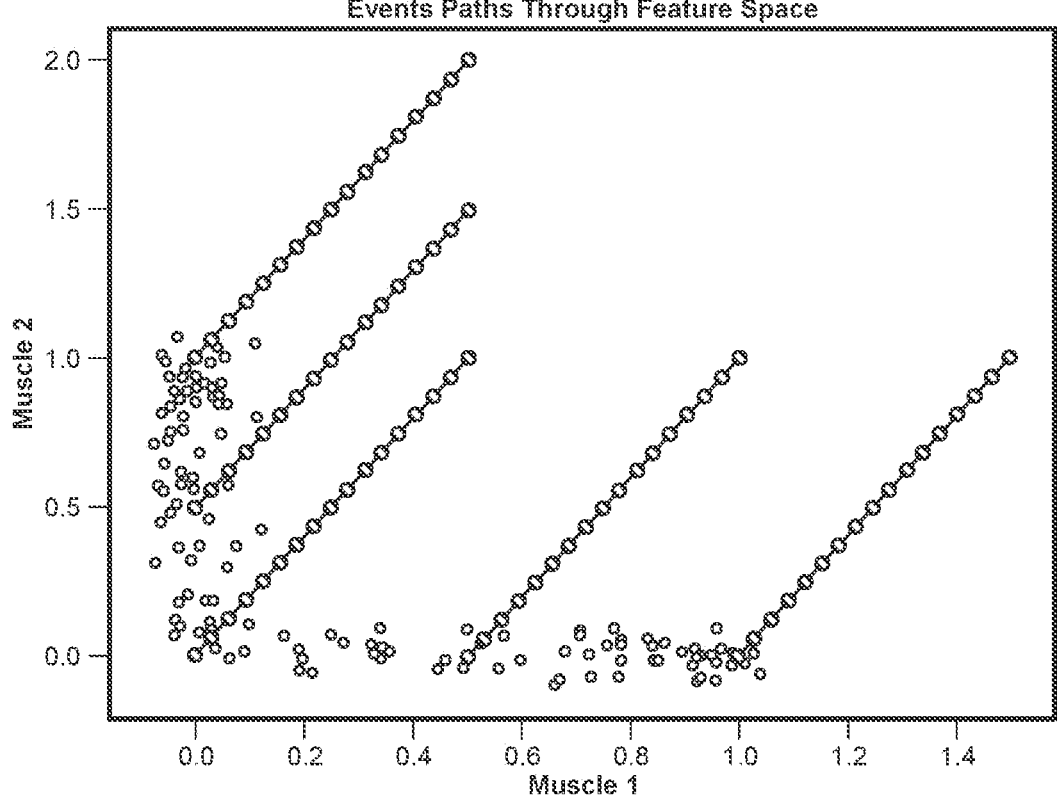

FIG. 34D is an illustration of example event paths through the feature space illustrated in FIG. 34C.

Figure 34E:
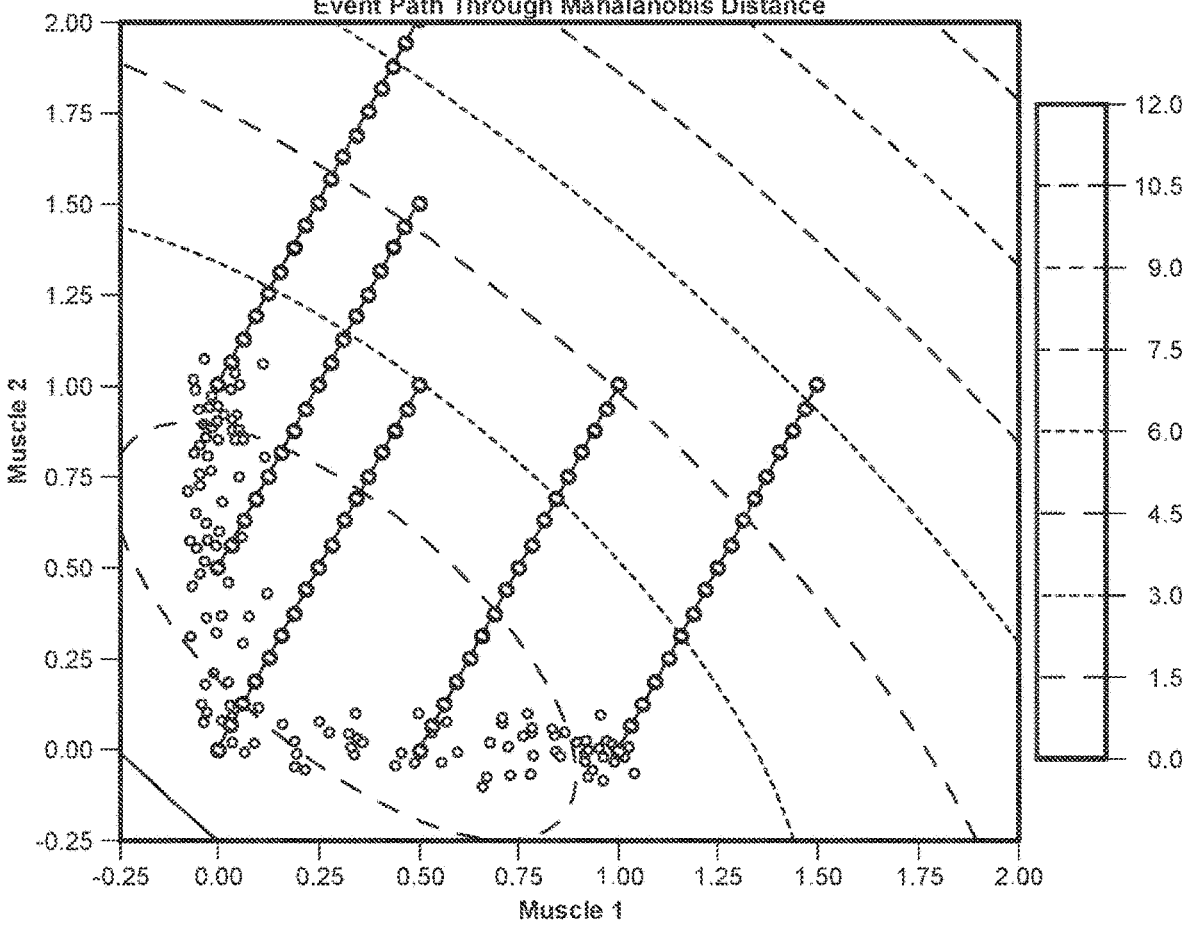

FIG. 34E is an illustration of the event paths of FIG. 34D in the context of a Mahalanobis distance metric.

Figure 34F:
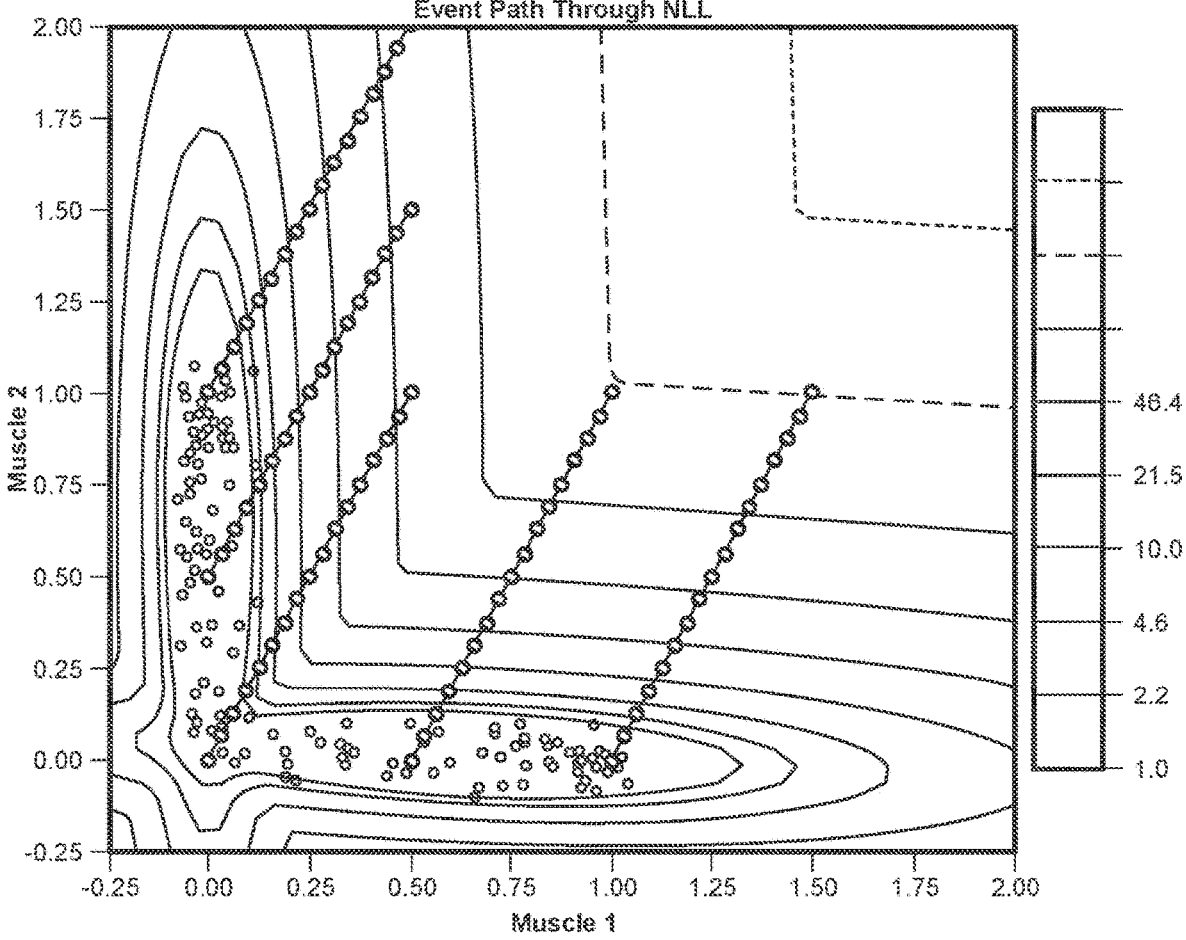

FIG. 34F is an illustration of the event paths of FIG. 34D in the context of a negative-log-likelihood based distance metric.

Figure 34G:
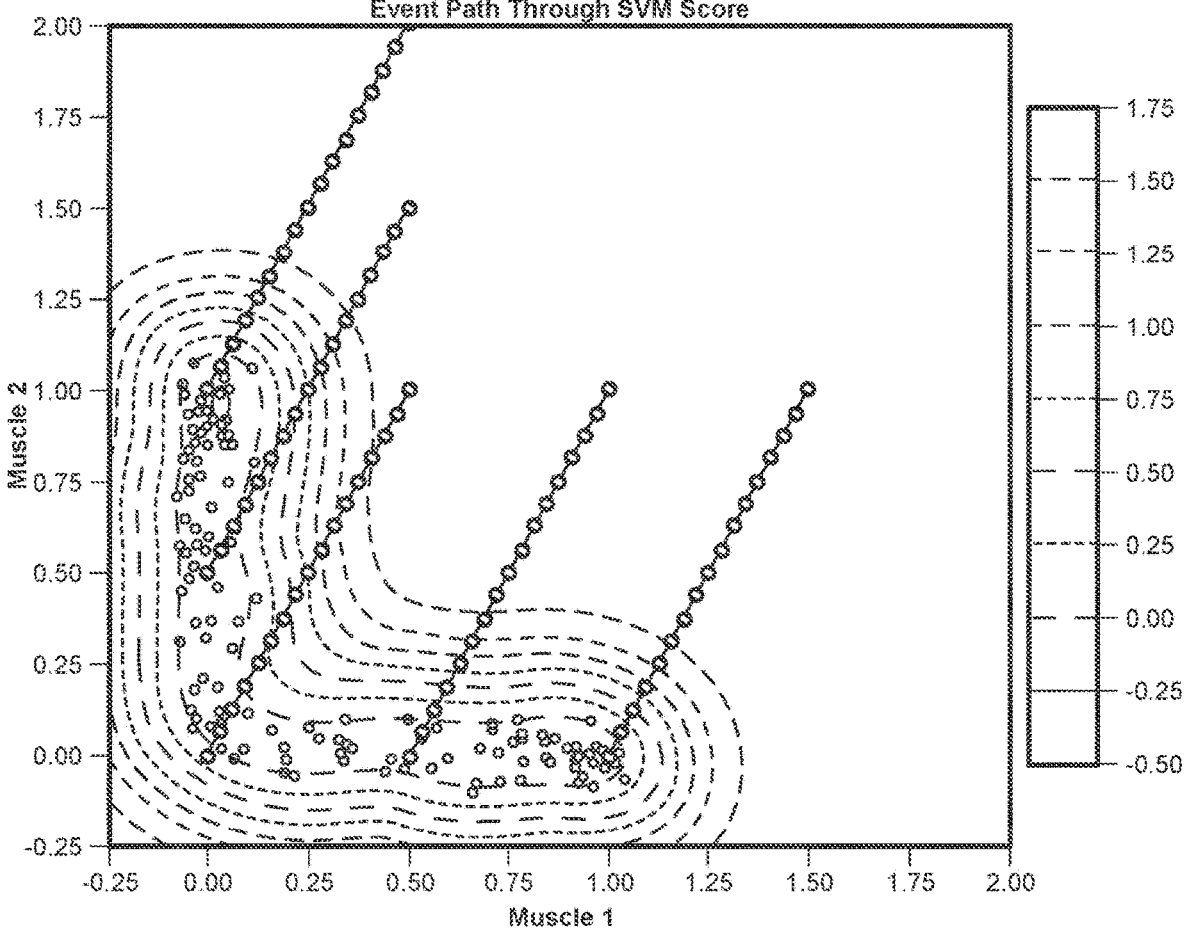

FIG. 34G is an illustration of the event paths of FIG. 34D in the context of a support vector machine score distance metric.

Figure 34H:
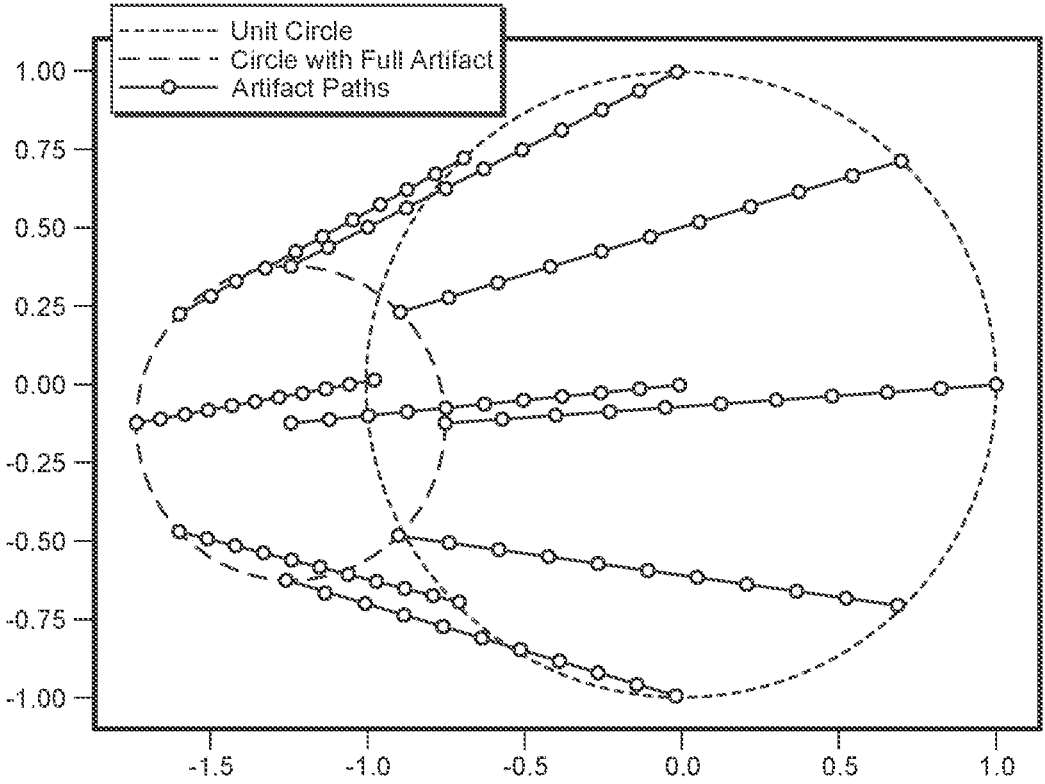

FIG. 34H is an illustration of an example plot of a 2D feature space.

Figure 34I:
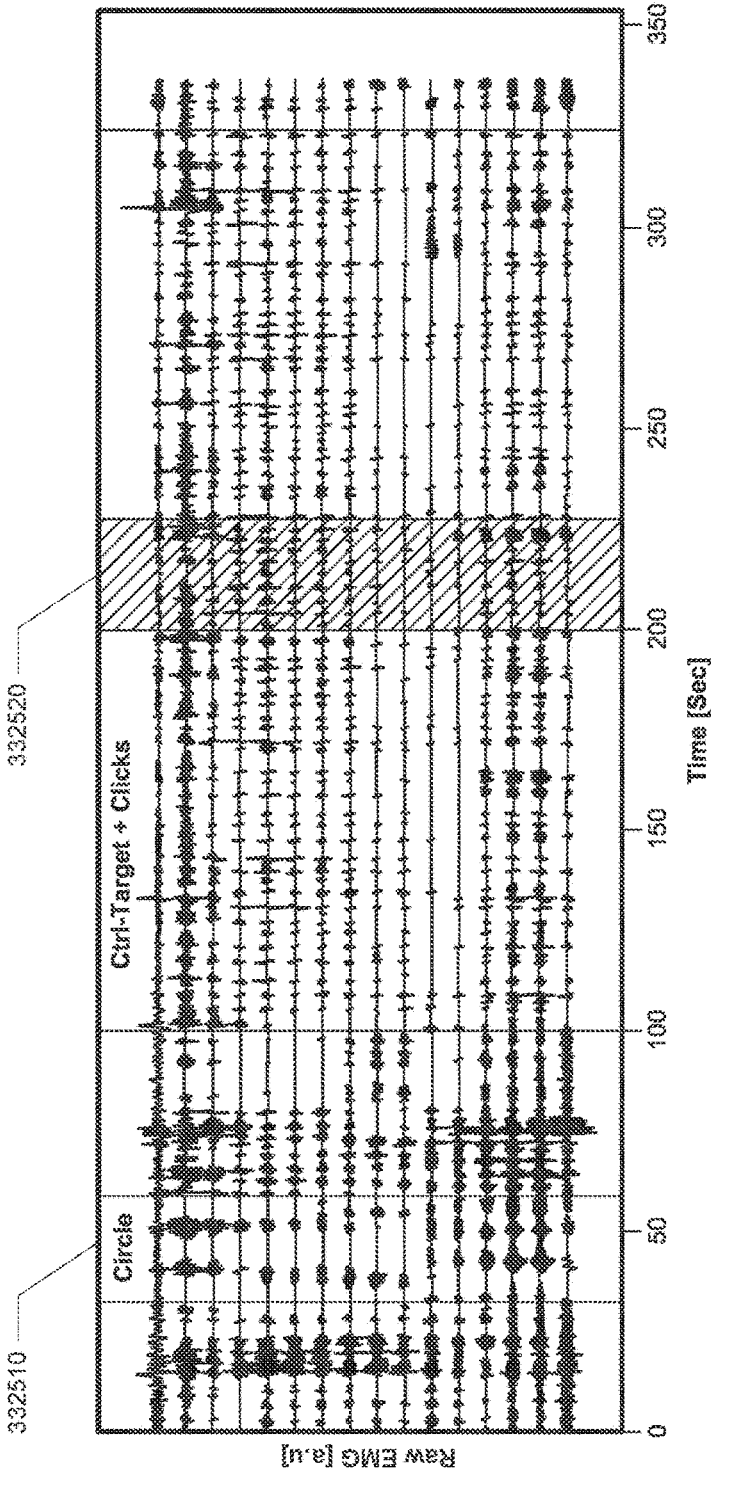

FIG. 34I is an illustration of a plot of neuromuscular data over time as a user performs various gestures.

Figure 34J:
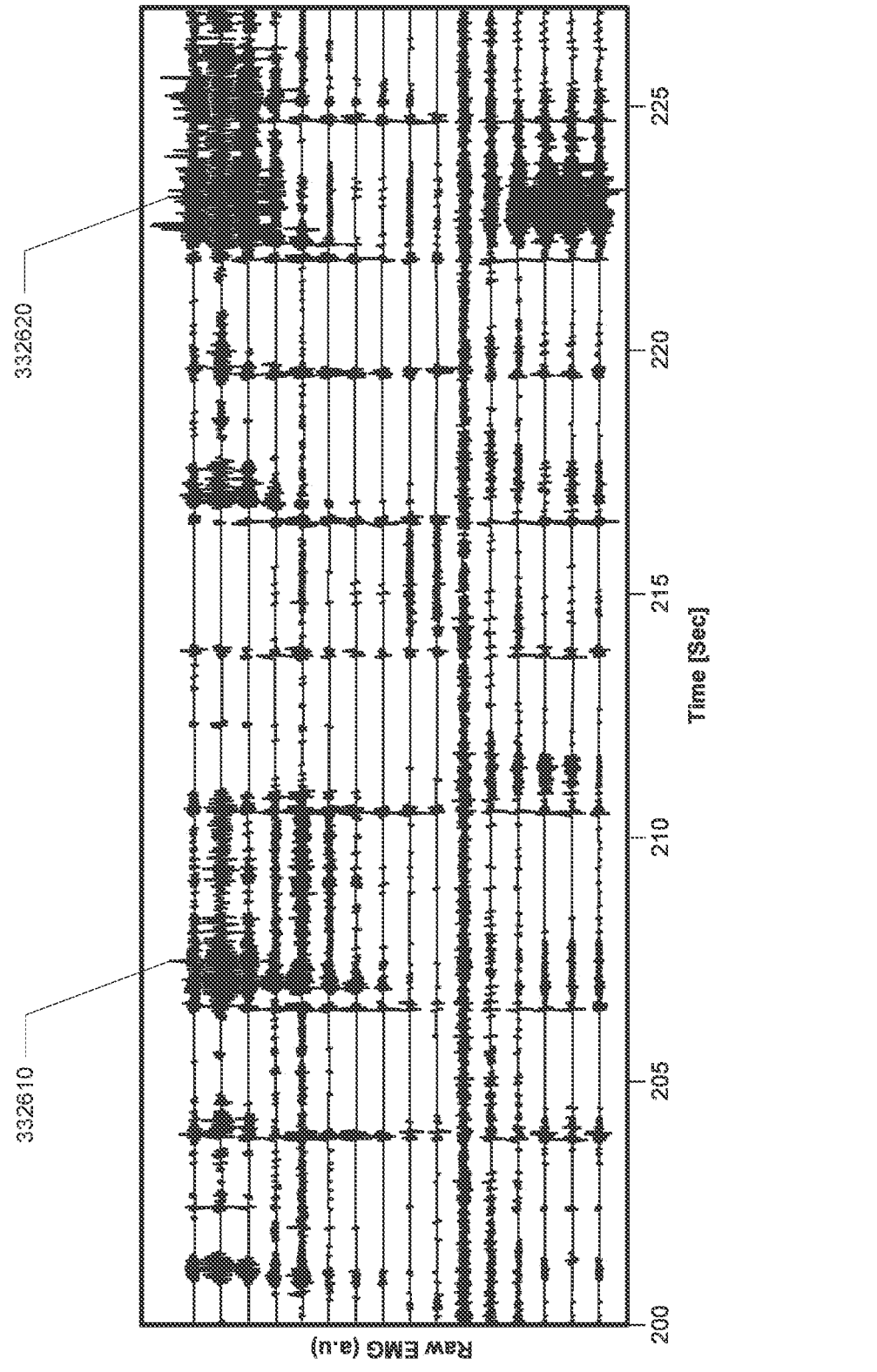

FIG. 34J is an illustration of a zoomed-in portion of the plot of FIG. 34I.

Figure 34K:
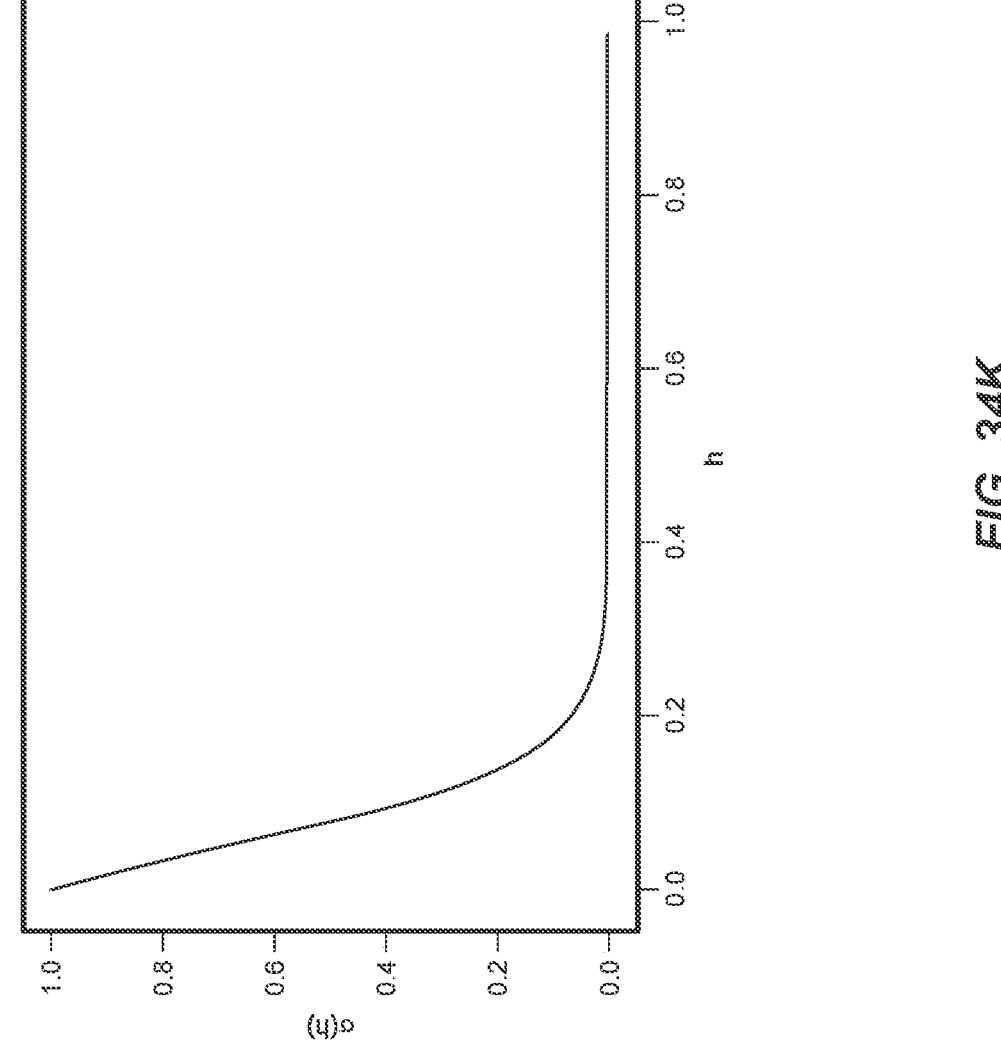

FIG. 34K is an illustration of a plot of an example function used in a modified one Euro filter.

Figures 34L, 34M:
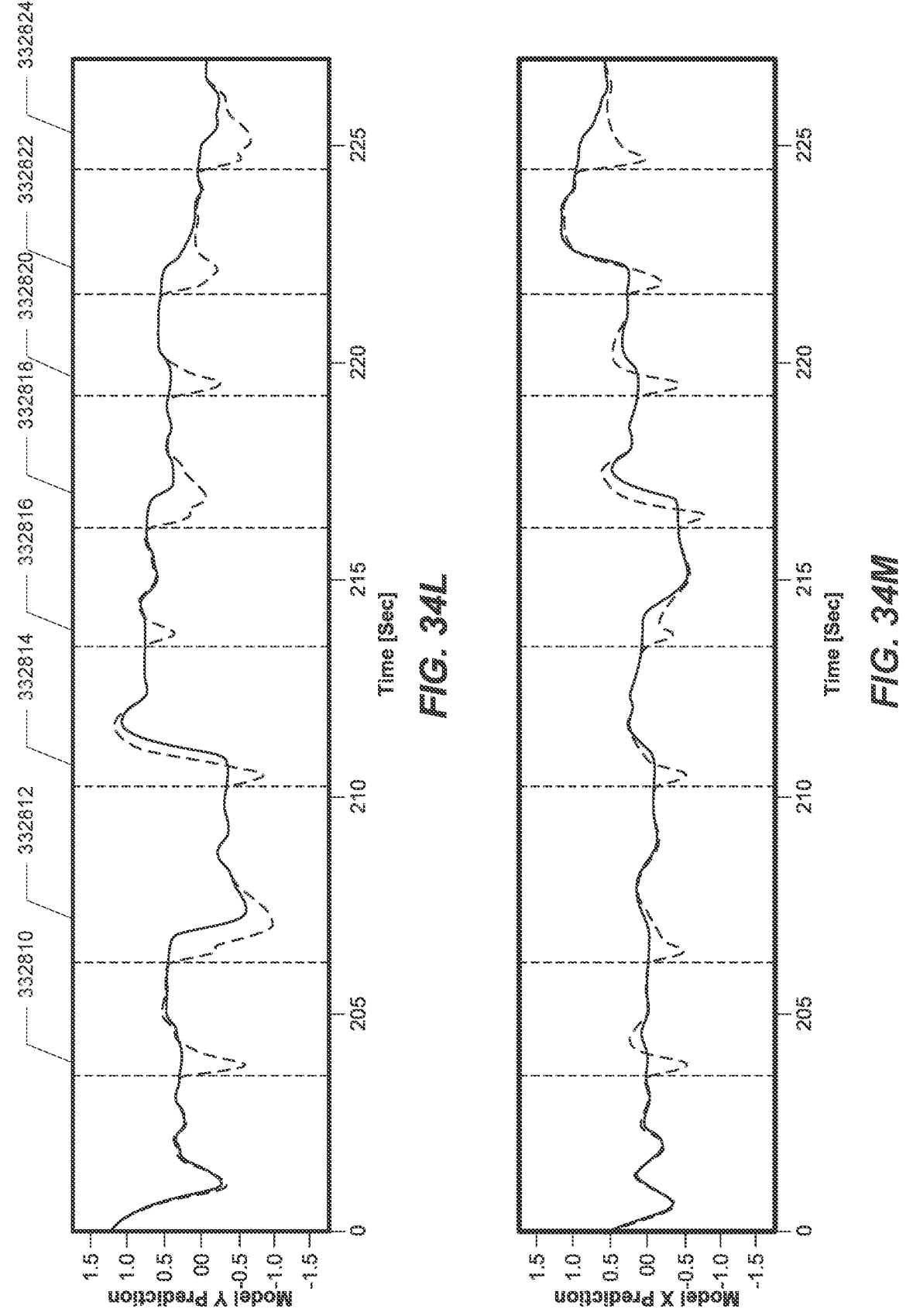

FIGS. 34L-M are illustrations of example plots of model predictions using a one Euro filter and a modified one Euro filter, respectively.

Figure 35A:
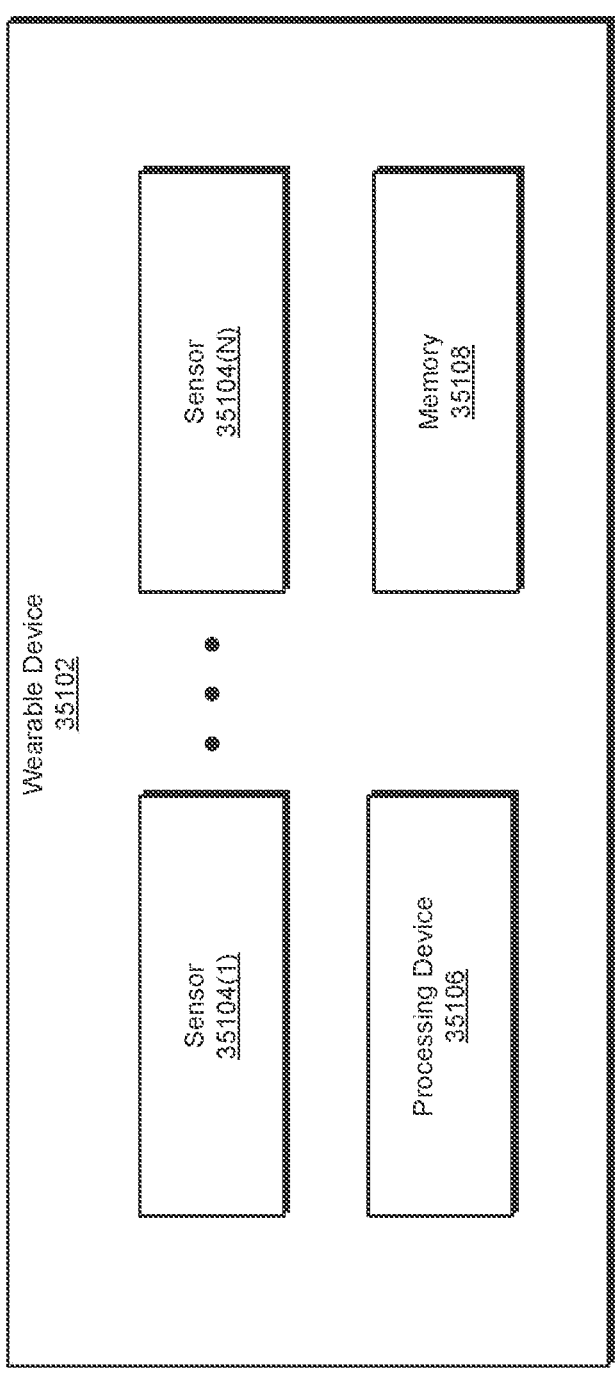

FIG. 35A is a block diagram of an exemplary wearable device for controlling computing devices via neuromuscular signals of users.

FIG. 35B is an illustration of an exemplary system for controlling computing devices via neuromuscular signals of users.

Figure 35C:
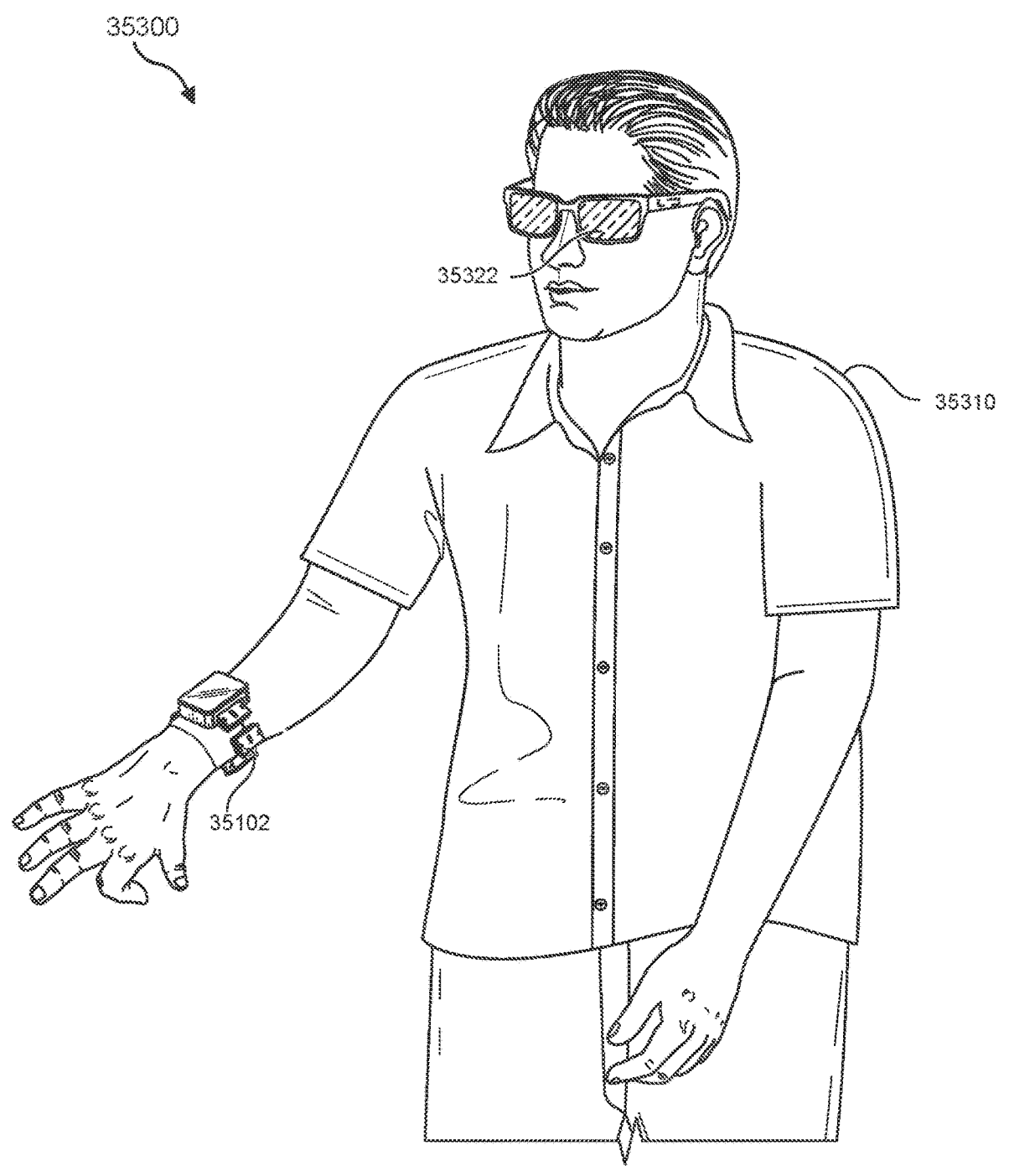

FIG. 35C is an illustration of a user wearing and operating an exemplary wearable device for controlling computing devices via neuromuscular signals.

Figures 35D, 35E:
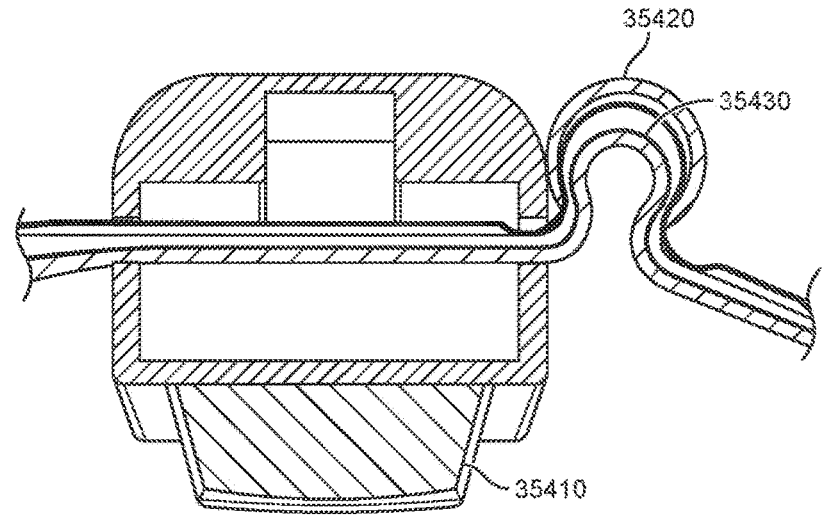

FIG. 35D is an illustration of an exemplary wearable device for controlling computing devices via neuromuscular signals of users.

FIG. 35E is an illustration of an exemplary wearable device for controlling computing devices via neuromuscular signals of users.

Figure 35F:
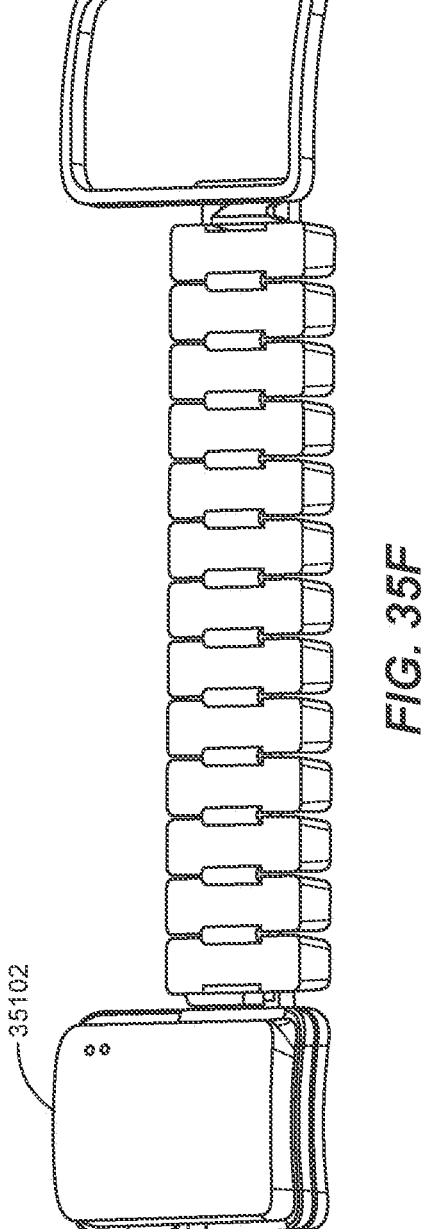

FIG. 35F is an illustration of an exemplary wearable device for controlling computing devices via neuromuscular signals of users.

Figure 35G:
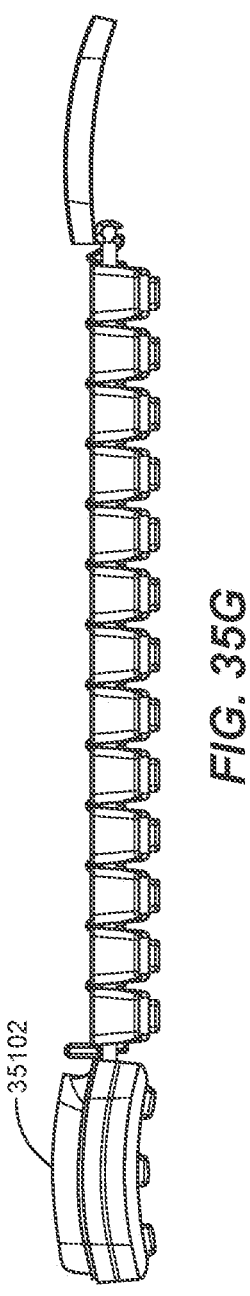

FIG. 35G is an illustration of an exemplary wearable device for controlling computing devices via neuromuscular signals of users.

FIG. 35H is an illustration of an exemplary wearable device for controlling computing devices via neuromuscular signals of users.

Figure 35I:
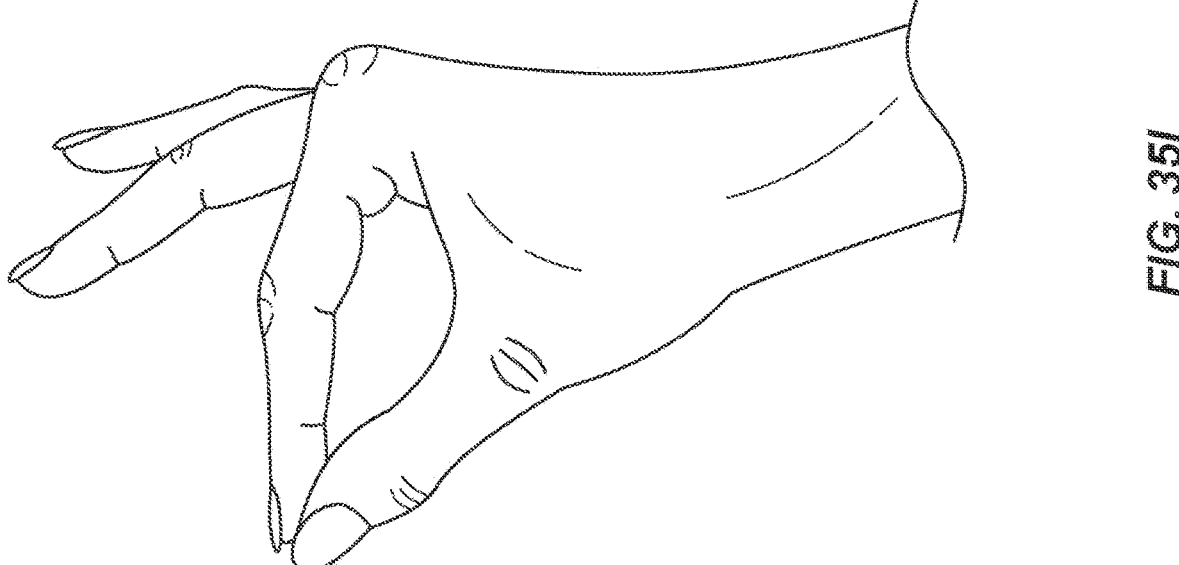

FIG. 35I is an illustration of an exemplary state of a body part of a user donning a wearable device for controlling computing devices via neuromuscular signals.

Figures 35J, 35K, 35L:
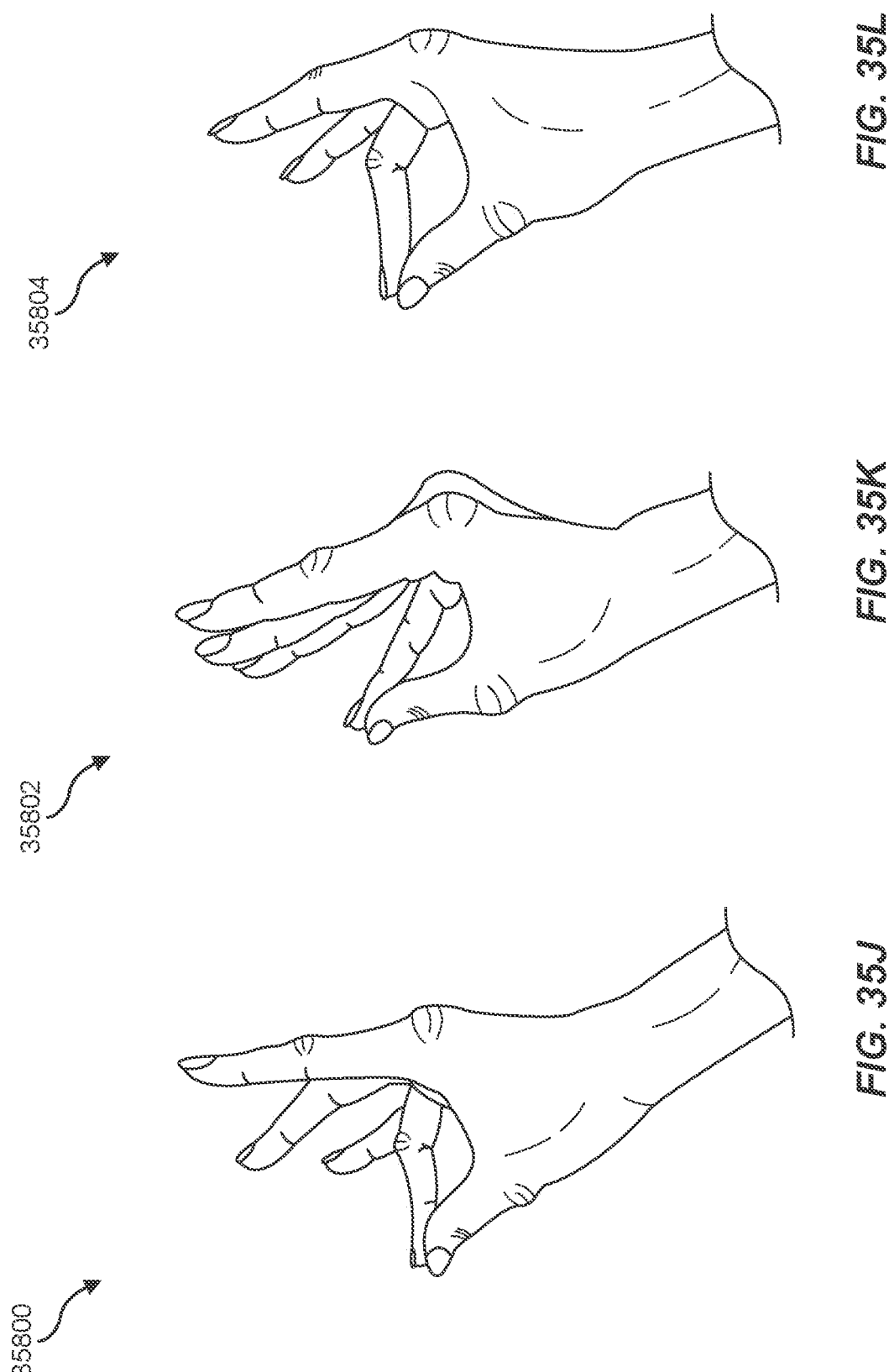

FIG. 35J is an illustration of an exemplary state of a body part of a user donning a wearable device for controlling computing devices via neuromuscular signals.

FIG. 35K is an illustration of an exemplary state of a body part of a user donning a wearable device for controlling computing devices via neuromuscular signals.

FIG. 35L is an illustration of an exemplary state of a body part of a user donning a wearable device for controlling computing devices via neuromuscular signals.

Figure 35M:
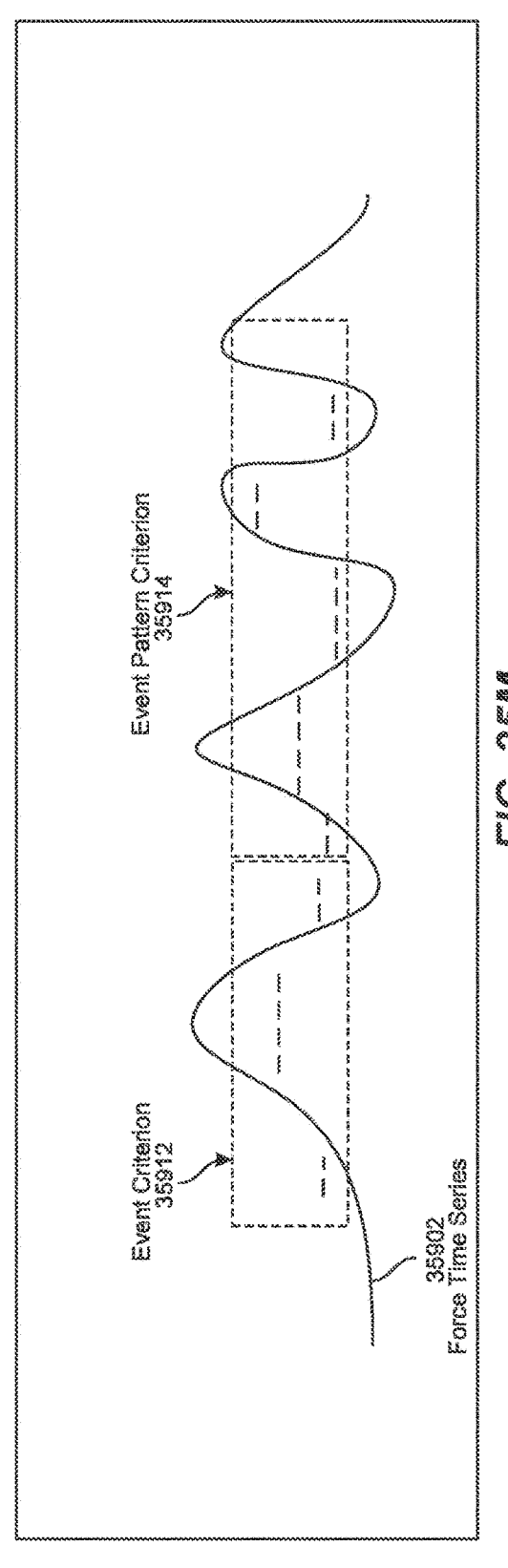

FIG. 35M is an illustration of an exemplary signal representative of a state pattern corresponding to a body part of a user donning a wearable device for controlling computing devices via neuromuscular signals.

Figure 35N:
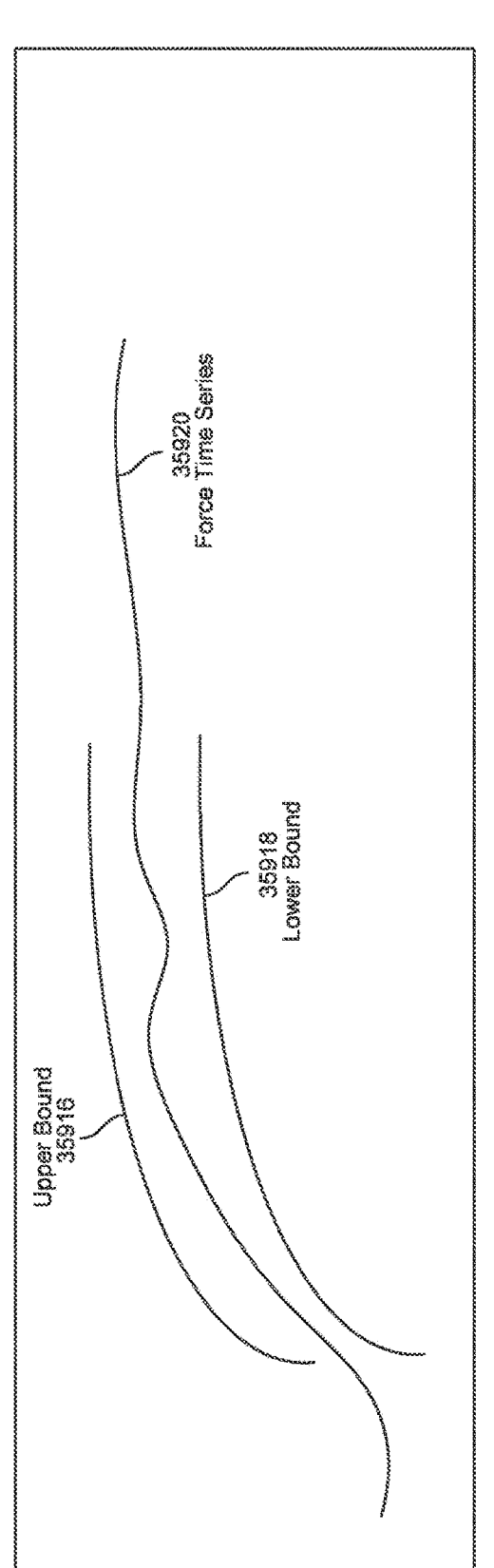

FIG. 35N is an illustration of an exemplary signal representative of a state pattern corresponding to a body part of a user donning a wearable device for controlling computing devices via neuromuscular signals.

Figures 35O, 35P, 35Q, 35R, 35S, 35T, 35U, 35V:
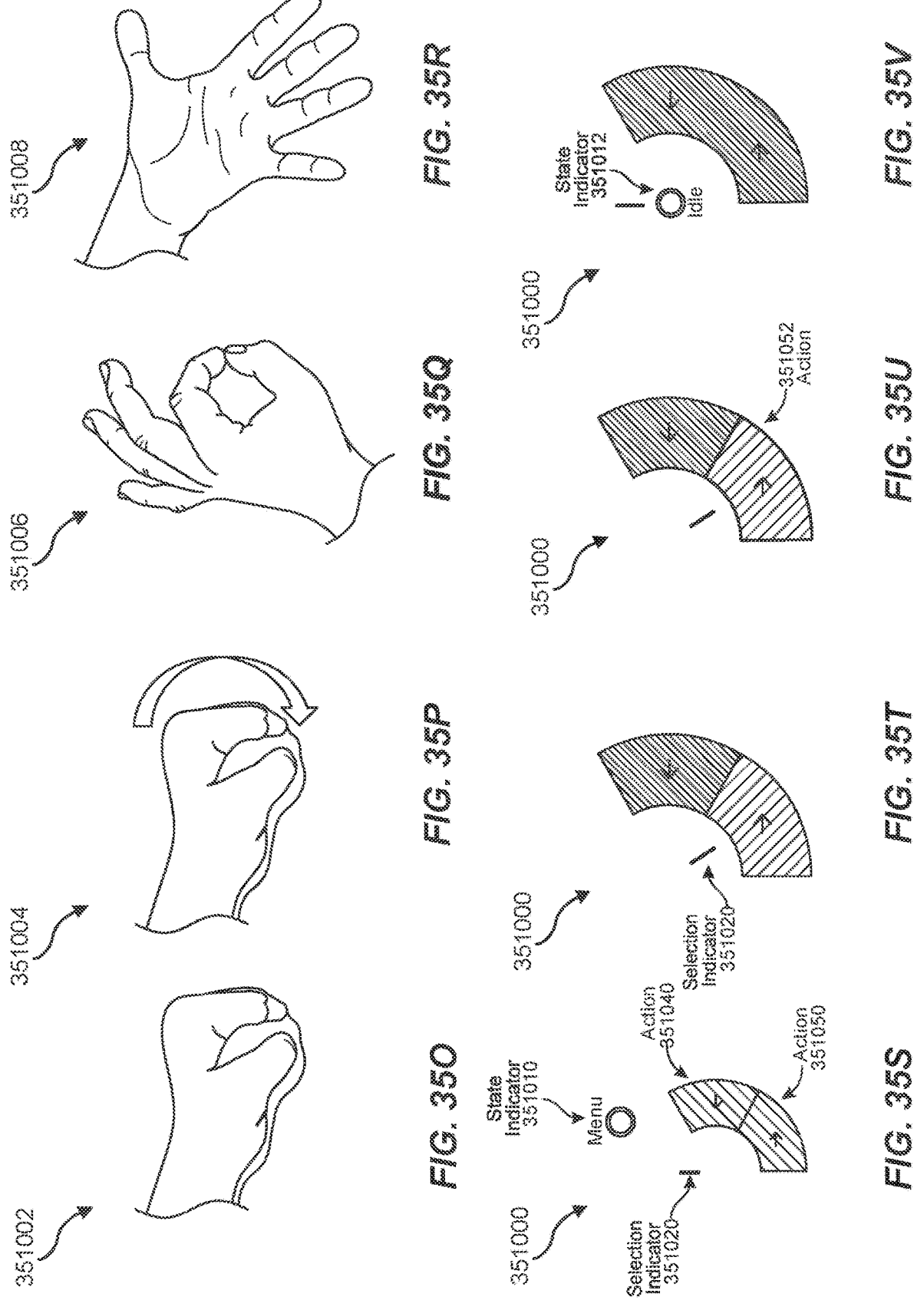

FIG. 35O is an illustration of an exemplary state of a body part of a user donning a wearable device for controlling computing devices via neuromuscular signals.

FIG. 35P is an illustration of an exemplary state of a body part of a user donning a wearable device for controlling computing devices via neuromuscular signals.

FIG. 35Q is an illustration of an exemplary state of a body part of a user donning a wearable device for controlling computing devices via neuromuscular signals.

FIG. 35R is an illustration of an exemplary state of a body part of a user donning a wearable device for controlling computing devices via neuromuscular signals.

FIG. 35S is an illustration of an exemplary action that is performed by a computing device in response to the state of the user's body part illustrated in FIG. 35O.

FIG. 35T is an illustration of an exemplary action that is performed by a computing device in response to the state of the user's body part illustrated in FIG. 35P.

FIG. 35U is an illustration of an exemplary action that is performed by a computing device in response to the state of the user's body part illustrated in FIG. 35Q.

FIG. 35V is an illustration of an exemplary action that is performed by a computing device in response to the state of the user's body part illustrated in FIG. 35R.

FIG. 36A is an illustration of an exemplary radial menu capable of being controlled by a wearable device via neuromuscular signals of users.

FIG. 36B is an illustration of an exemplary radial menu capable of being controlled by a wearable device via neuromuscular signals of users.

FIG. 36C is an illustration of an exemplary sequential menu capable of being controlled by a wearable device via neuromuscular signals of users.

FIG. 36D is an illustration of an exemplary sequential menu capable of being controlled by a wearable device via neuromuscular signals of users.

FIG. 36E is an illustration of an exemplary sequential menu capable of being controlled by a wearable device via neuromuscular signals of users.

Figure 36F:
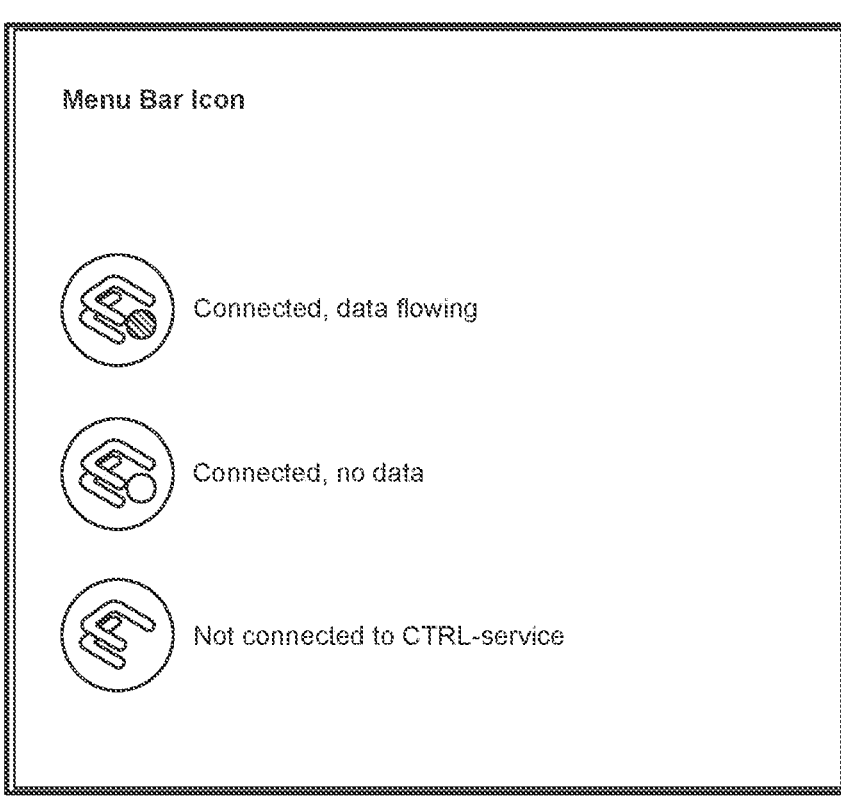

FIG. 36F is an illustration of an exemplary menu bar icon indicating whether a wearable device donned by a user is connected to a computing device.

Figure 36G:
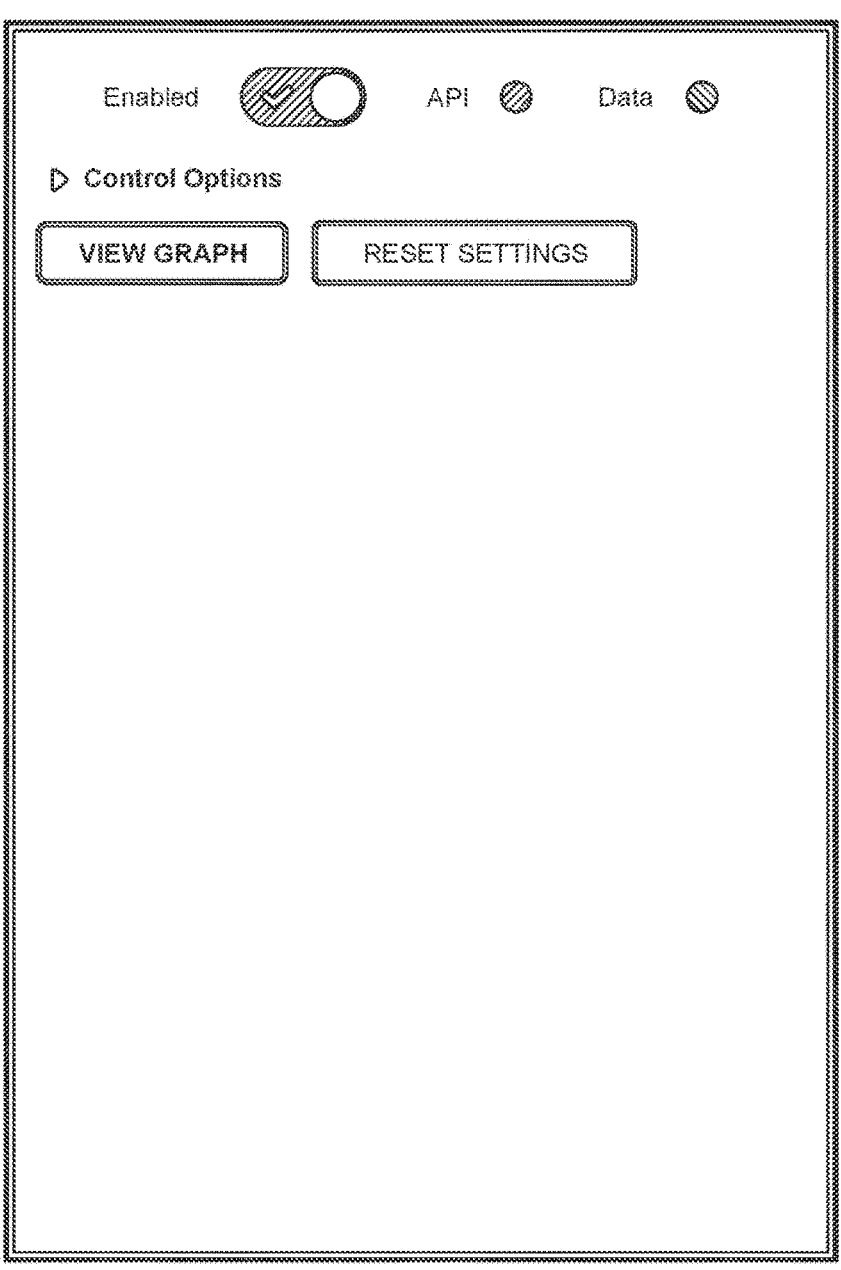

FIG. 36G is an exemplary popup menu display that enables a user to activate and/or deactivate certain mappings between possible states of the user's body parts and actions capable of being performed by a computing device.

Figure 36H:
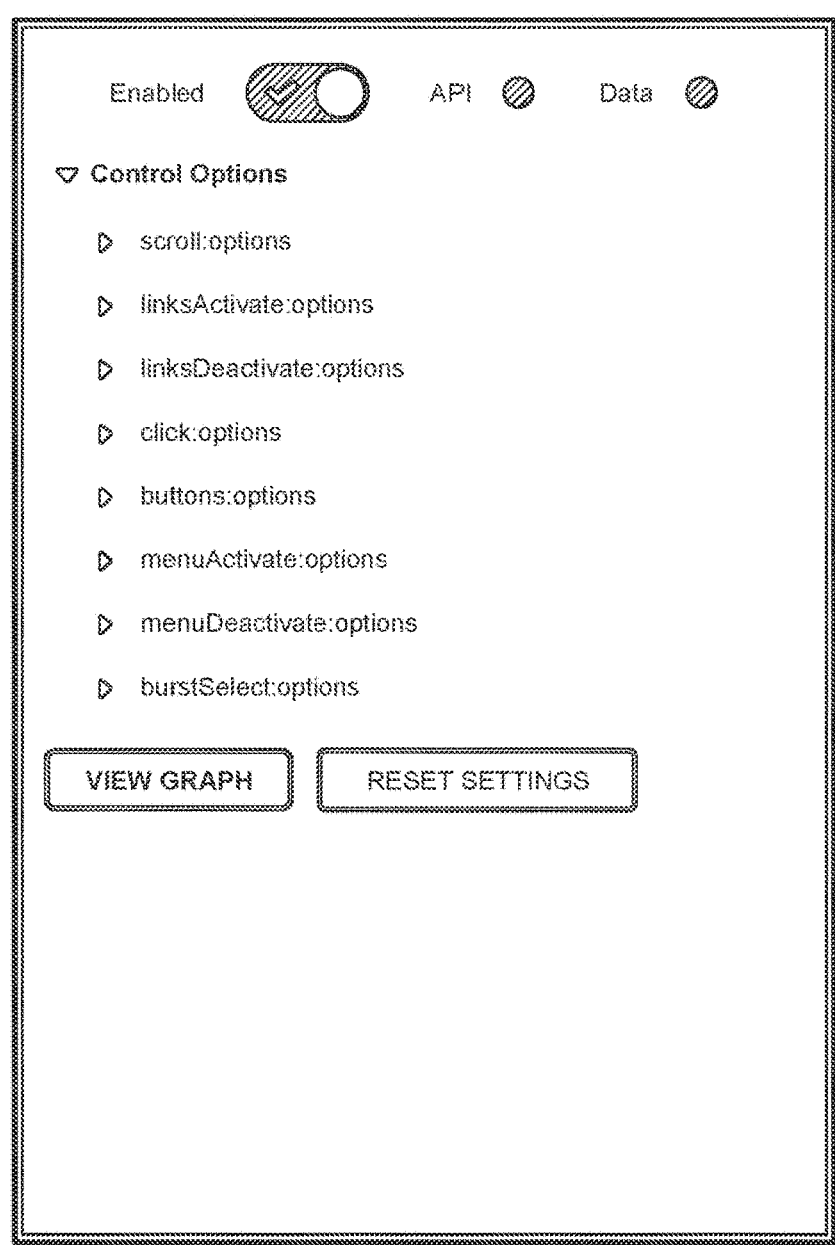

FIG. 36H is an exemplary popup menu display that enables a user to activate and/or deactivate certain mappings between possible states of the user's body parts and actions capable of being performed by a computing device.

Figure 36I:
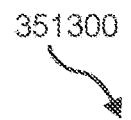

FIG. 36I is an exemplary popup menu display that enables a user to activate and/or deactivate certain mappings between possible states of the user's body parts and actions capable of being performed by a computing device.

Figure 36J:

FIG. 36J is an exemplary popup menu display that enables a user to activate and/or deactivate certain mappings between possible states of the user's body parts and actions capable of being performed by a computing device.

Figure 36K:

FIG. 36K is an exemplary popup menu display that enables a user to activate and/or deactivate certain mappings between possible states of the user's body parts and actions capable of being performed by a computing device.

Figure 36L:
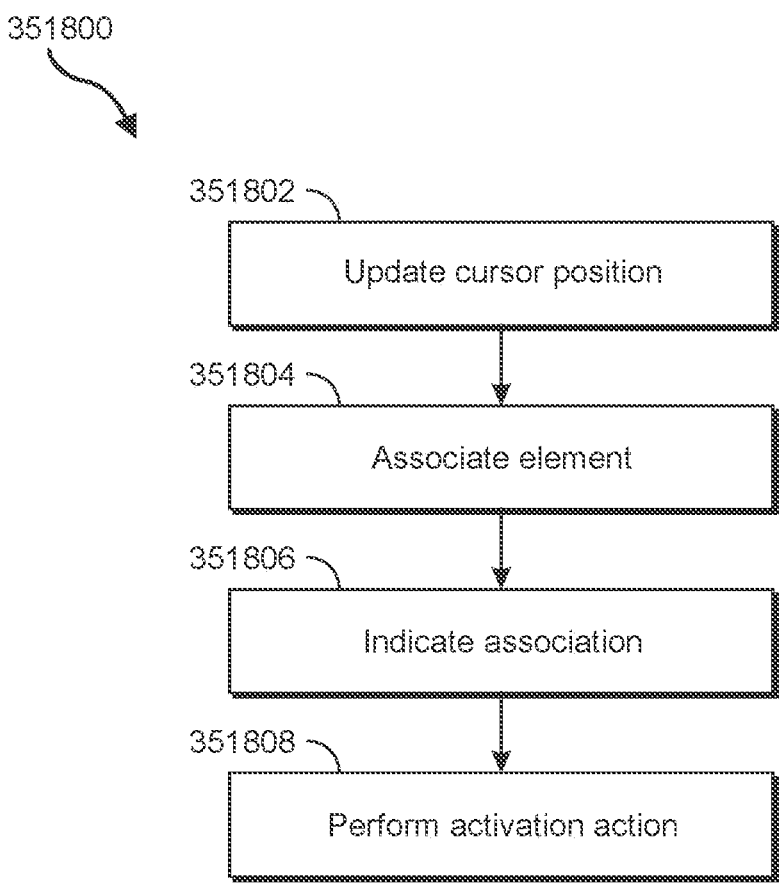

FIG. 36L is a flow diagram of an exemplary method for controlling a graphical user interface of a computing device via a wearable device donned by a user.

Figure 36M:
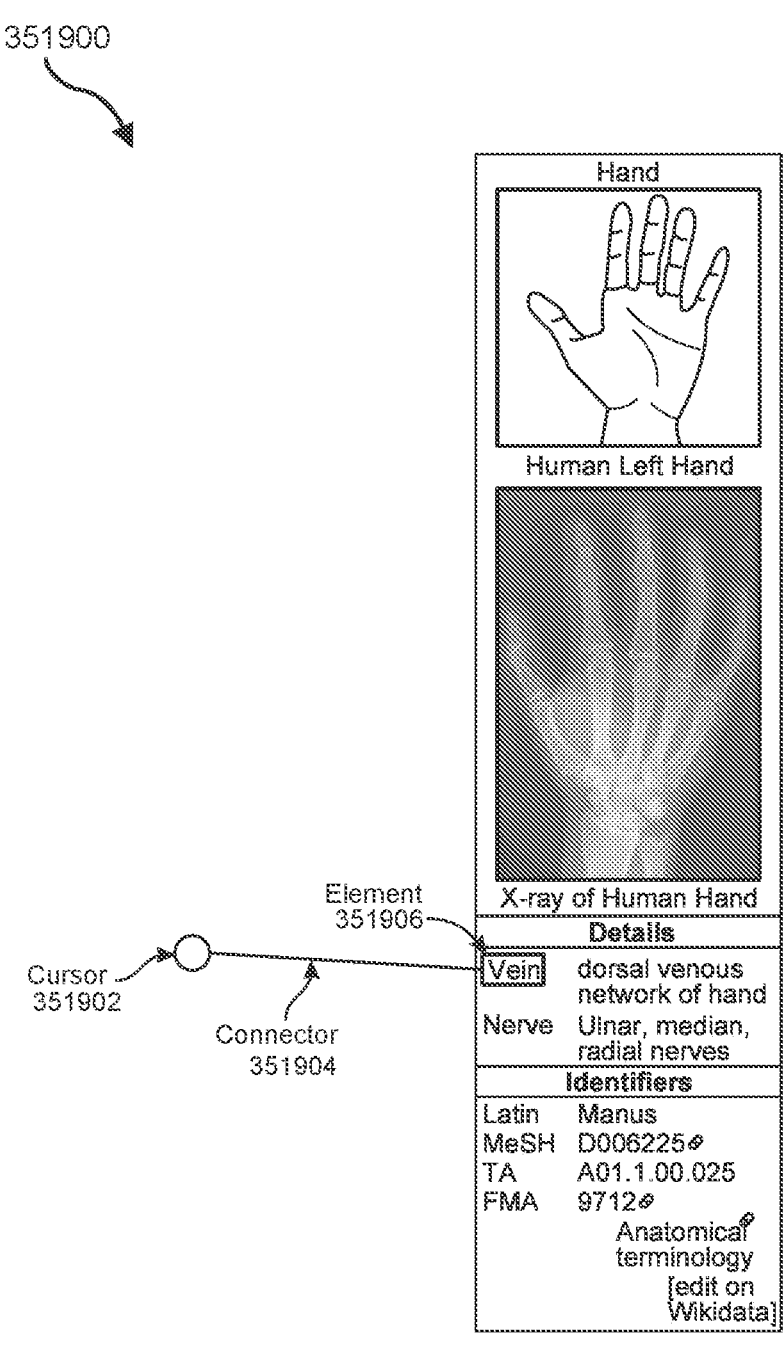

FIG. 36M is an illustration of an exemplary highlighted link activated in a web page in connection with a link-activate setting selected via the popup menu display illustrated in FIG. 36K.

Figure 36N:
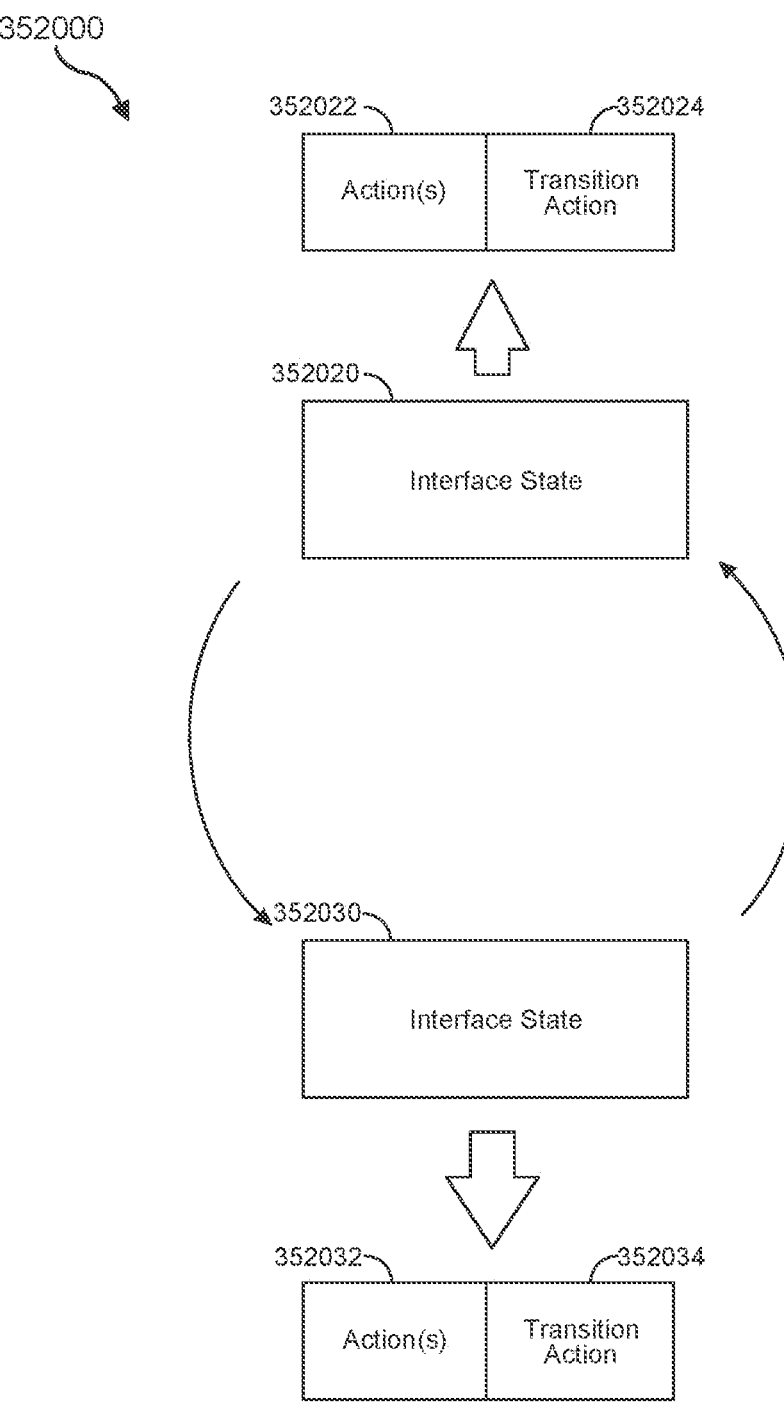

FIG. 36N is an illustration of an exemplary transition between mappings of possible states of the user's body parts and actions capable of being performed by a computing device.

Figures 36O, 36P:
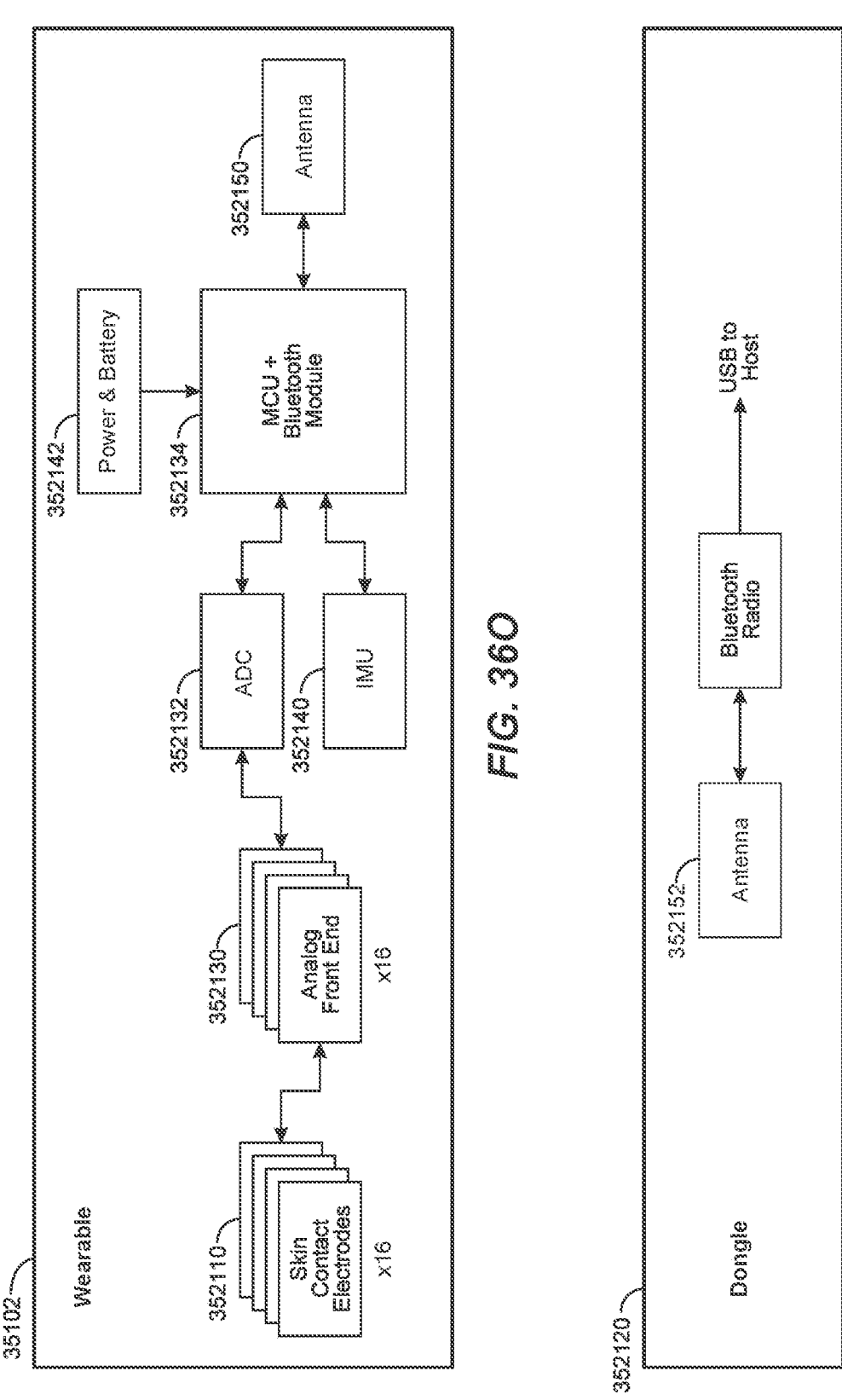

FIG. 36O is an illustration of exemplary wearable device for controlling computing devices via neuromuscular signals of users.

FIG. 36P is an illustration of exemplary dongle that is connected to a computing device and facilitates interfacing a wearable device with the computing device.

FIG. 36Q is a flowchart of an exemplary method for controlling computing devices via neuromuscular signals of users.

Figure 36R:

FIG. 36R is an illustration of an exemplary drawing application that includes a virtual drawing instrument whose width is capable of being controlled and/or modified in accordance with certain states of the user's body parts.

Figure 36S:
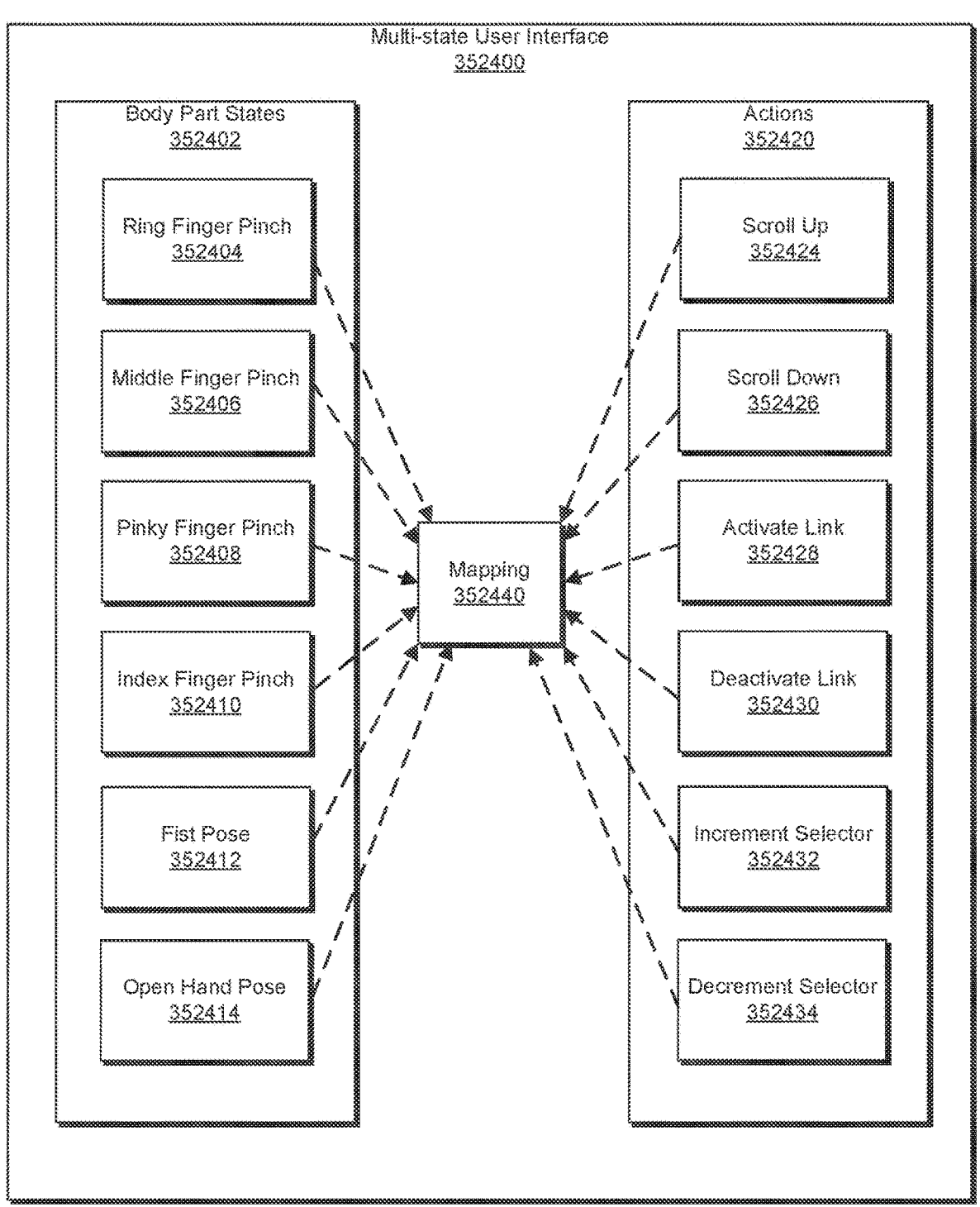

FIG. 36S is an illustration of an exemplary multi-state user interface that enables a user to select and/or define certain mappings between possible states of the user's body parts and actions capable of being performed by a computing device.

Figure 37A:
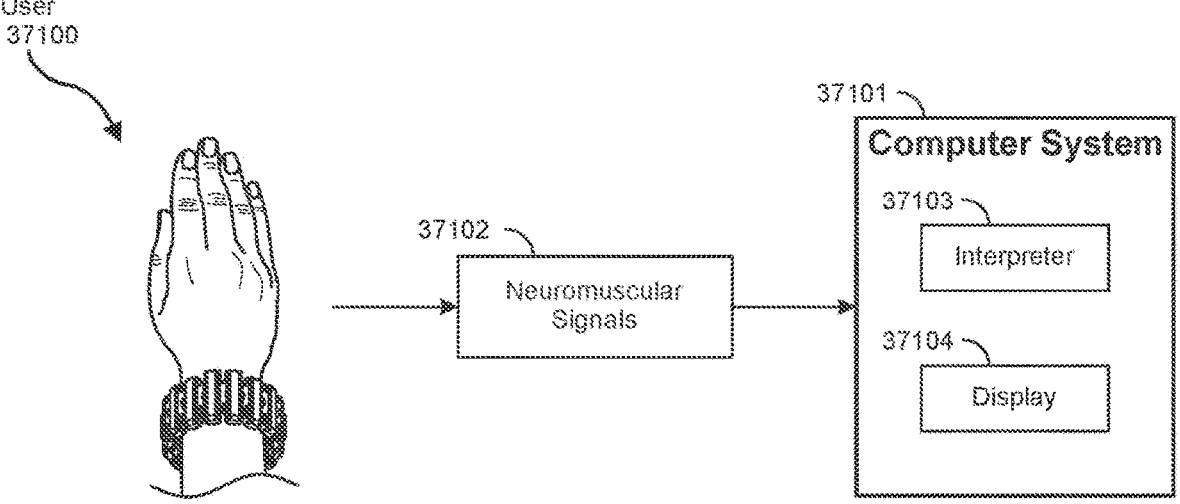

FIG. 37A illustrates an embodiment in which neuromuscular signals are measured from a user using neuromuscular sensors arranged around a band or other type of device worn by the user.

Figures 37B, 37C:
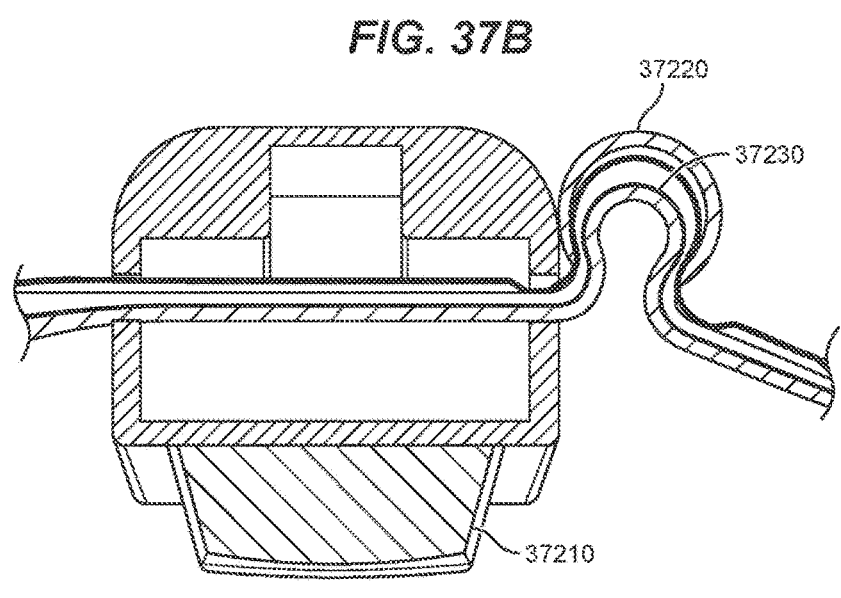

FIG. 37B illustrates a wearable system with multiple neuromuscular sensors arranged circumferentially around a band configured to be worn around a user's lower arm or wrist.

FIG. 37C illustrates a cross-sectional view through one of the sensors of the wearable device shown in FIG. 37B.

Figure 37D:
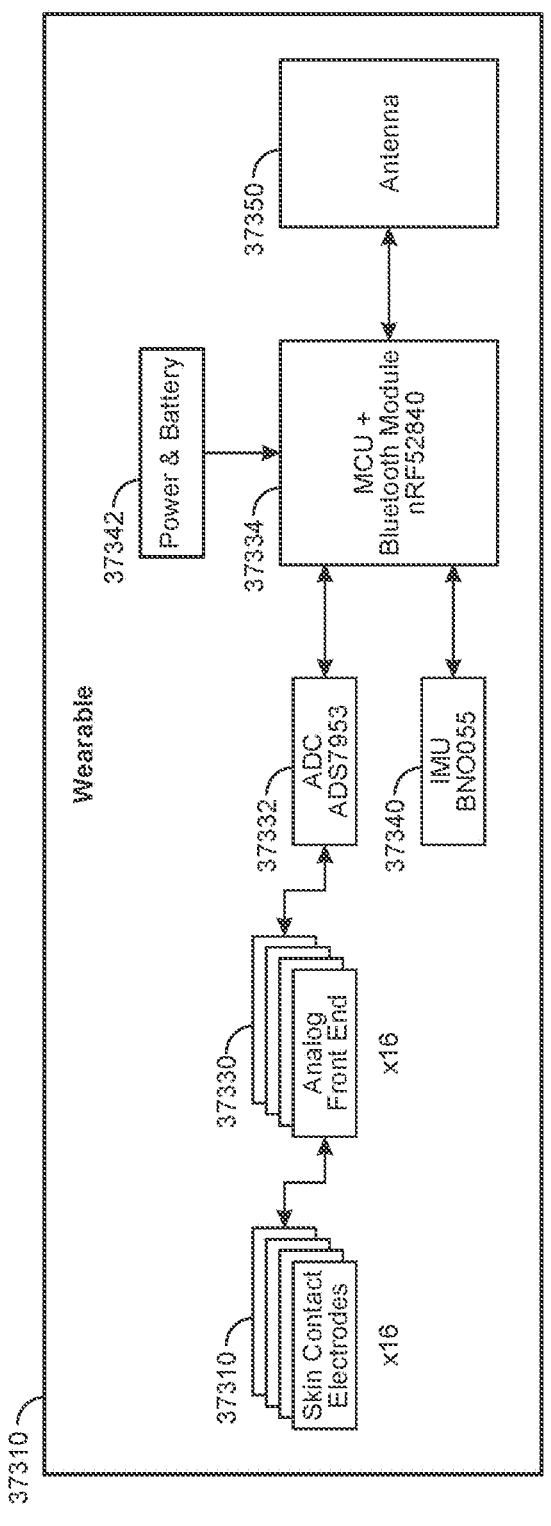
Figure 37E:
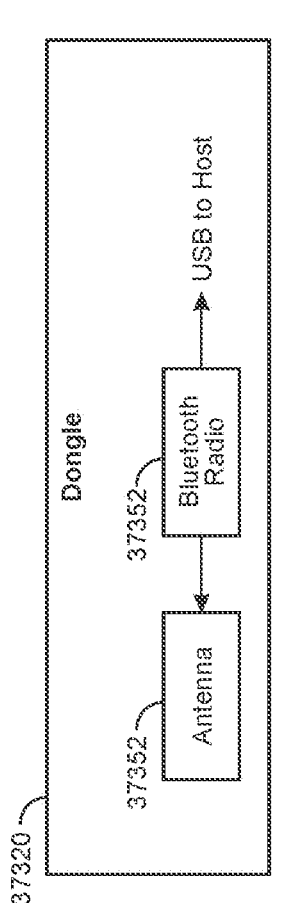

FIGS. 37D and 37E illustrate schematic diagrams with internal components of a wearable system with multiple EMG sensors.

Figure 37F:
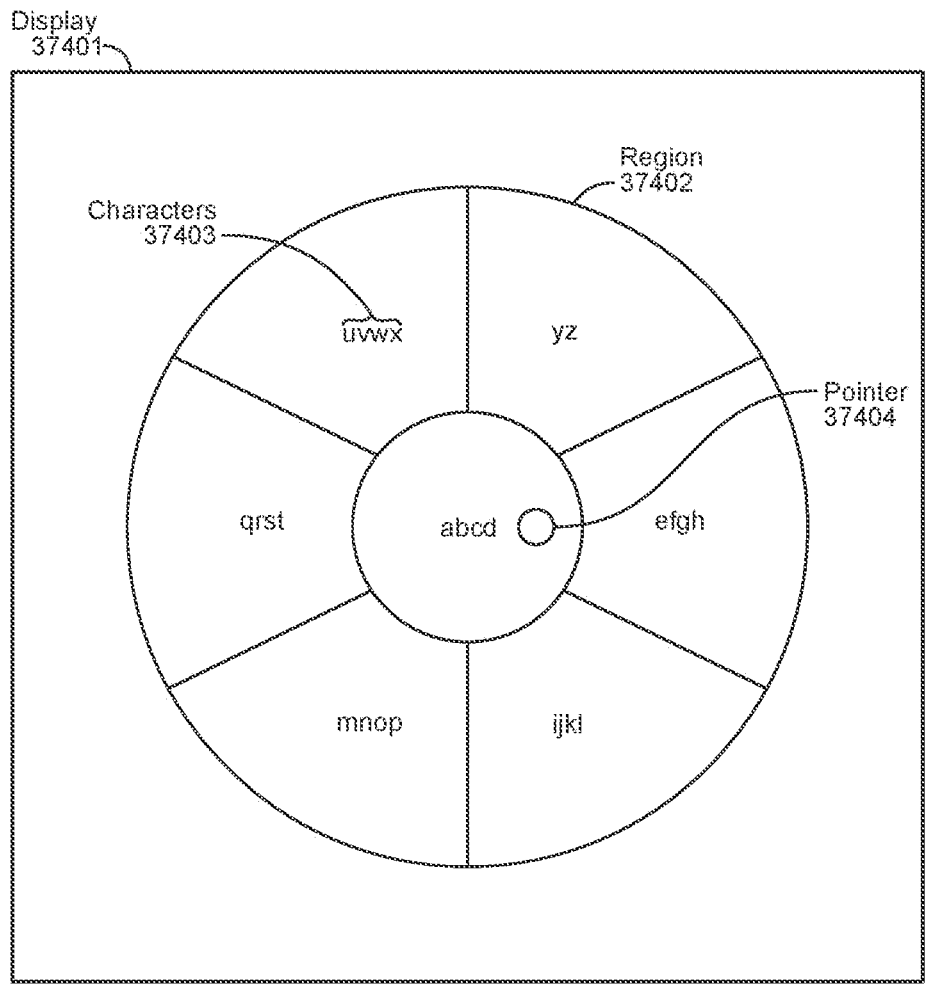

FIG. 37F illustrates an embodiment of a user interface that is displayed to the user in a 2D plane.

Figure 37G:
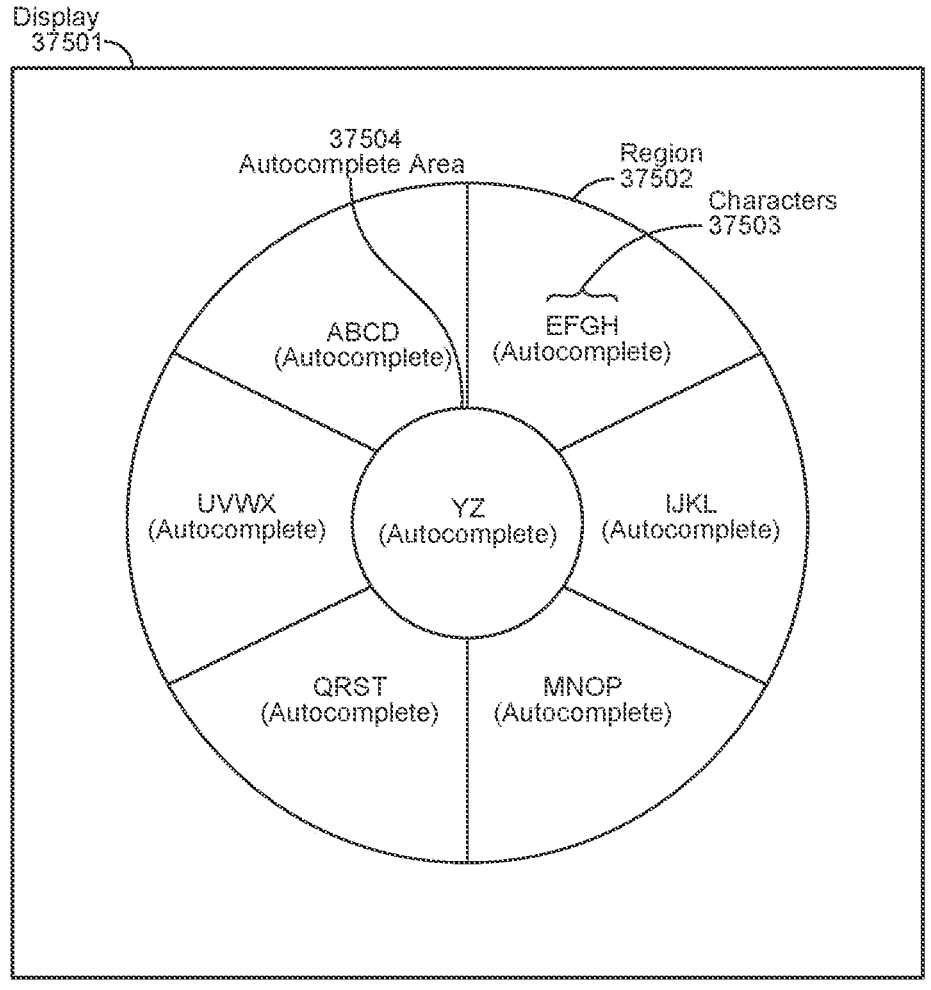

FIG. 37G illustrates an alternative embodiment of a user interface that is displayed to the user in a 2D plane.

Figure 37H:
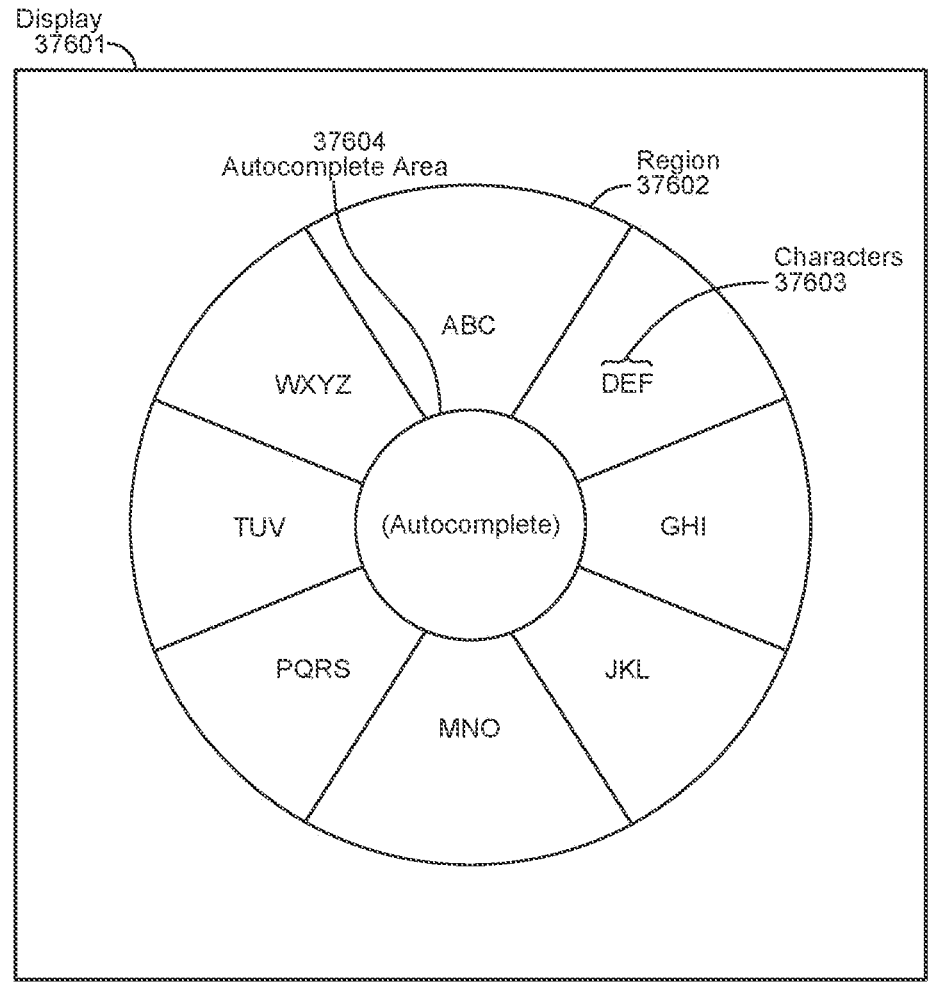
Figure 371:
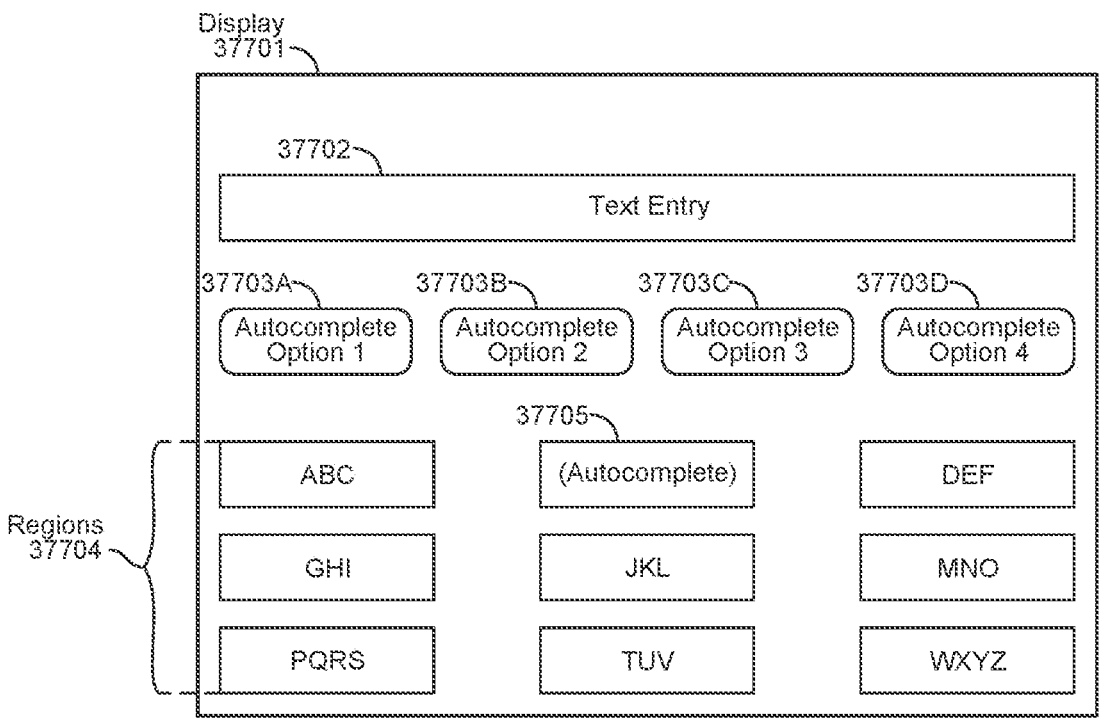

FIG. 37H illustrates an alternative embodiment of a user interface having a different type of control scheme.

FIG. 37I illustrates an alternative embodiment of a user interface having another different type of control scheme.

FIG. 37J illustrates a system having multiple sensors configured to record signals resulting from the movement of portions of a human body.

FIG. 37K is a flow diagram of a method for generating or training a statistical model using signals recorded from sensors.

Figure 37L:
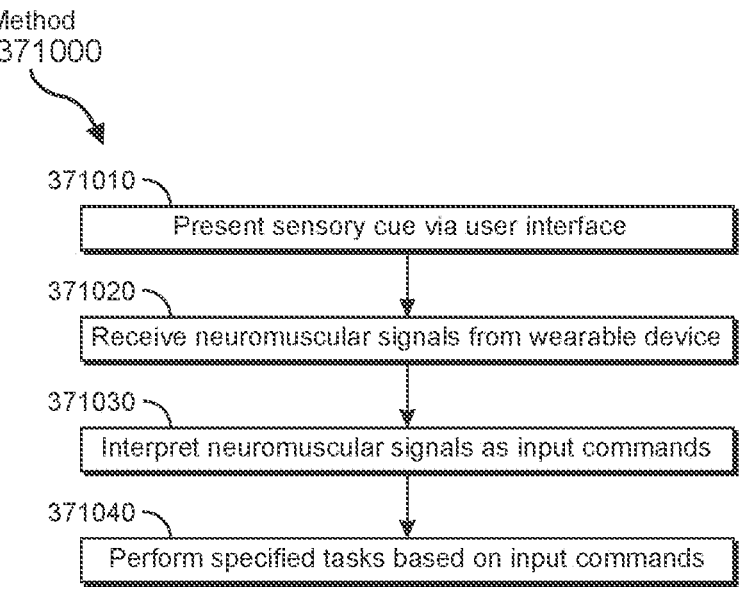

FIG. 37L is a flow diagram of a method for facilitating interactions with a user interface via neuromuscular signals.

Figure 37M:
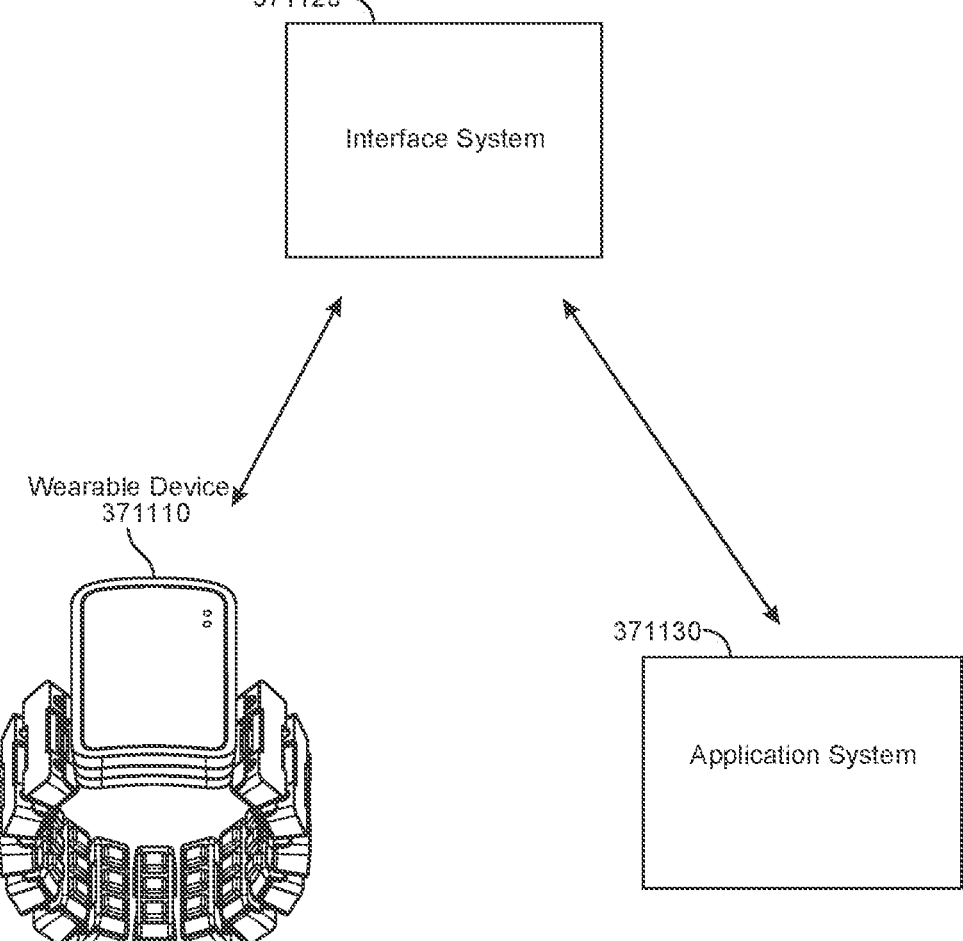

FIG. 37M illustrates a human computer interface system including a wearable device, an interface system, and an application system.

Figure 37N:
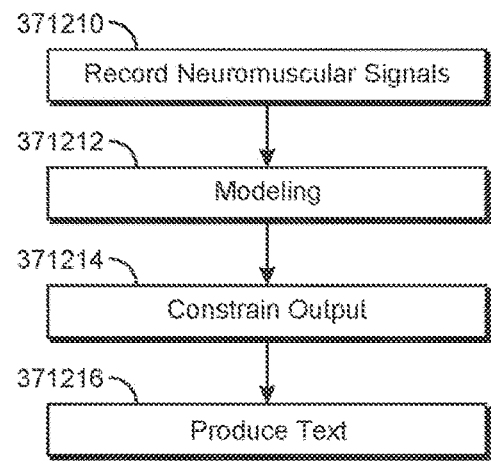

FIG. 37N is a flow diagram of a method for using a neuromuscular-based system trained to interpret typing gestures or other user activity.

Figure 37O:
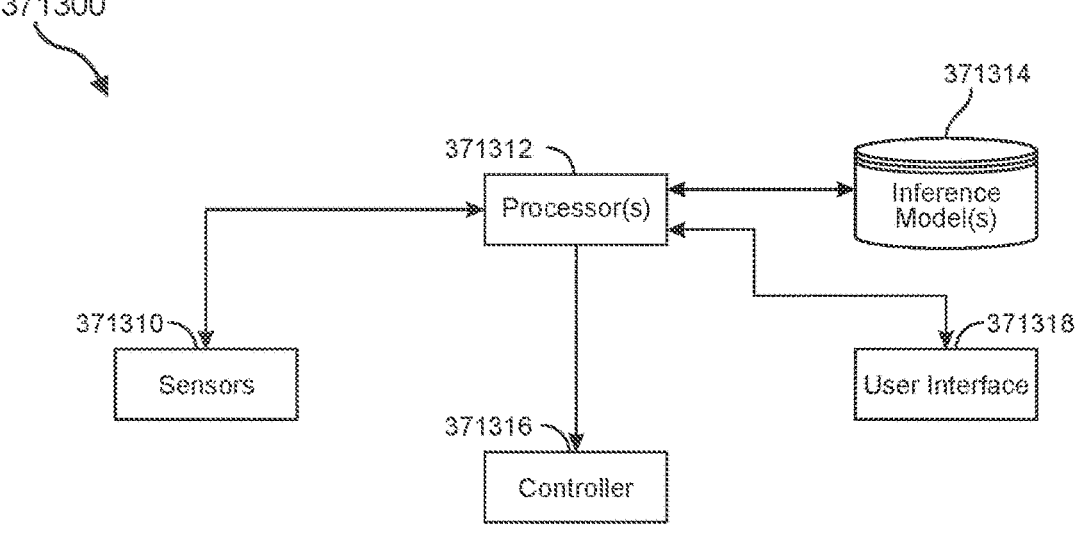

FIG. 37O illustrates an embodiment of a neuromuscular activity sensing system.

Figure 37P:
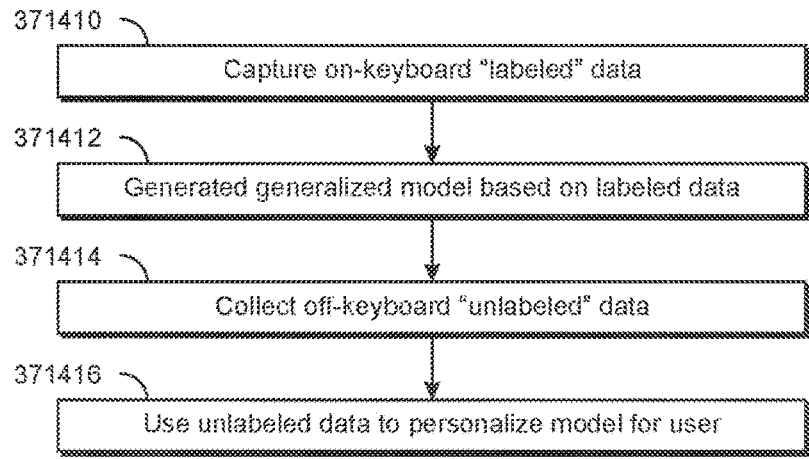

FIG. 37P is a flow diagram of a method for generating a personalized inference model trained to output characters based on neuromuscular data provided as input to the model.

Figure 37Q:
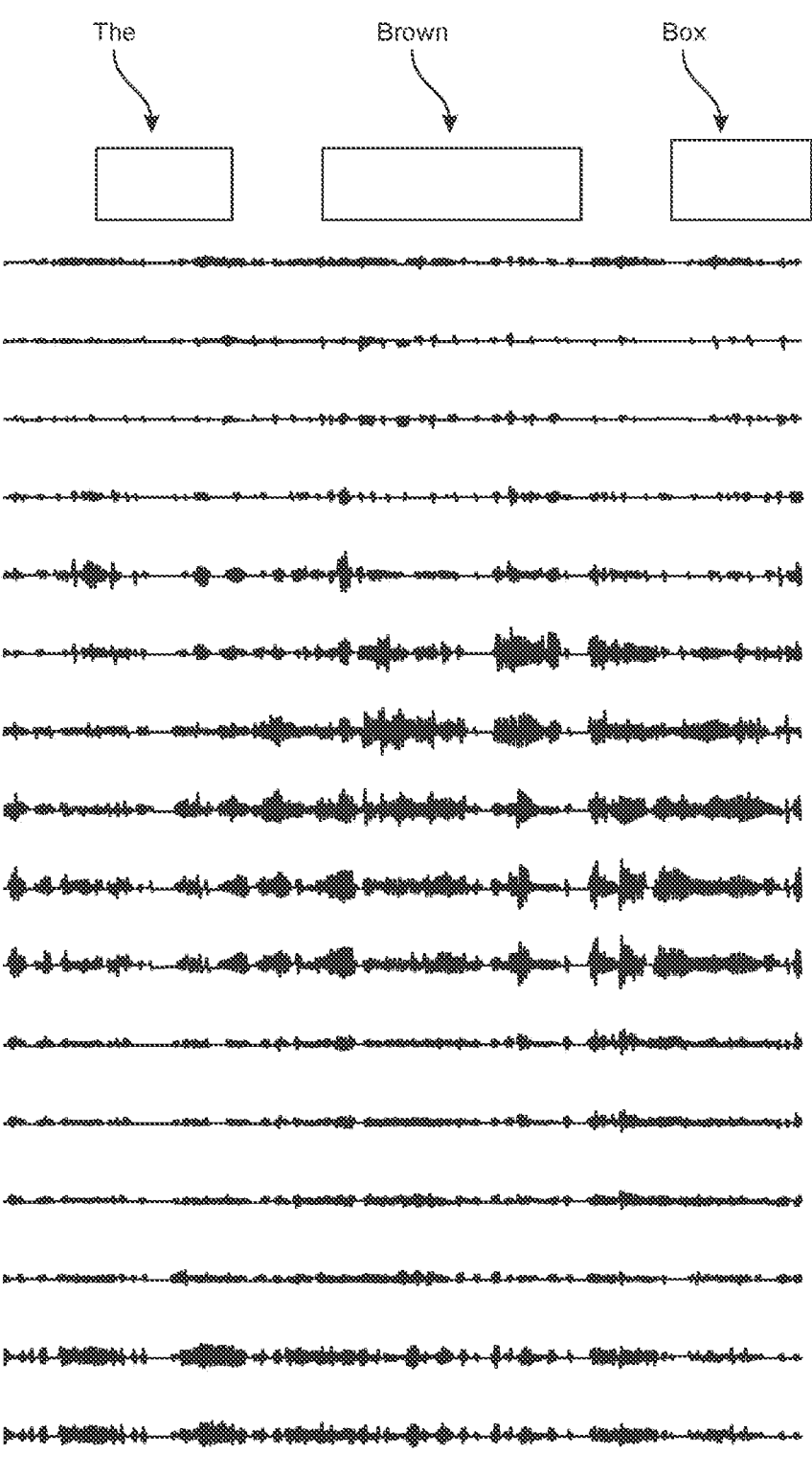

FIG. 37Q schematically illustrates how chunking of multi-channel neuromuscular signal data may be performed for character data.

FIG. 37R is a flow diagram of a method for iteratively training an inference model.

FIG. 37S is a flow diagram of a method for iteratively training a personalized typing model.

Figure 37T:
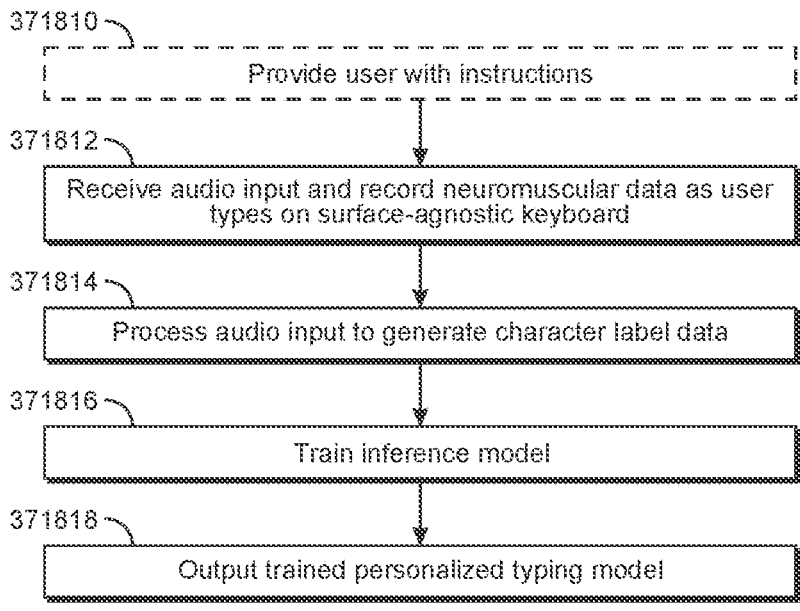

FIG. 37T is a flow diagram of an alternative method for iteratively training a personalized typing model.

Figure 37U:
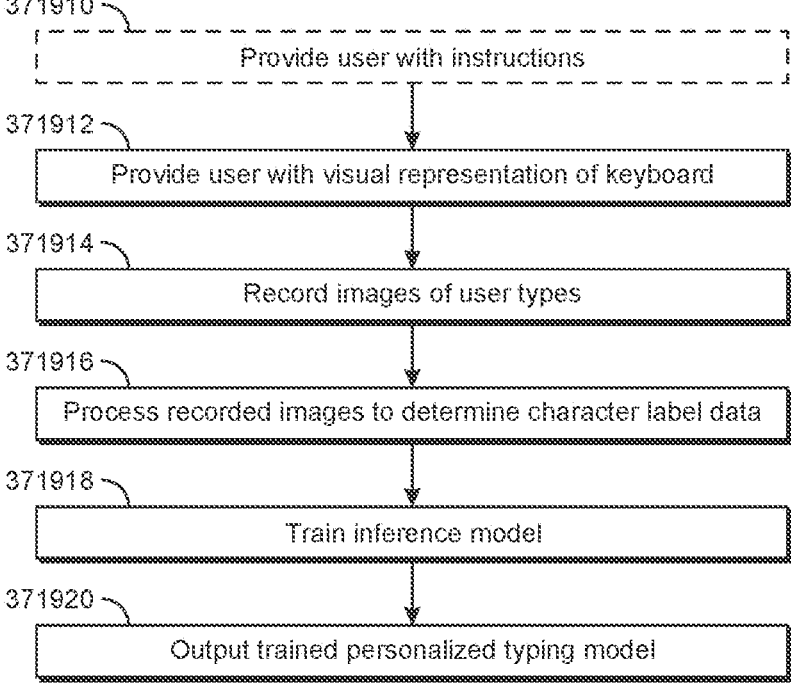

FIG. 37U is a flow diagram of another alternative method for iteratively training a personalized typing model.

Figure 37V:
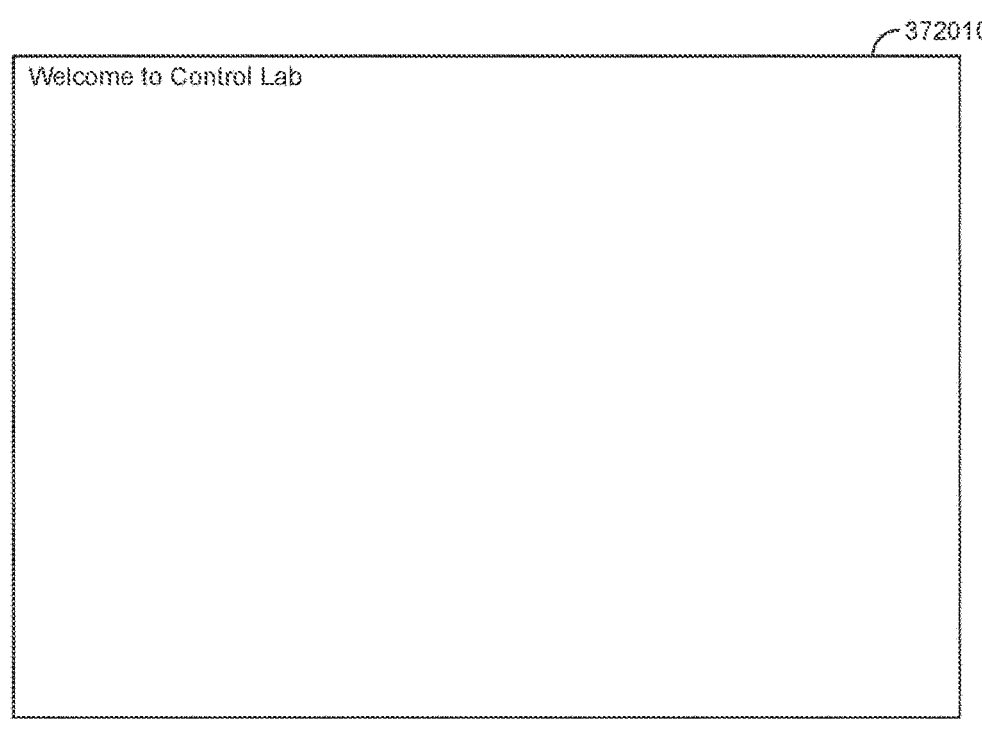

FIG. 37V illustrates an example interface in which a user may prompt the system to enter into an alternative input mode.

Figure 37W:
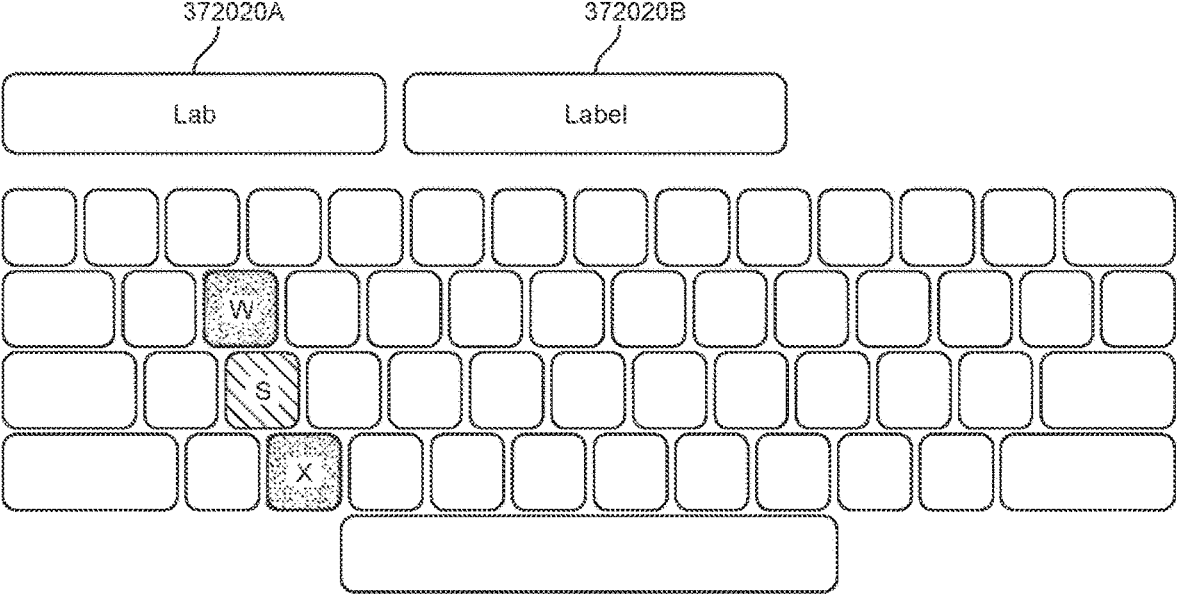

FIG. 37W illustrates a portion of a user interface that displays a representation of a keyboard when the user has engaged a "careful" typing mode through a gesture.

Figure 37X:
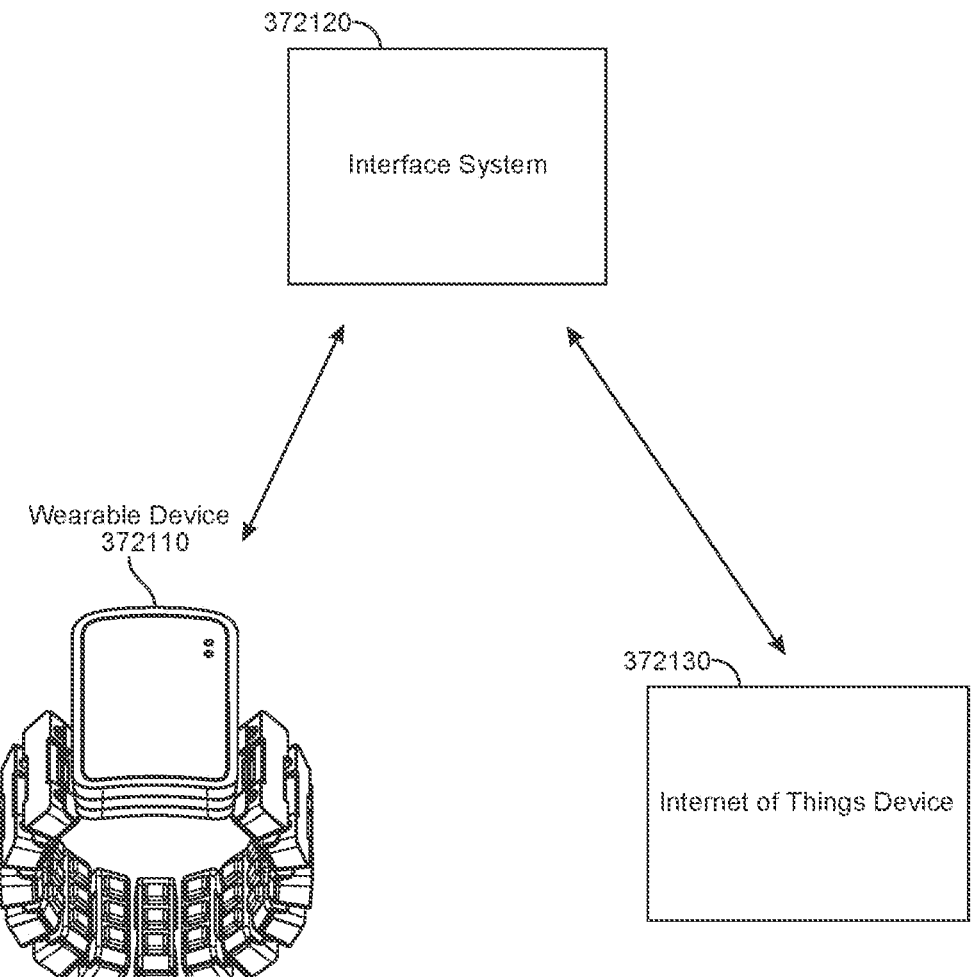

FIG. 37X illustrates a human computer interface system including a wearable device, an interface system, and an Internet of Things (IoT) device.

Figure 37Y:
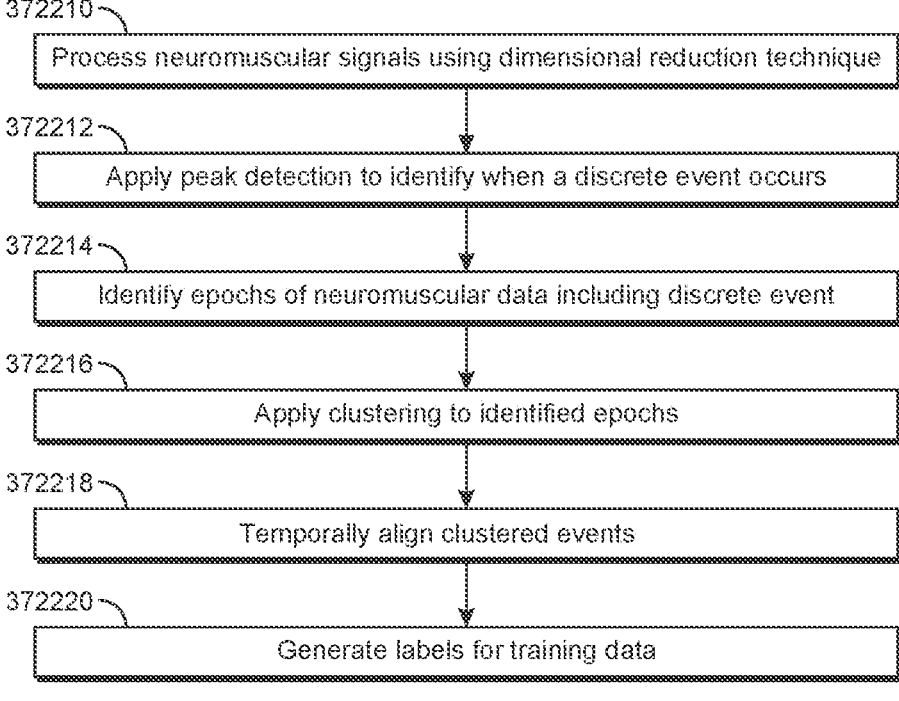

FIG. 37Y is a flow diagram of a method for generating training data for training an inference model.

Figure 37Z:
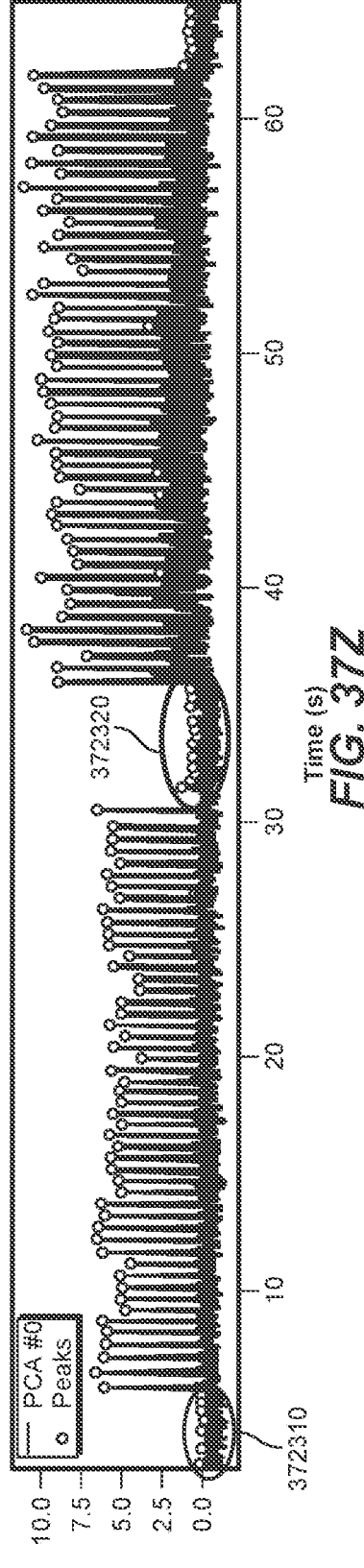

FIG. 37Z illustrates a plot of a first principal component analysis (PCA) component with the output of peak detection.

Figure 38A:
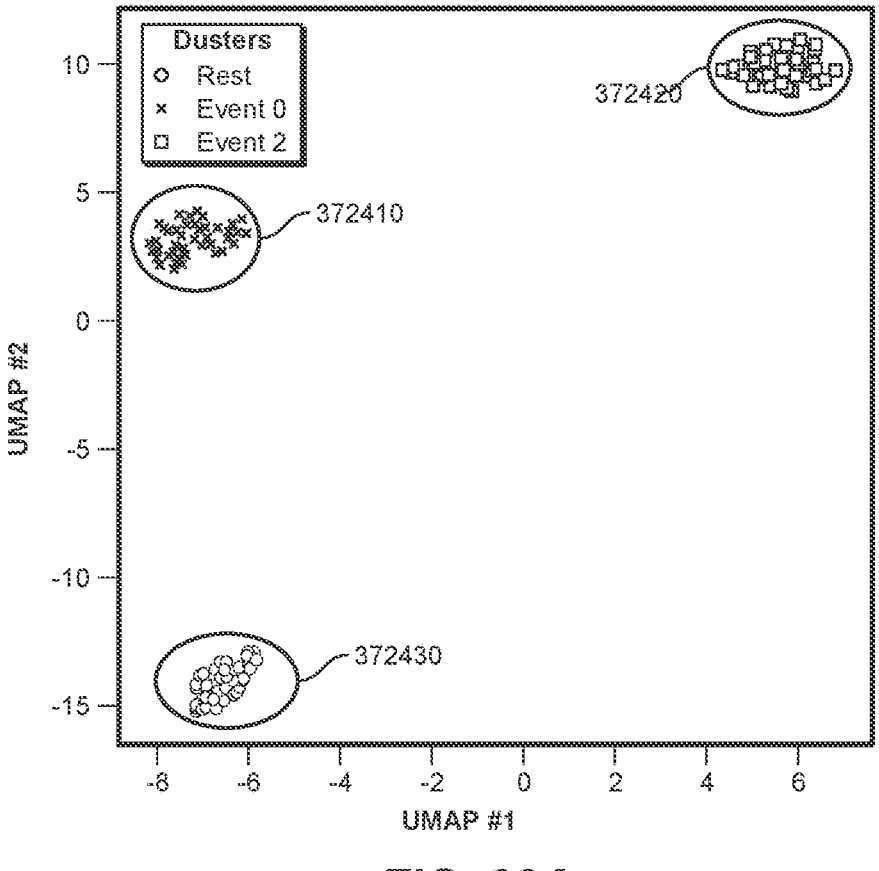

FIG. 38A illustrates an embodiment of three clusters that are separated from each other.

Figure 38B:
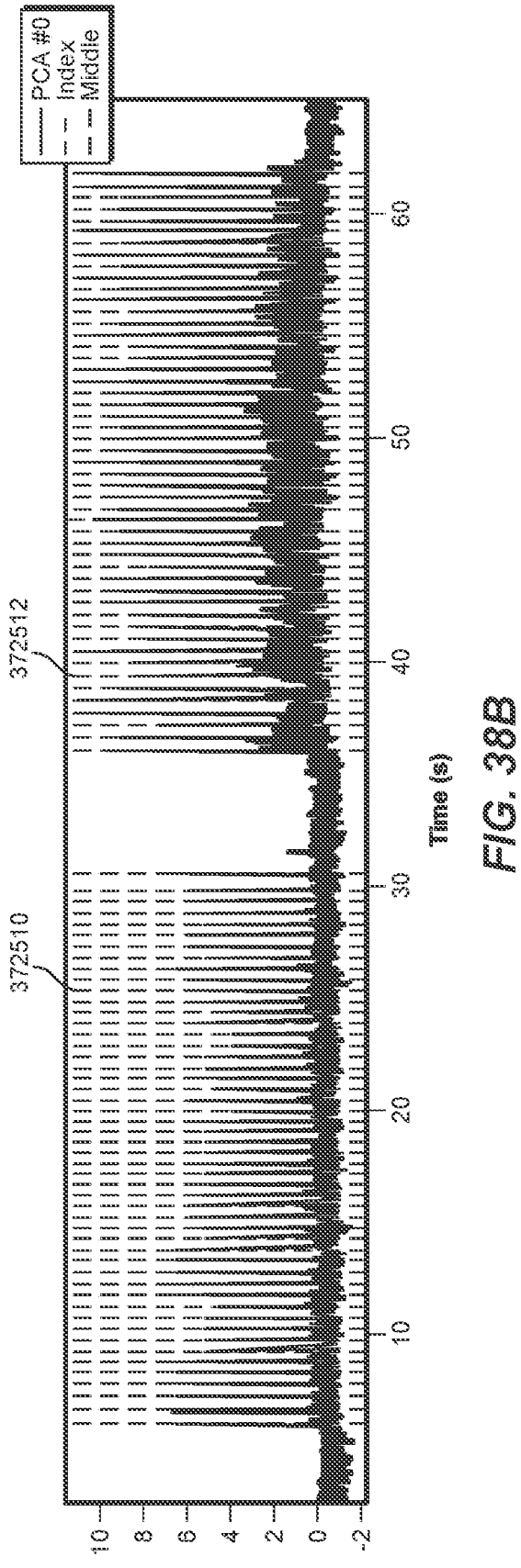

FIG. 38B illustrates an embodiment in which vertical dashed lines and solid lines indicate distinguished index taps and middle finger taps.

Figure 38C:
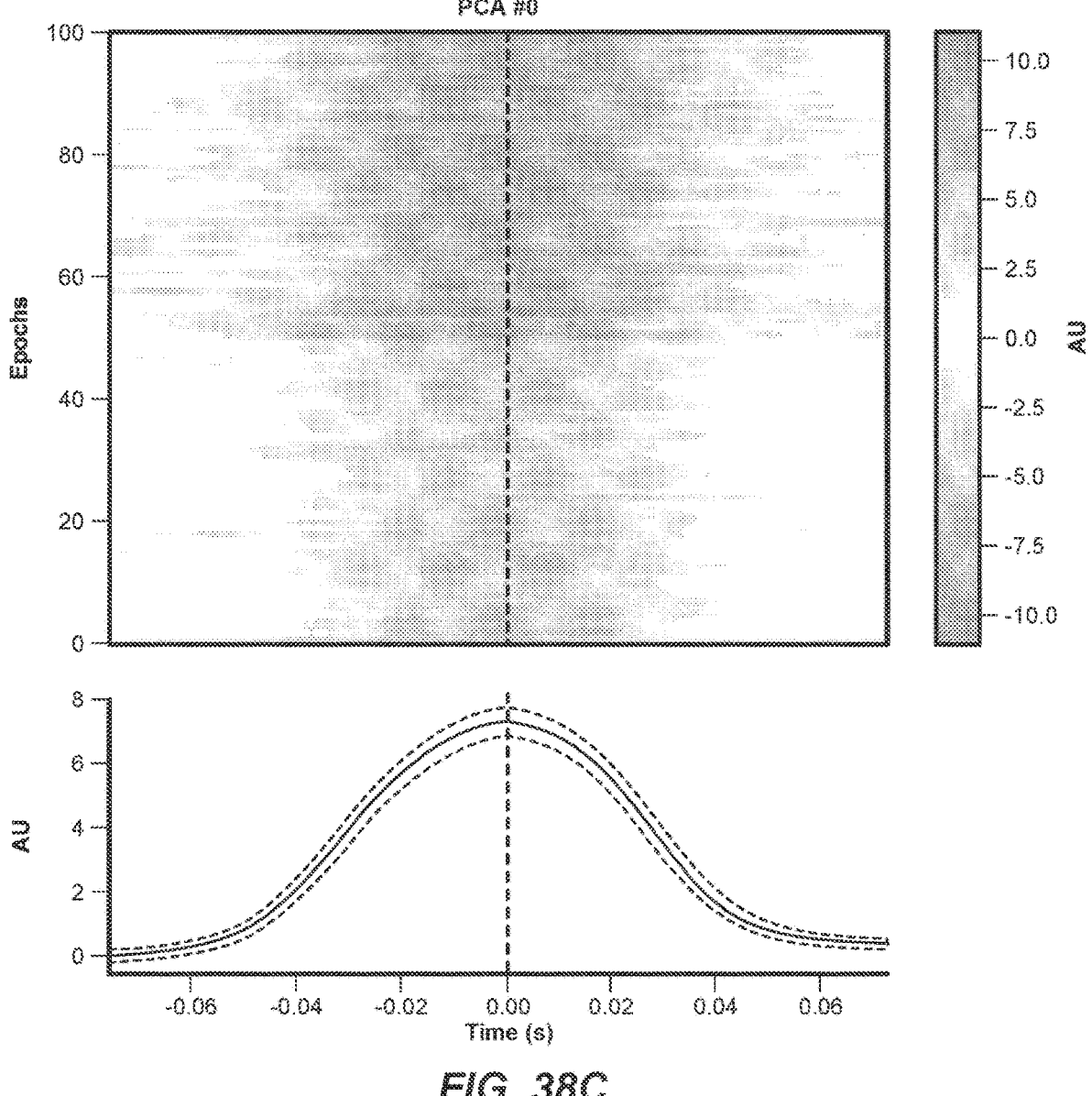

FIG. 38C illustrates each identified event as a row indicating the magnitude of the first principal component prior to temporal alignment.

Figure 38D:
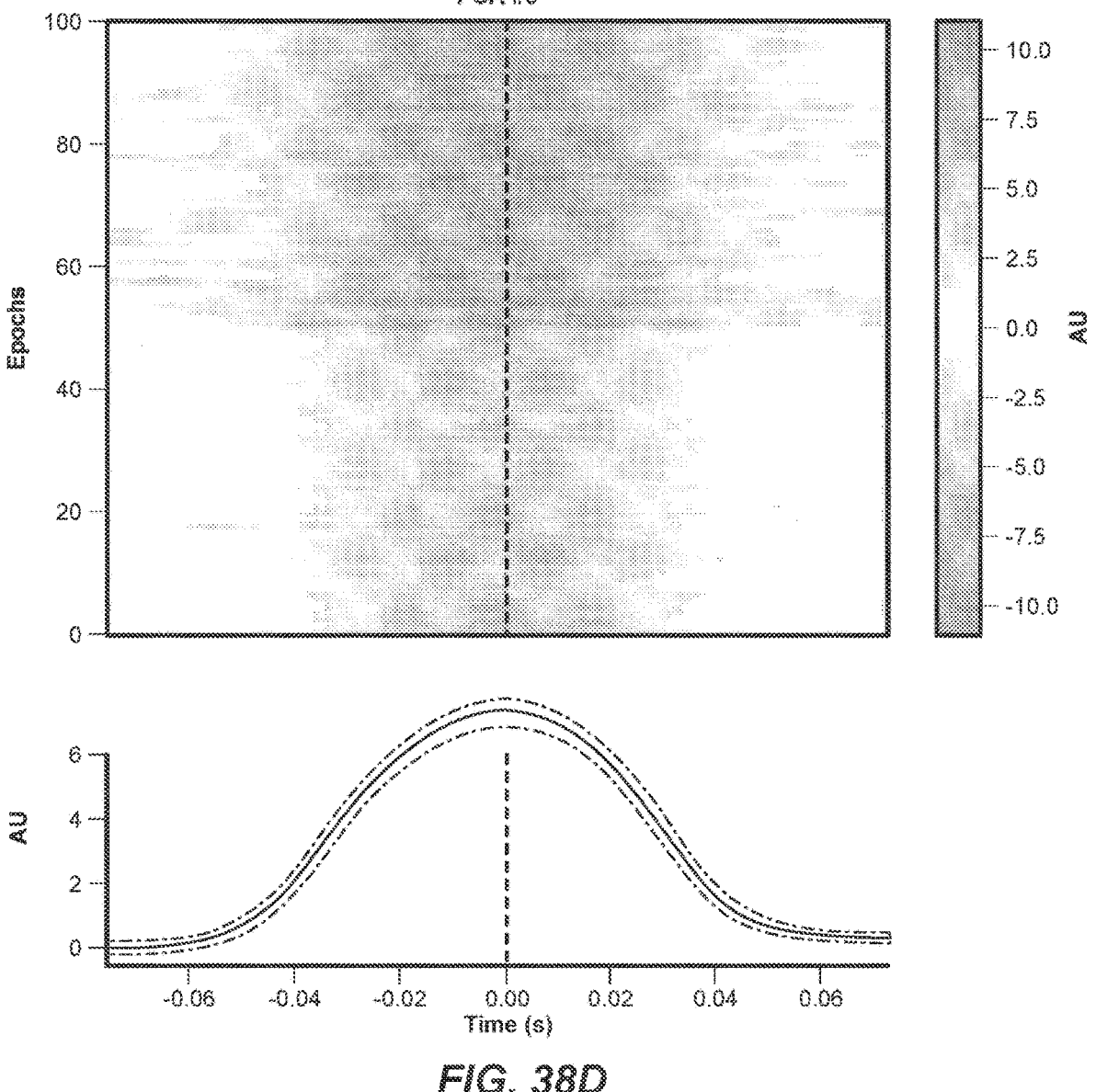

FIG. 38D illustrates the same identified events from FIG. 38C following temporal alignment.

Figure 38E:
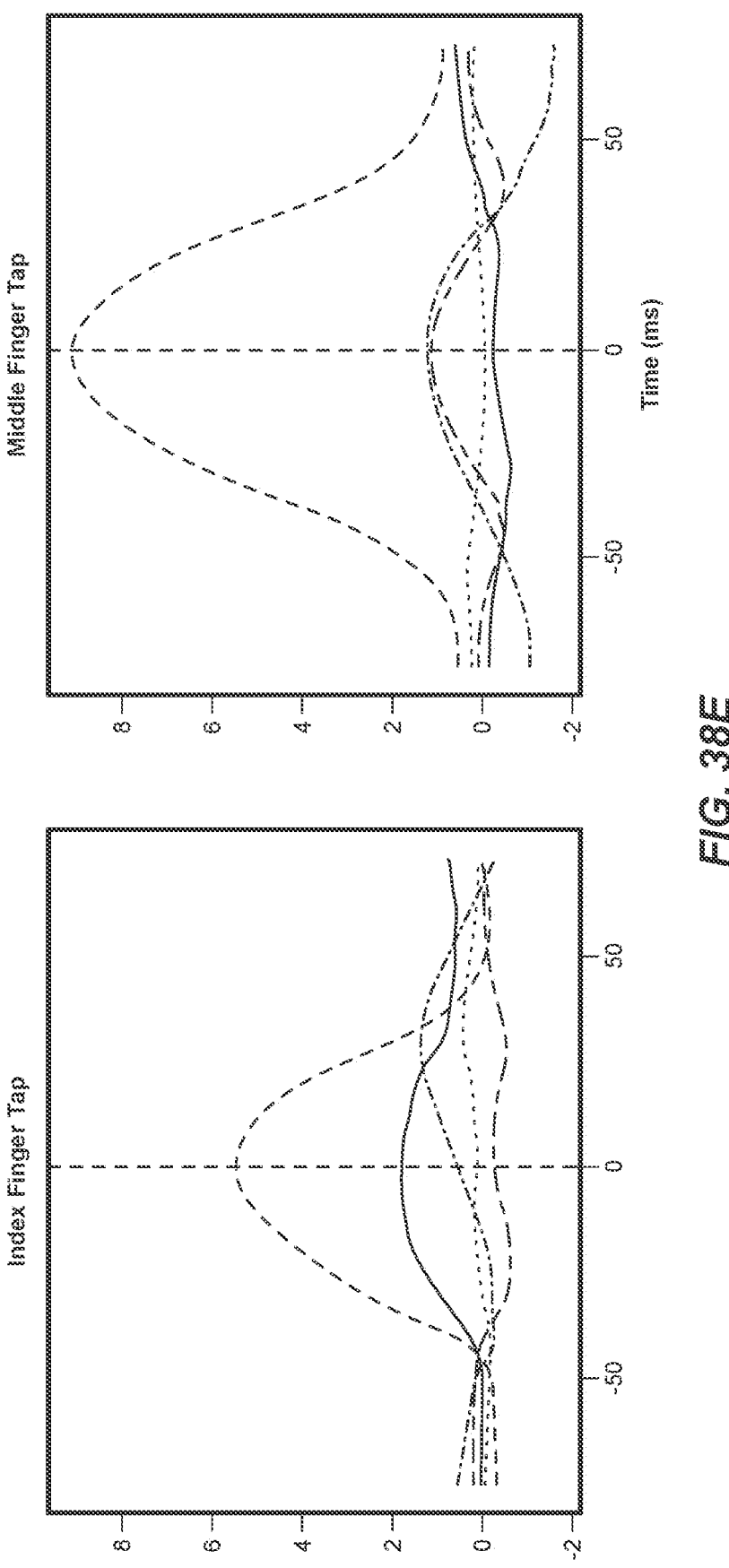

FIG. 38E illustrates an embodiment of index and middle finger tap templates.

Figure 38F:
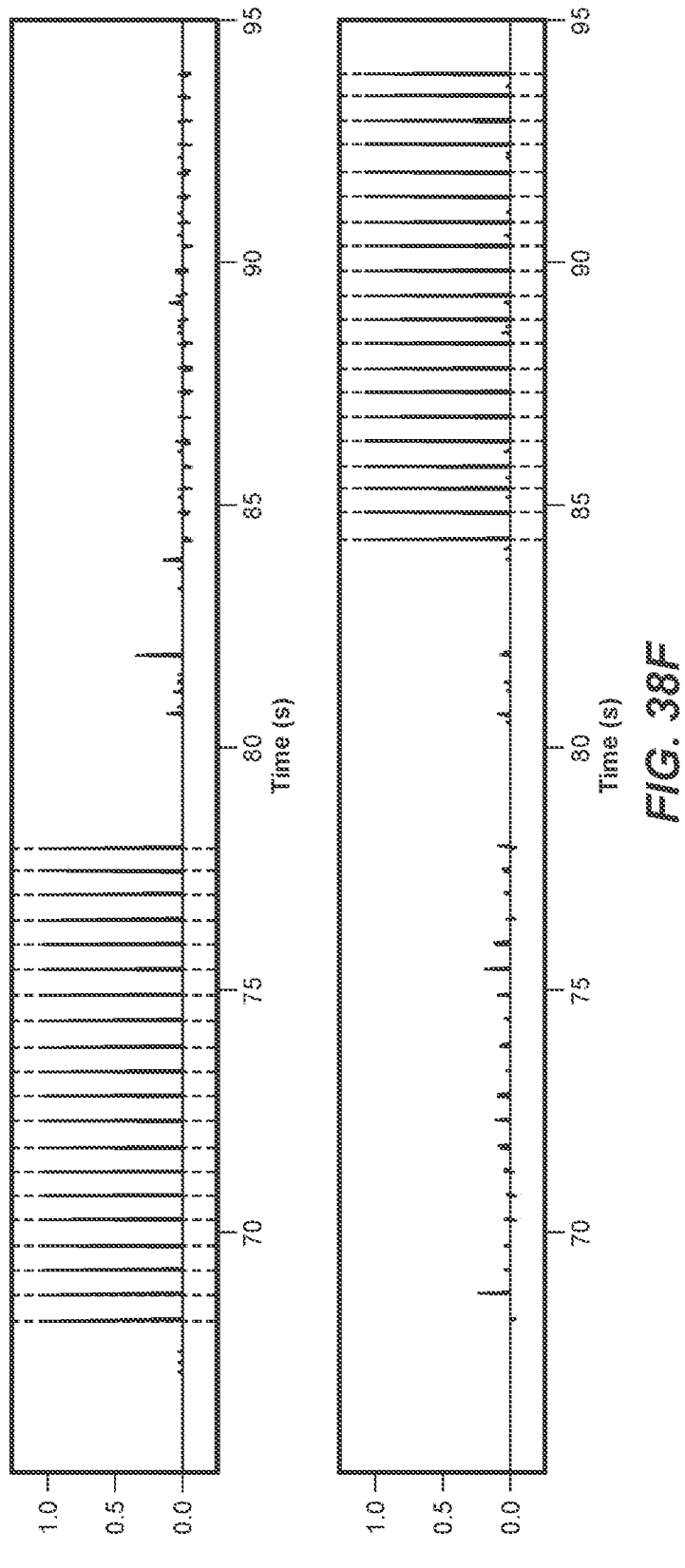

FIG. 38F illustrates a chart having example data for identifying and distinguishing two events.

Figure 39A:
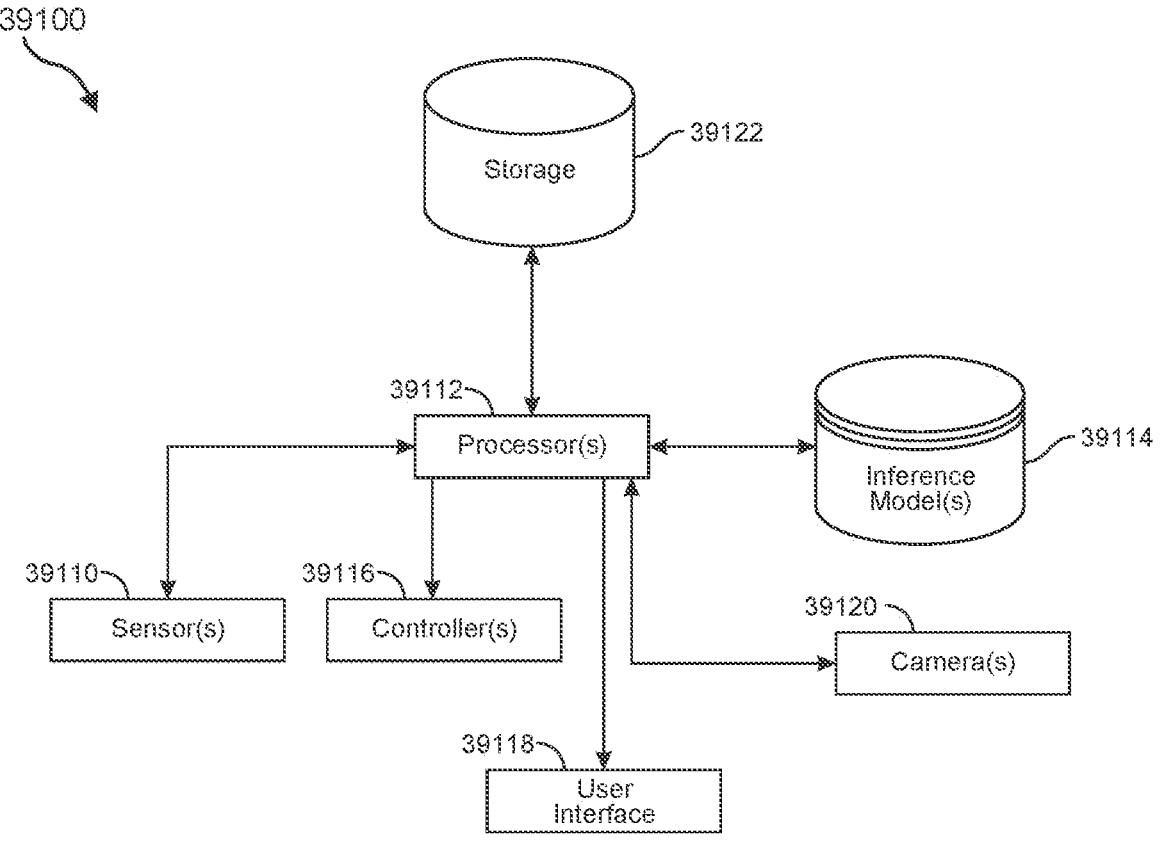

FIG. 39A is a block diagram of a computer-based system for processing sensor data and camera data, such as sensed signals obtained from neuromuscular sensors and image data obtained from a camera, in accordance with some embodiments of the technology described herein.

FIG. 39B-39E schematically illustrate patch type wearable systems with sensor electronics incorporated thereon, in accordance with some embodiments of the technology described herein.

Figure 39B:
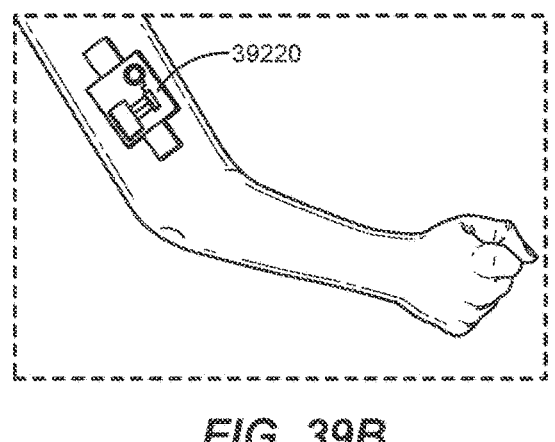
Figure 39C:
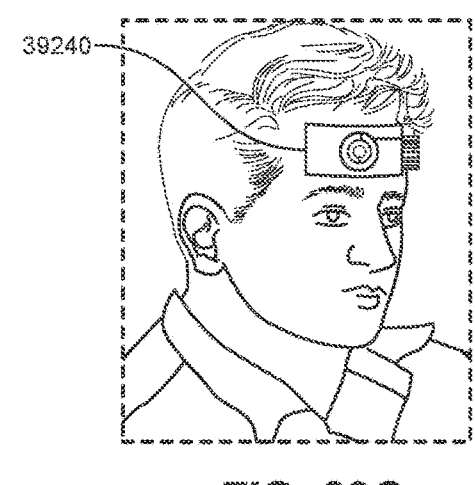
Figure 39D:
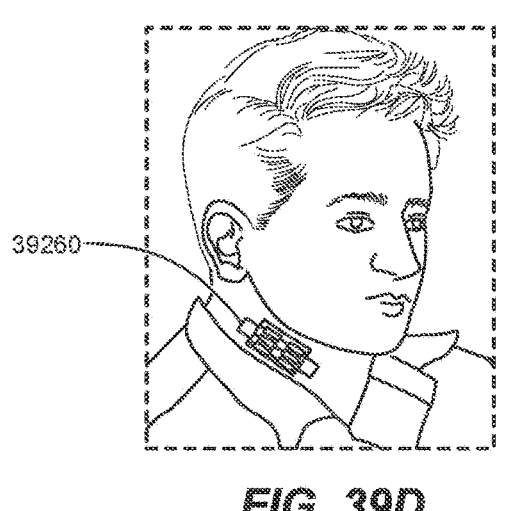
Figure 39E:
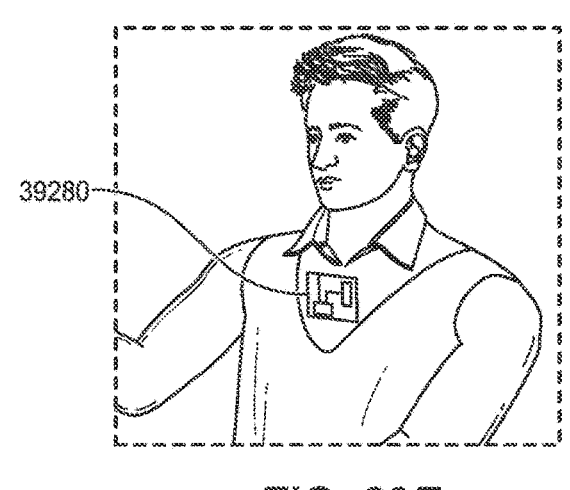
Figure 39F:
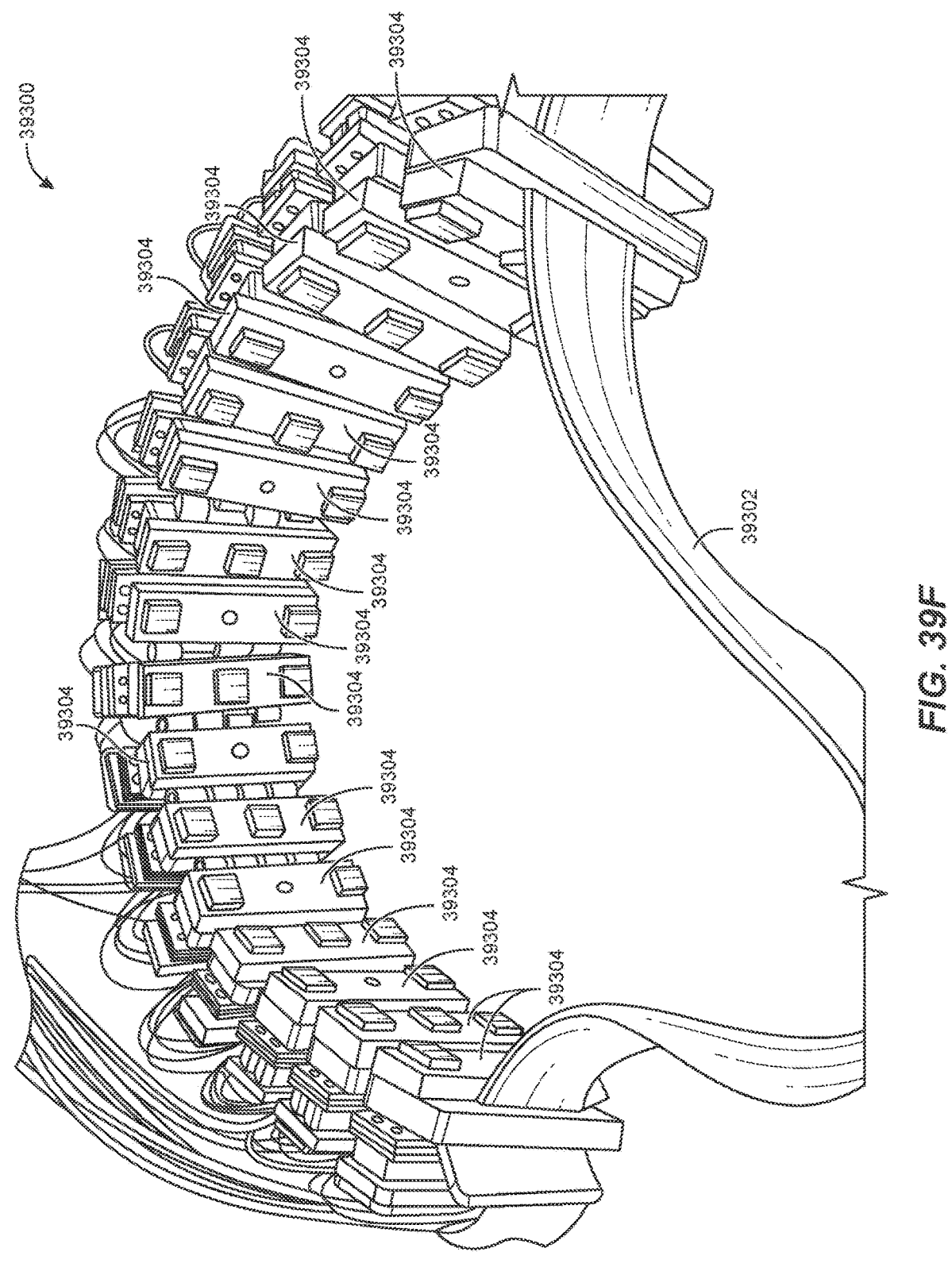

FIG. 39F illustrates a wearable system with neuromuscular sensors arranged on an adjustable belt, in accordance with some embodiments of the technology described herein.

Figures 39G, 39H:
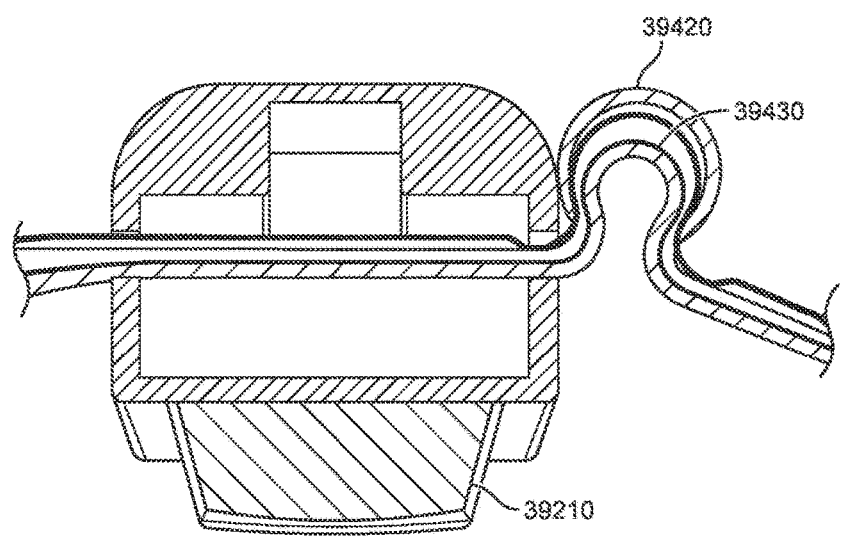

FIG. 39G illustrates a wearable system with sixteen neuromuscular sensors arranged circumferentially around a band, in accordance with some embodiments of the technology described herein; and FIG. 39H is a cross-sectional view through one of the sixteen neuromuscular sensors illustrated in FIG. 39G.

Figure 39I:
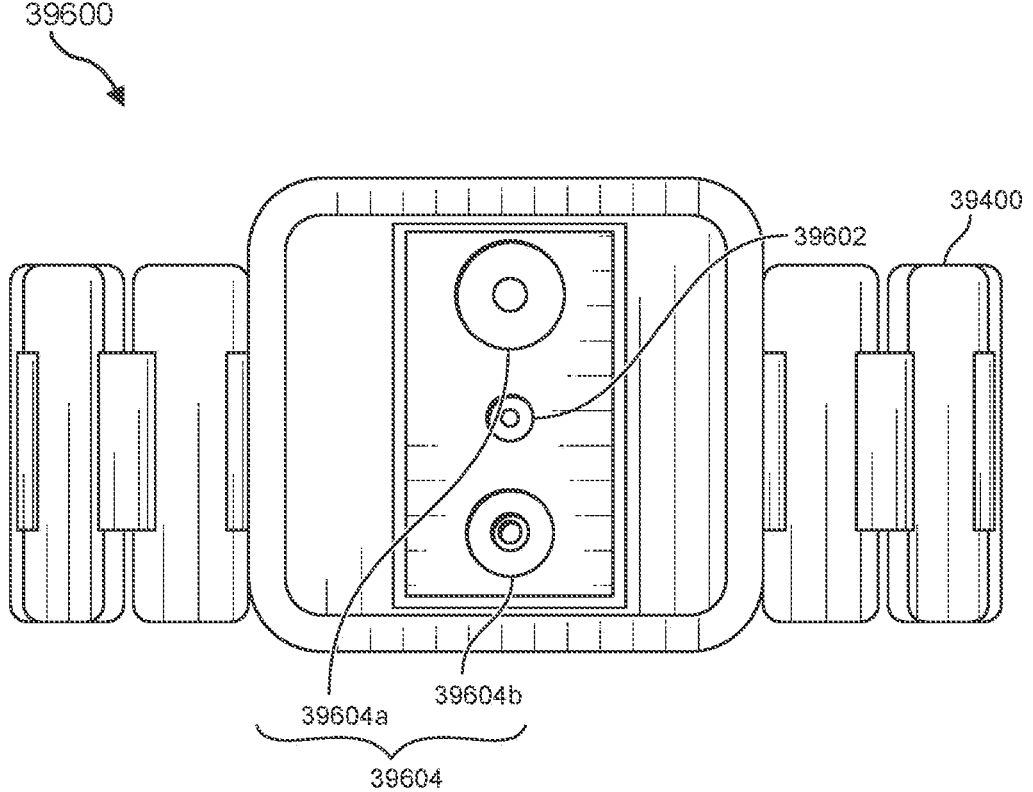

FIG. 39I schematically illustrates a camera usable in one or more system(s), in accordance with some embodiments of the technology described herein.

Figure 39J:
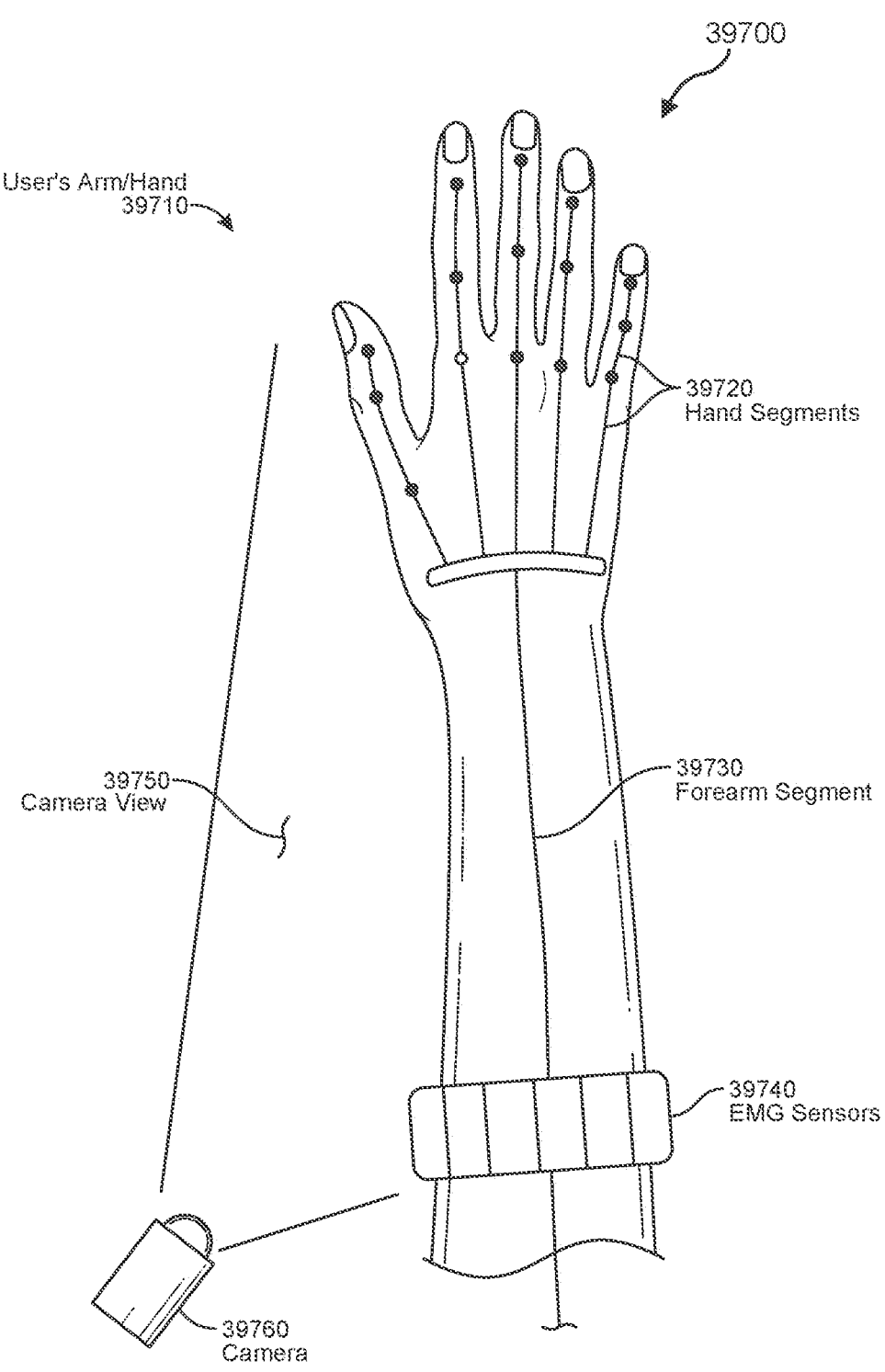

FIG. 39J is a diagram schematically illustrating an example implementation of a camera and a wearable system of neuromuscular sensors arranged on an arm, in accordance with some embodiments of the technology described herein.

Figure 39K:
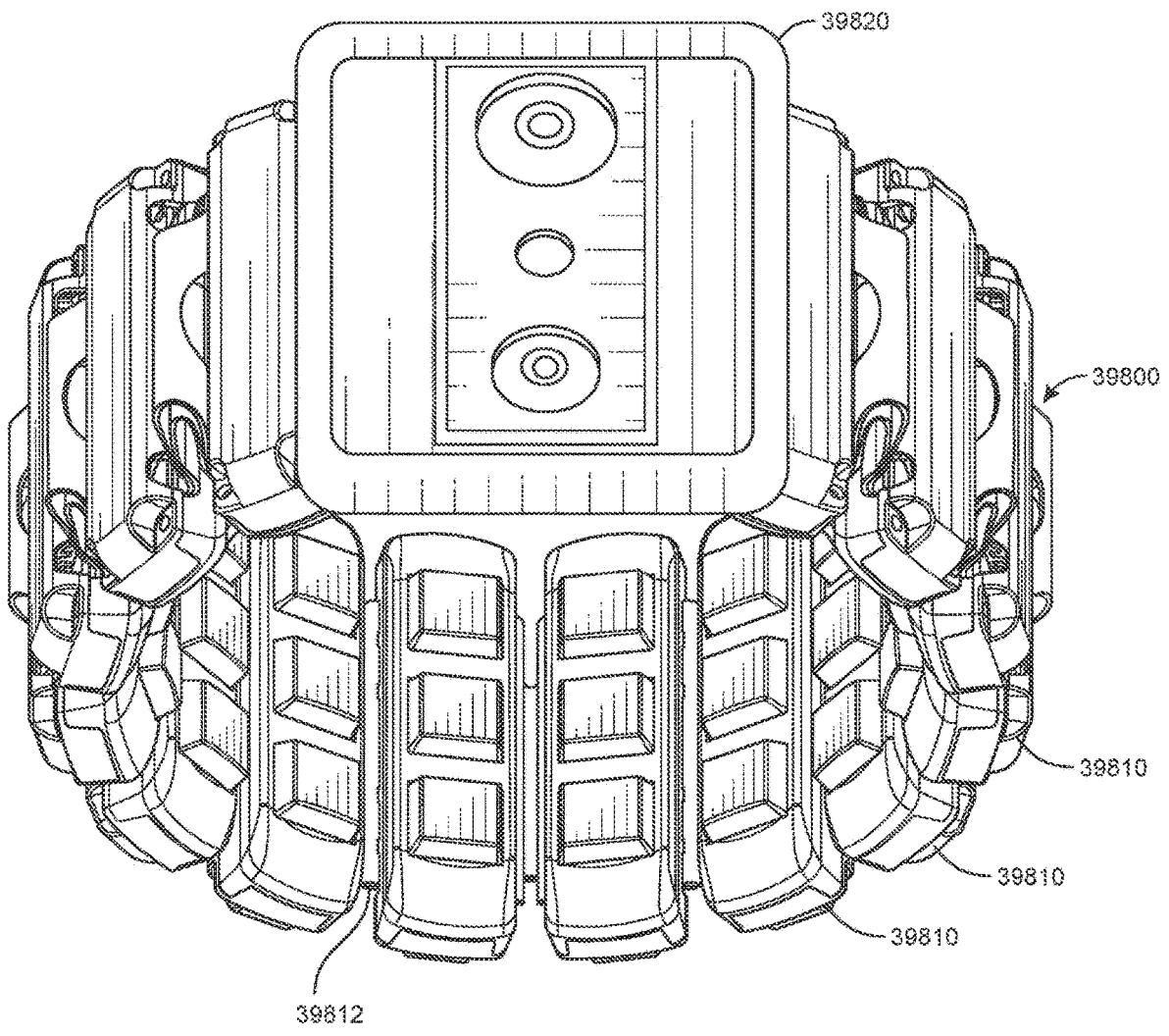

FIG. 39K is a diagram schematically illustrating another example implementation of a wearable system of a camera and neuromuscular sensors arranged on an arm, in accordance with some embodiments of the technology described herein.

Figure 39L:
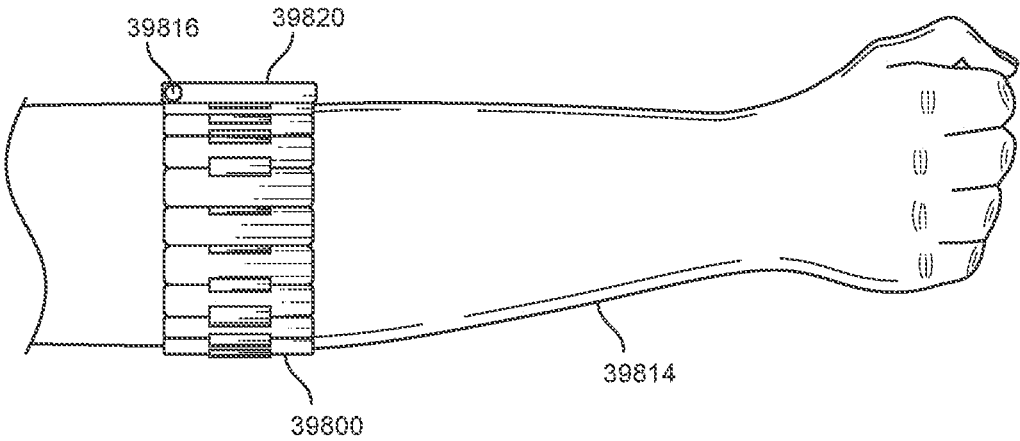
Figure 39M:
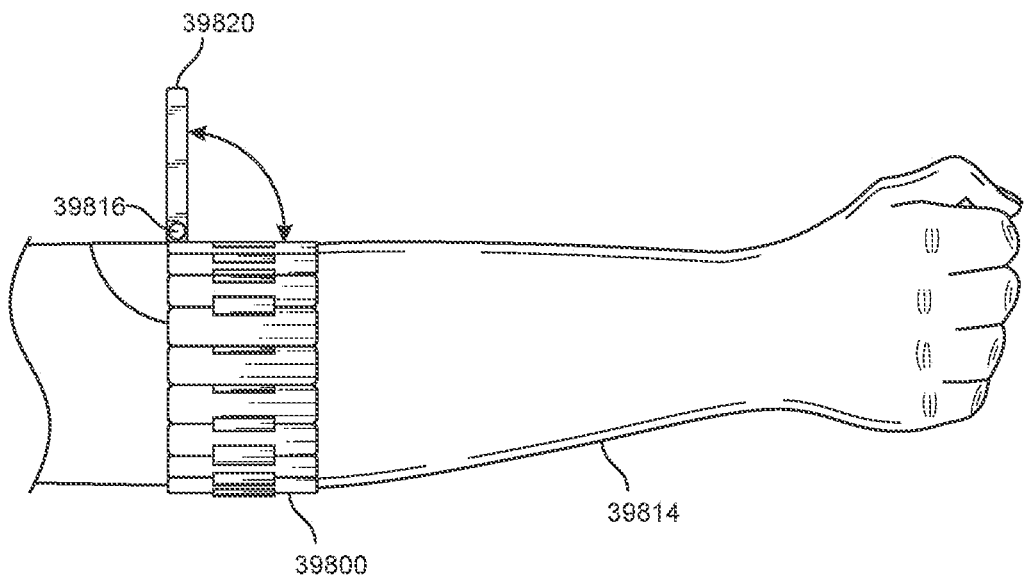

FIGS. 39L and 39M schematically illustrate a perpendicular orientation and an axial orientation of the camera of FIG. 39K, in accordance with some embodiments of the technology described herein.

Figure 39N:
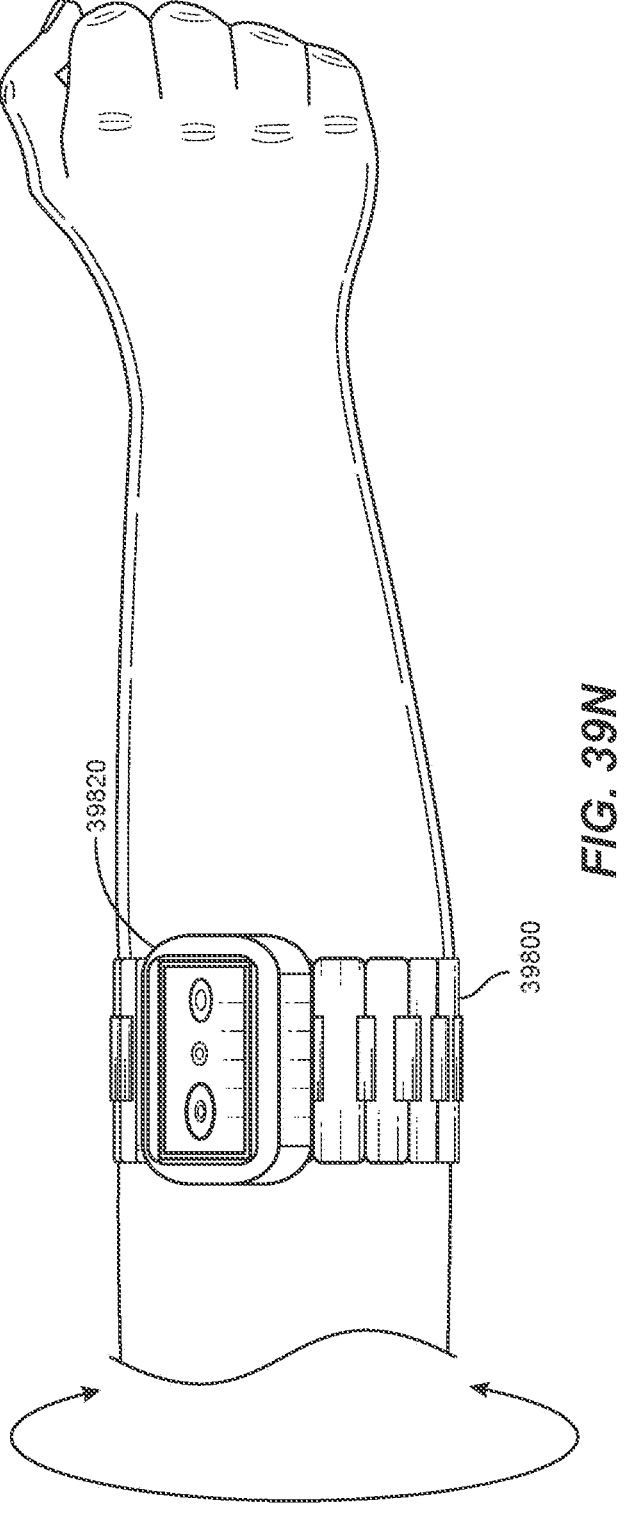
Figure 390:
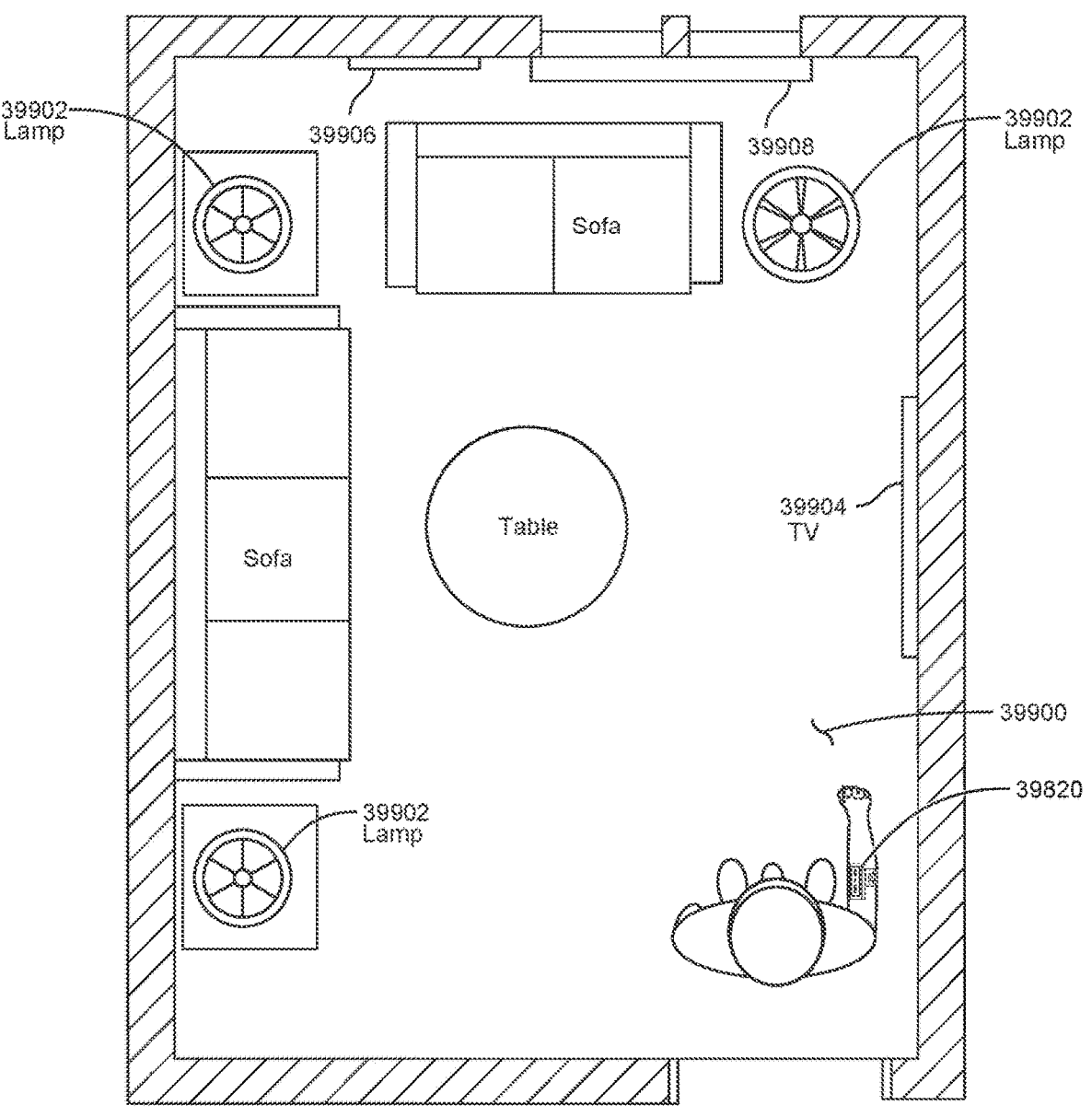

FIG. 39N shows that the wearable system comprising a camera that may be rotated in accordance with some embodiments of the technology described herein.

FIG. 39O schematically illustrates a living-room environment in which smart devices are located, in accordance with some embodiments of the technology described herein.

FIG. 39P is a block diagram of a distributed computer-based system that integrates an XR system with a neuromuscular activity system, in accordance with some embodiments of the technology described herein.

FIG. 39Q shows a flowchart of a process in which neuromuscular signals and camera data are used to capture information of an environment to generate a 3D map of the environment, in accordance with some embodiments of the technology described herein.

FIG. 39R shows a flowchart of a process to generate a 3D map usable to control smart devices of an environment, in accordance with some embodiments of the technology described herein.

Figure 39S:
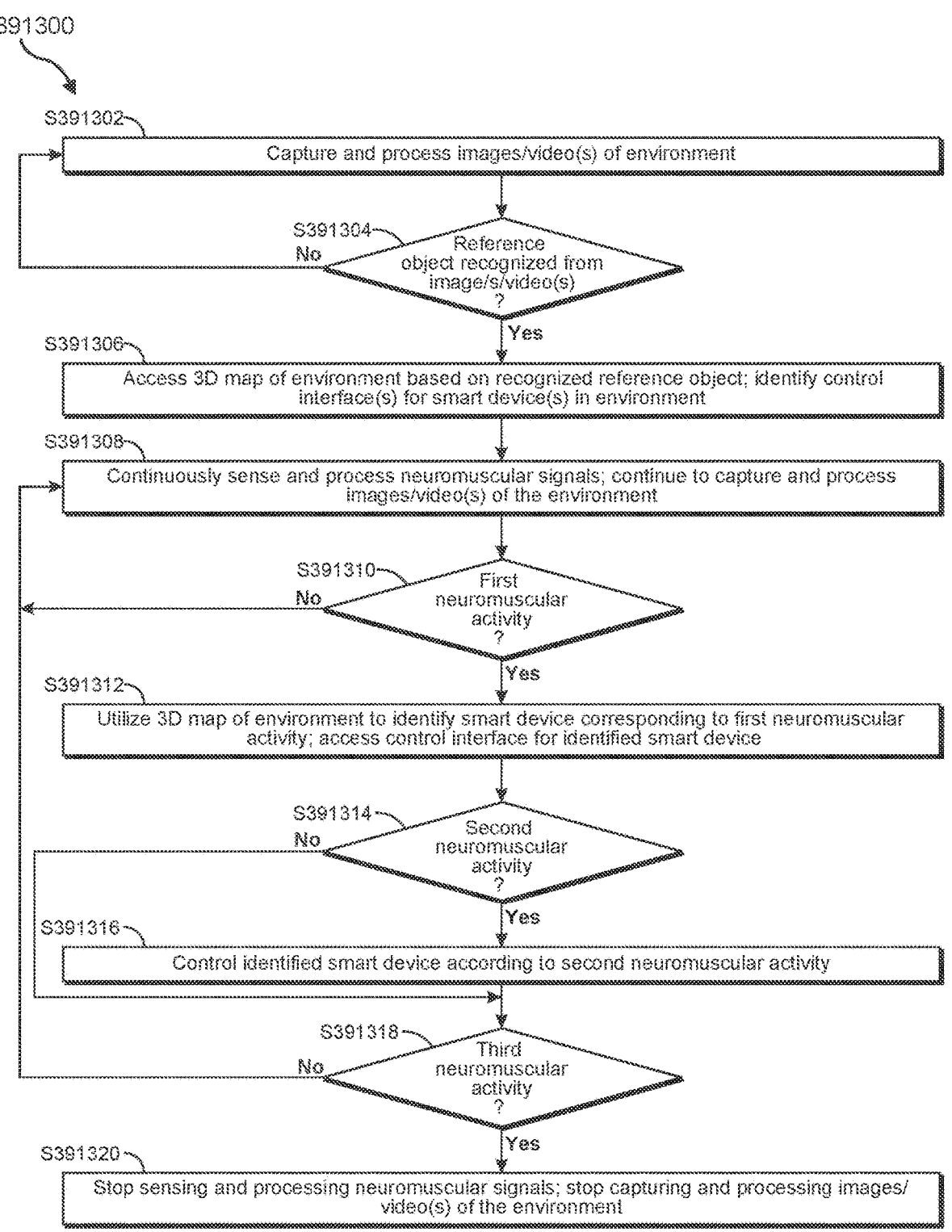

FIG. 39S shows a flowchart of a process in which neuromuscular signals and camera data are used in conjunction with a 3D map of an environment to control smart devices in the environment, in accordance with some embodiments of the technology described herein.

Figure 39U:
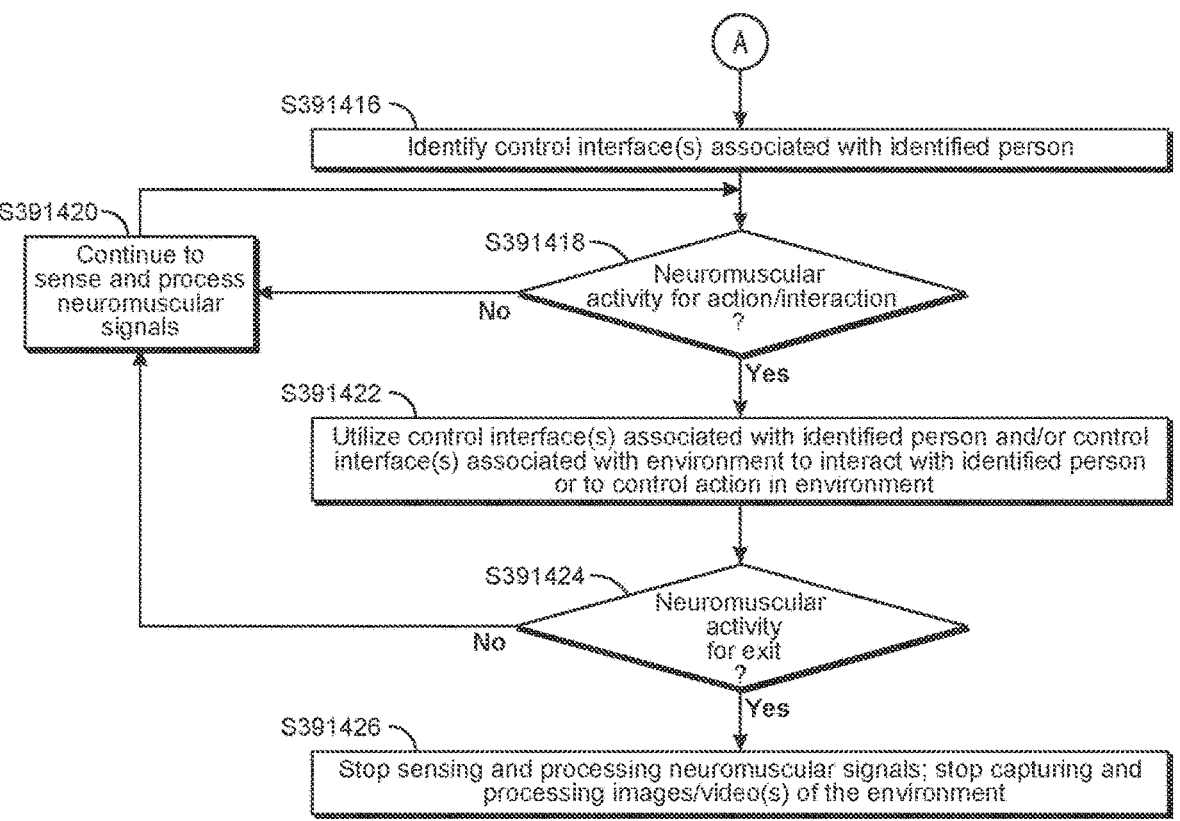

FIGS. 39T and 39U show a flowchart of a process in which neuromuscular signals and camera data are used to control interactions in an environment, including interactions with another person in the environment, in accordance with some embodiments of the technology described herein.

Figure 40A:
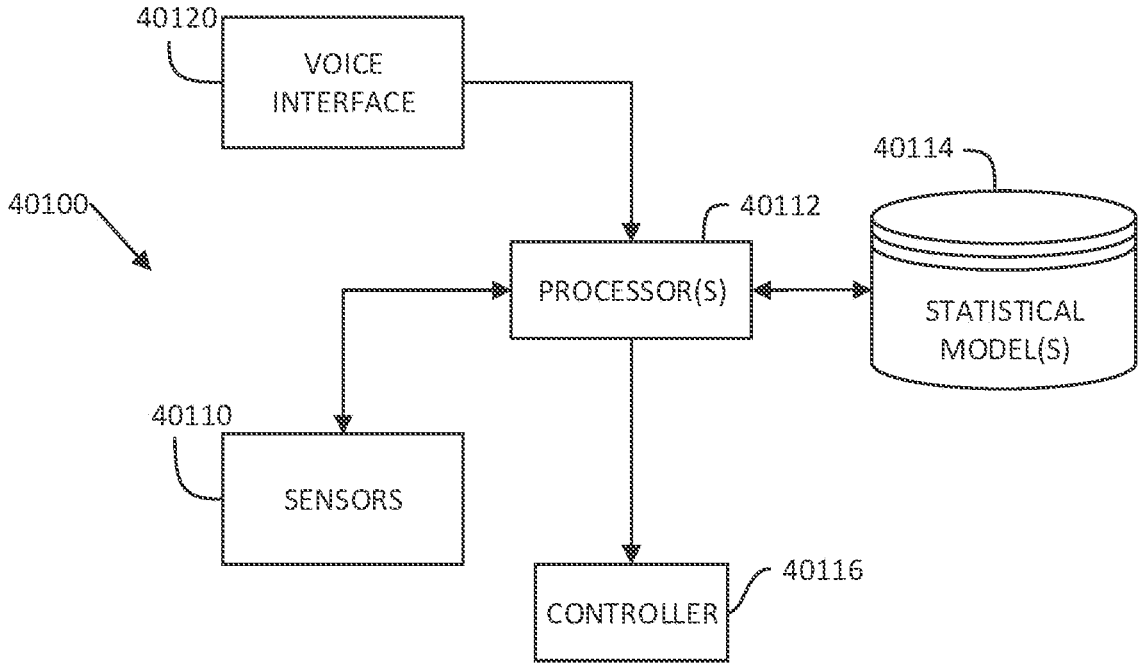

FIG. 40A is a schematic diagram of a computer-based system for using neuromuscular information to improve speech recognition in accordance with some embodiments of the technology described herein.

Figure 40B:
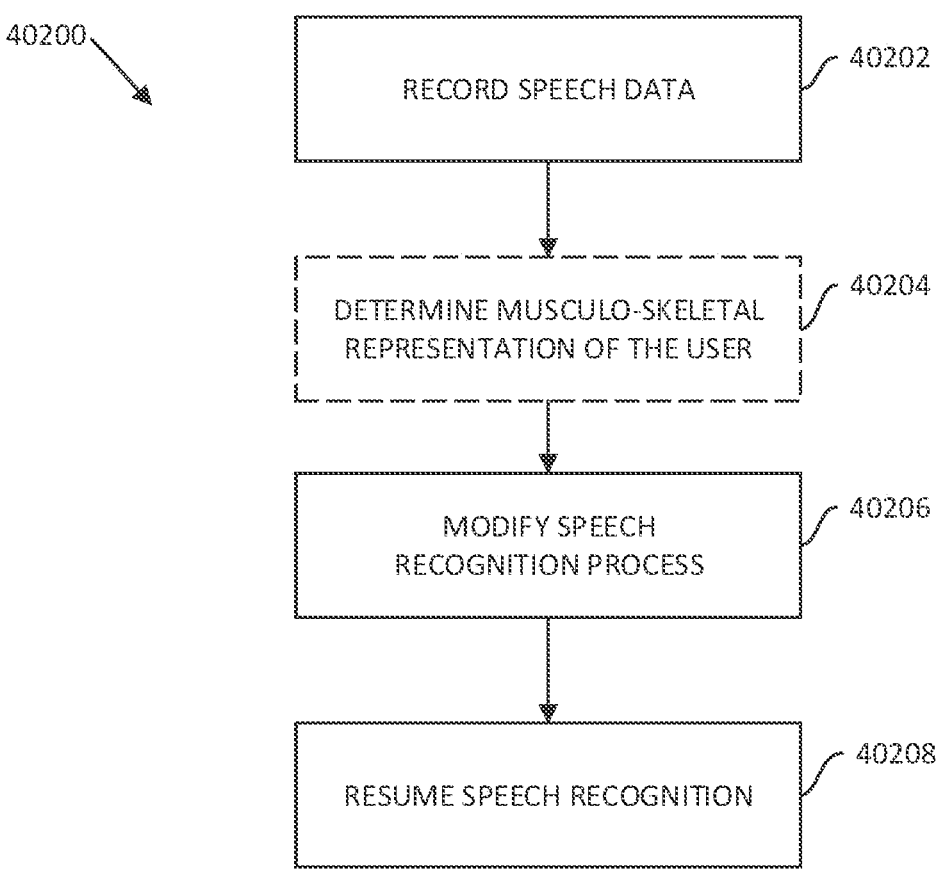

FIG. 40B is a flowchart of an illustrative process for using neuromuscular information to improve speech recognition, in accordance with some embodiments of the technology described herein.

Figure 40C:
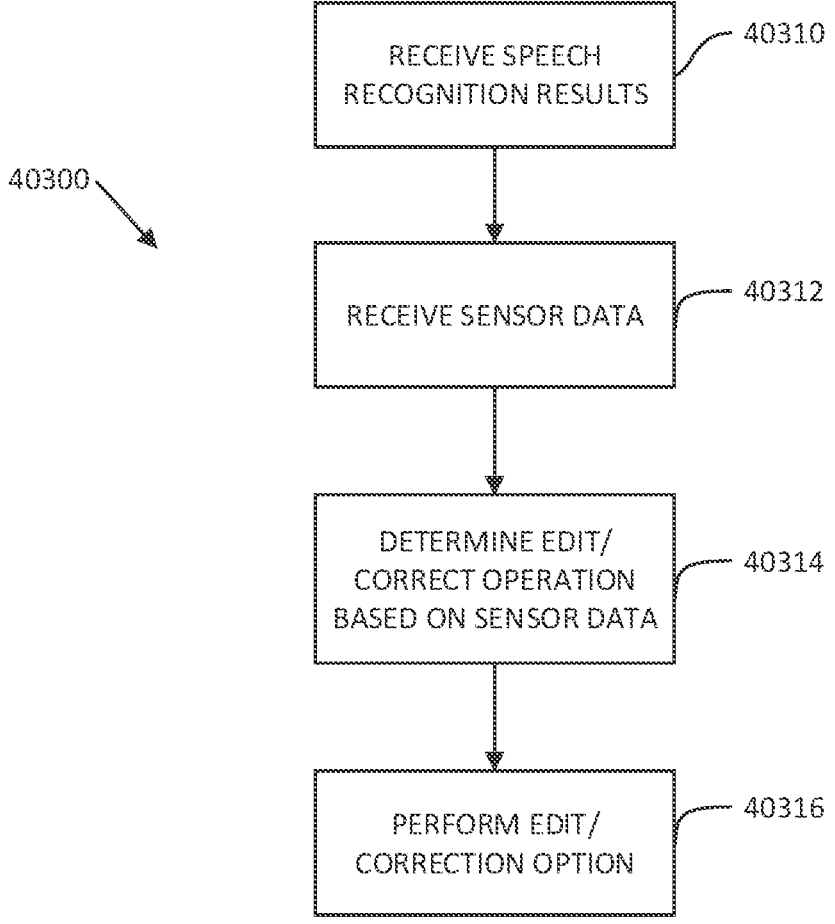

FIG. 40C is a flowchart of another illustrative process for using neuromuscular information to improve speech recognition, in accordance with some embodiments of the technology described herein.

Figure 40D:
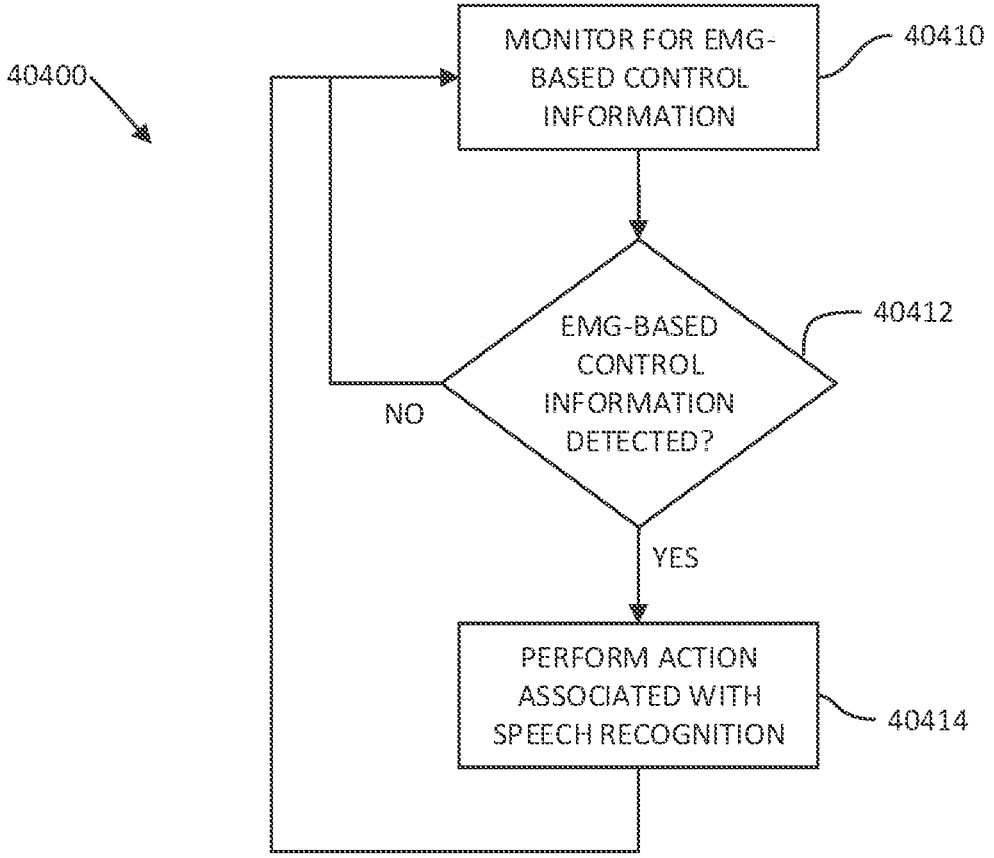

FIG. 40D is a flowchart of yet another illustrative process for using neuromuscular information to improve speech recognition, in accordance with some embodiments of the technology described herein.

Figure 40E:
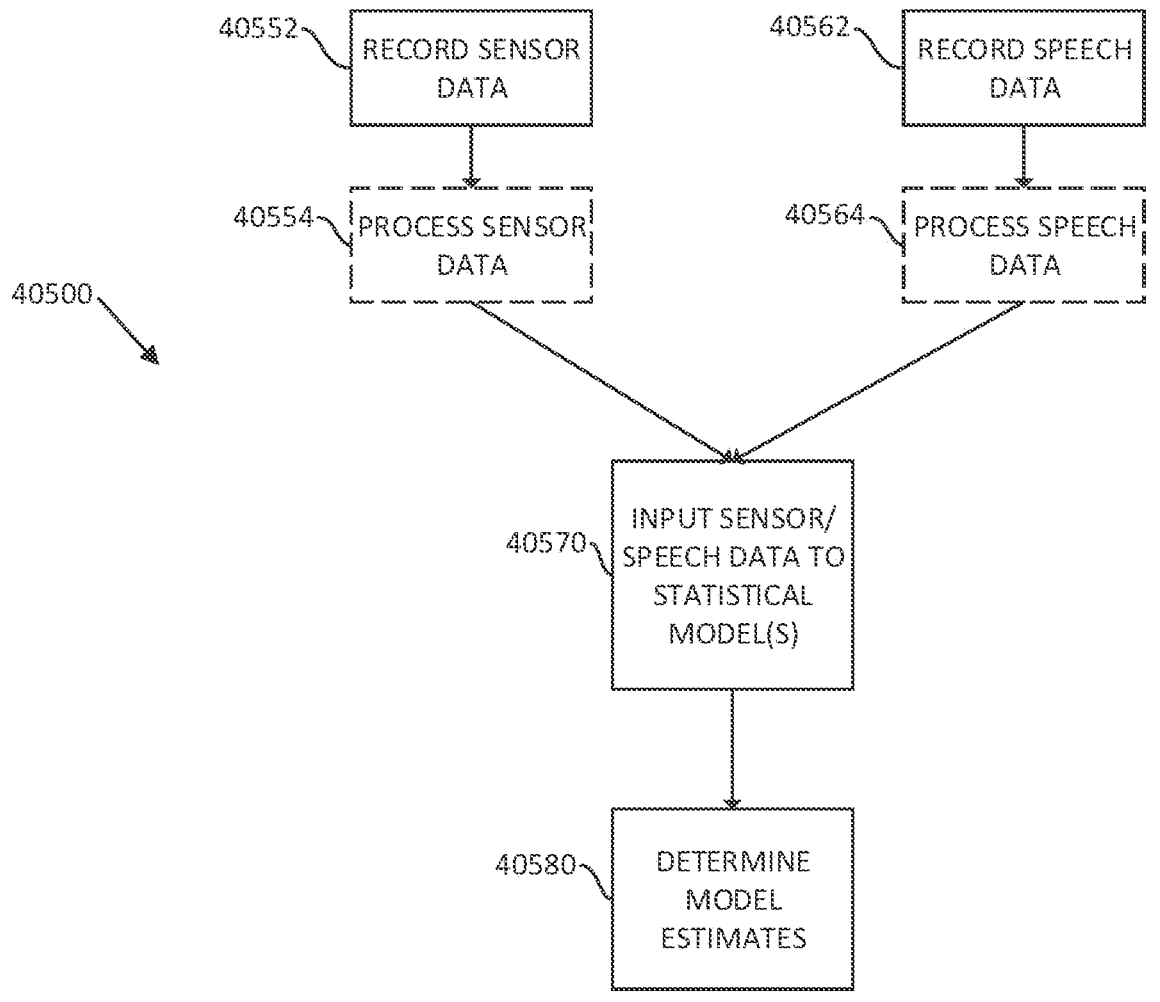

FIG. 40E is a flowchart of an illustrative process for using neuromuscular information to improve speech recognition in accordance with some embodiments of the technology described herein.

Throughout the drawings, identical reference characters and descriptions indicate similar, but not necessarily identical, elements. While the exemplary embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the present disclosure covers all modifications, equivalents, and alternatives falling within the scope of the appended claims.

DETAILED DESCRIPTION

The inventors have developed novel techniques for controlling AR systems as well as other types of XR systems, such as VR systems and MR systems. Various embodiments of the technologies presented herein offer certain advantages, including avoiding the use of an undesirable or burdensome physical keyboard or microphone; overcoming issues associated with time-consuming and/or high-latency processing of low-quality images of a user captured by a camera; allowing for capture and detection of subtle, small, or fast movements and/or variations in pressure on an object (e.g., varying amounts of force exerted through a stylus, writing instrument, or finger being pressed against a surface) that can be important for resolving, e.g., text input; collecting and analyzing various sensory information that enhances a control identification process, which may not be readily achievable using conventional input devices; and allowing for hand-based control to be possible in cases where a user's hand is obscured or outside a camera's field of view, e.g., in the user's pocket, or while the user is wearing a glove.

Some embodiments of the technology described herein are directed to coupling a system that senses neuromuscular signals, via neuromuscular sensors worn by a user, with a system that performs AR functions. In particular, a neuromuscular system that senses neuromuscular signals for the purpose of determining a position of a body part (e.g., a hand, an arm, etc.) may be used in conjunction with an AR system to provide an improved AR experience for a user. For instance, information gained within both systems may be used to improve the overall AR experience. The AR system may include a camera to capture image information regarding one or more body part(s) of the user, and this image information may be used to improve the user's interaction with an AR environment produced by the AR system. For example, a musculoskeletal representation associated with one or more body part(s) of the user may be generated based on sensor data from the neuromuscular sensors, and image data of the user, captured by the camera in the AR system, may be used to supplement the sensor data to, for instance, enable a more realistic visualization of the user relative to one or more object(s) in the AR environment. In one implementation of this example, the image data of the user may be used to determine an object of interest to the user, and the sensor data may provide muscle activation information used to determine a type of action to be performed relative to the object and/or an amount of force to be used for the action (e.g., a gentle push of the object, a forceful push of the object, a tap on the object, etc.). In another implementation, display information in the AR environment may be used as feedback to the user to permit the user to more accurately control his/her musculoskeletal input (e.g., movement input) to the neuromuscular system.

The inventors recognize that neither cameras nor neuromuscular sensors are by themselves ideal input systems. Cameras such as those that may be provided in an AR system may provide good positional information (relative both to other skeletal segments and to external objects) when, e.g., joint segments of the user are clearly within view, but may be limited by field of view restrictions and occlusion, and may be ill-suited for measuring forces. At the same time, signals measured or detected by neuromuscular sensors (e.g., electromyography (EMG) signals or another modality of neuromuscular signals as described herein) may, on their own, be insufficient for distinguishing between forces that a user is applying against himself/herself versus forces that he/she applies to an external object, and such signals may not provide sufficiently accurate information about skeletal geometry, for example finger lengths. According to some embodiments, it is appreciated that it would be beneficial to increase the accuracy of AR systems and neuromuscular-sensor-based systems to provide more accurate and more realistic user experiences.

Some conventional AR systems include camera-based technologies that are used to identify and map physical objects in the user's real-world environment. Such camera-based technologies are often insufficient in measuring and enabling a full range of possible physical and virtual interactions with physical objects in an AR environment generated by an AR system. To this end, some embodiments of the technology described herein are directed to an AR-based system comprising an improved AR system that provides an enriched AR user experience through interpretation of neuromuscular signals obtained via a wearable neuromuscular-sensor device worn by a user of the AR-based system. In some embodiments, motor activity states determined from the neuromuscular signals may be used to determine whether and how a user is interacting with a physical object in the AR environment. In other embodiments, the motor activity states determined from the neuromuscular signals may be used to change a mode of the AR system, e.g., to turn a physical object into one or more "augmented" object(s) by activating a set of control actions for the physical object in response to the determined motor activity states. In various embodiments, visual indicators based on the user's neuromuscular signals may be used to improve user experience when the user interacts with physical objects in the AR environment. Further examples of using neuromuscular signals to enhance interactions with physical objects in an AR environment are described in more detail below.

As will be appreciated, although various embodiments may be described herein with reference to an AR-based system, the scope of the present technology disclosed herein is such that those embodiments may be implemented using other types of XR-based systems.

In accordance with some embodiments of the technology disclosed herein, neuromuscular signals sensed and recorded by one or more wearable sensors may be used to determine information a user's interaction or desired interaction with a physical object in an AR environment generated by an AR-based system. Such signals may also be referred to as "sensed signals" herein. Sensed signals may be used directly as an input to an AR system (e.g. by using motor-unit action potentials as an input signal) and/or the sensed signals may be processed (including by using an inference model as described herein) for the purpose of determining a movement, a force, and/or a position of a part of the user's body (e.g. fingers, hand, wrist, etc.). For example, neuromuscular signals obtained by neuromuscular sensors arranged on a wearable device may be used to determine a force (e.g., a grasping force) applied to a physical object. The inventors have recognized that a number of muscular activation states of a user may be identified from the sensed signals and/or from information based on the sensed signals, to provide an improved AR experience. The muscular activation states may include, but are not limited to, a static gesture or pose performed by the user, a dynamic gesture or motion performed by the user, a sub-muscular activation state of the user, a muscular tensing or relaxation performed by the user, or any combination of the foregoing. As described herein, the user's interaction with one or more physical objects in the AR environment can take many forms, including but not limited to: selection of one or more objects, control of one or more objects, activation or deactivation of one or more objects, adjustment of settings or features relating to one or more objects, etc. As will be appreciated, the user's interaction may take other forms enabled by the AR system for the environment, and need not be the interactions specifically listed herein. For instance, control performed in an AR environment may include control based on activation of one or more individual motor units, e.g., control based on a detected sub-muscular activation state of the user, such as a sensed tensing of a muscle. As will be appreciated, the phrases "sensed", "obtained", "collected", "sensed and recorded", "measured", "recorded", and the like, when used in conjunction with a sensor signal from a neuromuscular sensor comprises a signal detected by the sensor. As will be appreciated, signal may be recorded, or sensed and recorded, without storage in a nonvolatile memory, or the signal may be recorded, or sensed and recorded, with storage in a local nonvolatile memory or in an external nonvolatile memory. For example, after detection, the signal may be stored at the sensor "as-detected" (i.e., raw), or the signal may undergo processing at the sensor prior to storage at the sensor, or the signal may be communicated (e.g., via a Bluetooth technology or the like) to an external device for processing and/or storage, or any combination of the foregoing.

Identification of one or more muscular activation state(s) may allow a layered or multi-level approach to interacting with physical objects in an AR environment. For instance, at a first layer/level, one muscular activation state may indicate that the user is interacting with a physical object; at a second layer/level, another muscular activation state may indicate that the user wants to activate a set of virtual controls and/or features for the physical object in the AR environment with which they are interacting; and at a third layer/level, yet another muscular activation state may indicate which of the activated virtual controls and/or features the user wants to use when interacting with the object. It will be appreciated that any number of muscular activation states and layers may be used without departing from the scope of this disclosure. For example, in some embodiments, one or more muscular activation state(s) may correspond to a concurrent gesture based on activation of one or more motor units, e.g., the user's hand bending at the wrist while pointing the index finger at the object. In some embodiments, one or more muscular activation state(s) may correspond to a sequence of gestures based on activation of one or more motor units, e.g., the user's hand grasping the object and lifting the object. In some embodiments, a single muscular activation state may both indicate a user's desire to interact with a physical object and to activate a set of virtual controls and/or features for interacting with the object.

As an example, sensor signals may be sensed and recorded for a first activity of the user, e.g., a first gesture performed by the user, and a first muscular activation state of the user may be identified from these sensed signals using, for example, a trained inference model, as discussed below. The first muscular activation state may indicate that the user is interacting with a particular physical object (e.g., a writing implement) in the user's environment. In response to the system detecting the first activity, feedback may be provided to identify the interaction with the physical object indicated by the first muscular activation state. Examples of the types of feedback that may be provided in accordance with some embodiments of the present technology are discussed in more detail below. Sensor signals may continue to be sensed and recorded, and a second muscular activation state may be determined. Responsive to identifying the second muscular activation state (e.g., corresponding to a second gesture, which may be the same as or different from the first gesture), the AR system may activate a set of virtual controls (e.g., controls for selecting writing characteristics for a writing implement) for the object. Sensor signals may continue to be sensed and recorded, and a third muscular activation state may be determined. The third muscular activation state may indicate a selection from among the virtual controls. For example, the third muscular activation state may indicate a selection of a particular line thickness of the writing implement.

According to some embodiments, the muscular activation states may be identified, at least in part, from raw (e.g., unprocessed) sensor signals collected by one or more of the wearable sensors. In some embodiments, the muscular activation states may be identified, at least in part, from information based on the raw sensor signals (e.g., processed sensor signals), where the raw sensor signals collected by the one or more of the wearable sensors are processed to perform, e.g., amplification, filtering, rectification, and/or other form of signal processing, examples of which are described in more detail below. In some embodiments, the muscular activation states may be identified, at least in part, from an output of a trained inference model that receives the sensor signals (raw or processed versions of the sensor signals) as input.

As disclosed herein, muscular activation states, as determined based on sensor signals in accordance with one or more of the techniques described herein, may be used to interact with one or more physical object(s) in an AR environment without the need to rely on cumbersome and inefficient input devices, as discussed above. For example, sensor data (e.g., signals obtained from neuromuscular sensors or data derived from such signals) may be sensed and recorded, and muscular activation states may be identified from the sensor data without the user having to carry a controller and/or other input device(s), and without having the user remember complicated button or key manipulation sequences. Also, the identification of the muscular activation states (e.g., poses, gestures, etc.) from the sensor data can be performed relatively fast, thereby reducing the response times and latency associated with issuing control signals to the AR system. Furthermore, some embodiments of the technology described herein enable user customization of an AR-based system, such that each user may define a control scheme for interacting with physical objects in an AR environment of an AR system of the AR-based system, which is typically not possible with conventional AR systems.

Signals sensed by wearable sensors placed at locations on a user's body may be provided as input to an inference model trained to generate spatial information for rigid segments of a multi-segment articulated rigid-body model of a human body. The spatial information may include, for example, position information of one or more segments, orientation information of one or more segments, joint angles between segments, and the like. Based on the input, and as a result of training, the inference model may implicitly represent inferred motion of the articulated rigid body under defined movement constraints. The trained inference model may output data useable for applications such as applications for rendering a representation of the user's body in an XR environment (e.g., the AR environment mentioned above), in which the user may interact with one or more physical and/or one or more virtual object(s), and/or applications for monitoring the user's movements as the user performs a physical activity to assess, for example, whether the user is performing the physical activity in a desired manner. As will be appreciated, the output data from the trained inference model may be used for applications other than those specifically identified herein.

For instance, movement data obtained by a single movement sensor positioned on a user (e.g., on a user's wrist or arm) may be provided as input data to a trained inference model. Corresponding output data generated by the trained inference model may be used to determine spatial information for one or more segments of a multi-segment articulated rigid-body model for the user. For example, the output data may be used to determine the position and/or the orientation of one or more segments in the multi-segment articulated rigid body model. In another example, the output data may be used to determine angles between connected segments in the multi-segment articulated rigid-body model.

As will be appreciated, an inference model used in conjunction with neuromuscular signals may involve a generalized skeletal geometry for a type of user (e.g., a typical adult male, a typical child, a typical adult female) or may involve a user-specific skeletal geometry for a particular user.

Different types of sensors may be used to provide input data to a trained inference model, as discussed below.

As described briefly herein, in some embodiments of the present technology, various muscular activation states may be identified directly from sensor data. In other embodiments, handstates, gestures, postures, and the like (which may be referred to herein individually or collectively as muscular activation states) may be identified based, at least in part, on the output of a trained inference model. In some embodiments, the trained inference model may output motor-unit or muscle activations and/or position, orientation, and/or force estimates for segments of a computer-generated musculoskeletal model. In one example, all or portions of the human musculoskeletal system can be modeled as a multi-segment articulated rigid body system, with joints forming the interfaces between the different segments, and with joint angles defining the spatial relationships between connected segments in the model.

As used herein, the term "gestures" may refer to a static or dynamic configuration of one or more body parts including a position of the one or more body parts and forces associated with the configuration. For example, gestures may include discrete gestures, such as placing or pressing the palm of a hand down on a solid surface or grasping a ball, continuous gestures, such as waving a finger back and forth, grasping and throwing a ball, or a combination of discrete and continuous gestures. Gestures may include covert gestures that may be imperceptible to another person, such as slightly tensing a joint by co-contracting opposing muscles or using sub-muscular activations. In training an inference model, gestures may be defined using an application configured to prompt a user to perform the gestures or, alternatively, gestures may be arbitrarily defined by a user. The gestures performed by the user may include symbolic gestures (e.g., gestures mapped to other gestures, interactions, or commands, for example, based on a gesture vocabulary that specifies the mapping). In some cases, hand and arm gestures may be symbolic and used to communicate according to cultural standards.

In some embodiments of the technology described herein, sensor signals may be used to predict information about a position and/or a movement of a portion of a user's arm and/or the user's hand, which may be represented as a multi-segment articulated rigid-body system with joints connecting the multiple segments of the rigid-body system. For example, in the case of a hand movement, signals sensed and recorded by wearable neuromuscular sensors placed at locations on the user's body (e.g., the user's arm and/or wrist) may be provided as input to an inference model trained to predict estimates of the position (e.g., absolute position, relative position, orientation) and the force(s) associated with a plurality of rigid segments in a computer-based musculoskeletal representation associated with a hand when the user performs one or more hand movements. The combination of position information and force information associated with segments of a musculoskeletal representation associated with a hand may be referred to herein as a "handstate" of the musculoskeletal representation. As a user performs different movements, a trained inference model may interpret neuromuscular signals sensed and recorded by the wearable neuromuscular sensors into position and force estimates (handstate information) that are used to update the musculoskeletal representation. Because the neuromuscular signals may be continuously sensed and recorded, the musculoskeletal representation may be updated in real time and a visual representation of a hand (e.g., within an AR environment) may be rendered based on current estimates of the handstate. As will be appreciated, an estimate of a user's handstate may be used to determine a gesture being performed by the user and/or to predict a gesture that the user will perform.

Constraints on the movement at a joint are governed by the type of joint connecting the segments and the biological structures (e.g., muscles, tendons, ligaments) that may restrict the range of movement at the joint. For example, a shoulder joint connecting the upper arm to a torso of a human subject, and a hip joint connecting an upper leg to the torso, are ball and socket joints that permit extension and flexion movements as well as rotational movements. By contrast, an elbow joint connecting the upper arm and a lower arm (or forearm), and a knee joint connecting the upper leg and a lower leg of the human subject, allow for a more limited range of motion. In this example, a multi-segment articulated rigid body system may be used to model portions of the human musculoskeletal system. However, it should be appreciated that although some segments of the human musculoskeletal system (e.g., the forearm) may be approximated as a rigid body in the articulated rigid body system, such segments may each include multiple rigid structures (e.g., the forearm may include ulna and radius bones), which may enable more complex movements within the segment that is not explicitly considered by the rigid body model. Accordingly, a model of an articulated rigid body system for use with some embodiments of the technology described herein may include segments that represent a combination of body parts that are not strictly rigid bodies. It will be appreciated that physical models other than the multi-segment articulated rigid body system may be used to model portions of the human musculoskeletal system without departing from the scope of this disclosure.

Continuing with the example above, in kinematics, rigid bodies are objects that exhibit various attributes of motion (e.g., position, orientation, angular velocity, acceleration). Knowing the motion attributes of one segment of a rigid body enables the motion attributes for other segments of the rigid body to be determined based on constraints in how the segments are connected. For example, the hand may be modeled as a multi-segment articulated body, with joints in the wrist and each finger forming interfaces between the multiple segments in the model. In some embodiments, movements of the segments in the rigid body model can be simulated as an articulated rigid body system in which position (e.g., actual position, relative position, or orientation) information of a segment relative to other segments in the model are predicted using a trained inference model.

For some embodiments of the present technology described herein, the portion of the human body approximated by a musculoskeletal representation is a hand or a combination of a hand with one or more arm segments. The information used to describe a current state of the positional relationships between segments, force relationships for individual segments or combinations of segments, and muscle and motor unit activation relationships between segments, in the musculoskeletal representation is referred to herein as the handstate of the musculoskeletal representation (see discussion above). It should be appreciated, however, that the techniques described herein are also applicable to musculoskeletal representations of portions of the body other than the hand including, but not limited to, an arm, a leg, a foot, a torso, a neck, or any combination of the foregoing.

In addition to spatial (e.g., position and/or orientation) information, some embodiments enable a prediction of force information associated with one or more segments of the musculoskeletal representation. For example, linear forces or rotational (torque) forces exerted by one or more segments may be estimated. Examples of linear forces include, but are not limited to, the force of a finger or hand pressing on a solid object such as a table, and a force exerted when two segments (e.g., two fingers) are pinched together. Examples of rotational forces include, but are not limited to, rotational forces created when a segment, such as in a wrist or a finger, is twisted or flexed relative to another segment. In some embodiments, the force information determined as a portion of a current handstate estimate includes one or more of pinching force information, grasping force information, and information about co-contraction forces between muscles represented by the musculoskeletal representation.

Figure 1:
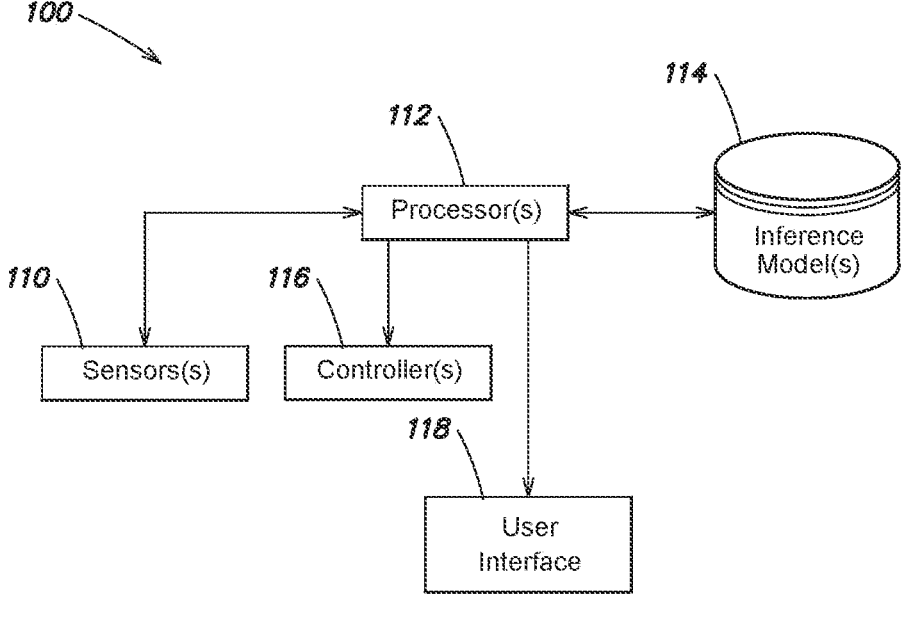
FIG. 1 is a schematic diagram of a computer-based system for processing neuromuscular sensor data, such as signals obtained from neuromuscular sensors, in accordance with some embodiments of the technology described herein.

Turning now to the figures, FIG. 1 schematically illustrates a system 100, for example, a neuromuscular activity system, in accordance with some embodiments of the technology described herein. The system 100 may comprise one or more sensor(s) 110 configured to sense and record signals resulting from activation of motor units within one or more portion(s) of a human body. The sensor(s) 110 may include one or more neuromuscular sensor(s) configured to sense and record signals arising from neuromuscular activity in skeletal muscle of a human body. The term "neuromuscular activity" as used herein refers to neural activation of spinal motor neurons or units that innervate a muscle, muscle activation, muscle contraction, or any combination of the neural activation, muscle activation, and muscle contraction. The one or more neuromuscular sensor(s) may include one or more electromyography (EMG) sensors, one or more mechanomyography (MMG) sensors, one or more sonomyography (SMG) sensors, a combination of two or more types of EMG sensors, MMG sensors, and SMG sensors, and/or one or more sensors of any suitable type able to detect neuromuscular signals. In some embodiments, information relating to an interaction of a user with a physical object in an AR environment may be determined from neuromuscular signals sensed by the one or more neuromuscular sensor(s). Spatial information (e.g., position and/or orientation information) and force information relating to the movement may be predicted based on the sensed neuromuscular signals as the user moves over time. In some embodiments, the one or more neuromuscular sensor(s) may sense muscular activity related to movement caused by external objects, for example, movement of a hand being pushed by an external object.

The one or more sensor(s) 110 may include one or more auxiliary sensor(s), such as one or more Inertial Measurement Unit(s) or IMU(s), which measure a combination of physical aspects of motion, using, for example, an accelerometer, a gyroscope, a magnetometer, or any combination of one or more accelerometers, gyroscopes and magnetometers. In some embodiments, one or more IMU(s) may be used to sense information about movement of the part of the body on which the IMU(s) is or are attached, and information derived from the sensed IMU data (e.g., position and/or orientation information) may be tracked as the user moves over time. For example, one or more IMU(s) may be used to track movements of portions (e.g., arms, legs) of a user's body proximal to the user's torso relative to the IMU(s) as the user moves over time.

In embodiments that include at least one IMU and one or more neuromuscular sensor(s), the IMU(s) and the neuromuscular sensor(s) may be arranged to detect movement of different parts of a human body. For example, the IMU(s) may be arranged to detect movements of one or more body segments proximal to the torso (e.g., movements of an upper arm), whereas the neuromuscular sensors may be arranged to detect motor unit activity within one or more body segments distal to the torso (e.g., movements of a lower arm (forearm) or a wrist). It should be appreciated, however, that the sensors (i.e., the IMU(s) and the neuromuscular sensor(s)) may be arranged in any suitable way, and embodiments of the technology described herein are not limited based on the particular sensor arrangement. For example, in some embodiments, at least one IMU and a plurality of neuromuscular sensors may be co-located on a body segment to track motor unit activity and/or movements of the body segment using different types of measurements. In one implementation, an IMU and a plurality of EMG sensors may be arranged on a wearable device structured to be worn around the lower arm or the wrist of a user. In such an arrangement, the IMU may be configured to track, over time, movement information (e.g., positioning and/or orientation) associated with one or more arm segments, to determine, for example, whether the user has raised or lowered his/her arm, whereas the EMG sensors may be configured to determine finer-grained or more subtle movement information and/or sub-muscular information associated with activation of muscular or sub-muscular structures in muscles of the wrist and/or the hand.

As the tension of a muscle increases during performance of a motor task, the firing rates of active neurons increases and additional neurons may become active, which is a process that may be referred to as motor-unit recruitment. The pattern by which neurons become active and increase their firing rate is stereotyped, such that expected motor-unit recruitment patterns, may define an activity manifold associated with standard or normal movement. In some embodiments, sensor signals may identify activation of a single motor unit or a group of motor units that are "off-manifold," in that the pattern of motor-unit activation is different than an expected or typical motor-unit recruitment pattern. Such off-manifold activation may be referred to herein as "sub-muscular activation" or "activation of a sub-muscular structure," where a sub-muscular structure refers to the single motor unit or the group of motor units associated with the off-manifold activation. Examples of off-manifold motor-unit recruitment patterns include, but are not limited to, selectively activating a higher-threshold motor unit without activating a lower-threshold motor unit that would normally be activated earlier in the recruitment order and modulating the firing rate of a motor unit across a substantial range without modulating the activity of other neurons that would normally be co-modulated in typical motor-unit recruitment patterns. In some embodiments, the one or more neuromuscular sensors may be arranged relative to the human body and used to sense sub-muscular activation without observable movement, i.e., without a corresponding movement of the body that can be readily observed. Sub-muscular activation may be used, at least in part, to interact with physical objects in an AR environment, in accordance with some embodiments of the technology described herein.

Some or all of the sensor(s) 110 may each include one or more sensing components configured to sense information about a user. In the case of IMUs, the sensing component(s) of an IMU may include one or more: accelerometer, gyroscope, magnetometer, or any combination thereof, to measure or sense characteristics of body motion, examples of which include, but are not limited to, acceleration, angular velocity, and a magnetic field around the body during the body motion. In the case of neuromuscular sensors, the sensing component(s) may include, but are not limited to, electrodes that detect electric potentials on the surface of the body (e.g., for EMG sensors), vibration sensors that measure skin surface vibrations (e.g., for MMG sensors), acoustic sensing components that measure ultrasound signals (e.g., for SMG sensors) arising from muscle activity, or any combination thereof. Optionally, the sensor(s) 110 may include any one or any combination of: a thermal sensor that measures the user's skin temperature (e.g., a thermistor); a cardio sensor that measure's the user's pulse, heart rate, a moisture sensor that measures the user's state of perspiration, and the like. Exemplary sensors that may be used as part of the one or more sensor(s) 110, in accordance with some embodiments of the technology disclosed herein, are described in more detail in U.S. Pat. No. 10,409,371 entitled "METHODS AND APPARATUS FOR INFERRING USER INTENT BASED ON NEUROMUSCULAR SIGNALS," which is incorporated by reference herein.

Figure 6B:
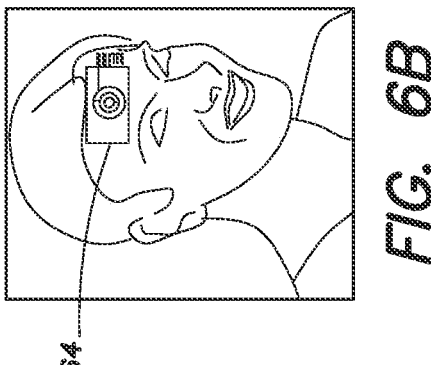
FIGS. 6A, 6B, 6C, and 6D schematically illustrate patch type wearable systems with sensor electronics incorporated thereon, in accordance with some embodiments of the technology described herein.
Figure 6D:
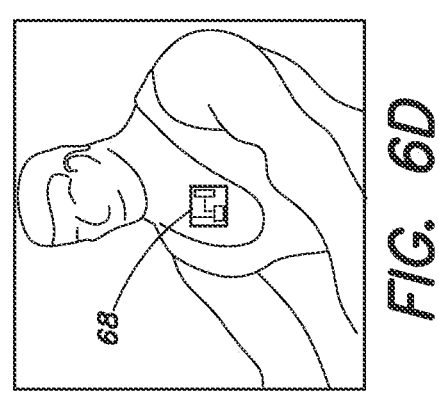
Figure 6A:
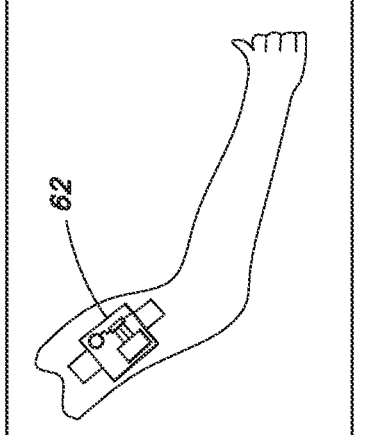
Figure 6C:
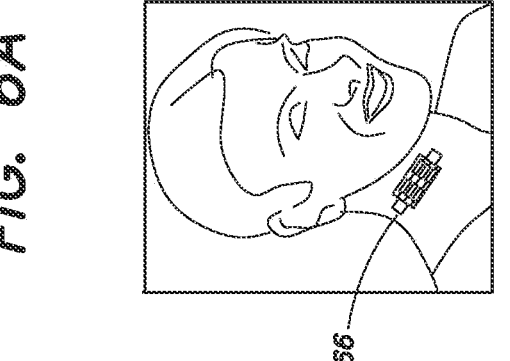

In some embodiments, the one or more sensor(s) 110 may comprise a plurality of sensors 110, and at least some of the plurality of sensors 110 may be arranged as a portion of a wearable device structured to be worn on or around a part of a user's body. For example, in one non-limiting example, an IMU and a plurality of neuromuscular sensors may be arranged circumferentially on an adjustable and/or elastic band, such as a wristband or an armband structured to be worn around a user's wrist or arm, as described in more detail below. In some embodiments, multiple wearable devices, each having one or more IMU(s) and/or one or more neuromuscular sensor(s) included thereon, may be used to determine information relating to an interaction of a user with a physical object based on activation from sub-muscular structures and/or based on movement that involve multiple parts of the body. Alternatively, at least some of the sensors 110 may be arranged on a wearable patch structured to be affixed to a portion of the user's body. FIGS. 6A-6D show various types of wearable patches. FIG. 6A shows a wearable patch 62 in which circuitry for an electronic sensor may be printed on a flexible substrate that is structured to adhere to an arm, e.g., near a vein to sense blood flow in the user. The wearable patch 62 may be an RFID-type patch, which may transmit sensed information wirelessly upon interrogation by an external device. FIG. 6B shows a wearable patch 64 in which an electronic sensor may be incorporated on a substrate that is structured to be worn on the user's forehead, e.g., to measure moisture from perspiration. The wearable patch 64 may include circuitry for wireless communication, or may include a connector structured to be connectable to a cable, e.g., a cable attached to a helmet, a heads-mounted display, or another external device. The wearable patch 64 may be structured to adhere to the user's forehead or to be held against the user's forehead by, e.g., a headband, skullcap, or the like. FIG. 6C shows a wearable patch 66 in which circuitry for an electronic sensor may be printed on a substrate that is structured to adhere to the user's neck, e.g., near the user's carotid artery to sense flood flow to the user's brain. The wearable patch 66 may be an RFID-type patch or may include a connector structured to connect to external electronics. FIG. 6D shows a wearable patch 68 in which an electronic sensor may be incorporated on a substrate that is structured to be worn near the user's heart, e.g., to measure the user's heartrate or to measure blood flow to/from the user's heart. As will be appreciated, wireless communication is not limited to RFID technology, and other communication technologies may be employed. Also, as will be appreciated, the sensors 110 may be incorporated on other types of wearable patches that may be structured differently from those shown in FIGS. 6A-6D.

In one implementation, the sensor(s) 110 may include sixteen neuromuscular sensors arranged circumferentially around a band (e.g., an elastic band) structured to be worn around a user's lower arm (e.g., encircling the user's forearm). For example, FIG. 7A shows an embodiment of a wearable system in which neuromuscular sensors 704 (e.g., EMG sensors) are arranged circumferentially around an elastic band 702. It should be appreciated that any suitable number of neuromuscular sensors may be used and the number and arrangement of neuromuscular sensors used may depend on the particular application for which the wearable system is used. For example, a wearable armband or wristband may be used to generate control information for controlling a robot, controlling a vehicle, scrolling through text, controlling a virtual avatar, or any other suitable control task. In some embodiments, the elastic band 702 may also include one or more IMUs (not shown).

Figure 7B:
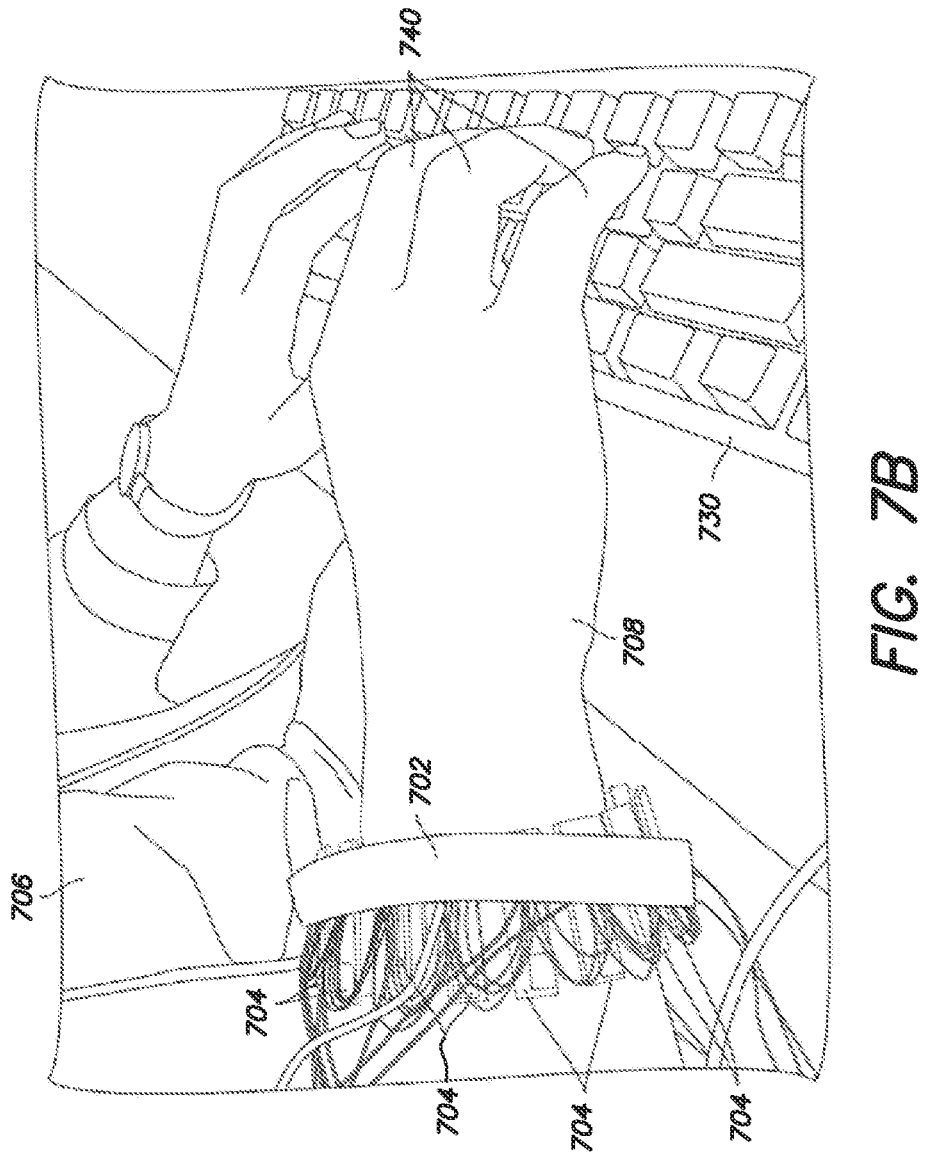
FIG. 7B illustrates a user wearing the wristband of FIG. 7A, while performing a typing task.

For example, as shown in FIG. 7B, a user 706 may wear the elastic band 702 on his/her hand 708. In this way, the neuromuscular sensors 704 (e.g., EMG sensors) may be configured to sense and record neuromuscular signals as the user 706 controls or manipulates a keyboard 730 using his/her fingers 740. In some embodiments, the elastic band 702 may also include one or more IMUs (not shown), configured to sense and obtain or record movement information, as discussed above.

Figure 8A:
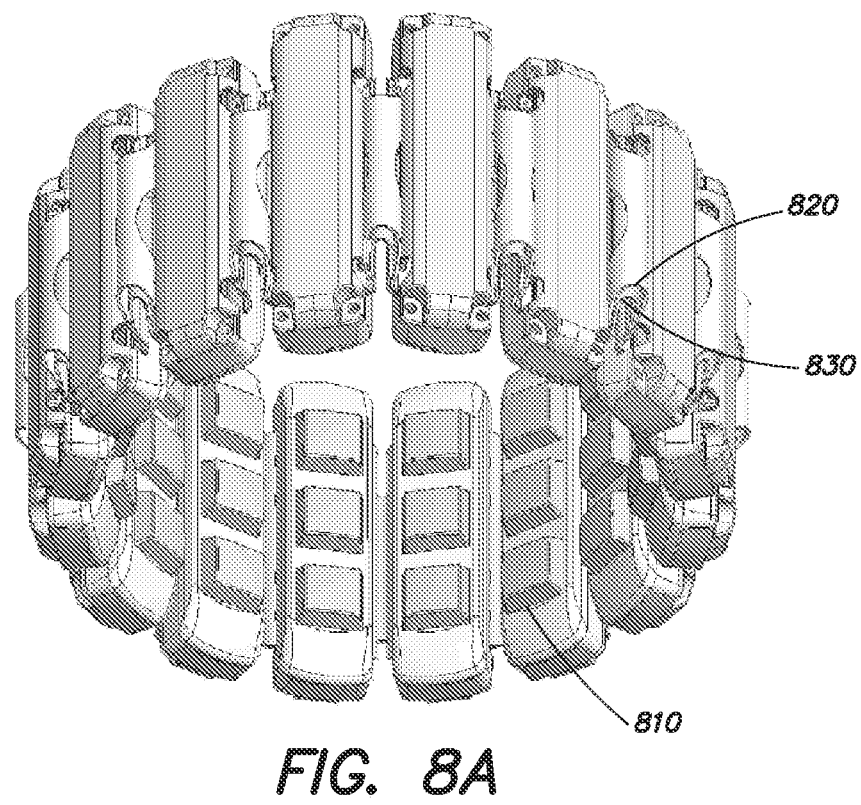
FIG. 8A illustrates a wearable system with sixteen EMG sensors arranged circumferentially around a band configured to be worn around a user's lower arm or wrist, in accordance with some embodiments of the technology described herein.

FIGS. 8A-8B and 9A-9B show other embodiments of a wearable system of the present technology. In particular, FIG. 8A illustrates a wearable system with a plurality of sensors 810 arranged circumferentially around an elastic band 820 structured to be worn around a user's lower arm or wrist. The sensors 810 may be neuromuscular sensors (e.g., EMG sensors). As shown, there may be sixteen sensors 810 arranged circumferentially around the elastic band 820 at a regular spacing. It should be appreciated that any suitable number of sensors 810 may be used, and the spacing need not be regular. The number and arrangement of the sensors 810 may depend on the particular application for which the wearable system is used. For instance, the number and arrangement of the sensors 810 may differ when the wearable system is to be worn on a wrist in comparison with a thigh. A wearable system (e.g., armband, wristband, thighband, etc.) can be used to generate control information for controlling a robot, controlling a vehicle, scrolling through text, controlling a virtual avatar, and/or performing any other suitable control task.

Figure 8B:
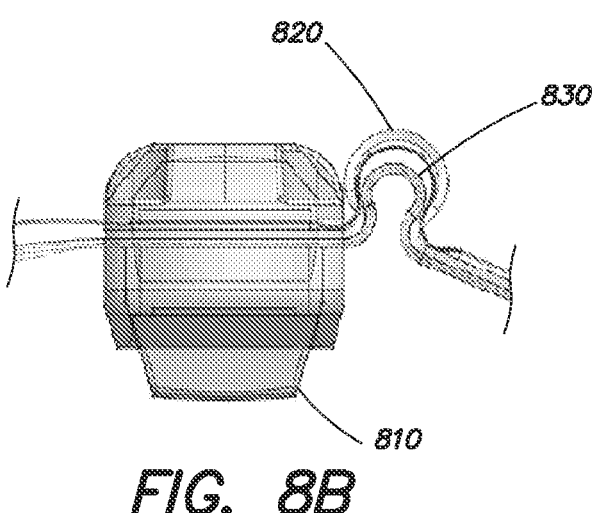
FIG. 8B is a cross-sectional view through one of the sixteen EMG sensors illustrated in FIG. 8A.

In some embodiments, the sensors 810 may include only a set of neuromuscular sensors (e.g., EMG sensors). In other embodiments, the sensors 810 may include a set of neuromuscular sensors and at least one auxiliary device. The auxiliary device(s) may be configured to continuously sense and record one or a plurality of auxiliary signal(s). Examples of auxiliary devices include, but are not limited to, IMUs, microphones, imaging devices (e.g., cameras), radiation-based sensors for use with a radiation-generation device (e.g., a laser-scanning device), heart-rate monitors, and other types of devices, which may capture a user's condition or other characteristics of the user. As shown in FIG. 8A, the sensors 810 may be coupled together using flexible electronics 830 incorporated into the wearable system. FIG. 8B illustrates a cross-sectional view through one of the sensors 810 of the wearable system shown in FIG. 8A.

In some embodiments, the output(s) of one or more of sensing component(s) of the sensors 810 can be optionally processed using hardware signal-processing circuitry (e.g., to perform amplification, filtering, and/or rectification). In other embodiments, at least some signal processing of the output(s) of the sensing component(s) can be performed using software. Thus, signal processing of signals sampled by the sensors 810 can be performed by hardware or by software, or by any suitable combination of hardware and software, as aspects of the technology described herein are not limited in this respect. A non-limiting example of a signal-processing procedure used to process recorded data from the sensors 810 is discussed in more detail below in connection with FIGS. 9A and 9B.

Figures 9A, 9B:
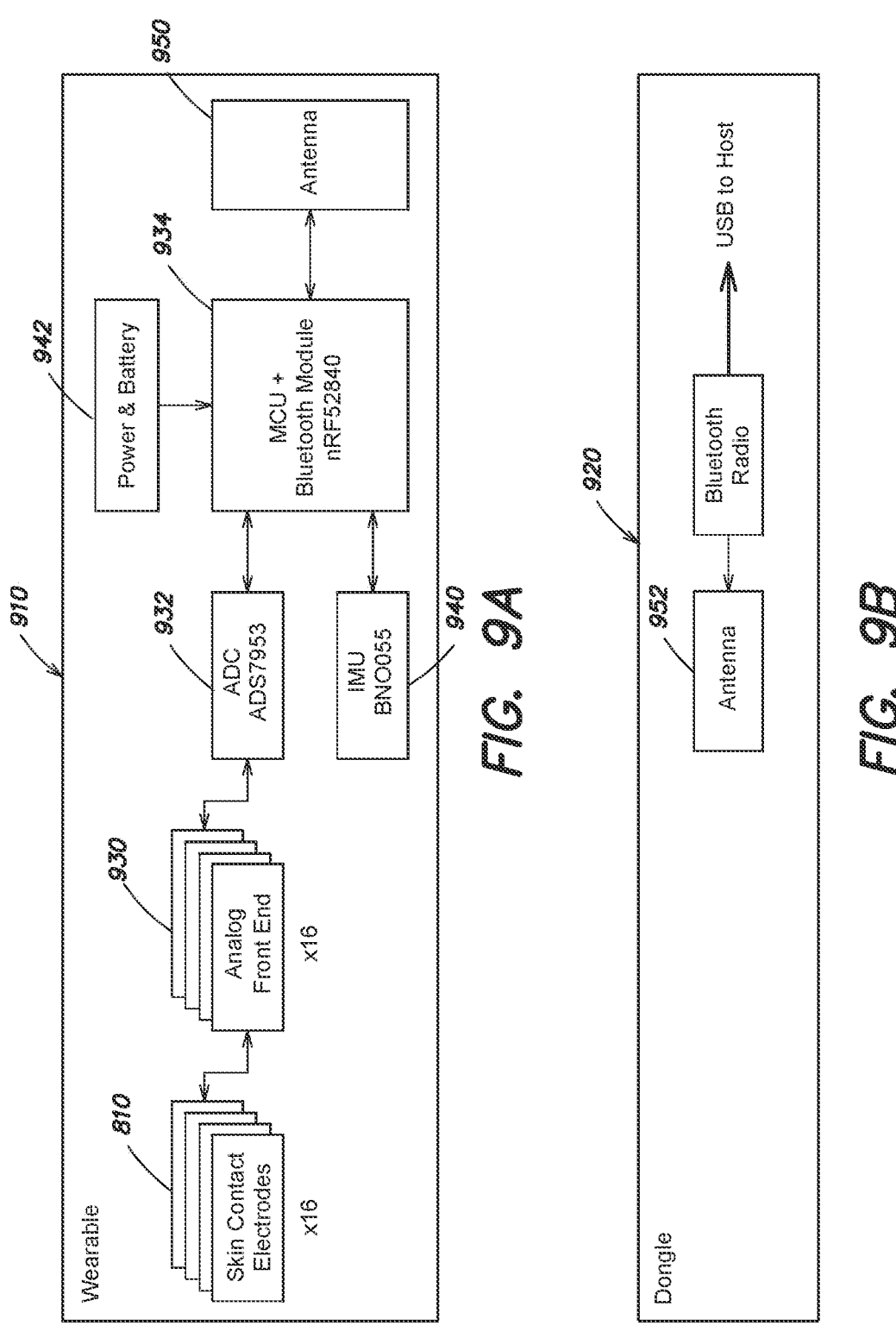
FIGS. 9A and 9B schematically illustrate components of a computer-based system in which some embodiments of the technology described herein are implemented.

FIGS. 9A and 9B illustrate a schematic diagram with internal components of a wearable system with sixteen sensors (e.g., EMG sensors), in accordance with some embodiments of the technology described herein. As shown, the wearable system includes a wearable portion 910 (FIG. 9A) and a dongle portion 920 (FIG. 9B). Although not illustrated, the dongle portion 920 is in communication with the wearable portion 910 (e.g., via Bluetooth or another suitable short range wireless communication technology). As shown in FIG. 9A, the wearable portion 910 includes the sensors 810, examples of which are described above in connection with FIGS. 8A and 8B. The sensors 810 provide output (e.g., signals) to an analog front end 930, which performs analog processing (e.g., noise reduction, filtering, etc.) on the signals. Processed analog signals produced by the analog front end 930 are then provided to an analog-to-digital converter 932, which converts the processed analog signals to digital signals that can be processed by one or more computer processors. An example of a computer processor that may be used in accordance with some embodiments is a microcontroller (MCU) 934. As shown in FIG. 9A, the MCU 934 may also receive inputs from other sensors (e.g., an IMU 940) and from a power and battery module 942. As will be appreciated, the MCU 934 may receive data from other devices not specifically shown. A processing output by the MCU 934 may be provided to an antenna 950 for transmission to the dongle portion 920, shown in FIG. 9B.

The dongle portion 920 includes an antenna 952 that communicates with the antenna 950 of the wearable portion 910. Communication between the antennas 950 and 952 may occur using any suitable wireless technology and protocol, non-limiting examples of which include radiofrequency signaling and Bluetooth. As shown, the signals received by the antenna 952 of the dongle portion 920 may be provided to a host computer for further processing, for display, and/or for effecting control of a particular physical or virtual object or objects (e.g., to perform a control operation in an AR environment).

Although the examples provided with reference to FIGS. 8A, 8B, 9A, and 9B are discussed in the context of interfaces with EMG sensors, it is to be understood that the wearable systems described herein can also be implemented with other types of sensors, including, but not limited to, mechanomyography (MMG) sensors, sonomyography (SMG) sensors, and electrical impedance tomography (EIT) sensors.

Returning to FIG. 1, in some embodiments, sensor data or signals obtained by the sensor(s) 110 may be optionally processed to compute additional derived measurements, which may then be provided as input to an inference model, as described in more detail below. For example, signals obtained from an IMU may be processed to derive an orientation signal that specifies the orientation of a segment of a rigid body over time. The sensor(s) 110 may implement signal processing using components integrated with the sensing components of the sensor(s) 110, or at least a portion of the signal processing may be performed by one or more components in communication with, but not directly integrated with, the sensing components of the sensor(s) 110.

The system 100 also includes one or more computer processor(s) 112 programmed to communicate with the sensor(s) 110. For example, signals obtained by one or more of the sensor(s) 110 may be output from the sensor(s) 110 and provided to the processor(s) 112, which may be programmed to execute one or more machine-learning algorithm(s) to process the signals output by the sensor(s) 110. The algorithm(s) may process the signals to train (or retrain) one or more inference model(s) 114, and the trained (or retrained) inference model(s) 114 may be stored for later use in generating selection signals and/or control signals for controlling an AR system, as described in more detail below. As will be appreciated, in some embodiments, the inference model(s) 114 may include at least one statistical model.

In some embodiments, the inference model(s) 114 may include a neural network and, for example, may be a recurrent neural network. In some embodiments, the recurrent neural network may be a long short-term memory (LSTM) neural network. It should be appreciated, however, that the recurrent neural network is not limited to being an LSTM neural network and may have any other suitable architecture. For example, in some embodiments, the recurrent neural network may be any one or any combination of: a fully recurrent neural network, a gated recurrent neural network, a recursive neural network, a Hopfield neural network, an associative memory neural network, an Elman neural network, a Jordan neural network, an echo state neural network, and a second-order recurrent neural network, and/or any other suitable type of recurrent neural network. In other embodiments, neural networks that are not recurrent neural networks may be used. For example, deep neural networks, convolutional neural networks, and/or feedforward neural networks may be used.

In some embodiments, the inference model(s) 114 may produce discrete outputs. Discrete outputs (e.g., discrete classifications) may be used, for example, when a desired output is to know whether a particular pattern of activation (including individual neural spiking events) is detected in the neuromuscular signals. For example, the inference model(s) 114 may be trained to estimate whether the user is activating a particular motor unit, activating a particular motor unit with a particular timing, activating a particular motor unit with a particular firing pattern, or activating a particular combination of motor units. On a shorter timescale, a discrete classification may be used in some embodiments to estimate whether a particular motor unit fired an action potential within a given amount of time. In such a scenario, these estimates may then be accumulated to obtain an estimated firing rate for that motor unit.

In embodiments in which an inference model is implemented as a neural network configured to output a discrete output (e.g., a discrete signal), the neural network may include an output layer that is a softmax layer, such that outputs of the inference model add up to one and may be interpreted as probabilities. For instance, outputs of the softmax layer may be a set of values corresponding to a respective set of control signals, with each value indicating a probability that the user wants to perform a particular control action. As one non-limiting example, the outputs of the softmax layer may be a set of three probabilities (e.g., 0.92, 0.05, and 0.03) indicating the respective probabilities that a detected pattern of activity is one of three known patterns.

It should be appreciated that when an inference model is a neural network configured to output a discrete output (e.g., a discrete signal), the neural network is not required to produce outputs that add up to one. For example, instead of a softmax layer, the output layer of the neural network may be a sigmoid layer, which does not restrict the outputs to probabilities that add up to one. In such embodiments, the neural network may be trained with a sigmoid cross-entropy cost. Such an implementation may be advantageous in cases where multiple different control actions may occur within a threshold amount of time and it is not important to distinguish an order in which these control actions occur (e.g., a user may activate two patterns of neural activity within the threshold amount of time). In some embodiments, any other suitable non-probabilistic multi-class classifier may be used, as aspects of the technology described herein are not limited in this respect.

In some embodiments, an output of the inference model(s) 114 may be a continuous signal rather than a discrete output (e.g., a discrete signal). For example, the model(s) 114 may output an estimate of a firing rate of each motor unit, or the model(s) 114 may output a time-series electrical signal corresponding to each motor unit or submuscular structure.

It should be appreciated that aspects of the technology described herein are not limited to using neural networks, as other types of inference models may be employed in some embodiments. For example, in some embodiments, the inference model(s) 114 may comprise a hidden Markov model (HMM), a switching HMM in which switching allows for toggling among different dynamic systems, dynamic Bayesian networks, and/or any other suitable graphical model having a temporal component. Any such inference model may be trained using sensor signals obtained by the sensor(s) 110.

As another example, in some embodiments, the inference model(s) 114 may be or may include a classifier that takes, as input, features derived from the sensor signals obtained by the sensor(s) 110. In such embodiments, the classifier may be trained using features extracted from the sensor signals. The classifier may be, e.g., a support vector machine, a Gaussian mixture model, a regression based classifier, a decision tree classifier, a Bayesian classifier, and/or any other suitable classifier, as aspects of the technology described herein are not limited in this respect. Input features to be provided to the classifier may be derived from the sensor signals in any suitable way. For example, the sensor signals may be analyzed as timeseries data using wavelet analysis techniques (e.g., continuous wavelet transform, discrete-time wavelet transform, etc.), Fourier-analytic techniques (e.g., short-time Fourier transform, Fourier transform, etc.), and/or any other suitable type of time-frequency analysis technique. As one non-limiting example, the sensor signals may be transformed using a wavelet transform and the resulting wavelet coefficients may be provided as inputs to the classifier.

In some embodiments, values for parameters of the inference model(s) 114 may be estimated from training data. For example, when the inference model(s) 114 is or includes a neural network, parameters of the neural network (e.g., weights) may be estimated from the training data. In some embodiments, parameters of the inference model(s) 114 may be estimated using gradient descent, stochastic gradient descent, and/or any other suitable iterative optimization technique. In embodiments where the inference model(s) 114 is or includes a recurrent neural network (e.g., an LSTM), the inference model(s) 114 may be trained using stochastic gradient descent and backpropagation through time. The training may employ a cross-entropy loss function and/or any other suitable loss function, as aspects of the technology described herein are not limited in this respect.

The system 100 also may include one or more controller(s) 116. For example, the controller(s) 116 may include a display controller configured to display a visual representation (e.g., a representation of a hand) on a display device (e.g., a display monitor). As discussed in more detail below, one or more computer processor(s) 112 may implement one or more trained inference models that receive, as input, sensor signals obtained by the sensor(s) 110 and that provide, as output, information (e.g., predicted handstate information) that is used to generate control signals that may be used to control, for example, an AR system.

The system 100 also may optionally include a user interface 118. Feedback determined based on the signals obtained by the sensor(s) 110 and processed by the processor(s) 112 may be provided via the user interface 118 to facilitate a user's understanding of how the system 100 is interpreting the user's muscular activity (e.g., an intended muscle movement). The user interface 118 may be implemented in any suitable way, including, but not limited to, an audio interface, a video interface, a tactile interface, and electrical stimulation interface, or any combination of the foregoing.

The system 100 may have an architecture that may take any suitable form. Some embodiments may employ a thin architecture in which the processor(s) 112 is or are included as a portion of a device separate from and in communication with the sensor(s) 110 arranged on the one or more wearable device(s). The sensor(s) 110 may be configured to wirelessly stream, in substantially real time, sensor signals and/or information derived from the sensor signals to the processor(s) 112 for processing. The device separate from and in communication with the sensors(s) 110 may be, for example, any one or any combination of: a remote server, a desktop computer, a laptop computer, a smartphone, a wearable electronic device such as a smartwatch, a health monitoring device, smart glasses, and an AR system.

Some embodiments employ a thick architecture in which the processor(s) 112 may be integrated with the one or more wearable device(s) on which the sensor(s) 110 is or are arranged. In yet further embodiments, processing of signals obtained by the sensor(s) 110 may be divided between multiple processors, at least one of which may be integrated with the sensor(s) 110, and at least one of which may be included as a portion of a device separate from and in communication with the sensor(s) 110. In such an implementation, the sensor(s) 110 may be configured to transmit at least some of the sensed signals to a first computer processor remotely located from the sensor(s) 110. The first computer processor may be programmed to train, based on the transmitted signals obtained by the sensor(s) 110, at least one inference model of the at least one inference model(s) 114. The first computer processor may then be programmed to transmit the trained at least one inference model to a second computer processor integrated with the one or more wearable devices on which the sensor(s) 110 is or are arranged. The second computer processor may be programmed to determine information relating to an interaction between a user wearing the one or more wearable device(s) and a physical object in an AR environment using the trained at least one inference model transmitted from the first computer processor. In this way, the training/fitting process and a real-time process that utilizes the trained at least one model may be performed separately by using different processors.

In some embodiments, a computer application that simulates and XR environment, (e.g., a VR environment, an AR environment, etc.) may be instructed to provide a visual representation by displaying a visual character, such as an avatar (e.g., via the controller(s) 116). Positioning, movement, and/or forces applied by portions of visual character within the XR environment may be displayed based on an output of the trained inference model(s). The visual representation may be dynamically updated as continuous signals are obtained by the sensor(s) 110 and processed by the trained inference model(s) 114 to provide a computer-generated representation of the character's movement that is updated in real-time.

Information obtained by or provided to the system 100, (e.g., inputs obtained from an AR camera, inputs obtained from the sensor(s) 110) can be used to improve user experience, accuracy, feedback, inference models, calibration functions, and other aspects in the overall system. To this end, in an AR environment for example, the system 100 may include an AR system that includes one or more processors, a camera, and a display (e.g., the user interface 118, or other interface via AR glasses or another viewing device) that provides AR information within a view of a user. The system 100 may also include system elements that couple the AR system with a computer-based system that generates a musculoskeletal representation based on sensor data (e.g., signals from at least one neuromuscular sensor). For example, the systems may be coupled via a special-purpose or other type of computer system that receives inputs from the AR system that generates a computer-based musculoskeletal representation. Such a system may include a gaming system, robotic control system, personal computer, or other system that is capable of interpreting AR and musculoskeletal information. The AR system and the system that generates the computer-based musculoskeletal representation may also be programmed to communicate directly. Such information may be communicated using any number of interfaces, protocols, and/or media.

As discussed above, some embodiments are directed to using an inference model 114 for predicting musculoskeletal information based on signals obtained by wearable sensors. As discussed briefly above in the example where portions of the human musculoskeletal system can be modeled as a multi-segment articulated rigid body system, the types of joints between segments in a multi-segment articulated rigid body model may serve as constraints that constrain movement of the rigid body. Additionally, different human individuals may move in characteristic ways when performing a task that can be captured in statistical patterns that may be generally applicable to individual user behavior. At least some of these constraints on human body movement may be explicitly incorporated into one or more inference model(s) (e.g., the model(s) 114) used for prediction of user movement, in accordance with some embodiments. Additionally or alternatively, the constraints may be learned by the inference model(s) 114 though training based on sensor data obtained from the sensor(s) 110, as discussed briefly above.

Some embodiments are directed to using an inference model for predicting information to generate a computer-based musculoskeletal representation and/or to update in real-time a computer-based musculoskeletal representation. For example, the predicted information may be predicted handstate information. The inference model may be used to predict the information based on IMU signals, neuromuscular signals (e.g., EMG, MMG, and/or SMG signals), external or auxiliary device signals (e.g., camera or laser-scanning signals), or a combination of IMU signals, neuromuscular signals, and external or auxiliary device signals detected as a user performs one or more movements. For instance, as discussed above, a camera associated with an AR system may be used to capture data of an actual position of a human subject of the computer-based musculoskeletal representation, and such actual-position information may be used to improve the accuracy of the representation. Further, outputs of the inference model may be used to generate a visual representation of the computer-based musculoskeletal representation in an AR environment. For example, a visual representation of muscle groups firing, force being applied, text being entered via movement, or other information produced by the computer-based musculoskeletal representation may be rendered in a visual display of an AR system. In some embodiments, other input/output devices (e.g., auditory inputs/outputs, haptic devices, etc.) may be used to further improve the accuracy of the overall system and/or to improve user experience.

Some embodiments of the technology described herein are directed to using an inference model, at least in part, to map muscular activation state information, which is information identified from neuromuscular signals obtained by neuromuscular sensors, to control signals. The inference model may receive as input IMU signals, neuromuscular signals (e.g., EMG, MMG, and SMG signals), external device signals (e.g., camera or laser-scanning signals), or a combination of IMU signals, neuromuscular signals, and external or auxiliary device signals detected as a user performs one or more sub-muscular activations, one or more movements, and/or one or more gestures. The inference model may be used to predict control information without the user having to make perceptible movements.

As discussed above, according to some embodiments of the present technology, camera information may be used to improve interpretation of neuromuscular signals and their relationship to movement, position, and force generation. As will be appreciated, the camera information may be, for example, an image signal corresponding to at least one image captured by a camera; thus, as used herein, an image from a camera may be understood to refer to an image signal from a camera. The camera may be a still camera, a video camera, an infrared camera, and the like, which is able to capture or record an image of a user. One or more filters may be used on the camera, so that the camera may capture images only within a particular range of wavelengths of light. As will be appreciated, the image may be a still image, a sequence of still images (or image sequence), a moving image (or video sequence), and the like, which may be captured and recorded as a signal. The terms "camera information," "camera data," and "camera signal," may be used herein to represent information about the user that may be captured by a camera. It should be understood that although various embodiments may refer to "a" camera or "the" camera, such embodiments may utilize two or more cameras instead of one camera. Further, the camera information may relate to any one or any combination of: an image produced by visible light, an image produced by non-visible (e.g., infrared) light, an image produced by light of a predetermined range of wavelengths, and an image produced by light of two or more different predetermined ranges of wavelengths. For example, non-visible light may be used to capture an image that shows heat distribution in the user's body, which may provide an indication of blood flow within the user, which in turn may be used to infer a condition of the user (e.g., a force being exerted by a finger of the user may have a different blood-flow pattern than a finger that is not exerting force).

A camera may be mounted on the user (e.g., on an head-mounted display worn by the user, or on a glove worn on the user's hand) or may be mounted external to the user to capture the user and/or the user's environment. When a camera is mounted on the user, the camera may be used to capture the user's environment and/or portions of the user's body (e.g., a hand-mounted camera may be used to capture an image of the user's other hand).

Figure 10:
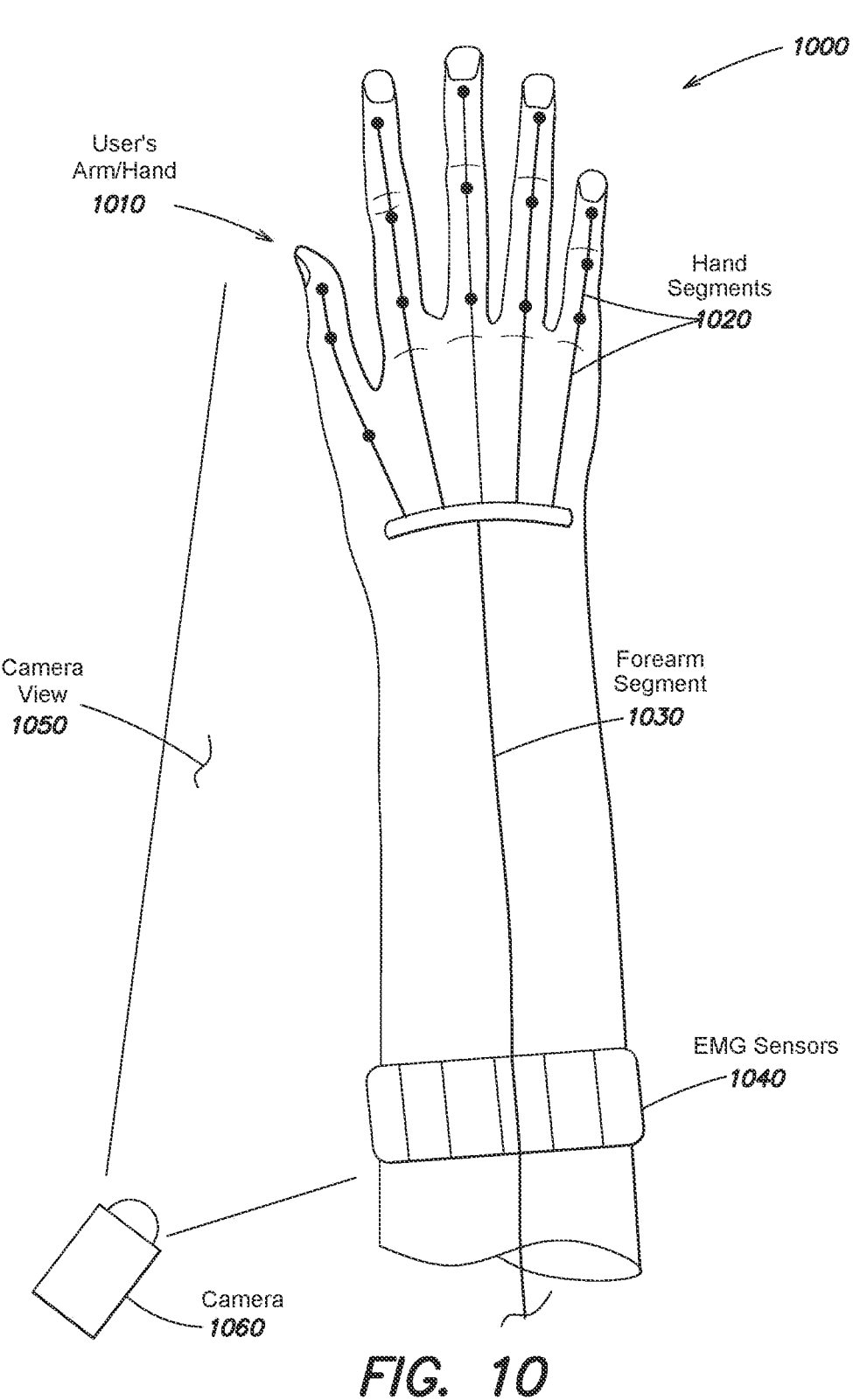
FIG. 10 is a diagram schematically showing an example of an implementation using EMG sensors and a camera, in accordance with some embodiments of the technology described herein.

FIG. 10 is a diagram showing an example implementation of a system 1000 that utilizes one or more EMG sensor(s) 1040 and a camera 1060, in accordance with some embodiments of the technology described herein. For example, FIG. 10 shows a user's arm and an attached hand ("arm/hand") 1010, which is made up of one or more joints and segments, and which can be depicted as a musculoskeletal representation. More particularly, the user's hand segments 1020 are connected by joints. The arm and hand positions and segment lengths of the arm and the hand can be determined by the system 1000 and positioned within a three-dimensional space of a model musculoskeletal representation. Further, the user's hand may also include an interpolated forearm segment 1030. As discussed above, a neuromuscular activity system may be used to determine one or more representations of a user's hand/arm positions. To this end, the user may wear a band comprising the one or more EMG sensor(s) 1040, which sense and record neuromuscular signals that are used to determine a musculoskeletal skeletal representation. Concurrently with the EMG sensor(s) 1040 sensing and recording the neuromuscular signals, a camera 1060 may be used to capture objects within the camera's field of view 1050. For example, in FIG. 10, the camera's field of view 1050 include the user's arm/hand 1010. Camera data in addition to the neuromuscular activity signals determined by the EMG sensors 1040 may be used to reconstruct positions, geometries, and forces being applied by the user's arm/hand 1010. Further, outputs from the system 1000 can be provided that allow the system 1000 to render a representation of the user's arm/hand 1010, such as within an AR environment of an AR system.

Figure 2:
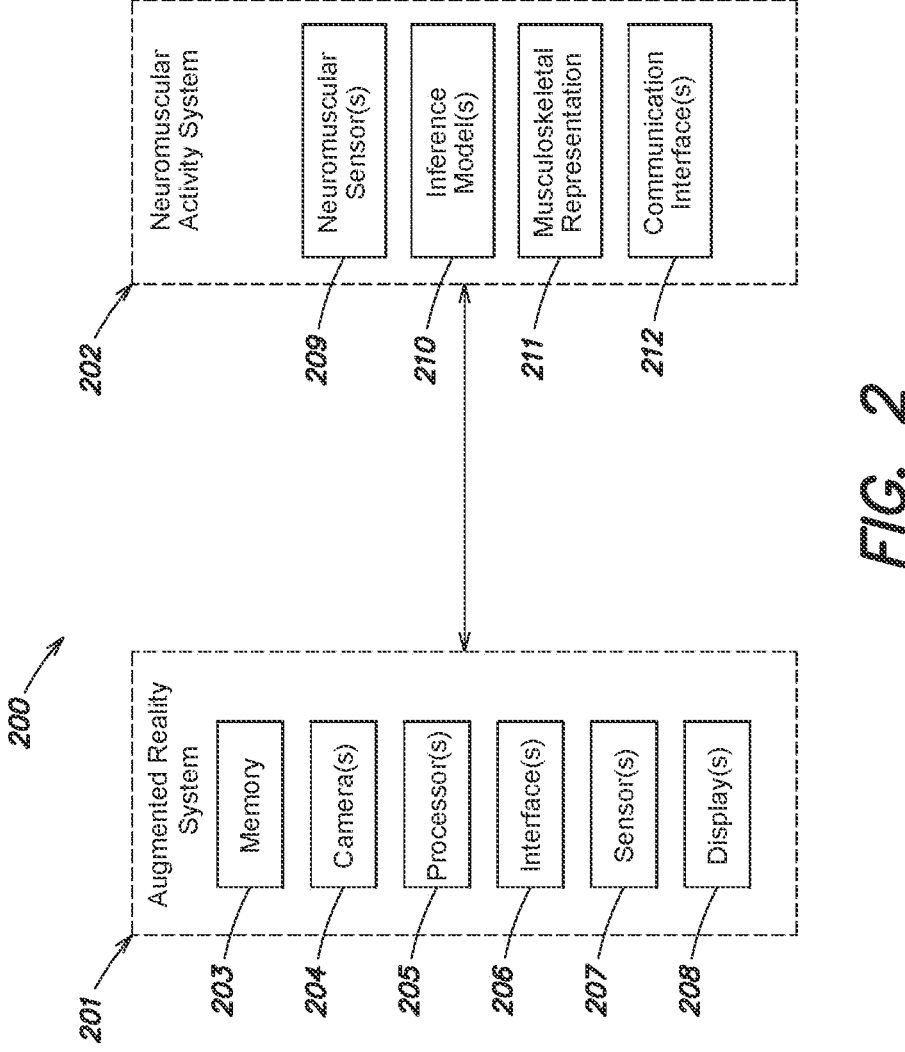
FIG. 2 is a schematic diagram of a distributed computer-based system that integrates an AR system with a neuromuscular activity system, in accordance with some embodiments of the technology described herein.

FIG. 2 illustrates a schematic diagram of an AR-based system 200, which may be a distributed computer-based system that integrates an AR system 201 with a neuromuscular activity system 202. The neuromuscular activity system 202 is similar to the system 100 described above with respect to FIG. 1.

Generally, an XR system such as the AR system 201 may take the form of a pair of goggles or glasses or eyewear, or other type of display device that shows display elements to a user that may be superimposed on the user's "reality." This reality in some cases could be the user's view of the environment (e.g., as viewed through the user's eyes), or a captured version (e.g., by camera(s)) of the user's view of the environment. In some embodiments, the AR system 201 may include one or more camera(s) 204, which may be mounted within a device worn by the user, that captures one or more views experienced by the user in the user's environment. The system 201 may have one or more processor(s) 205 operating within the device worn by the user and/or within a peripheral device or computer system, and such processor(s) 205 may be capable of transmitting and receiving video information and other types of data (e.g., sensor data).

The AR system 201 may also include one or more sensor(s) 207, such as microphones, GPS elements, accelerometers, infrared detectors, haptic feedback elements or any other type of sensor, or any combination thereof. In some embodiments, the AR system 201 may be an audio-based or auditory AR system, and the one or more sensor(s) 207 may also include one or more headphones or speakers. Further, the AR system 201 may also have one or more display(s) 208 that permit the AR system 201 to overlay and/or display information to the user in addition to provide the user with a view of the user's environment presented via the AR system 201. The AR system 201 may also include one or more communication interface(s) 206, which enable information to be communicated to one or more computer systems (e.g., a gaming system or other system capable of rendering or receiving AR data). AR systems can take many forms and are available from a number of different manufacturers. For example, various embodiments may be implemented in association with one or more types of AR systems or platforms, such as HoloLens holographic reality glasses available from the Microsoft Corporation (Redmond, Washington, USA); Lightwear AR headset from Magic Leap (Plantation, Florida, USA); Google Glass AR glasses available from Alphabet (Mountain View, California, USA); R-7 Smartglasses System available from Osterhout Design Group (also known as ODG; San Francisco, California, USA); Oculus Quest, Oculus Rift S, and Spark AR Studio available from Facebook (Menlo Park, California, USA); or any other type of AR or other XR device. Although discussed using AR by way of example, it should be appreciated that one or more embodiments of the technology disclosed herein may be implemented within one or more XR system(s).

The AR system 201 may be operatively coupled to the neuromuscular activity system 202 through one or more communication schemes or methodologies, including but not limited to, Bluetooth protocol, Wi-Fi, Ethernet-like protocols, or any number of connection types, wireless and/or wired. It should be appreciated that, for example, the systems 201 and 202 may be directly connected or coupled through one or more intermediate computer systems or network elements. The double-headed arrow in FIG. 2 represents the communicative coupling between the systems 201 and 202.

As mentioned above, the neuromuscular activity system 202 may be similar in structure and function to the system 100 described above with reference to FIG. 1. In particular, the system 202 may include one or more neuromuscular sensor(s) 209, one or more inference model(s) 210, and may create, maintain, and store a musculoskeletal representation 211. In an example embodiment, similar to one discussed above, the system 202 may include or may be implemented as a wearable device, such as a band that can be worn by a user, in order to collect (i.e., obtain) and analyze neuromuscular signals from the user. Further, the system 202 may include one or more communication interface(s) 212 that permit the system 202 to communicate with the AR system 201, such as by Bluetooth, Wi-Fi, or other communication method. Notably, the AR system 201 and the neuromuscular activity system 202 may communicate information that can be used to enhance user experience and/or allow the AR system 201 to function more accurately and effectively.

Although FIG. 2 shows a distributed computer-based system 200 that integrates the AR system 201 with the neuromuscular activity system 202, it will be understood that integration of these systems 201 and 202 may be non-distributed in nature. In some embodiments, the neuromuscular activity system 202 may be integrated into the AR system 201 such that the various components of the neuromuscular activity system 202 may be considered as part of the AR system 201. For example, inputs from the neuromuscular signals recorded by the neuromuscular sensor(s)

209 may be treated as another of the inputs (e.g., from the camera(s) 204, from the sensor(s) 207) to the AR system 201. In addition, processing of the inputs (e.g., sensor signals obtained) obtained from the neuromuscular sensor(s) 209 may be integrated into the AR system 201.

Figure 3:
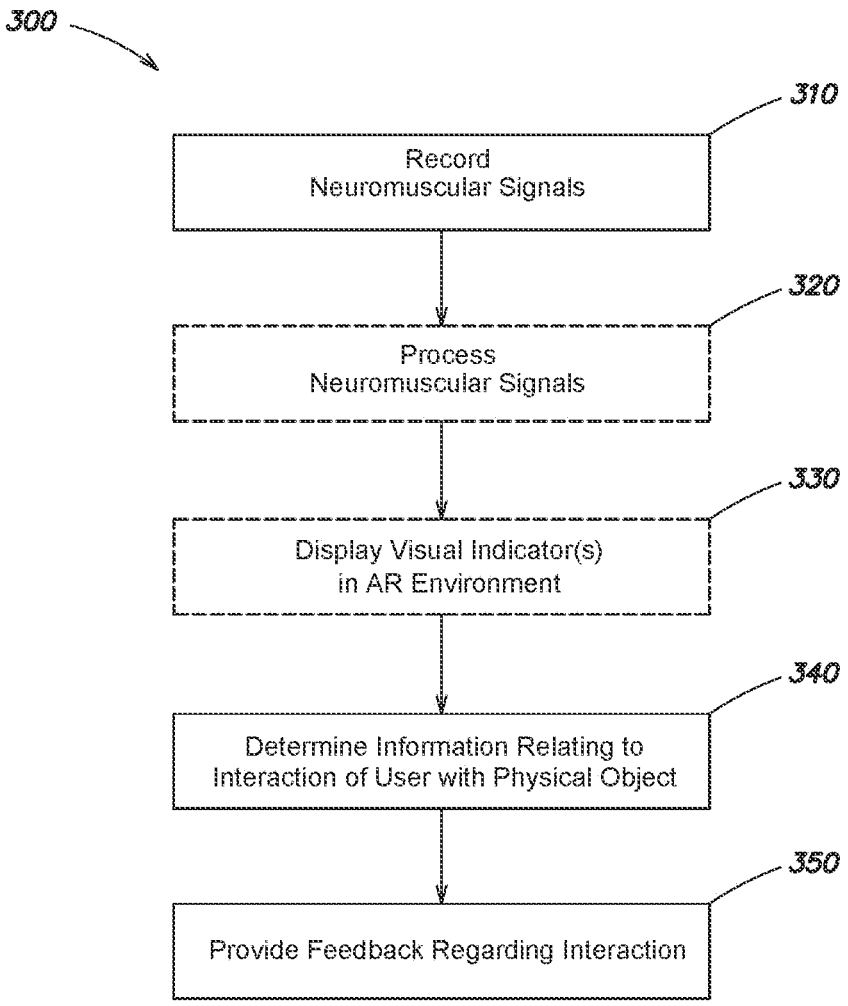
FIG. 3 is a flowchart of a process for using neuromuscular signals to provide an enhanced AR experience, in accordance with some embodiments of the technology described herein.

FIG. 3 illustrates a process 300 for using neuromuscular signals to provide a user with an enhanced interaction with a physical object in an AR environment generated by an AR system, such as the AR system 201, in accordance with some embodiments of the technology described herein. The process 300 may be performed at least in part by the neuromuscular activity system 202 and/or the AR system 201 of the AR-based system 200. At act 310, sensor signals (also referred to herein as "raw sensor signals") may be obtained (e.g., sensed and recorded) by one or more sensors of the neuromuscular activity system 202. In some embodiments, the sensor(s) may include a plurality of neuromuscular sensors 209 (e.g., EMG sensors) arranged on a wearable device worn by a user. For example, the sensors 209 may be EMG sensors arranged on an elastic band configured to be worn around a wrist or a forearm of the user to sense and record neuromuscular signals from the user as the user performs muscular activations (e.g., movements, gestures). In some embodiments, the EMG sensors may be the sensors 704 arranged on the band 702, as shown in FIG. 7A; in some embodiments, the EMG sensors may be the sensors 810 arranged on the band 820, as shown in FIG. 8A. The muscular activations performed by the user may include static gestures, such as placing the user's hand palm down on a table; dynamic gestures, such as waving a finger back and forth; and covert gestures that are imperceptible to another person, such as slightly tensing a joint by co-contracting opposing muscles, or using sub-muscular activations. The muscular activations performed by the user may include symbolic gestures (e.g., gestures mapped to other gestures, interactions, or commands, for example, based on a gesture vocabulary that specifies the mapping).

In addition to the plurality of neuromuscular sensors 209, in some embodiments of the technology described herein, the neuromuscular activity system 202 may include one or more auxiliary sensor(s) configured to obtain (e.g., sense and record) auxiliary signals that may also be provided as input to the one or more trained inference model(s), as discussed above. Examples of auxiliary sensors include IMUs, imaging devices, radiation detection devices (e.g., laser scanning devices), heart rate monitors, or any other type of biosensors able to sense biophysical information from a user during performance of one or more muscular activations. Further, it should be appreciated that some embodiments of the present technology may be implemented using camera-based systems that perform skeletal tracking, such as, for example, the Kinect system available from the Microsoft Corporation (Redmond, Washington, USA) and the LeapMotion system available from Leap Motion, Inc. (San Francisco, California, USA). It should be appreciated that any combination of hardware and/or software may be used to implement various embodiments described herein.

The process 300 then proceeds to act 320, where raw sensor signals, which may include signals sensed and recorded by the one or more sensor(s) (e.g., EMG sensors, auxiliary sensors, etc.), as well as optional camera input signals from one more camera(s), may be optionally processed. In some embodiments, the raw sensor signals may be processed using hardware signal-processing circuitry (e.g., to perform amplification, filtering, and/or rectification). In other embodiments, at least some signal processing of the raw sensor signals may be performed using software. Accordingly, signal processing of the raw sensor signals, sensed and recorded by the one or more sensor(s) and optionally obtained from the one or more camera(s), may be performed using hardware, or software, or any suitable combination of hardware and software. In some implementations, the raw sensor signals may be processed to derive other signal data. For example, accelerometer data obtained by one or more IMU(s) may be integrated and/or filtered to determine derived signal data associated with one or more muscle(s) during activation of a muscle or performance of a gesture.

The process 300 then proceeds to act 330, where one or more visual indicators may be optionally displayed in the AR environment, based, at least in part, on the neuromuscular signals obtained by the plurality of neuromuscular sensors 209. For example, the AR system 201 may operate in conjunction with the neuromuscular activity system 202 to overlay one or more visual indicators on or near a physical object within the AR environment. The one or more visual indicators may instruct the user that the physical object is an object that has a set of virtual controls associated with it such that, if the user interacted with the object (e.g., by picking it up), the user could perform one or more "enhanced" or "augmented" interactions with the object. The one or more visual indicator(s) may be displayed within the AR environment in any suitable way. For example, the physical object may change colors or glow, thereby indicating that it is an object capable of enhanced interaction. In another example, an indication of a set of virtual controls for the physical object, which may be activated by the user to control the physical object, may be overlaid on or displayed near the physical object in the AR environment. The user may interact with the indicator(s) of the set of virtual controls by, for example, performing a muscular activation to select one of the virtual controls. In response to the interaction of the user with the indicator(s) of the set of virtual controls, information relating to an interaction with the physical object may be determined. For example, if the physical object is a writing implement and a displayed indicator of the set of virtual controls indicates that the user may use the writing implement as a pen, a paintbrush, or a pointing device within the AR environment, the user may perform a gesture to select a paintbrush functionality, such that, when the user picks up the writing implement, it may be used to paint within the AR environment.

The process 300 then proceeds to act 340, where information relating to an interaction of the user with the physical object is determined, based, at least in part, on the neuromuscular signals obtained by the plurality of neuromuscular sensors 209 and/or information derived from the neuromuscular signals. Optionally, auxiliary signals from one or more auxiliary device(s) (e.g., a camera, an IMU, etc.) may supplement the neuromuscular signals to determine the information relating to the interaction of the user with the physical object. For example, based, at least in part, on the neuromuscular signals (and optionally supplemented with auxiliary signals), the AR-based system 200 may determine how tightly the user is grasping the physical object, and a control signal may be sent to the AR-based system 200 based on an amount of grasping force being applied to the physical object. Continuing with the example above, the physical object may be a writing implement, and applying different amounts of grasping force to a surface of the writing implement and/or pressing on different parts of the writing implement may transform the writing implement into an "enhanced" or "augmented" writing implement in which a set of virtual control actions for the physical object may be enabled or activated.

In some embodiments, the information relating to the interaction of the user with the physical object in the AR environment may be determined based on a combination of the neuromuscular signals and at least one other sensor (e.g., a camera, an IMU, etc.). For example, some embodiments may include at least one camera (e.g., as part of the AR system 201), which may be arranged or configured to capture one or more images. An example of such an arrangement is shown in FIG. 10. The neuromuscular signals obtained by the plurality of neuromuscular sensors 209 and the image(s) captured by the camera(s) may be used, for example, to determine a force that that the user is applying to the physical object. Neuromuscular signal data and auxiliary sensor data (e.g., camera data) may be combined in any other suitable way to determine information associated with the user's interaction with the physical object, and embodiments are not limited in this respect.

The process 300 then proceeds to act 350, where feedback based on the determined information about the interaction of the user with the physical object is provided. In some embodiments, the feedback is provided to the user interacting with the object. For example, the AR-based system 200 may provide feedback (e.g., visual feedback, auditory feedback, haptic feedback) to the user within the AR environment. In embodiments where visual feedback is provided within the AR environment, the visual feedback may be provided in any suitable way. For example, the physical object with which the user is interacting may change colors or glow indicating that the user is interacting with the object. Alternatively, the feedback may be provided using a visual indicator separate from the physical object. For example, an icon or other visual indicator may be displayed within the AR environment showing an interaction mode (e.g., paintbrush mode) for the object with which the user is interacting. In some embodiments that provide feedback to the user, the feedback may be provided using non-visual forms of feedback such as auditory or haptic feedback. The feedback may, for example, instruct the user that the physical object that he/she is interacting with may have augmented properties or functions that may not be available through ordinary real-world interactions with the object.

In some embodiments of the technology described herein, the AR system (e.g., the system 201) may include haptic circuitry able to deliver haptic signals to the user. The haptic signals may be used to provide feedback to the user, and may comprise any one or any combination of a vibration actuator, a skin-tap actuator, a low-voltage electrical jolt circuit, and a force actuator. Such haptic actuators are known in the art, and my involve electromagnetic transducers, motors, and the like. The haptic circuitry may be arranged on a wearable device worn by the user, and may be included on a wearable patch or a wearable band, such as those discussed above. For example, the haptic circuitry may be included on the band 702 together with one or more neuromuscular sensor(s).

The AR system may be controlled to provide feedback to the user as haptic feedback delivered via the haptic circuitry. In some embodiments, the AR system may be controlled in this regard by a controller within the AR system or by a controller of the AR-based system (e.g., the system 200) encompassing the AR system. In other embodiments, the AR system may be controlled in this regard by control signals from a controller external to the AR system and external to the AR-based system.

In some embodiments, feedback may be provided to the user as an altered functionality of the physical object itself, rather than being provided as an indication separate from the altered functionality. For example, feedback may be provided to the user based on a current functionality of one or more physical object(s). Using the example above, the user may pick up a writing implement in the AR environment and grip the writing implement with a certain amount of force. Gripping the writing implement with a particular amount of force may transform the physical writing implement into an augmented writing implement (or AR writing implement), which may have different writing characteristics for writing within the AR environment. When the user uses the augmented writing implement to write within the AR environment, an augmented functionality of the writing implement may be apparent through use of the physical object itself to write. For example, a color of writing produced by the augmented writing implement, and/or a pixel size of writing produced by the augmented writing implement, and/or some other writing characteristic or combination of writing characteristics may provide feedback about the augmented functionality of the physical object.

In some embodiments, feedback may be provided to someone other than the user interacting with the physical object. For example, in a shared AR environment that includes a first user who is interacting with the object and a second user who is not interacting with the object, an indication may be provided to the second user about an interaction between the first user and the physical object in the AR environment. Such feedback may enable the second user to understand how the first user is interacting with the physical object as well as one or more other physical object(s) in the AR environment without directly observing the first user interacting with the object. For example, the second user may be able to determine how forceful the first user is grasping a ball in the AR environment, which may not be visibly apparent by observing an interaction of the first user with the ball.

The feedback provided at act 350 may reflect information relating to the interaction of the user with the physical object in any suitable way. For example, in some embodiments, the information relating to the interaction may include force information relating to a force that the user is applying to the object (e.g., by pressing, grasping, etc.). In such embodiments, a visual rendering of the force may be displayed within the AR environment to let the user (or another user in a shared AR environment) visualize an amount of force being applied to the object. In other embodiments in which force information is included in the information relating to the interaction, the feedback may be provided using a non-visual technique. For example, auditory and/or haptic feedback may be provided, based, at least in part, on an amount of force being applied to the object.

As discussed above, in some embodiments of the technology disclosed herein, physical objects in an AR environment may be transformed into "augmented" objects. An augmented object may have a set of enhanced or augmented features in the AR environment, and such augmented features may not be available when the user interacts with the object in a real-world environment. For example, a writing implement, such as a pen, may typically be capable of writing only in a single color of ink supplied in the pen, and using a line width dictated in part by a tip of the pen. In some embodiments, such a pen may be transformed into an augmented pen endowed with a set of augmented features for use within the AR environment. For example, an augmented writing implement when used within the AR environment may have a set of augmented features that enable a selection from among multiple writing colors, line thicknesses, brush shapes, tip shapes, drawing modes (e.g., a pen up/down functionality such that writing only occurs when a certain amount of pressure is applied to the writing implement), and writing-implement types (e.g., paintbrush, spray can, pen, pencil, highlighter). In some embodiments, the augmented features may also include functions not typically associated with use of the object in a real-world environment. For example, an augmented writing implement may be used as a remote controller or as a pointer within the AR environment, for selection and/or manipulation of one or more other object(s) at a distance from the user in the AR environment. In yet further embodiments, a physical object that is not typically used as a writing implement (e.g., a stick, ruler, or other object that can be held in the user's hand) may be transformed into a writing implement for use within the AR environment, based, at least in part, on the user's interaction with the physical object. For example, the user may pick up a physical object (e.g., a stick) in their environment and "double grasp" the object (i.e., grasp the object twice) with greater than a threshold amount of force to transform the object into a writing instrument within the AR environment, thereby transforming the physical object into an augmented object that may be used for providing writing input within the AR environment.

In some embodiments, selection by the user (e.g., selection of a physical object and/or a function relating to the physical object) may be performed based, at least in part, on user context and/or user behavior. For example, selection of a physical object may be based, at least in part, on user behavior such as information about one or more recent interactions between the user and one or more physical objects. In another example, if the user had most recently controlled a particular device such as a smart speaker by pressing play on a new track, then the smart speaker may be automatically selected, and a muscular activation determined based, at least in part, on the sensed neuromuscular signals may be used to change the volume of the selected smart speaker. In a further example, selection of a physical object may be based, at least in part, on user context such as information about a current location of the user (e.g., which environment (e.g., room) the user currently is located). The information about the user's current location may be determined in any suitable way including, but not limited to, using NFC technology, RFID technology, another field-based technology, and a global positioning technology (e.g., GPS). Based, at least in part, on the location information, a physical object in the user's environment (e.g., a light switch in a particular room) may be selected for control.

Figure 4:
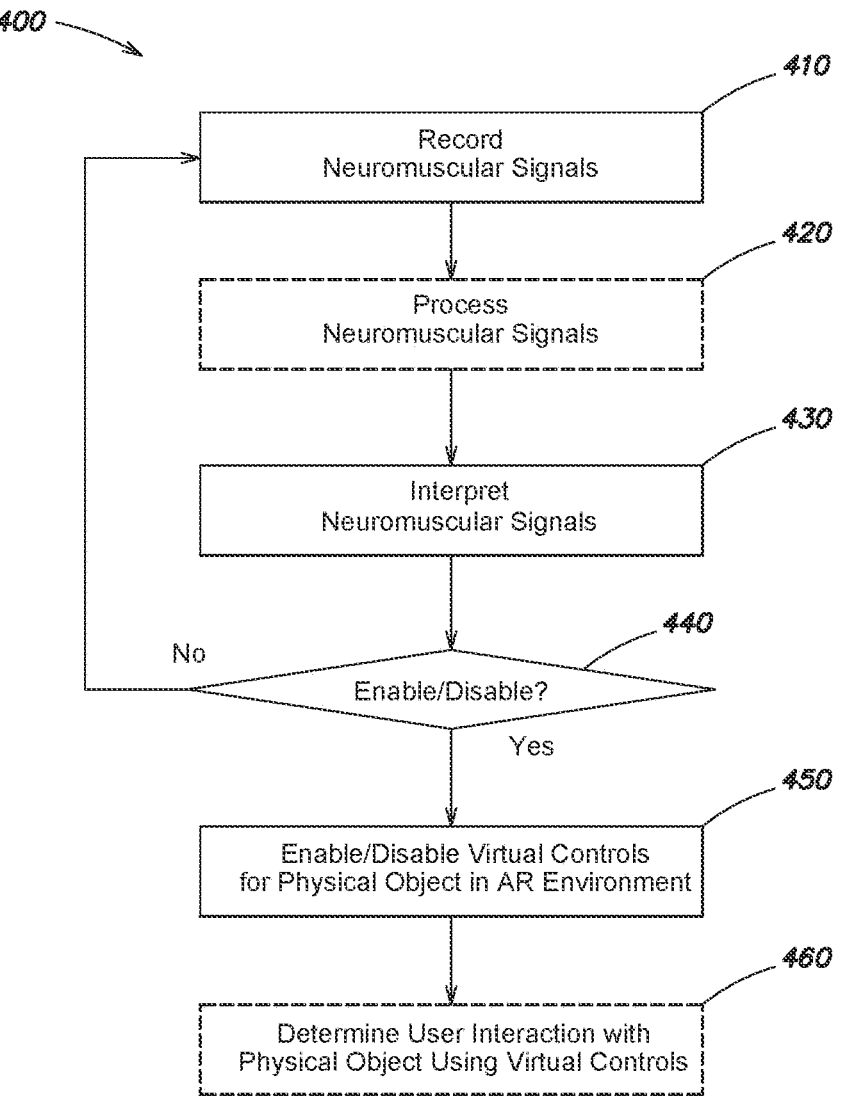
FIG. 4 is a flowchart of a process for providing virtual controls for physical objects in an AR environment, in accordance with some embodiments of the technology described herein.

FIG. 4 illustrates a process 400 for enabling and/or disabling virtual controls associated with an object in an AR environment, in accordance with some embodiments of the technology disclosed herein. At act 410, a plurality of neuromuscular signals are obtained by a plurality of neuromuscular sensors (e.g., the neuromuscular sensors 209) worn by a user. For example, the plurality of neuromuscular signals may be sensed and recorded by the plurality of neuromuscular sensors. The process 400 then proceeds to act 420, at which the plurality of neuromuscular signals may be optionally processed (e.g., amplified, filtered, rectified, etc.), examples of which are discussed above. The process 400 then proceeds to act 430, at which the plurality of neuromuscular signals and/or information derived from the plurality of neuromuscular signals are interpreted to, for example, determine a muscular activation performed by the user. Examples of interpreting neuromuscular signals may include, but are not limited to, processing the plurality of neuromuscular signals using one or more trained inference model(s) (e.g., the inference model(s) 114) to identify a muscular activation state that the user has performed, determining an amount of force applied to an object with which the user is interacting (e.g., an amount of force used to hold or grasp the object, an amount of force used to push against a stationary surface such as a table, etc.), determining co-contraction forces, and determining sub-muscular activation (e.g., activation of a single motor unit).

The process 400 then proceeds to act 440, where it is determined whether a set of virtual controls is to be enabled (if currently disabled) or disabled (if currently enabled), based, at least in part, on the interpreted neuromuscular signals. Determining whether to enable or disable a set of virtual controls may be made in any suitable way. Some embodiments map a particular muscle activation state (e.g., a particular gesture, or a particular muscle tension, or a particular sub-muscular activation, or any combination thereof) to a control signal for enabling or disabling the set of virtual controls associated with a physical object. For example, in some embodiments, the neuromuscular activity system (e.g., the neuromuscular activity system 202) may be configured to associate a pinch gesture involving the user's thumb and index finger with a command to enable or disable the set of virtual controls for the physical object. In other embodiments, the neuromuscular activity system may be configured to associate detection of a particular amount of force applied to the object with which the user is interacting with a command to enable or disable the set of virtual controls for the physical object. The amount of force applied to the object may be a static amount of force applied at a single point in time or a dynamic sequence of forces applied to the object (e.g., a double-squeeze of the object may enable or disable the set of virtual controls). In yet other embodiments, the neuromuscular activity system may be configured to associate activation of a single motor unit, or activation of a defined set of motor units, with a command to enable or disable the set of virtual controls for the physical object. At act 440, an output of the neuromuscular signal interpretation process at act 430 may be compared against stored information associating a muscle activation state or states to a control signal for enabling or disabling the set of virtual controls for the physical object to determine whether to enable or disable the set of virtual controls for the object. In some embodiments, the same muscle activation state(s) may be used to enable and disable virtual controls for all physical objects in the AR environment. In other embodiments, different muscle activation states may be associated with enabling and disabling virtual controls for different objects in the AR environment.

In some embodiments, the AR-based system (e.g., the system 200) may be configured to automatically enable virtual controls for physical objects in the AR environment without requiring the user to perform a muscular activation. For example, components of the AR-based system may be configured to determine which physical object(s) in the user's proximity that have virtual controls associated with the object(s), and the AR-based system may automatically enable virtual controls for those physical objects, and optionally may provide appropriate feedback to the user and/or one or more other user(s) (e.g., in a shared AR environment). Alternatively, the AR-based system may automatically enable virtual controls for a particular physical object in response to the user interacting with the object (e.g., when the user touches the object). Regardless of whether the AR-based system automatically enables virtual controls for object(s) or whether the user is required to perform muscular activation to enable the virtual controls, the AR-based system may disable virtual controls for an object in response to interpreting neuromuscular signals obtained from the user and/or information derived from the neuromuscular signals. In some embodiments, the muscular activation state(s) used to enable the virtual controls are the same as the muscular activation state(s) used to disable the virtual controls. In other embodiments, the muscular activation states used to enable and disable virtual controls for one or more object(s) in the AR environment are different.

If it is determined at act 440 that the virtual controls for the physical object in the AR environment should be enabled or disabled, the process proceeds to act 450, at which the virtual controls for the physical object are enabled or disabled. For example, a control signal may be sent to the AR system (e.g., the system 201) instructing the AR system to enable or disable virtual controls for a particular physical object, all physical objects within proximity of the user within the AR environment, or all physical objects within the user's field of view within the AR environment. In some embodiments, enabling a set of virtual controls for a physical object comprises providing an indication that the physical object has been transformed into an augmented object to which the virtual controls apply. Examples of providing an indication may include, but are not limited to, providing a visual, an audio, and/or a haptic indication within the AR environment to the user.

When virtual controls for an augmented or enhanced physical object are enabled, the process 400 optionally may proceed to act 460, where an interaction of the user with the object using the enabled set of virtual controls is determined. For example, if the augmented physical object is a writing implement and a set of enabled augmented features for the object includes a paintbrush mode, a pointer mode, and a remote control mode, the user may select one of the three modes by performing different muscular activations sensed and interpreted by the neuromuscular activity system (e.g., the system 202).

An AR environment may include a plurality of physical objects with which a user can interact. One or more of the plurality of physical objects in the AR environment may have a set of control actions associated with it. For example, as discussed above, the AR system (e.g., the system 201) of the AR-based system (e.g., the system 200) may be configured to associate a set of virtual controls with a physical object in the AR environment, and neuromuscular control signals obtained by the neuromuscular activity system (e.g., the system 202) may be used to enable or activate the set of virtual controls. From among the plurality of physical objects in the AR environment, the AR system may determine which object the user is interacting with, and may activate an appropriate set of control actions for the determined object.

Figure 5:
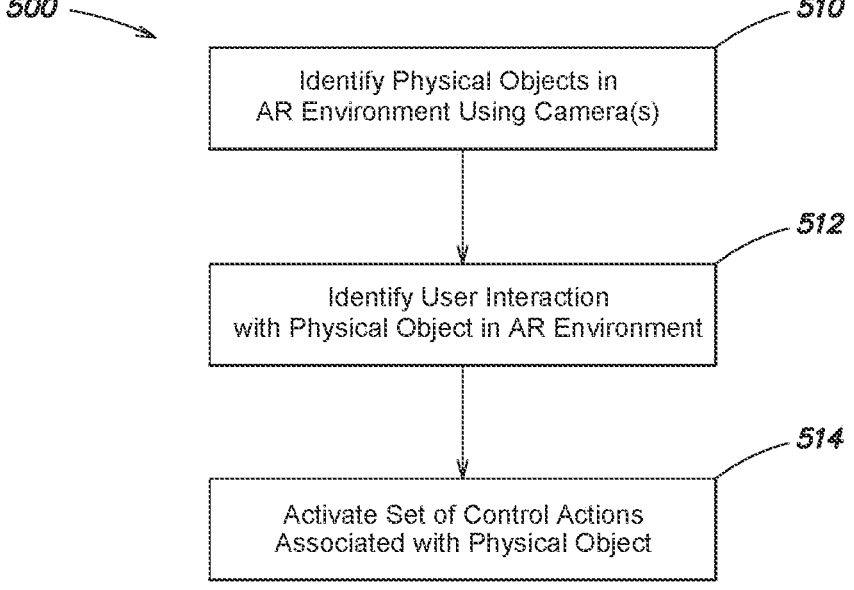
FIG. 5 is a flowchart of a process for activating a set of control actions for a physical object in an AR environment, in accordance with some embodiments of the technology described herein.

As described herein, AR components (e.g., cameras, sensors, etc.) may be used in combination with a neuromuscular controller (e.g., the one or more controller(s) 116) to provide enhanced functionally for interacting with physical objects in an AR environment. FIG. 5 illustrates a process 500 for activating a set of control actions associated with a physical object, in accordance with some embodiments of the technology disclosed herein. At act 510, physical objects in the AR environment are identified using one or more cameras (e.g., the camera(s) 204) associated with the AR-based system (e.g., the system 200). Images captured by camera(s) may be particularly useful in mapping environments and identifying physical objects in an AR environment. For example, if the user of the AR-based system is located in the user's kitchen, the camera(s) associated with the AR-based system may detect multiple physical objects in the user's AR environment, such as a refrigerator, a microwave oven, a stove, a pen, or an electronic device on a kitchen counter. As described above, in some embodiments, at least some of the physical objects in the AR environment may be associated with virtual controls that, when enabled, allow the user to interact with the objects in ways not possible when the user interacts with the objects in a real-world environment. In one exemplary embodiment of the technology disclosed herein, visual feedback may be provided to the user in the AR environment, to help guide or instruct the user in the real world. For example, a set of dials in the real world may be represented in the AR environment with overlaid visual interfaces and/or graphics, to inform the user about each dial, e.g., a type of the dial, a setting range of the dial, a purpose of the dial, or another characteristic of the dial as it relates to the real world and the user's interaction with the dial in the real world. In another example, visual instructions may be overlaid onto piano keys in an AR environment to instruct a user in the real world how to play a song on the piano. In another exemplary embodiment, if the stove in the kitchen was recently used and the surface of the stove is still hot, the AR system can present a warning label to the user in the AR environment, so that the user can avoid getting burned by the stove in real life. As another example, the AR system can present status information in the AR environment, to provide the user with information regarding the status of physical objects, e.g., device battery life, whether the device is switched on or off, etc.

The process 500 then proceeds to act 512, where an interaction of the user with a physical object in the AR environment is identified. The identification of the interaction may be made, at least in part, based on one or more images captured by the camera(s) associated with the AR system. For example, it may be determined from the one or more images that the user is holding a physical object (e.g., a writing implement), touching an object (e.g., a surface of a table) or reaching toward an object (e.g., a thermostat on the wall). In some embodiments, the identification of the interaction of the user with the object and/or a determination of how the user is interacting with the object may be made based, at least in part, on a plurality of neuromuscular signals obtained (e.g., sensed and recorded) by wearable sensors, as described above. For example, it may be determined based, at least in part, on the neuromuscular signals that the user is interacting with an object by pushing against the object with a force. After identifying the user's interaction with a physical object, the process 500 proceeds to act 514, where a set of control actions associated with the object with which the user is interacting is activated. For example, the set of control actions may be virtual controls, examples of which are described above.

In some embodiments, an interpretation of the neuromuscular signals by at least one trained inference model may be based, at least in part, on a particular object that the user is interacting with. For example, information about the physical object and/or information associated with an activated set of control actions may be provided as input to the trained inference model used to interpret the neuromuscular signals.

In some embodiments, an operation of the AR-based system may be modified based, at least in part, on an interaction of the user with a physical object in the AR environment. For example, a mode of the AR-based system may be changed from a coarse interaction mode (e.g., to determine whether a user is interacting with a physical object in the AR environment) into a higher-precision interaction mode for detecting finer-grained (e.g., more subtle or more detailed) interactions of the user with the physical object. The finer-grained interactions may include information about how the user is interacting with the physical object to perform different tasks within the AR environment using the physical object. The higher-precision interaction mode of the AR-based system may, for example, weight the neuromuscular signals more strongly than input from other sensors (e.g., a camera of the AR-based system) when determining information about one or more interaction(s) of the user with one or more physical object(s) in the AR environment.

In some embodiments, the neuromuscular signals may be used, at least in part, to affect how objects within the AR environment are digitized or rendered by the AR system. For some embodiments, AR applications may use one or more camera(s) to scan a physical environment to create a 3D model of the environment and physical objects within the physical environment so that, for example, virtual objects may be appropriately placed within an AR environment, which may be generated based on the physical environment, in a way that enables the virtual objects to interact properly with the physical objects in the AR environment. For example, a virtual character created within the generated AR environment may be presented as jumping up and down on a physical table in the AR environment. To ensure that the virtual character is represented within the AR environment correctly, properties about the table and its position are characterized in the 3D model of the physical environment created by the AR system. A potential limitation of camera-based scanning techniques for creating a 3D model of a physical environment is that non-visible properties of objects in the environment, which may include, but are not limited to, weight, texture, compressibility, bulk modulus, center of mass, and elasticity, are inferred from a visible appearance of the objects. In some embodiments, when a user interacts with a physical object in the physical environment (e.g., by picking up, pressing on, or otherwise manipulating the object), information about at least one non-visible property of the object may be determined with more specificity based on the neuromuscular signals obtained by the wearable sensors worn by the user, and this information about the non-visible properties of the object may be used to create a more accurate model of the object in the AR environment. For instance, neuromuscular signals obtained while the user picks up a soft furry pillow may differ from neuromuscular signals obtained while the user picks up a can of cold soda. Differences in, e.g., texture, temperature, and/or elasticity of a physical object may not be readily visible but may be sensed by one or more neuromuscular sensor(s) and/or one or more auxiliary sensor(s) and provided as feedback to the user.

The above-described embodiments can be implemented in any of numerous ways. For example, the embodiments may be implemented using hardware, software, or a combination thereof. When implemented in software, code comprising the software can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware or with one or more processors programmed using microcode or software to perform the functions recited above.

In this respect, it should be appreciated that one implementation of the embodiments of the present invention comprises at least one non-transitory computer-readable storage medium (e.g., a computer memory, a portable memory, a compact disk, etc.) encoded with a computer program (i.e., a plurality of instructions), which, when executed on a processor (or multiple processors), performs the above-discussed functions of the embodiments of the technologies described herein. The at least one computer-readable storage medium can be transportable such that the program stored thereon can be loaded onto any computer resource to implement the aspects of the present invention discussed herein. In addition, it should be appreciated that reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the present invention. As will be appreciated, a first portion of the program may be executed on a first computer processor and a second portion of the program may be executed on a second computer processor different from the first computer processor. The first and second computer processors may be located at the same location or at different locations; in each scenario the first and second computer processors maybe in communication with each other via e.g., a communication network.

In some embodiments of the present technology provided herein, a kit may be provided for controlling an AR system. The kit may include a wearable device comprising a plurality of neuromuscular sensors configured to sense a plurality of neuromuscular signals of a user, and a non-transitory computer-readable storage medium encoded with a plurality of instructions that, when executed by at least one computer processor, causes the at least computer processor to perform a method for enabling a user to interact with a physical object in an AR environment generated by the AR system. The method may comprise: receiving, as input, the plurality of neuromuscular signals sensed from the user by the plurality of neuromuscular sensors; determining, based at least in part on the plurality of neuromuscular signals, information relating to an interaction of the user with the physical object in the AR environment generated by the AR system; and instructing the AR system to provide feedback based, at least in part, on the information relating to an interaction of the user with the physical object. For example, the wearable device may comprise a wearable band structured to be worn around a part of the user, or a wearable patch structured to be worn on a part of the user, as described above.

Various aspects of the present invention may be used alone, in combination, or in a variety of arrangements not specifically discussed in the embodiments described above and therefore are not limited in their application to the details and arrangement of components set forth in the foregoing description and/or illustrated in the drawings. For example, aspects described in one embodiment may be combined in any manner with aspects described in other embodiments.

Also, embodiments of the invention may be implemented as one or more methods, of which at least one example has been provided. The acts performed as part of the method(s)

may be ordered in any suitable way. Accordingly, embodiments may be constructed in which acts are performed in an order different than illustrated and/or described, which may include performing some acts simultaneously, even though shown and/or described as sequential acts in illustrative embodiments.

Embodiments of the present disclosure may include or be implemented in conjunction with various types of artificial reality systems. Artificial reality is a form of reality that has been adjusted in some manner before presentation to a user, which may include, for example, a virtual reality, an augmented reality, a mixed reality, a hybrid reality, or some combination and/or derivative thereof. Artificial-reality content may include completely computer-generated content or computer-generated content combined with captured (e.g., real-world) content. The artificial-reality content may include video, audio, haptic feedback, or some combination thereof, any of which may be presented in a single channel or in multiple channels (such as stereo video that produces a three-dimensional (3D) effect to the viewer). Additionally, in some embodiments, artificial reality may also be associated with applications, products, accessories, services, or some combination thereof, that are used to, for example, create content in an artificial reality and/or are otherwise used in (e.g., to perform activities in) an artificial reality.

Artificial-reality systems may be implemented in a variety of different form factors and configurations. Some artificial reality systems may be designed to work without near-eye displays (NEDs). Other artificial reality systems may include an NED that also provides visibility into the real world (such as, e.g., augmented-reality system 1100 in FIG. 11) or that visually immerses a user in an artificial reality (such as, e.g., virtual-reality system 1200 in FIG. 12). While some artificial-reality devices may be self-contained systems, other artificial-reality devices may communicate and/or coordinate with external devices to provide an artificial-reality experience to a user. Examples of such external devices include handheld controllers, mobile devices, desktop computers, devices worn by a user, devices worn by one or more other users, and/or any other suitable external system.

Figure 11:
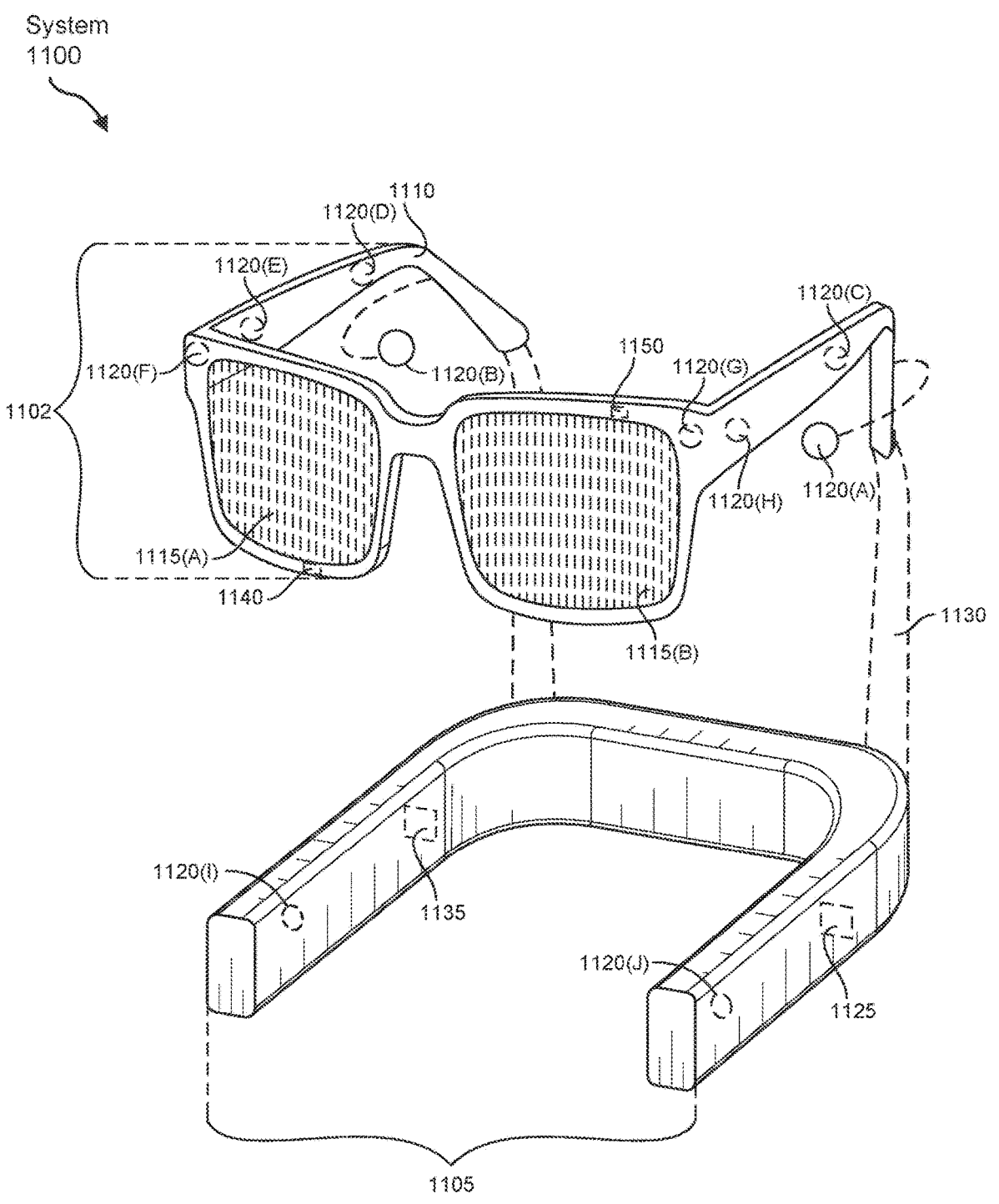
FIG. 11 is an illustration of exemplary augmented-reality glasses that may be used in connection with embodiments of this disclosure.

Turning to FIG. 11, augmented-reality system 1100 may include an eyewear device 1102 with a frame 1110 configured to hold a left display device 1115(A) and a right display device 1115(B) in front of a user's eyes. Display devices 1115(A) and 1115(B) may act together or independently to present an image or series of images to a user. While augmented-reality system 1100 includes two displays, embodiments of this disclosure may be implemented in augmented-reality systems with a single NED or more than two NEDs.

In some embodiments, augmented-reality system 1100 may include one or more sensors, such as sensor 1140. Sensor 1140 may generate measurement signals in response to motion of augmented-reality system 1100 and may be located on substantially any portion of frame 1110. Sensor 1140 may represent one or more of a variety of different sensing mechanisms, such as a position sensor, an inertial measurement unit (IMU), a depth camera assembly, a structured light emitter and/or detector, or any combination thereof. In some embodiments, augmented-reality system 1100 may or may not include sensor 1140 or may include more than one sensor. In embodiments in which sensor 1140 includes an IMU, the IMU may generate calibration data based on measurement signals from sensor 1140. Examples of sensor 1140 may include, without limitation, accelerometers, gyroscopes, magnetometers, other suitable types of sensors that detect motion, sensors used for error correction of the IMU, or some combination thereof.

In some examples, augmented-reality system 1100 may also include a microphone array with a plurality of acoustic transducers 1120(A)-1120(J), referred to collectively as acoustic transducers 1120. Acoustic transducers 1120 may represent transducers that detect air pressure variations induced by sound waves. Each acoustic transducer 1120 may be configured to detect sound and convert the detected sound into an electronic format (e.g., an analog or digital format). The microphone array in FIG. 11 may include, for example, ten acoustic transducers: 1120(A) and 1120(B), which may be designed to be placed inside a corresponding ear of the user, acoustic transducers 1120(C), 1120(D), 1120(E), 1120(F), 1120(G), and 1120(H), which may be positioned at various locations on frame 1110, and/or acoustic transducers 1120(I) and 1120(J), which may be positioned on a corresponding neckband 1105.

In some embodiments, one or more of acoustic transducers 1120(A)-(J) may be used as output transducers (e.g., speakers). For example, acoustic transducers 1120(A) and/or 1120(B) may be earbuds or any other suitable type of headphone or speaker.

The configuration of acoustic transducers 1120 of the microphone array may vary. While augmented-reality system 1100 is shown in FIG. 11 as having ten acoustic transducers 1120, the number of acoustic transducers 1120 may be greater or less than ten. In some embodiments, using higher numbers of acoustic transducers 1120 may increase the amount of audio information collected and/or the sensitivity and accuracy of the audio information. In contrast, using a lower number of acoustic transducers 1120 may decrease the computing power required by an associated controller 1150 to process the collected audio information. In addition, the position of each acoustic transducer 1120 of the microphone array may vary. For example, the position of an acoustic transducer 1120 may include a defined position on the user, a defined coordinate on frame 1110, an orientation associated with each acoustic transducer 1120, or some combination thereof.

Acoustic transducers 1120(A) and 1120(B) may be positioned on different parts of the user's ear, such as behind the pinna, behind the tragus, and/or within the auricle or fossa. Or, there may be additional acoustic transducers 1120 on or surrounding the ear in addition to acoustic transducers 1120 inside the ear canal. Having an acoustic transducer 1120 positioned next to an ear canal of a user may enable the microphone array to collect information on how sounds arrive at the ear canal. By positioning at least two of acoustic transducers 1120 on either side of a user's head (e.g., as binaural microphones), augmented-reality device 1100 may simulate binaural hearing and capture a 3D stereo sound field around about a user's head. In some embodiments, acoustic transducers 1120(A) and 1120(B) may be connected to augmented-reality system 1100 via a wired connection 1130, and in other embodiments acoustic transducers 1120(A) and 1120(B) may be connected to augmented-reality system 1100 via a wireless connection (e.g., a BLUETOOTH connection). In still other embodiments, acoustic transducers 1120(A) and 1120(B) may not be used at all in conjunction with augmented-reality system 1100.

Acoustic transducers 1120 on frame 1110 may be positioned in a variety of different ways, including along the length of the temples, across the bridge, above or below display devices 1115(A) and 1115(B), or some combination thereof. Acoustic transducers 1120 may also be oriented such that the microphone array is able to detect sounds in a wide range of directions surrounding the user wearing the augmented-reality system 1100. In some embodiments, an optimization process may be performed during manufacturing of augmented-reality system 1100 to determine relative positioning of each acoustic transducer 1120 in the microphone array.

In some examples, augmented-reality system 1100 may include or be connected to an external device (e.g., a paired device), such as neckband 1105. Neckband 1105 generally represents any type or form of paired device. Thus, the following discussion of neckband 1105 may also apply to various other paired devices, such as charging cases, smart watches, smart phones, wrist bands, other wearable devices, hand-held controllers, tablet computers, laptop computers, other external compute devices, etc.

As shown, neckband 1105 may be coupled to eyewear device 1102 via one or more connectors. The connectors may be wired or wireless and may include electrical and/or non-electrical (e.g., structural) components. In some cases, eyewear device 1102 and neckband 1105 may operate independently without any wired or wireless connection between them. While FIG. 11 illustrates the components of eyewear device 1102 and neckband 1105 in example locations on eyewear device 1102 and neckband 1105, the components may be located elsewhere and/or distributed differently on eyewear device 1102 and/or neckband 1105. In some embodiments, the components of eyewear device 1102 and neckband 1105 may be located on one or more additional peripheral devices paired with eyewear device 1102, neckband 1105, or some combination thereof.

Pairing external devices, such as neckband 1105, with augmented-reality eyewear devices may enable the eyewear devices to achieve the form factor of a pair of glasses while still providing sufficient battery and computation power for expanded capabilities. Some or all of the battery power, computational resources, and/or additional features of augmented-reality system 1100 may be provided by a paired device or shared between a paired device and an eyewear device, thus reducing the weight, heat profile, and form factor of the eyewear device overall while still retaining desired functionality. For example, neckband 1105 may allow components that would otherwise be included on an eyewear device to be included in neckband 1105 since users may tolerate a heavier weight load on their shoulders than they would tolerate on their heads. Neckband 1105 may also have a larger surface area over which to diffuse and disperse heat to the ambient environment. Thus, neckband 1105 may allow for greater battery and computation capacity than might otherwise have been possible on a stand-alone eyewear device. Since weight carried in neckband 1105 may be less invasive to a user than weight carried in eyewear device 1102, a user may tolerate wearing a lighter eyewear device and carrying or wearing the paired device for greater lengths of time than a user would tolerate wearing a heavy stand-alone eyewear device, thereby enabling users to more fully incorporate artificial reality environments into their day-to-day activities.

Neckband 1105 may be communicatively coupled with eyewear device 1102 and/or to other devices. These other devices may provide certain functions (e.g., tracking, localizing, depth mapping, processing, storage, etc.) to augmented-reality system 1100. In the embodiment of FIG. 11, neckband 1105 may include two acoustic transducers (e.g., 1120(I) and 1120(J)) that are part of the microphone array (or potentially form their own microphone subarray). Neckband 1105 may also include a controller 1125 and a power source 1135.

Acoustic transducers 1120(I) and 1120(J) of neckband 1105 may be configured to detect sound and convert the detected sound into an electronic format (analog or digital). In the embodiment of FIG. 11, acoustic transducers 1120(I) and 1120(J) may be positioned on neckband 1105, thereby increasing the distance between the neckband acoustic transducers 1120(I) and 1120(J) and other acoustic transducers 1120 positioned on eyewear device 1102. In some cases, increasing the distance between acoustic transducers 1120 of the microphone array may improve the accuracy of beamforming performed via the microphone array. For example, if a sound is detected by acoustic transducers 1120(C) and 1120(D) and the distance between acoustic transducers 1120(C) and 1120(D) is greater than, e.g., the distance between acoustic transducers 1120(D) and 1120(E), the determined source location of the detected sound may be more accurate than if the sound had been detected by acoustic transducers 1120(D) and 1120(E).

Controller 1125 of neckband 1105 may process information generated by the sensors on neckband 1105 and/or augmented-reality system 1100. For example, controller 1125 may process information from the microphone array that describes sounds detected by the microphone array. For each detected sound, controller 1125 may perform a direction-of-arrival (DOA) estimation to estimate a direction from which the detected sound arrived at the microphone array. As the microphone array detects sounds, controller 1125 may populate an audio data set with the information. In embodiments in which augmented-reality system 1100 includes an inertial measurement unit, controller 1125 may compute all inertial and spatial calculations from the IMU located on eyewear device 1102. A connector may convey information between augmented-reality system 1100 and neckband 1105 and between augmented-reality system 1100 and controller 1125. The information may be in the form of optical data, electrical data, wireless data, or any other transmittable data form. Moving the processing of information generated by augmented-reality system 1100 to neckband 1105 may reduce weight and heat in eyewear device 1102, making it more comfortable to the user.

Power source 1135 in neckband 1105 may provide power to eyewear device 1102 and/or to neckband 1105. Power source 1135 may include, without limitation, lithium ion batteries, lithium-polymer batteries, primary lithium batteries, alkaline batteries, or any other form of power storage. In some cases, power source 1135 may be a wired power source. Including power source 1135 on neckband 1105 instead of on eyewear device 1102 may help better distribute the weight and heat generated by power source 1135.

As noted, some artificial reality systems may, instead of blending an artificial reality with actual reality, substantially replace one or more of a user's sensory perceptions of the real world with a virtual experience. One example of this type of system is a head-worn display system, such as virtual-reality system 1200 in FIG. 12, that mostly or completely covers a user's field of view. Virtual-reality system 1200 may include a front rigid body 1202 and a band 1204 shaped to fit around a user's head. Virtual-reality system 1200 may also include output audio transducers 1206(A) and 1206(B). Furthermore, while not shown in FIG. 12, front rigid body 1202 may include one or more electronic elements, including one or more electronic displays, one or more inertial measurement units (IMUs), one or more tracking emitters or detectors, and/or any other suitable device or system for creating an artificial-reality experience.

Artificial reality systems may include a variety of types of visual feedback mechanisms. For example, display devices in augmented-reality system 1100 and/or virtual-reality system 1200 may include one or more liquid crystal displays (LCDs), light emitting diode (LED) displays, microLED displays, organic LED (OLED) displays, digital light project (DLP) micro-displays, liquid crystal on silicon (LCoS) micro-displays, and/or any other suitable type of display screen. These artificial reality systems may include a single display screen for both eyes or may provide a display screen for each eye, which may allow for additional flexibility for varifocal adjustments or for correcting a user's refractive error. Some of these artificial reality systems may also include optical subsystems having one or more lenses (e.g., concave or convex lenses, Fresnel lenses, adjustable liquid lenses, etc.) through which a user may view a display screen. These optical subsystems may serve a variety of purposes, including to collimate (e.g., make an object appear at a greater distance than its physical distance), to magnify (e.g., make an object appear larger than its actual size), and/or to relay (to, e.g., the viewer's eyes) light. These optical subsystems may be used in a non-pupil-forming architecture (such as a single lens configuration that directly collimates light but results in so-called pincushion distortion) and/or a pupil-forming architecture (such as a multi-lens configuration that produces so-called barrel distortion to nullify pincushion distortion).

In addition to or instead of using display screens, some of the artificial reality systems described herein may include one or more projection systems. For example, display devices in augmented-reality system 1100 and/or virtual-reality system 1200 may include micro-LED projectors that project light (using, e.g., a waveguide) into display devices, such as clear combiner lenses that allow ambient light to pass through. The display devices may refract the projected light toward a user's pupil and may enable a user to simultaneously view both artificial reality content and the real world. The display devices may accomplish this using any of a variety of different optical components, including waveguide components (e.g., holographic, planar, diffractive, polarized, and/or reflective waveguide elements), light-manipulation surfaces and elements (such as diffractive, reflective, and refractive elements and gratings), coupling elements, etc. Artificial reality systems may also be configured with any other suitable type or form of image projection system, such as retinal projectors used in virtual retina displays.

The artificial reality systems described herein may also include various types of computer vision components and subsystems. For example, augmented-reality system 1100 and/or virtual-reality system 1200 may include one or more optical sensors, such as two-dimensional (2D) or 3D cameras, structured light transmitters and detectors, time-of-flight depth sensors, single-beam or sweeping laser rangefinders, 3D LiDAR sensors, and/or any other suitable type or form of optical sensor. An artificial reality system may process data from one or more of these sensors to identify a location of a user, to map the real world, to provide a user with context about real-world surroundings, and/or to perform a variety of other functions.

The artificial reality systems described herein may also include one or more input and/or output audio transducers. Output audio transducers may include voice coil speakers, ribbon speakers, electrostatic speakers, piezoelectric speakers, bone conduction transducers, cartilage conduction transducers, tragus-vibration transducers, and/or any other suitable type or form of audio transducer. Similarly, input audio transducers may include condenser microphones, dynamic microphones, ribbon microphones, and/or any other type or form of input transducer. In some embodiments, a single transducer may be used for both audio input and audio output.

In some embodiments, the artificial reality systems described herein may also include tactile (i.e., haptic) feedback systems, which may be incorporated into headwear, gloves, body suits, handheld controllers, environmental devices (e.g., chairs, floormats, etc.), and/or any other type of device or system. Haptic feedback systems may provide various types of cutaneous feedback, including vibration, force, traction, texture, and/or temperature. Haptic feedback systems may also provide various types of kinesthetic feedback, such as motion and compliance. Haptic feedback may be implemented using motors, piezoelectric actuators, fluidic systems, and/or a variety of other types of feedback mechanisms. Haptic feedback systems may be implemented independent of other artificial reality devices, within other artificial reality devices, and/or in conjunction with other artificial reality devices.

By providing haptic sensations, audible content, and/or visual content, artificial reality systems may create an entire virtual experience or enhance a user's real-world experience in a variety of contexts and environments. For instance, artificial reality systems may assist or extend a user's perception, memory, or cognition within a particular environment. Some systems may enhance a user's interactions with other people in the real world or may enable more immersive interactions with other people in a virtual world. Artificial reality systems may also be used for educational purposes (e.g., for teaching or training in schools, hospitals, government organizations, military organizations, business enterprises, etc.), entertainment purposes (e.g., for playing video games, listening to music, watching video content, etc.), and/or for accessibility purposes (e.g., as hearing aids, visual aids, etc.). The embodiments disclosed herein may enable or enhance a user's artificial reality experience in one or more of these contexts and environments and/or in other contexts and environments.

Some augmented reality systems may map a user's and/or device's environment using techniques referred to as "simultaneous location and mapping" (SLAM). SLAM mapping and location identifying techniques may involve a variety of hardware and software tools that can create or update a map of an environment while simultaneously keeping track of a user's location within the mapped environment. SLAM may use many different types of sensors to create a map and determine a user's position within the map.

SLAM techniques may, for example, implement optical sensors to determine a user's location. Radios including WiFi, BLUETOOTH, global positioning system (GPS), cellular or other communication devices may be also used to determine a user's location relative to a radio transceiver or group of transceivers (e.g., a WiFi router or group of GPS satellites). Acoustic sensors such as microphone arrays or 2D or 3D sonar sensors may also be used to determine a user's location within an environment. Augmented reality and virtual reality devices (such as systems 1100 and 1200 of FIGS. 11 and 12, respectively) may incorporate any or all of these types of sensors to perform SLAM operations such as creating and continually updating maps of the user's current environment. In at least some of the embodiments described herein, SLAM data generated by these sensors may be referred to as "environmental data" and may indicate a user's current environment. This data may be stored in a local or remote data store (e.g., a cloud data store) and may be provided to a user's AR/VR device on demand.

When the user is wearing an augmented reality headset or virtual reality headset in a given environment, the user may be interacting with other users or other electronic devices that serve as audio sources. In some cases, it may be desirable to determine where the audio sources are located relative to the user and then present the audio sources to the user as if they were coming from the location of the audio source. The process of determining where the audio sources are located relative to the user may be referred to as "localization," and the process of rendering playback of the audio source signal to appear as if it is coming from a specific direction may be referred to as "spatialization."

Localizing an audio source may be performed in a variety of different ways. In some cases, an augmented reality or virtual reality headset may initiate a DOA analysis to determine the location of a sound source. The DOA analysis may include analyzing the intensity, spectra, and/or arrival time of each sound at the artificial reality device to determine the direction from which the sounds originated. The DOA analysis may include any suitable algorithm for analyzing the surrounding acoustic environment in which the artificial reality device is located.

For example, the DOA analysis may be designed to receive input signals from a microphone and apply digital signal processing algorithms to the input signals to estimate the direction of arrival. These algorithms may include, for example, delay and sum algorithms where the input signal is sampled, and the resulting weighted and delayed versions of the sampled signal are averaged together to determine a direction of arrival. A least mean squared (LMS) algorithm may also be implemented to create an adaptive filter. This adaptive filter may then be used to identify differences in signal intensity, for example, or differences in time of arrival. These differences may then be used to estimate the direction of arrival. In another embodiment, the DOA may be determined by converting the input signals into the frequency domain and selecting specific bins within the time-frequency (TF) domain to process. Each selected TF bin may be processed to determine whether that bin includes a portion of the audio spectrum with a direct-path audio signal. Those bins having a portion of the direct-path signal may then be analyzed to identify the angle at which a microphone array received the direct-path audio signal. The determined angle may then be used to identify the direction of arrival for the received input signal. Other algorithms not listed above may also be used alone or in combination with the above algorithms to determine DOA.

In some embodiments, different users may perceive the source of a sound as coming from slightly different locations. This may be the result of each user having a unique head-related transfer function (HRTF), which may be dictated by a user's anatomy including ear canal length and the positioning of the ear drum. The artificial reality device may provide an alignment and orientation guide, which the user may follow to customize the sound signal presented to the user based on their unique HRTF. In some embodiments, an artificial reality device may implement one or more microphones to listen to sounds within the user's environment. The augmented reality or virtual reality headset may use a variety of different array transfer functions (e.g., any of the DOA algorithms identified above) to estimate the direction of arrival for the sounds. Once the direction of arrival has been determined, the artificial reality device may play back sounds to the user according to the user's unique HRTF. Accordingly, the DOA estimation generated using the array transfer function (ATF) may be used to determine the direction from which the sounds are to be played from. The playback sounds may be further refined based on how that specific user hears sounds according to the HRTF.

In addition to or as an alternative to performing a DOA estimation, an artificial reality device may perform localization based on information received from other types of sensors. These sensors may include cameras, IR sensors, heat sensors, motion sensors, GPS receivers, or in some cases, sensors that detect a user's eye movements. For example, as noted above, an artificial reality device may include an eye tracker or gaze detector that determines where the user is looking. Often, the user's eyes will look at the source of the sound, if only briefly. Such clues provided by the user's eyes may further aid in determining the location of a sound source. Other sensors such as cameras, heat sensors, and IR sensors may also indicate the location of a user, the location of an electronic device, or the location of another sound source. Any or all of the above methods may be used individually or in combination to determine the location of a sound source and may further be used to update the location of a sound source over time.

Some embodiments may implement the determined DOA to generate a more customized output audio signal for the user. For instance, an "acoustic transfer function" may characterize or define how a sound is received from a given location. More specifically, an acoustic transfer function may define the relationship between parameters of a sound at its source location and the parameters by which the sound signal is detected (e.g., detected by a microphone array or detected by a user's ear). An artificial reality device may include one or more acoustic sensors that detect sounds within range of the device. A controller of the artificial reality device may estimate a DOA for the detected sounds (using, e.g., any of the methods identified above) and, based on the parameters of the detected sounds, may generate an acoustic transfer function that is specific to the location of the device. This customized acoustic transfer function may thus be used to generate a spatialized output audio signal where the sound is perceived as coming from a specific location.

Indeed, once the location of the sound source or sources is known, the artificial reality device may re-render (i.e., spatialize) the sound signals to sound as if coming from the direction of that sound source. The artificial reality device may apply filters or other digital signal processing that alter the intensity, spectra, or arrival time of the sound signal. The digital signal processing may be applied in such a way that the sound signal is perceived as originating from the determined location. The artificial reality device may amplify or subdue certain frequencies or change the time that the signal arrives at each ear. In some cases, the artificial reality device may create an acoustic transfer function that is specific to the location of the device and the detected direction of arrival of the sound signal. In some embodiments, the artificial reality device may re-render the source signal in a stereo device or multi-speaker device (e.g., a surround sound device). In such cases, separate and distinct audio signals may be sent to each speaker. Each of these audio signals may be altered according to the user's HRTF and according to measurements of the user's location and the location of the sound source to sound as if they are coming from the determined location of the sound source. Accordingly, in this manner, the artificial reality device (or speakers associated with the device) may re-render an audio signal to sound as if originating from a specific location.

As noted, artificial reality systems 1100 and 1200 may be used with a variety of other types of devices to provide a more compelling artificial reality experience. These devices may be haptic interfaces with transducers that provide haptic feedback and/or that collect haptic information about a user's interaction with an environment. The artificial-reality systems disclosed herein may include various types of haptic interfaces that detect or convey various types of haptic information, including tactile feedback (e.g., feedback that a user detects via nerves in the skin, which may also be referred to as cutaneous feedback) and/or kinesthetic feedback (e.g., feedback that a user detects via receptors located in muscles, joints, and/or tendons).

Haptic feedback may be provided by interfaces positioned within a user's environment (e.g., chairs, tables, floors, etc.) and/or interfaces on articles that may be worn or carried by a user (e.g., gloves, wristbands, etc.). As an example, FIG. 13 illustrates a vibrotactile system 1300 in the form of a wearable glove (haptic device 1310) and wristband (haptic device 1320). Haptic device 1310 and haptic device 1320 are shown as examples of wearable devices that include a flexible, wearable textile material 1330 that is shaped and configured for positioning against a user's hand and wrist, respectively. This disclosure also includes vibrotactile systems that may be shaped and configured for positioning against other human body parts, such as a finger, an arm, a head, a torso, a foot, or a leg. By way of example and not limitation, vibrotactile systems according to various embodiments of the present disclosure may also be in the form of a glove, a headband, an armband, a sleeve, a head covering, a sock, a shirt, or pants, among other possibilities. In some examples, the term "textile" may include any flexible, wearable material, including woven fabric, non-woven fabric, leather, cloth, a flexible polymer material, composite materials, etc.

One or more vibrotactile devices 1340 may be positioned at least partially within one or more corresponding pockets formed in textile material 1330 of vibrotactile system 1300. Vibrotactile devices 1340 may be positioned in locations to provide a vibrating sensation (e.g., haptic feedback) to a user of vibrotactile system 1300. For example, vibrotactile devices 1340 may be positioned against the user's finger(s), thumb, or wrist, as shown in FIG. 13. Vibrotactile devices 1340 may, in some examples, be sufficiently flexible to conform to or bend with the user's corresponding body part(s).

A power source 1350 (e.g., a battery) for applying a voltage to the vibrotactile devices 1340 for activation thereof may be electrically coupled to vibrotactile devices 1340, such as via conductive wiring 1352. In some examples, each of vibrotactile devices 1340 may be independently electrically coupled to power source 1350 for individual activation. In some embodiments, a processor 1360 may be operatively coupled to power source 1350 and configured (e.g., programmed) to control activation of vibrotactile devices 1340.

Vibrotactile system 1300 may be implemented in a variety of ways. In some examples, vibrotactile system 1300 may be a standalone system with integral subsystems and components for operation independent of other devices and systems. As another example, vibrotactile system 1300 may be configured for interaction with another device or system 1370. For example, vibrotactile system 1300 may, in some examples, include a communications interface 1380 for receiving and/or sending signals to the other device or system 1370. The other device or system 1370 may be a mobile device, a gaming console, an artificial reality (e.g., virtual reality, augmented reality, mixed reality) device, a personal computer, a tablet computer, a network device (e.g., a modem, a router, etc.), a handheld controller, etc. Communications interface 1380 may enable communications between vibrotactile system 1300 and the other device or system 1370 via a wireless (e.g., Wi-Fi, BLUETOOTH, cellular, radio, etc.) link or a wired link. If present, communications interface 1380 may be in communication with processor 1360, such as to provide a signal to processor 1360 to activate or deactivate one or more of the vibrotactile devices 1340.

Vibrotactile system 1300 may optionally include other subsystems and components, such as touch-sensitive pads 1390, pressure sensors, motion sensors, position sensors, lighting elements, and/or user interface elements (e.g., an on/off button, a vibration control element, etc.). During use, vibrotactile devices 1340 may be configured to be activated for a variety of different reasons, such as in response to the user's interaction with user interface elements, a signal from the motion or position sensors, a signal from the touch-sensitive pads 1390, a signal from the pressure sensors, a signal from the other device or system 1370, etc.

Although power source 1350, processor 1360, and communications interface 1380 are illustrated in FIG. 13 as being positioned in haptic device 1320, the present disclosure is not so limited. For example, one or more of power source 1350, processor 1360, or communications interface 1380 may be positioned within haptic device 1310 or within another wearable textile.

Figure 14:
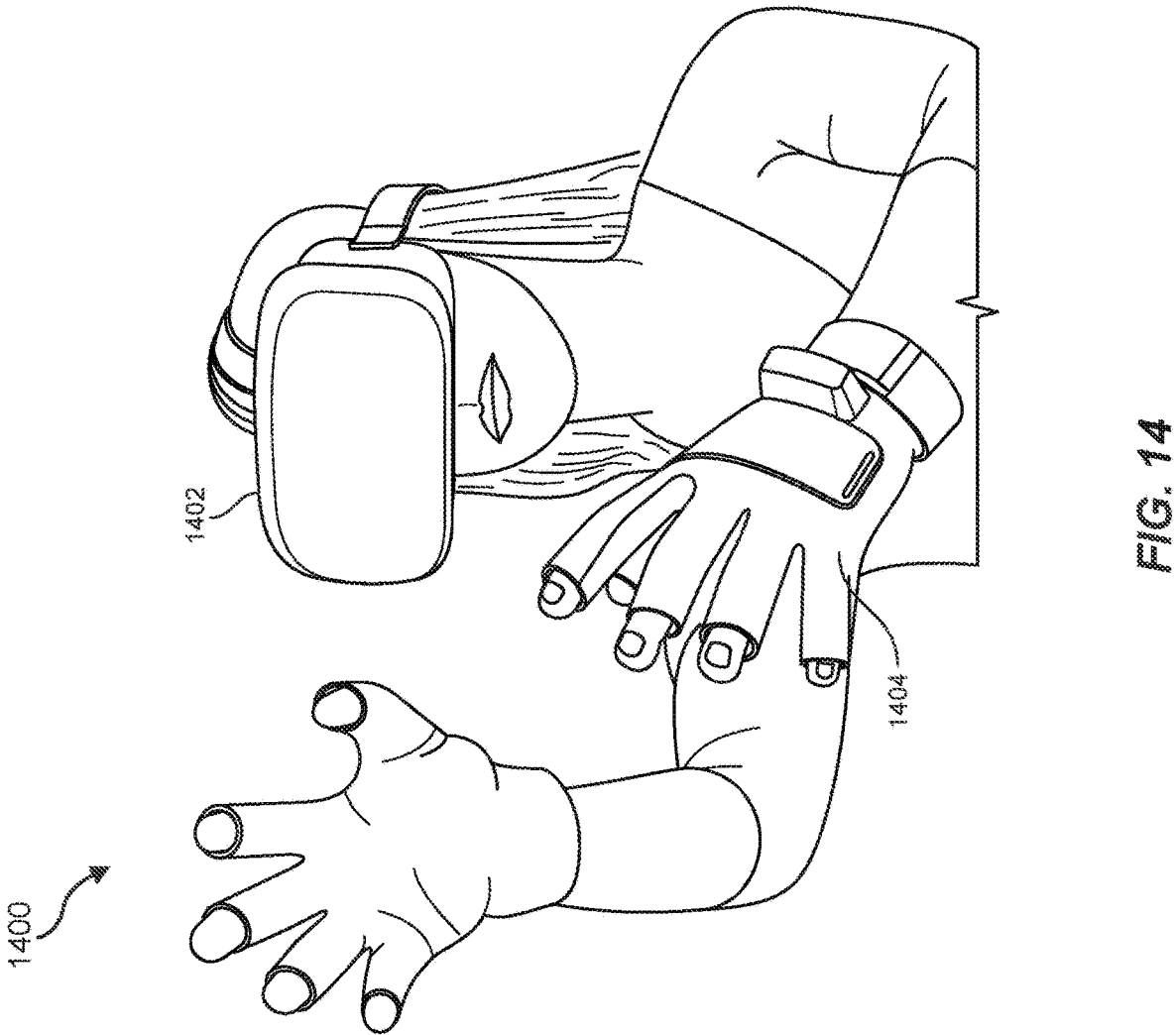
FIG. 14 is an illustration of an exemplary virtual-reality environment according to embodiments of this disclosure.

Haptic wearables, such as those shown in and described in connection with FIG. 13, may be implemented in a variety of types of artificial-reality systems and environments. FIG. 14 shows an example artificial reality environment 1400 including one head-mounted virtual-reality display and two haptic devices (i.e., gloves), and in other embodiments any number and/or combination of these components and other components may be included in an artificial reality system. For example, in some embodiments there may be multiple head-mounted displays each having an associated haptic device, with each head-mounted display and each haptic device communicating with the same console, portable computing device, or other computing system.

Figure 12:
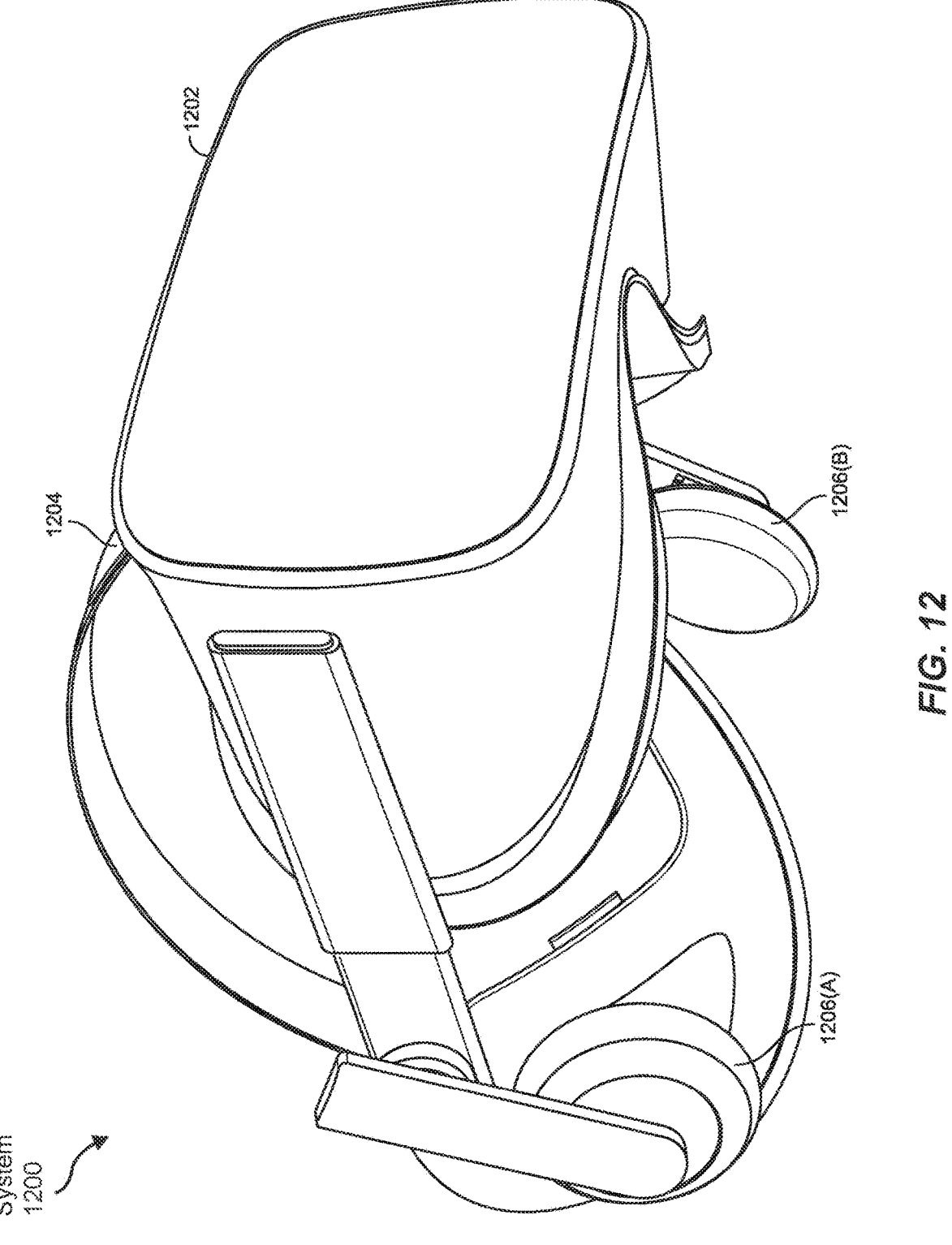
FIG. 12 is an illustration of an exemplary virtual-reality headset that may be used in connection with embodiments of this disclosure.

Head-mounted display 1402 generally represents any type or form of virtual-reality system, such as virtual-reality system 1200 in FIG. 12. Haptic device 1404 generally represents any type or form of wearable device, worn by a user of an artificial reality system, that provides haptic feedback to the user to give the user the perception that he or she is physically engaging with a virtual object. In some embodiments, haptic device 1404 may provide haptic feedback by applying vibration, motion, and/or force to the user. For example, haptic device 1404 may limit or augment a user's movement. To give a specific example, haptic device 1404 may limit a user's hand from moving forward so that the user has the perception that his or her hand has come in physical contact with a virtual wall. In this specific example, one or more actuators within the haptic device may achieve the physical-movement restriction by pumping fluid into an inflatable bladder of the haptic device. In some examples, a user may also use haptic device 1404 to send action requests to a console. Examples of action requests include, without limitation, requests to start an application and/or end the application and/or requests to perform a particular action within the application.

Figure 15:
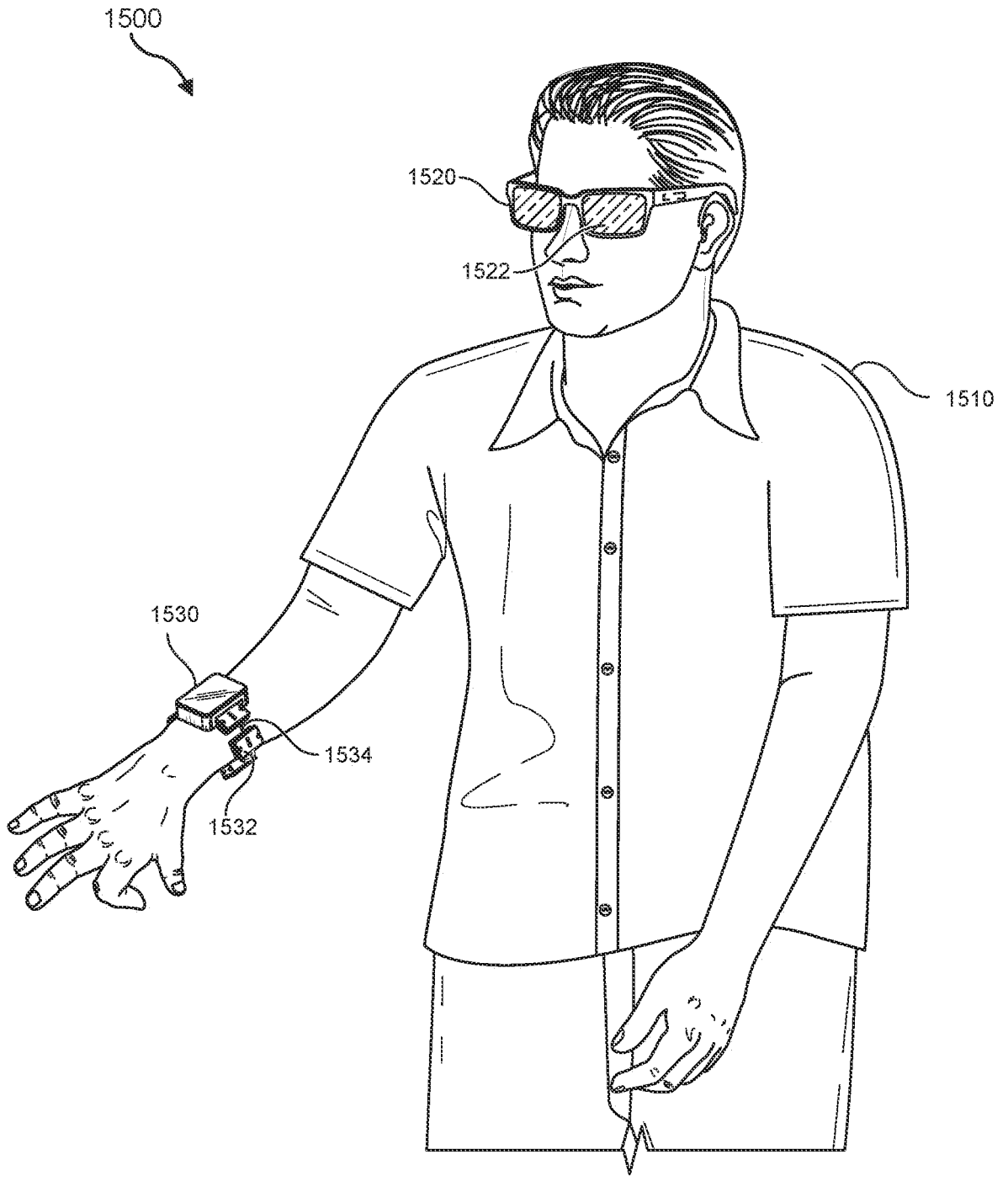
FIG. 15 is an illustration of an exemplary augmented-reality environment according to embodiments of this disclosure.

While haptic interfaces may be used with virtual-reality systems, as shown in FIG. 14, haptic interfaces may also be used with augmented-reality systems, as shown in FIG. 15.

FIG. 15 is a perspective view of a user 1510 interacting with an augmented-reality system 1500. In this example, user 1510 may wear a pair of augmented-reality glasses 1520 that may have one or more displays 1522 and that are paired with a haptic device 1530. In this example, haptic device 1530 may be a wristband that includes a plurality of band elements 1532 and a tensioning mechanism 1534 that connects band elements 1532 to one another.

One or more of band elements 1532 may include any type or form of actuator suitable for providing haptic feedback. For example, one or more of band elements 1532 may be configured to provide one or more of various types of cutaneous feedback, including vibration, force, traction, texture, and/or temperature. To provide such feedback, band elements 1532 may include one or more of various types of actuators. In one example, each of band elements 1532 may include a vibrotactor (e.g., a vibrotactile actuator) configured to vibrate in unison or independently to provide one or more of various types of haptic sensations to a user. Alternatively, only a single band element or a subset of band elements may include vibrotactors.

Haptic devices 1310, 1320, 1404, and 1530 may include any suitable number and/or type of haptic transducer, sensor, and/or feedback mechanism. For example, haptic devices 1310, 1320, 1404, and 1530 may include one or more mechanical transducers, piezoelectric transducers, and/or fluidic transducers. Haptic devices 1310, 1320, 1404, and 1530 may also include various combinations of different types and forms of transducers that work together or independently to enhance a user's artificial-reality experience. In one example, each of band elements 1532 of haptic device 1530 may include a vibrotactor (e.g., a vibrotactile actuator) configured to vibrate in unison or independently to provide one or more of various types of haptic sensations to a user.

In some embodiments, the systems described herein may also include an eye-tracking subsystem designed to identify and track various characteristics of a user's eye(s), such as the user's gaze direction. The phrase "eye tracking" may, in some examples, refer to a process by which the position, orientation, and/or motion of an eye is measured, detected, sensed, determined, and/or monitored. The disclosed systems may measure the position, orientation, and/or motion of an eye in a variety of different ways, including through the use of various optical-based eye-tracking techniques, ultrasound-based eye-tracking techniques, etc. An eye-tracking subsystem may be configured in a number of different ways and may include a variety of different eye-tracking hardware components or other computer-vision components. For example, an eye-tracking subsystem may include a variety of different optical sensors, such as two-dimensional (2D) or 3D cameras, time-of-flight depth sensors, single-beam or sweeping laser rangefinders, 3D LiDAR sensors, and/or any other suitable type or form of optical sensor. In this example, a processing subsystem may process data from one or more of these sensors to measure, detect, determine, and/or otherwise monitor the position, orientation, and/or motion of the user's eye(s).

Figure 16:
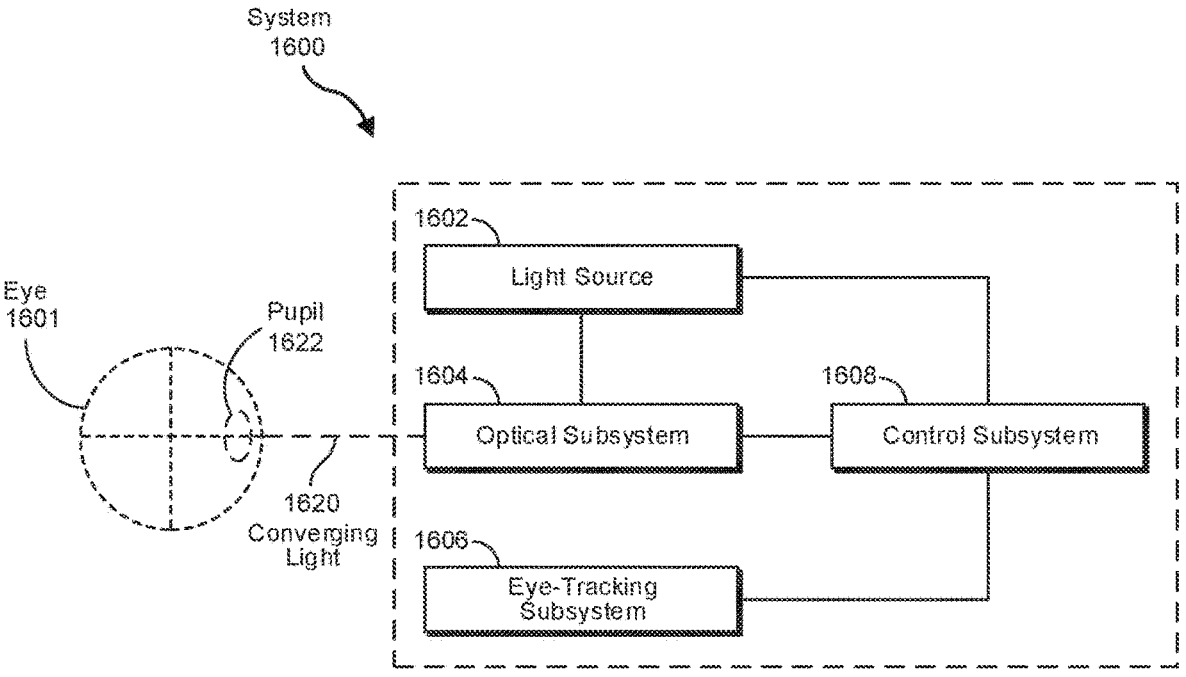
FIG. 16 an illustration of an exemplary system that incorporates an eye-tracking subsystem capable of tracking a user's eye(s).

FIG. 16 is an illustration of an exemplary system 1600 that incorporates an eye-tracking subsystem capable of tracking a user's eye(s). As depicted in FIG. 16, system 1600 may include a light source 1602, an optical subsystem 1604, an eye-tracking subsystem 1606, and/or a control subsystem 1608. In some examples, light source 1602 may generate light for an image (e.g., to be presented to an eye 1601 of the viewer). Light source 1602 may represent any of a variety of suitable devices. For example, light source 1602 can include a two-dimensional projector (e.g., a LCoS display), a scanning source (e.g., a scanning laser), or other device (e.g., an LCD, an LED display, an OLED display, an active-matrix OLED display (AMOLED), a transparent OLED display (TOLED), a waveguide, or some other display capable of generating light for presenting an image to the viewer). In some examples, the image may represent a virtual image, which may refer to an optical image formed from the apparent divergence of light rays from a point in space, as opposed to an image formed from the light ray's actual divergence.

In some embodiments, optical subsystem 1604 may receive the light generated by light source 1602 and generate, based on the received light, converging light 1620 that includes the image. In some examples, optical subsystem 1604 may include any number of lenses (e.g., Fresnel lenses, convex lenses, concave lenses), apertures, filters, mirrors, prisms, and/or other optical components, possibly in combination with actuators and/or other devices. In particular, the actuators and/or other devices may translate and/or rotate one or more of the optical components to alter one or more aspects of converging light 1620. Further, various mechanical couplings may serve to maintain the relative spacing and/or the orientation of the optical components in any suitable combination.

In one embodiment, eye-tracking subsystem 1606 may generate tracking information indicating a gaze angle of an eye 1601 of the viewer. In this embodiment, control subsystem 1608 may control aspects of optical subsystem 1604 (e.g., the angle of incidence of converging light 1620) based at least in part on this tracking information. Additionally, in some examples, control subsystem 1608 may store and utilize historical tracking information (e.g., a history of the tracking information over a given duration, such as the previous second or fraction thereof) to anticipate the gaze angle of eye 1601 (e.g., an angle between the visual axis and the anatomical axis of eye 1601). In some embodiments, eye-tracking subsystem 1606 may detect radiation emanating from some portion of eye 1601 (e.g., the cornea, the iris, the pupil, or the like) to determine the current gaze angle of eye 1601. In other examples, eye-tracking subsystem 1606 may employ a wavefront sensor to track the current location of the pupil.

Any number of techniques can be used to track eye 1601. Some techniques may involve illuminating eye 1601 with infrared light and measuring reflections with at least one optical sensor that is tuned to be sensitive to the infrared light. Information about how the infrared light is reflected from eye 1601 may be analyzed to determine the position(s), orientation(s), and/or motion(s) of one or more eye feature(s), such as the cornea, pupil, iris, and/or retinal blood vessels.

In some examples, the radiation captured by a sensor of eye-tracking subsystem 1606 may be digitized (i.e., converted to an electronic signal). Further, the sensor may transmit a digital representation of this electronic signal to one or more processors (for example, processors associated with a device including eye-tracking subsystem 1606). Eye-tracking subsystem 1606 may include any of a variety of sensors in a variety of different configurations. For example, eye-tracking subsystem 1606 may include an infrared detector that reacts to infrared radiation. The infrared detector may be a thermal detector, a photonic detector, and/or any other suitable type of detector. Thermal detectors may include detectors that react to thermal effects of the incident infrared radiation.

In some examples, one or more processors may process the digital representation generated by the sensor(s) of eye-tracking subsystem 1606 to track the movement of eye 1601. In another example, these processors may track the movements of eye 1601 by executing algorithms represented by computer-executable instructions stored on non-transitory memory. In some examples, on-chip logic (e.g., an application-specific integrated circuit or ASIC) may be used to perform at least portions of such algorithms. As noted, eye-tracking subsystem 1606 may be programmed to use an output of the sensor(s) to track movement of eye 1601. In some embodiments, eye-tracking subsystem 1606 may analyze the digital representation generated by the sensors to extract eye rotation information from changes in reflections. In one embodiment, eye-tracking subsystem 1606 may use corneal reflections or glints (also known as Purkinje images) and/or the center of the eye's pupil 1622 as features to track over time.

In some embodiments, eye-tracking subsystem 1606 may use the center of the eye's pupil 1622 and infrared or near-infrared, non-collimated light to create corneal reflections. In these embodiments, eye-tracking subsystem 1606 may use the vector between the center of the eye's pupil 1622 and the corneal reflections to compute the gaze direction of eye 1601. In some embodiments, the disclosed systems may perform a calibration procedure for an individual (using, e.g., supervised or unsupervised techniques) before tracking the user's eyes. For example, the calibration procedure may include directing users to look at one or more points displayed on a display while the eye-tracking system records the values that correspond to each gaze position associated with each point.

In some embodiments, eye-tracking subsystem 1606 may use two types of infrared and/or near-infrared (also known as active light) eye-tracking techniques: bright-pupil and dark-pupil eye tracking, which may be differentiated based on the location of an illumination source with respect to the optical elements used. If the illumination is coaxial with the optical path, then eye 1601 may act as a retroreflector as the light reflects off the retina, thereby creating a bright pupil effect similar to a red-eye effect in photography. If the illumination source is offset from the optical path, then the eye's pupil 1622 may appear dark because the retroreflection from the retina is directed away from the sensor. In some embodiments, bright-pupil tracking may create greater iris/pupil contrast, allowing more robust eye tracking with iris pigmentation, and may feature reduced interference (e.g., interference caused by eyelashes and other obscuring features). Bright-pupil tracking may also allow tracking in lighting conditions ranging from total darkness to a very bright environment.

In some embodiments, control subsystem 1608 may control light source 1602 and/or optical subsystem 1604 to reduce optical aberrations (e.g., chromatic aberrations and/or monochromatic aberrations) of the image that may be caused by or influenced by eye 1601. In some examples, as mentioned above, control subsystem 1608 may use the tracking information from eye-tracking subsystem 1606 to perform such control. For example, in controlling light source 1602, control subsystem 1608 may alter the light generated by light source 1602 (e.g., by way of image rendering) to modify (e.g., pre-distort) the image so that the aberration of the image caused by eye 1601 is reduced.

The disclosed systems may track both the position and relative size of the pupil (since, e.g., the pupil dilates and/or contracts). In some examples, the eye-tracking devices and components (e.g., sensors and/or sources) used for detecting and/or tracking the pupil may be different (or calibrated differently) for different types of eyes. For example, the frequency range of the sensors may be different (or separately calibrated) for eyes of different colors and/or different pupil types, sizes, and/or the like. As such, the various eye-tracking components (e.g., infrared sources and/or sensors) described herein may need to be calibrated for each individual user and/or eye.

The disclosed systems may track both eyes with and without ophthalmic correction, such as that provided by contact lenses worn by the user. In some embodiments, ophthalmic correction elements (e.g., adjustable lenses) may be directly incorporated into the artificial reality systems described herein. In some examples, the color of the user's eye may necessitate modification of a corresponding eye-tracking algorithm. For example, eye-tracking algorithms may need to be modified based at least in part on the differing color contrast between a brown eye and, for example, a blue eye.

FIG. 17 is a more detailed illustration of various aspects of the eye-tracking subsystem illustrated in FIG. 16. As shown in this figure, an eye-tracking subsystem 1700 may include at least one source 1704 and at least one sensor 1706. Source 1704 generally represents any type or form of element capable of emitting radiation. In one example, source 1704 may generate visible, infrared, and/or near-infrared radiation. In some examples, source 1704 may radiate non-collimated infrared and/or near-infrared portions of the electromagnetic spectrum towards an eye 1702 of a user. Source 1704 may utilize a variety of sampling rates and speeds. For example, the disclosed systems may use sources with higher sampling rates in order to capture fixational eye movements of a user's eye 1702 and/or to correctly measure saccade dynamics of the user's eye 1702. As noted above, any type or form of eye-tracking technique may be used to track the user's eye 1702, including optical-based eye-tracking techniques, ultrasound-based eye-tracking techniques, etc.

Sensor 1706 generally represents any type or form of element capable of detecting radiation, such as radiation reflected off the user's eye 1702. Examples of sensor 1706 include, without limitation, a charge coupled device (CCD), a photodiode array, a complementary metal-oxide-semiconductor (CMOS) based sensor device, and/or the like. In one example, sensor 1706 may represent a sensor having predetermined parameters, including, but not limited to, a dynamic resolution range, linearity, and/or other characteristic selected and/or designed specifically for eye tracking.

As detailed above, eye-tracking subsystem 1700 may generate one or more glints. As detailed above, a glint 1703 may represent reflections of radiation (e.g., infrared radiation from an infrared source, such as source 1704) from the structure of the user's eye. In various embodiments, glint 1703 and/or the user's pupil may be tracked using an eye-tracking algorithm executed by a processor (either within or external to an artificial reality device). For example, an artificial reality device may include a processor and/or a memory device in order to perform eye tracking locally and/or a transceiver to send and receive the data necessary to perform eye tracking on an external device (e.g., a mobile phone, cloud server, or other computing device).

FIG. 17 shows an example image 1705 captured by an eye-tracking subsystem, such as eye-tracking subsystem 1700. In this example, image 1705 may include both the user's pupil 1708 and a glint 1710 near the same. In some examples, pupil 1708 and/or glint 1710 may be identified using an artificial-intelligence-based algorithm, such as a computer-vision-based algorithm. In one embodiment, image 1705 may represent a single frame in a series of frames that may be analyzed continuously in order to track the eye 1702 of the user. Further, pupil 1708 and/or glint 1710 may be tracked over a period of time to determine a user's gaze.

In one example, eye-tracking subsystem 1700 may be configured to identify and measure the inter-pupillary distance (IPD) of a user. In some embodiments, eye-tracking subsystem 1700 may measure and/or calculate the IPD of the user while the user is wearing the artificial reality system. In these embodiments, eye-tracking subsystem 1700 may detect the positions of a user's eyes and may use this information to calculate the user's IPD.

As noted, the eye-tracking systems or subsystems disclosed herein may track a user's eye position and/or eye movement in a variety of ways. In one example, one or more light sources and/or optical sensors may capture an image of the user's eyes. The eye-tracking subsystem may then use the captured information to determine the user's inter-pupillary distance, interocular distance, and/or a 3D position of each eye (e.g., for distortion adjustment purposes), including a magnitude of torsion and rotation (i.e., roll, pitch, and yaw) and/or gaze directions for each eye. In one example, infrared light may be emitted by the eye-tracking subsystem and reflected from each eye. The reflected light may be received or detected by an optical sensor and analyzed to extract eye rotation data from changes in the infrared light reflected by each eye.

The eye-tracking subsystem may use any of a variety of different methods to track the eyes of a user. For example, a light source (e.g., infrared light-emitting diodes) may emit a dot pattern onto each eye of the user. The eye-tracking subsystem may then detect (e.g., via an optical sensor coupled to the artificial reality system) and analyze a reflection of the dot pattern from each eye of the user to identify a location of each pupil of the user. Accordingly, the eye-tracking subsystem may track up to six degrees of freedom of each eye (i.e., 3D position, roll, pitch, and yaw) and at least a subset of the tracked quantities may be combined from two eyes of a user to estimate a gaze point (i.e., a 3D location or position in a virtual scene where the user is looking) and/or an IPD.

In some cases, the distance between a user's pupil and a display may change as the user's eye moves to look in different directions. The varying distance between a pupil and a display as viewing direction changes may be referred to as "pupil swim" and may contribute to distortion perceived by the user as a result of light focusing in different locations as the distance between the pupil and the display changes. Accordingly, measuring distortion at different eye positions and pupil distances relative to displays and generating distortion corrections for different positions and distances may allow mitigation of distortion caused by pupil swim by tracking the 3D position of a user's eyes and applying a distortion correction corresponding to the 3D position of each of the user's eyes at a given point in time. Thus, knowing the 3D position of each of a user's eyes may allow for the mitigation of distortion caused by changes in the distance between the pupil of the eye and the display by applying a distortion correction for each 3D eye position. Furthermore, as noted above, knowing the position of each of the user's eyes may also enable the eye-tracking subsystem to make automated adjustments for a user's IPD.

In some embodiments, a display subsystem may include a variety of additional subsystems that may work in conjunction with the eye-tracking subsystems described herein. For example, a display subsystem may include a varifocal subsystem, a scene-rendering module, and/or a vergence-processing module. The varifocal subsystem may cause left and right display elements to vary the focal distance of the display device. In one embodiment, the varifocal subsystem may physically change the distance between a display and the optics through which it is viewed by moving the display, the optics, or both. Additionally, moving or translating two lenses relative to each other may also be used to change the focal distance of the display. Thus, the varifocal subsystem may include actuators or motors that move displays and/or optics to change the distance between them. This varifocal subsystem may be separate from or integrated into the display subsystem. The varifocal subsystem may also be integrated into or separate from its actuation subsystem and/or the eye-tracking subsystems described herein.

In one example, the display subsystem may include a vergence-processing module configured to determine a vergence depth of a user's gaze based on a gaze point and/or an estimated intersection of the gaze lines determined by the eye-tracking subsystem. Vergence may refer to the simultaneous movement or rotation of both eyes in opposite directions to maintain single binocular vision, which may be naturally and automatically performed by the human eye. Thus, a location where a user's eyes are verged is where the user is looking and is also typically the location where the user's eyes are focused. For example, the vergence-processing module may triangulate gaze lines to estimate a distance or depth from the user associated with intersection of the gaze lines. The depth associated with intersection of the gaze lines may then be used as an approximation for the accommodation distance, which may identify a distance from the user where the user's eyes are directed. Thus, the vergence distance may allow for the determination of a location where the user's eyes should be focused and a depth from the user's eyes at which the eyes are focused, thereby providing information (such as an object or plane of focus) for rendering adjustments to the virtual scene.

The vergence-processing module may coordinate with the eye-tracking subsystems described herein to make adjustments to the display subsystem to account for a user's vergence depth. When the user is focused on something at a distance, the user's pupils may be slightly farther apart than when the user is focused on something close. The eye-tracking subsystem may obtain information about the user's vergence or focus depth and may adjust the display subsystem to be closer together when the user's eyes focus or verge on something close and to be farther apart when the user's eyes focus or verge on something at a distance.

The eye-tracking information generated by the above-described eye-tracking subsystems may also be used, for example, to modify various aspect of how different computer-generated images are presented. For example, a display subsystem may be configured to modify, based on information generated by an eye-tracking subsystem, at least one aspect of how the computer-generated images are presented. For instance, the computer-generated images may be modified based on the user's eye movement, such that if a user is looking up, the computer-generated images may be moved upward on the screen. Similarly, if the user is looking to the side or down, the computer-generated images may be moved to the side or downward on the screen. If the user's eyes are closed, the computer-generated images may be paused or removed from the display and resumed once the user's eyes are back open.

The above-described eye-tracking subsystems can be incorporated into one or more of the various artificial reality systems described herein in a variety of ways. For example, one or more of the various components of system 1600 and/or eye-tracking subsystem 1700 may be incorporated into augmented-reality system 1100 in FIG. 11 and/or virtual-reality system 1200 in FIG. 12 to enable these systems to perform various eye-tracking tasks (including one or more of the eye-tracking operations described herein).

Figure 18:
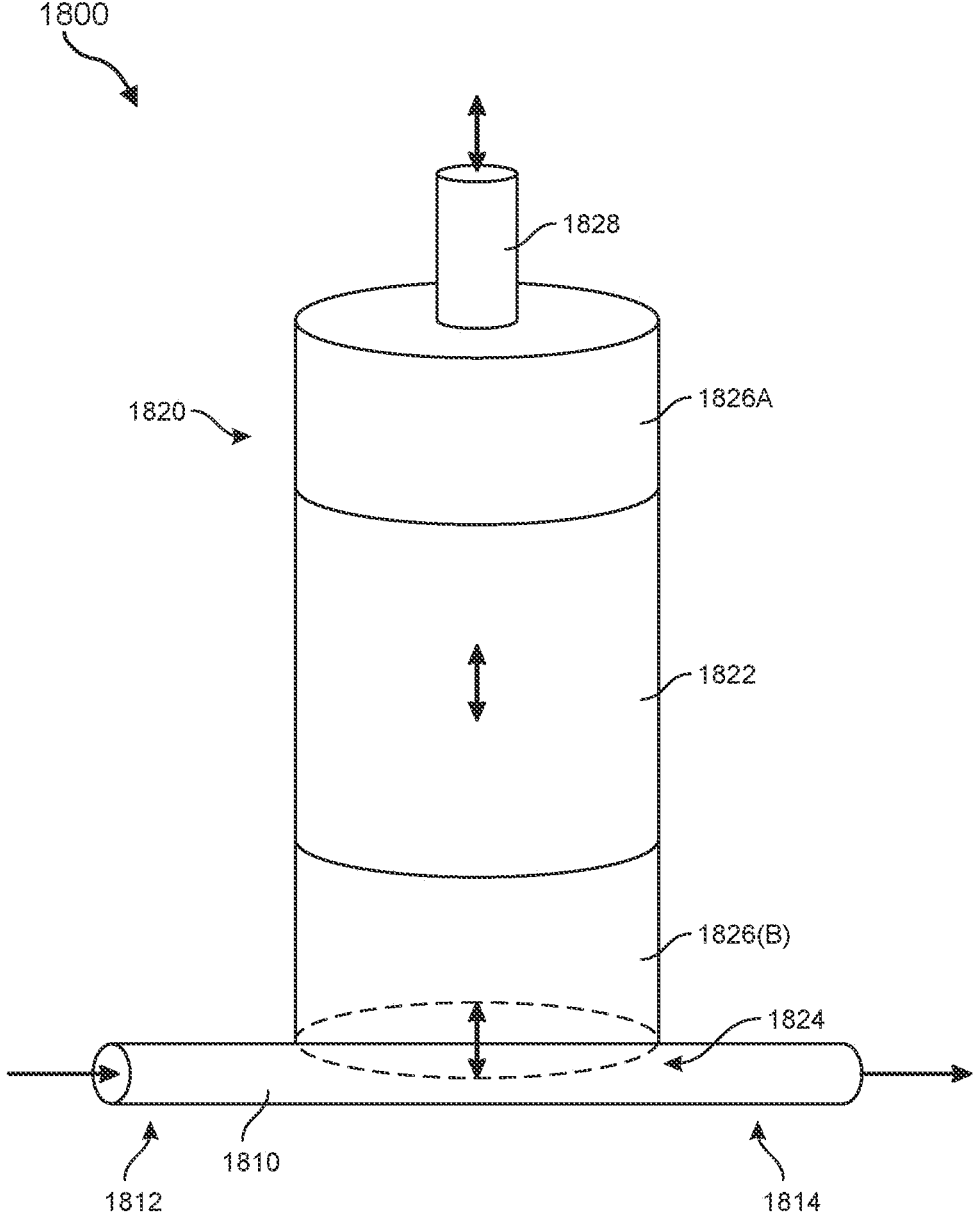
FIG. 18 is an illustration of an exemplary fluidic control system that may be used in connection with embodiments of this disclosure.

As noted above, the present disclosure may also include haptic fluidic systems that involve the control (e.g., stopping, starting, restricting, increasing, etc.) of fluid flow through a fluid channel. The control of fluid flow may be accomplished with a fluidic valve. FIG. 18 shows a schematic diagram of a fluidic valve 1800 for controlling flow through a fluid channel 1810, according to at least one embodiment of the present disclosure. Fluid from a fluid source (e.g., a pressurized fluid source, a fluid pump, etc.) may flow through the fluid channel 1810 from an inlet port 1812 to an outlet port 1814, which may be operably coupled to, for example, a fluid-driven mechanism, another fluid channel, or a fluid reservoir.

Fluidic valve 1800 may include a gate 1820 for controlling the fluid flow through fluid channel 1810. Gate 1820 may include a gate transmission element 1822, which may be a movable component that is configured to transmit an input force, pressure, or displacement to a restricting region 1824 to restrict or stop flow through the fluid channel 1810. Conversely, in some examples, application of a force, pressure, or displacement to gate transmission element 1822 may result in opening restricting region 1824 to allow or increase flow through the fluid channel 1810. The force, pressure, or displacement applied to gate transmission element 1822 may be referred to as a gate force, gate pressure, or gate displacement. Gate transmission element 1822 may be a flexible element (e.g., an elastomeric membrane, a diaphragm, etc.), a rigid element (e.g., a movable piston, a lever, etc.), or a combination thereof (e.g., a movable piston or a lever coupled to an elastomeric membrane or diaphragm).

As illustrated in FIG. 18, gate 1820 of fluidic valve 1800 may include one or more gate terminals, such as an input gate terminal 1826(A) and an output gate terminal 1826(B) (collectively referred to herein as "gate terminals 1826") on opposing sides of gate transmission element 1822. Gate terminals 1826 may be elements for applying a force (e.g., pressure) to gate transmission element 1822. By way of example, gate terminals 1826 may each be or include a fluid chamber adjacent to gate transmission element 1822. Alternatively or additionally, one or more of gate terminals 1826 may include a solid component, such as a lever, screw, or piston, that is configured to apply a force to gate transmission element 1822.

In some examples, a gate port 1828 may be in fluid communication with input gate terminal 1826(A) for applying a positive or negative fluid pressure within the input gate terminal 1826(A). A control fluid source (e.g., a pressurized fluid source, a fluid pump, etc.) may be in fluid communication with gate port 1828 to selectively pressurize and/or depressurize input gate terminal 1826(A). In additional embodiments, a force or pressure may be applied at the input gate terminal 1826(A) in other ways, such as with a piezoelectric element or an electromechanical actuator, etc.

In the embodiment illustrated in FIG. 18, pressurization of the input gate terminal 1826(A) may cause the gate transmission element 1822 to be displaced toward restricting region 1824, resulting in a corresponding pressurization of output gate terminal 1826(B). Pressurization of output gate terminal 1826(B) may, in turn, cause restricting region 1824 to partially or fully restrict to reduce or stop fluid flow through the fluid channel 1810. Depressurization of input gate terminal 1826(A) may cause gate transmission element 1822 to be displaced away from restricting region 1824, resulting in a corresponding depressurization of the output gate terminal 1826(B). Depressurization of output terminal 1826(B) may, in turn, cause restricting region 1824 to partially or fully expand to allow or increase fluid flow through fluid channel 1810. Thus, gate 1820 of fluidic valve 1800 may be used to control fluid flow from inlet port 1812 to outlet port 1814 of fluid channel 1810.

The following describes exemplary systems and methods for mitigating neuromuscular signal artifacts according to at least one embodiment of the present disclosure.

Sensors mounted on wearable devices are subjected to a number of conditions that may affect the quality of sensed signals. For instance, in the case of some neuromuscular sensors, sensed signals can be distorted by, for example, ambient electromagnetic radiation, imperfect contact between sensors (e.g., electrodes) and skin, and crosstalk resulting from electromagnetic interference. For some applications, high-fidelity neuromuscular sensor data may be desirable. For example, in an extended reality (XR) context (e.g., with virtual reality (VR) systems, augmented reality (AR) systems, and/or mixed reality systems), applications that use neuromuscular data to generate visualizations of a user's hand in real time or that use neuromuscular data to provide gesture-based input may rely on high-fidelity data in order to improve a user's sense of immersion and overall experience.

As will be described in greater detail below, systems and methods described herein may improve the fidelity of sensor data from wearable devices by selectively activating and/or differentially pairing sensors based on real-time conditions. For example, these systems and methods may selectively activate and/or differentially pair specific sensors based on real-time evaluations of sensor performance. In some examples, these systems and methods may selectively activate and/or differentially pair specific sensors for specific tasks (e.g., where a particular sensor pair is predicted to perform well producing sensor data for certain types of muscular activation and/or during certain types of movement). In this manner, a sensor-equipped wearable device may provide reliable neuromuscular sensor data even through a wide range of movements and under a wide range of conditions, thereby improving user experience and immersion for applications such as XR applications.

By improving the output of neuromuscular data provided by a wearable device, the systems and methods described herein may improve the functioning of the wearable device and of associated systems (e.g., XR systems). In addition, by selectively activating sensors, these systems and methods may reduce consumption of computational resources of the wearable device and/or associated systems, thereby improving the functioning of the wearable device and/or associated systems. In some examples, selectively activating sensors may reduce power consumption, thereby potentially extending battery life of the wearable device and/or associated systems. These systems and methods therefore represent an advancement in the fields of computing, wearable devices, neuromuscular sensing, and extended reality.

In some examples, systems and methods described herein may use neuromuscular data gathered from a wearable device with dynamically configured sensors to measure and/or model human anatomy (e.g., generate a musculoskeletal representation). Data from the neuromuscular sensors may be applied alone or combined with other sources, such as camera data.

In some examples, systems and methods described herein may predict information about the positioning and movements of portions of a user's arm and/or hand represented as a multi-segment articulated rigid body system with joints connecting the multiple segments of the rigid body system. Signals recorded by wearable neuromuscular sensors placed at locations on the user's body may be provided as input to an inference model trained to predict estimates of the position (e.g., absolute position, relative position, orientation) and/or forces associated with a plurality of rigid segments in a computer-based musculoskeletal representation associated with a hand when a user performs one or more movements. The position information and/or force information associated with segments of a musculoskeletal representation associated with a hand is referred to herein as a "handstate" of the musculoskeletal representation. In some examples, as a user performs different movements, a trained inference model may interpret neuromuscular signals recorded by the wearable neuromuscular sensors into position and force estimates (handstate information) that are used to update the musculoskeletal representation. As the neuromuscular signals are continuously recorded, the musculoskeletal representation is updated in real time (or near real time) and a visual representation of a hand (e.g., within a virtual reality environment) is optionally rendered based on the current handstate estimates.

Due to imperfect neuromuscular sensor data, the estimated handstate output may be noisy, inaccurate, and/or manifest discontinuities. Inaccurate handstate output within a virtual environment may break immersion as a virtual representation of a hand appears unnatural and/or to lack correspondence with the user's actual movements. In addition, where handstate is used for gesture-based input, inaccurate handstate output may interfere with the user's ability to successfully perform gesture-based input.

Accordingly, systems and methods described herein may address issues, such as unreliable neuromuscular sensor data, otherwise observable in the output from a trained inference model. For example, these systems and methods may dynamically configure sensor usage within a wearable device to select sensors (e.g., differential sensor pairs) that will provide more reliable sensor data (e.g., based on specific tasks, such as gathering neuromuscular sensor data for a certain class of movements; and/or based on current conditions, such as poor sensor contact with the skin and/or interfering signals).

All or portions of the human musculoskeletal system can be modeled as a multi-segment articulated rigid body system, with joints forming the interfaces between the different segments and joint angles defining the spatial relationships between connected segments in the model. Constraints on the movement at the joints are governed by the type of joint connecting the segments and the biological structures (e.g., muscles, tendons, ligaments) that restrict the range of movement at the joint. For example, the shoulder joint connecting the upper arm to the torso and the hip joint connecting the upper leg to the torso are ball and socket joints that permit extension and flexion movements as well as rotational movements. By contrast, the elbow joint connecting the upper arm and the forearm and the knee joint connecting the upper leg and the lower leg allow for a more limited range of motion. As described herein, a multi-segment articulated rigid body system is used to model portions of the human musculoskeletal system. However, it should be appreciated that some segments of the human musculoskeletal system (e.g., the forearm), though approximated as a rigid body in the articulated rigid body system, may include multiple rigid structures (e.g., the ulna and radius bones of the forearm) that provide for more complex movement within the segment that is not explicitly considered by the rigid body model. Accordingly, a model of an articulated rigid body system for use with some embodiments of the technology described herein may include segments that represent a combination of body parts that are not strictly rigid bodies.

In kinematics, rigid bodies are objects that exhibit various attributes of motion (e.g., position, orientation, angular velocity, acceleration). Knowing the motion attributes of one segment of the rigid body enables the motion attributes for other segments of the rigid body to be determined based on constraints in how the segments are connected. For example, the hand may be modeled as a multi-segment articulated body with the joints in the wrist and each finger forming the interfaces between the multiple segments in the model. In some embodiments, movements of the segments in the rigid body model can be simulated as an articulated rigid body system in which position (e.g., actual position, relative position, or orientation) information of a segment relative to other segments in the model are predicted using a trained statistical model, as described in more detail below.

The portion of the human body approximated by a musculoskeletal representation, as described herein as one non-limiting example, is a hand or a combination of a hand with one or more arm segments and the information used to describe a current state of the positional relationships between segments and force relationships for individual segments or combinations of segments in the musculoskeletal representation is referred to herein as the handstate of the musculoskeletal representation. It may be appreciated, however, that the techniques described herein are also applicable to musculoskeletal representations of portions of the body other than the hand including, but not limited to, an arm, a leg, a foot, a torso, a neck, or any combination of the foregoing.

Figure 19A:
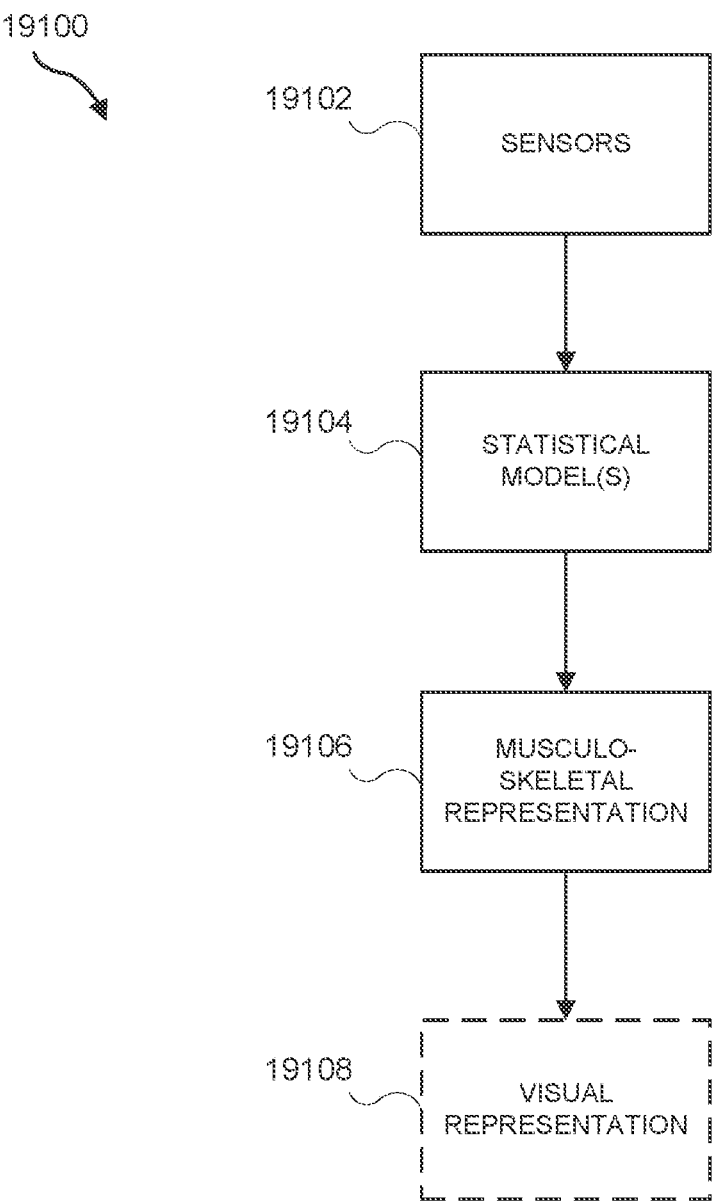
FIG. 19A is a schematic diagram of a computer-based system for generating a musculoskeletal representation based on neuromuscular sensor data in accordance with some embodiments of the technology described herein.

FIG. 19A illustrates a system 19100 in accordance with some embodiments. The system includes a plurality of sensors 19102 configured to record signals resulting from the movement of portions of a human body. Sensors 19102 may include autonomous sensors. As used herein, the term "autonomous sensors" refers to sensors configured to measure the movement of body segments without requiring the use of external devices. In some embodiments, sensors 19102 may also include non-autonomous sensors in combination with autonomous sensors. As used herein, the term "non-autonomous sensors" refers to sensors configured to measure the movement of body segments using external devices. Examples of external devices that include non-autonomous sensors include, but are not limited to, wearable (e.g. body-mounted) cameras, global positioning systems, and laser scanning systems.

Autonomous sensors may include a plurality of neuromuscular sensors configured to record signals arising from neuromuscular activity in skeletal muscle of a human body. The term "neuromuscular activity" as used herein refers to neural activation of spinal motor neurons that innervate a muscle, muscle activation, muscle contraction, or any combination of the neural activation, muscle activation, and muscle contraction. Neuromuscular sensors may include one or more electromyography (EMG) sensors, one or more mechanomyography (MMG) sensors, one or more sonomyography (SMG) sensors, a combination of two or more types of EMG sensors, MMG sensors, and SMG sensors, and/or one or more sensors of any suitable type that are configured to detect neuromuscular signals. In some embodiments, the plurality of neuromuscular sensors may be used to sense muscular activity related to a movement of the part of the body controlled by muscles from which the neuromuscular sensors are arranged to sense the muscle activity. Spatial information (e.g., position and/or orientation information) and force information describing the movement may be predicted based on the sensed neuromuscular signals as the user moves over time.

Autonomous sensors may include one or more Inertial Measurement Units (IMUs), which measure a combination of physical aspects of motion, using, for example, an accelerometer, a gyroscope, a magnetometer, or any combination of one or more accelerometers, gyroscopes and magnetometers. In some embodiments, IMUs may be used to sense information about the movement of the part of the body on which the IMU is attached and information derived from the sensed data (e.g., position and/or orientation information) may be tracked as the user moves over time. For example, one or more IMUs may be used to track movements of portions of a user's body proximal to the user's torso relative to the sensor (e.g., arms, legs) as the user moves over time.

In embodiments that include at least one IMU and a plurality of neuromuscular sensors, the IMU(s) and neuromuscular sensors may be arranged to detect movement of different parts of the human body. For example, the IMU(s) may be arranged to detect movements of one or more body segments proximal to the torso (e.g., an upper arm), whereas the neuromuscular sensors may be arranged to detect movements of one or more body segments distal to the torso (e.g., a forearm or wrist). It should be appreciated, however, that autonomous sensors may be arranged in any suitable way, and embodiments of the technology described herein are not limited based on the particular sensor arrangement. For example, in some embodiments, at least one IMU and a plurality of neuromuscular sensors may be co-located on a body segment to track movements of body segment using different types of measurements. In one implementation described in more detail below, an IMU sensor and a plurality of EMG sensors are arranged on a wearable device configured to be worn around the lower arm or wrist of a user. In such an arrangement, the IMU sensor may be configured to track movement information (e.g., positioning and/or orientation over time) associated with one or more arm segments, to determine, for example whether the user has raised or lowered their arm, whereas the EMG sensors may be configured to determine movement information associated with wrist or hand segments to determine, for example, whether the user has an open or closed hand configuration.

Each of the autonomous sensors includes one or more sensing components configured to sense information about a user. In the case of IMUs, the sensing components may include one or more accelerometers, gyroscopes, magnetometers, or any combination thereof to measure characteristics of body motion, examples of which include, but are not limited to, acceleration, angular velocity, and sensed magnetic field around the body. In the case of neuromuscular sensors, the sensing components may include, but are not limited to, electrodes configured to detect electric potentials on the surface of the body (e.g., for EMG sensors) vibration sensors configured to measure skin surface vibrations (e.g., for MMG sensors), and acoustic sensing components configured to measure ultrasound signals (e.g., for SMG sensors) arising from muscle activity.

In some embodiments, the output of one or more of the sensing components may be processed using hardware signal processing circuitry (e.g., to perform amplification, filtering, and/or rectification). In other embodiments, at least some signal processing of the output of the sensing components may be performed in software. Thus, signal processing of autonomous signals recorded by the autonomous sensors may be performed in hardware, software, or by any suitable combination of hardware and software, as aspects of the technology described herein are not limited in this respect.

In some embodiments, the recorded sensor data may be processed to compute additional derived measurements that are then provided as input to a statistical model, as described in more detail below. For example, recorded signals from an IMU sensor may be processed to derive an orientation signal that specifies the orientation of a rigid body segment over time. Autonomous sensors may implement signal processing using components integrated with the sensing components, or at least a portion of the signal processing may be performed by one or more components in communication with, but not directly integrated with the sensing components of the autonomous sensors.

In some embodiments, at least some of the plurality of autonomous sensors are arranged as a portion of a wearable device configured to be worn on or around part of a user's body. For example, in one non-limiting example, an IMU sensor and a plurality of neuromuscular sensors are arranged circumferentially around an adjustable and/or elastic band such as a wristband or armband configured to be worn around a user's wrist or arm. Alternatively, at least some of the autonomous sensors may be arranged on a wearable patch configured to be affixed to a portion of the user's body. In some embodiments, multiple wearable devices, each having one or more IMUs and/or neuromuscular sensors included thereon, may be used to predict musculoskeletal position information for movements that involve multiple parts of the body.

In some embodiments, sensors 19102 only include a plurality of neuromuscular sensors (e.g., EMG sensors). In other embodiments, sensors 19102 include a plurality of neuromuscular sensors and at least one "auxiliary" sensor configured to continuously record a plurality of auxiliary signals. Examples of auxiliary sensors include, but are not limited to, other autonomous sensors such as IMU sensors, and non-autonomous sensors such as an imaging device (e.g., a camera), a radiation-based sensor for use with a radiation-generation device (e.g., a laser-scanning device), or other types of sensors such as a heart-rate monitor.

System 19100 also includes one or more computer processors (not shown in FIG. 19A) programmed to communicate with sensors 19102. For example, signals recorded by one or more of the sensors may be provided to the processor(s), which may be programmed to execute one or more machine learning techniques that process signals output by the sensors 19102 to train one or more statistical models 19104, and the trained (or retrained) statistical model(s) 19104 may be stored for later use in generating a musculoskeletal representation 19106, as described in more detail below. Non-limiting examples of statistical models that may be used in accordance with some embodiments to predict handstate information based on recorded signals from sensors 19102 are discussed in more detail below with regard to FIG. 19E.

System 19100 also optionally includes a display controller configured to display a visual representation 19108 (e.g., of a hand). As discussed in more detail below, one or more computer processors may implement one or more trained statistical models configured to predict handstate information based, at least in part, on signals recorded by sensors 19102. The predicted handstate information is used to update the musculoskeletal representation 19106, which is then optionally used to render a visual representation 19108 based on the updated musculoskeletal representation incorporating the current handstate information. Real-time reconstruction of the current handstate and subsequent rendering of the visual representation reflecting the current handstate information in the musculoskeletal model may provide visual feedback to the user about the effectiveness of the trained statistical model to accurately represent an intended handstate. Not all embodiments of system 19100 include components configured to render a visual representation. For example, in some embodiments, handstate estimates output from the trained statistical model and a corresponding updated musculoskeletal representation are used to determine a state of a user's hand (e.g., in a virtual reality environment) even though a visual representation based on the updated musculoskeletal representation is not rendered (e.g., for interacting with virtual objects in a virtual environment in the absence of a virtually-rendered hand).

In some embodiments, a computer application configured to simulate a virtual reality environment may be instructed to display a visual representation of the user's hand. Positioning, movement, and/or forces applied by portions of the hand within the virtual reality environment may be displayed based on the output of the trained statistical model(s). The visual representation may be dynamically updated based on current reconstructed handstate information as continuous signals are recorded by the sensors 19102 and processed by the trained statistical model(s) 19104 to provide an updated computer-generated representation of the user's movement and/or exerted force that is updated in real-time.

As discussed above, some embodiments are directed to using a statistical model for predicting musculoskeletal information based on signals recorded from wearable autonomous sensors. The statistical model may be used to predict the musculoskeletal position information without having to place sensors on each segment of the rigid body that is to be represented in the computer-generated musculoskeletal representation. As discussed briefly above, the types of joints between segments in a multi-segment articulated rigid body model constrain movement of the rigid body. Additionally, different individuals tend to move in characteristic ways when performing a task that can be captured in statistical patterns of individual user behavior. At least some of these constraints on human body movement may be explicitly incorporated into statistical models used for prediction in accordance with some embodiments. Additionally or alternatively, the constraints may be learned by the statistical model through training based on ground truth data on the position and exerted forces of the hand and wrist in the context of recorded sensor data (e.g., EMG data). Constraints imposed in the construction of the statistical model are those set by anatomy and the physics of a user's body, while constraints derived from statistical patterns are those set by human behavior for one or more users from which sensor measurements are measured and used to train the statistical model. As described in more detail below, the constraints may comprise part of the statistical model itself being represented by information (e.g., connection weights between nodes) in the model.

As discussed above, some embodiments are directed to using a statistical model for predicting handstate information to enable the generation and/or real-time update of a computer-based musculoskeletal representation. The statistical model may be used to predict the handstate information based on IMU signals, neuromuscular signals (e.g., EMG, MMG, and SMG signals), external device signals (e.g., camera or laser-scanning signals), or a combination of IMU signals, neuromuscular signals, and external device signals detected as a user performs one or more movements.

Relative to tabletop research systems for neuromuscular recording, systems designed for independent use by a non-technical user, including wearable, wireless, and portable neuromuscular recording devices, are more susceptible to recording artifacts. Identifying, mitigating, and accounting for such artifacts is not trivial and doing so effectively enhances the accuracy of systems and methods for estimating the position, movement, and/or forces of a part of a user's body (e.g., hand).

During continuous recording of neuromuscular signals from neuromuscular sensors, artifacts may occasionally appear in the recorded signal data for various reasons including, but not limited to, sensor malfunction and environmental factors such as 60 Hz noise. Providing neuromuscular signals including such artifacts as input to a trained statistical model as described above may result in inaccurate model output estimates (e.g., handstate estimates). Detecting one or more artifacts in the continuously recorded neuromuscular signals in real-time and compensating for the detected artifacts prior to providing the neuromuscular signals as input to the trained statistical model may, however, produce model estimates that more closely represent the user's movements.

Figure 19B:
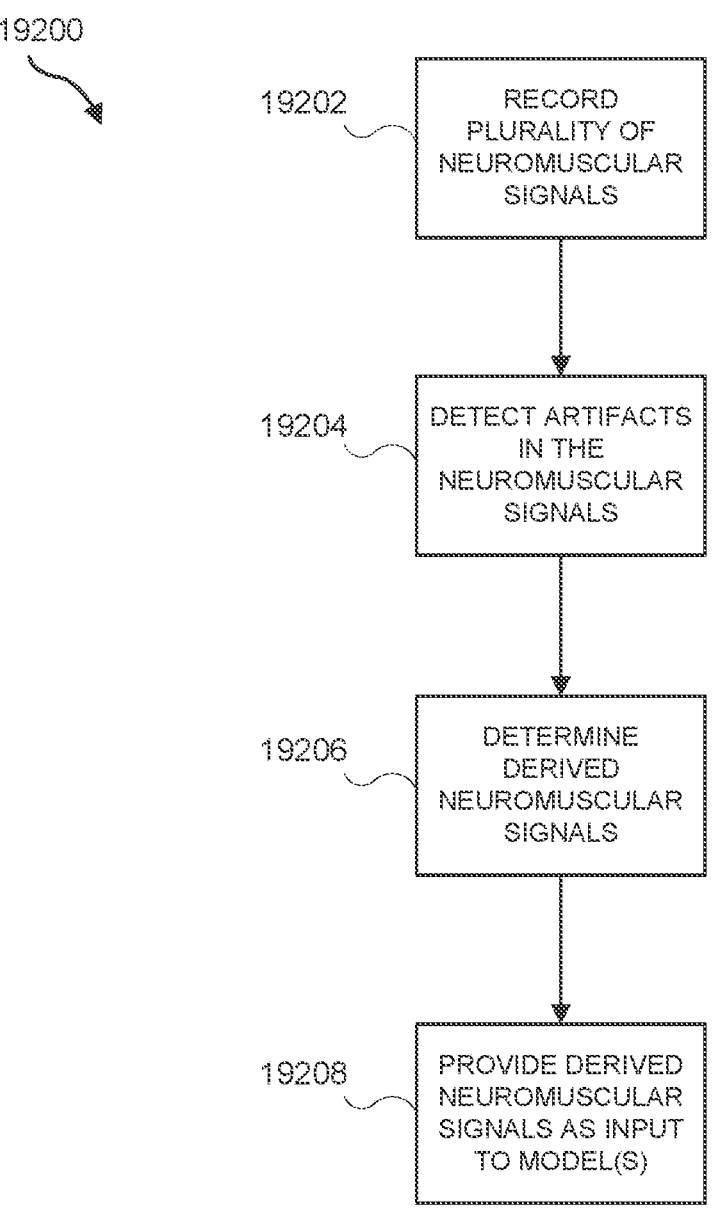
FIG. 19B is flowchart of a process for mitigating neuromuscular signal artifacts in accordance with some embodiments of the technology described herein.

FIG. 19B illustrates a process 19200 for detecting and mitigating artifacts in neuromuscular signal data in real-time in accordance with some embodiments. In act 19202, a plurality of neuromuscular signals are recorded from a plurality of neuromuscular sensors. Process 19200 proceeds to act 19204, where the neuromuscular signals are analyzed to detect one or more artifacts in the neuromuscular signals in real-time as the neuromuscular signals are continuously recorded. Process 19200 then proceeds to act 19206, where derived neuromuscular signals are determined when one or more artifacts are detected in the neuromuscular signals. The derived neuromuscular signals are signals in which the detected artifacts have been mitigated by, for example, processing the signal data to at least partially remove the artifact(s) (e.g., via a filter or other suitable technique as described below), replacing at least some of the signal data with other signal data, or replacing the signal data with an average of signal data from neighboring sensors (as described below). Examples of determining derived neuromuscular signals are discussed in further detail below. Process 19200 then proceeds to act 19208, where the derived neuromuscular signals are provided as input to a trained statistical model in place of the recorded neuromuscular signals. In some instances, when no artifacts are detected in the neuromuscular signals recorded from particular sensors, the neuromuscular signals from those sensors may be provided as input to the trained statistical model without processing the signals to mitigate artifacts.

Figure 19C:
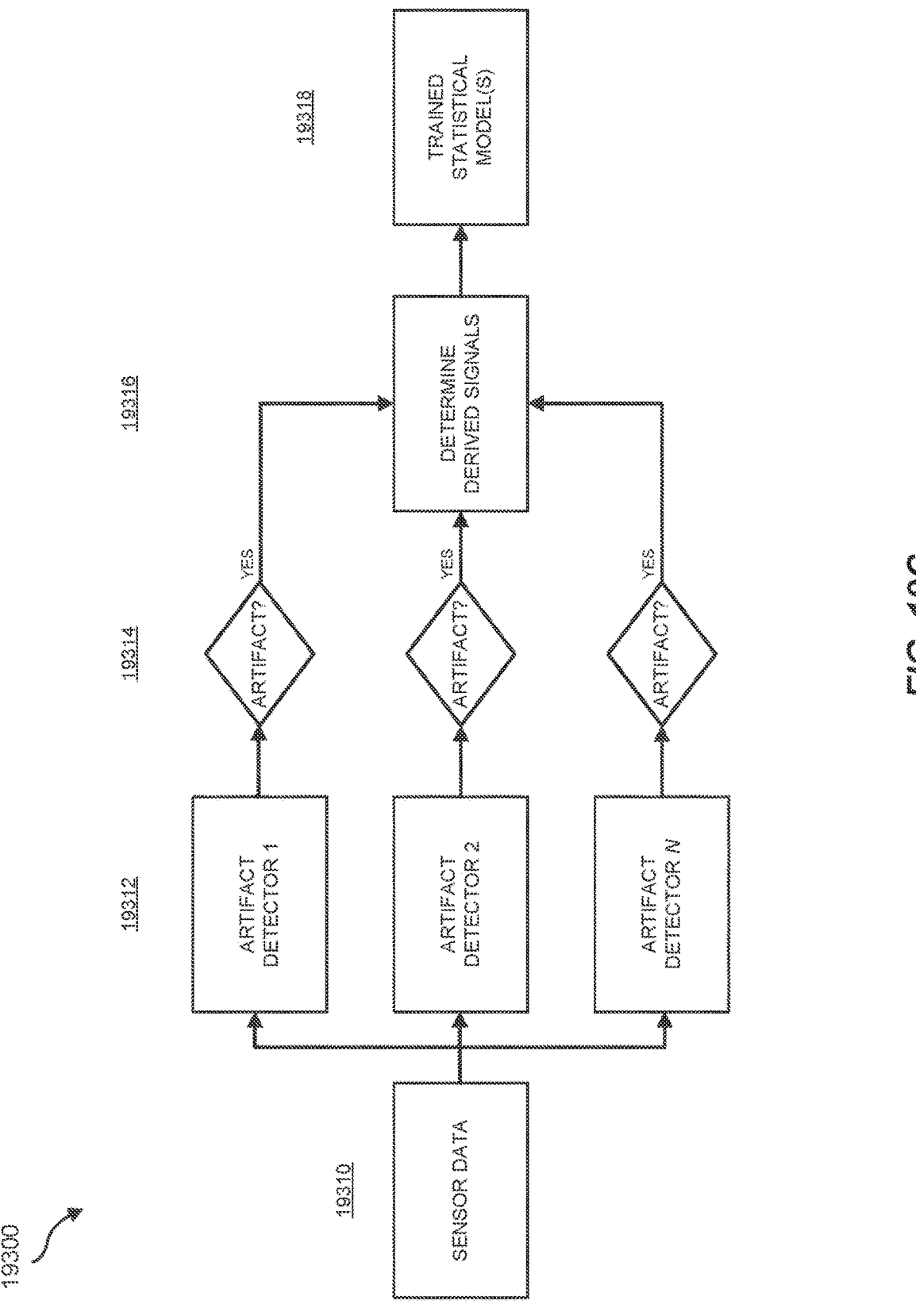
FIG. 19C is a flowchart of a process for mitigating neuromuscular signal artifacts using multiple detector circuits in accordance with some embodiments of the technology described herein.

FIG. 19C illustrates a system architecture 19300 for detecting and mitigating artifacts from recorded neuromuscular signals in accordance with some embodiments. Sensor data 19310 recorded by a plurality of neuromuscular sensors is analyzed by a plurality of detector circuits 19312, each of which is configured to detect a particular type of artifact by analyzing the sensor data. Detector circuits 19312 may be implemented using hardware, software, or a combination of hardware and software (as described below). After analyzing the neuromuscular signals, a decision 19314 is made as to whether the neuromuscular signals analyzed by the detector circuit 19312 include the artifact for which the detector circuit is configured to detect. In some embodiments, decision 19314 is made based, at least in part, on a quality metric associated with the neuromuscular signals analyzed by the detector circuit 19312. For example, the quality metric may represent a probability (e.g., a confidence level) that the neuromuscular signals include a particular artifact, and it may be determined that the neuromuscular signals include the artifact when the probability is higher than a threshold value. Detector circuits 19312 may be configured to process individual channels of neuromuscular sensor data or at least some of the detector circuits 19312 may be configured to process neuromuscular sensor data recorded by multiple channels to detect artifacts. In an implementation where each of N detector circuits 19312 is configured to process an individual channel of neuromuscular data to detect a particular artifact, the output of the artifact detection process may be a vector of N quality metrics, each of which corresponds to the analysis of the channel data by one of the detector circuits 19312. Detector circuits 19312 may be configured to detect any suitable signal artifact including, but not limited to, noise artifacts, skin-contact artifacts, skin lift-off artifacts, power line frequency (e.g., 50 Hz, 60 Hz) artifacts, clipped signal artifacts, inactive sensor artifacts, microfriction artifacts, data degeneration artifacts, and artifacts caused by movement of one or more neuromuscular sensors (e.g., the rotation of an armband containing a plurality of neuromuscular sensors that causes the mapping between the location of one or more neuromuscular sensors and the recorded signals of the neuromuscular sensors generated by underlying motor units to change).

When decision 19314 indicates that the neuromuscular sensor data includes an artifact detected by a corresponding detector circuit 19312, one or more derived neuromuscular signals 19316 are determined in which the artifact has been mitigated by, for example, at least partially removing the artifact or replacing the signals with other signals. The derived neuromuscular signals may be determined in any suitable way based on the decisions 19314 output from the detector circuits 19312 and one or more rules associated with those decisions. In some embodiments, information output from the detector circuits is used to determine whether to process the neuromuscular signals to mitigate the detected artifact(s) or whether to replace the neuromuscular sensor data with other sensor data or data derived from other sensor data.

The decision on whether to process the sensor data or replace the data may be made in any suitable way. In some embodiments, the decision of whether to process or replace the sensor data may be made on a detector circuit by detector circuit basis. For example, for some detector circuits, the neuromuscular signals may always be processed (rather than replaced) to mitigate a detected artifact based on the type of artifact that the detector circuit is configured to detect. For example, if the artifact detected is external 60 Hz noise, the neuromuscular signals may always be processed by filtering rather than being replaced. In other instances, the neuromuscular signals may always be replaced rather than being processed. For example, if the detector circuit is configured to detect artifacts corresponding to a disconnected or malfunctioning sensor, the neuromuscular signals may always be replaced (rather than being processed) with an average (or other metric) of neuromuscular signals from one or more neighboring sensors. In yet other instances, a determination of whether the neuromuscular signals analyzed by a particular detector circuit should be processed or replaced is made based, at least in part, on a quality factor determined as a result of the analysis by the detector circuit. For example, if the quality factor is less than a threshold value or within a first range, the neuromuscular sensor data may be replaced, whereas when the quality factor is greater than a threshold or within a second range, the neuromuscular sensor data may be processed.

In some embodiments, the decision on whether to process neuromuscular signals with detected artifact(s) or replace the neuromuscular signals may be made based on the output of multiple detector circuits. For example, if the detector circuits indicate that multiple artifacts in a particular neuromuscular sensor channel or group of neuromuscular sensors have been detected, it may be determined to replace the neuromuscular signals due to the poor quality of the recorded signals.

When it is determined to process the neuromuscular signals based on the decision 19314 for a particular detector circuit 19312, the processing may be performed in any suitable way to mitigate the detected artifact. For example, the neuromuscular signals may be filtered or otherwise processed to mitigate the detected artifact. The type of artifact and/or characteristics of the artifact that is detected may inform how the neuromuscular signals are processed. In some implementations the neuromuscular signals may be analyzed to determine one or more characteristics of the artifact by, for example, calculating a power spectrum to determine the frequency characteristics of the artifact, or fitting a generative model of certain artifact types to the neuromuscular signals. After determining the artifact characteristic(s) the neuromuscular signals may be processed to mitigate the artifact. For some types of artifacts (e.g., skin lift-off artifacts), the processing may involve filtering techniques (e.g., a high pass filter above a critical frequency). For other types of artifacts, the processing may involve subtracting at least some estimated artifact behavior from the recorded neuromuscular signals using, for example, a generative model.

When it is determined to replace the neuromuscular signals based on the decision 19314 for a particular detector circuit 19312 or collection of detector circuits 19312, the replacing may be performed in any suitable way to mitigate the detected artifact. For example, if the detected artifact occurs over a relatively short time period, the neuromuscular signal data for a particular sensor may be replaced with signal data from the same sensor recorded at an earlier point in time when the artifact was not present in the signal. Replacing the corrupted signal data (e.g., signal data with detected artifacts) with signal data from the same sensor may be preferred in some instances because the signal data used for replacement has been recorded for neuromuscular activity from the same muscle or muscles as the corrupted signal data. Alternatively, if the detected artifact occurs over a relatively long period of time or if the signal data from the sensor is unusable (e.g., if the sensor has been disconnected or has contact issues), the signal data may be replaced with signal data recorded by other sensors. For example, the signal data may be replaced based on signal data recorded by one or more sensors arranged adjacent to the sensor having the corrupted data. In some embodiments, the signal data for the corrupted sensor may be replaced with an average of signal data from two or more neighboring sensors to the corrupted sensor. For example, the two or more neighboring sensors may be arranged next to or near the corrupted sensor on a wearable device that includes the plurality of neuromuscular sensors. In some embodiments, the average of signal data may be a weighted average of signal data, where the weights are determined in any suitable way. In some embodiments, the weight for data recorded by a neuromuscular sensor with an artifact may be set to zero such that data from that sensor is not considered. In some embodiments, signal data from a neuromuscular sensor with an artifact may be imputed based on neuromuscular signal data derived from historical data of neuromuscular sensors in an array of neuromuscular sensors that are not experiencing an artifact. In certain embodiments, imputed signal data may be user-specific or based on data from a population of users. Signal data from a neuromuscular sensor experiencing an artifact may be inferred and the inference may comprise raw signal data or processed signal data (e.g., amplitude, cospectrum matrix, or another metric). In some embodiments, the inference about signal data from a neuromuscular sensor experiencing an artifact may be generated based on one or more of: general constraints about the neuromuscular system and human anatomy; personal constraints related to the user's physiology and/or anatomy; and session-specific constraints related to the particular positioning and impedance of a plurality of neuromuscular sensors.

When only a single detector circuit 19312 of a plurality of detector circuits detects an artifact in the analyzed neuromuscular signals, the neuromuscular signals may be processed or replaced based on one or more rules specifying how to process/replace data when the artifact is detected by the single detector circuit 19312. When multiple detector circuits detect artifacts in the analyzed neuromuscular signals, the neuromuscular signals may be processed or replaced based on one or more rules specifying how to process or replace data when multiple artifacts are detected. For example, the one or more rules may specify a processing hierarchy (or order) based on the detected artifacts such that processing to mitigate certain artifacts is performed prior to processing to mitigate other artifacts. Additionally, the one or more rules may specify that if any of the detector circuits 19312 detects an artifact with a quality value less than a particular threshold, the signal data is replaced (rather than processed) regardless of artifacts detected by the other detector circuits 19312. Any other rules may alternatively be used, and embodiments are not limited in this respect.

After the derived signals 19316 in which the signal artifacts have been mitigated are determined, the derived signals are provided as input to a trained statistical model 19318, which in turn is configured to output estimates (e.g., handstate estimates) based on the input signals. It should be appreciated that some neuromuscular signals may be processed/replaced when an artifact is detected, whereas other contemporaneously recorded neuromuscular signals (e.g., from other sensors) may not be processed/replaced when no artifacts are detected, and the combination of unprocessed (for mitigating artifacts) and derived signals may be provided as input to the trained statistical model.

Figure 19D:
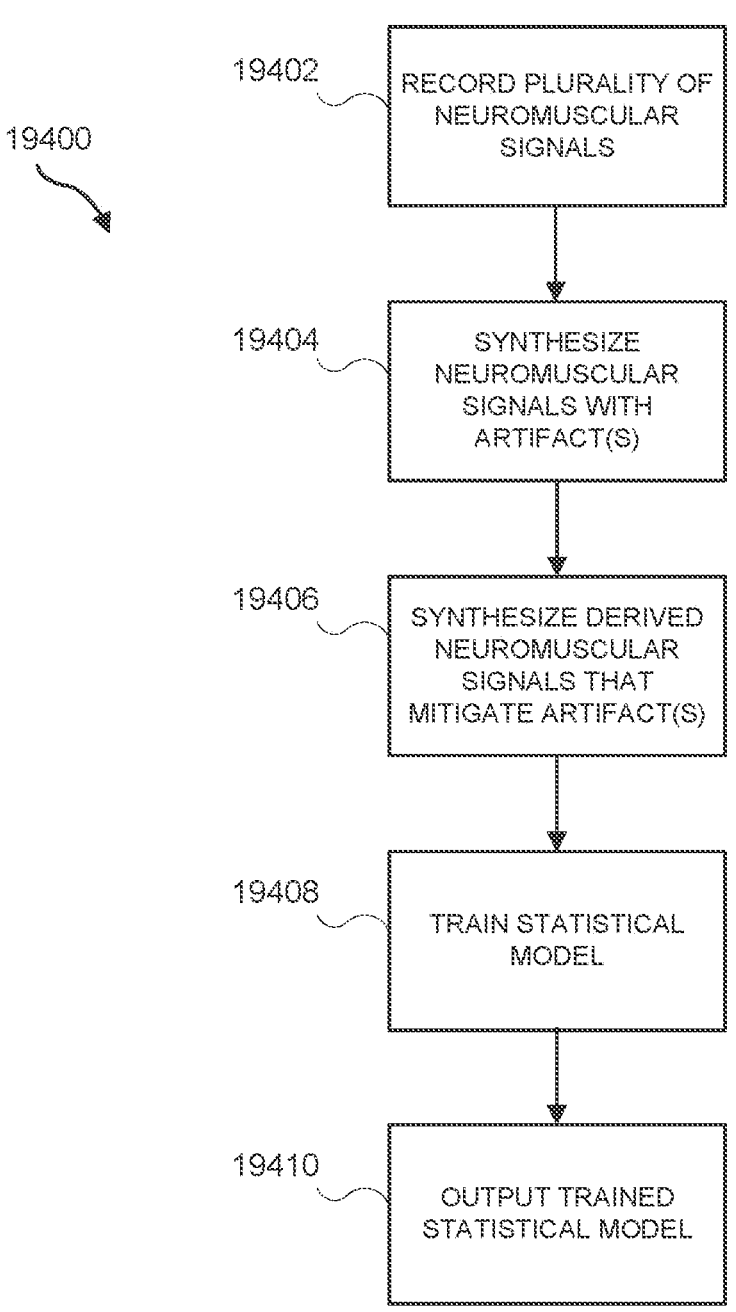
FIG. 19D is a flowchart of a process for training a statistical model using training data determined based on neuromuscular signal data with simulated artifacts in accordance with some embodiments of the technology described herein.

Trained statistical models used in accordance with some embodiments may be trained using training data that makes the model more robust to artifacts in the recorded signals. FIG. 19D illustrates a process 19400 for training a statistical model using training data that includes neuromuscular signals associated with artifacts. The artifacts may be recorded as part of the neuromuscular signals or the artifacts may be simulated and added to the recorded neuromuscular signals. Such a trained statistical model when used during runtime may be more robust to artifacts in the recorded neuromuscular signals. Process 19400 begins in act 19402 where neuromuscular signals are continuously recorded. Process 19400 then proceeds to act 19404 where neuromuscular signals with one or more artifacts are synthesized by modifying the recorded neuromuscular signals to include characteristics of the artifact. The synthesized neuromuscular signals may be created in any suitable way. For example, noise may be added to the neuromuscular signals to simulate the presence of noise in the recorded signals when used in a particular environment (e.g., an environment in which 60 Hz noise is prevalent). In some embodiments, synthesized neuromuscular signals based on some or all of the types of artifacts detected by the detection circuits described in connection with the architecture of FIG. 19C may be used in act 19404. Alternatively, the recorded neuromuscular signals used as training data to train the model may already have artifacts included in the recorded signals, making it unnecessary to simulate the artifacts and add the simulated artifacts into "clean" neuromuscular signals. For example, an armband with a plurality of neuromuscular sensors may be worn loosely in order to generate frequent contact artifacts caused by a neuromuscular sensor transiently losing low-impedance contact with the skin.

Process 19400 then proceeds to act 19406, where derived neuromuscular signals are synthesized in which the artifacts introduced to the neuromuscular signals in act 19404 have been mitigated. Realizing that the mitigation techniques described herein for mitigating signal artifacts may not entirely remove the signal artifacts, inclusion in the training data of synthesized derived neuromuscular signal data that mimics the operation of the mitigation techniques used during runtime results in a trained statistical model that may provide more accurate model estimates.

Process 19400 then proceeds to act 19408, where the statistical model is trained using training data that includes the synthesized derived neuromuscular signals. Following training, process 19400 proceeds to act 19410, where the trained statistical model is output for use during runtime as described above in connection with FIGS. 19A-19C.

In some embodiments, a denoising autoencoder as a component of a statistical model is used to identify and mitigate an artifact. A denoising autoencoder can be implemented by building a statistical model (e.g., a neural network) where input data comprises clean neuromuscular sensor data containing no (or few) artifacts combined with artifacts (e.g., noise), then training the model with the clean neuromuscular sensor data. In this manner, a system or method with a statistical model comprising a denoising autoencoder may provide robustness to neuromuscular artifacts. The artifacts added to the clean neuromuscular sensor data may have a statistical structure consistent with any suitable signal artifact including, but not limited to, noise artifacts, skin-contact artifacts, skin lift-off artifacts, power line frequency (e.g., 50 Hz, 60 Hz) artifacts, clipped signal artifacts, inactive sensor artifacts, microfriction artifacts, data degeneration artifacts, and artifacts caused by movement of one or more neuromuscular sensors (e.g., the rotation of an armband containing a plurality of neuromuscular sensors that causes the mapping between the location of one or more neuromuscular sensors and the recorded signals of the neuromuscular sensors generated by underlying motor units to change).

In some embodiments, simple quality metrics may be derived from the first few principal components of the log power spectra of the neuromuscular sensor data, which tend to be stereotyped across electrodes and between users and recording sessions. For example, linear and quadratic discriminant analysis may account for common causes of aberrant power spectra (e.g., to be able to identify artifacts including but not limited to: motion artifacts (low frequency), contact artifacts (broadband noise), power-line noise (60 Hz), artifacts caused by ground truth data systems that determine the position of a part of the user's body (e.g., joints of the hand), and IMU artifacts). In a variation of this embodiment, cospectral features of multi-channel neuromuscular data may be used to identify artifacts manifesting as correlational information between neuromuscular sensors.

Figure 19E:
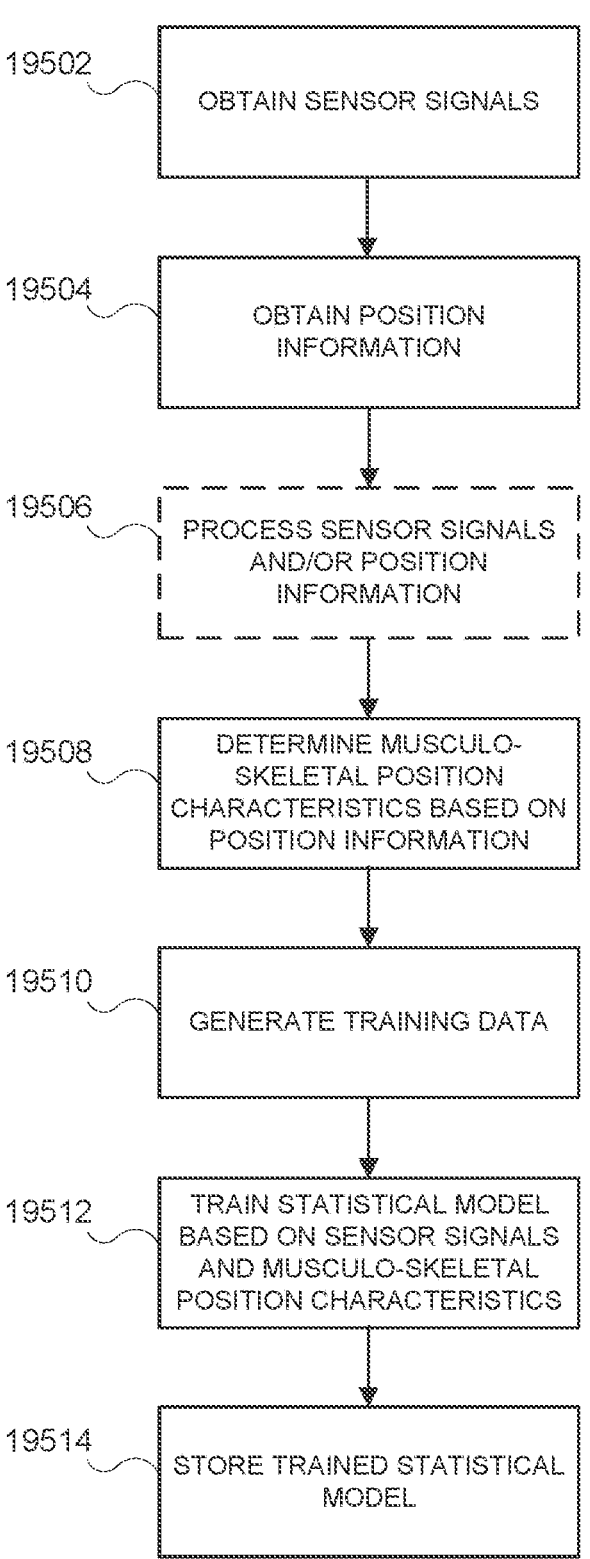
FIG. 19E is a flowchart of an illustrative process for generating a statistical model for predicting musculoskeletal position information using signals recorded from sensors, in accordance with some embodiments of the technology described herein.

FIG. 19E describes a process 19500 for generating (sometimes termed "training" herein) a statistical model using signals recorded from sensors 19102. Process 19500 may be executed by any suitable computing device(s), as aspects of the technology described herein are not limited in this respect. For example, process 19500 may be executed by one or more computer processors described with reference to FIGS. 9A and 9B. As another example, one or more acts of process 19500 may be executed using one or more servers (e.g., servers included as a part of a cloud computing environment). For example, at least a portion of act 19510 relating to training of a statistical model (e.g., a neural network) may be performed using a cloud computing environment.

Process 19500 begins at act 19502, where a plurality of sensor signals are obtained for one or multiple users performing one or more movements (e.g., typing on a keyboard). In some embodiments, the plurality of sensor signals may be recorded as part of process 19500. In other embodiments, the plurality of sensor signals may have been recorded prior to the performance of process 19500 and are accessed (rather than recorded) at act 19502.

In some embodiments, the plurality of sensor signals may include sensor signals recorded for a single user performing a single movement or multiple movements. The user may be instructed to perform a sequence of movements for a particular task (e.g., opening a door) and sensor signals corresponding to the user's movements may be recorded as the user performs the task he/she was instructed to perform. The sensor signals may be recorded by any suitable number of sensors located in any suitable location(s) to detect the user's movements that are relevant to the task performed. For example, after a user is instructed to perform a task with the fingers of his/her right hand, the sensor signals may be recorded by multiple neuromuscular sensors circumferentially (or otherwise) arranged around the user's lower right arm to detect muscle activity in the lower right arm that give rise to the right hand movements and one or more IMU sensors arranged to predict the joint angle of the user's arm relative to the user's torso. As another example, after a user is instructed to perform a task with his/her leg (e.g., to kick an object), sensor signals may be recorded by multiple neuromuscular sensors circumferentially (or otherwise) arranged around the user's leg to detect muscle activity in the leg that give rise to the movements of the foot and one or more IMU sensors arranged to predict the joint angle of the user's leg relative to the user's torso.

In some embodiments, the sensor signals obtained in act 19502 correspond to signals from one type of sensor (e.g., one or more IMU sensors or one or more neuromuscular sensors) and a statistical model may be trained based on the sensor signals recorded using the particular type of sensor, resulting in a sensor-type specific trained statistical model. For example, the obtained sensor signals may comprise a plurality of EMG sensor signals arranged around the lower arm or wrist of a user and the statistical model may be trained to predict musculoskeletal position information for movements of the wrist and/or hand during performance of a task such as grasping and twisting an object such as a doorknob.

In embodiments that provide predictions based on multiple types of sensors (e.g., IMU sensors, EMG sensors, MMG sensors, SMG sensors), a separate statistical model may be trained for each of the types of sensors and the outputs of the sensor-type specific models may be combined to generate a musculoskeletal representation of the user's body. In other embodiments, the sensor signals obtained in act 19502 from two or more different types of sensors may be provided to a single statistical model that is trained based on the signals recorded from the different types of sensors. In one illustrative implementation, an IMU sensor and a plurality of EMG sensors are arranged on a wearable device configured to be worn around the forearm of a user, and signals recorded by the IMU and EMG sensors are collectively provided as inputs to a statistical model, as discussed in more detail below.

In some embodiments, the sensor signals obtained in act 19502 are recorded at multiple time points as a user performs one or multiple movements. As a result, the recorded signal for each sensor may include data obtained at each of multiple time points. Assuming that n sensors are arranged to simultaneously measure the user's movement information during performance of a task, the recorded sensor signals for the user may comprise a time series of K n¬-dimensional vectors $\{xk|1{\leq}k{\leq}K\}$ at time points t1, t2, . . . , tK during performance of the movements.

In some embodiments, a user may be instructed to perform a task multiple times and the sensor signals and position information may be recorded for each of multiple repetitions of the task by the user. In some embodiments, the plurality of sensor signals may include signals recorded for multiple users, each of the multiple users performing the same task one or more times. Each of the multiple users may be instructed to perform the task and sensor signals and position information corresponding to that user's movements may be recorded as the user performs (once or repeatedly) the task he/she was instructed to perform. When sensor signals are collected by multiple users which are combined to generate a statistical model, an assumption is that different users employ similar musculoskeletal positions to perform the same movements. Collecting sensor signals and position information from a single user performing the same task repeatedly and/or from multiple users performing the same task one or multiple times facilitates the collection of sufficient training data to generate a statistical model that can accurately predict musculoskeletal position information associated with performance of the task.

In some embodiments, a user-independent statistical model may be generated based on training data corresponding to the recorded signals from multiple users, and as the system is used by a user, the statistical model is trained based on recorded sensor data such that the statistical model learns the user-dependent characteristics to refine the prediction capabilities of the system for the particular user.

In some embodiments, the plurality of sensor signals may include signals recorded for a user (or each of multiple users) performing each of multiple tasks one or multiple times. For example, a user may be instructed to perform each of multiple tasks (e.g., grasping an object, pushing an object, and pulling open a door) and signals corresponding to the user's movements may be recorded as the user performs each of the multiple tasks he/she was instructed to perform. Collecting such data may facilitate developing a statistical model for predicting musculoskeletal position information associated with multiple different actions that may be taken by the user. For example, training data that incorporates musculoskeletal position information for multiple actions may facilitate generating a statistical model for predicting which of multiple possible movements a user may be performing.

As discussed above, the sensor data obtained at act 19502 may be obtained by recording sensor signals as each of one or multiple users performs each of one or more tasks one or more multiple times. As the user(s) perform the task(s), position information describing the spatial position of different body segments during performance of the task(s) may be obtained in act 19504. In some embodiments, the position information is obtained using one or more external devices or systems that track the position of different points on the body during performance of a task. For example, a motion capture system, a laser scanner, a device to measure mutual magnetic induction, or some other system configured to capture position information may be used. As one non-limiting example, a plurality of position sensors may be placed on segments of the fingers of the right hand and a motion capture system may be used to determine the spatial location of each of the position sensors as the user performs a task such as grasping an object. The sensor data obtained at act 19502 may be recorded simultaneously with recording of the position information obtained in act 19504. In this example, position information indicating the position of each finger segment over time as the grasping motion is performed is obtained.

Next, process 19500 proceeds to act 19506, where the sensor signals obtained in act 19502 and/or the position information obtained in act 19504 are optionally processed. For example, the sensor signals or the position information signals may be processed using amplification, filtering, rectification, or other types of signal processing.

Next, process 19500 proceeds to act 19508, where musculoskeletal position characteristics are determined based on the position information (as collected in act 19504 or as processed in act 19506). In some embodiments, rather than using recorded spatial (e.g., x, y, z) coordinates corresponding to the position sensors as training data to train the statistical model, a set of derived musculoskeletal position characteristic values are determined based on the recorded position information, and the derived values are used as training data for training the statistical model. For example, using information about the constraints between connected pairs of rigid segments in the articulated rigid body model, the position information may be used to determine joint angles that define angles between each connected pair of rigid segments at each of multiple time points during performance of a task. Accordingly, the position information obtained in act 19504 may be represented by a vector of n joint angles at each of a plurality of time points, where n is the number of joints or connections between segments in the articulated rigid body model.

Next, process 19500 proceeds to act 19510, where the time series information obtained at acts 19502 and 19508 is combined to create training data used for training a statistical model at act 19510. The obtained data may be combined in any suitable way. In some embodiments, each of the sensor signals obtained at act 19502 may be associated with a task or movement within a task corresponding to the musculoskeletal position characteristics (e.g., joint angles) determined based on the positional information recorded in act 19504 as the user performed the task or movement. In this way, the sensor signals may be associated with musculoskeletal position characteristics (e.g., joint angles) and the statistical model may be trained to predict that the musculoskeletal representation will be characterized by particular musculoskeletal position characteristics between different body segments when particular sensor signals are recorded during performance of a particular task.

In embodiments comprising sensors of different types (e.g., IMU sensors and neuromuscular sensors) configured to simultaneously record different types of movement information during performance of a task, the sensor data for the different types of sensors may be recorded using the same or different sampling rates. When the sensor data is recorded at different sampling rates, at least some of the sensor data may be resampled (e.g., up-sampled or down-sampled) such that all sensor data provided as input to the statistical model corresponds to time series data at the same time resolution. Resampling at least some of the sensor data may be performed in any suitable way including, but not limited to using interpolation for upsampling and using decimation for downsampling.

In addition to or as an alternative to resampling at least some of the sensor data when recorded at different sampling rates, some embodiments employ a statistical model configured to accept multiple inputs asynchronously. For example, the statistical model may be configured to model the distribution of the "missing" values in the input data having a lower sampling rate. Alternatively, the timing of training of the statistical model occur asynchronously as input from multiple sensor data measurements becomes available as training data.

Next, process 19500 proceeds to act 19512, where a statistical model for predicting musculoskeletal position information is trained using the training data generated at act 19510. The statistical model being trained may take as input a sequence of data sets each of the data sets in the sequence comprising an n-dimensional vector of sensor data. The statistical model may provide output that indicates, for each of one or more tasks or movements that may be performed by a user, the likelihood that the musculoskeletal representation of the user's body will be characterized by a set of musculoskeletal position characteristics (e.g., a set of joint angles between segments in an articulated multi-segment body model). For example, the statistical model may take as input a sequence of vectors {xk|1≤k≤K} generated using measurements obtained at time points t1, t2, . . . , tK, where the ith component of vector xj is a value measured by the ith sensor at time tj and/or derived from the value measured by the ith sensor at time tj. In another non-limiting example, a derived value provided as input to the statistical model may comprise features extracted from the data from all or a subset of the sensors at and/or prior to time tj (e.g., a covariance matrix, a power spectrum, a combination thereof, or any other suitable derived representation). Based on such input, the statistical model may provide output indicating, a probability that a musculoskeletal representation of the user's body will be characterized by a set of musculoskeletal position characteristics. As one non-limiting example, the statistical model may be trained to predict a set of joint angles for segments in the fingers in the hand over time as a user grasps an object. In this example, the trained statistical model may output, a set of predicted joint angles for joints in the hand corresponding to the sensor input.

In some embodiments, the statistical model may be a neural network and, for example, may be a recurrent neural network. In some embodiments, the recurrent neural network may be a long short-term memory (LSTM) neural network. It should be appreciated, however, that the recurrent neural network is not limited to being an LSTM neural network and may have any other suitable architecture. For example, in some embodiments, the recurrent neural network may be a fully recurrent neural network, a recursive neural network, a variational autoencoder, a Hopfield neural network, an associative memory neural network, an Elman neural network, a Jordan neural network, an echo state neural network, a second order recurrent neural network, and/or any other suitable type of recurrent neural network. In other embodiments, neural networks that are not recurrent neural networks may be used. For example, deep neural networks, convolutional neural networks, and/or feedforward neural networks, may be used.

In some of the embodiments in which the statistical model is a neural network, the output layer of the neural network may provide a set of output values corresponding to a respective set of possible musculoskeletal position characteristics (e.g., joint angles). In this way, the neural network may operate as a non-linear regression model configured to predict musculoskeletal position characteristics from raw or pre-processed sensor measurements. It should be appreciated that, in some embodiments, any other suitable non-linear regression model may be used instead of a neural network, as aspects of the technology described herein are not limited in this respect.

In some embodiments, the neural network can be implemented based on a variety of topologies and/or architectures including deep neural networks with fully connected (dense) layers, Long Short-Term Memory (LSTM) layers, convolutional layers, Temporal Convolutional Layers (TCL), or other suitable type of deep neural network topology and/or architecture. The neural network can have different types of output layers including output layers with logistic sigmoid activation functions, hyperbolic tangent activation functions, linear units, rectified linear units, or other suitable type of nonlinear unit. Likewise, the neural network can be configured to represent the probability distribution over n different classes via, for example, a softmax function or include an output layer that provides a parameterized distribution e.g., mean and variance of a Gaussian distribution.

It should be appreciated that aspects of the technology described herein are not limited to using neural networks, as other types of statistical models may be employed in some embodiments. For example, in some embodiments, the statistical model may comprise a hidden Markov model, a Markov switching model with the switching allowing for toggling among different dynamic systems, dynamic Bayesian networks, and/or any other suitable graphical model having a temporal component. Any such statistical model may be trained at act 19512 using the sensor data obtained at act 19502.

As another example, in some embodiments, the statistical model may take as input, features derived from the sensor data obtained at act 19502. In such embodiments, the statistical model may be trained at act 19512 using features extracted from the sensor data obtained at act 19502. The statistical model may be a support vector machine, a Gaussian mixture model, a regression-based classifier, a decision tree classifier, a Bayesian classifier, and/or any other suitable classifier, as aspects of the technology described herein are not limited in this respect. Input features to be provided as training data to the statistical model may be derived from the sensor data obtained at act 19502 in any suitable way. For example, the sensor data may be analyzed as time series data using wavelet analysis techniques (e.g., continuous wavelet transform, discrete-time wavelet transform, etc.), Fourier-analytic techniques (e.g., short-time Fourier transform, Fourier transform, etc.), and/or any other suitable type of time-frequency analysis technique. As one non-limiting example, the sensor data may be transformed using a wavelet transform and the resulting wavelet coefficients may be provided as inputs to the statistical model.

In some embodiments, at act 19512, values for parameters of the statistical model may be estimated from the training data generated at act 19510. For example, when the statistical model is a neural network, parameters of the neural network (e.g., weights) may be estimated from the training data. In some embodiments, parameters of the statistical model may be estimated using gradient descent, stochastic gradient descent, and/or any other suitable iterative optimization technique. In embodiments where the statistical model is a recurrent neural network (e.g., an LSTM), the statistical model may be trained using stochastic gradient descent and backpropagation through time. The training may employ a cross-entropy loss function and/or any other suitable loss function, as aspects of the technology described herein are not limited in this respect.

Next, process 19500 proceeds to act 19514, where the trained statistical model is stored (e.g., in datastore—not shown). The trained statistical model may be stored using any suitable format, as aspects of the technology described herein are not limited in this respect. In this way, the statistical model generated during execution of process 19500 may be used at a later time, for example, to predict musculoskeletal position information (e.g., joint angles) for a given set of input sensor data, as described below.

In some embodiments, sensor signals are recorded from a plurality of sensors (e.g., arranged on or near the surface of a user's body) that record activity associated with movements of the body during performance of a task. The recorded signals may be optionally processed and provided as input to a statistical model trained using one or more techniques described above in connection with FIG. 19E. In some embodiments that continuously record autonomous signals, the continuously recorded signals (raw or processed) may be continuously or periodically provided as input to the trained statistical model for prediction of musculoskeletal position information (e.g., joint angles) for the given set of input sensor data. As discussed above, in some embodiments, the trained statistical model is a user-independent model trained based on autonomous sensor and position information measurements from a plurality of users. In other embodiments, the trained model is a user-dependent model trained on data recorded from the individual user from which the data associated with the sensor signals is also acquired.

After the trained statistical model receives the sensor data as a set of input parameters, the predicted musculoskeletal position information is output from the trained statistical model. As discussed above, in some embodiments, the predicted musculoskeletal position information may comprise a set of musculoskeletal position information values (e.g., a set of joint angles) for a multi-segment articulated rigid body model representing at least a portion of the user's body. In other embodiments, the musculoskeletal position information may comprise a set of probabilities that the user is performing one or more movements from a set of possible movements.

In some embodiments, after musculoskeletal position information is predicted, a computer-based musculoskeletal representation of the user's body is generated based, at least in part, on the musculoskeletal position information output from the trained statistical model. The computer-based musculoskeletal representation may be generated in any suitable way. For example, a computer-based musculoskeletal model of the human body may include multiple rigid body segments, each of which corresponds to one or more skeletal structures in the body. For example, the upper arm may be represented by a first rigid body segment, the lower arm may be represented by a second rigid body segment the palm of the hand may be represented by a third rigid body segment, and each of the fingers on the hand may be represented by at least one rigid body segment (e.g., at least fourth-eighth rigid body segments). A set of joint angles between connected rigid body segments in the musculoskeletal model may define the orientation of each of the connected rigid body segments relative to each other and a reference frame, such as the torso of the body. As new sensor data is measured and processed by the statistical model to provide new predictions of the musculoskeletal position information (e.g., an updated set of joint angles), the computer-based musculoskeletal representation of the user's body may be updated based on the updated set of joint angles determined based on the output of the statistical model. In this way the computer-based musculoskeletal representation is dynamically updated in real-time as sensor data is continuously recorded.

The computer-based musculoskeletal representation may be represented and stored in any suitable way, as embodiments of the technology described herein are not limited with regard to the particular manner in which the representation is stored. Additionally, although referred to herein as a "musculoskeletal" representation, to reflect that muscle activity may be associated with the representation in some embodiments, as discussed in more detail below, it should be appreciated that some musculoskeletal representations used in accordance with some embodiments may correspond to skeletal structures, muscular structures or a combination of skeletal structures and muscular structures in the body.

In some embodiments, direct measurement of neuromuscular activity and/or muscle activity underlying the user's movements may be combined with the generated musculoskeletal representation. Measurements from a plurality of sensors placed at locations on a user's body may be used to create a unified representation of muscle recruitment by superimposing the measurements onto a dynamically posed skeleton. In some embodiments, muscle activity sensed by neuromuscular sensors and/or information derived from the muscle activity (e.g., force information) may be combined with the computer-generated musculoskeletal representation in real time.

Figure 19F:
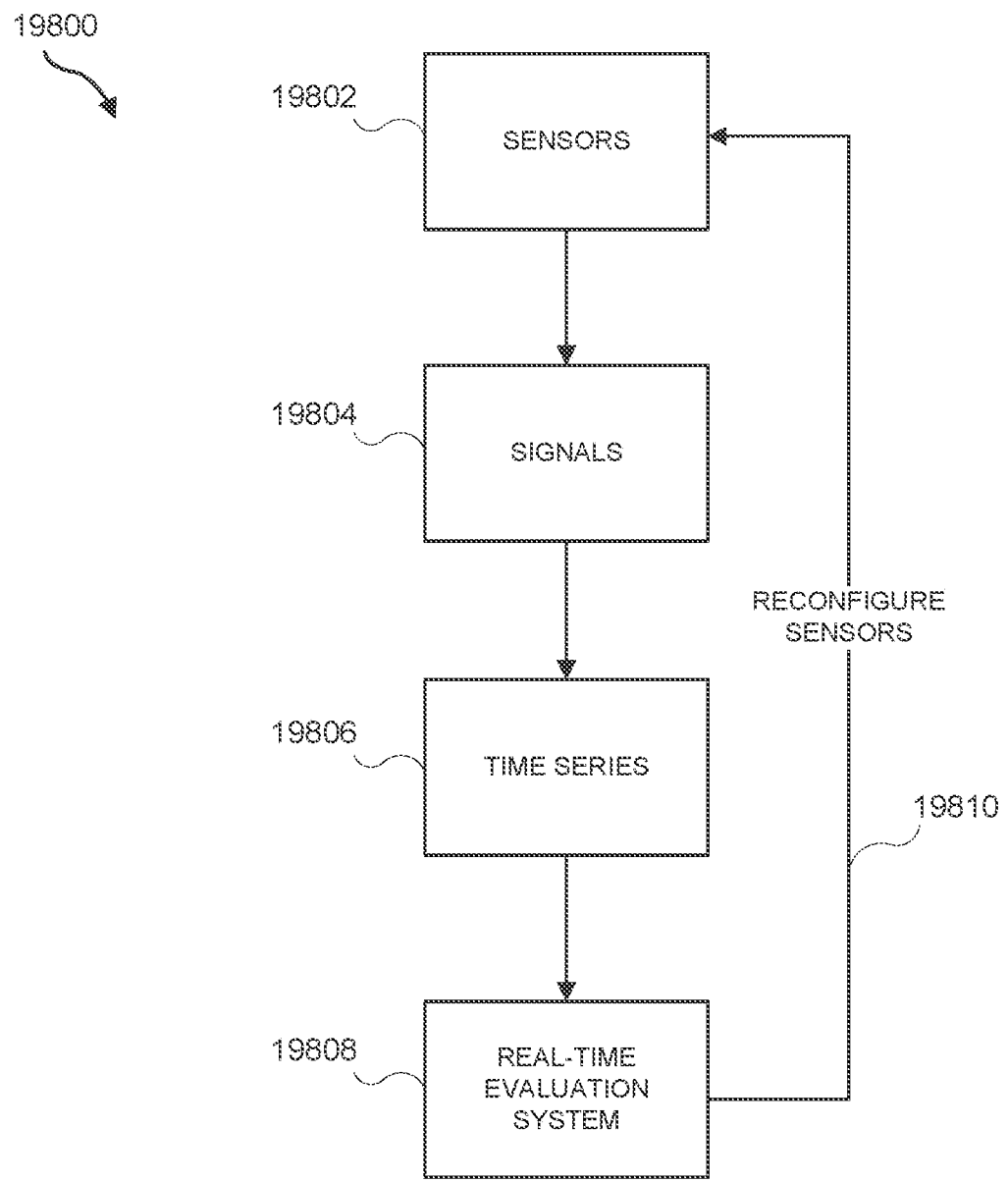
FIG. 19F is a diagram of a computer-based system for configuring neuromuscular sensors based on neuromuscular sensor data.

FIG. 19F shows a computer-based system 19800 for configuring neuromuscular sensors based on neuromuscular sensor data in accordance with some embodiments. The system includes a plurality of sensors 19802 configured to record signals resulting from the movement of portions of a human body. Sensors 19802 may include autonomous sensors.

System 19800 also includes one or more computer processors (not shown in FIG. 19F) programmed to communicate with sensors 19802. For example, signals 19804 recorded by one or more of the sensors 19802 may be provided to the processor(s), which may be programmed to identify a time series with values acquired via sensors 19802. The processor(s), as a part of a real-time system, may evaluate the quality of signals 19804 received from, e.g., a single sensor or a pair of differential sensors.

The term "differential sensors," as used herein, may refer to any pair or set of sensors whose signals are compared and/or combined (e.g., by subtracting one from another) to produce a composite signal (e.g., with the end of reducing or eliminating noise from the signals). For example, in the case of electrodes used as neuromuscular sensors, the raw voltage signal from an electrode in the absence of relevant neuromuscular activity may typically represent noise (e.g., ambient electromagnetic noise from the environment). On the assumption that two electrodes will experience the same noise, by subtracting the signal of an electrode only observing noise from the signal of an electrode whose signal represents relevant activity plus noise, the relevant signal may be isolated. However, as described herein, in some cases sensors may experience noise unevenly, and systems and methods described herein may dynamically configure differential sensor pairings to improve the resultant signal.

As discussed above, a real-time system may evaluate, based on received time series data, the performance of a sensor and/or a pair of differential sensors. For example, the real-time system can determine if a particular electrode in a pair of differential electrodes is not in contact with the user's skin. An electrode that is not in contact with the user's skin can generate signals characterized by out-of-range amplitude and frequency discontinuities. The real-time system can reconfigure the array of electrodes to replace or deactivate the channel of the electrode that is not in contact with the user's skin with another electrode determined to be in contact with the user's skin. Thus, the dynamically configurable arrangement of electrodes ensures that only electrodes in contact with the user skin are used to compute measurements.

In some instances, the real-time system configures multiple pairs of sensors in the arrangement, each pair of sensors being used to compute differential measurements. Sensors in each pair do not need to be located at equal distances. Differently stated, sensors in a first pair of sensors can be separated by a first distance, while sensors in a second pair of electrodes can be separated by a second distance, wherein the first distance is different from the second distance. Configuring pairs of sensors, where the sensors in one pair are separated by a different distance than the sensors in another pair results in a flexible and adaptable system capable of retrieving differential measurements from pairs of sensors known to be better predictors of, for example, an amount of applied force, gestures, and/or poses (collectively "interactions") performed by a user. Moreover, this flexible configuration enables the acquisition of differential measurements from electrodes paired according to the direction of a signal propagation (e.g., in a line down the arm or wrist), horizontally across the arm or wrist, or diagonally (both down and horizontally across the arm or wrist). Accordingly, the armband system can be configured to reduce and/or correct motion artifacts by selecting specific electrodes identified as motion resilient when the real-time system detects the infiltration of motion artifacts in the acquired signals.

In some implementations, the real-time system can activate sensors positioned at specific areas of the arm or wrist depending on an activity being performed by the user. For example, when the user engages in a typing task, the real-time system can determine such activity and accordingly can steer the sampling density to the underside arm nerves by, for example, activating and pairing sensors located in such region. For another example, the sampling density can focus on regions of the arm associated with the movement of a finger (e.g., for mission critical discrete controls) or configured in a distributed full arm or wrist sampling configuration when predictions are made regarding the user's handstate.

In some implementations, the configurable array of sensors can reduce the number of channels in the armband system that remain active at a given time. For example, the real-time system can determine that, for a specific task, predictions of interactions performed by a user can be computed from signals received from a first set of sensors, while the signals received from a second set of sensors are discarded or ignored. In such a case, the real-time system can activate the first set of sensors and deactivate the second set of sensors resulting in a more efficient use of computational resources.

In some examples, the systems and methods described herein may dynamically configure sensors in a way that is personalized to the particular user. For example, the shape of the user's arm or wrist, the fit of the wearable device on the user, the characteristics of the neuromuscular signals received from the user, surface qualities of the user's skin, and/or the hairiness of the user's arm may impact how suited various sensors are to producing accurate and/or useful signals (e.g., for a system that converts neuromuscular signals into musculoskeletal representations). In some examples, systems described herein may observe and evaluate sensor performance and quality during specific user-performed tasks. By determining that certain sensors provide more reliable performance during certain tasks for a given user, the systems and methods described herein may dynamically adjust the configurable array of sensors to use data from pairs of differential sensors that provide signals most representative of the user's activity for those tasks. Thus, for example, an XR system that consumes the neuromuscular signals to produce musculoskeletal representations of the user's hand may provide high-level information about activities that the user is engaged in (e.g., typing, interacting with particular types of virtual objects, etc.) or predicted to be engaging in so that systems described herein may adjust the configurable array of sensors according to a stored user profile.

In some examples, systems described herein may prospectively adjust the configurable array of sensors (e.g., based on information received about an application that the user has initiated, an input mode that the user has selected, a task that the user is predicted to start performing). Additionally or alternatively, systems described herein may adjust the configurable array of sensors in response to observed performance issues and/or errors (e.g., detecting that an electrode has come out of contact with the user's skin). In some examples, systems described herein may evaluate sensor performance before providing sensor data to subsystems that consume the sensor data (e.g., an inferential model that produces a musculoskeletal representation of the user's hand based on the neuromuscular sensor data). Additionally or alternatively, systems described herein may partly evaluate sensor performance based on performance issues observed by the subsystems that consume the sensor data. For example, an inferential model (and/or associated subsystems for interpreting neuromuscular data) may produce a musculoskeletal representation with a large expected error term. While systems described herein may attribute some of the error to the inferential model, in some embodiments systems described herein may attribute some of the error to sensor performance. These systems may therefore backpropagate the error to the sensor array, and a real-time system may reconfigure the sensor array at least partly in response to the backpropagated error.

Figure 19G:
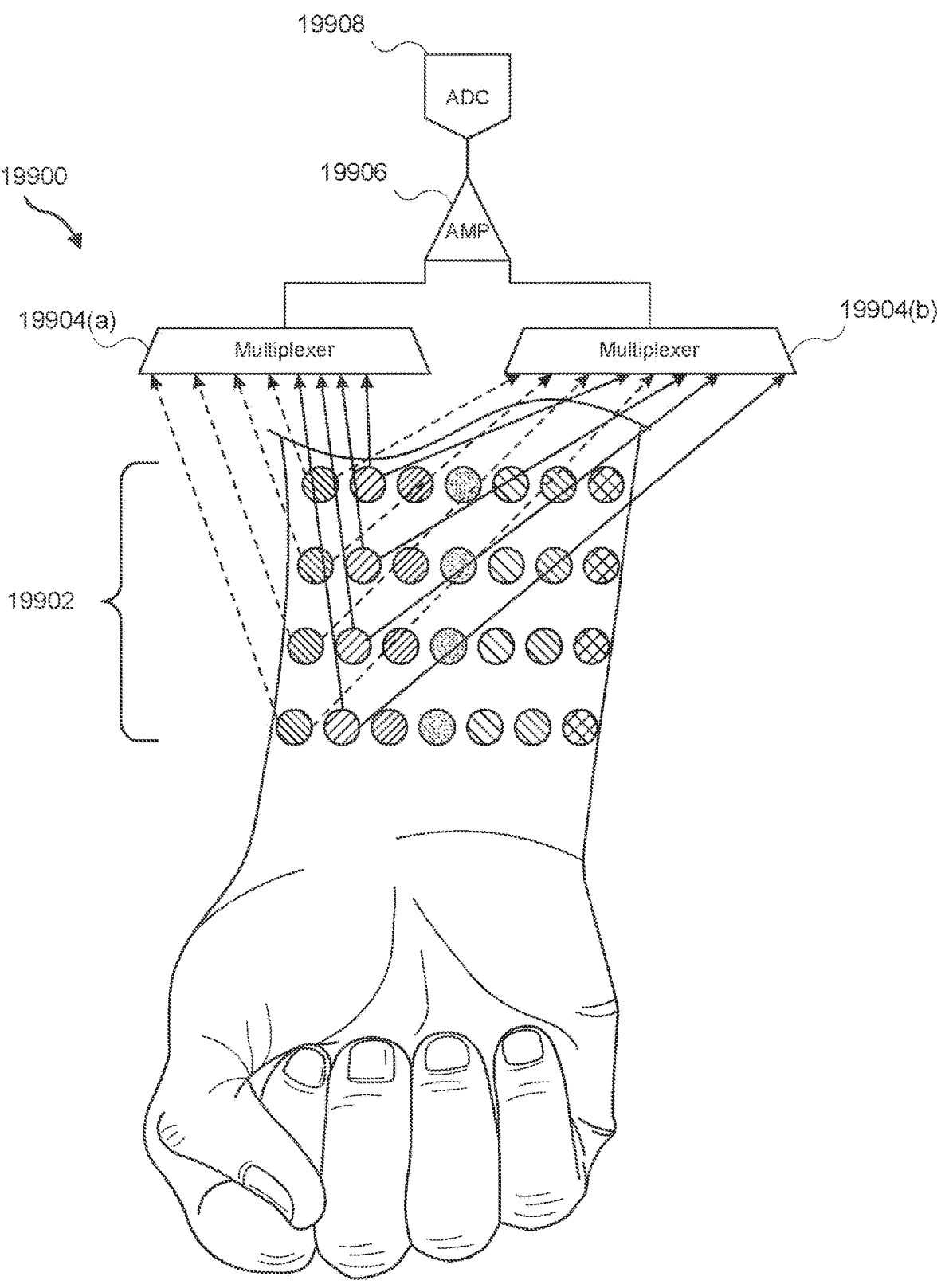
FIG. 19G is an illustration of a dynamically configurable array of neuromuscular sensors.

FIG. 19G shows an example of a system 19900 for a dynamically configurable array 19902 of electrodes. The dynamically configurable array can be integrated in the armband system shown in FIGS. 8A-8B and FIGS. 9A-9B. Electrodes in an array, as shown in FIG. 19G, can be wired to a fully switched/multiplexed matrix in a configuration that enables any electrode in the array to be paired with any other electrode in the same array. Thus, signals from dynamically configurable array 19902 may be received by multiplexers 19904 (*a*)-(*b*), which may pass the resultant signal to an amplifier 19906. Amplifier 19906 may, in turn, pass the signal to an analog-to-digital converter 19908.

Figure 19H:
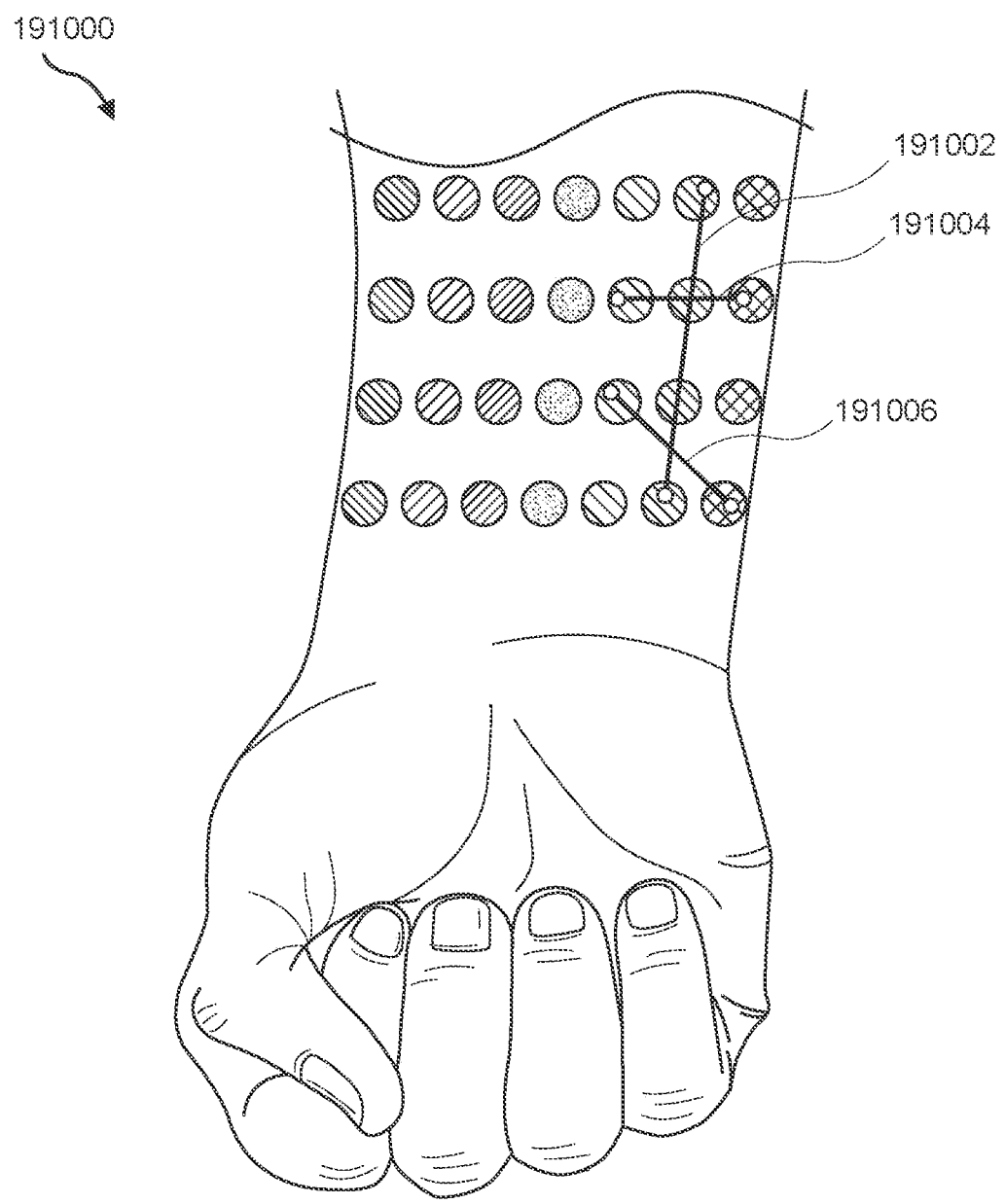
FIG. 19H is an illustration of potential differential pairings of neuromuscular sensors.

FIG. 19H shows example differential sensor pairings within the dynamically configurable array 19902 of electrodes shown in FIG. 19G. As shown in FIG. 19H, sensors that run longitudinally along the user's wrist may be paired, as illustrated by example pairing 191002. In another example, sensors that run horizontally across the user's wrist may be paired, as illustrated by pairing 191004. Furthermore, sensors that are positioned diagonally from each other (e.g., not positioned strictly longitudinally or horizontally from each other) may be paired, as illustrated by pairing 191006. In addition, it may be appreciated that the various example sensor pairings may involve differing sensor distances.

The following describes exemplary methods and apparatus for providing sub-muscular control according to at least one embodiment of the present disclosure.

Figure 20A:
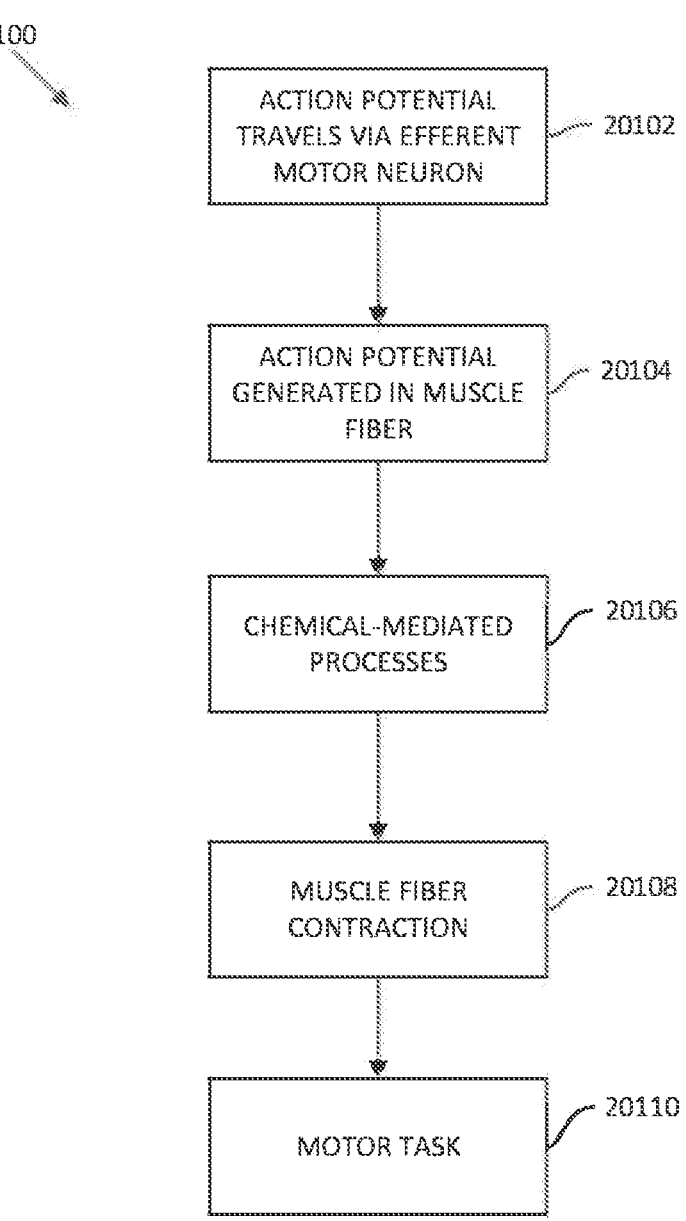
FIG. 20A is a flowchart of a biological process for performing a motor task in accordance with some embodiments of the technology described herein.

FIG. 20A illustrates a flowchart of a biological process 20100 for initiating a motor task by the coordinated movement of one or more muscles. In act 20102, action potentials are generated in one or more efferent spinal motor neurons. The motor neurons carry the neuronal signal away from the central nervous system and toward skeletal muscles in the periphery. For each motor neuron in which an action potential is generated, the action potential travels along the axon of motor neuron from its body in the spinal cord where the action potential is generated to the axon terminals of the motor neuron that innervate muscle fibers included in skeletal muscles. A motor neuron and the muscle fibers that it innervates are referred to herein as a motor unit. Muscle fibers in a motor unit are activated together in response to an action potential generated in the corresponding motor neuron of the motor unit. Individual muscles typically include muscle fibers from hundreds of motor units with the simultaneous contraction of muscle fibers in many motor units resulting in muscle contraction evidenced as perceptible muscle movement.

A chemical synapse formed at the interface between an axon terminal of a spinal motor neuron and a muscle fiber is called a neuromuscular junction. As an action potential transmitted along the axon of a motor neuron reaches the neuromuscular junction, process 20100 proceeds to act 20104, where an action potential is generated in the muscle fiber as a result of chemical activity at the neuromuscular junction. In particular, acetylcholine released by the motor neuron diffuses across the neuromuscular junction and binds with receptors on the surface of the muscle fiber triggering a depolarization of the muscle fiber. Although neuromuscular signals sensed on the body surface generated by the depolarization of individual muscle fibers are small (e.g., less than 100 $\mu V$), the collective action of multiple muscle fibers conducting simultaneously results in a detectable voltage potential that may be recorded by neuromuscular sensors (e.g., EMG sensors) located on the surface of the body. As noted above, the collective conduction of muscle fibers from many motor units results in muscle contraction and perceptible motion. Accordingly, when a user performs a movement or gesture, the corresponding recorded neuromuscular signals include contributions from multiple activated motor units.

Following generation of an action potential in the muscle fiber, process 20100 proceeds to act 20106, where the propagation of the action potential in the muscle fiber results in a series of chemical-mediated processes within the muscle fiber. For example, depolarization of a muscle fiber results in an influx of calcium ions into the muscle fiber. Calcium ions inside the muscle fiber bind with troponin complexes causing the troponin complexes to separate from myosin binding sites on actin filaments in the muscle fiber, thereby exposing the myosin binding sites.

Following these chemical-mediated processes, process 20100 proceeds to act 20108, where the muscle fiber contracts. Muscle fiber contraction is achieved due to the binding of exposed myosin heads with actin filaments in the muscle fiber creating cross-bridge structures. Process 20100 then proceeds to act 20110, where the collective contraction of muscle fibers in one or more muscles results in the performance of a motor task.

As the tension of a muscle increases during performance of a motor task, the firing rates of active neurons increases and additional neurons may become active, which is a process referred to as motor unit recruitment. The pattern by which neurons become active and increase their firing rate is stereotyped, such that the expected motor unit recruitment patterns define an activity manifold associated with standard or normal movement. Some embodiments are directed to teaching a user to activate a single motor unit or a group of motor units that are "off-manifold," in that the pattern of motor unit activation is different than an expected or typical motor unit recruitment pattern. Such off-manifold activation is referred to herein as, "sub-muscular activation" or "activation of a sub-muscular structure," where a sub-muscular structure refers to the single motor unit or the group of motor units associated with the off-manifold activation. Examples of off-manifold motor unit recruitment patterns include, but are not limited to, selectively activating a high-threshold motor unit without activating a lower-threshold motor unit that would normally be activated earlier in the recruitment order and modulating the firing rate of a motor unit across a substantial range without modulating the activity of other neurons that would normally be co-modulated in typical motor recruitment patterns. Sub-muscular activation is used in accordance with some embodiments of the technology described herein to generate control information, as described in more detail below.

When a user performs a motor task, such as moving their arm, a group of muscles necessary to perform the motor task is activated. When the motor task is performed while the user is wearing a wearable device that includes neuromuscular sensors, the neuromuscular signals recorded by the sensors on the surface of the body correspond to superimposed activity of all motor units in the muscles in the group activated during performance of the motor task. The neuromuscular signals may be analyzed and mapped to control signals to control a device based on the type of movement or gesture that the user performs. For example, if the user performs a thumbs-up gesture with their hand, a corresponding control signal to select an object in a user interface may be generated. The mapping between sensor signals and control signals may be implemented, for example, using an inference model trained to associate particular sensor signal inputs with control signal outputs. In some implementations, the inference model(s) can include one or more statistical models, one or more machine learning models, and/or a combination of one or more statistical model(s) and/or one or more machine learning model(s). A further discussion of the implementation of the inference model is provided below. In some embodiments, the output of the trained inference model may be musculoskeletal position information that describes, for example, the positions and/or forces of elements in a computer-implemented musculoskeletal model. As neuromuscular signals are continuously recorded, the musculoskeletal model may be updated with predictions of the musculoskeletal position information output from the inference model. Control signals may then be generated based on the updated musculoskeletal position information. In other embodiments, the output of the trained inference model may be the control information itself, such that a separate musculoskeletal model is not used.

As discussed above, each muscle in the human body typically includes muscle fibers from hundreds of motor units. During normal motor control, in systems that generate control signals based on activation of one or more muscles (e.g., when a user activates a muscle or performs a movement using a group of muscles), the joint activity of the motor units within each muscle are projected to a single dimension corresponding to the activation or tension of that muscle. By projecting the multidimensional sensor signals to a single dimension, information about activation of individual sub-muscular structures (e.g., one or more motor units) is lost, as only the collective activation of all motor units within each muscle used to perform the movement, gesture or pose is considered when determining a corresponding control signal to generate. Some embodiments of the technology described herein are directed to using neuromuscular sensors to identify activation of sub-muscular structures and to generate a control signal based, at least in part, on the identified activated sub-muscular structure. The inventors have recognized and appreciated that by identifying activation of sub-muscular structures, a control system can be designed that includes multiple sub-muscular control "channels," each of which corresponds to pattern of activation identified within one or more motor units. Accordingly, information about sub-muscular structure activation, which is typically lost in conventional neuromuscular sensor-based control systems that project down to a single dimension, is utilized in some embodiments to increase the amount of control information that can be used to control a device. Additionally, by training a user to activate individual motor units or groups of motor units, some embodiments are configured to generate control information based on recorded neuromuscular signals without perceptible movement of muscles or groups of muscles.

Throughout this disclosure EMG sensors are used as examples of the type of neuromuscular sensors configured to detect neuromuscular activity. However it should be appreciated that other types of neuromuscular sensors including, but not limited to, mechanomyography (MMG) sensors, electrical impedance tomography (EIT) sensors, and sonomyography (SMG) sensors may additionally or alternatively be used in combination with EMG sensors to detect neuromuscular activity in accordance with some embodiments. The neuromuscular signals recorded by the neuromuscular sensors may be used to identify activation of sub-muscular structures in accordance with the techniques described herein.

Figure 20B:
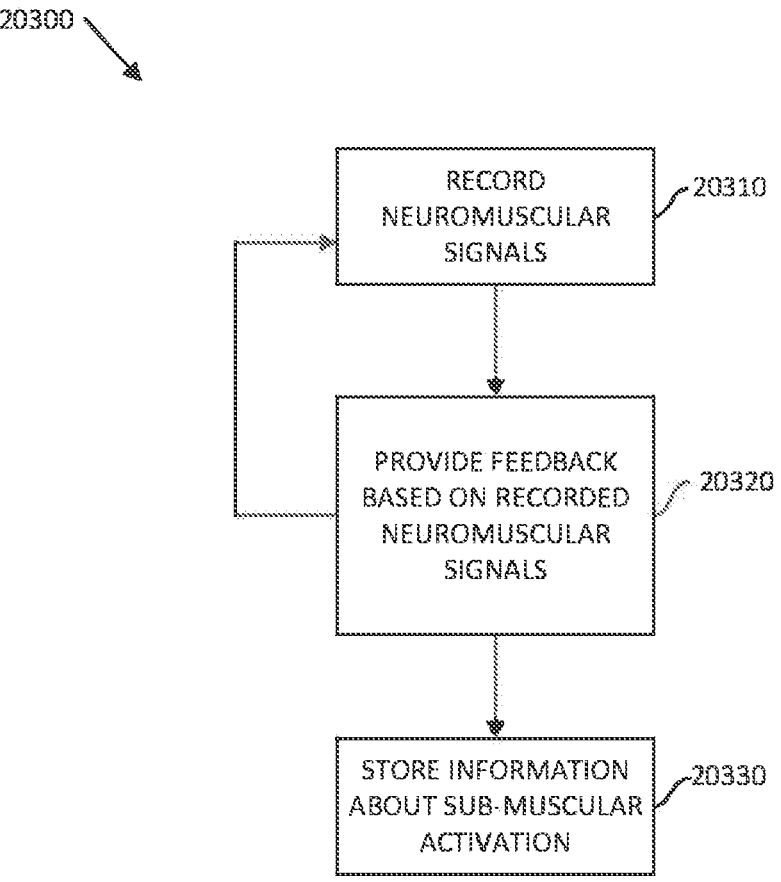
FIG. 20B is a flowchart of a process for training a user to activate sub-muscular structures in accordance with some embodiments of the technology described herein.

FIG. 20B illustrates a process 20300 for training a user to activate sub-muscular structures using neuromuscular signals and feedback generated by processing the recorded signals in accordance with some embodiments. In act 20310, a plurality of neuromuscular signals are recorded by a plurality of neuromuscular sensors worn by a user as the user activates one or more sub-muscular structures. Process 20300 then proceeds to act 20320 where feedback generated based on the recorded neuromuscular signals is provided to the user based on the recorded neuromuscular signals. The feedback may be provided via a user interface (e.g., user interface 118 in system 100). The feedback generated in act 20320 provides information to the user about the recorded neuromuscular signals which in turn enables the user to learn how to selectively activate sub-muscular structures. Although feedback is described in connection with process 20300 for training a user to activate sub-muscular structures, in some embodiments, feedback is provided to the user even after the system has been trained. Providing feedback as the user is using the system following training may facilitate the user's understanding of how the trained system is interpreting the user's intended sub-muscular activation and may alert the user as to whether further training of the system is needed.

In some embodiments, the feedback provided to the user in act 20320 is generated using the raw (e.g., unprocessed) neuromuscular signals recorded by the neuromuscular sensors. For example, the raw neuromuscular signals may be converted into audio signals that are played through an audio interface (e.g., a speaker). Alternatively, the raw neuromuscular signals may be displayed on a visual interface such as a display to provide feedback. In other embodiments, the raw neuromuscular signals may be analyzed to identify activation of particular sub-muscular structures. The inventors have recognized and appreciated that activation of sub-muscular structures is manifested in neuromuscular signals in characteristic ways (e.g., timing, waveform shape) that enables the separation of signals arising from one sub-muscular structure from another sub-muscular structure. Identifying activation of particular sub-muscular structures from the raw neuromuscular signals may be performed in any suitable way. For example, the raw neuromuscular signals may be decomposed into signal components (e.g., using independent component analysis, convolutive blind source separation, spike sorting protocols that include event detection followed by clustering or classification, or another suitable technique) corresponding to activation arising from individual motor units (e.g., individual spiking events in a motor unit) or groups of motor units.

Characteristics or "signatures" of sub-muscular activation identified in the recorded neuromuscular signals may be used to generate feedback provided to the user as the user activates sub-muscular structures. For example, the user may be provided with audio feedback that encodes activation of different sub-muscular structures using audio having different characteristics. In a simplified example, the system may analyze raw neuromuscular signals and identify activation of two motor units. Audio feedback may be generated including a first audio tone having a first pitch and a second audio tone having a second pitch, where the first audio tone corresponds to activation of one of the two motor units and the second audio tone corresponds to activation of the other of the two motor units. In some embodiments, the timing of the presentation of tones in the audio feedback may correspond to a timing of activation (e.g., neuromuscular spike activity) for the corresponding motor unit or other sub-muscular structure. In some embodiments, the amplitude of the tone may correspond to the rate or intensity with which the sub-muscular structure is activated.

The feedback received by the user provides the user with information about whether and when the system is able to detect a pattern of neuromuscular activity associated with particular sub-muscular structures, and allows the user to adapt their neuromuscular activity to learn how to activate sub-muscular structures, such as a single motor unit. For example, if the user receives audio feedback that includes tones having multiple pitches, the user is made aware of the pattern of activity for multiple sub-muscular structures that the system has identified as being activated. Based on this feedback, the user can consciously modify their neuromuscular activity in an attempt to invoke a particular activation pattern associated with a sub-muscular structure. As the user modifies their motor activity, the feedback provided to the user also changes based on the recorded neuromuscular signals to enable the user to understand in real-time how modifications in their activity were interpreted by the system. The user can continue to continuously modify their activity based on the provided feedback to learn how to activate particular patterns of sub-muscular activity.

When audio signals are used as feedback, audio characteristics other than pitch of a tone may be used to signify differences between identified activated sub-muscular structures in the recorded neuromuscular signals. For example, loudness, duration, timbre, or other perceptual audio characteristics of the audio feedback may be modulated to represent the identification of particular sub-muscular structures in the neuromuscular signals. Additionally, audio signals other than tones may also be used. For example, different activated sub-muscular structures may be represented in the audio feedback by different musical instruments.

Feedback other than audio feedback may alternatively be used in accordance with some embodiments. Non-limiting examples of feedback that may be provided to a user to facilitate training a user to activate sub-muscular structures include visual feedback, tactile/haptic feedback, and feedback provided via electrical stimulation. For any chosen feedback modality, perceptual characteristics of components of the feedback provided may be updated in real-time based on sub-muscular activation identified in recorded neuromuscular signals to enable the user to learn how to modify their neuromuscular activity to activate one or more sub-muscular structures using particular activation patterns. For example, the user may be trained to alternate firings of two motor units, create a rhythmic pattern of firings for a single motor unit, or modulate the rate of one or more motor units in a time-dependent manner, and the feedback may be provided to facilitate the training.

As described above, feedback provided to a user may be generated based on raw (e.g., unprocessed) sensor data. In other embodiments, feedback may be generated based on information derived from the recorded sensor data. For example, the recorded sensor data may be filtered or otherwise processed prior to being used to generate feedback provided to the user.

As described above, some embodiments employ an inference model trained to output information used to generate a control signal based on sensor data provided as input to the model. In some embodiments, feedback provided to a user is generated based on an output of the trained inference model. For example, a control signal generated based on the output of the trained inference model may be provided to a display controller (or other suitable controller) that updates a display with information that informs the user about particular sub-muscular structures that were activated. As the user modifies their neuromuscular activation based on the feedback provided on the display, the control signal generated by the system is also updated, resulting in an updated visual representation on the display. In this way, the feedback provided to the user may be presented in a form that mimics a game that encourages the user to complete a particular task, where completion of the task is associated with successful activation of a particular pattern of sub-muscular activity. Such feedback may be more easily comprehensible and useful for some users, enabling those users to learn how to sub-muscular structures in particular ways.

prehensible and useful for some users, enabling those users to learn how to sub-muscular structures in particular ways.

Realizing that different users may learn how to activate sub-muscular structures in different ways, some embodiments provide feedback to users in multiple different ways. The user may be able to select the type of feedback that is most useful to facilitate their training. In some embodiments, the type of feedback that is provided to the user may be determined and/or recommended, at least in part, by the system, based on a measure of the effectiveness of the feedback to help the user learn. For example, a measure of how long it takes a user to successfully complete a task associated with activating a sub-muscular structure may be used to determine which type of feedback is recommended by the system for a particular user.

As shown in process 20300, feedback may be provided continuously as the user learns to invoke a particular activation pattern and neuromuscular signals are continuously recorded as the user modifies their behavior in response to the feedback. The training may continue until it is determined that the user has successfully learned how to activate particular sub-muscular structures as desired (e.g., in a particular pattern). This determination may be made by the user or may be made, at least in part, using an automated process implemented, for example, using processor 112. For example, the signals recorded by the sensor may be compared to a template describing a known or desired activation pattern and when there is a sufficient match to the template, it may be determined to end the training for the particular sub-muscular activation pattern. The determination that a user has successfully trained a sub-muscular pattern may be made even when other sub-muscular structures or activity patterns are also observed in the recorded sensor data. For example, if the system is programmed to determine whether the user has activated motor unit A, it may be determined that the user has activated motor unit A when the system determines that motor units A, B and C (or other unidentified sources) have been activated, but not when the system determines that motor units C and D (but not A) have been activated. In some embodiments, the system is programmed to determine that the user has activated motor unit A when only motor unit A has been activated.

After it has been determined to stop training, process 20300 proceeds to act 20330 where information about the sub-muscular activation on which the user was training to activate is stored. In some embodiments, an inference model trained to map the recorded sensor data to one or more control signals associated with the sub-muscular structure may be stored and/or updated. For example, when the inference model is implemented as a neural network, the weights associated with the connections in the neural network may be updated to reflect the mapping between the recorded sensor data and a control signal output from or derived from output of the inference model.

The inventors have recognized that storing information about sub-muscular activation by a user enables the user to activate the same sub-muscular structure or structures across sessions. A second session of wearing a system with a plurality of neuromuscular sensors 110 and other components shown in FIG. 1 may occur minutes, hours, days, weeks, months, or even years after a first session. The stored representation of the sub-muscular activation by the user can be accessed and used as a control signal.

In general, inference models may be implemented that calibrate the neuromuscular sensor data recorded from the user in order to reliably derive information for one or more sub-muscular structures activated by the user. Calibration may be necessary for several reasons. For example, calibration may be necessary because, when a user wears a neuromuscular array in a second session, one or more of the neuromuscular sensors may be in a different position on the user's body than in the first session. When the neuromuscular sensors are arranged in a radial array on the wearable device as shown in FIGS. 7A and 8A, the location of the neuromuscular sensors on the body may rotate from session to session, and an inference model may be used to calibrate the neuromuscular sensor data in order to reliably identify the same sub-muscular structure (or structures) identified in the first session. In another example of why calibration may be necessary, the position of a radial neuromuscular array (e.g., the system shown in FIGS. 7A and 8A) may be located more distal or proximal on an arm of the user, and an inference model may be used to calibrate the neuromuscular sensor data in order to reliably identify the same sub-muscular structure (or structures) identified in the first session. In yet another example of why calibration may be necessary, a radial neuromuscular array (e.g., the system shown in FIGS. 7A and 8A) may be placed on the user's arm in the opposite orientation—that is, a side of the neuromuscular array that faced proximally in a first session may face distally in a second session, and an inference model may be used to identify whether the neuromuscular array is facing proximally or distally and the anatomical position of the neuromuscular sensors may be re-ordered in a processing step that precedes identification of the previously identified sub-muscular structure or structures.

The inventors have recognized that systems and methods that store information about sub-muscular activation by a user that enable the user to activate the same sub-muscular structure or structures across sessions are beneficial for identifying changes in sub-muscular activation across time in a user. Tracking changes in sub-muscular activation is beneficial for monitoring changes in the motor nervous system of the user. Changes in sub-muscular activation may change for any of several reasons, including but not limited to: muscle fatigue, training to strengthen or otherwise affect the pattern of sub-muscular activation (e.g., motor learning or strength training), diet, time-of-day, the amount and quality of sleep a user has had, the presence of compounds that affect the motor nervous system (e.g., pharmaceutical agents, drugs of abuse, caffeine, alcohol, and nicotine), peripheral neuropathy, neurodegeneration, peripheral nerve injury, brain injury, or other disorder that affects the motor system.

The inventors have recognized that while some users may be able to selectively activate sub-muscular structures while suppressing other neural activity, other users may have difficulty learning to selectively activate sub-muscular structures. In some embodiments, a control signal output from the system is mapped to a subset of motor units activated during a motor task (e.g., moving a hand up and down), wherein the subset of motor units are associated with a sub-muscular structure. During training, the user may initially move their hand up and down, thereby activating the motor units in the subset mapped to the control signal in addition to other motor units. Over time, the user may learn that producing smaller and smaller movements still results in the control signal being output from the system as long as the user's movements still activate the motor units in the subset. Eventually, with additional training the user may be able to generate the control signal without making perceptible movements as long as the motor units in the subset corresponding to the sub-muscular structure are activated. Training a user to make small movements to activate submuscular structures in accordance with some embodiments enables the creation of a control system in which user fatigue is reduced and in which the user can control a device discretely (e.g., when the user is in a place where making larger movements to generate control signals is not appropriate behavior) or independently of larger movements.

As discussed briefly above, activation of a particular sub-muscular structure may be observed in recorded sensor data as timings and/or signal waveform shapes that characterize the activation from that structure. The spatiotemporal activation patterns that characterize activation of a sub-muscular structure are also referred to herein as the structure's "signature." The ability of the system to effectively separate activations from different sub-muscular structures, and thus create separate control channels for activation associated with individual sub-muscular structures or multiple sub-muscular structures (e.g., combinatorial codes), may depend on how different the signatures are for the sub-muscular structures. Additionally, the set of sub-muscular structures whose signatures achieve the best separation may vary from user to user. Prior to training a user how to activate sub-muscular patterns of activation, a set of target sub-muscular structures that the user may be trained to activate may be identified.

Figure 20C:
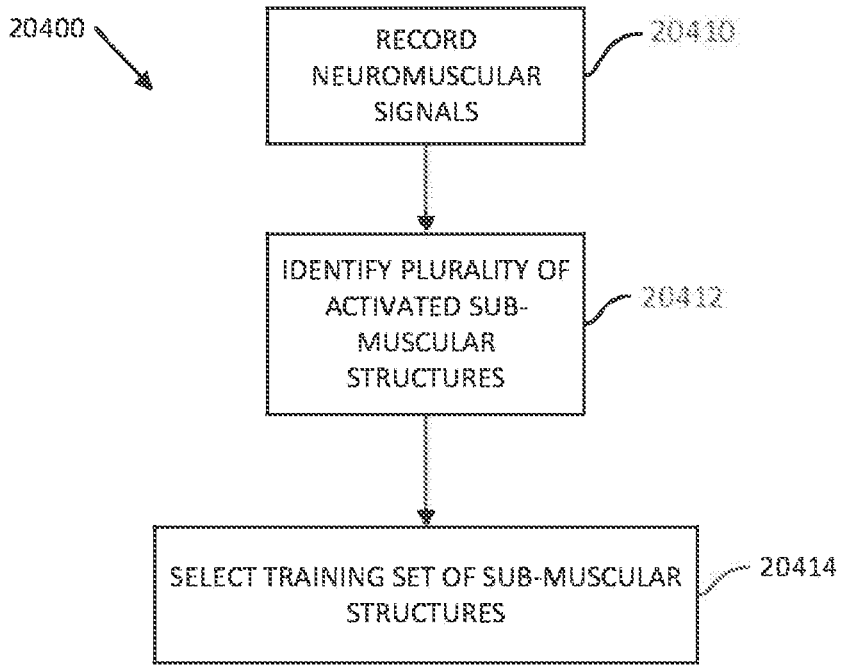
FIG. 20C is a flowchart of a process for selecting a set of sub-muscular structures for training in accordance with some embodiments of the technology described herein.

FIG. 20C illustrates a process 20400 for identifying a set of sub-muscular structures to be used as training targets in accordance with some embodiments. In act 20410, a plurality of neuromuscular signals is recorded from a plurality of sensors arranged on a wearable device as the user performs one or more movements or gestures. Process 20400 then proceeds to act 20412 where a plurality of activated sub-muscular structures (e.g., motor units) are identified based on the recorded neuromuscular signals. The plurality of activated sub-muscular structures may be identified in any suitable way. For example, the recorded neuromuscular signals may be decomposed into signal components that characterize activation of the plurality of activated sub-muscular structures. In some embodiments, the signal components may represent individual spiking events and identifying the plurality of activated sub-muscular structures may be performed by determining which of the individual spiking events are associated with activation of particular sub-muscular structures. Alternatively, the recorded neuromuscular signals may be analyzed in any other suitable way to identify a plurality of sub-muscular structures.

Process 20400 then proceeds to act 20414, where a subset of sub-muscular structures is selected for use in training. Selection of sub-muscular structures to include in the training set may be based, at least in part, on characteristics of activation associated with each of the sub-muscular structures identified in act 20412. As described above, to enable the system to distinguish between activation of different sub-muscular structures, the inventors have recognized that it is advantageous to train users to activate sub-muscular structures having different activation characteristics or signatures as manifested in the recorded sensor data. Examples of characteristics of activation that may be used in some embodiments to select sub-muscular structures to include in a training set include, but are not limited to, a type of motor unit associated with the sub-muscular structure, a motor unit action potential amplitude associated with the sub-muscular structure, a similarity of a waveform for activation of the sub-muscular structure to waveforms for activation of other sub-muscular structures, and activation rate and timing statistics associated with activation of the sub-muscular structure.

In some embodiments, the number of sub-muscular structures to include in the training set are determined based on a desired number of sub-muscular control channels for the control system. For example, to construct a neuromuscular-based control system with eight sub-muscular control channels, the plurality of activated sub-muscular structures identified in act 20412 may be analyzed to determine eight activated sub-muscular structures that have reliably separable characteristics of activation to include in the training set. It should be appreciated that not all of the sub-muscular structures selected for inclusion in the training set need be separable from other sub-muscular structures in the training set using the same activation characteristics. For example, a first sub-muscular structure in the training set may be separable from other structures in the training set based on signal waveform shape, whereas a second sub-muscular structure in the training set may be separable from other structures in the training set based motor unit action potential amplitude. Additionally, it should be appreciated that the sub-muscular structures selected for the training set may be separable based on a combination of characteristics of activation, and embodiments are not limited in this respect.

Selection of sub-muscular structures in act 20414 may be automatically performed by the one or more processors of the system 100 using criteria that maximize or increase the distance between activation characteristics or signatures of the activated sub-muscular structures. Alternatively, the selection of sub-muscular structures may be at least partially user driven. For example, users may be provided with feedback generated based on the recorded neuromuscular signals and the users may be able to select the sub-muscular structures to include in the training set. Permitting users to participate in the process of selecting sub-muscular structures allows the control system to implement a less robust source separation technique than would be required if the selection of sub-muscular structures for the training set was entirely automated by the system.

Following selection of a set of sub-muscular structures for the training set, the user may be trained to activate each of the sub-muscular structures in the set using, for example, training process 20300 shown in FIG. 20B and described above. Spatiotemporal information about the activated sub-muscular structures in the training set and/or the information that maps neuromuscular sensor signals to sub-muscular activation (e.g., a user-specified or trained inference model) may be stored by at least one storage device associated with the system for using the system to control a device once the user and the system have been trained.

The inventors have recognized that each time the user wears the wearable device including the neuromuscular sensors to begin a control session, it may be difficult, at least initially, for the system to recover activity from the same sub-muscular structures on which the system was trained. For example, the placement on the body of the wearable device including the sensors may be different each time the user uses the device. Accordingly, prior to using the system, including the trained inference model, to control a device, the system may be calibrated. The calibration may be automatically performed by the system when the user starts using the device or the calibration may be at least partially user-driven to relax the requirement that the system perform automatic calibration without user input. Additionally, it should be appreciated that calibration may be performed at any suitable time including during a control session.

Figure 20D:
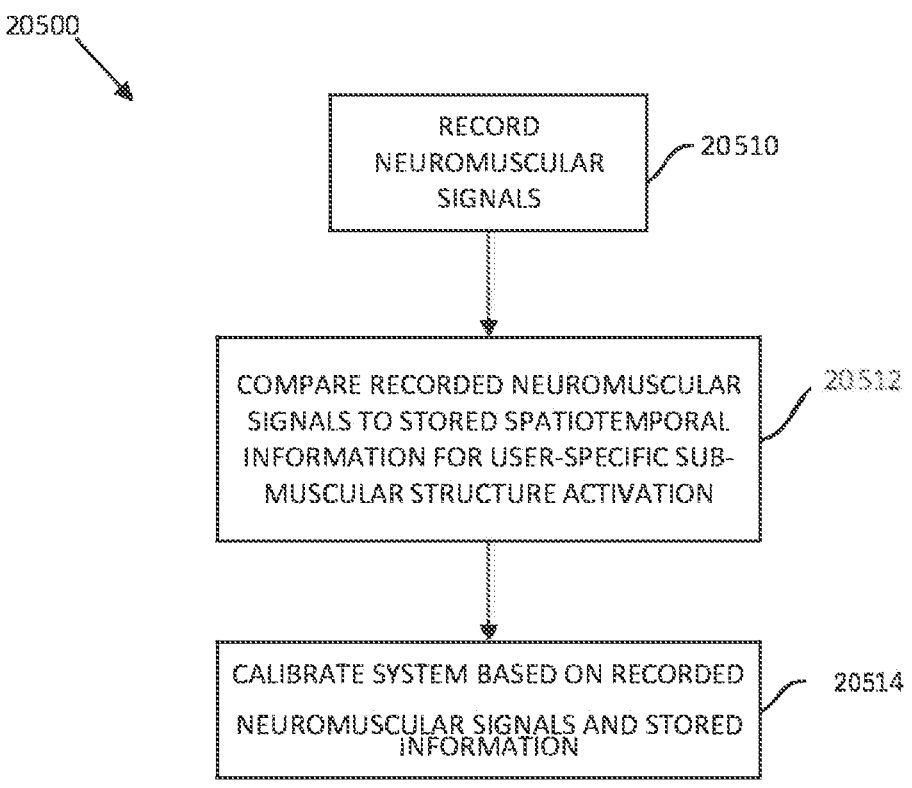
FIG. 20D is a flowchart of a process for calibrating a control system in accordance with some embodiments of the technology described herein.

FIG. 20D shows a process 20500 for calibrating the system in accordance with some embodiments. In act 20510, neuromuscular signals are recorded from sensors arranged on a wearable device worn by a user. Process 20500 then proceeds to act 20512, where the recorded neuromuscular signals are compared to information stored during the training process described above in connection with FIG. 20B. For example, the system may analyze the recorded neuromuscular signals to determine whether the system can automatically identify activation of sub-muscular structures using spatiotemporal information about the sub-muscular structures in the training set. The system may be configured to automatically identify the sub-muscular structures in the recorded sensor data by, for example, performing source separation on the recorded neuromuscular signals.

In embodiments in which the one or more processors of the system are not configured to perform automatic calibration, or in the case where automatic calibration fails, the user may provide input to facilitate the calibration process. For example, the user may be prompted to activate a plurality of sub-muscular structures in sequence, e.g., structure A, structure B, structure C. Feedback may be provided to the user as the user activates each of the sub-muscular structures to let the user know whether the system correctly interpreted the intended activation.

Process 20500 then proceeds to act 20514, where the system is calibrated based on the analysis of the recorded neuromuscular signals and the stored information. Calibration may be performed in any suitable way to enable the system to recover activation of the sub-muscular structures in the training set from the recorded neuromuscular signals. In some embodiments, the calibration may include transforming some of the recorded neuromuscular signals or information derived from the recorded neuromuscular signals to a representation that more closely aligns with the stored information. In other embodiments, the user may be provided with feedback instructing the user to adjust the positioning of the wearable device on the body and additional neuromuscular signals may be recorded until the system is able to reliably recover activation of the sub-muscular structures from the recorded sensor data.

After the system has been calibrated, the system may be used to derive information for a plurality of sub-muscular control channels from recorded signal data, generate control signal(s) based on the derived information, and provide the control signal to a control interface to control operation of a physical or virtual device. In this way, a control system capable of controlling a device using sub-muscular activation is provided.

Figure 20E:
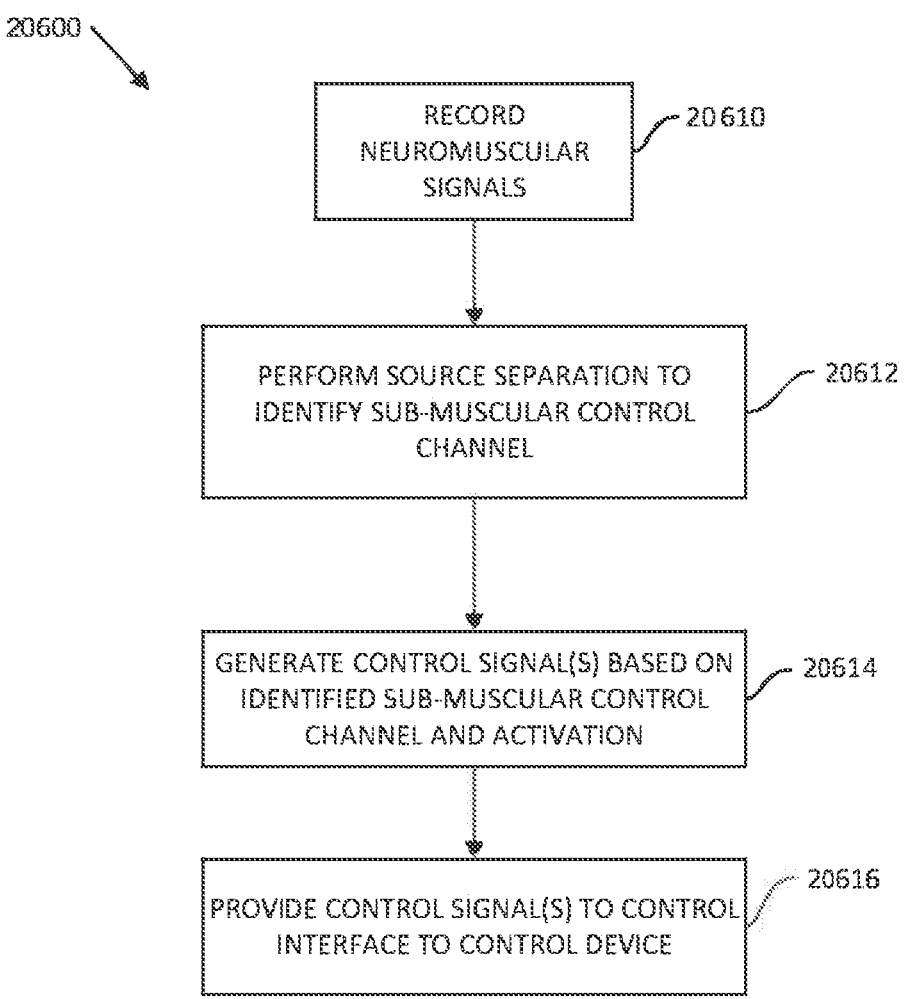
FIG. 20E is a flowchart of a process for using a calibrated control system to provide a control signal based on sub-muscular activation in accordance with some embodiments of the technology described herein.

FIG. 20E illustrates a process 20600 for providing a control signal to a device based on sub-muscular control information recorded from sensor data in accordance with some embodiments. In act 20610, a plurality of neuromuscular signals is recorded from neuromuscular sensors arranged near or on the surface of a user's body. One or more auxiliary sensors (e.g., IMU sensors) may also be used to record sensor data used for providing control information, and embodiments are not limited in this respect. Process 20600 then proceeds to act 20612 where a source separation process is performed on the recorded neuromuscular signals to identify a sub-muscular control channel associated with activation identified in the neuromuscular signals. Any suitable source separation technique, examples of which are discussed above, may be used to identify a sub-muscular control channel.

Process 20600 then proceeds to act 20614 where one or more control signals are generated based on the identified sub-muscular control channel and a pattern of activation represented in the recorded neuromuscular signals. For example, the neuromuscular signals may be provided as input to a trained inference model and an output of the trained inference model may be used to generate one or more control signals. In one implementation, the output of the trained inference model may be a set of one or more control signals. In another implementation, the control signal(s) may be generated based on the pattern of activation in the neuromuscular signals without the use of a trained inference model. Process 20600 then proceeds to act 20614 where the control signal(s) are provided to a control interface of a device to control an operation of the device. For example, the device may be a display and a control signal may be provided to a display controller of the display. The control signal may include instructions to update information displayed on the display. Alternatively, the device may be a computer or other computing device (e.g., a smartphone) and the control signal may be provided to a controller of the computing device to change an operation of the device. In yet a further example, the control signal may be used to control a device (e.g., a musical instrument) to provide an artistic expression. It should be appreciated that any device having a control interface may be controlled using control systems designed in accordance with the techniques described herein.

The following describes exemplary real-time spike detection and identification according to at least one embodiment of the present disclosure.

Figure 21A:
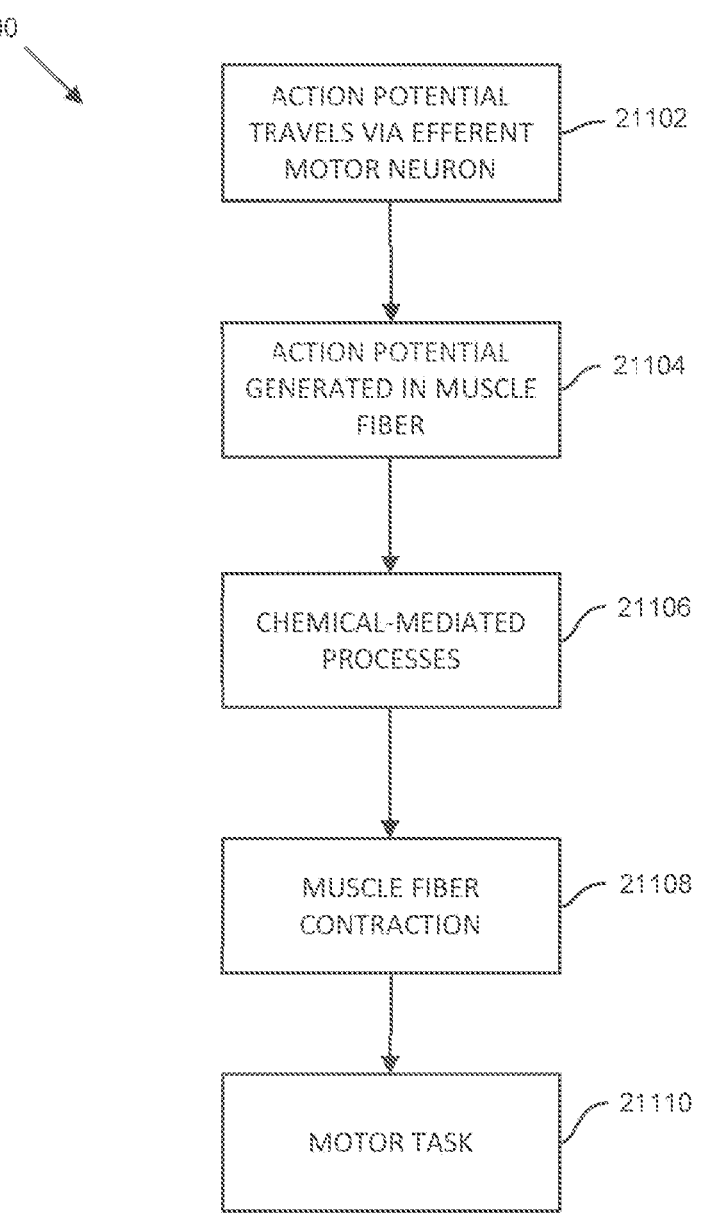
FIG. 21A is a flowchart of a biological process for performing a motor task in accordance with some embodiments of the technology described herein.

FIG. 21A illustrates a flowchart of a biological process 21100 for initiating a motor task by the coordinated movement of one or more muscles. In act 21102, action potentials are generated in one or more efferent spinal motor neurons. The motor neurons carry the neuronal signal (also referred to as "spikes" herein) away from the central nervous system and toward skeletal muscles in the periphery. For each motor neuron in which an action potential is generated, the action potential travels along the axon of the motor neuron from its body in the spinal cord where the action potential is generated to the axon terminals of the motor neuron that innervate muscle fibers included in skeletal muscles. A motor neuron and the muscle fibers that it innervates are referred to herein as a motor unit. Muscle fibers in a motor unit are activated together in response to an action potential generated in the corresponding motor neuron of the motor unit. Individual muscles typically include muscle fibers from hundreds of motor units with the simultaneous contraction of muscle fibers in many motor units resulting in muscle contraction evidenced as perceptible muscle movement and/or force.

A chemical synapse formed at the interface between an axon terminal of a spinal motor neuron and a muscle fiber is called a neuromuscular junction. As an action potential transmitted along the axon of a motor neuron reaches the neuromuscular junction, process 21100 proceeds to act 21104, where an action potential is generated in the muscle fiber as a result of chemical activity at the neuromuscular junction. In particular, acetylcholine released by the motor neuron diffuses across the neuromuscular junction and binds with receptors on the surface of the muscle fiber triggering a depolarization of the muscle fiber. Although neuromuscular signals sensed on the body surface generated by the depolarization of individual muscle fibers are small (e.g., less than 100 $\mu$V), the collective action of multiple muscle fibers conducting simultaneously results in a detectable voltage potential that may be recorded by neuromuscular (e.g., EMG) sensors located on the surface of the body. As noted above, the collective conduction of muscle fibers from many motor units results in muscle contraction and perceptible motion. Accordingly, when a user performs a movement or gesture, the corresponding recorded neuromuscular signals include contributions from multiple activated motor units.

Following generation of an action potential in the muscle fiber, process 21100 proceeds to act 21106, where the propagation of the action potential in the muscle fiber results in a series of chemical-mediated processes within the muscle fiber. For example, depolarization of a muscle fiber results in an influx of calcium ions into the muscle fiber. Calcium ions inside the muscle fiber bind with troponin complexes causing the troponin complexes to separate from myosin binding sites on actin filaments in the muscle fiber, thereby exposing the myosin binding sites.

Following these chemical-mediated processes, process 21100 proceeds to act 21108, where the muscle fiber contracts. Muscle fiber contraction is achieved due to the binding of exposed myosin heads with actin filaments in the muscle fiber creating cross-bridge structures. Process 21100 then proceeds to act 21110, where the collective contraction of muscle fibers in one or more muscles results in the performance of a motor task.

As the tension of a muscle increases, the firing rates of active motor neurons increases and additional motor neurons may become active, which is a process referred to as motor unit recruitment. The pattern by which motor neurons innervating a muscle become active and increase their firing rate is, in some cases, stereotyped. Some embodiments are directed to analyzing neuromuscular signals to detect and identify/classify spike events corresponding to firing of action potentials in one or more motor units.

When a user performs a motor task, such as moving their arm, a group of muscles necessary to perform the motor task is activated. When the motor task is performed while the user is wearing a wearable device that includes neuromuscular sensors (e.g., EMG sensors), the neuromuscular signals recorded by the sensors on the surface of the body correspond to superimposed activity of all motor units in the muscles in the group activated during performance of the motor task. The neuromuscular signals may be analyzed and mapped to control signals to control a device based on the type of movement or gesture that the user performs. In some embodiments, the analysis of neuromuscular signals involves the detection and identification of spike events in activated motor units.

A generative model of an EMG signal x(t) may take the form:

$$x(t)=\Sigma_i^N(s_i*t_i)(t)+\eta(t) \tag{1}$$

where t is the time, si is the spatiotemporal waveform of the i-th MUAP observed by an EMG recording device, ti is the spike train of the corresponding motor neuron and n (t) is the EMG measurement noise, where the spike train is represented as a time series of Dirac functions occurring each time the motor neuron fires.

As discussed above, a MUAP is an electrical potential generated by activation of muscle fibers in a corresponding motor unit. The spatiotemporal waveform of the MUAP as detected by a pair of EMG sensors (or a number of EMG sensors greater than two) depends primarily on the position of the motor unit relative to the array of EMG sensors. Tissue between the site of the muscle fiber(s) composing the motor unit and an EMG sensor filters the spatiotemporal waveform, so that the same EMG sensor (or EMG sensors) may measure a distinct spatiotemporal pattern due to different locations of the muscle fibers in the underlying tissue and, accordingly, unique filtering caused by tissue between the muscle fibers and an EMG sensor (or EMG sensors).

Some embodiments assume that the spatiotemporal waveform of the MUAP remains constant as long as the electrode positions and the conductive medium (e.g., the user's body) do not change. In practice, small variations in the spatiotemporal waveform for a MUAP may be introduced due to muscle contractions. For surface EMG sensors, the duration of a MUAP is on the order of 10-20 ms and may have an amplitude on the order of hundreds of microvolts. The duration of the MUAP is influenced largely based on the spacing between differential EMG electrodes and the velocity of the action potential wave traveling along the muscle fibers. The amplitude of the MUAP is influenced largely based on the distance from the motor unit to the EMG electrode pair and the number of muscle fibers in the motor unit.

The inventors have recognized that since the spatiotemporal waveform of a MUAP remains substantially constant, and as such encodes little or no information related to user intent, some embodiments are directed to extracting spike event information (e.g., spike train data) from neuromuscular signals as a measure of user intent. The extracted spike event information may be used to generate one or more outputs (e.g., one or more control signals, where the control signals may be used to change the state of a computerized system that is configured to receive the control signal). A mapping between spike event information and control signals may be implemented, for example, using an inferential model trained to associate particular spike event information with control signal outputs. In some embodiments, the output of the trained inferential model may be musculoskeletal position information that describes, for example, the positions and/or forces of rigid body segments in a computer-implemented musculoskeletal model. As neuromuscular signals are continuously recorded and spike events detected, the musculoskeletal model may be updated with predictions of the musculoskeletal position information output from the inferential model. Control signals may then be generated based on the updated musculoskeletal position information. In other embodiments, the output of the trained inferential model may be the control signals themselves, such that a musculoskeletal model is not used. In other embodiments, spike event information from a plurality of motor units may be combined, for example to enable two-dimensional control.

As described in more detail below, some embodiments detect spike events in recorded neuromuscular signals and identify a biological source (e.g., a motor unit or group of motor units) of the detected spike events. The output (e.g., a control signal) is then generated based on the detected spike event(s) and/or the identified biological source.

Throughout this disclosure EMG sensors are used as examples of the type of neuromuscular sensors configured to detect neuromuscular activity. However it should be appreciated that other types of neuromuscular sensors including, but not limited to, mechanomyography (MMG) sensors and sonomyography (SMG) sensors may additionally or alternatively be used in combination with EMG sensors to detect neuromuscular activity in accordance with some embodiments. The neuromuscular signals recorded by the neuromuscular sensors may be used to identify activation of sub-muscular structures in accordance with the techniques described herein.

As illustrated in FIG. 1, the system includes a plurality of sensors 110 configured to record signals resulting from the activation of motor units with portions of a human body. Sensors 110 may include a plurality of neuromuscular sensors configured to record signals arising from neuromuscular activity in skeletal muscle of a human body, as described above. The term "neuromuscular activity" as used herein refers to neural activation of spinal motor neurons that innervate a muscle, muscle activation, muscle contraction, or any combination of the neural activation, muscle activation, and muscle contraction. In some embodiments, spike event information describing when an action potential has occurred and/or a biological source of a detected spike event may be determined from the sensed neuromuscular signals.

Sensors 110 may include one or more Inertial Measurement Units (IMUs), which measure a combination of physical aspects of motion, using, for example, an accelerometer, a gyroscope, a magnetometer, or any combination of one or more accelerometers, gyroscopes and magnetometers. In some embodiments, IMUs may be used to sense information about movement of the part of the body on which the IMU is attached and information derived from the sensed data (e.g., position and/or orientation information) may be tracked as the user moves over time. For example, one or more IMUs may be used to track movements of portions of a user's body proximal to the user's torso relative to the sensor (e.g., arms, legs) as the user moves over time. In some embodiments, signals from an IMU may be used to filter, post-process, or otherwise refine the spike event(s) inferred by an inferential model.

In embodiments that include at least one IMU and a plurality of neuromuscular sensors, the IMU(s) and neuromuscular sensors may be arranged to detect movement of different parts of the human body. For example, the IMU(s) may be arranged to detect movements of one or more body segments proximal to the torso (e.g., an upper arm), whereas the neuromuscular sensors may be arranged to detect motor unit activity within one or more body segments distal to the torso (e.g., a forearm or wrist). It should be appreciated, however, that the sensors may be arranged in any suitable way, and embodiments of the technology described herein are not limited based on the particular sensor arrangement. For example, in some embodiments, at least one IMU and a plurality of neuromuscular sensors may be co-located on a body segment to track motor unit activity and/or movements of the body segment using different types of measurements. In one implementation described in more detail below, an IMU sensor and a plurality of EMG sensors are arranged on a wearable device configured to be worn around the lower arm or wrist of a user. In such an arrangement, the IMU sensor may be configured to track movement information (e.g., positioning and/or orientation over time) associated with one or more arm segments, to determine, for example whether the user has raised or lowered their arm, whereas the EMG sensors may be configured to determine sub-muscular information associated with activation of sub-muscular structures in muscles of the wrist or hand. In some embodiments, an IMU sensor may provide control signals that a user may volitionally control independently from one or more MUAPs.

Each of the sensors 110 includes one or more sensing components configured to sense information about a user. In the case of IMUs, the sensing components may include one or more accelerometers, gyroscopes, magnetometers, or any combination thereof to measure characteristics of body motion, examples of which include, but are not limited to, acceleration, angular velocity, and sensed magnetic field around the body. In the case of neuromuscular sensors, the sensing components may include, but are not limited to, electrodes configured to detect electric potentials on the surface of the body (e.g., for EMG sensors), vibration sensors configured to measure skin surface vibrations (e.g., for MMG sensors), and acoustic sensing components configured to measure ultrasound signals (e.g., for SMG sensors) arising from muscle activity. Exemplary sensors 110 that may be used in accordance with some embodiments are described in more detail in U.S. patent application Ser. No. 15/659,018 entitled "METHODS AND APPARATUS FOR PREDICTING MUSCULO-SKELETAL POSITION INFORMATION USING WEARABLE AUTONOMOUS SENSORS," incorporated by reference herein by its entirety.

In some embodiments, at least some of the plurality of sensors are arranged as a portion of a wearable device configured to be worn on or around part of a user's body. For example, in one non-limiting example, an IMU sensor and a plurality of neuromuscular sensors are arranged circumferentially around an adjustable and/or elastic band such as a wristband or armband configured to be worn around a user's wrist or arm. Alternatively, at least some of the sensors may be arranged on a wearable patch configured to be affixed to a portion of the user's body, at least some of the sensors may be implanted EMG sensors, or at least some of the sensors may be included as a portion of an electronic tattoo worn by the user. In some embodiments, multiple wearable devices, each having one or more neuromuscular sensors (and, optionally, one or more IMUs) included thereon may be used to generate control information based on MUAPs, sub-muscular structures, and/or movement that involve multiple parts of the body.

In some embodiments, multiple wearable devices, each having one or more IMUs and/or neuromuscular sensors included thereon may be used to generate control information based on MUAPs, activation associated with sub-muscular structures, and/or movement that involve multiple parts of the body.

In some embodiments, sensors 110 only include a plurality of neuromuscular sensors (e.g., EMG sensors). In other embodiments, sensors 110 include a plurality of neuromuscular sensors and at least one "auxiliary" sensor configured to continuously record a plurality of auxiliary signals. Examples of auxiliary sensors include, but are not limited to, IMU sensors, an imaging device (e.g., a camera), a radiation-based sensor for use with a radiation-generation device (e.g., a laser-scanning device), or other types of sensors such as a heart-rate monitor.

In some embodiments, the output of one or more of the sensing components may be optionally processed using hardware signal processing circuitry (e.g., to perform amplification, filtering, and/or rectification). In other embodiments, at least some signal processing of the output of the sensing components may be performed in software. Accordingly, signal processing of signals recorded by the sensors may be performed in hardware, software, or by any suitable combination of hardware and software, as aspects of the technology described herein are not limited in this respect.

In some embodiments, the recorded sensor data may be optionally processed to compute additional derived measurements that are then provided as input to a spike event detection process. For example, recorded signals from an IMU sensor may be processed to derive an orientation signal that specifies the orientation of a body segment over time. In another example, recorded signals from an IMU sensor may be processed to determine movement (e.g. high velocity movement) that may cause sensor movement artifacts or shifts in the spatial location of muscle fibers of a motor unit relative to one or more EMG sensors, each of which may cause spurious spike events to be detected. Accordingly, IMU sensor data may be used to filter or otherwise refine the output of an inferential model configured for detecting one or more MUAPs. Sensors may implement signal processing using components integrated with the sensing components, or at least a portion of the signal processing may be performed by one or more components in communication with, but not directly integrated with the sensing components of the sensors 110.

System 100 also includes one or more computer processors 112 programmed to communicate with sensors 110. For example, signals recorded by one or more of the sensors may be provided to the processor(s) 112, which may be programmed to execute one or more machine learning algorithms that process signals output by the sensors 110 to train one or more inferential models (e.g., statistical models 114), and the trained (or retrained) statistical model(s) 114 may be stored for later use in generating control signals, as described in more detail below.

In some embodiments, statistical model 114 may be a neural network and, for example, may be a recurrent neural network. In some embodiments, the recurrent neural network may be a long short-term memory (LSTM) neural network. It should be appreciated, however, that the recurrent neural network is not limited to being an LSTM neural network and may have any other suitable architecture. For example, in some embodiments, the recurrent neural network may be a fully recurrent neural network, a gated recurrent neural network, a recursive neural network, a Hopfield neural network, an associative memory neural network, an Elman neural network, a Jordan neural network, an echo state neural network, a second order recurrent neural network, and/or any other suitable type of recurrent neural network. In other embodiments, neural networks that are not recurrent neural networks may be used. For example, deep neural networks, convolutional neural networks, and/or feedforward neural networks, may be used.

In some embodiments, the output of an inferential model (e.g., a statistical model) provides discrete outputs. Discrete outputs (e.g., classification labels) may be used, for example, when a desired output is to know whether a particular pattern of activation (including individual neural spiking events) is detected in the neuromuscular signals. For example, the model may be trained to estimate whether the user is activating a particular motor unit, activating a particular motor unit with a particular timing, activating a particular motor unit with a particular firing pattern, or activating a particular combination of motor units. On a shorter timescale, discrete classification is used in some embodiments to estimate whether a particular motor unit fired an action potential within a given amount of time. In such a scenario, these estimates may then be accumulated to obtain an estimated firing rate for that motor unit.

In embodiments in which the statistical model is implemented as a neural network configured to output a discrete signal, the neural network may include a softmax layer such that the outputs add up to one and may be interpreted as probabilities. The output of the softmax layer may be a set of values corresponding to a respective set of control signals, with each value indicating a probability that the user wants to perform a particular control action. As one non-limiting example, the output of the softmax layer may be a set of three probabilities (e.g., 0.92, 0.05, and 0.03) indicating the respective probabilities that the detected pattern of activity is one of three known patterns.

It should be appreciated that when the statistical model is a neural network configured to output a discrete signal, the neural network is not required to produce outputs that add up to one. For example, instead of a softmax layer, the output layer of the neural network may be a sigmoid layer (which has no restriction that the probabilities add up to one). In such embodiments, the neural network may be trained with a sigmoid cross-entropy cost. Such an implementation may be advantageous in the case when multiple different control actions may occur within a threshold amount of time and it is not important to distinguish the order in which these actions occur (e.g., a user may activate two patterns of neural activity within the threshold amount of time). In some embodiments, any other suitable non-probabilistic multi-class classifier may be used, as aspects of the technology described herein are not limited in this respect.

In some embodiments, the output of the statistical model may be a continuous signal rather than a discrete signal. For example, the model may output an estimate of the firing rate of each motor unit or the model may output a time-series electrical signal corresponding to each motor unit or sub-muscular structure.

It should be appreciated that aspects of the technology described herein are not limited to using neural networks, as other types of statistical models may be employed in some embodiments. For example, in some embodiments, the statistical model may comprise a hidden Markov model (HMM), a switching HMM with the switching allowing for toggling among different dynamic systems, dynamic Bayesian networks, and/or any other suitable graphical model having a temporal component. Any such statistical model may be trained using recorded sensor signals.

As another example, in some embodiments, the statistical model is a classifier taking as input, features derived from the recorded sensor signals. In such embodiments, the classifier may be trained using features extracted from the sensor data. The classifier may be a support vector machine, a Gaussian mixture model, a regression based classifier, a decision tree classifier, a Bayesian classifier, and/or any other suitable classifier, as aspects of the technology described herein are not limited in this respect. Input features to be provided to the classifier may be derived from the sensor data in any suitable way. For example, the sensor data may be analyzed as time series data using wavelet analysis techniques (e.g., continuous wavelet transform, discrete-time wavelet transform, etc.), Fourier-analytic techniques (e.g., short-time Fourier transform, Fourier transform, etc.), and/or any other suitable type of time-frequency analysis technique. As one non-limiting example, the sensor data may be transformed using a wavelet transform and the resulting wavelet coefficients may be provided as inputs to the classifier.

In some embodiments, values for parameters of the statistical model may be estimated from training data. For example, when the statistical model is a neural network, parameters of the neural network (e.g., weights) may be estimated from the training data. In some embodiments, parameters of the statistical model may be estimated using gradient descent, stochastic gradient descent, and/or any other suitable iterative optimization technique. In embodiments where the statistical model is a recurrent neural network (e.g., an LSTM), the statistical model may be trained using stochastic gradient descent and backpropagation through time. The training may employ a cross-entropy loss function and/or any other suitable loss function, as aspects of the technology described herein are not limited in this respect.

System 100 also optionally includes one or more controllers 116. For example, controller 116 may be a display controller configured to display a visual representation (e.g., of a hand) on a display. As discussed in more detail below, one or more computer processors may implement one or more trained statistical models that receive as input sensor signals and provide as output information that is used to generate control signals.

In some embodiments, a computer application configured to simulate a virtual reality environment may be instructed to display a visual character such as an avatar (e.g., via controller 116). Positioning, movement, and/or forces applied by portions of visual character within the virtual reality environment may be displayed based on the output of the trained statistical model(s). The visual representation may be dynamically updated as continuous signals are recorded by the sensors 110 and processed by the trained statistical model(s) 104 to provide a computer-generated representation of the character's movement that is updated in real-time.

Some embodiments are directed to using a statistical model, at least in part, to map spike event information extracted from the neuromuscular signals to control signals. The statistical model may receive as input IMU signals, neuromuscular signals (e.g., EMG, MMG, and/or SMG signals), spike event information (e.g., spike train data) extracted from neuromuscular signals, external device signals (e.g., camera or laser-scanning signals), or a combination of IMU signals, neuromuscular signals, and external device signals detected as a user performs one or more muscular activations. In some embodiments, the statistical model may be used to predict the control information without the user having to make perceptible movements.

System 100 also optionally includes a user interface 118. Feedback determined based on the signals recorded by sensors 110 and processed by processor(s) 112 may be provided via user interface 118 to facilitate a user's understanding of how the system is interpreting the user's intended activation. User interface 118 may be implemented in any suitable way including, but not limited to, an audio interface, a video interface, a tactile interface, and electrical stimulation interface, or any combination of the foregoing. In general, control signals based on a user activating one or more MUAPs may require user training so that the user may effectively and reliably activate the intended one or more MUAPs to create intended control signals. In general, a user cannot detect the activation of a single MUAP, because the amount of force exerted by the muscle is below the detection limit of the proprioceptive system. In some embodiments of the invention, systems and methods provide sensory feedback to a user when they have activated a specified (i.e. desired) MUAP (and a model has detected the presence of the specified MUAP), so that the user may become more skillful at reliably activating that MUAP. For example, feedback may comprise auditory, visual, haptic, or multi-sensory feedback with sufficiently low latency for the user to learn the mapping between the sensory feedback and the preceding MUAP activation.

The architecture of system 100 may take any suitable form. Some embodiments employ a thin architecture in which processor 112 is included as a portion of a device separate from and in communication with the plurality of neuromuscular sensors 110 arranged on the one or more wearable devices. The neuromuscular sensors may be configured to wirelessly stream in substantially real-time, the plurality of neuromuscular signals and/or the information derived from the plurality of neuromuscular signals to processor 112 for processing including, but not limited to, spike event detection and biological source identification. The device separate from and in communication with the plurality of neuromuscular sensors may be, for example, a remote server, a desktop computer, a laptop computer, a smartphone, or a wearable electronic device such as a smartwatch, a health monitoring device, smart glasses, other wearable system (including head mounted wearable systems), or an augmented reality system.

Some embodiments employ a thick architecture in which processor 112 is integrated with the one or more wearable devices on which the neuromuscular sensors 110 are arranged. In yet further embodiments, the processing for spike event detection and/or biological source identification is divided between multiple processors, at least one of which is integrated with sensors 110 and at least one of which is included as a portion of a device separate from and in communication with the sensors 110. In such an implementation, the neuromuscular sensors may be configured to transmit at least some of the recorded neuromuscular signals to a first computer processor remotely located from the sensors. The first computer processor may be programmed to train, based on the transmitted neuromuscular signals, at least one spike detection model and/or at least one spike identification model. The first computer processor may then be programmed to transmit the trained at least one spike detection model and/or the at least one spike identification model to a second computer processor integrated with the one or more wearable devices on which the sensors are arranged. The second computer processor may be programmed to detect spike events and determine the biological source of the detected spike events using the at least one spike detection model and/or the at least one spike identification model transmitted from the first computer processor. In this way, the training/fitting process and the real-time process of using the trained model(s) may be separated by being performed by different processors.

Figure 21B:
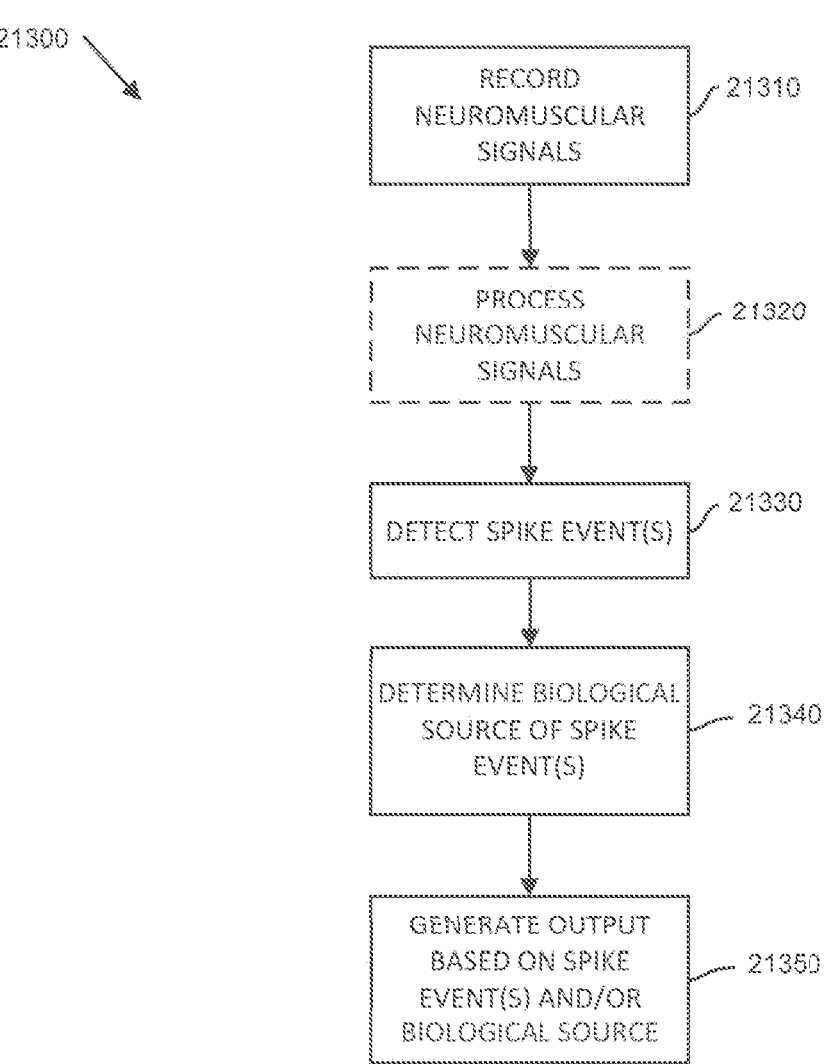
FIG. 21B is a flowchart of a substantially real-time process for detecting spike event information from neuromuscular data in accordance with some embodiments of the technology described herein.

FIG. 21B illustrates a process 21300 for generating an output based on one or more spike events detected in recorded neuromuscular signals in accordance with some embodiments. In act 21310, a plurality of neuromuscular signals are recorded by a plurality of neuromuscular sensors worn by a user as the user activates one or more motor units. Process 21300 then proceeds to act 21320 where the recorded neuromuscular signals are optionally processed prior to detection of spike events. For example, one or more time-lagged versions of the recorded signals may be generated and the time-lagged versions may subsequently be used for detection of spike events. The inventors have recognized that effective time lag values are on the order of the timescale of a motor unit action potential with the particular neuromuscular recording technique employed. For example, the motor unit action potentials measured using surface EMG recordings generally exhibit a time lag in a range of between 10 and 50 ms. In some embodiments, a time lag of 15 to 25 ms may also be effective.

Process 21300 then proceeds to act 21330, where at least one spike event is detected in the recorded neuromuscular signals. For example, in some embodiments, the recorded neuromuscular signals or information derived from the recorded neuromuscular signals (e.g., time-lagged versions of the recorded neuromuscular signals) are processed using one or more filters to detect spike events in the recorded neuromuscular signals. In some embodiments, the one or more filters includes a plurality of filters, each of which is configured to detect spikes generated from a particular biological source (e.g., from a particular motor unit). Example techniques for generating filters for use with some embodiments are described in more detail below.

Process 21300 then proceeds to act 21340, where biological source of the detected spike event(s) is determined. In embodiments that use a plurality of filters, each of which is configured to detect spike events generated by a particular biological source, the biological source determination in act 21340 may be based on the output of the plurality of filters and their associated biological sources for which they are configured to detect spike events. In other embodiments, the detection of one or more spike events in act 21330 and the determination of a biological source of the spike event(s) in act 21340 may be performed sequentially. Any suitable biological source for spike events may be determined in act 21340. For example, the biological source may be a single motor unit, a group of motor units, a muscle, or a group of muscles. In some embodiments, the ability of the system to determine a particular biological source for spike events may be based, at least in part, on a spatiotemporal resolution of the system in distinguishing between different spike events. For example, in some instances the system may not be able to determine which of a plurality of motor units a spike originated from, but the system may be able to determine a group of motor units from which the spike originated. In other instances, the system may not be able to determine within a muscle which of the motor units a spike originated from, but the system may be able to determine which muscle the spike originated from, and so on.

Process 21300 then proceeds to act 21350, where one or more outputs are generated based on the detected spike event(s) and/or the biological source of the spike event(s). Any suitable output may be generated for a particular application, and embodiments are not limited in this respect. In some embodiments, the output may be compressed data representing the recorded neuromuscular signals. For example, rather than storing "raw" neuromuscular signals, the system may be configured to store only information about the detected spike events such as their timing characteristics and/or their biological source information. Storing such compressed data may be beneficial, for example, for transmission of the data (e.g., over one or more wireless networks) to an external device and/or for logging data for health/fitness/ergonomics monitoring applications without having to store the raw recorded data.

In some embodiments, the output generated in act 21350 is information used to update a musculoskeletal model. As described briefly above, some embodiments employ a musculoskeletal model that is updated with musculoskeletal position information describing, for example, positions and/or forces of rigid body segments in the model. Spike event information determined in acts 21330 and/or 21340 may be provided as input to the musculoskeletal model as part of the updating process. Control signals may then be generated based on the updated musculoskeletal model.

In some embodiments, the output generated in act 21350 is a control signal used to control an external device. Rather than mapping recorded neuromuscular signals directly to control signals using, for example, a trained statistical model, some embodiments map spike event information (e.g., detected spike events and/or biological source information for the spike events) to control signals. In such an implementation, one or more control signals may be generated based on the identified biological source(s) and a pattern of activation represented in the detected spike event information. For example, the spike event information may be provided as input to a trained statistical model and an output of the trained statistical model may be used to generate the one or more control signals. In one implementation, the output of the trained statistical model may be a set of one or more control signals. In another implementation, the control signal(s) may be generated based on the spike event information without the use of a trained statistical model. The generated control signal(s) may then be provided to a control interface of a device to control an operation of the device. For example, the device may be a display and a control signal may be provided to a display controller of the display. The control signal may include instructions to update information displayed on the display. Alternatively the device may be a computer or other computing device (e.g., a smartphone) and the control signal may be provided to a controller of the computing device to change an operation of the device. In yet a further example, the control signal may be used to control a device (e.g., a musical instrument) to provide an artistic expression. It should be appreciated that any device having a control interface may be controlled using control systems designed in accordance with the techniques described herein.

In some embodiments, the one or more control signals are generated based, at least in part, on the spike event information in substantially real-time. As used herein the term "substantially real-time" means that the spike event information determination process occurs and/or the control signals are generated shortly after the electrical event occurs while the neuromuscular data is being recorded, rather than happening off-line at a time when the neuromuscular signals are not being recorded. In some embodiments, spike event information is detected within 5 seconds, within 1 second, within 500 ms, within 100 ms, or within 50 ms of the occurrence of the electrical event.

The spike event information used to generate output in act 21350 may include information about the spatiotemporal pattern of detected spike events (e.g., spike rate, spatial distribution of spike events, biological source of spike events). In some embodiments, one or more control signals may be generated based, at least in part, on at least one characteristic of the spatiotemporal pattern of the detected spike events. For example, the one or more control signals may be generated based, at least in part, on a spike rate and/or a spatial distribution of spike events detected from the neuromuscular signals.

In general, control signals based on MUAPs from one or more motor units may be used as one or more discrete controls (i.e. a button or set of buttons that, when activated cause a computing device to change an operation), one or more continuous controls (i.e. a one-dimensional controller such as to control the volume of a speaker or the temperature of a thermostat, a two-dimensional controller such as to navigate a cursor on a two-dimensional screen, or a higher-dimensional controller such as to control a robotic arm with three or more degrees of freedom). In some embodiments, control signals based on MUAPs may comprise composite controls based on a particular sequence of activation of one or more MUAPs in order to achieve a greater number of discrete controls (i.e. degrees of freedom (DOF)) than the number of MUAPs identified. In an alternative or complementary embodiment for achieving a greater number of discrete controls (i.e. DOFs), a user may simultaneously (or near-simultaneously, within a defined period of time) activate two or more MUAPs that achieve unique discrete controls than the unitary activation of a MUAP. One skilled in the art will recognize that continuous controls as described above are generally not truly continuous and represent quantized control across a range of values.

Figure 21C:
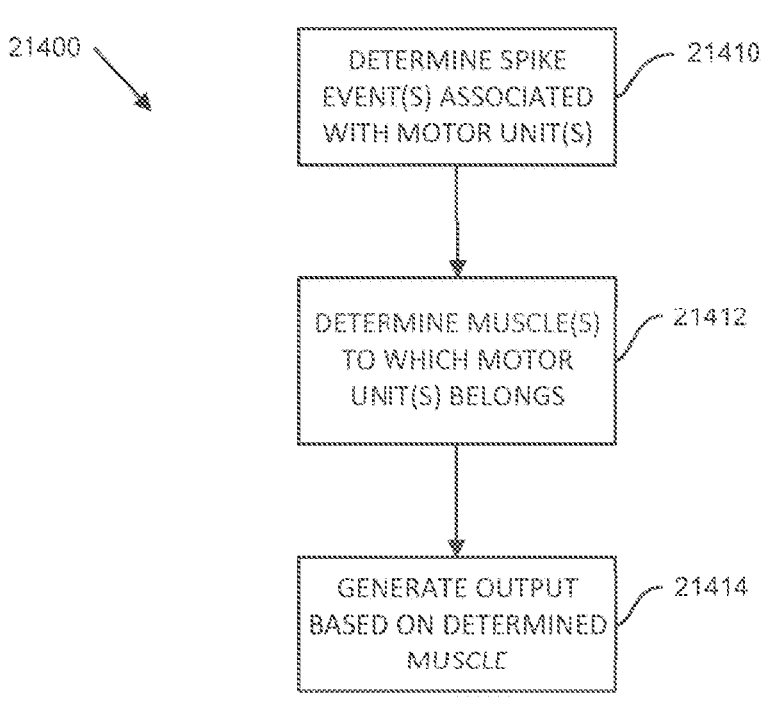
FIG. 21C is a flowchart of a process for associating spike events with muscles in accordance with some embodiments of the technology described herein.

In some embodiments, the motor unit(s) from which a detected spike event(s) originated from may be mapped to one or more muscles. FIG. 21C illustrates a process 21400 for performing muscle classification in accordance with some embodiments. In act 21410, spike event information is determined, for example, in accordance with at least a portion of process 21300 described above. Process 21400 then proceeds to act 21410, where one or more muscles to which the identified motor unit belongs is determined. The muscle(s) may be determined in any suitable way. For example, similarities between spatial profiles and correlations in spiking activity arising from multiple motor units may indicate that the multiple motor units belong to the same muscle. Alternatively, the muscular (or sub-muscular) source may be inferred based on the spatial pattern of signals recorded on a plurality of neuromuscular sensors on the skin of a user (or, optionally, implanted in a user). Process 21400 then proceeds to act 21414, where output is generated based, at least in part, on the determined muscle associated with the spike event information. In some embodiments, the identification of a particular muscle relating to detected spike events may be used to further describe information about the spike events relative to the identified muscle. For example, as described above, each muscle in the human body may be characterized by a particular pattern of motor unit recruitment that describes an order by which additional motor units are recruited when needed. In some embodiments, the information about a motor unit recruitment pattern of a muscle may be used, at least in part, to determine where the motor unit or group of motor units falls within the motor unit recruitment pattern for the determined muscle.

Figure 21D:
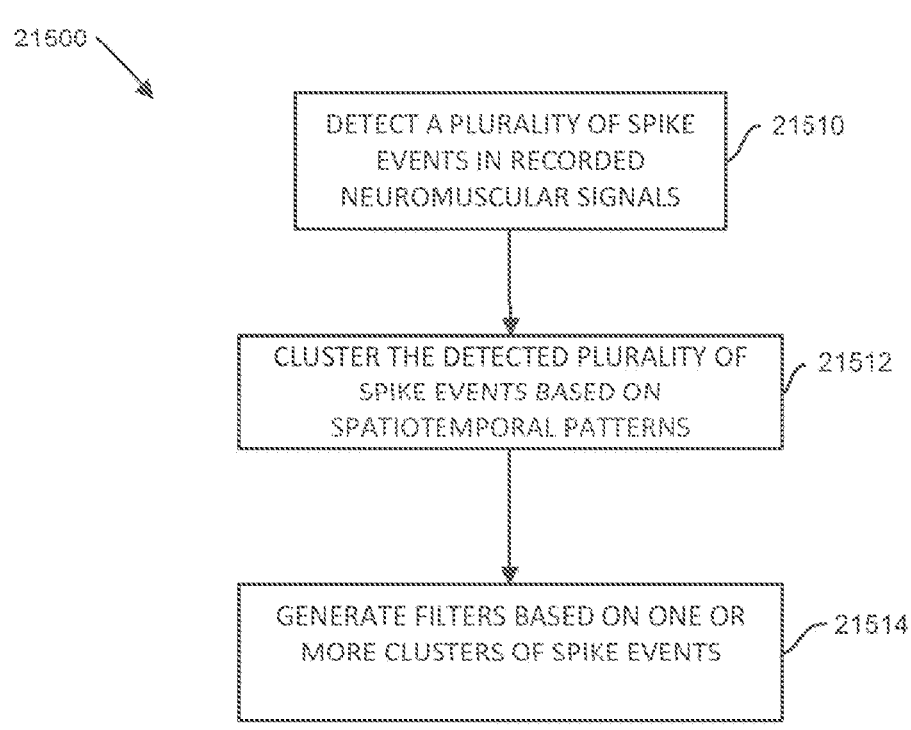
FIG. 21D is a flowchart of a process for generating filters for use with a substantially real-time spike event decoder in accordance with some embodiments of the technology described herein.
Figure 21E:
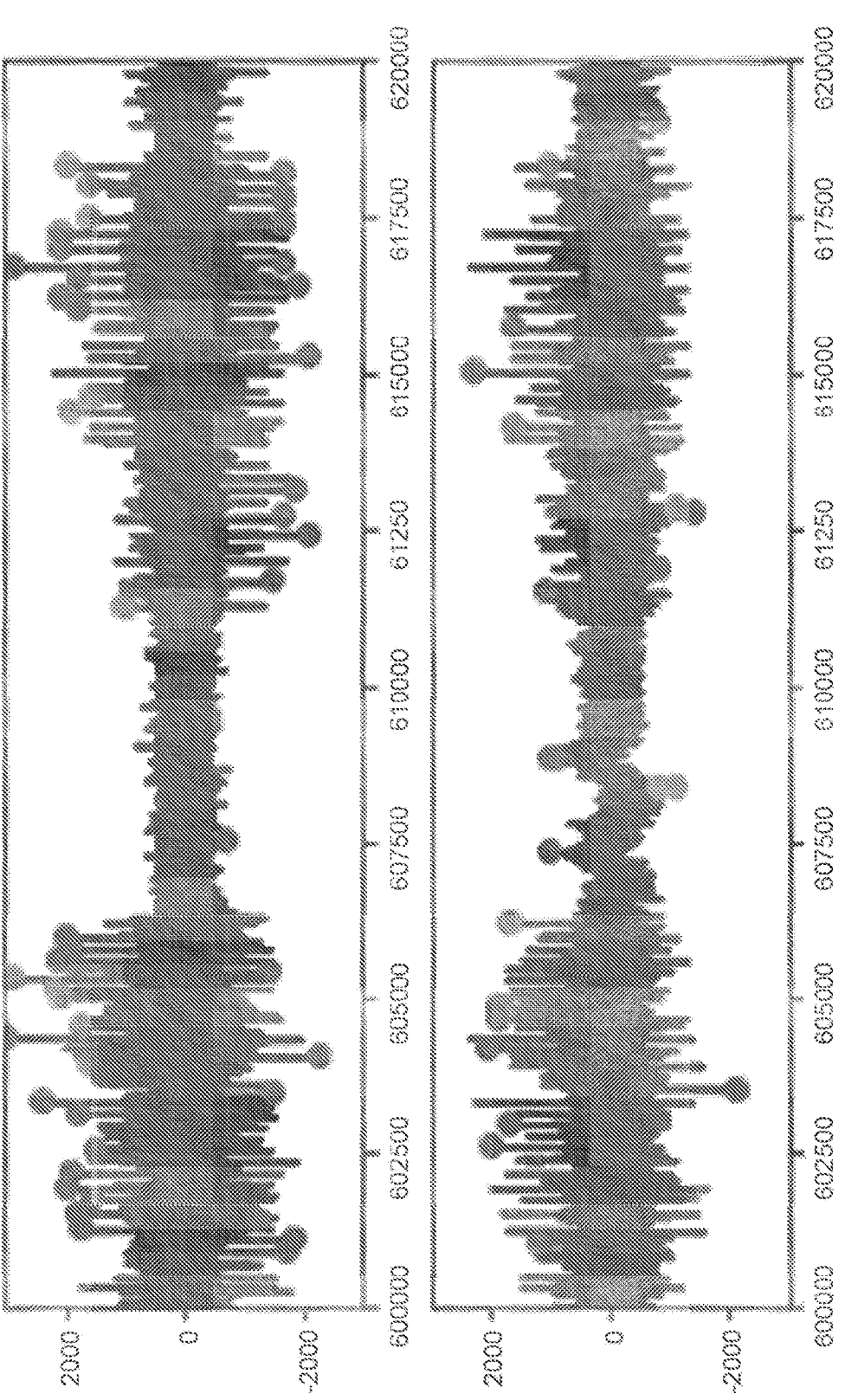
FIG. 21E illustrates a plot for detecting spike events in two channels of recorded neuromuscular data during periods of low activity, in accordance with some embodiments of the technology described herein.

Some embodiments are directed to a process for generating one or more filters used to decode spike events from recorded neuromuscular signals. FIG. 21D illustrates a process 21500 for generating a plurality of filters, each of which represents spike activity within a biological source (e.g., a motor unit). The plurality of filters, once generated, may be used to process neuromuscular signals and provide outputs in substantially real-time as the neuromuscular signals are recorded. Additionally, in some embodiments, as additional neuromuscular data is recorded, filter parameters may be updated such that the filters are dynamically updated. In act 21510, a plurality of spike events are detected in recorded neuromuscular signals. For example, neuromuscular signals may be recorded during periods of relatively low activity, and then spike events may be detected using thresholding of the recorded data. FIG. 21E shows an example of the detection of putative spike events in two EMG sensor channels during periods of low activity. The putative spike events detected in the EMG recordings may be analyzed to eliminate false positives. For example, putative spike events having one or more particular characteristics (e.g., a duration longer than a threshold duration) may be discarded.

Figure 21F:
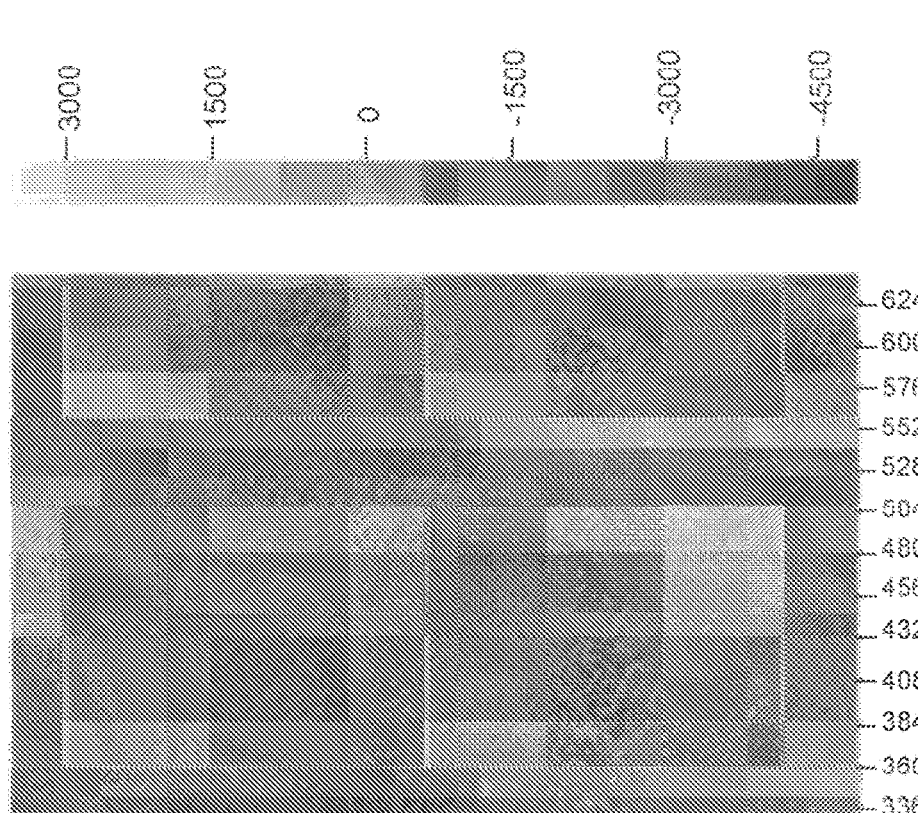
FIG. 21F is a color figure illustrating a plot of clustering spike events to identify spike events with similar spatiotemporal profiles, in accordance with some embodiments of the technology described herein.

After the plurality of spike events have been detected, process 21500 proceeds to act 21512, where the detected spike events are clustered, based on their spatiotemporal characteristics, to identify spike events likely arising from the same biological source. Clustering of spike events may occur in any suitable way. In one simplistic example of clustering, a window (e.g., a 10 ms window) around each of the peaks of the spike events may be used to define the temporal bounds of the event. Each spike event may then be defined as a vector of values, where each vector includes N×M samples, where N corresponds to the number of samples in the window for the event, and M corresponds to the number of neuromuscular sensors. For example, if the sampling rate of the neuromuscular data is 4 kHz, and the window for each spike event is 10 ms, N=40. Assuming an array of 15 neuromuscular sensors, the number of values in each spike event vector would be 40*15=600 values. After defining vectors for all of the detected spike events, a similarity metric may be used to identify vectors having values that cluster together, and thus are likely to represent spike events generated from a common biological source. For example, Principal Component Analysis (PCA) or some other suitable technique may be used to reduce the dimensionality of each of the spike event vectors, and k-means clustering or another suitable clustering technique may be used to cluster the lower-dimensional vectors into clusters of spike waveforms that have similar spatiotemporal characteristics. Other non-limiting examples of dimensionality reduction techniques include t-Distributed Stochastic Neighbor Embedding, deep auto-encoders, and Uniform Manifold Approximation and Projection (UMAP). Other non-limiting examples of clustering methods include agglomerative clustering, Density-Based Spatial Clustering of Applications with Noise (DBSCAN), Hierarchical Density-Based Spatial Clustering of Applications with Noise (HDBSCAN). In another example, the vectors for each of the spike events are used to create an affinity matrix of the different spike events and a measure of similarity of the vectors, for example, using correlations, may be used to identify the clusters of spike waveforms having similar spatiotemporal characteristics. FIG. 21F illustrates the results of a clustering process in which clusters of spike waveforms having similar spatiotemporal characteristics have been identified.

Figure 21G:
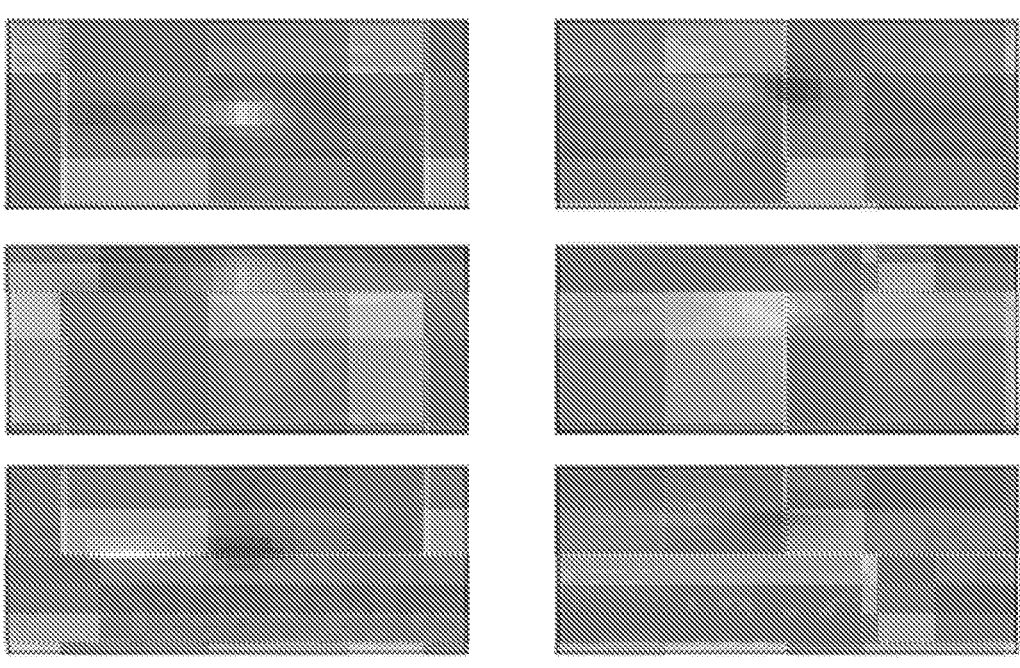
FIG. 21G is a color figure illustrating six spatiotemporal profiles generated for each of six clusters of spike events, in accordance with some embodiments of the technology described herein.

Each of the clusters of spike event data includes a plurality of spike events that represent a distribution of spike events generated by a particular biological source (e.g., a motor unit). The process then proceeds to act 21514, where a plurality of filters are generated based on the spike events within each of the clusters, resulting in a set of filters, each of which is configured to detect spike events for its associated biological source (i.e., MUAP spike event). Act 21512 serves to produce labeled spike event data from the unlabeled data detected in act 21510. The labeled spike event data from act 21512 may then be used, at least in part, to generate filters in act 21514. In some embodiments, the spatiotemporal response function for each cluster may be determined by, for example, calculating the mean of each of the spike event vectors in the cluster. FIG. 21G illustrates example spatiotemporal profiles calculated for six clusters using this technique. The spatiotemporal profiles may then be used to generate the filters in act 21514. For example, some embodiments use a beamforming formulation to determine filters for automatic spike decoding. An example of a beamforming formulation that may be used to generate filters in accordance with some embodiments is the minimum variance distortionless response (MVDR) filter, described in more detail below. In some embodiments, multiple filters may be used to disambiguate multiple motor units that are present in one cluster, such as motor units that are located near each other anatomically. For instance, multiple MVDR filters may be combined to disambiguate multiple motor units that are present in one MVDR cluster.

Instead of using filters to perform automatic spike event detection from neuromuscular data, some embodiments employ neural networks to detect spike event data, and the labeled data output from act 21512 in process 21500 may be used to train the neural network. Any suitable neural network architecture may be used including, but not limited to, convolutional neural networks and recurrent neural networks. When recurrent neural networks are used, a convolutional layer may be used as the first layer of the network.

Beamforming methods use e filters to determine source signals from multidimensional sensor signals. Beamforming methods commonly use purely spatial filters. However, the inventors have recognized that spatial filtering alone is not suitable for detecting spike events in neuromuscular signals due to the large number of similarly localized sources relative to the small number of sensor channels. Accordingly, some embodiments use a time-lagged representation of the recorded neuromuscular signals to increase their effective dimensionality and exploit the consistent spatiotemporal response function for each source. Any suitable beamforming technique may be used, examples of which include, but are not limited to MVDR, described in more detail below, and linear constrained minimum variance (LCMV), according to which the filters weights are, where L is the matrix of spatiotemporal response profiles (i.e. the collection of all h vectors in the MVDR notation below) and C is the sensor signal covariance matrix (equivalent to in the MVDR notation below). The outputs of the filtered signals may then be thresholded to determine whether a spike event occurs. Each filter corresponds to a biological source (e.g., an individual motor unit), so spike detection and identification of the spike's biological source occur as a single process.

Some embodiments are directed to using a plurality of MVDR filters to perform real-time spike detection in neuromuscular signals. Similar to matched filtering, the use of MVDR filters maintains a target signal as much as possible, but also minimizes the noise of any other signals that are present in the recorded neuromuscular signals. Assuming S sources, each of which has a stereotyped signal profile or template across channels and time, let xs(t) be a binary variable indicating whether source s is triggered at time t. xs(t) will have a value of 1 for only a single time step at a time, not for the duration of the emission. Let $hsc(\tau)$ be the profile of the stereotyped profile of source s as measured in channel c at time $\tau$. Then the measured signal will be $y_c(t)=(\Sigma h_{sc}(t)*x_s(t)+n_c(t)=\Sigma_s\Sigma_\tau h_x(t-\tau)x_s(t)+n_c(t))$, where * is the convolution operator and nc(t) is additional noise on channel c at time t. In order to make the derivation more mathematically straightforward, y, x, and h may be unwrapped into time-lagged vectors for each time-step. The template, instead of being a 2D matrix of size C×T for C channels and T timesteps, is unwrapped into a CT×1 vector, which is equivalent to concatenating successive time frames of the template on top of each other. The stacked template is then $h_s=[h_{s}(0), h_{s1}(1), h_{s2}(0), \ldots, h_{sc-1}(0), h_{s0}(1), \ldots, h_{sc-1}(t-1)]^T$. The stacked observation is $y(t)=[y_0(t), y_1(t), y_2(t), \ldots, y_{c-1}(t), y_0(t+1), \ldots, y_{c-1}(t+T-1)]^T$ and the stacked noise is $n(t)=[n_0(t), n_1(t), n_2(t), \ldots, n_{c-1}(t), n_0(t+1), \ldots, n_{c-1}(t+T-1)]^T$. Then the model can be rewritten as $y(t)=\Sigma_s h_s x_s(t)+n(t)$. Assuming a single source of interest, then $y(t)=hx(t)+n(t)$. To find a filter, w that can be applied to y (t) recover x(t), the estimate of which may be provided as $x(t)=w^T y(t)=w^T(hx(t)+n(t))$. The MVDR filter is the filter w that satisfies the following optimization $w=min_w E[x^2]$, such that $w^T h=1$. Manipulating the term $E[x^2]$ yields $E[x^2]=E[(w^T y(t))^2]=E[(w^T y(t)y^T(t)w)]=w^T E[y(t)y^T(t)]w=w^T\varphi_{yy}w$, where $\varphi_{yy}$ is the correlation matrix for all of the entries of y. Thus, the optimization becomes $w=min_w w^T\varphi_{yy}w$, such that $w^T h=1$. This problem has a closed-form solution, which is $w=(\varphi_{yy}^{-1}h)/(h^T\varphi_{yy}^{-1h})$. To compute this filter, an estimate of the template h and the covariance of the observation $\varphi_{yy}$ is required. In some embodiments, $\varphi_{yy}$ is computed as the sample covariance matrix from the observation. The estimated signal is then $x(t)=w^T(hx(t)+n(t))=(hx(t)+n(t)) (h^T\varphi_{yy}^{-1})/(h^T\varphi_{yy}^{-1h})=x(t)(h^T\varphi_{yy}^{-1}n(t))/(h^T\varphi_{yy}^{-1}h)$.

Figure 21H:
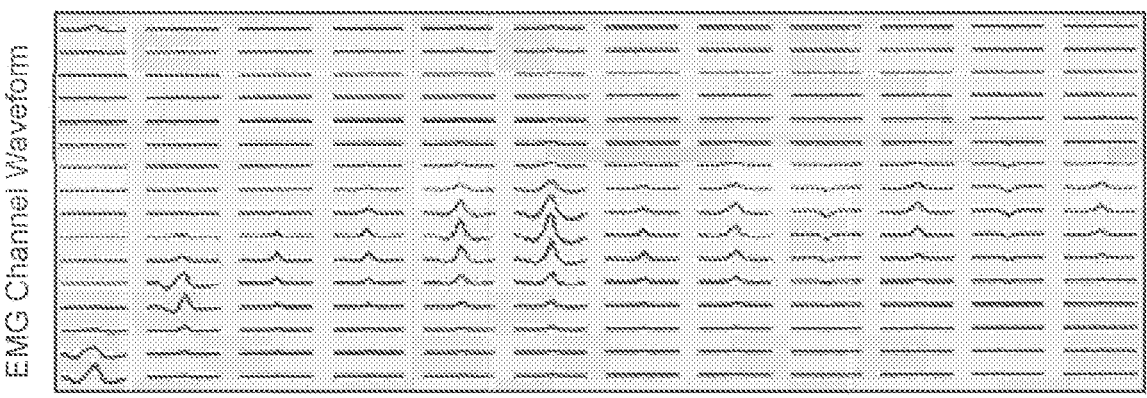
FIG. 21H illustrates a set of EMG channel waveforms associated with a number of biological sources, that may be produced in accordance with some embodiments of the technology described herein.

FIG. 21H illustrates a set of EMG channel waveforms associated with a number of biological sources, that may be produced in accordance with some embodiments of the technology described herein. As shown, each column reflects a spatiotemporal waveform as detected from one biological source (i.e., one motor unit) and each row is (average/template) waveform produced from one EMG channel.

Figure 21I:
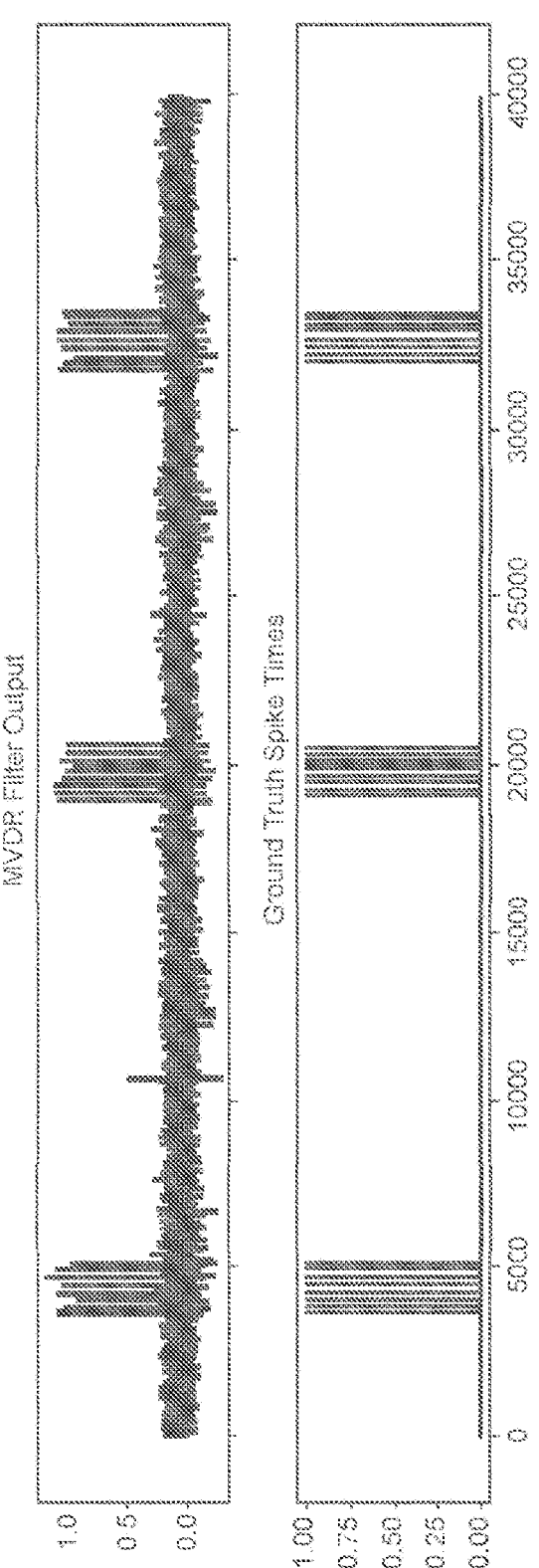
FIG. 21I shows output of an MVDR-based spike event decoder configured in accordance with some embodiments of the technology described herein.
Figure 21J:
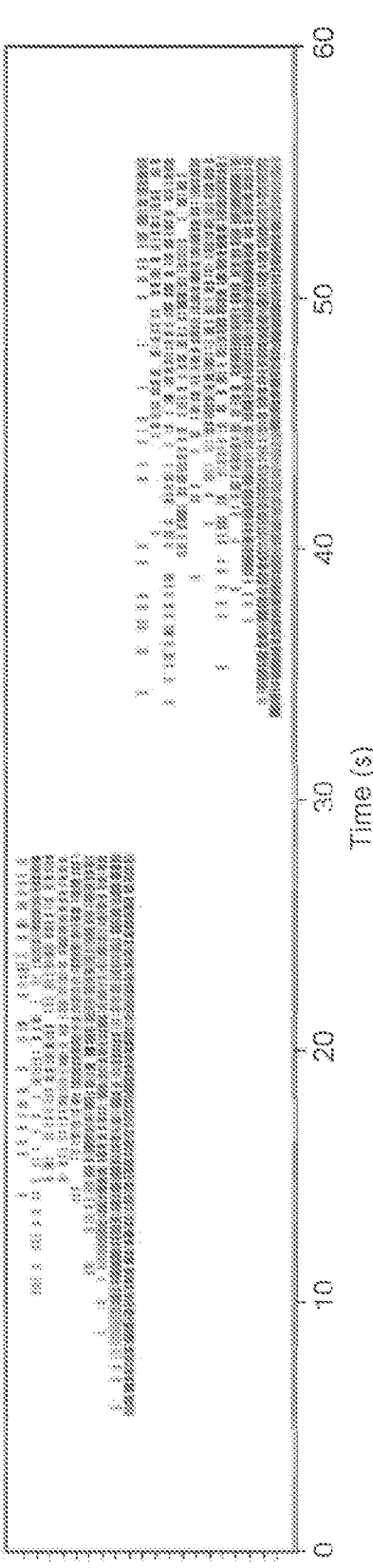
FIG. 21J shows output of an MVDR-based spike event decoder including MVDR filters for each of a plurality of motor units, wherein the decoder is configured in accordance with some embodiments of the technology described herein.
Figure 21K:
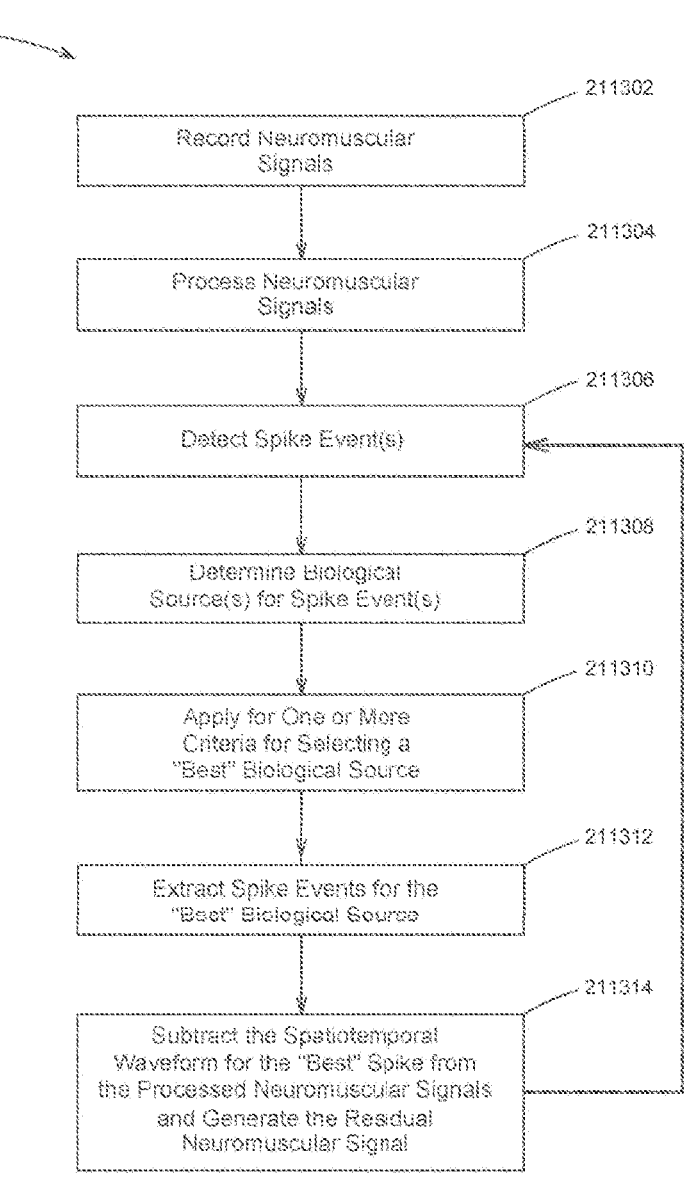
FIG. 21K is a flowchart of a substantially real-time process for detecting spike event information from neuromuscular data in accordance with some embodiments of the technology described herein.

FIG. 21I illustrates an exemplary output of an automatic spike detector using an MVDR filter to process streaming recorded neuromuscular data. As shown, the MVDR filter output is similar to the ground truth spike times indicating that the accuracy of the automatic spike detection is high. When a plurality of MVDR filters are used, each of which corresponds to an individual motor unit, spike event information for each motor unit may be determined, as shown in FIG. 21K.

For beamforming techniques such as MVDR, training/ fitting the model comprises determining the spatiotemporal response functions. The spatiotemporal patterns for each biological source (e.g., each motor unit) may be determined by first performing spike sorting on an initial set of collected data. To generate the filters, approaches that work in real-time on streaming data and approaches that do not work in real-time (e.g., iterative techniques) may be used. For example, in some embodiments, the spatiotemporal response functions for biological sources are determined using matrix factorization technique. For example, Negro et al. Journal of Neural Engineering (2016) uses a multi-step iterative algorithm to decompose the time-lagged sensor signals into components corresponding to each source and detecting the spike events from each source. An advantage of matrix factorization is that it does not require training or parameter fitting, as it acts over the data to effectively accomplish this, e.g., by its iterative nature. More generally, the spatiotemporal response functions can be obtained by any spike decomposition or spike sorting method, of which non-limiting examples include those used by commercially-available spike sorting software packages KiloSort, Moun-tainSort, and combinations of the techniques used therein. In some non-limiting embodiments, estimates of the spatio-temporal response functions are updated, for example by repeating these estimation procedures with additional accu-mulated data or performing reverse correlation based on the timings of detected spikes during real-time operation of the detectors.

In some embodiments, spike events may be detected in the neuromuscular data. For example, raw neuromuscular data may be thresholded. Alternatively, the recorded neuro-muscular data may be whitened or filtered, for example, with wavelets. The detected spike events may then be clustered to identify similar spike events. The spike events in the cluster may then be used to determine the spatiotemporal patterns for each biological source (e.g. by taking the cluster means) for the beamforming filters. Thresholds on the filter outputs may be set by applying the beamforming filters to the data from which the clusters were determined, and determining which threshold results in an appropriate balance between false negatives (failing to identify a member of the cluster) and false positives (e.g. identifying an event from another cluster).

In some embodiments, the clusters are accepted, rejected, or ranked based on quality criteria. Non-limiting examples of quality criteria can reflect intra- and inter-cluster dis-tances, amplitudes of spatiotemporal response functions, biological plausibility of spatiotemporal response functions, and biological plausibility of spike times for events within the cluster (e.g. do multiple events occur within a motor neuron's refractory period). In some embodiments, the event detection and clustering technique described above is repeated multiple times in an iterative manner. For example, after the clusters are identified, the best cluster (e.g., the cluster with the largest amplitude events or the most tightly clustered cluster) is selected and beamforming is used on recorded neuromuscular data to detect spike events corre-sponding to that cluster, e.g., for a first biological source. The detected spike events are convolved with the spatiotem-poral pattern and the result is subtracted from the recorded neuromuscular signals to be used on further iterations for event detection and clustering, essentially eliminating the contribution of the first biological source to the neuromus-cular signals. A stopping criterion, e.g., when there are no more clusters that pass a quality criterion or when the residual signal has variance comparable to that of the noise (which can be estimated from a period of minimal neuro-muscular activity), may be used to determine when to stop the iteration.

For embodiments that employ neural networks rather than beamforming techniques, there is typically no closed-form solution for the optimal weights in the network. Neural networks that employ supervised learning also require train-ing data with accurate ground-truth labels. Therefore, it can be helpful to generate synthetic training data for training the neural network. Synthetic data may be generated by simu-lating neuromuscular data having spike times with a random point process (e.g. Poisson process, renewal process), con-volving the spike events with spatiotemporal profiles of the spikes. The spatiotemporal profiles can be the cluster cen-ters, samples from within the cluster, interpolations between samples within the clusters, or samples from a model fit from the cluster), and then adding noise. The noise can include Gaussian noise and also spatiotemporal profiles from other motor units (e.g., synthetically generated from a mathematical model, obtained from data from other users, or semisynthetic, e.g., scaled or otherwise transformed profile obtained from another user).

For neural networks, the first convolutional layer of the networks can be initialized with the linear filters determined from beamforming methods, and connections to the output layer may be skipped so that the rest of the network can act as a correction to the beamforming estimates.

In some embodiments, the filters are saved and re-used across user sessions. Due to changes in sensor placement, reusing the filters may require calibration or registration of the signals across sessions.

The inventors have recognized that any of the spike identification systems and methods described herein may optionally comprise a "spike peeling" workflow for itera-tively identifying and extracting spikes from distinct bio-logical sources (i.e. motor units). Spike peeling comprises identifying one spike action potential (i.e. one biological source, generally a motor unit) at a time and extracting the spatiotemporal pattern of that biological source from the recording, potentially revealing more spikes in the residual. The purpose of this technique is to be able to extract spikes from a recording in an unsupervised and potentially online manner. In some embodiments, spike peeling may be used to generate a session-specific "spike bank" to extract as many spikes as possible from a recording.

FIG. 21K is a flow chart showing a substantially real-time process for detecting spike event information from neuro-muscular data in accordance with some embodiments of the technology described herein. In particular, FIG. 21L shows an example process 211300 for spike peeling according to some embodiments. Such a process may be performed, for example, using various system or computer-based elements as described herein. At block 211302, neuromuscular signals are recorded from a user. Next, the neuromuscular signals are processed at block 211304 and one or more spike events are detected at block 211306 (such as, for example, using beamforming techniques as described herein). At block 211308, the system determines the best biological source(s) for one or more spike event(s) that are detected. A first biological source is selected at block 211310 by applying criteria to determine a "best" biological source (i.e. motor unit) to extract, and the spike events (spike times) are extracted (i.e. saved for use as a control signal or other use) at block 211312. After the spike events for the best biological source are extracted, the spatiotemporal waveform for that biological source (e.g. a spatiotemporal template for that biological source) is subtracted from the processed neuromuscular signals to generate a residual neuromuscular signal at block 211314. Next, spike event(s) are detected from the residual processed neuromuscular signals again and workflow 211306 through 211314 repeats one or more times until no biological source is present in the signal that meets a minimum threshold for selection as a biological source of spike events.

One benefit of spike peeling is that it may be possible to group spikes into "muscles" based on their co-activations and sort spikes within muscles to approximate a recruitment curve.

One effective workflow for spike peeling selects the "best" spike to extract next based on the product of its highest amplitude and the log of the number of spikes assigned to it in the clustering process. The inventors have recognized that using just the highest amplitude as a criterion for selecting the next spike for extraction tends to pick up artifacts that are localized in a single sample in a single electrode, whereas using a criterion based only on the number of detected spikes tends to pick up common low-amplitude patterns that are not spike-like (i.e. not physiologically plausible). The combination of spike amplitude and number of detected spikes is most effective, in at least some instances, to identify spatiotemporal patterns that exhibit physiological characteristics.

The following describes exemplary camera-guided interpretation of neuromuscular signals according to at least one embodiment of the present disclosure.

Some embodiments are directed to coupling a system that senses neuromuscular signals via neuromuscular sensors with a system that performs extended reality (XR) functions. As will be appreciated, XR functions may include augmented reality (AR) functions, virtual reality (VR) functions, mixed reality (MR) functions, and the like. In particular, a system that senses neuromuscular signals for the purpose of determining a position of a body part (e.g., a hand, an arm, etc.) may be used in conjunction with an XR system to provide an improved XR experience for a user. For instance, information gained within both systems may be used to improve the overall XR experience. In embodiments where a musculoskeletal representation associated with the body part is generated based on sensor data, a camera in an XR system may capture data that is used to improve the accuracy of a model of the musculoskeletal representation and/or may be used to calibrate the model. Further, in another implementation, sensor data may provide muscle activation information, which may be visualized and displayed to a user in an XR environment. In yet another implementation, display information in the XR environment may be used as feedback to the user to permit the user to more accurately control his/her musculoskeletal input (e.g., movement input) to the system. Further, control features may be provided that permit neuromuscular signals to control XR system elements, including operation of the XR system itself.

The inventors recognize that neither cameras nor neuromuscular sensors are by themselves ideal input systems. Cameras such as those provided by an XR system may provide good positional information (relative both to other skeletal segments and to external objects) when joint segments are clearly within view, but may be limited by field of view restrictions and occlusion, and may be ill-suited for measuring forces. At the same time, measurements of signals by neuromuscular sensors (e.g., electromyography (EMG) signals or another modality of neuromuscular signal as described herein) may, on their own, be insufficient for distinguishing between forces that a user is applying against himself/herself versus forces that he/she applies to an external object, and such signals may not provide sufficiently accurate information about skeletal geometry, for example finger lengths. According to some embodiments, it is appreciated that it would be beneficial to increase the accuracy of XR systems and neuromuscular-sensor-based systems to provide more accurate and more realistic user experiences.

As will be appreciated, an inference model may involve a generalized skeletal geometry for a type of user (e.g., a typical adult male, a typical child, a typical adult female) or may involve a user-specific skeletal geometry for a particular user (e.g., Jane Miller, Henry Smith).

According to some embodiments, a system is configured to use camera information to improve interpretation of neuromuscular signals and their relationship to movement and force generation. For example, inside-out cameras and/or other camera systems associated with XR systems may be used in association with neuromuscular signals to more accurately represent the position of segments of a user's body, movement of a user's body, and/or representations of force exerted by segments of a user's body. For example, camera information, such as images, video, time series of images, etc., may be used to calibrate neuromuscular systems by providing ground truth labels for data from neuromuscular signals. In one implementation, a system may perform a calibration operation using prompts (e.g., hand gestures, verbal information provided visually or audibly (e.g., words (e.g., "fist") or phrases (e.g., "make a thumbs up gesture")) provided to a user through an XR display or other screen (which may include a smartphone, smartwatch, tablet computer, laptop, desktop computer, AR display, VR display, etc.), where the user is asked to match his/her hand posture to that of a projected hand on the XR display, with the camera optionally assisting with detection of when a match occurs. Further, other types of camera data may be used to calibrate a neuromuscular system, such as calibrating a geometric model of skeletal geometry using camera data. For instance, finger lengths of a geometric model may be verified and/or corrected using camera data. In another example, camera information may be used to determine that two or more parts of a user's body are touching (e.g. the tips of the thumb and index finger touching in a 'pinch' pose). In such a case, images may be processed to automatically identify one or more parts of a user's body (i.e. hand, fingers, and/or wrist) and determine the relative position of the parts of a user's body. For example, the processed camera information may be translated to quaternions or another mathematical framework for representing the segments and joints of a part of a user's body.

In some embodiments, neuromuscular signals, camera data, or both may be used to provide a real-time determination of musculoskeletal representations or gestures. For instance, as neuromuscular (e.g., EMG) and IMU information may be used to determine a more accurate musculoskeletal representation, other data such as camera data may be used to create an even more accurate and consistent representation. Further, it is appreciated that multiple signals can be used, including, but not limited to, signals from one or more cameras, neuromuscular signals from one or more devices, among other types of sensor data, to determine real-time musculoskeletal representations. Other data, such as IMU data and/or camera data, may be used to train and improve an inference model for musculoskeletal representation as well as improve the real-time representation of skeletal position. As will be appreciated, an inference model may be a model that utilizes statistical inference based on a probability distribution to deduce a result; in this regard, an inference model may comprise a statistical model.

As used herein, the term "gestures" refers to a static or dynamic configuration of one or more body parts including the position of the one or more body parts and forces associated with the configuration. For example, gestures include discrete gestures, such as placing or pressing the palm of a hand down on a solid surface or grasping a ball, continuous gestures, such as waving a finger back and forth, grasping and throwing a ball, or a combination of discrete and continuous gestures. Gestures may include covert gestures that are imperceptible to another person, such as slightly tensing a joint by co-contracting opposing muscles or using sub-muscular activations. Gestures may be defined by an application configured to prompt a user to perform the gestures or, alternatively, gestures may be arbitrarily defined by a user. The gestures performed by the user may include symbolic gestures (e.g., gestures mapped to other gestures, interactions, or commands, for example, based on a gesture vocabulary that specifies the mapping). In some cases, hand and arm gestures may be symbolic and used to communicate according to cultural standards.

In some embodiments, a system may combine neuromuscular signals and camera data (e.g., camera signals or image signals from a camera) to infer or reconstruct the position of segments (i.e., skeletal segments) of the user's body. The system may be adapted to adjust a level of influence given to each signal based on the quality of that signal. In the case of a camera signal (e.g., an image signal from a camera), there may be field of view or occlusion restrictions that cause the signal to be unreliable or inaccurate. In the case of neuromuscular signals such as a signal from an EMG sensor, there may be EMG artifacts produced that cause the EMG signal to be unreliable (or other artifacts present in neuromuscular signals derived from an alternative modality of neuromuscular signal, as described below). In such cases, the system may be configured to assess a quality level of each of the signals to determine whether either or both should be used (e.g., to determine a handstate or gesture). The system may also use weighting or another combining method to adjust the degree to which a signal is used between the different types of signal sources (e.g., the different sensor types). Also, when confidence in a particular signal source is high, the signal from that source may be used to train and/or correct another source or model. For instance, a quality of the neuromuscular signals may be assessed in cases where the hand is in clear view of the camera, and a retraining of the handstate model may be performed.

In some embodiments, a system may include a first inference model for generating a musculoskeletal representation based on neuromuscular signals and a second model for generating a musculoskeletal representation based on camera input (i.e., input obtained from a camera). The system may be configured to transition between the use of the first inference model and the use of the second inference model for representing a user's handstate based, at least in part, on information associated with the camera input, such as whether all or a portion of the user's hand is within the camera's field of view. For example, when the user's hand (or another portion of the user's body) is within the camera's field of view, the second inference model may be used to determine the position of the segments of the user's hand, whereas when the user's hand is completely or partially outside the camera's field of view (including cases wherein the user's body is completely or partially occluded), the first inference model may be used to determine the position of the segments of the user's hand representing the handstate. As an alternative implementation, a single inference model that receives both neuromuscular signals and camera input may be used, and the contribution of the inputs may be weighted, as described above. In instances in which the user's hand is out of the field of view of the camera, the camera-input weight may be set to zero or some other small value to reflect the unreliability of the camera input for estimating position information when the user's hand is out of the camera's field of view.

In some embodiments, data from one or more cameras may be used to determine the position of an arm, a hand, a forearm, or another part of the user's body. Also, camera data may be used to combat drift in an IMU-based estimate of forearm position, with the IMU information being used to measure forearm orientation and the neuromuscular signals being used to determine hand and wrist configuration and forces. In this embodiment, positional tracking reference marks on a band of neuromuscular sensors (e.g., a band of EMG sensors) may be used, especially when the camera is used to refine the IMU-based system for tracking one or more position(s) of articulated rigid bodies. As will be appreciated, data from a single camera may be used or data from two or more cameras may be used.

According to some embodiments, camera data may be used for determining whether an object (e.g., a hand, finger, or another physical object) is subjected to a force. For instance, camera data may be used to distinguish between whether someone is moving freely or pressing against object(s) and/or surface(s) (which may include another part of the user's body), determine which object(s) and/or surfaces is or are being interacted with, which position(s) on the surface(s) and/or object(s) are being touched, and can assist with estimating a skeletal configuration, position, and/or force. It is appreciated that although camera data can be used to determine whether a force is being applied, camera data is not particularly suited to determining a magnitude of the force(s) applied. To this end, other input signals (e.g., neuromuscular signals) can be used to determine an amount of force applied and also assist with determining the skeletal configuration and/or position.

When an XR user is applying self force(s) against the user's own body (e.g., the user is pinching his or her own arm), the camera can assist with determining the skeletal configuration and/or position (e.g. which joint segments are involved in touching the arm), and the neuromuscular sensors can be used to determine the intensity of the force. In this way, a more accurate representation of the arm position(s) and/or the hand position(s) and force(s) can be constructed. Further, it is more generally appreciated that the physical context as determined by the cameras could inform priors for estimating the musculoskeletal representation from neuromuscular signals, for example if users are more likely to perform certain movements in specific environments.

Some embodiments are directed to predicting information about the position and movements of portions of a user's arm and/or hand, which may be represented as a multi-segment articulated rigid body system with joints connecting the multiple segments of the rigid body system. For example, in the case of a hand movement, signals sensed and recorded by wearable neuromuscular sensors placed at locations on the user's body (e.g., the user's arm and/or wrist) may be provided as input to an inference model trained to predict estimates of the position (e.g., absolute position, relative position, orientation) and the force(s) associated with a plurality of rigid segments in a computer-based musculoskeletal representation associated with a hand when the user performs one or more hand movements. The combination of position information and force information associated with segments of a musculoskeletal representation associated with a hand is colloquially referred to herein as a "handstate" of the musculoskeletal representation. As a user performs different movements, a trained inference model interprets neuromuscular signals recorded by the wearable neuromuscular sensors into position and force estimates (handstate information) that are used to update the musculoskeletal representation. Because the neuromuscular signals are continuously sensed and recorded, the musculoskeletal representation is updated in real time and a visual representation of a hand (e.g., within an extended reality environment) may be rendered based on the current handstate estimates. As will be appreciated, an estimate of a user's handstate may be used to determine a gesture being performed by the user and/or to predict a gesture that the user will perform.

According to some embodiments, musculoskeletal representations (e.g., hand-rendering) may include actual visual representations of biomimetic (realistic) hands, synthetic (robotic) hands, as well as abstract "internal representations" that serve as input for gesture control (e.g., to other applications, systems, etc.). That is, the hand's position and/or force may be provided to downstream algorithms (e.g., control algorithms in an XR system) but may not be directly rendered. In some embodiments, camera data may be used to assist in creating actual visual representations (e.g., improving an XR version of a user's hands based on the camera data).

According to some embodiments, information received in an EMG context (e.g., force) may be used to control modes of a computer system (e.g., an XR system). For instance, a detection of force (e.g., beyond a threshold amount, such as applied by a finger or a hand) may be used to control the XR system, such as to, for example, open a help dialog interface, open a global system properties menu, or perform a mode switching function. Such dual-mode inputs may also include, for example, submitting a "wake" signal to an XR system or other type of system having heavy computing costs (e.g., high usage of electrical power) because the system wakes or is responsive to the user engaging the system with a position-, force-, or gesture-related event (e.g., the user clenching his or her first results in a wake signal being sent to the XR system). In another implementation, any number of combinations of neuromuscular signals may be used in conjunction with camera data to control a computer system. For instance, in a scenario where a user is selecting an object in an XR environment, the camera data may be used to determine the user's posture, and an EMG signal may be used to inform the XR system that the object has been selected for action (e.g., by detecting a force applied through the EMG signal). It should be appreciated that any combination of modes of control using different types of input data may be performed.

Some embodiments are directed to coupling a system that senses neuromuscular signals with a system that performs XR functions (e.g., AR functions, VR functions, etc.). In particular, a system that senses neuromuscular signals for the purpose of determining a position of a body part (e.g., a hand, an arm, etc.) may be used in conjunction with an XR system to provide an improved XR experience for a user. For instance, information gained within both systems may be used to improve the overall XR experience. In one example, a camera in an AR system may capture data that is used to improve the accuracy of a model of a musculoskeletal representation, used to calibrate the model and/or to control the system(s) using any combination of camera and neuromuscular signals. Further, in another implementation, muscle activation data may be visualized and displayed to a user in an XR environment. In yet another example, display information in the XR environment may be used as feedback to the user to permit the user to more accurately control their musculoskeletal input to the system. Further, control features may be provided that permit neuromuscular signals to control XR system elements.

Figure 22A:
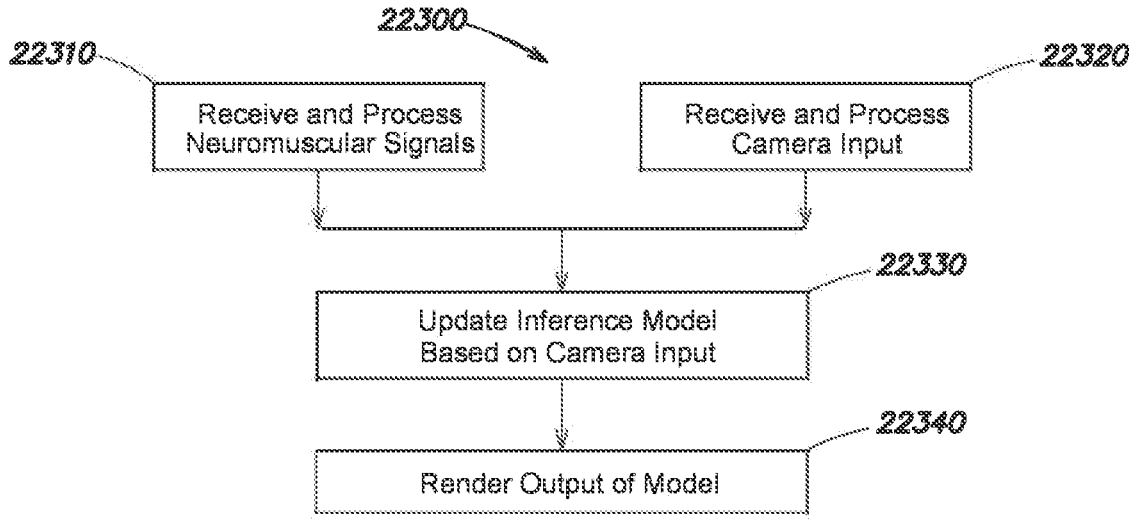
FIG. 22A is a flowchart of a process for processing neuromuscular signals and camera data in accordance with some embodiments of the technology described herein.

FIG. 22A shows a flowchart of a process 22300 for processing neuromuscular signals and camera or signals inputs in accordance with some embodiments of the technology described herein. The process 22300 may be implemented on a system such as, for example, the AR-based system 200, the AR system 201, the neuromuscular activity system 202, and/or a separate computer system to which the systems 201, 202 provide signal inputs. In one implementation, the process 22300 may be performed by the neuromuscular activity system 202. In act 22310, sensor signals may be sensed and recorded by one or more sensor(s) (also referred to herein as "raw sensor signals") of the neuromuscular activity system 202. In some embodiments, the sensor(s) may include a plurality of neuromuscular sensors 209 (e.g., EMG sensors) arranged on a wearable device worn by a user. For example, the sensors 209 may be EMG sensors arranged on an elastic band configured to be worn around a wrist or a forearm of a user to record neuromuscular signals from the user as the user performs various movements or gestures. In some embodiments, the EMG sensors may be the sensors 704 arranged on the band 702, as shown in FIG. 7A; in some embodiments, the EMG sensors may be the sensors 810 arranged on the elastic band 820, as shown in FIG. 8A. The gestures performed by the user may include static gestures, such as placing the user's hand palm down on a table; dynamic gestures, such as waving a finger back and forth; and covert gestures that are imperceptible to another person, such as slightly tensing a joint by co-contracting opposing muscles, pressing on an object or surface, or using sub-muscular activations. The gestures performed by the user may include symbolic gestures (e.g., gestures mapped to other gestures, interactions, or commands, for example, based on a gesture vocabulary that specifies the mapping).

In addition to a plurality of neuromuscular sensors, some embodiments of the technology described herein may include one or more auxiliary sensor(s) configured to record auxiliary signals that may also be provided as input to the one or more trained inference model(s), as discussed above. Examples of auxiliary sensors include IMUs, imaging devices, radiation detection devices (e.g., laser scanning devices), heart rate monitors, or any other type of biosensor configured to sense and record biophysical information from a user during performance of one or more movements or gestures. According to one embodiment, as shown in the process 22300 of FIG. 22A at act 22320, the system receives and processes one or more camera inputs. Such inputs may include one or more raw signals, such as signals of images, video, stream, etc., or signals of one or more pre-processed forms, such as signals of a representation of a detected object, a 3D model, etc., and/or other information, such as information reflecting a state of the camera inputs. Further, it should be appreciated that some embodiments may be implemented using camera-based systems that perform skeletal tracking, such as, for example, the Kinect system available from the Microsoft Corporation (Redmond, Washington, USA) and the LeapMotion system available from Leap Motion, Inc. (San Francisco, California, USA). It should be appreciated that any combination of hardware and/or software may be used to implement various embodiments described herein.

The acts 22310 and 22320 may also include processing acts themselves, where raw sensor signals, which may include the signals sensed and recorded by the one or more sensor(s) (e.g., EMG sensors, IMUs) and/or the camera input signals from the one more camera(s), are optionally processed. In some embodiments, the raw sensor signals may be processed using hardware signal-processing circuitry (e.g., to perform amplification, filtering, and/or rectification). In other embodiments, at least some signal processing of the raw sensor signals may be performed using software. Accordingly, signal processing of the raw sensor signals, sensed and recorded by the one or more sensor(s) and/or obtained from the one or more camera(s), may be performed using hardware, or software, or any suitable combination of hardware and software. In some implementations, the raw sensor signals may be processed to derive other signal data. For example, accelerometer data recorded by one or more IMU(s) may be integrated and/or filtered to determine derived signal data associated with one or more muscles during activation of a muscle or performance of a gesture.

The process 22300 then proceeds to act 22330, where the raw sensor signals (e.g., the neuromuscular signals and the camera input signals) or the processed versions of the raw sensor signals are optionally provided as input to the trained inference model(s), which is or are configured to produce user-movement information, such as handstate information, as described above.

The process 22300 then proceeds to act 22340, where outputs of the trained inference model(s) are provided. For instance, in some embodiments, control outputs of the system are provided based on the raw sensor signals, the processed sensor signals, and/or the outputs of the trained inference model(s) (e.g., handstate information and/or other rendered output of the trained inference model(s), etc.). For example, in some embodiments, the AR system 201 may receive a rendered output that the AR system 210 (or other system display) can display as a rendered gesture.

According to some embodiments, one or more computer processors (e.g., the processor(s) 112 of the system 100, or the processor(s) 205 of the AR-based system 200) may be programmed to identify one or more muscular activation states of a user from raw sensor signals (e.g., signals sensed and recorded by the sensor(s) discussed above and/or camera input signals) and/or information based on these signals. The information based on the signals the raw sensor signals may include information associated with processed sensor signals (e.g., processed EMG signals) and/or information associated with outputs of the trained inference model(s) (e.g., handstate information). The one or more muscular activation states of the user may include a static gesture performed by the user, a dynamic gesture performed by the user, a sub-muscular activation state of the user, and/or a muscular tensing performing by the user. The one or more muscular activation states of the user may be defined by one or more pattern(s) of muscle activity and/or one or more motor unit activation(s) detected in the raw sensor signals and/or information based on the raw sensor signals, associated with various movements or gestures performed by the user.

Figure 22B:
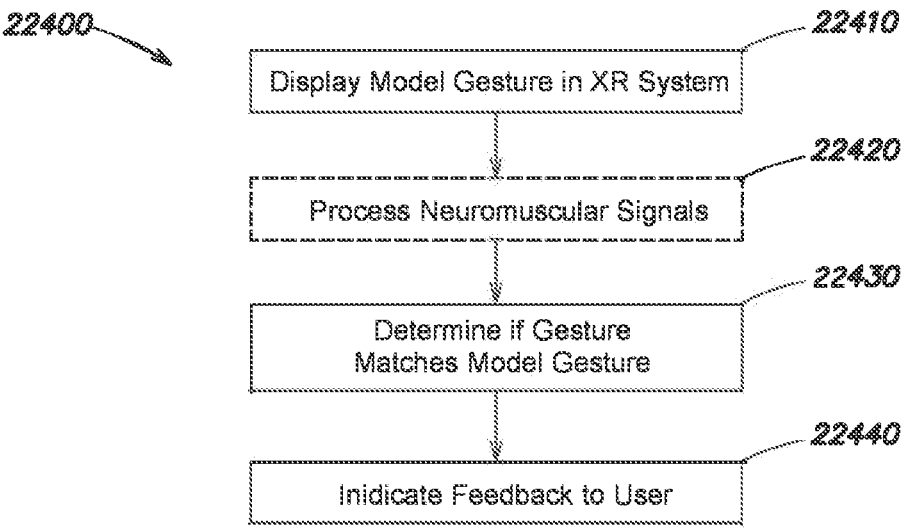
FIG. 22B is a flowchart of a process for processing gesture information in an XR system in accordance with some embodiments of the technology described herein.

FIG. 22B is a flowchart of a process 22400 for processing gesture information in an AR-based system in accordance with some embodiments of the technology described herein. In particular, there may be a number of different use scenarios wherein an AR system may be used in association with a neuromuscular activity system for providing a user experience. As shown in FIG. 22B, according to the process 22400, at act 22410, the AR-based system may be configured to display a model gesture to a user within a display of the AR-based system. For example, the AR-based system may be adapted to display a throwing motion or other gesture type that the user would like to mimic or learn. To this end, the AR-based system may display an example of a gesture to the user while the user tries to emulate that particular gesture. At act 22420, a neuromuscular activity system processes neuromuscular signals produced by the user while emulating that gesture. At act 22430, the neuromuscular activity system determines whether the emulated gesture matches a model of that gesture. Such a determination may be made, for example, using one or more 3D reference model(s) and comparing outputs of an inference model that measures or compares the user's emulated gesture versus a reference model of the gesture. Acceptable matches may occur within certain predefined ranges or error levels between two or more reference models. It should be appreciated that camera data (e.g., input signals from a camera) may also be used (either alone or in combination with the neuromuscular signals) to determine whether a match occurs. For instance, in such cases where neuromuscular signals (e.g., EMG signals) are not available, a match may be detected exclusively using camera data.

Further, the inference model may also be trained to provide an indication of a match between models. At act 22440, feedback may be provided to the user (discussed in more detail below in connection with FIG. 22C), such as a display indication within an AR display (e.g., a light or other indicator identifying that the gesture was matched or was not matched); an audio output (e.g., an audio signal for spoken words such as "great job", "match", etc.); haptic feedback; electrical stimulation; and/or other output perceivable by the user. It should be appreciated that one aspect of such a comparison may include a prediction as to whether the gesture will be completed correctly (or incorrectly). For example, hardware and/or software in the AR-based system may perform a routine for a predictive measure that is capable of determining whether the user is likely to successfully complete the gesture. In one example implementation, an audio output may be presented to the user when the predictive measure indicates that the user will be unsuccessful.

As will be appreciated, the feedback to the user may relate to a user's position relative to a camera. For example, if the user is wholly or partially occluded from the camera's field of view, the feedback may inform the user when a relevant part of the user's body is in view.

It should be appreciated that, in some embodiments, some outputs may be delivered to the user before completion of the gesture, based on a prediction of the gesture (e.g., the user may receive an electric stimulus indicating that the user's attempt at performing the gesture will be unsuccessful before the user completes the gesture). Also, it should be appreciated that although a matching operation may be performed for purposes of training an inference model, calibration of the AR-based system, and/or training of the user in an AR context, data that pairs, e.g., EMG signals and joint angles may be used to train and/or correct a musculoskeletal inference model in real time to create more accurate joint-angle predictions. However, for a gesture classifier, it may be desirable to determine specifically whether the user is performing a given gesture. In such a case, one or more camera(s) (e.g., the camera(s) 204) may be used to obtain information usable to provide training and/or classification data, such as gesture labels, by detecting matches or targeting joint angles against which to regress the model.

Figure 22C:
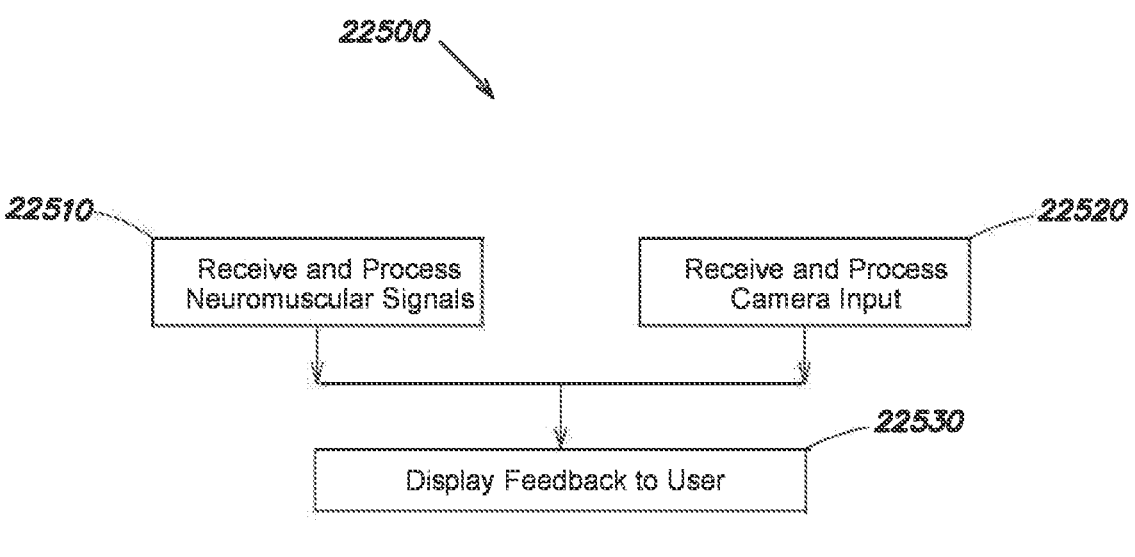
FIG. 22C is a flowchart of a process for integrating neuromuscular signals and camera data and providing feedback to a user in accordance with some embodiments of the technology described herein.

FIG. 22C is a flowchart of a process 22500 for integrating neuromuscular signals and camera input signals, and providing feedback to a user, in accordance with some embodiments of the technology described herein. The process 22500 may be performed by the AR-based system 200 of FIG. 2. At act 22510, the neuromuscular activity system 202 receives and processes signals in a similar manner as discussed above with reference to FIG. 22A. Further, at act 22520, the system 200 receives and processes camera input in a manner similar to that discussed above with reference to FIG. 22A (e.g., at the act 22320). At act 22530, the system 200 displays feedback to the user (e.g., within one or more of the display(s) 208 of the AR-based system 200). Alternatively, the system 200 may provide feedback in any number of different ways, such as audio feedback, haptic feedback, or other output perceivable by the user. To this end, the neuromuscular activity system 202 may be capable of providing output to other parts of the AR-based system 200 for the purpose of displaying or generating feedback output. In some implementations, the AR-based system 200 may have one or more audio outputs, displays, indicators and/or other type of output device capable of providing or rendering feedback to the user. Alternatively, the system 200 may be configured to provide or render an output signal (e.g., a control signal) to one or more third-party systems (e.g., a manager system, monitor system, supervisor system, or other type of third-party system).

Figure 22D:
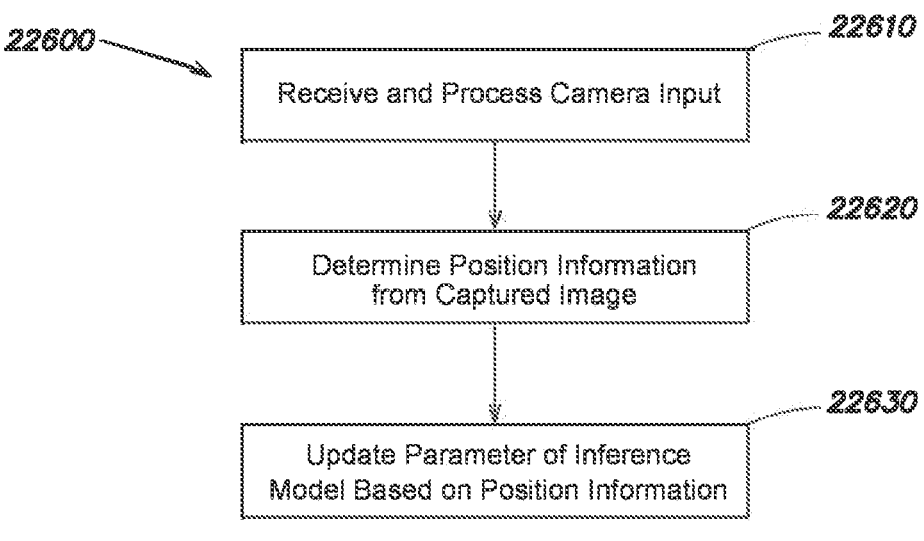
FIG. 22D is a flowchart of a process for updating an inference model based on camera data in accordance with some embodiments of the technology described herein.

FIG. 22D is a flowchart of a process 22600 for updating an inference model based on camera data in accordance with some embodiments of the technology described herein. The process 22600 may be performed by the AR-based system 200 of FIG. 2. At act 22610, the system 200 receives and processes camera input (e.g., an input signal of a captured image). In one embodiment, at act 22620, the system 200 determines position information from the captured image or from other input (e.g., neuromuscular data). At act 22630, the system 200 may update a parameter of the inference model based on the determined position information. For example, in a situation where the neuromuscular activity system 202 determines a hand position and/or an arm position, camera input data (e.g., an image of the hand and/or the arm) may be used to correct position information for that particular inference model in a calibration action, i.e., to calibrate the inference model. In cases where there are two or more sources of data (e.g., camera data and EMG data), the inference model may require that the data from the sources be simultaneously acquired. For instance, there may be error or drift within a signal corresponding to EMG-based position information, and a ground truth position determined from a camera input signal may be used to adjust a parameter of an EMG-based inference model. In this way, accuracy of the EMG-based inference model may be improved by use of both the EMG and camera input signals to calibrate the EMG-based inference model. Such a process may be used as part of a calibration operation where a user performs discrete gestures and/or performs gestures in real time in a "normal" operation, and an inference model for the gestures needs to be adjusted based on ground truth data generated by a signal source other than the source providing the neuromuscular signals for the model; the other signal source may, for example be a camera. In some embodiments, camera data may be used to estimate continuous joint angles (e.g., for a regression model) or to identify discrete gestures (e.g., for a classifier).

Figure 22E:
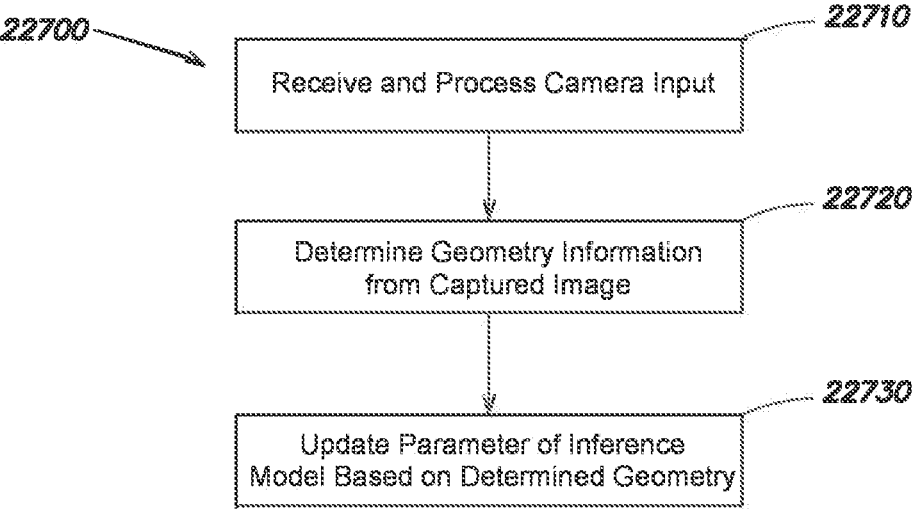
FIG. 22E is a flowchart of a process for updating an inference model based on camera data in accordance with some embodiments of the technology described herein.

FIG. 22E is a flowchart of a process 22700 for updating an inference model based on camera data in accordance with some embodiments of the technology described herein. The process 22700 may be performed by the AR-based system 200 of FIG. 2. Similar to the act 22610 of FIG. 22D, at act 22710 the system 200 receives and processes camera input (e.g., an input signal of a captured image). At act 22720, the system 200 determines geometry information from the captured image. For instance, when capturing an image of a hand, geometrical information such as segment lengths, joint positions, and other geometrical relations of a hand may be captured. At act 22730, such geometrical information may be used to update one or more parameters of an inference model. In one example implementation, the system 200 may correct a geometry used by an EMG model of a hand. It is appreciated, for example, that an image captured by a camera may more accurately portray a geometry of a hand of the user than an image generated using EMG-based signals. For instance, an image of a segment length of a finger as captured by a camera may be used to update an EMG-based inference model of hand geometry. This may be especially pertinent when the EMG-based inference model is corrected or updated for use with that particular user.

Figure 22F:
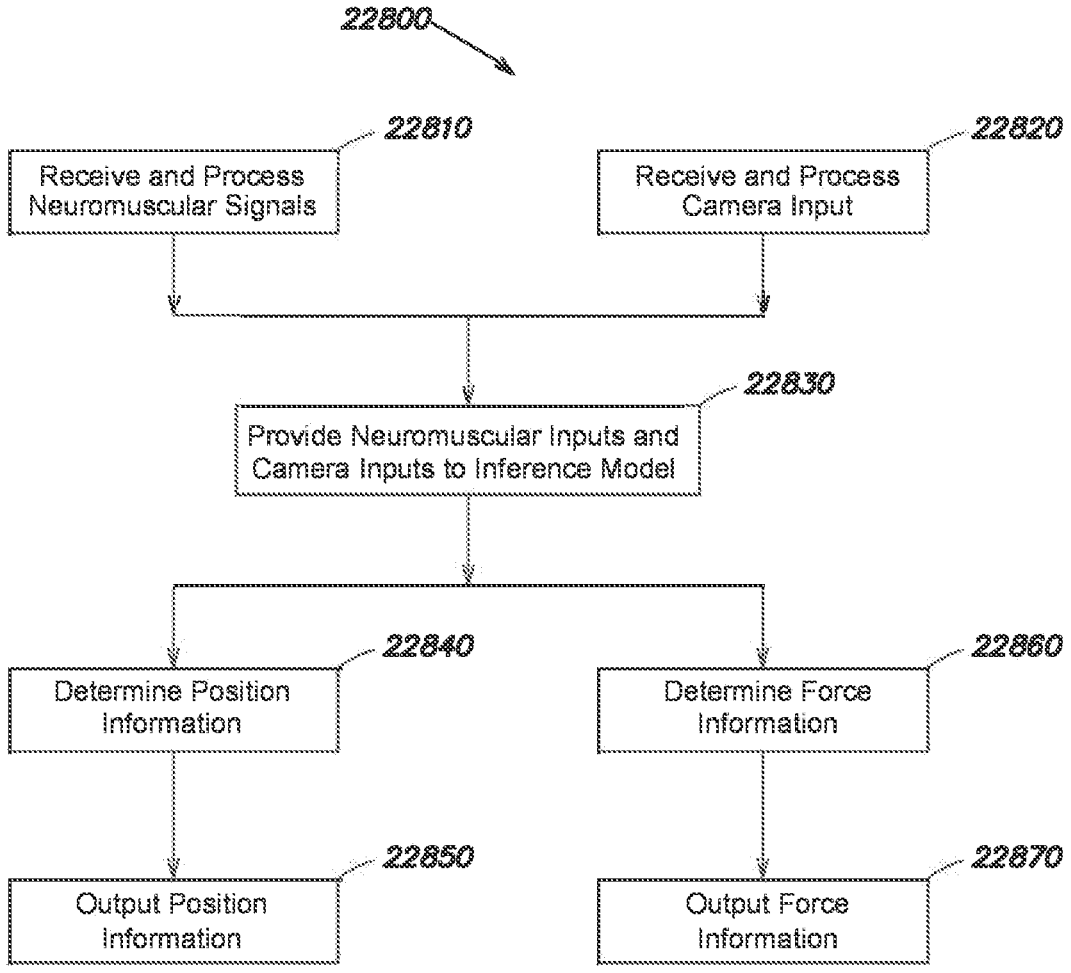
FIG. 22F is a flowchart of a process for determining position information and force information, in accordance with some embodiments of the technology described herein.

FIG. 22F is a flowchart 22800 of a process for determining position information and force information in accordance with some embodiments of the technology described herein. In particular, as discussed above, it may be beneficial to use both neuromuscular signals and camera input signals to more accurately determine position and force information within an AR environment. The process 22800 may be performed by the AR-based system 200 of FIG. 2. At act 22810, the neuromuscular activity system 202 receives and processes neuromuscular input signals. Further, at act 22820, the AR system 201 receives and processes at least one camera input signal. At act 22830, the neuromuscular input signals and the camera input signal(s) are provided to an inference model. Based on both inputs, the system 200 may determine position information (e.g., at act 22840), and may determine force information (e.g., at act 22860). The position information and the force information may be used, for example, to render a representation of a user's hand within an AR display. For example, the representation may indicate a more accurate position of the user's hand and finger appendages as well as any forces that may be applied to any of the hand and/or the finger appendages. In one specific example, the system 200 may more accurately render the user's hand position where the user's thumb is pressing on the index finger of the same hand. The camera input may be particularly useful, as it may provide a visual indication that the index finger and the thumb are in contact, while the neuromuscular signals may indicate that forces are being applied by the index finger and the thumb at some relative level (e.g., the index finger and the thumb are being pressed together with a light amount of force). In this way, the system 200 may more accurately represent handstate information of the user's hand. Optionally, the system 200 may provide position information and force information as outputs, at acts 22850 and 22870, respectively. Such outputs may be used by one or more other systems to provide indications, render outputs or other representations, and/or control other systems.

In some implementations, the camera input signals may be processed to determine whether one or more fingers are in contact with the user's thumb and, if so, which fingers are in contact with the thumb. In one embodiment, if there is contact, a magnitude of the force between the thumb and the contacting fingers then may be estimated as an affine transformation as a function of the logarithm of a signal power recorded from the neuromuscular sensors that provided the neuromuscular input signals (e.g., EMG signal power) or with another signal processing technique for inferring a magnitude of force. Coefficients of the affine transformation function can be determined by a calibration stage in which the user first lightly touches the fingers and then later produces a maximum voluntary contraction corresponding to a pinch force between the fingers. In this implementation, the inference model may output a force in units of a fraction of the maximum voluntary contraction. In some implementations, the coefficients of the affine transformation function can be specific to the set of fingers contacting the thumb. Similarly, affine transformation functions of EMG signal power can be calibrated for cases where the user is applying forces against objects or surfaces.

Figure 22G:
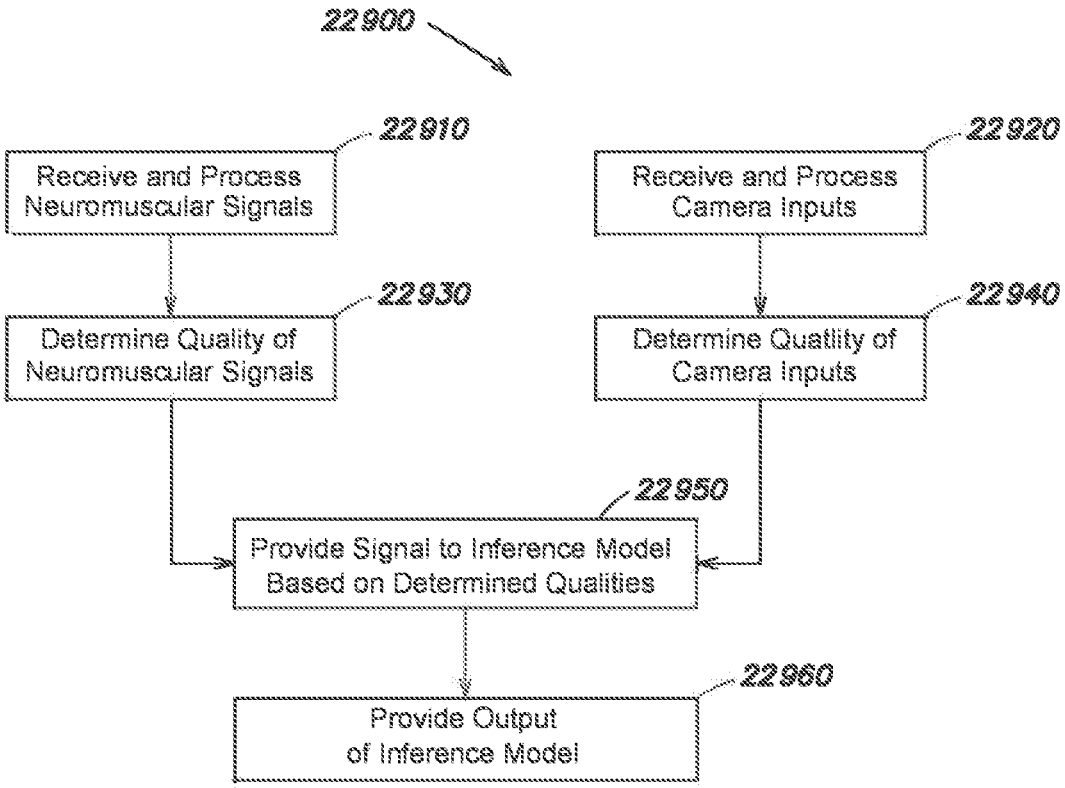
FIG. 22G is a flowchart of a process for determining qualities of input signals and performing model functions based on those qualities, in accordance with some embodiments of the technology described herein.

FIG. 22G is a flowchart of a process 22900 for determining qualities of input signals and performing model functions based on those qualities, in accordance with some embodiments of the technology described herein. The process 22900 may be performed by the AR-based system 200 of FIG. 2. For example, it is appreciated that certain input signals may be more reliable than others in certain situations. For example, a camera input signal may be less reliable for information when an object to be modeled is occluded from view or not within the camera's view at all. Similarly, neuromuscular signals may include errors generated by varying physical conditions, noise, or other interference. Therefore, it may be beneficial for a system to adaptively determine the qualities of particular input signals so that a model may be properly updated.

At act 22910, the system 200 receives and processes neuromuscular signals (e.g. as received by the neuromuscular activity system 202). At act 22920, the AR system 201 receives and processes one or more camera input signal(s). At act 22930, the system 200 determines a quality of the neuromuscular signals. For instance, the neuromuscular activity system 202 or another suitable system may determine whether the neuromuscular signals should be used and, if so, to what level. For instance, certain portions of the neuromuscular signals may be accurate (e.g., a force measurement) but other portions of the neuromuscular signals may not (e.g., absolute forearm position). Certain portions of the neuromuscular signals may be reliable within certain time frames, and under varying conditions. For example, EMG signals having a substantial power (e.g., power above a predetermined threshold) at low (e.g., less than 20 Hz) or high (e.g., greater than 500 Hz) frequencies may indicate a low quality of the EMG signals.

At act 22940, the system 200 may determine a quality of the camera input signals. As discussed above, a camera signal may be determined to be of a particular quality level when certain objects are within a field of view, and a camera signal may be determined to be at a lower quality level when objects are occluded or not within the field of view. At act 22950, the system 200 may provide a signal to an inference model based on the determined qualities of the camera input signal(s) and the neuromuscular signals. For example, one or more camera input signal(s) or neuromuscular signals may be filtered or deprecated prior to being input into the inference model. In another implementation, the inference model may be trained under varying conditions and may be trained to be responsive to signals of different quality. In another implementation, separate Bayesian predictions and confidences may be determined from each of the two types of input, and Bayesian approaches may be used to combine the two predictions (e.g., by taking a weighted average). At act 22960 the system 200 provides an output of the inference model.

Figure 22H:
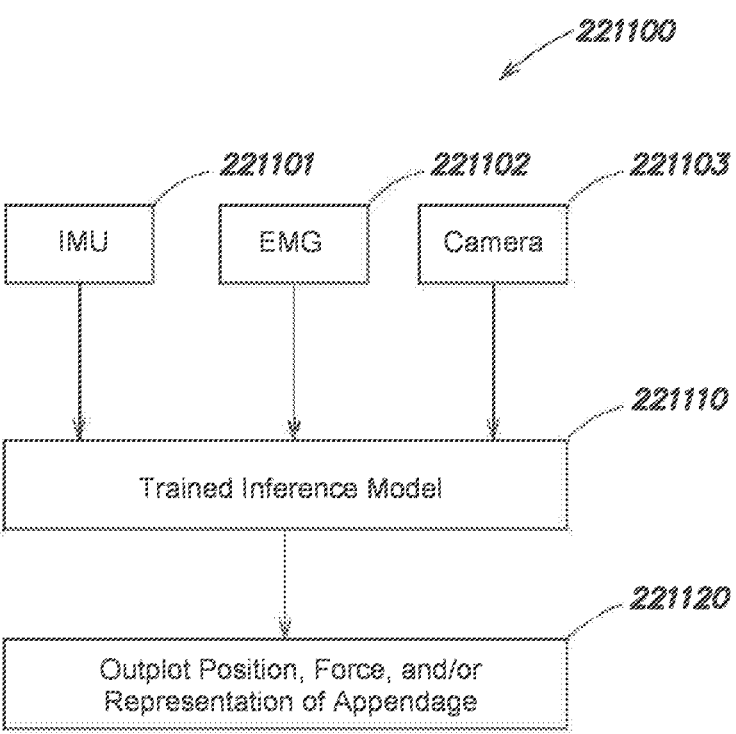
FIG. 22H is a diagram showing a trained inference model with representative inputs and outputs, in accordance with some embodiments of the technology described herein.

FIG. 22H is a diagram showing a process 221100 of processing inputs to a trained inference model in accordance with some embodiments of the technology described herein. For example, it is appreciated that a more accurate representation of a musculoskeletal representation may be obtained by using IMU inputs (221101), EMG inputs (221102), and camera inputs (221103). Each of these inputs 221101, 221102, 221103 may be provided to a trained inference model 221110. The inference model 221110 may be structured to provide one or more outputs, such as position, force, and/or a representation of a musculoskeletal state. Such outputs may be provided to one or more system (s), such as an AR system for indication or display, as discussed above, or for providing feedback to a user. It should be appreciated that any of the inputs 221101, 221102, 221103 may be used in any combination with any other input to derive an output from the trained inference model. For instance, forearm positional information may be derived based on a combination of the IMU input 221101 and the camera input 221103. In one implementation, an estimate of forearm position may be generated based on the IMU input 221101 and adjusted based on ground truth data obtained from the camera input 221103. Also, forearm position and/or forearm orientation may be derived using the camera input 221103 alone without the IMU input 221101. In another scenario, the EMG input 221102 (e.g., EMG signals) may be used to derive force-only information to augment posture-only information provided by a camera-model system. Other combinations of inputs may be used to obtain a desired output and are within the scope of various embodiments descried herein.

It should also be appreciated that such outputs may be derived with or without generating any musculoskeletal representation. It should also be appreciated that one or more outputs may be used as control inputs to any other system, such as an output of an EMG-based control signal that is used as a control input signal provided to an AR system.

It is appreciated that any embodiment described herein may be use alone or in any combination with any other embodiment described herein. Further, portions of an embodiment described herein may be combined with portions of one or more other embodiments described herein. Additionally, embodiments described herein may be used in whole or in part with embodiments described in U.S. patent application Ser. No. 16/257,979, filed Jan. 25, 2019, entitled "CALIBRATION TECHNIQUES FOR HANDSTATE REPRESENTATION MODELING USING NEUROMUSCULAR SIGNALS," which is incorporated by reference herein, and U.S. patent application Ser. No. 15/659,504, filed Jul. 25, 2017, entitled "SYSTEM AND METHOD FOR MEASURING THE MOVEMENTS OF ARTICULATED RIGID BODIES," which is incorporated by reference herein.

The following describes exemplary neuromuscular text entry, writing and drawing in augmented reality systems according to at least one embodiment of the present disclosure.

The inventors have developed novel techniques for providing input to extended reality (XR) systems, which include inter alia augmented reality (AR), virtual reality (VR), and mixed reality (MR) systems. Various embodiments described herein offer certain advantages, including, but not limited to, avoiding the use of an undesirable or burdensome physical keyboard, joystick, or other controller; overcoming issues associated with time consuming and high latency processing of low quality images of the user captured by a camera; allowing for the capture and detection of subtle, small, or fast movements and/or variations in force exerted by a user (e.g., varying amounts of force exerted through a stylus, writing instrument, or finger being pressed against a surface) that can be important for resolving text input and other control signals; collecting and analyzing various physiological and/or behavioral information detected from the user that enhances the identification process and is not readily obtained by conventional input devices; allowing instances where the user's hand is obscured or outside the camera's field of view, e.g., in the user's pocket, or while the user is wearing a glove; and allowing better user operability and navigability within the XR environment.

Other embodiments account for scenarios in which an individual either does not have access to input devices or may otherwise want to provide input to the XR system without the use of input devices. For example, an individual may want to provide input to the XR system in a covert manner without being noticed by other individuals.

In accordance with some embodiments, signals recorded or detected from wearable sensors are used to identify and provide input to an XR system. Various forms of input, for example, discrete control signals, continuous (e.g., 2D) control signals, text entry via a keyboard or other mode of text entry, writing, and/or drawing, may be identified from the recorded or detected signals and/or information based on the recorded or detected signals to enable improved techniques for providing input (such as text) to the XR system. In some embodiments, various forms of input may be identified based on a mode of the system that senses signals via the wearable sensors and provides input to the XR system. The user can manually, or the system can automatically, switch between input modes based, at least in part, on neuromuscular data detected from the user. In one embodiment, the system can enter a typing mode and can identify text from the user to be provided to the XR system based on one or more tapping or typing actions performed by the user (e.g., tapping on a surface of a physical keyboard, tapping on a surface that has a virtual keyboard projected thereon by the XR system, tapping on a surface that does not have a keyboard projected on it, or performing gestures in mid-air that correspond to typing-style movements). The systems and methods described herein can identify text input from the user based on the recorded or detected signals and/or information based on the recorded or detected signals. In another embodiment, the system can enter a writing mode and text input can be provided to the XR system by identifying one or more writing actions performed by the user (e.g., writing on a surface with a physical or virtual writing implement) based on the recorded or detected signals and/or information based on the recorded or detected signals. In yet another embodiment, the system can enter a drawing mode and input can be provided to the XR system by identifying one or more drawing actions (e.g., drawing one or more line segments and/or curves on a surface) performed by the user based on the recorded or detected signals and/or information based on the recorded or detected signals. In another embodiment, the system can enter a one-handed mode (i.e., a mode where the user uses only one hand to provide input), and input can be provided to the XR system by identifying one or more one-handed actions (for example, gestures such as squeezing, pinching, and/or tapping of various fingers and combinations of fingers) performed by the user based on the recorded or detected signals and/or information based on the recorded or detected signals.

In some embodiments, the XR system may provide visual feedback by displaying an indication of the identified input to the user, which may facilitate text entry or other information provided as input to the XR system. The indication can be displayed via a user interface presented within an XR environment provided by the XR system. For example, a display associated with the XR system can overlay a visual representation of the identified input in the user interface or provide audio feedback to the user about the identified input. In some embodiments, the indication may be rendered by the AR system onto a surface with which the user is interacting.

In some embodiments, the system described herein senses signals via the wearable sensors and provides input to the XR system such that the system smoothly transitions from a first input mode to a second input mode without requiring an explicit mode switch instruction from the user. This provides for a flexible approach to providing input to the XR system. For example, the system described herein may be operating in a typing mode where the user is providing text input to the system by typing on a physical keyboard. The user may stop typing on the physical keyboard and resume providing text input by writing with a stylus. In response, the system may automatically detect the change in input mode and seamlessly switch from the typing mode to a writing mode. In some embodiments, the user may switch to different forms of text entry while the system is in the same mode. For example, the user may begin by typing on a physical keyboard, and resume text entry by typing on a virtual keyboard or using typing motions without any virtual representation of a keyboard. In this scenario, the manner in which the user is providing text input has changed even though the system remains in the typing mode. In some embodiments, the visual feedback provided by the XR system may continue uninterrupted regardless of the mode or the form of text entry.

Figure 23A:
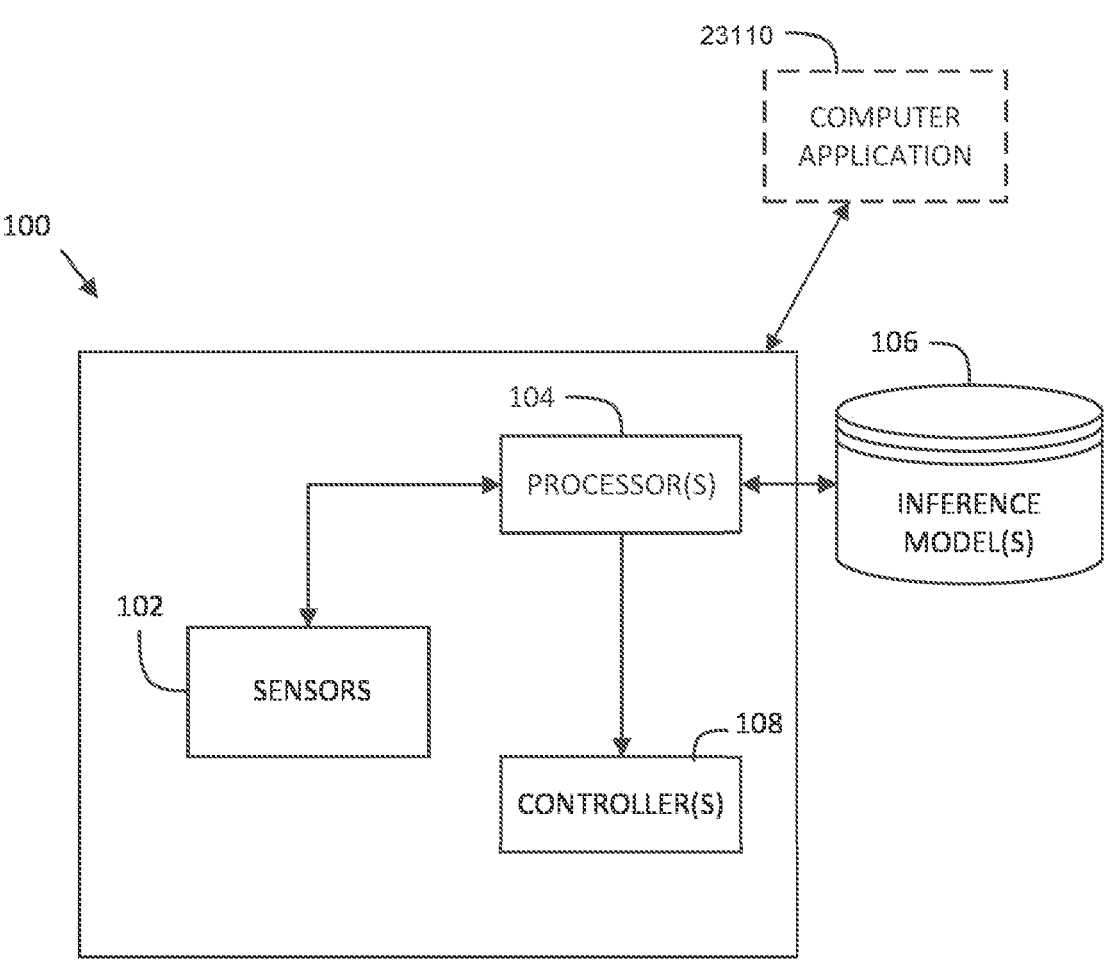
FIG. 23A is a schematic diagram of a computer-based system for processing neuromuscular sensor data in accordance with some embodiments of the technology described herein.

In some embodiments, as shown in FIG. 23A, the system 100 optionally includes a computer application 23110 that is configured to simulate a virtual reality (VR), augmented reality (AR), and/or a mixed reality (MR) environment (collectively, extended reality, "X Reality" or "XR" systems or environments), and the computer application 23110 can display a visual character such as an avatar (e.g., via controller 108) in an XR environment. Positioning, movement, and/or forces applied by portions of the visual character within the virtual reality environment may be displayed in the XR environment based on the output of the trained inference model(s). The visual representation in the XR environment may be dynamically updated as continuous signals are recorded by the sensors 102, processed by computer processor(s), and sent to the inference model(s)

106 for trained or inferred outputs, so that the system can provide a computer-generated representation of the visual character's movement that is updated in real-time in the XR environment.

Information generated in either system (e.g., XR camera inputs from an XR system, neuromuscular sensor inputs from a computer-based system that generates the musculoskeletal representation based on sensor data) can be used to improve the user experience, accuracy, feedback, inference models, calibration functions, and other aspects in the overall system. To this end, in an XR environment for example, system 100 may include an XR system that includes one or more of the following: processors, a camera (e.g., one or more camera(s) contained in a head-mounted display), a display (e.g., via XR glasses or other viewing device), or any other auxiliary sensor(s) that provides XR information within a view of the user or provides XR information to the user. In some embodiments, information from a camera contained in the head-mounted display in the XR system may be used in combination with information from the neuromuscular sensors to interpret movement, gestures, and/or actions performed by the user. System 100 may also include system elements that couple the XR system with a computer-based system that generates the musculoskeletal representation based on sensor data. For example, the systems may be coupled via a special-purpose or other type of computer system that receives inputs from the XR system and the system that generates the computer-based musculoskeletal representation. Such a system may include a gaming system, robotic control system, personal computer, or other system that is capable of interpreting XR and musculoskeletal information. The XR system and the system that generates the computer-based musculoskeletal representation may also be programmed to communicate directly. Such information may be communicated using any number of interfaces, protocols, or media.

Figure 23B:
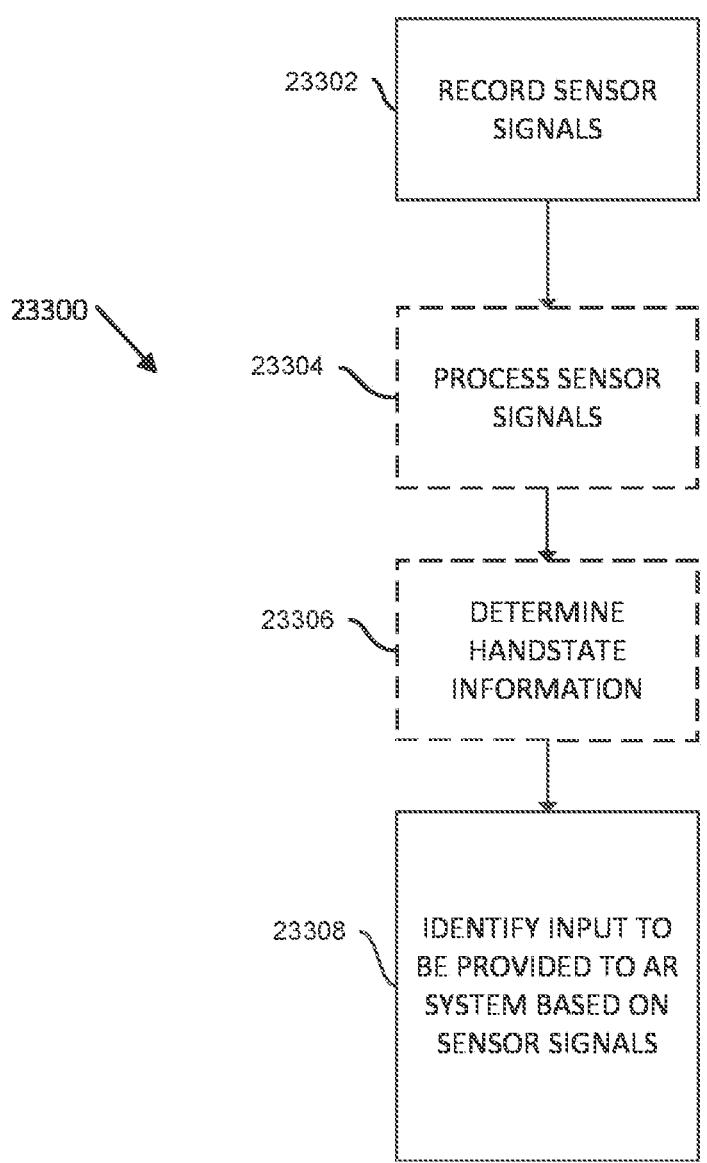
FIG. 23B is a flowchart of a process for providing input to an AR system in accordance with some embodiments of the technology described herein.

FIG. 23B illustrates a process 23300 for identifying and providing input to an XR system. In particular, process 23300 is described with respect to identifying and providing input to an AR system, such as AR system 201, in accordance with some embodiments. The process 23300 may be performed by the neuromuscular activity system 202. In act 23302, sensor signals may be recorded by one or more sensors 102 (also referred to herein as "raw sensor signals") of the neuromuscular activity system 202. In some embodiments, the sensors include a plurality of neuromuscular sensors (e.g., EMG sensors) arranged on a wearable device worn by a user. For example, EMG sensors may be arranged on an elastic band configured to be worn around a wrist or forearm of the user to record neuromuscular signals from the user as the user performs various movements or gestures. In some embodiments, the EMG sensors may be the sensors 704 arranged on the band 702, as shown in FIG. 7A; in some embodiments, the EMG sensors may be the sensors 810 arranged on the elastic band 820, as shown in FIG. 8A.

As used herein, the term "gestures" refers to a static or dynamic configuration of one or more body parts including the position of the one or more body parts and forces associated with the configuration. For example, gestures performed by the user include static/discrete gestures (also referred to as "pose") that indicate a static configuration of one or more body parts. For example, a pose can include a fist, an open hand, statically placing or pressing the palm of the hand down on a solid surface or grasping a ball. A pose can indicate the static configuration by providing positional information (e.g., segment coordinates, joint angles, or similar information) for the pose, or by providing an identifier corresponding to a pose (e.g., a parameter, function argument, or variable value). The gestures performed by the user may include dynamic/continuous gestures that indicate a dynamic configuration of one or more body parts. The dynamic configuration can describe the position of the one or mode body parts, the movement of the one or more body parts, and forces associated with the dynamic configuration. For example, a dynamic gesture can include waving a finger back and forth, throwing a ball or grasping and throwing a ball. Gestures may include covert gestures that are imperceptible to another person, such as slightly tensing a joint by co-contracting opposing muscles, or using sub-muscular activations. Gestures may be defined by an application configured to prompt a user to perform the gestures or, alternatively, gestures may be arbitrarily defined by a user. The gestures performed by the user may include symbolic gestures (e.g., gestures mapped to other gestures, interactions, or commands, for example, based on a gesture vocabulary that specifies the mapping). In some cases, hand and arm gestures may be symbolic and used to communicate according to cultural standards.

In some embodiments, the movements or gestures performed by the user may include tapping or typing actions such as, tapping or typing actions on a surface of a physical keyboard, tapping or typing actions on a surface that has a virtual keyboard projected thereon by the AR system 201, tapping or typing actions without any virtual representation of a keyboard and/or typing actions or other gestures performed in mid-air (e.g., not on a surface).

In some embodiments, the movements or gestures performed by the user may include writing actions such as, writing actions performed on a surface with a physical stylus, a physical writing implement, or fingertip or fingertips of the user (e.g., a user might be imagining that he is holding a pen or stylus by holding his fingertips together in a writing position), writing actions performed on a surface with a virtual stylus or virtual writing implement, and/or writing actions performed with a physical writing implement, a virtual writing implement, or fingertip(s) of the user in mid-air and not on a particular surface.

In some embodiments, the movements or gestures performed by the user may include drawing actions such as, drawing actions performed on a surface including drawing one or more line segments and/or curves and/or swiping through a virtual keyboard (e.g., virtual swipe keyboard) projected by the AR system 201.

In some embodiments, the movements or gestures performed by the user may include one-handed actions such as one-handed chord gestures including squeezes, taps or pinches with various fingers or combinations of fingers of one hand.

In addition to a plurality of neuromuscular sensors, some embodiments include one or more auxiliary sensors configured to record auxiliary signals that may also be provided as input to the one or more trained inference models. Examples of auxiliary sensors include IMU sensors, imaging devices, radiation detection devices (e.g., laser scanning devices), heart rate monitors, or any other type of biosensors configured to record biophysical information from the user during performance of one or more movements or gestures mentioned above. In some embodiments, the neuromuscular signals may be associated or correlated with information detected from the auxiliary sensors (e.g., auxiliary signals providing information indicative of a user's physiological state and/or behavior). For example, the auxiliary signals may be used together with the neuromuscular signals to interpret the user's movements, gestures, actions or otherwise augment and enhance the neuromuscular signals or the input identification process described in detail below.

Process 23300 then proceeds to act 23304, where the raw sensor signals recorded by the sensors 102 are optionally processed. In some embodiments, the raw sensor signals may be processed using hardware signal processing circuitry (e.g., to perform amplification, filtering, and/or rectification). In other embodiments, at least some signal processing of the raw sensor signals may be performed in software. Accordingly, signal processing of the raw sensor signals recorded by the sensors may be performed in hardware, software, or by any suitable combination of hardware and software. In some implementations, the raw sensor signals may be processed to derive other signal data. For example, accelerometer data recorded by one or more IMU sensors may be integrated and/or filtered to determine derived signal data associated with one or more muscles during activation of a muscle or performance of a gesture.

Process 23300 then proceeds to act 23306, where the raw sensor signals or the processed sensor signals are optionally provided as input to a trained inference model(s) configured to output information representing user activity, such as handstate information and/or muscular activation state information (e.g., a gesture or pose), as described above.

Process 23300 then proceeds to act 23308, where input to be provided to the AR system 201 is identified based on the raw sensor signals, the processed sensor signals, and/or the outputs of the trained inference model(s) (e.g., the handstate information). In some embodiments, input to be provided to the AR system 201 may be identified based on the movements, gestures, or actions identified from the raw sensor signals, the processed sensor signals, and/or the outputs of the trained inference model(s). For example, text input to be provided to the AR system 201 may be identified based on the tapping or typing actions, writing actions, drawing actions, and/or one-handed actions. Input other than or in addition to text input may be identified, for example, a drawing may be identified based on the drawing actions.

According to some embodiments, the one or more computer processors 104 of system 100 may be programmed to identify the input to be provided to the AR system 201 from signals recorded by sensors 102 (e.g., the raw sensor signals) and/or information based on these signals. The information based on the signals recorded by sensors 102 may include information associated with processed sensor signals (e.g., processed EMG signals) and/or information associated with outputs of the trained inference model (e.g., handstate information).

According to some embodiments, input to be provided to the AR system 201 may be identified based on signals output from the auxiliary sensors (e.g., one or more IMU sensors, one or more cameras or imaging devices associated with neuromuscular activity system 202 or augmented reality system 201) in addition to the signals recorded by the neuromuscular sensors. Such auxiliary sensors can provide additional information regarding the movement of the pen, stylus, fingertip(s), when the user performs the various movements, gestures and/or actions. The additional information can be used to improve the accuracy of the identification process.

In some embodiments, the identified input may be provided to the AR system 201. The AR system 201 may provide visual feedback by displaying an indication of the identified input to the user (and/or may provide other forms of feedback such as audio or haptic feedback). The visual feedback may facilitate text entry, for example, by prompting the user to adjust the way various movements, gestures, and/or actions are performed. The visual feedback may be useful in situations where the user provides input using an object or the user's hand/fingertip, which does not leave physical marks when writing or drawing on a surface, for example. In some embodiments, the indication of the identified input includes text input identified based on the tapping or typing actions, writing actions, drawing actions, and/or one-handed actions performed by the user. In some embodiments, the indication of the identified input includes a listing of one or more suggested or predicted words or phrases for text input. For example, multiple options, guesses or alternative words may be presented to the user. The user may select from among the presented items by, for example, performing certain movements or gestures (that are identified based on neuromuscular signals) or using alternative control schemes (e.g., a cursor/pointer). In some embodiments, the indication of the identified input includes one or more virtual ink marks associated with one or more strokes made by a writing implement. In some embodiments, the indication of the identified input includes a drawing identified based on drawing actions performed by the user. In some embodiments, the indication may be displayed via a user interface presented with an augmented reality environment provided by the AR system 201. For example, the indication may be provided on a virtual document in the user interface or as a representation shown in the AR environment to be floating in space. In some embodiments, the indication may be rendered onto a surface that the user is interacting with by the AR system 201. The indication may be rendered onto the surface where the user is typing, for example, as a scrolling tickertape or a line-oriented typewriter. The indication may be rendered onto the surface where the user is writing, for example, as virtual ink on the surface.

Figure 23C:
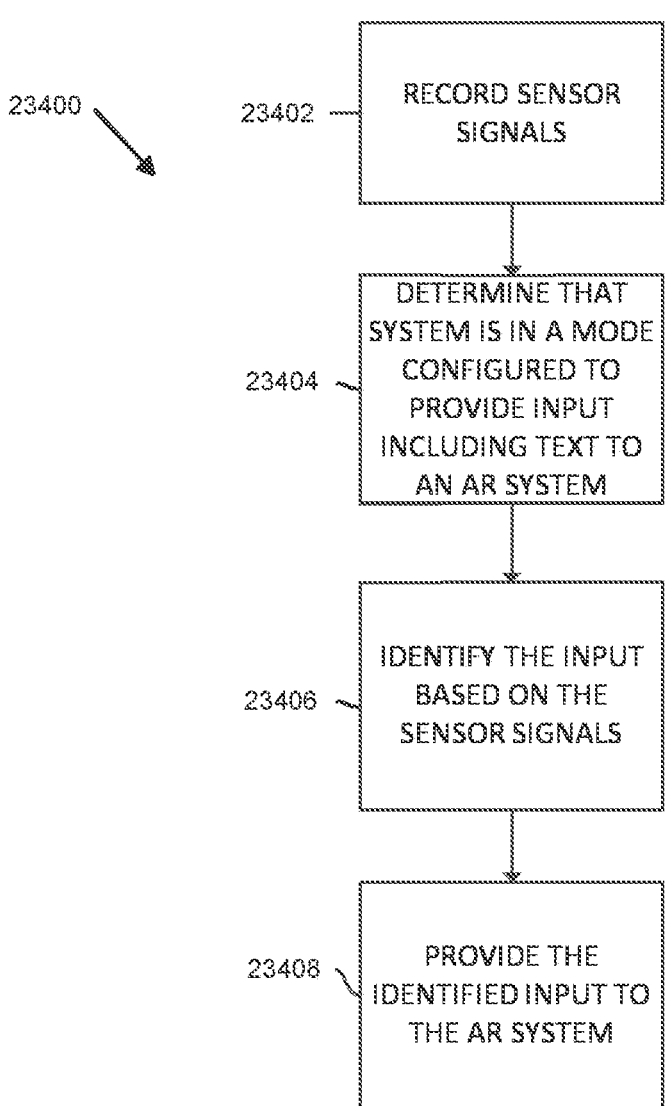
FIG. 23C is a flowchart of a process for providing input to an AR system based on one or more neuromuscular signals in accordance with some embodiments of the technology described herein.

FIG. 23C illustrates a process 23400 for identifying and providing input to an XR system. In particular, process 23400 is described with respect to identifying and providing input to an AR system, such as AR system 201, in accordance with some embodiments. The process 23400 may be performed by the neuromuscular activity system 202. In act 23402, sensor signals are recorded by one or more sensors such as neuromuscular sensors (e.g., EMG sensors) and/or auxiliary sensors (e.g., IMU sensors, imaging devices, radiation detection devices, heart rate monitors, or any other type of biosensors) of the neuromuscular activity system 202.

In act 23404, a determination may be made that the neuromuscular activity system 202 is in a mode configured to provide input including text to the AR system 201. The mode may include a typing mode in which a user may perform tapping or typing actions on a physical or virtual keyboard to provide text input, a writing mode in which a user may perform writing actions with a physical or virtual writing implement (e.g., pen, stylus, etc.) and/or fingertip(s) to provide text input, a drawing mode in which a user may perform drawing actions with a physical or virtual writing implement (e.g., pen, stylus, etc.) and/or fingertip(s) to provide text and/or drawing input, a one-handed mode in which a user may perform one-handed actions to provide text input, and/or a mode in which discrete and/or continuous control signals may be provided as input to the AR system 201.

In some embodiments, the mode determination may be made based on a user selection of the mode. In other words, the mode that the neuromuscular activity system 202 is in may be determined in response to receiving a user selection of the mode. The user selection may be received from a user interface displayed in an AR environment provided by the AR system 201. The user interface may identify and display a number of modes from which the user may select a particular mode. For example, a list of available modes, such as, typing mode, writing mode, drawing mode, and/or one-handed mode may be provided and the user may select a mode from the list.

In some embodiments, the mode determination may be made based on the sensor signals and/or information based on the sensor signals. In other words, the mode that the neuromuscular activity system 202 is in may be determined based on the sensor signals and/or information based on the sensor signals. In one embodiment, a particular gesture performed by the user may be identified based on the sensor signals and/or information based on the sensor signals, and the mode may be determined by identifying the mode corresponding to the particular gesture. For example, different gestures may be mapped to different modes and a particular mode may be determined based on a corresponding gesture performed by the user. The mode entered based on a particular gesture or muscular activation state may depend on the state of the system (e.g., a current mode of the system) and/or may be personalized according to a user's preferred settings. In some embodiments, the mode may be determined as the user performs one or more actions associated with the corresponding mode. For example, when the user starts performing typing actions, the neuromuscular activity system 202 may be configured to recognize that the input mode is a typing mode and when the user starts performing writing actions, the neuromuscular activity system 202 may be configured to recognize that the input mode is a writing mode. The neuromuscular activity system 202 may switch from one mode to another mode based on detection of different actions performed by the user. For example, the user may switch between performing typing actions and writing actions and the system may determine that the input mode should switch between the typing mode and the writing mode accordingly without interrupting text entry.

In some embodiments, the mode determination may be made based on a signal received from the AR system 201. In other words, the neuromuscular activity system 202 may be configured to operate in a mode determined in response to receiving a signal from the AR system. The AR system 201 may generate the signal in response to detection of an event for which input within an AR environment provided by the AR system is desired. For example, text input may be desired to complete a portion of a form presented in a user interface displayed in the AR environment. Presentation of the form may trigger a signal to be generated by the AR system indicating that text input is desired. The signal may identify the various modes that are available for providing the input. The AR system 201 may communicate the signal to the neuromuscular activity system 202 and the neuromuscular activity system 202 may switch to particular available mode to provide the text input.

In act 23406, the input to be provided to the AR system 201 may be identified based on the raw or processed signals and/or information based on the recorded signals (e.g., handstate and/or muscular activation state information). In some embodiments, the one or more computer processors of system 100 may be programmed to identify the input based on the sensor signals, the handstate information, detection of a gesture or muscular activation state, and/or a combination of any of the foregoing.

Figure 23D:
FIGS. 23D-23F depict exemplary scenarios in which user input may be provided to an XR system in accordance with some embodiments of the technology described herein.

In some embodiments, the input to be provided to the AR system 201 may be further identified based on the current mode of the neuromuscular activity system 202. When the neuromuscular activity system 202 is in a typing mode, input to be provided to the AR system 201 for the typing mode may be identified by identifying one or more tapping or typing actions performed by a user based on the sensor signals and/or information based on the sensor signals. For example, tapping or typing actions performed on a surface of a physical keyboard or a surface that has a virtual keyboard projected thereon by the AR system may be identified based on the sensor signals and text input for the typing mode may be identified based on the tapping/typing actions. FIG. 23D depicts a user performing typing actions on a physical keyboard 23902 placed on a table. Input to be provided to the AR system may be identified based on the neuromuscular signals and/or muscular activation state(s) associated with these typing actions (as detected by wearable portion 23910) and indications of the identified input may be displayed to the user via the virtual headset 23904.

Figure 23E:
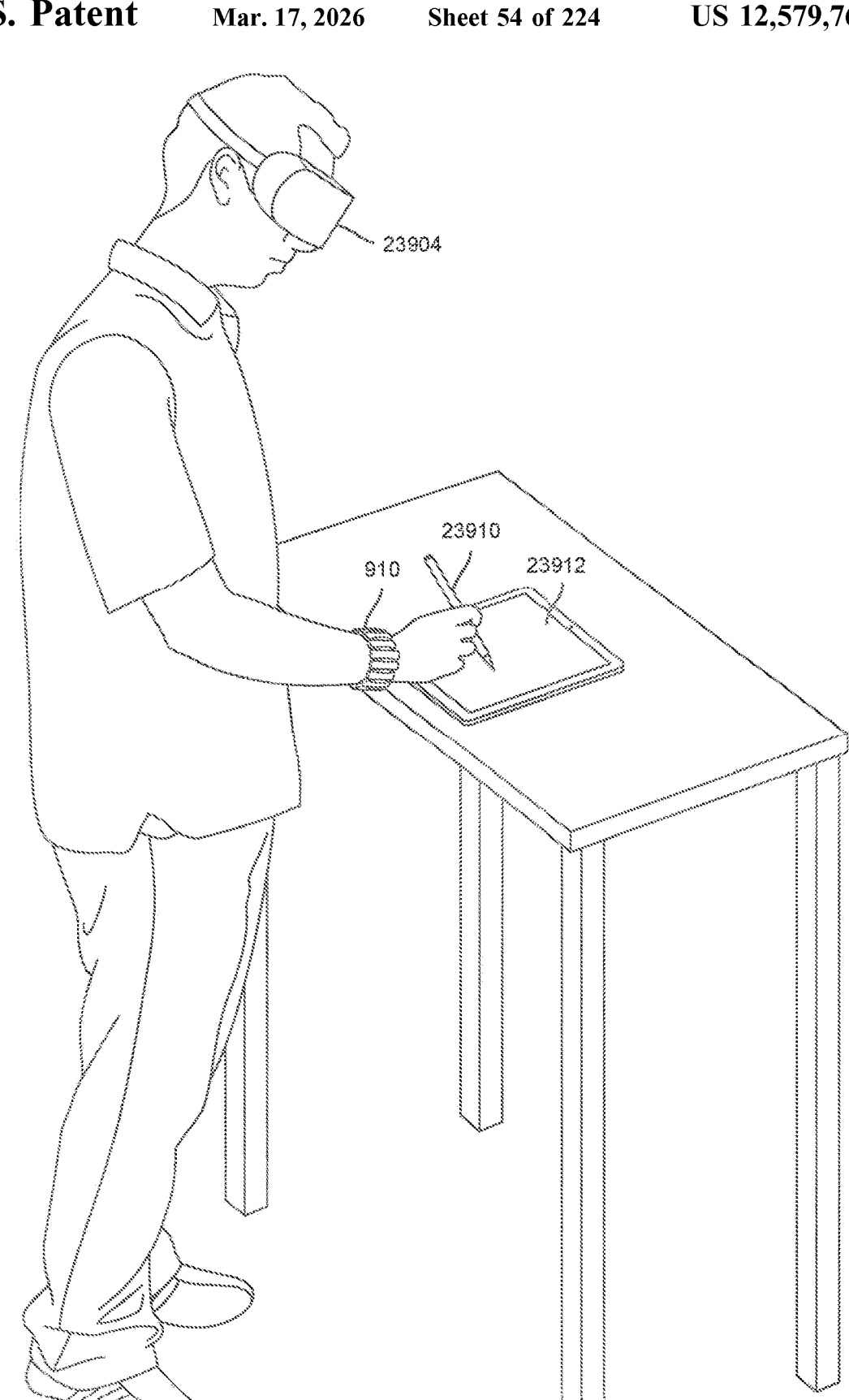

When the neuromuscular activity system 202 is in a writing mode, input to be provided to the AR system 201 for the writing mode may be identified by identifying one or more writing actions performed by the user based on the sensor signals and/or information based on the sensor signals. For example, writing actions performed on a surface with a physical writing implement, a virtual writing implement and/or fingertip(s) of the user may be identified based on the sensor signals and text input for the writing mode may be identified based on the writing actions. FIG. 23E depicts a user performing writing actions on an optional tablet device 23912 using an optional stylus 23910. Input to be provided to the AR system may be identified based on the neuromuscular signals and/or muscular activation state(s) associated with these writing actions (as detected by the wearable portion 23910) and indications of the identified input may be displayed to the user via the virtual headset 23904.

Figure 23F:
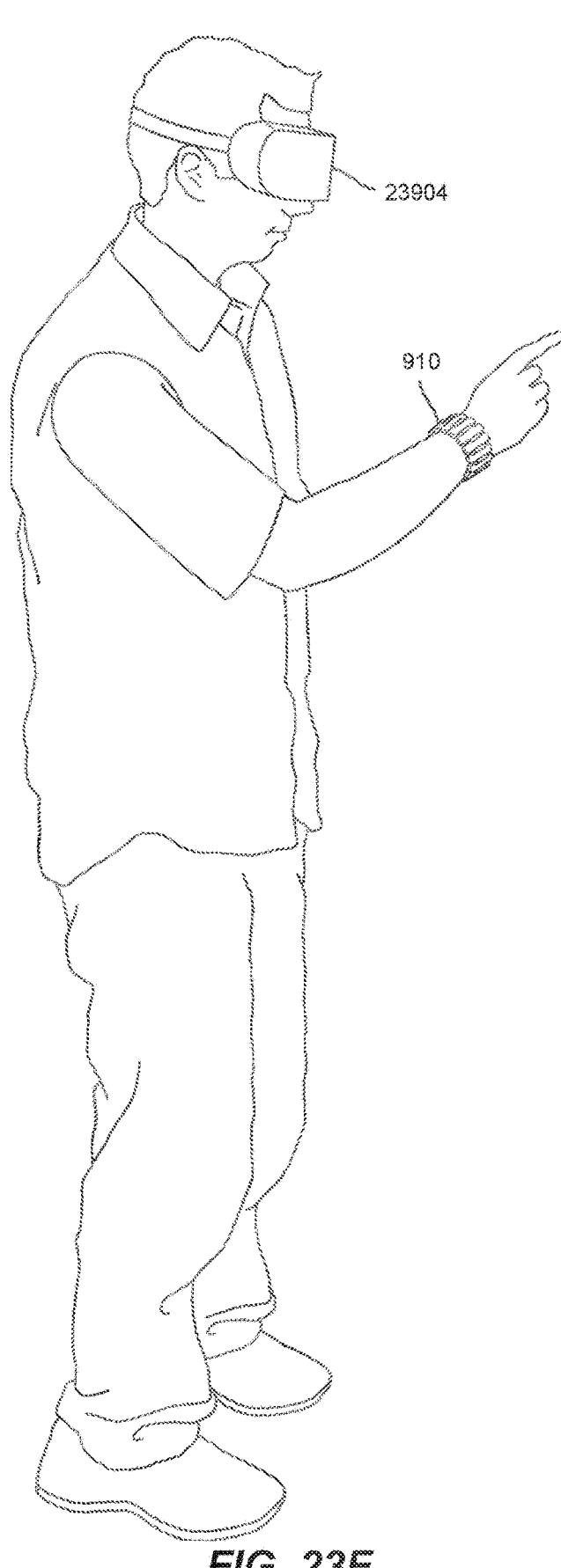

When the neuromuscular activity system 202 is in a drawing mode, input to be provided to the AR system for the drawing mode may be identified by identifying one or more drawing actions (e.g., drawing a number of line segments and/or curves on a surface) performed by the user based on the sensor signals and/or information based on the sensor signals. Input (e.g., text input and/or drawing input) for the drawing mode may be identified based on the drawing actions. In some embodiments, the input for the drawing mode may include one or more line segments and/or curves. In some embodiments, the input for the drawing mode may include input determined based on a sequence of pixel positions controlled by the drawing actions performed by the user. FIG. 23F depicts a user performing drawing actions mid-air (i.e., without using any writing instruments). Input to be provided to the AR system may be identified based on the neuromuscular signals and/or muscular activation state(s) associated with these drawing actions (as detected by wearable portion 23910) and indications of the identified input may be displayed to the user via the virtual headset 23904. In this scenario and other scenarios described herein, an auxiliary sensor (e.g., a camera) (not shown) may be provided as part of the virtual headset or as a separate component and may provide additional information (e.g., position of the hand) that maybe used to further interpret the user actions and associated neuromuscular signals and/or muscular activation state(s).

In some embodiments, both the text input and the drawing may be identified based on the drawing actions performed by the user. In some implementations, processing of the sensor signals may be performed by multiple processors. The neuromuscular sensors may be configured to communicate at least some of the sensor signals to a first computer processor and a second computer processor, where drawings may be identified by the first computer processor and text input (e.g., handwriting) may be identified by the second computer processor. The text input and the drawing from the first and second computer processors may be combined such that the text overlays or annotates the drawing, or is stored as metadata for later processing (e.g., search and filtering). In other implementations, the drawing may be identified based on the drawing actions performed by the user and the text input may be identified from the drawing. For example, the drawing may be identified from the sensor signals and text may be identified from the drawing by running a handwriting recognition process on the drawing.

When the neuromuscular activity system 202 is in a one-handed mode (i.e., a mode where the user uses only one hand to provide input), input to be provided to the AR system for the one-handed mode may be identified by identifying one or more one-handed actions (for example, squeezing, pinching, and/or tapping of various fingers and combinations of fingers) performed by the user based on the sensor signals and/or information based on the sensor signals. Text input for the one-handed mode may be identified based on the one-handed actions.

In some embodiments, one or more gestures may be identified in addition to the typing/tapping, writing, drawing, and/or one-handed actions to allow editing and/or correction of identified text. For example, one or more delete gestures may be recognized in addition to writing actions (based on which text input is identified) that allow deletion of identified letters or words in the text input. The one or more delete gestures may include a gesture to delete a single letter, a gesture to delete a previous word, and/or a gesture to delete a selected word. In some embodiments, the selection of the word to be deleted may be accomplished using neuromuscular controls, for example, cursor navigation. The one or more delete gestures may involve manipulating an object being held by a user (e.g., a stylus or pencil). For example, the one or more delete gestures may include flipping the object, such as a pencil, to an eraser position and then swiping or pressing an imaginary button on the object with a particular finger to initiate deletion of one or more letters or words.

In some embodiments, one or more gestures (such as newline gestures that indicate the end of a line of text and start of a new line of text, space gestures that indicate a space break in text, and/or other gestures) may be identified and combined with recognizing text input to allow the user to compose longer sequences of text without having to physically move his hand (e.g., to the right or down a virtual page in a virtual document). For example, a swipe or flick in a particular direction may be used as a newline gesture and a "pen up" motion may be used for space or word breaks.

In act 23408, the input identified in act 23406 may be provided to the AR system 201. Text input and/or drawing input identified based on the sensor signals and/or information based on the sensor signals may be provided to the AR system 201. The one or more computer processors of system 100 may identify and provide the input to the AR system.

In some embodiments, the neuromuscular activity system 202 may switch between different modes, for example typing, writing, drawing, and/or one-handed modes, for providing input. For example, a user may provide text-based input by tapping on a surface of a physical keyboard, writing on a surface with a stylus, swiping though a virtual swipe keyboard projected in the AR environment, or using a custom movement-free mapping from neuromuscular signals to text. These different approaches may all be integrated with the AR system 201 though a common application programming interface (API). In other words, the different forms of text input may be identified by the neuromuscular activity system 202 and provided to the AR system 201, where the AR system receives the different forms of text input via a common text API.

In some embodiments, the input to be provided to the AR system 201 may be identified from multiple sources, where the sources may include the neuromuscular signals and at least one source other than the neuromuscular signals. For example, the at least one source may include a physical input device such as a physical keyboard or stylus. Input received from the multiple sources may be combined and the combined input may be provided to the AR system 201. In some implementations, the common API may receive input from the multiple sources. In some embodiments, visual feedback provided by the AR system may continue regardless of the source, the mode or the form of text entry.

In some embodiments, when used in combination with physical input devices, the neuromuscular activity system 202 may learn to emulate the physical input devices using the neuromuscular signals, thereby allowing seamless switching between the physical input devices and their virtual emulations.

It will be appreciated that the disclosure is not limited to the use of typing, writing, drawing, and/or one-handed modes or identifying input based on tapping/typing actions, writing actions, drawing actions, and/or one-handed actions, and other modes or actions can be used. For example, two-handed actions other that typing, tapping, writing, or drawing on a surface, such as, combinations of fingertip squeezes, hand gestures, or finger movements on both hands may be used without departing from the scope of this disclosure.

The following describes exemplary neuromuscular control of an augmented reality system according to at least one embodiment of the present disclosure.

In accordance with some embodiments of the technology described herein, signals sensed by one or more wearable sensors may be used to control an XR system. The inventors have recognized that a number of muscular activation states of a user may be identified from such sensed and recorded signals and/or from information based on or derived from such sensed and recorded signals to enable improved control of the XR system. Neuromuscular signals may be used directly as an input to an XR system (e.g. by using motor-unit action potentials as an input signal) and/or the neuromuscular signals may be processed (including by using an inference model as described herein) for the purpose of determining a movement, a force, and/or a position of a part of the user's body (e.g. fingers, hand, wrist, etc.). Various operations of the XR system may be controlled based on identified muscular activation states. An operation of the XR system may include any aspect of the XR system that the user can control based on sensed and recorded signals from the wearable sensors. The muscular activation states may include, but are not limited to, a static gesture or pose performed by the user, a dynamic gesture or motion performed by the user, a sub-muscular activation state of the user, a muscular tensing or relaxation performed by the user, or any combination of the foregoing. For instance, control of an XR system may include control based on activation of one or more individual motor units, e.g., control based on a detected sub-muscular activation state of the user, such as a sensed tensing of a muscle. Identification of one or more muscular activation state(s) may allow a layered or multi-level approach to controlling operation(s) of the XR system. For instance, at a first layer/level, one muscular activation state may indicate that a mode of the XR system is to be switched from a first mode (e.g., an XR interaction mode) to a second mode (e.g., a control mode for controlling operations of the XR system); at a second layer/level, another muscular activation state may indicate an operation of the XR system that is to be controlled; and at a third layer/level, yet another muscular activation state may indicate how the indicated operation of the XR system is to be controlled. It will be appreciated that any number of muscular activation states and layers may be used without departing from the scope of this disclosure. For example, in some embodiments, one or more muscular activation state(s) may correspond to a concurrent gesture based on activation of one or more motor units, e.g., the user's hand bending at the wrist while pointing the index finger. In some embodiments, one or more muscular activation state(s) may correspond to a sequence of gestures based on activation of one or more motor units, e.g., the user's hand bending at the wrist upwards and then downwards. In some embodiments, a single muscular activation state may both indicate to switch into a control mode and indicate the operation of the XR system that is to be controlled. As will be appreciated, the phrases "sensed and recorded", "sensed and collected", "recorded", "collected", "obtained", and the like, when used in conjunction with a sensor signal comprises a signal detected or sensed by the sensor. As will be appreciated, the signal may be sensed and recorded or collected without storage in a nonvolatile memory, or the signal may be sensed and recorded or collected with storage in a local nonvolatile memory or in an external nonvolatile memory. For example, after detection or being sensed, the signal may be stored at the sensor "as-detected" (i.e., raw), or the signal may undergo processing at the sensor prior to storage at the sensor, or the signal may be communicated (e.g., via a Bluetooth technology or the like) to an external device for processing and/or storage, or any combination of the foregoing.

As an example, sensor signals may be sensed and recorded while the user performs a first gesture. The first gesture, which may be identified based on the sensor signals, may indicate that the user wants to control an operation and/or an aspect (e.g., brightness) of a display device associated with an XR system. In response to the XR system detecting the first gesture, a settings screen associated with the display device may be displayed by the XR system. Sensor signals may continue to be sensed and recorded while the user performs a second gesture. Responsive to detecting the second gesture, the XR system may, e.g., select a brightness controller (e.g., a slider control bar) on the settings screen. Sensor signals may continue to be sensed and recorded while the user performs a third gesture or series of gestures that may, e.g., indicate how the brightness is to be controlled. For example, one or more upward swipe gestures may indicate that the user wants to increase the brightness of the display device and detection of the one or more upward swipe gestures may cause the slider control bar to be manipulated accordingly on the settings screen of the XR system.

According to some embodiments, the muscular activation states may be identified, at least in part, from raw (e.g., unprocessed) sensor signals obtained (e.g., sensed and recorded) by one or more of the wearable sensors. In some embodiments, the muscular activation states may be identified, at least in part, from information based on the raw sensor signals (e.g., processed sensor signals), where the raw sensor signals obtained by one or more of the wearable sensors are processed to perform, e.g., amplification, filtering, rectification, and/or other form of signal processing, examples of which are described in more detail below. In some embodiments, the muscular activation states may be identified, at least in part, from an output of a trained inference model that receives the sensor signals (raw or processed versions of the sensor signals) as input.

In contrast to some conventional techniques that may be used for controlling XR systems, muscular activation states, as determined based on sensor signals in accordance with one or more of the techniques described herein, may be used to control various aspects and/or operations of the XR system, thereby reducing the need to rely on cumbersome and inefficient input devices, as discussed above. For example, sensor data (e.g., signals obtained from neuromuscular sensors or data derived from such signals) may be recorded and muscular activation states may be identified from the recorded sensor data without the user having to carry a controller and/or other input device, and without having the user remember complicated button or key manipulation sequences. Also, the identification of the muscular activation states (e.g., poses, gestures, etc.) from the recorded sensor data can be performed relatively fast, thereby reducing the response times and latency associated with controlling the XR system. Furthermore, some embodiments of the technology described herein enable user-customizable control of the XR system, such that each user may define a control scheme for controlling one or more aspects and/or operations of the XR system specific to that user.

Figure 24A:
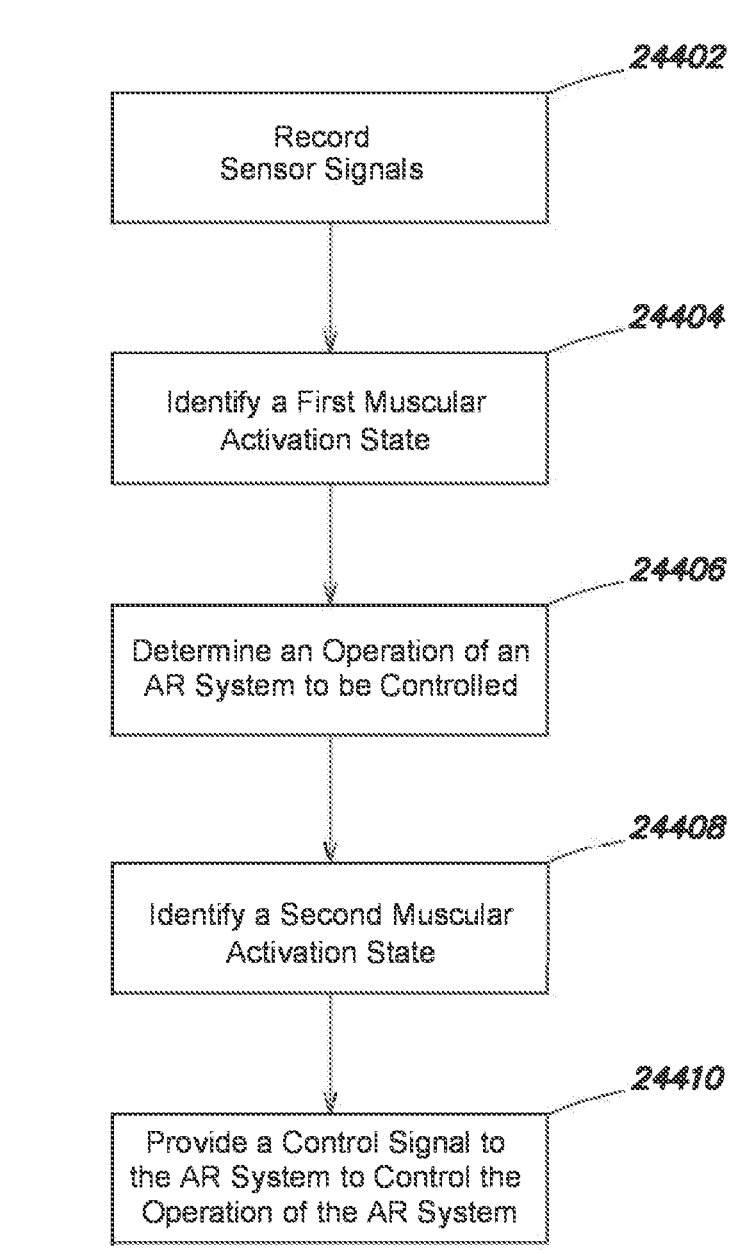
FIG. 24A is a flowchart of a process for controlling an AR system based on one or more muscular activation states of a user, in accordance with some embodiments of the technology described herein.

FIG. 24A illustrates a process 24400 for controlling an AR system, such as the AR system 201 of the AR-based system 200 comprising the AR system 201 and the neuromuscular activity system 202, in accordance with some embodiments of the technology described herein. The process 24400 may be performed at least in part by the neuromuscular activity system 202 of the AR-based system 200. In act 24402, sensor signals are sensed and recorded by one or more sensor(s), such as neuromuscular sensors (e.g., EMG sensors) and/or auxiliary sensors (e.g., IMUs, imaging devices, radiation detection devices, heart rate monitors, other types of biosensors, etc.) of the neuromuscular activity system 202. For example, the sensor signals may be obtained from a user wearing a wristband on which the one or more sensor(s) is or are attached.

In act 24404, a first muscular activation state of the user may be identified based on raw signals and/or processed signals (collectively "sensor signals") and/or information based on or derived from the raw signals and/or the processed signals, as discussed above (e.g., handstate information). In some embodiments, one or more computer processor(s) (e.g., the processor(s) 104 of the system 100, or the processor(s) 205 of the AR-based system 200) may be programmed to identify the first muscular activation state based on any one or any combination of: the sensor signals, the handstate information, static gesture information (e.g., pose information, orientation information), dynamic gesture information (movement information), information on motor-unit activity (e.g., information on sub-muscular activation) etc.

In act 24406, an operation of the AR system to be controlled is determined based on the identified first muscular activation state of the user. For example, the first muscular activation state may indicate that the user wants to control a brightness of a display device associated with the AR system. In some implementations, in response to the determination of the operation of the AR system to be controlled, the one or more computer processors (e.g., 104 of the system 100 or 205 of the system 200) may generate and communicate a first control signal to the AR system. The first control signal may include identification of the operation to be controlled. The first control signal may include an indication to the AR system regarding the operation of the AR system to be controlled. In some implementations, the first control signal may trigger an action at the AR system. For example, receipt of the first control signal may cause the AR system to display a screen associated with the display device (e.g., a settings screen via which brightness can be controlled). In another example, receipt of the first control signal may cause the AR system to communicate to the user (e.g., by displaying within an AR environment provided by the AR system) one or more instructions about how to control the operation of the AR system using muscle activation sensed by the neuromuscular activity system. For instance, the one or more instructions may indicate that an upward swipe gesture can be used to increase the brightness of the display and/or a downward swipe gesture can be used to decrease the brightness of the display. In some embodiments, the one or more instructions may include a visual demonstration and/or a textual description of how one or more gesture(s) can be performed to control the operation of the AR system. In some embodiments, the one or more instructions may implicitly instruct the user, for example, via a spatially arranged menu that implicitly instructs that an upward swipe gesture can be used to increase the brightness of the display. Optionally, the receipt of the first control signal may cause the AR system to provide one or more audible instructions about how to control the operation of the AR system using muscle activation sensed by the neuromuscular activity system. For instance, the one or more voiced instructions may instruct that moving an index finger of a hand toward a thumb of the hand in a pinching motion can be used to decrease the brightness of the display and/or that moving the index finger and the thumb away from each other may increase the brightness of the display.

In act 24408, a second muscular activation state of the user may be identified based on the sensor signals and/or information based on or derived from the sensor signals (e.g., handstate information). In some embodiments, the one or more computer processors (e.g., 104 of the system 100 or 205 of the system 200) may be programmed to identify the second muscular activation state based on any one or any combination of: neuromuscular sensor signals, auxiliary sensor signals, handstate information, static gesture information (e.g., pose information, orientation information), dynamic gesture information (movement information), information on motor-unit activity (e.g., information on sub-muscular activation) etc.

In act 24410, a control signal may be provided to the AR system to control the operation of the AR system based on the identified second muscular activation state. For example, the second muscular activation state may include one or more second muscular activation states, such as, one or more upward swipe gestures to indicate that the user wants to increase the brightness of the display device associated with the AR system, one or more downward swipe gestures to indicate that the user wants to decrease the brightness of the display device, and/or a combination of upward and downward swipe gestures to adjust the brightness to a desired level. The one or more computer processors may generate and communicate one or more second control signal(s) to the AR system. In some implementations, the second control signal(s) may trigger the AR system to increase the brightness of the display device based on the second muscular activation state. For example, receipt of the second control signal(s) may cause the AR system to increase or decrease the brightness of the display device and manipulate a slider control in the settings screen to indicate such increase or decrease.

In some embodiments, the first muscular activation state and/or the second muscular activation state may include a static gesture (e.g., an arm pose) performed by the user. In some embodiments, the first muscular activation state and/or the second muscular activation state may include a dynamic gesture (e.g., an arm movement) performed by the user. In other embodiments, the first muscular activation state and/or the second muscular activation state may include a sub-muscular activation state of the user. In yet other embodiments, the first muscular activation state and/or the second muscular activation state may include muscular tensing performed by the user, which may not be readily seen by someone observing the user.

Although FIG. 24A describes controlling a brightness of the display device based on two (e.g., first and second) muscular activation states, it will be appreciated that such control can be achieved based on one muscular activation state or more than two muscular activation states, without departing from the scope of this disclosure. In a case where there is only one muscular activation state, that muscular activation state may be used to determine or select the operation of the AR system to be controlled and also to provide the control signal to the AR system to control the operation. For example, a muscular activation state (e.g., an upward swipe gesture) may be identified that indicates that the user wants to increase the brightness of the display and a control signal may be provided to the AR system to increase the brightness based on the single muscular activation state.

Although FIG. 24A has been described with respect to control signals generated and communicated to the AR system to control the brightness of a display device associated with the AR system, it will be understood that one or more muscular activation states may be identified and appropriate one or more control signal(s) may be generated and communicated to the AR system to control different aspects/operations of the AR system. For example, a control signal may include a signal to turn on or off the display device associated with the AR system.

In some embodiments, a control signal may include a signal for controlling an attribute of an audio device associated with the AR system, such as, by triggering the audio device to start or stop recording audio or changing the volume, muting, pausing, starting, skipping and/or otherwise changing the audio associated with the audio device.

In some embodiments, a control signal may include a signal for controlling a privacy mode or privacy setting of one or more devices associated with the AR system. Such control may include enabling or disabling certain devices or functions (e.g., cameras, microphones, and other devices) associated with the AR system and/or controlling information that is processed locally vs. information that is processed remotely (e.g., by one or more servers in communication with the AR system via one or more networks).

In some embodiments, a control signal may include a signal for controlling a power mode or a power setting of the AR system.

In some embodiments, a control signal may include a signal for controlling an attribute of a camera device associated with the AR system, such as, by triggering a camera device (e.g., a head-mounted camera device) to capture one or more frames, triggering the camera device to start or stop recording a video, or changing a focus, zoom, exposure or other settings of the camera device.

In some embodiments, a control signal may include a signal for controlling a display of content provided by the AR system, such as by controlling the display of navigation menus and/or other content presented in a user interface displayed in an AR environment provided by the AR system.

In some embodiments, a control signal may include a signal for controlling information to be provided by the AR system, such as, by skipping information (e.g., steps or instructions) associated with an AR task (e.g., AR training). In an embodiment, the control signal may include a request for specific information to be provided by the AR system, such as display of a name of the user or other person in the field of view, where the name may be displayed as plain text, stationary text, or animated text.

In some embodiments, a control signal may include a signal for controlling communication of information associated with the AR system to a second AR system associated with another person different from the user of the AR system or to another computing device (e.g., cell phone, smartwatch, computer, etc.). In one embodiment, the AR system may send any one or any combination of text, audio, and video signals to the second AR system or other computing device. In another embodiment, the AR system may communicate covert signals to the second AR system or other computing device. The second AR system or other computing device may interpret the information sent in the signals and display the interpreted information in a personalized manner (i.e., personalized according to the other person's preferences). For example, the covert signals may cause the interpreted information to be provided only to the other person via, e.g., a head-mounted display device, earphones, etc.

In some embodiments, a control signal may include a signal for controlling a visualization of the user (e.g., to change an appearance of the user) generated by the AR system. In one embodiment, a control signal may include a signal for controlling a visualization of an object or a person other than the user, where the visualization is generated by the AR system.

In some embodiments, a first muscular activation state detected from the user may be used to determine that a wake-up mode of the AR system is to be controlled. A second muscular activation state detected from the user may be used to control an initialization operation of the wake-up mode of the XR system.

It will be appreciated that while FIG. 24A describes a first muscular activation state and a second muscular activation state, additional or alternative muscular activation state(s) may be identified and used to control various aspects/operations of the AR system, to enable a layered or multi-level approach to controlling the AR system. For instance, the AR system may be operating in a first mode (e.g., a game playing mode) when the user desires a switch to a second mode (e.g., a control mode) for controlling operations of the AR system. In this scenario, a third muscular activation state of the user may be identified based on the raw signals and/or processed signals (i.e., the sensor signals) and/or the information based on or derived from the sensor signals (e.g., handstate information), where the third muscular activation state may be identified prior to the first and second muscular activation states. The operation of the AR system may be switched/changed from the first mode to the second mode based on the identified third muscular activation state. As another example, once in the control mode, a fourth muscular activation state may be identified based on the sensor signals and/or the information based on the sensor signals (e.g., handstate information), where the fourth muscular activation state may be identified after the third muscular activation state and prior to the first and second muscular activation states. A particular device or function (e.g., display device, camera device, audio device, etc.) associated with the AR system may be selected for control based on the fourth muscular activation state.

In some embodiments, a plurality of first (and/or a plurality of second, and/or a plurality of third) muscular activation states may be detected or sensed from the user. For example, the plurality of first muscular activation states may correspond to a repetitive muscle activity of the user (e.g., a repetitive tensing of the user's right thumb, a repetitive curling of the user's left index finger, etc.). Such repetitive activity may be associated with a game-playing AR environment (e.g., repeated pulling of a firearm trigger in a skeet-shooting game, etc.).

In some embodiments, the AR system may have a wake-up or initialization mode and/or an exit or shut-down mode. The muscular activation states detected or sensed from the user may be used to wake up the AR system and/or to shut down the AR system.

According to some embodiments, the sensor signals and/or the information based on the sensor signals may be interpreted based on information received from the AR system. For instance, information indicating a current state of the AR system may be received where the received information is used to inform how the one or more muscular activation state(s) are identified from the sensor signals and/or the information based on the sensor signals. As an example, when the AR system is currently displaying information, certain aspects of the display device may be controlled via the one or more muscular activation state(s). When the AR system is currently recording video, certain aspects of the camera device may be controlled via the same one or more muscular activation state(s) or via one or more different muscular activation state(s). In some embodiments, one or more same gestures could be used to control different aspects of the AR system based on the current state of the AR system.

The following describes exemplary feedback from neuromuscular activation within various types of virtual and/or augmented reality environments according to at least one embodiment of the present disclosure.

It is appreciated that there may be difficulty observing, describing, and communicating about neuromuscular activity, such as that performed by a person by moving one or more body part(s), such as an arm, a hand, a leg, a foot, etc. In particular, it may be difficult to process a timing and/or an intensity of motor-unit activations and muscle activations in such body part(s) in order to provide feedback to a person who performed or is performing certain movements of his or her body part(s). Skilled motor acts to be performed by humans may require precise coordinated activations of motor units and muscles, and learning such skilled acts may be hindered by difficulties in observing and communicating about motor-unit activations and muscle activations. Difficulty communicating about these activations can also be a hindrance to coaches, trainers (both human and automated/semi-automated ones), medical providers, and others who instruct humans to perform certain acts in athletics, performing arts, rehabilitation, and other areas.

As will be appreciated, precise feedback regarding these activations is desirable for people learning to use neuromuscular control technology to control one or more system(s)

(e.g., robotic systems, industrial control systems, gaming systems, AR systems, VR systems, other XR systems, etc.).

In some embodiments of the present technology described herein, systems and methods are provided for performing sensing and/or measurement(s) of neuromuscular signals, identification of activation of one or more neuromuscular structure(s), and delivering feedback to a user to provide information about the user's neuromuscular activation(s). In some embodiments, such feedback may be provided as any one or any combination of a visual display, an XR display (e.g., a MR, AR, and/or VR display), haptic feedback, an auditory signal, a user interface, and other types of feedback able to assist the user in performing certain movements or activities. Further, neuromuscular signal data may be combined with other data to provide more accurate feedback to the user. Such feedback to the user may take various forms, e.g., timing(s), intensity (ies), and/or muscle activation(s) relating to the neuromuscular activations of the user. Feedback may be delivered to the user instantaneously (e.g., in real-time or near real-time with minimal latency) or at some point in time after completing the movements or activities.

As will be appreciated, some systems of the present technology described herein may be used within an AR environment and/or a VR environment to provide such feedback to users. For instance, visualization of muscle and motor-unit activation(s) can be projected over a user's body within a display produced by an AR or VR system. Other feedback types, such as, for example, auditory tones or instructions, haptic buzzes, electrical feedback, etc., may be provided alone or in combination with visual feedback. Some embodiments of the present technology may provide a system that is capable of measuring or sensing a user's movement(s) through neuromuscular signals, comparing the movement(s) to a desired movement or movements, and providing feedback to the user about any differences or similarities between the desired movement(s) and the measured or sensed (i.e., actual) movement(s) of the user.

In some embodiments of the technology described herein, sensor signals may be used to predict information about a position and/or a movement of one or more portion(s) of a user's body (e.g., a leg, an arm, and/or a hand), which may be represented as a multi-segment articulated rigid-body system with joints connecting the multiple segments of the rigid-body system. For example, in the case of a hand movement, signals sensed by wearable neuromuscular sensors placed at locations on the user's body (e.g., the user's arm and/or wrist) may be provided as input to one or more inference model(s) trained to predict estimates of the position (e.g., absolute position, relative position, orientation) and the force(s) associated with a plurality of rigid segments in a computer-based musculoskeletal representation associated with a hand, for example, when the user performs one or more hand movements. The combination of position information and force information associated with segments of the musculoskeletal representation associated with a hand may be referred to herein as a "handstate" of the musculoskeletal representation. As a user performs different movements, a trained inference model may interpret neuromuscular signals sensed by the wearable neuromuscular sensors into position and force estimates (handstate information) that are used to update the musculoskeletal representation. Because the neuromuscular signals may be continuously sensed, the musculoskeletal representation may be updated in real-time, and a visual representation of one or more portion(s) of the user's body may be rendered (e.g., a hand within an AR or VR environment) based on current estimates of the handstate determined from the neuromuscular signals. As will be appreciated, an estimate of the user's handstate, determined using the user's neuromuscular signals, may be used to determine a gesture being performed by the user and/or to predict a gesture that the user will perform.

In some embodiments of the present technology, a system that senses neuromuscular signals may be coupled with a system that performs XR (e.g., AR or VR or MR) functions. For example, a system that senses neuromuscular signals used for determining a position of a body part (e.g., a hand, an arm, etc.) of a user may be used in conjunction with an AR system, such that the combined system may provide an improved AR experience for the user. Information gained by these systems may be used to improve the overall AR experience for the user. In one implementation, a camera included in the AR system may capture data that is used to improve an accuracy of a model of a musculoskeletal representation and/or to calibrate the model. Further, in another implementation, muscle activation data obtained by the system via sensed neuromuscular signals may be used to generate a visualization that may be displayed to the user in an AR environment. In yet another implementation, information displayed in the AR environment may be used as feedback to the user to permit the user to more accurately perform, e.g., gestures, or poses, or movements, etc., used for musculoskeletal input to the combined system. Further, control features may be provided in the combined system, which may permit predetermined neuromuscular activity to control aspects of the AR system.

In some embodiments of the present technology, musculoskeletal representations (e.g., handstate renderings) may include different types of representations that model user activity at different levels. For instance, such representations may include any one or any combination of an actual visual representation of a biomimetic (realistic) hand, a synthetic (robotic) hand, a low-dimensional embedded-space representation (e.g., by utilizing Principal Component Analysis (PCA), Isomaps, Local Linear Embedding (LLE), Sensible PCA, and/or another suitable technique to produce a low-dimensional representation), as well as an "internal representation" that may serve as input information for a gesture-based control operation (e.g., to control one or more function(s) of another application or another system, etc.). That is, in some implementations, hand-position information and/or force information may be provided as inputs for downstream algorithms but need not be directly rendered. As mentioned above, data captured by a camera may be used to assist in creating actual visual representations (e.g., improving an XR version of the user's hand using a hand image captured by the camera).

As discussed above, it may be beneficial to measure (e.g., sense and analyze) neuromuscular signals, to determine identifications of an activation of one or more neuromuscular structure(s), and to deliver feedback to the user to provide information about the user's neuromuscular activations. In some embodiments of the technology described herein, in order to obtain a reference for determining human movement, a system may be provided for measuring and modeling a human musculoskeletal system. All or portions of the human musculoskeletal system can be modeled as a multi-segment articulated rigid body system, with joints forming the interfaces between the different segments and joint angles defining the spatial relationships between connected segments in the model.

Constraints on the movement at a joint are governed by the type of joint connecting the segments and the biological structures (e.g., muscles, tendons, ligaments) that may restrict the range of movement at the joint. For example, the shoulder joint connecting the upper arm to a torso or a human subject, and a hip joint connecting an upper leg to the torso, are ball and socket joints that permit extension and flexion movements as well as rotational movements. By contrast, an elbow joint connecting the upper arm and a lower arm (or forearm), and a knee joint connecting the upper leg and a lower leg of the human subject, allow for a more limited range of motion. In this example, a multi-segment articulated rigid body system may be used to model portions of the human musculoskeletal system. However, it should be appreciated that although some segments of the human musculoskeletal system (e.g., the forearm) may be approximated as a rigid body in the articulated rigid body system, such segments may each include multiple rigid structures (e.g., the forearm may include ulna and radius bones), which may enable more complex movements within the segment that is not explicitly considered by the rigid body model. Accordingly, a model of an articulated rigid body system for use with some embodiments of the technology described herein may include segments that represent a combination of body parts that are not strictly rigid bodies. It will be appreciated that physical models other than the multi-segment articulated rigid body system may be used to model portions of the human musculoskeletal system without departing from the scope of this disclosure.

Continuing with the example above, in kinematics, rigid bodies are objects that exhibit various attributes of motion (e.g., position, orientation, angular velocity, acceleration). Knowing the motion attributes of one segment of the rigid body enables the motion attributes for other segments of the rigid body to be determined based on constraints in how the segments are connected. For example, the hand may be modeled as a multi-segment articulated body, with the joints in the wrist and each finger forming interfaces between the multiple segments in the model. Movements of the segments in the rigid body model can be simulated as an articulated rigid body system in which position (e.g., actual position, relative position, or orientation) information of a segment relative to other segments in the model are predicted using a trained inference model, as described in more detail below.

For some embodiments of the present technology, the portion of the human body approximated by a musculoskeletal representation may be a hand or a combination of a hand with one or more arm segments. The information used to describe a current state of the positional relationships between segments, force relationships for individual segments or combinations of segments, and muscle and motor-unit activation relationships between segments in the musculoskeletal representation is referred to herein as the "handstate" of the musculoskeletal representation (see other discussions of handstate herein). It should be appreciated, however, that the techniques described herein are also applicable to musculoskeletal representations of portions of the body other than the hand, including, but not limited to, an arm, a leg, a foot, a torso, a neck, or any combination of the foregoing.

In addition to spatial (e.g., position and/or orientation) information, some embodiments of the present technology enable a prediction of force information associated with one or more segments of the musculoskeletal representation. For example, linear forces or rotational (torque) forces exerted by one or more segments may be estimated.

Examples of linear forces include, but are not limited to, the force of a finger or hand pressing on a solid object such as a table, and a force exerted when two segments (e.g., two fingers) are pinched together. Examples of rotational forces include, but are not limited to, rotational forces created when a segment, such as in a wrist or a finger, is twisted or flexed relative to another segment. In some embodiments, the force information determined as a portion of a current handstate estimate includes one or more of: pinching force information, grasping force information, and information about co-contraction forces between muscles represented by the musculoskeletal representation. It should be appreciated that there may be multiple forces associated with a segment of a musculoskeletal representation. For example, there are multiple muscles in a forearm segment, and force acting on the forearm segment may be predicted based on an individual muscle or based on one or more group(s) of muscles (e.g., flexors, extensors, etc.).

As used herein, the term "gestures" may refer to a static or dynamic configuration of one or more body parts including a position of the one or more body parts and forces associated with the configuration. For example, gestures may include discrete gestures, such as placing or pressing the palm of a hand down on a solid surface, or grasping a ball, or pinching two fingers together (e.g., to form a pose); or continuous gestures, such as waving a finger back and forth, grasping and throwing a ball, rotating a wrist in a direction; or a combination of discrete and continuous gestures. Gestures may include covert gestures that may be imperceptible to another person, such as slightly tensing a joint by co-contracting opposing muscles or using sub-muscular activations. In training an inference model, gestures may be defined using an application configured to prompt a user to perform the gestures or, alternatively, gestures may be arbitrarily defined by a user. The gestures performed by the user may include symbolic gestures (e.g., gestures mapped to other gestures, interactions, or commands, for example, based on a gesture vocabulary that specifies the mapping). In some cases, hand and arm gestures may be symbolic and used to communicate according to cultural standards.

In accordance with some embodiments of the technology described herein, signals sensed by one or more wearable sensor(s) may be used to control an XR system. The inventors have discovered that a number of muscular activation states of a user may be identified from such sensed signals and/or from information based on or derived from such sensed signals to enable improved control of the XR system. Neuromuscular signals may be used directly as an input to an XR system (e.g. by using motor-unit action potentials as an input signal) and/or the neuromuscular signals may be processed (including by using an inference model as described herein) for the purpose of determining a movement, a force, and/or a position of a part of the user's body (e.g. fingers, hand, wrist, leg, etc.). Various operations of the XR system may be controlled based on identified muscular activation states. An operation of the XR system may include any aspect of the XR system that the user can control based on sensed signals from the wearable sensor(s). The muscular activation states may include, but are not limited to, a static gesture or pose performed by the user, a dynamic gesture or motion performed by the user, a sub-muscular activation state of the user, a muscular tensing or relaxation performed by the user, or any combination of the foregoing. For instance, control of the XR system may include control based on activation of one or more individual motor units, e.g., control based on a detected sub-muscular activation state of the user, such as a sensed tensing of a muscle. Identification of one or more muscular activation state(s) may allow a layered or multi-level approach to controlling operation(s) of the XR system. For instance, at a first layer/level, one muscular activation state may indicate that a mode of the XR system is to be switched from a first mode (e.g., an XR interaction mode) to a second mode (e.g., a control mode for controlling operations of the XR system); at a second layer/level, another muscular activation state may indicate an operation of the XR system that is to be controlled; and at a third layer/level, yet another muscular activation state may indicate how the indicated operation of the XR system is to be controlled. It will be appreciated that any number of muscular activation states and layers may be used without departing from the scope of this disclosure. For example, in some embodiments, one or more muscular activation state(s) may correspond to a concurrent gesture based on activation of one or more motor units, e.g., the user's hand bending at the wrist while pointing the index finger. In some embodiments, one or more muscular activation state(s) may correspond to a sequence of gestures based on activation of one or more motor units, e.g., the user's hand bending at the wrist upwards and then downwards. In some embodiments, a single muscular activation state may both indicate to switch into a control mode and indicate the operation of the XR system that is to be controlled. As will be appreciated, the phrases "sensed and recorded", "sensed and collected", "recorded", "collected", "obtained", and the like, when used in conjunction with a sensor signal comprises a signal detected or sensed by the sensor. As will be appreciated, the signal may be sensed and recorded or collected without storage in a nonvolatile memory, or the signal may be sensed and recorded or collected with storage in a local nonvolatile memory or in an external nonvolatile memory. For example, after detection or being sensed, the signal may be stored at the sensor "as-detected" (i.e., raw), or the signal may undergo processing at the sensor prior to storage at the sensor, or the signal may be communicated (e.g., via a Bluetooth technology or the like) to an external device for processing and/or storage, or any combination of the foregoing.

According to some embodiments of the present technology, the muscular activation states may be identified, at least in part, from raw (e.g., unprocessed) sensor signals obtained (e.g., sensed) by one or more wearable sensor(s). In some embodiments, the muscular activation states may be identified, at least in part, from information based on the raw sensor signals (e.g., processed sensor signals), where the raw sensor signals obtained by the one or more wearable sensor(s) are processed to perform, e.g., amplification, filtering, rectification, and/or other form of signal processing, examples of which are described in more detail below. In some embodiments, the muscular activation states may be identified, at least in part, from an output of one or more trained inference model(s) that receive the sensor signals (raw or processed versions of the sensor signals) as input(s).

As noted above, muscular activation states, as determined based on sensor signals in accordance with one or more of the techniques described herein, may be used to control various aspects and/or operations of an XR system. Such control may reduce the need to rely on cumbersome and inefficient input devices (e.g., keyboards, mouses, touchscreens, etc.). For example, sensor data (e.g., signals obtained from neuromuscular sensors or data derived from such signals) may be obtained and muscular activation states may be identified from the sensor data without the user having to carry a controller and/or other input device, and without having the user remember complicated button or key manipulation sequences. Also, the identification of the neuromuscular activation states (e.g., poses, gestures, varying degrees of force associated with the neuromuscular activation states, etc.) from the sensor data can be performed relatively fast, thereby reducing the response times and latency associated with controlling the XR system. Signals sensed by wearable sensors placed at locations on the user's body may be provided as input to an inference model trained to generate spatial and/or force information for rigid segments of a multi-segment articulated rigid-body model of a human body, as mentioned above. The spatial information may include, for example, position information of one or more segments, orientation information of one or more segments, joint angles between segments, and the like. Based on the input, and as a result of training, the inference model may implicitly represent inferred motion of the articulated rigid body under defined movement constraints. The trained inference model may output data useable for applications such as applications for rendering a representation of the user's body in an XR environment, in which the user may interact with physical and/or virtual objects, and/or applications for monitoring the user's movements as the user performs a physical activity to assess, for example, whether the user is performing the physical activity in a desired manner. As will be appreciated, the output data from the trained inference model may be used for applications other than those specifically identified herein. For instance, movement data obtained by a single movement sensor positioned on the user (e.g., on the user's wrist or arm) may be provided as input data to a trained inference model. Corresponding output data generated by the trained inference model may be used to determine spatial information for one or more segments of a multi-segment articulated rigid body model for the user. For example, the output data may be used to determine the position and/or the orientation of one or more segments in the multi-segment articulated rigid body model. In another example, the output data may be used to determine angles between connected segments in the multi-segment articulated rigid-body model.

Figure 25A:
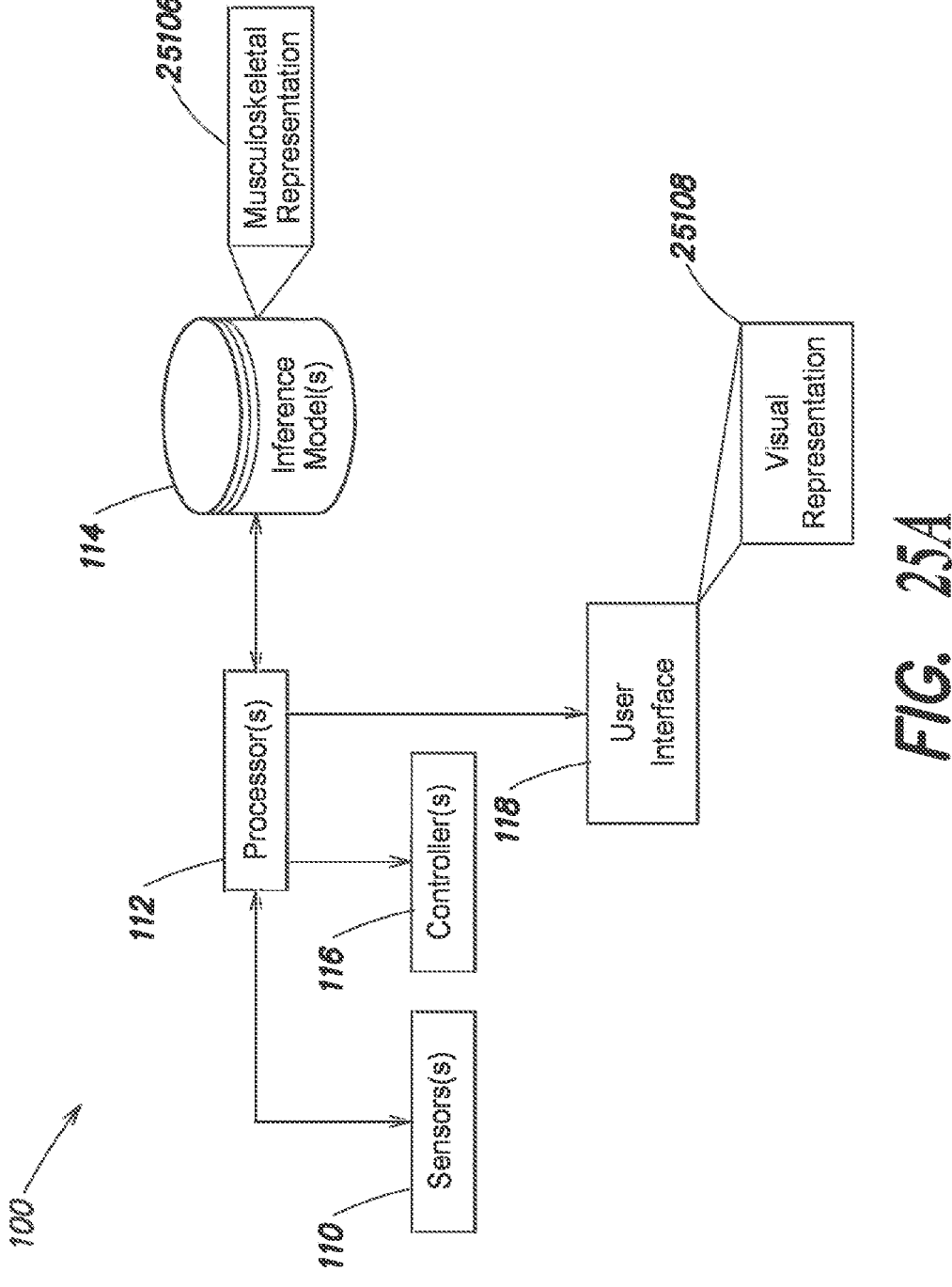
FIG. 25A is a schematic diagram of a computer-based system for processing neuromuscular sensor data, such as signals obtained from neuromuscular sensors, to generate a musculoskeletal representation, in accordance with some embodiments of the technology described herein.

FIG. 25A schematically illustrates an exemplary configuration of system 100, for example, a neuromuscular activity system, in accordance with some embodiments of the technology described herein. The system may comprise one or more sensor(s) 110 configured to sense (e.g., detect, measure, and/or record) signals resulting from activation of motor units within one or more portion(s) of a human body. Such activation may involve a visible movement of the portion(s) of the human body, or a movement that may not be readily seen with a naked eye. The sensor(s) 110 may include one or more neuromuscular sensor(s) configured to sense signals arising from neuromuscular activity in skeletal muscle of a human body (e.g., carried on a wearable device) without requiring the use of auxiliary devices (e.g., cameras, global positioning systems, laser scanning systems) and also without requiring the use of an external sensor or device (i.e., not carried on the wearable device), as discussed below with reference to FIGS. 7A and 8A. As will be appreciated, although not required, one or more auxiliary device(s) may be used in conjunction with the neuromuscular sensor(s).

The term "neuromuscular activity" as used herein refers to neural activation of spinal motor neurons or units that innervate a muscle, muscle activation, muscle contraction, or any combination of the neural activation, muscle activation, and muscle contraction. The one or more neuromuscular sensor(s) may include one or more electromyography (EMG) sensors, one or more mechanomyography (MMG) sensors, one or more sonomyography (SMG) sensors, a combination of two or more types of EMG sensors, MMG sensors, and SMG sensors, and/or one or more sensors of any suitable type able to detect neuromuscular signals. In some embodiments of the present technology, information relating to an interaction of a user with a physical object in an XR environment (e.g., an AR, MR, and/or VR environment) may be determined from neuromuscular signals sensed by the one or more neuromuscular sensor(s). Spatial information (e.g., position and/or orientation information) and force information relating to the movement may be predicted based on the sensed neuromuscular sensor(s) may sense muscular activity related to movement caused by external objects, for example, movement of a hand being pushed by an external object.

The term "neuromuscular activity state" or "neuromuscular activation state" may comprise any information relating to one or more characteristics of a neuromuscular activity, including but not limited to: a strength of a muscular or sub-muscular contraction, an amount of force exerted by a muscular or sub-muscular contraction, a performance of a pose or a gesture and/or any varying amount of force(s) associated with that performance, spatio-temporal positioning of one or more body parts or segments, a combination of position information and force information associated with segments of a musculoskeletal representation associated with a hand (e.g., handstate) or other body part, any pattern by which muscles become active and/or increase their firing rate, and angles between connected segments in a multi-segment articulated rigid-body model. Accordingly, the term "neuromuscular activity state" or "neuromuscular activation state" is meant to encompass any information relating to sensed, detected, and/or recorded neuromuscular signals and/or information derived from those neuromuscular signals.

The one or more sensor(s) 110 may include one or more auxiliary sensor(s), such as one or more photoplethysmography (PPG) sensors, which detect vascular changes (e.g., changes in blood volume) and/or one or more Inertial Measurement Unit(s) or IMU(s), which measure a combination of physical aspects of motion, using, for example, an accelerometer, a gyroscope, a magnetometer, or any combination of one or more accelerometers, gyroscopes and magnetometers. In some embodiments, one or more IMU(s) may be used to sense information about movement of the part of the body on which the IMU(s) is or are attached, and information derived from the sensed IMU data (e.g., position and/or orientation information) may be tracked as the user moves over time. For example, one or more IMU(s) may be used to track movements of portions (e.g., arms, legs) of a user's body proximal to the user's torso relative to the IMU(s) as the user moves over time.

In embodiments that include at least one IMU and one or more neuromuscular sensor(s), the IMU(s) and the neuromuscular sensor(s) may be arranged to detect movement of different parts of a human body. For example, the IMU(s) may be arranged to detect movements of one or more body segments proximal to the torso (e.g., movements of an upper arm), whereas the neuromuscular sensors may be arranged to detect motor unit activity within one or more body segments distal to the torso (e.g., movements of a lower arm (forearm) or a wrist). It should be appreciated, however, that the sensors (i.e., the IMU(s) and the neuromuscular sensor(s)) may be arranged in any suitable way, and embodiments of the technology described herein are not limited based on the particular sensor arrangement. For example, in some embodiments, at least one IMU and a plurality of neuromuscular sensors may be co-located on a body segment to track motor unit activity and/or movements of the body segment using different types of measurements. In one implementation, an IMU and a plurality of EMG sensors may be arranged on a wearable device structured to be worn around the lower arm or the wrist of a user. In such an arrangement, the IMU may be configured to track, over time, movement information (e.g., positioning and/or orientation) associated with one or more arm segments, to determine, for example, whether the user has raised or lowered his/her arm, whereas the EMG sensors may be configured to determine finer-grained or more subtle movement information and/or sub-muscular information associated with activation of muscular or sub-muscular structures in muscles of the wrist and/or the hand.

As the tension of a muscle increases during performance of a motor task, the firing rates of active neurons increase, and additional neurons may become active, which is a process referred to as motor-unit recruitment. A motor unit is made up of a motor neuron and skeletal muscle fibers innervated by that motor neuron's axonal terminals. Groups of motor units often work together to coordinate a contraction of a single muscle; all of the motor units within a muscle are considered a motor pool.

The pattern by which neurons become active and increase their firing rate may be stereotyped, such that the expected motor unit recruitment patterns may define an activity manifold associated with standard or normal movement. In some embodiments, sensor signals may identify activation of a single motor unit or a group of motor units that are "off-manifold," in that the pattern of motor-unit activation is different than an expected or typical motor-unit recruitment pattern. Such off-manifold activation may be referred to herein as, "sub-muscular activation" or "activation of a sub-muscular structure," where a sub-muscular structure refers to the single motor unit or the group of motor units associated with the off-manifold activation. Examples of off-manifold motor-unit recruitment patterns include, but are not limited to, selectively activating a high-threshold motor unit without activating a lower-threshold motor unit that would normally be activated earlier in the recruitment order and modulating the firing rate of a motor unit across a substantial range without modulating the activity of other neurons that would normally be co-modulated in typical motor-unit recruitment patterns. The one or more neuromuscular sensor(s) may be arranged relative to the human body to sense sub-muscular activation without observable movement, i.e., without a corresponding movement of the body that can be readily observed by naked eyes. Sub-muscular activation may be used, at least in part, to provide information to an AR or VR system and/or to interact with a physical object in an AR or VR environment produced by the AR or VR system.

The system 100 also includes one or more computer processor(s) 112 programmed to communicate with the sensor(s) 110. For example, signals obtained by one or more of the sensor(s) 110 may be output from the sensor(s) 110 and provided to the processor(s) 112, which may be programmed to execute one or more machine learning algorithm(s) to process the signals output by the sensor(s) 110. The algorithm(s) may process the signals to train (or retrain) one or more inference model(s) 114, and the trained (or retrained) inference model(s) 114 may be stored for later use in generating a musculoskeletal representation. As will be appreciated, in some embodiments of the present technology, the inference model(s) 114 may include at least one statistical model. Non-limiting examples of inference models that may be used in accordance with some embodiments of the present technology to predict, e.g., handstate information based on signals from the sensor(s) 110 are discussed in U.S. patent application Ser. No. 15/659,504 filed Jul. 25, 2017, entitled "SYSTEM AND METHOD FOR MEASUR-ING THE MOVEMENTS OF ARTICULATED RIGID BODIES," which is incorporated by reference herein in its entirety. It should be appreciated that any type or combination of types of inference model(s) may be used, such as ones that are pre-trained, ones that are trained with user input, and/or ones that are periodically adapted or retrained based on further input.

Some inference models may have a long-standing focus on producing inferences achieved through building and fitting probability models to compute quantitative measures of confidence to determine relationships that are unlikely to result from noise or randomly. Machine-learning models may strive to produce predictions by identifying patterns, often in rich and unwieldy datasets. To some extent, robust machine-learning models may depend on datasets used during a training phase, which may be inherently related to data analysis and statistics. Accordingly, as used herein, the term "inference model" should be broadly construed to encompass inference models, machine-learning models, statistical models, and combinations thereof built to produce inferences, predictions, and/or otherwise used in the embodiments described herein.

In some embodiments of the present technology, the inference model(s) 114 may include a neural network and, for example, may be a recurrent neural network. In some embodiments, the recurrent neural network may be a long short-term memory (LSTM) neural network. It should be appreciated, however, that the recurrent neural network is not limited to be an LSTM neural network and may have any other suitable architecture. For example, in some embodiments, the recurrent neural network may be any one or any combination of: a fully recurrent neural network, a gated recurrent neural network, a recursive neural network, a Hopfield neural network, an associative memory neural network, an Elman neural network, a Jordan neural network, an echo state neural network, a second order recurrent neural network, and/or any other suitable type of recurrent neural network.

In other embodiments, neural networks that are not recurrent neural networks may be used. For example, deep neural networks, convolutional neural networks, and/or feedforward neural networks, may be used.

In some embodiments of the present technology, the inference model(s) 114 may produce one or more discrete output(s). Discrete outputs (e.g., classification labels) may be used, for example, when a desired output is to know whether a particular pattern of activation (including individual biologically produced neural spiking events) is currently being performed by a user, as detected via neuromuscular signals obtained from the user.

For example, the inference model(s) 114 may be trained to estimate whether the user is activating a particular motor unit, activating a particular motor unit at a particular timing, activating a particular motor unit with a particular firing pattern, and/or activating a particular combination of motor units. On a shorter timescale, a discrete classification may be output and used in some embodiments to estimate whether a particular motor unit fired an action potential within a given amount of time. In such a scenario, estimates from the inference model(s) 114 may then be accumulated to obtain an estimated firing rate for that motor unit.

In embodiments of the present technology in which an inference model is implemented as a neural network configured to output a discrete output (e.g., a discrete signal), the neural network may include a softmax layer, such that the outputs of the inference model add up to one and may be interpreted as probabilities. For instance, outputs of the softmax layer may be a set of values corresponding to a respective set of control signals, with each value indicating a probability that the user wants to perform a particular control action. As one non-limiting example, the outputs of the softmax layer may be a set of three probabilities (e.g., 0.92, 0.05, and 0.03) indicating the respective probabilities that a detected pattern of activity is one of three known patterns.

It should be appreciated that when an inference model is a neural network configured to output a discrete output (e.g., a discrete signal), the neural network is not required to produce outputs that add up to one. For example, instead of a softmax layer, the output layer of the neural network may be a sigmoid layer, which does not restrict the outputs to probabilities that add up to one. In such embodiments of the present technology, the neural network may be trained with a sigmoid cross-entropy cost. Such an implementation may be advantageous in cases where multiple different control actions may occur within a threshold amount of time and it is not important to distinguish an order in which these control actions occur (e.g., a user may activate two patterns of neural activity within the threshold amount of time). In some embodiments, any other suitable non-probabilistic multi-class classifier may be used, as aspects of the technology described herein are not limited in this respect.

In some embodiments of the technology described herein, an output of the inference model(s) 114 may be a continuous signal rather than a discrete output (e.g., a discrete signal). For example, the model(s) 114 may output an estimate of a firing rate of each motor unit, or the model(s) 114 may output a time-series electrical signal corresponding to each motor unit or sub-muscular structure. Further, the model may output an estimate of a mean firing rate of all of the motor units within a designated functional group (e.g., within a muscle or a group of muscles).

It should be appreciated that aspects of the technology described herein are not limited to using neural networks, as other types of inference models may be employed in some embodiments. For example, in some embodiments, the inference model(s) 114 may comprise a Hidden Markov Model (HMM), a switching HMM in which switching allows for toggling among different dynamic systems, dynamic Bayesian networks, and/or any other suitable graphical model having a temporal component. Any of such inference models may be trained using sensor signals obtained by the sensor(s) 110.

As another example, in some embodiments of the present technology, the inference model(s) 114 may be or may include a classifier that takes, as input, features derived from the sensor signals obtained by the sensor(s) 110. In such embodiments, the classifier may be trained using features extracted from the sensor signals. The classifier may be, e.g., a support vector machine, a Gaussian mixture model, a regression-based classifier, a decision-tree classifier, a Bayesian classifier, and/or any other suitable classifier, as aspects of the technology described herein are not limited in this respect. Input features to be provided to the classifier may be derived from the sensor signals in any suitable way. For example, the sensor signals may be analyzed as time-series data using wavelet analysis techniques (e.g., continuous wavelet transform, discrete-time wavelet transform, etc.), covariance techniques, Fourier-analytic techniques (e.g., short-time Fourier transform, Fourier transform, etc.), and/or any other suitable type of time-frequency analysis technique. As one non-limiting example, the sensor signals may be transformed using a wavelet transform and the resulting wavelet coefficients may be provided as inputs to the classifier.

In some embodiments, values for parameters of the inference model(s) 114 may be estimated from training data. For example, when the inference model(s) is or includes a neural network, parameters of the neural network (e.g., weights) may be estimated from the training data. In some embodiments, parameters of the inference model(s) 114 may be estimated using gradient descent, stochastic gradient descent, and/or any other suitable iterative optimization technique. In embodiments where the inference model(s) 114 is or includes a recurrent neural network (e.g., an LSTM), the inference model(s) 114 may be trained using stochastic gradient descent and backpropagation through time. The training may employ any one or any combination of: a squared-error loss function, a correlation loss function, a cross-entropy loss function and/or any other suitable loss function, as aspects of the technology described herein are not limited in this respect.

The system 100 also may include one or more controller(s) 116. For example, the controller(s) 116 may include a display controller configured to display a visual representation (e.g., a representation of a hand) on a display device (e.g., a display monitor).

As discussed herein, the processor(s) 112 may implement one or more trained inference model(s) that receive, as input, sensor signals obtained by the sensor(s) 110 and that provide, as output, information (e.g., predicted handstate information) used to generate control signals that may be used to control, for example, an AR or VR system.

The system 100 also may include a user interface 118. Feedback determined based on the signals obtained by the sensor(s) 110 and processed by the processor(s) 112 may be provided to the user via the user interface 118 to facilitate the user's understanding of how the system 100 is interpreting the user's muscular activity (e.g., an intended muscle movement). The user interface 118 may be implemented in any suitable way, including, but not limited to, an audio interface, a video interface, a tactile interface, and electrical stimulation interface, or any combination of the foregoing. The user interface 118 may be configured to produce a visual representation 25108 (e.g., of a hand, an arm, and/or other body part(s) or a user), which may be displayed via a display device associated with the system 100.

As discussed herein, the computer processor(s) 112 may implement one or more trained inference model(s) configured to predict handstate information based, at least in part, on sensor signals obtained by the sensor(s) 110. The predicted handstate information may be used to update a musculoskeletal representation or model 25106, which may be used to render the visual representation 25108 (e.g., a graphical representation) based on the updated musculoskeletal representation or model 25106. Real-time reconstruction of a current handstate and subsequent rendering of the visual representation 25108 reflecting current handstate information in the musculoskeletal representation or model 25106 may be used to provide visual feedback to the user about the effectiveness of the trained inference model(s), to enable the user to, e.g., make adjustments in order to represent an intended handstate accurately. As will be appreciated, not all embodiments of the system 100 include components configured to render the visual representation 25108. For example, in some embodiments, handstate estimates output from the trained inference model and a corresponding updated musculoskeletal representation 25106 may be used to determine a state of the user's hand (e.g., in a VR environment) even though no visual representation based on the updated musculoskeletal representation 25106 is rendered.

The system 100 may have an architecture that may take any suitable form. Some embodiments of the present technology may employ a thin architecture in which the processor(s) 112 is or are included as a portion of a device separate from and in communication with the sensor(s) 110 arranged on one or more wearable device(s). The sensor(s) 110 may be configured to wirelessly stream, in substantially real-time, sensor signals and/or information derived from the sensor signals to the processor(s) 112 for processing. The device separate from and in communication with the sensors(s) 110 may be, for example, any one or any combination of: a remote server, a desktop computer, a laptop computer, a smartphone, a wearable electronic device such as a smartwatch, a health monitoring device, smart glasses, and an AR system.

Some embodiments of the present technology may employ a thick architecture in which the processor(s) 112 may be integrated with one or more wearable device(s) on which the sensor(s) 110 is or are arranged. In some embodiments, processing of sensed signals obtained by the sensor(s) 110 may be divided between multiple processors, at least one of which may be integrated with the sensor(s) 110, and at least one of which may be included as a portion of a device separate from and in communication with the sensor(s) 110. In such an implementation, the sensor(s) 110 may be configured to transmit at least some of the sensed signals to a first computer processor remotely located from the sensor(s) 110. The first computer processor may be programmed to train, based on the transmitted signals obtained by the sensor(s) 110, at least one inference model of the inference model(s) 114.

The first computer processor may then be programmed to transmit the trained at least one inference model to a second computer processor integrated with the one or more wearable devices on which the sensor(s) 110 is or are arranged. The second computer processor may be programmed to determine information relating to an interaction between the user who is wearing the one or more wearable device(s) and a physical object in an AR environment using the trained at least one inference model transmitted from the first computer processor. In this way, the training process and a real-time process that utilizes the trained at least one model may be performed separately by using different processors.

In some embodiments of the present technology, a computer application configured to simulate an XR environment (e.g., a VR environment, an AR environment, and/or an MR environment) may be instructed to display a visual representation of the user's hand (e.g., via the controller(s) 116). Positioning, movement, and/or forces applied by portions of the hand within the XR environment may be displayed based on an output of the trained inference model(s). The visual representation may be dynamically updated based on current reconstructed handstate information using continuous signals obtained by the sensor(s) 110 and processed by the trained inference model(s) 114 to provide an updated computer-generated representation of the user's movement and/or handstate that is updated in real-time.

Information obtained by or provided to the system 100 (e.g., inputs from an AR camera, inputs from the sensor(s) 110 (e.g., neuromuscular sensor inputs), inputs from one or more auxiliary sensor(s) (e.g., IMU inputs), and/or any other suitable inputs) can be used to improve user experience, accuracy, feedback, inference models, calibration functions, and other aspects in the overall system. To this end, in an AR environment for example, the system 100 may include or may operate in conjunction with an AR system that includes one or more processors, a camera, and a display (e.g., the user interface 118, or another interface via AR glasses or another viewing device) that provides AR information within a view of the user. For example, the system 100 may include system elements that couple the AR system with a computer-based system that generates the musculoskeletal representation based on sensor data (e.g., signals from at least one neuromuscular sensor). In this example, the systems may be coupled via a special-purpose or other type of computer system that receives inputs from the AR system and the system that generates the computer-based musculoskeletal representation. Such a computer-based system may include a gaming system, robotic control system, personal computer, medical device, or another system that is capable of interpreting AR and musculoskeletal information. The AR system and the system that generates the computer-based musculoskeletal representation may also be programmed to communicate directly. Such information may be communicated using any number of interfaces, protocols, and/or media.

As discussed above, some embodiments of the present technology are directed to using an inference model 114 for predicting musculoskeletal information based on signals obtained by wearable sensors. Also as discussed briefly above, the types of joints between segments in a multi-segment articulated rigid body model constrain movement of the rigid body. The inference model 114 may be used to predict the musculoskeletal position information without having to place a sensor on each segment of the rigid body that is to be represented in the computer-generated musculoskeletal representation. Additionally, different individuals tend to move in characteristic ways when performing a task that can be captured in statistical or data patterns of individual user behavior. At least some of these constraints on human body movement may be explicitly incorporated in one or more inference model(s) (e.g., the model(s) 114) used for prediction of user movement, in accordance with some embodiments. Additionally or alternatively, the constraints may be learned by the inference model(s) 114 though training based on sensor data obtained from the sensor(s) 110. Constraints imposed on a construction of an inference model may be those set by human anatomy and by physics of a human body, while constraints derived from statistical or data patterns may be those set by human behavior for one or more users from which sensor data has been obtained. Constraints may comprise part of the inference model itself being represented by information (e.g., connection weights between nodes) in the inference model.

As mentioned above, some embodiments of the present technology are directed to using an inference model for predicting information to generate a computer-based musculoskeletal representation and/or to update in real-time a computer-based musculoskeletal representation. For example, the predicted information may be predicted handstate information. The inference model may be used to predict the handstate information based on IMU signals, neuromuscular signals (e.g., EMG, MMG, and/or SMG signals), external or auxiliary device signals (e.g., camera or laser-scanning signals), or a combination of IMU signals, neuromuscular signals, and external device signals detected as a user performs one or more movements. For instance, as discussed above, a camera associated with an AR system may be used to capture data of an actual position of a human subject of the computer-based musculoskeletal representation, and such actual-position information may be used to improve the accuracy of the representation. Further, outputs of the inference model may be used to generate a visual representation of the computer-based musculoskeletal representation in an XR environment. For example, a visual representation of muscle groups firing, force being applied, text being entered via movement, or other information produced by the computer-based musculoskeletal representation may be rendered in a visual display of an XR system. In some embodiments, other input/output devices (e.g., auditory inputs/outputs, haptic devices, etc.) may be used to further improve the accuracy of the overall system and/or to improve user experience. As mentioned above, XR may encompass any one or any combination of AR, VR, MR, and other machine-produced-reality technologies.

As stated above, FIG. 2 illustrates a schematic diagram of an XR-based system 200 according to some embodiments of the present technology. The XR-based system may be a distributed computer-based system that integrates an XR system 201 with a neuromuscular activity system 202. The neuromuscular activity system 202 may be similar to the system 100 described above with respect to FIG. 25A. As will be appreciated, instead of the XR system 201, the XR-based system 200 may comprise an AR system, a VR system, or a MR system.

Generally, the XR system 201 may take the form of a pair of goggles or glasses or eyewear, or other type of device that shows display elements to a user that may be superimposed on "reality." This reality in some cases could be the user's view of the environment of his or her own body part(s) (e.g., arms and hands, legs and feet, etc., as viewed through the user's eyes), or those of another person or an avatar, or a captured view (e.g., by camera(s)) of the user's environment. In some embodiments, the XR system 201 may include one or more camera(s) 204, which may be mounted within a device worn by the user, that captures one or more views experienced by the user in the user's environment, including the user's own body part(s). The XR system 201 may have one or more processor(s) 205 operating within the device worn by the user and/or within a peripheral device or computer system, and such processor(s) 205 may be capable of transmitting and receiving video information and other types of data (e.g. sensor data). As discussed herein, captured video(s) of the user's body part(s) (e.g., hands and fingers) may be used as additional inputs to inference models, so that the inference models can more accurately predict the user's handstates, movements, and/or gestures. For example, information obtained from the captured video(s) can be used to train the inference models to recognize neuromuscular activation patterns or other motor-control signals, including by mapping or otherwise associating recorded images in the video(s) with the neuromuscular patterns detected during any one or more movement(s), gestures(,) and/or pose(s) as recorded.

The XR system 201 may also include one or more sensor(s) 207, such as microphones, GPS elements, accelerometers, infrared detectors haptic feedback elements, or any other type of sensor, or any combination thereof, that would be useful to provide any form of feedback to the user based on the user's movements and/or motor activities. In some embodiments, the XR system 201 may be an audio-based or auditory XR system, and the one or more sensor(s) 207 may also include one or more headphones or speakers.

Further, the XR system 201 may also have one or more display(s) 208 that permit the XR system 201 to overlay and/or display information to the user in addition to the users' reality view. The XR system 201 may also include one or more communication interface(s) 206, which enable information to be communicated to one or more computer systems (e.g., a gaming system or other systems capable of rendering or receiving XR data). XR systems can take many forms and are provided by a number of different manufacturers. Although discussed by way of example, it should be appreciated that one or more embodiments may be implemented within one type or a combination different types of XR systems (e.g., AR, MR, and/or VR systems).

The XR system 201 may be operatively coupled to the neuromuscular activity system 202 through one or more communication schemes or methodologies, including but not limited to: the Bluetooth protocol, Wi-Fi, Ethernet-like protocols, or any number of connection types, wireless and/or wired. It should be appreciated that, for example, the systems 201 and 202 may be directly connected or coupled through one or more intermediate computer systems or network elements. The double-headed arrow in FIG. 2 represents the communicative coupling between the systems 201 and 202.

As mentioned above, the neuromuscular activity system 202 may be similar in structure and function to the system 100 described above with reference to FIG. 25A. In particular, the system 202 may include one or more neuromuscular sensor(s) 209, one or more inference model(s) 210, and may create, maintain, and store a musculoskeletal representation 211. In some embodiments of the present technology, similar to one discussed above, the system 202 may include or may be implemented as a wearable device, such as a band that can be worn by a user, in order to collect (i.e., obtain) and analyze neuromuscular signals from the user. Further, the system 202 may include one or more communication interface(s) 212 that permit the system 202 to communicate with the XR system 201, such as by Bluetooth, Wi-Fi, and/or another communication method. Notably, the XR system 201 and the neuromuscular activity system 202 may communicate information that can be used to enhance user experience and/or allow the XR system 201 to function more accurately and effectively. In some embodiments, the systems 201 and 202 may cooperate to determine a user's neuromuscular activity and to provide real-time feedback to the user regarding the user's neuromuscular activity.

Although FIG. 2 describes a distributed computer-based system 200 that integrates the XR system 201 with the neuromuscular activity system 202, it will be understood integration of these systems 201 and 202 may be non-distributed in nature. In some embodiments of the present technology, the neuromuscular activity system 202 may be integrated into the XR system 201 such that the various components of the neuromuscular activity system 202 may be considered as part of the XR system 201. For example, inputs of neuromuscular signals obtained by the neuromuscular sensor(s) 209 may be treated as another of the inputs (e.g., from the camera(s) 204, from the sensor(s) 207) to the XR system 201. In addition, processing of the inputs (e.g., sensor signals) obtained from the neuromuscular sensor(s) 209 as well as from one or more inference model(s) 210 can be performed by the XR system 201.

Figure 25B:
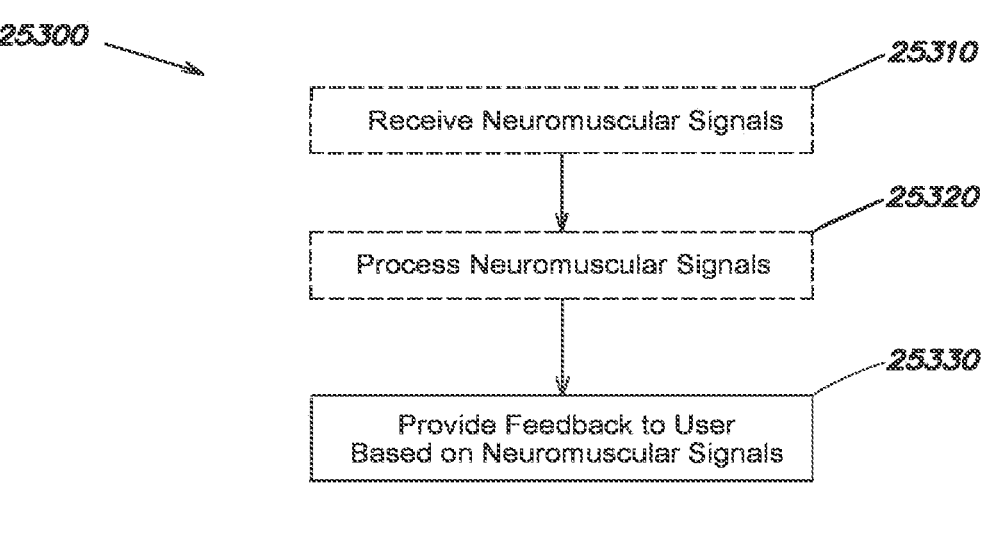
FIG. 25B shows a flowchart of a process for using neuromuscular signals to provide feedback to a user, in accordance with some embodiments of the technology described herein.

FIG. 25B shows a flowchart of a process 25300 for using neuromuscular signals to provide feedback to a user, in accordance with some embodiments of the present technology. As discussed above, there are challenges involved with observation, detection, measurement, processing, and/or communication of neuromuscular activity. The systems and methods disclosed herein are capable of obtaining (e.g., detecting, measuring, and/or recording) and processing neuromuscular signals to determine muscular or sub-muscular activations (e.g., signal characteristics and/or patterns) and/ or other suitable data from motor-unit and muscular activities, and providing feedback regarding such activations to the user. In some embodiments, a computer system may be provided along with one or more sensor(s) for obtaining (e.g., detecting, measuring, and/or recording) neuromuscular signals. As discussed herein, the sensor(s) may be provided on a band that can be placed on an appendage of the user, such as an arm or wrist of the user. In some embodiments, the process 25300 may be performed at least in part by the neuromuscular activity system 202 and/or the XR system 201 of the XR-based system 200.

At block 25310, the system obtains neuromuscular signals. The neuromuscular signals may comprise one or more muscular activation state(s) of the user, and these states may be identified based on raw signals obtained by one or more sensor(s) of the neuromuscular activity system 202 and/or processed signals (collectively "sensor signals") and/or information based on or derived from the sensor signals (e.g., handstate information). In some embodiments, one or more computer processor(s) (e.g., the processor(s) 112 of the system 100, or the processor(s) 205 of the XR-based system 201) may be programmed to identify the muscular activation state(s) based on any one or any combination of: the sensor signals, the handstate information, static gesture information (e.g., pose information, orientation information), dynamic gesture information (movement information), information on motor-unit activity (e.g., information on sub-muscular activation), etc.

In some embodiments, the sensor(s) 209 of the neuromuscular activity system 202 may include a plurality of neuromuscular sensors 209 arranged on a wearable device worn by a user. For example, the sensors 209 may be EMG sensors arranged on an adjustable band configured to be worn around a wrist or a forearm of the user to sense and record neuromuscular signals from the user as the user performs muscular activations (e.g., movements, gestures). In some embodiments, the EMG sensors may be the sensors 704 arranged on the band 702, as shown in FIG. 7A; in some embodiments, the EMG sensors may be the sensors 810 arranged on the elastic band 820, as shown in FIG. 8A. The muscular and/or sub-muscular activations performed by the user may include static gestures, such as placing the user's hand palm down on a table; dynamic gestures, such as waving a finger back and forth; and covert gestures that are imperceptible to another person, such as slightly tensing a joint by co-contracting opposing muscles, or using sub-muscular activations. The muscular activations performed by the user may include symbolic gestures (e.g., gestures mapped to other gestures, interactions, or commands, for example, based on a gesture vocabulary that specifies the mapping).

In addition to the plurality of neuromuscular sensors 209, in some embodiments of the technology described herein, the neuromuscular activity system 202 may include one or more auxiliary sensor(s) configured to obtain (e.g., sense and/or record) auxiliary signals that may also be provided as input to the one or more trained inference model(s), as discussed above. Examples of auxiliary sensors include IMUs, imaging devices, radiation detection devices (e.g., laser scanning devices), heart rate monitors, or any other type of biosensors able to sense biophysical information from a user during performance of one or more muscular activations. Further, it should be appreciated that some embodiments of the present technology may be implemented using camera-based systems that perform skeletal tracking, such as, for example, the Kinect™ system available from the Microsoft Corporation (Redmond, Washington, USA) and the LeapMotion™ system available from Leap Motion, Inc. (San Francisco, California, USA). It should be appreciated that any combination of hardware and/or software may be used to implement various embodiments described herein.

The process 25300 then proceeds to block 25320, the neuromuscular signals are processed. At block 25330, feedback is provided to the user based on the processed neuromuscular signals. It should be appreciated that, in some embodiments of the present technology, the neuromuscular signals may be recorded; however, even in such embodiments, the processing and the providing of feedback may occur continuously, such that the feeding may be presented to the user in near real-time. Feedback that is provided in real-time or near real-time may be used advantageously in situations where the user is being trained, e.g., real-time visualizations provided to the user and/or a coach or trainer to train the user to perform particular movements or gestures properly. In some other embodiments, the neuromuscular signals may be recorded and analyzed at later times, and then presented to the user (e.g., during a review of a performance of a previous task or activity). In these other embodiments, the feedback (e.g., visualizations) may be provided much later, e.g. when analyzing a log of neuromuscular activity for the purposes of diagnoses and/or for tracking ergonomic/fitness/skill/compliance/relaxation. In skill-training scenarios (e.g. athletics, performing arts, industry), information regarding neuromuscular activity can be provided as feedback for training the user to perform one or more particular skill(s). In some cases, a target or desired pattern of neuromuscular activation may also be presented together with the feedback, and/or deviations of the user's actual or realized pattern from the target pattern may be presented or emphasized, such as by providing the user an auditory tone, a haptic buzz, a visual indication, template comparison feedback, or another indication. The target pattern for a task (e.g., a movement, etc.) may be produced from one or more previous pattern(s) of activation of the user or another person, such as during one or more instance(s) when the user or another individual performed particularly the task well (e.g., sat at a desk with his or her arms and hands in an ergonomic position to minimize wrist stain; threw a football or shot a basketball using proper technique; etc.). Further, it should be appreciated that comparison feedback to a target model or deviation information may be provided to the user in real-time, or later (e.g., in an offline review), or both. In certain embodiments, the deviation information can be used to predict an outcome of a task or activity, such as whether the user "sliced" a trajectory of a golf ball with a bad swing, hit a tennis ball with too much force and/or at too steep of an angle to cause the ball to land out-of-bounds, etc.

In some embodiments of the present technology, feedback is provided in the form of a visual display to convey musculoskeletal and/or neuromuscular activation information to a user. For instance, within an XR display, indications may be displayed to the user that identify a visualization of the activations or some other representation indicating that the neuromuscular activity performed by the user is acceptable (or not). In one example, in an XR implementation, visualization of muscular activation and/or motor-unit activation may be projected over the user's body. In this implementation, visualization of activated muscles within, e.g., an arm of the user may be displayed over the arm of the user within an XR display so the user can visualize various ranges of motions for his or her arm via an XR headset. For instance, as depicted in FIG. 25K, a user 251602 may observe a visualization of muscular activations and/or motor-unit activations in the user's arm 251604 during throwing of a ball, by looking at the arm 251604 through an XR headset 251606 during the throwing. The activation are determined from the user's neuromuscular signals sensed by sensors of a wearable system 251608 (e.g., the wearable system 800) during the throwing.

In another example, in an AR implementation, another person (e.g., a coach, a trainer, a physical therapist, an occupational therapist, etc.) may wear an AR headset to observe the user's activity while the user wears, e.g., an arm band on which neuromuscular sensors are attached (e.g., to observe while the user pitches a baseball, writes or draws on a canvas, etc.). For instance, as depicted in FIG. 25L, a coach 251702 may observe a visualization of muscular activations and/or motor-unit activations in one or both arm(s) 251704 of a golfer 251706 during swinging of a golf club by the golfer. The activations are determined from the golfer's neuromuscular signals sensed by sensors of a wearable system 251708 (e.g., the wearable system 800) worn by the golfer 251706. The visualizations may be seen by the coach 251702 via an AR headset 251710.

In some embodiments of the present technology, the feedback may be visual and may take many one or more form(s), and may be combined with other types of feedback, such as non-visual feedback. For instance, auditory, haptic, electrical, or other feedback may be provided to the user in addition to visual feedback.

Figure 25C:
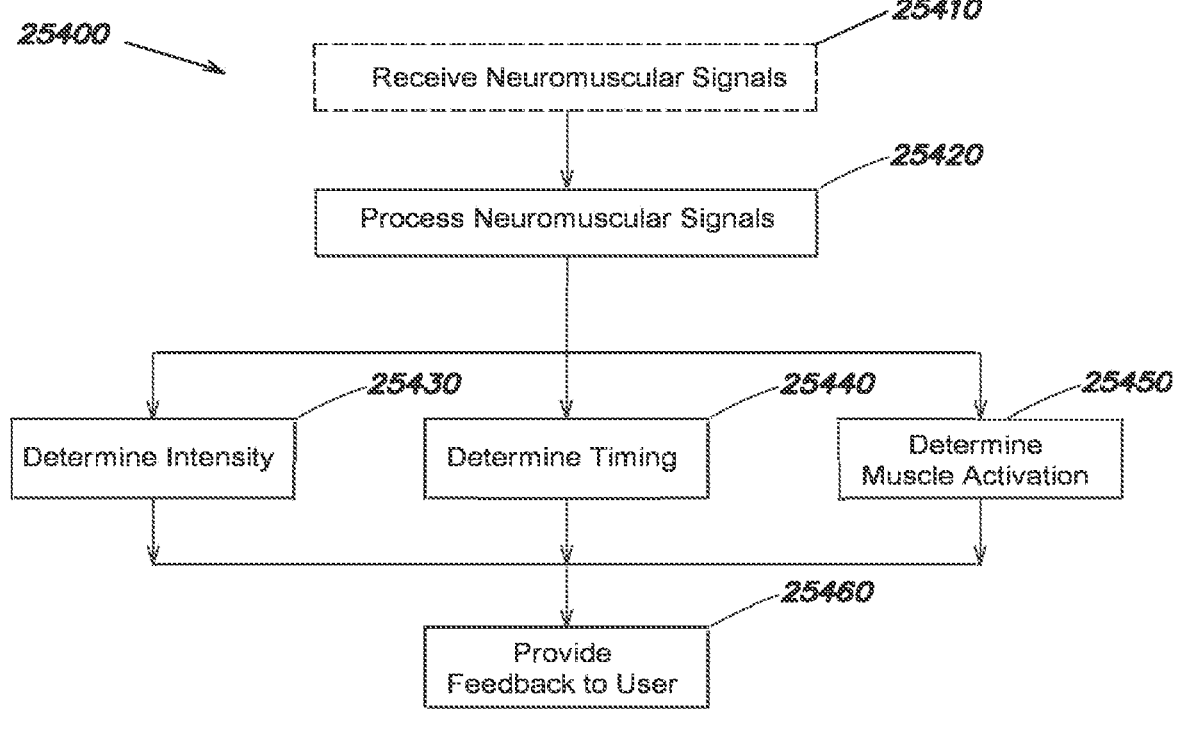
FIG. 25C shows a flowchart of a process for using neuromuscular signals to determine intensity, timing, and/or muscle activation, in accordance with some embodiments of the technology described herein.

FIG. 25C shows a flowchart of a process 25400 in which neuromuscular signals are used to determine intensity, timing, and/or occurrence of one or more muscle activation(s), in accordance with some embodiments of the technology described herein. Systems and methods according to these embodiments may help overcome the difficulty in observing, describing, and/or communicating about neuromuscular activity, such as a timing and/or an intensity of motor-unit and/or muscle activations. Skilled motor acts may require precise coordinated activations of motor units and/or muscles, and learning to perform skilled acts may be hindered by difficulties with observing and communicating about such activations.

Further, difficulty communicating about such activations can be a hindrance to coaches and medical providers. As will be appreciated, feedback regarding a person's performance of skilled motor acts is needed in neuromuscular control technology, where the person may use neuromuscular signals to control one or more devices.

In some embodiments of the present technology, the process 25400 may be performed at least in part by a computer-based system such as the neuromuscular activity system 202 and/or the XR system 201 of the XR-based system 200. More specifically, neuromuscular signals may be obtained from a user wearing one or more neuromuscular sensor(s), and, at block 25410, the neuromuscular signals may be received by the system. For example, the sensor(s) may be arranged on or within a band (e.g., the bands of the wearable systems 700 and 800) and positioned over an area of the user's body, such as an arm or a wrist. At block 25420, the received neuromuscular signals are processed to determine one or more aspects of these signals. For example, at block 25430, the system may determine an intensity of an activation (e.g., a contraction) of a particular motor unit or an intensity of one or more group(s) of motor units of the user. In this example, the system may determine a firing rate of the motor unit(s) and/or associated force(s) generated by the motor unit(s). The system may provide information about the determined intensity as feedback to the user, at act 25460, and this feedback may be provided alone or in combination with other information derived from the neuromuscular signals. At block 25440, the system may determine a timing of activities of a particular motor unit. In certain embodiments, maximal muscular activation or contraction states of a particular user can be previously recorded and used as a comparator to current muscular activation or contraction states of the user as detected and recorded during the user's performance of a movement or exercise. For example, if the user's maximal velocity for throwing a baseball is 100 mph, i.e., a fastball, the muscular activation or contraction states of the user's arm and shoulder muscles, as detected during such throwing of a fastball, can be used to visually compare the previously recorded muscular-activation or contraction states with the currently recorded states during the user's successive performances of throwing a fastball. In another example, a user with motor neuropathy can be monitored in real-time during treatment by a medical provider by comparing previously recorded forearm muscular activation states with current muscular activation states detected as the user, e.g., draws on a canvas, and such real-time comparison feedback of current versus previous muscular activation states can be presented to the user and/or the medical provider. At block 25440, the system may also determine a timing of one or more particular motor-unit activation(s). For example, how the motor unit(s) function over a period of time may be determined from the neuromuscular signals, and feedback regarding such a timing determination may be provided to the user (e.g., at block 25460). For instance, a sequence and timing of activities of particular motor unit(s) may be presented to the user, alone or in conjunction with model or target information previously collected from the user or from a different person. Also, specific information relating to, e.g., one or more particular muscle activation(s) may be determined at block 25450 and presented to the user as feedback at block 25460. As will be appreciated, the blocks 25430, 25440, and 25450 may be performed concurrently or sequentially or, in some embodiments, only one or two of these acts may be performed while the other one or two of these acts may be omitted.

Figures 25D, 25E:
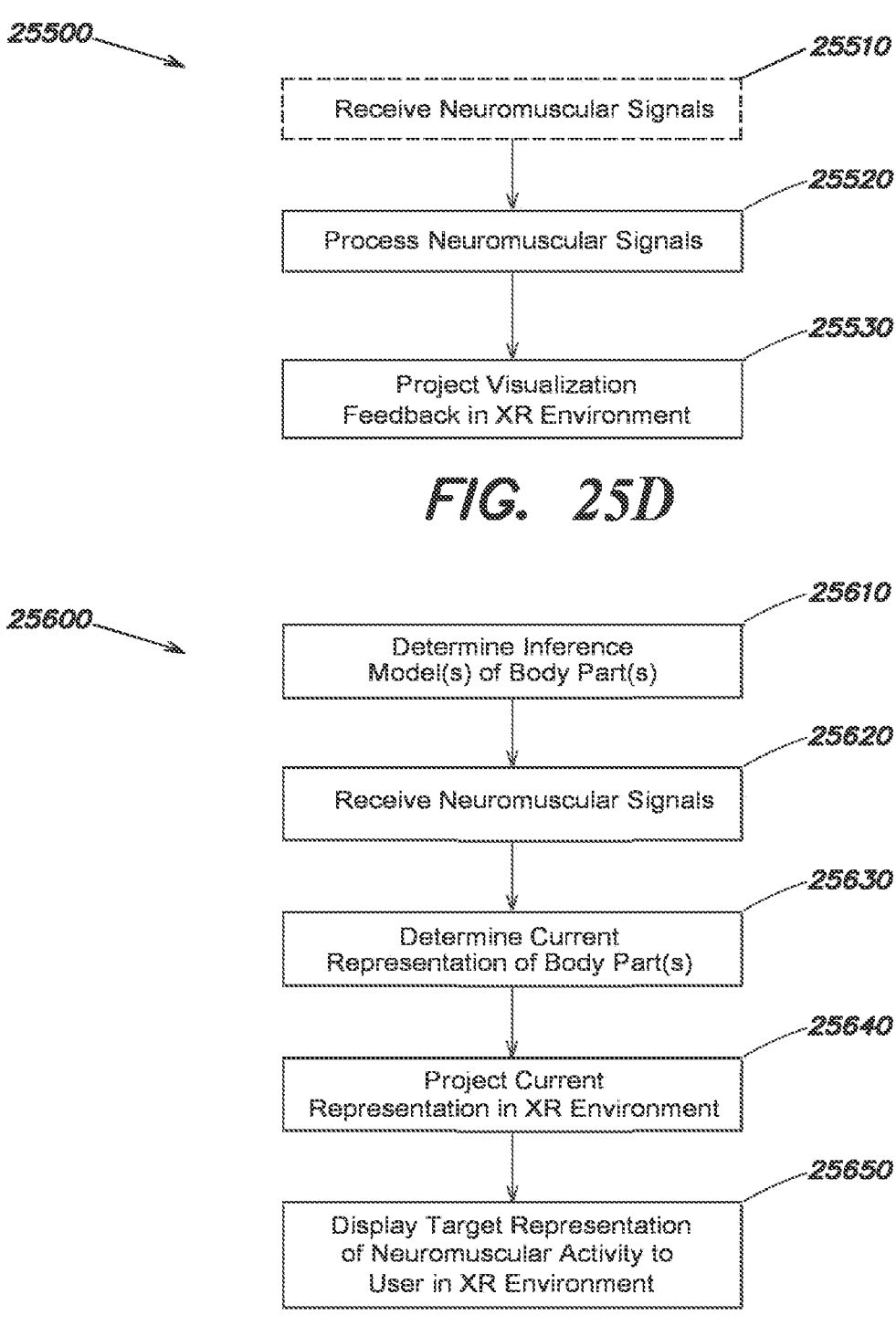
FIG. 25D shows a flowchart of a process for using neuromuscular signals to provide a projected visualization feedback in an AR environment, in accordance with some embodiments of the technology described herein.
FIG. 25E shows a flowchart of a process for using neuromuscular signals to provide current and target musculoskeletal representations in an AR environment, in accordance with some embodiments of the technology described herein.

FIG. 25D shows a flowchart of a process 25500 in which neuromuscular signals are processed to produce a visualization, which may be projected in an XR environment, in accordance with some embodiments of the technology presented herein. In particular, in the XR environment, the visualization may be projected over a body part of the user, such as an arm of the user, to provide the user with feedback information that may involve the body part. For instance, in one implementation, the projection may include a visual indication that shows muscle-group activations and/or degrees of joint angles within the projected feedback information. In one such scenario, a muscular representation (e.g., an animated view of muscle activations) may be projected over a view of the user's arm, and indications of particular activations and/or joint angles as measured by the received and processed neuromuscular signals may be shown by the muscular representation. The user then may adjust his/her movement to achieve a different result. In an exercise scenario, the user may use the XR visualization as feedback to slightly vary his/her intensity or movement to achieve a desired muscle activation (e.g., to activate a certain muscle group to be exercised) at a certain intensity level) and may do so at a given joint angle as provided in the feedback. In this way, the user can monitor and control the intensity of his or her muscular activation(s) or track ranges of motion of one or more joints. It can be appreciated that such feedback would be advantageous in other scenarios, including but not limited to: physical rehabilitation scenarios where the user works to strengthen muscles and/or surrounding ligaments, tendons, tissues, etc., or to increase a joint's range of motion; athletic performance scenarios, such as throwing a baseball, shooting a basketball, swinging a golf club or tennis racquet, etc.; and coaching or instructional scenarios where another person alone, or in combination with the user, views the user's muscular activation and/or joint-angle feedback and provides corrective instruction to the user.

FIG. 25E shows a flowchart for a process 25600 in which neuromuscular signals are processed to produce a visualization, which may be displayed in an XR environment, in accordance with some embodiments of the present technology. In particular, the process 25600 may be executed to enable the user to view a visualization of a target or desired neuromuscular activity within the XR environment as well as a visualization of a realized neuromuscular activity performed by the user. The process 25600 may be executed at least in part by a computer-based system such as the neuromuscular activity system 202 and/or the XR system 201 of the XR-based system 200. In skill-training scenarios (e.g. athletics, performing arts, industry, etc.), information regarding a target neuromuscular activity can be provided as extra feedback for the user. In some cases, a target pattern of neuromuscular activation may be presented to the user in a display (e.g., within an XR display, or another type of display) and/or deviations of a realized pattern obtained from the user's neuromuscular signals from the target pattern may be presented or emphasized. Such deviations may be presented to the user in one or more form(s), such as an auditory tone, a haptic buzz, a visual indication (e.g., a visual representation of the realized pattern superimposed to a visual representation of the target pattern in which deviations are highlighted), and the like. It can be appreciated that in some instances deviations between the realized pattern and the targeted pattern can be generated and provided to the user in real-time or near real-time, while in other instances such deviations can be provided "offline" or after fact, such as upon the user's request at a later time.

One way to create the target pattern may be from one or more previously performed realized pattern(s) of activation during one or more instance(s) when the user or another individual performed a desired activation task particularly well. For example, in one scenario, an expert (e.g., an athlete) may perform the desired activation task well, and neuromuscular signals may be obtained from the expert during performance of that task. The neuromuscular signals may be processed to obtain visual target neuromuscular activations, which may be displayed as feedback to the user within, e.g., a display in an XR environment. In various embodiments of the present technology, the feedback can be shown to the user as a separate example display, as activations that are grafted or projected onto the user's appendage(s), and/or as activations that may be compared to the user's actual or realized activations.

In FIG. 25E, at block 25610, the system determines an inference model built according to the user's body or body part (e.g., hand, arm, wrist, leg, foot, etc.). The inference model may be or may include one or more neural network model(s), as discussed above, trained to classify and/or assess neuromuscular signals captured from a user. The inference model may be trained to recognize one or more pattern(s) that characterize a target neuromuscular activity. At block 25620, the system receives neuromuscular signals from one or more sensor(s) worn by the user during performance of a task corresponding to the target neuromuscular activity, and at block 25630, the system determines a current representation of one or more part(s) of the user's body (e.g., appendage(s) and/or other body part(s)) based on the received neuromuscular signals and the inference model.

At block 25640, the system projects the current representation of the user's body part(s) within the XR environment. For example, the XR display may display a graphical representation of the user's body over an actual view of the body part(s) (e.g., of an arm) or an avatar can be presented that mimics the user's appearance in the XR environment.

Further, neuromuscular status information may be displayed within this representation, such an indication of muscular activity within one or more muscle groups. At block 25650, the XR display may also display a target representation of neuromuscular activity. For instance, the target representation may be displayed on the same display as the current representation of the user's body part(s), and may be shown as an image that is projected onto a view of the user, e.g., an actual appendage of the user or onto the user's avatar or through some other representation of the user's appendage, which need not connect directly to the user. As discussed above, such feedback may be provided to the user by itself or in combination with other types of feedback indicating the user's performance of the task, such as haptic feedback, audio feedback, and/or other types of feedback.

Figure 25F:
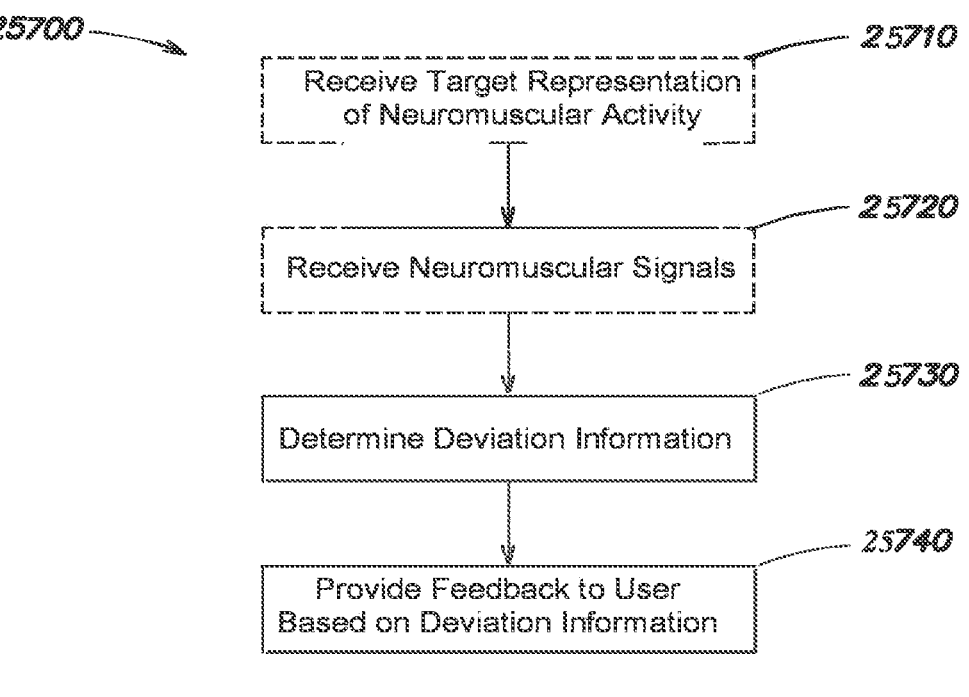
FIG. 25F shows a flowchart of a process for using neuromuscular signals to determine deviations from a target musculoskeletal representation, and to provide feedback to a user, in accordance with some embodiments of the technology described herein.

FIG. 25F shows a flowchart for another process 25700 in which neuromuscular signals, which are obtained from a user during performance of a task (e.g., a movement), are processed to determine deviations of the user's performance from a target performance, and providing feedback to the user in the form of deviation information, in accordance with some embodiments of the present technology. Such deviation information, resulting from the process 25700, may help the user achieve or perform, e.g., a desired movement that closely resembles the target performance. In one implementation, deviation information may be input into the system automatically and may be derived from previously processed inputs relating to a correct or best way of performing a given task, activity, or movement. In another implementation, in addition to or alternative to the automatically input deviation information, deviation information may be manually input by the user to help the user achieve movement(s) closer to a target for the given task, activity, or movement. For instance, deviations of a realized pattern, determined from the user's performance, from a target pattern, corresponding to a target performance, may be presented or emphasized to the user as feedback in the form of, e.g., an auditory tone that increases in loudness according to a deviation amount, a haptic buzz that increases in amplitude according to the deviation amount, or a visual indication showing the deviation amount) and/or the user can update deviation information manually by, e.g., make a drawing or an annotation within the XR environment.

The process 25700 may be executed at least in part by a computer-based system such as the neuromuscular activity system 202 and/or the XR system 201 of the XR-based system 200. At block 25710, the system may receive a target representation of neuromuscular activity. For instance, the target representation may identify a target movement and/or one or more target muscle activation(s). The target representation of neuromuscular activity may be a recorded signal provided to the system and used as a reference signal. At block 25720, the system may receive neuromuscular signals obtained from a user wearing one or more neuromuscular sensor(s) while performing an act (e.g., a movement, a gesture, etc.) to be evaluated. For instance, the user may wear a band (e.g., the bands in FIGS. 7A and 8A) carrying sensors that sense the neuromuscular signals from the user and provides the sensed neuromuscular signals to the system in real time and provide feedback to the user (in real time, near-real time, or at a later period (e.g., in a review session)). At block 25730, the system may determine deviation information derived by comparing a target activity to a measured activity based on the received neuromuscular signals. The feedback provided to the user may include parameters that determine a quality measure of an entire act performed by the user (e.g., a complex movement comprising multiple muscle activations and/or physical movement) and/or specific elements of the act (e.g., a specific muscle activation). In some embodiments, joint angles, motor-unit timing(s), intensity (ies), and/or muscle activation(s) relating to the user's neuromuscular activations may be measured in relation to the target activity. In particular, comparisons may be performed between models (e.g., a target model and a user model to be evaluated). Further, in some embodiments, the target model may be adapted to specifics of the user model to provide more accurate comparisons (e.g., normalizing the target model to a specific user based on differences in sizes between the user and a model performer of the target model).

At block 25740, feedback can be provided to the user based on the deviation information. In particular, the deviation information may indicate to the user that an activity or task was performed correctly or incorrectly, or was performed to some measured quality within a range. Such feedback may be visual, such as by an indication within an XR display that a particular muscle group was not activated via a projection on the user's arm (e.g., a projection of a muscle group colored red on the user's arm) or that the particular muscle group was only partially activated (e.g., activated to 75% as opposed to an intended 90% of maximal contraction). Also, a display of timing(s), intensity (ies), and/or muscle activation(s) relating to the user's neuromuscular activations may be displayed to the user within the XR display (e.g., as projection onto the user's body or onto the user's avatar). As discussed above, the visual feedback may be provided alone or in combination with other feedback, such as auditory (e.g., by a voice indication that the user's movement is unsatisfactory), haptic (such as a haptic buzz, resistive tension, etc.), and/or other feedback. Such deviation information may be helpful for the user to improve his or her performance of the activity or task and to more accurately track the target activity. This type of feedback could assist users developing their ability to use control systems involving neuromuscular signals. For example, visualization of neuromuscular activations could help a user learn to activate atypical combinations of muscles or motor units.

Figure 25G:
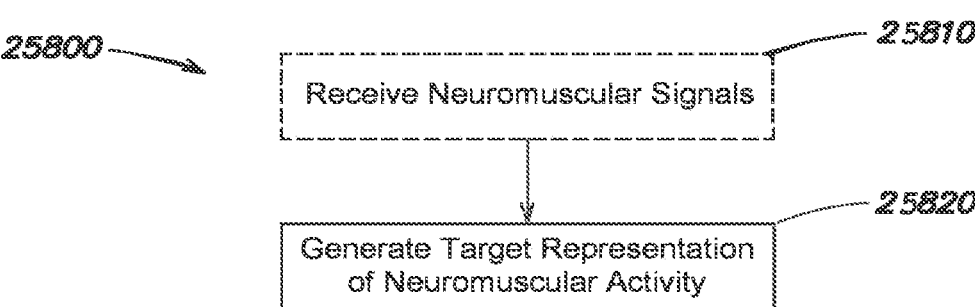
FIG. 25G shows a flowchart of a process for using neuromuscular signals to obtain target neuromuscular activity, in accordance with some embodiments of the technology described herein.

FIG. 25G shows a flowchart for a process 25800 for generating a target neuromuscular activity based on received neuromuscular signals, in accordance with some embodiments of the present technology. The process 25800 may be executed at least in part by a computer-based system such as the XR-based system 200. As discussed above, the system may use a target activity as a reference by which the user's activity may be assessed or measured. To elicit such a target activity, a neuromuscular system or other type of system (e.g., the neuromuscular activity system 202) may receive neuromuscular signals (e.g., at block 25810) and may generate a model of a target neuromuscular activity based on these signals. Such neuromuscular signals may be used in addition to other types of signals and/or data such as, for example, camera data. Such neuromuscular signals may be sampled from an expert performer (e.g., an athlete, a trainer, or another suitably skilled person) and modeled for use as the target activity. For instance, a golf swing activity may be captured from one or more golfing professional(s), modeled, and stored as a target activity for use in a golf training exercise, game, or other system.

In some instances, neuromuscular signals sampled from the user's previous performances of an activity can be used to assess user's progress over time, based on computed deviations between user's previous performances and a current performance of the user (e.g., for training and/or rehabilitation over time). In this way, the system can track the user's performance progress in relation to a reference activity.

Figure 25H:
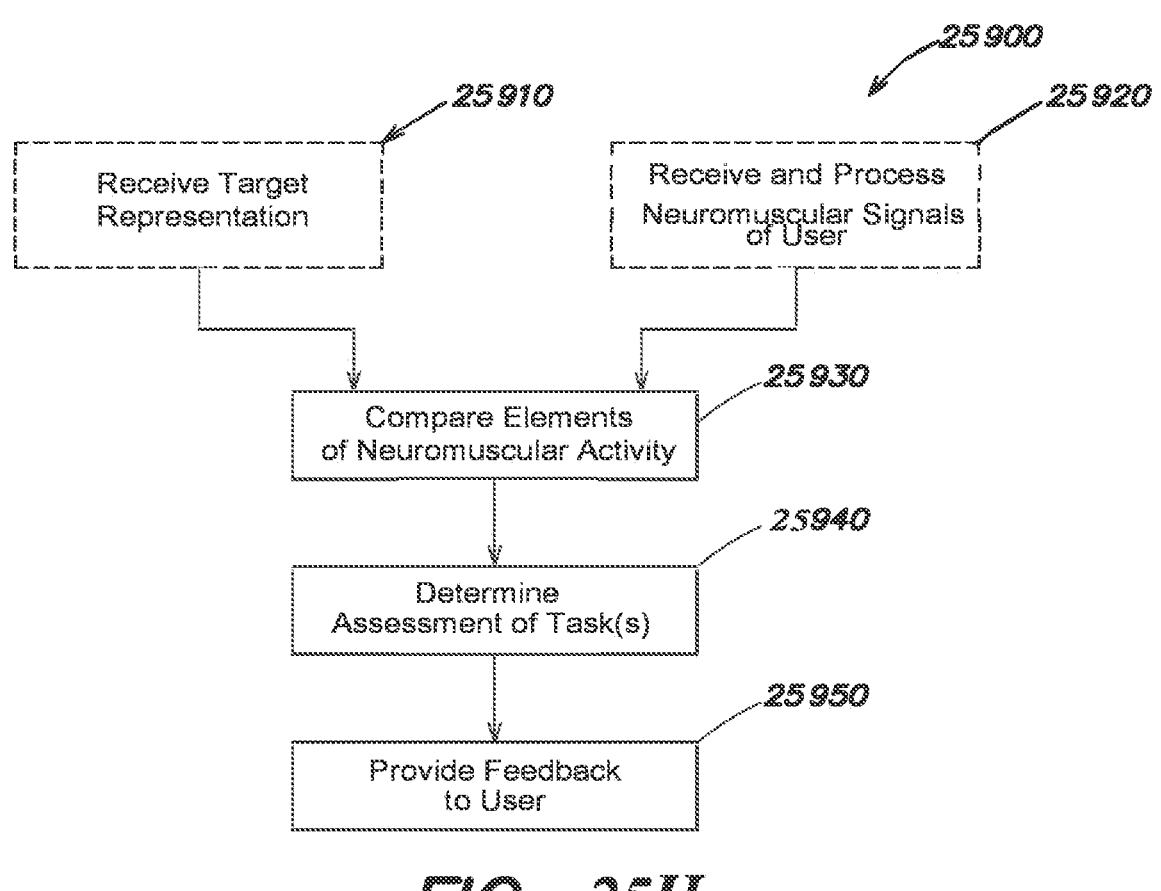
FIG. 25H shows a flowchart of a process for using neuromuscular activity to assess one or more task(s) and to provide feedback, in accordance with some embodiments of the technology described herein.

FIG. 25H shows a flowchart for a process 25900 for assessing one more task(s) based on compared neuromuscular activity, in accordance with some embodiments of the present technology. The process 25900 may be executed at least in part by a computer-based system such as the XR-based system 200. As discussed above, inference models may be trained and used to model a user's neuromuscular activity as well as a target or model activity. Also, as discussed above with reference to FIG. 25G, the system may be capable of receiving a target neuromuscular activity (e.g., at block 25910) to be used as a reference. Such target activity may be preprocessed and stored in memory (e.g., within a processing system, a wearable device, etc.) for future comparisons. At block 25920, the system may receive and process neuromuscular signals of the user being monitored. For example, sensors of a wearable system (e.g., 700 shown in FIG. 7A, 800 shown in FIG. 8A) may be worn by the user to sense the neuromuscular signals from the user, and the neuromuscular signals may be provided to the system for processing (e.g., processing via one or more inference model(s), as discussed above). At block 25930, the system may compare elements of neuromuscular activity from the sensed signals to the stored reference.

At block 25940, the system may determine an assessment of one or more task(s). The assessment may be an overall assessment of a complex movement and/or an assessment of one or more specific element(s), such as a muscle movement. At block 25950, feedback may be provided to the user by the system (e.g., in an XR display with or without other feedback channels, as described above).

In some implementations, the feedback provided to the user be provided in real-time or near real-time, as is advantageous for training. In other implementations, the feedback (e.g., a visualization) may be provided at a later time, e.g., when analyzing a log of neuromuscular activity for purposes of diagnoses and/or for ergonomic/fitness/skill/compliance/ relaxation tracking. In some embodiments, such as monitoring (in real-time) a compliance-tracking task, the user may receive feedback in near real-time. For example, the user may be instructed to tighten a screw, and, based on the user's neuromuscular activity, the system could estimate how tightly the user turned the screw and provide feedback to adjust his or her performance of this task accordingly (e.g., by presenting text and/or an image in an XR environment signaling that the user needs to continue tightening the screw). Further, although a target activity may require a high level of skill to be performed well (e.g., to hit a golf ball accurately), it should be appreciated that the system may be used to measure any activity requiring any level of skill.

In some embodiments of the technology described herein, information about the user's muscle activations may be available long before the user would otherwise get feedback about his or her performance of a task corresponding to the muscle activations. For example, a golfer may have to wait multiple seconds for an outcome of a swing (e.g., waiting to see whether a ball hit by the golfer deviates from a desired trajectory), and a tennis player may have to wait for an outcome of a swing (e.g., waiting to see ball to hit the ground before learning whether a serve was in play or out of bounds). In cases such as these, the system may present immediate feedback derived from neuromuscular data (possibly in conjunction with other data such as that from one or more auxiliary sensor(s)), for example, a tone to indicate that the system has detected that the serve will land out of bounds.

Advance feedback such as this can be used to, e.g., abort a performance of the task when permissible (e.g., if an error is detected during the golfer's backswing) or to facilitate training with more immediate feedback. The system can be trained, for example, by having the user indicate (e.g., with voice) whether each instance of a motor act (a completed golf swing in this example) was successful, to provide supervised training data.

In some embodiments, feedback presented to a user during performance of a task or after completion of the task may relate to the user's ability to perform the task accurately and/or efficiently. For example, neuromuscular signals recorded during a performance of the task (e.g., tightening a bolt) may be used to determine whether the user performed the task accurately and/or optimally, and feedback may be provided to instruct the user about how to improve performance of the task (e.g., provide more force, position hands and/or fingers in an alternate configuration, adjust hands and/or arms and/or fingers relative to each other, etc.). In some embodiments, the feedback regarding the performance of the task may be provided to the user before the task has been completed, in order to guide the user through proper performance of the task. In other embodiments, the feedback may be provided to the user, at least in part, after the task has been completed to allow the user to review his or her performance of the task, in order to learn how to perform the task correctly.

In some other embodiments relating to physical skill training, augmentation and instrumentations, the system may be used to monitor, assist, log, and/or help the user in a variety of scenarios. For example, the system may be used in a following (e.g., counting) activity, such as knitting or an assembly-line activity. In such cases, the system may be adapted to follow along the user's movements, align his or her activities with instruction(s), step(s), pattern(s), recipe (s), etc.

Further, the system may be adapted to provide error detection and/or alerting functions. For instance, the system can prompt the user with help, documents, and/or other feedback to make the user more efficient and to keep the user on track with performing a task. After the task has been performed, the system may compute metrics about task performance (e.g., speed, accuracy).

In some embodiments of the present technology, the system may be capable of providing checklist monitoring to assist the user in performing an overall activity or set of tasks. For instance, surgeons, nurses, pilots, artists, etc., who perform some types of activities may benefit by having an automated assistant that is capable of determining whether certain tasks for an activity were performed correctly. Such a system may be capable of determining whether all tasks (e.g., physical-therapy steps) on a checklist were executed properly, and may be capable of providing some type of feedback to the user that tasks on the checklist were completed.

Aspects described herein may be used in conjunction with control assistants. For instance, control assistants may be provided for smoothing input actions of the user in order to achieve a desired output control, such as within a surgical mechanical device to smooth shaky hands (e.g., Raven), within a CAD program (e.g., AutoCAD) to control drafting input, within a gaming application, as well as within some other type(s) of applications.

Aspects described herein may be used in other applications such as life logging applications or other applications where activity detection is performed and tracked. For instance, various elements may be implemented by systems (e.g., activity trackers such as Fitbit® available from Fitbit, Inc., (San Francisco, California, USA), and the like) that can detect and recognize different activities, such as eating, walking, running, biking, writing, typing, brushing teeth, etc. Further, various implementations of such system may be adapted to determine, e.g., how often, how long, how much the recognized activities were performed. The accuracy of such systems may be improved using neuromuscular signals, as neuromuscular signals may be more accurately interpreted than existing inputs recognized by these systems. Some further implementations of such systems may include applications that assist users to learn physical skills. For example, a user's performance of activities requiring physical skills such as performing music, athletics, controlling a yoyo, knitting, magic tricks, etc.) may be improved by a system that can detect and provide feedback on the user's performance of such skills. For instance, in some implementations, the system may provide visual feedback and/or feedback that may be presented to the user in a gamified form. In some implementations, feedback may be provided to the user in the form of coaching (e.g., by an artificial-intelligence inference engine and/or an expert system), which may assist the user in learning and/or performing a physical skill.

Figure 25I:
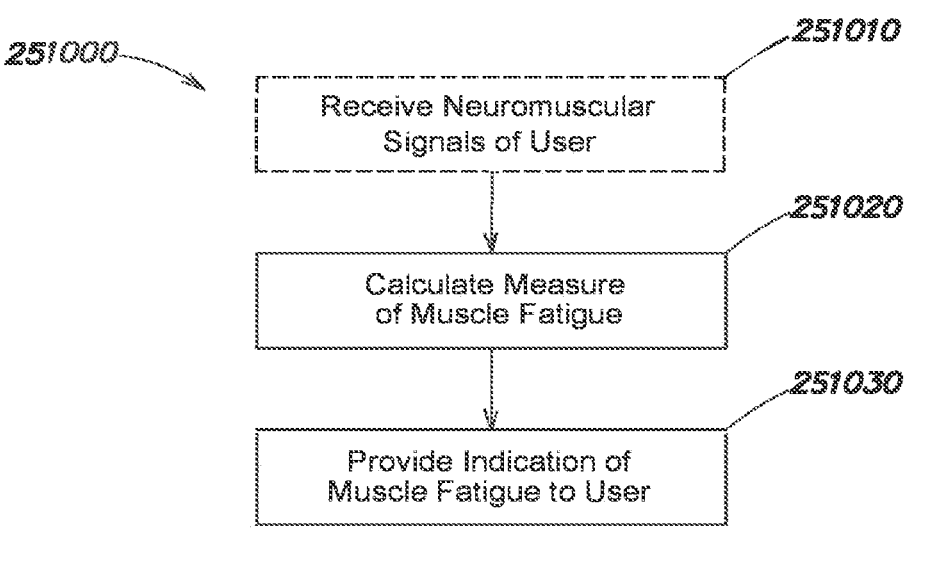
FIG. 25I shows a flowchart of a process for using neuromuscular signals to monitor muscle fatigue, in accordance with some embodiments of the technology described herein.

FIG. 25I shows a flowchart for process 251000 for monitoring muscle fatigue, in accordance with some embodiments of the technology described herein. In particular, it is realized that there may be a benefit in observing muscle fatigue in a user and providing indications of muscle fatigue to the user (or to another system, or to another person (e.g., trainer), etc.). The process 251000 may be executed at least in part by a computer-based system such as the XR-based system 200. At block 251010, the system receives neuromuscular signals of the user being monitored via one or more sensor(s) (e.g., on the wearable systems 700 and 800 shown in FIGS. 7A and 8A, or another sensor arrangement). At block 251020, the system may calculate or determine a measure of muscle fatigue from the user's neuromuscular signals. For instance, fatigue may be calculated or determined as a function of spectral changes in EMG signals over time, using historical neuromuscular signals collected for the user. Alternatively, fatigue may be assessed based on a firing pattern of one or more motor unit(s) of the user. Other methods for calculating or determining fatigue based on neuromuscular signals may be used, such as an inference model that translates neuromuscular signals into a subjective fatigue score. At block 251030, the system may provide an indication of muscle fatigue to the user (or to another system, a third party (e.g., a trainer, medical provider), or another entity (e.g., a vehicle that monitors muscle fatigue)). For instance, the indication can be provided visually (e.g., by a projection in an XR environment, or another type of visual indication), audibly (e.g., a voice indicating fatigue is occurring), or another type of indication. In this way, more detailed information regarding the user may be collected and presented as feedback.

For example, in safety or ergonometric applications, the user may be provided with immediate feedback (e.g., a warning) indicating, e.g., muscle activation and fatigue level, which can be detected by spectral changes in data captured by EMG sensors or another suitable type of sensor, and the user also may be provided with an historical view of a log of the user's muscle activations and fatigue levels, potentially within a postural context. The system may provide as feedback a suggestion to change a technique (for physical tasks) or to change a control scheme (for virtual tasks) as a function of the user's fatigue. For instance, the system may be used to alter a physical rehabilitation training program, such as by increasing an amount of time to a next session, based on a fatigue score determined within a current rehabilitation session. A measure of fatigue may be used in association with other indicators to warn the user or others of one or more issue(s) relating to the user's safety. For instance, the system may help in determining ergonometric issues (e.g., to detect whether the user is lifting too much weight, or typing inappropriately or with too much force, etc.) and recovery monitoring (e.g., to detect whether the user is pushing himself or herself too hard after an injury). It should be appreciated that various embodiments of the system may use fatigue level as an indicator or as input for any purpose.

In some embodiments of the present technology, systems and methods are provided for assisting, treating, or otherwise enabling a patient with an injury or a disorder that affects his or her neuromuscular system by delivering feedback about the patient's neuromuscular activity (i.e. in an immersive experience such as via XR displays, haptic feedback, auditory signals, user interfaces, and/or other feedback types to assist the patient in performing certain movements or activities). For a patients taking part in neuro-rehabilitation, which may be required due to injury (e.g., peripheral nerve injury and/or spinal cord injury), stroke, cerebral palsy, or another cause, feedback about patterns of neuromuscular activity may be provided that permit the patients to gradually increase neuromuscular activity or otherwise improve their motor-unit outputs. For example, a patient may only be able to activate a small number of motor units during an early phase of therapy, and the system may provide feedback (e.g., 'high-gain feedback') showing a virtual or augmented part of the patient's body moving a greater degree than actually occurs. As therapy progresses, the gain provided for feedback can be reduced as the patient achieves better motor control. In other therapeutic examples, a patient may have a motor disorder such as a tremor and be guided through feedback specific to the patient's neuromuscular impairment (e.g. that shows less tremor in the feedback). Thus, feedback may be used to show small incremental changes in neuromuscular activation (e.g., each increment being recognized as achievable by the patient), to encourage the patient's rehabilitation progress.

Figure 25J:
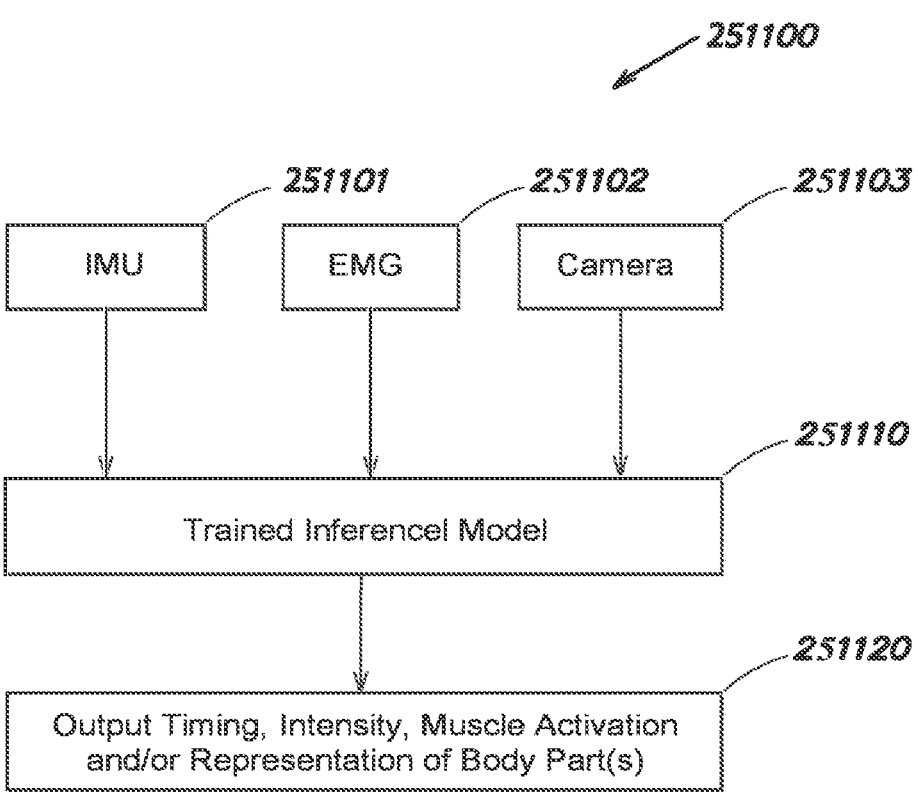
FIG. 25J shows a flowchart of a process for providing data to a trained inference model to obtain musculoskeletal information, in accordance with some embodiments of the technology described herein.
Figure 25K:
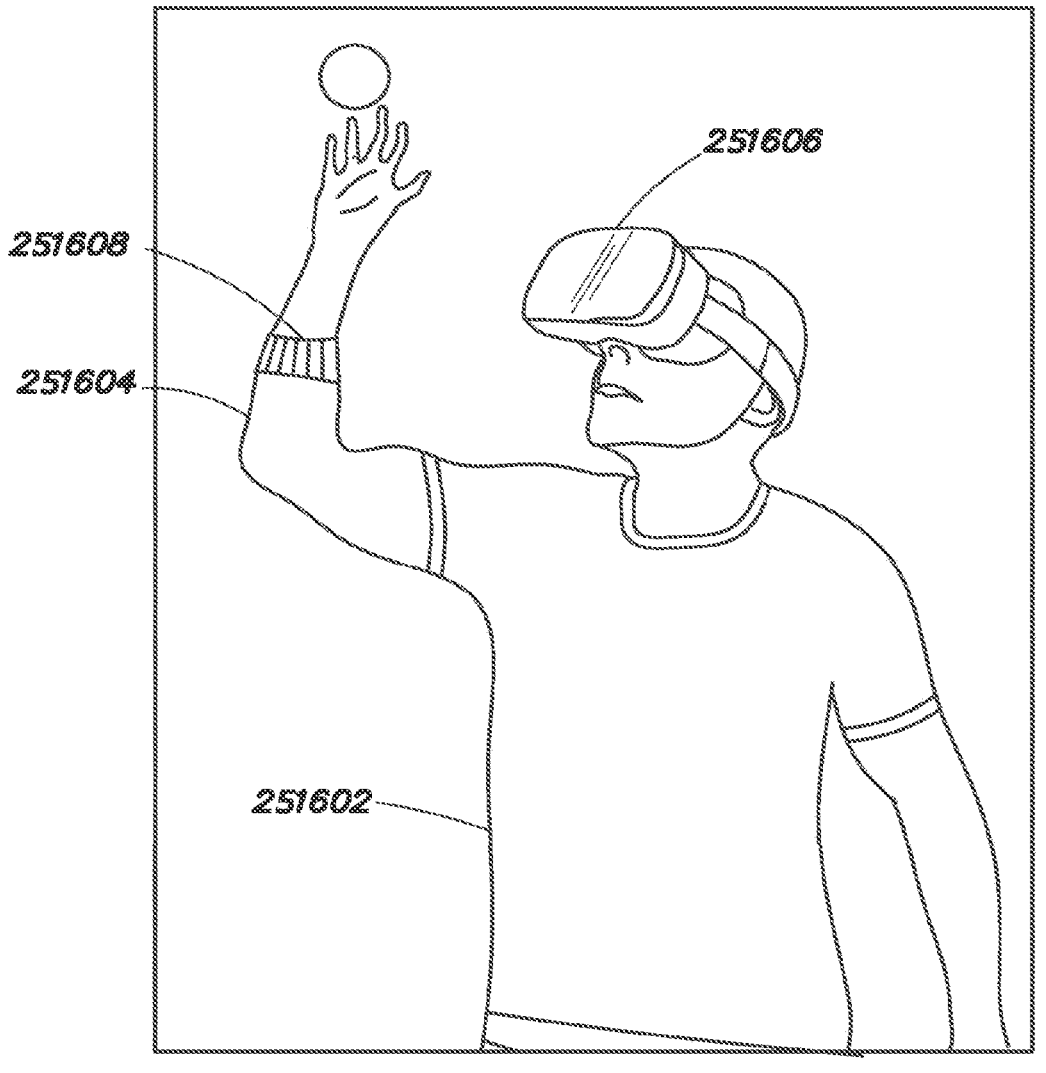
FIG. 25K shows an example of an XR implementation in which feedback about a user may be provided to the user via an XR headset.
Figure 25L:
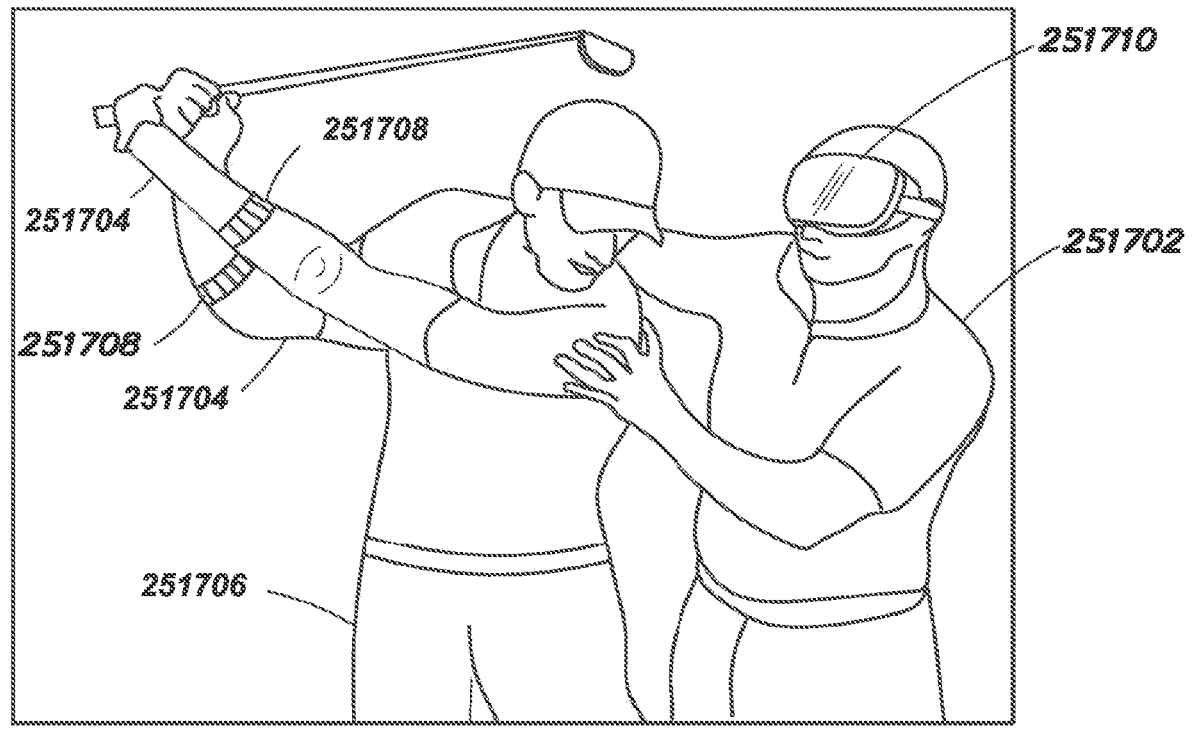
FIG. 25L shows an example of an XR implementation in which feedback about a user may be provided to another person assisting the user.

FIG. 25J shows a flowchart of a process 251100 in which inputs are provided to a trained inference model, in accordance with some embodiments of the technology described herein. For example, the process 251100 may be executed at least in part by a computer-based system such as the XR-based system 200. In various embodiments of the present technology, a more accurate musculoskeletal representation may be obtained by using IMU inputs (251101), EMG inputs (251102), and camera inputs (251103). Each of these inputs may be provided to a trained inference model 251110.

The inference model may be capable of providing one or more outputs such as position, force, and/or a representation of the musculoskeletal state. Such outputs may be utilized by the system or provided to other systems to produce feedback for the user. It should be appreciated that any of the inputs may be used in any combination with any other input to derive any output, either alone or in combination with any output list or any other possible output. For instance, forearm positional information may be derived based on a combination of IMU data and camera data. In one implementation, an estimate of forearm position may be generated based on IMU data and adjusted based on ground-truth camera data. Also, forearm position and/or forearm orientation may be derived using camera data alone without IMU data. In another scenario, EMG signals may be used to derive force-only information to augment posture-only information provided by a camera-model system. Other combinations of inputs and output are possible and within the scope of various embodiments descried herein.

It should also be appreciated that such outputs may be derived with or without generating any musculoskeletal representation. It should also be appreciated that one or more outputs may be used as control inputs to any other system, such as an EMG-based control that is used to control an input mode of an XR system, or vice-versa.

The following describes exemplary electromagnetic interference reduction in extended reality environments according to at least one embodiment of the present disclosure.

Extended reality systems, such as augmented reality or virtual reality systems, often include one or more sensors configured to detect the actions or intent of a user. Such sensors may be included in a control device, such as a wearable device configured to be worn by the user. For example, a wearable control device may include a plurality of electromyography (EMG) sensors that include electrodes designed to contact the skin of a user when the device is worn. EMG signals generated by these EMG sensors may, in turn, be used to generate a control signal that may be used to modify the extended reality experience of the user. However, these EMG signals are often susceptible to noise, such as electromagnetic noise generated by an electronic circuit of the control device and/or other components (such as magnetic trackers). Unfortunately, these noise signals often have undesirable effects on the control signal and, hence, on the extended reality experience of the user.

As is explained in greater detail below, the instant disclosure describes a variety of approaches to reducing or substantially eliminating the effects of noise, from any source, on detected sensor signals. For example, a control device according to the principles described herein may include an analog circuit with an amplifier configured to receive sensor signals from a plurality of electrodes, an analog-to-digital converter (ADC) configured to receive analog sensor signals from the analog circuit and to provide digital sensor signals, and a processor configured to receive the digital sensor signals and provide digital control signals based on the sensor signals.

In some examples, the control device may be configured to reduce the effects of electromagnetic noise. For example, the amplifier and/or the ADC may be configured to reduce noise signals, and an anti-aliasing filter may also be introduced into the analog circuit to prevent problematic undersampling of the noise signal. The control device may also be shielded, and the arrangement of components within the control device may be configured to reduce the amplitude of the noise signal. Improved control signals may then be generated by the control device, allowing improved control of an extended reality view in response to the control signals.

Figure 26A:
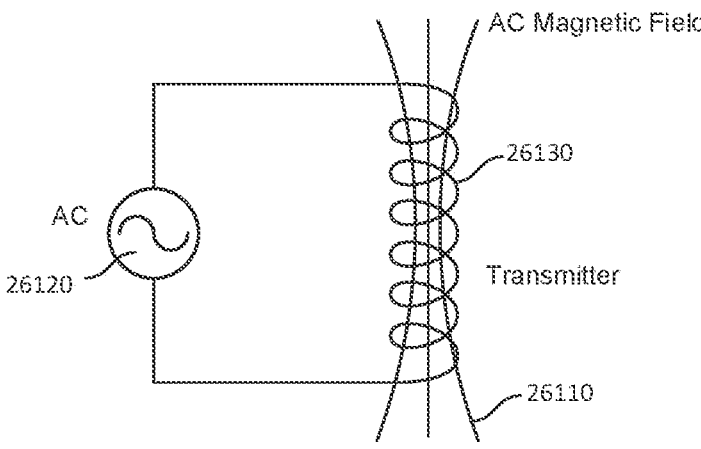
FIGS. 26A-26C illustrate, respectively, how an AC magnetic field is generated in a magnetic tracking system transmitter, how the generated AC magnetic field induces a current in a closed-loop conductor, and how the generated AC magnetic field induces a voltage in an open-loop conductor.

FIG. 26A illustrates generation of a magnetic field 26110 by passing AC current from a current source 26120 through coil 26130. In some examples, the coil 26130 may be a component of the transmitter of a magnetic tracker.

Figure 26B:
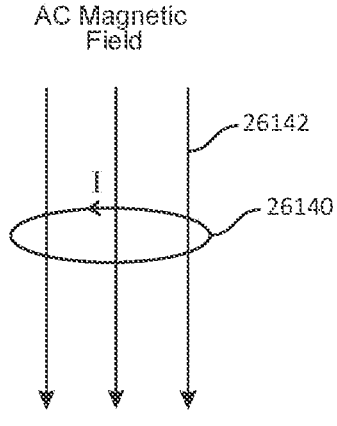

FIG. 26B illustrates that an alternating magnetic field 26142 (that may be generated by the transmitter of a magnetic tracker) may induce a current (denoted I) in a closed-loop conductor 26140. The current I may be an alternating current, so the arrow direction may be arbitrary. This may create noise problems, particularly when the closed-loop conductor is located near the transmitter.

Figure 26C:
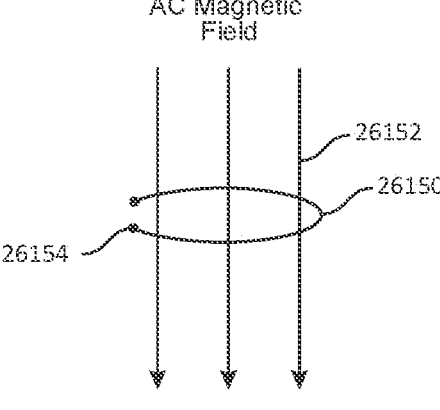

FIG. 26C illustrates that the alternating magnetic field 26152 (that may be generated by the transmitter of a magnetic tracker) may induce an alternating voltage in an open-loop conductor 26150. A noise voltage may be generated between the open ends of the open-loop conductor (e.g., end 26154). This may also create noise problems, particularly when the open-loop conductor is located near the transmitter. In general, an open-loop or closed-loop conductor located close to the magnetic tracker transmitter may result in a noise signal (a noise voltage and/or a noise current) being induced in the conductor.

Figure 26D:
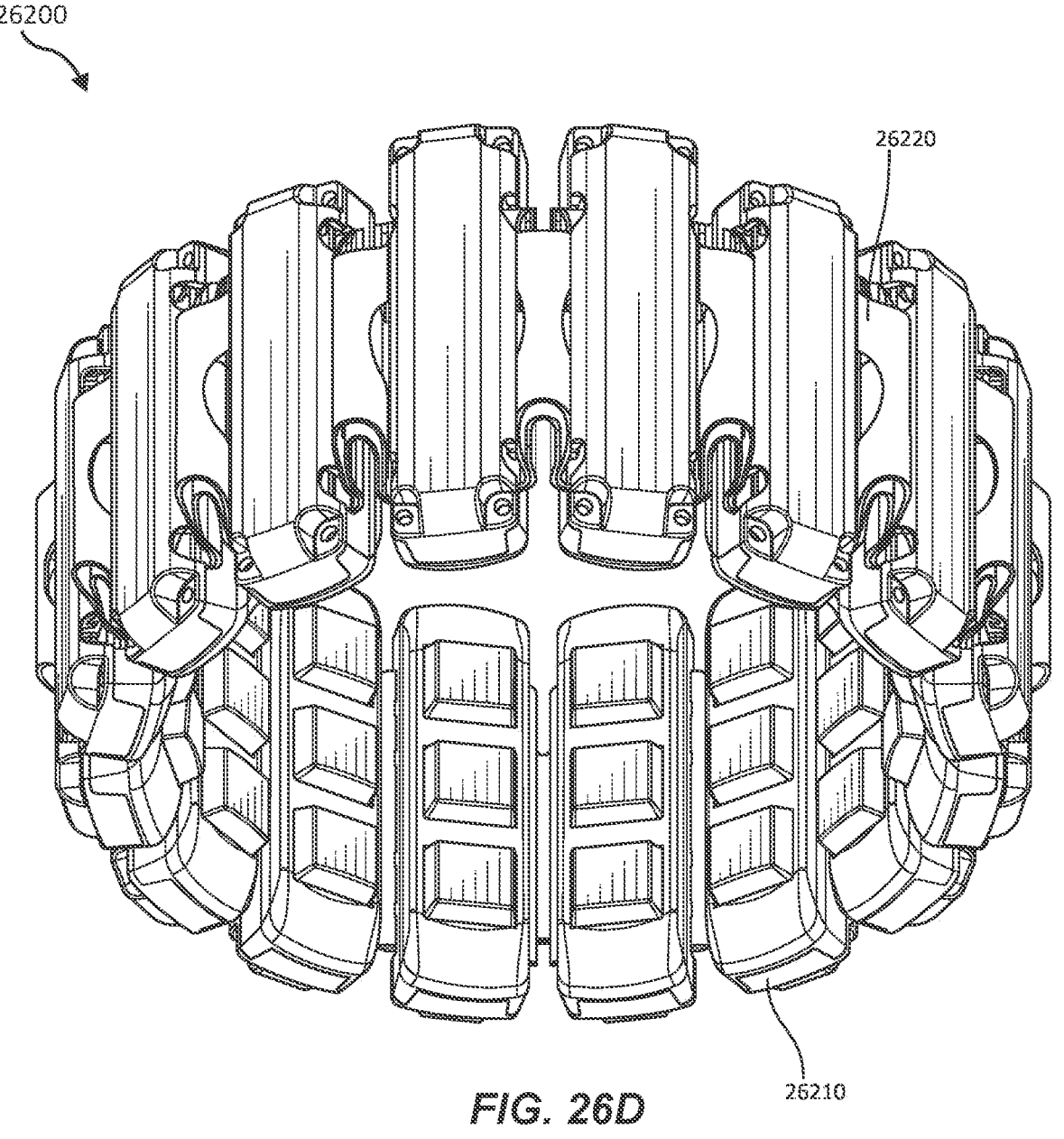
FIG. 26D illustrates a wearable system with sixteen EMG sensors arranged circumferentially around an elastic band configured to be worn around a user's lower arm or wrist, in accordance with some embodiments.

FIG. 26D illustrates an example device, that may include one or more of the following: a human-machine interface, an interface device, a control device, and/or a control interface. In this example, the device may include a control device 26200, which in this example includes sixteen neuromuscular sensors 26210 (e.g., EMG sensors) arranged circumferentially around an elastic band 26220 configured to be worn around a user's lower arm or wrist. As shown, EMG sensors 26210 are arranged circumferentially around elastic band 26220. Any suitable number of neuromuscular sensors may be used. The number and arrangement of neuromuscular sensors may depend on the particular application for which the control device is used. For example, a wearable control device configured as an armband, wristband, or chest-band may be used to generate control information for controlling an augmented reality system, controlling a robot, controlling a vehicle, scrolling through text, controlling a virtual avatar, or any other suitable control task. As shown, the sensors may be coupled together using flexible electronics incorporated into the wireless device.

Figure 26E:
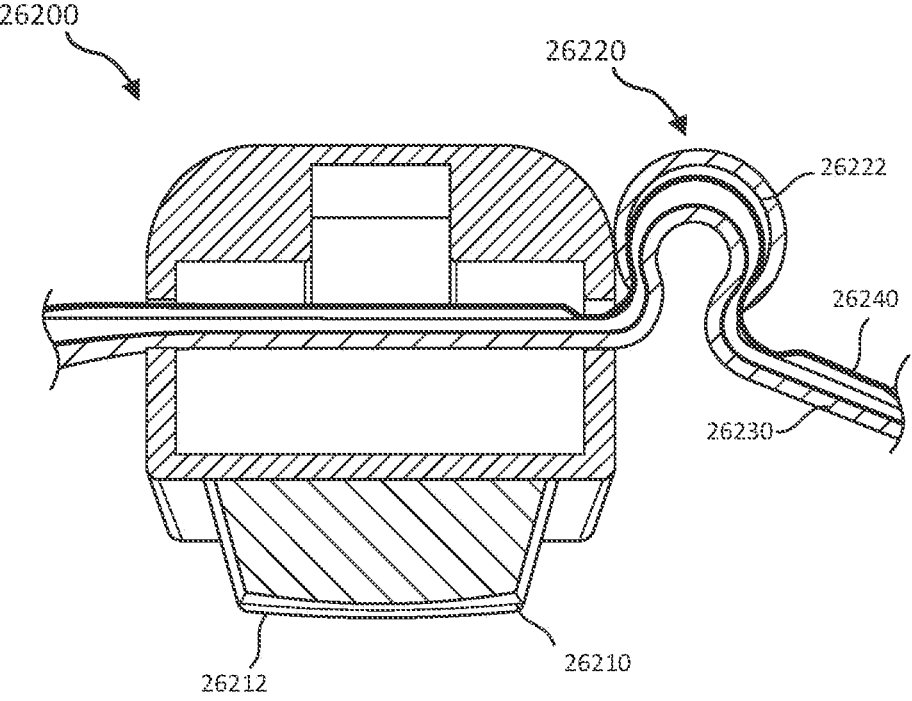
FIG. 26E is a cross-sectional view through one of the sixteen EMG sensors illustrated in FIG. 26D.

FIG. 26E illustrates a cross-sectional view through one of the sensors 26210 of the control device 26200 shown in FIG. 26D. The sensor 26210 may include a plurality of electrodes located within a skin-contacting surface 26212. The elastic band 26220 may include an outer flexible layer 26222 and an inner flexible layer 26230, that may at least in part enclose a flexible electrical connector 26240 which may interconnect the sensors.

In some embodiments, the output of one or more of the sensing components may be optionally processed using hardware signal processing circuit (e.g., to perform amplification, filtering, and/or rectification). In some embodiments, at least some signal processing of the output of the sensing components may be performed in software. Thus, signal processing of signals sampled by the sensors may be performed in hardware, software, or by any suitable combination of hardware and software, as aspects of the technology described herein are not limited in this respect. A non-limiting example of a signal processing chain used to process sensor data from sensors 26210 is discussed in more detail below, for example, with reference to FIGS. 26F and 26G.

Figure 26F:
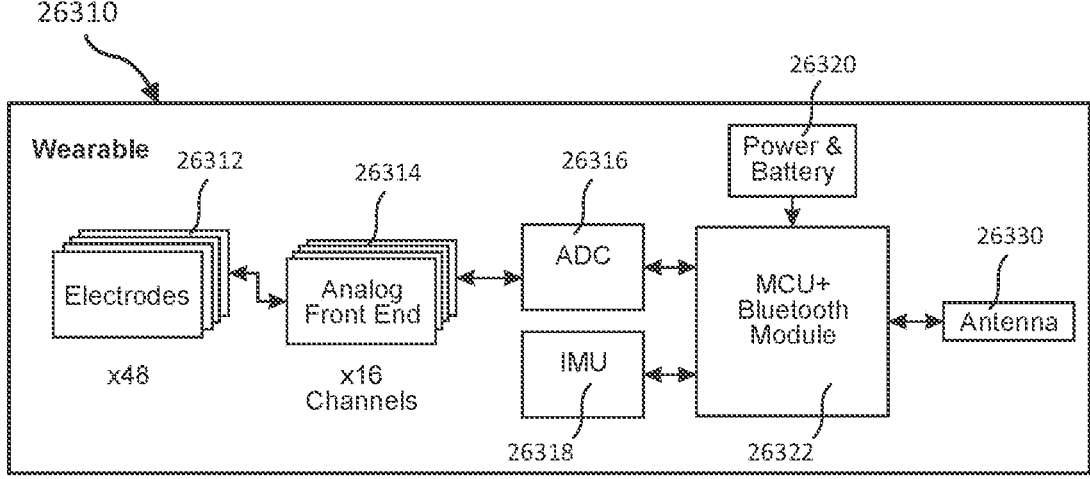
FIGS. 26F and 26G schematically illustrate components of a computer-based system on which some embodiments are implemented.
Figure 26G:
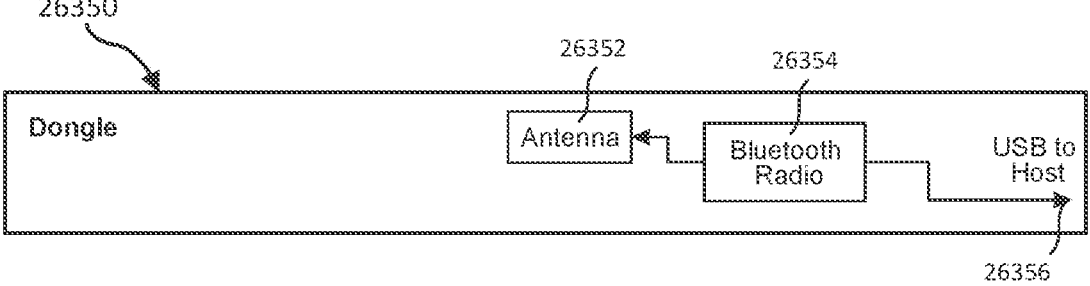

FIGS. 26F and 26G illustrate a schematic diagram with internal components of an apparatus including EMG sensors. In some examples, there may be sixteen EMG sensors, though this and other numerical examples are non-limiting and other numbers of sensors may be used. The apparatus may include a control device 26310 (FIG. 26F) and a dongle portion 26350 (FIG. 26G) in communication with the control device 26310 (e.g., via BLUETOOTH or another suitable short range wireless communication technology). In some examples, the function of the dongle portion may be included within a head-mounted device, allowing the control device to communicate with the head-mounted device.

FIG. 26F shows that the control device 26310 may include a plurality of sensors 26312, that may include the example EMG sensors 26210 described in connection with FIGS. 26D and 26E, or other sensors. The sensor signals from the sensors 26312 may be provided to analog front end 26314, that may be configured to perform analog processing (e.g., noise reduction, filtering, etc.) of the sensor signals. The processed analog signals may then be provided to analog-to-digital converter 26316, which converts the processed analog signals to digital signals that may be processed by one or more computer processors. An example computer processor, that may be used in accordance with some embodiments, is microcontroller (MCU) 26322. The MCU may also receive signals from other sensors (e.g., an inertial sensor such as inertial measurement unit (IMU) sensor 26318, or other suitable sensors). The control device 26310 may also include, or receive power from, a power supply 26320, that may include a battery module or other power source. The output of the processing performed by MCU 26322 may be provided to antenna 26330 for transmission to the dongle portion 26350 shown in FIG. 26G, or to another device such as a head-mounted device.

FIG. 26G shows an example dongle portion 26350 that may include an antenna 26352, that may be configured to communicate with antenna 26330 associated with control device 26310. Communication between antennas 26330 and 26352 may occur using any suitable wireless technology and protocol, non-limiting examples of which include radiofrequency signaling and BLUETOOTH. As shown, the signals received by antenna 26352 of dongle portion 26350 may be received by a BLUETOOTH radio (or other receiver circuit), and provided to a host computer through output 26356 (e.g., a USB output) for further processing, display, and/or for effecting control of a particular physical or virtual object or objects.

In some examples, the dongle may be inserted into a separate computer device, that may be located within the same environment as the user, but not carried by the user. This separate computer may receive signals from the control device and further process these signals to provide control signals to the head-mounted device. In some examples, the dongle may be network enabled, allowing communication with a remote computer through the network, and the remote computer may provide control signals to the head-mounted device to modify an extended reality (XR) image (e.g., VR or AR image) presented to the user. In some examples, a dongle may be inserted into a head-mounted device to provide improved communications functionality, and the head-mounted device may perform further processing (e.g., modification of the XR image) based on the control signal received from the control device 26310.

In some examples, an apparatus may not include a separate dongle portion. The configuration of the dongle portion may be included in a head-mounted device, such as an extended reality headset, or other device such as a remote computer device. In some examples, the circuit described above in FIG. 26G may be provided by (e.g., integrated within) components of the head-mounted device. In some examples, the control device may communicate with the head-mounted device using the described wireless communications, and/or a similar schematic circuit, or a circuit having similar functionality.

A head-mounted device may include an antenna similar to antenna 26352 described above in relation to FIG. 26G. The antenna of a head-mounted device may be configured to communicate with the antenna associated with the control device. Communication between antennas of the control device and the head-mounted device may occur using any suitable wireless technology and protocol, non-limiting examples of which include radiofrequency signaling and BLUETOOTH. Signals, such as control signals, received by an antenna of a head-mounted device may be received by a BLUETOOTH radio (or other receiver circuit) and provided to a processor within the head-mounted device, that may be programmed to modify an extended reality view for the user in response to the control signals.

Although the examples provided with reference to FIGS. 26D, 26E and FIGS. 26F, 26G are discussed in the context of interfaces with EMG sensors, techniques described herein for reducing electromagnetic interference may also be implemented in wearable interfaces with other types of sensors including, but not limited to, mechanomyography (MMG) sensors, sonomyography (SMG) sensors, and electrical impedance tomography (EIT) sensors.

In some examples, electromagnetic interference may be reduced by increasing the distance between a device and its associated analog circuit and a magnetic tracker transmitter that generates an AC magnetic field. In some embodiments, a shielding material may be arranged around at least a portion of the analog circuit to shield the circuit, at least in part, from the effects of the AC magnetic field. In yet further embodiments, one or more components of the analog circuit of the EMG control device may be configured to reduce electromagnetic interference induced on one or more conductors of the EMG control device. One or more of the various techniques for reducing electromagnetic interference described herein may be used alone or in combination.

Figure 26H:
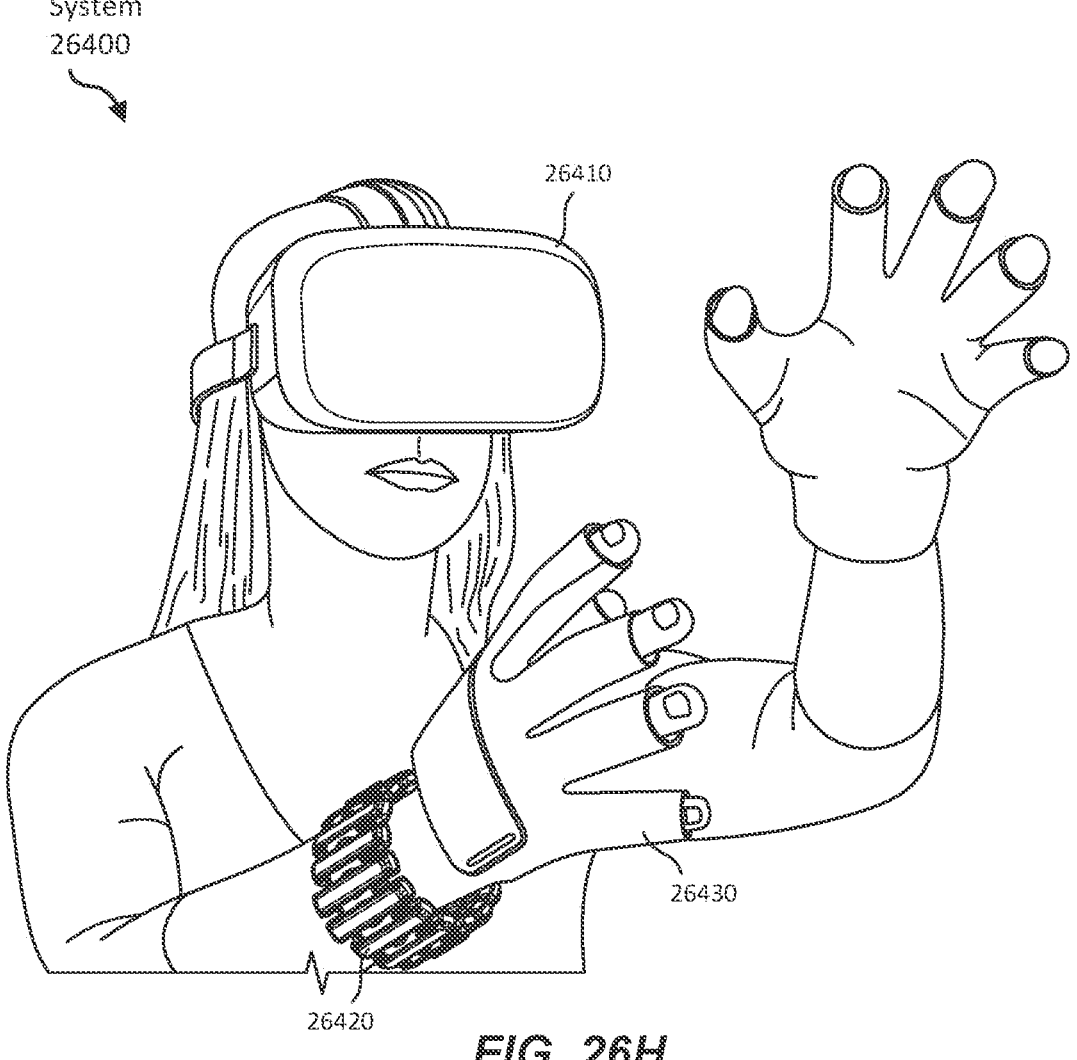
FIG. 26H illustrates components of an extended reality system, in accordance with some embodiments.

FIG. 26H illustrates an example XR system 26400, such as an augmented reality system or virtual reality system, that may include a headset 26410 and a control device 26420 (that may represent a wearable control device). In some examples, the system 26400 may include a magnetic tracker. In some examples, the transmitter for the magnetic tracker may be associated with (e.g., mounted on or in) the control device 26420, and the receiver for the magnetic tracker may be mounted on the headset 26410. In some examples, the transmitter for the magnetic tracker may be associated with (e.g., mounted on or in) the headset, or otherwise located within the environment. In some embodiments, the system 26400 may also include one or more optional control gloves 26430. In some examples, many or all functions of a control glove may be provided by the control device 26420. In some examples, the control glove 26430 may include a plurality of magnetic tracker receivers. The orientation and/or location of various parts of the hand of a user may be determined using magnetic tracker receivers, or other sensors.

In some examples, the control glove 26430 (that may be more simply referred to as a glove) may include one or more magnetic tracker receivers. For example, a finger of the glove may include at least one receiver coil, and detection of a tracker signal from the at least one receiver coil induced by a magnetic tracker transmitter may be used to determine the position and/or orientation of at least portion of the finger. One or more receiver coils may be associated with each portion of a hand, such as a finger (such as the thumb), palm, and the like. The glove may also include other sensors providing sensor signals indicative of the position and/or configuration of the hand, such as electroactive sensors. Sensor signals, such as magnetic tracker receiver signals, may be transmitted to a control device, such as a wearable control device. In some examples, a control device (such as a wrist-mounted control device) may be in communication with a control glove, and receive sensor data from the control glove using wired and/or wireless communication. For example, a flexible electrical connector may extend between a control device (e.g., a wrist-mounted control device) and the glove.

In some examples, the control device 26420 may include an EMG control interface similar to the device illustrated in FIGS. 26D-26E. Locating the magnetic tracker transmitter on or near the control device 26420 may result in the introduction of noise into the signals recorded by the control device 26420 due to induced currents and/or voltages. In some embodiments, electromagnetic interference caused by the magnetic tracker transmitter may be reduced by locating the transmitter at a distance further away from the control device 26420. For example, the transmitter may be mounted on the headset 26410, and the magnetic tracker receiver may be mounted on the control device 26420. This configuration works well, for example, when the user keeps their arms away from their head, but may not work as well if the user moves their arms in close proximity to the headset. However, many XR applications do not require extensive proximity between the head and the hands of the user.

Electromagnetic interference reduction techniques may be integrated with magnetic trackers having configurations similar to the configuration shown in FIG. 26H, or other configurations, such as configurations in which the magnetic tracker transmitter is positioned in a computer device separate from the headset 26410 shown in FIG. 26H, or at another remote locations, such as located within the same room as the user.

In some examples, electromagnetic interference may be reduced by increasing the physical distance between the magnetic tracker transmitter and the EMG control interface. In some embodiments, electromagnetic noise induced in the circuit of the EMG control interface may be reduced, at least in part, prior to analog-to-digital conversion using additional circuit components introduced in the analog signal chain. Although introducing additional circuit components into the analog signal chain increases the amount of area that the analog signal chain circuit consumes on a printed circuit broad, in some embodiments, the increase in area is offset by noise reduction benefits, such as those described in more detail below.

Figure 26I:
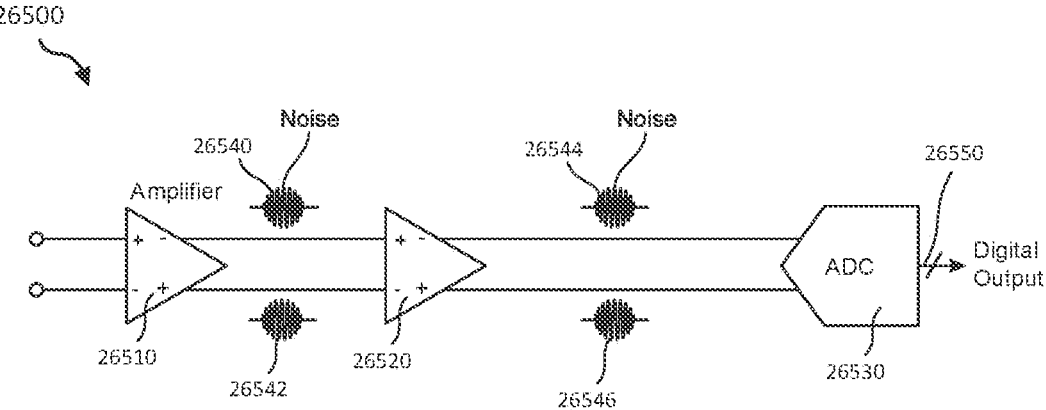
FIG. 26I illustrates a fully differential analog circuit in accordance with some embodiments.

FIG. 26I illustrates a portion of a device 26500, including an electromagnetic interference reduction circuit in which the analog circuit of the device (e.g., the input analog signal chain of device, such as an EMG control interface) may include one or more fully differential amplifiers. As shown, the analog circuit may include a first fully differential amplifier stage 26510 that receives a differential input signal from the sensors (such as EMG sensors, described in relation to FIG. 26D) and a second fully differential amplifier stage 26520 coupled to the output of the first fully differential amplifier stage 26510, which provides a signal to the ADC (analog to digital converter) 26530. In such a configuration, electromagnetic noise induced within the analog circuit is reduced due to subtraction of the differential signals at the output of each of the fully differential amplifier stages. The first fully differential amplifier 26510 may be configured to cancel common mode noise signals in the sensor data. In this context, the term "cancel" may refer to subtraction of a signal from a similar signal (or vice versa) to give an approximately null result. Various noise signals may arise from a similar source (such as the transmitter signal), and hence may have similar amplitudes and phases, and may be canceled using subtraction of one signal from another. In some examples, noise signals 26540 and 26542, that may be induced by the transmitter signal within circuit traces (e.g., PCB tracks) may effectively cancel each other out due to the operation of the fully differential amplifier 26520. The ADC 26530 (which may be a differential ADC) is coupled to the output of the fully differential amplifier 26520, and may be configured to subtract the noise signal from both input connections provided as input to the ADC (e.g., noise signals 26544 and 26546). This may be achieved, for example, by digitizing the difference signal between the two inputs. The ADC 26530 may thereafter convert the noise-reduced signal into a digital representation. Hence, the ADC may be configured to effectively cancel out the noise signals 26544 and 26546 so that the output 26550 has a reduced noise component.

In some examples, the ADC 26530 may be a differential ADC, configured to output a digital signal based on the difference between two analog input voltages. If there is similar noise signal in both analog input voltages, the difference between the input voltages, and hence the digital signal, may be generally independent of the electromagnetic noise. For example, noise signals 26544 and 26546 may be present in both ADC inputs, and may have reduced or effectively no effect on the output of ADC 26530 functioning as a differential ADC. In some examples, two digital signals may be generated, and digital subtraction (or division, or other comparison method) may be used to remove common mode noise signals. Alternatively, a difference signal may be generated and digitized. In this context, a common mode noise signal may refer to similar noise signals present in multiple sensor signals, or data channels derived therefrom.

In some examples, a device may include an analog circuit configured so that a first noise signal present at the non-inverting input of a differential amplifier may be similar to, and in phase with, a second noise signal generated at the inverting input of the differential amplifier. The differential amplifier may then effectively subtract the second noise signal from the first noise signal, so that the differential amplifier output may be effectively noise free, or have reduced noise in the differential amplifier output (e.g., compared to the output of a non-differential amplifier used in a similar circuit). In some examples, a device may include one or more fully differential amplifiers, where the difference between the two output voltages may be based on the difference between the two input voltages (optionally including multiplication by the gain, if any). For both differential amplifiers and fully differential amplifiers, the noise signal may be a common mode signal, having a similar form in both inputs, that is thereby greatly reduced or substantially eliminated in the output voltage(s). In some examples, negative feedback may be provided to reduce the gain and/or improve the signal bandwidth.

Figure 26J:
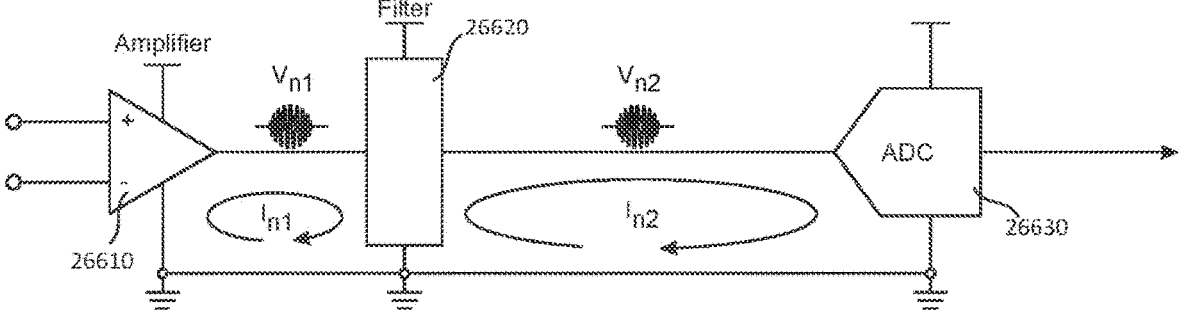
FIGS. 26J and 26K illustrate an analog circuit for filtering electromagnetic noise induced by an electromagnetic field in accordance with some embodiments.
Figure 26K:
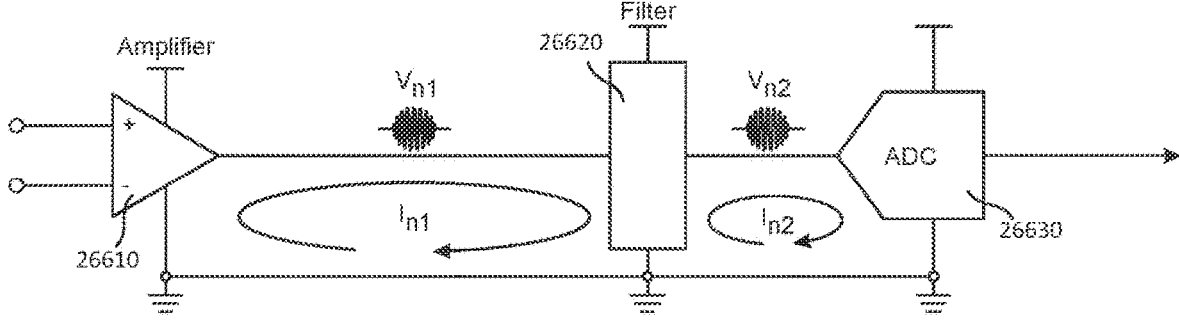

FIGS. 26J and 26K illustrate an example in which an anti-aliasing filter is included in the analog circuit (e.g., the EMG control interface) of an example control device. As shown in both FIGS. 26J and 26K, amplifier 26610 may receive a differential signal from one or more sensors, such as one or more EMG sensors. Anti-aliasing filter 26620 may be located between the output of amplifier 26610 and the ADC 26630, and may be configured to filter noise on the trace (e.g., a PCB conducting track or other electrical conductor) between the output of the amplifier 26610 and the ADC 26630. The configuration shown in FIG. 26J may experience a larger induced noise voltage (Vn2) and noise current (In2) between the anti-aliasing filter 26620 and the ADC 26630, compared to the induced noise voltage (Vn1) and noise current (In1) generated between the amplifier 26610 and the anti-aliasing filter 26620 (e.g., Vn2>Vn1, and In2>In1).

FIG. 26K shows a configuration in which the anti-aliasing filter 26620 is located close to the ADC 26630, such that the induced noise voltage and noise currents observed at the input to the ADC 26630 are reduced compared to the configuration in FIG. 26J. For example, in the configuration of FIG. 26K, the following relationships may be observed; Vn1>Vn2, and In1>In2. The longer the trace between the anti-aliasing filter 26620 and the ADC 26630, the larger the resulting induced noise voltage/current may be introduced at the input of the ADC. Noise signals may be reduced by locating the anti-aliasing filter close to the ADC, thereby reducing the conducting track length between the output of the anti-aliasing filter and the ADC. In some examples, the electrically conducting path between the output of the anti-aliasing filter and the input of the ADC may be less than approximately 15 mm, such as less than approximately 10 mm. In some examples, the electrical conductor between the filter 26620 and the ADC 26630 may be shielded, for example using an electrically conducting and/or magnetically shielding layer or other suitable structure.

In some examples, the ADC and anti-aliasing filter may be integrated into a single package, for example, a single integrated circuit (IC, or chip). Shielding may be located proximate, adjacent, or within the ADC/anti-aliasing chip to reduce noise generation in the chip.

Figure 26L:
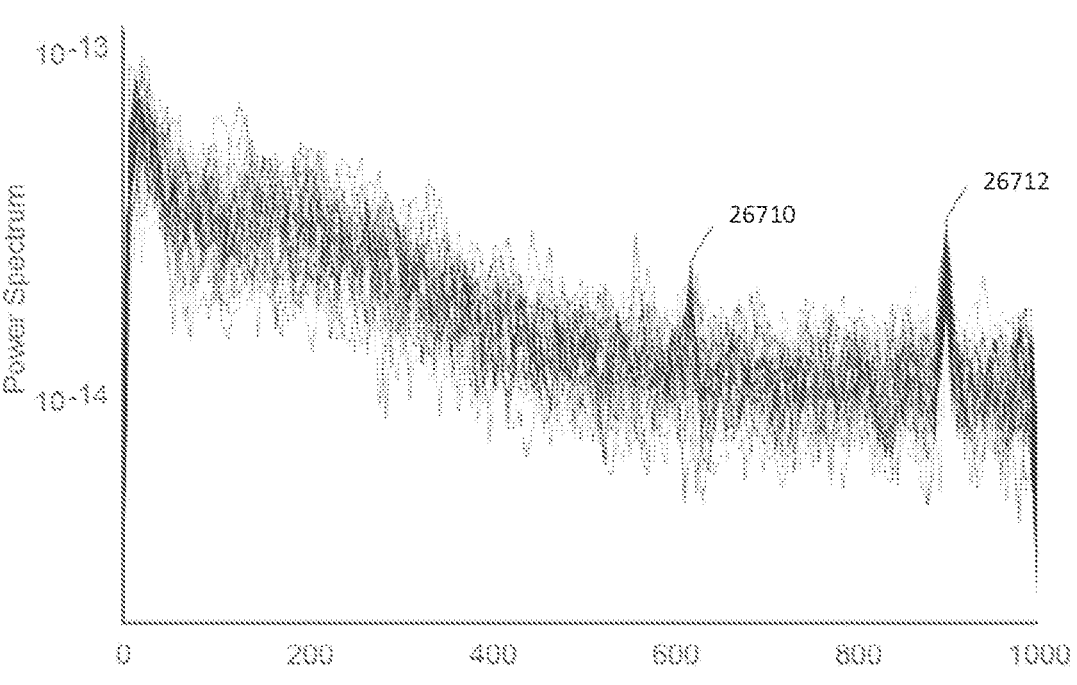
FIGS. 26L and 26M illustrate results of an experiment in which the configuration of FIG. 26J was used.
Figure 26M:
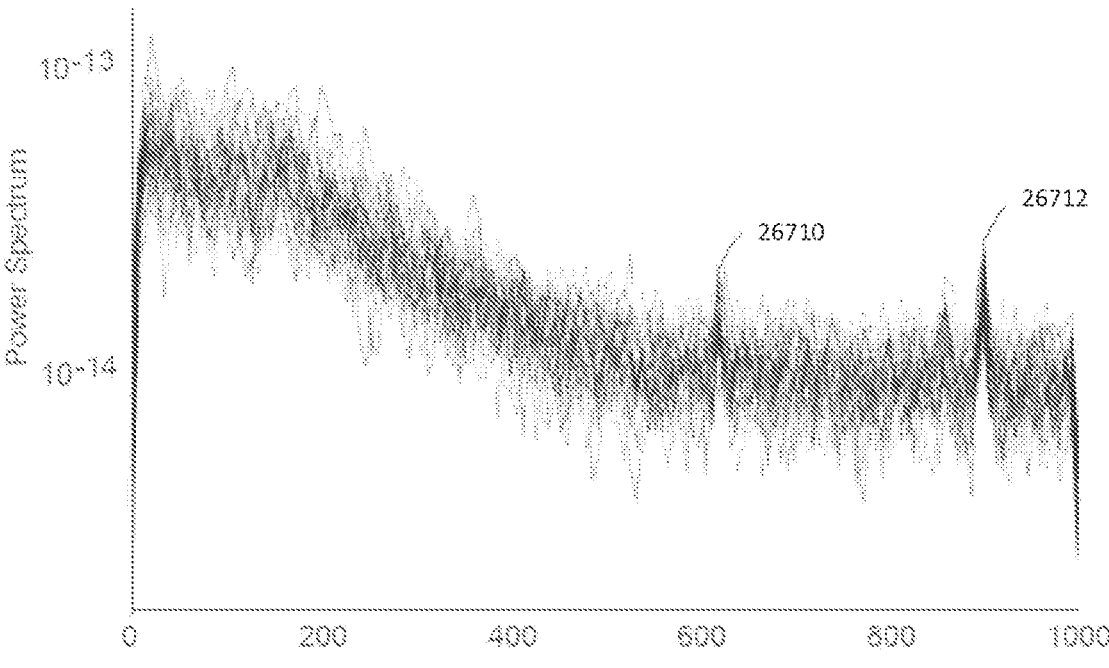

FIGS. 26L-C illustrate results from an experiment in which the effects of locating the anti-aliasing filter closer to (as shown in FIG. 26K) or farther from (as shown in FIG. 26J) the ADC were observed. FIGS. 26L and 26M show the power spectrum for two channels of a 16 channel EMG control interface when the anti-aliasing filter was located a distance of 24 cm from the ADC of the EMG control interface. Two noise peaks 26710 and 26712 may be observed at approximately 600 Hz and 900 Hz in both channels.

Figure 26N:
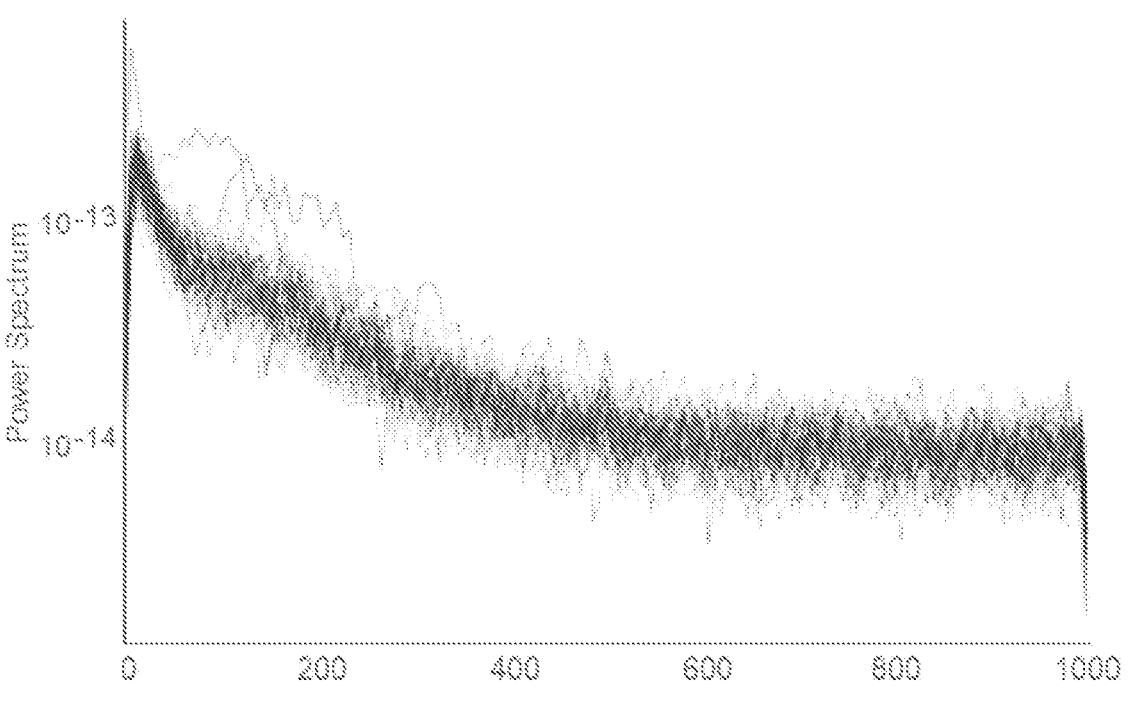
FIG. 26N illustrates results of an experiment in which the configuration of FIG. 26K was used, showing removal of noise peaks previously observable in a power spectrum for the first channel.

FIG. 26N shows results for the first channel of the 16-channel EMG control interface, when the anti-aliasing filter was located a distance of 1.5 cm from the ADC of the EMG control interface. The noise peaks previously observable in FIG. 26L are attenuated, and may no longer be observable when the distance between the anti-aliasing filter and the input of the ADC is reduced. A similar improvement was seen for the second channel, where the noise peaks previously observable in FIG. 26M were no longer visible when the anti-aliasing filter was located closer to the ADC. The x-axis unit is frequency in Hz.

In some embodiments, attenuation of noise generated by an external electromagnetic source may be achieved using a higher-order anti-aliasing filter arranged between an input amplifier and an ADC within an analog-signal chain of an EMG control interface. The higher-order anti-aliasing filter may, for example, in combination with the amplifier, provide a transfer function such that the amplified in-band signals are at least 90 dB higher than the attenuated noise signals.

Figure 26O:
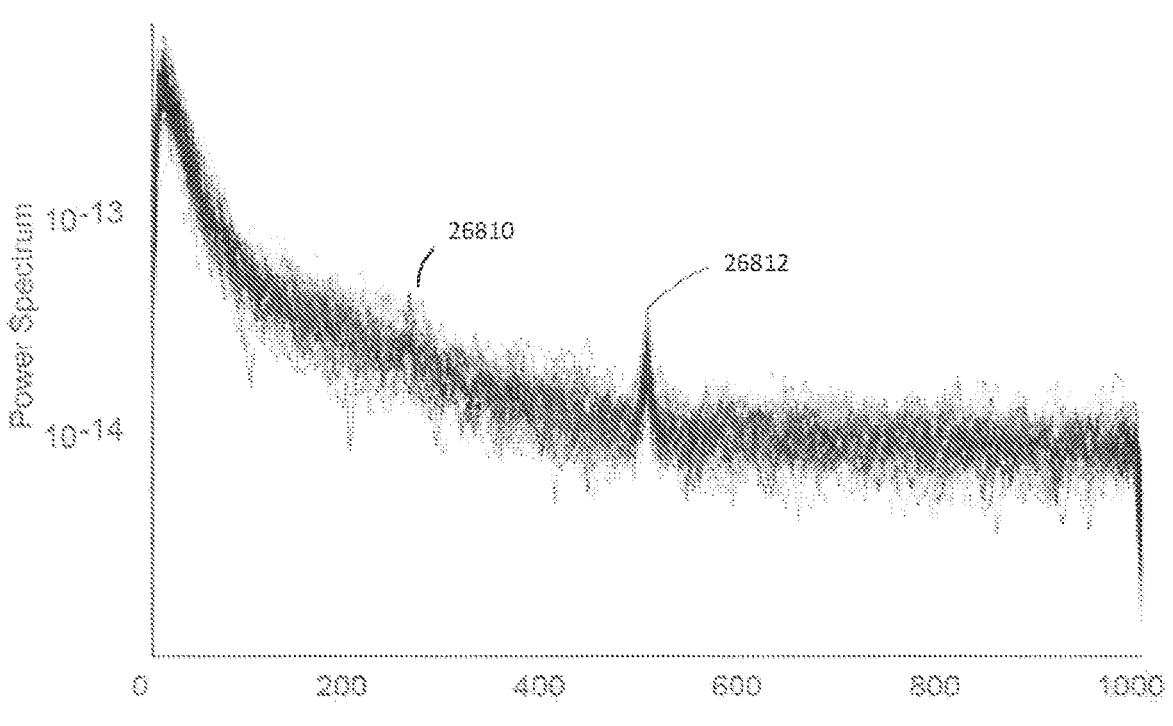
FIGS. 26O and 26P illustrate results of an experiment in which the configuration of FIG. 26K was used with a single anti-aliasing filter, where
Figure 26P:
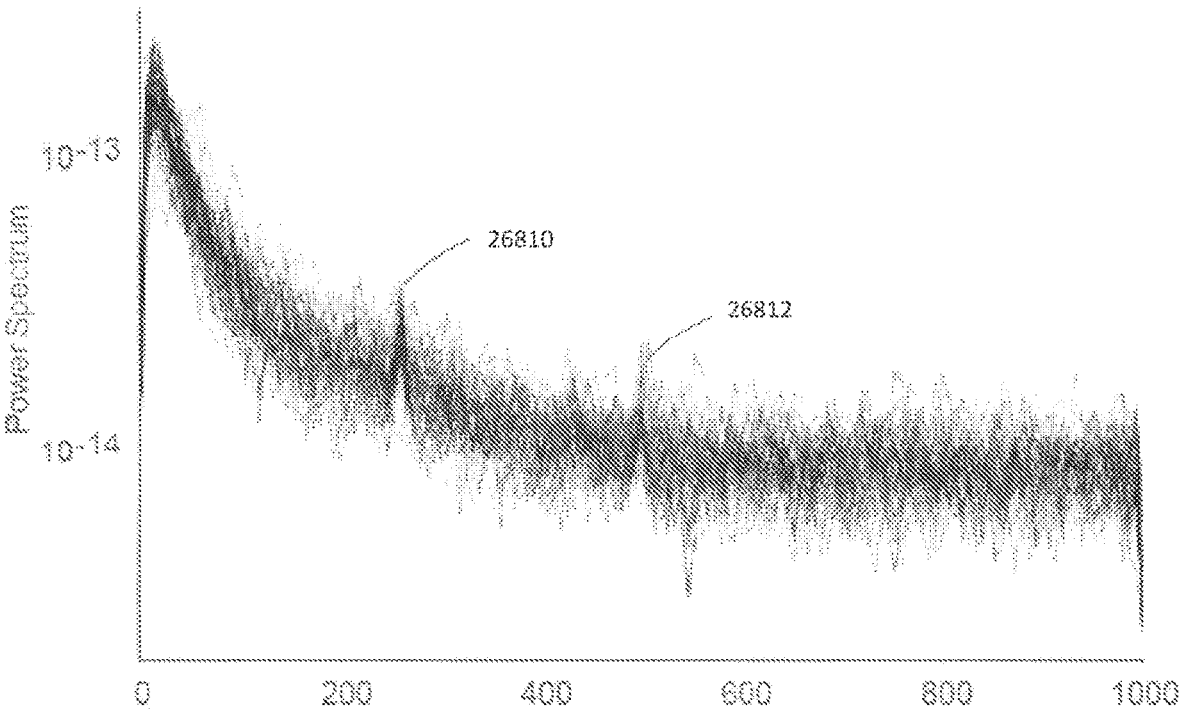
Figure 26Q:
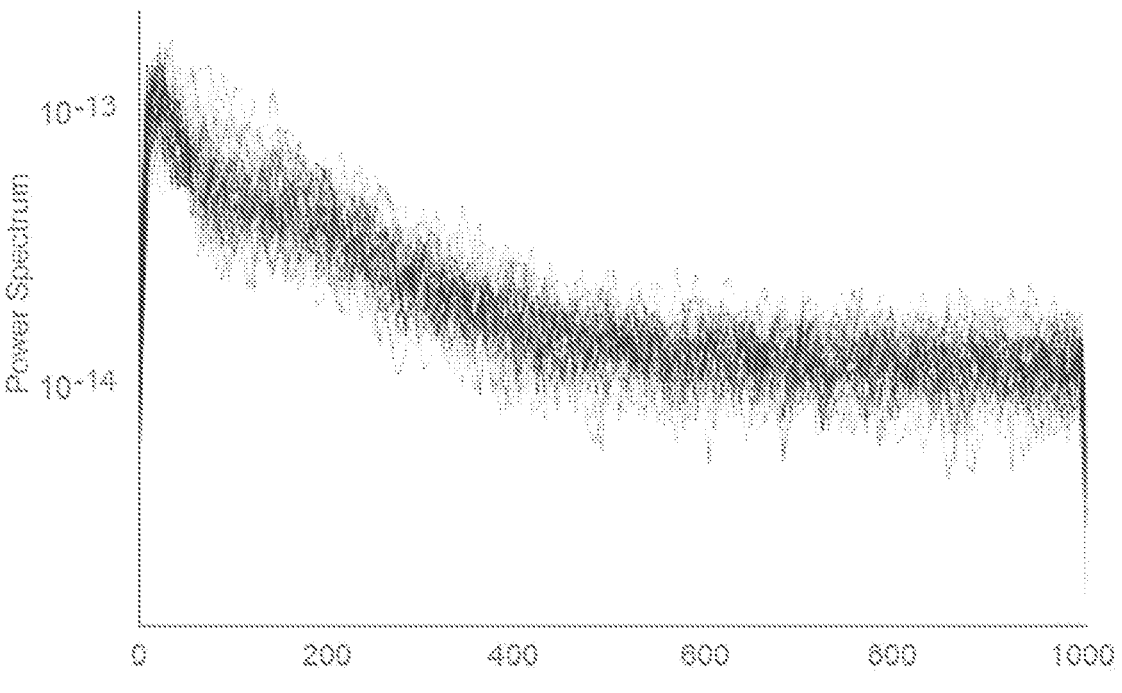
FIGS. 26Q and 26R illustrate results of an experiment in which an additional anti-aliasing filter was used, thereby creating a two-stage filter, where
Figure 26R:
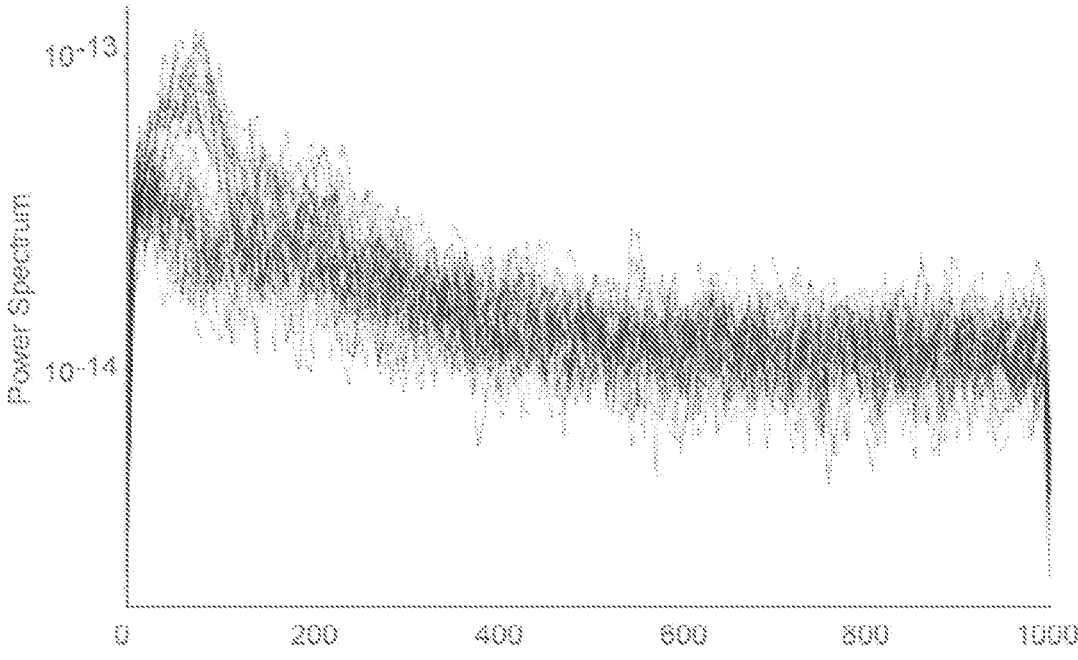

FIGS. 26O-R illustrate results from an experiment in which the effect of implementing a higher-order anti-aliasing filter was observed. FIGS. 26O and 26P illustrate two channels of a 16-channel EMG control interface, where a single anti-aliasing filter was arranged 1.5 cm from the ADC of the EMG control interface. A first noise peak 26810 at approximately 250 Hz is observed in the channel shown in FIG. 26P and a second noise peak 26812 at approximately 500 Hz is observed in both channels shown in FIGS. 26O and 26P. FIGS. 26Q and 26R illustrate the same two channels of the 16-channel EMG control interface, where a second anti-aliasing filter is added close to the amplifier output such that the analog signal chain may include two filters (or alternatively, a two-stage filter). As observed in FIGS. 26Q and 26R, the previously observed noise peaks at 250 and 500 Hz are no longer observed, providing evidence that a higher-order filter attenuated the noise induced in the analog signal chain. For these plots, the x-axis unit is frequency in Hz.

In some embodiments, electromagnetic noise may be reduced by changing a characteristic of the ADC circuit. Conventional ADC circuit is often susceptible to the aliasing effect, as discussed above. In some embodiments, a continuous-time ADC is used in the analog signal chain of the EMG control interface, which does not have the same aliasing properties. Although continuous-time ADCs may be more expensive and consume more power than a conventional ADC circuit, the tradeoff of improved electromagnetic interference reduction may be suitable for some applications.

Figure 26S:
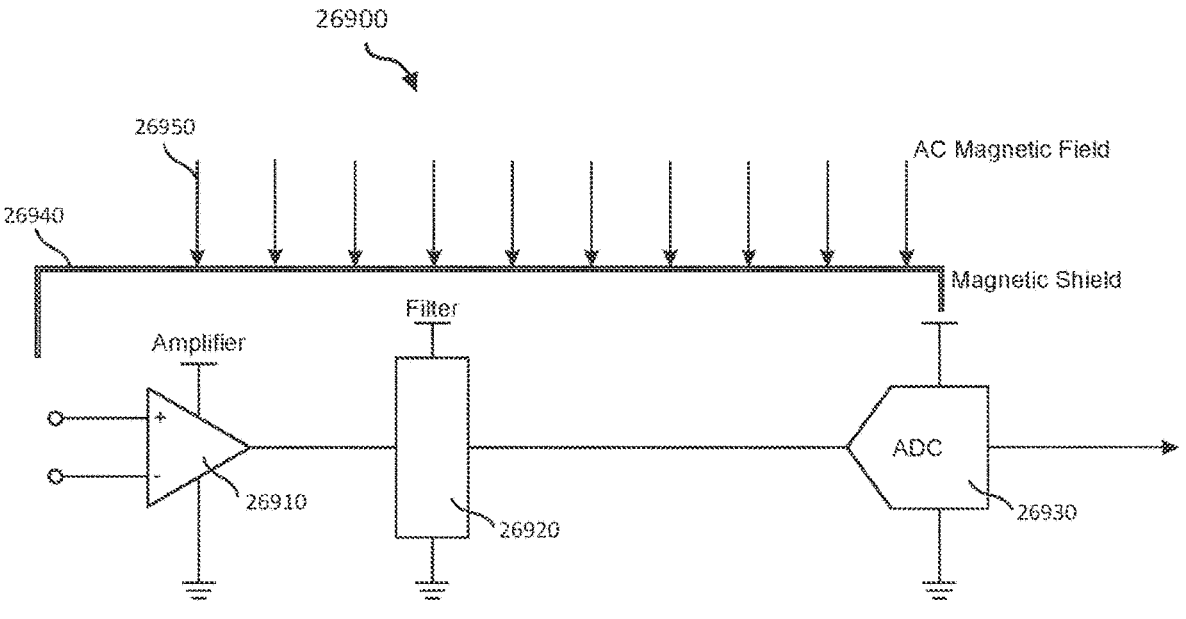
FIG. 26S illustrates a technique for reducing electromagnetic noise using a shielding material, in accordance with some embodiments.

FIG. 26S illustrates example approaches for reducing electromagnetic interference, in accordance with some embodiments. The figure shows an analog circuit portion of a device 26900, (e.g., including an EMG control interface), that may include an amplifier 26910, an anti-aliasing filter 26920, and ADC 26930. The device also includes a shielding material 26940, that may be configured to shield the analog circuit from an electromagnetic field schematically represented by arrows 26950. In some embodiments, the shielding material 26940 includes a magnetic shielding material, such as a composition including a ferrite material, and may be configured such that the magnetic shielding material redirects the AC magnetic field around the analog circuit.

In some examples, the shielding material may include an electrically conductive material. A shielding material may include a metal layer, such as an aluminum layer, having a metal layer thickness of 2 mm or less, for example, a thickness of 1 mm or less. In some embodiments, multiple layers of shielding material may be used, for example, if one layer of magnetic shielding does not offer the desired attenuation of noise signals. The shielding material as disclosed herein can be formed from or include any suitable material (including flexible and lightweight materials) provided it achieves the functionality described herein. In addition to the those mentioned above, such materials include but are not limited to: one or more metals and/or alloys or compounds (e.g., those comprising aluminum, bronze, tin, copper, and/or mu-metals), carbon-filled nylon, conductive paint (e.g., silver and/or carbon-based paint), conductive fabric (e.g., silver nanowire), conductive polymers (e.g., carbon or graphene filled polylactic acid (PLA)), conductive plastics, conductive rubbers, conductive silicones, or combinations thereof. The shielding material may also include one or more non-conductive components that may be combined with any one or more conductive components, such as the aforementioned examples.

Figure 26T:
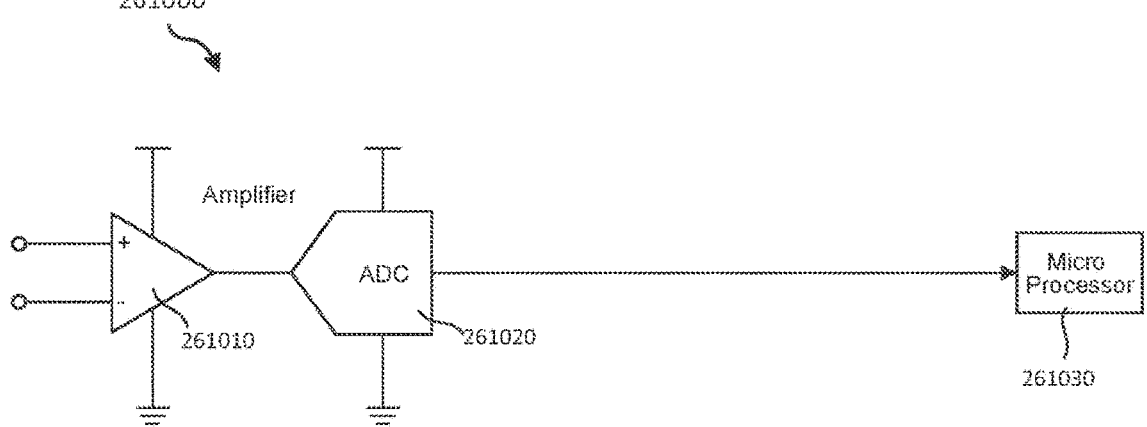
FIG. 26T illustrates a technique for reducing electromagnetic noise by employing an ADC for each channel of a multi-channel control interface, in accordance with some embodiments.

FIG. 26T illustrates an example technique for reducing electromagnetic interference in accordance with some embodiments. FIG. 26T shows a portion of a device 261000 including an analog circuit including an ADC 261030 located within each analog channel. The ADC may be located as close to the output of amplifier 261020 as possible. By locating an ADC close to each amplifier output for the analog channels, the analog signal may be converted into a corresponding digital signal as it is outputted by the amplifier 26610, using a trace that may be around a few mm in length. In some embodiments, the trace length may not exceed 20 mm to avoid noise signal generation through an AC magnetic field. The digital signal may then be provided to microprocessor 261010. Noise generation may not be a problem for the digital signals in this example.

In some examples, a method of reducing electromagnetic interference in an analog circuit of a control device for an extended reality (XR) system may include: providing an analog signal chain circuit that includes at least one amplifier and an analog-to-digital converter coupled to an amplifier by one or more electrical conductors; and reducing electromagnetic interference induced on the one or more electrical conductors by an external AC magnetic field by configuring at least one component of the control device to reduce the electromagnetic interference. The step of reducing the electromagnetic interference may include providing, in the analog signal chain circuit, at least one fully differential amplifier configured to subtract electromagnetic noise present on the one or more electrical conductors, that may include providing at least two fully differential amplifiers in the analog signal chain circuit. Reducing the electromagnetic interference may also include providing, in the analog signal chain circuit, at least one anti-aliasing filter arranged between an amplifier and the analog-to-digital converter, and/or arranging an anti-aliasing filter to be closer to the analog-to-digital converter than an amplifier. An anti-aliasing filter may include an anti-aliasing filter having at least two stages. In addition, reducing the electromagnetic interference may include forming a shielding material around at least a portion of the analog signal chain circuit. In one example, the method may also include providing, in the analog signal chain circuit, a plurality of analog-to-digital converters, each of which is configured to process the output of a single signal channel of a plurality of signal channels. In another example, the method may also include reducing the electromagnetic interference by integrating a magnetic tracker receiver within the control device and configuring a distance between the magnetic tracker receiver and a magnetic tracker transmitter of the XR system to reduce the electromagnetic interference.

Figure 26U:
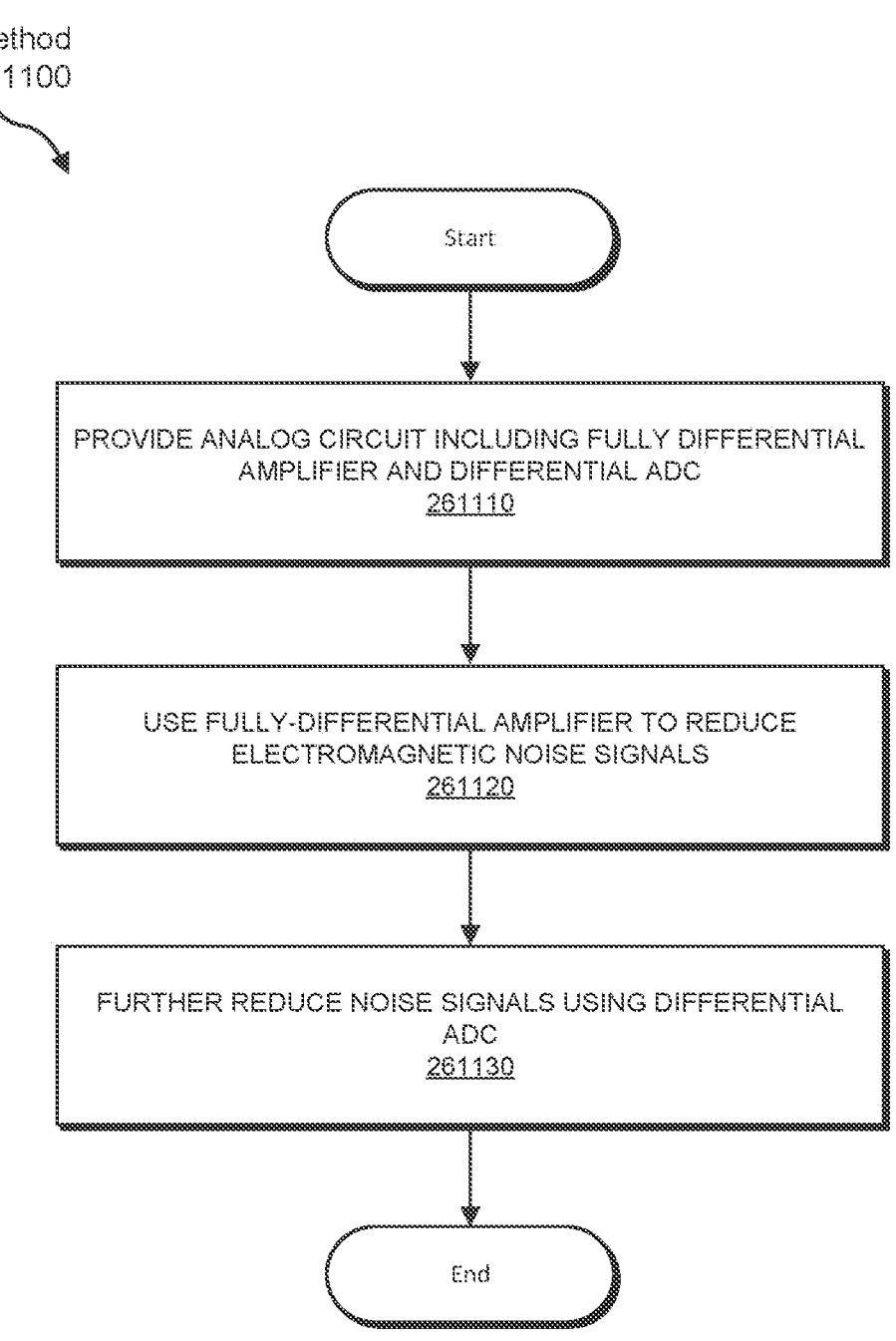
FIGS. 26U-26V show example methods, in accordance with some embodiments.

FIG. 26U illustrates an example method 261100 for reducing electromagnetic noise in an analog circuit of a device, such as a control device for an extended reality (XR) system. In this example, the method may include: providing an analog circuit including a differential amplifier (such as a fully differential amplifier) and an analog-to-digital converter (ADC, such as a differential ADC) (261110), where the ADC is coupled to the amplifier by one or more electrical conductors; reducing the electromagnetic noise induced in the analog circuit by using the differential amplifier to cancel common mode noise signals (261120); and further reducing the noise signal using the differential ADC (261130). In this example, a differential ADC may output a digital signal based on the difference between two analog input voltages. If there is similar noise signal in both analog input voltages, the difference between the input voltages, and hence the digital signal, may be generally independent of the electromagnetic noise.

Figure 26V:
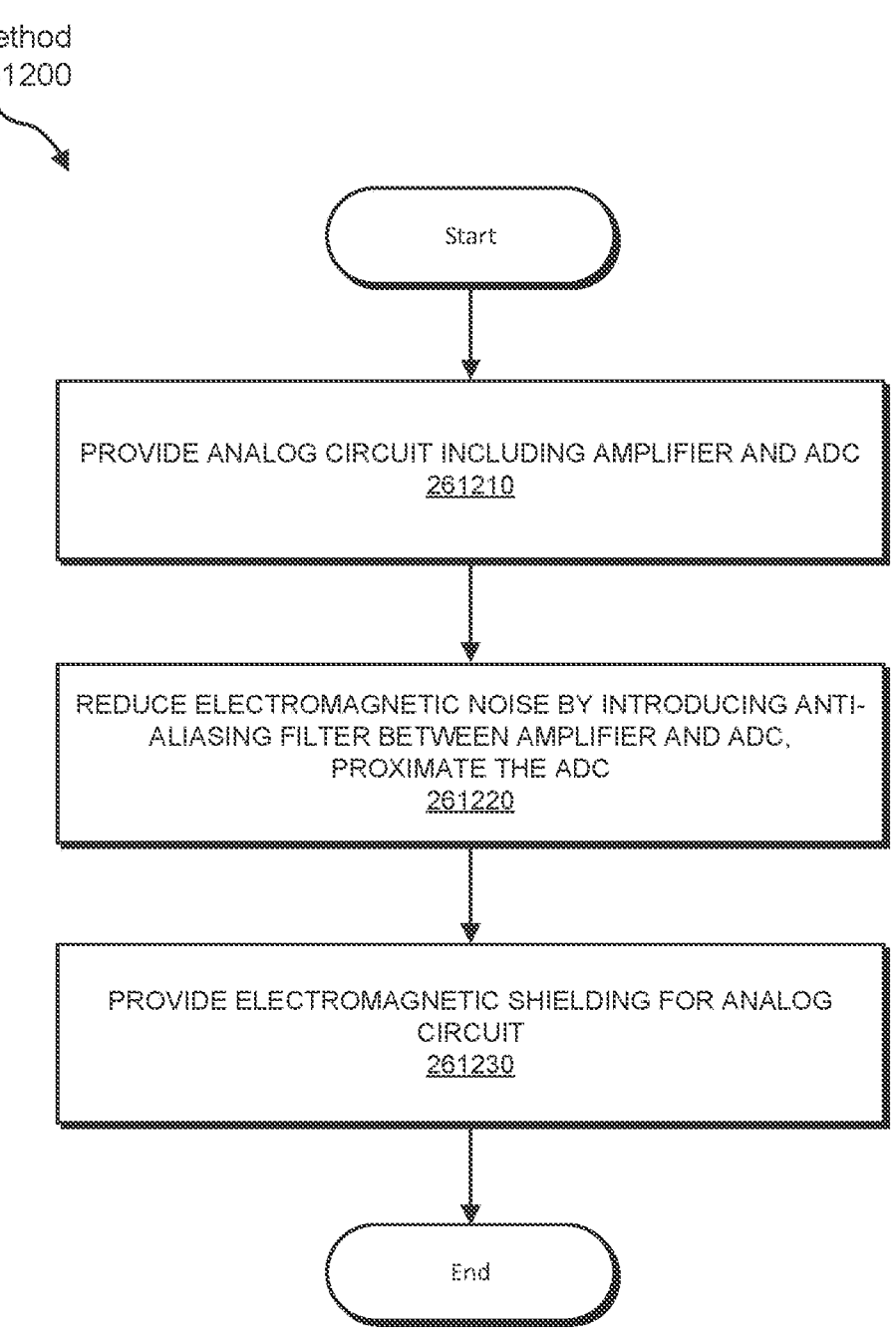

FIG. 26V illustrates another example method 261200 of reducing electromagnetic noise in the analog circuit of a device, such as a control device for an extended reality (XR) system, such as an augmented reality or virtual reality system. In this example, the method may include: providing an analog circuit including a differential amplifier and an analog-to-digital converter (ADC) (261210), where the ADC is coupled to the amplifier by one or more electrical conductors; reducing the electromagnetic noise induced in the analog circuit by providing at least one anti-aliasing filter located between the amplifier and the analog-to-digital converter (ADC), proximate the ADC (261220); and (optionally) providing shielding, at least for the analog circuit portion of the device, from electromagnetic radiation (261230). The analog circuit may be configured to receive sensor signals, such as EMG signals. The electrical connection between the anti-aliasing filter and the ADC may have a length of less than or approximately 15 mm, such as less than or approximately 5 mm, and in some examples less than or approximately 3 mm. In some examples, the anti-aliasing filter and ADC may be combined into a single package, or combined within a single shielded component, or combination of components having at least a partially shielded enclosure.

In some examples, electromagnetic noise reduction may include the use of hardware, software, or a combination thereof. When implemented in software, the software code may be executed on any suitable processor or collection of processors, whether provided in a single computer or distributed among multiple computers. Any component or collection of components that perform the functions described above may be generically considered as one or more controllers that control the above-discussed functions. The one or more controllers may be implemented in numerous ways, such as with dedicated hardware or with one or more processors programmed using microcode or software to perform the functions recited above.

In some examples, a device may include at least one non-transitory computer readable storage medium (e.g., a computer memory, a portable memory, a compact disk, etc.) encoded with a computer program (i.e., a plurality of instructions), which, when executed on a processor, performs the above-discussed functions of the described examples. The computer-readable storage medium may be transportable such that the program stored thereon may be loaded onto any computer resource to implement any suitable aspects of the described examples. In addition, the reference to a computer program which, when executed, performs the above-discussed functions, is not limited to an application program running on a host computer. Rather, the term computer program may be used herein to reference any type of computer code (e.g., software or microcode) that may be employed to program a processor to implement the one or more aspects of the described example.

In some examples, a device (such as a control device for an extended reality (XR) system) includes an analog signal chain circuit including at least one amplifier configured to amplify analog electrical signals recorded from a body of a user on which the device is worn, and an analog-to-digital converter configured to convert the amplified analog electrical signals to digital signals. In these examples, at least one component of the device is configured to reduce electromagnetic interference induced on one or more conductors within the analog signal chain circuit by an external AC magnetic field.

In some examples, the amplifier may include at least one fully differential amplifier configured to reduce the electromagnetic interference. In some examples, the amplifier may include at least two fully differential amplifiers. In some examples, the analog signal chain circuit may further include an anti-aliasing filter arranged between an amplifier and a respective analog-to-digital converter, where the anti-aliasing filter is configured to reduce electromagnetic interference. In some examples, the anti-aliasing filter may include an anti-aliasing filter arranged closer to the analog-to-digital converter than the amplifier. In some examples, the distance between the anti-aliasing filter and the analog-to-digital converter is less than 2 cm. The anti-aliasing filter may have one or more stages, such as at least two stages. An example device may further include a shielding material formed around at least a portion of the analog signal chain circuit, where the shielding material is configured to reduce the electromagnetic interference.

In some examples, a device includes a plurality of signal channels, where each signal channel is configured to record an analog electrical signal from the body of the user. The analog signal chain circuit may further include a plurality of analog-to-digital converters, each of which is configured to process the analog electrical signal from one of the plurality of signal channels. In some examples, the control device may include a magnetic tracker receiver. The distance between the magnetic tracking receiver and the magnetic tracking system transmitter of the XR system may be configured to reduce the electromagnetic interference. An example device, such as a control device, may include a plurality of EMG sensors configured to record a plurality of EMG signals from the body of the user, with an amplifier coupled to one or more of the plurality of EMG sensors. The analog-to-digital converter may include a continuous-time analog-to-digital converter configured to reduce the electromagnetic interference.

In some examples, a method of reducing electromagnetic interference in an analog circuit of a control device for an extended reality (XR) system includes: providing an analog signal chain circuit including at least one amplifier and an analog-to-digital converter coupled to an amplifier by one or more electrical conductors; and reducing electromagnetic interference induced on the one or more electrical conductors by an external AC magnetic field by configuring at least one component of the control device to reduce the electromagnetic interference. The step of reducing the electromagnetic interference may include providing, in the analog signal chain circuit, at least one fully differential amplifier configured to subtract electromagnetic noise present on the one or more electrical conductors, that may include providing at least two fully differential amplifiers in the analog signal chain circuit. Reducing the electromagnetic interference may also include providing, in the analog signal chain circuit, at least one anti-aliasing filter arranged between an amplifier and the analog-to-digital converter, and/or arranging an anti-aliasing filter to be closer to the analog-to-digital converter than an amplifier. An anti-aliasing filter may include an anti-aliasing filter having at least two stages. Reducing the electromagnetic interference may include forming a shielding material around at least a portion of the analog signal chain circuit. An example method may further include providing, in the analog signal chain circuit, a plurality of analog-to-digital converters, each of which is configured to process output of a single signal channel of a plurality of signal channels. An example method may further include reducing the electromagnetic interference by integrating a magnetic tracker receiver within the control device such that a distance between the magnetic tracker receiver and a magnetic tracker transmitter of the XR system is configured to reduce the electromagnetic interference. In some examples, the magnetic tracker transmitter may be located within or supported by a head-mounted device or positioned in another location away from the sensors within the control device. The control device may include one or more magnetic tracker receiver coils, and/or receive signals from one or more magnetic tracker receiver coils. Receiver coils may be located on, for example, the hand, wrist, limb segments, joints, head, or other locations on the user's body.

In some examples, an extended reality (XR) system may include a head-mounted device, such as a headset configured to be worn on a user's head, and a control device configured to be worn on the user's arm or wrist. In these examples, the control device includes an analog signal chain circuit including at least one amplifier configured to amplify analog electrical signals recorded from a body of the user and an analog-to-digital converter configured to convert the amplified analog electrical signals to digital signals. In addition, at least one component of the XR system may be configured to reduce electromagnetic interference induced on one or more conductors within the analog signal chain circuit by an external AC magnetic field.

As detailed above, an electromagnetic field, such as a transmitter signal, may induce noise signals within the receiver of an apparatus. This transmitter signal may be generated by passing an alternating current from an alternating voltage source through a coil. The transmitter signal may generate a noise signal within a closed-loop or open-loop conductor within the receiver due, for example, to an interaction with the transmitter signal. A closed-loop or open-loop conductor may be formed, at least in part, by conducting tracks within the receiver circuit.

An example control device may include EMG sensors arranged circumferentially around a band, such as an elastic band configured to be worn around a body part of a user, such as the lower arm, wrist, one or more fingers, ankle, foot, head, or chest. Any suitable number of neuromuscular sensors may be used. The number and arrangement of neuromuscular sensors within a device may depend on the particular application for which the control device is used. In some examples, the sensors of an apparatus may be coupled together, for example, using flexible electronics incorporated into a control device, for example, within a flexible band.

In some examples, an apparatus, such as a control device (e.g., including an armband, wristband, and/or a head-mounted device) may be configured to generate a control signal for controlling an external device. The external device that may be controlled by the apparatus may include one or more of the following: an augmented reality system, a robot, an appliance (such as a television, radio, or other audiovisual device), an in-house system (such as heating or air conditioning), a vehicle, or other electronic device including a screen (e.g., to scroll through text, interact with a user interface, or control the operation of software). In some examples, an apparatus may be configured to control a virtual avatar within an augmented reality or virtual reality environment, or to perform any other suitable control task.

In some embodiments, the output of one or more of the sensors may be optionally processed using hardware signal processing circuit (e.g., to perform amplification, filtering, and/or rectification). In some embodiments, at least some signal processing of the output of the sensors may be performed in software. Thus, signal processing of signals sampled by the sensors may be performed in hardware, software, or by any suitable combination of hardware and software, as aspects of the technology described herein are not limited in this respect.

An example device may include a control device and one or more dongle portions in communication with the control device (e.g., via BLUETOOTH or another suitable short-range wireless communication technology). The control device may include one or more sensors, that may include electrical sensors including one or more electrodes. The electrical outputs from the electrodes, that may be referred to as sensor signals, may be provided to an analog circuit configured to perform analog processing (e.g., filtering, etc.) of the sensor signals. The processed sensor signals may then be provided to an analog-to-digital converter (ADC), that may be configured to convert analog signals to digital signals that may be processed by one or more computer processors. Example computer processors may include one or more microcontrollers (MCU), such as the nRF52840 (manufactured by NORDIC SEMICONDUCOTR). The MCU may also receive inputs from one or more other sensors. The device may include one or more other sensors, such as an orientation sensor, that may be an absolute orientation sensor and may include an inertial measurement unit. An example orientation sensor may include a BNO055 inertial measurement unit (manufactured by BOSCH SEN-SORTEC). The device may also include a dedicated power supply, such as a power and battery module. The output of the processing performed by MCU may be provided to an antenna for transmission to the dongle portion or another device. Other sensors may include mechanomyography (MMG) sensors, sonomyography (SMG) sensors, electrical impedance tomography (EIT) sensors, and other suitable type of sensors.

A dongle portion may include one or more antennas configured to communicate with the control device and/or other devices. Communication between device components may use any suitable wireless protocol, such as radio-frequency signaling and BLUETOOTH. Signals received by the antenna of dongle portion may be provided to a computer through an output, such as a USB output, for further processing, display, and/or for effecting control of a particular physical or virtual object or objects.

In some examples, a magnetic tracker transmitter may be provided by a separate device, such a separate computer device that may not be supported by a user. For example, a magnetic tracker transmitter may be located at a fixed location relative to the environment (e.g., a room) in which the user is located.

In some examples, a device according to the principles disclosed herein may include a higher-order anti-aliasing filter to attenuate the noise signals. This filter, plus the amplifier block, may offer a transfer function such that the amplified in-band signals are at least 90 dB higher than the attenuated noise signals. Such a configuration may use traces between ADC inputs and anti-aliasing filters outputs that are as short as practically possible. The noise signal coupled into unprotected traces may be negligible if such traces are kept short (e.g., approximately 3 mm in length, or less.)

In some examples, an ADC may be located within each analog channel, and may be located as close to the amplifier output as possible. For example, the analog signal may be converted into a corresponding digital form soon after it is outputted by the amplifier, for example, using a trace (e.g., a PCB track or other electrical conductor) having a length of approximately 3 mm or less. In some examples, the trace length may be approximately equal to or less than 2 mm to substantially avoid noise generation through the alternating electromagnetic field.

Examples include various methods and apparatuses for reducing electromagnetic interference in sensors used in extended reality (XR) environments, such as augmented reality (AR) or virtual reality (VR) environments. As is explained in greater detail below, positional tracking may be used in XR environments (such as AR or VR environments) to track movements, for example, with six degrees of freedom. A corresponding computing device may be configured to estimate a position of an object relative to the environment using one or more positional tracking approaches. Positional tracking may include magnetic tracking, in which the magnitude of a magnetic field may be measured in different directions.

An example apparatus may include a control device, that may be configured to be worn on the wrist of a user, and a head-mounted device. The control device, such as a wearable control device, may be configured to be supported on the wrist or lower arm of a user, and may include one or more sensors. The head-mounted device may include a headset, augmented reality spectacles, or other device configured to be supported by the head of a user, for example, by one or more frame elements, straps, and/or other support elements. The headset may take the form of a visor or helmet, or may be supported by a frame similar to those of spectacles. The head-mounted device may be configured to provide an extended reality environment to a user, such as a virtual reality or augmented reality environment. The control device and the head-mounted device may be in communication with one another, such as via wireless or wired communication components. The control device may detect gestures or other movements of the hands of the user, and provide control signals to the head-mounted device. The control signals may be used to modify augmented or virtual reality image elements displayed to a user. In some examples, control signals may be used to control real (physical) devices, that may be viewed by the user as part of an extended reality experience. In some examples, the apparatus may include a control element used to send control signals to a computer device.

An example magnetic tracker (that may also be referred to as a magnetic tracking system or magnetic tracker) may determine the intensity of a magnetic field using one or more electromagnetic sensors, such as magnetic sensors. The magnetic tracker may include a base station having a transmitter configured to generate an alternating or static electromagnetic field, and one or more sensors that may be configured to send sensor data to a computing device. The sensor data may be related to a position and/or orientation of the sensor with respect to the transmitter. The magnetic tracker may also be configured to enable the determination of object orientation. For example, if a tracked object is rotated, the distribution of the magnetic field along various axes (e.g., orthogonal axes in relation to the sensor) may change. The resulting change in the sensor signal may be used to determine the orientation of the sensor, and, optionally, the orientation of an object on which the sensor is located.

In one embodiment, an example apparatus may include an improved human-machine interface for XR devices, such as AR or VR devices, and an apparatus configured to control computing devices or other electronic devices. This example apparatus may also include a control device configured to receive and process electrical signals derived from the body of a user to provide a control signal. The control signal may be used for object manipulation within an XR environment, control of a computing device, or control of any other suitable electronic device. The control device may include one or more sensors, that may include one or more of an electromyography (EMG) sensor, mechanomyography (MMG) sensor, sonomyography (SMG) sensor, electrical impedance tomography (EIT) sensor, and/or any other suitable sensor.

In some examples, an apparatus, such as a control device, may include one or more printed circuit boards (PCBs), that may be electrically interconnected. In some examples, a PCB may include a plurality of electrically conducting traces, which in some examples may be configured to sense signals, such as signals from the body of a user. The apparatus may be configured to include one or more electronic circuits configured to provide signal amplification, data acquisition, wireless transmission, or other suitable signal acquisition and processing operations.

An apparatus including a magnetic tracker may allow, for example, manipulation of objects in XE environments. An alternating or static magnetic field produced by a transmitter of a magnetic tracker may induce voltage and/or current within an apparatus. For example, electromagnetic fields generated by the transmitter may induce electrical signals within the apparatus, for example, due to electromagnetic coupling to electrical conductors within the apparatus, such as copper tracks within a PCB. In some examples, copper tracks may help form electrically conducting loops, and stray signals may be induced within such loops. The stray signals may induce noise signals within the device, and the noise signals may have the same frequency as the transmitter. The transmitter frequency may be, for example, in the range of approximately 10 kHz to approximately 50 kHz. The transmitter frequency may be higher than the frequency of signals obtained from the body of the user, for instance higher than electromyography signals, which normally are in the frequency range of between approximately 20 Hz to approximately 3 kHz. A sampling frequency, that may be twice the frequency of the biometric signals (e.g., approximately 6 kHz), may be used to convert the analog signals into digital. Even though the induced noise frequency may be much higher than the biometric signals from human bodies, after the analog-digital conversion stage, the noise may be under-sampled, and alias signals originating from the under-sampling of the noise signal may be introduced into the frequency band of the biometric signals. Effectively, high-frequency noise signals may be "down-converted" in the frequency band and be combined with the biometric signals of interest. The noise signal may become stronger as the transmitter is moved closer to the apparatus.

Positional tracking may be used in XR environments to track movements with up to and including six degrees of freedom. Computer devices may be configured, with hardware and/or software, to estimate the positions of objects relative to the environment using positional tracking technologies. Magnetic tracking is a technique in which the magnitude of a magnetic field may be measured in different directions to track positions of one or more objects in an environment.

A magnetic tracking system (or magnetic tracker) may be configured to measure the intensity of an inhomogeneous magnetic field using one or more electromagnetic sensors. An example magnetic tracker may include a transmitter configured to generate an alternating or static electromagnetic field, and one or more electromagnetic sensors configured to provide a respective sensor position (e.g., with respect to the transmitter) to a computer device. The orientation of an object may also be determined using a magnetic tracker. For instance, if a tracked object is rotated, the distribution of the magnetic field along the various axes may change, and these changes may be used to determine the object's orientation.

An example apparatus may include control devices configured as human-machine interfaces, and may be used for immersive XR applications (such as virtual reality applications), and more generally to control computer devices. An example interface device may be configured to process electrical signals derived from the body of a user, and may be used to achieve realistic object manipulation in an XR environment. Example devices may include one or more sensors, including one or more electromyography (EMG) sensors, mechanomyography (MMG) sensors, sonomyography (SMG) sensors, electrical impedance tomography (EIT) sensors, and/or other suitable sensors. Example devices may include one or more printed circuit boards (PCBs), that may include boards connected together, that may include many (e.g., thousands) of electrically conductive traces routed together to achieve certain functionalities such as sensing signals from a user body, signal amplification, data acquisition, wireless transmission, and/or other suitable signal acquisition and processing operations.

Example devices including a magnetic tracker may enable, for example, manipulation of objects in XR environments. However, an alternating or static magnetic field produced by the transmitter of a magnetic tracker may induce a voltage or current within open or closed electrically conductive loops within the device. An electrically conductive loop may include device components (e.g., copper traces on a PCB, electronic components, wires, and the like), resulting in noise being introduced into the device. The introduced noise may fluctuate at the same frequency used by the magnetic tracker, that may operate, for example, at a frequency within a range of 10 kHz to 50 kHz. In some examples, a magnetic tracker transmitter and/or a corresponding magnetic tracker receiver may include at least one coil, such as a 3-axis coil arrangement. Signal processing may be used to establish the three-dimensional relationship between transmitter and receiver coil arrangements.

Magnetic tracker frequencies may be higher than frequencies associated with signals recorded and/or derived from the user's body. For instance, frequencies associated with EMG signals typically range between ~20 Hz to ~3 KHz. In some examples, a device may use a signal sampling frequency twice as large as the highest frequency of the signal of interest (e.g., around ~ 6 kHz) to convert the analog signals into digital signals (e.g., using analog to digital conversion (ADC) circuit). Despite the induced noise frequency being substantially higher than the frequency of the recorded biometric signals, when the high frequency noise is provided as input to the ADC circuit, it may be under-sampled and an aliased image of the noise may interfere with the frequency band of interest associated with the biometric signals. The high frequency noise signal may be "down-converted" into the frequency band of interest by the ADC circuit. In some examples, a device is configured to reduce electromagnetic interference in a control device, such as a wearable control device.

In some examples, an apparatus may include a control device for an extended reality system. The control device may include analog signal chain circuit including at least one amplifier configured to amplify analog electrical signals recorded from a body of a user on which the control device is worn, and an analog-to-digital converter configured to convert the amplified analog electrical signals to digital signals, where at least one component of the control device is configured to reduce electromagnetic interference induced on one or more conductors within the analog signal chain circuit by an external AC magnetic field. In some examples, an amplifier may include at least one fully differential amplifier configured to reduce the electromagnetic interference. In some examples, an amplifier includes at least two fully differential amplifiers. In some examples, the analog signal chain circuit may further include at least one anti-aliasing filter arranged between an amplifier and the analog-to-digital converter, where an anti-aliasing filter may be configured to reduce the electromagnetic noise within the analog circuit. In some examples, an anti-aliasing filter may be located closer to the analog-to-digital converter than the associated amplifier. In some examples, a distance between the anti-aliasing filter and the analog-to-digital converter may be less than 20 mm, and in some examples may be less than 5 mm, such as less than 2 mm. In some examples, an anti-aliasing filter may have at least two stages. In some examples, the control device may further include a shielding material formed around at least a portion of analog circuit.

In some examples, a device, such as a control device, may further include a plurality of signal channels, where each signal channel is configured to record an analog electrical signal from the body of the user, and where the analog circuit further includes a plurality of analog-to-digital converters, each of which is configured to process the analog electrical signal within one of the plurality of signal channels. The analog circuit may include a plurality of signal channels, and each signal channel may include an analog-to-digital converter.

In some examples, a device, such as a control device, may further include a magnetic tracking system receiver (also referred to as a magnetic tracker receiver), where, in some examples, a distance between the magnetic tracker receiver and the magnetic tracker transmitter of the XR system may be configured to reduce the electromagnetic noise in the analog circuit. For example, the magnetic tracker receiver may be located adjacent or otherwise proximate the head of the user. In some examples, the control device may further include a plurality of EMG sensors configured to record a plurality of EMG signals from the body of the user, where an amplifier coupled to one or more of the plurality of EMG sensors. In some examples, the analog-to-digital converter may include a continuous-time analog-to-digital converter configured to reduce the electromagnetic interference. In some examples, the magnetic tracker system may be trained, for example, by comparison of receiver signals with analysis of images determined using an optical imaging system, or using a training process where a user places body parts, such as hands, into predetermined configurations. Magnetic tracker receivers may be distributed over the body of a user, for example, distributed over the torso, limb segments, and joints of a user. The magnetic tracking data may also be used in conjunction with a musculo-skeletal model of the user.

Some embodiments are directed to methods of reducing electromagnetic interference in analog circuit of a control device for an extended reality system. An example method may include providing an analog circuit including at least one amplifier and an analog-to-digital converter coupled to an amplifier by one or more electrical conductors, and reducing electromagnetic interference induced on the one or more electrical conductors by an external AC magnetic field by configuring at least one component of the control device to reduce the electromagnetic interference.

In some examples, a method reducing the electromagnetic interference includes providing in the analog signal chain circuit at least one fully differential amplifier configured to subtract electromagnetic noise present on the one or more electrical conductors. In some examples, the analog circuit may include at least one fully differential amplifier, such as at least two fully differential amplifiers. In some examples, reducing the electromagnetic interference includes providing in the analog circuit at least one anti-aliasing filter arranged between an amplifier and the analog-to-digital converter. In some examples, reducing the electromagnetic interference further includes arranging an anti-aliasing filter closer to the analog-to-digital converter than to an amplifier. In some examples, an anti-aliasing filter may include an anti-aliasing filter having at least two stages. In some examples, reducing the electromagnetic interference may include forming a shielding material around at least a portion of the analog signal chain circuit.

In some examples, a method includes reducing electromagnetic noise induced in an analog circuit by using the fully differential amplifier to reduce the effect of electromagnetic noise signals (e.g., present in both inputs of the fully differential amplifier) on the outputs of the fully differential amplifier, and further reducing the noise signal using the differential analog-to-digital converter configured to receive the outputs of the fully differential amplifier. The electromagnetic noise may be generated by a transmitter of a magnetic tracker system. The analog circuit may be configured to receive and process sensor signals from a plurality of electromyography sensors. In some examples, a method may further include using an anti-aliasing filter to further reduce the electromagnetic noise.

In some examples, the method may further include providing in the analog signal chain circuit a plurality of analog-to-digital converters, each of which is configured to process output of a single signal channel of a plurality of signal channels. In some examples, reducing the electromagnetic interference may include integrating a magnetic tracking system receiver with the control device such that a distance between the magnetic tracking system receiver and a magnetic tracking system transmitter of the XR system is configured to reduce the electromagnetic interference.

Some embodiments are directed to an XR system. The XR system may include a headset configured to be worn on a user's head, and a control device configured to be worn on the user's arm or wrist. The control device may include analog signal chain circuit including at least one amplifier configured to amplify analog electrical signals recorded from a body of the user, and an analog-to-digital converter configured to convert the amplified analog electrical signals to digital signals, where at least one component of the XR system is configured to reduce electromagnetic interference induced on one or more conductors within the analog signal chain circuit by an external AC magnetic field. All combinations of the concepts discussed herein are contemplated as being part of the disclosed subject matter (provided such concepts are not mutually inconsistent).

In some examples, an apparatus may include at least one physical processor, and physical memory including computer-executable instructions that, when executed by the physical processor, cause the physical processor to provide control signals to an extended reality headset (or other head-mounted device) based on detected EMG signals and/or to perform any of the other methods described herein.

In some examples, a non-transitory computer-readable medium may include one or more computer-executable instructions that, when executed by at least one processor of a computing device, cause the computing device to provide control signals to an extended reality headset (or other head-mounted device) based on detected EMG signals and/or to perform any of the other methods described herein.

The following describes exemplary systems and methods for improving handstate representation model estimates according to at least one embodiment of the present disclosure.

In some computer applications that generate musculoskeletal representations of the human body, it may be desirable for the application to provide a more realistic representation of body position, movement, and force. Systems and methods described herein may improve musculoskeletal representations (e.g., representations of the hand) by applying smoothing functions to an inferential model to reduce noise and/or jitter. By reducing noise and/or jitter, these systems and methods may improve user experience in virtual environments that use the musculoskeletal representations for visualizing body parts (e.g., a hand) and for providing movement-based input (e.g., hand gestures).

Accordingly the systems and methods described herein improve the functioning of a computer that processes musculoskeletal representations. Furthermore, these systems and methods improve the functioning of extended reality systems (e.g., a virtual reality (VR) system, an augmented reality (AR) system, or a mixed reality system) that process and/or consume musculoskeletal representation models. These systems and methods therefore represent an advancement in the fields of computing and extended reality.

An application may involve a virtual environment tracking the spatial position of the user's hand and virtually rendering the hand. Although there are camera-based systems used to track human movement, they may fail to realistically track (and render) a user's body part (e.g. hand), at least because such systems may not account for realistic physics, human anatomy (including joint kinematics), and stereotyped and common gestures. Some embodiments described herein may improve systems for tracking (and, e.g., rendering) a part of a user's body (e.g. a hand) in order to more realistically render the position and/or movement of a part of a user's body. More realistic rendering of a part of a user's body (e.g., by more realistically approximating natural kinematics and gestures) may enhance immersion in virtual environments.

Systems and methods described herein may measure and/or model human anatomy using wearable neuromuscular sensors. Data from the neuromuscular sensors may be applied alone or combined with other sources, such as camera data.

In some examples, systems and methods described herein may predict information about the positioning and movements of portions of a user's arm and/or hand represented as a multi-segment articulated rigid body system with joints connecting the multiple segments of the rigid body system. Signals recorded by wearable neuromuscular sensors placed at locations on the user's body are provided as input to an inference model trained to predict estimates of the position (e.g., absolute position, relative position, orientation) and/or forces associated with a plurality of rigid segments in a computer-based musculoskeletal representation associated with a hand when a user performs one or more movements. The position information and/or force information associated with segments of a musculoskeletal representation associated with a hand is referred to herein as a "handstate" of the musculoskeletal representation. As a user performs different movements, a trained inference model may interpret neuromuscular signals recorded by the wearable neuromuscular sensors into position and force estimates (handstate information) that are used to update the musculoskeletal representation. As the neuromuscular signals are continuously recorded, the musculoskeletal representation is updated in real time (or near real time) and a visual representation of a hand (e.g., within a virtual reality environment) is optionally rendered based on the current handstate estimates.

Due to imperfect neuromuscular sensor data and/or imperfectly trained inference models, the estimated handstate output produced by a trained inference model may be noisy and/or jittery. The presence of handstate jitter within a virtual environment may break immersion as a virtual representation of a hand appears unnatural and/or to lack correspondence with the user's actual movements. In addition, where handstate is used for gesture-based input, handstate jitter may interfere with the user's ability to successfully perform gesture-based input.

Accordingly, systems and methods described herein address issues, such as noise or jitter, otherwise observable in the output from a trained inference model. For example, these systems and methods may include a temporal smoothing function within the trained inference model. Additionally or alternatively, these systems and methods may include a temporal smoothing function that post-processes output from the trained inference model. The temporal smoothing function may include any of a variety of functions including, without limitation, a total variation loss function or a finite difference loss function.

The temporal smoothing function may temporally smooth the output of the trained inference model. For example, the temporally smooth output may include one or more predicted joint angles, and a total variation loss function may apply a penalty corresponding to a reduced angular velocity of the one or more predicted joint angles. Applying such a loss penalty may reduce large differences in time-series or sequential output from the trained inference model and help generate more realistic representations (including, e.g., visual representations) of the user's hand or another suitable portion of the user's body.

All or portions of the human musculoskeletal system can be modeled as a multi-segment articulated rigid body system, with joints forming the interfaces between the different segments and joint angles defining the spatial relationships between connected segments in the model. Constraints on the movement at the joints are governed by the type of joint connecting the segments and the biological structures (e.g., muscles, tendons, ligaments) that restrict the range of movement at the joint. For example, the shoulder joint connecting the upper arm to the torso and the hip joint connecting the upper leg to the torso are ball and socket joints that permit extension and flexion movements as well as rotational movements. By contrast, the elbow joint connecting the upper arm and the forearm and the knee joint connecting the upper leg and the lower leg allow for a more limited range of motion. As described herein, a multi-segment articulated rigid body system is used to model portions of the human musculoskeletal system. However, some segments of the human musculoskeletal system (e.g., the forearm), though approximated as a rigid body in the articulated rigid body system, may include multiple rigid structures (e.g., the ulna and radius bones of the forearm) that provide for more complex movement within the segment that is not explicitly considered by the rigid body model. Accordingly, a model of an articulated rigid body system for use with some embodiments of the technology described herein may include segments that represent a combination of body parts that are not strictly rigid bodies.

In kinematics, rigid bodies are objects that exhibit various attributes of motion (e.g., position, orientation, angular velocity, acceleration). Knowing the motion attributes of one segment of the rigid body enables the motion attributes for other segments of the rigid body to be determined based on constraints in how the segments are connected. For example, the hand may be modeled as a multi-segment articulated body with the joints in the wrist and each finger forming the interfaces between the multiple segments in the model. In some embodiments, movements of the segments in the rigid body model can be simulated as an articulated rigid body system in which position (e.g., actual position, relative position, or orientation) information of a segment relative to other segments in the model are predicted using a trained inference model, as described in more detail below.

The portion of the human body approximated by a musculoskeletal representation as described herein as one non-limiting example, is a hand or a combination of a hand with one or more arm segments and the information used to describe a current state of the positional relationships between segments and force relationships for individual segments or combinations of segments in the musculoskeletal representation is referred to herein as the handstate of the musculoskeletal representation. It may be appreciated, however, that the techniques described herein are also applicable to musculoskeletal representations of portions of the body other than the hand including, but not limited to, an arm, a leg, a foot, a torso, a neck, or any combination of the foregoing.

In addition to spatial (e.g., position/orientation) information, some embodiments are configured to predict force information associated with one or more segments of the musculoskeletal representation. For example, linear forces or rotational (torque) forces exerted by one or more segments may be estimated. Examples of linear forces include, but are not limited to, the force of a finger or hand pressing on a solid object such as a table, and a force exerted when two segments (e.g., two fingers) are pinched together. Examples of rotational forces include, but are not limited to, rotational forces created when segments in the wrist or fingers are twisted or flexed. In some embodiments, the force information determined as a portion of a current handstate estimate includes one or more of pinching force information, grasping force information, or information about co-contraction forces between muscles represented by the musculoskeletal representation.

Figure 27A:
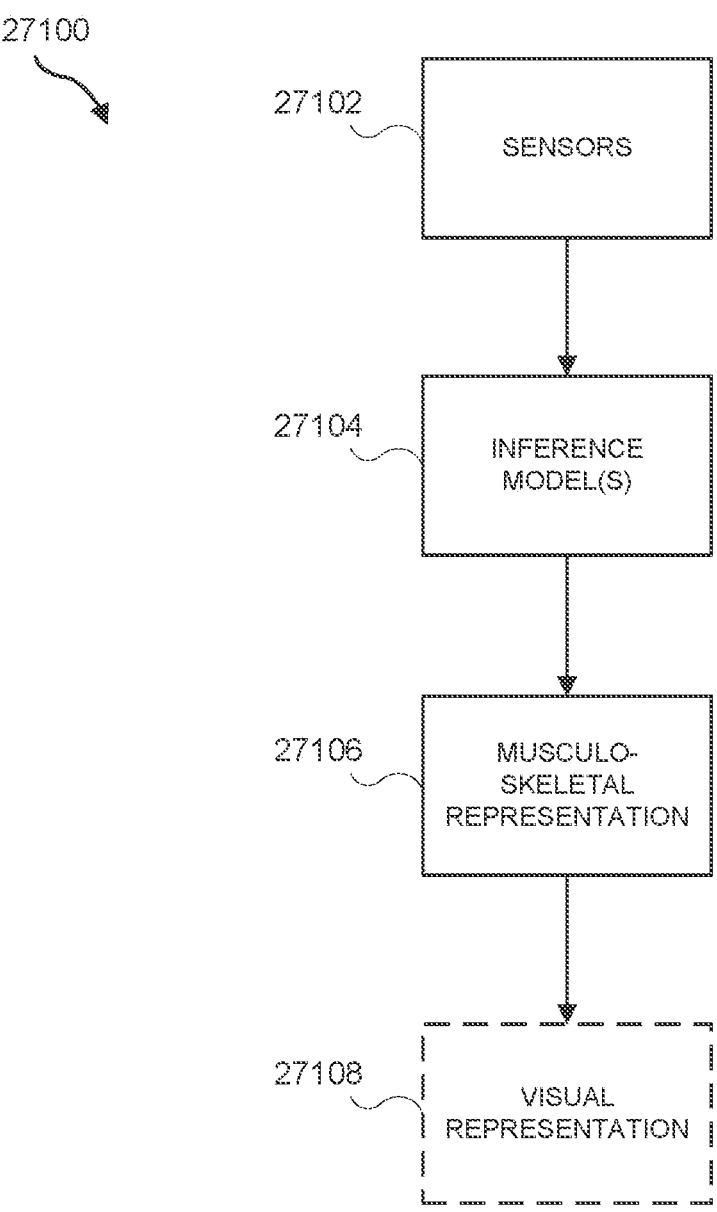
FIG. 27A is a diagram of a computer-based system for generating a musculoskeletal representation based on neuromuscular sensor data.

FIG. 27A illustrates a system 27100 in accordance with some embodiments. The system includes a plurality of sensors 27102 configured to record signals resulting from the movement of portions of a human body. Sensors 27102 may include autonomous sensors. As used herein, the term "autonomous sensors" refers to sensors configured to measure the movement of body segments without requiring the use of external devices. Examples of external devices used in non-autonomous sensors include, but are not limited to, wearable (e.g. body-mounted) cameras, global positioning systems, or laser scanning systems. In some embodiments, sensors 27102 may also include non-autonomous sensors in combination with autonomous sensors. As used herein, the term "non-autonomous sensors" refers to sensors configured to measure the movement of body segments using external devices.

Autonomous sensors may include a plurality of neuromuscular sensors configured to record signals arising from neuromuscular activity in skeletal muscle of a human body. The term "neuromuscular activity" as used herein refers to neural activation of spinal motor neurons that innervate a muscle, muscle activation, muscle contraction, or any combination of the neural activation, muscle activation, and muscle contraction. Neuromuscular sensors may include one or more electromyography (EMG) sensors, one or more mechanomyography (MMG) sensors, one or more sonomyography (SMG) sensors, one or more electrical impedance tomography (EIT) sensors, a combination of two or more types of EMG sensors, MMG sensors, SMG sensors, EIT sensors, and/or one or more sensors of any suitable type that are configured to detect neuromuscular signals. In some embodiments, the plurality of neuromuscular sensors may be used to sense muscular activity related to a movement of the part of the body controlled by muscles from which the neuromuscular sensors are arranged to sense the muscle activity. Spatial information (e.g., position and/or orientation information) and force information describing the movement may be predicted based on the sensed neuromuscular signals as the user moves over time.

Autonomous sensors may include one or more Inertial Measurement Units (IMUs), which measure a combination of physical aspects of motion, using, for example, an accelerometer, a gyroscope, a magnetometer, or any combination of one or more accelerometers, gyroscopes and magnetometers. In some embodiments, IMUs may be used to sense information about the movement of the part of the body on which the IMU is attached and information derived from the sensed data (e.g., position and/or orientation information) may be tracked as the user moves over time. For example, one or more IMUs may be used to track movements of portions of a user's body proximal to the user's torso relative to the sensor (e.g., arms, legs) as the user moves over time.

In embodiments that include at least one IMU and a plurality of neuromuscular sensors, the IMU(s) and neuromuscular sensors may be arranged to detect movement of different parts of the human body. For example, the IMU(s) may be arranged to detect movements of one or more body segments proximal to the torso (e.g., an upper arm), whereas the neuromuscular sensors may be arranged to detect movements of one or more body segments distal to the torso (e.g., a forearm or wrist). Notwithstanding the provided examples, autonomous sensors may be arranged in any suitable way, and embodiments of the technology described herein are not limited based on the particular sensor arrangement. For example, in some embodiments, at least one IMU and a plurality of neuromuscular sensors may be co-located on a body segment to track movements of body segment using different types of measurements. In one implementation described in more detail below, an IMU sensor and a plurality of EMG sensors are arranged on a wearable device configured to be worn around the lower arm or wrist of a user. In such an arrangement, the IMU sensor may be configured to track movement information (e.g., positioning and/or orientation over time) associated with one or more arm segments, to determine, for example whether the user has raised or lowered their arm, whereas the EMG sensors may be configured to determine movement information associated with wrist or hand segments to determine, for example, whether the user has an open or closed hand configuration.

Each of the autonomous sensors includes one or more sensing components configured to sense information about a user. In the case of IMUs, the sensing components may include one or more accelerometers, gyroscopes, magnetometers, or any combination thereof to measure characteristics of body motion, examples of which include, but are not limited to, acceleration, angular velocity, and sensed magnetic field around the body. In the case of neuromuscular sensors, the sensing components may include, but are not limited to, electrodes configured to detect electric potentials on the surface of the body (e.g., for EMG sensors) vibration sensors configured to measure skin surface vibrations (e.g., for MMG sensors), and acoustic sensing components configured to measure ultrasound signals (e.g., for SMG sensors) arising from muscle activity.

In some embodiments, the output of one or more of the sensing components may be processed using hardware signal processing circuitry (e.g., to perform amplification, filtering, and/or rectification). In other embodiments, at least some signal processing of the output of the sensing components may be performed in software. Thus, signal processing of autonomous signals recorded by the autonomous sensors may be performed in hardware, software, or by any suitable combination of hardware and software, as aspects of the technology described herein are not limited in this respect.

In some embodiments, the recorded sensor data may be processed to compute additional derived measurements that are then provided as input to an inference model, as described in more detail below. For example, recorded signals from an IMU sensor may be processed to derive an orientation signal that specifies the orientation of a rigid body segment over time. Autonomous sensors may implement signal processing using components integrated with the sensing components, or at least a portion of the signal processing may be performed by one or more components in communication with, but not directly integrated with the sensing components of the autonomous sensors.

In some embodiments, at least some of the plurality of autonomous sensors are arranged as a portion of a wearable device configured to be worn on or around part of a user's body. For example, in one non-limiting example, an IMU sensor and a plurality of neuromuscular sensors are arranged circumferentially around an adjustable and/or elastic band such as a wristband or armband configured to be worn around a user's wrist or arm. Alternatively, at least some of the autonomous sensors may be arranged on a wearable patch configured to be affixed to a portion of the user's body. In some embodiments, multiple wearable devices, each having one or more IMUs and/or neuromuscular sensors included thereon may be used to predict musculoskeletal position information for movements that involve multiple parts of the body.

In some embodiments, sensors 27102 only includes a plurality of neuromuscular sensors (e.g., EMG sensors). In other embodiments, sensors 27102 includes a plurality of neuromuscular sensors and at least one "auxiliary" sensor configured to continuously record a plurality of auxiliary signals. Examples of auxiliary sensors include, but are not limited to, other autonomous sensors such as IMU sensors, and non-autonomous sensors such as an imaging device (e.g., a camera), a radiation-based sensor for use with a radiation-generation device (e.g., a laser-scanning device), or other types of sensors such as a heart-rate monitor.

System 27100 also includes one or more computer processors (not shown in FIG. 27A) programmed to communicate with sensors 27102. For example, signals recorded by one or more of the sensors may be provided to the processor (s), which may be programmed to execute one or more machine learning techniques that process signals output by the sensors 27102 to train one or more inference models 27104, and the trained (or retrained) inference model(s) 27104 may be stored for later use in generating a musculoskeletal representation 27106, as described in more detail below. In some implementations, the inference model(s) can include one or more statistical models, one or more machine learning models, and/or a combination of one or more statistical model(s) and/or one or more machine learning model(s). Non-limiting examples of inference models that may be used in accordance with some embodiments to predict handstate information based on recorded signals from sensors 27102 are discussed in more detail below.

System 27100 also optionally includes a display controller configured to display a visual representation 27108 (e.g., of a hand). As discussed in more detail below, one or more computer processors may implement one or more trained inference models configured to predict handstate information based, at least in part, on signals recorded by sensors 27102. The predicted handstate information is used to update the musculoskeletal representation 27106, which is then optionally used to render a visual representation 27108 based on the updated musculoskeletal representation incorporating the current handstate information. Real-time reconstruction of the current handstate and subsequent rendering of the visual representation reflecting the current handstate information in the musculoskeletal model may provide visual feedback to the user about the effectiveness of the trained inference model to accurately represent an intended handstate. Not all embodiments of system 27100 include components configured to render a visual representation. For example, in some embodiments, handstate estimates output from the trained inference model and a corresponding updated musculoskeletal representation are used to determine a state of a user's hand (e.g., in a virtual reality environment) even though a visual representation based on the updated musculoskeletal representation is not rendered (e.g. for interacting with virtual objects in a virtual environment in the absence of a virtually-rendered hand).

In some embodiments, a computer application configured to simulate a virtual reality environment may be instructed to display a visual representation of the user's hand. Positioning, movement, and/or forces applied by portions of the hand within the virtual reality environment may be displayed based on the output of the trained inference model(s). The visual representation may be dynamically updated based on current reconstructed handstate information as continuous signals are recorded by the sensors 27102 and processed by the trained inference model(s) 27104 to provide an updated computer-generated representation of the user's movement and/or exerted force that is updated in real-time.

As discussed above, some embodiments are directed to using an inference model for predicting musculoskeletal information based on signals recorded from wearable autonomous sensors. The inference model may be used to predict the musculoskeletal position information without having to place sensors on each segment of the rigid body that is to be represented in the computer-generated musculoskeletal representation. As discussed briefly above, the types of joints between segments in a multi-segment articulated rigid body model constrain movement of the rigid body. Additionally, different individuals tend to move in characteristic ways when performing a task that can be captured in statistical patterns of individual user behavior. At least some of these constraints on human body movement may be explicitly incorporated into inference models used for prediction in accordance with some embodiments.

Additionally or alternatively, the constraints may be learned by the inference model though training based on ground truth data on the position and exerted forces of the hand and wrist in the context of recorded sensor data (e.g., EMG data). Constraints imposed in the construction of the inference model are those set by anatomy and the physics of a user's body, while constraints derived from statistical patterns are those set by human behavior for one or more users from which sensor measurements are measured and used to train the inference model. As is described in more detail below, the constraints may comprise part of the inference model itself being represented by information (e.g., connection weights between nodes) in the model.

As discussed above, some embodiments are directed to using an inference model for predicting handstate information to enable the generation and/or real-time update of a computer-based musculoskeletal representation. The inference model may be used to predict the handstate information based on IMU signals, neuromuscular signals (e.g., EMG, MMG, and SMG signals), external device signals (e.g., camera or laser-scanning signals), or a combination of IMU signals, neuromuscular signals, and external device signals detected as a user performs one or more movements.

Although it is appreciated that inference modeling can be used to predict handstate information, it should be appreciated that the states of other parts of the body may be modeled and predicted using inference models. To this end, there may be other types of devices having one or more sensor types that can be used on other parts of the body to predict their position and any associated forces, movements, or accelerations using, for example, IMU, neuromuscular signals, or other external device signals.

According to one aspect, it is appreciated that the best estimate of the model at any particular time point may not be the correct or most accurate representation. Thus, in a system where sensor outputs are received in real-time, including noise, high variation outputs (e.g., highly variant movement data), or other signals that may drastically change the state of the inference model, it may be beneficial to include in the inference model(s) some type of loss function or penalization term that reduces errors and/or otherwise improves the reliability that the output response models the user's intended movement. In some cases, a loss function may be configured to generate an output response that adheres to realistic physics, anatomy of a user's body part (e.g. a hand), natural joint kinematics, and/or common gestures (i.e. a 'thumbs up' gesture) rather than optimizing for accuracy of an estimate of the movement, position, and/or force of a part of the user's body (e.g., a handstate). In some instances, preset movements may be stored, and it may be determined whether a user's movement corresponds to a particular preset movement (e.g., a 'thumbs up' gesture). In some example implementations, the system may be capable of rendering the preset movement rather than an interpretation of the actual movement (e.g., an estimated handstate). Also, in some cases, a tradeoff may be made between an increased time lag and accuracy in the modeled movement.

Systems described herein many use any of a variety of techniques to modify the inference model to enact one or more loss functions or penalization terms. For instance, the inference model may be trained with one more loss functions described herein. In one implementation, the system may be programmed to train the model with one more loss functions to promote smoothness of the model outputs. For example, the system may be configured to train the inference model with an error function includes the error in the estimates of the time derivatives of joint angles and forces. The error function may include an error in estimates of one or more derivatives of various orders, including first-order derivatives (velocity), second-order derivatives (acceleration), third-order derivatives (jerk), fourth-order derivatives (jounce or snap), or higher-order derivatives (crackle, pop, lock, drop, shot, put, etc.).

In some embodiments, to address, e.g., noise or jitter issues, in the output from the trained inference model, the systems described herein may include a total variation loss function within the trained inference model in order to temporally smooth the output of the trained inference model. For example, the temporally smooth output may include one or more predicted joint angles, and the total variation loss function may apply a penalty corresponding to a reduced angular velocity of the one or more predicted joint angles. Applying such a loss penalty may reduce large differences in time-series or sequential output from the trained inference model and help generate more realistic visual representations of the user's hand or another suitable portion of the user's body.

In some embodiments, the total variation loss function (LTV) includes Equation (1) shown below:

$$L_{TV} = \lambda \sum_i |y_i - y_{i-1}| \tag{1}$$

where (i) $\lambda$ is a regularization strength, (ii) yi is a predicted joint angle at time i, and (iii) yi−1 is a predicted joint angle at time (i−1).

In some embodiments, the total variation loss function (LTV) includes Equation (2) shown below:

$$L_{TV} = (\lambda/(N-1)) \sum_i^{N-1} |y_i - y_{i-1}|^{\beta} \tag{2}$$

where (i) N is a number of timepoints, (ii) $\lambda$ is a regularization strength, (iii) $y_i$ is a predicated joint angle at time i, (iv) $y_{i-1}$ is a predicted joint angle at time (i−1), and (v) $\beta$ is a sparsity parameter.

In some embodiments, varying the regularization weight, $\lambda$, may improve or diminish the performance of the model with respect to providing temporally smooth output. In some embodiments, the loss function may be varied by using the sparsity parameter, $\beta$, which is the exponent of the loss function and corresponds to a sparsity penalty.

In some embodiments, the finite difference loss function (LnFD) includes Equation (3) shown below:

$$L_{FD}^n = \lambda \sum_i |(1-\delta)^n y_i| \tag{3}$$

where (i) n is a derivative order, (ii) $\lambda$ is a regularization strength, (iii) $y_i$ is a predicted joint angle at time i, and (iv) $\delta$ is a shift operator where $\delta y_i = y_{i-1}$.

In some embodiments, the finite difference loss function (LnFD) includes Equation (4) shown below:

$$L_{FD}^n = (\lambda/(N-n)) \sum_i^{N-n} |(1-\delta)^n y_i|^{\beta} \tag{4}$$

where (i) N is a number of timepoints, (ii) n is a derivative order, (iii) $\lambda$ is a regularization strength, (iv) $y_i$ is a predicted joint angle at time i, and (v) $\delta$ is a shift operator where $\delta y_i = y_{i-1}$, and (vi) $\beta$ is a sparsity parameter.

In some embodiments, varying the regularization weight, $\lambda$, may improve or diminish the performance of the model with respect to providing temporally smooth output. In some embodiments, the loss function may be varied by using the sparsity parameter, $\beta$, which is the exponent of the loss function and corresponds to a sparsity penalty. In some embodiments, the derivative order, n, may be selected according to the desired order of derivative of the joint angles. For example, n=2 may relate to the penalty corresponding to an acceleration of the one or more predicted joint angles. In another example, n=3 may relate to the penalty corresponding to a jerk of the one or more predicted joint angles. In some embodiments, the shift operator, $\delta$, may be used to push the time-series backward in time. For example, where n=2, the expression $(1-\delta)^2 y_i$ may resolve to $(1-2\delta+\delta^2)y_i$ which in turn may yield $y_i-2y_{i-1}+y_{i-2}$. In another example, where n=3, the expression $(1-\delta)^3 y_i$ may resolve to $(1-3\delta+3\delta^2-\delta^3)y_i$, which in turn may yield $y_i-3y_{i-1}+3y_{i-2}-y_{i-3}$.

In some examples, the systems and methods described herein may use multiple different temporal smoothing functions and/or multiple different sets of parameters for a temporal smoothing function for different aspects of the handstate (e.g., for the angles of different joints). For example, these systems and methods may apply the total variation loss function to the wrist and the finite distance loss function to the fingers. In another example, these systems and methods may apply a higher derivative order (e.g., jerk) with the finite distance loss function to the thumb and a relatively lower derivative order (e.g., acceleration) with the finite distance loss function to the pinky finger. In some examples, the systems described herein may determine that a particular temporal smoothing function and/or a particular parameterization of the function results in more accurate smoothed output. These systems may apply a particular function and/or parameterization for a particular aspect of the handstate in any of a variety of ways. For example, smoothing functions and parameterizations may be applied to the various joints of a hand based on observed performance across a group of users. Additionally or alternatively, smoothing functions and parameterizations may be applied to the various joints of a hand based on feedback from a user (e.g., allowing the user to test multiple configurations and allowing the user to select a preferred configuration; receiving feedback from a user that the quality of a handstate representation is poor (overall or for a particular joint) and modifying the smoothing function configuration in response; performing tests with a user that prompt the user to produce a handstate representation under various smoothing functions and parameterizations and selecting a smoothing function with parameterization that results in the user producing the handstate representation that is most faithful to the prompt; etc.).

In some embodiments, the system determines position information of a spatial relationship between connected segments of the musculoskeletal representation. Further, the system determines forces exerted by the musculoskeletal representation. Collectively, the position information and/or force information is referred to as a handstate of the musculoskeletal model. The system determines the musculoskeletal representation based on the position information and determined force.

In some embodiments, the smoothed output may be used to determine the musculoskeletal representation which can be then used to render, for example, a visual representation based on the updated musculoskeletal representation that incorporates the current handstate information or may otherwise be used as a control input for one or more systems. Such a visual representation may be shown, for example, within a virtual reality environment. In other embodiments, the output may be used to control one or more systems such as a robotic system that is responsive to handstate information. In such systems, it may be useful to provide a model with smoothing effect that restricts outputs responsive to situational outputs that provide inaccurate representations.

In some embodiments, adjustment of one or more parameters of the loss function of the model may be performed responsive to one or more control inputs. For example, it is appreciated that the trained model may record its own measure of accuracy which can be used as control input for adjusting one or more parameters of the loss function of the model. In some embodiments, the system may receive an estimate of an accuracy of the inference model which may be used as a control function for adjusting of one or more parameters of the loss function of the model. For example, an accuracy of the inference model may comprise a likelihood or confidence metric. Further, the system may determine quality metrics associated with incoming neuromuscular data received from neuromuscular sensors, IMUs, or other external sensors. In some embodiments, the system may balance smoothness and error minimization—that is, the system may perform in an adjusted response mode that makes the model less susceptible to input changes yet may not necessarily accurately reflect the current state of the body part. Responsive to these estimates and/or determined quality metrics, the system may alter one or more parameters of the loss function to temporally smooth an output of the model. Such a temporally smoothed output from the model may be provided as a control input to another system and/or rendered such as by a visualization (e.g., a virtual representation, including a virtual reality (VR) environment, an augmented reality (AR) environment, or a mixed environment).

In other embodiments, the model may be responsive to external inputs, such as situational inputs provided in a virtual representation. For instance, after a rendering of the model in the VR environment, one or more parameters of the loss function of the model may be controlled responsive to environmental situation information within the VR environment, such as a spatial relationship of the modeled representation (e.g., of a hand) in relation to one or more objects within the virtual reality environment. For instance, a smoothing effect (or a change in a dynamic smoothing effect) can be enforced on the model as the visual representation of the hand approaches an object within the VR environment. For example, a user is more likely to recognize a movement as non-natural or non-smooth if their (virtual or real) body part (e.g. hand) is in proximity to an object (a virtual object in a virtual environment or a real object in a real/augmented environment), so dynamic smoothing based on virtual object proximity to a rendered part of the user's body (e.g. hand) may enhance the user's experience of immersive virtual reality.

Figure 27B:
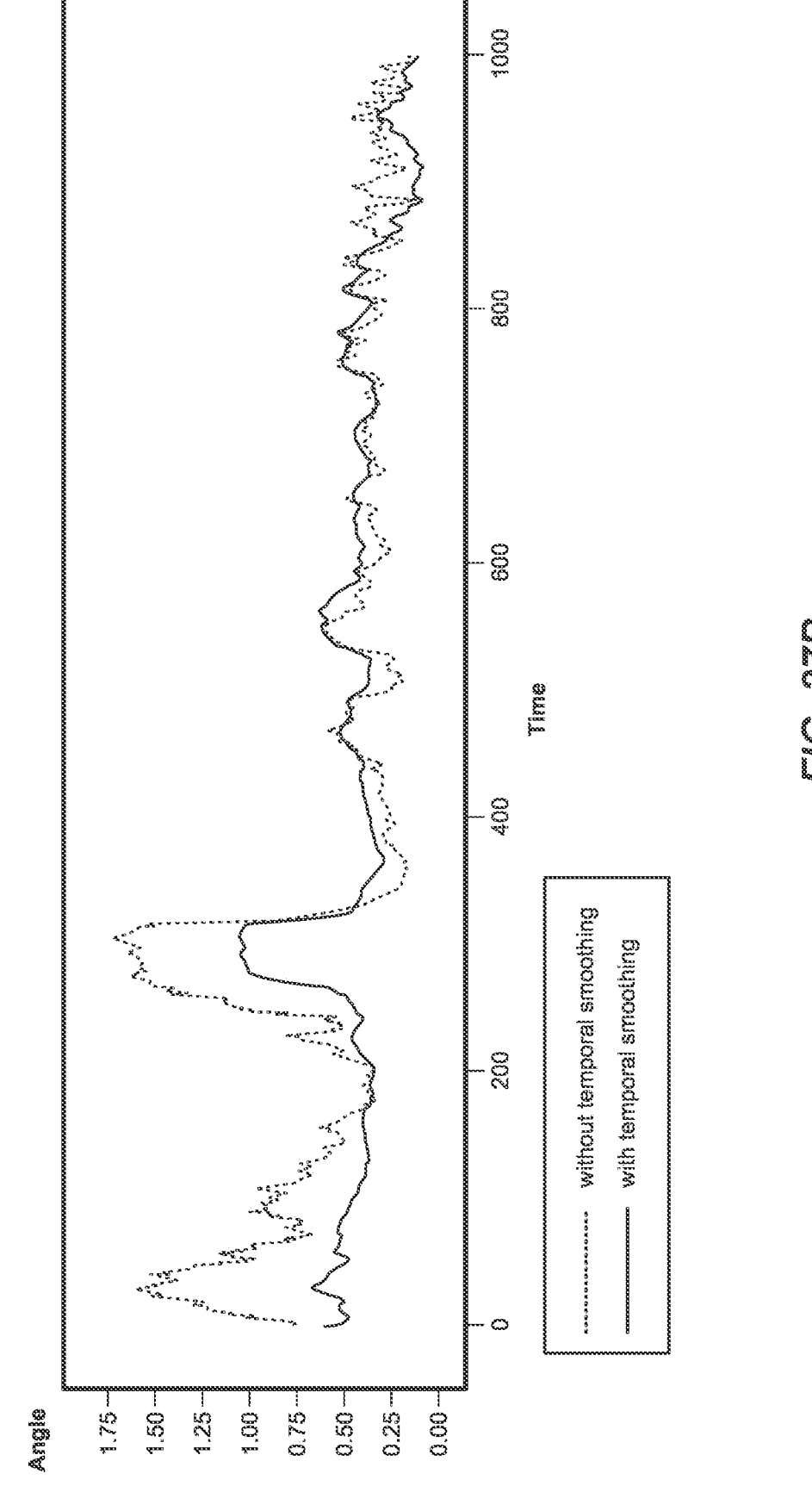
FIG. 27B. is an illustration of an example graph comparing an aspect of a musculoskeletal representation with and without applying a temporal smoothing function.

FIG. 27B illustrates an example graph 27302 of a computer-generated musculoskeletal representation with and without temporal smoothing as described herein. As shown in FIG. 27B, a musculoskeletal representation may be produced by an inferential model using neuromuscular sensor data with or without temporal smoothing. In the example shown in graph 27302, without temporal smoothing, the representation of a joint angle (e.g., the metacarpophalangeal joint of the user's right index finger) may change erratically. If visually represented to a user, the user's index finger would appear to be rapidly jittering even if the user were holding the finger substantially still. If the user were attempting gesture-based inputs involving their index finger, an interface system might register inputs based on gestures that the user didn't make and/or might fail to correctly recognize gestures that the user did make. However, with temporal smoothing the musculoskeletal representation may appear natural to the user (e.g., without jitter and/or erratic movements that the user didn't make) and/or gestures performed by the user to a gesture-based input system may be registered with fewer false positives and/or false negatives.

The following describes exemplary methods and apparatuses for low latency body state prediction based on neuromuscular data according to at least one embodiment of the present disclosure.

The present disclosure is generally directed to predicting body part states of a human user using trained inferential models. In some computer applications that generate musculoskeletal representations of the human body, it may be desirable for an application to know the spatial positioning, orientation, and movement of a user's body to provide a realistic representation of body movement to the application. For example, in an artificial-reality (AR) environment, tracking the spatial position of the user's hand may enable the application to accurately represent hand motion in the AR environment, which may allow the user to interact with (e.g., by grasping or manipulating) virtual objects within the AR environment. In a user interface application, detecting the presence or absence of a pose or gesture of the user may be used as a binary control input (e.g., mode switching) to a computer. An important feature of computer applications that generate musculoskeletal representations of the human body is low latency between a movement of the user's body and the representation of that movement by the computer application (e.g., displaying a visual representation to the user).

The time delay between onsets of neuromuscular activity (e.g., as indicated by electromyography (EMG) signals measured by a wearable device) and muscle contraction in a human body part may range from tens of milliseconds to hundreds of milliseconds or more, depending on physiological differences between individuals and the particular body part. Therefore, at any point in time, a neuromuscular activity signal corresponds to motion that may occur tens of milliseconds, or more, in the future.

Systems, methods, and apparatuses of the present disclosure for predicting a state of a body part, or a portion of a body part, based on neuromuscular activity data may achieve lower body state latency (e.g., the latency from recorded neuromuscular data to the output of a trained inferential model that predicts the state of the body part or the portion of the body part of the user) by temporally shifting neuromuscular activity signal data relative to ground truth measurements of body state. The temporally shifted data set may be used as an input for training an inferential model and/or as input to a previously trained inferential model.

In some embodiments, a method is provided that includes receiving neuromuscular activity signals in response to movement of a body part of a user via one or more neuromuscular sensors (e.g., neuromuscular sensors on a wearable device donned by the user), determining a ground truth (e.g., directly observed) measurement associated with a corresponding movement of the body part of the user, time shifting the neuromuscular activity signals to substantially align with a timing of the corresponding movement, and training an inferential model using the time shifted neuromuscular activity signals.

All or portions of the human musculoskeletal system may be modeled as a multi-segment articulated rigid body system, with joints forming the interfaces between the different segments and joint angles defining the spatial relationships between connected segments in the model. Constraints on the movement at the joints may be governed by the type of joint connecting the segments and the biological structures (e.g., muscles, tendons, ligaments, etc.) that restrict the range of movement at the joint. For example, the shoulder joint connecting the upper arm to the torso and the hip joint connecting the upper leg to the torso are ball and socket joints that permit extension and flexion movements as well as rotational movements. By contrast, the elbow joint connecting the upper arm and the forearm and the knee joint connecting the upper leg and the lower leg allow for a more limited range of motion. A musculoskeletal representation may be a multi-segment articulated rigid body system used to model portions of the human musculoskeletal system. However, some segments of the human musculoskeletal system (e.g., the forearm), though approximated as a rigid body in the articulated rigid body system, may include multiple rigid structures (e.g., the ulna and radius bones of the forearm) that provide for more complex movement within the body segment that is not explicitly considered by rigid body models. Accordingly, a musculoskeletal representation may include body segments that represent a combination of body parts that are not strictly rigid bodies.

In some embodiments, a trained inferential model may be configured to predict a state of a portion of the body of a user. Such a body state may include a force, a movement, a pose, or a gesture of a body part or a portion of a body part. For example, the body state may include the positional relationships between body segments and/or force relationships for individual body segments and/or combinations of body segments in the musculoskeletal representation of the portion of the body of the user.

A predicted force may be associated with one or more segments of a musculoskeletal representation of the portion of the body of the user. Such predicted forces may include linear forces or rotational (e.g., torque) forces exerted by one or more segments of the musculoskeletal representation. Examples of linear forces include, without limitation, the force of a finger or a hand pressing on a solid object such as a table or a force exerted when two segments (e.g., two fingers) are squeezed together. Examples of rotational forces include, without limitation, rotational forces created when segments in the wrist and/or fingers are twisted and/or flexed. In some embodiments, the predicted body state may include, without limitation, squeezing force information, pinching force information, grasping force information, twisting force information, flexing force information, or information about co-contraction forces between muscles represented by the musculoskeletal representation.

A predicted movement may be associated with one or more segments of a musculoskeletal representation of the portion of the body of the user. Such predicted movements may include linear/angular velocities and/or linear/angular accelerations of one or more segments of the musculoskeletal representation. The linear velocities and/or the angular velocities may be absolute (e.g., measured with respect to a fixed frame of reference) or relative (e.g., measured with respect to a frame of reference associated with another segment or body part).

As used herein, the term "pose" may refer to a static configuration (e.g., the positioning) of one or more body parts. For example, a pose may include a fist, an open hand, statically pressing the index finger against the thumb, pressing the palm of a hand down on a solid surface, grasping a ball, or a combination thereof. As used herein, the term "gesture" may refer to a dynamic configuration of one or more body parts, the movement of the one or more body parts, forces associated with the dynamic configuration, or a combination thereof. For example, gestures may include waving a finger back and forth, throwing a ball, grasping a ball, or a combination thereof. Poses and/or gestures may be defined by an application configured to prompt a user to perform the pose and/or gesture. Additionally or alternatively, poses and/or gestures may be arbitrarily defined by a user.

In some embodiments, a body state may describe a hand of a user, which may be modeled as a multi-segment articulated body. The joints in the wrist and each finger may form the interfaces between the multiple segments in the model. In some embodiments, a body state may describe a combination of a hand with one or more arm segments of the user. The methods described herein are also applicable to musculoskeletal representations of portions of the body other than the hand including, without limitation, an arm, a leg, a foot, a torso, a neck, or a combination thereof.

Systems and methods of the present disclosure that compensate for electromechanical delay in the musculoskeletal system may achieve lower latency and/or increased accuracy in predicting body state as compared to traditional methods. Electromechanical delay in the musculoskeletal system may be defined as the time between the arrival of a motor neuron action potential at a neuromuscular synapse and force output (e.g., movement) of a part of the body directed by the motor neuron action potential. The time delay between onsets of neuromuscular activity (e.g., as indicated by EMG signals from a wearable device donned by the user) and muscle contraction may range from tens of milliseconds to more than hundreds of milliseconds, depending on the physiology of the user and the body part directed by the motor neuron action potential. Therefore, at any point in time, the EMG signals may correspond to motion of the body part that occurs tens of milliseconds, or more, in the future.

In some examples, an inferential model trained on neuromuscular signals temporally shifted relative to ground truth measurements of the body part state may evaluate the relationship between the neuromuscular signal and the body part's corresponding motion, rather than between the neuromuscular signal and motion corresponding to an earlier neuromuscular signal. Further, the introduction of this temporal shift may reduce the latency between the ground truth body state and the predicted body state output by the trained inferential model, thereby improving the user experience associated with the application (e.g., an artificial-reality application, a user interface application, etc.) because the body part representation (e.g., a visual representation on a head-mounted display) is more reactive to the user's actual motor control.

Electromechanical delays may vary between individuals and parts of a user's body (e.g., different delays for a hand vs. a leg due to their different sizes). In some examples, the amount that neuromuscular signals are shifted relative to ground truth data about the position of the arm, hand, wrist, and/or fingers may be optimized according to particular physiology shared between users (e.g., age or gender) or personalized for a specific user based on their personal electromechanical delay (e.g., for muscles of the forearm that control hand and finger movements). Training an inferential model using neuromuscular signals temporally shifted relative to ground truth measurements of the state may account for any or all factors known to influence electromechanical delays in the human neuromuscular system including, without limitation, body temperature, fatigue, circadian cycle, drug consumption, diet, caffeine consumption, alcohol consumption, gender, age, flexibility, muscle contraction level, or a combination thereof.

In some examples, an appropriate temporal shift may be identified by generating multiple training datasets with multiple temporal shifts. In some examples, the temporal shifts may be different respective time intervals. For example, a set of training datasets may be created with time intervals ranging from 5 ms to 100 ms in increments of 5 ms or from 10 ms to 150 ms in increments of 10 ms, or some other combination of starting time interval, ending time interval, and time increment. The multiple training datasets may be used to train multiple inferential models. The latency and accuracy of these models may then be assessed by comparing the models to the ground truth data. A model may be selected that exhibits a desired balance of latency and accuracy. The desired balance may depend on the task performed by the user. For example, a task prioritizing precise movement (e.g., tele-surgery) may accept greater latency in exchange for greater accuracy, while a task prioritizing rapid movement (e.g., a video game) may accept lower accuracy in exchange for lower latency.

In some examples, an inferential model trained using an appropriate delay time interval may be selected without generating multiple training datasets. For example, an inferential model may be trained using a known appropriate delay time interval. The known appropriate delay time interval may depend on a known electromechanical delay time and/or a known characteristic latency of the system. The known electromechanical delay time may be specific to a force, a movement, a pose, a gesture, a body part, a specific user, a user having a physiological characteristic (e.g., a specific age, sex, activity level, or other characteristic influencing electromechanical delays in the human neuromuscular system), or a combination thereof. The known electromechanical delay time may be directly determined by a clinician according to known methods for the particular user and/or estimated based on known electromechanical delay times for users sharing a physiological characteristic with the user.

In some examples, an appropriate delay time interval may be determined using a known electromechanical delay time for a body part, a user, and/or a category of users. For example, when the known electromechanical delay associated with the body part is 40 ms, the time intervals may be selected ranging from 20 to 60 ms. Prediction accuracies may be generated for inferential models trained using time-shifted training datasets generated using the selected time intervals. One or more of the inferential models may be selected for use in predicting body part state using the generated prediction accuracies. By selecting time intervals based on a known electromechanical delay time, the selection of the appropriate delay time interval may focus on time intervals likely to combine sufficient accuracy and low latency. As a result, fewer time intervals may be tested and/or a range of time intervals may be tested at a higher resolution (e.g., a 1 ms resolution rather than a 5 ms or a 10 ms resolution).

Figure 28A:
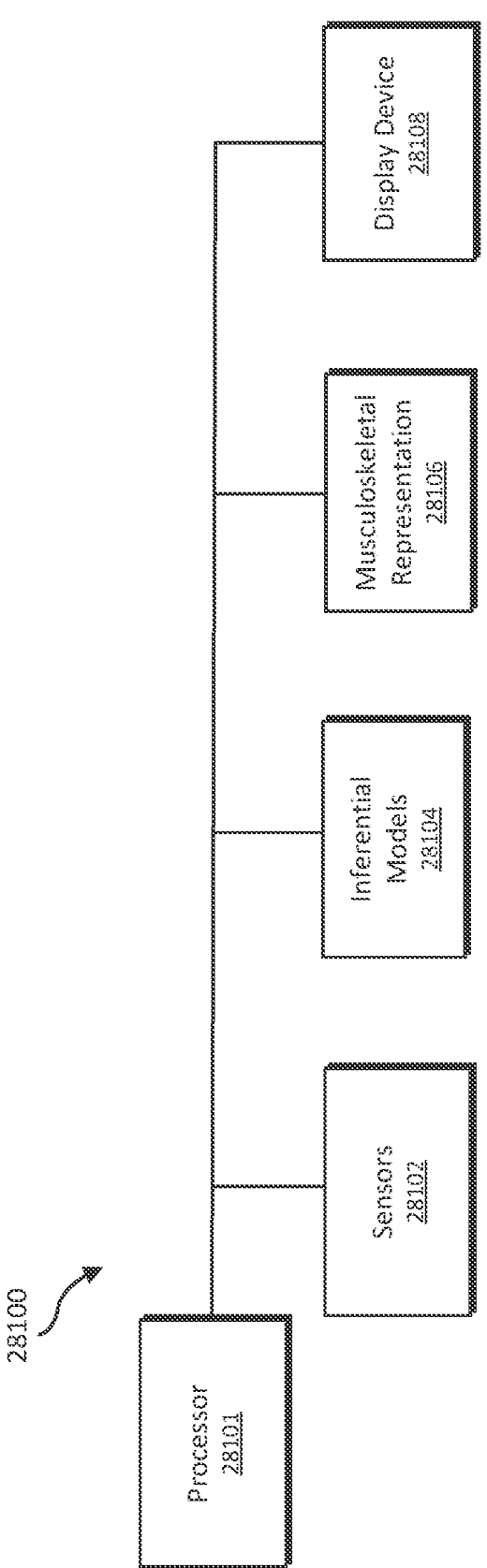
FIG. 28A is an illustration of an example block diagram of a system for predicting body state information, in accordance with embodiments of the present disclosure.

FIG. 28A illustrates a system 28100 in accordance with embodiments of the present disclosure. The system 28100 may include a plurality of sensors 28102 configured to record signals resulting from the movement of portions of a human body. Sensors 28102 may include autonomous sensors. In some examples, the term "autonomous sensors" may refer to sensors configured to measure the movement of body segments without requiring the use of external devices. In additional embodiments, sensors 28102 may also include non-autonomous sensors in combination with autonomous sensors. In some examples, the term "non-autonomous sensors" may refer to sensors configured to measure the movement of body segments using external devices. Examples of non-autonomous sensors may include, without limitation, wearable (e.g., body-mounted) cameras, global positioning systems, laser scanning systems, radar ranging sensors, or a combination thereof.

Autonomous sensors may include a plurality of neuromuscular sensors configured to record signals arising from neuromuscular activity in muscles of a human body. The term "neuromuscular activity," as used herein, may refer to neural activation of spinal motor neurons that innervate a muscle, muscle activation, muscle contraction, or a combination thereof. Neuromuscular sensors may include one or more electromyography (EMG) sensors, one or more mechanomyography (MMG) sensors, one or more sonomyography (SMG) sensors, one or more sensors of any suitable type that are configured to detect neuromuscular signals, or a combination thereof. In some examples, sensors 28102 may be used to sense muscular activity related to a movement of the body part controlled by muscles. Sensors 28102 may be configured and arranged to sense the muscle activity. Spatial information (e.g., position and/or orientation information) and force information describing the movement may be predicted based on the sensed neuromuscular signals as the user moves over time.

Autonomous sensors may include one or more Inertial Measurement Units (IMUs), which may measure a combination of physical aspects of motion, using, for example, an accelerometer, a gyroscope, a magnetometer, or a combination thereof. In some examples, IMUs may be used to sense information about the movement of the body part on which the IMU is attached and information derived from the sensed data (e.g., position and/or orientation information) may be tracked as the user moves over time. For example, one or more IMUs may be used to track movements of portions of a user's body proximal to the user's torso (e.g., arms, legs) as the user moves over time.

Some embodiments may include at least one IMU and a plurality of neuromuscular sensors. The IMU(s) and neuromuscular sensors may be arranged to detect movement of different parts of the human body. For example, the IMU(s) may be arranged to detect movements of one or more body segments proximal to the torso (e.g., an upper arm), whereas the neuromuscular sensors may be arranged to detect movements of one or more body segments distal to the torso (e.g., a forearm or wrist). Autonomous sensors may be arranged in any suitable way, and embodiments of the present disclosure are not limited to any particular sensor arrangement. For example, at least one IMU and a plurality of neuromuscular sensors may be co-located on a body segment to track movements of the body segment using different types of measurements. In some examples, an IMU sensor and a plurality of EMG sensors may be arranged on a wearable device configured to be worn around the lower arm (e.g., the forearm) or wrist of a user. In such an arrangement, the IMU sensor may be configured to track movement information (e.g., position, velocity, acceleration, and/or orientation over time) associated with one or more arm segments. The movement information may determine, for example, whether the user has raised or lowered their arm. The EMG sensors may be configured to determine movement information associated with wrist or hand segments to determine, for example, whether the user has an open or closed hand configuration.

Each of the autonomous sensors may include one or more sensing components configured to sense information about a user. In the case of IMUs, the sensing components may include one or more accelerometers, gyroscopes, magnetometers, or any combination thereof, to measure characteristics of body motion. Examples of characteristics of body motion may include, without limitation, acceleration, angular velocity, linear velocity, and sensed magnetic field around the body. The sensing components of the neuromuscular sensors may include, without limitation, electrodes configured to detect electric potentials on the surface of the body (e.g., for EMG sensors), vibration sensors configured to measure skin surface vibrations (e.g., for MMG sensors), acoustic sensing components configured to measure ultrasound signals (e.g., for SMG sensors) arising from muscle activity, or a combination thereof.

In some examples, the output of sensors 28102 may be processed using hardware signal processing circuitry (e.g., to perform amplification, filtering, and/or rectification). In some examples, at least some signal processing of the output of sensors 28102 may be performed in software. Thus, signal processing of autonomous signals recorded by the autonomous sensors may be performed in hardware, software, or by any suitable combination of hardware and software, as embodiments of the present disclosure are not limited in this respect.

In some examples, the recorded sensor data from sensors 28102 may be processed to compute additional derived measurements that may be provided as input to an inferential models 28104, as described in more detail below. For example, recorded signals from an IMU sensor may be processed to derive an orientation signal that specifies the orientation of a rigid body segment over time. Autonomous sensors may implement signal processing using components integrated with the sensing components or a portion of the signal processing may be performed by one or more components in communication with, but not directly integrated with, the sensing components of the autonomous sensors.

In some examples, the plurality of autonomous sensors may be arranged as a portion of a wearable device configured to be worn (e.g., donned) on or around part of a user's body. For example, an IMU sensor and/or a plurality of neuromuscular sensors may be arranged circumferentially around an adjustable and/or elastic band such as a wristband or armband that is configured to be worn around a user's wrist or arm. In some examples, an IMU sensor and/or a plurality of neuromuscular sensors may be arranged and/or attached to a portion and/or multiple portions of the body including, without limitation, an ankle, a waist, a torso, a neck, a head, a foot, a shin, a shoulder, or a combination thereof. Additionally or alternatively, the autonomous sensors may be arranged on a wearable patch configured to be affixed to a portion of the user's body. In some examples, multiple wearable devices, each having one or more IMUs and/or neuromuscular sensors included thereon, may be used to predict musculoskeletal position information for movements that involve multiple parts of the body.

In some examples, sensors 28102 may only include a plurality of neuromuscular sensors (e.g., EMG sensors). In some examples, sensors 28102 may include a plurality of neuromuscular sensors and at least one "auxiliary" or additional sensor configured to continuously record a plurality of auxiliary signals. Examples of auxiliary sensors may include, without limitation, other autonomous sensors such as IMU sensors, non-autonomous sensors such as imaging devices (e.g., a camera), radar ranging sensors, radiation-based sensors, laser scanning devices, and/or other types of sensors such as heart-rate monitors.

System 28100 also may include at least one processor 28101 programmed to communicate with sensors 28102. For example, signals recorded by one or more of sensors 28102 may be provided to processor 28101, which may be programmed to execute one or more machine learning algorithms that process signals output by sensors 28102 to train one or more inferential models 28104. The trained (or retrained) inferential models 28104 may be stored for later use in generating a musculoskeletal representation 28106, as described in more detail below. Non-limiting examples of inferential models 28104 that may be used to predict body state information based on recorded signals from sensors 28102 are discussed in detail below.

System 28100 may include a display device 28108 configured to display a visual representation of a body state (e.g., a visual representation of a hand). As discussed in more detail below, processor 28101 may use one or more trained inferential models 28104 configured to predict body state information based, at least in part, on signals recorded by sensors 28102. The predicted body state information may be used to update musculoskeletal representation 28106, which may be used to render a visual representation on display device 28108 (e.g., a head-mounted display). Real-time reconstruction of the current body state and subsequent rendering of a visual representation on display device 28108 reflecting the current body state information in the musculoskeletal model may provide visual feedback to the user about the effectiveness of inferential model 28104 to accurately represent an intended body state. In some examples, a metric associated with musculoskeletal representation 28106 (e.g., a likelihood metric for one or more hand gestures or a quality metric that represents a confidence level of estimating a position, movement, and/or force of a segment of a multi-segment articulated rigid body system such as a hand) may be provided to a user or other third-party.

In some examples, a computer application configured to simulate an artificial reality environment may be instructed to display a visual representation of the user's hand on display device 28108. Positioning, movement, and/or forces applied by portions of the hand within the artificial-reality environment may be displayed based on the output of the trained inferential model(s). The visual representation of the user's positioning, movement, and/or force may be dynamically (e.g., in real-time) updated based on current reconstructed body state information as signals are continuously recorded by sensors 28102 and processed by trained inferential models 28104.

As discussed above, some embodiments may be directed to using inferential models 28104 for predicting musculoskeletal representation 28106 based on signals recorded from sensors 28102 (e.g., wearable autonomous sensors). Inferential models 28104 may be used to predict the musculoskeletal position information without having to place sensors 28102 on each segment of the rigid body that is to be represented in the computer-generated musculoskeletal representation 28106. The types of joints between segments in a multi-segment articulated rigid body model may constrain movement of the rigid body. Additionally, different users may tend to move in individual ways when performing a task that may be captured in statistical patterns of individual user movement. At least some of these constraints on human body movement may be explicitly incorporated into inferential models 28104 used for prediction. Additionally or alternatively, the constraints may be learned by inferential models 28104 though training based on recorded data from sensors 28102. Constraints imposed on the construction of inferential models 28104 may be constraints set by the anatomy and physics of a user's body, while constraints derived from statistical patterns may be constraints set by human behavior for one or more users from which sensor measurements are recorded.

As discussed above, some embodiments may be directed to using inferential models 28104 for predicting body state information to enable the generation and/or real-time update of a computer-based musculoskeletal representation 28106. Inferential models 28104 may be used to predict the body state information based on signals from sensors 28102 including, without limitation, IMU signals, neuromuscular signals (e.g., EMG, MMG, and SMG signals), external device signals (e.g., camera, radar, or laser-scanning signals), or a combination thereof, as a user performs one or more movements.

Figure 28B:
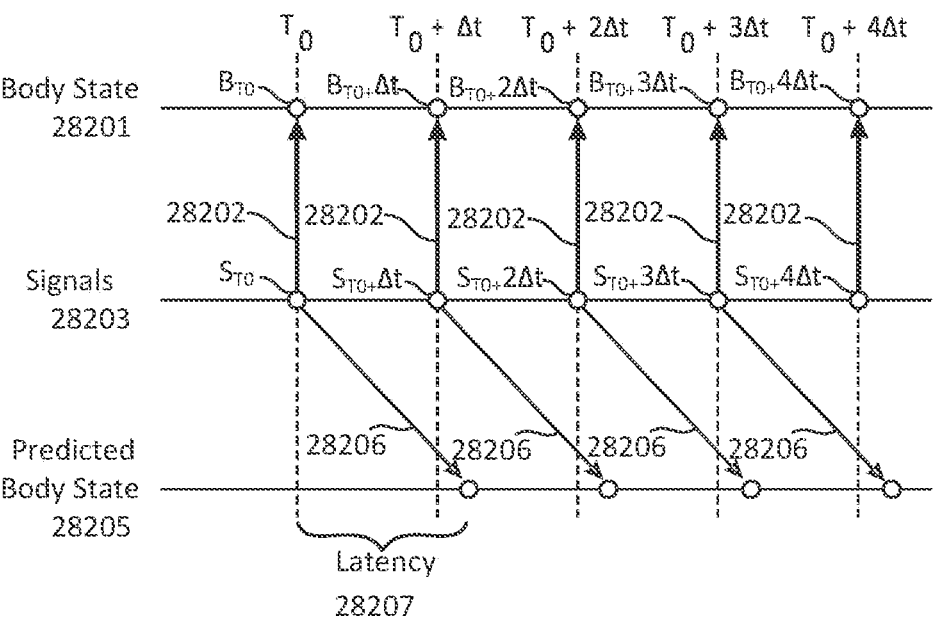
FIG. 28B is an illustration of an example chart depicting the effect of latency on predicting body state information, in accordance with embodiments of the present disclosure.

FIG. 28B illustrates an example chart depicting the effect of latency on predicting body state information, in accordance with embodiments of the present disclosure. A system may be configured to obtain repeated (e.g., periodic) measurements of neuromuscular signals 28203 and body state 28201 (e.g., ground truth body state) as a user performs one or more movements. For example, neuromuscular signals 28203 and ground truth body state 28201 may be time-series data (e.g., data recorded over a period of time), including explicitly and/or implicitly timestamped measurements (e.g., tuples of measurement value and measurement time, and/or a sequence of measurement values with a known sampling time interval and a known start time). The system may be configured to align samples of body state 28201 and signals 28203 based on acquisition time. The alignment of body state 28201 and signals 28203 samples may involve up sampling, down-sampling, interpolation, other signal processing techniques, or a combination thereof. For example, the system may align body state samples {BT0, BT0+Δt, BT0+2Δt, BT0+3Δt, BT0+4Δt, . . . } and signal samples {ST0, ST0+Δt, ST0+2Δt, ST0+3Δt, ST0+4Δt, . . . } respectively as shown in FIG. 28B.

The system may be configured to train an inferential model(s) using body state 28201 as ground truth data for signals 28203. In some examples, the term "ground truth data" may be used interchangeably with the term "label time series data." Label time series data may be data collected over a period of time at a constant time interval or a variable time interval. A conventional system may be configured to predict the current body state sample using the current signal sample (e.g., predict BT0 from ST0 represented in FIG. 28B as arrow 28202 connecting the signal sample to the body state at the same time). Due to electromechanical delay, the body state BT0+Δt may be the result of prior muscle activity. The body state BT0+Δt may therefore be more accurately predicted using an earlier signal sample (e.g., ST0). Furthermore, prediction of body state from signal samples requires processing time. This processing time may include time delays associated with temporal integration of signals, signal recording and conditioning, transmission of signal data (e.g., from a wearable sensor to the processing system), memory access, processor instruction execution, and processing signal data using the inferential model. Such time delays may range between 10 ms and 100 ms, or greater.

Predicted body state 28205 may depict when samples generated using signals 28203 are output by the trained inferential model (as indicated by arrows 28206 connecting samples of signals 28203 with predicted body states 28205). As shown in FIG. 28B, by the time the trained inferential model outputs predict body state BT0, the most recently measured body part state may be BT0+Δt. As used herein, latency may be a time period (e.g., an average time period, a median time period, or other suitable time period) between the measurement of a body state and the output of the corresponding predicted body state 28205 (e.g., latency 28207 between measured body state BT0 and predicted body state BT0). Latency may diminish the quality of the user experience, as a user may perceive the output of the system (e.g., a visual representation of the body state displayed on a head-mounted display (HMD)) to lag behind the user's actual movements.

Figure 28C:
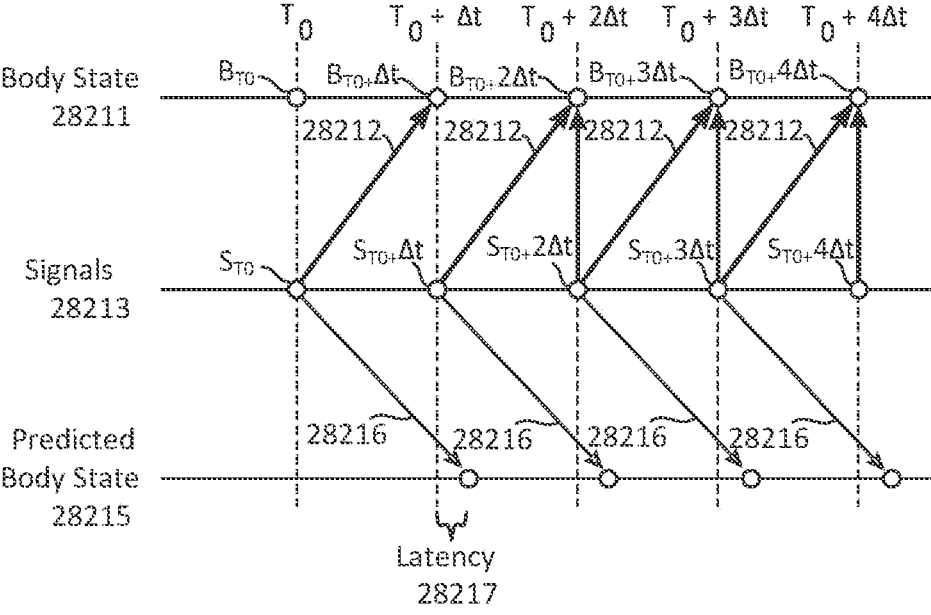
FIG. 28C is an illustration of an example chart depicting latency reduction in predicting body state information, in accordance with embodiments of the present disclosure.

FIG. 28C shows a chart depicting the effect on latency 28217 of training an inferential model using time shifted training data, in accordance with embodiments of the present disclosure. As described above with reference to FIG. 28B, the system may obtain multiple samples of body state 28211 (e.g., ground truth body state) and signals 28213. In some examples, rather than pairing samples of signals 28213 and body state 28211 acquired at the same time, the system may be configured to pair samples of signals 28213 with samples of body state 28211 acquired at later times (as indicated by arrows 28212 connecting samples of signals 28213 with samples of body state 28211). For example, the system may pair signal sample ST0 with body state sample BT0+Δt. In this manner, the system may create a training dataset by time-shifting either the signals 28213 or the ground truth body state 28211. The system may be configured to train an inferential model using the time-shifted training dataset. For example, the inferential model may then be trained to predict body state 28211 from the signals 28213 using the time-shifted training dataset.

Predicted body state 28215 depicts when samples generated using signals 28213 are output by the trained inferential model (as indicated by arrows 28216 connecting samples of signals 28213 with predicted body states 28215). In this example, by the time the trained inferential model outputs predicted body state BT0+Δt, the most recently measured body part state is also BT0+Δt. As shown, latency 28217 between when body state BT0+Δt occurs and when the trained inferential model outputs predicted body state BT0+Δt may be reduced compared to latency 28207 shown in FIG. 28B by predicting BT0+Δt from ST0. As discussed herein, the inferential model may be trained to predict BT0+Δt from ST0 at least in part because electromechanical delay causes signals measured at time T0 to affect later occurring body states (e.g., the body state at T0+Δt). Thus, for an appropriate choice of delay time interval Δt, training the inferential model to predict BT0+Δt from ST0 may improve body state prediction accuracy. Example methods for choosing delay time interval Δt are discussed below with reference to FIGS. 28D and 28E.

Figure 28D:
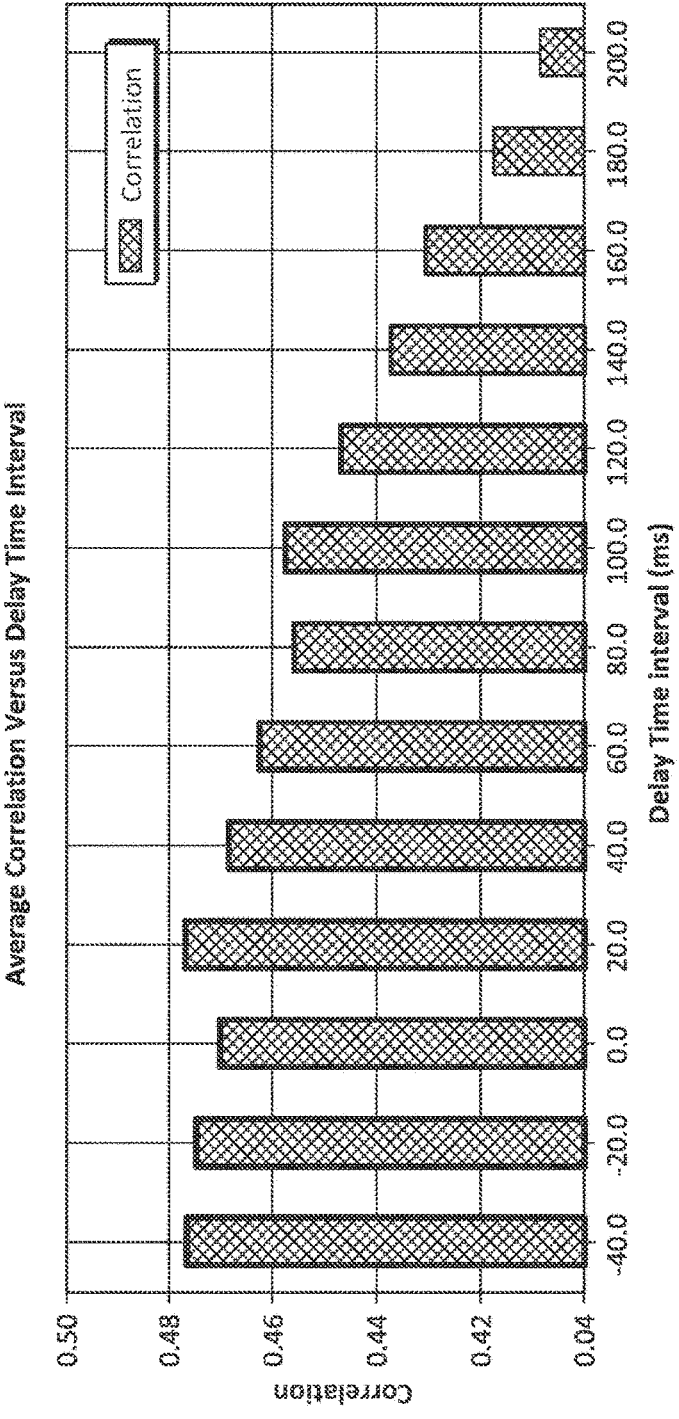
FIG. 28D is an illustration of an example chart depicting a relationship between delay time interval and body state prediction accuracy, in accordance with embodiments of the present disclosure.

FIG. 28D shows a chart 28300 depicting an empirical relationship between delay time interval Δt and body state prediction accuracy, in accordance with embodiments of present disclosure. The empirical relationship may be used to select a trained inferential model that exhibits a desired balance of latency and body state prediction accuracy. The independent variable depicted in FIG. 28D is the delay time interval between a neuromuscular signal sample and a body state sample. Positive time interval values correspond to pairing the neuromuscular signal sample with a body state sample obtained after the neuromuscular signal sample. Negative time interval values correspond to pairing the neuromuscular signal sample with a body state sample obtained before the neuromuscular signal sample. The zero time interval (0.0 ms) value corresponds to pairing the signal sample with a body state sample obtained at the same time as the signal sample. The response variable depicted in the chart of FIG. 28D may be a measure of the prediction accuracy of a model trained using a training dataset time-shifted by the time interval. The depicted measure may be a correlation value between measured and predicted joint angles in a musculoskeletal representation of a hand. In some examples, other measures of the prediction accuracy may be used, such as a mean squared error between characteristic values of a musculoskeletal representation of a body part. Such characteristic values may include, without limitation, joint angles, forces, or spatial coordinates of a body part. Similarly, a likelihood of correctly predicting a known pose or gesture (e.g., a first pose or transitioning from an open hand to a first pose) may be used as measure of the prediction accuracy. For example, the body part states and the predicted body part states may be binary labels indicating the presence or absence of a pose or gesture. The trained inferential model may have a false positive, false negative, true positive, or true negative prediction rate. The measure of prediction accuracy may depend on at least one of these prediction rates.

As shown in chart 28300, body state prediction accuracy (e.g., correlation between measured and predicted joint angles) may improve as the delay time interval value increases from zero to 20 milliseconds. Prediction accuracy decreases thereafter as the delay time interval value increases. As shown, shifting the measured signals relative to the body state labels by 40 ms reduces latency without reducing prediction accuracy. As described herein, depending on the task, an inferential model trained using a shorter or longer time interval (e.g., a time interval in the range 10 to 100 ms) may be selected for use in predicting body state.

In some examples, an inferential model may be selected for use in predicting body state based on a prediction accuracy criterion (e.g., correlation between measured and predicted joint angles) and the delay time interval Δt used to generate the training dataset for training the inferential model. For example, of the inferential models satisfying a prediction accuracy criterion (e.g., accuracy above a set threshold), the selected inferential model may be the inferential model trained using the training dataset generated using the largest time interval. For example, two inferential models may satisfy the accuracy criterion (e.g., both models having an accuracy above an acceptable threshold). The first model may have greater accuracy than the second model, but the time interval used to generate the training dataset for training the first model may be less than the time interval used to generate the training dataset for training the second model. In this example, the second inferential model may be selected to predict the body state, as this second inferential model may have acceptable prediction accuracy and lower latency than the first inferential model.

The accuracy criterion may depend on the greatest accuracy observed across the inferential models. For example, the accuracy criterion may be expressed as a deviation from an accuracy of the most accurate model. When the deviation in accuracy for an inferential model is less than a threshold value, the inferential model may satisfy the accuracy criterion. The threshold value may be an absolute difference in accuracy (e.g., the most accurate model has a prediction accuracy of 85% and the second model has at least an accuracy of 80%). The threshold value may alternatively be a relative difference in accuracy (e.g., the less accurate model is at least 95% as accurate as the most accurate model).

FIG. 28E shows two charts depicting user dependence in the empirical relationship between time interval and prediction accuracy, in accordance with embodiments of the present disclosure. The dependence of prediction accuracy on delay time interval may vary between users. As shown in the charts of FIG. 28E, the dependence of prediction accuracy on delay time interval may vary between user A as shown in chart 28402 and user B as shown in chart 28404. Accordingly, a system may be personalized to a user by selecting an inferential model trained using a delay time interval appropriate for the user and/or training an inferential model using a training dataset generated with a delay time interval appropriate for the user. The appropriate delay time interval may depend on a known electromechanical delay time and/or a characteristic latency of the system. For example, user A and user B may have different electromechanical delay times depending on physiological characteristics (e.g., user age, sex, activity level, or other characteristic known to influence electromechanical delays in the human neuromuscular system).

Figure 28F:
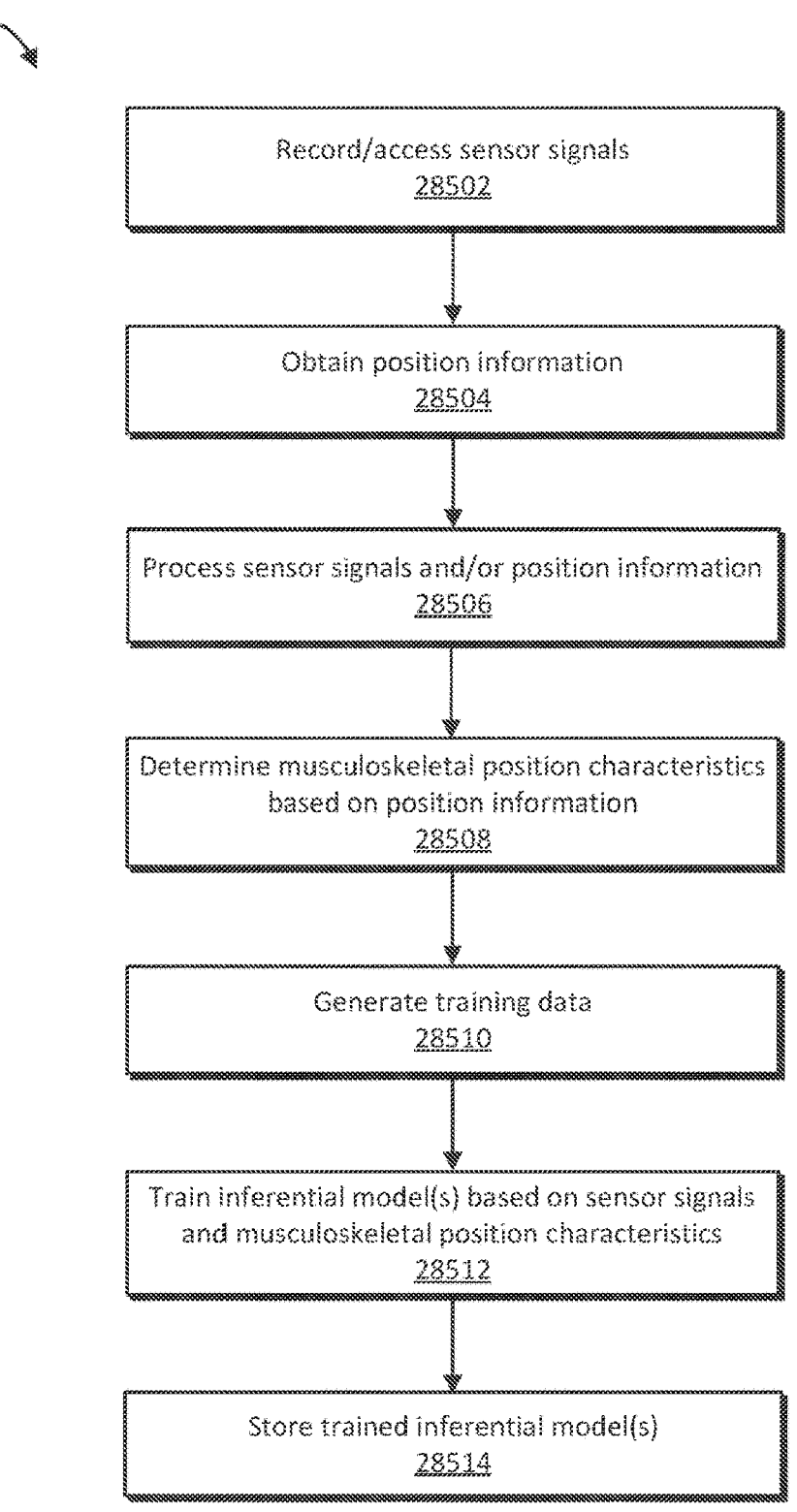
FIG. 28F is an illustration of a flowchart of an example method for generating an inferential model for predicting musculoskeletal position information using signals recorded from sensors, in accordance with embodiments of the present disclosure.

FIG. 28F describes a method 28500 for generating (e.g., training) an inferential model using signals recorded from sensors (e.g., sensors 28102). Method 28500 may be executed using any suitable computing device(s), as embodiments of the present disclosure are not limited in this respect. For example, method 28500 may be executed by one or more computer processors described with reference to FIGS. 28A and 28H. As another example, one or more operations of method 28500 may be executed using one or more servers (e.g., servers included as a part of a cloud computing environment). For example, at least a portion of the operations in method 28500 may be performed using a cloud computing environment and/or a processor(s) of a wearable device such as wearable device 28700 of FIG. 28H, 28810 of FIG. 28I, 1100 of FIG. 11, 1200 of FIG. 12, 1320 of FIG. 13, 1404 of FIG. 14, or 1530 of FIG. 15. Although the operations of method 28500 are shown in FIG. 28F as being performed in a certain order, the operations of method 28500 may be performed in any order.

Method 28500 may include operation 28502, in which a plurality of sensor signals (e.g., neuromuscular signals, IMU signals, etc.) are obtained for one or more users performing one or more movements (e.g., playing an artificial-reality game). In some examples, the plurality of sensor signals may be recorded as part of method 28500. Additionally or alternatively, the plurality of sensor signals may have been recorded prior to the execution of method 28500 and are accessed (rather than recorded) at operation 28502.

In some examples, the plurality of sensor signals may include sensor signals recorded for a single user performing a single movement and/or multiple movements. The user may be instructed to perform a sequence of movements for a particular task (e.g., grasping a game controller, providing a user input to a computer, etc.) and sensor signals corresponding to the user's movements may be recorded as the user performs the task that the user was instructed to perform. The sensor signals may be recorded by any suitable number and/or type of sensors located in any suitable location(s) to detect the user's movements that are relevant to the task performed. For example, after a user is instructed to perform a task with the fingers of the user's right hand, the sensor signals may be recorded by multiple neuromuscular sensors arranged (e.g., circumferentially) around the user's lower right arm to detect muscle activity in the lower right arm that causes the right hand movements and one or more IMU sensors arranged to predict the joint angle of the user's arm relative to the user's torso. As another example, after a user is instructed to perform a task with the user's leg (e.g., to kick an object), sensor signals may be recorded by multiple neuromuscular sensors arranged (e.g., circumferentially) around the user's leg to detect muscle activity in the leg that causes the movements of the foot and one or more IMU sensors arranged to predict the joint angle of the user's leg relative to the user's torso.

In some examples, the sensor signals obtained in operation 28502 may correspond to signals from one type of sensor (e.g., one or more IMU sensors or one or more neuromuscular sensors) and an inferential model may be trained based on the sensor signals recorded using the particular type of sensor, resulting in a sensor-type specific trained inferential model. For example, the obtained sensor signals may include a plurality of EMG sensor signals arranged (e.g., circumferentially) around the lower arm or wrist of a user and the inferential model may be trained to predict musculoskeletal position information for movements of the wrist and/or hand during performance of a task such as grasping and turning an object such as a game controller or a doorknob.

In embodiments that provide predictions based on multiple types of sensors (e.g., IMU sensors, EMG sensors, MMG sensors, SMG sensors, etc.), a separate inferential model may be trained for each of the different types of sensors and the outputs of the sensor-type specific models may be combined to generate a musculoskeletal representation of the user's body. In some examples, the sensor signals obtained in operation 28502 from two or more different types of sensors may be provided to a single inferential model that is trained based on the signals recorded from the different types of sensors. For example, an IMU sensor and a plurality of EMG sensors may be arranged on a wearable device configured to be worn around the forearm of a user, and signals recorded by the IMU and EMG sensors are collectively provided as inputs to an inferential model, as discussed in more detail below.

In some examples, a user may be instructed to perform a task multiple times and the sensor signals and position information may be recorded for each of multiple repetitions of the task by the user. In some examples, the plurality of sensor signals may include signals recorded for multiple users, each of the multiple users performing the same task one or more times. Each of the multiple users may be instructed to perform the task and sensor signals and position information corresponding to that user's movements may be recorded as the user performs (once or repeatedly) the task according to the instructions. When sensor signals are collected from multiple users and combined to generate an inferential model, an assumption may be made that different users employ similar musculoskeletal positions to perform the same movements. Collecting sensor signals and position information from a single user performing the same task repeatedly and/or from multiple users performing the same task one or multiple times facilitates the collection of sufficient training data to generate an inferential model that may accurately predict musculoskeletal position information associated with performance of the task.

In some examples, a user-independent inferential model may be generated based on training data corresponding to the recorded signals from multiple users, and as the system is used by a user, the inferential model may be trained based on recorded sensor data such that the inferential model learns the user-dependent characteristics to refine the prediction capabilities of the system and increase the prediction accuracy for the particular user.

In some examples, the plurality of sensor signals may include signals recorded for a user (or each of multiple users) performing each of multiple tasks one or multiple times. For example, a user may be instructed to perform each of multiple tasks (e.g., grasping an object, pushing an object, pulling open a door, etc.) and signals corresponding to the user's movements may be recorded as the user performs each of the multiple tasks the user(s) were instructed to perform. Collecting such signal data may facilitate developing an inferential model for predicting musculoskeletal position information associated with multiple different actions that may be performed by the user. For example, training data that incorporates musculoskeletal position information for multiple actions may facilitate generating an inferential model for predicting which of multiple possible movements a user may be performing.

As discussed above, the sensor data obtained at operation 28502 may be obtained by recording sensor signals as each of one or multiple users perform each of one or more tasks one or more times. In operation 28504, ground truth data (e.g., label time series data) may be obtained by multiple sensors including, without limitation, an optical sensor, an inertial measurement sensor, a mutual magnetic induction measurement sensor, a pressure sensor, or a combination thereof. The ground truth data may indicate a body part state of the user(s). For example, as the user(s) perform the task(s), position information describing the spatial position of different body segments during performance of the task(s) may be obtained in operation 28504. In some examples, the position information may be obtained using one or more external devices or systems that track the position of different points on the body during performance of a task. For example, a motion capture system, a laser scanner, a device to measure mutual magnetic induction, some other system configured to capture position information, or a combination thereof may be used. As one non-limiting example, a plurality of position sensors may be placed on segments of the fingers of the hand of a user and a motion capture system may be used to determine the spatial location of each of the position sensors as the user performs a task such as grasping an object. Additionally or alternatively, neuromuscular signals may be obtained at operation 28502 and may be used alone or in combination with one or more images from the motion capture system or IMU signals to determine the spatial location(s) of user body parts (e.g., fingers) as the user performs a task. The sensor data obtained at operation 28502 may be recorded simultaneously with recording of the position information obtained in operation 28504. In this example, the position information indicating the position of each finger segment over time as the grasping motion is performed is obtained.

Method 28500 may proceed to operation 28506, in which the sensor signals obtained in operation 28502 and/or the position information obtained in operation 28504 are optionally processed. For example, the sensor signals and/or the position information signals may be processed using, without limitation, amplification, filtering, rectification, other types of signal processing, or a combination thereof.

Method 28500 may proceed to operation 28508, in which musculoskeletal position characteristics are determined based on the position information (as collected in operation 28504). In some examples, rather than using recorded spatial (e.g., x, y, z) coordinates corresponding to the position sensors as training data to train the inferential model, a set of derived musculoskeletal position characteristic values are determined based on the recorded position information, and the derived values are used as training data for training the inferential model. For example, using information about constraints between connected pairs of rigid segments in the articulated rigid body model, the position information may be used to determine joint angles between each connected pair of rigid segments at each of multiple time points during performance of a task. Accordingly, the position information obtained in operation 28504 may be represented by a vector of n joint angles at each of a plurality of time points, where n is the number of joints or connections between segments in the articulated rigid body model.

Method 28500 may proceed to operation 28510, in which the time series information obtained at operations 28502 and 28508 may be combined to create training data used for training an inferential model. The obtained data may be combined using any suitable method. In some examples, each of the sensor signals obtained at operation 28502 may be associated with a task or movement within a task corresponding to the musculoskeletal position characteristics (e.g., joint angles) determined based on the positional information obtained in operation 28504 as the user performed the task or movement. In this way, the sensor signals may be associated with musculoskeletal position characteristics (e.g., joint angles) and the inferential model may be trained to predict that the musculoskeletal representation will be characterized by particular musculoskeletal position characteristics between different body segments when particular sensor signals are recorded during performance of a particular task.

In embodiments including sensors of different types (e.g., IMU sensors and neuromuscular sensors) that are configured to simultaneously record different types of movement information (e.g., position information, velocity information, acceleration information) during performance of a task, the sensor data for the different types of sensors may be recorded using the same or different sampling rates. When the sensor data is recorded at different sampling rates, at least some of the sensor data may be resampled (e.g., up-sampled or down-sampled) such that all sensor data provided as input to the inferential model corresponds to time series data at the same time resolution (e.g., the time period between samples). Resampling at least some of the sensor data may be performed using any suitable method including, without limitation, using interpolation for up-sampling sensor data and using decimation for down-sampling sensor data.

Additionally or alternatively, some embodiments may employ an inferential model configured to accept multiple inputs asynchronously. For example, the inferential model may be configured to model the distribution of the "missing" values in the input data having a lower sampling rate. Additionally or alternatively, the timing of training of the inferential model may occur asynchronously as input from multiple sensor data measurements becomes available (e.g., after signal conditioning) as training data.

Combining the time series information obtained at operations 28502 and 28508 to create training data for training an inferential model at operation 28510 may include generating one or more training datasets. As described herein, the one or more training datasets may be generated by time-shifting the sensor signals obtained at operation 28502 or by time-shifting the ground truth data obtained at operation 28504 or 28508 by one or more time intervals.

Method 28500 may proceed to operation 28512, in which an inferential model for predicting musculoskeletal position information may be trained using the training data generated at operation 28510. The inferential model being trained may use a sequence of data sets as an input, and each of the data sets in the sequence may include an n-dimensional vector of sensor data. The inferential model may provide output that indicates, for each of one or more tasks or movements that may be performed by a user, the likelihood that the musculoskeletal representation of the user's body will be characterized by a set of musculoskeletal position characteristics (e.g., a set of joint angles between segments in an articulated multi-segment body model). For example, the inferential model may use as input a sequence of vectors $\{xk|1{\le}k{\le}K\}$ generated using measurements obtained at time points t1, t2, . . . , tK, where the ith component of vector xj may be a value measured by the ith sensor at time tj and/or derived from the value measured by the ith sensor at time tj. In another non-limiting example, a derived value provided as input to the inferential model may include features extracted from the data for all, or a subset of, the sensors at and/or prior to time tj (e.g., a covariance matrix, a power spectrum, any other suitable derived representation, or a combination thereof). Based on such input, the inferential model may provide output indicating a probability that a musculoskeletal representation of the user's body will be characterized by a set of musculoskeletal position characteristics. As one non limiting example, the inferential model may be trained to predict a set of joint angles for segments in the fingers of a hand over time as a user grasps an object. In this example, the trained inferential model may output, a set of predicted joint angles for joints in the hand corresponding to the sensor input.

In some examples, the inferential model may be a neural network. In some examples, the inferential model may be a recurrent neural network. The recurrent neural network may be a long short-term memory (LSTM) neural network. However, the recurrent neural network is not limited to an LSTM neural network and may have any other suitable architecture. For example, the recurrent neural network may be, without limitation, a fully recurrent neural network, a recursive neural network, a variational autoencoder, a Hopfield neural network, an associative memory neural network, an Elman neural network, a Jordan neural network, an echo state neural network, a second order recurrent neural network, any other suitable type of recurrent neural network, or a combination thereof. In some examples, neural networks that are not recurrent neural networks may be used. For example, deep neural networks, convolutional neural networks, feedforward neural networks, or a combination thereof may be used.

In some examples in which the inferential model is a neural network, the output layer of the neural network may provide a set of output values corresponding to a respective set of possible musculoskeletal position characteristics (e.g., joint angles). In this example, the neural network may operate as a non-linear regression model configured to predict musculoskeletal position characteristics from raw and/or processed (e.g., conditioned) sensor measurements. In some examples, other suitable non-linear regression models may be used instead of a neural network, as the present disclosure is not limited in this respect.

In some examples, the neural network may be implemented based on multiple and/or different types of topologies and/or architectures including deep neural networks with fully connected (e.g., dense) layers, Long Short-Term Memory (LSTM) layers, convolutional layers, Temporal Convolutional Layers (TCL), other suitable types of deep neural network topology and/or architectures, or a combination thereof. The neural network may have different types of output layers including, without limitation, output layers with logistic sigmoid activation functions, hyperbolic tangent activation functions, linear units, rectified linear units, other suitable types of nonlinear units, or a combination thereof. In some examples, the neural network may be configured to represent the probability distribution over n different classes via a softmax function. In some examples, the neural network may include an output layer that provides a parameterized distribution (e.g., a mean and/or a variance of a Gaussian distribution).

Embodiments of the present disclosure are not limited to using neural networks as other types of inferential models may be employed. In some examples, the inferential model may include, without limitation, a hidden Markov model, a Markov switching model that allows switching among different dynamic systems, dynamic Bayesian networks, any other suitable graphical model having a temporal component, or a combination thereof. Any such inferential model may be trained at operation 28512 using the sensor data obtained at operation 28502.

As another example, the inferential model may use as input features derived from the sensor data obtained at operation 28502. In such embodiments, the inferential model may be trained at operation 28512 using features extracted from the sensor data obtained at operation 28502. The inferential model may include, without limitation, a support vector machine, a Gaussian mixture model, a regression-based classifier, a decision tree classifier, a Bayesian classifier, any other suitable classifier, or a combination thereof. Input features to be provided as training data to the inferential model may be derived from the sensor data obtained at operation 28502 using any suitable method. For example, the sensor data may be analyzed as time series data using, without limitation, wavelet analysis techniques (e.g., a continuous wavelet transform, a discrete-time wavelet transform, etc.), Fourier-analysis techniques (e.g., short-time Fourier transform, discrete-time Fourier transform, Fourier transform, etc.), any other suitable type of time-frequency analysis technique, or a combination thereof. As one non-limiting example, the sensor data may be transformed using a wavelet transform and the resulting wavelet coefficients may be provided as inputs to the inferential model.

In some examples, at operation 28512, values for parameters of the inferential model may be estimated from the training data generated at operation 28510. For example, when the inferential model is a neural network, parameters of the neural network (e.g., weights) may be estimated from the training data. Parameters of the inferential model may be estimated using, without limitation, gradient descent, stochastic gradient descent, any other suitable iterative optimization technique, or a combination thereof. In embodiments in which the inferential model is a recurrent neural network (e.g., an LSTM neural network), the inferential model may be trained using stochastic gradient descent and backpropagation through time. The training may employ a cross-entropy loss function and/or any other suitable loss function, as the present disclosure is not limited in this respect.

Method 28500 may proceed to operation 28514, in which the trained inferential model may be stored (e.g., in a datastore, a local database, a remote cloud database, a memory, etc.). The trained inferential model may be stored using any suitable format, device(s) and/or method. In this way, the inferential model generated during execution of method 28500 may be used at a later time. For example, a state prediction system may be configured using the trained inferential model to predict body part state from neuromuscular activity time series data (e.g., predict musculoskeletal position information such as joint angles from a given set of input sensor data), as described below.

In some examples, sensor signals may be recorded from a plurality of sensors (e.g., arranged on or near the surface of a user's body) that record activity associated with movements of the body during performance of a task. The recorded signals may be optionally processed (e.g., conditioned) and provided as input to an inferential model trained using one or more techniques described above in reference to FIG. 28F. In some examples, autonomous signals may be continually recorded, and the continuously recorded signals (raw or processed) may be continuously and/or periodically provided as input to the trained inferential model for prediction of musculoskeletal position information (e.g., joint angles) for the given set of input sensor data. As discussed above, in some examples, the trained inferential model may be a user-independent model trained based on autonomous sensor and position information measurements from a plurality of users. In some examples, the trained model may be a user-dependent model trained on data recorded from the individual user from which the data associated with the sensor signals is also acquired.

After the trained inferential model receives the sensor data as a set of input parameters, the predicted musculoskeletal position information may be output from the trained inferential model. As discussed above, in some examples, the predicted musculoskeletal position information may include a set of musculoskeletal position information values (e.g., a set of joint angles) for a multi-segment articulated rigid body model representing at least a portion of the user's body. In some examples, the musculoskeletal position information may include a set of probabilities that the user is performing one or more movements from a set of possible movements.

In some examples, after musculoskeletal position information is predicted, a computer-based musculoskeletal representation of the user's body may be generated based, at least in part, on the musculoskeletal position information output from the trained inferential model. The computer-based musculoskeletal representation may be generated using any suitable method. For example, a computer-based musculoskeletal model of the human body may include multiple rigid body segments, each of which corresponds to one or more skeletal structures in the body. For example, the upper arm may be represented by a first rigid body segment, the lower arm may be represented by a second rigid body segment, the palm of the hand may be represented by a third rigid body segment, and each of the fingers on the hand may be represented by at least one rigid body segment. A set of joint angles between connected rigid body segments in the musculoskeletal model may define the orientation of each of the connected rigid body segments relative to each other and a reference frame, such as the torso of the body. As new sensor data is measured and processed by the inferential model to provide new predictions of the musculoskeletal position information (e.g., an updated set of joint angles), the computer-based musculoskeletal representation of the user's body may be updated based on the updated set of joint angles determined based on the output of the inferential model. In this way, the computer-based musculoskeletal representation may be dynamically updated in real time as sensor data is continuously recorded.

The computer-based musculoskeletal representation may be represented and stored using any suitable devices and methods. For example, the computer-based musculoskeletal representation may be stored in memory (e.g., memory 28821 of FIG. 28I). Although referred to herein as a "musculoskeletal" representation to reflect that muscle activity may be associated with the representation, some musculoskeletal representations may correspond to skeletal structures, muscular structures, or a combination of skeletal structures and muscular structures in the body.

In some examples, direct measurement of neuromuscular activity and/or muscle activity underlying the user's movements may be combined with the generated musculoskeletal representation. Measurements from a plurality of sensors placed on a user's body may be used to create a unified representation of muscle recruitment by superimposing the measurements onto a dynamically-posed skeleton. In some examples, muscle activity sensed by neuromuscular sensors and/or information derived from the muscle activity (e.g., force information) may be combined with the computer-generated musculoskeletal representation in real time.

Figure 28G:
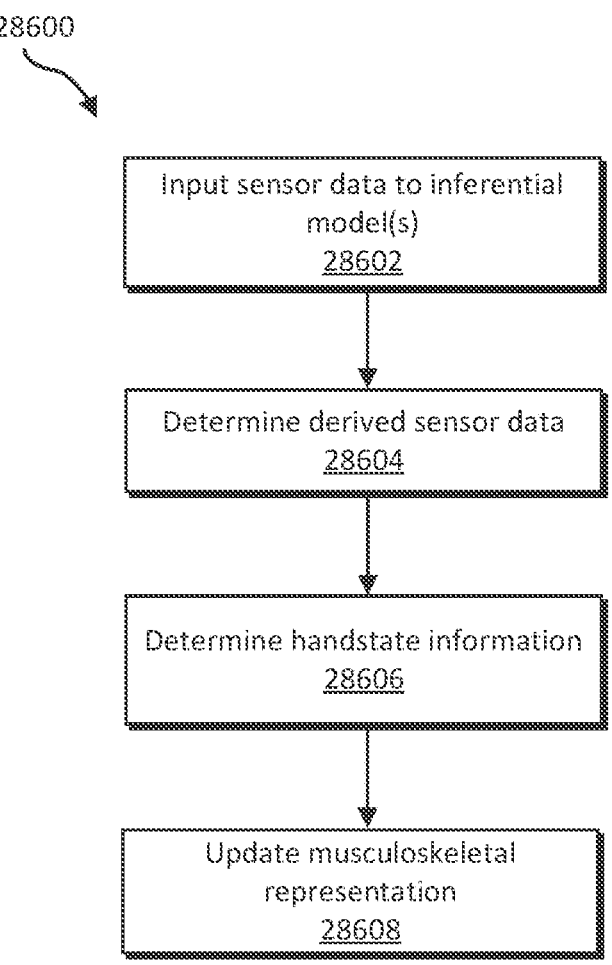
FIG. 28G is an illustration of a flowchart of an example method for determining body state information, in accordance with embodiments of the present disclosure.

FIG. 28G illustrates a method 28600 for determining body state information based on recorded sensor data in accordance embodiments of the present disclosure. Although the operations of method 28600 are shown in FIG. 28G as being performed in a certain order, the operations of method 28600 may be performed in any order. In operation 28602, sensor data may be recorded by one or more sensors and provided as input to one or more trained inferential models used to predict a body state, as described above. In some examples, the sensors may include a plurality of neuromuscular sensors (e.g., EMG sensors) arranged on a wearable device worn by a user. For example, EMG sensors may be arranged (e.g., circumferentially) on an elastic band configured to be worn around a wrist or forearm of the user to record neuromuscular signals from the user as the user exerts force and/or performs various movements, poses, and/or gestures. Examples of wearable devices that may be used in accordance with embodiments of the present disclosure include wearable device 28700 of FIG. 28H, 800 of FIG. 28I, 1320 of FIG. 13, 1404 of FIG. 14, or 1530 of FIG. 15., which are described in more detail below.

Additionally or alternatively, some embodiments may include one or more auxiliary sensors configured to continuously record auxiliary signals that may also be provided as input to the one or more trained inferential models. Examples of auxiliary sensors may include, without limitation, IMU sensors, imaging devices, radiation detection devices (e.g., laser scanning devices), heart rate monitors, any other type of biosensors configured to continuously record biophysical information from the user during performance of one or more movements or gestures, or a combination thereof.

Method 28600 may proceed to operation 28604, in which derived signal data is optionally determined based on the signals recorded by the sensors. For example, accelerometer data recorded by one or more IMU sensors may be integrated and/or filtered to determine derived signal data associated with one or more muscles during performance of a gesture. The derived signal data may be provided as input to the trained inferential model(s) in addition to, or as an alternative to, raw signal data or otherwise processed raw signal data recorded by the sensors.

Method 28600 may proceed to operation 28606, in which body state information is determined based on the output of the trained inferential model(s). Gestures performed by the user may include discrete gestures, such as placing the user's hand palm down on a table, and/or continuous movement gestures, such as waving a finger back and forth. The neuromuscular signals may be recorded continuously during user movements including during performance of the gesture and may be provided continuously as input to the trained inferential model, resulting in real-time estimation of the positions and/or forces of the user's body part (e.g., body state information) as output of the trained inferential model(s). Method 28600 may proceed to operation 28608, in which the real-time body state predictions output from the trained inferential model(s) are used to update a musculo-skeletal representation associated with a hand. In some examples, the musculoskeletal representation represents rigid segments within a hand and the joints connecting the rigid segments. In other embodiments, the musculoskeletal representation may include at least some rigid segments corresponding to an arm connected to the hand. Accordingly, the phrase "musculoskeletal representation associated with a hand" should be understood to include both musculoskeletal representations of the hand and/or musculoskeletal representations that include a representation of the hand and at least a portion of an arm connected to the hand.

Figure 28H:
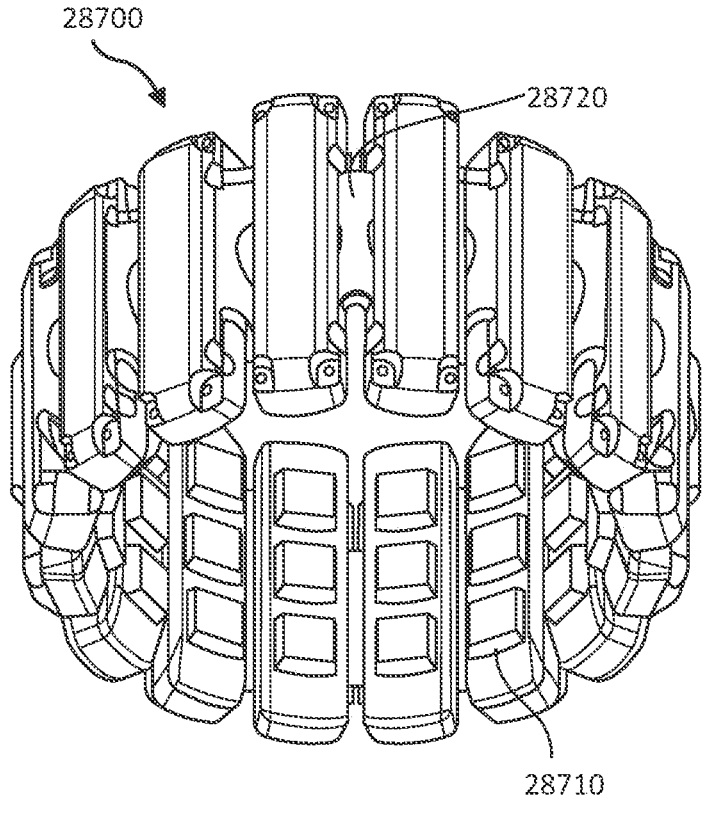
FIG. 28H is an illustration of a perspective view of an example wearable device with sensors, in accordance with embodiments of the present disclosure.

FIG. 28H illustrates a perspective view of an example wearable device 28700 that includes sixteen sensors 28710 (e.g., EMG sensors) arranged circumferentially around an elastic band 28720 configured to be worn around a body part of a user (e.g., a user's lower arm or wrist). As shown, sensors 28710 may be arranged circumferentially around elastic band 28720. Any suitable number of sensors 28710 may be used. The number and arrangement of sensors 28710 may depend on the particular application for which the wearable device is used. For example, a wearable armband or wristband may be used to generate control information for controlling an artificial reality system, a robot, a vehicle, scrolling through text, controlling a virtual avatar, or any other suitable control task.

In some examples, sensors 28710 may include a set of neuromuscular sensors (e.g., EMG sensors). In other embodiments, sensors 28710 may include a set of neuro-muscular sensors and at least one "auxiliary" sensor configured to record (e.g., periodically, continuously, or on demand) auxiliary signals. Examples of auxiliary sensors may include, without limitation, other sensors such as IMU sensors, microphones, imaging sensors (e.g., a camera), radiation based sensors, laser-scanning devices, or other types of sensors such as a heart-rate monitor.

In some examples, the output of one or more of the sensing components (e.g., sensors 28710) may be processed using hardware signal processing circuitry (e.g., to perform amplification, filtering, and/or rectification). In some examples, at least some signal processing of the output of the sensing components may be performed in software. Thus, signal processing of signals sampled by the sensors may be performed in hardware, software, or by any suitable combination of hardware and software, as aspects of the technology described herein are not limited in this respect. Non-limiting examples of a signal processing system used to process data recorded from sensors 28710 are discussed in more detail below in reference to FIG. 28I.

Figure 28I:
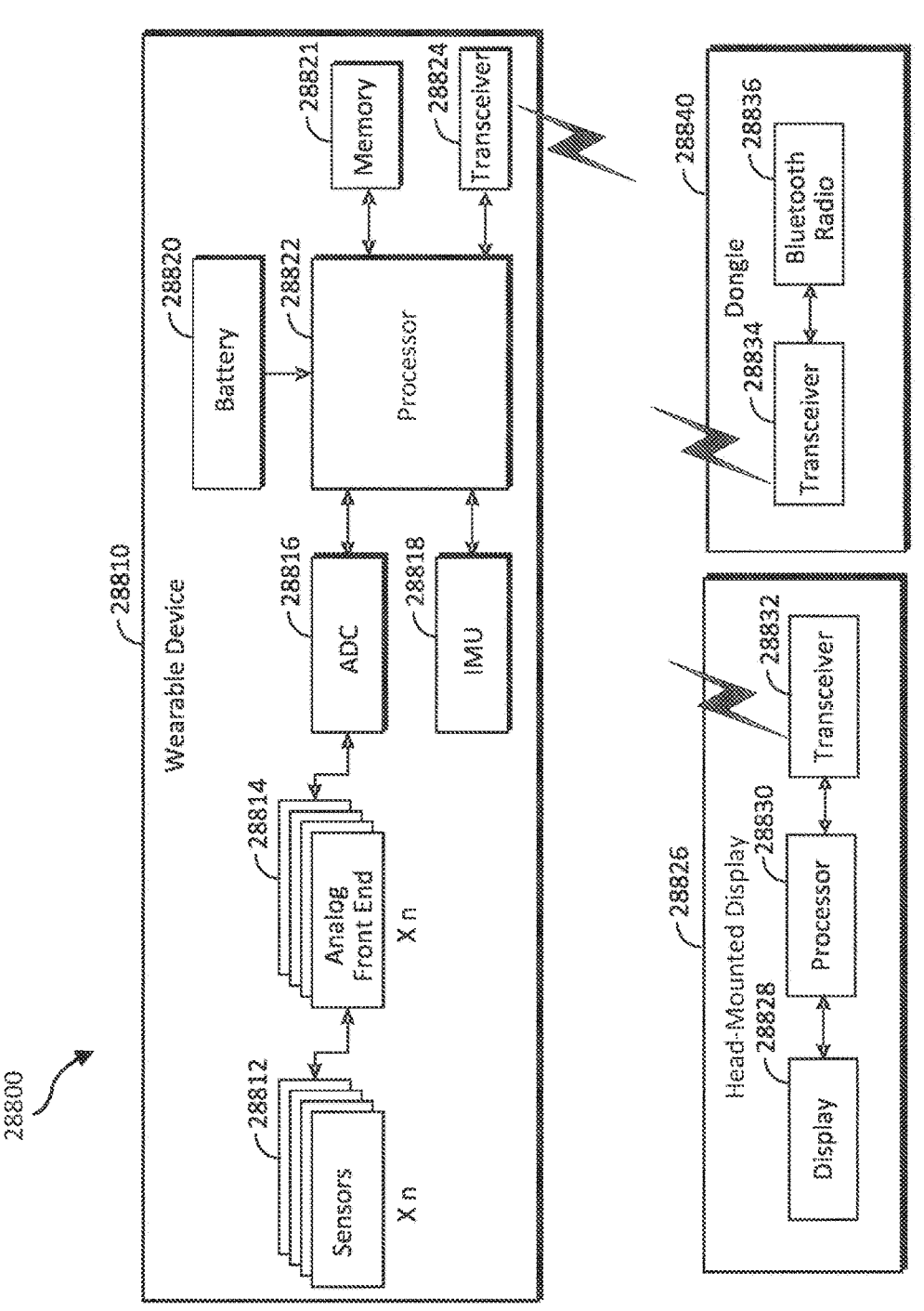
FIG. 28I is an illustration of an example block diagram of a wearable device and a head-mounted display, in accordance with embodiments of the present disclosure.

FIG. 28I illustrates an example block diagram of a wear-able system 28800 with multiple sensors, in accordance with embodiments of the present disclosure. As shown in FIG. 28I, wearable system 28800 may include a wearable device 28810, a head-mounted display (HMD) 28826 and a dongle 28840. Wearable device 28810, HMD 28826, and dongle 28840 may communicate to each other via wireless communication (e.g., via Bluetooth™ or other suitable short-range wireless communication technology) or wired communication. Wearable device 28810 may include sensors 28812 (e.g., EMG sensors), examples of which are described above in reference to FIGS. 28F and 28G. Data from sensors 28812 and/or data from sensors of HMD 28826 may be used to generate the ground truth data (e.g., label time series data). The output of sensors 28812 may be provided to analog front end 28814 that may be configured to perform analog signal processing (e.g., noise reduction, filtering, amplification, etc.) on the recorded signals from sensors

28812. The processed analog signals from analog front end 28814 may be provided to analog-to-digital converter (ADC) 28816, which may convert the analog signals to digital signals so that the signals may be processed by processor 28822 and/or processor 28830 of HMD 28826.

Processor 28822 and/or processor 28830 (e.g., a micro-controller, a central processing unit, a digital signal proces-sor, a graphics processor, etc.) may execute instructions stored in memory 28821 that implement the methods of the present disclosure including, without limitation, generating one or more training datasets by time-shifting neuromuscu-lar activity time series data and/or label time series data received from sensors 28812 by one or more time intervals, training one or more inferential models based on the neu-romuscular activity time series data using the one or more training datasets, and configuring a state prediction system to predict the body part state of a user using the trained inferential models. As shown in FIG. 28I, processor 28822 may also receive inputs from other sensors (e.g., IMU sensor 28818, an image sensor, etc.) that may be configured to track a position of a body part of the user. Power may be provided to processor 28822 and the other electronic components of wearable device 28810 by battery 28820. The output of the signal processing performed by processor 28822 (e.g., a musculoskeletal representation of the user's body) may be provided to transceiver 28824 for transmission to dongle 28840 and/or HMD 28826.

Dongle 28840 may include transceiver 28834 configured to communicate with transceiver 28824 of wearable device 28810 and/or transceiver 28832 of HMD 28826. Commu-nication between transceivers 28834, 28824, and 28828 may use any suitable wireless technology and protocol, non-limiting examples of which include WiFi, Near Field Com-munication, and/or Bluetooth™. Bluetooth™ radio 28836 may be configured to act as a gateway device to coordinate communication among various wearable devices of system 28800 including HMD 28826 and wearable device 28810. In additional embodiments, wearable device 28810, HMD 28826, and/or dongle 28840 may communicate with each other via a wired connection.

Signals received from sensors 28812 may be processed using inferential model(s) as described above to predict a body part state of the user's body. HMD 28826 may receive the body part state from wearable device 28810 and/or instructions executed on processor 28830 of HMD 28826 may determine the body part state using the trained one or more inferential models. Processor 28830 of HMD 28826 may generate a visual representation of the body part state of a user of wearable device 28810 using the determined body part state. The visual representation of the user's body part state may be displayed to the user on display 28828 of HMD 28826. The visual representation of the user's body part state displayed to the user wearing HMD 28826 may be in conjunction with an artificial-reality application. In some examples, HMD 28826 may be eyewear device 1102 of FIG. 11, virtual-reality system 1200 of FIG. 12, HMD 1402 of FIG. 14, or augmented reality glasses 1520 of FIG. 15

FIG. 28J is a flow diagram illustrating an example method 28900 of predicting a body state based on neuromuscular data. At operation 28910, method 28900 may include receiv-ing neuromuscular activity data over a first time series from a first sensor on a wearable device donned by a user. Operation 28910 may be performed in a variety of ways, for example, neuromuscular sensors of a wearable device may periodically generate time series data that indicates neuro-muscular activity of the user.

At operation 28920, method 28900 may include receiving ground truth data from a second, different sensor that indicates a body part state of a body part of the user over a second time series. Operation 28920 may be performed in a variety of ways. For example, the ground truth data may be label time series data that indicates a body part state of the user as the user performs a task. The body part state may be or include position information corresponding to the spatial position of different body segments of the user during performance of the task. The position information may be obtained using one or more external devices (e.g., a camera, an IMU) that tracks the position of different points on the user's body during performance of the task.

At operation 28930, method 28900 may include generating one or more training datasets by time-shifting at least a portion of the neuromuscular activity data over the first time series relative to the second time series, to associate the neuromuscular activity data with at least a portion of the ground truth data. Operation 28930 may be performed in a variety of ways. For example, an appropriate time interval may be identified by generating multiple training datasets with multiple temporal shifts. The temporal shifts may be different respective time intervals based on factors including electromechanical delay time of the user (e.g., a user's muscle response time) and/or a known characteristic latency of the system. The time shift interval may determine system latency and may be based on the accuracy requirements of the task. For example, a task prioritizing precise movement (e.g., tele-surgery) may accept greater latency in exchange for greater accuracy, while a task prioritizing rapid movement (e.g., a video game) may accept lower accuracy in exchange for lower latency.

At operation 28940, method 28900 may include training one or more inferential models based on the one or more training datasets. Operation 28940 may be performed in a variety of ways. For example, the inferential models may be trained using a sequence of data sets as input, and each of the data sets in the sequence may include an n-dimensional vector of sensor data (e.g., sensor data from neuromuscular sensors, IMU sensors, etc.). The inferential model may provide output that indicates, for each task or movement performed by a user, the likelihood that the musculoskeletal representation of the user's body will be characterized by a set of musculoskeletal position characteristics. The inferential model may be used to predict body states and create a musculoskeletal representation associated with body parts of a user. A visual representation of the body part of the user may be displayed to the user. For example, a visual representation of the body part of the user may be displayed to the user on a head-mounted display.

Accordingly, the present disclosure includes systems, methods, and apparatuses that may be employed to predict a body part state of a user. For example, an artificial-reality system may include a wearable device(s) that includes sensors and systems configured to predict a body part state of the user. A virtual representation of the predicted state of the body part (e.g., a hand) may be displayed to the user on an HMD. The HMD may also display a virtual object (e.g., a game controller, a sports object) being held by the virtual representation of the hand. The virtual representation of the predicted state of the body part displayed to the user in connection with audio/video content of an artificial-reality application may create a more compelling artificial reality experience compared to conventional systems, such as by reducing a latency between predicted and actual body movements.

The following describes exemplary systems and methods for a deep spike decoder according to at least one embodiment of the present disclosure.

Neuromuscular signals arising from the human central nervous system may reflect neural activation that results in the contraction of one or more muscles in the human body. Neuromuscular sensors (e.g., electromyography (EMG) sensors), placed on the surface of the human body may record neuromuscular activity produced when skeletal muscle cells are activated. The neuromuscular activity measured by neuromuscular sensors may result from neural activation, muscle excitation, muscle contraction, or a combination thereof. Signals recorded by neuromuscular sensors may be used to assess neuromuscular dysfunction in patients with motor control disorders. In some applications, neuromuscular signals may be used as control signals for devices such as prosthetic limbs. Neuromuscular signals may be generated by spinal motor neurons and the muscle fibers they target. Motor unit action potentials are a fundamental unit of neuromuscular control.

Coordinated movements of skeletal muscles in the human body that collectively result in the performance of a motor task originate with neural signals arising in the central nervous system. The neural signals travel from the central nervous system to muscles via spinal motor neurons. Spinal motor neurons each have a cell body in the spinal cord and axon terminals on one or more muscle fibers. In response to receiving the neural signals, the muscle fibers may contract, resulting in muscle movement. A spinal motor neuron and the muscle fiber(s) it innervates are collectively referred to as a "motor unit." Muscles typically include muscle fibers from hundreds of motor units. Simultaneous contraction of muscle fibers in multiple motor units is usually required for muscle contraction and resulting muscle movement.

Muscles may exhibit a characteristic pattern of motor unit recruitment. In other words, the number of motor units activated may depend on a strength of a desired muscle contraction. When a motor unit is activated, a motor unit action potential (MUAP) is generated in each of the muscle fibers of the motor unit. Neuromuscular sensors, such as EMG sensors, may be used to record biological signals that result in motor activity (e.g., contraction of a muscle, relaxation of a muscle). In the case of EMG sensors arranged on the surface of the human body, the biological signals recorded may relate to the generation of MUAPs in muscle fibers of a motor unit. A MUAP may only be present when the corresponding motor unit is triggered by its motor neuron.

Some examples of the present disclosure are directed to analyzing neuromuscular signals to train an inference model to determine at least one spatiotemporal waveform and a corresponding weight. The weight may be applied to the spatiotemporal waveform by training the inference model to determine parameters for a biophysical (e.g., musculoskeletal) model that simulates a motor unit. The inference model associated with the neuromuscular signals may detect spike events in a motor neuron of a motor unit that results in the generation of MUAPs in the muscle fibers of the motor unit. Control signals that are generated based on the identified spike events may be used in some examples to control the operation of a device (e.g., an artificial reality device). In some examples, training sessions may be used to train a user to isolate and volitionally control a single motor unit.

Figure 29A:
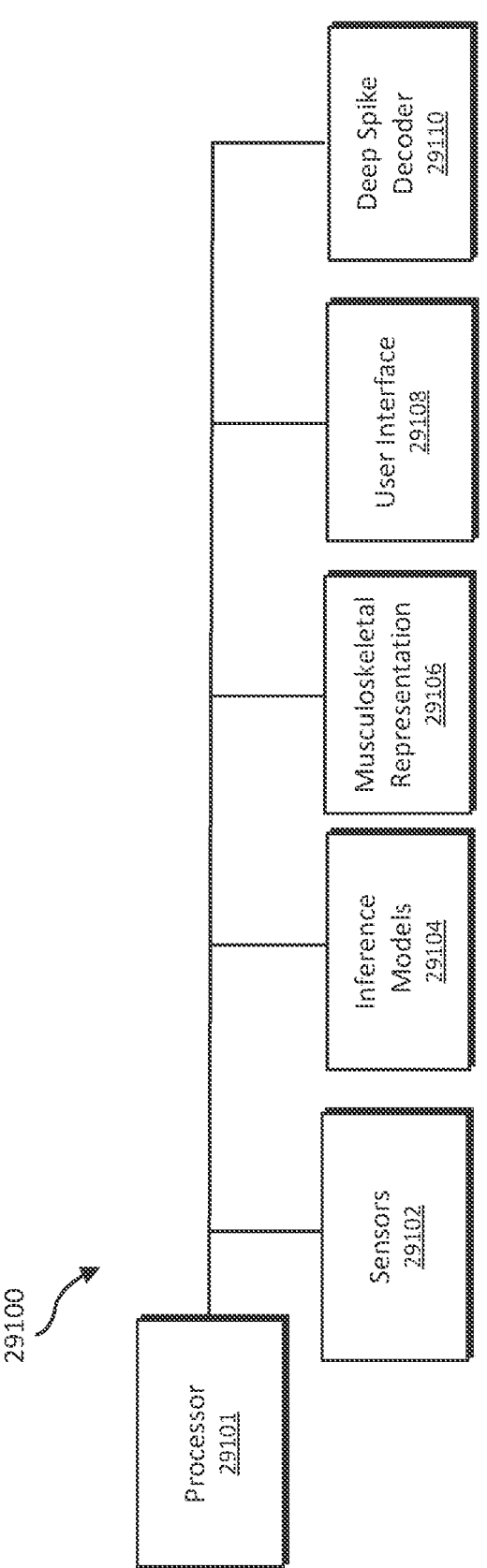
FIG. 29A is a block diagram of a system for processing neuromuscular signals, according to at least one embodiment of the present disclosure.

The following will provide, with reference to FIG. 29A, a description of an example block diagram of a system for training an inference model to process neuromuscular signals. A description of a chart representing neuromuscular signal data acquired by neuromuscular sensors arranged on a wearable device is presented in reference to FIG. 29B. A method for detecting a spike event in neuromuscular signal data acquired by neuromuscular sensors arranged on a wearable device is presented in reference to FIG. 29C. The description of FIGS. 29D-29F discloses a user interface for training a user to isolate and control a single motor unit. A method for training an inference model to determine a spatiotemporal waveform and a weight to determine parameters of a biophysical model simulating a motor unit is presented in reference to FIG. 29G. At least, FIGS. 8A-15 illustrate various types of example artificial reality devices that may be used with embodiments of the present disclosure.

General principles regarding how neuromuscular signals are used to activate muscles are described as follows. Motor unit action potentials may be generated in one or more efferent spinal motor neurons. The motor neurons may carry the neuronal signal (also referred to as "spikes" herein) away from the central nervous system and toward skeletal muscles in the periphery of the body. For each motor neuron in which an action potential is generated, the action potential travels along the axon of the motor neuron from the spinal cord where the action potential is generated to the axon terminals of the motor neuron that innervate muscle fibers included in skeletal muscles. A motor neuron and the muscle fibers that it innervates are referred to herein as a motor unit. Muscle fibers in a motor unit are activated together in response to an action potential generated in the corresponding motor neuron of the motor unit, referred to as a motor unit action potential (MUAP). Individual muscles typically include muscle fibers from hundreds of motor units with the simultaneous contraction of muscle fibers in many motor units resulting in muscle contraction evidenced as perceptible muscle movement.

A chemical synapse formed at the interface between an axon terminal of a spinal motor neuron and a muscle fiber is called a neuromuscular junction. As an action potential transmitted along the axon of a motor neuron reaches the neuromuscular junction, an action potential is generated in the muscle fiber as a result of chemical activity at the neuromuscular junction. In particular, acetylcholine released by the motor neuron diffuses across the neuromuscular junction and binds with receptors on the surface of the muscle fiber triggering a depolarization of the muscle fiber. Although neuromuscular signals sensed on the body surface generated by the depolarization of individual muscle fibers are small (e.g., less than 100 μV), the collective action of multiple muscle fibers conducting simultaneously results in a detectable voltage potential that may be recorded by neuromuscular sensors (e.g., EMG sensors) located on the surface of the body. As noted above, the collective conduction of muscle fibers from many motor units results in muscle contraction and perceptible motion. Accordingly, when a user performs a movement or gesture, the corresponding recorded neuromuscular signals include contributions from multiple activated motor units.

Following generation of an action potential in the muscle fiber, the propagation of the action potential in the muscle fiber results in a series of chemical-mediated processes within the muscle fiber. For example, depolarization of a muscle fiber results in an influx of calcium ions into the muscle fiber. Calcium ions inside the muscle fiber bind with troponin complexes, causing the troponin complexes to separate from myosin binding sites on actin filaments in the muscle fiber, thereby exposing the myosin binding sites. Following these chemical-mediated processes, the muscle fiber contracts. Muscle fiber contraction is achieved due to the binding of exposed myosin heads with actin filaments in the muscle fiber creating cross-bridge structures. The collective contraction of muscle fibers in one or more muscles results in the performance of a motor task. As the tension of a muscle increases, the firing rates of active motor neurons may increase, and additional motor neurons may become active in a process referred to as motor unit recruitment. The pattern by which motor neurons innervating a muscle become active and increase their firing rate may be stereotyped (e.g., may proceed in a particular order). Some examples of the present disclosure are directed to analyzing neuromuscular signals to detect, identify, and/or classify spike events corresponding to the firing of action potentials in one or more motor units. Some of these examples are described in the following discussion.

When a user performs a motor task, such as moving their arm, hand, or fingers, a group of muscles necessary to perform the motor task is activated. When the motor task is performed while the user is wearing a wearable device that includes neuromuscular sensors (e.g., EMG sensors), such as wristband 800 of FIG. 8A, the neuromuscular signals recorded by the sensors on the surface of the body may correspond to superimposed activity of all motor units in the muscles in the group activated during performance of the motor task. In some examples, the neuromuscular signals may be analyzed and mapped to control signals to control a device, such as the artificial reality devices described herein, based on the type of movement or gesture that the user performs. In some examples, the analysis of neuromuscular signals involves the detection and/or identification of spike events in activated motor units.

In some examples, a generative model of an EMG signal x (t) may take the following form:

$$x(t) = \sum t \wedge N_{\overline{\underline{i}}}(s\_i * t\_i)(t) + \eta(t) \tag{1}$$

Where t is the time, s_i is the spatiotemporal waveform of the i-th MUAP observed by an EMG recording device (e.g., wristband 800 of FIG. 8A), t_i is the spike train of the corresponding motor neuron and n (t) is the EMG measurement noise. The spike train may be represented as a time series of Dirac functions occurring each time the motor neuron fires.

As discussed above, a MUAP is an electrical potential generated by activation of muscle fibers in a corresponding motor unit. The spatiotemporal waveform of the MUAP as detected by an array of EMG sensors may depend on the position of the motor unit relative to the array of EMG sensors. Some examples may assume that the spatiotemporal waveform of the MUAP remains constant as long as the electrode positions and the conductive medium (e.g., the user's body) do not change. In some examples, small variations in the spatiotemporal waveform of a MUAP may be introduced due to muscle contractions. For EMG sensors positioned on the skin of the user's body, the time duration of a MUAP may be on the order of 20 ms (e.g., 10-30 ms) and may have an amplitude on the order of hundreds of microvolts (e.g., 100-900 microvolts). The duration of the MUAP may be influenced largely based on the spacing between differential EMG sensor electrodes and the velocity of the action potential wave traveling along the muscle fibers. The amplitude of the MUAP may be influenced largely based on the distance from the motor unit to the EMG sensor electrodes and the number of muscle fibers in the motor unit.

Since the spatiotemporal waveform of a MUAP may remain substantially constant and may therefore encode little or no information related to user intent, some examples of the present disclosure are directed to extracting spike event information (e.g., spike train data) from neuromuscular signals as a measure of user intent. For example, the extracted spike event information may be used to generate one or more outputs (e.g., one or more control signals). In some examples, a mapping between spike event information and control signals may be implemented using an inference model trained to associate particular spike event information with control signal outputs. In some examples, the output of the trained inference model may be musculoskeletal position information that describes, for example, the positions and/or forces of rigid body segments in a computer-implemented musculoskeletal model. The musculoskeletal model may include, without limitation, any predicted position of the user, an orientation of the user, a joint angle of the user, a linear force exerted by the user, a rotational force exerted by the user, a movement of the user, a pose of the user, a gesture of the user, or a combination thereof.

As neuromuscular signals are continuously recorded and spike events detected, the musculoskeletal model may be updated with predictions of the musculoskeletal position information output from the inference model. Control signals may then be generated based on the updated musculoskeletal position information. In some embodiments, the output of the trained inference model may be the control signals themselves, such that a separate musculoskeletal model is not used. For example, spike event information may be used to generate control signals for controlling an artificial reality device, a robot, a vehicle, scrolling through text, controlling a virtual avatar, playing a musical instrument (e.g., a piano), activating a discrete control (e.g., a button), activating a continuous control, navigating in a two-dimensional (or higher dimensional) space, or any other suitable control task.

In some examples, the described systems and methods provide for a computerized system to use a biophysical model. The computerized system may train an inference model using neuromuscular signals to determine one or more spatiotemporal waveforms and corresponding weights. Training the inference model may include determining one or more parameters for the biophysical model simulating at least one motor unit of the user. One or more spatiotemporal waveforms may relate to action potentials in one or more motor units of the user. In some embodiments, there is provided a simulator of fake or simulated spikes in a modeled arm and signals expected at each electrode to generate the spatiotemporal waveforms. The simulated biophysical model may provide a means for predicting a spike waveform and location in a cross section of the arm rather than a spatiotemporal waveform template on sixteen EMG channels. This implementation may allow for personalized anatomy based on ultrasound, x-ray, imaging, etc.

In some examples, the disclosed systems and methods may provide for a computerized system to implement cross session template calibration. The inference model may be trained using neuromuscular signals and one or more calibration parameters from the user. The calibration parameters may relate to a rotational shift, a longitudinal shift, and/or a skew shift of neuromuscular sensors arranged on one or more wearable devices. In some embodiments, the simulation-based biophysical model may be combined with cross session template calibration. Here, the inference model may be trained using the neuromuscular signals and the calibration parameters to determine one or more spatiotemporal waveforms and corresponding weights. Training the inference model may include determining one or more parameters for the biophysical model simulating motor units of the user. It is noted that one or more spatiotemporal waveforms may relate to firing of an action potential in one or more motor units of the user.

In some examples, the described systems and methods may address the spike-decomposition problem without using explicitly labelled data. Ground-truth labels for MUAPs may generally involve invasive electrode recordings that may be uncomfortable for the user, require a well-trained physiologist, and provide low-bandwidth data (e.g., monitor only a small number of motor units). Unlike neural networks that employ supervised learning and require training data with accurate ground-truth labels, the presently described neural networks or other suitable inference models may present a solution that is biophysically informed and self-supervised. In some examples, a deep neural network (DNN) may be trained to factorize a spatiotemporal signal (e.g., an EMG signal) into its constituent parts, namely, the spike trains, and the motor unit spatiotemporal templates that constitute it. During the inference process, an EMG frame may be input into the DNN, where it is passed into the first "half" of the DNN (e.g., the initial portion of the DNN), to produce spike trains. The spike trains may then be passed onto the last "half" of the DNN (e.g., the latter portion of the DNN), where they may be convolutionally combined with learned spatiotemporal templates, to reproduce the original EMG frame. In some examples, the process for last "half" of the DNN may be optional. For example, the EMG frame may be passed into the first "half" of the DNN, to produce spike trains, that are used as control signals (e.g., to control a device) without requiring reproduction of the original EMG frame.

FIG. 29A is a block diagram of a system 29100 for processing neuromuscular signals, according to at least one embodiment of the present disclosure. System 29100 may include a plurality of sensors 29102 configured to record signals resulting from the movement of portions of a human body. Sensors 29102 may include, without limitation, neuromuscular sensors, inertial measurement units (IMU), wearable (e.g., body-mounted) cameras, global positioning systems, laser scanning systems, radar ranging sensors, or a combination thereof.

Sensors 29102 may include a plurality of neuromuscular sensors configured to record signals arising from neuromuscular activity in muscles of a human body. The term "neuromuscular activity," as used herein, may refer to neural activation of spinal motor neurons that innervate a muscle, muscle activation, muscle contraction, and/or any combination thereof. Neuromuscular sensors may include one or more electromyography (EMG) sensors, one or more mechanomyography (MMG) sensors, one or more sonomyography (SMG) sensors, one or more sensors of any suitable type that are configured to detect neuromuscular signals, and/or any combination thereof. In some examples, sensors 29102 may be used to sense muscular activity related to a movement of the body part controlled by muscles. Sensors 29102 may be configured and arranged to sense the muscle activity. Spatial information (e.g., position and/or orientation information) and force information describing the movement may be predicted based on the sensed neuromuscular signals as the user moves over time.

Some embodiments may include a plurality of neuromuscular sensors. The neuromuscular sensors may be arranged to detect movement of different parts of the human body. For example, the neuromuscular sensors may be arranged to detect movements of one or more body segments distal to the torso (e.g., a forearm or wrist). In some examples, a plurality of EMG sensors may be arranged on a wearable device configured to be worn around the lower arm (e.g., the forearm) or wrist of a user. The EMG sensors may be configured to determine movement information associated with wrist or hand segments to determine, for example, whether the user has an open or closed hand configuration.

Each of sensors 29102 may include one or more sensing components configured to sense information about a user. In the case of IMUs, the sensing components may include one or more accelerometers, gyroscopes, magnetometers, or any combination thereof, to measure characteristics of body motion. Examples of characteristics of body motion may include, without limitation, acceleration, angular velocity, linear velocity, and sensed magnetic field around the body. The sensing components of the neuromuscular sensors may include, without limitation, electrodes configured to detect electric potentials on the surface of the body (e.g., for EMG sensors), vibration sensors configured to measure skin surface vibrations (e.g., for MMG sensors), acoustic sensing components configured to measure ultrasound signals (e.g., for SMG sensors) arising from muscle activity, or a combination thereof.

In some examples, the output of sensors 29102 may be processed using hardware signal processing circuitry (e.g., to perform amplification, filtering, and/or rectification). In some examples, at least some signal processing of the output of sensors 29102 may be performed in software. Thus, signal processing of neuromuscular signals recorded by sensors 29102 may be performed in hardware, software, or by any suitable combination of hardware and software, as embodiments of the present disclosure are not limited in this respect.

In some examples, sensors 29102 may be arranged as a portion of a wearable device configured to be worn (e.g., donned) on or around part of a user's body. For example, a plurality of neuromuscular sensors may be arranged circumferentially around an adjustable and/or elastic band such as a wristband or armband that is configured to be worn around a user's wrist or arm. In some examples, an IMU sensor and/or a plurality of neuromuscular sensors may be arranged and/or attached to a portion and/or multiple portions of the body including, without limitation, an ankle, a waist, a torso, a neck, a head, a foot, a shin, a shoulder, or a combination thereof. Additionally or alternatively, sensors 29102 may be arranged on a wearable patch configured to be affixed to a portion of the user's body. In some examples, multiple wearable devices, each having sensors 29102 included thereon, may be used to predict musculoskeletal position information for movements that involve multiple parts of the body.

System 29100 may include at least one processor 29101 programmed to communicate with sensors 29102. For example, signals recorded by one or more of sensors 29102 may be provided to processor 29101, which may be programmed to execute one or more machine learning algorithms configured to process signals output by sensors 29102 to train one or more inference models 29104. The trained (or retrained) inference models 29104 may be stored for later use in generating a musculoskeletal representation 29106, as described in more detail below. Non-limiting examples of inference models 29104 that may be used to train a user to isolate and volitionally control a single motor unit are discussed in further detail below.

System 29100 may include a user interface 29108 configured to interface with a user when training inference models 29104. As discussed in more detail below, processor 29101 may use one or more trained inference models 29104 configured to generate a biophysical model based, at least in part, on signals recorded by sensors 29102. As described with reference to FIGS. 29D-29F below, user interface 29108 may receive training parameters from the user and/or display training parameters/results to the user. The biophysical model may be used to update musculoskeletal representation 29106, which may be used to render a visual representation on a display device (e.g., a head-mounted display, a digital monitor, etc.) and/or provide a control signal to a device. Real-time reconstruction of the current body state and subsequent rendering of a visual representation on user interface 29108 reflecting the current body state information in the musculoskeletal model may provide visual feedback to the user about the effectiveness of inference models 29104 to accurately represent an intended body state. In some examples, a metric associated with musculoskeletal representation 29106 (e.g., a likelihood metric for one or more hand gestures or a quality metric that represents a confidence level of estimating a position, movement, and/or force of a segment of a multi-segment articulated rigid body system such as a hand) may be provided to a user, a device, or a third-party.

As discussed above, some embodiments may be directed to using inference models 29104 to train a user to volitionally control a single motor unit based on signals recorded from sensors 29102 (e.g., wearable sensors). Inference models 29104 may be used to train a user to volitionally control a single motor unit without having to place sensors 29102 on each segment of the rigid body that is to be represented in the computer-generated musculoskeletal representation 29106. The types of joints between segments in a multi-segment articulated rigid body model may constrain movement of the rigid body. Additionally, different users may tend to move in different (e.g., unique) ways when performing a task that may be captured in statistical patterns of individual user movement. Inference models may be personalized to the user by applying weights specific to the user. At least some of these constraints on human body movement may be explicitly incorporated into inference models 29104 used for prediction. Additionally or alternatively, the constraints associated with a particular user may be learned by inference models 29104 through training based on recorded data from sensors 29102 and/or user training through user interface 29108. Constraints imposed on the construction of inference models 29104 may be constraints set by the anatomy and physics of a particular user's body, while constraints derived from statistical patterns may be constraints set by human behavior for one or more users from which sensor measurements may be recorded.

In some examples, embodiments of the present disclosure may provide for system 29100 to train inference models 29104 using neuromuscular signals from sensors 29102 to determine one or more spatiotemporal waveforms and corresponding weights. System 29100 may train inference models 29104 in any suitable manner. In one example, system 29100 may train an inference model with the following parameters:

DSD: The Deep-Spike-Decoder DNN. It is characterized by both W_d and W_e.

N_c: The number of channels on a device for recording neuromuscular activity. For example, N_c=16, but it may be made arbitrarily large (or small) without loss of generality.

N_m: The maximum number of motor units the DNN is allowed to find. For example, N_m=10, but it may be made arbitrarily large (or small) without loss of generality.

N_T: The number of time samples in an EMG input frame, X. For example, N_T=64, but it can be made arbitrarily large (or small) without loss of generality.

N_t: The number of time samples of a MUAP template. For example, N_t=40, but it can be made arbitrarily large (or small) without loss of generality.

f_d (.; W_d): The decoder function (portion) of the DNN, parameterized by weights W_d, taking input '.'

W_d: The weights comprising the decoder portion of the net. Those weights may parameterize a deep nonlinear convolutional net.

f_e (.; W_e): The encoder function (portion) of the DNN, parameterized by weights $We, taking input '.'

W_e: The weights comprising the encoder portion of the net. Those weights may specifically and explicitly constitute a 3-dimensional cube $\in R\hat{}(N\_m \times N\_c \times N\_t)$.

$X \in R\hat{}(N\_c \times N\_T)$: The EMG input into the DNN.

$\hat{X} \in R\hat{}(N\_c \times N\_T)$: The reconstructed EMG output.

$S \in R\hat{}(N\_m \times N\_T)$: The spike train output.

The entire chain of the DNN may therefore operate in the following manner:

S=f_d (X;W_d)

$\hat{X}$=f_e (S;W_e)

During training both S and $\hat{X}$ may be computed. During the inference phase, only the spike trains S may be needed.

Architecture:

Some embodiments of the DNN architecture(s) used are described below. Other types of inference models with varying structures may be used in the embodiments described herein.

A decoder may be implemented in any suitable manner. In some embodiments, the decoder f_d may constitute a deep convolutional neural network (CNN), which may be assigned the task of simultaneously peak-picking and blindly clustering those peaks into its underlying and unique spike trains. In some embodiments, a Dense Nets architecture may be used. Additionally or alternatively, a Tiramisu Net may be used.

In some embodiments, because the decoder is tasked with implicitly peak-picking, it may be desirable for the network to have access to the original high-frequency content of the signal at later layers, which both architectures allow for. The delta between Dense Nets to Tiramisu Nets, at the conceptual level, however, may be the use of upsampling and downsampling paths as in U-net architecture. For image segmentation, it may achieve superior performance since it may explicitly leverage the idea of combining context information with high-resolution information at different levels of granularity. Since segmentation algorithms may generally need to perform some form of edge detection (spikes being the temporal analogue in this case), this makes Tiramisu Nets a suitable choice here. The Tiramisu architecture may also be computationally more efficient, since for the same number of parameters this architecture performs fewer number of convolution operations by virtue of performing them at different levels of granularity.

As with the decoder, an encoder may be implemented in any suitable manner. In some embodiments, an encoder may be a strictly a linear model. This is because from latent spike trains, it is desired to go back to the original EMG, and the generative biophysical model is indeed linear (or very close to it). Furthermore, forcing the encoder to be linear means that we can place biophysical interpretability on top of it. The imposition of interpretability here may be important for a number of reasons, some more subtle than others. In some embodiments, the encoder weights, W_e, can be approximated using canonical decomposition to significantly reduce the number of parameters of the network.

If the net is not forced to go through the linear biophysical model, then there may be one or more avenues available for the decoder to "cheat," in coming up with the latent representation owing to the power of universal approximation. The universal approximation theorem states that a feed-forward network with a single hidden layer containing a finite number of neurons can approximate continuous functions on compact subsets of R^n, under mild assumptions on the activation function. The theorem thus states that simple neural networks can represent a wide variety of interesting functions when given appropriate parameters. In this case, the latent representation need not be unique spike trains and can become anything arbitrary. If, on the other hand, the encoder is forced to take spike trains as intended, and only be allowed to reconstruct with a linear convolutional model, then the combinatorial solution space is pruned towards the truth. Secondly, in some application classes, explicit spatiotemporal motor units may be desired. Under the biophysical constraint, the encoder weights may be the spatiotemporal motor units themselves.

In this aspect, the encoder model f_e takes in the inferred spike train S, and subjects it to a (separable) linear convolution with its weights W_e. Here, each $1 \times N\_T$ spike train out of the maximum allowable N_"mus" spike trains is convolved with its corresponding $N_c \times N_t$ spatiotemporal slice from $W\_{e} \in \mathbb{R}\hat{}\{\{N\}\_{m} \times \{N\}\_{c} \times \{N\}\_{t}\}$. The results are then all summed up together across all $N_{mus}$ to give the EMG reconstruction $\hat{X}$.

Gumbel-Softmax:

The spike trains S are what exist on the boundary between the decoder and encoder. Concretely, the spiketrain matrix S is the top slice taken from an element-wise (e.g., pixel-wise) transformation of the penultimate tensor $P \in \mathbb{R}^{2 \times N_m \times N_T}$. In some embodiments, this transformation is a simple softmax operation. In other words, we would have:

$$S = \text{sm}(P)$$

where the softmax operation "sm" is applied on the first dimension to yield yield $S \in \mathbb{R}^{N_m \times N_T}$ Framed in such a way, the DNN effectively learns to create "spikes" (e.g., place a high probability value) where a spike may exist. However, the value of those spikes need not be necessarily 1, since the DNN may wish to bake MUAP scale into the spike value. At least, there is nothing stopping it from doing so. This, coupled with a sparsifying loss (see below) on the spike train matrix, means that there may be additional incentive for the spikes to be as low as the reconstruction loss will tolerate.

In some embodiments, the systems described herein may force the DNN to make a "hard" decision of spike/no-spike for every spatiotemporal pixel. In other words, it may be desirable for the DNN to learn how to make a categorical decision, on whether or not there is a spike present, and not the probability of whether or not a spike exists. Furthermore, it may be desirable to be able to backpropagate into this categorical decision-making function.

In some embodiments, the Gumbel-Softmax may be used to address the above discussed issues. The Gumbel-Softmax distribution may allow for defining a continuous distribution, over a simplex that can approximate discrete categories. Where the normal softmax on logits x across all categories C may be defined as:

$$P(y_i) = e^{x_i} / \sum_{j=1}^{C} e^{x_j}$$

Here, instead a proxy using the gumbel-distribution may be defined, whereby:

$$P(z_i) = e^{(log(P(y_i))+g_i)/\tau} / \sum_{j=1}^{C} e^{(log(P(y_j))+g_j)/\tau}$$

Here, two new terms are added, the temperature $\tau$, and a draw from a gumbel distribution g "G" (0,1). The gumbel draw can be computed by:

$$g = -\log(-\log(u))$$

where u "U" (0,1) is a draw from a uniform distribution. For categorical distributions, as the temperature term t is lowered over training, (similar to annealing), the distribution (for each pixel in our case) may begin to approximate a one-hot vector (e.g., a 1×N matrix, where all vector elements are zero except one), leading the DNN to be able to make a "decision" on spike/non-spike. During the training phase, there is an annealing scheduler, but some experiments have shown this to be robust across a lot of annealing schedules, so long as cooling eventually occurs. During the inference phase, the stochastic element g is dropped altogether, and the temperature term is set to 1.

In some embodiments, it has been empirically found that it is not desirable to cool too quickly, and instead let the DNN train as it normally would with a high temperature. This is to allow the other weights across the DNN a chance to converge to their respective values, before the DNN is forced to make hard decisions on spike/no-spike. In some embodiments, the softmax function is replaced with the gumbel-softmax function.

Having discussed embodiments of the architecture, below are described illustrative loss functions that may be utilized and the rationales for use therein, but the described systems and methods are not so limited. One or more loss functions may be used independently or in combination and such use is within the scope of the embodiments described herein.

Main Loss Terms $L_r$: Reconstruction loss.
$L_l$: Local sparsity loss.
$L_s$: Spike train loss.
$L_p$: Parsimony loss.
$L_u$: Uniqueness loss.

In some aspects, the described systems and methods provide for a computerized system to train an inference model using neuromuscular signals to determine one or more spatiotemporal waveforms and corresponding weights. The computerized system may reconstruct the neuromuscular signals based on the spatiotemporal waveforms and corresponding weights. The system may determine an error value between the neuromuscular signals and the reconstructed neuromuscular signals using a reconstruction loss function. In some embodiments, the reconstruction loss function may include a reconstruction mean square error loss using a fourth power to emphasize spike terms over noise-related terms. In some embodiments, an entropy loss function may be used to enforce 0 or 1 as probability of a spike term. Further details on these aspects are provided below.

In some embodiments, because the heart of the deep spike decoder is that of a biophysically inspired auto-encoder, there exists loss L_r, which may drive the reconstruction of the EMG data based on the factorization that may be forced upon it. In certain embodiments, the reconstruction loss L_r may be given by the mean-square error:

$$L_r = \|X - X\|_2$$

Other loss function variants, such as the 4th norm, may be used with similar results.

In some examples, system 29100 may process neuromuscular signals using trained inference models 29104 to determine one or more spike events. In some examples, deep spike decoder 29110 may include a loss function(s). The loss function may predict the error within the deep convolutional neural network of deep spike decoder 29110. The loss function may be used to update the weights of deep spike decoder 29110. The system may determine an error value between the neuromuscular signals and the reconstructed neuromuscular signals using a local sparsity loss function. The local sparsity loss function may enforce that spike pulse trains are sparse signals. In some examples, the local sparsity loss function may include a refractory loss function to enforce that a motor unit has a refractory period after a firing of an action potential in the motor unit. For example, the refractory loss function may apply a temporal window corresponding to the refractory period to enforce that the motor unit did not fire more than once within the refractory period.

In some embodiments, a spike train loss attempts to encode priors based on the statistics of the spike train matrix S that may be inferred. Compared to the sampling time of the device, spikes may be rare events—in other words, sparse events. This global statistic maybe used to push S to be as sparse as possible-provided that reconstruction is not violated.

$$L_s = \|S\|_1$$

How exactly sparse the spike trains may generally depend on the data.

In some aspects, the described systems and methods provide for a computerized system to train an inference model using neuromuscular signals to determine one or more spatiotemporal waveforms and corresponding weights. The computerized system reconstructs the neuromuscular signals based on the spatiotemporal waveforms and corresponding weights. The system determines an error value between the neuromuscular signals and the reconstructed neuromuscular signals using a parsimony loss function. The parsimony loss function may enforce that the at least one spatiotemporal waveform is smooth and/or sparse across the plurality of neuromuscular sensors. In some examples, the parsimony loss function may include an N-neighbor parsimony loss function. The N-neighbor parsimony loss function may enforce that the at least one spatiotemporal waveform has clustered sparsity across N consecutive neuromuscular sensors of the plurality of neuromuscular sensors. For example, the N consecutive neuromuscular sensors may include three or more consecutive neuromuscular sensors.

In some embodiments, L1-L2 loss may be applied to a partition of the spatiotemporal weights (e.g., as described by the encoder weights). This partition may emphasize group sparsity across motor units and across electrode neighborhoods. In some embodiments, L1-L2 loss may be applied to only the temporal waveforms obtained by the canonical decomposition of the encoder weights. In this aspect, only motor unit group sparsity may be enforced.

In some embodiments, the parsimony loss may contribute to the success of the DSD. The cardinality problem may be important for spike-decomposition and may describe how the DNN may learn to infer the number of motor units present. This discrete counting problem may be challenging, as a neural network may use whatever parameters are available to it to explain the data. This may be similar to an unsupervised clustering problem on a meta level as well, where not only should clustering be learned, but the number of clusters may also be inferred.

In some embodiments, a recurrent solution whereby this problem is side stepped to an extent may be implemented, whereby a DNN progressively "peels" out one motor unit after another. However, in some situations, without a robust and recurrent angle of attack, the (feedforward) DNN may be forced to instead utilize the concept of parsimony. In this case, the latent space may be over-parameterized (in this case, the number of MUAPs allowed) by allowing it to use as many MUAPs as it needs, up to a certain upper limit. However, the net may then be penalized for using more MUAPs than are needed.

In particular, in some embodiments MUAPs may be encoded in the weight tensor W, and so their non-zero support may be penalized in the joint electrode-cardinality space. Put another way, in some embodiment the DNN may reconstruct the EMG signal using as few MUAPs as it can get away with, where the support of each motor unit may be limited to as few channels as possible.

Similar to the cardinality-electrode space, there may be a strong prior for the temporal space of the W tensor as well. MUAP waveforms may be smooth phenomena due to the biophysics of propagation. This prior can be accounted for by incurring a loss on high-frequency content and encoded by taking the first temporal difference of the waveforms then computing its L2 norm.

In some embodiments, these two concepts may be combined into group-sparsity, the L1LQ norm (e.g., where Q=2). This combined group-sparsity may generate a parsimonious set of MUAPs, as described above. The following equations describe the parsimony loss:

Let $W'_e$ be the temporal derivative tensor, given by:

$$W'_e = W_e[:, :, 1:] - W_e[:, :, 0:-1]$$

The parsimony loss $L_p$ is then given by:

$$L_p = \left\| \left( \sum_{i=1}^{t} W'_e[:, :, i]^2 \right)^{1/2} \right\|_1$$

where i loops over all temporal slices of the tensor, and recalling that every $W'_e[:,:,i] \in \mathbb{R}^{N_m \times N_c}$.

In some aspects, the described systems and methods provide for a computerized system to train an inference model using neuromuscular signals to determine one or more spatiotemporal waveforms and corresponding weights. The computerized system reconstructs the neuromuscular signals based on the spatiotemporal waveforms and corresponding weights. The system may determine an error value between the neuromuscular signals and the reconstructed neuromuscular signals using a uniqueness loss function. With the reconstruction loss, the biophysical reconstruction fidelity may be tested. With the spikiness loss, it may be desired to encode priors on individual spike trains. With the parsimony loss, it may be desired to encode priors on individual MUAPs. Finally, with the uniqueness loss, it may be desired encode a joint prior on the cross MUAP-spike train interactions amongst each other.

In particular, some embodiments may not use two or more MUAPs and their corresponding spike trains to explain the same phenomena. In even more particular terms, some embodiments may penalize multiple explanations of co-occurrence of energy on the same channel and the same time.

In one example, let $E \in R^{(N_m \times N_m)}$ denote a matrix with 0 in the diagonal elements, and 1 otherwise.

Furthermore, let $M = \sum_{i=1}^{t} |We[:,:,i]|$, where $M \in \mathbb{R}^{N_m \times N_c}$. This matrix may represent the collapsed temporal energy for each MUAP's channel.

Lastly, for the spike train matrix $S \in \mathbb{R}^{/N_m \times N_T}$, a dilated version S' of this spike train matrix may be defined, where each spike train may be convolved with a filter of length t, composed of all 1s. The rationale here is that it may be desired to encode the refractory period t of the spike trains, to create the buffer unto which crosstalk of spike train is penalized. Put differently, if this dilation did not exist, then spikes offset by even a small number of samples explaining the same phenomenon (with their MUAPs' energies looking very similar) may not be penalized.

In embodiments that penalize consistent cross-spike train occurrences seeking to explain the same data on the same channel and the same time, the uniqueness loss $L\_u$ becomes:

$$L_u = \left\| S'S'^T \odot MM^T \odot E \right\|_1$$

The term E may simply stops self-penalization, and here $\odot$ is the hadamard element-wise product.

In some embodiments, with all four loss terms enumerated, a final loss term L may be determined. Weight terms for each of the four losses may be assigned. For example, the reconstruction weight may be set to 1, so that all the remaining losses are relative to the reconstruction loss. Therefore, in the end, we have:

$$L\_total = L\_r + \alpha L\_s + \beta L\_p + \gamma L\_u$$

where $\alpha$, $\beta$ and $\gamma$ are loss hyper-parameters to be tuned during validation.

In some aspects, the described systems and methods provide for a computerized system to use a biophysical model. The computerized system trains an inference model using neuromuscular signals to determine one or more spatiotemporal waveforms and corresponding weights. Here, training the inference model includes determining one or more parameters for the biophysical model simulating at least one motor unit of the user. It is noted that one or more spatiotemporal waveforms The simulated biophysical model provides a means for predicting a spike waveform and location in a cross section of the arm rather than a spatiotemporal waveform template on, e.g., sixteen channels. In some aspects, the described systems and methods provide for a computerized system to implement cross session template calibration. The inference model may be may be combined with cross-session template calibration. Training the inference model includes determining one or more parameters for the biophysical model simulating motor units of the user. In some embodiments, one or more spatiotemporal waveforms may relate to firing of an action potential in one or more motor units of the user.

FIG. 29B illustrates an example set of neuromuscular signal waveforms (e.g., EMG channel waveforms) associated with a number of biological sources (e.g., motor units of a user). Each column may represent a spatiotemporal waveform that is detected from one motor unit. Each row may represent a waveform (e.g., an average waveform) produced from one neuromuscular sensor channel (e.g., an EMG channel). In some examples, a user may don a wearable device that includes neuromuscular sensors that generate channel waveforms 29201(1) . . . 29201(n). Channel waveforms 29201(1) . . . 29201(n) may be generated from neuromuscular sensors (e.g., EMG sensors) arranged circumferentially around an elastic band and configured to be worn around a body part of a user (e.g., a user's lower arm or wrist). Although FIG. 29B shows sixteen channel waveforms generated by sixteen neuromuscular sensors, any suitable number of channels/sensors may be used. The number and arrangement of the neuromuscular sensors may depend on the particular application for which the wearable device is used. For example, a wearable armband or wristband (e.g., wristband 800 of FIG. 8A) may be used to generate control information for controlling an artificial reality system, a prosthetic limb, a robot, a vehicle, scrolling through text, controlling a virtual avatar, or any other suitable control task.

FIG. 29C illustrates a method 29300 for detecting one or more spike events detected in recorded neuromuscular signals, according to at least one embodiment of the present disclosure. In step 29310, a plurality of neuromuscular signals may be recorded by a plurality of neuromuscular sensors worn by a user as the user activates one or more motor units. Method 29300 may then proceed to step 29320, in which the recorded neuromuscular signals may optionally be preprocessed prior to detection of spike events. For example, one or more time-lagged versions of the recorded signals may be generated, and the time-lagged versions may subsequently be used for detection of spike events. In some examples, the recorded neuromuscular signals may optionally be preprocessed using signal denoising, frequency filtering, spatial transformations, signal whitening processes, or a combination thereof.

Method 29300 may then proceed to step 29330, where at least one spike event is detected in the recorded neuromuscular signals, such as according to the example techniques described herein. For example, the recorded neuromuscular signals or information derived from the recorded neuromuscular signals (e.g., time-lagged versions of the recorded neuromuscular signals) may be processed using one or more inference models to detect spike events in the recorded neuromuscular signals.

In some examples, one or more outputs may be generated based on the detected spike event(s). Any suitable output may be generated for a particular application, and embodiments are not limited in this respect. In some examples, the output may be compressed data representing the recorded neuromuscular signals. For example, rather than storing "raw" neuromuscular signals, the system may be configured to store only information about the detected spike events such as their timing characteristics and/or their biological source information. Storing such compressed data may be beneficial, for example, for transmission (e.g., over one or more wireless networks) of the data and/or of a control signal to an external device and/or for logging data for other (e.g., health, fitness, ergonomics, etc.) monitoring applications without having to store the raw recorded data.

In some examples, the generated output may include information used to update a musculoskeletal model. Some examples may employ a musculoskeletal model that is updated with musculoskeletal position information describing, for example, positions, poses, and/or forces of rigid body segments in the model. Spike event information determined in step 29330 may be provided as input to the musculoskeletal model as part of the updating process. Control signals may then be generated based on the updated musculoskeletal model.

In some examples, the generated output may be a control signal used to control an external device. Rather than mapping recorded neuromuscular signals directly to control signals using a trained inference model, some examples may map spike event information (e.g., detected spike events and/or biological source information for the spike events) to control signals. For example, the spike event information may be provided as input to a trained inference model and an output of the trained inference model may be used to generate the one or more control signals. In some examples, the output of the trained inference model may be a set of one or more control signals. In another example, the control signal(s) may be generated based on the spike event information without the use of a trained inference model. The generated control signal(s) may then be provided to a control interface of a device to control an operation of the device (e.g., an artificial reality device). For example, the device may be a display and a control signal may be provided to a display controller of the display. The control signal may include instructions to update information displayed on the display. Alternatively the device may be a computer or other computing device (e.g., a smartphone) and the control signal may be provided to a controller of the computing device to change an operation of the device. In another example, the control signal may be used to control a device (e.g., a musical instrument) to provide an artistic expression. Other non-limiting control signal examples may include: spike event information may be used to generate control signals for controlling a robot, controlling a vehicle, scrolling through text, controlling a virtual avatar, activating a discrete control (e.g., a button), activating a continuous (e.g., one-dimensional) control, navigating in a two-dimensional (or higher dimensional) space, or any other suitable control task. Any device having a control interface may be controlled using control systems designed in accordance with the techniques described herein.

In some examples, the one or more control signals may be generated based, at least in part, on the spike event information in substantially real-time. As used herein, the term "substantially real-time" means that the spike event information determination process occurs and/or the control signals may be generated shortly after the electrical event occurs while the neuromuscular data is being recorded, rather than happening off-line at a time when the neuromuscular signals are not being recorded. In some examples, spike event information may be detected within 5 seconds, within 1 second, within 500 ms, within 100 ms, or within 10 ms of the occurrence of the electrical event.

Throughout portions of this disclosure, EMG sensors are used as examples of the type of neuromuscular sensors configured to detect neuromuscular activity. However it should be appreciated that other types of neuromuscular sensors including, but not limited to, mechanomyography (MMG) sensors, sonomyography (SMG) sensors, and electrical impedance tomography (EIT) sensors may additionally or alternatively be used in combination with EMG sensors to detect neuromuscular activity in accordance with some examples. The neuromuscular signals recorded by the neuromuscular sensors may be used to detect and/or sort spike event information in accordance with the techniques described herein.

In some examples, a computer processor may be programmed to generate the musculoskeletal model to include a variety of information. For example, the musculoskeletal model may include a predicted position of the user, an orientation of the user, a joint angle of the user, a linear force exerted by the user, a rotational force exerted by the user, a movement of the user, a pose of the user, a gesture of the user, or any combination thereof.

In some examples, the systems and methods described herein may relate to creating personalized models to detect poses based on neuromuscular data for the user. In some embodiments, a set of poses and/or forces associated with each of these poses may be detected. The set of poses may include, for example, a rest pose (for which no or little force estimate is determined), pinches of each finger to the thumb, an open hand pose, and a fist.

Detection of poses and estimation of forces associated with each pose of a part of a user's body (e.g., the fingers, hand, and/or wrist) using neuromuscular signals and a generalized inference model may be sub-optimal for some users. On the other hand, systems and methods for training and implementing personalized models that infer the user's pose and the forces associated with that pose can provide improved reliability and sensitivity of pose detection for that user. Higher-quality pose inference may enable a user to more effectively use poses as control signals for computers, computing machines, or other devices.

One potential approach for personalizing an inference model may include building and training an inference model from scratch for each user. However, such an approach may be limited because it generally requires a large amount of data to be collected from each user for training. Collecting a sufficiently large training data set to train an inference model from scratch for an individual user may be cumbersome for the user. On the other hand, using a smaller training data set for training a personalized inference model typically results in sub-par performance, such as model instability and overtraining.

According to some embodiments of the present disclosure, personalizing an inference model for pose detection and force estimation by adapting a previously trained generalized inference model may be an effective approach that may improve the quality of model inferences while requiring a small training data set from a user. For example, various example embodiments of personalized pose models may work by adapting a generalized inference model.

In one embodiment for personalization of a pose inference model based on neuromuscular data, the model architecture of the generalized model may be maintained, and new model weights may be learned to better fit the model for the user.

In another embodiment for personalization of a pose inference model based on neuromuscular data, a linear pre-layer may be added to the model. The linear pre-layer may alter the input signal and may help the model make better predictions.

In another embodiment for personalization of a pose inference model based on neuromuscular data, generative models can be used to pre-label the poses and then the model can be trained to learn a light-weighted set of templates to alter the neuromuscular data for better predictions.

A generalized model for inferring poses and forces associated with the poses can be described with models that use at least one parameter θg and a fixed model architecture f to estimate y about the probability of a given pose and the relative force level, e.g., y=f(x|θg). To measure the quality of the model predictions, a loss function can be implemented (e.g., L (y,y0) where y0 is the ground truth).

In some embodiments, a user can generate a training data set for personalizing an inference model for poses and forces by wearing an armband with a plurality of neuromuscular sensors (e.g., surface electromyography (sEMG) sensors) while performing a set of poses according to prompts provided to the user (e.g., through a web browser of a computer or other device wirelessly connected to the armband containing the plurality of sEMG sensors). A user can be prompted (e.g., with verbal prompts and/or graphical indicators) to perform each pose in a set of poses with varying force(s). Generally, the pose can be performed several times (e.g., twice, three times, more than three times, etc.) and a next prompt can be provided for the user to perform a next pose in the set of poses. For example, the set of poses can include a rest pose (minimal muscle activation in the forearm), a fist, an open hand, and pinches of each of the mitten fingers (i.e., index, middle, ring, and pinky fingers) to the thumb. The neuromuscular (e.g., sEMG) signals associated with each pose can be recorded and associated with label data corresponding to a pose and/or the relative amounts of force(s) associated with the pose. The neuromuscular and label data can then be supplied as input for training an inference model, as described below. Example methods and user interfaces for generating a training data set for personalizing an inference model for poses and forces are described below with reference to FIGS. 29D-29F.

Techniques for personalizing an inference model for poses and forces may start with the original model architecture ŷ=f(x|θ), which may be trained to learn new weights for a particular user. In one embodiment, the model weights of the inference model can be fine tuned by initializing them as θ=θg, where θg corresponds to the model weights of a generalized inference model for poses and forces, and a personal training data set (generated as described above) may be used to adjust the weights θ. In another example, the model weights of the inference model can be retrained from scratch by initializing θ randomly, and a personal training data set (generated as described above) can be used to identify a new set of model weights, θ*.

Figure 29D:
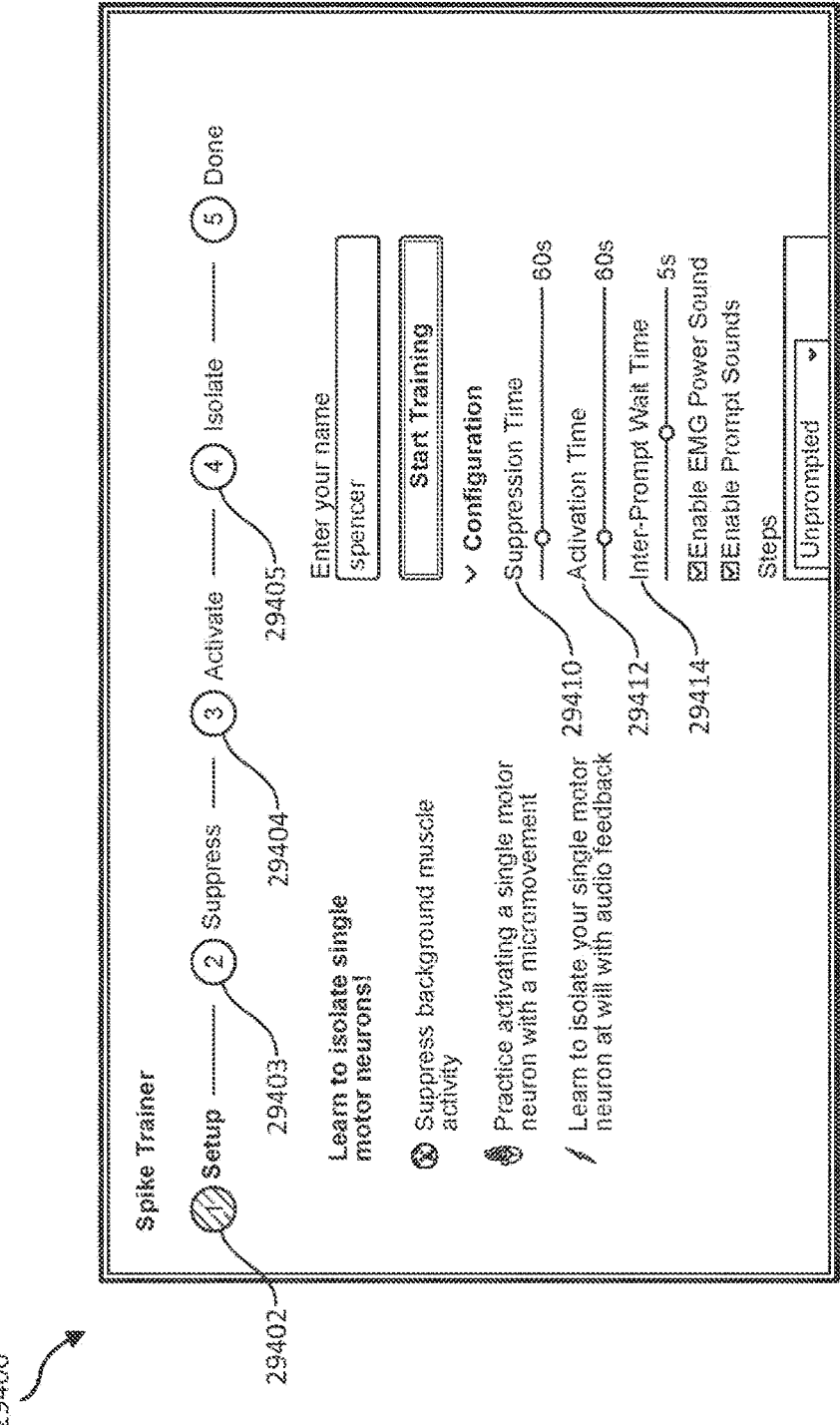
FIG. 29D illustrates a user interface in a first state for training a user to isolate a single motor unit, according to at least one embodiment of the present disclosure.
Figure 29E:
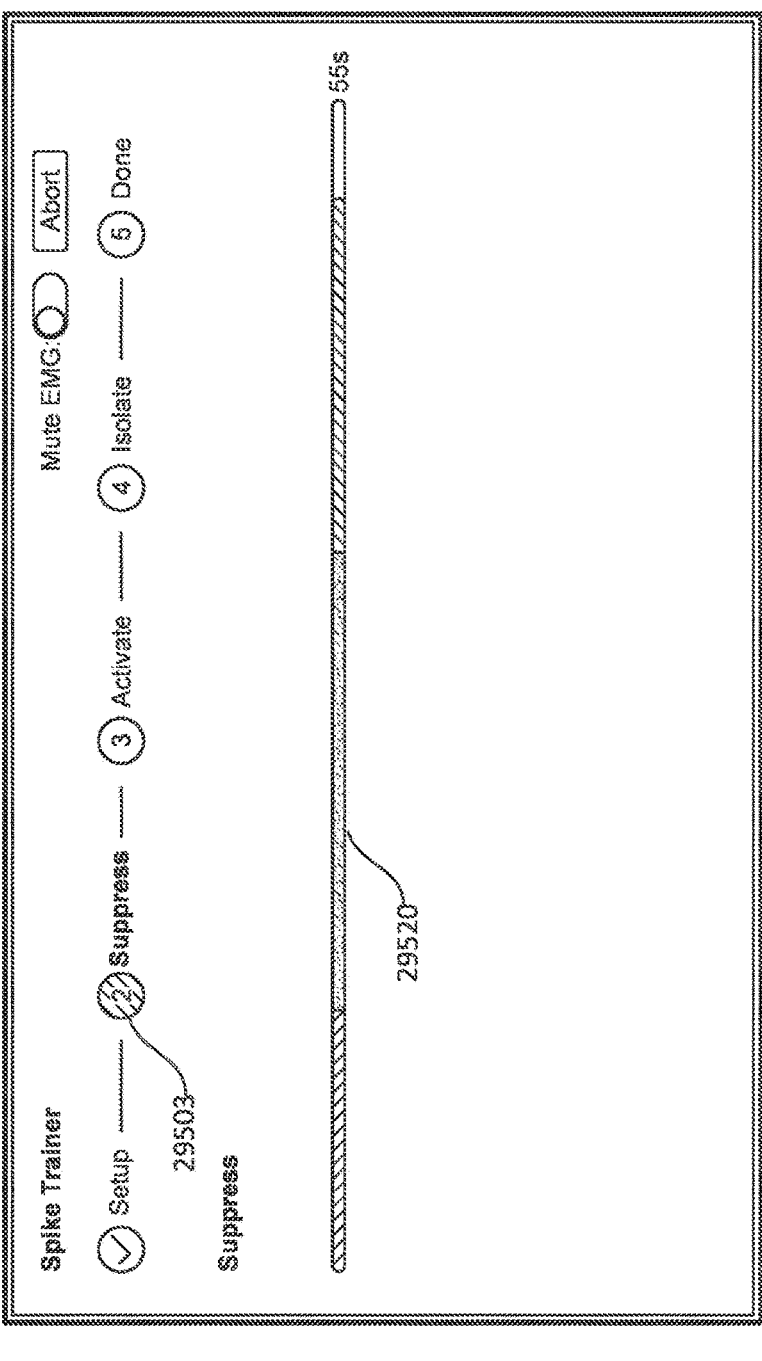
FIG. 29E illustrates the user interface in a second state for training a user to suppress neuromuscular signal activity, according to at least one embodiment of the present disclosure.

FIGS. 29D-29F illustrate, in various respective states, a user interface 29400 for training a user to isolate and activate a single motor unit, according to at least one embodiment of the present disclosure. The user interface 29400 may be used to train users for reliable, volitional MUAP control. In some examples, the user interface 29400 may be or include user interface 29108 of FIG. 29A. Motor units are the fundamental basis of motor control and therefore machine control based on volitional activation of individual motor units may provide a high bandwidth of machine control based on neuromuscular activity. In some examples, training a user to isolate and activate a single motor unit may include one or more steps designed to: (i) measure and account for user baseline neuromuscular signal activity during a resting or dormant state (e.g., a suppression step), (ii) detect active neuromuscular signals from a user while the user performs one or more fine motor movements (e.g., a micromovement), and/or (iii) train the user during prompted and unprompted block sessions to isolate and activate a single motor unit based on sensory feedback (e.g., including auditory feedback, visual feedback, haptic feedback, or a combination thereof). The baseline neuromuscular signals and the active neuromuscular signals may be compared to determine that the user is activating at least one motor unit. The sensory-based training feedback may be provided to the user to train the user to volitionally control the at least one motor unit.

In some examples, training a user to isolate and activate a single motor unit may include personalizing the inference model to the user (e.g., to a particular user). Personalizing the inference model may include adapting, with at least one computer processor, a previously trained generalized inference model by applying weights to the inference model that are specific to the user. In some examples, a linear pre-layer may be added to the generalized inference model. The linear pre-layer may alter the input signal to improve the predictions from the inference model. The generalized inference model may be trained more quickly and efficiently because only the pre-layer weights are personalized to the user. Moreover, less personal training data may be required to train the generalized inference model adequately due to the reduced number of parameters, compared to examples that do not implement a linear pre-layer. This may be an effective approach that improves the quality of the inference model while requiring a smaller training data set from the user. In some examples, the architecture of the generalized inference model, as described above, may be maintained. The generalized inference model may be a model that is applied to a broad population of users. Maintaining the generalized inference model and applying it to a broad population of users with personalized model weights may allow for a computationally efficient and accurate model across the population of users. The systems and methods described herein may learn new model weights to better fit the inference model to the user.

The linear pre-layer may be applied to alter an input signal to the generalized inference model to personalize the inference model for one or more poses and/or one or more forces in a variety of ways. For example, the input signal can be altered cooperatively $x \rightarrow \tilde{x}$ so that the new prediction $\tilde{y}$ can achieve a smaller loss value $L(\tilde{y}, y0) < L(y, y0)$, where $\tilde{y} = f(\tilde{x}|\theta g)$. According to this embodiment, an example process for personalizing an inference model for poses and forces may include initializing two variables A and b as A=0 and b=0. The variable $\tilde{x}$ may be initialized according to $\tilde{x} = x + Ax + b$. A partial derivative $\Delta x = \partial L (f(\tilde{x}), y0)/\partial x$ may be backpropagated in accordance with a machine learning technique. Regression (e.g., Ridge regression) may be used to fit $\tilde{A}, \tilde{b}$ such that $\tilde{A}x + \tilde{b} \approx -\alpha \cdot \Delta x + Ax + b$, where $\alpha$ is the learning rate and regression (e.g., Ridge regression) may be used to avoid overfitting. Variables may then be set according to $A \leftarrow \tilde{A}$ and $b \leftarrow \tilde{b}$. Next, it may be determined whether a loss function threshold is reached. If it is determined that the loss function threshold has not been reached, the process returns to and repeat from the step of initializing the variable $\tilde{x}$ according to $\tilde{x} = x + Ax + b$. If it is determined that the loss function threshold has been reached, the process may end. Using this technique of applying a linear pre-layer, the model may be trained more quickly (compared to processes that do not apply a linear pre-layer) because only the pre-layer weights are adapted. Moreover, less personal training data may be required to train the model adequately due to the reduced number of parameters to fit. Another potential advantage of using this technique may include bootstrapping by retraining $\tilde{x}$ based on adapted variables $\tilde{A}$ and $\tilde{b}$.

In some examples, the regression (e.g., Ridge regression) discussed above may employ any suitable regression technique including, but not limited to, L2 norm with a linear fit, which may weight A to be as small as possible.

As described below with reference to training the user to detect a single motor unit, personalizing the inference model to the user may include providing sensory-based training feedback (e.g., visual, auditory, haptic, or multi-sensory feedback) to the user and updating the corresponding weight based on the actions taken by the user in response to the sensory-based training feedback.

In some examples, systems and methods for training users for individual MUAP control may include several steps. As illustrated in FIG. 29D, the user interface 29400 may guide the user through the steps. In a first setup step 29402, a user may be instructed to don (e.g., wear) a wearable device for measuring neuromuscular signals The wearable device may include a radial array of surface electromyography electrodes worn on each of a user's two forearms or wrists to measure neuromuscular signals corresponding to the muscles of the forearm that control most movements and forces of the fingers, hand, and wrist. The wearable device may be communicably coupled to a computer training system. The wearable device may be or include wristband 800 of FIG. 8A. The wearable device may include sensors 29102 of FIG. 29A. The wearable device may be configured to record signals using the one or more sensors when worn on the body of a user. The recorded signals may include neuromuscular signals such as electromyography (EMG) signals, mechanomyography (MMG) signals, and/or sonomyography (SMG) signals. In some examples, the recorded signals may further include position, velocity, and/or acceleration information acquired from one or more inertial measurement unit (IMU) sensors, or other position-tracking sensors. In some examples, the wearable device may include a processor (e.g., processor 29101 of FIG. 29A) configured to perform analog processing (e.g., noise reduction, filtering, etc.) and analog to digital conversion of the recorded signals. The user may enter parameters for the training session into the user interface 29400 including suppression time 29410, activation time 29412, and inter-prompt wait time 29414.

In a second step, the training system or method may provide instructions, equipment, and/or materials to the user so the user may suppress (e.g., relax) portion(s) of their neuromuscular system being recorded by the array of neuromuscular sensors. Non-limiting examples of such instructions, equipment, and/or materials may include one or more of the following: providing a calming booklet or pamphlet, musical or rhythmic sounds, white noise, a reclining or lounge chair, visual imagery (photos, videos, etc.), step-by-step instructions for relaxation on a display screen or mobile application, meditation or yoga poses, menthol or eucalyptus scents, instructions to relax a muscle or muscle group, etc. Relaxing the appropriate muscle or muscles reduces the background activity of neuromuscular activity (e.g., the EMG signals), so that individual motor units may be more easily isolated and resolved. The user may also be provided instructions such as a particular hand pose that reduces background levels of neuromuscular activity or to take deep breaths to reduce overall physiological arousal and muscle activation.

In a third step, the training system or method may record a calibration data set of neuromuscular signals from the user (e.g., a baseline of EMG measurements) while the user maintains a relaxed posture and calm state (e.g., suppression step 29503 of FIG. 29E). The calibration data set may be used in subsequent steps of the process to estimate a noise floor (e.g., corresponding both to noise due to impedance at the skin-electrode contact and noise corresponding to background neuromuscular activity in the user). For example, the system may record one minute of calibration data from the user. As illustrated in FIG. 29E, during recording of the calibration data in the suppression step, the user interface 29400 may display progress bar 29520 that indicates the amount of time elapsed during the suppression step.

In some examples, the user interface 29400 may provide feedback about the level of muscle tone (e.g., the level of muscle activation) in real-time or substantially real-time via visual, auditory, haptic, or multi-sensory feedback. For example, the root mean squared noise (or other similar metric) may be calculated and converted to an audio signal audible to the user with instructions for the user to minimize the volume of the audible signal. In this step, the user's baseline EMG levels may be detected and accounted for in subsequent steps. To achieve an accurate baseline EMG level, an appropriate threshold of detection may be determined based on the individual's neuromuscular activity. In this step, any non-volitional user activity may be accounted for so that it does not interfere with volitional activity readings (e.g., so-called "background noise" in EMG readings). In this way, the user's signal-to-noise (SNR) ratio may be determined and accounted for. In some examples, the EMG data may be collected for approximately 1 minute in one or more block sessions. After the block sessions, the user's EMG threshold value may be determined. For example, the user's threshold value may be determined based on the bottom quartile of the EMG readings associated with the quietest signal.

In a fourth step, the training system or method may prompt the user with appropriate instructions to select and execute a task (e.g., a movement with minimal muscle activation such as a micro-movement, a gesture, and/or a pose) intended to activate a single motor unit or a small set of motor units. In some examples, the user may be prompted to execute a pose during the training session. The pose may indicate a static configuration of one or more body parts. The static configuration may describe the position of one or more body parts. For example, a pose may include a fist, an open hand, statically pressing the index finger against the thumb, pressing the palm of a hand down on a solid surface, or grasping a ball. The pose may indicate the static configuration by providing positional information (e.g., segment coordinates, joint angles, or similar information) for the pose, or by providing an identifier corresponding to a pose (e.g., a parameter, function argument, or variable value). A gesture may indicate a dynamic configuration of one or more body parts. The dynamic configuration may describe the position of the one or more body parts, the movement of the one or more body parts, and forces associated with the dynamic configuration. For example, the gesture may include waving a finger back and forth, grasping a ball, or throwing a ball.

In some examples, the user may be provided with sensory feedback (e.g., visual, auditory, and/or haptic) about the amount of neuromuscular activity caused by the task (e.g., the micro-movement and/or pose) so that the user may volitionally cause motor activation that falls within an appropriate range. In this step, the user may engage in one or more tasks including micromovements such as snapping a finger, slightly moving the wrist, posing, gesturing, or performing any other activity that results in slight contraction(s) of a muscle.

Over a defined period of time or multiple periods of time, the user may attempt to activate one or a small number of resolvable motor units by performing the task(s). Active neuromuscular signals may be measured from the user while the user performs the tasks (e.g., the physical movements). For example, as illustrated in FIG. 29F, the user may be prompted to perform the micromovements based on visual signals displayed in icon 29624. The user may be provided with visual feedback of the neuromuscular signal data in substantially real-time during the training session, or other means of feedback (e.g., audio) may be provided. The user may be presented with specific auditory feedback that correlates to the intensity of their EMG readings. If the user is presented with feedback, the user may utilize the feedback in substantially real-time to attempt to repeatedly generate appropriate muscle activations to permit reliable detection of MUAPs. For example, effective movements (e.g., micromovements and/or imperceptible movements) may cause feedback to include a low amplitude beep. The goal of the training step is to permit the user to become adept at isolating a single motor unit and training themselves to activate the single motor unit on command. During training, the user may close their eyes, take deep breaths, attempt to concentrate on something specific or not concentrate at all. The user may perform the one or more micromovements for a period of time (e.g., approximately 30 seconds) in one or more block sessions. The prompted learning time period may be displayed to the user on display bar 29622. The EMG data, including raw signals, may be measured and recorded during this training step.

In some examples, a user may be trained to selectively activate a first motor unit of a plurality of motor units in a muscle. The plurality of motor units may have a stereotyped recruitment order (e.g., an activation of additional motor units to increase contractile strength) in which a second motor unit is recruited before the first motor unit. The system may determine, based on the neuromuscular signals, a first spike rate for the first motor unit and a second spike rate for the second motor unit, and may provide feedback to the user based on the first spike rate, the second spike rate, and at least one weighting factor associated with the first spike rate and/or the second spike rate. The system may update the at least one weighting factor based on whether the task (e.g., selective activation of the first motor unit while suppressing activation of the second motor unit) was completed successfully. The updated weighting factor may dynamically change the feedback provided to the user to enable the user to selectively activate the first motor unit while suppressing activation of the second motor unit. The individually controllable weighting factors may be dynamically updated as the user learns how to selectively activate one of the two motor units.

By dynamically updating the weighting factor(s) in a particular way as the user learns, the boundary between activation of one motor unit relative to activation of another motor unit in the same muscle may be improved. Such a dynamic weighting scheme may enable the user to learn how to activate one motor unit and suppress activity of another motor unit, even when the motor unit being suppressed is typically recruited before the motor unit being activated in a physiological recruitment order of motor units for the muscle.

In some examples, visual feedback may be provided to a user as the user learns how to selectively activate one of two motor units. In this embodiment, each of the two selected motor units may be mapped to an opposite direction of a one-dimensional pointer (e.g., a cursor) on display bar 29622. For example, a spike rate of the first motor unit may be mapped to a leftward cursor movement and a spike rate of the second motor unit may be mapped to a rightward cursor movement. During each session of training, the goal of the user may include moving the cursor towards a left target or right target.

In some embodiments, a weighting factor may be used to train the user that is dynamically updated as the user learns how to control the cursor. By adjusting the weighting factor, the amount the cursor moves may be changed in response to the difference in spike rates, so the user may learn to move the cursor in a particular direction. The amount of feedback (e.g., intensity of the auditory feedback, speed of cursor movement, etc.) and the type of feedback (e.g., switching between feedback modes, adding another feedback mode, etc.) provided to the user may be updated based upon how the user reacts to the feedback during a training session. For example, if during training the user fails to move the cursor towards the desired direction, the weighting factor may be adjusted such that the task becomes easier. If the user succeeds in moving the cursor towards the desired direction, the weighting factor may be adjusted so the task becomes harder. For example, initially the weighting factor may be set such that even a small difference between the spiking rates of the two motor units may cause a large movement in the cursor, thereby encouraging the user that they can successfully perform the task. As the user learns to suppress activation of one of the motor units, the weighting factor may be dynamically changed to further train the user to suppress the motor unit activation during trials in which it is not desired. The weighting factor may be dynamically changed slowly or more abruptly depending on the desired level of difficulty or estimated time for training.

In a fifth step, the training system or method may apply a MUAP (spike) decomposition algorithm (e.g., an algorithm that applies beam-forming and annealing steps) and take the calibration data set acquired in the third step as input in order to identify one or more individual MUAPs activated by the user. In this step, the system or method may be used to train (e.g., modify) a general inference model with personalized weights so that the system may better detect individual MUAPs from the user. In this step, the neuromuscular signal data may be provided as input to a computerized system (e.g., processor 29101 of FIG. 29A) for decoding individual motor units from neuromuscular signal data (e.g., using deep spike decoder 29110 of FIG. 29A). For example, the computerized system may apply one or more techniques for analyzing neuromuscular signal data for spike decomposition, including but not limited to: clustering, beamforming, simulated annealing, and calculation of the variance and/or amplitude of the neuromuscular signal data. The system may then deploy deep spike decoder 29110 to identify the signal associated with the MUAP in order to use that MUAP activation (e.g., the intended movement) to provide a control signal to a device.

In a sixth step, the user may be instructed to activate the identified and decoded MUAP and is provided with feedback (e.g., visual, auditory, and/or haptic feedback) when the intended MUAP is activated and decoded by the inference model trained in the fifth step. The inference model may compare the measured baseline neuromuscular signals to the active neuromuscular signals to determine that the user is activating the MUAP. For example, the user may be instructed to activate the motor unit at their discretion (e.g., unprompted with regard to the timing of a MUAP). Additionally or alternatively, the user may be prompted to activate the motor unit at a specified time. For example, the user may be provided a visual and/or auditory prompt (e.g., a countdown of "3 . . . 2 . . . 1") to cause a MUAP to occur at a specified time. Control signals based on activating a MUAP that is measured by a plurality of neuromuscular sensors may be particularly useful if a user may volitionally activate the MUAP at a specified time. In this case, prompted MUAP activation may be of particular value in training a user. As illustrated in FIG. 29F, in some examples, the user interface 29400 may prompt individual motor unit activation by visually activating icon 29624. The sixth step may be repeated any number of times to improve the user's ability to activate the motor unit(s). In some embodiments, the user may indicate that they prefer to train a new motor unit (or motor units) and return to steps four through six.

FIG. 29G is a flow diagram illustrating a method 29700 of training an inference model to determine at least one spatiotemporal waveform and a corresponding weight to be applied to the at least one spatiotemporal waveform. At operation 29710, a plurality of neuromuscular sensor may be configured to record a plurality of neuromuscular signals from a user, wherein the plurality of neuromuscular sensors may be arranged on one or more wearable devices. Operation 29710 may be performed in a variety of ways, such as by arranging EMG sensors circumferentially around an elastic band. The number and arrangement of neuromuscular sensors may depend on the particular application for which the wearable device is used. Operation 29710 may be performed such as described above with reference to FIG. 29B.

At operation 29720, the method 29700 may include training, using the plurality of neuromuscular signals, an inference model to determine at least one spatiotemporal waveform and a corresponding weight to be applied to the at least one spatiotemporal waveform, wherein the at least one spatiotemporal waveform is related to firing of an action potential in at least one motor unit of the user and training the inference model comprises determining one or more parameters for a biophysical model simulating the at least one motor unit of the user. Operation 29720 may be performed in a variety of ways, such as in a way described above with reference to FIGS. 29A and 29C-29F.

Embodiments of the present disclosure are directed to analyzing neuromuscular signals of a user to train an inference model to determine at least one spatiotemporal waveform and a corresponding weight. The weight may be applied to the spatiotemporal waveform by training the inference model to determine parameters for a biophysical model that simulates a motor unit. The inference model associated with the neuromuscular signals may detect spike events in a motor neuron of a motor unit that results in the generation of MUAPs in the muscle fibers of the motor unit. Control signals that may be generated based on the identified spike events may be used in some examples to control the operation of a device (e.g., an artificial reality device). In some examples, training sessions may be used to train a user to isolate and volitionally control a single motor unit.

The following describes exemplary methods and apparatus for gesture detection and classification according to at least one embodiment of the present disclosure.

Examples of the present disclosure are directed to detection of signals from a user and control of an artificial reality device based on the detected signals. As is explained in greater detail below, embodiments of the present disclosure may include systems having a head-mounted device configured to present an artificial reality view to a user and a control device including a plurality of electromyography (EMG) sensors. One or more processors, that may be located in any system component, may be programmed to detect EMG signals corresponding to user gestures associated with the EMG data received from the sensors and to classify the EMG signals to identify gesture types. The control signal may trigger the head-mounted device to modify the artificial reality view, for example, based on the gesture type(s).

Accurate control of objects (real or virtual) within an artificial reality environment may be useful to maintain an immersive experience. Gestures may be a useful way of controlling objects and need not require interaction with any real physical object. For example, actions such as pressing the key of a keyboard, turning a dial, pressing a button, selecting an item from a menu (among many other actions) may be simulated by a user gesture. A tapping gesture may simulate a key press. Furthermore, identification of which body part (e.g., which finger) has been used to perform a gesture allows further control of an artificial reality environment.

Features from any of the embodiments described herein may be used in combination with one another in accordance with the general principles described herein. These and other embodiments, features, and advantages will be more fully understood upon reading the following detailed description in conjunction with the accompanying drawings and claims.

Figure 30A:
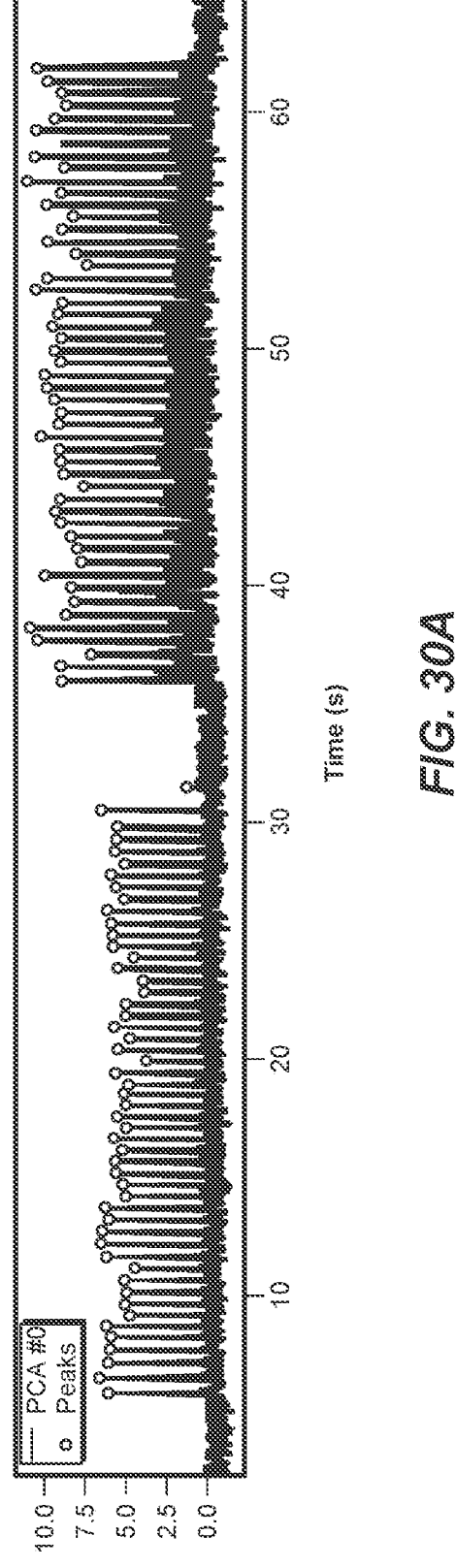
FIG. 30A shows an example of a first component extracted from the application of the PCA.

The following provides, with reference to FIGS. 30A-32T, detailed descriptions of gesture-identification models, including unsupervised and self-supervised models. FIGS. 30A-30W illustrate event detection and classification, where the term "events" may include gestures such as finger taps. FIGS. 30X-32O further illustrate time-dependence, clustering, training, and accuracy of various models. FIGS. 32P-32Q illustrate an example control device. FIG. 9A-9B illustrate a schematic of a control device. FIG. 32R illustrates an example system including a head-mounted device. FIGS. 32S-32T illustrate example computerized methods, and FIGS. 31 and 32 illustrate example AR/VR applications.

This disclosure is directed to event detector models that may be used to detect user gestures. Such detector models may involve recording a series of EMG signals (datasets) while one or more users perform different gestures. In some examples, example gestures may include finger taps (e.g., simulated keypresses), but other types of gestures may analogously be used to implement example event detector models.

Gestures may include discrete events that span a finite period of time and may be characterized, in some embodiments, by one or more electromyography signals (including electromyography wavelets) representing muscle activations. Configuring systems to detect and classify such gestures using machine learning techniques may involve a significant amount of labeled training samples. Hence, systems that may rapidly learn gestures from few samples and capture and interpret meaningful features from human gestures in an unsupervised or self-supervised way are highly desirable. Examples described herein provide such unsupervised and/or self-supervised models.

FIG. 30A shows a first component that may be extracted from the application of a principal component analysis (PCA, vertical lines), and detected peaks (dots). Multiple events are shown, divided into two groups separated by a rest period. The illustrated events may be detected using a peak detection process, which may also detect peaks registered during the resting period, corresponding to local maxima during rest.

The dataset may include EMG signals corresponding to index and middle finger taps. The dataset may be divided into a training set including 50 consecutive finger taps for each finger, recorded at approximately 2 Hz, and a test set including 20 consecutive finger taps for each finger, recorded at approximately 2 Hz. The above datasets may represent less than 2 minutes of recorded data. Any other suitable data sets may also be used as a training set.

A covariance mapped to the tangent space may be selected as a feature. A short time window (30 ms) and a stride of 5 samples, corresponding to a data rate of 400 Hz, may be used for the feature extraction. The dimensionality of the feature space may be reduced to find events in the dataset through the application of a Principal Component Analysis (PCA) on 5 components. Thereafter, the data may be centered (e.g., by removing the median) and finally, the local maximum (peak) may be identified on the first component.

Figure 30B:
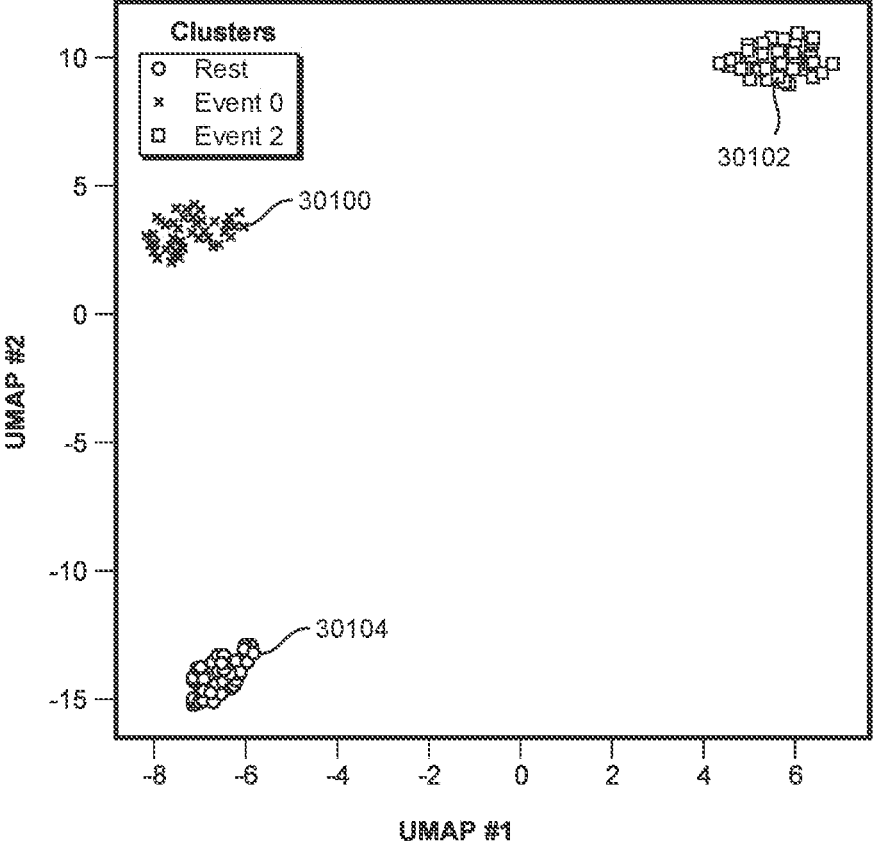
FIG. 30B shows example clusters produced from the detected events.

FIG. 30B shows clusters that may be produced from the detected events (including detected events registered during the resting period). Three clusters are shown, one for each type of finger tap (data groups 30100 and 30102, corresponding to index and middle finger taps). An extra cluster may arise for those events registered during the resting period (that may not be considered to be useful events). This extra cluster 30104 may be located in the lower left corner, indicating a cluster with low energy samples. This cluster may be removed by dropping all corresponding events below, for example, a predetermined energy level threshold.

Data around each event may be sliced in epochs in preparation for the cluster analysis. In one example, a window of 150 ms may be centered around each event to slice the data, and any other suitable window size may be used in a similar manner. Thereafter, each of the epochs may be vectorized and subjected to a K-Means clustering process to extract the three clusters. For visualization purposes, a dimensionality reduction process based on Uniform Manifold Approximation and Projection (UMAP) may be applied to plot the clusters shown in FIG. 30B, including approximately fifty events for each class of event.

Figure 30C:
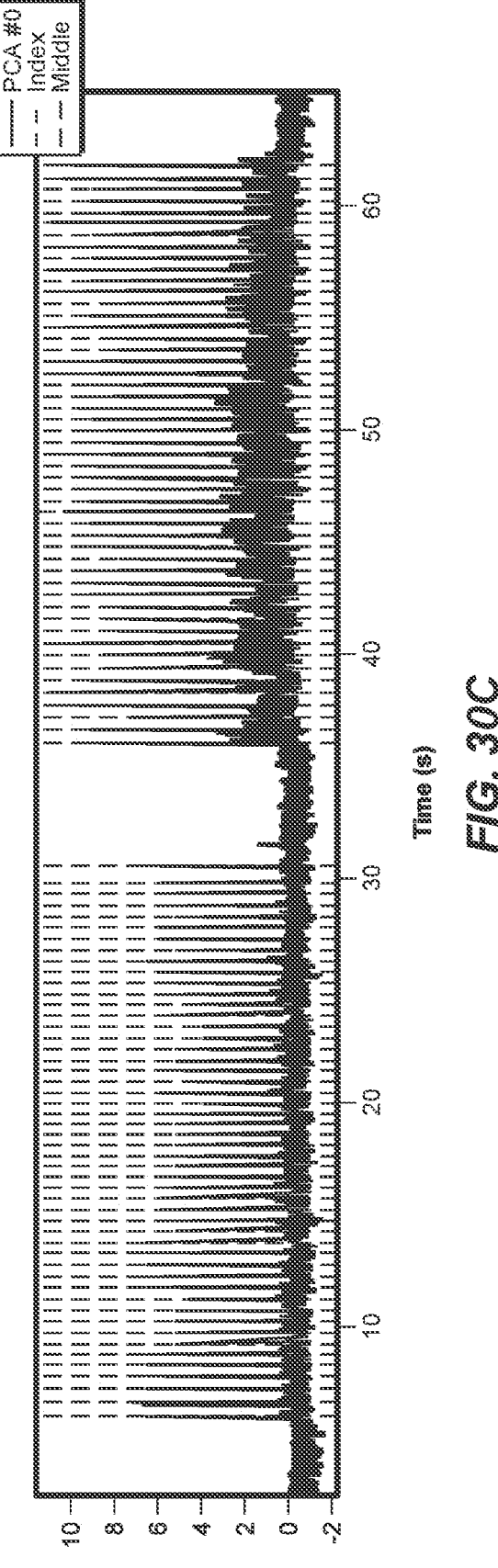
FIG. 30C shows an example plot of the first component from a PCA performed over the detected discrete events.

FIG. 30C shows a plot of the first component from a Principal Component Analysis (PCA), which may be performed over the detected discrete events. The data may be plotted with respect to the first component resulting from a Principal Component Analysis. In this example, index finger events are shown first (on the left), followed by the resting period, and then the middle finger events on the right.

In some examples, timing adjustments may be performed on the registered events. The timing of each event may be associated with the local maxima on the first component identified using the execution of a PCA analysis. The ground truth may then be generated from the acquired samples to train an event detection model.

Figure 30D:
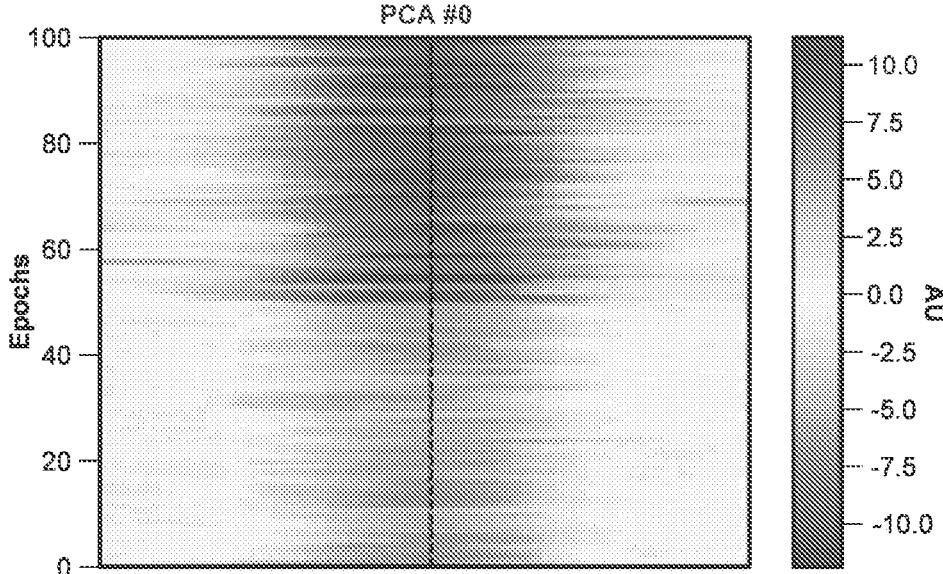
FIGS. 30D-30E illustrate epochs corresponding to discrete events showing synchronization quality aspects.
Figure 30E:
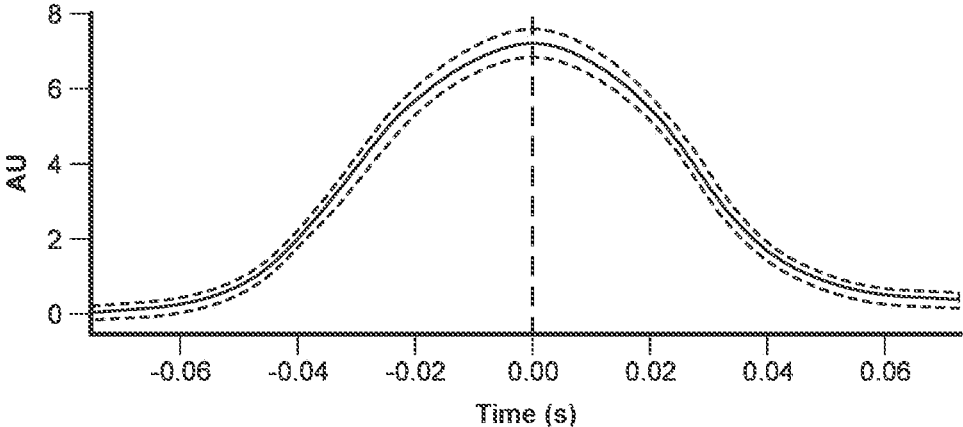

FIGS. 30D and 30E illustrate epochs corresponding to discrete events showing synchronization quality aspects. Some jitter and misalignment of the different epochs may be present.

In some examples, jitter and misalignments may be reduced or eliminated by finding an optimal offset for each epoch by analyzing the autocorrelation between the epoch and the average across all the event. Accordingly, different offsets (−10 to 10 samples) may be tested, and the timing that maximizes the correlation may then be selected. The testing process may be executed iteratively until all epochs are properly aligned.

Figure 30F:
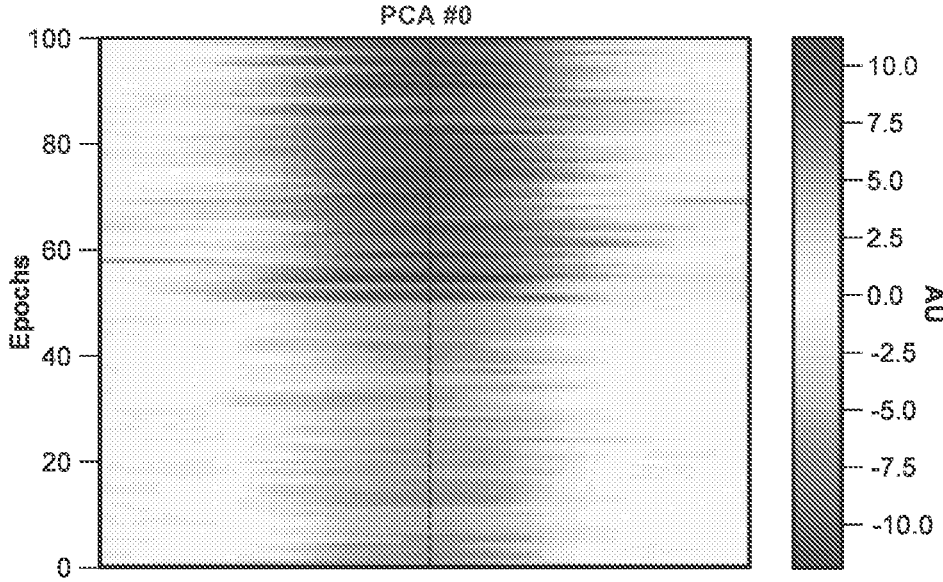
FIGS. 30F-30G show aligned epochs corresponding to detected discrete events.
Figure 30G:
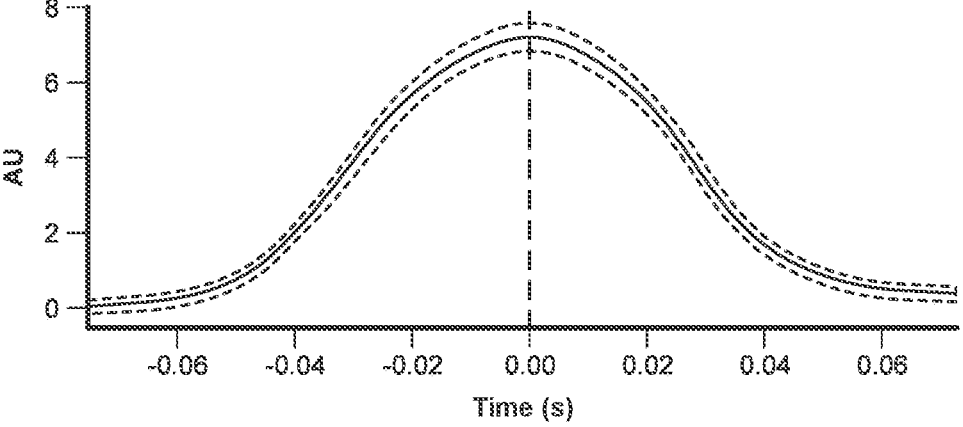

FIGS. 30F and 30G show aligned epochs corresponding to detected discrete events.

Figure 30H:
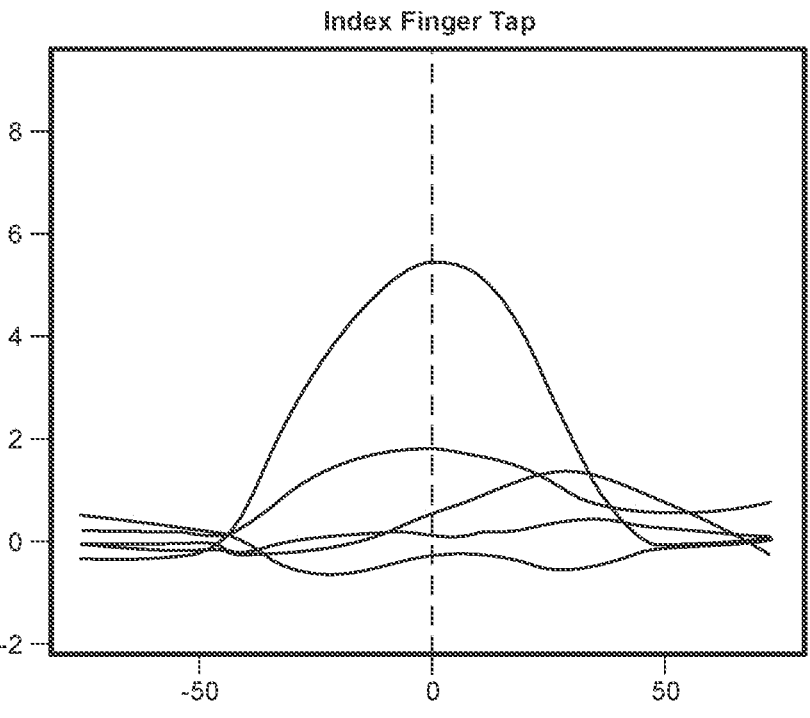
FIGS. 30H-30I show templates corresponding to a PCA analysis performed over the average of two different gestures.
Figure 30I:
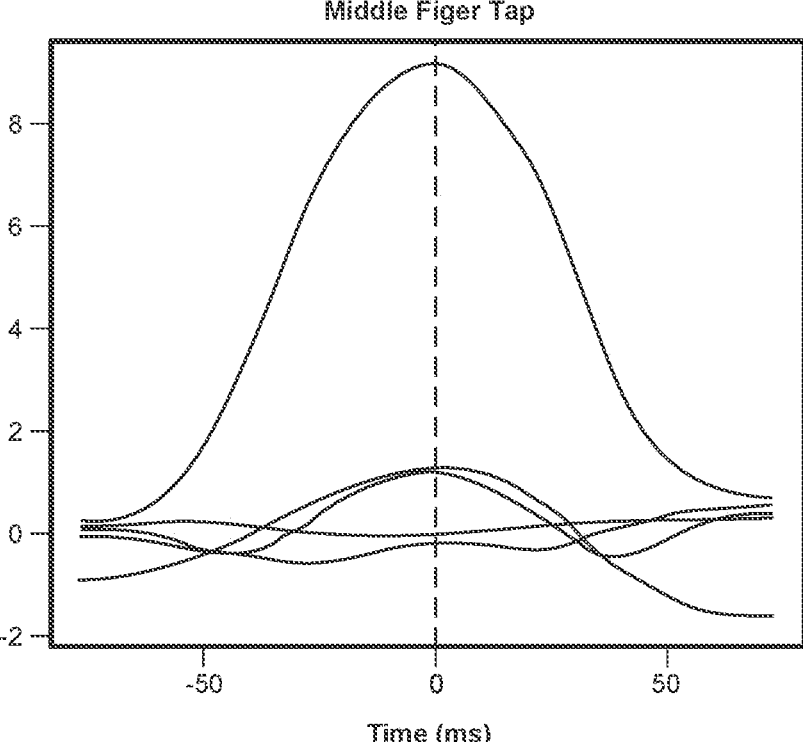

FIGS. 30H and 30I show plots of two templates corresponding to a PCA analysis which may be performed over the average of two different gestures. FIG. 30H corresponds to index finger tap data, and FIG. 30I corresponds to middle finger tap data. The templates may be based on the average energy of each event's epoch obtained after synchronization. The first PCA component (from five components of a PCA) may significantly differ in amplitude between the two finger taps (index vs. middle), and the other components may have different signal forms.

A binary time series may be labeled with a value of one when an event is detected (the event occurred) and a zero when the event is not detected (e.g., the event may not have occurred). A model to predict such a time series may be trained based on the labeled samples. The output of the model then may be compared against a predetermined energy threshold and debounced to configure the event detector.

Exemplary parameters may be configured for the model's ground truth. After re-synchronization, the events may be centered around the peak of the first PCA component. The model may rely on the full event time course, and the model may predict the event once a user finished its execution. Accordingly, the labels may be shifted or offset based on the event timing. This parameter may be referred to as "offset."

In some examples, the model may not perfectly predict the right single time sample corresponding to an event. Accordingly, the model may be configured to predict a value, such as 1, on several consecutive time samples surrounding the center of the event. This parameter may be referred to as a "pulse width."

In some examples, the offset may be set at 75 ms after the event peak (approximately 30 samples after the event's peak) and the pulse width may be set as 25 ms. These examples, and other examples, are non-limiting, and other parameter values may be used depending of particularities of the signals used during the training of the event detector model.

Figures 30J, 30K:
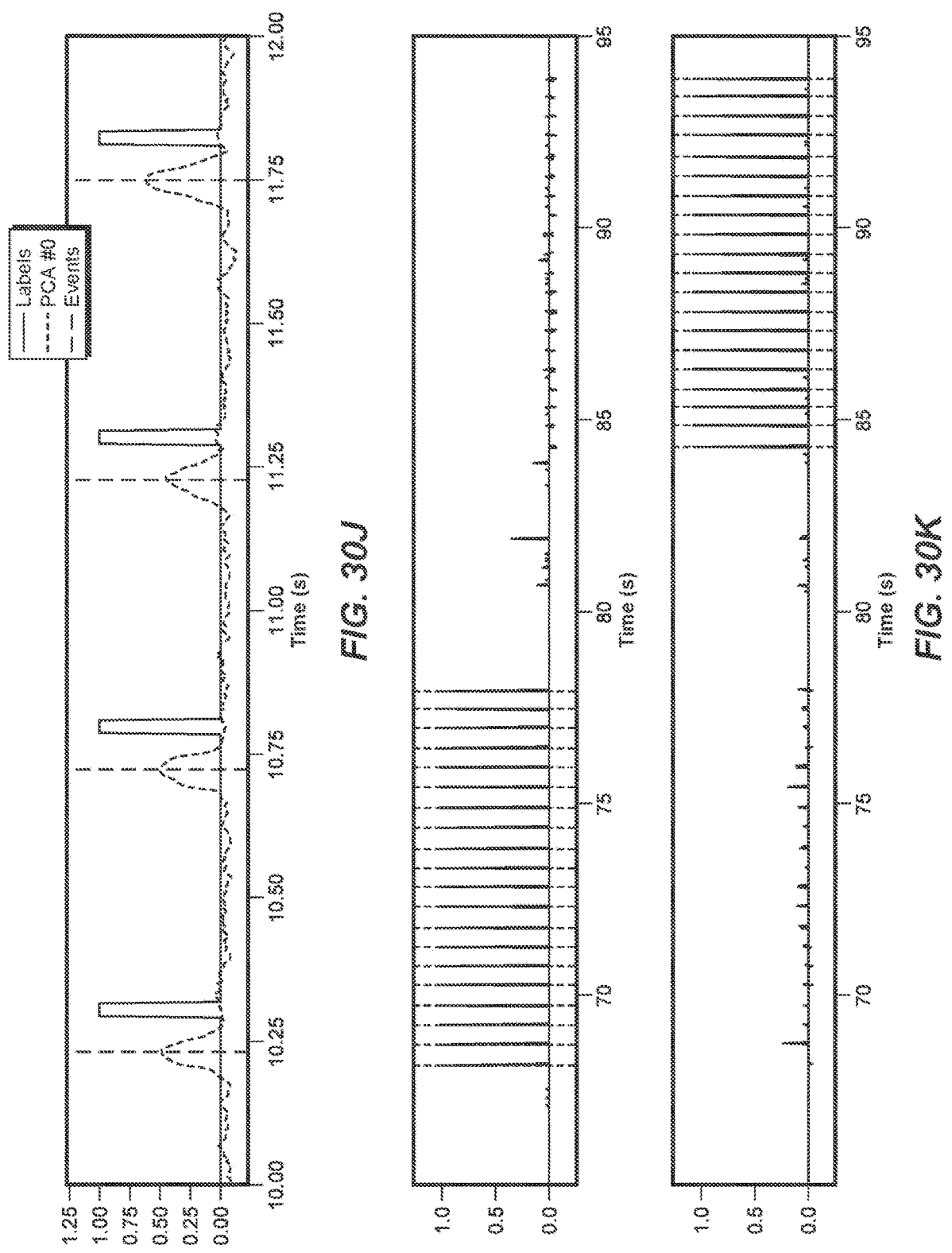
FIG. 30J shows example detected events on the first PCA component and respective labels generated from two seconds of data.
FIG. 30K shows an example of detection of discrete events using a testing set.

FIG. 30J illustrates events that may be detected using the first PCA component, with respective labels, that may be generated for 2 seconds of data. The event detector model may be implemented as a multilayer perceptron (MLP) model or other suitable machine learning model. Features may be collected from a 150 ms (approximately 60 samples) sliding window over the PCA features (e.g., for each time sample a vector with a vectorization of the previous 60 time samples of the five PCA components (i.e., 300 dimensions) may be generated).

The model may be trained to predict the labels used. The model may be applied on a test set, and the inferenced outputs may be compared to a predetermined threshold and debounced to elicit the identification of discrete events.

FIG. 30K illustrates detection of discrete events on a test set, including two outputs from the model (solid lines), as well as discrete events (dashed lines) that may be produced from the test set.

Figure 30L:
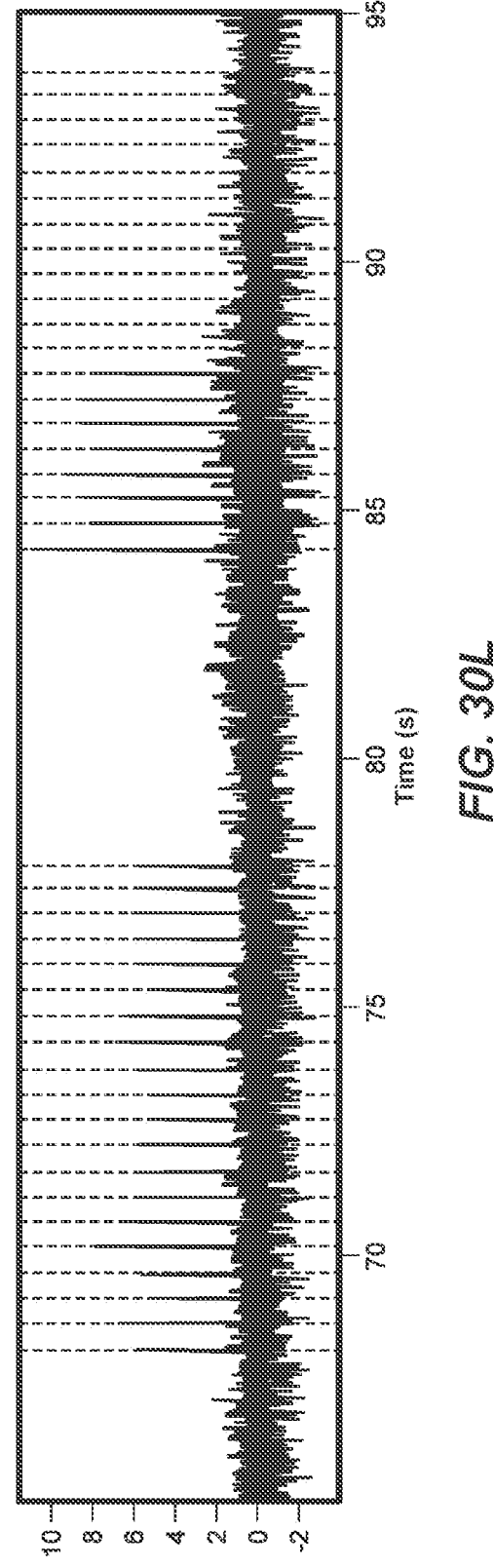
FIG. 30L shows an example of discrete events detected in a testing dataset.

FIG. 30L illustrates that discrete events may be detected in a test dataset, including, for example, five components produced using a PCA analysis conducted over the test set, and events that may be detected in the same set. All possible events may be detected by the model, and there may be clear disambiguation between the two types of discrete events.

In some examples, events may be classified from snapshots taken from the EMG signals. Snapshots taken around the time events may be detected or registered by the event detector. The event classifier model may be trained to distinguish between different types or classes of events. Such a classification is possible in part because each event is associated with a class or type of event corresponding to a characteristic or stereotypical signal associated with specific muscle activations synchronized with the occurrence of the event. Eighteen datasets may be used, and each dataset may be gathered from a different user. The datasets include recordings of EMG signals capture from key down, key up, and tap events. The total number of events used per user may be approximately 160 (80 for each finger index and middle).

The covariance may be estimated using a 40 ms time window and a stride of 2.5 ms, resulting from a feature sampling frequency of 400 Hz. The covariances may be then projected in the tangent space, and the dimension may be reduced by selecting the diagonal and two adjacent channels (represented in the matrix by the values located above and below the diagonal). A feature space of a dimension size of 48 is produced by the application of the above operations.

A window of signal ranging from −100 ms to +125 ms around each key press event may be extracted (e.g., sliced and buffered). Such windows may include approximately 90 EMG sample values. At the end of the aforementioned operations, a dataset of size 160×90×48 (N_events×N_time-_samples×N_features) may be obtained for each user.

Figure 30M:
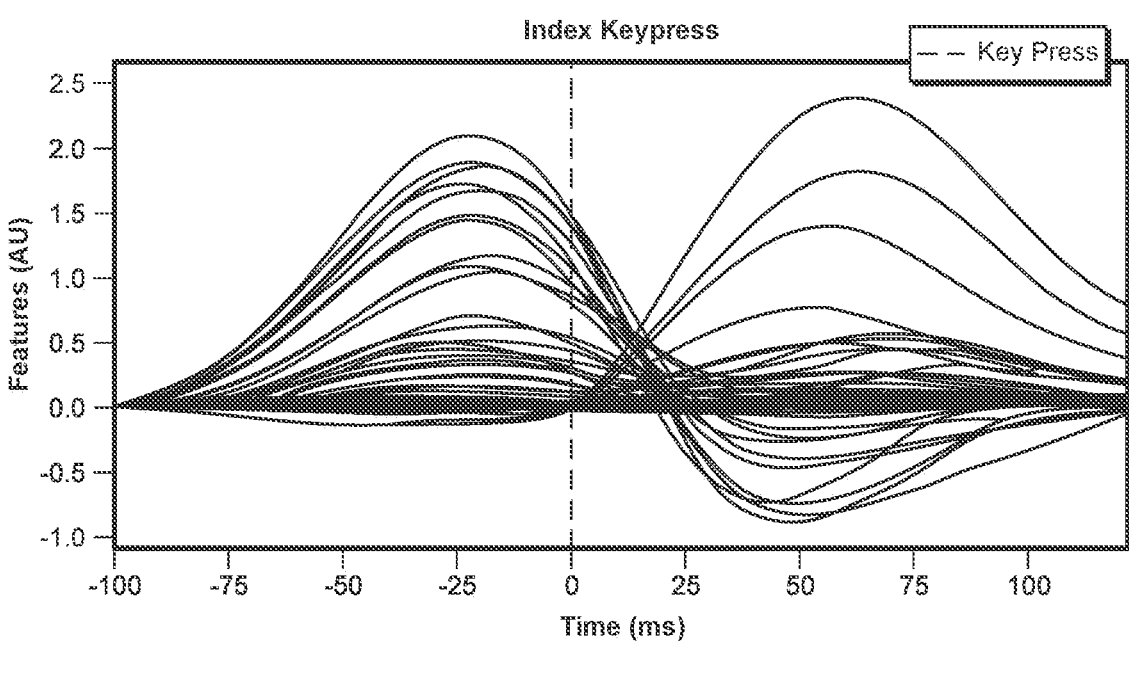
FIGS. 30M-30N show examples of an index finger tap event model and a middle finger tap event model.
Figure 30N:
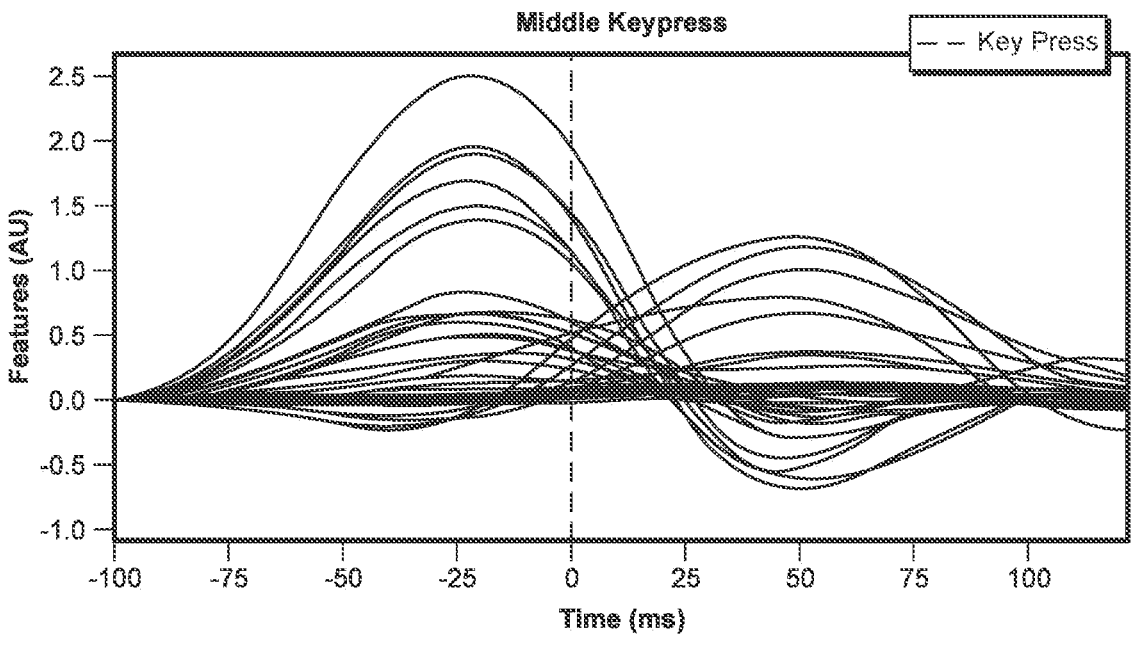

FIGS. 30M and 30N show examples of an index finger tap event model and a middle finger tap event model, respectively. Models of each event may be produced by averaging the EMG values of each event class (e.g., index tap and middle tap) for all occurrences of such events. Examples of the tap events are shown in FIGS. 30M and 30N.

In the event models shown in FIGS. 30M and 30N, two signals may be identified, one corresponding to the key press and one for the key release. The same features may appear to be active in both the index finger key press class and the middle finger key press class, but their respective amplitudes vary appreciably and provide a good basis for discrimination.

Figure 30O:
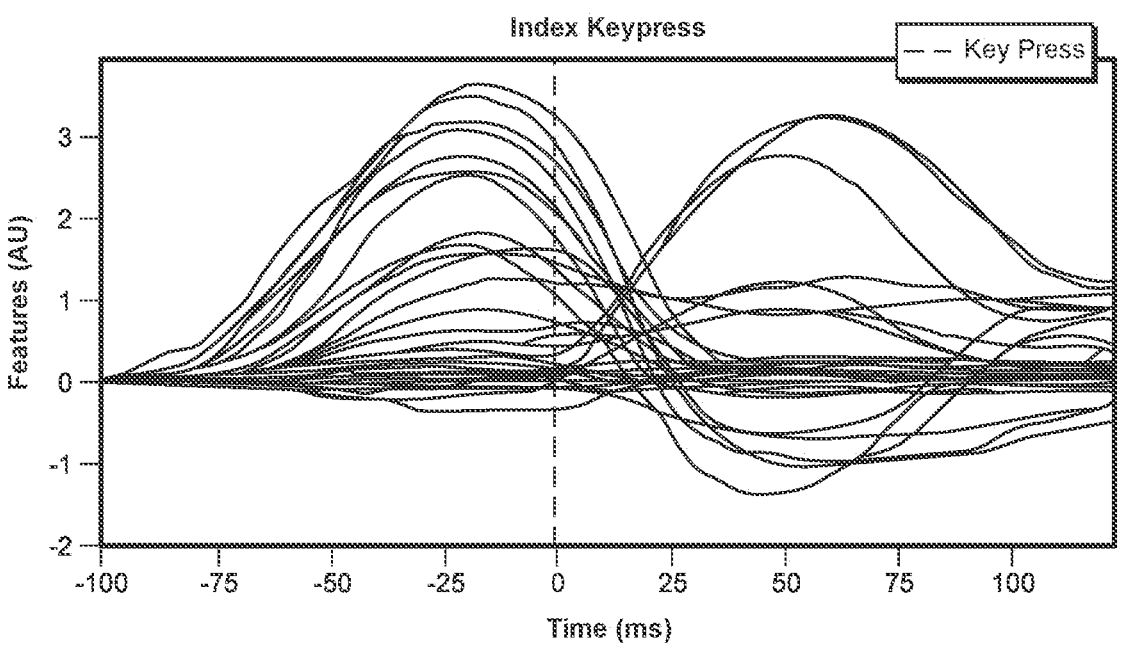
FIGS. 30O-30T show examples of user-specific event models for two classes of events.
Figure 30P:
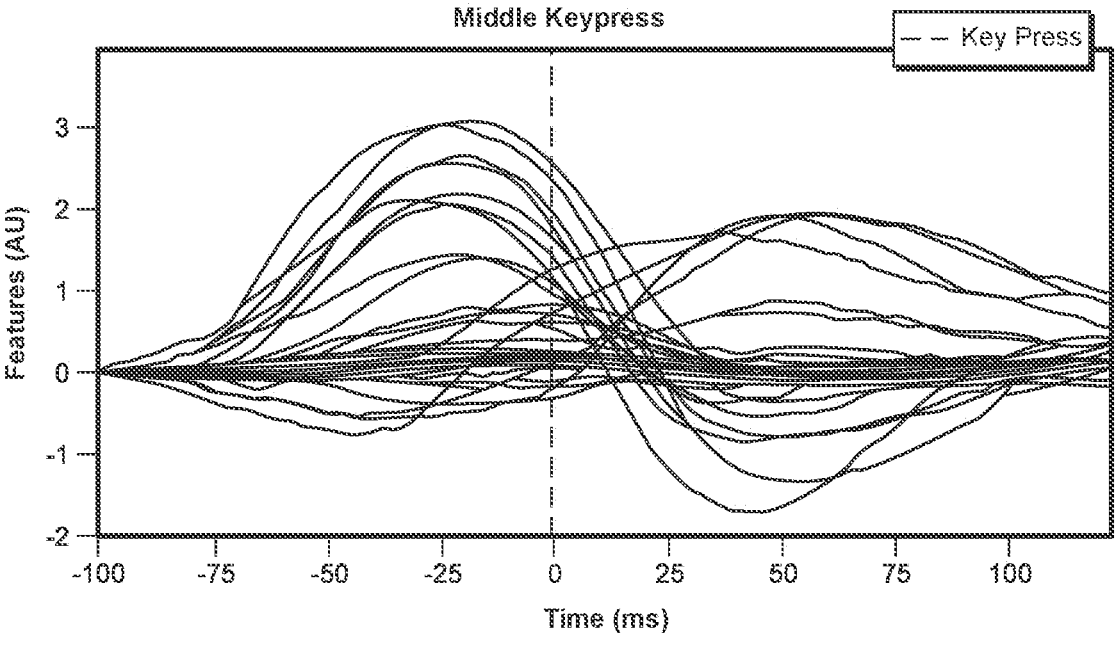
Figure 30Q:
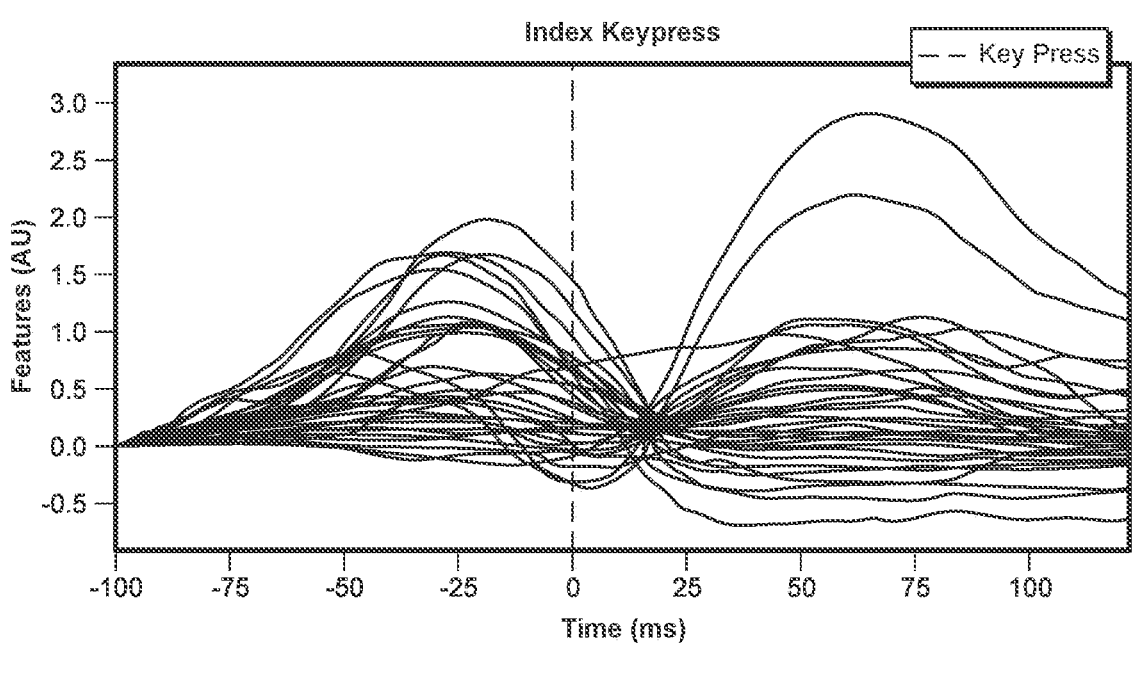
Figure 30R:
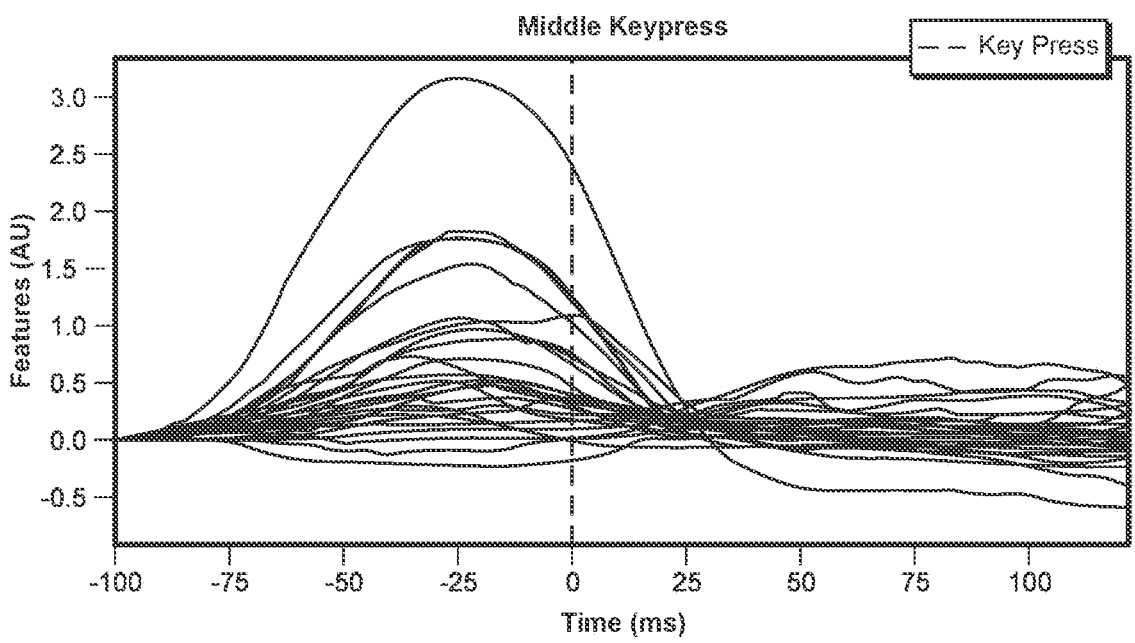
Figure 30S:
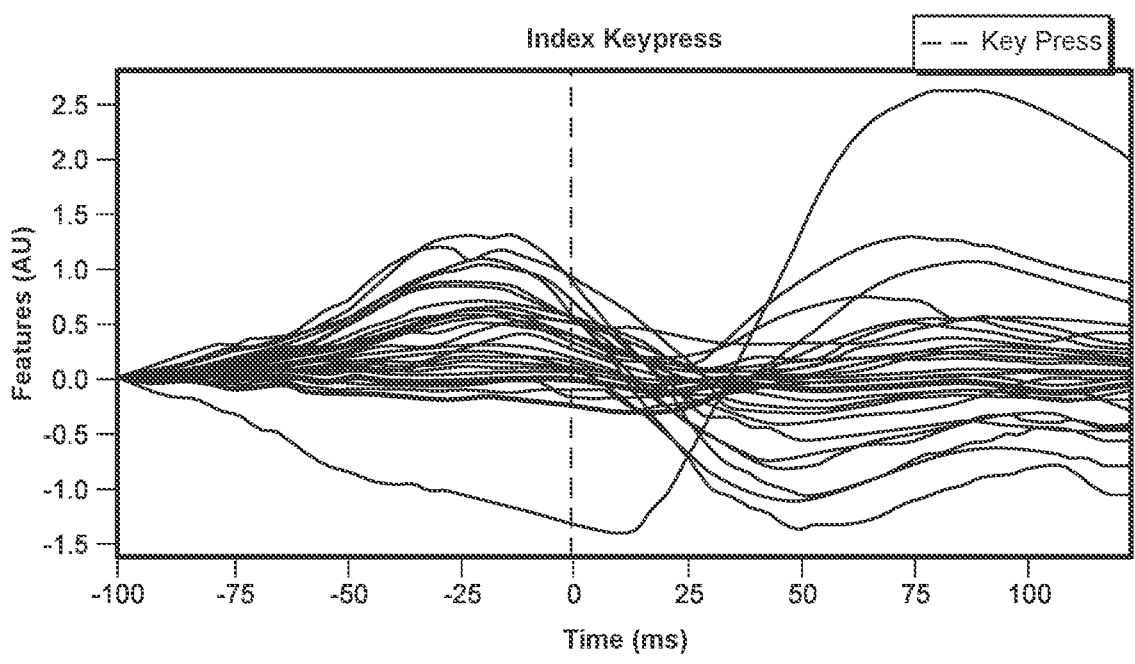
Figure 30T:
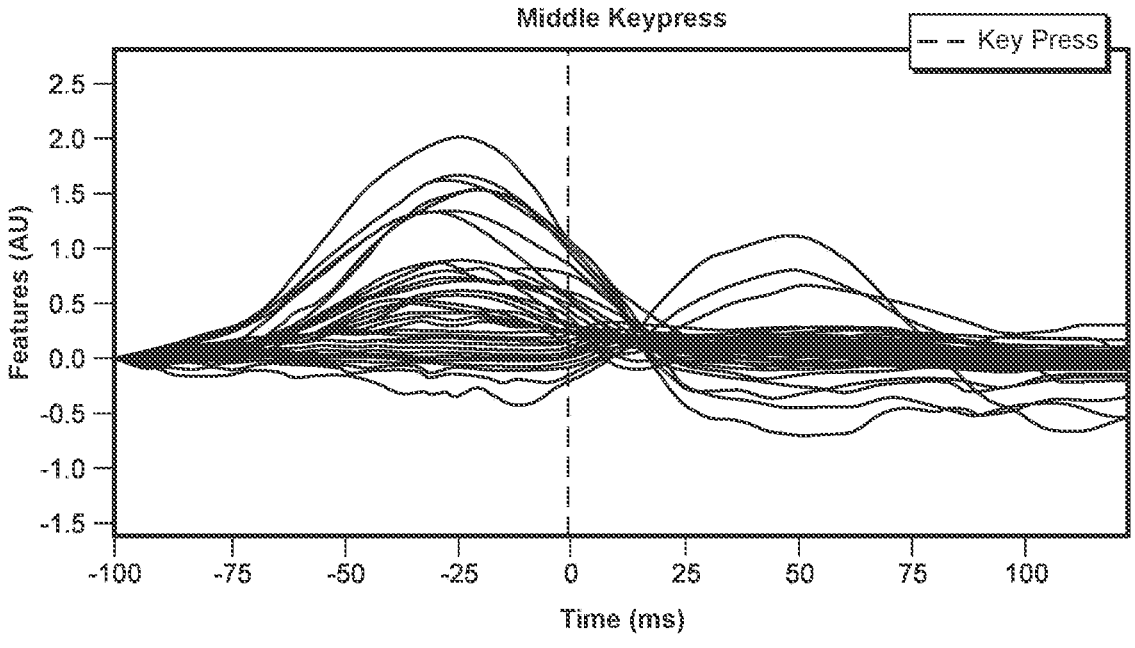

FIGS. 30O-30T illustrate examples of user-specific event models for two classes of events. FIGS. 30O, 30Q, and 30S correspond to index keypresses, and FIGS. 30P, 30R, and 30T correspond to middle finger keypresses. Each user may show different patterns for each event class. While the timing is generally the same, great differences in amplitude may be observed among signals.

Several classification models may be used to implement single user event classification models. In some examples, each trial may be vectorized into a large vector (with dimensions corresponding to number of times points x features). Once such large vectors are generated, a classifier may be produced based on logistic regression, random forest, or multilayer perceptron, and may be implemented in a gesture classification model.

In some examples, the dimensionality of the data (on the feature dimension) may be reduced by applying a spatial filter then, vectorizing the result and using a classifier. Examples of spatial filters may be based, for example, on extraction of Common Spatial Patterns (CSP), or xDawn enhancement of evoked potentials in ensemble with a Linear Discriminant Analysis (LDA). Through the application of CSP, a subspace that maximizes the difference in variance of the sources may be determined. In an xDawn approach, spatial filters may be estimated from class averages rather than raw data (which may increase the signal-to-noise ratio (SNR)).

In some examples, a model may be developed by a method including one or more of the following approaches: concatenating an event model of each class (e.g., middle finger keypress and index finger key press) to each trial; estimating the covariance matrix; tangent space mapping, and applying LDA. Such approaches may produce a compact representation of the signal, and may be effective with low SNR.

A stratified random split with 90% training and 10% test may be used in part to conserve class balance. A random split may also be used. A 99% accuracy in average across users may be achieved using the linear regression classifier, with 95% for the worst user.

Figure 30U:
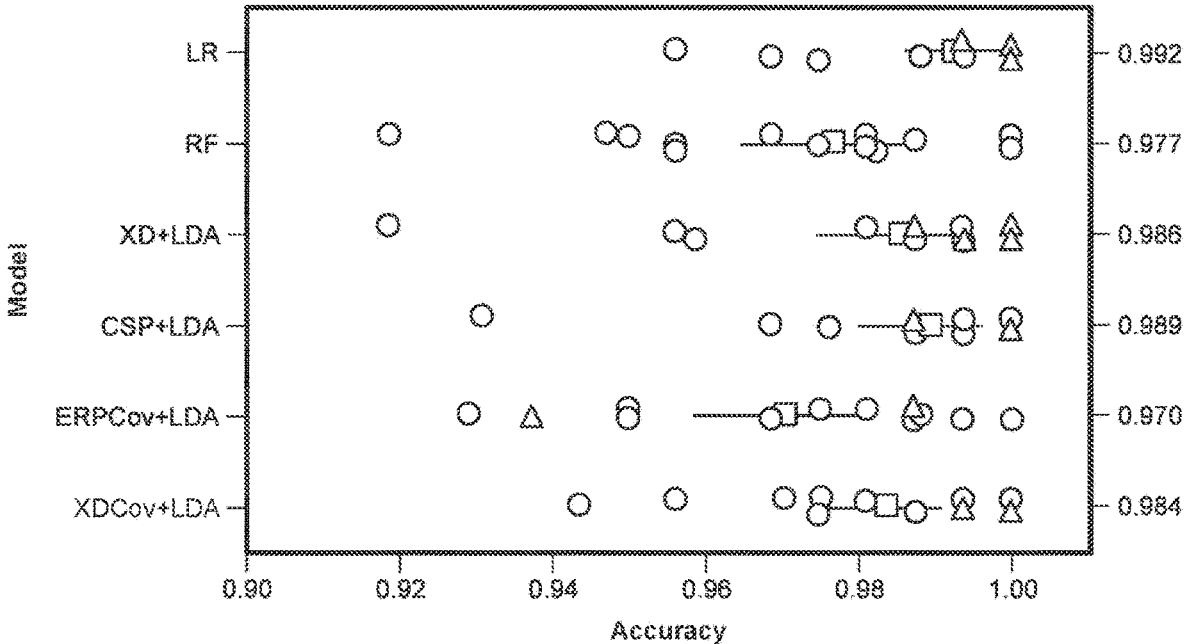
FIG. 30U shows example accuracy levels achieved by various single user event classification models.

FIG. 30U shows accuracy levels achieved by each of the tested models for single user event classification. Each dot in the plot represents a single user. The classifiers may generally perform at analogous accuracy levels to those shown in FIG. 30U.

Training set size may be modified. The size of the training set may be changed in the split, from 5% to 90%. The amount of test data may remain fixed at 10%. Two classifiers may be used, LR and XDCov+LDA. Ten stratified random splits with 10% test and variable train size may be used for cross validation.

A plateau of accuracy may be reached at around 80 events. Twenty events may be used to achieve an accuracy of 95% with a classifier based on logistic regression. The classifier based on XDCov+LDA may take a greater number of events to converge.

Figure 30V:
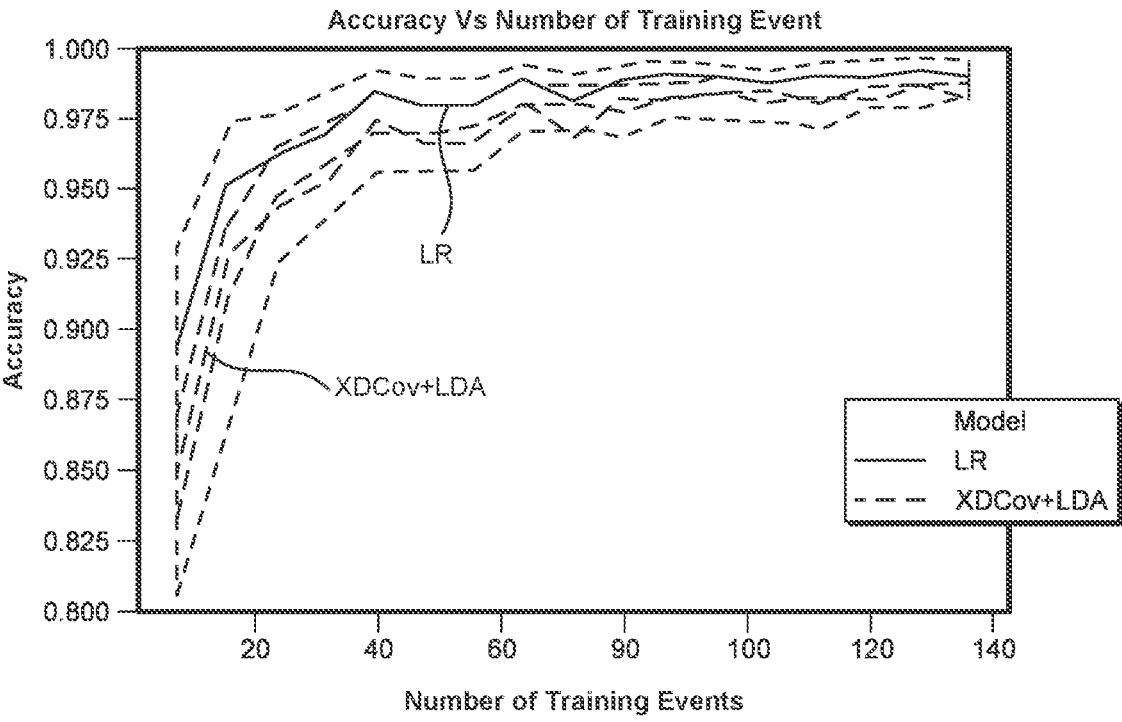
FIG. 30V shows example accuracy levels achieved by two single user event classification models.

FIG. 30V shows example accuracy levels that may be achieved by two different implementations of single user event classification models, as a function of the number of training events. Results are shown for LR (solid line) and XDCov+LDA (dashed line) approaches. The remaining dashed and dotted lines give a qualitative indication of possible uncertainties for the LR results (upper dotted line and generally lower middle dashed line) and XDCov+LDA results (remaining dashed line and lower dotted line).

Window size may also be adjusted. The size of the window used to classify the event may impact the latency of the event detection. Accordingly, the model's performance may vary depending on the window size parameter, which may be adjusted accordingly.

In some implementations, a single time point for the classification may be used to uncover which time point contains information. Alternatively, an increasing window size (containing all past time points), from, for example, −100 ms to +125 ms after the keypress event may be used. For each time point or window size, a user specific model may be trained, and the performance of the resulting classifier(s) or mode(s) may then be evaluated. A logistic regression model or other suitable model, as discussed above, may be used to implement a classifier. Cross validation may be achieved using 10 stratified random splits with 10% reserved for testing purposes and 90% used for of training purposes. These numerical values, and other values discussed herein, are exemplary and not limiting.

Figure 30W:
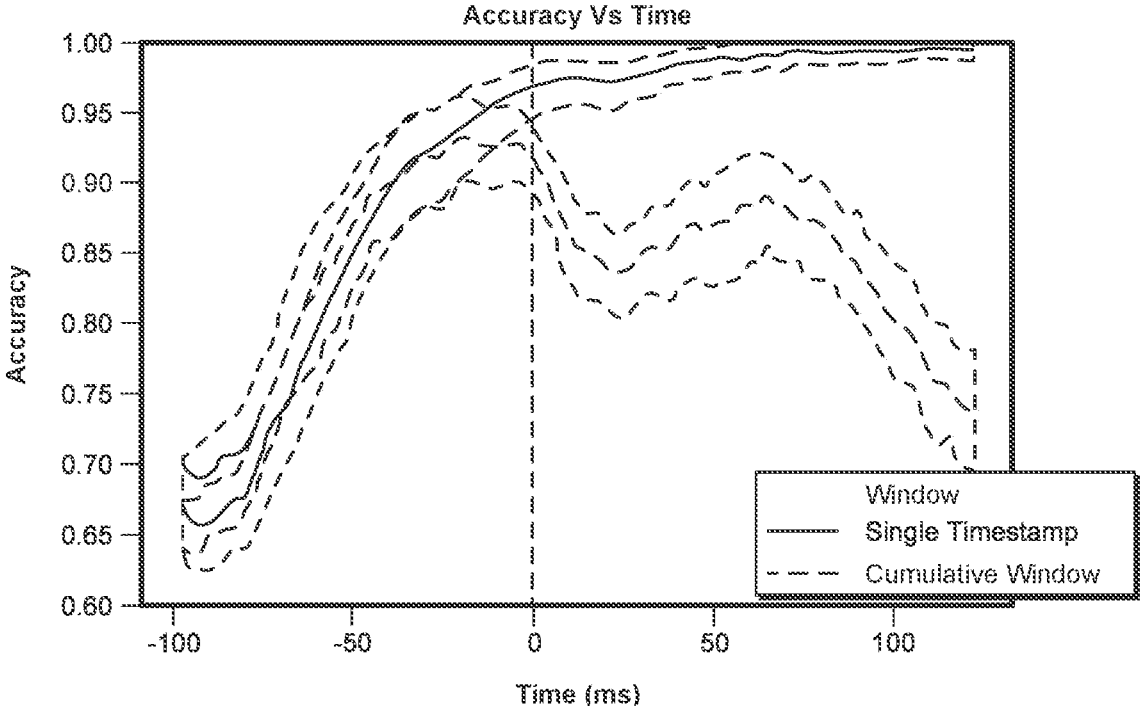
FIG. 30W shows example accuracy levels versus time for two single user event classification models (single stamp and cumulative window size).

FIG. 30W shows example accuracy levels that may be achieved by a single time stamp and a cumulative window size. The results indicate that most time points in the window may contain information that allow the model to classify them above the chance level (with, e.g., approx. 50% accuracy). Maximum accuracy may be reached at −25 ms for a key press, and around +70 ms for key release. Using a cumulative window including all past time samples, a maximum accuracy level may be reached at the end of the window. An average accuracy level of 95% may be reached using all timestamps before the key press event. Waiting for the release wave may boost the accuracy by providing complementary information. The remaining dashed and dotted lines represent a qualitative indication of possible uncertainties.

A generalization across time may be used to determine how independent time samples. As part of the generalization across time, a classifier may be trained at a single time point, and then the classifier may be tested at another time point. This approach may determine if the different processes involved in the event are stationary. If the same combination of source is similarly active across two different time points, then it may be implied that the single user model may be transferred or used to classify events produced by other users.

A classifier based on logistic regression may be trained for each user and each time point. The accuracy of each classifier may then be evaluated for every other time point (for the same user). The accuracy across all users may then be averaged, as well as the structure of the accuracy matrix.

Figure 30X:
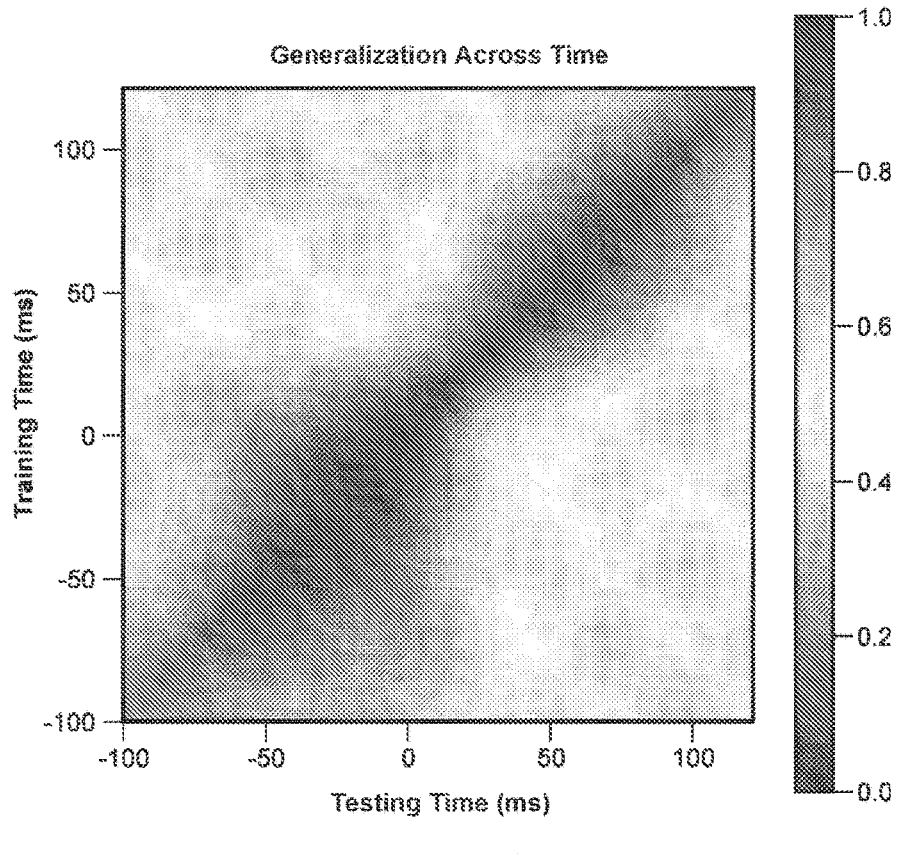
FIG. 30X shows a generalization across time executed to determine the independence of time samples.

FIG. 30X shows a generalization across time that may be executed to determine the independence of time samples. Two clusters may be observed in the accuracy matrix, one corresponding to the key press and another corresponding to the key release. From the observed transfer within each of the clusters, it may be implied that each time sample does not carry much complementary information, and that using a carefully selected subset of samples may be sufficient to achieve an optimal accuracy (or alternatively, compressing the feature space with Singular Value Decomposition SVD may be useful).

In some examples, generalized cross-user classification models may be used. A classifier may be trained with the data collected from several users, and the trained classifier obtained may be tested for its performance on a test user. As discussed above, several types of classifiers may be implemented to determine an optimal type of classifier. Data extracted from one user may be left out for cross validation purposes. On average, the accuracy achieved across the implemented models may be around 82%. A large variance across users may also be observed.

Figure 30Y:
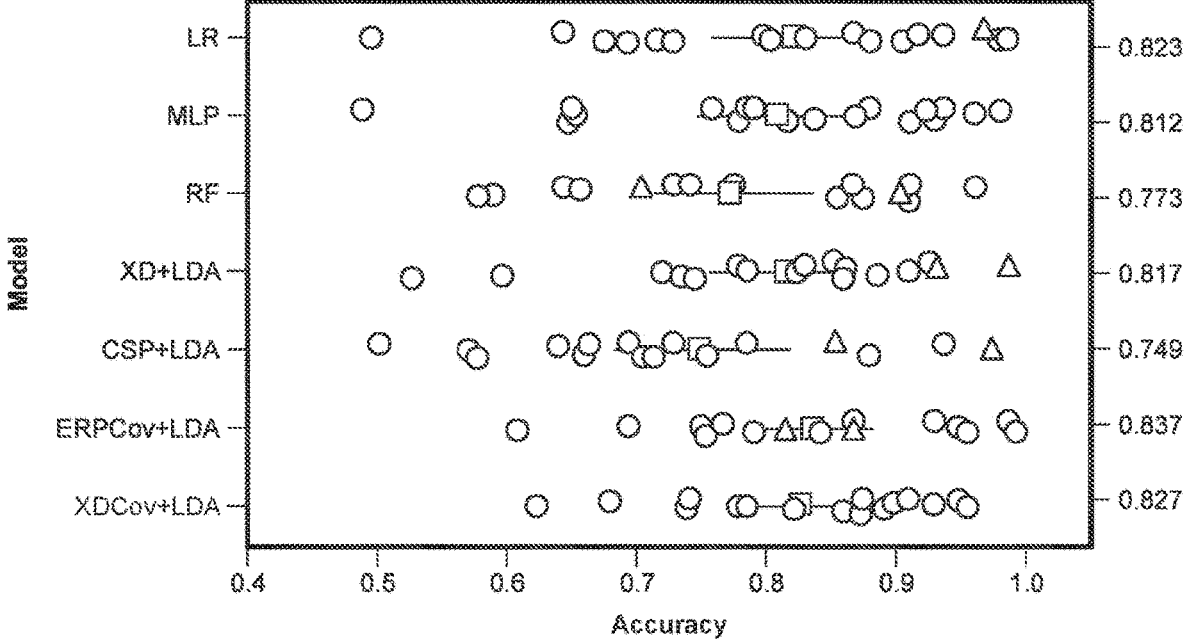
FIG. 30Y shows example accuracy levels for generalized cross-user classification models.
Figure 30Z:
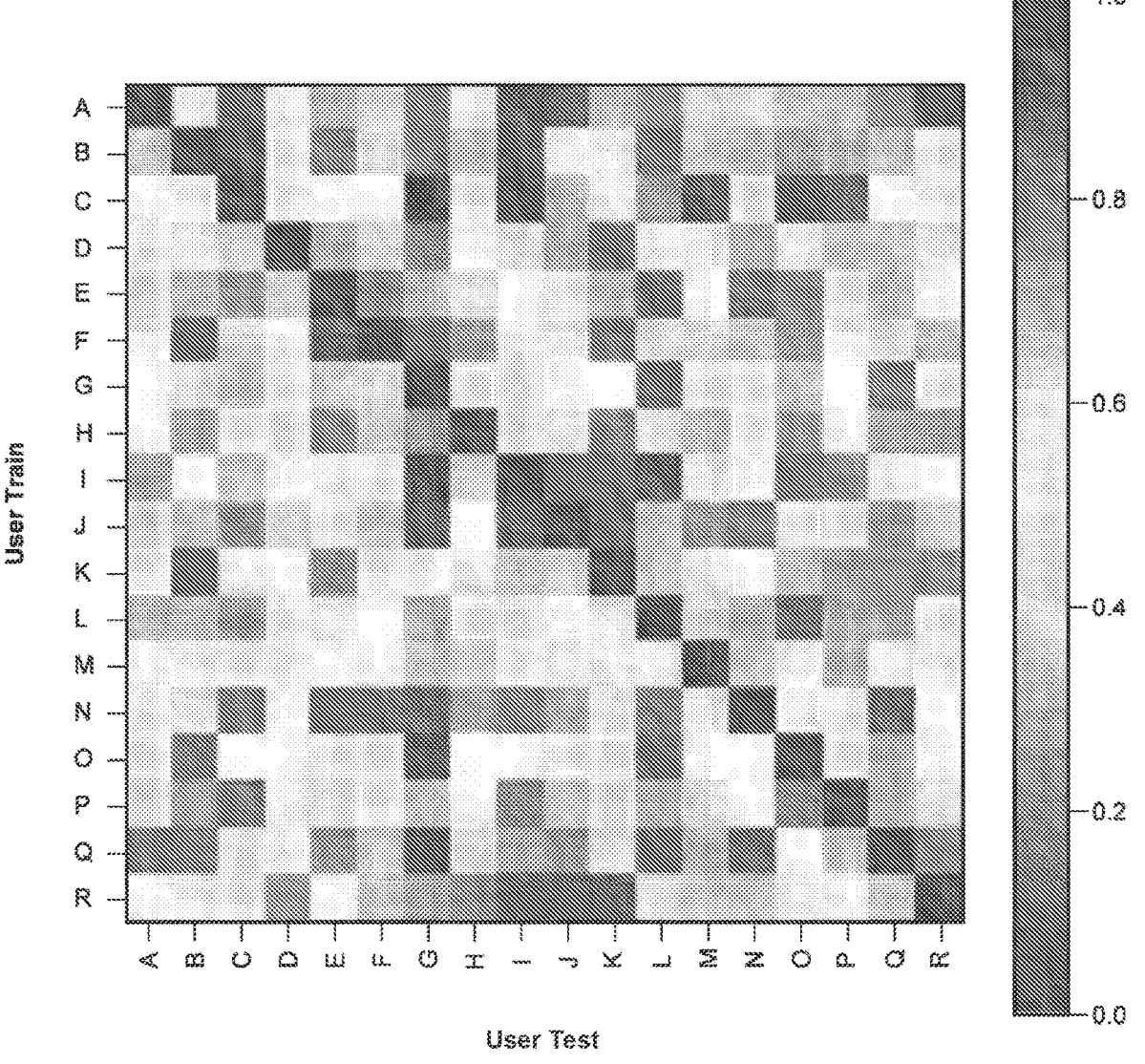
FIG. 30Z shows an example of transferability of user specific classifiers based on linear regression.

FIG. 30Y illustrates accuracy levels of generalized cross-user classification models, and shows that some classifiers may reach 100% accuracy, while others may only reach an accuracy below 60%. FIG. 30Z also indicates that reasonable accuracy levels may be achieved using classifiers based on linear regression.

In some examples, model transfer across pairs of users may be used. A classifier model may be trained based on data extracted from one user, and then the accuracy of the model may then be evaluated in relation to the data for every other user. The classifier model may be based on logistic regression.

FIG. 30Z illustrates transferability of user specific classifiers based on linear regression, showing that a large variability of transfer accuracy may be observed. Some user specific models may adequately be transferred to some other users. Some user specific models appear to be good recipients (e.g., the user model for "Alex" shown in FIG. 30Z) with good transfer to most other users, while other user specific models (e.g., the user model for "Rob") do not appear to have a good match with other users.

In some examples, user adaptation may also be used. Based on the investigation of single user event classification models, even classes derived from a single user may be separated, and a relatively small amount of labeled training data may be used to obtain a reasonably accurate single user event classification model.

From the generalized cross-user classification model results, it may be inferred that some user specific classification models transfer adequately to other users. Based on these initial results, the following examples follow. In some examples, models from other (different) users may be used get a good estimate of labels for a present user. Also, using this estimation of labels, a user specific model may be trained to obtain a performance close to that of a single user model trained with labeled data.

User embedding may also be used. An embedding space where the two event classes may be clustered may be generated. The user transfer matrix suggests that, for each test user, there are generally some (e.g., two) single user models that may adequately transfer. A user embedding space including the outputs of a collection of single user models may be constructed. Specifically, a simple nearest-centroid classifier over a covariance feature (XDCov+MDM) may be built. The advantage of the XDCov+MDM approach with respect to linear regression or other alternative probabilistic models is that an event may still contribute to cluster separability even if the model may be calibrated inappropriately.

The output of the XDCov+MDM model may be a function of the softmax applied over the distance to the centroid of each event class. In some examples (e.g., binary classifications), one dimension may be used for each user specific mode. The number of dimensions, however, may be extended depending on the classification type, such as a classification that may be made from a pool of more than two possible classes, for example, greater than a binary classification.

The embedding associated with a user may be trained with samples derived from all the users, minus one user, from a group of users. Thereafter, the samples associated with the user not used in the training of the embedding may be projected into the trained embedding. Thus, a space of X−1 dimensions may be produced, where X is the number of users from the group of users.

Figure 31A:
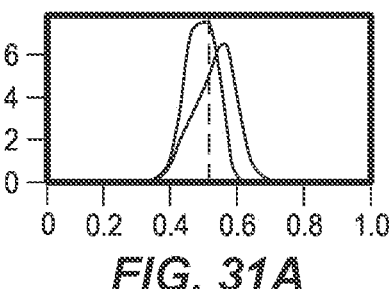
Figure 31B:
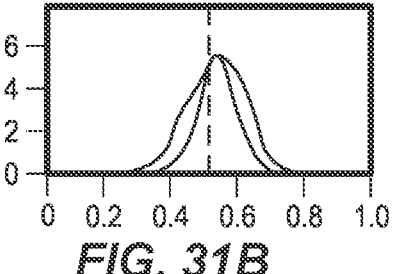
Figure 31C:
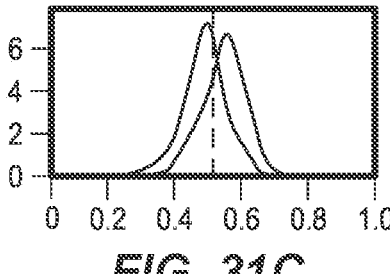
Figure 31D:
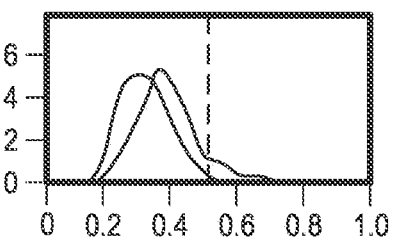
Figure 31E:
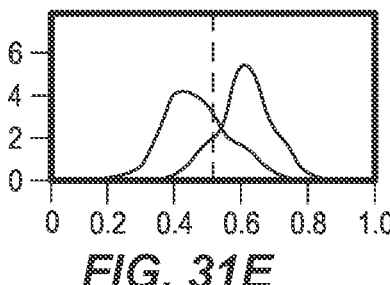
Figure 31F:
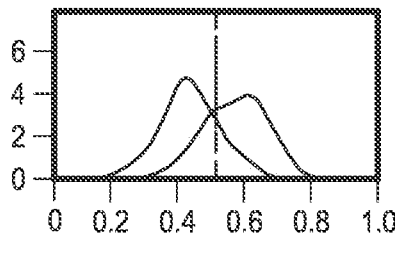
Figure 31G:
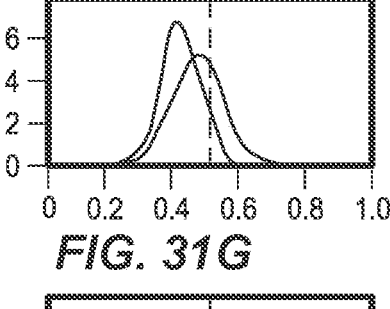
Figure 31H:
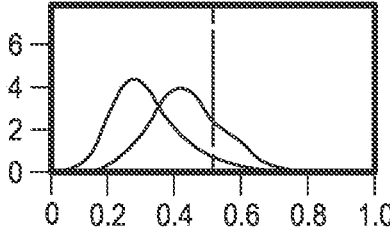
Figure 31I:
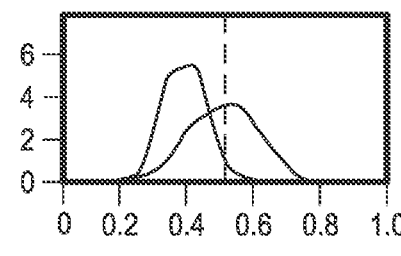
Figures 31J, 31K, 31L, 31M, 31N, 31O, 31P, 31Q:
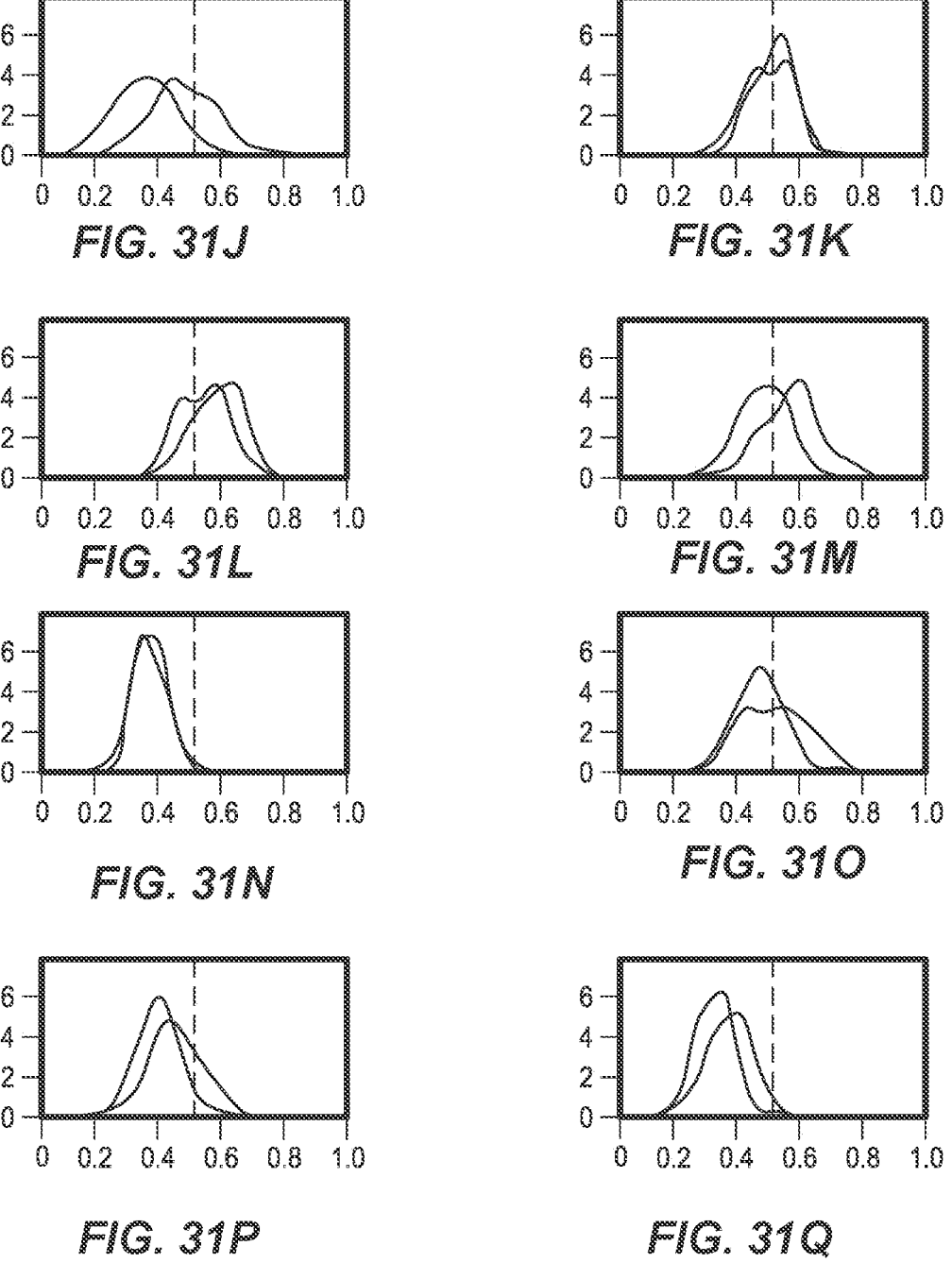

FIGS. 31A-31Q show example distributions of the two classes of gestures (index finger taps and middle finger taps), for each dimension. A separation of the two classes may be distinguished in some models, while other models show approximately identical distributions. In some examples, when the models are not optimally calibrated, (i.e. the optimal separation between the class may not be at 0.5), the model may still effectively separate the two classes.

After producing the embedding as discuss above, a clustering process may be executed to separate the clusters corresponding to the different types of event classes (such as index finger tap and middle finger tap or pinches or snaps or other gesture types to be separated). For example, a K-means process may be run on the set of data points produced using the embedding.

FIGS. 32A and 32B illustrate examples of separated clusters using UMAP and PCA, showing that such clusters may be plotted using either Uniform Manifold Approximation and Projection (UMAP), as in FIG. 32A, or Principal Component Analysis (PCA), as shown in FIG. 32B. A number of clusters (e.g., two clusters) may be seen, which may each correspond to a different event class (such as a gesture type) and a different label. As the embedding space conveys a meaning (which may be termed "proba"), each cluster may be associated with their corresponding class.

A self-supervised user model may also be developed. After a set of labels may be produced using, for example, the clustering technique, such labels may be used to train a user specific model from the original dataset. An XDCov and a linear displacement analysis, or other suitable classification model may be implemented, for example, if it is known that the chosen classification model does not overfit the model substantially and may be insensitive to noise included in the labeled data.

FIG. 32C illustrates example accuracy levels achieved using a self-supervised model, showing that an approximately 99% accuracy on the estimation of labels or classification may be achieved after training the self-supervised model. In this example, two training iterations may be sufficient.

An accuracy of 98% may be achieved using the full training set, which may include the data points of all the users from the group of users.

FIG. 32D illustrates accuracy levels achieved using a supervised user specific model and a self-supervised user specific model, showing that the self-supervised model performs better than a user specific model trained with labeled data. The remaining dashed and dotted lines give a qualitative indication of possible uncertainties.

The window size may be adjusted to improve the performance of the self-supervised model. Observing the accuracy of the self-supervised model as the window size increases may be used to determine an optimal window size. Data from one user may be omitted for cross validation of the model. For the clustering and user specific model, a 10 fold random split with 10% of test data and 90% training data may be used. In this case, it may be determined that the self-supervised model performed better with a full window size. This may be explained by the observation that, in this instance, a small window size did not produce a separable cluster. Accordingly, a large window size may be used to obtain labeled data, then a user specific model may be trained using a relatively small window size, for example, using the labels.

FIG. 32E illustrates window size determination for a user specific (solid line) and a self-supervised model (lower dashed line). The remaining dashed and dotted lines give a qualitative indication of possible uncertainties.

A similar approach may be used to study data size effects. An ensemble of single user models may be used to evaluate performance. Cross validation may include leaving one user out for the alignment, then using the same 10 fold random split with 10% of test data and an increasing training size from 5 to 90%. The ensemble approach may reach an accuracy of 96% after 30 events, and then the accuracy may plateau after that for larger numbers of events.

Supervised domain adaptation may use a Canonical Partial Least Square (CPLS) model. In some examples, a method based on domain adaptation may be used instead of building a user specific model, for example, by determining a data transformation that may result in adequate transfer across users. A CPLS model may be used to perform the domain adaptation. A transformation function may be determined to align models of each event class (e.g., different gesture types such as index finger tap, middle finger tap, index finger to thumb pinch, middle finger to thumb pinch, finger snap, etc.) for one user with models for each event class of another user.

FIG. 32F-32G illustrate models of each event class associated with a first user.

FIGS. 32H-32I illustrate models of each event class associated with a second user.

FIGS. 32J-32K show the alignment of models for event classes associated with the first user and the second user, showing that models of event classes for one user may be aligned with corresponding models of event classes for another user. The vertical dashed lines correspond to the key press. The alignment may be efficient, in part because the original models of each event classes of the two users may be substantially different, yet they may become nearly identical after alignment.

Data distribution after alignment may be studied by considering the UMAP embedding of the data before and after transformation.

FIGS. 32L-32M show example data before and after transformation. FIG. 32L shows that the original data may be unambiguously separated, and the largest variation may be seen across the two users. After transformation, the two event classes of events may match at a high degree of accuracy, for example, as shown in FIG. 32M.

The transformation process for each pair of users from the group of users may be studied. The user-to-user transfer matrix may be reproduced after performing the alignment. A single user model may be trained, and then for each test user, the data may be aligned, and the accuracy of the model may be tested on the transformed data. Cross validation may include, for a test user, estimating the event class model on the first 40 events (or other number of events), then performing domain adaptation, and finally testing the accuracy of the model on the remaining events (e.g., 120 events). Numerical values used in these (and other) examples are exemplary and not limiting.

FIG. 32N illustrates the transfer across users, from all users in a group of users, showing that the process may enhance the transfer of a single user model to any other users.

The amount of data needed to reach optimal adaptation may be determined. Performance evaluation may be made using an ensemble of a single user model, in part because it may be possible to adapt data between pairs of users. Cross validation may include leaving one user out of the alignment, and thereafter using a 10 fold random split with 10% of test data and increasing the training size from 5 to 90%. Numerical values are exemplary and not limiting.

FIG. 32O illustrates determination of data size for a supervised domain adaptation based on a transfer function, showing accuracy versus the number of training events. The results show that the ensemble may reach an accuracy of 96% after 30 events, and may plateau after that. The remaining dashed and dotted lines give a qualitative indication of possible uncertainties.

FIGS. 32P-32Q illustrate an example device, that may include one or more of the following: a human-machine interface, an interface device, a control device, and/or a control interface. In some examples, the device may include a control device 302600, which in this example (as shown in FIG. 32P) may include a number of (e.g., 16) neuromuscular sensors 302610 (e.g., EMG sensors) arranged circumferentially around an elastic band 302620 configured to be worn around a user's lower arm or wrist. In some examples, EMG sensors 302610 may be arranged circumferentially around elastic band 302620. The band may include a flexible electronic connection 302640 (shown in FIG. 32Q), which may interconnect separate sensors and electronic circuitry that may, in some examples, be enclosed in one or more sensor housings 302660. Each sensor 302610 may have a skin contacting portion 302650, which may include one or more electrodes. Any suitable number of neuromuscular sensors 302610 may be used. The number and arrangement of neuromuscular sensors may depend on the particular application for which the control device is used. For example, a wearable control device configured as an arm-band, wristband, or chest-band may be used to generate control information for controlling an augmented reality system, controlling a robot, controlling a vehicle, scrolling through text, controlling a virtual avatar, or any other suitable control task. As shown, the sensors may be coupled together using flexible electronics incorporated into the wireless device.

FIG. 32Q illustrates a cross-sectional view through one of the sensors 302610 of the control device 302600 shown in FIG. 32P. The sensor 302610 may include a plurality of electrodes located within a skin-contacting surface 302650. The elastic band 302620 may include an outer flexible layer 302622 and an inner flexible layer 302630, that may at least in part enclose a flexible electrical connector 302640.

In some embodiments, the output of one or more of the sensing components may be optionally processed using a hardware-based signal processing circuit (e.g., to perform amplification, filtering, rectification, and/or another suitable signal processing function). In some embodiments, at least some signal processing of the output of the sensing components may be performed in software. Thus, signal processing of signals sampled by the sensors may be performed in hardware, software, or by any suitable combination of hardware and software, as aspects of the technology described herein are not limited in this respect. A non-limiting example of an analog circuit used to process signal data from sensors 302610 is discussed in more detail herein, with reference to FIGS. 9A and 9B.

Although the examples provided with reference to FIGS. 32P, 32Q and FIGS. 9A, 9B are discussed in the context of interfaces with EMG sensors, examples may also be implemented in control devices, such as wearable interfaces, used with other types of sensors including, but not limited to, mechanomyography (MMG) sensors, sonomyography (SMG) sensors, and electrical impedance tomography (EIT) sensors. The approaches described herein may also be implemented in wearable interfaces that communicate with computer hosts through wires and cables (e.g., USB cables, optical fiber cables).

FIG. 32R illustrates an example system 302800 that may include a headset 302810 and a control device 302820 (that may represent a wearable control device). In some examples, the system 302800 may include a magnetic tracker. In these examples, the transmitter for the magnetic tracker may be mounted on the control device 302820, and the receiver for the magnetic tracker may be mounted on the headset 302810. In other examples, the transmitter for the magnetic tracker may be mounted on the headset or otherwise located within the environment. In some embodiments, the system 302800 may also include one or more optional control gloves 302830. In some examples, many or all functions of a control glove may be provided by the control device 302820. In some examples, the system may be an augmented reality and/or virtual reality system. In some examples, the control glove 302830 may include a plurality of magnetic tracker receivers, using which the orientation and/or location of various parts of the hand of a user may be determined. In some examples, the control device 302820 may be similar to that shown in FIGS. 32P and 32Q. In some examples, the control device may include an electronic circuit similar to that shown in FIG. 9A (and/or FIG. 9B).

In some examples, the control glove 302830 (that may be more simply referred to as a glove) may include one or more magnetic tracker receivers. For example, a finger of the glove may include at least one receiver coil, and detection of a tracker signal from the at least one receiver coil induced by a magnetic tracker transmitter may be used to determine the position and/or orientation of at least portion of the finger. One or more receiver coils may be associated with each portion of a hand, such as a finger (such as the thumb), palm, and the like. The glove may also include other sensors providing sensor signals indicative of the position and/or configuration of the hand, such as electroactive sensors. Sensor signals, such as magnetic tracker receiver signals, may be transmitted to a control device, such as a wearable control device. In some examples, a control device (such as a wrist-mounted control device) may be in communication with a control glove, and receive sensor data from the control glove using wired and/or wireless communication. For example, a flexible electrical connector may extend between a control device (e.g., a wrist-mounted control device) and the glove. In some examples, the control device may include a glove, and/or may include a wrist-strap.

In some examples, the control device 302820 may include an EMG control interface similar to the device illustrated in FIGS. 32P and 32Q. Locating the magnetic tracker transmitter on or near the control device 302820 may result in the introduction of noise into the signals recorded by the control device 302820 due to induced currents and/or voltages. In some embodiments, electromagnetic interference caused by the magnetic tracker transmitter may be reduced by locating the transmitter at a distance further away from the control device 302820. For example, the transmitter may be mounted on the headset 302810, and the magnetic tracker receiver may be mounted on the control device 302820. This configuration works well, for example, when the user keeps their arms away from their head, but may not work as well if the user moves their arms in close proximity to the headset. However, many applications do not require extensive proximity between the head and the hands of the user.

The control device, such as wearable control device 302820, may include an analog circuit including at least one amplifier configured to amplify analog electrical signals originating from a body of the user (e.g., from electrodes in contact with the skin, and/or one or more other sensors), and an analog-to-digital converter configured to convert the amplified analog electrical signals to digital signals that may be used to control the system, such as a virtual reality (VR) and/or augmented reality (AR) system.

In some examples, an augmented reality system may include a magnetic tracker. The magnetic tracker may include a transmitter positioned in the headset, or other location, and one or more receivers, that may be associated with tracked objects or body parts of a user (such as hands, or other limbs or portions thereof, or joints) of a user.

FIG. 32S shows an example method of classifying an event (302900), including obtaining electromyography (EMG) data from a user (302910), the EMG data including an EMG signal corresponding to an event, detecting the EMG signal corresponding the event (302920), classifying the EMG signal as being from an event type (302930), and generating a control signal based on the event type (302940). An example method may further include triggering the head-mounted device to modify the artificial reality view controlling an artificial reality environment based on the control signal.

FIG. 32T shows an example method of classifying an event (303000), including detecting an EMG signal corresponding to an event (303010), classifying the EMG signal as corresponding to an event type using a trained model (303020), and generating a control signal for an artificial reality environment based on the event type (303030). The control signal may trigger the head-mounted device to modify the artificial reality view.

In some examples, FIGS. 32S and 32T may represent flow diagram of exemplary computer-implemented methods for detecting at least one gesture, and using the at least one detected gesture type to control an artificial reality system, such as an augmented reality system or virtual reality system. One or more steps shown in the figures may be performed by any suitable computer-executable code and/or computer device, such as a control device, a head-mounted device, other computer device in communication with the control device, or a computer device in communication with a device providing sensor signals. In some examples, one or more of the steps shown in FIGS. 32S and/or 32T may represent an algorithm whose structure includes and/or is represented by multiple sub-steps, using approaches such as those described herein. In some examples, steps of a particular example method may be performed by different components of a system including, for example, a control device and a head-mounted device.

In some examples, event detection and classification may be performed by unsupervised or self-supervised models, and these approaches may be used to detect user gestures. Models may be trained for a particular user, or in some examples a model may be trained on a different user, and the training data for the different user adapted for use with a present user. In example training approaches, EMG data may be detected, and optionally recorded for analysis. A model may be trained using EMG data that may be obtained as one or more users perform one or more gestures. Example gestures include finger taps (e.g., simulated keypresses), other finger movements (such as finger curls, swipes, pointing gestures, and the like), or other types of gestures and/or sensor data may be analogously used to train example event detector models.

In some embodiments, by building an embedding space including a single user model, clearly separable clusters of events may be obtained. Clustering techniques may be implemented to determine labels for each event, and a user specific model may be then trained using the labeled data. By using at least one of these techniques, a very high accuracy rate (e.g., 98% accuracy rate) may be reached in a purely unsupervised fashion. For instance, using a relatively small number of samples (e.g., less than 40 event samples), a relatively high (e.g., 95% accuracy) may be achieved.

Further, in some embodiments, single-user event templates may be adapted to other users, reducing further the amount of additional data that may be needed for use of the models with the adapted users. For instance, domains may be adapted using PLS by aligning datasets across pairs of users. For instance, a PLS may be trained to align event templates across users. An ensemble of aligned user templates may lead to a high accuracy (e.g., 96% accuracy), requiring very few event data to be collected (e.g., less than 10 events).

Poses may be defined as body positions that are static over time and in theory may be maintained indefinitely. In contrast, in some examples, gestures may be defined as including dynamic body positions, that may have a start time and an end time, per occurrence. Accordingly, gestures may be defined as discrete events of a particular gesture type. Representative examples of gesture types include snaps, finger taps, finger curls or bends, pointing, swiping, turning, grasping, or other finger motions. In some examples, gestures may include movements of at least a portion of the arm, wrist, or hand, or other muscle activation. In some examples, visually perceptible movement of the user may not be required, and a gesture may be defined by a muscle activation pattern, independent of any visually perceptible movement of a portion of the user's body.

A generic event detector may generate an output signal when a gesture event is detected, for example, in a continuous stream of electromyography (EMG) data. A control signal for a computer device, such as an artificial reality system, may be based on the output signal of the generic event detector. The generic event detector may produce an output signal each time a user performs a gesture. In some examples, the output signal may be produced independently of the type of performed gesture. In some examples, an event classifier may execute when the event detector detects an event, such as a gesture. The event classifier may determine information related to the gesture, such as a gesture type, performed by the user. The gesture type may include one or more of the following: a physical action performed, the body part (such as a finger or other body part) used to perform the physical action, an intended action of the user, other physical action(s) performed the same or an approximately same time. A control signal may also be based on a combination of sensor data from one or more sensor types. A corresponding control signal may be sent to an augmented reality (AR) system, and the control signal may be based, at least in part, on the gesture type. The control signal may modify the artificial reality display by one or more of the following: selection of an item, performance of a task, movement of an object by a degree and/or direction that may be, at least in part, determined by the gesture type, interaction with a user interface of an object (e.g., a real or virtual object), or other action. In some embodiments, gestures may be classified as a particular gesture type based on one or more electromyography signals, such as electromyography wavelets.

In some examples, a method of detecting events, such as gestures, may include obtaining first set of electromyography (EMG) data including EMG signals corresponding to a gesture of a first user, training a first classifier by clustering event data determined from the obtained first set of EMG signals, labeling a second set of obtained EMG data using the first classifier, and training an event detector using the labeled second set of EMG data.

In some examples, a method for classifying events, such as gestures, may include one or more of the following steps; generating a plurality of single user event classifiers, generating a multi-user event classifier using the plurality of single user classifiers, labeling electromyography (EMG) data using the generated multi-user classifier, generating data transformations corresponding to a plurality of users, generating a single user classifier correlated with a first user of the plurality of users, labeling received EMG data for a second user of the plurality of users using the data transformation for the second user and the single user classifier for the first user, and training the event detector using the labeled EMG data.

In some examples, a method for training an event detector, such as a gesture detector, is provided. The method may include one or more of the following steps; obtaining electromyography (EMG) data including EMG signals corresponding to the gesture, generating feature data from the EMG data, detecting events in the feature data, generating epochs using the feature data, where each epoch may be centered around one of the detected events, clustering the epochs into types, where at least one of the types may correspond to the gesture, aligning the epochs by type to generate aligned epochs, training a labeling model using the aligned epochs, labeling the feature data using the labeling model to generate labeled feature data, and training an event detector using the labeled feature data.

In some examples, a method for training an event classifier may include one or more of the following steps; obtaining electromyography (EMG) data including EMG signals corresponding to a plurality of gestures, generating feature data from the EMG data, detecting events in the feature data using an event detector, generating epochs using the feature data, each epoch centered around one of the detected events, generating a single-user event classification model using the epochs, labeling the EMG data using the single-user event classification model, and training an event classifier using the labeled EMG data.

In some examples, a method of generating a single-user event classification model using epochs may include one or more of the following steps; generating vectorized epochs using the epochs, and generating the single-user event classification model by training one or more of a logistic regression, random forest, or multilayer perceptron classifier using the vectorized epochs. In some examples, wherein generating a single-user event classification model using the epochs includes generating spatially-filtered, reduced-dimension epochs using the epochs, generating vectorized epochs using the spatially-filtered, reduced-dimension epochs, and generating the single-user event classification model by training one or more of a logistic regression, random forest, or multilayer perceptron classifier using the vectorized epochs. In some examples, wherein generating a single-user event classification model using the epochs includes generating one or more event models using the epochs, each event model corresponding to a gestures, generating combined epochs by combining each of the epochs with the one or more event models, and generating the single-user event classification model by training one or more of a logistic regression, random forest, or multilayer perceptron classifier using the combined epochs.

In some examples, a method for training an event classifier is provided. The method may include one or more of the following steps; obtaining electromyography (EMG) data including EMG signals corresponding to a plurality of gestures for a plurality of users, generating feature data from the EMG data, detecting events in the feature data using an event detector, generating epochs using the feature data, each epoch centered around one of the detected events, generating a cross-user event classification model using the epochs, labeling the EMG data using the cross-user event classification model, and training an event classifier using the labeled EMG data.

In some examples, a method for training an event classifier is provided. The method may include one or more of the following steps; generating an embedding model using a plurality of single user event classification models, generating embedded events using the embedding model and electromyography (EMG) data including EMG signals corresponding to a plurality of gestures for a user, clustering the embedded events into clusters corresponding to the plurality of gestures, associating labels with the EMG data based on the clustered embedded events, and training an event classifier for the user using the EMG data and associated labels.

In some examples, a method for training an event classifier is provided. The method may include one or more of the following steps; generating, for each of a plurality of users, an event template for each of a plurality of events, determining alignment transformations between the event templates for each of the plurality of events across the plurality of users, transforming EMG data for a first user using ones of the determined alignment transformations for a second user, associating labels with the EMG data using the transform EMG data and a single user event classification model of the second user, and training an event classifier for the user using the EMG data and associated labels.

In some examples, a system for gesture detection is provided. The system may include at least one processor, and at least one non-transitory memory including instructions that, when executed by the at least one processor, cause the system for gesture detection to perform operations including associating, using an event detector, an event label with a portion of electromyography data, in response to associating the event label with the portion of electromyography data associating, using an event classifier, a gesture label with the portion of electromyography data, and outputting an indication of at least one of the event label or the gesture label.

Examples described herein may include various suitable combinations of example aspects, provided such aspects are not incompatible.

Example systems and methods may include user-based models for detecting gestures in an accurate and unsupervised manner. Event detector models are provided that may be trained on a limited set of user data for a particular user, and using labels and clustering methods, the accuracy of the event detector may be increased while limiting the number of event data instances.

By building an embedding space including a single user model, clearly separable cluster of events may be obtained. Clustering techniques may be implemented to determine labels of each event and a user specific model may be then trained using the labeled data. In some examples, 98% accuracy may be reached by applying this process, in a purely unsupervised fashion. Also, 95% accuracy may be reached using a limited number (e.g., 40) of event samples.

Domain adaptation with PLS may include the one or more of the following. Dataset across pairs of users may be aligned by training a PLS to align the event templates. An ensemble of aligned single user may lead to 96% accuracy. The alignment requires very little data to be performed (such as less than 10 events).

A generic event detector may emit an output signal when a gesture event is detected in a continuous stream of electromyography (EMG) data. An example generic event detector may produce an output signal each time a user performs a gesture, and the output signal may be produced independently of the type of performed gesture.

An event classifier may execute when the event detector identifies a gesture event. The event classifier may then determine the gesture type performed by a user.

In some examples, a method for detecting events may include one or more of the following: obtaining first set of electromyography (EMG) data including EMG signals corresponding to a gesture of a first user; training a first classifier by clustering event data determined from the obtained first set of EMG signals; and labeling a second set of obtained EMG data using the first classifier; and training an event detector using the labeled second set of EMG data. Example approaches may include providing a general event detector.

In some examples, a method for classifying events may include one or more of the following: generating a plurality of single user event classifiers; generating a multi-user event classifier using the plurality of single user classifiers; labeling electromyography (EMG) data using the generated multi-user classifier; generating data transformations corresponding to a plurality of users; generating a single user classifier correlated with a first user of the plurality of users;

labeling received EMG data for a second user of the plurality of users using the data transformation for the second user and the single user classifier for the first user; and training the event detector using the labeled EMG data. Example approaches may include providing a general event classifier.

In some examples, a method for training an event detector may include one or more of the following: obtaining electromyography (EMG) data including EMG signals corresponding to a gesture; generating feature data from the EMG data; detecting events in the feature data; generating epochs using the feature data, each epoch centered around one of the detected events; clustering the epochs into types, at least one the types corresponding to the gesture; aligning the epochs by type to generate aligned epochs; training a labeling model using the aligned epochs; labeling the feature data using the labeling model to generate labeled feature data; and training an event detector using the labeled feature data. Example approaches may include generating a classifier to label unlabeled data, and then generating an event detector using the labeled data.

In some examples, a method for training an event classifier may include one or more of the following: obtaining electromyography (EMG) data including EMG signals corresponding to a plurality of gestures; generating feature data from the EMG data; detecting events in the feature data using an event detector; generating epochs using the feature data, each epoch centered around one of the detected events; generating a single-user event classification model using the epochs; labeling the EMG data using the single-user event classification model; and training an event classifier using the labeled EMG data. Example approaches may include generating a single-user event classification model to label unlabeled data, then generating an event classifier using the labeled data.

In some examples, generating a single-user event classification model using the epochs may include one or more of the following: generating vectorized epochs using the epochs; and generating the single-user event classification model by training one or more of a logistic regression, random forest, or multilayer perceptron classifier using the vectorized epochs. Example approaches may include generating a single-user event classification model from vectorized trials.

In some examples, generating a single-user event classification model using the epochs may include one or more of the following: generating spatially-filtered, reduced-dimension epochs using the epochs; generating vectorized epochs using the spatially-filtered, reduced-dimension epochs; and generating the single-user event classification model by training one or more of a logistic regression, random forest, or multilayer perceptron classifier using the vectorized epochs. This approach may be used to generate a single-user event classification model from reduced dimension data generated by spatially filtering the trials.

In some examples, generating a single-user event classification model using the epochs may include one or more of the following: generating one or more event models using the epochs, each event model corresponding to a gesture; generating combined epochs by combining each of the epochs with the one or more event models; and generating the single-user event classification model by training one or more of a logistic regression, random forest, or multilayer perceptron classifier using the combined epochs. Example approaches may include generating a single-user event classification model by generating event templates and concatenating the event templates with the trials.

In some examples, a method for training an event classifier includes one or more of the following: obtaining electromyography (EMG) data including EMG signals corresponding to a plurality of gestures for a plurality of users; generating feature data from the EMG data; detecting events in the feature data using an event detector; generating epochs using the feature data, each epoch centered around one of the detected events; generating a cross-user event classification model using the epochs; and labeling the EMG data using the cross-user event classification model; and training an event classifier using the labeled EMG data. Example approaches may include generating a cross-user event classification model to label unlabeled data, and then generating an event classifier using the labeled data.

In some examples, a method for training an event classifier may include one or more of the following: generating an embedding model using a plurality of single user event classification models; generating embedded events using the embedding model and electromyography (EMG) data including EMG signals corresponding to a plurality of gestures for a user; clustering the embedded events into clusters corresponding to the plurality of gestures; associating labels with the EMG data based on the clustered embedded events; and training an event classifier for the user using the EMG data and associated labels. Example approaches may include generating a user independent event classification model to label unlabeled data from an ensemble of single-user event classification models, and then generating an event classifier using the labeled data.

In some examples, a method for training an event classifier may include one or more of the following: generating, for each of a plurality of users, an event template for each of a plurality of events; determining alignment transformations between the event templates for each of the plurality of events across the plurality of users; transforming EMG data for a first user using at least one of the determined alignment transformations for a second user; associating labels with the EMG data using the transform EMG data and a single user event classification model of the second user; and training an event classifier for the user using the EMG data and associated labels. Example approaches may include using alignment transformations between users to transform data for labeling by a single user-specific event classification model, then generating an event classifier using the labeled data.

In some examples, a system for gesture detection may be configured to use an event detector to identify gestures and an event classifier to classify gestures, where the event detector may be trained using a training method (such as a training method described herein). In some examples, a system for gesture detection may include: at least one processor; and at least one non-transitory memory including instructions that, when executed by the at least one processor, cause the system for gesture detection to perform operations including: associating, using an event detector, an event label with a portion of electromyography data; in response to associating the event label with the portion of electromyography data associating, using an event classifier, a gesture label with the portion of electromyography data; and outputting an indication of at least one of the event label or the gesture lab.

Exemplary computer-implemented methods may be performed by any suitable computer-executable code and/or computing system, where one or more steps of the method may represent an algorithm whose structure may include and/or may be represented by multiple sub-steps.

In some examples, a system includes at least one physical processor, and physical memory including computer-executable instructions that, when executed by the physical processor, cause the physical processor to perform one or more methods or method steps as described herein. In some examples, a computer-implemented method may include the detection and classification of gestures, and control of an artificial reality system using detected gesture types.

In some examples, a non-transitory computer-readable medium includes one or more computer-executable instructions that, when executed by at least one processor of a computing device, cause the computing device to perform one or more method steps as described herein. In some examples, a computer-implemented method may include the detection and classification of gestures, and control of an artificial reality system using detected gesture types.

Examples include a control device including a plurality of electromyography (EMG) sensors, and/or other sensors, and at least one physical processor programmed to receive sensor data, detect sensor signals corresponding to user gestures within the sensor data, classify the sensor signals to identify gesture types, and provide control signals based on the gesture types. The control signals may trigger the head-mounted device to modify the artificial reality view.

The following describes exemplary systems and methods for control schemes based on neuromuscular data according to at least one embodiment of the present disclosure.

The present disclosure is generally directed to systems and methods for generating user control schemes based on neuromuscular data. The disclosed systems and methods may comprise feature space or latent space representations of neuromuscular data to train users and for users to achieve greater neuromuscular control of machines and computers. In certain embodiments, the systems and methods employ multiple distinct inferential models (e.g., full control schemes using inferential models trained in multiple regions of a feature space). A control scheme as discussed herein may be regarded as a set of input commands and/or input modes that are used alone or in combination to reliably control computers and/or electronic devices. For example, neuromuscular data (e.g., gathered from wearable devices with neuromuscular sensors) may be provided as input to a trained inferential model which identifies an intended input command on the part of the user. In certain scenarios, independently trained models may lack both contextual information and invariances needed to be part of a full control scheme for a control application. The systems and methods described herein may allow for the selective utilization of one or more trained models based on the circumstances surrounding the data inputs (e.g., directing the system to use one model to interpret data within a feature space and another model to interpret data that lies within a different region of the feature space). In one example embodiment, systems and methods described herein may allow a user using an armband or wristband with neuromuscular sensors to have finer control of a virtual pointer on a 2D map and may also allow for better control of a user's interactions with the 2D map and its various functional features.

Generally speaking, machine learning models may perform better when provided input from a specific subset/subregion of a feature space, rather than from arbitrary locations in the feature space. When input is from the relevant region in the feature space, model output may tend to be more reasonable. However, when data inputs fall outside of that region, model performance may suffer. The term "feature space" can comprise one or more vectors or data points that represent one or more parameters or metrics associated with neuromuscular signals such as electromyography ("EMG") signals. As an example, an EMG signal possesses certain temporal, spatial, and temporospatial characteristics, as well as other characteristics such as frequency, duration, and amplitude, for example. A feature space can generated based on one or more of such characteristics or parameters.

The disclosed systems and methods allow for full control schemes by better identifying when data inputs fall within one or more regions or point clouds of a feature space and applying the appropriately trained model(s) for specific data points that lie within the various regions of the feature space. In certain embodiments, the systems and methods disclosed herein can select from different types of control schemes or input modes and can apply the applicable trained machine learning model(s) to the inputs based on the type of schemes and/or modes selected. The selection of different schemes and/or input modes can be done manually by a user or automatically by the system. For example, the disclosed systems and methods may allow the user to maintain effective control over a connected machine if the user switches between different types of control schemes or input modes. Such schemes and modes include but are not limited to surface typing, typing on the user's leg, using a first and wrist to control a virtual pointer in 2D, drawing, writing, or any other specific or general activity that a user can perform. In one example embodiment, a user could be typing on a surface, and the disclosed systems and methods are able to detect that activity and apply a trained inferential model or machine learning model that was trained based on a set of training data inputs obtained from one or more users while typing various words and phrases while keeping their hands on a surface. If the systems and methods detect that the user is now typing on their leg, a different model can be used to infer typing outputs with that model having been trained on data inputs from one or more users who typed various words and phrase on their legs. In this way, the systems and methods herein can apply the more appropriately trained model to produce more accurate outputs depending on the specific user activity.

In another embodiment, the user can be performing hand gestures and want to switch to a drawing mode. Because the inferential models trained to classify hand gestures accurately can differ from the inferential models trained to identify a user's drawing actions, it would be advantageous for the systems and methods to apply the appropriately trained inferential models to the activity upon which training data was used to generate the models. In another embodiment, a user could be performing discrete hand gestures such as snapping, pinching, etc. and can switch to performing continuous hand gestures such as making a first with varying levels of force, holding a pinch with various levels of force, etc. In another example, a user could be performing a series of index finger to thumb pinches and then want to switch to a series of middle finger to thumb pinches. In any of these examples, the disclosed systems and methods can implement a more appropriately trained inferential model to predict the user's intended action(s) in one input mode and use another more appropriately trained model to predict the user's intended action(s) in another input mode. The systems and methods disclosed herein can automatically detect a user's transition from one input mode or control scheme to another based on any one or more of the following: processed neuromuscular input data, spatio-temporal data from an IMU device (e.g., comprising an accelerometer, gyroscope, magnetometer, etc.), infrared data, camera and/or video based imaging data. The user can also instruct the systems and methods to switch between modes or control schemes based on neuromuscular input data (e.g., specific handstates, gestures, or poses) and/or verbal commands.

In certain embodiments, a neuromuscular armband or wristband can be implemented in the disclosed systems and methods. In other embodiments, the user can be utilizing the wrist band in combination with grasping a virtual or physical object including but not limited to a real or virtual remote control, gaming device, steering wheel, mobile phone, ball, pen/stylus, etc.

Using the systems and methods disclosed herein, a 2D linear model may perform well when the data inputs are from the subregion of a feature space where the model was trained. In some examples, such subregions may be identified within a feature space using a feature extraction and/or clustering technique. For example, a cluster of data points within a feature space may define a subregion, where the size of the subregion is estimated as the covariance of the data points and the distance from the center of the subregion is determined by the Mahalanobis distance of a point from the cluster of data points. Thus, if the Mahalanobis distance (or analogous metric) of an input places the input within the subregion, systems and methods described herein may apply an inferential model corresponding to the subregion to interpret the input. Conversely, if the Mahalanobis distance (or analogous metric) of an input places the input outside the subregion but within an alternate subregion, systems and methods described herein may apply an alternate inferential model corresponding to the alternate subregion to interpret the input.

In some examples, an input may not fall within any previously defined subregion of a feature space, for which there is an associated inferential model. In these examples, the systems and methods may handle the input in any of a variety of ways. For example, the systems and methods may identify a new default inferential model and apply the new default inferential model to interpret the input. In another example, the systems and methods may determine the nearest defined subregion (e.g., where "nearest" is determined according to Mahalanobis distance or an analogous metric) and apply the inferential model corresponding to the nearest subregion in the feature space to interpret the input. Additionally or alternatively, the systems and methods described herein may notify the user that the user's input is subject to misinterpretation and/or prompt the user to modify future input to comport more closely with a defined subregion of the feature space (e.g., by entering a training interface that provides feedback to the user regarding whether and/or how closely the user's input aligns with a currently selected input mode and/or with any input mode). In some examples, the systems and methods described herein may generate a new inferential model based on receiving inputs outside any defined subregion. For example, these systems and methods may prompt a user to perform actions intended by the user to represent specific inputs and then train a new model (or modify a copy of an existing model) to correspond to a new subregion defined by the user's prompted actions.

By applying appropriately trained models to differing neuromuscular data, the systems and methods described herein may improve the functioning of human-computer interface systems, representing an improvement in the function of a computer that interprets neuromuscular data as well as an advancement in the fields of interface devices, augmented reality, and virtual reality.

Features from any of the embodiments described herein may be used in combination with one another in accordance with the general principles described herein. These and other embodiments, features, and advantages will be more fully understood upon reading the following detailed description in conjunction with the accompanying drawings and claims.

By way of illustration, FIG. 33A shows an example feature space 33110. In one example, feature space 33110 may represent a mapping of a user's movements, including, e.g., wrist motion. As shown in FIG. 33A, most of the user's wrist motion may ordinarily stay within subregion 33120 of feature space 33110. In the case where the user's wrist motions are used as inputs for manipulating a 2D laser pointer, inputs that fall within subregion 33120 of feature space 33110 may allow for reliable control of the 2D laser pointer within the system.

When mapped data inputs fall outside of subregion 33120 of feature space 33110 (e.g., if the user squeezes their first during wrist rotation as opposed to using an open-hand-or even uses a more tightly held first rather than a more loosely held one) the performance of the 2D model for inferring wrist rotation outputs may deteriorate. With varying degrees of force that can accompany the making of a fist, the user may not perceive a slight change in the amount of force applied in making a first as being significant. However, an inferential model trained on certain parameters may vary in performance under certain situations and circumstances. In a feature space defined for certain events (e.g., a tightly held first versus a loosely held fist), the difference in mapped data points or vectors can be significant and thus affect system performance. In the example shown in FIG. 33A, when a user squeezes their fist, a cursor being controlled by the user through neuromuscular inputs to the system (e.g., with wrist rotation) may suddenly jump and no longer be positioned where the user intends it to be. This is can be referred to as an "event artifact," which can be attributed to the changes in force associated with a user's first being squeezed during wrist rotation versus it being in a relaxed state during wrist rotation. The user's squeezing of their first can cause a transition of data inputs from the EMG sensors to a different subregion of 2D space in the feature space, one outside of subregion 33120 where the 2D model has not been trained. Once outside subregion 33120 of feature space 33110, there may be still be some degree of control possible, but the model's output may be regarded as essentially undefined. Accordingly, any shifting in subregions of a feature space during user activity may be attributed to the user changing input modes or control schemes or may be attributed to the user staying within the same input mode or control scheme but changing a parameter in that input mode or control scheme.

The systems and methods disclosed herein may eliminate, mitigate, and/or otherwise address event artifacts by using a plurality of trained models under certain data collection scenarios. Various embodiments of the present disclosure may detect when the transitions between subregions in a feature space are occurring or have occurred. Transitions between subregions in a feature space may be detected in any of a variety of ways, thereby allowing the systems and methods described herein to determine whether the incoming data set is or is not well-suited for a particular trained inferential model. For example, the systems and methods described herein may detect transitions from one subregion to another calculating the Mahalanobis distance from a user input (or of a cluster of user inputs over a recent time period) to one or more subregions (e.g., the subregion corresponding to the most recently selected control mode along with other subregions representing other control modes). In various other examples, the systems and methods described herein may detect transitions from one subregion to another by using a binary classifier, a multinomial classifier, a regressor (to estimate distance between user inputs and subregions), and/or support vector machines.

Once a change in a subregion of a feature space occurs, the systems and methods described herein may employ a better-trained, and thus better-suited, inferential model to analyze the neuromuscular inputs and infer more accurate outputs. In this way, by employing the best-suited trained model for any given user activity, the system may implement full control schemes by recognizing poor performance using a specific model and calling on other more suited models as a function of where the mapped input data sets are landing in a feature space. Although the present disclosure describes improving control schemes by selecting one of multiple models for use, some implementations of model selection may be understood as an overarching model that contains and/or implements each of the multiple models. For example, an overarching model may functionally use the subregion within which an input falls as a key feature in determining how other characteristics of the input will be interpreted. In some examples, multiple models may be blended together by computing blending or mixing coefficients that indicate a level of trust or weight to give to each candidate model for a given input.

As described above by way of example in connection with FIG. 33A, a user could be performing the previously described wrist 2D movement with their first squeezed. By way of illustration, FIG. 33B shows the feature space 33110 of FIG. 33A with a transition 33230 from subregion 33120 (where the user is moving their wrist while their first is loose) to a subregion 33232 (where inputs are observed when the user is moving their wrist while their first is squeezed). A first squeeze could be used for a discrete/instantaneous event (e.g., to engage or disengage a particular feature within a given application), as well for a continuous/hold event (e.g., to maintain activation of a particular feature within a given application). In the case of a continuously held event, inputs (e.g., involving 2D movements of the wrist) that may otherwise normally fall within subregion 33120 may fall instead within subregion 33232.

When a set of inputs lies within a subregion (such as subregion 33232) that differs from another subregion (such as subregion 33120), in light of this difference, an inferential model previously trained for subregion 33120 may not provide accurate outputs for the set of inputs that fall within subregion 33232. In certain embodiments of the present disclosure, a new inferential model may be trained on data that falls within subregion 33232, and systems described herein may use that new inferential model whenever the system detects that data is being generated from the user in the vicinity of subregion 33232. Accordingly, the disclosed systems can determine which models to employ, and when to employ them, to exhibit the most accurate level of complete control across different input modes and control schemes. In certain embodiments, disclosed systems may determine the distance(s) between the various subregions in the feature space (e.g., subregions 33120 and 33232) and may blend the outputs of the two models together to get an output that is invariant to one or more parameters (e.g., a 2D pointer output that is invariant to a first squeeze during performance of the 2D movements). For example, inputs with a loose first may provide a blend factor of (1, 0), directing the system to rely on the inferential model that was trained on (or otherwise adapted for) wrist movements with a loose fist. Similarly, inputs with a squeezed first may provide a blend factor of (0, 1), directing the system to rely on the inferential model that was trained on (or otherwise adapted for) wrist movements with a squeezed fist. Inputs that fall between subregions 33120 and 33232 (e.g., in terms of Mahalanobis distance) may provide a blend factor of (1–a, a), where a indicates the proportion of the distance of the inputs from subregion 33120 as compared to the proportion of the distance of the inputs from subregion 33232, directing the system to partially rely on each inferential model (or to combine the outputs of both inferential models to yield a final output). However, inputs that are far from both subregions 33120 and 33232 may yield a blend factor of (0, 0), directing the system to rely on neither the inferential model associated with subregion 33120 nor the inferential model associated with subregion 33232.

Accordingly, in certain embodiments, the system and methods disclosed herein can allow a user to exhibit 2D control with the same amount of precision and accuracy irrespective of the state of the user's hand (e.g., whether the user's hand is in a closed or open state). In other embodiments, the disclosed systems and methods can afford a user better control when selecting from one or more options presented in one or more locations within a virtual or on-screen 2D map. For example, different options can be presented to the user on the virtual or on-screen visualization, and the user can navigate to those options using 2D wrist rotation and select from the options by performing another hand gesture such as clenching the fist.

Further to the embodiments discussed herein, a 2D wrist rotation model may be trained using a loose first while making the wrist rotations. The subregions within the feature space can be determined and analyzed in this embodiment as follows. In a first step, the system may collect data, e.g., tangent space input features, while the user is using a loose first to train a 2D model, which may have previously been generated as a generalized model based on various users using a loose first during performance of 2D wrist movements. In this step, the user may be prompted make sure the unit circle is properly traversed and both fast and slow motions are used. By way of illustration, FIG. 33C shows an example graphical user interface for online training of an inference model for 2D movement via wrist rotation. As shown in FIG. 33C, in a state 33302, the graphical user interface includes a circle 33310 for a cursor 33320 to traverse. As the user rotates their wrist clockwise, cursor 33320 traces a path 33322 along circle 33310. In a state 33304, as the user rotates their wrist counterclockwise, cursor 33320 traces a path 33324 along circle 33310.

In addition to training with a loose fist, a 2D wrist rotation model may be trained using a squeezed first while making the wrist rotations. For example, the system may collect data, e.g., tangent space input features, when the user makes a squeezed first to perform the same 2D training model as above. As discussed above, the user may be prompted to get a wide range of wrist motions that would cover unit circles and include both fast motion and slow motions.

After collecting data as described above, systems described herein may analyze the data. For example, for each data set (i.e., the data collected with a loose first and the data collected with a squeezed fist), the systems may compute the mean and the covariance of the data points. Additionally or alternatively, the systems may analyze the distances between data points using any of a variety of techniques, including: (i) a hyperplane of control; (ii) a one-class support vector machine with a Gaussian kernel that can distinguish between being in and out of the target region(s) in the feature space, as well as a distance of how far the data points are from the target region(s) for any given model; (iii) placing a margin between various data clusters and determine a blending factor based on signed distance to the margin, etc.; (iv) training neural networks to identify placement (or lack thereof) within the data sets and/or to distinguish between the data sets; and (v) performing a regression to model the data sets.

As an illustration of the difference in neuromuscular input data for wrist rotation between loose-fist and squeezed-fist scenarios, FIG. 33D shows a plot 33400 comparing the distribution of data points used for training a loose-fist model and data points used for training a squeezed-fist model. As shown in FIG. 33D, the Mahalanobis distances of loose-fist data points from the mean of the loose-fist cluster are consistently low, whereas the Mahalanobis distances of squeezed-fist data points from the mean of the loose-fist cluster are significant. As can be seen in FIG. 33D, the two distributions vary statistically and/or structurally. The disclosed systems and methods may leverage this difference in the distributions to implement full control schemes using various inferential models.

While, for simplicity, the discussion above has focused on one or two subregions within the feature space, in various examples there may be more than two subregions in the feature space (e.g., each with a corresponding inferential model trained on data points from within the respective subregion). For example, as described above in connection with FIGS. 33A and 33B, a user could be performing wrist 2D movement with their first squeezed instead of loose. Likewise, a user could be performing the previously described wrist 2D movement with their thumb pressed against the fist. By way of illustration, FIG. 33E shows the feature space 33110 of FIGS. 33A-33B with a transition 33540 from subregion 33120 (where the user is moving their wrist while their first is loose) to a subregion 33542 (where inputs are observed when the user is moving their wrist while their thumb is pressed). A thumb press could be used for a discrete/instantaneous event (e.g., to engage or disengage a particular feature within a given application), as well as for a continuous/hold event (e.g., to maintain activation of a particular feature within a given application). In the case of a continuously held thumb press event, inputs (e.g., involving 2D movements of the wrist) that may otherwise normally fall within subregion 33120 may fall instead within subregion 33542.

The transitions between subregions as shown in FIG. 33E can be interpreted as discrete or unique events or different continuous events. For example, a discrete event can be a quick transition between regions and then back again, and a continuous event can include a scenario where the data collected lingers within a defined region of the feature space. In certain embodiments, the relationship between subregions within the feature space and interpretable representations of the feature space is utilized to implement the disclosed system and methods herein. In certain embodiments, the disclosed systems and methods map out subregions in the feature space and provide feedback to a user about which subregions the processed neuromuscular input data is residing in or traveling between.

In certain embodiments, the systems and methods disclosed herein allow for full control schemes by implementing blended linear functions. For example, the disclosed systems and methods can blend a "loose fist" 2D linear model and a "squeezed fist" 2D linear model as shown in Equation (1) below:

$$y = (1 - \alpha(x))W_{loose}x + \alpha(x)W_{squeezed}x \tag{1}$$

which can be rearranged as shown in Equation (2) below:

$$y = W_{loose}x + \alpha(x)\,(W_{squeezed} - W_{loose})x \qquad (2)$$

or as shown in Equation (3) below:

$$y = W_{loose}x + \alpha(x)\,W_{correction}x \qquad (3)$$

The second term on the right-hand side of Equation (3) can be interpreted as a correction which happens whenever the user exits the "loose fist" subregion for the collected data inputs in the feature space and moves towards the "squeezed fist" subregion.

In certain embodiments, systems described herein calculate the blending function (i.e., $\alpha(x)$) and determine how much of the correction to apply, depending on where the input or inputs are within the feature space. In certain embodiments, the correction to be applied can be learned from data inputs and/or can be computed geometrically by projecting the action along the vector that connects the mean of the "loose fist" distribution to the mean of the "squeezed fist" distribution.

In another embodiment, the system and methods disclosed herein can employ one or more "contaminated" nonlinear models. Such a process may provide extra model capacity by first learning a linear model and then teaching a non-linear model to emulate the linear one. Once that is accomplished, the systems and methods disclosed herein can exploit the extra capacity in the nonlinear model to make it robust to the multiple regions in the feature space and transition between them. In some embodiments, the nonlinear model could be a neural network or any other model—e.g., a blended linear model in which the existing linear model is held fixed, but extra capacity is added by learning the blending function and corrections to some baseline model.

In various embodiments, the system and methods disclosed herein can adapt their data interpretations by turning off data input interpretations when certain data is not desired (e.g., not deemed suitable for a given inferential model). For example, if the system detects that the user is generating inputs that fall within a subregion of feature space not intended or desired for that given activity, the system can ignore those data inputs until they fall back within the subregion of interest in the feature space.

In some embodiments, the systems and methods described herein relate to processing, analyzing, visualizing, and training users based on neuromuscular signal data (e.g., sEMG data) obtained in a high-dimensional feature space and presenting that data in a lower dimensional feature space (e.g., two dimensional (2D) latent space). The systems and methods described herein may comprise training users via a visual interface of the latent space and presenting a mapping of detected and processed neuromuscular signal data. Using the described systems and methods, a user's performance (and a computer model's detection of that performance) can be improved for certain handstate configurations or poses as detected by one or more inferential models. Using a feedback loop, the user's poses can be more accurately classified by a machine control system. In certain embodiments, the system can further comprise a closed loop human-machine learning component wherein the user and computer are both provided with information regarding the received and processed neuromuscular signal data and a 2D latent space with latent vector plotting of the neuromuscular signal data. This approach allows the user to adjust their performance of handstate configurations (e.g., poses and gestures) and for the computer to more accurately classify the user's handstates into discrete poses and gestures based on one or more inferential models.

As discussed above, the systems and methods disclosed herein can provide feedback to the user regarding a feature space and how plotted vectors or data points within that feature space are being mapped. The feedback can come in any appropriate form, including but not limited to visual, haptic, and/or auditory feedback. The plotted points can be generated based on processed neuromuscular signal data. The neuromuscular signal data can be collected and processed during various time windows, as set by the system or the user for the task at hand. The plotted vectors or data points can be visually presented to the user and defined subregions within the feature space can be presented as well. The defined subregions in the feature space can correspond to subregions where a particular inference model produces the most accurate output(s) for processed neuromuscular data as inputs to the model. In an example embodiment, the user can be performing 2D control of a virtual cursor on a screen and may want to switch to various hand gestures to control the machine system. While the user is performing the 2D control via wrist rotations, they can visualize the subregion of the feature space into which their mapped vectors are falling. Once the user switches to performing a hand gesture (e.g., a finger pinch), the user can visualize the new subregion of the feature space into which their mapped vectors are now falling.

In some embodiments, the systems and methods described herein relate to detecting and processing a plurality of neuromuscular signal data from a higher-dimensional feature space into a lower-dimensional feature space including, but not limited to, a 2D latent space. In certain embodiments, a user receives feedback (e.g., in real-time or close to real-time) about how their neuromuscular data (sEMG data) is mapping onto or being presented or plotted within the lower-dimensional feature space, and how a machine learning inferential model is using position(s) in that the lower-dimensional feature space to extract event, gesture, or other control signal information. In one embodiment, visual feedback can be presented to the user such that the user can adjust neuromuscular activity and receive immediate feedback about how that change in output is reflected in the feature space mapping and how the machine learning inferential model is classifying certain handstates, events, poses, or gestures within the lower-dimensional feature space.

In certain embodiments, an events model that has been trained across multiple users (e.g., a generalized model) can be implemented to process and classify neuromuscular signal data (e.g., sEMG data) from a user into discrete events. The generalized model can comprise a generated feature space model including multiple vectors representing processed neuromuscular signal data. Such neuromuscular signal data can be acquired from users using a wrist/armband with EMG sensors as described herein. The vectors can be represented as latent vectors in a latent space model as further described below.

In certain embodiments, the neuromuscular signal data inputs from a user can be processed into their corresponding latent vectors, and the latent vectors can be presented in a lower-dimensional space. The various latent vectors can be mapped within latent classification regions in the lower-dimensional space, and the latent vectors can be associated with discrete classifications or classification identifiers. In some embodiments, each latent vector may include two values that can be mapped to x and y coordinates in a 2D visualization and represented as a latent vector point in the 2D visualization. Such a latent representation of processed neuromuscular signal data may provide useful information and may prove more informative for certain data sets compared to larger or more dimensioned vector spaces representing the neuromuscular signal data. For example, using the disclosed systems and methods, a user can be presented with one or more latent representations of their neuromuscular activity as feedback on a real-time basis using a 2D mapped visualization, and the user can adjust behavior and learn from the representations to generate more effective control signals to control, for example, a computing device. Providing a user with immediate feedback allows the user to understand how their neuromuscular activity is being interpreted by the machine model. The discrete classifications in the latent space can be defined and represented by the system in various ways. The latent vectors can correspond to various parameters, including discrete poses or gestures (e.g., fist, open hand), finite events (e.g., snapping or tapping a finger), and/or continuous gestures performed with varying levels of force (e.g., loose first versus tight fist). As described herein, the disclosed systems and methods can allow for a personalized and robust classification of a data set collected from a user during performance of any one or more actions corresponding to a desired set of parameters.

In an embodiment that involves classification of discrete user hand poses or gestures, processed neuromuscular signal data can be represented and visualized in a 2D latent space with latent vectors. The latent space can be generated such that any higher dimensioned data space can be visualized in a lower-dimensional space, e.g., by using any suitable encoder appropriate to the machine learning problem at hand. These encoders can be derived from various classes of problems, including auto-encoding, simple regression or classification, or other machine learning latent space generation techniques. In certain embodiments, the encoder(s) can be derived from a classification problem (e.g., classifying specific hand gestures) and a neural network can be trained to discriminate a finite number of poses of the hand (e.g., seven different poses of the hand). In this embodiment, the latent representation can be constrained to a lower-dimensional space (e.g., a two-dimensional space) before generating the actual classification of the data set. Any suitable loss function may be associated with the neural network, provided that the loss function remains constant across the various mappings in the latent space and classifications of processed neuromuscular input during any given user session. In one embodiment, the network used to generate the latent space and latent vectors is implemented using an autoencoder comprising a neural network and has a network architecture comprising a user embedding layer followed by a temporal convolution, followed by a multi-layer perceptron in order to reach the two-dimensional latent space. From the two-dimensional latent space, latent vectors can be mapped to classification probabilities for the seven classes via a final linear layer. As used herein, a "user embedding layer" comprises a vector unique to each user that defines a user-dependent transformation intended to adapt the model to the user's unique data characteristics (e.g., unique EMG data patterns for certain gestures performed by a user). The addition of such a unique vector can increase the reliability of the inferential model. This embedding layer can be determined via one or more personalized training procedures, which can tailor a generalized model by adjusting one or more of its weights based on processed EMG data as collected from the user during the performance of certain activities.

FIGS. 33F and 33G show example plots that are generated from collected and processed user neuromuscular data and that represent 2D visualizations of latent vectors representing classifications of users' hand poses. The plots represent various latent vector points and latent regions. In an exemplary embodiment, data was collected from 6 subjects during a session using a neuromuscular armband as disclosed herein. The latent vector points and plots generated for the 6 subjects (e.g., subjects 0-5) based on a generalized model are presented in the top rows of FIG. 33F and FIG. 33G. Each of the 6 subjects performed one of seven hand poses sequentially, namely: (1) a resting hand (the active null state); (2) a closed fist; (3) an open hand; (4) an index finger to thumb pinch ("index pinch"); (5) a middle finger to thumb pinch ("middle pinch"); (6) a ring finger to thumb pinch ("ring pinch"); and (7) a pinky finger to thumb pinch ("pinky pinch"). The EMG signal data associated with those hand poses was collected, processed using a generalized model trained from data acquired from multiple users, and associated latent vectors were displayed onto a 2D representational latent space as shown in the top rows of FIG. 33F. Each of the seven classifications of poses can be seen based on different coloring in the 7 latent spaces. After the users performed the gestures using the generalized model, each of the 6 subjects underwent a guided training session where they were instructed to perform each of the seven poses in sequence over several repetitions, and EMG signal data was collected and processed to personalize classification models to better detect the specific user's poses. The latent vector points after training are shown in the bottom rows of FIG. 33F and FIG. 33G. The bottom rows of FIG. 33F and FIG. 33G represent latent vector points generated after one session of personalized training.

As can be seen in FIGS. 33F and 33G, the sizes of the latent spaces vary across users. After one session of personalized training, the latent spaces representing the seven classifications can be visualized as more uniform in size and the latent vectors can be seen as being appropriately pushed towards the right pose classifications (e.g., subjects 2 and 3). As reflected in the latent space visualizations, personalized training enables more uniformly sized classification zones. With more uniformly sized zones in the latent space, a user of the armband can better visualize and fit their mapped neuromuscular activity reliably in a classification zone as intended (as further described herein).

In some embodiments, the mapping into latent space positions for the various classifications can vary between individuals and between personalized models for a particular individual. The described systems and methods provide solutions to account for this variability across individuals and between personalized models for a given individual. In certain embodiments, real-time feedback can be presented to the user so the user can adjust their behavior to ensure that the latent vectors are mapped more closely together and/or within a defined portion of the latent space. This can allow the user to exert more accurate control over the machine whether they are using a generalized machine learning model or a personalized model. Such an embodiment with visual and other types of sensory feedback for improving user-machine control is discussed further below.

In other embodiments, visualizations of mapped latent vectors can be used to determine how effective a generalized model may be performing for any given user. If, for example, a user is performing a gesture repeatedly with the same amount of force, and the generalized model is mapping the vectors across a wide range of the latent space or region or within only a very small range of the latent space or region, then the generalized model may not be working well for that specific user in terms of output accuracy. In that instance, the systems and methods described herein would indicate to the user that they should train another model to better represent their neuromuscular activity in the machine control scheme. Using the described systems and methods, one can infer a model is working well for a specific user if the latent vector regions are clearly separable in the latent vector space.

In certain embodiments, the systems and methods disclosed herein can be used for error diagnosis for a data set. For example, the disclosed systems and methods can be used to analyze and understand that a particular collected data set (e.g., processed EMG signal data) has bad metrics associated with it. By way of an exemplary embodiment, EMG signal data was collected and processed from a subject performing the seven poses as described above, either with or without rest between poses. The processed data is represented and depicted in FIG. 33H. Plot 33802 represents latent vectors associated with user rest between poses and plot 33804 represents latent vectors associated with no rest between poses.

As seen in FIG. 33H, as compared to the training and validation subjects from the same experiment, this dataset has a very small domain in the projected space, and further that the rest class contains a great deal of information. Given that the latent vectors are being mapped into a very small domain in FIG. 33H, it can be deduced that the specific model used for that person was not optimal for that individual and that another model can be tried for that individual to improve accuracy. Further, if this phenomenon was observed across multiple users, then one can deduce that the model is not performing well across users and the model therefore needs to be inspected further. In certain embodiments, this 2D visualization can be systematically generated across users and/or across sessions to systemically monitor model performance for a given user or a set of users.

To visualize how personalization of poses using a training module affects a low-dimensional model as generated according to an embodiment, visualizations shown in FIG. 33I can be generated. Plot 33902 represents a latent vector representation using a generalized pose model. Plot 33904 represents a latent vector representation using a personalized pose model. Plot 33906 represents a latent vector representation using the generalized model without rest between poses. Plot 33908 represents a latent vector representation using the personalized model without rest between poses.

As can be seen in FIG. 33I, the 2D model provides useful insight into how the system is classifying the various user poses. As can be seen, this pathology in the representation as viewed with the generalized model appears to be related to poor personalization. In this particular example, one can deduce that the model is not performing well for this specific user, and that the model may have been inadequately trained or trained on an improper data set. Further, one can rule out any user behavioral errors during performance of the tasks based on the narrowly defined region in which the latent vectors were falling. That the model congregated data points into a more concentrated region suggests the model is deficient in some respect. Such information can be used to reassess the sufficiency of the model, including by looking at the underlying data quality fed into the model and possibly diagnose any underfitting or overfitting of data by the model.

In another embodiment, the systems and methods described herein comprise an interactive feedback loop to provide feedback to the user. The system and methods can also comprise a closed loop human-machine learning configuration, wherein regions of a 2D latent space are defined and associated with certain classifications (e.g., hand poses or gestures), finite events (e.g., snapping or tapping a finger), and/or continuous gestures performed with varying levels of force (e.g., loose first versus tight fist). In various embodiments, the system can provide visual feedback to the user during a user's performance of activities as they are sensed in real-time through neuromuscular EMG sensors. For example, if the user is making an index finger to thumb pinch, the system can present a user interface showing a latent space representation of that gesture. As the user makes each of the discrete pinches, a vector associated with that activity can be plotted as a data point on the screen. The various regions of the latent space can be labeled so that the user can identify the regions and associate them with the activities. In certain embodiments, the various regions of the latent space can be labeled with text or images that show the gesture in the region. For example, each region can illustrate a different finger pinch or handstate configuration. Alternatively, each region can be labeled using a color-coded legend shown to the side of the latent space visualization or any other legend or key associated with specific finger pinches and handstate configurations. In certain embodiments, the user can visualize their previous gestures more saliently in order to track their progress. For example, more recent data mappings can be shown in different colors (hues and saturations, opacity levels or transparency levels, etc.) or with special effects or animations (e.g., comet trails, blinking/flashing, blinds, dissolving, checkerboxes, sizing alterations, etc.). Certain embodiments can also include auditory or haptic feedback in addition to visual feedback. Such embodiments can include auditory sound effects or haptic feedback to designate the various classifications or a transition from one classification to another (e.g., beeps or vibrations for every single mapped point or only when a mapped point goes into another latent region based on the previously mapped region). In one embodiment, if a user is performing a first gesture and a second gesture is mapped to a region in the latent space adjacent to the region of the latent space associated with the first gesture, the system can present a visual indicator showing the user that their data mappings are getting close to the adjacent region or are starting to fall within the adjacent region (e.g., highlighting a boundary between two latent regions). In various embodiments, the latent regions for the visual display can be assigned using a variety of labeling techniques, which include but are not limited to arbitrary labels; selectable or modifiable labels that the user can toggle through; visual depictions, logos, or images; slightly visible or invisible labels associated with auditory and/or haptic feedback or other types of sensory feedback. The user may toggle through or select from various labels by providing neuromuscular input (e.g., snapping, flicking, etc.) and/or voice input (e.g., oral commands) into the system. In certain embodiments, the user can assign custom labels either before or during mapping of the latent vector points.

In certain embodiments, if the user repeatedly performs an index finger pinch and the user notices that the visualization displays points for each of the index finger pinches in a latent region associated with a different classification (e.g., a pinky finger pinch), the user can perform model personalization based on that specific gesture (or a combination of gestures) to better personalize their model and more accurately detect that specific gesture (or a combination of gestures).

In an embodiment where the user is trained using the systems and methods described herein, the latent regions can be labeled based on the expected hand gesture to be classified. For instance, the latent regions may be labeled as "Index Pinch," "Middle Pinch," etc., as shown, for example, in FIG. 33J. FIG. 33J depicts a labeled latent space with hand pose classifications and vectors represented as data points during user training.

As the user makes a middle finger to thumb pinch, data point 331010 circled in FIG. 33J can be displayed. If the user performs the middle finger to thumb pinch again, data point 331020 circled in FIG. 33J can be displayed. If the user then performs an index finger to thumb pinch, data point 331030 circled in FIG. 33J can be displayed. In this way, the system can provide real-time visual feedback to the user as to how the system is analyzing, mapping, and classifying the various processed EMG signal inputs. If a user performs a middle pinch, but the data point appears in the index pinch latent space or appears close to the line separating the two latent spaces, the user can adjust how they are performing their index finger to thumb pinch and their middle finger to thumb pinch in order to adapt to the machine learning algorithm model being employed by the system. For example, if the user rotates their wrist slightly in either the clockwise or counter-clockwise direction, and the user sees how that wrist rotation affects the system's mapping and/or classification of their pinches, the user can adapt their wrist rotation as appropriate for the system to accurately identify the user's pinches.

In another embodiment, the system is able to detect and account for the user changing the position of their wrist while performing a gesture repeatedly. For example, a user can perform an index pinch and the system can properly classify the pinch and associate and plot a corresponding first latent vector that can be presented to the user. The user can instruct the system that it is going to perform the same gesture again. When the user performs the gesture again, they can do so with a slight modification (e.g., different wrist angle or degree of rotation). Based on the processed EMG data for that second gesture, the system can associate and plot a corresponding second latent vector that can be presented to the user. The system can quantify the distance between the first and second latent vectors and use that calculation to improve its ability to detect that specific gesture classification.

In another embodiment, the disclosed systems and methods can improve their personalization models by analyzing training data and remapping the classification boundaries within the latent space based on that training data. For example, if a user notifies the system about its next intended pose of an index pinch (or the system instructs the user to perform an index pinch), the system can modify the size and spacing of the latent spaces associated with index pinch (and the other classifications) if a mapped latent vector falls outside of the designated latent region for the index pinch classification.

In another embodiment, the user can repeatedly perform middle finger to thumb pinches while rotating their wrist in both clockwise and counterclockwise directions while aiming to maintain all of the associated data points within the defined middle finger to thumb latent space. As the user is performing this activity, the system can detect that pattern (either on its own in an unsupervised learning fashion or can be told that the user is going to perform the various rotations of the pinch in a supervised learning fashion) and learn to process the additional data associated with the wrist rotation and either account for or ignore certain data when it is trying to determine if the user is performing the middle finger to thumb pinch. In this way, the disclosed systems and methods can learn and generate more personalized models for each individual user.

In another embodiment, the user can be presented with an instruction screen instructing the user to perform only an index finger to thumb pinch, and the system can be instructed to recognize only index finger to thumb pinches and present those latent vectors to the user during the training session. If the system processes an EMG neuromuscular data input and initially associates a vector with that input that falls outside of the designated latent space for that classification, the system can learn from that EMG neuromuscular input and re-classify that input by associating it with the proper, designated classification. This can be an iterative process until the system reliably classifies the neuromuscular input data into the correct latent spaces and thus classifications. The degree of reliability of classification can be set by the user, e.g. 80% accurate hit rate, 90% accurate hit rate, etc.

As described above, the various modes of feedback to the user during a training session can vary depending on session training goals and how well the user is responding to the various types of feedback. In addition to the types of feedback mentioned above, additional types of feedback may be provided using extended reality systems and devices such as virtual reality and augmented reality devices. In these implementations, the latent visualizations can be presented to the user in an immersive or augmented environment where the training can be executed in a more user friendly and efficient fashion. Any of the above-described sensory indicators can be presented in virtual or augmented environments with the appropriate accessory hardware devices, including head-mounted displays and smart glasses.

In various embodiments, the subregions of the 2D latent representations as described with respect to FIGS. 33F-33J may correspond with differing subregions in a feature space as described with respect to FIGS. 33A, 33B, and 33E. Accordingly, systems described herein may apply differing inferential models to inputs falling in the various respective subregions of the 2D latent representations. Furthermore, in those embodiments in which subregions of the 2D latent representations are adjusted in response to user feedback, boundaries within the feature space delineating the use of differing inferential models may likewise be adjusted.

In another example embodiment, the systems and methods disclosed herein can be used to assess the efficacy of a particular inferential model. A user could be performing a hand gesture such as an index finger to thumb pinch and then can hold that pinch by rotating their wrist. In an embodiment, the visualization presented to the user can show mapped vectors or data points in a well-defined region with the pinching gesture when the wrist is in a neutral position, and as the user rotates their wrist while holding the pinching gesture, the mapped vectors can start to appear at the periphery of the previously well-defined region and/or may begin to exit the previously well-defined region altogether. The ability to visualize this transition from neuromuscular inputs that are interpreted well by the inferential model to neuromuscular inputs that are not interpreted well by the same inferential model would allow the user to modify their behavior to better fit the inferential model. In this example, if there is a specific range of wrist rotational angles that result in mapped vector points residing within the defined subregion, and other wrist rotational angles that result in mapped vector points falling outside of that sub-region, the user will know to stay within a certain range of rotation angles to best maximize their ability to control the machine via the inferential model. The ability to visualize the point(s) at which the quality of the outputs of the inferential model begin to deteriorate can be used to fine-tune the inferential model. For example, additional neuromuscular inputs can be fed into the inferential model to better train that model under certain scenarios and/or circumstances. Alternatively, the limits of any particular inferential model can be visualized such that the limits of the inferential model can be assessed and another inferential model can be trained on those data points that did not result in quality outputs from the first inferential model.

In certain embodiments, a plurality of inferential models can be trained on more limited sets of data. For example, inferential models can be trained and thus specialized and more accurate in detecting certain patterns of neuromuscular activity (e.g. forces, movements, Motor Unit Action Potentials, gestures, poses, etc.). Each of the inferential models can be implemented as part of the disclosed systems and methods herein such that accurate detection and/or classification of the neuromuscular activity can be improved by the selective application of one of the inferential models. In such an exemplary embodiment, there could be four inferential models trained on robust data sets to detect each of the finger pinches (e.g., one robust inferential model for the index finger to thumb pinch, another robust inferential model for the middle finger to thumb pinch, etc.). Depending on which pinch the user is performing, the systems and methods disclosed herein could select the appropriate inferential model into which to feed the processed neuromuscular data. Such a setup may result in more accuracy and greater flexibility in adding and updating models than a single model trained to detect all four hand gestures.

The various inferential models can be organized based on various input modes or control schemes. Such input modes and control schemes can comprise one or more of the following: user handstate configurations, hand poses, hand gestures (discrete and continuous), finger taps, wrist rotations, and varying levels of forces being applied during the performance of any one or more of the foregoing; typing actions from the user; pointing actions; drawing actions from the user; and other events or actions that can be performed by the user or detected by the systems disclosed herein.

In order to train and produce the various inferential models that correspond to the various input models and control schemes that the systems described herein may implement, systems described herein may gather user neuromuscular data. In some implementations, a user can be presented with an online training application. The online training application loads a Graphical User Interface (GUI) operatively coupled to the wearable system via, for example, Bluetooth. A user can select from a set of online training tasks provided by the GUI. One example of such an interface may be the interface illustrated in FIG. 33C. Although the discussion of FIG. 33C centered around control based on wrist rotation, a similar interface may be used for training other control schemes, such as the user controlling a cursor within a 2D plane with the tip of their finger. For example, users can wear the wearable device in their right wrist or arm and select a first training task in which users are prompted to drag a cursor within the interface along the edge of a circle with, for example, the tip of their finger on their right hand. The wearable device records EMG signals from users while they perform the training task such user data is saved to later train the user-specific machine learning model.

Likewise, users can select a second training task in which users are prompted via the GUI to move a cursor from within a circle to the edge of the circle as shown in FIG. 33K. For example, in state 331102 of the interface, a user may drag the cursor diagonally up and to the left to the edge of the circle. In state 331104 of the interface, a user may drag the cursor diagonally up and to the right to the edge of the circle. In state 331106 of the interface, a user may drag the cursor diagonally down and to the left to the edge of the circle.

As in the previously described training task, the wearable device records EMG signals from users while they perform the training task such users' data is saved to later train the user-specific machine learning model. Such user data is saved and used to train a user-specific inference model. The protocols described above can be used to train a user-specific inference model without the need of having predefined ground truth data. Thus, the ground truth data is generated via one or more of the available training protocols based on user-specific data. Accordingly, some memory resources can be saved by not relying and having in memory predefined ground truth data that may be larger than the user-specific data. In addition, the generation of the user-specific inference model may be perceived by users as near-instantaneous, i.e., the users can start using the armband device with the user-specific inference model rapidly after providing the user-specific data. In some instances, the training of the user-specific inference model can be executed in the user's local machine while in other instances, the training of the specific inference model can be executed remotely in the cloud.

Some individuals may be limited in the type of movements (or extent of forces) they can generate with a part of their body for any of various reasons including but not limited to: muscle fatigue, muscular atrophy, injury, neuropathy, repetitive stress injury such as carpal tunnel disorder, other peripheral nerve disorder (including degenerative nerve disorders such as multiple sclerosis or ALS), motor disorder of the central nervous system, chronic fatigue syndrome, deformity or other atypical anatomy, or other health-related reasons. Thus, the training and implementation of user-specific inference models for two-dimensional control are particularly well-suited to individuals whose motor system and/or anatomy is atypical. In some embodiments, a user-specific inference model may be periodically assessed to determine whether a user's ability to perform the movements and/or forces used to train (and/or retrain) a user-specific inference model are no longer feasible. This may occur, for example, if a user's injury resolves and his or her range of motion increases, thereby affecting the quality of the user-specific inference model trained during a time when the user's range of motion was reduced (e.g. due to injury). The systems and methods described herein may be configured to automatically detect the increased error rates of the model and cause a user interface to be presented to re-train the subject. Similarly, the systems and methods described herein may be further configured for a user who indicates that they have a neurodegenerative or muscular atrophy condition, thereby causing a user interface for retraining the user-specific inference model to be presented from time-to-time.

In some implementations a linear model can be used to implement the user-specific machine learning model. A linear model was selected because it is a good choice in cases in which the input data is such that the various classes are approximately linearly separated however, other models such as deep feed forward network, convolutional neural network, and recurrent neural network can likewise be selected.

Some human computer interfaces rely on generic inference models trained by aggregating data from multiple users. Such systems may reach an accuracy and performance plateau in part because the performance of generic models usually grows logarithmically with the number of training users. Moreover, in at least some cases it is unlikely that a certain type of generic model would reach the same accuracy and performance as a user-specific model. The examples provided below are in the context of a linear regression inference model. However, similar user-specific models can be implemented using various model architectures including but not limited to, a multilayer perceptron, a deep neural network (e.g., convolutional neural networks, recurrent neural networks, etc.), or other suitable type of prediction models.

In some instances, a linear model can be used to implement the user-specific inference model. A linear model is an adequate choice in cases in which the input data and the required model are approximately linearly related. Linear models describe one or more continuous response variables as a function of one or more predictor variables. Such a linear model can be implemented via linear regression, a support vector machine, or other suitable method or architecture. The hypothesis of multivariate linear model between n input variables and m output variables can be given (using vector and matrix notation) by Equation (4) below:

$$h\_\theta(x) = \Theta^\wedge T x + \theta\_0 \qquad (4)$$

Where:

$$\Theta = \begin{bmatrix} \theta_{11} & \cdots & \theta_{1m} \\ \vdots & \ddots & \vdots \\ \theta_{n1} & \cdots & \theta_{nm} \end{bmatrix} \in \mathcal{R}^{n \times m}, h_\theta, \theta_0 \in \mathcal{R}^m, X \in \mathcal{R}^n$$

It is noted that the above expressions correspond to multivariate linear regression models however, an analogous approach can be applied in the case of univariate linear regression. The cost function for multiple features is given by Equation (5) below:

$$J(\Theta, \theta_0; \{x_t, y_t\}) = \frac{1}{2T} \sum_{t=1}^{T} |h_\theta(x_t) - y_t|^2 \qquad (5)$$

The cost J can be minimized with respect to parameters $\Theta$ and $\theta\_0$. Various regularization schemes may be applied to optimize the model to enhance robustness to noise and procure an early stopping of the training to avoid overfitting of the inference model.

The above computations can be applied to build a user-specific machine learning model that takes as input EMG signals via the wearable device and outputs a set of numerical coordinates that can be mapped to a two-dimensional space. For example, the user-specific machine learning model can be used to predict, based on movements, hand poses, gestures, and/or forces, cursor positions within a graphical interface, effectively replacing a mouse, D pad, or similar peripheral devices. For example, a user may control a cursor rendered within a 2D graphical interface with the wearable device because the wearable device is configured (after the online training) to convert neuromuscular signals into X and Y cursor positions (control signals). Users can move the cursor within the 2D interface space by, for example, moving their fingers up, down, left, right, in diagonal, or other suitable movement as shown in FIGS. 33L-33N. The suitable movement may be idiosyncratic or unique to a user based on their comfort and preference.

Notably, non-linear models can be analogously implemented to incorporate additional features to the user-specific model, for instance clicking on a graphical object in two dimensional space (i.e. a button or hyperlink on a webpage), activating widgets, or other analogous operations that can be performed with additional functional interactive elements present in the user interface.

In some implementations, one or more various filters can be used to filter noisy signals for high precision and responsiveness. The filters can be applied to address temporal and/or spatial parameters of collected neuromuscular signals. For example, a one Euro filter can be implemented with a first order low-pass filter with an adaptive cutoff frequency: at low velocity, a low cutoff frequency (also known as corner frequency or break frequency) stabilizes the signal by reducing jitter. As the velocity of a control signal (e.g. for a cursor in 2D space) increases, the cutoff is increased to reduce lag. A one Euro filter can adapt a cutoff frequency of a low-pass filter for each new sample according to an estimate of a signal's velocity (second order), more generally its derivative value. The filter can be implemented using exponential smoothing as shown in Formula (6):

$$\hat{X_1} = X_1 \qquad (6)$$

$$\hat{X_i} = \alpha X_i + (1 - \alpha)\hat{X_{i-1}}, \, i \geq 2$$

where the smoothing factor $\alpha \in [0,1]$, instead of being constant, is adaptive, i.e., dynamically computed using information about the rate of change (velocity) of the signal. This aims to balance the jitter versus lag trade-off because a user may be more sensitive to jitter at low velocity and more sensitive to lag at high velocity. The smoothing factor can be defined as shown in Equation (7):

$$\alpha = \frac{1}{1 + \dfrac{\tau}{Te}} \qquad (7)$$

where T_e is the sampling period computed from the time difference between the EMG samples, T_e equals (T_i−T_(i−1)), and t is a time constant computed using the cutoff frequency $\tau = 1/(2\pi f\_C)$.

The cutoff frequency f_C is designed to increase linearly as the rate of change (i.e., velocity), increases as shown in Equation (8):

$$f_c = f_{c_{min}} + \beta |\hat{X_i}| \qquad (8)$$

where f_(C_min)>0 is the minimum cutoff frequency, $\beta>0$ is the velocity coefficient and (X_i)ˆ is the filtered rate of change. The rate of change $(X\_i)\hat{}$ is defined as the discrete derivative of the signal expressed in terms of Formula (9):

$$\dot{X}_1 = 0 \tag{9}$$

$$\dot{X}_1 = \frac{X_i - \widetilde{X_{i-1}}}{T_e}, i \geq 2,$$

The above may then be filtered using exponential smoothing with a constant cutoff frequency f_(C_d), which can be by default f_(C_d)=1. Accordingly, a one Euro filter can be implemented to enable users to control, for example, graphical objects rendered in a two-dimensional space at a velocity proportional to the velocity at which users perform gestures while wearing the armband system (e.g., moving a hand from left to right and vice versa). In other embodiments, the signal can be further subjected to a leaky integrator in order to keep the responsiveness of the signal to spikes in activity while controlling the amount of time the signal is high.

After the user-specific inference model is trained, the system can execute self-performance evaluations. Such self-performance evaluations can be executed by predicting via the user-specific inference model a set of positions or coordinates in a two-dimensional space using as input a set of neuromuscular signals (e.g., EMG signals) known to be associated with a predetermined path or shape. Accordingly, a fitness level or accuracy of the user-specific inference model can be determined by comparing the shape or path denoted by the set of positions or coordinates with the predetermined shape. When the denoted shape departs or deviates from the predetermined shape or path, it can be inferred that the user-specific inference model needs to be retrained or needs further tuning. The system then provides, depending on determined fitness or accuracy deficiencies, a subsequent training task to retrain or tune the user-specific inference model with user data acquired via the subsequent training task.

In some implementations, the self-performance evaluation can be executed while the user is, for example, interacting with an application or game. In such a case, the system can determine accuracy or fitness levels by establishing whether the model predictions match movements or actions expected to be performed by a user. For instance, if a user is expected to perform a gesture wearing the armband system (e.g., perform a gesture to move a cursor to an upper left quadrant in a two dimensional space) the system can determine whether the user-specific inference model predicts, based on the neuromuscular signals received from the armband system, whether the cursor is rendered in the expected position. In some instance, when the expected position is different from the actual position, the system can conclude that the user-specific inference model needs to be further tuned or retrained. As discussed above, the system can provide a subsequent training task for the user which may be designed to specifically retrain the aspects of the user-specific inference model for which errors above a threshold value were identified. New user neuromuscular data acquired by the subsequent training task can then be used to retrain or further tune the user-specific inference model.

In some embodiments, a graphical user interface is provided to calculate a set of metrics that can be used to evaluate the quality of the user-specific model. Such metrics can include path efficiency, stability, consistency, reachability, combinatorics, and other suitable metrics.

By way of illustration, FIG. 33O shows a visual representation of a path efficiency metric. In some implementations, path efficiency metrics can be computed by displaying on the GUI a path, for example, the arrowed path shown in FIG. 33O and instructing users to follow the path via movements including (finger movements, hand movements, wrist movements) while wearing an armband system. Such movements will cause a cursor indicator (circle) to move in the two-dimensional space defined by the GUI. Path efficiency can be measured as a function of the difference between the arrowed path and the path drawn by cursor indicator (while controlled by a user) on the two-dimensional space. In other words, a strong path efficiency metric value is associated with user movements that follow the displayed path while a weak path efficiency metric value is associated with user movements that depart from the displayed path. Other configurations different from the example provided in FIG. 33O are shown with respect to FIG. 33P below which shows different path forms.

In some embodiments, stability metrics can be computed by displaying on the GUI a circle shape divided in a predetermined number of sections or slices as shown in FIG. 33Q. In some instances, users can be prompted to hover a cursor over a particular circle section using the armband system that records neuromuscular data and inputs those data into a trained user-specific model for two-dimensional control. Stability metrics can be produced by measuring whether a user hovers over an indicated section. In some other instances, users can be prompted to hover over a particular circle section and hold the cursor in such a section for a duration that exceeds a predetermined amount of time. In such a case, stability is measured as a function of whether the user is able to hover over the indicated target section and whether the user held the cursor over the indicated circle section for the required time. FIG. 33R illustrates different GUI configurations that can be displayed for the user to compute stability metric values.

In some embodiments, reachability metrics can be computed by displaying on the GUI a circle shape divided in a predetermined number of sections as shown in FIG. 33S. In some instances, users can be prompted to hover a cursor over a particular circle section using the armband system. Reachability metric values can be computed by determining the number of indicated sections (i.e. sections of a slice at particular distances from the center of a target circle) a user is able to successfully reach. The example shown in FIG. 33S shows a circle divided into 64 sections of different sizes. For example, the circle can be analogously divided into fewer or more sections. It is understood that sections located closer to the center of the circle may be more difficult to be reached. Accordingly, a user's ability to successfully reach such sections represents a higher reachability metric value. FIG. 33T illustrates different GUI configurations that can be displayed for the user to compute different reachability metric values.

In some embodiments, combinatorics metrics can be computed by displaying on the GUI a circle shape divided in a predetermined number of sections as shown in FIG. 33U. In some instances, users can be prompted to hover a cursor over a particular circle section using the armband system and perform a hand gesture, or hand or arm movement, of by applying a force corresponding to a click. Combinatoric metric values can be computed as a function of whether a task has been accomplished successfully. For example, the user may receive a positive value when the user successfully navigates to the indicated section and performs a click. In another example, the user may receive a partial score value when the user only succeeds at hovering the cursor over the indicated circle section but does not succeed at clicking on the circle section.

In some implementations, a further level of granularity to compute the metrics described above can be implemented by providing cursor indicators that vary in size as shown with respect to FIG. 33V.

One skilled in the art will recognize that any target area shape and configuration of target sections within the shape may be used to assess stability, reachability, combinatorics, or another metric for effective two-dimensional control based on neuromuscular data and a trained user-specific inference model.

While the present disclosure largely represents the feature spaces described herein as two-dimensional for simplicity, feature spaces may have any suitable dimensionality based on any of a variety of variables. In one example, a dimension of the feature space may correspond to the activation of a muscle and/or to a pair of opposing muscles (which, e.g., may not typically be active simultaneously). For example, a continuous 1D output could be generated by two muscles, one which controls the positive dimension, and one which controls the negative dimension. By way of example, FIG. 34A illustrates a plot of a continuous 1D output representing the activation of a pair of opposing muscles. FIG. 34B illustrates a plot of the activation of each of the pair of the opposing muscles separately. Similarly, a continuous 2D output could may be generated with four muscles (two pairs of opposing muscles).

Continuing the example above, systems described herein may map and/or plot the samples of neuromuscular activity that generate the 1D signal to a feature space, as illustrated in FIG. 34C. This may result in a subregion of expected neuromuscular data (e.g., representing cases in which only one of the pair of muscles is activated at any given time). However, sometimes both muscles may be active at the same time (e.g., above a noise threshold). This may tend to happen during discrete or continuous events (e.g., such as those described earlier, when a user introduces an additional movement or gesture, whether transitory or sustained). By way of illustration, FIG. 34D shows a plot of example event paths through the feature space of FIG. 34C (i.e., the evolution of the neuromuscular data over time during an event). These event paths may be removed from the cluster of data points that represent the 1D signal. Accordingly, a single inferential model trained on the 1D signal may not handle events (such as the first squeeze or thumb press described earlier) well. Thus, systems and methods described herein may determine the subregion within which a particular input falls to determine what inferential model to apply to the input.

As discussed earlier, the systems described herein may use of a variety of metrics and methods to determine whether a particular input falls within a subregion. By way of illustration, FIG. 34E shows the event paths of FIG. 34D in comparison with the Mahalanobis distance from the cluster of inputs representing the original 1D signal. As may be appreciated from FIG. 34E, while the Mahalanobis distance does differentiate the data points of the original 1D signal from the data points of the event paths to a degree (e.g., data points with a Mahalanobis distance of 3.0 or greater are all data points on the event paths), some ambiguity remains (e.g., at a Mahalanobis distance between 1.5 and 3.0, there are both some data points from the original 1D signal and some data points on the event paths). As an alternative, FIG. 34F shows the event paths of FIG. 34D in comparison with a distance metric based on a negative log likelihood (NLL)

as determined by a Gaussian mixture model. As may be appreciated from FIG. 34F, almost all data points from the original 1D signal fall within an NLL of 1.0 and the remainder fall within an NLL of 2.2, whereas most of the data points on the event paths fall outside of these bounds. Another alternative is illustrated in FIG. 34G, which shows the event paths of FIG. 34D in comparison with a distance metric based on a support vector machine (SVM) score. Similar to the negative log likelihood of the Gaussian mixture model the SVM score successfully distinguishes many of the data points between the original 1D signal and the data points of the event paths.

Similar principles to those described above may be applied to feature spaces that describe two pairs of opposing muscles. If a user performs certain gestures (e.g., a "click" gesture), the user may activate all four muscles simultaneously, which may cause 2D output that previously assumed the activation of only one muscle in each pair at a time to become unpredictable (e.g., result in artifacts that deviate from the 2D output that would otherwise be expected). Accordingly, the systems described herein may detect when the artifacts occur and use a model trained to apply a correction function to the original 2D model. For example, if x represents the neuromuscular input, and the original 2D model is y=f2d(x), a model trained to account for artifacts may be y=f2d(x)+fcorrection(x), where fcorrection(x) is 0 when no event is occuring and is y0−f2d(x). Thus, the correction term in the model trained to account for artifacts may function as a detector for whether an input falls outside a default subregion of the feature space.

The correction function may be implemented in any suitable manner. In some examples, the systems described herein may use a radial basis function network to implement the correction function, which may have the advantage of being nonlinear, interpretable, and easy to train without requiring a large amount of data.

By way of illustration, FIG. 34H shows a plot of a 2D feature space (e.g., representing the possible activations of two pairs of muscles). A unit circle in FIG. 34H represents the set of expected data points. However, the circle with full artifacts represents the set of data points that may be observed during a particular event (e.g., the user making a "click" gesture). Artifact paths illustrate how inputs that would normally fall on the unit circle become projected onto the circle with full artifacts during an event. A correction function may therefore reverse such a projection, effectively mapping data points observed on the circle with full artifacts back onto the unit circle.

As mentioned earlier, in some examples a one Euro filter may be applied to filter noisy neuromuscular signals for high precision and responsiveness (e.g., before applying inferential models to the signals). In one example, a one Euro filter may be an exponential infinite impulse response filter with an adaptive time constant, as in Equation (10):

$$\tau = \frac{\tau_0}{1 + \alpha |\overline{\nabla x}|} \tag{10}$$

where is a lowpassed filtered version of

The one Euro filter may provide responsive output when activity varies a lot and stable output when activity is static (e.g., when tied to the movement of a cursor, the cursor may move responsively but remain stable when the user does not gesture for the cursor to move). However, the one Euro filter's timescale may be reduced when a large gradient is generated (e.g., when the user performs a clicking gesture), which may introduce instability in the cursor position. By way of illustration, FIG. 34I shows a plot 332500 of neuromuscular (e.g., EMG) data over time as a user performs various gestures. For example, at a time 332510 the user may be performing gestures to move a cursor around a circle. At a time 332520, the user may be performing clicking gestures while performing cursor movement gestures. FIG. 34J shows plot 332500 zoomed in to show the details of time 332510. As shown in FIG. 34J, click gesture events, such as events 332610 and 332620, may introduce artifacts into the neuromuscular data, possibly causing inferential models to misinterpret the neuromuscular data as involving cursor movement.

Accordingly, the systems described herein may gate the responsiveness of the one Euro filter responsive to events. For example, the one Euro filter may be modified by introducing a click-related gating variable h>0 and modifying the one Euro filter's adaptive time constant as shown in Equation (11):

$$\tau = \frac{\tau_0}{1 + \sigma(h)\left(\alpha|\overline{\nabla x}|\right)} \tag{11}$$

where $\sigma(h)$ is sigmoid given by a function such as that shown in Equation (12) by way of example:

$$\sigma(h) = (1 - g_{min})\frac{1 + \exp(-\beta\theta)}{1 + \exp(\beta(h - \theta))} + g_{min} \tag{12}$$

An illustration of a plot of an example $\sigma(h)$ is also shown in FIG. 34K. Thus, when h is larger than $\Theta$ the responsiveness of the filter is suppressed while when h is smaller than $\Theta$ the filter is equivalent to the one Euro filter. The gated filter may be referred to herein as a "two Euro filter."

In some embodiments, the systems and methods disclosed herein may use a regularized linear model trained on one-Euro-filtered features. For example, given neuromuscular data features x(t) and desired output y(t), some embodiments may search for a set of weights w* that minimize the mean squared error for the data set as shown in Equation (13):

$$w^\star = \operatorname{argmin}_w \frac{1}{2T} \sum_t \left(y_t - w^T x_t\right)^T \left(y_t - w^T x_t\right) \tag{13}$$

The solution to Equation (13) can be analytically found and w* can be defined as w*=C−1U.

In another embodiment, the systems described herein may use a ridge regression model. In this embodiment, a regularized version of linear regression where an additional term proportional to the L2-norm of the weights is added to the cost, as shown in Equation (14):

$$w^\star = \operatorname{argmin}_w \frac{1 - \rho}{2T} \sum_t \left(y_t - w^T x_t\right)^T \left(y_t - w^T x_t\right) + \rho\sigma^2 w^T w \tag{14}$$

where $\sigma 2$ is the mean second moment of the inputs x(t). This leads to Equations (15):

$$w^\star = \operatorname{argmin}_w \frac{1}{2} w^T \left[(1 - \rho)C + \rho\sigma^2 I\right] w - (1 - \rho)w^T U \tag{15}$$

$$w^\star = (1 - \rho)\left[(1 - \rho)C + \rho\sigma^2 I\right]^{-1} U$$

Where the matrix of $[(1-\rho)C+\rho\sigma 21]$ is called the shrunk covariance of C.

In another step, systems described herein may perform a linear regression using the shrunk covariance estimator of C, instead of C itself. This may be expressed in the optimization cost function as shown in Equation (16):

$$w^\star = \left[(1 - \rho)C + \rho\sigma^2 I\right]^{-1} U \tag{16}$$

Where this solution is proportional to the ridge regression solution as shown in Equation (17):

$$w^\star_{ridge} = (1 - \rho)w^\star_{shrunk} \tag{17}$$

Using the shrunk covariance solution may keep the output power high even when the regulatory parameter approaches 1.

Using the shrunk covariance 2D model, the systems and methods disclosed herein may apply a two Euro filter to enhance performance. The application of the two Euro filter using the shrunk covariance 2D model may provide outputs that filter out otherwise disruptive events, such as click events. By way of illustration, FIGS. 34L and 34M show plots of model predictions using a one Euro filter (shown in the dashed line) and the two Euro filter described above (shown in the solid line). During events 332810, 332812, 332814, 332816, 332818, 332820, 332822, 332824 (e.g., the user clicking), the predicted position of a 2D cursor based on the user's movements experience disruptions when using the one Euro filter (possibly causing the cursor to appear to jump or jitter). However, the two Euro filter effectively filters out the artifacts caused by these events.

A wearable device equipped with an array of neuromuscular sensors implemented to control and interact with computer-based systems and to enable users to engage with interactive media in unrestrictive ways is disclosed herein. The wearable system ("armband system") can be worn on the arm or wrist and used to control other devices (e.g., robots, Internet of things (IoT) devices and other suitable computing devices) and elements of interactive media based on neuromuscular signals that correlate to hand and arm movements, poses, gestures, and forces (isometric or other) recognized by the armband system. Some interactive tasks enabled by the armband system include selecting and activating graphical objects displayed on a two-dimensional space, moving graphical objects in a two-dimensional space, hovering over graphical objects, and other suitable interactions. Such interactions are based on hand and arm movements, poses, gestures, and forces recognized by the armband system.

The armband system recognizes arm and hand movements, poses, gestures, and forces via a user-specific inference model and maps such actions into a two-dimensional space, e.g., a computer screen, smart TV or other suitable device. The inference model can include one or more statistical models, one or more machine learning models, and/or a combination of one or more statistical model and/or one or more machine learning model. The inference model is user specific, because it is trained with data recorded from the user's neuromuscular activity and related movements and forces generated. The user neuromuscular signals are collected via the armband system. Thereafter, the inference model is trained with the collected user data to build a user-specific inference model. The user-specific inference model is adapted to the user and can handle user-specific characteristics or particularities associated with movements, poses, forces, and/or gestures performed by individual users. Accordingly, after training, the armband system is adapted into a personalized human computer interface.

The following describes exemplary devices, systems, and methods for controlling computing devices via neuromuscular signals of users according to at least one embodiment of the present disclosure.

Human computer interfaces (HCIs) often encompass and/or refer to the means and/or mechanisms with which humans communicate with, instruct, and/or control computers. Examples of such HCIs include, without limitation, mice, keyboards, touchscreens, touchpads, joysticks, styluses, buttons, handheld controllers, combinations or variations of one or more of the same, and/or any other suitable HCIs.

Some interactions between humans and computers may necessitate and/or call for the use and/or application of multiple HCIs simultaneously. In some examples, a user may switch back and forth between different HCIs to engage with interactive media presented and/or displayed on a computer. For example, a user may switch between using a mouse and using a keyboard multiple times during a single interactive media session. Moreover, as computing devices become more portable, the development of HCIs may become more complex due at least in part to design tradeoffs resulting from size constraints and/or mobility requirements of portable devices. Unfortunately, as the portability of computing devices becomes even more ubiquitous, traditional HCIs may become less desirable and/or convenient for users. The instant disclosure, therefore, identifies and addresses a need for additional devices, systems, and methods for controlling computing devices via neuromuscular signals of users.

As will be described in greater detail below, the various devices, systems, and methods described herein may involve the use of a wearable device capable of detecting and/or sensing neuromuscular signals traversing through a user's body. For example, a user may wear a smart wristband with multiple surface electromyography (EMG) sensors that detect and/or sense neuromuscular signals traversing the user's arm, wrist, and/or hand. In this example, the smart wristband may be communicatively coupled to a nearby computing device. In response to certain neuromuscular signals detected via the user's body, the smart wristband may direct the computing device to perform one or more actions that account for those neuromuscular signals.

Accordingly, the smart wristband may enable the user to engage with interactive media presented and/or displayed on the computing device in less restrictive ways than traditional HCIs. The smart wristband may be used to control certain elements of interactive media based at least in part on EMG signals that correlate to predefined states of one or more body parts of the user. The smart wristband may enable the user to direct the computing device to perform certain interactive tasks. Examples of such interactive tasks include, without limitation, map navigation, page browsing, gaming controls, flight controls, interactions with graphical objects presented on a display, cursor control, link and/or button selection, combinations of one or more of the same, and/or any other suitable interactive tasks.

In some implementations, a wearable device may facilitate web browsing based at least in part on configured and/or programed controls or commands. Such controls and/or commands may include and/or involve scrolling up or down a webpage, moving a cursor across a webpage, and/or clicking on one or more webpage elements. In one example, the wearable device may enable users to control web browsing interactions, thereby emulating controls and/or commands provided by traditional HCIs. In another example, the wearable device may also facilitate and/or emulate flight controls, such as pitch, yaw, roll, and/or throttle. Additional examples of such controls and/or commands include, without limitation, activating, selecting, pitching, rotating, rolling, and/or dragging visual objects, navigating, combinations of one or more of the same, and/or any other suitable controls and/or commands.

In some implementations, a wearable device may be used to transition between different mappings of body part states and responsive actions. For example, the wearable device may detect and/or sense certain neuromuscular signals traversing a user's body. In this example, those neuromuscular signals may correspond to and/or represent a specific state of one or more of the user's body parts. As a result, the wearable device may be able to detect and/or sense one or more positions, movements, forces, contractions, poses, and/or gestures made by those body parts of the user. One mapping may cause the wearable device and/or the target computing device to perform a certain action in response to the detection of a specific state of those body parts. However, another mapping may cause the wearable device and/or the target computing device to perform a different action in response to the detection of the same state of those body parts. The wearable device may enable the user to transition between those mappings via neuromuscular signals.

In some implementations, one or more states of the user's body parts may correspond to and/or represent control actions used to interact with a radial menu presented on a display. For example, a first pose may cause the wearable device to direct a computing device to display a radial menu for selection by the user. In this example, a wrist movement (e.g., rotation) may cause the wearable device to direct the computing device to select an item or option available in the radial menu. Additionally or alternatively, a finger pinch pose may cause the wearable device to direct the computing device to click a selected menu item. Further, an open hand pose may cause the wearable device to direct the computing device to close the radial menu.

In some examples, the terms "wearable" and "wearable device" may refer to any type or form of computing device that is worn by a user of an artificial-reality system and/or visual display system as part of an article of clothing, an accessory, and/or an implant. In one example, a wearable device may include and/or represent a wristband secured to and/or worn by the wrist of a user. Additional examples of wearable devices include, without limitation, armbands, pendants, bracelets, rings, jewelry, anklebands, clothing, electronic textiles, shoes, clips, headsets, headbands, head-mounted displays, gloves, glasses, variations or combinations of one or more of the same, and/or any other suitable wearable devices.

The following will provide, with reference to FIGS. 35A-35H and 36O-36P, detailed descriptions of various devices, systems, components, and/or implementations for controlling computing devices via neuromuscular signals of users. The discussion corresponding to FIGS. 35I-36M and 36R will provide detailed descriptions of exemplary neuromuscular signals, exemplary states of body parts capable of being detected via neuromuscular signals, and/or exemplary actions performed in response to the detection of such body part states. The discussion corresponding to FIG. 36N will provide detailed descriptions of exemplary transitions between different mappings of body part states and responsive actions. Additionally, the discussion corresponding to FIG. 36Q will provide detailed descriptions of an exemplary method for controlling computing devices via neuromuscular signals of users. Finally, the discussion corresponding to FIGS. 36R and 36S will provide detailed descriptions of types of exemplary artificial reality devices and/or systems capable of being controlled by neuromuscular signals of users.

FIG. 35A illustrates an exemplary wearable device 35102 capable of controlling computing devices via neuromuscular signals of users. As illustrated in FIG. 35A, exemplary wearable device 35102 may include and/or represent a set of sensors 35104(1)-(N) that detect and/or sense neuromuscular signals traversing the body of a user. In some examples, exemplary wearable device 35102 may also include and/or represent a processing device 35106 communicatively coupled to sensors 35104(1)-(N) and/or memory 35108. In such examples, memory 35108 may include and/or store one or more trained inferential models that determine amounts of force associated with the neuromuscular signals detected by the sensors 35104(1)-(N). Additionally or alternatively, memory 35108 may include and/or store computer-executable instructions that, when executed by processor 35106, cause processor 35106 to (1) identify an amount of force associated with the neuromuscular signals as determined by the one or more trained inferential models, (2) determine that the amount of force satisfies a threshold force value, and/or in accordance with the determination that the amount of force satisfies the threshold force value, (3) generate a first input command for an HCI system (such as HCI system 35200 in FIG. 35B).

In some examples, processing device 35106 may determine, based at least in part on those neuromuscular signals, a state of at least one body part of the user. Additionally or alternatively, processing device 35106 may generate one or more input commands for a separate computing system (not necessarily illustrated in FIG. 35A). Such input commands may account for the state of the user's body part.

In some examples, sensors 35104(1)-(N) may each constitute and/or represent any type or form of sensor capable of detecting and/or sensing neuromuscular signals via a user's body. In one example, sensors 35104(1)-(N) may include and/or represent one or more neuromuscular sensors and/or EMG sensors arranged circumferentially around wearable device 35102. Additional examples of sensors 35104(1)-(N) include, without limitation, mechanomyography (MMG) sensors, sonomyography (SMG) sensors, combinations or variations of one or more of the same, and/or any other suitable sensors. Any suitable number and/or arrangement of sensors 35104(1)-(N) may be applied to wearable device 35102.

In some embodiments, sensors 35104(1)-(N) may include one or more EMG sensors, MMG sensors, and/or SMG sensors as well as one or more auxiliary sensors that record auxiliary signals and/or information. Examples of such auxiliary sensors include, without limitation, inertial measurement unit (IMU) sensors, position-tracking sensors, microphones, imaging sensors (e.g., cameras), radiation-based sensors for use with radiation-generation devices (e.g., laser-scanning devices), heart-rate monitors, combinations or variations of one or more of the same, and/or any other suitable auxiliary sensors.

In some examples, sensors 35104(1)-(N) may be communicatively coupled to one another and/or to processing device 35106 by flexible electronics, connectors, and/or wiring. Additionally or alternatively, sensors 35104(1)-(N) may be integrated with and/or into an elastic band of wearable device 35102.

In some embodiments, the output of one or more of sensors 35104(1)-(N) may be processed, amplified, rectified, and/or filtered via hardware signal processing circuitry. Additionally or alternatively, the output of one or more of sensors 35104(1)-(N) may be processed, amplified, rectified, and/or filtered via signal processing software or firmware. Accordingly, the processing of neuromuscular signals may be performed in hardware, software, and/or firmware.

As illustrated in FIG. 35A, exemplary wearable device 35102 may also include one or more processors, such as processing device 35106. In some examples, processing device 35106 may include and/or represent any type or form of hardware-implemented processing device capable of interpreting and/or executing computer-readable instructions. In one example, processing device 35106 may access and/or modify certain software modules to facilitate controlling computing devices via neuromuscular signals of users. Examples of processing device 35106 include, without limitation, physical processors, central processing units (CPUs), microprocessors, microcontrollers, field-programmable gate arrays (FPGAs) that implement softcore processors, application-specific integrated circuits (ASICs), portions of one or more of the same, variations or combinations of one or more of the same, and/or any other suitable processing device.

As illustrated in FIG. 35A, exemplary wearable 35102 may further include one or more memory devices, such as memory 35108. Memory 35108 generally represents any type or form of volatile or non-volatile storage device or medium capable of storing data and/or computer-readable instructions. In one example, memory 35108 may store, load, and/or maintain one or more trained inferential models that perform certain tasks, classifications, and/or determinations in connection with controlling computing devices via neuromuscular signals. Examples of memory 35108 include, without limitation, Random Access Memory (RAM), Read Only Memory (ROM), flash memory, Hard Disk Drives (HDDs), Solid-State Drives (SSDs), optical disk drives, caches, variations or combinations of one or more of the same, and/or any other suitable storage memory.

In some examples, wearable device 35102 may include and/or incorporate a wearable band. For example, wearable device 35102 may include and/or represent a strap and/or band designed and/or dimensioned to at least partially encompass the user's wrist and/or arm. The strap and/or band may include and/or contain a variety of different materials. Examples of such materials include, without limitation, cottons, polyesters, nylons, elastics, plastics, neoprene, rubbers, metals, woods, composites, combinations or variations of one or more of the same, and/or any other suitable materials. The strap and/or band may be defined and/or formed in a variety of shapes and/or sizes with the aim of securing wearable device 35102 to the user's wrist and/or arm. In one example, the strap and/or band may include and/or represent one or more segments, links, and/or sections. Additionally or alternatively, the strap and/or band may be adjustable to provide a one-size-fits-most feature.

In some embodiments, wearable device 35102 may include and/or incorporate one or more additional components that are not represented and/or illustrated in FIG. 35A. For example, although not necessarily illustrated and/or labeled in this way in FIG. 35A, wearable device 35102 may also include and/or incorporate circuitry, transistors, resistors, capacitors, diodes, transceivers, sockets, wiring, and/or circuit boards, among other components.

In some examples, when wearable device 35102 is worn by the user, sensors 35104(1)-(N) may interface and/or make physical contact with the user's skin. In one example, wearable device 35102 may be communicatively coupled to a computing system (such as a virtual reality headset, an augmented reality headset, a laptop, a desktop, a smart television, a monitor, etc.). In this example, the user may put and/or place his or her body in a certain state and/or condition to control and/or modify the presentation or performance of the computing system. As the user puts and/or places his or her body in that state and/or condition, the user's body may generate and/or produce neuromuscular signals representative, indicative, and/or suggestive of that state or condition.

In some example, the neuromuscular signals may traverse and/or travel through the user's body. For example, the user may make a pose and/or gesture that generates neuromuscular signals that traverse down his or her arm toward the hand. In one example, one or more of sensors 35104(1)-(N) may detect and/or sense the neuromuscular signals as they traverse down the arm toward the hand. In response to detecting and/or sensing those signals, one or more of sensors 35104(1)-(N) may generate and/or produce data representative of those signals.

In some examples, those sensors may provide and/or deliver a version of the data representative of the detected neuromuscular signals to at least one processing device (e.g., processing device 35106, a processor incorporated in the computing system to which wearable device 35102 is communicatively coupled, and/or a processor incorporated in an intermediary communication link or dongle). This data may undergo certain processing and/or conversions prior to being provided and/or delivered to the processing device. Accordingly, the version of data provided and/or delivered to the processing device may be any derivation and/or processed representation of the output received from the sensors. Examples of this version of the data include, without limitation, raw data produced and/or output by the sensors, digital conversions and/or representations of analog signals output by the sensors, processed digital representations of signals output by the sensors, combinations or variations of one or more of the same, and/or any other suitable version of data representative of neuromuscular signals.

In this example, the processing device may analyze and/or evaluate the data representative of the neuromuscular signals to determine the state of one or more body parts of the user. For example, the processing device may implement a trained inferential model. The processing device may input and/or feed the data representative of the neuromuscular signals to the inferential model. From that data, the trained inferential model may then output and/or produce a classification that identifies and/or indicates the state of such body parts. Accordingly, the processing device may determine the state of such body parts based at least in part on the output of the inferential model.

Various states of the user's body parts may be discernible and/or detectable based at least in part on neuromuscular signals traversing the user's body. Examples of such body part states include, without limitations, relative positions of certain body parts, movements of certain body parts, forces applied and/or exerted by certain body parts, isometric contractions made by certain body parts, poses made by certain body parts, gestures made by certain body parts, activations of certain body parts (e.g., muscles), changes in activation of certain body parts, combinations of one or more of the same, and/or any other discernible or detectable states of such body parts.

In some examples, the processing device may be able to determine the amount of force produced and/or exerted by one or more body parts of the user based at least in part on the neuromuscular signals detected by sensors 35104(1)-(N). For example, from the data representative of the detected neuromuscular signals, the trained inferential model may output and/or produce an indication or measurement that identifies and/or specifies the amount of force exerted by those body parts. In response to determining the state of those body parts and the amount of force produced by those body parts, the processing device may generate one or more input commands for the computing system. Such input commands may account for the state of the user's body parts and the amount of force produced and/or exerted by those body parts.

In some examples, the processing device may cause the computing system to which wearable device 35102 is communicatively coupled to perform one or more actions mapped to the state of those body parts and/or the amount of force exerted by those body parts. For example, the processing device may direct the computing system to perform those actions by sending and/or providing those input commands to the computing system. In one example, the processing device may determine and/or identify one or more characteristics of those actions to be regulated in accordance with the amount of force produced by the user's body parts. In this example, the processing device may formulate the input command to account for the amount of force produced by the user's body parts such that the characteristics of those actions correspond to the amount of force produced by the user's body parts.

Various actions may be mapped to different states of the user's body parts. Examples of such actions include, without limitation, scrolling through a graphical user interface (GUI), selecting a visual element of a GUI, clicking on a visual element of a GUI, displaying a visual element in a GUI, drawing and/or painting a visual element on a GUI, moving a cursor displayed on a GUI, associating a cursor of the computing system with a visual element displayed in a GUI based at least in part on an updated position of the cursor relative to the visual element, providing a feedback indication (whether visual, auditory, and/or haptic) of an association made between a cursor of the computing system and a visual element displayed in a GUI, inputting data, modifying interface controls, navigating or scrolling a GUI, transitioning from one mapping to another, combinations or variations of one or more of the same, and/or any other suitable actions.

Similarly, various degrees of force may be mapped to and/or be commensurate with different characteristics of such actions. For example, one characteristic may include and/or represent the scrolling speed with which the GUI is scrolled. In one example, as the amount of force produced by the user's body parts increases, so too may the scrolling speed. Conversely, as the amount of force produced by the user's body parts decreases, so too may the scrolling speed.

As another example, one characteristic may include and/or represent the width of a virtual drawing instrument and/or a virtual paint brushstroke. In one example, as the amount of force produced by the user's body parts increases, so too may the width of the virtual drawing instrument and/or the virtual paint brushstroke. Conversely, as the amount of force produced by the user's body parts decreases, so too may the width of the virtual drawing instrument and/or the virtual paint brushstroke.

Various forms of feedback may be provided to the user as the computing system performs the actions mapped to the state of the user's body parts. For example, one feedback indication of an association made between the cursor of the computing system and a visual element of the GUI may involve and/or entail modifying one or more characteristics (e.g., color, size, transparency, shadow, font, animation, shape, fill, emphasis, orientation, animation, line type, and/or line width) of the visual element of the GUI. Another exemplary feedback indication of an association made between the cursor of the computing system and a visual element of the GUI may involve and/or entail adding, to the GUI, at least one further visual element that represents the association.

Associations may be made between the cursor of the computing system and the visual element for a variety of reasons. For example, the processing device and/or the computing system may determine that an updated position of the cursor is within a certain distance of the visual element of the GUI. In one example, the processing device and/or the computing system may identify the position of the visual element within the GUI and/or the position(s) of one or more additional visual elements within the GUI. In this example, the processing device and/or the computing system may determine that the updated position of the cursor is closer to the position of the virtual element than the additional virtual elements within the GUI. In response to determining that the updated position of the cursor is within the certain distance of the visual element, the processing device and/or the computing system may associate the cursor with the visual element (instead of, e.g., the additional virtual elements).

As another example, the processing device and/or the computing system may determine the speed at which the cursor moved or is moving within the GUI to reach the updated position. The processing device and/or the computing system may then associate the cursor with the visual element based at least in part on the speed at which the cursor moved or is moving to reach the updated position.

In a further example, the processing device and/or the computing system may detect a direction in which the cursor moved or is moving within the GUI to reach the updated position. The processing device and/or the computing system may then associate the cursor with the visual element based at least in part on the direction in which the cursor moved or is moving to reach the updated position.

In some examples, the processing device and/or the computing system may maintain one or more mappings between possible states of the body parts and responsive actions capable of being performed by the computing system. For example, the processing device and/or the computing system may maintain a first mapping between possible states of a body part and a first set of actions as well as a second mapping between possible states of the body part and a second set of actions. In one example, the processing device and/or the computing system may activate the first mapping and/or deactivate the second mapping such that one or more of the actions in the first set are performed in response to one or more detected states of the body part.

In some examples, the user may be able to switch between the mappings by changing the state of one or more body parts. For example, the user may make a pose and/or gesture with his or her hand. As the user does so, sensors 35104 (1)-(N) may detect and/or sense certain neuromuscular signals generated by the user's body in connection with the pose and/or gesture. In this example, the processing device and/or the computing system may determine the state of the user's body parts based at least in part on those neuromuscular signals.

In some examples, this state of the user's body parts may correspond and/or be mapped to a transition command and/or action that causes the processing device and/or the computing system to switch mappings. In such examples, in response to determining this state of the user's body parts, the processing device and/or the computing system may transition from one mapping to another mapping. For example, the processing device and/or the computing system may deactivate one mapping and activate another mapping. As a result of this mapping transition, the computing device may be configured and/or programmed to perform one or more actions assigned by the other mapping to the possible state of a body part in response to the subsequent detection of that body part state.

In some examples, the processing device and/or computing system may map any number of conditions to a single action. In these examples, to initiate performance of the action, the processing device and/or computing system may ensure and/or determine that all the conditions have been satisfied. For example, the processing device and/or computing system may map the rotation of the user's arm while making a first pose to navigating a radial menu in a certain direction. In this example, the user may be able to navigate the radial menu in that direction by rotating his or her arm while making a first pose. However, if the user rotates his or her arm without making a first post, the user's arm rotation may have no effect on the radial menu.

FIG. 35B illustrates an exemplary HCl system 35200 that includes wearable device 35102, an interface system 35220, and/or an application system 35230. In some examples, wearable device 35102, interface system 35220, and/or application system 35230 may each include an instance of processing device 35106 and/or memory 35108. In addition, HCl system 35200 may include one or more additional wearable devices capable of implementing and/or performing any of the same functionality as wearable device 35102. Accordingly, any of the tasks described above as being performed by wearable device 35102 in connection with FIG. 35A may additionally or alternatively be performed by interface system 35220, application system 35230, and/or any additional wearable devices included in HCl system 35200.

In some examples, wearable device 35102 may communicate with interface system 35220 and/or application system 35230. In such examples, when worn on the body of a user, wearable device 35102 may detect neuromuscular signals traversing the user's body via sensors 35104(1)-(N). Wearable device 35102 may record, store, and/or analyze those neuromuscular signals.

In some implementations, wearable device 35102 may record, store, and/or analyze auxiliary position, velocity, and/or acceleration information together with the neuromuscular signals. In such implementations, wearable device 35102 may perform analog processing (e.g., noise reduction, filtering, etc.) and/or analog-to-digital conversion of recorded neuromuscular signals. Wearable device 35102 may communicate with interface system 35220 via any suitable wireless technology, protocol, and/or signaling. In one example, wearable device 35102 may provide and/or transfer the recorded neuromuscular signals, features extracted from such signals, and/or commands or instructions based on such signals to interface system 35220 and/or application system 35230.

In some examples, interface system 35220 may receive the recorded neuromuscular signals, features extracted from such signals, and/or commands or instructions based on such signals from wearable device 35102. In one example, interface system 35220 may generate data, commands, and/or instructions for use or consumption by application system 35230. In another example, interface system 35220 may identify and/or determine the current state of a body part of the user by implementing and/or applying an inferential model. In this example, interface system 35220 may communicate and/or disclose the identified or determined current state of the user's body part to application system 35230. For example, interface system 35220 may provide the position, orientation, joint angle, force, movement, contraction, pose, and/or gesture information to application system 35230. Interface system 35220 may communicate with application system 35230 via any suitable wireless technology, protocol, and/or signaling.

In some examples, the state of the user's body part may include and/or represent a relative position, orientation, joint angle, force, movement, pose, or gesture of that body part. In one example, the state of the user's body part may describe a configuration of one or more segments in a musculoskeletal representation of that body part and/or the user's body. In this example, the musculoskeletal representation may model that body part and/or the user's body as a multi-segment articulated rigid body system. The musculoskeletal representation may also model certain joints that form the interfaces between the different segments and/or certain joint angles that define the spatial relationships between connected segments.

In the model, the spatial relationships between the connected segments may conform and/or be subject to human anatomical constraints. In some examples, the musculoskeletal segments may be modeled as rigid bodies. Additionally or alternatively, the musculoskeletal segments in the model may conform and/or be subject to inter-segment movements (e.g., a forearm modeled as a semi-rigid segment to account for the motion of the ulna and radius bones). In one example, position, orientation, and/or joint angle of the segments, as well as their respective time derivatives (e.g. linear or angular velocity or acceleration), may be described and/or modeled as one or more fixed coordinate systems.

In some examples, the state of the user's body part may include and/or represent the amount of force applied by and/or to that body part. For example, wearable device 35102 may measure, identify and/or determine the amount of linear force and/or rotational (torque) force exerted by one or more segments of the musculoskeletal representation based at least in part on neuromuscular signals traversing the user's body.

Examples of such linear forces include, without limitation, the force of a finger or hand pressing on a solid object (e.g., a table), the force exerted when two segments (e.g., two fingers) are pinched together, variations or combinations of one or more of the same, and/or any other suitable linear forces. Examples of such rotational forces include, without limitation, the force created as segments in the wrist or fingers are twisted or flexed, the force created by twisting or flexing the user's arm or waist, variations or combinations of one or more of the same, and/or any other suitable rotational forces. In some embodiments, the state of the user's body part may include and/or involve pinching force information, grasping force information, and/or information about co-contraction forces between muscles represented by the musculoskeletal representation.

In some examples, the state of the user's body part may include and/or represent a pose made by the user's body and/or one or more of the user's body parts. In one example, a pose may indicate a static configuration and/or positioning of one or more body parts. In this example, the static configuration may describe the position of those body parts relative to one another. For example, a pose may include and/or represent clenching a fist, forming an open hand, statically pressing the user's index finger against the user's thumb, pressing the palm of one hand down on a solid surface, and/or gripping or holding a ball.

In some examples, the state of the user's body part may correspond to and/or represent positional information (e.g., segment coordinates, joint angles, or similar information) for a pose. Additionally or alternatively, the state of the user's body part may correspond to and/or represent an identifier assigned and/or specific to a pose (e.g., a parameter, function argument, or variable value).

In some examples, the state of the user's body part may include and/or represent a gesture made by the user's body and/or one or more of the user's body parts. In one example, a gesture may indicate a dynamic configuration of one or more body parts. In this example, the dynamic configuration may describe the position of those body parts relative to one another, the movement of those body parts relative to one another, and/or forces applied to and/or exerted by those body parts. For example, a gesture may constitute and/or represent waving a finger back and forth, throwing a ball, and/or grasping or palming a ball. Additionally or alternatively, a gesture may constitute and/or represent the activation and/or change in activation of certain muscles in the user's body.

In some embodiments, wearable device 35102 may generate, store, and/or record state information that describes states of the user's body parts. In one example, such state information may describe a pose and/or gesture made with a hand of the user. In this example, such state information may also include a data-based model of the user's hand as a multi-segment representation. The joints in the user's wrist and fingers may form interfaces between the multiple segments in the data-based model.

In various embodiments, the state of the user's body state may describe a hand in combination with one or more arm segments. In other embodiments, the state of the user's body state may describe portions of the user's body other than the hand or fingers, such as an arm, a leg, a foot, a torso, a neck, variations or combinations of one or more of the same, and/or any other suitable body parts of the user.

The inferential model implemented by wearable device 35102, interface system 35120, and/or application system 35130 may include and/or represent at least one statistical or machine learning model. For example, the inferential model may include and/or represent a neural network (e.g., a recurrent neural network) used to determine and/or classify body part states based at least in part on neuromuscular signals. In one example, the neural network may include and/or represent a long short-term memory (LSTM) neural network. Additionally or alternatively, the neural network may include and/or represent a fully recurrent neural network, a gated recurrent neural network, a recursive neural network, a Hopfield neural network, an associative memory neural network, an Elman neural network, a Jordan neural network, an echo state neural network, a second order recurrent neural network, deep neural networks, convolutional neural networks, feedforward neural networks, variations or combinations of one or more of the same, and/or any other suitable type of neural network.

In some examples, the inferential model may include and/or represent a supervised machine learning model in which the user makes certain positions, movements, forces, contractions, poses, and/or gestures with his or her body. In such examples, the inferential model may obtain sensor data samples representative of those positions, movements, forces, contractions, poses, and/or gestures via wearable device 35102. The inferential model may then be trained (or further trained) based at least in part on those sensor data samples. In other examples, the inferential model may include and/or represent an unsupervised machine learning model that is trained without the user making such positions, movements, forces, contractions, poses, and/or gestures with his or her body. The inferential model may also be trained from data samples collected from multiple users.

In some implementations, the recorded neuromuscular signals may exhibit spatio-temporal (e.g., spatio-frequential) patterns that depend on way in which the user wears wearable device 35102. For example, one body part state may be associated with a first spatio-temporal pattern when the user is donning wearable device 35102 in a first manner (e.g., where the electrodes are in contact with certain areas of the user's skin) and a second spatio-temporal pattern when the user rotates wearable device 35102 on his or her body or when the user moves wearable device 35102 to a different part of the body (e.g., from a lower arm position to an upper arm position). Accordingly, the inferential model may be trained to identify one or more body part states by the exhibited spatio-temporal patterns.

In some implementations, wearable device 35102 may be configured to determine a rotation and/or position of wearable device 35102. In such implementations, wearable device 35102 may be able to select and/or apply an inferential model trained and/or adapted for identifying body parts states at the determined rotation and/or position. In other words, wearable device 35102 may be configured to auto-calibrate by adapting to any rotation and/or arm position offset without interfering with the user experience. By auto-calibrating in this way, wearable device 35102 may be able to account for the manner in which the user is donning wearable device 35102 relative to the user's underlying musculature and other anatomy that has the potential to affect the recording of the neuromuscular signals traversing the user's body. Moreover, wearable device 35102 may be able to adapt to users with varying body types and/or abnormalites, including those who have suffered injured or missing muscles, different adipose tissue or fat, and/or other anatomic variables.

In some examples, HCl system 35200 may build an inferential model that classifies neuromuscular signal patterns for auto-calibration by (1) building a new statistical model/experiment class that takes a set of preprocessed neuromuscular signals as input, (2) generating a batch of training data by randomly applying a rotation offset to the preprocessed signals, (3) producing positive labels when the augmented offset is zero and null labels when the augmented offset is not zero, (4) calibrating the batch of training data to have an offset of zero, and (5) training an inferential model and evaluating its performance by testing different rotation offsets.

In some examples, application system 35230 may receive body state information from interface system 35220. In response to this information, application system 35230 perform certain actions on one or more applications.

Examples of such actions include, without limitation, changing an execution state of an application (e.g., starting, stopping, suspending, or resuming the application), communicating with an application (e.g., providing commands and/or data to the application), moving a cursor in connection with an application, associating a cursor with a visual element displayed in a GUI, presenting and/or highlighting a visual element within a GUI, selecting and/or clicking on a visual indicator displayed in a GUI, transitioning from one mapping to another, and/or any other suitable actions.

In some examples, application system 35230 may be configured to provide a GUI to the user donning wearable device 35102. In one example, the GUI may generate and/or deliver visual, auditory, and/or haptic feedback in response to commands, instructions, and/or data received from application system 35230. For example, a user donning wearable device 35102 may interact with graphical controls and/or indicators displayed in the GUI of application system 35230 via wearable device 35102. As an additional example, the GUI may generate and/or deliver auditory prompts and/or feedback through speakers incorporated into HCl system 35200. As a further example, the GUI may provide haptic prompts and/or feedback via one or more actuators that apply certain forces to the user's body (e.g., vibrations generated by a linear resonant actuator or eccentric rotating mass actuator).

In some embodiments, wearable device 35102, interface system 35220, and/or application system 35230 may be combined into a single standalone computing device or unit. In other embodiments, wearable device 35102 may include and/or represent a single standalone computing device or unit, and interface system 35220 and application system 35230 may be combined into a different standalone computing device or unit. In further embodiments, wearable device 35102 and interface system 35220 may be combined into a single standalone computing device or unit, and application system 35230 may include and/or represent a different standalone computing device or unit. In additional embodiments, wearable device 35102, interface system 35220, and/or application system 35230 may each include and/or represent a separate standalone computing device or unit.

In some examples, wearable device 35102 may implement and/or be configured with one or more trained inferential models. In such examples, wearable device 35102 may record neuromuscular signals, use the trained inferential models to identify one or more states of the user's body parts, and/or provide one or more indications of the identified body states to a separate computing device implementing interface system 35220 and/or application system 35230. Additionally or alternatively, wearable device 35102 may communicate and/or disclose certain features extracted from the recorded neuromuscular signals and/or one or more commands or instructions based on such signals to a separate computing device implementing interface system 35220 and/or application system 35230.

In some examples, the separate computing device implementing interface system 35220 and/or application system 35230 may identify and/or determine the states of the user's body parts by feeding the recorded neuromuscular signals and/or certain features extracted from such signals into one or more trained inferential models. The identified states may be mapped to specific actions capable of being executed and/or performed by the computing device implementing application system 35230. For example, a given body part state may cause application system 35230 to execute and/or perform one or more actions in connection with an application running on that computing device.

In some examples, wearable device 35102 or another portion of HCl system 35200 may determine whether the amount of force exerted by the user satisfies multiple threshold force values. In one example, each of these threshold force values may be associated with a different action and/or input command. For example, wearable device 35102 or another portion of HCl system 35200 may determine that the amount of force exerted by the user while performing a certain hand gesture satisfies a first threshold force value and a second threshold force value. In this example, the first threshold force value and the second threshold force value may differ from one another.

In response to the determination that the amount of force exerted by the user satisfies the first and second threshold force values, wearable device 35102 or another portion of HCl system 35200 may generate a first input command corresponding to the first threshold force value having been satisfied and a second input command corresponding to the second threshold force value having been satisfied. In this example, the first and second input commands may differ from one another.

In some examples, wearable device 35102 or another portion of HCl system 35200 may forego generating input commands corresponding to threshold force values that have not been satisfied. For example, wearable device 35102 or another portion of HCl system 35200 may determine that the amount of force exerted by the user while performing a certain hand gesture does not satisfy a first threshold force value. In response to this determination, wearable device 35102 or another portion of HCl system 35200 may forgo generating an input command corresponding to the first threshold force value in connection with that gesture.

In some examples, wearable device 35102 or another portion of HCl system 35200 may determine that the amount of force exerted by the user satisfies one threshold force value but not another threshold force value. For example, wearable device 35102 or another portion of HCl system 35200 may determine that the amount of force exerted by the user while performing a certain gesture satisfies a first threshold force value but does not satisfy a second threshold force value. In response to this determination, wearable device 35102 or another portion of HCl system 35200 may generate a first input command corresponding to the first threshold force value having been satisfied but forgo generating a second input command corresponding to the second threshold force value having been satisfied. Alternatively, in response to this determination, wearable device 35102 or another portion of HCl system 35200 may generate a first input command corresponding to the first threshold force value having been satisfied and a second input command corresponding to the second threshold force value having not been satisfied.

In some examples, wearable device 35102 or another portion of HCl system 35200 may determine whether the user implemented and/or performed certain combinations of hand gestures and force. For example, wearable device 35102 or another portion of HCl system 35200 may determine that the user exerted a first amount of force while performing a first hand gesture. In this example, wearable device 35102 or another portion of HCl system 35200 may determine that the user exerted a second amount of force while performing a second hand gesture. Additionally or alternatively, wearable device 35102 or another portion of HCl system 35200 may determine that the first amount of force satisfies a first threshold force value and the second amount of force satisfies a second threshold force value.

In response to the determination that the first amount of force satisfies the first threshold force value, wearable device 35102 or another portion of HCl system 35200 may generate a first input command that accounts for the first amount of force exerted by the user while performing the first hand gesture. Moreover, in response to the determination that the second amount of force satisfies the second threshold force value, wearable device 35102 or another portion of HCl system 35200 may generate a second input command that accounts for the second amount of force exerted by the user while performing the second hand gesture.

In some examples, wearable device 35102 or another portion of HCl system 35200 may determine whether the user increases or decreases the amount of force exerted while performing a single hand gesture or pose. For example, wearable device 35102 or another portion of HCl system 35200 may determine and/or identify a single hand gesture (e.g., forming and/or holding a first) performed by the user over a certain period of time. In this example, wearable device 35102 or another portion of HCl system 35200 may determine and/or identify a first amount of force exerted by the user at a first point in time while performing that hand gesture. In response, wearable device 35102 or another portion of HCl system 35200 may generate a first input command that accounts for the first amount of force exerted by the user while performing that hand gesture.

Subsequently, wearable device 35102 or another portion of HCl system 35200 may determine and/or identify a second amount of force exerted by the user at a second point in time while performing that hand gesture. In response, wearable device 35102 or another portion of HCl system 35200 may generate a second input command that accounts for the second amount of force exerted by the user while performing that hand gesture. Accordingly, wearable device 35102 or another portion of HCl system 35200 may generate multiple input commands that correspond to and/or are commensurate with a varying scale of force exerted by the user while performing that hand gesture over time.

As a specific example, wearable device 35102 or another portion of HCl system 35200 may determine and/or identify a first formed and/or held by the hand of the user. In this example, the user may increase and/or decrease the amount of force applied to the first over time. For example, wearable device 35102 or another portion of HCl system 35200 may formulate a first input command to control the speed of a cursor implemented on application system 35230 based at least in part on the amount of force applied to the first at a first point in time. Subsequent to the first point time, wearable device 35102 or another portion of HCl system 35200 may detect an increase and/or decrease in the amount of force exerted by the user in forming or holding the fist. In response, wearable device 35102 or another portion of HCl system 35200 may formulate a second input command to increase and/or decrease the speed of the cursor implemented on HCl system 35200 based at least in part on the increase and/or decrease in the amount of force exerted by the user. Accordingly, light first squeezes may correspond to and/or result in relatively slow cursor speeds, whereas heavy first squeezes may correspond to and/or result in relatively fast cursor speeds (or vice versa).

In some examples, wearable device 35102 or another portion of HCl system 35200 may rely in part on photographic data to determine and/or identify certain hand gestures performed by the user. For example, wearable device 35102 or another portion of HCl system 35200 may identify photographic data representative of the one or more hand gestures as captured by a camera incorporated into an artificial-reality system. In one example, the camera may generate and/or capture this photographic data of the hand gestures from a head-mounted display worn by the user. Additionally or alternatively, the camera may generate and/or capture this photographic data of the hand gestures from a mount, pedestal, and/or base positioned in the surrounding environment of the user.

In one example, wearable device 35102 or another portion of HCI system 35200 may provide the photographic data to one or more trained inferential models to enable such trained inferential models to determine the one or more hand gestures based at least in part on the neuromuscular signals detected by the sensors and the photographic data. By doing so, wearable device 35102 or another portion of HCI system 35200 may be able to improve the accuracy of its hand gesture detection and/or identification, thereby mitigating the number of false positives and/or negatives produced by the trained inferential models. For example, the neuromuscular signals detected by the sensors may indicate and/or suggest that a certain hand gesture performed by the user is either an index finger pinch or a middle finger pinch. However, without further information, the trained inferential models may be unable to conclusively decide on the hand gesture being one or the other. In this example, the trained inferential models may rely on a combination of those neuromuscular signals and photographic data representative of the user's hands captured at the time of the gesture to accurately determine that the user is performing an index finger pinch or a middle finger pinch.

FIG. 35C is an illustration of an exemplary implementation 35300 in which a user 35310 is donning and/or operating wearable device 35102 along with a head-mounted display 35322. In one example, wearable device 35102 may be communicatively coupled to head-mounted display 35322. In this example, the user may be able to control and/or manipulate one or more visual elements presented via head-mounted display 35322 by making certain poses, gestures, and/or isometric contractions with his or her right hand. More specifically, such poses, gestures, and/or isometric contractions may involve and/or entail certain neuromuscular signals that are detected by sensors 35104(1)-(N) of wearable device 35102. In response to those neuromuscular signals, a processing device of wearable device 35102 and/or head-mounted display 35322 may be able to discern and/or identify the poses, gestures, and/or contractions made by the user's right hand. Head-mounted display may then manipulate and/or modify one or more visual elements presented to the user based at least in part on such poses, gestures, and/or contractions.

FIG. 35D illustrates an exemplary implementation of wearable device 35102 with sixteen sensors 35410 (e.g., EMG sensors) arranged circumferentially around an elastic band 35420. As illustrated in FIGS. 35D and 35E, elastic band 35420 may be dimensioned and/or configured to be worn around a user's lower arm or wrist. In some examples, the number and/or arrangement of sensors 35410 may depend on the particular application for which the wearable device 35102 is used and/or deployed. For example, wearable device 35102 may be used and/or deployed to generate control information for controlling a virtual reality system, an augmented reality system, a robot, a vehicle, a computer application, a scrolling feature, a virtual avatar, and/or any other suitable control task.

As illustrated in FIG. 35D, sensors 35410 may be coupled together using flexible electronics 351630 incorporated into wearable device 35102. FIG. 35E illustrates an exemplary cross-sectional view through one of the sensors 35410 of wearable device 35102 in FIG. 35D. FIGS. 35F, 35G and 35H illustrate an alternative implementation of wearable device 35102 capable of executing and/or performing one or more the of signal processing techniques described herein without external assistance. Accordingly, wearable device 35102 in FIGS. 35F, 35G, and 35H may include and/or incorporate a physical compute module and/or unit that, along with the neuromuscular sensors, is integrated into the elastic band.

FIGS. 35I-35L illustrate exemplary pinch poses 35700, 35802, 35804, and 35806 made by a user. As illustrated in FIG. 35I, exemplary pinch pose 35700 may involve and/or represent a positioning of the user's right index finger and right thumb in a pinch pose. Accordingly, pinch pose 35700 may be executed and/or performed as the user pinches, presses, and/or holds his or her right index finger and right thumb together. In one example, pinch pose 35700 may be mapped to a click action such that, when the user executes and/or performs pinch pose 35700 for a predetermined duration, application system 35230 in FIG. 35B may direct and/or cause a corresponding application to click and/or select a certain feature and/or visual element presented in a GUI of that application. This clicking and/or selection of the feature or visual element may be executed and/or performed in connection with the current cursor position.

In another example, pinch pose 35700 may be mapped to an activation action, such as activation action 351900 in FIG. 36M. For example, when the user executes and/or performs pinch pose 35700 for a predetermined duration, application system 35230 in FIG. 35B may direct and/or cause a cursor 351902 in FIG. 36M to move toward element 351906 in a GUI of a corresponding application. As cursor 351902 approaches element 351906, the application may activate element 351906 due at least in part to an association between element 351906 and cursor 351902.

In some examples, the application may provide one or more feedback indicators of this association to the user. Such feedback indicators may inform the user that the HCI system has detected pinch pose 35700. For example, the application may indicate and/or show the activation of this association with a connector 351904 between cursor 351902 and element 351906. Additionally or alternatively, the application may indicate and/or show the activation of this association with a box that surrounds and/or encompasses element 351906.

As another example, the application may indicate and/or show the activation of this association by modifying a certain characteristic or feature of a GUI. For example, the application may transition the appearance of cursor 351902 from an empty circle to a filled circle (e.g., as the user holds pinch pose 35700 for the predetermined duration). In this example, the circle may appear empty at the initiation of pinch pose 35700 and then appear to fill as pinch pose 35700 is held over the predetermined duration. In a further example, the application may modify and/or alter the shape and/or color of cursor 351902.

In one example, element 351906 may include and/or represent a hyperlink. In this example, to activate element 351906, the application may cause the GUI to render and/or display a webpage linked to or by element 351906. To exit and/or return from this webpage, the user may execute and/or perform another pose and/or gesture represented in the active mapping. For example, if an open hand pose is mapped to an exit and/or return action, the user may accomplish exiting and/or returning from this webpage by executing and/or performing the open hand pose.

As illustrated in FIG. 35J-35L, exemplary pinch pose 35800 may involve and/or represent a positioning of the user's right ring finger and right thumb in a pinch pose. Accordingly, pinch pose 35800 may be executed and/or performed as the user pinches, presses, and/or holds his or her right ring finger and right thumb together. In one example, pinch pose 35800 may be mapped to a click action such that, when the user executes and/or performs pinch pose 35800 for three seconds, application system 35230 in FIG. 35B may direct and/or cause a corresponding application to display an identifier for the action in a status bar of a GUI. Additionally or alternatively, application system 35230 in FIG. 35B may direct and/or cause the application to display a countdown of the remaining time required for pinch pose 35800 to be held by the user. Once the user has held pinch pose 35800 for the three seconds, application system 35230 in FIG. 35B may direct and/or cause the application to perform the mapped action and/or terminate the display of the action identifier and/or the countdown.

In one example, pinch pose 35802 in FIG. 35K may be mapped to a scrolling action such that, when the user executes and/or performs pinch pose 35802, application system 35230 in FIG. 35B may direct and/or cause a corresponding application to scroll up a GUI. In this example, pinch pose 35804 in FIG. 35L may be mapped to another scrolling action such that, when the user executes and/or performs pinch pose 35804, application system 35230 in FIG. 35B may direct and/or cause the application to scroll down the GUI.

FIGS. 35M and 35N illustrate exemplary time and amplitude criteria for discrete event detection that may be used in connection with some embodiments. As illustrated in FIG. 35M, a first portion of force time series 35902 may satisfy an event criterion 35912, and a second portion of force time series 35902 may satisfy an event pattern criterion 35914. In one example, event criterion 35912 and event pattern criterion 35914 may be specified and/or defined in any suitable way (such as minimum and/or maximum amplitude values, degree of force maximum and/or thresholds or limits, etc.). As illustrated in FIG. 35N, force time series 35920 may satisfy force time series criteria by falling within upper bound 35916 and lower bound 35918 over a certain time interval.

In some implementations, a combination of pose and force may be used for one-dimensional control. For example, the identified body state may include and/or represent a pose and a force. In this example, the identified pose may dictate and/or influence the responsive action, whereas the identified degree of force may dictate and/or influence a specific characteristic of the responsive action. For example, if the action includes scrolling a GUI in a certain direction, the identified degree of force may dictate and/or influence the speed of that scrolling (e.g., the speed of scrolling may be proportional to the degree of force). As an additional example, if the action includes painting pixels or voxels in a virtual painting application, the identified degree of force may dictate and/or influence the width of the virtual brush-stroke.

FIG. 36R illustrates an exemplary drawing application 352300 that includes a virtual drawing instrument whose width may be controllable and/or modifiable by certain states of the user's body parts. As illustrated in FIG. 36R, drawing application 352300 may include a virtual drawing instrument 352302 capable of drawing lines of varying widths. In some examples, the user may be able to control and/or modify the width of such lines based at least in part on the identified degree of force applied in the user's body state. For example, the user may apply one degree of force that causes application system 35230 to select a width 352310 for lines drawn by visual drawing instrument 352302 and/or another degree of force that causes application system 35230 to select a width 352312 for lines drawn by visual drawing instrument 352302. In this example, the user may apply a further degree of force that causes application system 35230 to select a width 352314 for lines drawn by visual drawing instrument 352302 and/or an even further degree of force that causes application system 35230 to select a width 352316 for lines drawn by visual drawing instrument 352302. Additionally or alternatively, these degrees of force may be used to increase and/or decrease the width of visual drawing instrument 352302 by discrete increments and/or decrements.

In some embodiments, application system 35230 may be configured to provide visual feedback of both the identified pose and the identified force. For example, when the action includes scrolling a GUI, application system 35230 may display a cursor in connection with that scrolling. In this example, the cursor may be presented and/or shown as a horizontal line with a bar extending above or below the line, depending on the scrolling direction. Further, the distance to which the bar extends above or below the line (e.g., the height of the bar) may depend on the identified degree of force applied to the pose. As an additional example, when the action includes painting virtual pixels or voxels, application system 35230 may vary the size of a cursor depending on the identified degree of force. In this example, the size of the cursor may indicate the position of the virtual brush-stroke.

FIGS. 35O-35V illustrate exemplary interactions between a user and an exemplary radial menu 351000 in accordance with some embodiments. In some implementations, application system 35230 may be configured to present and/or display radial menu 351000. In one example, application system 35230 may incorporate radial menu 351000 into a GUI (e.g., a web browser) and/or a multi-state user interface (e.g., multi-state user interface 352000 in FIG. 36N). As illustrated in FIGS. 35S-35V, radial menu 351000 may include certain visual indicators, such as an interface state indicator 351010, a selection indicator 351020, an action indicator 351040, and/or action indicator 351050.

In some examples, interface state indicator 351010 may indicate a transition from a disabled radial menu (e.g., a mode in which the user is not able to interact with the radial menu) to an enabled radial menu (e.g., a mode in which the user is able to interact with the radial menu). In such examples, selection indicator 351020 may indicate a currently selected action (e.g., either action indicator 351040 or action indicator 351050). In one example, application system 35230 may perform an action associated with the selected action indicator. For example, if radial menu 351000 is used with a web browser, action indicator 351040 may be associated with a forward action, and/or action indicator 351050 may be associated with a backward action.

FIGS. 35O-35R illustrate exemplary poses and/or gestures suitable for use in connection with radial menu 351000. In some examples, wearable device 35102 may detect and/or record a plurality of neuromuscular signals via the body of a user. For example, wearable device 35102 may detect and/or record neuromuscular signals from the arm and/or wrist of the user. In this example, wearable device 35102, interface system 35220, and/or application system 35230 may be configured to determine and/or identify a first pose using the recorded signals inputted to an inferential model. Application system 35230 may be configured to provide commands and/or instructions to control aspects of radial menu 351000 in response to the identification of the first pose.

FIG. 35O illustrates an exemplary first pose 351002. In some examples, first pose 351002 may be mapped to a command and/or instruction to display, enter, and/or activate radial menu 351000 within a GUI of application system 35230. In such examples, prior to the identification of first pose 351002, some or all of radial menu 351000 may be withheld and/or hidden from view within the GUI. In one example, state indicator 351010 may be displayed within the GUI upon identification of first pose 351002.

As shown in FIG. 35S, state indicator 351010 may include and/or represent a circle. In one example, as the user holds first pose 351002 for the predetermined duration, the circle may transition from empty to filled. Once first pose 351002 has been held for the predetermined duration, selection indicator 351020 and/or action indicators 351040 and 351050 may be displayed within the GUI. Alternatively, selection indicator 351020 and/or action indicators 351040 and 351050 may be displayed upon identification of first pose 351002. In another example, state indicator 351010, selection indicator 351020, and/or action indicators 351040 and 351050 may be displayed prior to identification of first pose 351002.

FIG. 35P illustrates an exemplary gesture 351004 that includes and/or represents a first pose combined with a specific movement of the user's wrist. In some examples, the specific movement may involve and/or entail a flexion, extension, deviation, and/or rotation of the user's wrist while he or she holds the first pose. In such examples, the first post combined with the specific movement may be mapped to a command and/or instruction to select a visual indicator in radial menu 351000 (e.g., either action indicator 351040 or action indicator 351050). In one example, the flexion of the wrist may be mapped to selecting action indicator 351050, and the extension of the wrist may be mapped to selecting action indicator 351040.

As shown in FIG. 35T, radial menu 351000 may be configured to indicate and/or identify a selected action indicator within the GUI. For example, in response to a certain pose and/or gesture made by the user, selection indicator 351020 may change from the position shown in FIG. 35S to the position shown in FIG. 35T. In this example, upon completion of this change, selection indicator 351020 may identify and/or point toward action indicator 351050.

More generally, the selection of a visual indicator (such as action indicator 351050) may be demonstrated and/or confirmed using visual, auditory, or haptic feedback. For example, in response to the selection of the visual indicator, application system 35230 may play a sound (e.g., a click sound) and/or cause an actuator to vibrate with haptic feedback for user. In some examples, visual feedback may include and/or represent the change of a characteristic of a visual element within radial menu 351000 in response to the selection of the visual indicator. Examples of such a characteristic change include, without limitation, a position change, an orientation change, a color change, a size change, a transparency change, a fill change, an emphasis change, a shadow change, an animation change, a font change, a line type change, a line width change, combinations or variations of one or more of the same, and/or any other suitable characteristic changes.

FIG. 35Q illustrates an exemplary finger pinch pose 351006. In some examples, finger pinch pose 351006 may be mapped to a command and/or instruction to click a visual indicator in radial menu 351000 (e.g., either action indicator 351040 or action indicator 351050). In some implementations, the effect of the click may be analogous to a mouse button click and/or a keypress in certain conventional computer systems. In one example, rather than mapping simply finger pinch pose 351006 to the click command, the combination of finger pinch pose 351006 and a certain degree of force may be mapped to the click command. For example, the user may clench his or her fingers with at least a threshold amount of force while maintaining finger pinch pose 351006 to initiate and/or cause the execution of the click command.

As shown in FIG. 35U, radial menu 351000 may be configured to click (e.g., engage with or activate a function of) the currently selected action indicator. In one example, application system 35230 may click action indicator 351052 in response to an identified click gesture. In this example, upon performing the click action, application system 35230 may cause the visual indicator to appear to depress and/or release (e.g., similar to the pressing and/or releasing of a physical button).

FIG. 35R illustrates an exemplary open hand pose 351008. In some examples, open hand pose 351008 may be mapped to a command and/or instruction to hide, exit, and/or deactivate radial menu 351000. In some implementations, the user may need to hold open hand pose 351008 for a predetermined amount of time before application system 35230 executes and/or performs the deactivation command. Following identification of open hand pose 351008, some or all of radial menu 351000 may be obscured and/or hidden from view within the GUI.

As shown in FIG. 35V, a state indicator 351012 may include and/or represent a circle. In one example, as the user holds open hand pose 351008 for the predetermined duration, the circle may transition from empty to filled (or from filled to empty), and/or selection indicator 351020 and action indicators 351040 and 351050 may no longer be displayed within the GUI. Alternatively, selection indicator 351020 and/or action indicators 351040 and 351050 may disappear from the GUI upon identification of open hand pose 351008. In another example, state indicator 351010, selection indicator 351020, and/or action indicators 351040 and 351050 may remain displayed within the GUI following the deactivation command However, radial menu 351000 may not recognize and/or response to a subsequent selection (e.g., a wrist gesture) or click (e.g., a finger pinch pose) command until receiving a subsequent activation command.

FIG. 36A illustrates an exemplary implementation of radial menu 351000 in accordance with some embodiments. As illustrated in FIG. 36A, radial menu 351000 may be superimposed over a webpage 351102. In one example, when associated with webpage 351102, radial menu 351000 may function and/or serve as a navigation menu that enabling the user to move back to a previous page or forward to subsequent page depending on the menu button selected (e.g., using a wrist gesture) and/or clicked (e.g., using a finger pinch pose) by the user in the superimposed navigation menu. In this example, the user may cause the superimposed menu to disappear from webpage 351102 by holding open hand pose 351008 as described above.

FIGS. 36B and 36C illustrate alternative implementations of an exemplary radial menu 351110 in accordance with some embodiments. As illustrated in FIGS. 36B and 36C, radial menu 351110 may include a set of action indicators (e.g., indicator 351111 and indicator 351113). The indicators may be displayed in the GUI along a substantially circular arc. In one example, a first body state may be mapped to the selection of the next indicator in a given sequence. For example, in response to identification of the first body state, application system 35230 may deselect indicator 351111 and/or select indicator 351113. Additionally or alternatively, application system 35230 may demonstrate and/or conform the selection and/or deselection of a visual indicator using visual, auditory, and/or haptic feedback.

In some embodiments, the first body state and a second body state may represent counterparts of one another. For example, the first body state may include a wrist extension, and the second body state may include a wrist flexion. Additionally or alternatively, the first body state may include a clockwise wrist rotation, and the second body state may include a counterclockwise wrist rotation. In a further example, the first body state may include a radial deviation, and the second body state may include an ulnar deviation.

FIGS. 36D and 36E illustrate implementations of an exemplary sequential menu 351120 in accordance with some embodiments. In certain examples, sequential menu 351120 may include and/or represent a sequence of visual indicators (depicted as "A" through "F"). In such examples, sequential menu 351120 may provide a suitable spatial arrangement among these visual indicators (e.g., throughout the rows and columns in illustrated in FIGS. 36D and 36E). In one example, a first body state may be mapped to the selection of the next visual indicator in the sequence, and a second body state may be mapped to the selection of the previous visual indicator in the sequence. For example, in response to identification of the second body state, application system 35230 may deselect subsequent indicator 351123 and/or select prior indicator 351121.

FIG. 36N illustrates a state diagram of an exemplary multi-state user interface 352000 in accordance with some embodiments. Multi-state user interface 352000 may be implemented by any suitable computing system, including any of the devices incorporated into HCI system 35200 in FIG. 35B (e.g., wearable device 35102, interface system 35220 and/or application system 35230). In one example, multi-state user interface 352000 may receive body state information from wearable device 35102, interface system 35220, and/or application system 35230. Multi-state user interface 352000 may then identify, determine, and/or recognize certain body states, as defined by the user or by default, based at least in part on such information. In some cases, certain hand and arm poses and/or gestures may be symbolic and/or communicate according to cultural standards.

Multi-state user interface 352000 may be configured and/or programmed with multiple interface states (e.g., interface state 352020 and interface state 352030). Each of the multiple interface states may implement and/or represent mappings between one or more body states to a set of responsive actions. As an example, interface state 352020 may implement and/or represent a first mapping from a first set of body states to a first set of responsive actions 352022, and interface state 352030 may implement and/or represent a second mapping from a second set of body states to a second set of actions 352032. The first set of body states may differ from the second set of body states, and the first set of actions 352022 may differ from the second set of actions 352032. Alternatively, the same body states may map to differing responsive actions in different interface states. Further, differing body states may map to the same actions across different interface states.

In some embodiments, multi-state user interface 352000 may provide information about the current status of HCI system 35200 via one or more visual, auditory, or haptic indicators. For example, multi-state user interface 352000 may be configured to display a connection status between interface system 35220 (or application system 35230) and wearable device 35102. FIG. 36F illustrates an exemplary menu bar icon 351200 that demonstrates different appearances of a menu button displaying such a connection status. This menu button may be displayed in a menu bar of multi-state user interface 352000 (or another application running on application system 35230).

The menu button may change in appearance to indicate the status of interface system 35220. For example, a first appearance of the menu button may indicate that wearable device 35102 is connected and sending data to interface system 35220. In this example, a second appearance of the menu button may indicate that wearable device 35102 is connected and but not sending data to interface system 35220 or application system 35230. Finally, a third appearance of the menu button may indicate that wearable device 35102 is not connected to interface system 35220.

In some implementations, multi-state user interface 352000 may be configured to provide and/or indicate its current state and/or setting of interface 352000 (e.g., whether interface state 352020 or interface state 352030 is currently active), a current body state, and/or a current action corresponding to the identified body state. For example, when a body state mapped to a responsive action includes a pose held for a predetermined duration, multi-state user interface 352000 may provide an indication that the HCI system 35200 has recognized the pose. Furthermore, multi-state user interface 352000 may provide an indication of the remaining time necessary for the user to hold the pose before initiating performance of the action mapped to the pose.

In some implementations, multi-state user interface 352000 may include one or more graphical elements for displaying the current interface state, the current body state, and/or the responsive action. For example, the title bar, the menu bar, and/or the status bar of a GUI may display the current interface state, the current body state, and/or the responsive action. Additionally or alternatively, multi-state user interface 352000 may modify a visual characteristic (e.g., size, shape, fill, emphasis, orientation, animation, etc.) of one or more elements of the GUI (e.g., cursor, control element, indicator element, etc.) to indicate the current interface state, current body state, and/or the responsive action.

In some embodiments, multi-state user interface 352000 may be configured to indicate current interface state, the current body state, and/or the responsive action with visual, auditory, or haptic feedback. For example, the transition to a new interface state or the performance of a responsive action may be accompanied by a graphical presentation, sound, and/or vibration provided to the user.

In some embodiments, multi-state user interface 352000 may be configurable and/or programmable by a user. Accordingly, the user may be able to specify and/or select mappings between certain body states and responsive actions for one or more interface states. FIG. 36S illustrates an exemplary multi-state user interface 352400 that enables the user to select and/or define certain mappings between body part states 352402 and actions 352420. As illustrated in FIG. 36S, body part states 352402 may include and/or represent a ring finger pinch 352404, a middle finger pinch 352406, a pinky finger pinch 352408, an index finger pinch 352410, a first pose 352412, and/or an open hand pose 352414. In this example, actions 352420 may include and/or represent a scroll up 352424, a scroll down 352426, an activate link 352428, a deactivate link 352430, an increment selector 352432, and/or a decrement selector 352434.

In some examples, the user may be able to select and/or define a mapping 352440 between one or more of body part states 352402 and actions 352420 via multi-state user interface 352400. For example, the user may direct multi-state user interface 352400 to map ring finger pinch 352404 to scroll up 352424 via mapping 352440 such that, when the user makes a ring finger pinch pose, the page and/or browser displayed on application system 35230 scrolls up. Additionally or alternatively, the user may direct multi-state user interface 352400 to map pinky finger pinch 352408 to map pinky finger pinch 352408 to scroll down 352424 via mapping 352440 such that, when the user makes a pinky finger pinch pose, the page and/or browser displayed on application system 35230 scrolls down.

FIGS. 36G-36K illustrate exemplary portions and/or views of a multi-state user interface 351300 that enables a user to specify and/or select the mappings. For example, multi-state user interface 351300 in FIG. 36G may include and/or represent a popup box and/or dialog that appears in response to certain user input. In this example, multi-state user interface 351300 may facilitate enabling and/or disabling body state control (e.g., using the "enabled" button). In addition, multi-state user interface 351300 may indicate a current status of HCl system 35200 (e.g., using the "API" and "Data" indicators). As illustrated in FIG. 36H, multi-state user interface 351300 may include a drop-down menu control from which the user is able to select certain display settings and/or map certain body states to responsive actions.

Through multi-state user interface 351300, the user may modify the mappings between body states and actions. For example, if multi-state user interface 351300 includes and/or represents a web browser, the user may configure web navigation settings by selecting setting options shown in a drop-down menu of the web browser. As shown in FIG. 36I, multi-state user interface 351300 may enable the user to click on and/or select "scroll: options" to configure a type of pose that initiates a scrolling control or feature. In this example, the user may map the scroll-down action with a ring finger pinch pose (as shown in FIG. 35J) and the scroll-up action with a pinky finger pinch (as shown in FIG. 35K). Accordingly, when the user holds a ring finger pinch pose, the web browser may receive a scroll-down command from application system 35230. The web browser may then scroll down the displayed webpage.

As an additional example, FIG. 36J illustrates an exemplary "link activate" setting used to highlight links included in a web page. As shown in FIG. 36J, multi-state user interface 351300 may enable the user to click on "linksActivate: options" to configure a type of pose and predetermined pose duration that initiates the activation and/or rendering of a link displayed in a webpage. In the example, the user may map the link-activation action to a middle finger pinch pose (as shown in FIG. 35L). Accordingly, when the user holds a middle finger pinch pose for the selected pose duration, the web browser may receive an activate-link command from application system 35230. The web browser may then activate and/or render a link associated with the current cursor position.

As a further example, FIG. 36K illustrates an exemplary "click action" setting used to map a pose to a click action. As shown in FIG. 36K, multi-state user interface 351300 may enable the user to click on "click: options" to configure a type of pose and predetermined pose duration that initiates a click action in an application (e.g., emulating a trackball or mouse click). In this example, the user may map the click action to an index finger pinch pose (as shown in FIG. 35I). Accordingly, when the user holds an index finger pinch pose for the selected pose duration, the application may receive a click command from application system 35230. The application may then perform the click action on a control and/or feature associated with the current cursor position.

In some examples, multi-state user interface 351300 may be configured and/or programmed as a plugin or API for use with existing applications. For example, multi-state user interface 351300 may be formatted and/or packaged to provide a body state recognition functionality as a web browser plugin for use with existing web browsers running on application system 35230.

FIG. 36L illustrates an exemplary method 351800 for assisted user interface navigation in accordance with some embodiments. Method 351800 may facilitate convenient selection and/or activation of elements in a GUI by associating such elements with the current position of the user's cursor. Upon making this association, the user may activate one or more of those elements in the GUI to initiate a certain action in the application. As a result, the user may be able to interact with an application running on application system 35230 in FIG. 35B without necessitating precise control over the cursor position.

As illustrated in FIG. 36L, method 351800 may include a step 351802 of updating a cursor position in a GUI of an application. In this example, method 351800 may also include a step 351804 of associating an element of the GUI with the updated cursor position. The element may be any suitable feature of the GUI, including a hyperlink, a data entry field, an/or a control indicator. In one example, this association may be formed and/or initiated as a result of the cursor being positioned within a certain distance and/or range of the element. For example, application system 35230 may be configured to associate the cursor with the closest applicable element within the GUI, especially if the determined distance between the cursor and that element is within a predetermined threshold or range.

Method 351800 may further include a step 351806 of providing a feedback indication of the association to the user. For example, application system 35230 may provide a visual, auditory, or haptic indication of the association to the user. In one example, application system 35230 may provide auditory prompts and/or feedback representative of the association using speakers associated with HCl system 35200. As a further example, application system 35230 may provide haptic prompts or feedback representative of the association using actuators that apply forces to the user's body. Additionally or alternatively, application system 35230 may provide a visual indication of the association by modifying a characteristic of the cursor and/or the associated element.

Method 351800 may additionally include a step 351808 of performing an activation action based at least in part on the association between the cursor and the element. For example, an activation action may be mapped to a specific body state. In response to the identification of the mapped body state, application system 35230 may determine whether the cursor is associated with a certain element of the GUI. If the cursor is associated with that element of the GUI, application system 35230 may perform the mapped activation action on the associated element.

FIGS. 36O and 36P illustrate an exemplary block diagram of wearable device 35102 with sixteen EMG sensors. As shown in FIG. 36O, wearable device 35102 may include sensors 352110 that record neuromuscular signals traversing the user's body. The output of the sensors 352110 may be provided to analog front end 352130, which performs analog processing (e.g., noise reduction, filtering, etc.) on the recorded signals. The processed analog signals may then be provided to analog-to-digital converter (ADC) 352132, which converts the analog signals to digital signals for further processing by a computer processor (MCU) 352134. In one example, MCU 352134 may receive inputs from other sensors (e.g., IMU sensor 352140) and/or electric current from power and battery module 352142. The output of the processing performed by MCU 352134 may be provided to antenna 352150 for transmission to dongle 352120 shown in FIG. 36P.

In one example, dongle 352120 in FIG. 36P may communicate with the wearable device 35102 (e.g., via Bluetooth or another suitable short-range wireless communication technology). In this example, dongle 352120 may include antenna 352152 configured to communicate with antenna 352150 of wearable device 35102. The signals received by antenna 352152 of dongle 352120 may be provided to a host computer for further processing, display, and/or effecting control of a particular physical or virtual element of that host computer.

FIG. 36Q is a flow diagram of an exemplary method 352200 for controlling computing devices via neuromuscular signals of users. The steps shown in FIG. 36Q may be performed during the operation of an HCl system implemented and/or deployed by a user. Additionally or alternatively, the steps shown in FIG. 36Q may also incorporate and/or involve various sub-steps and/or variations consistent with the descriptions provided above in connection with FIGS. 35A-36P.

As illustrated in FIG. 36Q, method 352200 may include a step 352210 in which one or more neuromuscular signals are detected and/or sensed from a forearm or wrist of a user. For example, a user donning wearable device 35102 may make a pose and/or gesture that causes neuromuscular signals to traverse down the user's arm toward his or her hand. In this examples, wearable device 35102 may include and/or incorporate a plurality of sensors that detect, sense, and/or measure those neuromuscular signals.

As illustrated in FIG. 36Q, method 352200 may also include a step 352220 in which an amount of force associated with the one or more neuromuscular signals are determined. For example, wearable device 35102 or another portion of HCl system 35200 may include and/or incorporate at least one processor that implements one or more trained inferential models. In this example, the one or more trained inferential models may analyze and/or consume data representative of the neuromuscular signals. Upon doing so, the one or more trained inferential models may determine the amount of force associated with the neuromuscular signals.

As illustrated in FIG. 36Q, method 352200 may also include a step 352230 in which the amount of force associated with the one or more neuromuscular signals is determined to have satisfied a threshold force value. For example, wearable device 35102 or another portion of HCl system 35200 may include and/or incorporate at least one processor that determines that the amount of force associated with the neuromuscular signals satisfies a threshold force value. In this example, the threshold force value may represent a certain level of force associated with a specific action to be performed by HCl system 35200.

As illustrated in FIG. 36Q, method 352200 may further include a step 352240 in which a first input command is generated in accordance with the determination that the amount of force satisfies the threshold force value. For example, wearable device 35102 or another portion of HCl system 35200 may include and/or incorporate at least one processor that generates a first input command for HCl system 35200 in response to the determination that the amount of force satisfies the threshold force value. In this example, the first input command may direct and/or cause HCl system 35200 to perform a specific action that corresponds to the amount of force exerted by the user.

The following describes exemplary systems, methods, and interfaces for performing inputs based on neuromuscular control according to at least one embodiment of the present disclosure.

While computing devices have evolved over time from large machines that sit on desktops to portable devices that fit in pockets, devices and interfaces used to provide text input to computing devices remain largely unchanged. The keyboard (and the QWERTY keyboard in particular) remains the most widely used device for providing text input to a computing device. Due to the proliferation of computing devices in society, typing on a keyboard has therefore become an important skill to interact with such devices. Typing on a keyboard, however, can be cumbersome to learn, and remains a relatively slow method of inputting text.

Still further, in some forms of text entry, the number of characters that can be input by a user may exceed the number of buttons or other input mechanisms. For example, numerical keypads on a phone may associate a set of characters with each number and may enable a user to select a character among the several present on each number sequentially (e.g., "A", B," or "C" can be associated with the number "2"). However, mechanical, electrical, or other input mechanisms for machine control may be cumbersome and imprecise. Moreover, interactions with other types of devices that do not have traditional text input user interfaces may also be difficult to work with. For example, the number of Internet of Things (IoT) devices is growing rapidly, with many different types of devices and appliances being connected to (and controlled through) the internet. Interaction with these IoT devices may also be cumbersome in at least some instances.

The embodiments described herein may include methods, systems, and apparatuses to provide different ways of interacting with devices and different methods of inputting text to a computing device. These methods may leverage users' skilled knowledge of how to type on a keyboard, but without requiring a physical keyboard to do so. To this extent, some embodiments described herein are directed to a human-computer interface (HCl) system that maps neuromuscular signal recordings to text input for a computing device to enable a user to type without requiring the user to press keys on a physical keyboard or interact with a touchscreen displayed on a computing device. These alternative forms of text input may be beneficial for users having physical disabilities or injury. Still further, other embodiments may provide new forms of machine control based on inferring intent from a user's neuromuscular activity. In various embodiments, interpreting neuromuscular signals may be used in place of, or in addition to, conventional computer-based input methods and devices.

In some embodiments described herein, computers systems and methods are provided for detecting neuromuscular signals (e.g., as detected from a user) and interpreting these signals as text inputs. In some instances, interfaces may be provided using visual, haptic, audible, and/or other sensory means (or any combination thereof) to indicate which characters are being input by the user, so as to provide feedback to the user. Such user interfaces may be displayed to the user in a 2D plane or other arrangement (e.g., in a computer-based interface such as computer display provided in various computer systems, such as, for example, a standard computer monitor, smartphone, watch, heads-up-display (HUD), automotive display, projected interface, display such as those provided in an extended reality (XR), mixed reality (MR), augmented reality (AR) or virtual reality (VR) environment (e.g., XR, MR, AR, VR, headset etc.) or any other suitable graphical user interface, and indications of characters that are input may be displayed or presented to the user.

The user may use such feedback to adjust their neuromuscular activity in order to more accurately control their input within the 2D display (e.g., using neuromuscular activity that causes movement, forces, and selection gestures and combining that with feedback to control inputs). In some embodiments, the systems described herein receive neuromuscular signals from the user and translate those signals into movement control in a 2D plane. The systems then use selection control to input text into a computer system. In general herein, the visual interface is described as a 2D plane and may also be referred to as displayed on a 2D display, but one skilled in the art will recognize that the interface may employ other arrangements than a 2D plane (e.g., in a three-dimensional display) and immersive three-dimensional displays such as those made possible in AR or VR systems. For example, such movement control and selection control methods may be used along a defined surface in 3D space, such as a surface projected in 3D space (e.g., a curved display, a 3D rectangular surface, along an object surface in 3D space, etc.

In some embodiments, the systems described herein display characters that are capable of being input to the system within regions of a computer interface (e.g., any type of a computer-based display), with characters associated with the regions. In some cases, for example, a user may navigate to a region of the 2D display (or other display type) associated with a character they intend to input to the system. For example, a cursor can be shown on the display to indicate user navigation. In another example, a region to which a user has navigated can be indicated by changing the visual representation of that region of the display (e.g. by changing the color, shape, border width, etc.) and/or by providing other sensory feedback to a user (e.g., haptic or auditory). In some embodiments, navigation is based on an inference model that takes as input a plurality of neuromuscular signals from a device placed on a portion of the user's body (e.g., the forearm or wrist to record muscles that control movements of the fingers, hand, and wrist) and outputs a velocity, direction, and/or position of a cursor. Two-dimensional control generally corresponds to a movement or force, though in some cases may be based on muscle activations that do not cause a movement, force, or perceived proprioceptive signal (e.g., activation of a single motor unit or a small number of motor units).

In some embodiments, a user may select a letter in the region to which they have navigated the cursor, generally by performing a dynamic or static gesture, where the gesture can be determined based on the output of one or more inference models that take(s) as input(s) a plurality of neuromuscular signals from a device placed on a portion of the user's body (e.g., the forearm or wrist to record muscles that control movements of the fingers, hand, and wrist) and outputs a likelihood (and, optionally, a force) associated with a set of gestures. For example, a gesture may be a tap of a finger or a pinch of two fingers together. Multiple gestures may enable selection among a plurality of options (e.g., if several characters are present in a region to disambiguate among the group of characters). For example, a particular character may be selected among four options in a particular region by tapping one of the four fingers on a surface or by pinching one of the four fingers to the thumb).

The description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. It, however, will be clear and apparent that the subject technology is not limited to the specific details set forth herein and may be practiced without these specific details. In some instances, well-known structures and components are shown in block diagram form to avoid obscuring the concepts of the subject technology.

The terms "computer", "processor", "computer processor", "computing device" or the like should be expansively construed to cover any kind of electronic device with data processing capabilities including, by way of non-limiting examples, a digital signal processor (DSP), a microcontroller, a field programmable gate array (FPGA), an application specific integrated circuit (ASIC), or any other electronic computing device comprising one or more processors of any kind, or any combination thereof.

As used herein, the phrase "for example," "such as", "for instance" and variants thereof describe non-limiting embodiments of the presently disclosed subject matter. Reference in the specification to "one case", "some cases", "other cases", or variants thereof means that a particular feature, structure or characteristic described in connection with the embodiment(s) is included in at least one embodiment of the presently disclosed subject matter. Thus the appearance of the phrase "one case", "some cases", "other cases" or variants thereof does not necessarily refer to the same embodiment(s).

It is appreciated that, unless specifically stated otherwise, certain features of the presently disclosed subject matter, which are, for clarity, described in the context of separate embodiments, may also be provided in combination in a single embodiment. Conversely, various features of the presently disclosed subject matter, which are, for brevity, described in the context of a single embodiment, may also be provided separately or in any suitable sub-combination.

FIG. 37A shows an exemplary implementation in which neuromuscular signals are measured from a user 37100 using, for example, one or more neuromuscular sensors arranged around a band or other type of device worn by the user. For example, a band may include EMG sensors (or other types of neuromuscular sensors) arranged circumferentially around an elastic band as discussed further below. It should be appreciated that any suitable number of neuromuscular sensors may be used, and the number and arrangement of neuromuscular sensors used may depend on the particular application for which the wearable device is used.

The neuromuscular signals (e.g., signals 37102) received by the neuromuscular sensors may be provided as an input to a computer system 37101. It should be appreciated that the signals may be provided in raw form to the computer system, may be preprocessed, or may otherwise be analyzed and/or made into an interpreted or processed form as determined by one or more computer-based systems residing on the band or in any other location. Computer system 37101 may include a display 37104, which may be used to display, in some embodiments, a 2D representation to visually indicate which characters are being input by the user, so as to provide feedback to the user. Computer system 37101 may also include an interpreter 37103 that is capable of receiving neuromuscular signals (in any form) and determining one or more text-based inputs. It should be appreciated that a computer system for the disclosed technology may include one or more of the components shown in FIG. 37A, or the components may be located in one or more systems, including a distributed network, on a system worn or used by a user (e.g., in a band, watch, mobile phone, or any other system), or the components may comprise any combination of the foregoing. Further, the system may comprise various hardware, firmware, and/or software components and accessories.

An example wearable system will now be described with reference to FIGS. 37B-37E. The wearable device 37200 may be configured to sense neuromuscular signals. FIGS. 37B-37C and 37D-37E show several embodiments of a wearable system in which various embodiments may be practiced. In particular, FIG. 37B illustrates a wearable system with sixteen neuromuscular sensors 37210 (e.g., EMG sensors) arranged circumferentially around an elastic band 37220 configured to be worn around a user's lower arm or wrist. As shown, neuromuscular sensors 37210 (e.g., EMG sensors) are arranged circumferentially around elastic band 37220. It should be appreciated that any suitable number of neuromuscular sensors may be used. The number and arrangement of neuromuscular sensors may depend on the particular application for which the wearable device is used. For example, a wearable armband or wristband can be used to generate control information for controlling an augmented reality system, controlling a robot, controlling a vehicle, scrolling through text, controlling a virtual avatar, or any other suitable control task.

In some embodiments, sensors 37210 include a set of neuromuscular sensors (e.g., EMG sensors). In other embodiments, sensors 37210 can include a set of neuromuscular sensors and at least one "auxiliary" sensor configured to continuously record auxiliary signals. Examples of auxiliary sensors include, but are not limited to, other sensors such as IMU sensors, microphones, imaging sensors (e.g., a camera), radiation based sensors for use with a radiation-generation device (e.g., a laser-scanning device), or other types of sensors such as a heart-rate monitor. As shown the sensors 37210 may be coupled together using flexible electronics 37230 incorporated into the wearable device. FIG. 37C illustrates a cross-sectional view through one of the sensors 37210 of the wearable device shown in FIG. 37B.

In some embodiments, the output of one or more of the sensing components can be optionally processed using hardware signal processing circuitry (e.g., to perform amplification, filtering, and/or rectification). In other embodiments, at least some signal processing of the output of the sensing components can be performed in software. Thus, signal processing of signals sampled by the sensors can be performed in hardware, software, or by any suitable combination of hardware and software, as aspects of the technology described herein are not limited in this respect. A non-limiting example of a signal processing chain used to process recorded data from sensors 37210 are discussed in more detail below in connection with FIGS. 37D and 37E.

FIGS. 37D and 37E illustrate a schematic diagram with internal components of a wearable system with sixteen EMG sensors, in accordance with some embodiments of the technology described herein. As shown, the wearable system includes a wearable portion 37310 (FIG. 37D) and a dongle portion 37320 (FIG. 37E) in communication with the wearable portion 37310 (e.g., via Bluetooth or another suitable short-range wireless communication technology). As shown in FIG. 37D, the wearable portion 37310 includes the sensors 37210, examples of which are described in connection with FIGS. 37B and 37C. The output of the sensors 37210 is provided to analog front end 37330 configured to perform analog processing (e.g., noise reduction, filtering, etc.) on the recorded signals. The processed analog signals are then provided to analog-to-digital converter 37332, which converts the analog signals to digital signals that can be processed by one or more computer processors. An example of a computer processor that may be used in accordance with some embodiments is microcontroller (MCU) 37334 illustrated in FIG. 37D. As shown, MCU 37334 may also include inputs from other sensors (e.g., IMU sensor 37340), and power and battery module 37342. The output of the processing performed by MCU may be provided to antenna 37350 for transmission to dongle portion 37320 shown in FIG. 37E.

Dongle portion 37320 includes antenna 37352 configured to communicate with antenna 37350 included as part of wearable portion 37310. Communication between antenna 37350 and 37352 may occur using any suitable wireless technology and protocol, non-limiting examples of which include radiofrequency signaling and Bluetooth. As shown, the signals received by antenna 37352 of dongle portion 37320 may be provided to a host computer for further processing, display, and/or for effecting control of a particular physical or virtual object or objects.

Although the examples provided with reference to FIGS. 37B, 37C and FIGS. 37D, 37E are discussed in the context of interfaces with EMG sensors, it is understood that the techniques described herein for reducing electromagnetic interference can also be implemented in wearable interfaces with other types of sensors including, but not limited to, mechanomyography (MMG) sensors, sonomyography (SMG) sensors, and electrical impedance tomography (EIT) sensors.

In some embodiments, the trained statistical models may be a neural network and, for example, may be a recurrent neural network. In some embodiments, the recurrent neural network may be a long short-term memory (LSTM) neural network. It should be appreciated, however, that the recurrent neural network is not limited to be an LSTM neural network and may have any other suitable architecture. For example, in some embodiments, the recurrent neural network may be a fully recurrent neural network, a gated recurrent neural network, a recursive neural network, a Hopfield neural network, an associative memory neural network, an Elman neural network, a Jordan neural network, an echo state neural network, a second order recurrent neural network, and/or any other suitable type of recurrent neural network. In other embodiments, neural networks that are not recurrent neural networks may be used. For example, deep neural networks, convolutional neural networks, and/or feedforward neural networks, may be used. In some implementations, the statistical model can be an unsupervised machine learning model, e.g., users are not required to perform a predetermined set of gestures for which the statistical model was previously trained to predict or identify.

Processor-executable instructions can be in many forms, such as program modules, executed by one or more compute devices, and can include routines, programs, objects, components, data structures, etc. that perform particular tasks or implement particular data types, and the functionality can be combined and/or distributed as appropriate for various embodiments. Data structures can be stored in processor-readable media in a number of suitable forms. For simplicity of illustration, data structures may be shown to have fields that are related through location in the data structure. Such relationships may likewise be achieved by assigning storage for the fields with locations in a processor-readable medium that conveys relationship(s) between the fields. However, any suitable mechanism/tool can be used to establish a relationship between information in fields of a data structure, including through the use of pointers, tags or other mechanisms/tools that establish relationship between data elements.

All or portions of the human musculoskeletal system can be modeled as a multi-segment articulated rigid body system, with joints forming the interfaces between the different segments and joint angles defining the spatial relationships between connected segments in the model. Constraints on the movement at the joints are governed by the type of joint connecting the segments and the biological structures (e.g., muscles, tendons, ligaments) that restrict the range of movement at the joint. For example, the shoulder joint connecting the upper arm to the torso and the hip joint connecting the upper leg to the torso are ball and socket joints that permit extension and flexion movements as well as rotational movements. By contrast, the elbow joint connecting the upper arm and the forearm and the knee joint connecting the upper leg and the lower leg allow for a more limited range of motion. As described herein, a multi-segment articulated rigid body system is used to model portions of the human musculoskeletal system. However, it should be appreciated that some segments of the human musculoskeletal system (e.g., the forearm), though approximated as a rigid body in the articulated rigid body system, may include multiple rigid structures (e.g., the ulna and radius bones of the forearm) that provide for more complex movement within the segment that is not explicitly considered by the rigid body model. Accordingly, a model of an articulated rigid body system for use with some embodiments of the technology described herein may include segments that represent a combination of body parts that are not strictly rigid bodies.

In kinematics, rigid bodies are objects that exhibit various attributes of motion (e.g., position, orientation, angular velocity, acceleration). Knowing the motion attributes of one segment of the rigid body enables the motion attributes for other segments of the rigid body to be determined based on constraints that regulate how the segments are connected. For example, the hand may be modeled as a multi-segment articulated body with the joints in the wrist and each finger forming the interfaces between the multiple segments in the model. In some embodiments, movements of the segments in the rigid body model can be simulated as an articulated rigid body system in which position (e.g., actual position, relative position, or orientation) information of a segment relative to other segments in the model are predicted using at least one of a trained statistical model, a trained machine learning model, or a combination thereof, as described in more detail below.

The portion of the human body approximated by a musculoskeletal representation as described herein as one non-limiting example, is a hand or a combination of a hand with one or more arm segments and the information used to describe a current state of the positional relationships between segments and force relationships for individual segments or combinations of segments in the musculoskeletal representation is referred to herein as the handstate of the musculoskeletal representation. It should be appreciated, however, that the techniques described herein are also applicable to musculoskeletal representations of portions of the body other than the hand including, but not limited to, an arm, a leg, a foot, a torso, a neck, or any combination of the foregoing.

In addition to spatial (e.g., position/orientation) information, some embodiments are configured to predict force information associated with one or more segments of the musculoskeletal representation. For example, linear forces or rotational (torque) forces exerted by one or more segments may be estimated. Examples of linear forces include, but are not limited to, the force of a finger or hand pressing on a solid object such as a table, and a force exerted when two segments (e.g., two fingers) are pinched together. Examples of rotational forces include, but are not limited to, rotational forces created when segments in the wrist or fingers are twisted or flexed. In some embodiments, the force information determined as a portion of a current handstate estimate includes one or more of pinching force information, grasping force information, or information about co-contraction forces between muscles represented by the musculoskeletal representation.

As discussed above, interfaces may be provided that visually indicate which characters are being input by the user. Such interfaces may be displayed to the user in a 2D plane such as in a display 37401 shown in FIG. 37F. Display 37401 can include one or more graphical elements, including one or more defined regions (e.g., region 37402) including one or more characters (e.g., characters 37403). The interfaces described herein may also comprise other means of presenting feedback, including but not limited to auditory means, haptic means, and/or other sensory means, or any combination of the foregoing.

Display 37401 may also show a location of a pointer or cursor within the display (e.g., pointer 37404), and the system may be adapted to translate movement control in a 2D plane responsive to the received neuromuscular signals. In some embodiments, navigation is based on one or more inference model(s) that take(s) as input a plurality of neuromuscular signals from a device placed on a portion of the user's body (e.g., the forearm or wrist to record muscles that control movements of the fingers, hand, and wrist) and outputs a velocity, direction, and/or position of a pointer or cursor. The user may use such visual feedback to adjust their neuromuscular activity in order to more accurately control their input (e.g., movement and selection activities) within the 2D display. For instance, the user may move the cursor or pointer 37404 to a particular region (e.g., the center region shown in FIG. 37F, the region having text inputs "abcd"). When the pointer is located within the desired region, the user may perform some action, such as a discrete or continuous gesture to select a particular character displayed within the selected region (e.g., character "c" of the group of characters "abcd"). Once the gesture is detected, the selected character may be provided as input (e.g., such as an entry within an application, for example a chat window, email, word processing, or other application type). In some embodiments, other selection mechanisms may be used, such as a rotating selection among the options (e.g., an automated highlight of an option of "abcd" as it rotates within the display between other options), a time spent within the region (e.g., a selection of a character "a" after the cursor or pointer is located for a predetermined time within the region), a selection option to scroll or pan through different sets of characters, or other selection mechanisms.

As discussed, alternative interfaces having different display and control schemes may be used. For instance, as shown in FIG. 37G, an interface may be provided which includes one or more "autocomplete" or "autosuggest" areas within the display (e.g., autocomplete area 37504). In some embodiments, an autocomplete area may be displayed within a region, and a user may select among a number of autocomplete options by, for example, providing an appropriate neuromuscular input. For instance, in some embodiments, one or more autocomplete (or autocorrect) options may be selected by performing an appropriate discrete gesture. For example, as shown in FIG. 37G, a user may have positioned a cursor within region 37502, permitting the user to select characters "E", "F", "G" or "H" within that region. Based on the user's input and/or previous text selection, the system may display an appropriate autocomplete option. For instance, if the user navigates to region 37502, the display may show, in an autocomplete area, four options, each associated with a particular gesture or series of gestures (e.g., number of finger taps or flick of one of the fingers). In some embodiments, autocomplete options may be based upon a natural language model that determines one or more probable characters based upon current and/or previous inputs. The user can select from one of the options by either using a specific gesture alone or a gesture in combination with the user controlling a pointer (not shown).

FIG. 37H shows another implementation of an alternate interface having a different type of control scheme according to various embodiments. In particular, display 37601 includes a circular type arrangement of regions (e.g., region 37602), each of the regions having associated groups of text (e.g., character group 37603 of text characters "D", "E", and "F") with a center region being an autocomplete area (e.g., autocomplete area 37604). Either single characters can be displayed within this autocomplete area and/or probable words, numbers, or special characters (e.g., as computed using a language model). The user can select from one of the options by either using a specific gesture alone or a gesture in combination with the user controlling a pointer (not shown).

FIG. 37I shows yet another example interface having a different type of control scheme according to various embodiments. In particular, display 37701 includes a matrix type arrangement of regions (e.g. regions 37704) in which possible text and/or autocomplete regions may be displayed. Further, display 37701 may have one or more autocomplete options 1-4 (items 37703A-37703D) which include possible words associated with text entry area 37702. As different characters are input, they may be displayed in area 37702, and autocomplete option items 37703A-37703D may be adjusted as text that is entered to permit the user to auto-complete possible words formed with the text entered in area 37702. Similarly, autocomplete area 37705 may be associated with characters only within regions 37704, permitting the user to more easily select the next character for input within area 37702. The user can select from one of the options by either using a specific gesture alone or a gesture in combination with the user controlling a pointer (not shown).

Other arrangements and configurations of displays and control schemes may be provided. As discussed, in some embodiments, variations in the control scheme and 2D display options may be provided, depending on the application, user-type, user preferences, or computing environment, among other considerations.

For example, such variations may include, without limitation, the following variations, either alone or in combination with any other variation(s) A first example is text input based on 2D navigation and character selection by user time in region or single click. For example, the user controls movement within a 2D plane (or other shape onto which 2D movements can be effectively mapped such as in a virtual reality or augmented reality environment), and that movement is translated to different regions of the 2D plane, permitting the user to perform a selection activity. The selection activity may be performed by the user performing a dynamic or static gesture (e.g., a tap, pinch, pose, etc.). The selection activity may also be performed without an additional gesture (e.g., responsive to the user controlling the cursor to a selected region and remaining within the region for a predetermined amount of time, without leaving the region).

Another example is text input based on 2D navigation and character selection with multi-click. In some embodiments, it is appreciated that 2D movement control using neuromuscular activity may be more easily performed by a user if they are provided larger 2D regions within or over which to navigate, and "multi-click" operations may be performed by the user within a selected region using different dynamic or static gestures. In one example, multiple characters are grouped within a same region, and in response to a movement into or within that region by the user, the user is permitted to perform a selection activity of a particular character within the group by performing a particular dynamic or static gesture, thereby selecting the particular character.

A third example involves different shapes of regions for 2D navigation. In some embodiments, the regions containing characters can be shaped and/or arranged in a number of alternate ways, depending on system requirements and capabilities, user preferences and skill level for using a system or method of this type, and display platform (e.g., a laptop screen, computer screen, smartphone screen, tablet screen, smartwatch screen, VR, AR, or mixed reality system, etc.). In some embodiments, a user can specify a number of regions. For example, regions containing characters to which a user can navigate can be arranged as: a) a circle with slices and/or center region, b) a grid of squares or rectangles, c) other shapes or layouts in a layout or display amenable to navigation with two-dimensional control.

A fourth example involves characters assigned to each region. In some embodiments, the regions containing characters can contain an equal number of characters per region or a variable number of characters per region (e.g., based on the frequency of use of a particular character or likelihood that a character is often used after another). In some embodiments, the character composition of a region of the display can be dynamic and change based on previous or current text input. In some embodiments, the identity or order of characters assigned to each region can take different forms. For example, the system can use an alphabetical order assignment, a qwerty-based assignment, or another assignment protocol (e.g., by associating likelihood of using a letter with regions that are easier to access and, in embodiments with more than one character per region (e.g., requiring multiple discrete events to select among the several characters present in the region), associating more commonly used letters with gestures or poses (e.g., discrete events controls) that are more comfortable, convenient, and/or reliable.

A fifth example involves autocomplete functionality. In some embodiments, multiple autocomplete, autocorrect, and/or autosuggest options may be displayed and may be based on, for example, based on a natural language model. The user can navigate a cursor to a specified 'autocomplete' region in the display and then can select among several autocomplete, autocorrect, and/or autosuggest options by completing an appropriate discrete gesture. For example, up to four autocomplete, autocorrect, and/or autosuggest options can be displayed in a horizontal fashion to indicate to a user which of the four "mitten" fingers to tap or pinch (e.g., pinch the fingertip to the thumb) in order to select the displayed option. In some cases, fewer than four autocomplete, autocorrect, and/or autosuggest options can be displayed, causing one or more certain regions to be empty and thus causing no action to be performed upon a user's completion of a tap or pinch of a finger corresponding to an empty field. Multiple autocomplete, autocorrect, and/or autosuggest options may be displayed based on a natural language model. For example, a user may navigate the cursor to a region associated with an autocomplete, autocorrect, and/or autosuggest option and select an option with a specified gesture.

In general, selection for text entry can occur when a particular gesture is recognized based on one or more inference models for gestures that take(s) as input(s) a plurality of neuromuscular signals measured from a part of a user's body (e.g. measured on the user's wrist or forearm). In various embodiments, a selection for character input can occur upon detection of a specific gesture (among several enabled gestures) and/or upon detection of a repeated gesture (e.g., one could tap an index finger once for selecting a first item and twice (within a particular time window) for selecting a second item).

Particular gestures can be used for additional functionality. For example, a first pose may be used to delete characters, an open hand pose can be used as a space bar, and a tap of the thumb can be used as a punctuation pose to change the displayed characters in the regions of the character display region from letters to punctuation characters.

FIG. 37J illustrates a system 37800 in accordance with some embodiments. The system includes a plurality of sensors 37802 configured to record signals resulting from the movement of portions of a human body. Sensors 37802 may include autonomous sensors. In some embodiments, the term "autonomous sensors" may generally refer to sensors configured to measure the movement of body segments without requiring the use of external devices. In some embodiments, sensors 37802 may also include non-autonomous sensors in combination with autonomous sensors. In some examples, the term "non-autonomous sensors" may generally refer to sensors configured to measure the movement of body segments using external devices. Examples of external devices used in non-autonomous sensors include, but are not limited to, wearable (e.g. body-mounted) cameras, global positioning systems, or laser scanning systems.

Autonomous sensors may include a plurality of neuromuscular sensors configured to record signals arising from neuromuscular activity in skeletal muscle of a human body. The term "neuromuscular activity" as used herein may generally to neural activation of spinal motor neurons that innervate a muscle, muscle activation, muscle contraction, or any combination of the neural activation, muscle activation, and muscle contraction. Neuromuscular sensors may include one or more electromyography (EMG) sensors, one or more mechanomyography (MMG) sensors, one or more sonomyography (SMG) sensors, a combination of two or more types of EMG sensors, MMG sensors, and SMG sensors, and/or one or more sensors of any suitable type that are configured to detect neuromuscular signals. In some embodiments, the plurality of neuromuscular sensors may be used to sense muscular activity related to a movement of the part of the body controlled by muscles from which the neuromuscular sensors are arranged to sense the muscle activity. Spatial information (e.g., position and/or orientation information) and force information describing the movement may be predicted based on the sensed neuromuscular signals as the user moves over time.

Autonomous sensors may include one or more Inertial Measurement Units (IMUs), which may measure a combination of physical aspects of motion, using, for example, an accelerometer, a gyroscope, a magnetometer, or any combination of one or more accelerometers, gyroscopes and magnetometers. In some embodiments, IMUs may be used to sense information about the movement of the part of the body on which the IMU is attached and information derived from the sensed data (e.g., position and/or orientation information) may be tracked as the user moves over time. For example, one or more IMUs may be used to track movements of portions of a user's body proximal to the user's torso relative to the sensor (e.g., arms, legs) as the user moves over time.

In embodiments that include at least one IMU and a plurality of neuromuscular sensors, the IMU(s) and neuromuscular sensors may be arranged to detect movement of different parts of the human body. For example, the IMU(s) may be arranged to detect movements of one or more body segments proximal to the torso (e.g., an upper arm), whereas the neuromuscular sensors may be arranged to detect movements of one or more body segments distal to the torso (e.g., a forearm or wrist). It should be appreciated, however, that autonomous sensors may be arranged in any suitable way, and embodiments of the technology described herein are not limited based on the particular sensor arrangement.

FIG. 37K describes a method 37900 for generating (sometimes termed "training" herein) a statistical model using signals recorded from sensors 37802. Method 37900 may be executed by any suitable computing device(s), as aspects of the technology described herein are not limited in this respect. For example, method 37900 may be executed by one or more computer processors described with reference to FIG. 37J or other computer processors, among other types and configurations of processors. As another example, one or more acts of method 37900 may be executed using one or more servers (e.g., servers included as a part of a cloud computing environment). For example, at least a portion of act 37910 relating to training of a statistical model (e.g., a neural network) may be performed using a cloud computing environment.

The sensors 37802 of FIG. 37J may detect movements and may send sensors signals to a specified device or location (at step 37902 of method 37900). For example, in some embodiments, at least one IMU and a plurality of neuromuscular sensors may be co-located on a body segment to track movements of the body segment using different types of measurements. In one implementation described in more detail below, an IMU sensor and a plurality of EMG sensors are arranged on a wearable device configured to be worn around the lower arm or wrist of a user. In such an arrangement, the IMU sensor may be configured to track movement information (e.g., positioning and/or orientation over time) associated with one or more arm segments, to determine, for example whether the user has raised or lowered their arm, whereas the EMG sensors may be configured to determine movement information associated with wrist or hand segments to determine, for example, whether the user has an open or closed hand configuration. Thus, at 37904 of method 37900, the system may obtain position and/or orientation information of the user wearing the wearable device.

Each of the autonomous sensors may include one or more sensing components configured to sense information about a user. In the case of IMUs, the sensing components may include one or more accelerometers, gyroscopes, magnetometers, or any combination thereof to measure characteristics of body motion, examples of which include, but are not limited to, acceleration, angular velocity, and sensed magnetic field around the body. In the case of neuromuscular sensors, the sensing components may include, but are not limited to, electrodes configured to detect electric potentials on the surface of the body (e.g., for EMG sensors) vibration sensors configured to measure skin surface vibrations (e.g., for MMG sensors), and acoustic sensing components configured to measure ultrasound signals (e.g., for SMG sensors) arising from muscle activity.

In some embodiments, the output of one or more of the sensing components may be processed using hardware signal processing circuitry (e.g., to perform amplification, filtering, and/or rectification) at step 37906 of method 37900. In other embodiments, at least some signal processing of the output of the sensing components may be performed in software. Thus, signal processing of autonomous signals recorded by the autonomous sensors may be performed in hardware, software, or by any suitable combination of hardware and software, as aspects of the technology described herein are not limited in this respect.

In some embodiments, the recorded sensor data may be processed to compute additional derived measurements that are then provided as input to a statistical model and/or a machine learning model, as described in more detail below. For example, recorded signals from an IMU sensor may be processed to derive an orientation signal that specifies the orientation of a rigid body segment over time. Autonomous sensors may implement signal processing using components integrated with the sensing components, or at least a portion of the signal processing may be performed by one or more components in communication with, but not directly integrated with the sensing components of the autonomous sensors.

In some embodiments, at least some of the plurality of autonomous sensors are arranged as a portion of a wearable device configured to be worn on or around part of a user's body. For example, an IMU sensor and a plurality of neuromuscular sensors are arranged circumferentially around an adjustable and/or elastic band such as a wristband or armband configured to be worn around a user's wrist or arm. Alternatively, at least some of the autonomous sensors may be arranged on a wearable patch configured to be affixed to a portion of the user's body. In some embodiments, multiple wearable devices, each having one or more IMUs and/or neuromuscular sensors included thereon, may be used to predict musculoskeletal position information for movements that involve multiple parts of the body (e.g., at step 37908 of method 37900).

In some embodiments, sensors 37802 only include a plurality of neuromuscular sensors (e.g., EMG sensors). In other embodiments, sensors 37802 include a plurality of neuromuscular sensors and at least one "auxiliary" sensor configured to continuously record a plurality of auxiliary signals. Examples of auxiliary sensors include, but are not limited to, other autonomous sensors such as IMU sensors, and non-autonomous sensors such as an imaging device (e.g., a camera), a radiation-based sensor for use with a radiation-generation device (e.g., a laser-scanning device), or other types of sensors such as a heart-rate monitor.

System 37800 may also include one or more computer processors (not shown in FIG. 37J) programmed to com-municate with sensors 37802. For example, signals recorded by one or more of the sensors may be provided to the processor(s), which may be programmed to execute one or more machine learning techniques that process signals output by the sensors 37802 to generate training data (e.g., at act 37910 of method 37900) and train one or more statistical models 37804 and/or machine learning models (not shown in FIG. 37J) (e.g., at step 37912 of method 37900). The trained (or retrained) inferential models (e.g., statistical model(s) 37804) may then be stored (e.g., at step 37914 of method 37900) for later use in generating a musculoskeletal representation 37806, as described in more detail below. As used herein, the term inferential model includes, but is not limited to, pure statistical models, pure machine learning models, or any combination thereof. Non-limiting examples of statistical models that may be used in accordance with some embodiments to predict handstate information based on recorded signals from sensors 37802 are discussed in detail below.

System 37800 also optionally includes a display controller configured to display a visual representation 37808 (e.g., of a hand). As discussed in more detail below, one or more computer processors may implement one or more trained statistical models configured to predict handstate information based, at least in part, on signals recorded by sensors 37802. The predicted handstate information is used to update the musculoskeletal representation 37806, which is then optionally used to render a visual representation 37808 based on the updated musculoskeletal representation incorporating the current handstate information. Real-time reconstruction of the current handstate and subsequent rendering of the visual representation reflecting the current handstate information in the musculoskeletal model may provide visual feedback to the user about the effectiveness of the trained statistical model to accurately represent an intended handstate. Not all embodiments of system 37800 include components configured to render a visual representation. For example, in some embodiments, handstate estimates output from the trained statistical model and a corresponding updated musculoskeletal representation are used to determine a state of a user's hand (e.g., in a virtual reality environment) even though a visual representation based on the updated musculoskeletal representation is not rendered (e.g., for interacting with virtual objects in a virtual or augmented reality environment in the absence of a virtually-rendered hand).

In some embodiments, a computer application configured to simulate a virtual reality environment may be instructed to display or render a visual representation of the user's hand within a user interface (e.g., a graphical user interface). Positioning, movement, and/or forces applied by portions of the hand within the virtual reality environment may be displayed based on the output of the trained statistical model(s). The visual representation may be dynamically updated based on current reconstructed handstate information as continuous signals are recorded by the sensors 37802 and processed by the trained statistical model(s) 37804 to provide an updated computer-generated representation of the user's position, movement, and/or exerted force.

In some embodiments, the term "gestures" generally refers to a static or dynamic configuration of one or more body parts including the position of the one or more body parts and forces associated with the configuration. For example, gestures may include discrete gestures, such as pressing the palm of a hand down on a solid surface or grasping a ball or pinching one or more fingers, continuous gestures, such as a waving a finger back and forth or throwing a ball or snapping or tapping one or more fingers, or making a first or rolling a wrist, or a combination of discrete and continuous gestures such as grasping and throwing a ball. Gestures may be defined by an application configured to prompt a user to perform the gestures or, alternatively, gestures may be arbitrarily defined by a user. In some cases, hand and arm gestures may be symbolic and used to communicate according to cultural standards. A user may want to have a particular personalization for a particular task. In some implementations, the one or more computer processors may be further programmed to re-personalize the musculoskeletal representation by re-applying a particular desired personal characteristic to a musculoskeletal representation that has been anonymized using one or more of the techniques described herein.

FIG. 37L illustrates an example method 371000 for interpreting input commands received through neuromuscular signals sensed at a wearable device (e.g., wearable device 37200 of FIG. 37A-37B). In some embodiments, the method 371000 may include presenting, via a user interface, at least one sensory cue (step 371010). For instance, the computer system 37101 may instantiate a user interface such as that shown in FIG. 37F, 37G, or 37H. The UI may be configured to provide a sensory cue such as an auditory cue, a haptic cue, an olfactory cue, an environmental cue, a visual cue, or other type of cue. The computer system 37101 may then receive, from one or more neuromuscular sensors of a wearable device, one or more neuromuscular signals generated by a user wearing the wearable device (step 371020). In such cases, the user (e.g., user 37100) may generate the neuromuscular signals in response to the at least one sensory cue being presented to the user via the user interface (step 371020). The wearable device 37200 may include one or more neuromuscular sensors 37210 configured to detect neuromuscular signals. The computer system 37101 may interpret the one or more received neuromuscular signals as input commands with respect to the sensory cue provided by the user interface, such that the input commands initiate performance of one or more specified tasks within the user interface (step 371030). The computer system 37101 may then perform the one or more specified tasks within the user interface according to the interpreted input commands (step 371040).

In some cases, carrying out the specified task includes navigating to a specified display region in the user interface that corresponds to a text input that is available for selection, and selecting the text input located at the specified display region within the user interface. For instance, in FIG. 37F, carrying out the specified task may include navigating to region 37402 (and potentially moving the pointer 37404 to that region) and selecting one or more of the characters in that region (in this case, "y" or "z"). Other regions may also be selected, or may be selected in sequence on after another to provide inputs spelling out a word. Thus, in this manner, a user 37100 may wear a wearable device 37200, have that device interpret their neuromuscular signals as commands, and carry out those commands by moving the pointer within the display 37401 and selecting text including words, letters, pictures, or other selectable items. In some cases, as noted above, users may perform gestures with their fingers or hand. The wearable device 37200 may detect these gestures and select specified words or characters as inputs within the user interface.

For instance, as shown in FIG. 37F, a user interface shown in display 37401 may include multiple display regions (e.g., 37402). Within each display region, various potential text inputs may be mapped to each display region in a mapping.

For instance, characters "mnop" may be mapped to one region, while characters "qrst" are mapped to another location. Selection of a particular text input in the specified display region may be based, at least in part, on a recognized gesture determined from the received neuromuscular signals. The gesture may include a user moving their hand or wrist in a manner that navigates the pointer 37404 to a particular region. Lingering in that region or performing a finger tap or finger pinch gesture may select one or more of the characters in that region. In some cases, the mapping of characters to regions may include a mapping of specified text inputs to specified gestures. Thus, in some embodiments, numbers may be mapped to finger tap gestures, while lower-case letters may be mapped to pointer finger taps, and upper-case letters may be mapped to middle finger taps or to finger-thumb pinches, etc.

In some cases, interpreting the neuromuscular signals received from the wearable device sensors as input commands with respect to the sensory cue provided by the user interface may include interpreting the received neuromuscular signals from the user as a velocity control, a directional control, and/or positional control of a cursor used to select particular text inputs within the user interface. The system may thus track how gestures are provided, including the velocity, direction, and/or position of the wearable device as the user moves their hand or other body parts. This velocity, direction, and/or position may then be used when interpreting the gesture and mapping it to an input command.

In some embodiments, interpreting the received neuromuscular signals as input commands with respect to the sensory cue provided by the user interface may include recognizing a user gesture based on the received neuromuscular signals. This recognized user gesture may then control a selection of a particular text input. If the user's intent on selecting a particular portion of text is unclear, the systems described herein may disambiguate the text input displayed within the user interface based on which user gesture was recognized. Users may not only provide a single selection, but may provide a series of inputs. The systems herein may be configured to automatically determine, based on the received neuromuscular signals, which series of likely text inputs were provided by the user.

In other cases, carrying out the specified command includes predicting, from a language model, various characters that are to be selected as typed inputs based on the input commands and providing the predicted characters as typed inputs within the user interface. As will be explained further below, the inputs provided by the user 37100 through neuromuscular signals detected by the wearable device 37200 may be indicative of typed letters that were "typed" by the user, whether at a physical keyboard or typed elsewhere. The language model may be used to predict which characters were typed by the user and then input those characters into the user interface.

In some embodiments, interpreting the received neuromuscular signals as input commands with respect to the at least one sensory cue provided by the user interface may include recognizing at least one user gesture based on the received neuromuscular signals. This recognized user gesture is then used to control selection of a particular typed input. In some cases, this typed input may be provided via a surface-agnostic gesture performed by the user. Such surface-agnostic gestures may be performed on substantially any surface, including in the air or on the user's leg, etc. These embodiments will be described in greater detail with regard to FIGS. 37M-37W.

FIG. 37M depicts a human computer interface system 371100 comprising wearable device 371110, interface system 371120, and application system 371130. As described herein, wearable device 371110 includes one or more sensors and can communicate with interface system 371120 and/or application system 371130. Wearable device 371110 may be configured to enable recording of signals using the one or more sensors when worn on the body of a user. The recorded signals may include neuromuscular signals such as electromyography (EMG) signals, mechanomyography (MMG) signals, and/or sonomyography (SMG) signals. In some implementations, the recorded signals can further include position, velocity, and/or acceleration information acquired from one or more inertial measurement unit (IMU) sensors, or other position-tracking sensors. In some implementations, wearable device 371110 can be configured to perform analog processing (e.g., noise reduction, filtering, etc.) and analog to digital conversion of the recorded signals. Wearable device 371110 can communicate with interface system 371120 using any suitable wireless technology and protocol, non-limiting examples of which include radiofrequency signaling, Bluetooth, Zigbee, WiFi, or the like. For example, wearable device 371110 can provide the recorded signals, or features extracted from the recorded signal, to interface system 371120.

Interface system 371120 can be configured to receive the recorded signals from wearable device 371110 and generate data and/or instructions for use by application system 371130. In some implementations, interface system 371120 can be configured to identify a state of a part of the body of the user using one or more inference models and the received signals or features extracted from the received signals can be provided as input to the inference model(s). Interface system 371120 can be configured to communicate identified states of a part of the user's body to application system 371130. For example, interface system 371120 can provide predicted position, orientation, joint angle, force, movement, pose, or gesture information to application system 371130. Interface system 371120 can be configured to communicate with application system 371130 using any suitable wireless technology and protocol, non-limiting examples of which include radiofrequency signaling, Bluetooth, Zigbee, WiFi, or the like.

A state of a part of the user's body can include position, orientation, joint angle, force, movement, pose, or gesture information associated with the body part of the user. A state can describe a configuration of one or more segments in a musculoskeletal representation of the part of the body of a user. Such a musculoskeletal representation can model the body part of the user as a multi-segment articulated rigid body system, with joints forming the interfaces between the different segments and joint angles defining the spatial relationships between connected segments in the model. The spatial relationships between the connected segments in the model can be subject to anatomical constraints. The segments can be modeled as rigid bodies, or can be modeled as rigid bodies subject to inter-segment movements (e.g., a model for a forearm segment can be semi-rigid to account for the motion of the ulna and radius bones of the forearm). Position, orientation, and/or joint angle information for the segments, and time derivatives thereof (e.g., linear or angular velocity or acceleration), can be described with respect to one or more fixed coordinate systems, and/or with respect to the positions and orientations of other segments or body parts of the user.

A force can include a linear force and/or a rotational (torque) force exerted by one or more segments of the musculoskeletal representation. Examples of linear forces include, but are not limited to, the force of a finger or hand pressing on a solid object such as a table, and a force exerted when two segments (e.g., two fingers) are pinched together. Examples of rotational forces include, but are not limited to, rotational forces created when segments in the wrist or fingers are twisted or flexed. In some embodiments, the indicated body state information can include one or more of pinching force information, grasping force information, or information about co-contraction forces between muscles represented by the musculoskeletal representation.

Body state information may comprise or relate to a pose and can indicate a static configuration of one or more body parts. The static configuration can describe the position of one or more body parts. For example, a pose can include a fist, an open hand, statically pressing the index finger against the thumb, pressing the palm of a hand down on a solid surface, or grasping a ball. A pose can indicate the static configuration by providing positional information (e.g., segment coordinates, joint angles, or similar information) for the pose, or by providing an identifier corresponding to a pose (e.g., a parameter, function argument, or variable value). Body state information may comprise or relate to a gesture and can indicate a dynamic configuration of one or more body parts. The dynamic configuration can describe the position of the one or more body parts, the movement of the one or more body parts, and forces associated with the dynamic configuration. For example, a gesture can include waving a finger back and forth, throwing a ball, or grasping and throwing a ball.

In some embodiments, body state information can describe a hand of the user (e.g., hand state information), which may be modeled as a multi-segment articulated body. The joints in the wrist and each finger can form the interfaces between the multiple segments in the model. In various embodiments, a body state can describe a combination of a hand with one or more arm segments. It should be appreciated, however, that the techniques described herein are also applicable to musculoskeletal representations of portions of the body other than the hand including, but not limited to, an arm, a leg, a foot, a torso, a neck, or any combination of the foregoing.

In some implementations, as described herein, the recorded signals can exhibit spatio-temporal (e.g., spatio-frequential) patterns that depend on the manner or way a user wears the wearable device. For example, a state can be associated with a first spatio-temporal pattern when a user is wearing the wearable system in a first manner (e.g., in a manner in which the electrodes are in contact with certain areas of the user's skin) and a second spatio-temporal pattern when the user rotates the wearable system on the body or when the user moves the wearable system to a different part of the body (e.g., from a lower arm position to an upper arm position). Thus the inference model can be trained to identify one or more body states using the exhibited spatio-temporal patterns.

In some implementations, the wearable system may be configured to determine a rotation and/or position of the wearable system and to select a corresponding inference model trained or adapted for identifying body state in the determined position and/or rotation. Differently stated, the wearable system may be configured to auto-calibrate, such that the device adapts to any rotation and/or arm position offset without interfering with the user experience, also referred to herein as auto-calibration to account for the way the system is worn by the user in relation to their underlying musculature and other anatomy that affects the neuromuscular signals recorded by the wearable system. In some implementations, the wearable system can be configured to adapt to users that may have injured or missing muscles, different adipose tissue or fat, and other anatomic variables. Although discussed with regards to multiple inference models, it is appreciated that the embodiments discussed herein can, in some instances, be implemented as a single inference model. It is also appreciated that the one or more inference models may be trained from data collected from multiple users.

An inference model that classifies neuromuscular signal patterns for auto-calibration may be built by performing one or more of the following steps: 1) build a new statistical model or experiment class that takes as input a set of preprocessed neuromuscular signals, 2) generate a batch of training data by randomly applying a rotation offset to the preprocessed signals, 3) produce positive labels when the augmented offset is 0, and null otherwise, 4) take the batch of training data and calibrate it to have calibrated data at offset=0, and 5) train an inference model and evaluate its performance by testing different rotation offsets.

Application system 371130 may be configured to receive body state information from interface system 371120. In response to the received indications, application system 371130 may be configured to perform actions on one or more applications executing on application system 371130. The actions can include changing an execution state of an application (e.g., starting, stopping, suspending, or resuming the application) or communicating with the application (e.g., providing commands and/or data to the application). As described herein, application system 371130 may be configured to provide a user interface. The user interface can be configured to provide visual, auditory, haptic, and/or other sensory feedback to commands and/or data received from application system 371130. For example, a user can interact with graphical controls and indicators displayed by the user interface on a display associated with application system 371130. As an additional example, the user interface can provide auditory prompts and/or feedback using speakers associated with the computing system. As a further example, the user interface can provide haptic prompts or feedback using controllers that apply forces to the user (e.g., vibrations using a linear resonant actuator or eccentric rotating mass actuator).

It should be appreciated that the functionality described above with regards to wearable device 371110, interface system 371120, and application system 371130 may be combined or divided between one or more computing devices. In an exemplary embodiment, wearable device 371110 can be configured with one or more trained inference models. Wearable device 371110 can record signals, use the one or more trained inference models to identify one or more states of a part of the user's body, and provide an indication of the identified body state to a separate computing device implementing application system 371130. In an additional exemplary embodiment, wearable device 371110 can be configured to provide the recorded signals, and/or features extracted from the recorded signals, to a separate computing device implementing interface system 371120 and application system 371130. The separate computing device, which can be configured to implement interface system 371120 using a device driver, application, emulator, or the like, can identify the one or more states of a part of the user's body using one or more trained inference models and the received recorded signals, and/or extracted features. The identified states can be mapped to data or instructions and at least some of the data or instructions may be provided to one or more applications running on a separate computing device (e.g., one or more computing devices in the cloud). In an additional embodiment, wearable device 371110 can implement the functionality of interface system 371120 and application system 371130.

At least some of the systems and methods described herein relate to generating text based on neuromuscular signals recorded using one or more neuromuscular sensors arranged on one or more wearable devices while a user wearing the wearable device(s) performs typing movements. FIG. 37N schematically illustrates a process for using a neuromuscular-based system trained to interpret typing gestures, or other user activity in accordance with some embodiments. The typing gesture may be single-key gestures (e.g., pressing the key for the letter "x") or multiple-key gestures performed concurrently (e.g., pressing the "Shift" key and the key for the letter "x" at the same time to output a capital "X") or at least partially in succession within a certain time duration (e.g., pressing the "Ctrl"+ "Alt" and "Delete" keys at least partially in succession to perform a command, bring up a menu, or perform some other keyboard shortcut). The embodiments described herein relate to processing neuromuscular data as a user performs conventional typing gestures (e.g., as one would use with a keyboard) without requiring the use of a physical keyboard. However, it should be appreciated that one or more of the techniques described herein may also be used to interpret other types of neuromuscular data associated with a user's intent to type including, but not limited to, sub-muscular activations in which the user is trained to activate individual or small groups of motor units without performing movements.

In act 371210, neuromuscular signals are recorded from a plurality of neuromuscular sensors arranged on a wearable device. In act 371212, the recorded signals (or information (e.g., features) derived from the signals) are provided as input to one or more inference models, which interpret the signals (or information derived from the signals) to generate one or more FIG. 1n act 371214, the predictions output from the inference model(s) may be constrained using, for example, a language model, as discussed in more detail below. In act 371216, a final predicted character or characters are provided as text. Various aspects for training and using inference models to output one or more characters based on recorded neuromuscular signals are provided in the sections that follow. In the disclosed system and methods described herein that comprise labeling one or more data sets, the accuracy of the labeling can be confirmed by the user or the system. For example, after one or more neuromuscular inputs, the user can be prompted to confirm the accuracy of the inputted text prior to the system labeling the character data for incorporation into the inferential mode(s). Alternatively, the system can automatically detect the accuracy of the recorded neuromuscular signals and associated text inputs based on the frequency of user-initiated "backspace" key presses during typing of the data set(s).

FIG. 37O schematically illustrates a system 371300, for example, a neuromuscular activity sensing system, in accordance with some embodiments of the technology described herein. The system 371300 includes a plurality of sensors 371310 (e.g., neuromuscular sensors) configured to sense and record signals arising from neuromuscular activity in skeletal muscle of a human body. The sensors 371310 may include any or all of the sensors identified above in conjunction with sensors 37802 of FIG. 37J. In some embodiments, the plurality of neuromuscular sensors may be arranged relative to the human body and used to sense muscular activity related to a movement of the part of the body controlled by muscles from which the muscular activity is sensed by the neuromuscular sensors. Spatial information (e.g., position and/or orientation information) and force information describing the movement may be predicted based on the sensed neuromuscular signals as the user moves over time.

In some embodiments, sensor data recorded by the sensors 371310 may be optionally processed by processor(s) 371312 to compute additional derived measurements, which may then be provided as input to one or more inference models, as described in more detail below. For example, recorded signals from an IMU may be processed to derive an orientation signal that specifies the orientation of a segment of a rigid body over time. The sensors 371310 may implement signal processing using components integrated with the sensing components of the sensors 371310, or at least a portion of the signal processing may be performed by one or more components in communication with, but not directly integrated with, the sensing components of the sensors 371310.

The system 371300 also includes one or more computer processors 371312 programmed for one-way or two-way communication with sensors 371310. For example, signals recorded by one or more of the sensors 371310 may be output from the sensor(s) 371310 and provided to the processor(s) 371312, which may be programmed to execute one or more machine-learning algorithms to process the signals output by the sensor(s) 371310. The algorithm(s) may process the signals to train (or retrain) one or more inference models 371314, and the resulting trained (or retrained) inference model(s) 371314 may be stored for later use in generating control signals. The processor(s) 371312 may be in one-way or two-way communication with the inference model(s) 371314.

In some embodiments, the inference model(s) 371314 may produce discrete outputs. Discrete outputs (e.g., discrete classifications) may be used, for example, when a desired output is to know whether a particular pattern of activation (including individual neural spiking events) is currently being performed by a user. For example, the inference model(s) 371314 may be trained to estimate whether the user is activating a particular motor unit, activating a particular motor unit with a particular timing, activating a particular motor unit with a particular firing pattern, or activating a particular combination of motor units. On a shorter time scale, a discrete classification may be used in some embodiments to estimate whether a particular motor unit fired an action potential within a given amount of time. In such a scenario, these estimates may then be accumulated to obtain an estimated firing rate for that motor unit.

In embodiments in which an inference model is implemented as a neural network configured to output a discrete output, the neural network may include an output layer that is a softmax layer, such that outputs of the inference model add up to one and may be interpreted as probabilities. For instance, the outputs of the softmax layer may be a set of values corresponding to a respective set of control signals, with each value indicating a probability that the user wants to perform a particular control action. As one non-limiting example, the outputs of the softmax layer may be a set of three probabilities (e.g., 0.92, 0.05, and 0.03) indicating the respective probabilities that a detected pattern of activity is one of three known patterns.

It should be appreciated that when an inference model is a neural network configured to output a discrete output (e.g., a discrete signal), the neural network is not required to produce outputs that add up to one. For example, for some embodiments, instead of a softmax layer, the output layer of the neural network may be a sigmoid layer, which does not restrict the outputs to probabilities that add up to one. In such embodiments, the neural network may be trained with a sigmoid cross-entropy cost. Such an implementation may be advantageous in cases where multiple different control actions may occur within a threshold amount of time and it is not important to distinguish an order in which these control actions occur (e.g., a user may activate two patterns of neural activity within the threshold amount of time). In some embodiments, any other suitable non-probabilistic multi-class classifier may be used, as aspects of the technology described herein are not limited in this respect. In some embodiments, an output of the inference model(s) 371314 may be a continuous signal rather than a discrete signal. For example, the inference model(s) 371314 may output an estimate of a firing rate of each motor unit, or the inference model(s) 371314 may output a time-series electrical signal corresponding to each motor unit or submuscular structure.

It should be appreciated that aspects of the technology described herein are not limited to using neural networks, as other types of inference models may be employed in some embodiments. For example, in some embodiments, the inference model(s) 371314 may comprise a hidden Markov model (HMM), a switching HMM in which switching allows for toggling among different dynamic systems, dynamic Bayesian networks, and/or any other suitable graphical model having a temporal component. Any such inference model may be trained using recorded sensor signals.

As another example, in some embodiments, the inference model(s) 371314 may be a classifier that takes, as input, features derived from the recorded sensor signals. In such embodiments, the classifier may be trained using features extracted from the sensor signals. The classifier may be, e.g., a support vector machine, a Gaussian mixture model, a regression-based classifier, a decision tree classifier, a Bayesian classifier, and/or any other suitable classifier, as aspects of the technology described herein are not limited in this respect. Input features to be provided to the classifier may be derived from the sensor signals in any suitable way. For example, the sensor signals may be analyzed as time-series data using wavelet analysis techniques (e.g., continuous wavelet transform, discrete-time wavelet transform, etc.), Fourier-analytic techniques (e.g., short-time Fourier transform, Fourier transform, etc.), and/or any other suitable type of time-frequency analysis technique. As one non-limiting example, the sensor signals may be transformed using a wavelet transform and the resulting wavelet coefficients may be provided as inputs to the classifier.

In some embodiments, values for parameters of the inference model(s) 371314 may be estimated from training data. For example, when the inference model(s) 371314 is a neural network, parameters of the neural network (e.g., weights) may be estimated from the training data. In some embodiments, parameters of the inference model(s) 371314 may be estimated using gradient descent, stochastic gradient descent, and/or any other suitable iterative optimization technique. In embodiments where the inference model(s) 371314 is a recurrent neural network (e.g., an LSTM), the inference model(s) 371314 may be trained using stochastic gradient descent and backpropagation through time. The training may employ a squared error or cross-entropy loss function and/or any other suitable loss function, as aspects of the technology described herein are not limited in this respect.

The system 371300 also may optionally include one or more controller(s) 371316. For example, the controller(s) 371316 may include a display controller configured to display a visual representation (e.g., a representation of a hand). As discussed in more detail below, the one or more computer processors 371312 may implement one or more trained inference models that receive, as input, signals sensed and recorded by the sensors 371310 and that provide, as output, information (e.g., predicted hand state information) that may be used to generate control signals and control an augmented reality system.

The system 371300 also may optionally include a user interface 371318. Feedback determined based on the signals recorded by the sensors 371310 and processed by the processor(s) 371312 may be provided via the user interface 371318 to facilitate a user's understanding of how the system 371300 is interpreting the user's intended activation. The user interface 371318 may be implemented in any suitable way, including, but not limited to, an audio interface, a video interface, a tactile interface, and electrical stimulation interface, or any combination of the foregoing.

In some cases, the embodiments described herein may train an inference model for predicting typing movements based on neuromuscular signals using bootstrapping. In some cases, collecting a large amount of labeled training data to train an inference model to map neuromuscular signals to characters (e.g., letters) may be cumbersome. At least some of the embodiments described herein may be directed to using a bootstrapping technique to generate a personalized inference model for a user without requiring the user to provide large amounts of labeled training data used to train and therefore personalize the inference model. As described in more detail below, some embodiments are directed to using a generalized model trained on data collected from a group of users, and then supplementing the generalized model with additional training data collected from a user for which a personalized inference model is to be created.

FIG. 37P shows a process for generating a personalized inference model trained to output characters based on neuromuscular data provided as input to the model in accordance with some embodiments. In act 371410, neuromuscular data is recorded as a user is typing using an input device. In some instances, the input device may be a physical keyboard coupled to a computing system configured to determine the identity of keys pressed by the user. In other instances, the input device may be a representation of a keyboard without requiring use of a physical keyboard. In such instances, an external device (e.g., a camera) may be used to determine which key the user pressed. Regardless of the type of input device used, the output of act 371410 includes recorded neuromuscular data and an identity of keys (or representations of keys) that the user pressed during recording of the neuromuscular data. The ground truth data (identity of the keys) enables the neuromuscular data to be labeled, and the labeled neuromuscular data may be used to train an inference model to predict the identity of keys based on the neuromuscular data. In some embodiments, the neuromuscular data and ground truth data collected in act 371410 may be collected from a plurality of users to create a training dataset of labeled data that may be used to train a generalized (e.g., user-independent) model. In other embodiments, a small amount of neuromuscular data and ground truth data may be collected from a user for which the personalized inference model is to be created, and the small amount of labeled data may be used to create a "lightly trained" model that may further be trained using unlabeled "off-keyboard" data, examples of which are described in more detail below.

The process of FIG. 37P then proceeds to act 371412, where the labeled neuromuscular data recorded in act 371410 is used to train an inference model to produce a generalized (or lightly trained) inference model that maps neuromuscular data to the identity of particular keys on a keyboard. The generalized inference model may be trained, for example, by applying each exemplar in the labeled training data set to the inference model such that the model more accurately represents the mapping between the recorded neuromuscular signals and the ground truth data (i.e., identity of keys).

The process of FIG. 37P then proceeds to act 371414, where surface-agnostic (e.g., without a physical keyboard or "off-keyboard") unlabeled training data is recorded from a user for whom a personalized inference model is to be generated. The "off-keyboard" data comprises neuromuscular data for which ground truth data is not known. For example, the neuromuscular data may be recorded while the user is typing on a surface (e.g., a table) or midair and without using a physical keyboard to record the keystrokes. The data recorded in act 371414 is considered to be "unlabeled" because the ground truth data is not known. The process of FIG. 37P then proceeds to act 371416, where the unlabeled data collected in act 371414 is used to retrain the generalized (or lightly trained) model generated in act 371412. Exemplary techniques for training an inference model using off-keyboard data are discussed in more detail below.

One of the challenges with assigning key (e.g., character) labels to continuously recorded neuromuscular data while a user performs typing movements is that neuromuscular data corresponding to multiple instances of the same key presses (e.g., multiple presses of the "s" key) may have slightly different alignments. Accordingly, some embodiments employ connectionist temporal classification (CTC) to train the inference model when implemented as a neural network (e.g., an LSTM network). A CTC network has a continuous output (e.g., a softmax output), which is fitted through training to model the probability of a label (e.g., that the user has pressed a certain key). Labeled sequences (e.g., for the key "s") are considered equivalent if they differ only in alignment.

CTC is a technique that helps resolve alignment issues often observed in data collection, but further enables collection of data where exact alignments are not available. In particular, in a CTC architecture, the loss function is invariant to the exact timing of the labels in that the objective function is marginalized over all alignments. In this instance, a CTC architecture may be used to allow for collection of "off-keyboard" data for use in training a typing inference model.

Systems and methods for surface-agnostic (e.g., without a physical keyboard or "off-keyboard") text entry based on neuromuscular signal data inputs to an inference model generally involve each user generating training data so that a personalized inference model can be trained. However, traditional generalized models for surface-agnostic text entry can exhibit sub-par performance in at least some instances. As described herein, aspects of a training data set for training a personalized inference model for surface-agnostic text entry may include the following: 1) neuromuscular signal data measured by a plurality of neuromuscular sensors (e.g., a radial array of surface electromyography (sEMG) electrodes worn on each of a user's two forearms or wrists to measure neuromuscular signals corresponding to the muscles of the forearm that control most movements and forces of the fingers, hand, and wrist), and 2) character label data that represents the intended key press by the user (i.e., ground truth data for training a model to infer an intended key press based on neuromuscular signal inputs).

In an exemplary embodiment, each of the two data types above (neuromuscular signal data and character label data) may contain timestamps and may be co-registered in time, so that a particular time segment of neuromuscular signal data may be aligned with character label data.

The embodiments described herein include various systems and methods for generating training data for training an inference model for surface-agnostic text input that takes as input neuromuscular signal data from a plurality of neuromuscular sensors worn on a user's forearm or wrist. The embodiments described herein may also include systems and methods for generating neuromuscular signal data and co-registered character label data (comprising all or part of the user training data) without having to type on a physical keyboard and/or use a keylogger to generate character label data. In some embodiments, these systems and methods for generating training data may not require the use of a physical keyboard (which may be mechanical, touchscreen based, etc.) and/or a keystroke logger or keylogger.

In an exemplary embodiment, there may be two or more characteristics of character label data sets used for training surface-agnostic text entry inference models. First, the composition of the character label data can be known (i.e., the user intends to type "The brown fox jumps over the fence."). Second, the character label data can be temporally aligned to the neuromuscular signal data. FIG. 37Q shows schematically how chunking of multi-channel neuromuscular signal data (16 channels of surface EMG data in the example of FIG. 37Q) may be performed for character data. In the example shown in FIG. 37Q, three words ("The," "Brown," and "Fox") are aligned to the appropriate portion of sEMG data (e.g., 'chunked') with gaps representing periods between typing of each of the words.

In some cases, the embodiments described herein may include various techniques (which may be implemented as systems or methods) that sufficiently detect and collect character label data and do not require a physical keyboard or keylogger. These various embodiments may be used individually or in combination (either concurrently or sequentially).

For example, the embodiments described herein may generate off-keyboard training data by providing text of increasing complexity. In one embodiment, a user puts on neuromuscular sensors which can be worn on a user's forearm(s) or wrist(s). In this embodiment, character label data can be generated by providing a user with increasingly complex verbal or written prompts while they are typing on a surface, in midair, on their lap, etc. Text prompts provided to the user early in the process can comprise one or more simple or complex characters, which may enable reliable registration of neuromuscular signal data with the character label data. The epochs associated with neuromuscular data obtained during typing can be used to build a first, relatively less accurate, inference model for surface-agnostic text input. This inference model can be used to chunk (register) sEMG data in subsequent phases of training data generation that can use more complex text prompts. In this embodiment, the composition of the character training data may be provided according to user prompts, and the registration of the data (timing relative to neuromuscular data, i.e., chunking) may be performed according to the output of simple inference models for surface agnostic text input. These simple inference models can be made more accurate and able to parse and infer text entry as more training data is acquired, e.g., in an iterative process.

In this exemplary embodiment, the following process may be employed after the user has put on the neuromuscular sensors on their forearm(s) or wrist(s) as shown in FIG. 37R. In act 371610, a user optionally can be provided with instructions to enter text on a surface (e.g., a table or desk that is not an electrical or mechanical keyboard) with their hands in a traditional keyboard 'home position' and further guided to maintain a relaxed pose in the home position unless otherwise prompted to enter text. By maintaining a relaxed position between text prompts, the user can facilitate chunking and registration of their neuromuscular data to character label data, because the neuromuscular signal level is low between text prompts and high while the user types on the surface according to the text prompt.

In act 371612, the user can be provided with a first text prompt to type without a physical keyboard (e.g., by typing on a desk surface, in midair, or on their lap). The first text prompt can be simple (e.g., a single letter or short word), so that the registration (i.e. chunking) of neuromuscular data to this character label data can be performed reliably. For example, an algorithm for chunking a simple text prompt may include identifying the epoch of neuromuscular data (e.g., average rectified sEMG signals or root mean squared sEMG) that exceeds a threshold and is the first such event that follows the time when the text prompt was delivered. In some embodiments, act 371612 may include providing a plurality of text prompts before proceeding to act 371614.

For this and at least some other embodiments described herein, any of the text prompts provided to the user can be delivered visually via a screen, booklet, AR/VR headset, or using another suitable technique, audibly via a set of headphones, smart speaker, other speaker, or verbally by a technician, or by another technique appropriate for the user (e.g., braille if the user is blind).

In act 371614, the neuromuscular signal data and temporally registered character label data may be provided as input to train an inference model (e.g., a neural network that includes an LSTM architecture). The inference model can be trained to infer which key (i.e., character) the user intends to press and provide that inference (e.g., likelihood estimate) as a control signal for the system disclosed herein. In act 371616, the user may be provided with additional text prompts that can be more complicated (e.g., words with more characters, phrases, etc.), and the user can 'type' them on a virtual keyboard of the surface that may or may not have any visual contours.

In act 371618, the system determines whether the inference model requires additional training. Any suitable metric may be used to determine whether the model requires additional training. For example, it may be determined whether the inference model has achieved a threshold level of performance as set by the user, and the performance level can be determined subjectively by the user or objectively by the system, including, but not limited to, the system analyzing neuromuscular data associated with keystroke errors (e.g., the frequency of backspace commands initiated by the user). When it is determined in act 371618 that additional training is required, the process returns to act 371614, where additional training may be performed and the acts 371614 and 371616 continued to be performed iteratively, with increasingly complex text prompts and inference models being employed that can both more reliably register (i.e. chunk) neuromuscular data associated with the more complex text prompts and more accurately infer the intended character input by the user. This iterative process can continue until the inference model achieves a threshold level of performance as set by the user or the system as determined in act 371618, after which the trained inference model is output in act 371620. This exemplary embodiment for generating training data may be repeated as needed, depending on the level of system performance desired.

In some cases, the embodiments described herein may generate off-keyboard training data by leveraging a generalized model for a chunking key and a user-defined control signal. In another exemplary embodiment of a system and method as disclosed herein, an action gesture, verbalization, button press (e.g., via a traditional physical keyboard, mouse, touchscreen, or similar), or (virtual) keystroke can be used to indicate the beginning and/or end of a user's entry of prompted text. By relying on the user to provide a marker for the onset and offset of an epoch of entry of prompted text onto a surface according to the positions of a keyboard layout (but without an actual keyboard present), neuromuscular data may be more easily chunked, registered in time with prompted text, and used as input for training an inference model for surface-agnostic text entry.

This embodiment can comprise the following process, which may be employed after the user has put on the neuromuscular sensors on their forearm(s) or wrist(s) as shown in FIG. 37S. In act 371710, a user optionally can be provided instructions to enter text on a surface (i.e. a table or desk that is not an electrical or mechanical keyboard), or in midair with their hands starting in a traditional keyboard 'home position' and further guided to maintain a relaxed pose in the home position unless otherwise prompted to enter text. By maintaining a relaxed position between text prompts, the user can facilitate chunking and registration of their neuromuscular data to character label data, because the neuromuscular signal level is low between text prompts and high while the user types on the surface according to the text prompt. In act 371712, the user can be provided a text prompt which may be a word, phrase, or sentence.

In act 371714, a 'text entry' control signal provided by a user to a computing machine coordinating the training data process can be received. The text entry control signal indicates that the user will commence executing the motor commands to enter the prompted text. In various embodiments, the 'text entry' control signal may comprise one or more of the following: (i) a physical or electrical button, switch, or other similar control (e.g., one on a traditional physical keyboard, implemented via a touchscreen display (e.g., an app), foot pedal, or other controller or joystick, etc.), (ii) a gesture (e.g., a snap, finger pinch, finger flick, fist, etc.) provided as a control signal via the output of a previously trained inference model that takes as input a plurality of neuromuscular signals and provides as output a likelihood about a specific gesture or other neuromuscular control signal generated by the user, (iii) a verbalization (e.g., the user performs an audible utterance, a microphone detects the sound, and a speech recognition algorithm identifies that the appropriate 'text entry' control signal has been received, (iv) activation of a single motor unit or a plurality of single motor units either one or a plurality of times within a specified duration, wherein the motor unit activity is detected by a neuromuscular sensor (or plurality of neuromuscular sensors), or (v) by implementing a generalized model for detecting based on a plurality of neuromuscular signals that a user has pressed the spacebar, enter key, or other large key on the-surface agnostic keyboard.

In act 371716, the user can enter the prompted text by performing the appropriate movements (e.g., taps, etc.) on a surface-agnostic keyboard. In act 371718, the user can provide another 'text entry' control signal, indicating they have completed entering the prompted text.

It should be understood that acts 371714-371718 can be repeated to collect sufficient data for training an inference model for surface-agnostic text input according to a specified schedule. In some instances, a user may specify a preferred level of accuracy for an inference model for surface-agnostic text input, which can determine the number of times steps three through five are repeated. It should be appreciated that the larger the training data set (e.g., due to repeating acts 371714-371718), the better the expected accuracy of a subsequently trained inference model for surface-agnostic text input. In other instances, the system can be programmed with a preferred level of accuracy including, but not limited to, determining the amount of errors associated with text input based on the frequency of the user pressing the backspace key.

In act 371720, the neuromuscular signal data and temporally registered character label data can be provided as input to train an inference model (e.g., a neural network that includes an LSTM architecture). The inference model can be trained to infer which key (i.e. character) the user intends to press. The trained personalized inference model is output in act 371722.

In some embodiments, the embodiments described herein may generate off-keyboard training data with the user speaking while typing. In some cases, no text prompts are provided to the user. Rather, the user can speak the words they type as they type them, and the spoken words can be recorded by a microphone. The recorded sounds can be provided as input to a speech recognition process, and the output of the speech recognition process can be used to identify the identity and timing of the characters the user has entered into the surface-agnostic virtual keyboard.

This embodiment may comprise the following process after the user has put on the neuromuscular sensors on their forearm(s) or wrist(s) as shown in FIG. 37T. In act 371810, a user optionally can be provided with instructions to enter text on a surface (i.e. a table or desk that is not an electrical or mechanical keyboard), or in midair with their hands in a traditional keyboard 'home position' and further guided to maintain a relaxed pose in the home position unless otherwise prompted to enter text. By maintaining a relaxed position between text prompts, the user facilitates chunking and registration of their neuromuscular data to character label data, because the neuromuscular signal level is low between text prompts and high while the user types on the surface according to the text prompt.

In act 371812, the user can audibly speak words and type them concurrently (or approximately concurrently or at a defined interval). In act 371814, a microphone can record the user's speech, provide it as input to a speech recognition process, and the system can generate character label data (e.g., which characters the user input and the timestamp relative to neuromuscular data) based on the spoken words. In act 371816, the neuromuscular signal data and temporally registered character label data can be provided as input to train an inference model (e.g., a neural network that includes an LSTM architecture). The inference model can be trained to infer which key (i.e. character) the user intends to press. The trained personalized inference model is output in act 371818.

In still other embodiments, the embodiments described herein may generate off-keyboard training data by using machine vision to generate character label data. In some cases, a non-functional representation of a keyboard can be placed or projected onto a typing surface or in midair, and a camera can be used to image or record the user's movements as they type to determine the identity and timing of characters to be used as label data. This embodiment may include one or more of the following acts after the user has put on the neuromuscular sensors on their forearm(s) or wrist(s) as shown in FIG. 37U.

In act 371910, a user optionally can be provided with instructions to enter text on a surface (i.e. a table or desk that is not an electrical or mechanical keyboard) with their hands in a traditional keyboard 'home position' and further guided to maintain a relaxed pose in the home position unless otherwise prompted to enter text. By maintaining a relaxed position between text prompts, the user can facilitate chunking and registration of their neuromuscular data to character label data, because the neuromuscular signal level is low between text prompts and high while the user types on the surface according to the text prompt.

In act 371912, an image, printout, or other visible non-functional representation of a keyboard can be placed or projected on the surface onto which the user will 'type.' In variations of the embodiment, any of several methods for creating a visible non-functional representation of a keyboard can be used, including: (i) a projector may project an image of a keyboard onto the typing surface, (ii) a paper printout or other physical representation of a keyboard, (iii) virtual keyboard object in an augmented, virtual, or mixed reality environment, or (iv) other non-functional representation of a keyboard, or any combination of any of the foregoing.

In act 371914, a camera (or plurality of cameras) is configured to have the non-functional representation of a keyboard in its field of view and capture and/or record images (static or dynamic images as in a video recording) as the user types self-generated text (i.e., without prompting). In act 371916, the images or recordings can be input to one or more machine vision processes that can identify the user's fingers (and, optionally, hand or other portion of the user's body), and determine which character on the non-functional representation of the keyboard the user presses. The output of act 371916 can provide character label data (identity of characters and timestamp of the characters). It should be understood that a user may, if desired, confirm the accuracy of the output prior to the system creating the character label data.

In act 371918, the neuromuscular signal data and temporally registered character label data can be provided as input to train an inference model (e.g. a neural network that includes an LSTM architecture). The inference model can be trained to infer which key (i.e. character) the user intends to press. The trained personalized inference model is output in act 371920.

In some cases, the embodiments described herein may detect good home position and account for variations in a user's posture. The embodiments described herein indicate that the pattern of neuromuscular signals recorded from the forearm(s) or wrist(s) while a user enters text using systems and/or methods for surface-agnostic text entry (e.g., without a keyboard) may vary from session to session if a user's posture changes. That is, the pattern of neuromuscular signals associated with pressing a specific 'virtual' key on a surface (e.g., the letter 'c' or the sequence of letters to spell 'cardinals') may differ according to the user's posture while typing that 'virtual' key. For example, during text entry, a user may be seated upright at a desk, slouched on their chair, standing at a desk, reclining on a couch with her fingers on her legs, etc. The embodiments described herein indicate that an inference model can be trained based on neuromuscular data to predict labels representing a user's posture, typing location, surface onto which they are pressing their fingers to enter text, etc. In some exemplary embodiments, a generalized model can be trained to detect a posture or position for typing across users.

In other exemplary embodiments, a user can provide label data, or data can be collected from the user directly or indirectly, that corresponds to their posture, position, and/or typing surface location. A personalized inference model can be trained to predict their posture and/or typing position based on neuromuscular signal data recorded from the user (e.g., sEMG from their wrist or forearm). In one exemplary embodiment, neuromuscular data can be collected when a user begins to use a system or method for surface-agnostic text input, and the neuromuscular data can be combined with data from other auxiliary sensors that can be input to an inference model for predicting a user's posture and/or pose. The output of the inference model can reflect the user's position or posture (or the likelihood of the user's position or posture). The listing of auxiliary sensors suitable for the purpose described herein can comprise one or more of the following: an IMU, an infrared sensor, a pyroelectric infrared sensor, a heat sensor, a magnetic sensor, a gyroscopic sensor, an accelerometer sensor, etc. It should be understood that any spatiotemporal-related sensor can be used as an auxiliary sensor.

The user's position or posture can be used to adjust an inference model for surface-agnostic text input (or, alternatively, to select among several inference models tuned for particular postures) in order to improve the accuracy of text entry detection by the user. Feedback can also be provided to a user if their detected posture is unsuitable for accurate inference about text entry, so that the user may adjust their posture.

Systems and methods for text input without a keyboard, touchscreen, or other mechanical or electrical system (i.e. based on typing motions by a user onto a table or other surface) based on neuromuscular signals recorded from the wrist or forearm of the user and inference models trained to predict which virtual key a user intends to press based on the measured neuromuscular signal data can be generally referred to as surface-agnostic text input. Systems and methods for surface-agnostic text input would benefit from additional gesture-based functionality, as described herein.

A user may engage and interact with a system or method for surface-agnostic text input in keyboard text entry mode in order to type specific letters, characters, and/or words. The user can also initiate various inputs and/or commands by using certain gestures. In general, a control feature of a gesture can be the force associated with the gesture, and control gestures can include dynamic gestures, static gestures, and compound gestures of multiple sequential and/or concurrent gestures. A user's gesture can be detected by providing as input the same neuromuscular signal data recorded from the user's forearm or wrist to an inference model for gesture detection. The output of the inference model for gesture detection can be a likelihood of a gesture among a set of specified gestures and, for at least some gestures, an estimate of the force with which the user makes the gesture. Gestures described herein as machine control inputs take the output of the inference model for gesture detection and provide it as a control signal to a text entry functionality of a machine. The user can initiate these gestures while remaining in keyboard text entry mode, or, alternatively, the gestures can take the user out of the keyboard text entry mode and into a gesture mode. In either embodiment, the user's ability to interact with the display and virtual keyboard can be enhanced to enable more complicated and efficient text and character inputs and navigation on the display.

In one exemplary embodiment, the user can input a capital letter by exerting a relatively larger amount of force during a "finger tap," by "double finger" tapping, or by "finger tapping" and holding/pushing firmly on the surface with that same finger. By way of examples, a user can input a capital letter "D" (i) by tapping the user's left middle finger with a relatively larger amount of force than needed to input a lowercase letter "d," (ii) by tapping and pressing firmly, or just pressing firmly onto a surface, with the user's left middle finger, (iii) by double tapping the user's left middle finger, or (iv) with another suitable gesture or compound gesture. In another exemplary embodiment, the user can initiate "caps lock" by (i) tapping all of the fingers at once on both hands, (ii) by double tapping all of the fingers on both hands, (iii) by tapping and holding firmly all of the fingers on both hands, or (iv) with another suitable gesture or compound gesture. The user can exit from "caps lock" by again performing one of the foregoing gestures.

In another exemplary embodiment, the user can delete a previously typed word, phrase, or sentence by using a specified 'delete' gesture. In an exemplar embodiment, a snap gesture can be used as a delete key. In an alternative embodiment, a gesture may be used to change the functionality of a subsequent activation of the surface-agnostic text entry system. For example, activating a 'delete' virtual key on a surface-agnostic text input system can in general cause a single character to be deleted and can provide an altered function of deleting an entire word if there is a preceding first gesture to change the delete mode.

In another exemplary embodiment, a set of gestures permits a user to accept among one or more autocorrect or autosuggest options provided by a natural language model module of the surface agnostic text entry system. While the user is typing in the keyboard text entry mode, the system can prompt the user to accept a word or phrase that can include a suggested word based on a preliminary set of characters (referred to herein as "autocomplete") and a suggested word to correct a mis-typed word (referred to herein as "autocorrect"). In general, suggestions can be automatically suggested based on a natural language model that takes as input a set of characters and/or words that a user has already entered (and may, optionally, include a personalized language model based on aa user's history of text entry such as proper nouns) and visually presented to the user on a visual interface of a system for surface-agnostic text input. Next, the user may optionally select one of the autosuggested words or phrases with a specified gesture.

In one exemplary embodiment, a user can scroll or toggle through the suggested words or phrases by, for example, tapping a finger and the user can accept one of the words or phrases by pinching one or more mitten fingers to the thumb. Alternatively, the user can select directly from the various suggested words or phrases without scrolling or toggling through the options by pinching a specific mitten finger with the thumb. In this exemplary embodiment, option 1 from the suggested words or phrases can be selected by pinching the index finger with the thumb, option 2 from the suggested words or phrases can be selected by pinching the middle finger with the thumb, and so on. The user can be presented with and can select from multiple suggested words or phrases at the same time and the visual layout of the suggested words or phrases can indicate to the user which gesture to perform. For example, four autosuggestions may be provided in a horizontal display arrangement, so that the user intuitively understands which of the four fingers of their right hand to pinch to their thumb. In another example, up to eight suggestions can be presented that can be chosen from specific mitten finger and thumb pinches from either the left or right hands.

In general, any of the preceding gesture control frameworks based on a pinch of a finger to the thumb can be replaced with another suitable gesture (or, alternatively, a single motor unit control), including the use of a flick of any of the four mitten fingers (i.e. a dynamic gesture), wherein the finger is held by the thumb while the user activates the extensor muscle for that finger, then the user releases the finger and permits it to extend. In another exemplary embodiment, the user can toggle through one or more series of suggestions by tapping a finger and then selecting from one of those suggestions by initiating a pinch as described herein. FIGS. 37V and 37W show exemplary portions of a user interface that include a text entry box 372010 and autosuggestion options 372020A and 372020B generated based on a current word being typed in the text entry box 372010.

In another exemplary embodiment, the embodiments described herein may suggest a word to replace a previously input word that may have one or more typographical errors (e.g., autocorrection). The user can select from one or more suggested words or phrases using a gesture or combination of gestures, as described herein.

In another exemplary embodiment, a user can disengage and/or exit from the keyboard text entry mode by performing a specified gesture. For example, an open hand gesture of both hands can be used to open and/or exit from a text entry mode of a surface-agnostic text input system. Once exited from the keyboard text entry mode, the user can stay in a gesture mode or can perform other actions outside of text or character entry. In one exemplary embodiment, the user can enter into a 2D movement/pointing/mouse mode by making a certain gesture or set of gestures. For example, a user can rotate their wrist to enter into the 2D movement/pointing/mouse mode, and then use their index finger to point to various portions of the display to move a mouse cursor. An example of using a 2D movement mode to perform typing is described in more detail below. Alternatively, the user can move a hand on their work surface, in midair, or on their lap to control the positioning of a cursor on the display. The user can use another gesture to implement a click, for example by using the other hand to click or double-click text or a character by, for example, tapping or double tapping their index finger. The user can tap and hold and draft their index finger firmly on the work surface or their lap to highlight desired text or characters.

In another exemplary embodiment, a user can initiate a "cut," "copy," or "pasting" function using a specific gesture. For example, a user can mimic a "cutting" action using their index and middle fingers to cut a word or phrase from the inputted text or characters.

In some embodiments, a user can prompt the system to enter into one or more alternative input modes, including, but not limited to, the following input modes: a "careful typing" mode, "new language" mode, "symbol" mode, "special character" mode, a "computer settings" mode (volume, brightness, etc.), "mouse" mode, etc. As discussed above, in order to initiate one or more of the alternative modes, the user can perform one or more gestures with any specific or a loosely defined degree or degrees of force (e.g., a loosely held first versus a tightly squeezed fist). Detection of a gesture can either initiate a specific alternative input mode, or detection of the gesture may result in presentation of potential alternative input modes to a user (e.g., on a screen) from which the user can select one of the input modes. When in one of the alternative input modes, the user can be presented with visual display options (such as text and/or images) and the user can leverage this concurrent visual feedback to select from one or more input options within the mode from the visual display.

In one exemplary embodiment, a user can activate a "careful" typing mode by squeezing their left hand to make a first (or performing some other gesture). When in "careful" typing mode, the system can present the user with a display of different input options such as different letter keys or numbers. These input options can relate to a "finger tap" previously initiated or performed by the user. For example, if a user intended to type a "j" with an index finger prior to entering into "careful" typing mode, and the user engages the mode, the system can present the user with one or more of the following letter options associated with the reach of the index finger: "j," "y," "u," "h," "n," and/or "m." The user may scroll through these various letter options by tapping the same index finger (or any other finger) with a relatively lighter amount of force and then tapping the same index finger (or any other finger) with a relatively heavier amount of force to select the desired input letter once it is highlighted on the display. In another embodiment, the user can select the desired input option once it is highlighted using a thumb to mimic pressing the "spacebar" or some other key on a surface upon which the hand is resting. Once the user selects the desired input from the various options, the system can exit from the "careful" typing mode and input the selected letter and present it on the user's typing screen. Alternatively, if the user wants to exit the "careful" typing mode without selecting an input, the user can do so by squeezing the left hand again to make another fist.

FIG. 37W illustrates a portion of a user interface that displays a representation of a keyboard when the user has engaged the "careful" typing mode through a gesture. As shown, three characters on the keyboard—'w,' 's,' and 'x'—have been highlighted as possible character candidates that the system determines the user may have typed, with one character—'s' being emphasized to show the user that the system has determined that character as the most likely candidate. The user may then select the most likely candidate or one of the other highlighted candidates by, for example, performing a gesture, cycling through the candidates by typing with the same finger, or using some other suitable technique.

In another embodiment, the system can also enter into "careful" typing mode automatically without the user initiating it by performing a gesture. By way of example, if the system is either unable to detect the user's desired input, or if the system can only detect the desired input below a certain level of confidence, the system can automatically enter into the "careful" typing mode. The user can interact with the system in the "careful" typing mode by selecting from one of several potential inputs, as described above, or the user can exit the mode by initiating or performing a specific gesture. Further, based on what the user selects during the "careful" typing mode, the system can better detect future desired inputs, by for example, associating the neuromuscular data signal(s) obtained prior to initiating "careful" typing mode with the selected user input during the "careful" typing mode so that the system can more accurately detect future desired user input without the need to utilize the "careful" typing mode as frequently moving forward.

In another exemplary embodiment, the user can enter into a "new language" mode by squeezing their right hand or using another appropriate gesture. Once this mode is initiated, the new language mode can present various options to the user on the visual display such as "Spanish, "French," "German," etc. If the user engages the language mode after attempting to input or inputting the letter "e," by way of example, the user can select "Spanish" using a specific gesture as described above (e.g., tapping through the options using the left middle finger) and then can select "é" for a Spanish accented "e" by using a specific gesture as described above (e.g., pressing the spacebar).

For any or all of the foregoing embodiments, it should be understood that the user's hands can be positioned on top of a surface, held in mid-air, or placed on the user's legs. Further, while the foregoing embodiments described specific gestures used in specific embodiments, it should be understood that any other gesture or gestures can be used to achieve the functionality described herein. For embodiments that incorporate an autosuggest and/or autocorrect functionality, the embodiments described herein indicate that it may be beneficial to retain multiple potential inferences about the intended text entry by a user in a surface-agnostic text input system or method and to update the likelihood of a sequence of text entry based on a natural language model so that autocorrections and/or autocomplete suggestions can be generated for selection by the user.

Specifically, the embodiments described herein indicate that the output of a CTC network can be input to a natural language model to further improve the accuracy of the inference model predictions. In one embodiment, a beam search algorithm can be applied to the lattice of predicted keystrokes, and the system or method can update the likelihood of a character sequence according to the natural language model. For example, maximum likelihood decoding can show various autosuggestions and/or autocorrections in approximate real-time as a user enters text in a surface-agnostic text input system or method.

FIG. 37X illustrates an embodiment in which a wearable device 372110 may be implemented to control an Internet of Things (IoT) device 372130 through an interface system 372120. Voice-controlled (i.e. voice-enabled) connected devices (including IoT devices (e.g., 372130) and other connected devices such as smartphones, tablets, smartwatches, and smart glasses or other head-mounted displays) are widely implemented in the home, office, and on-the-go environments. Such devices can be connected to one another via a Wi-Fi network, Bluetooth connection, or via any other suitable wired or wireless means. Verbal commands to such connected devices permit control of these systems at a distance. However, at least in some instances, verbal commands may be cumbersome or inefficient for an intended task or series of tasks.

Consistent with at least some embodiments, the embodiments described herein may provide systems and methods that enable control of one or more connected devices based on gestures, poses, and/or other spatiotemporal patterns of muscle activation that cause movements and/or forces across joints that offer significant advantages relative to voice control alone. For example, the wearable device 372110 as described herein for human-machine control can detect neuromuscular signals, and at least in part based on those signals, enable (1) discreet two-way communications (e.g., communicating discretely through muscle activations), (2) dynamic control of one or more devices, and/or (3) identification of and smart access to devices, systems, and/or networks.

In various social contexts as on a bus or plane, people may not want to bring too much attention to themselves while interacting with one or more connected devices. Machine control of these devices based at least in part on neuromuscular signals as described herein permits a user to activate, control, or otherwise use one or more connected devices in a discreet manner appropriate for certain settings. For example, changing the volume of connected (i.e. 'smart') earbuds or a headset may be done discretely by a user tapping a finger on their leg. Further, in some instances, a method of multimodal control (i.e. where control can be exerted by a combination of different forms of control) as contemplated by an embodiment herein can leverage neuromuscular signals and offer a higher degree of access to and control of connected devices than would be possible using a modality of control in isolation.

Additionally, in some situations, voice commands alone may not be able to control a device with sufficient precision. In such situations, a user may execute a gesture alone or in combination with the voice command in order to more accurately and conveniently control a connected device via the systems and methods described herein. For example, a user may rotate their thumb to adjust the volume of a connected device to a desired setting, or a user may mimic spinning a wheel to adjust the brightness, quality, intensity, or wavelength associated with lighting devices.

In other situations, control and authentication for connected devices can be sub-optimal, particularly in environments in which a connected device is accessed by many users (i.e. a speaker or door lock in a connected home). According to certain embodiments of the invention described herein, access control and authentication of a user of a connected device may be achieved by detecting a unique neuromuscular signal associated with a user (i.e., as recorded by an armband or wristband array of neuromuscular sensors using wearable device 372110). A connected device enabled for authentication and/or access control via neuromuscular signals may automatically recognize a user in proximity to the connected device based on their unique pattern of neuromuscular signals, permitting that user to access and control the connected device and/or for a personalized user profile of the connected device to be activated. For example, a user wearing an apparatus with an array of neuromuscular sensors as described herein may enter a room with a connected light fixture configured for neuromuscular authentication and thereby cause the connected light to load a particular color palette or light level personalized for that user.

At least some of the embodiments described herein indicate that systems and methods as described herein for using neuromuscular signals to create controls based on gestures, poses, movements, or forces exerted across a user's joints may be particularly advantageous when paired with smart earbuds, smart glasses (or other smart head mounted displays), smartphones, smartwatches, connected tablets, other wearable or handheld personal computing devices, or any other external smart device including but not limited to thermostats, garage door openers, car doors, gates, locks, etc. Whereas many connected devices are configured to recognize voice commands, the systems and methods as described herein for machine control and interaction based on neuromuscular signals can enable a user to interact with auditory (e.g. via a 'hearable' or other connected headphone or speaker system) or visual (e.g. on a screen of a smartwatch or smartphone or other screen) cues using commands based on poses, gestures, or other movements and/or forces as derived from neuromuscular signals.

For example, a wearable wristband apparatus with a plurality of neuromuscular sensors may be configured to permit a user to respond to a smart assistant (e.g. via a wearable or handheld device with visual, haptic, and/or auditory alerts) with small, subtle gestures (i.e., via a finger tap on the user's leg to accept a meeting invitation or to confirm a hotel reservation, or a swipe gesture on a tabletop to ignore a notification, or a pinch gesture to play a video received from a friend, or a flick gesture to send a message to a colleague).

The embodiments described herein indicate that environments with multiple connected devices may require specific controls, so that a user can direct their intention for control to a particular connected device. Exemplary embodiments of the systems and methods for human machine control as described herein may permit a gesture or other pattern of neuromuscular activation to be used to switch from one connected device to another for subsequent control, where the subsequent control may be exerted by neuromuscular control signals, voice signals, and/or another modality of control.

For various embodiments, the systems described herein may indicate that combining voice control with neuromuscular control based on gestures, poses, and/or other patterns of movement and/or force exerted by the neuromuscular system can enable more reliable, diverse, discrete, and/or personalized forms of machine control. By way of a non-limiting example, the embodiments described herein indicate that user authentication based at least in part on neuromuscular activity may be used to activate a smart wallet for payment processing.

As noted above, gestures and/or poses may refer to a static or dynamic configuration of one or more body parts including the position of the one or more body parts and forces associated with the configuration(s). For example, gestures can include discrete orientations, such as placing or pressing the palm of a hand down on a solid surface or grasping a ball, continuous gestures, such as waving a finger back and forth, grasping and throwing a ball, or a combination of discrete and continuous gestures or poses. Gestures may also include covert gestures that are imperceptible to another person, such as slightly tensing a joint by co-contracting opposing muscles or using sub-muscular activations. Gestures may be defined by an application configured to prompt a user to perform the gestures or, alternatively, gestures may be arbitrarily defined by a user. The gestures performed by the user may include symbolic gestures (e.g., gestures mapped to other gestures, interactions, or commands, for example, based on a gesture vocabulary that specifies the mapping). In some cases, hand and arm gestures may be symbolic and used to communicate according to cultural standards. Non-limiting examples of gestures include the following: up/down/left/right movements, circular movements, single finger or multiple finger taps, specific sequences of finger taps, swipes, clicks, "thumbs up" and "thumbs down" signs, pointing, making of fists with varying amounts of pressure and tightness, wrist rolls, flat hand motions, flicks, two-finger pinches, multiple finger pinches, either alone or in any combination of or specific sequences involving one or more of the foregoing.

In the various embodiments as contemplated herein, a user may initiate a control signal for a connected computing device based on neuromuscular signals that do not cause perceptible movements or forces to be generated. In these embodiments, a neuromuscular control signal may comprise the activation of a single motor unit (comprising a spinal motor neuron and the muscle fibers onto which it forms a neuromuscular junction) and/or a plurality of motor neurons recorded through a plurality of neuromuscular sensors. In general, the activation of a motor unit is referred to as a motor unit action potential (MUAP). For example, a user may cause the volume of a connected speaker to increase with a MUAP from a first motor unit and may cause the volume to decrease with a MUAP from a second motor unit.

The embodiments described herein indicate that MUAPs elicited from a plurality of motor units may be used to increase the effective degrees of freedom (DOFs) for controlling a machine, IoT device, or other connected device by activating multiple motor units concurrently (or within a specified duration) or in a specified sequence. In some instances, an aspect of the control signal may require a user to activate some motor units and not activate other units. For example, a control scheme based on a user controlling three motor units labeled A, B, and C may cause a particular control signal to be transmitted to a connected computing device based on concurrently, consecutively, or within a specified duration, activating motor units A and B but not activating motor unit C. In some instances, a control signal based on motor unit activation may require a certain frequency (or count) of MUAPs within a threshold period of time. For example, pausing a video on a connected screen may require that motor unit A fires five MUAPs within two seconds, though one skilled in the art will recognize that the required plurality of MUAPs may be greater or less than five, and the duration for counting the MUAPs may be shorter or longer than two seconds.

The table below lists various exemplary and non-limiting methods and/or forms of control a user may exert based on neuromuscular signals, as contemplated herein.

| Feature | Interaction | Potential Control Scheme |
| --- | --- | --- |
| TV control-replace remote | Select app<br>Browse apps/channels<br>Play/pause<br>Go back<br>Go home<br>Menu navigation-scroll<br>Typing | Up/Down/Left/Right/Select<br>Finger taps<br>Swiping<br>Any combination of the foregoing |
| Smart speaker control | Volume up/down<br>Mute/unmute<br>Previous/next<br>Play/pause | Up/Down/Left/Right/Select<br>Swiping<br>Any combination of the foregoing |
| Smart lightbulb control | Lights on/off<br>Dim up/down | Up/Down/Left/Right/Select<br>Swiping<br>Any combination of the foregoing |
| Bidirectional communication | Yes/no (to virtual assistant question)<br>Confirm (purchase, reservation, etc) | Thumb up/down |
| Smart oven control | Oven on/off<br>Temp up/down<br>Preheat/bake/broil on/off | Up/Down/Left/Right/Select<br>Any combination of the foregoing |
| Smart thermostat control | Thermostat On/Off<br>Temp up/down | Up/Down/Left/Right/Select<br>Any combination of the foregoing |
| Smart alarm system control | Camera up/down/left/right<br>Zoom in/out<br>Range increase/decrease | Up/Down/Left/Right/Select<br>Any combination of the foregoing |

-continued

| Feature | Interaction | Potential Control Scheme |
| --- | --- | --- |
| Smart camera control | Camera up/down/left/right<br>Zoom in/out | Up/Down/Left/Right<br>Any combination of the foregoing |
| Smart display video control | Volume up/down<br>Mute/unmute<br>Accept/decline/end call<br>Typing | Up/Down/Left/Right/Select<br>Finger taps<br>Any combination of the foregoing |
| Virtual assistant activation without speaking | Virtual assistant wake<br>Virtual assistant stop | Fist + pressure (at varying levels)<br>Any combination of the foregoing |
| Phone controls mid-call | Pick up/hang up<br>Volume<br>Mute/unmute | Up/Down/Left/Right/Select<br>Any combination of the foregoing |
| Videochat controls mid-call | Pick up/hang up<br>Volume<br>Mute/unmute<br>Video filters | Up/Down/Left/Right/Select<br>Poses<br>Any combination of the foregoing |
| Audio controls in transit | Volume up/down<br>Fwd/back 10 seconds<br>Play/pause<br>Mute/unmute | Up/Down/Left/Right/Select<br>Any combination of the foregoing |
| Song controls on plane or subway or with company at home | Previous/next<br>Play/pause<br>Mute/unmute | Up/Down/Left/Right/Select<br>Any combination of the foregoing |
| Car dashboard controls | Play/pause song<br>Mute/unmute<br>Temp on/off<br>Accept/decline call<br>Volume up/down | Up/Down/Left/Right/Select<br>Any combination of the foregoing |
| Unique neuromuscular signal | User authorization | N/a |
| Unlock front door | Hover | N/a |
| Notification | Engage<br>Ignore | Swipe |
| List | Scroll through<br>Select | Wrist roll<br>Fist |
| Audiobook<br>Radio<br>News<br>Weather<br>Music<br>Phone call | Play/pause song<br>Mute/unmute<br>Temp on/off<br>Accept/decline call<br>Volume up/down | Up/down/left/right/Select |
| Menu | Navigate<br>Select | Up/down/left/right/Select |

In another exemplary embodiment as described herein, three interactive primitives (i.e. basic forms of human machine control) may be used for controlling a connected earbud device or connected headset or head mounted display (or other wearable connected device): "Flick" as a discrete input (where a flick gesture corresponds to flexing a finger (e.g. a middle finger)), holding the finger in place with the thumb, activating the extensor muscles for that finger, and causing the thumb to release the finger so that it rapidly extends. One or more "pinch taps" as discrete inputs (where a pinch tap gesture corresponds to a transient gesture in which a finger (e.g. an index finger) flexes so that the tip of the finger touches the tip of the thumb, then is released by extending the finger and/or thumb). A "wrist roll" primitive may also be used for one-dimensional rotary control similar to the directionality associated with a UI input wheel (where a wrist roll corresponds to a clockwise and/or counterclockwise rotation of the hand which may, optionally, be in a first pose about the wrist joint).

Notifications are often an important part of smart or virtual assistant systems available through smart earbuds or head mounted displays (or other smart connected devices).

In another exemplary embodiment, a flick gesture may be used as a dismissal mechanism for notifications, as this gesture is similar to a dismissal mechanism with which people may already be familiar.

In another exemplary embodiment relating to a calendar application, a smart or virtual assistant may notify a user that their next meeting is coming up, permitting the use of the primitives as follows: "Flick" will dismiss the notification outright. This may be analogous to dismissing a notification on the user's mobile device or desktop. With this gesture, the smart or virtual assistant will not bother the user again about the notification. Index "pinch tap" may set a "standard" snooze alarm. The smart or virtual assistant may notify the user again in a few minutes with this gesture. A middle "pinch tap" may engage a timer function of a smart or virtual assistant. Once the timer mode is engaged, the user may define the duration of a timer to be implemented by the smart or virtual assistant by rolling her wrist to select the timer duration.

As the user rolls their wrist clockwise, for example, the duration of the timer may increase, and the smart or virtual assistant may provide auditory feedback to the user (i.e. '1 minute', '2 minutes', '3 minutes', etc.). If the user accidentally selects a timer duration greater than intended, the user may roll their wrist counterclockwise while receiving further auditory feedback from the smart or virtual assistant, so that the user may select an intended timer duration. Once the correct duration has been selected, another "pinch tap" gesture may set the timer and the smart or virtual assistant will notify the user after the appropriate amount of time. At any point in this process, a "flick" gesture may enable a user to exit the timer setting module.

FIG. 37Y illustrates a process for generating training data for training an inference model (e.g., a neural network) in accordance with some embodiments. In act 372210, multiple neuromuscular signals are processed using a dimensional reduction technique including, but not limited to, a principal component analysis (PCA) or another suitable dimensional reduction technique (e.g., non-negative matrix factorization, linear discriminant analysis). In some instances, the neuro-muscular signals may be processed before applying a dimensional reduction technique, for example, to remove artifacts, apply filters, temporally average, and/or otherwise extract features of interest in the neuromuscular signals. As discussed above, PCA is a non-limiting example of a technique for reducing dimensionality. In one implementation using PCA, five components of the data are specified, the data is normalized by removing the median, and a peak detection algorithm is applied to detect local maxima (i.e. peaks) of the first component. In some cases, the received neuromus-cular signals may include multi-dimensional neuromuscular signals. In such cases, the systems herein may calculate a dimensionally reduced signal from the multi-dimensional neuromuscular signals, where the dimensionally reduced signal includes at least one fewer dimension.

FIG. 37Z shows a plot of the first PCA component (in solid black line) with the output of peak detection (in hollow circles). Event occurrences can be clearly resolved in sets of about 50 events according to the specified training regime (e.g., between about 5 and 31 seconds and between about 36 and 64 seconds). In the data shown in FIG. 37Z, the first set of peaks corresponds to index finger taps (e.g., events), and the second set of peaks corresponds to middle finger taps (e.g., events). As shown in FIG. 37Z, the peak detection algorithm identified each event (no false negatives). How-ever, the peak detection algorithm also detected spurious events (false positives) that are spurious events corresponding to local maxima occurring during the rest phase (e.g., periods 372310 and 372320) between sets of finger taps.

The process of FIG. 37Y then proceeds to act 372212, where a peak detection algorithm is applied to data corre-sponding to one or more reduced dimensions (e.g., a prin-cipal component) over time to identify epochs when the signal present in the principal component is large. For example, a clustering algorithm can be applied to some or all detected events. In the example of the data shown in FIG. 37Z, three clusters corresponding to one cluster for each type of finger tap and a third cluster corresponding to all spurious events may be identified. The embodiments described herein indicate that the peak picking algorithm effectively identifies when a finger tap occurs, but that it is typically insufficient for distinguishing between finger taps of one finger (e.g., the index finger) from another finger (e.g., the thumb).

The process of FIG. 37Y then proceeds to act 372214, where the epochs of neuromuscular data occurring in a time window extending for some 10s to 100s of milliseconds before, during, and after an event identified based on peak detection in the dominant principal component are collected. For example, an epoch (temporal slice) of data around each event can be generated by taking a window of, for example, 150 ms centered around each event. It should be appreciated that windows of shorter or longer duration may also be used to generate clusters.

The process of FIG. 37Y then proceeds to act 372216, where a clustering algorithm is applied to the collected epochs of neuromuscular data to distinguish which finger was responsible for the tap (i.e., to distinguish the different classes of events (e.g., index or middle finger tap)). For example, a vector can be generated corresponding to each epoch and the vectors can then be input to a k-means clustering algorithm to extract the three clusters. For visu-alization purposes, uniform manifold approximation and projection (UMAP) can be applied to plot the clusters. FIG. 38A shows that the expected three clusters (e.g., clusters 372410 and 372420 for the two fingers that performed taps, and cluster 372430 for the spurious event cluster) are clearly separated. The spurious event cluster (i.e., cluster 372430) can be distinguished by identifying the cluster that has the lowest energy, and these events removed from subsequent analysis.

As shown in FIG. 38A, approximately 50 events of each class are present in the clusters corresponding to event 0 (cluster 372410) and event 2 (cluster 372420), which rep-resent finger taps from different fingers. To confirm that clustering has successfully distinguished finger taps of dif-ferent fingers, class event categories can be plotted with the PCA data generated previously to confirm that all events of the same type are consecutive, per the training protocol. The vertical dashed lines 372510 and the vertical dashed lines 372512 in FIG. 38B indicate index and middle finger taps, respectively.

The process of FIG. 37Y then proceeds to act 372218, where clustered events are aligned temporally (e.g., using an iterative algorithm) so that templates can be generated that distinguish taps from different fingers. For example, as discussed further herein, templates may distinguish taps by one finger from taps of another finger according to the temporal profile of a plurality of principal components after the first principal component (which was used in act 372212 to detect events generally). In one implementation, the timing of events can be adjusted so all events are well aligned. An event may be recognized at its onset rather than the peak of the first principal component. Temporal adjustment may be employed to reduce the latency of event detection and enable more responsive machine control.

The identified timing of events from act 372212 can be relatively noisy and the maxima can shift by a few samples and thus create jitter that reduces the fidelity of templates for distinguishing events in later steps. An optimal offset for each epoch can be identified by calculating the autocorrelation between the epoch and a template (averaged across all events). In one exemplary embodiment, an appropriate offset can be identified by testing various offsets (e.g., −10 to 10 samples) and selecting the offset that maximizes the correlation across events. The amount of offset can vary between events, and the process can be performed iteratively until all epochs are aligned.

FIG. 38C shows each identified event (e.g., finger tap) as a row with shading indicating the magnitude of the first principal component prior to temporal alignment. FIG. 38D shows the same identified events (PCA #0) following temporal alignment. After temporal alignment, a template for each event can be plotted for each of the first five principal components. In the case of the index and middle finger tap templates shown in FIG. 38E, the first PCA component differs primarily in amplitude between the two finger taps, and the subsequent components exhibit a distinct profile between events.

The process of FIG. 37Y then proceeds to act 372220, where, based on the detected and clustered events, labels relating to which finger caused the tap are generated. The labels can be used to train a neural network (e.g., a multi-layer perception (MLP)) based on time-delayed features of the neuromuscular signals in order to build a classifier that, once trained, may accurately predict the identity and timing of each discrete event. For example, labels can be created by generating a binary time series with 1 when a specified event occurs and 0 otherwise. A model can then be trained to predict this time series. In inference time, a threshold can be used with a debounce algorithm, or other suitable technique, applied to the output of the model to achieve event detection.

After temporal alignment, the events are typically centered around the peak of the first PCA component and in some instances it may be preferred to predict the event once the user has completed it. Accordingly, the labels may need to be shifted with reference to the event timing, which may be referred to as an offset parameter. Moreover, at least in some cases, a model may not be able to predict the single time sample corresponding to an event, and some temporal flexibility may improve the quality of model output, which can be achieved by implementing the model to predict a 1 for several consecutive time samples around the event (e.g., the pulse width). For example, the offset may be set to be 75 ms after the event peak and the pulse width may be set to be 25 ms. It should be appreciated that other suitable offsets may be used to improve the quality of the model output.

In an exemplary embodiment, the model to be trained is a simple MLP that has input features corresponding to a 150 ms sliding window over the PCA features (e.g., for each time sample a vector is created comprising the last 60 time samples for the 5 PCA components (e.g., 300 dimensions)). It should be understood that other artificial neural networks can alternatively be employed. The model can be trained to predict the extracted labels, and for inference time, the model can be applied on the test data and the output of the model can be thresholded and debounced to obtain the events.

In some cases, the systems described herein may be configured to analyze the received neuromuscular signals to identify a time of occurrence for one or more peaks in the neuromuscular signals that represent discrete muscle activation events. The systems may then identify one or more time windows surrounding the identified peaks in the neuromuscular signal, group the identified time windows into clusters, where each cluster represents a different discrete muscle activation event, temporally align the clusters representing the identified discrete muscle activation events, and then identify at least one specific muscle activation for each temporally aligned cluster.

FIG. 38F shows example data for identifying and distinguishing two events using the techniques described herein. For example, timing and epochs between taps may be analyzed to distinguish between two different fingers (or other body parts) performing a gesture such as a tap. Once identified, the specific body part (e.g., a user's pointer finger) may be used when selecting text or typing characters or when controlling IoT devices. For instance, certain text or characters or IoT devices may be mapped to each finger or to different body parts. Then, when the specified body part is identified and its movements and/or gestures are identified (e.g., using the wearable device 372110 of FIG. 37X), a specific portion of text may be selected, or a specific character may be selected within the UI, or a specific IoT device may be controlled. Other fingers or body parts may select other text or typed characters or may control other IoT devices, even when using the same input commands or gestures. Thus, by determining which finger or other body part is performing the movement, specific commands or inputs associated with or mapped to that body part may be implemented within the UI or in relation to an IoT device or other electronic device. In some cases, due to this mapping, different fingers may cause different tasks to be performed or may perform different options within the UI, even if the fingers (or other body parts) are performing the same gesture, as each finger is mapped to a different input command. For example, if a double tap gesture turns on an IoT device, a double tap with a pointer finger may turn on a coffee maker, while a double tap with a middle finger will turn on an alarm clock, etc.

Accordingly, the embodiments described herein allow users to select input text, provide typed inputs, and/or control IoT devices using muscle movements detected by a wearable device. The neuromuscular signals detected by the wearable device may be converted into input commands and may allow the user to interact with a user interface, selecting different characters or words for input, typing different letters with or without a physical keyboard, and controlling operations on IoT devices using inputs. Because the embodiments described herein may be configured to distinguish between which fingers (or other body parts) are performing the gestures, different commands may be mapped to each finger, allowing a user to initiate certain tasks with each finger, allowing the user a great deal of control over how text is selected or typed, or how IoT devices are controlled using their input neuromuscular signals.

The following describes exemplary systems and methods for contextualized interactions with an environment according to at least one embodiment of the present disclosure.

The present technology disclosed herein provides mapping systems and mapping methods that enable a user to create an electronic 3D map of an environment through a combination of neuromuscular sensing technology and imaging technology. A 3D map may be generated in which objects in the environment are mapped. As described below, the 3D map may include image information as well as location and depth information for the objects. The 3D map also may include additional information, e.g., information identifying which of the objects is a remotely controllable object, i.e., a smart device. The 3D map also may include self-identification information, in which an object in the environment may serve as a reference object for the environment and also may serve as a searchable object used to identify a 3D map corresponding to the environment.

In some embodiments of the present technology, the 3D map may be a map of a real-world environment, and may be employed to control one or more smart device(s) in the real-world environment via neuromuscular activities of a user. In some embodiments, the 3D map may comprise a map of an XR environment, and may include information regarding virtual objects as well as real-world objects in the XR environment.

The present technology also provides systems and methods that utilize a 3D map of an environment to enable a user to control or interact with one or more object(s) in the environment remotely via neuromuscular activities of the user. For example, in the case of a real-world environment that contains a plurality of objects, certain neuromuscular activities of the user (e.g., a pointing of a finger of the user, a closing of a hand of the user to form a fist, a turning of a wrist of the user, etc.) may be targeted or used to select a smart device to be controlled (e.g., a remotely controllable window shade), and also may be used to control the smart device (e.g., to raise or lower the window shade).

In another example, a 3D map of an environment may be used with a XR-based system, described below, such that the environment is an XR environment. The XR environment may be an AR environment, or a VR environment, or an MR environment, or any other type of environment that enables a user to experience aspects of a real-world environment in combination with aspects of a virtual environment. In the XR environment, the user may interact with a virtual object (e.g., paint on a virtual canvas) and also may interact with a real-world smart device (e.g., to adjust the remotely controllable window shade) via certain neuromuscular activities. In some embodiments, the user may interact with another person, in the real-world environment or in the XR environment, via neuromuscular activities performed by the user.

In some embodiments of the present technology, neuromuscular signals corresponding to neuromuscular activity of the user may be sensed by one or more wearable sensors worn by the user, as described in more detail below. The neuromuscular signals may be used to determine information about the user's desired remote interaction with one or more object(s) in the environment. As mentioned above, the environment may be a real-world one or one generated by an XR-based system, or a combination of both. Such neuromuscular signals may also be referred to as "sensed signals" herein. Sensed signals may be used directly as an input to a control system for the environment (e.g., by using motor-unit action potentials as an input signal) and/or the sensed signals may be processed (including by using an inference model as described herein) for the purpose of determining a movement, a force, and/or a position of a part of the user's body (e.g., fingers, hand, wrist, etc.).

For example, neuromuscular signals obtained by neuromuscular sensors arranged on a wearable device worn by the user may be used to determine a force (e.g., a grasping force) applied by the user to a physical object. A number of muscular activation states of the user may be identified from the sensed signals and/or from information derived from the sensed signals, to provide an improved user experience in the environment. The muscular activation states may include, but are not limited to, a static gesture or pose performed by the user, a dynamic gesture or motion performed by the user, a sub-muscular activation state of the user, a muscular tensing or relaxation performed by the user, or any combination of the foregoing. The user's interaction with one or more object(s) in the environment can take many forms, including but not limited to: selection of one or more object(s), control of one or more object(s), activation or deactivation of one or more object(s), adjustment of settings or features relating to one or more object(s), etc. The user's interaction(s) may also be with another person in the environment.

As will be appreciated, the user's interaction may take other forms enabled by the control system for the environment, and need not be the interactions specifically listed herein. For instance, a control operation performed in the environment may include control based on activation of one or more individual motor units, e.g., control based on a sensed or detected sub-muscular activation state of the user, such as a sensed tensing of a muscle.

It should be understood that the phrases "sensed", "detected", "obtained", "collected", "sensed and recorded", "measured", "recorded", and the like, when used herein in conjunction with a sensed signal from a neuromuscular sensor comprises a signal detected by the sensor. Also as will be appreciated, a sensed signal may be stored in a nonvolatile memory before being processed, or processed before being stored in the nonvolatile memory. A sensed signal may be cached before being processed. For example, after detection, the sensed signal may be stored in a memory of the neuromuscular sensor "as-detected" (i.e., raw), or the sensed signal may undergo processing at the neuromuscular sensor prior to storage of the sensed signal and/or storage of a processed signal in the memory of the neuromuscular sensor, or the sensed signal may be communicated (e.g., via a wireless technology, a direct wired connection, and/or other know communication technologies) to an external device for processing and/or storage, or any combination of the foregoing. Optionally, the sensed signal may be processed and utilized without storage in a nonvolatile memory.

Identification of one or more muscular activation state(s) of the user may allow a layered or multi-level approach to interacting remotely with an object in the environment. For instance, in an XR environment, at a first layer/level, one muscular activation state may indicate that the user is interacting with or intends to interact with an object (e.g., a window shade of a window); at a second layer/level, another muscular activation state may indicate a desired control operation (e.g., to open the window shade); at a third layer/level, yet another activation state may indicate that the user wants to activate a set of virtual controls and/or features for the object (e.g., a set of virtual scenery images for different seasons to appear on panes of the window); and at a fourth layer/level, yet another muscular activation state may indicate which of the activated set of virtual controls and/or features the user wants to use when interacting with the object (e.g., virtual scenery images for summer). It should be appreciated that any number of muscular activation states and layers may be used without departing from the scope of this disclosure. For example, in some embodiments, one or more muscular activation state(s) may correspond to a concurrent gesture based on activation of one or more motor units, e.g., the user's hand bending at the wrist while pointing the index finger at the object. In some embodiments, one or more muscular activation state(s) may correspond to a sequence of gestures based on activation of one or more motor units, e.g., the user's hand grasping the object and lifting the object. In some embodiments, a single muscular activation state may both indicate a user's desire to interact with an object and to activate a set of controls and/or features for interacting with the object.

As an example, neuromuscular sensors may sense signals for neuromuscular activities of the user. The sensed signals may be inputted to a computer processor of the control system, which may identify or detect a first muscular activation state of the user using, for example, a trained inference model, as discussed below. The first muscular activation state may correspond to, e.g., a first gesture performed by the user, and may indicate that the user is interacting with or intends to interact with a particular object (e.g., a lamp) in the environment. Optionally, in response to the detecting the first muscular activation state, feedback may be provided to identify the interaction with the object indicated by the first muscular activation state. The neuromuscular sensors may continue to sense signals for neuromuscular activity of the user, and a second muscular activation state may be determined from the sensed signals. Responsive to identifying the second muscular activation state (e.g., corresponding to a second gesture, which may be the same as or different from the first gesture), the control system may activate a set of virtual controls for the object (e.g., controls for turning the lamp on or off, selecting a lamplight brightness level, selecting a lamplight color, etc.). The neuromuscular sensors may continue to sense signals for neuromuscular activity of the user, and a third muscular activation state may be determined, and so on.

In some embodiments of the present technology, muscular activation states may be identified, at least in part, from raw (e.g., unprocessed) sensor signals collected by one or more wearable sensor(s). In some embodiments, muscular activation states may be identified, at least in part, from information based on or derived from raw sensor signals (e.g., processed sensor signals), where the raw sensor signals collected by the one or more of the wearable sensor(s) are processed using one or more technique(s), e.g., amplification, filtering, rectification, and/or other forms of signal processing. In some embodiments, muscular activation states may be identified, at least in part, from one or more output(s) of a trained inference model that receives the sensor signals (raw or processed versions of the sensor signals) as inputs.

In some embodiments of the present technology, muscular activation states of a user, as determined based on sensed signals in accordance with one or more techniques described herein, may be used to interact with one or more object(s) in an environment without requiring the user to rely on cumbersome, inefficient, and/or inconvenient input devices. For example, sensor data (e.g., sensed signals or data derived from such signals) may be obtained from neuromuscular sensors worn by or mounted on the user, and muscular activation states may be identified from the sensor data without the user having to carry a controller and/or other input device(s), and without having the user remember complicated button or key manipulation sequences. Also, the identification of the muscular activation states (e.g., poses, gestures, etc.) from the sensor data can be performed relatively fast, thereby reducing response times and latency associated with issuing control signals to the control system, thus enabling the user to have real-time or nearly real-time interactions in the environment.

As mentioned above, sensed signals obtained by neuromuscular sensors placed at locations on the user's body may be provided as input(s) to one or more inference model(s) trained to generate spatial information for rigid segments of a multi-segment articulated rigid-body model of a human body (i.e., a model of a human musculoskeletal system). The spatial information may include, for example, position information of one or more segments, orientation information of one or more segments, joint angles between segments, and the like. All or portions of the human musculoskeletal system can be modeled as a multi-segment articulated rigid body system, with joints forming the interfaces between the different segments, and with joint angles defining the spatial relationships between connected segments in the model. Based on the input(s), and as a result of training, the inference model(s) may implicitly represent inferred motion of the articulated rigid body under defined movement constraints. The trained inference model(s) may output data useable for applications such as applications for rendering a representation of the user's body, or a portion thereof, in an XR game environment, and/or applications that utilize certain muscular activation states to control smart devices in a real-world environment.

For instance, movement data obtained by a single movement sensor positioned on the user (e.g., on the user's wrist or arm) may be provided as input data to a trained inference model. Corresponding output data generated by the trained inference model may be used to determine spatial information for one or more segments of a multi-segment articulated rigid-body model for the user. For example, the output data may be used to determine the position and/or the orientation of the user's upper arm segment and lower arm segment, which are connected by an elbow joint. The output data may be used to determine an angle between these two connected segments via the multi-segment articulated rigid-body model for the user. Different types of sensors may be used to provide input data to a trained inference model, as discussed below.

In some embodiments of the present technology, sensed signals provided to one or more trained inference model(s) may determine that the user is standing with an outstretched forearm pointing forward. The trained inference model(s) also may determine that a finger of the outstretched forearm has moved from a relaxed bent position to a flexed and pointing position, or that a wrist of the outstretched arm has bent upward or downward, or that the outstretched forearm has rotated clockwise or counterclockwise, etc. As discussed below, muscular activation states identified from the sensed signals may be used in conjunction with a 3D map of an environment to enable the user to, e.g., enter the environment and interact with a smart device remotely via neuromuscular signals. Further, as will be discussed below, by orienting the user in the environment (e.g., via locating a reference object in the environment relative to the user), the user may control and/or interact with a plurality of different smart devices individually (e.g., by using a finger to point at a smart-device window shade in the environment and bending the wrist upward to open the window shade) or collectively (e.g., by using a finger to point at one of several smart-device lamps in the environment and performing a pinching motion with two or more fingers to dim all of the lamps in the environment). As will be appreciated, the output data from the trained inference model(s) may be used for applications other than those specifically identified herein.

In some embodiments of the present technology, various muscular activation states may be identified directly from sensed signals. In other embodiments, as discussed above, muscular activation states, which may comprise handstates (described below), gestures, postures, and the like, may be identified based, at least in part, on results from processing the sensed signals using one or more trained inference model(s). For example, the trained inference model(s) may output motor-unit or muscle activations and/or position, orientation, and/or force estimates for segments of a computer-generated musculoskeletal model. As used herein, the term "gestures" may refer to a static or dynamic configuration of one or more body parts including a position of the one or more body parts and forces associated with the configuration. For example, gestures may include discrete gestures, such as placing or pressing the palm of a hand down on a solid surface or grasping a ball, continuous gestures, such as waving a finger back and forth, grasping and throwing a ball, or a combination of discrete and continuous gestures. Gestures may include covert gestures that may be imperceptible to another person, such as slightly tensing a joint by co-contracting opposing muscles or using sub-muscular activations. In training an inference model, gestures may be defined using an application configured to prompt a user to perform the gestures or, alternatively, gestures may be arbitrarily defined by a user. The gestures performed by the user may include symbolic gestures (e.g., gestures mapped to other gestures, interactions, or commands, for example, based on a gesture vocabulary that specifies the mapping). In some cases, hand and arm gestures may be symbolic and used to communicate according to cultural standards.

In some embodiments of the present technology, sensed signals may be used to predict information about a position and/or a movement of a portion of a user's arm and/or the user's hand, which may be represented as a multi-segment articulated rigid-body system with joints connecting the multiple segments of the rigid-body system. For example, in the case of a hand movement, sensed signals obtained by neuromuscular sensors placed at locations on the user's body (e.g., the user's arm and/or wrist) may be provided as input to an inference model trained to predict estimates of the position (e.g., absolute position, relative position, orientation) and the force(s) associated with a plurality of rigid segments in a computer-based musculoskeletal representation associated with a hand when the user performs one or more hand movements. The combination of position information and force information associated with segments of a musculoskeletal representation associated with a hand may be referred to herein as a "handstate" of the musculoskeletal representation. As a user performs different movements, a trained inference model may interpret neuromuscular signals as position and force estimates (handstate information) that may be output as control signals to control or interact with a smart device in the environment or with another person in the environment. Because the user's neuromuscular signals may be continuously sensed, the user's handstate may be updated in real time and a visual representation of the user's hand (e.g., within an XR environment) may be rendered in real time based on current estimates of the user's handstate. As will be appreciated, an estimate of the user's handstate may be used to determine a gesture being performed by the user and/or to predict a gesture that the user will perform.

Constraints on movement at a joint are governed by the type of joint connecting the segments and the biological structures (e.g., muscles, tendons, ligaments) that may restrict the range of movement at the joint. For example, a shoulder joint connecting the upper arm segment to a torso of a human subject, and a hip joint connecting an upper leg segment to the torso, are ball and socket joints that permit extension and flexion movements as well as rotational movements. In contrast, an elbow joint connecting the upper arm segment and a lower arm segment (or forearm), and a knee joint connecting the upper leg segment and a lower leg segment of the human subject, allow for a more limited range of motion. In this example, a multi-segment articulated rigid body system may be used to model portions of the human musculoskeletal system. However, it should be appreciated that although some segments of the human musculoskeletal system (e.g., the forearm) may be approximated as a rigid body in the articulated rigid body system, such segments may each include multiple rigid structures (e.g., the forearm may include ulna and radius bones), which may enable more complex movements within the segment that may not be explicitly considered by the rigid body model. Accordingly, a model of an articulated rigid body system for use with some embodiments of the technology described herein may include segments that represent a combination of body parts that are not strictly rigid bodies. It will be appreciated that physical models other than the multi-segment articulated rigid body system discussed herein may be used to model portions of the human musculoskeletal system without departing from the scope of this disclosure.

Continuing with the example above, in kinematics, rigid bodies are objects that exhibit various attributes of motion (e.g., position, orientation, angular velocity, acceleration). Knowing the motion attributes of one segment of a rigid body enables the motion attributes for other segments of the rigid body to be determined based on constraints in how the segments are connected. For example, the hand may be modeled as a multi-segment articulated body, with joints in the wrist and each finger forming interfaces between the multiple segments in the model. In some embodiments, movements of the segments in the rigid body model can be simulated as an articulated rigid body system in which position (e.g., actual position, relative position, or orientation) information of a segment relative to other segments in the model are predicted using a trained inference model.

For some embodiments of the present technology, the portion of the human body approximated by a musculoskeletal representation may be a hand or a combination of a hand with one or more arm segments. As mentioned above, the information used to describe a current state of the positional relationships between segments, force relationships for individual segments or combinations of segments, and muscle and motor unit activation relationships between segments, in the musculoskeletal representation is referred to as the handstate of the musculoskeletal representation. It should be appreciated, however, that the techniques described herein are also applicable to musculoskeletal representations of portions of the body other than the hand, including, but not limited to, an arm, a leg, a foot, a torso, a neck, or any combination of the foregoing.

In addition to spatial (e.g., position and/or orientation) information, some embodiments of the present technology enable a prediction of force information associated with one or more segments of the musculoskeletal representation. For example, linear forces or rotational (torque) forces exerted by one or more segments may be estimated. Examples of linear forces include, but are not limited to, the force of a finger or hand pressing on a solid object such as a table, and a force exerted when two segments (e.g., two fingers) are pinched together. Examples of rotational forces include, but are not limited to, rotational forces created when a segment, such as in a wrist or a finger, is twisted or flexed relative to another segment. In some embodiments, the force information determined as a portion of a current handstate estimate includes one or more of pinching force information, grasping force information, and information about co-contraction forces between muscles represented by the musculoskeletal representation. In some embodiments, force information may be used to set of speed for controlling a smart device. For instance, in the previous example of a window shade, a light touching of two fingers may be used as an instruction to close the window shade slowly, whereas a more forceful or strong pinching of the two fingers may be used as an instruction to close the window shade quickly.

Turning now to the figures, FIG. 39A schematically illustrates a system 39100 (e.g., a neuromuscular activity system), in accordance with some embodiments of the technology described herein. The system 39100 may comprise one or more sensor(s) 39110 configured to sense signals resulting from activation of motor units within one or more portion(s) of a human body. The sensor(s) 39110 may include one or more neuromuscular sensor(s) configured to sense signals arising from neuromuscular activities in skeletal muscle of a human body. The term "neuromuscular activity" as used herein refers to neural activation of spinal motor neurons or units that innervate a muscle, muscle activation, muscle contraction, or any combination of the neural activation, muscle activation, and muscle contraction. The one or more neuromuscular sensor(s) may include one or more electromyography (EMG) sensors, one or more mechanomyography (MMG) sensors, one or more sonomyography (SMG) sensors, a combination of two or more types of EMG sensors, MMG sensors, and SMG sensors, and/or one or more sensors of any suitable type able to detect neuromuscular signals. In some embodiments, information relating to an interaction of a user in an environment corresponding to a 3D map may be determined from neuromuscular signals sensed by the one or more neuromuscular sensor(s). Spatial information (e.g., position and/or orientation information) and force information relating to movement (readily visible or covert) may be predicted based on the sensed signals as the user interacts with the environment over time. In some embodiments, the neuromuscular sensor(s) may sense muscular activity related to movement caused by external objects, for example, movement of the user's hand being pushed by an external object.

The sensor(s) 39110 may include one or more auxiliary sensor(s), such as one or more Inertial Measurement Unit(s) or IMU(s), which measure a combination of physical aspects of motion, using, for example, an accelerometer, a gyroscope, a magnetometer, or any combination of one or more accelerometers, gyroscopes and magnetometers. In some embodiments of the present technology, one or more IMU(s) may be used to sense data about movement of the part of the user's body on which the IMU(s) is or are attached, and information derived from the sensed IMU data (e.g., position and/or orientation information) may be tracked as the user moves over time. For example, one or more IMU(s) may be used to track movements of portions (e.g., arms, legs) of the user's body proximal to the user's torso relative to the IMU(s) as the user moves over time.

In embodiments that include at least one IMU and one or more neuromuscular sensor(s), the IMU(s) and the neuromuscular sensor(s) may be arranged to detect movement of different parts of a human body. For example, the IMU(s) may be arranged to detect movements of one or more body segments proximal to the user's torso (e.g., movements of an upper arm), whereas the neuromuscular sensors may be arranged to detect motor unit activity within one or more body segments distal to the user's torso (e.g., movements of a lower arm (forearm) or a wrist). It should be appreciated, however, that the sensors (i.e., the IMU(s) and the neuromuscular sensor(s)) may be arranged in any suitable way, and embodiments of the technology described herein are not limited based on any particular sensor arrangement. For example, in some embodiments, at least one IMU and a plurality of neuromuscular sensors may be co-located on a body segment of the user to track motor-unit activity and/or movements of the body segment using different types of measurements. In one implementation, an IMU and a plurality of EMG sensors may be arranged on a wearable device structured to be worn around the lower arm or the wrist of the user. In such an arrangement, the IMU may be configured to track, over time, movement information (e.g., positioning and/or orientation) associated with one or more arm segments, to determine, for example, whether the user has raised or lowered his/her arm, whereas the EMG sensors may be configured to determine finer-grained or more subtle movement information and/or sub-muscular information associated with activation of muscular or sub-muscular structures in muscles of the wrist and/or the hand.

As the tension of a muscle increases during performance of a motor task, the firing rates of active neurons increases and additional neurons may become active, which is a process that may be referred to as motor-unit recruitment. The pattern by which neurons become active and increase their firing rate is stereotyped, such that expected motor-unit recruitment patterns, may define an activity manifold associated with standard or normal movement. In some embodiments of the present technology, sensed signals may identify activation of a single motor unit or a group of motor units that are "off-manifold," in that the pattern of motor-unit activation is different from an expected or typical motor-unit recruitment pattern. Such off-manifold activation may be referred to herein as "sub-muscular activation" or "activation of a sub-muscular structure," where a sub-muscular structure refers to the single motor unit or the group of motor units associated with the off-manifold activation. Examples of off-manifold motor-unit recruitment patterns include, but are not limited to, selectively activating a higher-threshold motor unit without activating a lower-threshold motor unit that would normally be activated earlier in the recruitment order, and modulating the firing rate of a motor unit across a substantial range without modulating the activity of other neurons that would normally be co-modulated in typical motor-unit recruitment patterns. In some embodiments, one or more neuromuscular sensor(s) may be arranged relative to the user's body and used to sense sub-muscular activations without observable movement, i.e., without a corresponding movement of the user's body that can be readily observed. Sub-muscular activation may be used, at least in part, to interact with objects in a real-world environment as well as an XR environment, in accordance with some embodiments of the present technology.

Some or all of the sensor(s) 39110 may each include one or more sensing components configured to sense information about the user. In the case of IMUs, the sensing component(s) of an IMU may include any one or any combination of: an accelerometer, a gyroscope, a magnetometer, which may be used to measure or sense characteristics of body motion of the user, examples of which include, but are not limited to, acceleration, angular velocity, and a magnetic field around the user's body during the body motion. In the case of neuromuscular sensors, the sensing component(s) may include, but are not limited to, electrodes that detect electric potentials on the surface of the body (e.g., for EMG sensors), vibration sensors that measure skin surface vibrations (e.g., for MMG sensors), acoustic sensing components that measure ultrasound signals (e.g., for SMG sensors) arising from muscle activity, or any combination thereof. Optionally, the sensor(s) 39110 may include any one or any combination of: a thermal sensor that measures the user's skin temperature (e.g., a thermistor); a cardio sensor that measures the user's pulse and/or heart rate, a moisture sensor that measures the user's state of perspiration, and the like. Exemplary sensors that may be used as part of the one or more sensor(s) 39110, in accordance with some embodiments of the technology disclosed herein, are described in more detail in U.S. Pat. No. 10,409,371 entitled "METH-ODS AND APPARATUS FOR INFERRING USER INTENT BASED ON NEUROMUSCULAR SIGNALS," which is incorporated by reference herein.

In some embodiments, the one or more sensor(s) 39110 may comprise a plurality of sensors 39110, and at least some of the plurality of sensors 39110 may be arranged as a portion of a wearable device structured to be worn on or around a part of the user's body. For example, in one non-limiting example, an IMU and a plurality of neuromuscular sensors may be arranged circumferentially on an adjustable band (e.g., an elastic band), such as a wristband or an armband structured to be worn around the user's wrist or arm, as described in more detail below. In some embodiments, multiple wearable devices, each having one or more IMU(s) and/or one or more neuromuscular sensor(s) included thereon, may be used to determine information relating to an interaction of the user with an object based on activation from sub-muscular structures and/or based on movement(s) that involve multiple parts of the user's body. Alternatively, at least some of the plurality of sensors 39110 may be arranged on a wearable patch structured to be affixed to a portion of the user's body.

FIGS. 39B-39E show various types of wearable patches. FIG. 39B shows a wearable patch 39220 in which circuitry for an electronic sensor may be printed on a flexible substrate that is structured to adhere to an arm, e.g., near a vein to sense blood flow in the user. The wearable patch 39220 may be an RFID-type patch, which may transmit sensed information wirelessly upon interrogation by an external device. FIG. 39C shows a wearable patch 39240 in which an electronic sensor may be incorporated on a substrate that is structured to be worn on the user's forehead, e.g., to measure moisture from perspiration. The wearable patch 39240 may include circuitry for wireless communication, or may include a connector structured to be connectable to a cable, e.g., a cable attached to a helmet, a heads-mounted display, or another external device. The wearable patch 39240 may be structured to adhere to the user's forehead or to be held against the user's forehead by, e.g., a headband, skullcap, or the like. FIG. 39D shows a wearable patch 39260 in which circuitry for an electronic sensor may be printed on a substrate that is structured to adhere to the user's neck, e.g., near the user's carotid artery to sense flood flow to the user's brain. The wearable patch 39260 may be an RFID-type patch or may include a connector structured to connect to external electronics. FIG. 39E shows a wearable patch 39280 in which an electronic sensor may be incorporated on a substrate that is structured to be worn near the user's heart, e.g., to measure the user's heartrate or to measure blood flow to/from the user's heart. As will be appreciated, wireless communication is not limited to RFID technology, and other communication technologies may be employed. Also, as will be appreciated, the sensor(s) 39110 may be incorporated on other types of wearable patches that may be structured differently from those shown in FIGS. 39B-39E.

In some embodiments of the present technology, the sensor(s) 39110 may include sixteen neuromuscular sensors arranged circumferentially around a band (e.g., an elastic band, an adjustable belt, etc.) structured to be worn around the user's lower arm (e.g., encircling the user's forearm). For example, FIG. 39F shows an embodiment of a wearable system 39300 in which neuromuscular sensors 39304 (e.g., EMG sensors) are arranged on an adjustable belt 39302. It should be appreciated that any suitable number of neuromuscular sensors may be used, and the number and arrangement of neuromuscular sensors used may depend on the particular application for which the wearable system 39300 is used. For example, a wearable armband or wristband may be used to sense information for controlling a robot, controlling a vehicle, scrolling through text, controlling a virtual avatar, or any other suitable control task. In some embodiments, the adjustable belt 39302 may also include one or more IMU(s) (not shown).

FIGS. 39G and 39H show other embodiments of a wearable system of the present technology. In particular, FIG. 39G illustrates a wearable system 39400 that includes a plurality of sensors 39410 arranged circumferentially around an elastic band 39420 structured to be worn around the user's lower arm or wrist. The sensors 39410 may be neuromuscular sensors (e.g., EMG sensors). As shown, there may be sixteen sensors 39410 arranged circumferentially around the elastic band 39420 at a regular spacing. It should be appreciated that any suitable number of the sensors 39410 may be used, and the spacing need not be regular. The number and arrangement of the sensors 39410 may depend on the particular application for which the wearable system is used. For instance, the number and arrangement of the sensors 39410 may differ when the wearable system is to be worn on a wrist in comparison with a thigh. As mentioned above, the wearable system (e.g., armband, wristband, thigh-band, etc.) can be used to sense information for controlling a robot, controlling a vehicle, scrolling through text, controlling a virtual avatar, and/or performing any other suitable control task.

In some embodiments of the present technology, the sensors 39410 may include only a set of neuromuscular sensors (e.g., EMG sensors). In other embodiments, the sensors 39410 may include a set of neuromuscular sensors and at least one auxiliary device. The auxiliary device(s) may be configured to continuously or intermittently collect one or a plurality of auxiliary signal(s). Examples of auxiliary devices include, but are not limited to, IMUs, microphones, imaging devices (e.g., cameras), radiation-based sensors for use with a radiation-generation device (e.g., a laser-scanning device), heart-rate monitors, and other types of devices, which may capture the user's condition or other characteristics of the user. As shown in FIG. 39G, the sensors 39410 may be coupled together using flexible electronics 39430 incorporated into the wearable system. FIG. 39H illustrates a cross-sectional view through one of the sensors 39410 of the wearable system shown in FIG. 39G.

In some embodiments of the present technology, the output(s) of one or more of sensing component(s) of the sensors 39410 can be optionally processed using hardware signal-processing circuitry (e.g., to perform amplification, filtering, and/or rectification). In other embodiments, at least some signal processing of the output(s) of the sensing component(s) can be performed using software. Thus, signal processing of sensed signals detected by the sensors 39410 can be performed by hardware or by software, or by any suitable combination of hardware and software, as aspects of the technology described herein are not limited in this respect.

Returning to FIG. 39A, in some embodiments, sensed signals obtained by the sensor(s) 39110 may be optionally processed to compute additional derived measurements, which may then be provided as input to an inference model, as mentioned above described in more detail below. For example, sensed signals obtained from an IMU may be processed to derive an orientation signal that specifies an orientation of a segment of a rigid body over time. The sensor(s) 39110 may implement signal processing using components integrated with the sensing components of the sensor(s) 39110, or at least a portion of the signal processing may be performed by one or more other component(s) in communication with, but not directly integrated with, the sensing components of the sensor(s) 39110.

The system 39100 also includes one or more computer processor(s) 39112 programmed to communicate with the sensor(s) 39110. For example, sensed signals obtained by one or more of the sensor(s) 39110 may be output from the sensor(s) 39110 (in raw form or in processed form, as discussed above) and provided to the processor(s) 39112, which may be programmed to execute one or more machine-learning algorithm(s) to process the sensed signals. The algorithm(s) may process the sensed signals to train (or retrain) one or more inference model(s) 39114, and the trained (or retrained) inference model(s) 39114 may be stored for later use in generating selection signals and/or control signals for controlling an object in an environment or a 3D map, as described below. As will be appreciated, in some embodiments, the inference model(s) 39114 may include at least one statistical model.

In some embodiments of the present technology, the inference model(s) 39114 may include a neural network and, for example, may be a recurrent neural network. In some embodiments, the recurrent neural network may be a long short-term memory (LSTM) neural network. It should be appreciated, however, that the recurrent neural network is not limited to being an LSTM neural network and may have any other suitable architecture. For example, in some embodiments, the recurrent neural network may be any one or any combination of: a fully recurrent neural network, a gated recurrent neural network, a recursive neural network, a Hopfield neural network, an associative memory neural network, an Elman neural network, a Jordan neural network, an echo state neural network, and a second-order recurrent neural network, and/or another suitable type of recurrent neural network. In other embodiments, neural networks that are not recurrent neural networks may be used. For example, deep neural networks, convolutional neural networks, and/or feedforward neural networks may be used.

In some embodiments of the present technology, the inference model(s) 39114 may produce discrete outputs. Discrete outputs (e.g., discrete classifications) may be used, for example, when a desired output is to know whether a particular pattern of activation (including individual neural spiking events) is detected in the sensed neuromuscular signals. For example, the inference model(s) 39114 may be trained to estimate whether the user is activating a particular motor unit, activating a particular motor unit with a particular timing, activating a particular motor unit with a particular firing pattern, or activating a particular combination of motor units. On a shorter timescale, a discrete classification may be used in some embodiments to estimate whether a particular motor unit fired an action potential within a given amount of time. In such a scenario, these estimates may then be accumulated to obtain an estimated firing rate for that motor unit.

In embodiments in which an inference model is implemented as a neural network configured to output a discrete output (e.g., a discrete signal), the neural network may include an output layer that is a softmax layer, such that outputs of the inference model add up to one and may be interpreted as probabilities. For instance, outputs of the softmax layer may be a set of values corresponding to a respective set of control signals, with each value indicating a probability that the user wants to perform a particular control action. As one non-limiting example, the outputs of the softmax layer may be a set of three probabilities (e.g., 0.92, 0.05, and 0.03) indicating the respective probabilities that a detected pattern of activity is one of three known patterns. However, it should be appreciated that when an inference model is a neural network configured to output a discrete output (e.g., a discrete signal), the neural network is not required to produce outputs that add up to one. For example, instead of a softmax layer, the output layer of the neural network may be a sigmoid layer, which does not restrict the outputs to probabilities that add up to one. In such embodiments, the neural network may be trained with a sigmoid cross-entropy cost. Such an implementation may be advantageous in cases where, for example, multiple different control actions may occur within a threshold amount of time and it is not important to distinguish an order in which these control actions occur (e.g., a user may activate two patterns of neural activity within the threshold amount of time). It should be understood that any other suitable non-probabilistic multi-class classifier may be used, as aspects of the technology described herein are not limited in this respect.

In some embodiments of the present technology, an output of the inference model(s) 39114 may be a continuous signal rather than a discrete output (e.g., a discrete signal). For example, the inference model(s) 39114 may output an estimate of a firing rate of each motor unit, or the inference model(s) 39114 may output a time-series electrical signal corresponding to each motor unit or sub-muscular structure.

It should be understood that aspects of the technology described herein are not limited to using neural networks, as other types of inference models may be employed in some embodiments. For example, in some embodiments, the inference model(s) 39114 may comprise a hidden Markov model (HMM), a switching HMM in which switching allows for toggling among different dynamic systems, dynamic Bayesian networks, and/or another suitable graphical model having a temporal component. Any such inference model may be trained using sensed signals obtained by the sensor(s) 39110.

As another example, in some embodiments, the inference model(s) 39114 may be or may include a classifier that takes, as input, features derived from the sensed signals obtained by the sensor(s) 39110. In such embodiments, the classifier may be trained using features extracted from the sensed signals. The classifier may be, e.g., a support vector machine, a Gaussian mixture model, a regression-based classifier, a decision tree classifier, a Bayesian classifier, and/or another suitable classifier, as the present technology is not limited in this respect. Input data to be provided to the classifier may be derived from the sensed signals in any suitable way. For example, the sensed signals may be analyzed as timeseries data using wavelet analysis techniques (e.g., continuous wavelet transform, discrete-time wavelet transform, etc.), Fourier-analytic techniques (e.g., short-time Fourier transform, Fourier transform, etc.), and/or another suitable type of time-frequency analysis technique. As one non-limiting example, the sensed signals may be transformed using a wavelet transform, and the resulting wavelet coefficients may be provided as input data to the classifier.

In some embodiments of the present technology, values for parameters of the inference model(s) 39114 may be estimated from training data. For example, when the inference model(s) 39114 is or includes a neural network, parameters of the neural network (e.g., weights) may be estimated from the training data. In some embodiments, parameters of the inference model(s) 39114 may be estimated using gradient descent, stochastic gradient descent, and/or another suitable iterative optimization technique. In embodiments where the inference model(s) 39114 is or includes a recurrent neural network (e.g., an LSTM), the inference model(s) 39114 may be trained using stochastic gradient descent and backpropagation through time. The training may employ a cross-entropy loss function and/or another suitable loss function, as aspects of the present technology are not limited in this respect.

The system 39100 also may include one or more controller(s) 39116. For example, the controller(s) 39116 may include a display controller configured to display a visual representation (e.g., a representation of a hand) on a display device (e.g., a display monitor). As discussed herein, the one or more computer processor(s) 39112 may implement one or more of the inference model(s) 39114, which receive, as input, sensed signals obtained by the sensor(s) 39110, and which provide, as output, information (e.g., predicted hand-state information) that may be used to generate control signals that may be used to control, for example, a smart device or other controllable object in an environment defined by a 3D map.

The system 39100 also may optionally include a user interface 39118. Feedback determined based on the sensed signals obtained by the sensor(s) 39110 and processed by the processor(s) 39112 may be provided to the user via the user interface 39118, to facilitate a user's understanding of how the system 39100 is interpreting the user's muscular activity (e.g., an intended muscle movement). The user interface 39118 may be implemented in any suitable way, including, but not limited to, an audio interface, a video interface, a tactile interface, and electrical stimulation interface, or any combination of the foregoing.

The system 39100 may have an architecture that may take any suitable form. Some embodiments of the present technology may employ a thin architecture, in which the processor(s) 39112 is or are included as a portion of a device separate from and in communication with the sensor(s) 39110, which may be arranged on one or more wearable device(s). The sensor(s) 39110 may be configured to wirelessly stream, in substantially real time, sensed signals (in raw or processed form) and/or information derived from the sensed signals to the processor(s) 39112 for processing. The device separate from and in communication with the sensors(s) 39110 may be, for example, any one or any combination of: a remote server, a desktop computer, a laptop computer, a smartphone, a wearable electronic device such as a smartwatch, a health monitoring device, smart glasses, an XR-based system, and a control system of an environment for which a 3D map may be used to identify smart devices and other controllable objects in the environment.

Some embodiments of the present technology may employ a thick architecture in which the processor(s) 39112 may be integrated with the one or more wearable device(s) on which the sensor(s) 39110 is or are arranged. In yet further embodiments, processing of sensed signals obtained by the sensor(s) 39110 may be divided between multiple processors, at least one of which may be integrated with the sensor(s) 39110, and at least one of which may be included as a portion of a device separate from and in communication with the sensor(s) 39110. In such an implementation, the sensor(s) 39110 may be configured to transmit at least some of the sensed signals to a first computer processor remotely located from the sensor(s) 39110. The first computer processor may be programmed to train, based on the sensed signals transmitted to the first computer processor, at least one inference model of the inference model(s) 39114. The first computer processor may be programmed to transmit the trained at least one inference model to a second computer processor integrated with the one or more wearable device(s) on which the sensor(s) 39110 is or are arranged. The second computer processor may be programmed to determine information relating to an interaction between the user wearing the one or more wearable device(s) and an object in an environment of a 3D map using the trained at least one inference model transmitted from the first computer processor. In this way, the training process and a real-time process that utilizes the trained at least one inference model may be performed separately by using different processors.

In some embodiments of the present technology, the controller(s) 39116 may instruct a computer application of an XR system that simulates an XR environment to provide a visual representation by displaying a virtual object. For example, the virtual object may be a character (e.g., an avatar), an imaginary image (e.g., a scene representing a desired season), a tool (e.g., a paintbrush). In one example, positioning, movement, and/or forces applied by portions of a virtual character within the XR environment may be displayed based on an output of the trained at least one inference model. The visual representation may be dynamically updated through use of continuously sensed signals obtained by the sensor(s) 39110 and processed by the trained inference model(s) 39114 to provide a computer-generated representation of the virtual character's movement that is updated in real-time.

Information obtained by or provided to the system 39100, (e.g., inputs obtained from a camera, inputs obtained from the sensor(s) 39110, etc.) can be used to improve user experience when the user interacts with in an environment of a 3D map, including accuracy of interactions and/or control operations, feedback, inference models, calibration functions, and other aspects of the system 39100. To this end, for an XR environment generated by an XR system that operates with the system 39100, the XR system may include at least one processor, at least one camera, and at least one display that provides XR information within a view of the user. The at least one display may be the user interface 39118, a display interface provided to the user via AR glasses, or another viewing device viewable by the user. The system 39100 may include system elements that couple the XR system with a computer-based system that generates musculoskeletal representations based on sensor data (e.g., sensed signals from at least one neuromuscular sensor). In some embodiments of the present technology, these systems may be incorporated as subsystems of the system 39100. In other embodiments, these systems may be coupled via a special-purpose or other type of computer system that receives inputs from the XR system and the computer-based system, and that generates XR musculoskeletal representations from the inputs. Such a system may include a gaming system, a robotic control system, a personal computer, or another system that is capable of interpreting XR information and musculoskeletal information. In some embodiments, the XR system and the computer-based system may be configured to communicate directly with each other, such that the computer-based system generates XR musculoskeletal representations for the XR environment. In this regard, information may be communicated using any number of interfaces, protocols, and/or media.

In some embodiments of the present technology, the system 39100 may include one or more camera(s) 39120, which may be used in conjunction with sensed signals from the sensor(s) 39110 to provide an enhanced user experience in an environment containing smart devices. In various embodiments, such smart devices may be identifiable via a 3D map of the environment. In various other embodiments, such smart devices may be identified via the sensed signals and information obtained by the camera(s) 39120 to enable such a 3D map of the environment to be generated, as discussed in more detail below.

As noted above, in some embodiments of the present technology an inference model may be used to predict information used to generate a computer-based musculo-skeletal representation and/or to update in real-time a computer-based musculoskeletal representation. For example, the predicted information may be predicted handstate information. The inference model may be used to predict the information based on IMU signals, neuromuscular signals (e.g., EMG, MMG, and/or SMG signals), camera signals, external or auxiliary device signals (e.g., laser-scanning signals), or a combination of such signals when such signals are detected as the user performs one or more movement(s) and/or as the user undergoes other types of neuromuscular activity. For example, the camera(s) 39120 may be used with an XR system to capture data of an actual position of the user's hand. The captured data may be used to generate a computer-based musculoskeletal representation of the user's hand, and such actual-position information may be used by an inference model to improve the accuracy of the representation and to generate a visual representation (e.g., a virtual hand) in an XR environment produced by the XR system. For example, a visual representation of muscle groups firing, force being applied, an object being lifted via movement of the user, and/or other information relating to the computer-based musculoskeletal representation may be rendered in a visual display of in the XR environment of the XR system.

In some embodiments of the present technology, an inference model may be used to map muscular activation state information, which is information identified from sensed neuromuscular signals obtained by neuromuscular sensors, to control signals. The inference model may receive as input IMU signals, neuromuscular signals (e.g., EMG, MMG, and SMG signals), camera signals, external or auxiliary device signals, or a combination of such signals, which are detected and/or captured as the user performs one or more sub-muscular activation(s), one or more movement(s), and/or one or more gesture(s). The inference model may be used to predict control information without the user having to make perceptible movements.

According to some embodiments of the present technology, the camera(s) 39120 may be used to capture information to improve interpretation of neuromuscular signals and their relationship to movement, position, and force generation, to capture information in response to certain neuromuscular signals, to capture information that may be used to identify an environment corresponding to a 3D map, and/or to capture information use to generate a 3D map of an environment. As will be appreciated, the captured information may be, for example, an image signal corresponding to images captured by the camera(s) 39120. The camera(s) 39120 may comprise a still camera, a video camera, an infrared camera, a stereoscopic camera, a panoramic camera, and the like, which is or are able to capture one or more 3D image(s) of the user and/or one or more 3D images of an environment of interest to the user or surrounding the user. Optionally, the camera(s) 39120 may be equipped with one or more filter(s) so that the camera(s) 39120 may capture 3D images only within a particular range of wavelengths of light.

The information captured by the camera(s) 39120 may include a sequence of still 3D images (image sequence) and/or one more 3D moving image(s) (video sequence(s)), which may be captured as one or more signal(s); thus, reference to capturing an image should be understood to encompass capturing an image signal. The terms "camera information," "camera data," and "camera signal," may be used herein to represent information about the user and/or information about the user's environment, which may be captured by a camera. It should be understood that although various embodiments may refer to "a" camera or "the" camera, such embodiments may utilize two or more cameras instead of one camera. Further, the camera information may relate to any one or any combination of: a 3D image produced by visible light, a 3D image produced by non-visible (e.g., infrared) light, a 3D image produced by light of a certain range of wavelengths, a 3D image produced by light of two or more different ranges of wavelengths, a 3D image produced using stereoscopic technologies, a 3D image produced by providing a 2D image with depth information, etc. For example, non-visible light may be used to capture a 3D image of an object that has a different heat distribution from other nearby objects (e.g., a radiator) user's body, which may provide an indication of blood flow within the user, which in turn may be used to infer a condition of the user (e.g., a force being exerted by a finger of the user may have a different blood-flow pattern than a finger that is not exerting force).

In some embodiments, the camera(s) 39120 may comprise a camera 39600 as schematically shown in FIG. 39I. The camera 39600 may include an imaging portion 39602 configured to capture one or more digital image(s) comprising a plurality of pixels of image data. For example, the imaging portion 39602 may comprise a red-green-blue (RGB) camera and/or a near-infrared (NIR) camera. The camera 39600 may further include a depth portion 39604 configured to detect a distance from the camera 39600 to one or more surface(s) in a field of view of the camera. For example, the depth portion 39604 may include an illumination device 39604*a* (e.g., an infrared (IR) diode) configured to transmit IR light, and a detector 39604*b* configured to receive IR light reflected from the surface(s) in the field of view. Distance or depth may be determined using known time-of-flight techniques. The depth portion 39604 and the imaging portion 39602 may be arranged to capture image data and detect depth data in the same field of view, such that the pixels of image data may each be provided with corresponding depth data.

The camera 39600 may be mounted on the user's head (e.g., on a headband, a hat, a cap, a helmet, eyewear, etc.) so that the user's head may be used to aim the camera 39600 in desired directions to capture images. Alternatively, the camera 39600 may be mounted on the user's arm (e.g., on a glove, a wristband, an armband, etc.) so that the user's arm may be used to aim the camera 39600 in desired directions to capture images. The images may be captured as still images or as scans of video images. The camera 39600 may also include other types of lights, bulbs, or lamps, including but not limited to halogen, UV, black, incandescent, metal halide, fluorescent, neon, and/or light emitting diodes (LEDs). The camera 39600 may communicate with onboard processors and/or remote processors, such that the captured images may either be processed on, e.g., the armband worn by the user or via remote computers or processing units in communication with the armband.

The camera(s) 39120 (e.g., the camera 39600) may include circuitry (e.g., a controller) configured to receive control signals from the processor(s) 39112 based on one or more neuromuscular activation state(s) determined from sensed signals. For example, a first activation state may be recognized by the processor(s) 39112 as the user's desire to capture an image or initiate a video scan; a second activation state may be recognized by the processor(s) 39112 as the user's desire to stop a video scan; a third activation state may be recognized by the processor(s) 39112 as the user's desire to identify a specific object (e.g., a smart device or controllable object amongst other objects); a fourth activation state may be recognized by the processor(s) 39112 as the user's desire to control a designated smart device or controllable object to perform a specific function; a fifth activation state may be recognized by the processor(s) 39112 as the user's desire to perform an interaction with another person. The foregoing activation states may be in any order or may be stand-alone steps. As will be appreciated, the camera(s) 39120 and the processor(s) may communicate wirelessly (e.g., via Bluetooth technologies, near-field communication (NFC) technologies, etc.) or through a wired connection.

FIG. 39J is a schematic diagram showing an example implementation of a system 39700 that utilizes one or more EMG sensor(s) 39740 and a camera 39760, in accordance with some embodiments of the technology described herein. For example, the system 39700 may comprise the system 39100. The user's arm 39702 and the user's hand 39704 are attached and may comprise an arm/hand portion 39710 of the user's body. The arm/hand portion 39710 comprises a plurality of joints and segments, which can be depicted as a musculoskeletal representation. More particularly, the user's hand segments 39720 are connected by joints. Any one or any combination of arm positions, hand positions, and segment lengths of the arm 39702 and the hand 39704 may be determined by the system 39700 and positioned within a three-dimensional space of a model musculoskeletal representation of the arm/hand portion 39210. Further, in addition to the hand segments 39720, the musculoskeletal representation of the user's arm/hand portion 39710 may include a forearm segment 39730. The system 39700 may be used to determine one or more musculoskeletal representation(s) of the user's arm/hand portion 39710, which may be used to determine one more position(s) of the arm/hand portion 39710. To this end, the user may wear a band comprising the EMG sensor(s) 39740, which sense the user's neuromuscular signals used to determine the musculoskeletal representation(s). Concurrently with the EMG sensor(s) 39740 sensing the neuromuscular signals, a camera 39760 may be used to capture objects within the camera's field of view 39750. For example, in FIG. 39H, the camera's field of view 39750 may be in a same general direction of extension of the user's arm/hand portion 39710, and may include a part of the user's arm/hand portion 39710. In this example, the camera 39760 may be mounted on the user's head, as discussed above, such that the user may change the camera's field of view 39750 via head motion. Data captured by the camera 39760 in addition to the sensed signals obtained by the EMG sensors 39740 may be used to generate a 3D map of an environment, identify smart devices in the environment, control one or more smart device(s) in the environment, interact with another person in the environment, etc. Further, the system 39700 may render a representation of the user's arm/hand portion 39710 based on the sensed signals, such as within an AR environment.

FIG. 39K-39N schematically illustrate embodiments of the present technology in which a wearable system 39800 comprises a plurality of neuromuscular sensors 39810 (e.g., EMG sensors) and a camera 39820 (e.g., the camera 39600) arranged on an arm band 39812 structured to be worn on an arm 39814 of the user. Optionally, an IMU, a GPS, and/or other auxiliary device (not shown) may be arranged on the arm band 39812 together with the camera 39820 and the neuromuscular sensors 39810.

In FIG. 39L, the camera 39820 is shown in a perpendicular orientation to capture images that are perpendicular to the user's arm 39814. When the user's arm 39814 is held directly outward from the user's torso while the user is standing on a ground surface, such that the user's arm 39814 is parallel to the ground surface, the arm band 39812 may be rotated on the user's arm such that the camera 39820 may face upward to capture images of a ceiling of an environment, i.e., the camera 39820 may have a field of view pointing upwards from the user's arm 39814. Based on a mapping of the environment (which may include the ceiling and features above, beyond, below, and/or in front of the user), the disclosed embodiments herein can employ geometric techniques to orient the arm band 39812 and the camera 39820 in the environment, and thus be able to identify the specific spatial location in the environment surrounding the user at any given time (e.g., in front of the user even when the camera is pointed orthogonal to a plane formed by the user's arm).

In some embodiments of the present technology, the camera 39820 may be arranged to pivot about a hinge 39816 or other type of pivoting device. For example, the hinge 39816 may enable the camera 39820 to be adjusted from the perpendicular orientation shown in FIG. 39L (see also FIG. 39K) to an axial orientation shown in FIG. 39M, which is 90° from the perpendicular orientation. In the axial orientation, when the user's arm 39814 is held directly outward from the user's torso while the user is standing on the ground surface, such that the user's arm 39814 is parallel to the ground surface, the field of view of the camera 39820 may be aligned generally with a lengthwise direction of the user's arm 39814. Thus, when the camera 39820 is in the axial orientation, the user easily may use a finger on the arm 39814 to point forward at an object in the field of view of the camera 39820. The double-headed arrow in FIG. 39N shows that the wearable system 39800 comprising the camera 39820 may be rotated around the user's arm 39814.

In an example implementation, the user may use the camera 39820 to capture images and/or video(s) for generation of a 3D map of an environment (e.g., a living room 39900, schematically shown in FIG. 39O) by performing any one or any combination of: standing inside the environment at a central location and scanning the arm 39814 in an arc while the torso is in a fixed position; by holding the arm 39814 in a fixed position relative to the torso and rotating the torso in place at the central location through an angle from 0° to 360°; by walking around a perimeter of the environment while a field of view of the camera 39820 is aimed inwards away from the perimeter; and while meandering in the environment while the field of view of the camera changes randomly. The images/video(s) captured by the camera 39820 may include still images of a standard aspect ratio; still images of a panoramic, wide-angle, or other non-standard aspect ratio; and/or one or more video scan(s). As discussed above, via the neuromuscular sensors 39810, the user may use various gestures to control the camera 39820, to impart information to be used to generate the 3D map of the living room 39900, which may include an entirety of the living room 39900 (including walls, ceiling, and floor). For example, a first gesture corresponding to a first activation state may be performed to cause the camera 39820 to capture a still image or initiate a video scan; a second gesture corresponding to a second activation state may be performed to cause the camera 39820 to stop a video scan; a third gesture corresponding to a third activation state may be performed to cause a specific object (e.g., a lamp 39902, a television 39904, a window shade 39908, etc.) in the field of view of the camera 39820 to be identified as a smart device in captured camera data corresponding to the living room 39900; a fourth gesture corresponding to a fourth activation state may be performed to cause an object in the field of view of the camera 39820 to be designated a reference object 39906 for the living room 39900. As will be appreciated, the 3D map generated for the living room 39900 may be identified based on the reference object 39906. Optionally, a plurality of reference objects may be designated for an environment of a 3D map (e.g., a primary reference object and a secondary reference object, to ensure a correct correlation between the environment and the 3D map).

In some embodiments of the present technology, images/video(s) captured by the camera(s) 39120 when the user is in an environment may be processed by the computer processor(s) 39112 to determine one or more reference object(s) in the environment. If a reference object is recognized for the environment, the processor(s) may access a storage device 39122 to retrieve a 3D map of the recognized environment. Further, the processor(s) 39112 also may activate a control interface for the recognized environment, to enable the user to interact with smart devices in the recognized environment via neuromuscular activation states (e.g., gestures, movements, etc.). Thus, instead of using a conventional interface to control the smart devices in the recognized environment (e.g., a conventional Internet-of-Things type smartphone interface), the smart devices in the environment may be controlled by the user's neuromuscular activity when the reference object(s) for the environment is or recognized and the corresponding 3D map is retrieved. In an embodiment, the storage device 39122 may store a plurality of different maps for a plurality of different environments. In another embodiment, the storage device 39122 may store a plurality of maps for a single environment, with each map identifying a different set of smart devices usable by the user. For example, User A may be permitted to control a lamp and a sound system via neuromuscular activity via Map A corresponding to Control Interface A, whereas User B may be permitted to control the lamp, the sound system, and a television via neuromuscular activity via Map B corresponding to Control Interface B.

In some embodiments of the present technology, the 3D map may be utilized for an XR environment. FIG. 39P illustrates a schematic diagram of an XR-based system 391000, which may be a distributed computer-based system that integrates an XR system 391001 with a neuromuscular activity system 391002. The neuromuscular activity system 391002 may be the same as or similar to the system 39100 described above with respect to FIG. 39A.

The XR system 39201 may take the form of a pair of goggles or glasses or eyewear, or other type of display device that shows display elements to a user that may be superimposed on the user's "reality." This reality in some cases could be the user's view of the environment (e.g., as viewed through the user's eyes), or a captured version of the user's view of the environment. For instance, the XR system 391001 may include one or more camera(s) 391004, which may be mounted within a device worn by the user, that captures one or more view(s) experienced by the user in the environment. The XR system 391001 may include one or more processor(s) 391005 operating within a device worn by the user and/or within a peripheral device or computer system, and such processor(s) 391005 may be capable of transmitting and receiving video information and other types of data (e.g., sensor data).

The XR system 391001 may also include one or more sensor(s) 391007, such as any one or any combination of a microphone, a GPS element, an accelerometer, an infrared detector, a haptic feedback element, and the like. In some embodiments of the present technology, the XR system 391001 may be an audio-based or auditory XR system, and the sensor(s) 391007 may also include one or more headphones or speakers. Further, the XR system 391001 may also include one or more display(s) 391008 that permit the XR system 391001 to overlay and/or display information to the user in addition to provide the user with a view of the user's environment presented via the XR system 391001. The XR system 391001 may also include one or more communication interface(s) 391006, which enable information to be communicated to one or more computer systems (e.g., a gaming system or other system capable of rendering or receiving XR data). XR systems can take many forms and are available from a number of different manufacturers. For example, various embodiments may be implemented in association with one or more types of XR systems or platforms, such as HoloLens holographic reality glasses available from the Microsoft Corporation (Redmond, Washington, USA); Lightwear AR headset from Magic Leap (Plantation, Florida, USA); Google Glass AR glasses available from Alphabet (Mountain View, California, USA); R-7 Smartglasses System available from Osterhout Design Group (also known as ODG; San Francisco, California, USA); Oculus Quest, Oculus Rift S, and Spark AR Studio available from Facebook (Menlo Park, California, USA); or any other type of XR device.

The XR system 391001 may be operatively coupled to the neuromuscular activity system 391002 through one or more communication schemes or methodologies, including but not limited to, Bluetooth protocol, Wi-Fi, Ethernet-like protocols, or any number of connection types, wireless and/or wired. It should be appreciated that, for example, the systems 391001 and 391002 may be directly connected or coupled through one or more intermediate computer systems or network elements. The double-headed arrow in FIG. 39P represents the communicative coupling between the systems 391001 and 391002.

As mentioned above, the neuromuscular activity system 391002 may be similar in structure and function to the system 39100. In particular, the neuromuscular activity system 391002 may include one or more neuromuscular sensor(s) 391009, one or more inference model(s) 391010, and may create, maintain, and store one or more musculoskeletal representation(s) 391011. In an example embodiment, similar to one discussed above, the neuromuscular activity system 391002 may include or may be implemented as a wearable device, such as a band that can be worn by the user, in order to collect (i.e., obtain) and analyze neuromuscular signals from the user. Further, the neuromuscular activity system 391002 may include one or more communication interface(s) 391012 that permit the neuromuscular activity system 391002 to communicate with the XR system 391001, such as by Bluetooth, Wi-Fi, or another means of communication. Notably, the XR system 391001 and the neuromuscular activity system 391002 may communicate information that can be used to enhance user experience and/or allow the XR system 391001 to function more accurately and effectively.

In some embodiments, the XR system 391001 or the neuromuscular activity system 391002 may include one or more auxiliary sensor(s) configured to obtain auxiliary signals that may also be provided as input to the one or more trained inference model(s), as discussed above. Examples of auxiliary sensors include IMUs, GPSs, imaging devices, radiation detection devices (e.g., laser scanning devices), heart rate monitors, or any other type of biosensors able to sense biophysical information from the user during performance of one or more muscular activation(s). Further, it should be appreciated that some embodiments of the present technology may be implemented using camera-based systems that perform skeletal tracking, such as, for example, the Kinect system available from the Microsoft Corporation (Redmond, Washington, USA) and the LeapMotion system available from Leap Motion, Inc. (San Francisco, California, USA). It also should be appreciated that any combination of hardware and/or software may be used to implement various embodiments described herein.

Although FIG. 39P shows a distributed computer-based system 391000 that integrates the XR system 391001 with the neuromuscular activity system 391002, it should be understood that integration of these systems 391001 and 391002 may be non-distributed in nature. In some embodiments, the neuromuscular activity system 391002 may be integrated into the XR system 391001 such that various components of the neuromuscular activity system 391002 may be considered as part of the XR system 391001. For example, inputs from the neuromuscular signals sensed by the neuromuscular sensor(s) 391009 may be treated as another of the inputs (e.g., from the camera(s) 391004, from the sensor(s) 391007) to the XR system 391001. In addition, processing of the inputs (e.g., sensed signals) obtained from the neuromuscular sensor(s) 391009 may be integrated into the XR system 391001 (e.g., performed by the processor(s) 391005).

As noted above, the present technology involves, in some aspects, a computerized map system. The map system may generate an electronic three-dimensional (3D) map of an environment (e.g., room in a house, an office of a building, a warehouse indoor environment, etc.), and the 3D map may identify objects in the environment that may be controlled remotely. The map system may comprise a plurality of neuromuscular sensors, one or more camera(s), one or more computer processor(s), and one or more memory device(s). The neuromuscular sensors may be attached to a wearable device, which may be worn by a user to sense neuromuscular signals from the user. As discussed herein, the neuromuscular signals may be processed to determine neuromuscular activities of the user. The neuromuscular activities may result from a readily visible movement by the user or from sub-muscular changes in the user, which may not be readily visible. The computer processor(s) may generate the 3D map based on the neuromuscular signals sensed by the plurality of neuromuscular sensors and image information captured by the camera(s), and may store the 3D map in the memory device(s). The camera(s) may be controlled to capture one or more image(s) and/or one or more video scan(s) based on a neuromuscular activity recognized by the computer processor(s) from the neuromuscular signals. Known image-processing techniques may be used to stitch together two or more images and/or two or more video sequences.

For instance, the map system may generate a 3D map of a real-world room by capturing a video scan of the room and/or capturing one or more still image(s) of the room (referred to collectively as "captured video/images"). The captured video/images may be stored in the memory device(s). Of the various real-world objects in the captured video/images, the user may identify one or more controllable object(s) (i.e., smart device(s)), which may be controlled remotely as so-called "Internet of Things" (IoT) object(s). For example, the room may include an IoT controllable lamp, an IoT controllable sound system, and an IoT controllable videogame monitor. The user may identify these IoT controllable objects via neuromuscular activities detected during or after capturing of the captured video/images. In one example, in the case of a video scan, during capturing of the video scan the user may point his/her index finger to each of the IoT controllable objects. In another example, the user may update a previously existing 3D map of the room by identifying the IoT controllable object(s) via neuromuscular activities.

More specifically, the plurality of neuromuscular sensors and the camera(s) may be attached to a wearable device worn on an arm of the user. The computer processor(s) may be programmed to control the camera(s) to capture a still image or a video scan when, e.g., the user's index finger is pointed. In this example, the user may point the index finger to initiate a video capture or recording of the room, and may move the arm (and consequently the camera(s)) to scan various parts of the room for the video capture. Optionally, the user may identify particular objects of interest in the room (e.g., IoT controllable objects) by performing another neuromuscular activity during the video capture. For example, the user may move the index finger up and down to identify an object of interest in the room. Each object of interest may be electronically tagged or labeled to enable the object to be identified in the 3D map of the room.

The neuromuscular sensors may output one or more signal(s) to the computer processor(s) and/or to the memory device(s). These signal(s) may be processed by the computer processor(s) to determine each pointing instance during the video scan, in which the user moves his/her index finger up and down, and to correlate each such instance to an IoT controllable object. As will be appreciated, each IoT controllable object may have a corresponding IoT control system (e.g., a corresponding IoT control interface) accessible by the computer processor(s), such that the computer processor(s) may communicate instruction signals to the IoT controllable object via the IoT control system.

In order to obtain depth information, the camera(s) may include an infrared (IR) distance sensor comprising circuitry for IR transmission and IR reception. The IR distance sensor may be configured to transmit IR light outward and receive reflected IR light resulting from the transmitted IR light impinging on surfaces (i.e., reflection surfaces) and reflecting back towards the IR distance sensor. Using known techniques, a processor in the IR distance sensor and/or the computer processor(s) may determine a distance between each reflection surface and the IR distance sensor based on an elapsed time between transmission of the IR light and reception of the reflected IR light. As will be appreciated, the IR distance sensor and the camera(s) may be aligned, so that an imaging region of the camera(s) may be correlated with distance information from the IR distance sensor. Using known techniques, each pixel of an array of pixels of an image captured by the camera(s) may be associated with depth or distance information for that pixel.

Alternatively, the camera(s) may comprise a stereoscopic camera able to record 3D still images or 3D video, or may comprise a plurality of cameras mounted relative to each other to obtain image information or video information that may be combined to produce stereoscopic information.

The present technology also involves, in some aspects, using recognized neuromuscular activities of a user to control smart devices in an IoT-enabled environment. In this regard, an IoT interaction system is provided that may comprise a plurality of neuromuscular sensors, one or more camera(s), one or more computer processor(s), and one or more memory device(s). The IoT interaction system may be a real-world system or an XR-based system. The neuromuscular sensors may be attached to a wearable device, which may be worn by the user to sense neuromuscular signals from the user. The computer processor(s) may process image data captured by the camera(s) to determine whether an object in the image data corresponds to a reference object of a 3D map stored in the memory device(s). If a match is found, the 3D map corresponding to the reference object may be accessed, and control interfaces for smart devices in an environment corresponding to the 3D map may be activated.

The computer processor(s) may process the sensed signals from the neuromuscular sensors to determine neuromuscular activities of the user while the user is in the environment corresponding to the 3D map. Recognized neuromuscular activities may be used to control smart devices in the environment. If the IoT interaction system is an XR-based system, the may be enabled to have a virtual experience with a real-world object. For example, the user may interact with a real-world window of a room via neuromuscular activities, e.g., to open a window shade covering the window. The interaction may be via detection of the user pointing to the window shade and/or via a relative movement of the user's fingers to indicate that the window shade is to be opened. The recognized predetermine neuromuscular activities may indicate the user's desire to see a view of animation through the window (e.g., a clockwise turn of the user's wrist may cause an animated bird to appear at the window, a counterclockwise turn of the user's wrist may cause a fall foliage scene to appear through the window, etc.).

The present technology also involves, in some aspects, using recognized neuromuscular activities of a user to interact with a person in an environment (e.g., an XR environment). In this regard, an XR-based system is provided that may comprise a plurality of neuromuscular sensors, one or more camera(s), one or more computer processor(s), and one or more memory device(s). The neuromuscular sensors may be attached to a wearable device, which may be worn by the user to sense neuromuscular signals from the user. The computer processor(s) may process image data captured by the camera(s) to determine whether an object in the environment is a person. Such determination may be based on shape, movement, facial characteristics, and the like. Optionally, the computer processor(s) may be equipped with a detector configured to detect a signal emanating from a device worn by a person in the environment. If the computer processor(s) determine that a person is present, the computer processor(s) may determine an identity of the person. For example, facial-recognition processing may be performed on facial characteristics in the captured image data. In another example, the signal emanating from the device worn by the user may provide the person's identification. Once the person is identified, the user may interact with the person in the environment using neuromuscular activities.

For example, recognized neuromuscular activities may be used to play a game with the person in the environment, sent messages to the person's smartphone, send haptic signals to the person, etc.

Implementation A—Generation of 3D Map

According to some embodiments of an implementation of the present technology, a computerized system for obtaining a 3D map of an environment is provided, which may be the system 39100. The system may comprise a plurality of neuromuscular sensors, at least one camera, and at least one computer processor. The plurality of neuromuscular sensors may be configured to sense neuromuscular signals from a user. For example, the plurality of neuromuscular sensors may be arranged on at least one wearable device structured to be worn by the user to obtain the neuromuscular signals. The at least one camera may be configured to capture information about objects in the environment based on or in response to signals from the plurality of neuromuscular sensors. The at least one computer processor may be coupled to a memory and may be programmed to: generate a 3D map of the environment based on or in response to the signals from the plurality of neuromuscular sensors or information obtained from the signals from the plurality of neuromuscular sensors, and cause the 3D map to be stored in the memory. The 3D map may comprise information identifying the objects in the environment.

In various embodiments of this implementation, the system may include GPS circuitry, which may provide GPS data to be associated with the 3D map. For example, the GPS circuitry may be configured to provide GPS coordinates for objects in the environment based on or in response to signals from the plurality of neuromuscular sensors.

In various embodiments of this implementation, the neuromuscular signals from the plurality of neuromuscular sensors may cause a plurality of images of the environment to be captured and/or may cause at least one video scan of the environment to be captured. The at least one computer processor may generate the 3D map by joining together the plurality of images or joining together portions of the at least one video scan. For example, the at least one computer processor may be programmed to "close loops" and join together the plurality of images or to join together portions of the at least one video scan using Simultaneous Localization and Mapping (SLAM) technology, (e.g., Visual SLAM or VSLAM, ORB-SLAM, DynaSLAM, and the like) and/or Real-Time Appearance-Based Mapping (RTAB-Map) technology. Feature-tracking algorithms (e.g., Scale-Invariant Feature Transform (SIFT), Speeded-Up Robust Features (SURF), Good Features To Track (GFTT), Binary Robust Independent Elementary Features (BRIEF), and the like) may be used in conjunction with SLAM technology. As will be appreciated, other image-joining technologies known in the art may be used instead of or in conjunction with those identified herein.

As can be appreciated, some of the embodiments of the present technology described herein may generate or utilize a 3D map of an environment as seen from a predetermined rotational axis, in which a camera may be rotated through an angular sector (e.g., 90°, 180°, 270°, 360°, etc.) to capture video(s) and/or images, and in which depth may be one of the dimensions; these embodiments may involve 3D maps that may be partial maps. In other embodiments of the present technology, a 3D map may involve rotations through multiple different rotational axes (e.g., three mutually orthogonal axes); maps for these embodiments may result from video(s) and/or images taken through any angle from multiple different center points along the multiple different rotational axes, with established geometric relationships between the multiple different center points.

The at least one computer processor used to generate a 3D map may include one or more local processor(s) at a location of the environment being mapped and/or one or more remote processor(s) at a location remote from the environment being mapped. In some embodiments, the local processor(s) may be located on a wearable device on which a camera and neuromuscular sensors are located (e.g., on the wearable system 39800 of FIG. 39K) or may be located within one or more server(s) of a local-area network (LAN) to which the wearable device belongs. As will be appreciated, communication within the LAN may be via any one or any combination of: Wi-Fi, 3G, 4G, 5G, Bluetooth, other streaming technologies, and also conventional hardwiring. In some embodiments, the remote processor(s) may be located at a distant facility (e.g., in a different city, in a different state, in a different country, etc.) from the wearable device and may be in communication with the wearable device via a global communication network (e.g., the Internet). As will be appreciated, although some computations used to generate a 3D map may be relatively simple and thus may require a relatively small amount of computing power and consequently can be performed on a simple processor that may be carried on the wearable device, other computations may require a significantly greater amount of computing power and consequently a simple processor may not be sufficient. Thus, it may be advantageous for some or all of the computations used to generate a 3D map to be performed on one or more specialized (e.g., high computing power) mapping computer(s) equipped with one or more graphics processing unit(s) (GPUs), which may perform. For instance, data from the neuromuscular sensors and the camera may be streamed or uploaded to a remote cloud facility where the data may be accessed by the specialized computer(s) to generate a 3D map from the data.

In various embodiments of this implementation, the at least one computer processor may be programmed to identify a first neuromuscular activity from the neuromuscular signals. Each occurrence of the first neuromuscular activity may cause an image of the environment to be captured or a video scan of the environment to be captured. The at least one computer processor may be further programmed to determine a second neuromuscular activity from the neuromuscular signals, and to correlate the second neuromuscular activity to a controllable object (e.g., a smart device) in the environment. The 3D map may be generated such that the 3D map includes information on which of the objects in the environment is a controllable object, such that the controllable object(s) may be identified from the 3D map. That is, in a case where the environment includes a plurality of controllable objects, each of the of controllable objects may be identified on the 3D map.

In various embodiments of this implementation, the first neuromuscular activity and/or the second neuromuscular activity may comprise any one or any combination of: a pointing of a finger of the user, an unpointing of a finger of the user, a making of a first of the user, an unmaking of a first of the user, a clockwise wrist movement of the user, a counterclockwise wrist movement of the user, a palm up gesture of the user, and a palm down gesture of the user, or any other suitable arm, finger, hand, or wrist movement or gesture. As will be appreciated, the at least one computer processor may be programmed to recognize one or more other types of neuromuscular activity for the first neuromuscular activity and or the second neuromuscular activity.

In various embodiments of this implementation, the information captured about the objects in the environment may comprise any one or any combination of: a visual image of each of the objects in the environment, one or more depth value(s) of each of the objects in the environment, and one or more angular value(s) of each of the objects in the environment. For example, for each of the objects in the environment, an angular value of the object may correspond to an angle between the object and a predetermined origin for the 3D map. A vertex of this angle may correspond to a camera location of the at least one camera during capturing of the information about the objects in the environment. The depth value of an object in the environment may be a line-of-sight distance between the at least one camera and the object. Depending on the sizes of the various objects in the environment, one or more depth value(s) and/or angular value(s) may be used for the various embodiments disclosed herein.

In various embodiments of this implementation, the at least one camera may be arranged on the at least one wearable device. For example, the at least one camera may comprise a camera arranged on a head-wearable device. The head-wearable device may be one of: a head band, a hat, a helmet, and eyewear. In another example, the at least one wearable device may comprise a band structured to encircle a wrist or a forearm of the user. The plurality of neuromuscular sensors may be arranged circumferentially on the band, and the at least one camera may comprise a camera mounted on the band and arranged radially external to one or more of the plurality of neuromuscular sensors.

In various embodiments of this implementation, the at least one camera may comprise a stereoscopic camera able to capture 3D images/video(s).

In various embodiments of this implementation, the at least one camera may comprise: an imaging portion, and a depth determination portion. The imaging portion may comprise an RGB camera. The imaging portion may comprise at least two optical paths. The depth determination portion may comprise an infrared-light transmitter and receiver. The transmitter may be configured to transmit infrared light to one or more surface(s), and the receiver may be configured to receive reflected infrared light from the surface(s).

In various embodiments of this implementation, the information about the objects in the environment, captured by the at least one camera, may comprise images, with each of the images being formed of an array of pixels. Each pixel of the array of pixels may comprise depth data and visual data.

In various embodiments of this implementation, the at least one computer processor may be programmed to: identify and label a particular object of the objects in the 3D map as a reference object for the environment, and identify and label others of the objects in the 3D map relative to the reference object, such that identification of a physical location of the reference object in the 3D map enables identification of physical locations of the others of the objects in the 3D map.

In various embodiments of this implementation, the reference object for the environment may be determinable based on any one or any combination of: a shape of the reference object, a color or a combination of colors of the reference object, a symbol on the reference object, and a surface relief structure on the reference object. For example, the 3D map may be retrieved from the memory device when a match is found between the reference object identified for the 3D map and an object in an image captured by a camera.

FIG. 39Q shows a flow chart of a process flow 391100 for an embodiment of this implementation. At S391102, neuromuscular sensors on the user sense the user's neuromuscular signals, and the sensed signals are processed. For example, the neuromuscular sensors may be attached to a band worn around the user's arm. At S391104, if a determination is made that the neuromuscular signals include one or more signal(s) corresponding to a first neuromuscular activity, the process flow 391100 proceeds to S391106; if not, the process flow 391100 returns to S391102. For example, the first neuromuscular activity may be the user forming a first to start imaging the user's current environment. At S391106, 3D images/video(s) is or are captured while neuromuscular signals of the user continue to be sensed and processed. For example, the images/video(s) may be captured by a 3D camera attached to the band worn around the user's arm.

At S391108, if a determination is made that the neuromuscular signals include one or more signal(s) corresponding to a second neuromuscular activity, the process flow 391100 proceeds to S391110; if not, the process flow 391100 returns to S391106. For example, the second neuromuscular activity may be the user pinching a thumb and index finger together. At S391110, an object appearing in the images/video(s) when the second neuromuscular activity occurred is tagged. For example, the second neuromuscular activity may be performed by the user to indicate a reference object for the environment. The reference object may be an object used to identify the environment from other environments. The environment may have one reference object or a plurality of reference objects. As will be appreciated, a field of view of the 3D camera may be aligned with a direction of the user's arm or may be orthogonal to that direction or at some other angle to that direction, such that the user's hand or a portion thereof may or may not be captured in the image(s). Optionally, if captured in the image(s), the user's hand can facilitate identification of the object as a reference object; however, as described herein, it is not necessary to capture the user's hand to know where a finger of the hand is pointing, because neuromuscular signals obtained from the user via one or more neuromuscular sensors(s) (e.g., EMG sensor(s)) on a wearable system worn by the user, and image information obtained from a camera on the wearable system, may be provided to a trained inference model to determine when and where the finger of the user's hand is pointing. It should be understood that identification of a particular object may be achieved by extrapolating a direction of pointing of the user's finger to an object determined from the image information. When the environment has objects that are spaced far apart from each other, a single extrapolation may be sufficient to identify the particular object. On the other hand, when the environment has multiple objects that are close to each other, multiple extrapolations may be used to identify the particular object. For example, in the case of multiple extrapolations, each extrapolation may be from the user's finger pointing at the object from different perspectives, and an intersection of the extrapolations may be used to identify the particular object.

The process flow then proceeds to S391112 at which a determination is made as to whether the neuromuscular signals include one or more signal(s) corresponding to a third neuromuscular activity. If so, the process flow 391100 proceeds to S391114; if not, the process flow 391100 returns to S391106. For example, the third neuromuscular activity may be the user pointing a finger. At S391114, an object appearing in the image(s) when the third neuromuscular activity occurred is tagged. For example, the third neuromuscular activity may be performed by the user to indicate a smart device in the environment. The process flow then proceeds to S391116, at which a determination is made as to whether the neuromuscular signals include one or more signal(s) corresponding to a fourth neuromuscular activity, which may indicate the user's desire to stop capturing information about the environment. If not, the process flow 391100 returns to the S391106 to enable another reference object and/or another smart device to be tagged. If so, the process flow 391100 proceeds to S391118, at which the sensing and processing neuromuscular signals stops, the capturing of the image(s) stops, and sensor data corresponding to the sensed and processed neuromuscular signals, and camera data corresponding to the image(s) is stored. The stored sensor data and/or the stored camera data may include raw data, or processed data, or both raw data and processed data. The data may be stored such that the data is searchable based on the tagged reference object(s).

The process flow 391100 of FIG. 39Q may be used to obtain information about the environment to produce a 3D map of the environment.

FIG. 39R shows a flow chart of a process flow 391200 for another embodiment of this implementation. At S391202, a plurality of captured images of an environment, or portions of one or more video scan(s) of the environment, are stitched together to form a 3D map of the environment. For example, the image(s) from the process flow 391100 of FIG. 39Q may be used in this regard. At S391204, the 3D map of the environment is updated to identify each object tagged as a smart device (e.g., based on the third neuromuscular activity at S391114 in FIG. 39Q). At S391206, for each smart device identified on the 3D map, a link is formed between the smart device and a control interface for that smart device. Thus, when the 3D map of the environment is accessed for use, each smart device identified in the 3D map is activated to be remotely controllable. At S391208, the 3D map of the environment is updated to identify each object tagged as a reference object (e.g., based on the second neuromuscular activity at S391110 in FIG. 39Q). At S391210, the updated 3D map is stored in a memory device such that the 3D map is searchable based on the reference object(s) identified on the 3D map for the environment. As will be appreciated, the link to the smart device may be any means for remotely controlling the smart device using IoT technology. In some embodiments, the link may be a user interface known in the art that enables communication of instructions from the user to the smart device via a server that processes the instructions and transmits control signals to the smart device. For example, the communication may be via Wi-Fi, Bluetooth, LAN, WAN, and/or any suitable technology, wired or wireless, for sending the instructions to the server. The server may be programmed to receive the instructions from the user interface, and to transmit appropriate control signals to the smart device. The transmission may be via Wi-Fi, Bluetooth, LAN, WAN, and/or any suitable technology, wired or wireless, for sending the control signals to the smart device. Thus, when a 3D map of an environment is accessed for use, user interfaces for smart devices in the environment may be accessed and activated for use, such that instructions determined from recognized neuromuscular activity of the user may be transmitted via the user interfaces to one or more server(s) corresponding to the smart devices, to process the instructions and control the smart devices of the environment in a manner analogous to control of smart devices conventionally via instructions received via, e.g., a tablet computer, a smartphone and/or one or more other input devices.

Implementation B—Use of 3D Map

According to some embodiments of an implementation of the present technology, a computerized system for remote control of devices is provided, which may be the system 39100, or the system 391000, or a variation of these systems 39100, 391000. The system may comprise a plurality of neuromuscular sensors, at least one camera, and at least one computer processor. The plurality of neuromuscular sensors may be arranged on at least one wearable device structured to be worn by a user to sense neuromuscular signals from the user. The at least one camera may be configured to capture information about an environment of interest to the user. The at least one computer processor may be programmed to access map information of the environment based on the information about the environment captured by the at least one camera. The map information may comprise information for controlling at least one controllable object in the environment. The at least one computer processor also may be programmed to, in response to a neuromuscular activity recognized from the neuromuscular signals sensed by the plurality of neuromuscular sensors, control the at least one controllable object to change from a first state to a second state.

In various embodiments of this implementation, the map information of the environment may be stored in a memory, and the at least one computer processor may be programmed to retrieve the map information from the memory based on information recognized from the information about the environment captured by the at least one camera. For example, the recognized information may be visible in the environment and may comprise any one or any combination of: a QR code, a graphical symbol, a string of alphanumeric text, a 3D object having a specific shape, and a physical relationship between at least two objects. The recognized information may comprise a reference object for the environment. As an example, if the camera detects a small desk and/or a small office lamp, the system can use that information and help identify the given environment as a home office environment; if the camera detects a couch and/or an ottoman, the system can use that information and help identify the environment as a living room or a family room; if the camera detects architectural lighting and/or ceiling fixtures, the system can use that information and help identify the environment as an office space or a warehouse; if the camera detects natural light in a range of wavelengths and/or detects a motor vehicle, the system can use that information and help identify the environment as outdoors; etc.

In various embodiments of this implementation, the map information may comprise map data on a physical relationship between two or more controllable objects in the environment. For example, the map data may comprise one or a plurality of established center point(s), and the physical relationship between the two or more controllable objects in the environment may be determined from the established center point(s). The map data may comprise 3D panoramic data of objects in the environment. In one example, the 3D panoramic data may comprise a partial view of the environment. In another example, the 3D panoramic data may comprise a representation of the environment through a single rotational axis or multiple different rotational axes.

In various embodiments of this implementation, the environment may be an XR environment comprising virtual objects and real-world objects. The at least one computer processor may be programmed to: determine, from the information about the environment captured by the at least one camera, a reference object in the environment; and to determine, from the map information, location information of the virtual objects and location information of the real-world objects. The map information may comprise location information of the at least one controllable object relative to the reference object.

In various embodiments of this implementation, the neuromuscular activity recognized from the neuromuscular signals sensed by the plurality of neuromuscular sensors results from the user performing at least one gesture relative to the at least controllable object while the user is in the environment. The at least one gesture may comprise any one or any combination of: the user moving at least one finger relative to the at least one controllable object (e.g., the user moving the at least one finger upward or downward relative to the at least one controllable object); the user moving a wrist relative to the at least one controllable object (e.g., the user tilting the wrist upward or downward relative to the at least one controllable object); the user moving an arm relative to the at least one controllable object (e.g., the user moving the arm upward or downward relative to the at least one controllable object); and the user using two or more fingers to perform a pinching motion relative to the at least one controllable object.

In various embodiments of the present implementation, the at least one controllable object may comprise a plurality of controllable objects. The at least one gesture may comprise a gesture relative to one of the plurality of controllable objects. The at least one computer processor may be programmed to, in response to the neuromuscular activity recognized from the neuromuscular signals sensed by the plurality of neuromuscular sensors, control each of the plurality of controllable objects to change from a first state to a second state.

In various embodiments of the present implementation, the environment may be any one or any combination of: one or more room(s) in a home; one or more room(s) in an business; one or more floor(s) of a multistory building; and an outdoor region.

In various embodiments of the present implementation, the at least one controllable object comprises any one or any combination of: a lamp, a display device, an electronic game, a window shade, a sound system, a lock, and a food or beverage preparation device.

FIG. 39S shows a flow chart of a process flow 391300 for an embodiment of this implementation. At S391302, images/video(s) of an environment is or are captured by a camera. For example, the images/video(s) may be captured by a camera attached to a band worn around a user's arm. At S391304, the images/video(s) are processed to determine whether a reference object can be recognized. If not, the process flow 391300 returns to S391302. If so, at S391306, a 3D map of the environment is accessed based on the recognized reference object. Also, at S391306, one or more control interface(s) are identified for one or more smart device(s) in the environment. For example, the control interface(s) may be linked to the 3D map (e.g., see S391206 in FIG. 39R). At S391308, the user's neuromuscular signals are sensed continuously by neuromuscular sensors, and the images/video(s) continue to be captured. For example, the neuromuscular sensors may be attached to the band on which the camera is attached. The process flow 391300 proceeds to S391310, at which a determination is made as to whether the neuromuscular signals include one or more signal(s) corresponding to a first neuromuscular activity. If so, the process flow 391300 proceeds to S391312; if not, the process flow 391300 returns to S391308. For example, the first neuromuscular activity may be the user pointing a finger. At S391312, the 3D map is utilized to identify a smart device corresponding to the first neuromuscular activity, and a control interface for the identified smart device is accessed (e.g., via a link to the 3D map). A field of view of the 3D camera may be aligned with a direction of the user's arm, such that the user's finger may be captured in the images/ video(s), to facilitate identification of the smart device. For example, the smart device may be a window shade (e.g., 908 in FIG. 39O).

At S391314, a determination is made as to whether the neuromuscular signals include one or more signal(s) corresponding to a second neuromuscular activity. If not, the process flow 391300 proceeds to S391318. If so, the process flow 391300 proceeds to S391316, at which the identified smart device is controlled according to the second neuromuscular activity. Continuing with the previous example of the window shade, if the second neuromuscular activity is the user pinching a thumb and index finger together, the window shade may be controlled to close the window shade via an electronic mechanism activated by the control interface linked to the 3D map. At S391318, a determination is made as to whether the neuromuscular signals include one or more signal(s) corresponding to a third neuromuscular activity. If not, the process flow 391300 returns to S391308. If so, the process flow 391300 proceeds to S391320, at which the sensing and processing of neuromuscular signals stops, and the capturing of the image(s) stops.

In some embodiments of this implementation, the user may wear the wearable system 39800, which may continuously stream image data, or periodically stream image data (e.g., A seconds of imaging "on" then B seconds of imaging "off" in an ABAB, etc., repeated sequence), or occasionally stream image data (e.g., C seconds "on" then "off" until a neuromuscular event is detected), while the user is in the environment. In these embodiments, the image data may be used to continuously or periodically or occasionally "localize" or determine the user's location and/or orientation in the environment. In the case of image data that is occasionally streamed, the C seconds of image data may be stored (e.g., in cache) and updated with a new C seconds of image data when the user, e.g., points his or her finger while in the environment; processing of the new C seconds of image data and the neuromuscular signals therefore may be performed together when the user performs an activity, but otherwise processing is held off to conserve use of processing resources. In this regard, in order to conserve processing resources, difference techniques may be used to store different information between, e.g., a plurality of image frames, instead of storing the image frames in their entirety. For example, if the user is moving slowly in the environment and the image frames show slow variations of a wall as the user is moving, data corresponding to the variations may be stored instead of data of the entirety of the image frames.

In some embodiments of this implementation, the wearable system 39800 worn by the user may include an IMU sensor, which may help to localize the user in the environment (i.e., determine the user's position and orientation). For example, data from the IMU sensor may improve localization processing by taking into consideration human arm constraints (discussed above) to give a more accurate determination of the user's arm orientation (e.g., angle(s)). Localization of the user may be determined more quickly by using known human arm constraints to eliminate impossible arm positions from being part of the localization processing. For instance, a typical human arm may be rotated though an arc of, e.g., +135° (based on a maximum possible arc of +180° corresponding to a complete circle). Constraints on the user's arm position/orientation would eliminate the possibility that the user is pointing to an object that would require the user's arm to be rotated greater than +135°, thus eliminating unnecessary calculations.

Implementation C—Hardware, Including Programmed Hardware

According to some embodiments of an implementation of the present technology, an electronic apparatus is provided. The apparatus may comprise: a wearable carrier; a plurality of neuromuscular sensors attached to the carrier; a camera system; and at least one computer processor configured to communicate electronically with the plurality of neuromuscular sensors and the camera system. The apparatus may further comprise a communication interface configured to transmit signals between the plurality of neuromuscular sensors, the camera system, and the at least one computer processor. The communication interface may comprise any one or any combination of: a wiring that directly interconnects the plurality of neuromuscular sensors and the camera system; a wiring that directly interconnects the plurality of neuromuscular sensors and the at least one computer processor; a wiring that directly interconnects the camera system and the at least one computer processor; a wired communication bus interconnecting the plurality of neuromuscular sensors, the camera system, and the at least one computer processor; a wireless signal transmitter; and a wireless signal receiver.

In various embodiments of this implementation, the at least one processor may be attached to the carrier, and may be configured to access a memory device to retrieve information and to store information. The memory device may be attached to the carrier.

In an embodiment of this implementation, the camera system may comprise at least two optical paths. For example, the camera system may comprise a stereoscopic camera.

In various embodiments of this implementation, the camera system may comprise: an imaging portion and a depth determination portion. The imaging portion may comprise any one or any combination of: a still-image camera, an RGB camera, a panoramic camera, and a video camera. The imaging portion may be equipped with various types of lenses and/or filters. For example, the imaging portion may be equipped with a wide-angle or fisheye lens, which may enable the imaging portion to capture a larger area of an environment, which in some sense may serve to speed up tracking of objects in the environment. The depth determination portion may comprise a light-beam transmitter and receiver. For example, the light-beam transmitter and receiver may be an infrared-beam transmitter and receiver. The at least one computer processor may comprise a controller configured to control the imaging portion and the depth determination portion to capture data simultaneously.

In various embodiments of this implementation, the at least one computer processor may be programmed to: receive image signals from the imaging portion; receive depth signals from the depth determination portion; generate correlation data correlating at least a portion of the image signals with at least a portion of the depth signals; and cause the memory device to store the correlation data.

In various embodiments of this implementation, the carrier may be structured to be worn by a user. In one example, the carrier may be structured to be worn on a hand of the user (e.g., a glove). In another example, the carrier may be an arm band structured to be worn on an arm of the user (e.g., an elastic band, an adjustable belt). In this example, the arm band may be sized to encircle a wrist or a forearm portion of the user, and the plurality of neuromuscular sensors are arranged circumferentially on the arm band. The plurality of neuromuscular sensors may comprise EMG sensors.

In various embodiments of this implementation, the camera system may be arranged circumferentially on the arm band together with the plurality of neuromuscular sensors. For example, the camera system may be arranged on the arm band radially external to one or more of the plurality of neuromuscular sensors. The camera system may be arranged on the arm band to be movable to and from a perpendicular orientation, in which the camera system points radially outward from the arm band when the arm band is worn on the arm of the user, and an axial orientation, in which the camera system points axially in a direction parallel to a central axis of the arm band when the arm band is worn on the arm of the user. The camera system may be attached to a hinge that is structured to pivot the camera system from the perpendicular orientation to the axial orientation, to enable the camera system to capture image information in the perpendicular orientation, or the axial orientation, or an orientation between the perpendicular orientation and the axial orientation.

In various embodiments of the present implementation, the apparatus may further comprise a second carrier structured to be worn on a head of the user. The camera system may be attached to the second carrier.

In various embodiments of the present implementation, the apparatus may further comprise an auxiliary device attached to the wearable carrier or the second wearable carrier. The auxiliary device may comprise any one or any combination of: an IMU, a GPS, a radiation detector, a heart-rate monitor, a moisture (e.g., perspiration) detector, etc.

Implementation D—Interactions Via Neuromuscular Activity

According to some embodiments of an implementation of the present technology, a computerized system for performing interactions via neuromuscular activity is provided. The system may comprise: a plurality of neuromuscular sensors; a camera system; and at least one computer processor. The plurality of neuromuscular sensors, which may be configured to sense neuromuscular signals from a user, may be arranged on at least one wearable device worn by the user to obtain the neuromuscular signals. The camera system, which may be configured to capture information about an environment of interest to the user, may comprise an imaging portion and a depth determination portion. The at least one computer processor may be programmed to: receive the captured information from the camera system and the neuromuscular signals from the plurality of neuromuscular sensors; recognize the environment from the captured information; access control information associated with the environment recognized from the captured information, with the control information comprising information for performing at least one function associated with the environment; and, in response to a neuromuscular activity recognized from the neuromuscular signals, cause the at least one function to be performed.

In various embodiments of this implementation, the environment may be an outdoor region, and the control information may comprises information for performing an outdoor function. The outdoor function may be a transportation-related function. In one example, the transportation-related function may be to start an automobile. In another example, the transportation-related function may be to cause a request to be transmitted for a pickup at the outdoor region. The at least one computer processor may be programmed to transmit the request via an Internet transmission to a transportation service vendor.

In various embodiments of this implementation, the at least one computer processor may be programmed to determine whether a person is present in the environment based on the captured information. For example, the at least one computer processor may be programmed to determine that a person is present in the environment based on an one or any combination of: a recognized general shape of the person; a recognized presence of at least one limb on the person; a recognized facial characteristic of the person; a recognized movement of the person; and a recognized object carried by the person. The at least one computer processor may be further programmed such that, if it is determined that a person is in the environment, an identity of the person may be determined based on recognized facial characteristics of the person.

In various embodiments of this implementation, the system may further comprise a communication interface configured to transmit electronic signals to an external device and to receive electronic signals from the external device. The external device may be any one or any combination of: a smart device; a smartphone; a haptic device; a game; and a display device. In some embodiments, the at least one computer processor may be programmed to determine an identity of a person in the environment based on recognized facial characteristics of the person; to access an interactive control application based on the identity of the person; and to utilize the interactive control application to cause any one or any combination of: a personal message to be transmitted to a smartphone of the person, a game move to be performed in an electronic game played by the person, an activation of a haptic device worn by the person, an image to be displayed on a display device viewable by the person in the environment, and permit the person to control of a function of the environment. The at least one computer processor may be programmed to cause permission to be granted to the person to control any one or any combination of: the electronic game, the display device, a smartphone of the user, and a haptic device worn by the user.

In various embodiments of this implementation, the at least one computer processor may be programmed to utilize the interactive control application to generate an XR environment in which the user and the person may interact. In one example, the at least one computer processor may be programmed to enable the user to interact with the person in the XR environment based on neuromuscular activities recognized from the neuromuscular signals sensed by the plurality of neuromuscular sensors. In another example, the at least one computer processor may be programmed to utilize the interactive control application to: turn on an electronic device operable by the user and the person, and, in response to one or more neuromuscular activities recognized from the neuromuscular signals sensed by the plurality of neuromuscular sensors, control at least one operation of the electronic device. For instance, the electronic device may be a game playable by the user and the person, and, in response to the one or more neuromuscular activities recognized from the neuromuscular signals, the at least one computer processor controls any one or any combination of: a game-player movement, a game effect, and a game setting.

FIGS. 39T and 39U show a flow chart of a process flow 391400 for an embodiment of this implementation. At S391402, images/video(s) of an environment is or are captured by a camera. For example, the images/video(s) may be captured by a camera attached to a band worn around a user's arm. At S391404, the images/video(s) are processed to determine whether a reference object can be recognized. If not, the process flow 391400 returns to S391402. If so, at S391406, a 3D map of the environment is accessed based on the recognized reference object. Also, at S391406, one or more control interface(s) are identified for the environment. For example, the control interface(s) may be for communication functions linked to the environment of the 3D map. At S391408, the user's neuromuscular signals are sensed continuously by neuromuscular sensors, and the images/video (s) continue to be captured. For example, the neuromuscular sensors may be attached to the band on which the camera is attached. The process flow 391400 proceeds to S391410, at which a determination is made as to whether a person is detected in the environment. For example, detection may be via a determination that an object in the images/video(s) is shaped like a human. If a person is detected, the process flow 391400 proceeds to S391412; if not, the process flow 391400 returns to S391408.

At S391412, processing is performed to identify the person. For example, if the person is carrying a smartphone or other electronic device (e.g., another neuromuscular armband or wristband), a signal from the smartphone or other electronic device may be detected by electronic circuitry (e.g., NFC circuitry, RFID circuitry, etc.) attached to the band on which the camera is attached. In another example, facial detection may be used to identify the person from the images/video(s). In yet another example, the person may be wearing a wearable system (e.g., the wearable system 39800 in FIG. 39K), which may provide an identification signal useable to identify the person. At S391414, if the person cannot be identified, the process flow 391400 returns to S391408. If the person is identified at S391414, the process flow 391400 proceeds to S391416, at which one or more control interface(s) associated with the identified person is or are identified and accessed for use.

At S391418, a determination is made as to whether the neuromuscular signals include one or more signal(s) corresponding to a neuromuscular activity for an action in the environment or an interaction with the identified person. If so, the process flow 391400 proceeds to S391422; if not, the process flow 391400 returns to S391418 via S391420, where the user's neuromuscular signals continue to be sensed and processed to determine whether there is neuromuscular activity for an action in the environment or an interaction with the identified person.

At S391422 the control interface(s) associated with the identified person and/or the control interface(s) associated with the environment is or are used to interact with the identified person (e.g., send a text message to the identified person's smartphone) and/or to control an action in the environment (e.g., initiate XR functions in the environment). At S391424, a determination is made as to whether the neuromuscular signals include one or more signal(s) corresponding to a neuromuscular activity to exit control operations and interactions in the environment. If not, the process flow 391400 proceeds to S391418 via S391420. If so, the process flow 391400 proceeds to S391426, at which at which the sensing and processing of neuromuscular signals stops, and the capturing of the images/video(s) stops. If the system interacts with the identified person, such interactions can comprise any one or any combination of: sending discrete text or email messages to the identified person's mobile phone or computer, synchronizing one or more smart devices between the user and the identified person, sending a message or communication in an XR environment that the identified person can see in the XR environment, etc.

In some embodiments, two or users may interact with the XR environment. Each user (e.g., User A and User B) may be uniquely identified to the XR system by a wearable device (e.g., the wearable system 39800 in FIG. 39K). In such a case, no facial recognition would be necessary, because each user's wearable device would be registered to a different account in the XR system, such that each wearable device would uniquely identify the user to the XR system. Thus, each user may interact with objects in the XR environment independently of the other user, and also may interact with the other user in the XR environment. Further, each user may be associated with a different 3D map for the same XR environment (e.g., User A may be a child and may only have control of lamps in the XR environment of User A's 3D map, while User B may have control of a television and a video-game system in the XR environment of User B's 3D map). In an embodiment, when multiple users are in the same XR environment at the same time, the XR system may enable all the users to share control of each other's controllable objects (e.g., User A and User B may both perform control operations with the video-game system). In this regard, User A's 3D map may be merged or stitched together with User B's 3D map when User A and User B are both in the same XR environment.

In a cloud-based embodiment, an environment may be associated with a plurality of users, and each of the users may be equipped with a wearable band (e.g., the wearable system 39800 in FIG. 39K) useable to control one or more object(s) in the environment. For example, the environment may be a workplace having multiple different regions, and the plurality of users may be employees of the workplace. Employees A and C may be associated with Map A1 of region A and Map C of region C of the environment. Employees B and D may be associated with Map A2 of region A and Map B of region B of the environment. Maps A1, A2, B, and C may be stored remotely in a cloud facility, which may be controlled by workplace management personnel. Thus, the workplace management personnel may authorize a first group of employees to have permission to control a first group of object(s) within region A via Map A1, and may authorize a second group of employees to have permission to control a second group of object(s) within the same region A via Map A2.

Workplace management personnel may control each employee's authorization details via the employees wearable band, and may change an employee's authorization(s) via the employee's wearable band. Each wearable band may be associated with an identification code, which may be used to associate the wearable band with one or more 3D maps of the regions of the environment. For instance, the environment may be a warehouse having several stock rooms, and Map A1 may permit a group of employees to operate heavy machinery in region A while Map A2 may permit another group of employees to operate light machinery in region A. As will be appreciated, some employees may be associated with Maps A1 and A2, and thus may be permitted to operate light machinery and heavy machinery. As will be appreciated, various other types of control may be set up for the regions of the environment by the workplace management personnel using the 3D maps for the regions of the environment, and the description above is illustrative of just one example.

Each wearable band may emit an identification signal when in the environment (e.g., using RFID technology, NFC technology, GPS technology and the like). Such a signal may be used to determine which employee is in the environment, and roughly where the employee is in the environment (e.g., which region of the environment); the localization techniques described above (e.g., using a video stream) may be used to determine a more exact location of the user (e.g., where the employee is located within the region of the environment). In some embodiments, such a signal may be used access one or more 3D maps, which may enable the employee corresponding to the signal to control object(s) in the environment or to interact in other ways with the environment (e.g., to enable a first employee in the environment to interact with a second employee in the environment via a neuromuscular action indicating a desire to transfer a control authorization from the first employee to the second employee; to enable the first employee to send a haptic warning signal to the second employee; etc.).

As will be appreciated, cloud-based storage of 3D maps and other information useable by management personnel may enable centralized oversight of a workplace environment that may encompass regions in multiple cities and/or multiple states and/or multiple countries. For example, the management personnel can control employees by controlling authorizations or permissions granted to each of the employees, which may differ from employee to employee based on each employee's wearable band and the 3D map(s) associated with each employee's wearable band.

The following describes exemplary systems and methods for text input using neuromuscular information.

Systems and methods are described herein for providing an improved speech recognition system in which speech data provided as input to the system is augmented with neuromuscular signals (e.g., recorded using electromyography (EMG)). The improved speech recognition system may exhibit better performance (e.g., accuracy, speed) compared to speech recognition systems that receive only speech data as input. For example, a musculo-skeletal representation (including, but not limited to, body position information and biophysical quantities such as motor unit and muscle activation levels and forces) determined based on the neuromuscular signals may encode contextual information represented in a user's movements or activation of their muscles, that may be used to enhance speech recognition performance. In another example, the described systems and methods may interpret parts of speech from the user's movements or activations to enhance speech recognition performance. In some embodiments, the described systems and methods provide for modifying an operation of a speech recognition system (e.g., by enabling and disabling speech recognition with a wake word/phrase or gesture, applying formatting such as bold, italics, underline, indent, etc., entering punctuation, and other suitable modifications). In some embodiments, the described systems and methods provide for using recognized neuromuscular information, e.g., for one or more gestures, to change an interaction mode (e.g., dictation, spelling, editing, navigation, or another suitable mode) with the speech recognition system or speech recognizer. In some embodiments, the described systems and methods provide for using EMG-based approaches (e.g. EMG-based scrolling and clicking) to select text for editing, error corrections, copying, pasting, or another suitable purpose. In some embodiments, the described systems and methods provide for selection of options from list of choices, e.g., with audio feedback for "eyes-busy" situations like driving ("did you mean X or Y?"). In some embodiments, the described systems and methods provide for a hybrid neuromuscular/speech input that gracefully switches from one mode to the other, and uses both modes when available to increase accuracy and speed. In some embodiments, the described systems and methods provide for text input using a linguistic token, such as phonemes, characters, syllables, words, sentences, or another suitable linguistic token, as the basic unit of recognition.

Some embodiments are directed to a system for using neuromuscular information to improve speech recognition. The system includes a plurality of neuromuscular sensors arranged on one or more wearable devices. The plurality of neuromuscular sensors is configured to continuously record a plurality of neuromuscular signals from a user. The system further includes at least one storage device configured to store one or more trained statistical models and at least one computer processor. The computer processor is programmed to provide as an input to the one or more trained statistical models. The plurality of neuromuscular signals or signals are derived from the plurality of neuromuscular signals. The computer processor is further programmed to determine based, at least in part, on an output of the one or more trained statistical models, at least one instruction for modifying an operation of a speech recognizer and provide the at least one instruction to the speech recognizer. In some embodiments, the instruction for modifying the operation of the speech recognizer is determined directly from the plurality of neuromuscular signals. For example, the instruction may be output from a trained statistical model after applying the plurality of neuromuscular signals as inputs to the trained statistical model. In some embodiments, a musculo-skeletal representation of the user is determined based on the output of the one or more trained statistical models, and the instruction for modifying the operation of the speech recognizer is determined based on the musculo-skeletal representation.

Some embodiments are directed to a system for using neuromuscular information to improve speech recognition. The system includes a plurality of neuromuscular sensors arranged on one or more wearable devices. The plurality of neuromuscular sensors is configured to continuously record a plurality of neuromuscular signals from a user. The system further includes at least one storage device configured to store one or more trained statistical models, at least one input interface configured to receive the audio input, and at least one computer processor. The computer processor is programmed to obtain the audio input from the input interface and obtain the plurality of neuromuscular signals from the plurality of neuromuscular sensors. The computer processor is further programmed to provide as input to the one or more trained statistical models, the audio input and/or the plurality of neuromuscular signals or signals derived from the plurality of neuromuscular signals. The computer processor is further programmed to determine the text based, at least in part, on an output of the one or more trained statistical models.

Some embodiments are directed to a system for text input based on neuromuscular information. The system includes a plurality of neuromuscular sensors arranged on one or more wearable devices. The plurality of neuromuscular sensors is configured to continuously record a plurality of neuromuscular signals from a user. The system further includes at least one storage device configured to store one or more trained statistical models and at least one computer processor. The computer processor is programmed to obtain the plurality of neuromuscular signals from the plurality of neuromuscular sensors and provide the plurality of neuromuscular signals, or signals derived from the plurality of neuromuscular signals, as input to the one or more trained statistical models. The computer processor is further programmed to determine one or more linguistic tokens based, at least in part, on an output of the one or more trained statistical models.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

Automated speech recognition (ASR) is a computer-implemented process for converting speech to text using mappings between acoustic features extracted from input speech and language-based representations such as phonemes. Some ASR systems take as input, information other than speech to improve the performance of the ASR system. For example, an ASR system may take as input both visual information (e.g., images of a user's face) and audio information (e.g., speech) and may determine a speech recognition result based one or both of the types of inputs.

The inventors have recognized and appreciated that existing techniques for performing speech recognition may be improved by using musculo-skeletal information about the position and/or movement of a user's body (including, but not limited to, the user's arm, wrist, hand, neck, throat, tongue, or face) derived from recorded neuromuscular signals to augment the analysis of received audio when performing speech recognition.

The human musculo-skeletal system can be modeled as a multi-segment articulated rigid body system, with joints forming the interfaces between the different segments and joint angles defining the spatial relationships between connected segments in the model. Constraints on the movement at the joints are governed by the type of joint connecting the segments and the biological structures (e.g., muscles, tendons, ligaments) that restrict the range of movement at the joint. For example, the shoulder joint connecting the upper arm to the torso and the hip joint connecting the upper leg to the torso are ball and socket joints that permit extension and flexion movements as well as rotational movements. By contrast, the elbow joint connecting the upper arm and the forearm and the knee joint connecting the upper leg and the lower leg allow for a more limited range of motion. As described herein, a multi-segment articulated rigid body system is used to model the human musculo-skeletal system. However, it should be appreciated that some segments of the human musculo-skeletal system (e.g., the forearm), though approximated as a rigid body in the articulated rigid body system, may include multiple rigid structures (e.g., the ulna and radius bones of the forearm) that provide for more complex movement within the segment that is not explicitly considered by the rigid body model. Accordingly, a model of an articulated rigid body system for use with some embodiments of the technology described herein may include segments that represent a combination of body parts that are not strictly rigid bodies.

In kinematics, rigid bodies are objects that exhibit various attributes of motion (e.g., position, orientation, angular velocity, acceleration). Knowing the motion attributes of one segment of the rigid body enables the motion attributes for other segments of the rigid body to be determined based on constraints in how the segments are connected. For example, the arm may be modeled as a two-segment articulated rigid body with an upper portion corresponding to the upper arm connected at a shoulder joint to the torso of the body and a lower portion corresponding to the forearm, wherein the two segments are connected at the elbow joint. As another example, the hand may be modeled as a multi-segment articulated body with the joints in the wrist and each finger forming the interfaces between the multiple segments in the model. In some embodiments, movements of the segments in the rigid body model can be simulated as an articulated rigid body system in which orientation and position information of a segment relative to other segments in the model are predicted using a trained statistical model, as described in more detail below.

FIG. 40A illustrates a system 40100 in accordance with some embodiments. The system includes a plurality of autonomous sensors 40110 configured to record signals resulting from the movement of portions of a human body (including, but not limited to, the user's arm, wrist, hand, neck, throat, tongue, or face). As used herein, the term "autonomous sensors" refers to sensors configured to measure the movement of body segments without requiring the use of external sensors, examples of which include, but are not limited to, cameras or global positioning systems. Autonomous sensors 40110 may include one or more Inertial Measurement Units (IMUs), which measure a combination of physical aspects of motion, using, for example, an accelerometer and a gyroscope. In some embodiments, IMUs may be used to sense information about the movement of the part of the body on which the IMU is attached and information derived from the sensed data (e.g., position and/or orientation information) may be tracked as the user moves over time. For example, one or more IMUs may be used to track movements of portions of a user's body proximal to the user's torso (e.g., arms, legs) as the user moves over time.

Autonomous sensors 40110 may also include a plurality of neuromuscular sensors configured to record signals arising from neuromuscular activity in skeletal muscle of a human body. The term "neuromuscular activity" as used herein refers to neural activation of spinal motor neurons that innervate a muscle, muscle activation, muscle contraction, or any combination of the neural activation, muscle activation, and muscle contraction. Neuromuscular sensors may include one or more electromyography (EMG) sensors, one or more mechanomyography (MMG) sensors, one or more sonomyography (SMG) sensors, and/or one or more sensors of any suitable type that are configured to detect neuromuscular signals. In some embodiments, the plurality of neuromuscular sensors may be used to sense muscular activity related to a movement of the part of the body controlled by muscles from which the neuromuscular sensors are arranged to sense the muscle activity. Spatial information (e.g., position and/or orientation information) describing the movement (e.g., for portions of the user's body distal to the user's torso, such as hands and feet) may be predicted based on the sensed neuromuscular signals as the user moves over time.

In embodiments that include at least one IMU and a plurality of neuromuscular sensors, the IMU(s) and neuromuscular sensors may be arranged to detect movement or activation of different parts of the human body (including, but not limited to, the user's arm, wrist, hand, neck, throat, tongue, or face). For example, the IMU(s) may be arranged to detect movements of one or more body segments proximal to the torso, whereas the neuromuscular sensors may be arranged to detect movements of one or more body segments distal to the torso. It should be appreciated, however, that autonomous sensors 40110 may be arranged in any suitable way, and embodiments of the technology described herein are not limited based on the particular sensor arrangement. For example, in some embodiments, at least one IMU and a plurality of neuromuscular sensors may be co-located on a body segment to track movements of body segment using different types of measurements. In one implementation, an IMU sensor and a plurality of EMG sensors are arranged on a wearable device configured to be worn around the user's neck and/or proximate to the user's face. In one implementation described in more detail below, an IMU sensor and a plurality of EMG sensors are arranged on a wearable device configured to be worn around the lower arm or wrist of a user. In such an arrangement, the IMU sensor may be configured to track movement or activation information (e.g., positioning and/or orientation over time) associated with one or more arm segments, to determine, for example whether the user has raised or lowered their arm, whereas the EMG sensors may be configured to determine movement or activation information associated with wrist or hand segments to determine, for example, whether the user has an open or closed hand configuration.

Each of autonomous sensors 40110 includes one or more sensing components configured to sense movement information or activation information from the user. The movement or activation sensed by the autonomous sensors 40110 may correspond to muscle activation at a fixed point in time (e.g., the user making a thumbs up gesture or tensing arm muscles) or may correspond to the user performing a movement over a period of time (e.g., the user moving their arm in an arc). The autonomous sensors 40110 may sense movement information when the user performs a movement, such as a gesture, a movement of a portion of the user's body (including, but not limited to, the user's arm, wrist, hand, neck, throat, tongue, or face), or another suitable movement. The autonomous sensors 40110 may sense activation information when the user performs an activation, such as forces applied to external objects without movement, balanced forces (co-contraction), activation of individual muscle fibers (e.g., muscle fibers too weak to cause noticeable movement), or another suitable activation. In the case of IMUs, the sensing components may include one or more accelerometers, gyroscopes, magnetometers, or any combination thereof to measure characteristics of body motion, examples of which include, but are not limited to, acceleration, angular velocity, and sensed magnetic field around the body. In the case of neuromuscular sensors, the sensing components may include, but are not limited to, electrodes configured to detect electric potentials on the surface of the body (e.g., for EMG sensors) vibration sensors configured to measure skin surface vibrations (e.g., for MMG sensors), and acoustic sensing components configured to measure ultrasound signals (e.g., for SMG sensors) arising from muscle activity.

In some embodiments, the output of one or more of the sensing components may be processed using hardware signal processing circuitry (e.g., to perform amplification, filtering, and/or rectification). In other embodiments, at least some signal processing of the output of the sensing components may be performed in software. Thus, signal processing of autonomous signals recorded by autonomous sensors 40110 may be performed in hardware, software, or by any suitable combination of hardware and software, as aspects of the technology described herein are not limited in this respect.

In some embodiments, the recorded sensor data may be processed to compute additional derived measurements that are then provided as input to a statistical model, as described in more detail below. For example, recorded signals from an IMU sensor may be processed to derive an orientation signal that specifies the orientation of a rigid body segment over time. Autonomous sensors 40110 may implement signal processing using components integrated with the sensing components, or at least a portion of the signal processing may be performed by one or more components in communication with, but not directly integrated with the sensing components of the autonomous sensors.

In some embodiments, at least some of the plurality of autonomous sensors 40110 are arranged as a portion of a wearable device configured to be worn on or around part of a user's body. For example, in one non-limiting example, an IMU sensor and a plurality of neuromuscular sensors are arranged circumferentially around an adjustable and/or elastic band such as a wristband or armband configured to be worn around a user's wrist or arm. Alternatively or additionally, at least some of the autonomous sensors may be arranged on a wearable patch configured to be affixed to a portion of the user's body.

In one implementation, 16 EMG sensors are arranged circumferentially around an elastic band configured to be worn around a user's lower arm. For example, FIG. 7A shows EMG sensors 704 arranged circumferentially around elastic band 702. It should be appreciated that any suitable number of neuromuscular sensors may be used and the number and arrangement of neuromuscular sensors used may depend on the particular application for which the wearable device is used. For example, a wearable armband or wristband may be used to predict musculo-skeletal position information for hand-based motor tasks, whereas a wearable leg or ankle band may be used to predict musculo-skeletal position information for foot-based motor tasks. For example, as shown in FIG. 7B, a user 706 may be wearing elastic band 702 on hand 708. In this way, EMG sensors 704 may be configured to record EMG signals as a user controls keyboard 710 using fingers 712. In some embodiments, elastic band 702 may also include one or more IMUs (not shown), configured to record movement or activation information, as discussed above.

In some embodiments, multiple wearable devices, each having one or more IMUs and/or neuromuscular sensors included thereon may be used to predict musculo-skeletal position information for movements that involve multiple parts of the body.

System 40100 also includes voice interface 40120 configured to receive audio input. For example, voice interface 40120 may include a microphone that, when activated, receives speech data, and processor(s) 40112 may perform automatic speech recognition (ASR) based on the speech data. Audio input including speech data may be processed by an ASR system, which converts audio input to recognized text. The received speech data may be stored in a datastore (e.g., local or remote storage) associated with system 40100 to facilitate the ASR processing. In some embodiments, ASR processing may be performed in whole or in part by one or more computers (e.g., a server) remotely located from voice interface 40120. For example, in some embodiments, speech recognition may be performed locally using an embedded ASR engine associated with voice interface 40120, a remote ASR engine in network communication with voice interface 40120 via one or more networks, or speech recognition may be performed using a distributed ASR system including both embedded and remote components. Additionally, it should be appreciated that computing resources used in accordance with the ASR engine may also be located remotely from voice interface 40120 to facilitate the ASR processing described herein, as aspects of the invention related to ASR processing are not limited in any way based on the particular implementation or arrangement of these components within system 40100.

System 40100 also includes one or more computer processor(s) 40112 programmed to communicate with autonomous sensors 40110 and/or voice interface 40120. For example, signals recorded by one or more of the autonomous sensors 40110 may be provided to processor(s) 40112, which may be programmed to perform signal processing, non-limiting examples of which are described above. In another example, speech data recorded by voice interface 40120 may be provided to processor(s) 40112, which may be programmed to perform automatic speech recognition, non-limiting examples of which are described above. Processor (s) 40112 may be implemented in hardware, firmware, software, or any combination thereof. Additionally, processor(s) 40112 may be co-located on a same wearable device as one or more of the autonomous sensors or the voice interface or may be at least partially located remotely (e.g., processing may occur on one or more network-connected processors).

System 40100 also includes datastore 40114 in communication with processor(s) 40112. Datastore 40114 may include one or more storage devices configured to store information describing a statistical model used for predicting musculo-skeletal position information based on signals recorded by autonomous sensors 40110 in accordance with some embodiments. Processor(s) 40112 may be configured to execute one or more machine learning algorithms that process signals output by the autonomous sensors 40110 to train a statistical model stored in datastore 40114, and the trained (or retrained) statistical model may be stored in datastore 40114 for later use in generating a musculo-skeletal representation. Non-limiting examples of statistical models that may be used in accordance with some embodiments to predict musculo-skeletal position information based on recorded signals from autonomous sensors are discussed in more detail below.

In some embodiments, a set of training data, including sensor data from the autonomous sensors 40110 and/or speech data from the voice interface 40120, is obtained for training the statistical model. This training data may also be referred to as ground truth data. The training data may be obtained by prompting the user at certain times to perform a movement or activation and capturing the corresponding sensor data and/or speech data. Alternatively or additionally, the training data may be captured when the user is using a device, such as a keyboard. For example, the captured training data may include the user's EMG signal data and the user's corresponding key presses from a key logger. Alternatively or additionally, the training data may include ground truth joint angles corresponding to the user's movement or activation. The ground truth joint angles may be captured using, e.g., a camera device, while the user performs the movement or activation. Alternatively or additionally, the training data may include sensor data corresponding to a movement or activation performed by the user and annotated with speech data corresponding to the user speaking at the same time as performing the movement or activation. For example, the user may perform a gesture, such as a thumbs up gesture, and speak a word, such as "edit," to indicate that the gesture relates to an edit function. Alternatively or additionally, the training data may be captured when the user is using a writing implement or instrument, such as a pen, a pencil, a stylus, or another suitable writing implement or instrument. For example, the captured training data may include EMG signal data recorded when the user is prompted to write one or more characters, words, shorthand symbols, and/or another suitable written input using a pen. Optionally, the motion of the writing implement or instrument may be recorded as the user writes. For example, an electronic stylus (or another device configured to record motion) may record motion of the electronic stylus as the user writes a prompted word using the electronic stylus. Accordingly, the captured training data may include recorded EMG signal data and the corresponding recorded motion of the writing implement or instrument as the user writes one or more letters, words, shorthand symbols, and/or another suitable written input using the writing implement or instrument.

In some embodiments, processor(s) 40112 may be configured to communicate with one or more of autonomous sensors 40110, for example, to calibrate the sensors prior to measurement of movement or activation information. For example, a wearable device may be positioned in different orientations on or around a part of a user's body and calibration may be performed to determine the orientation of the wearable device and/or to perform any other suitable calibration tasks. Calibration of autonomous sensors 40110 may be performed in any suitable way, and embodiments are not limited in this respect. For example, in some embodiments, a user may be instructed to perform a particular sequence of movements or activations and the recorded movement or activation information may be matched to a template by virtually rotating and/or scaling the signals detected by the sensors (e.g., by the electrodes on EMG sensors). In some embodiments, calibration may involve changing the gain(s) of one or more analog to digital converters (ADCs), for example, in the case that the signals detected by the sensors result in saturation of the ADCs.

System 40100 optionally includes one or more controllers 40116 configured to receive a control signal based, at least in part, on processing by processor(s) 40112. As discussed in more detail below, processor(s) 40112 may implement one or more trained statistical models 40114 configured to predict musculo-skeletal position information based, at least in part, on signals recorded by autonomous sensors 40110 worn by a user. One or more control signals determined based on the output of the trained statistical model(s) may be sent to controller 40116 to control one or more operations of a device associated with the controller. In some embodiments, system 40100 does not include one or more controllers configured to control a device. In such embodiments, data output as a result of processing by processor(s) 40112 (e.g., using trained statistical model(s) 40114) may be stored for future use or transmitted to another application or user.

In some embodiments, during real-time tracking, information sensed from a single armband/wristband wearable device that includes at least one IMU and a plurality of neuromuscular sensors is used to reconstruct body movements, such as reconstructing the position and orientation of both the forearm, upper arm, wrist and hand relative to a torso reference frame using a single arm/wrist-worn device, and without the use of external devices or position determining systems. For brevity, determining both position and orientation may also be referred to herein generally as determining movement.

As discussed above, some embodiments are directed to using a statistical model for predicting musculo-skeletal position information based on signals recorded from wearable autonomous sensors. The statistical model may be used to predict the musculo-skeletal position information without having to place sensors on each segment of the rigid body that is to be represented in a computer-generated musculo-skeletal representation of user's body. As discussed briefly above, the types of joints between segments in a multi-segment articulated rigid body model constrain movement of the rigid body. Additionally, different individuals tend to move in characteristic ways when performing a task that can be captured in statistical patterns of individual user behavior. At least some of these constraints on human body movement may be explicitly incorporated into statistical models used for prediction in accordance with some embodiments. Additionally or alternatively, the constraints may be learned by the statistical model through training based on recorded sensor data. Constraints imposed in the construction of the statistical model are those set by anatomy and the physics of a user's body, while constraints derived from statistical patterns are those set by human behavior for one or more users from which sensor measurements are measured. As described in more detail below, the constraints may comprise part of the statistical model itself being represented by information (e.g., connection weights between nodes) in the model.

In some embodiments, system 40100 may be trained to predict musculo-skeletal position information as a user moves or activates muscle fibers. In some embodiments, the system 40100 may be trained by recording signals from autonomous sensors 40110 (e.g., IMU sensors, EMG sensors) and position information recorded from position sensors worn by one or more users as the user(s) perform one or more movements. The position sensors, described in more detail below, may measure the position of each of a plurality of spatial locations on the user's body as the one or more movements are performed during training to determine the actual position of the body segments. After such training, the system 40100 may be configured to predict, based on a particular user's autonomous sensor signals, musculo-skeletal position information (e.g., a set of joint angles) that enable the generation of a musculo-skeletal representation without the use of the position sensors.

As discussed above, some embodiments are directed to using a statistical model for predicting musculo-skeletal position information to enable the generation of a computer-based musculo-skeletal representation. The statistical model may be used to predict the musculo-skeletal position information based on IMU signals, neuromuscular signals (e.g., EMG, MMG, and SMG signals), or a combination of IMU signals and neuromuscular signals detected as a user performs one or more movements.

FIG. 40B describes a process 40200 for using neuromuscular information to improve speech recognition. Process 40200 may be executed by any suitable computing device (s), as aspects of the technology described herein are not limited in this respect. For example, process 40200 may be executed by processor(s) 40112 described with reference to FIG. 40A. As another example, one or more acts of process 40200 may be executed using one or more servers (e.g., servers included as a part of a cloud computing environment). For example, at least a portion of act 40204 relating to determining a musculo-skeletal representation of the user may be performed using a cloud computing environment. Although process 40200 is described herein with respect to processing IMU and EMG signals, it should be appreciated that process 40200 may be used to predict neuromuscular information based on any recorded autonomous signals including, but not limited to, IMU signals, EMG signals, MMG signals, SMG signals, or any suitable combination thereof and a trained statistical model trained on such autonomous signals.

Process 40200 begins at act 40202, where speech data is obtained for one or multiple users from voice interface 40120. For example, voice interface 40120 may include a microphone that samples audio input at a particular sampling rate (e.g., 16 kHz), and recording speech data in act 40202 may include sampling audio input by the microphone. Sensor data for a plurality of neuromuscular signals may be obtained from sensors 40110 in parallel, prior to, or subsequent to obtaining the speech data from voice interface 40120. For example, speech data corresponding to a word from the user may obtained at the same time as sensor data corresponding to a gesture from the user to change the formatting of the word. In another example, speech data corresponding to a word from the user may obtained, and at a later time, sensor data may be obtained corresponding to a gesture from the user to delete the word. In yet another example, sensor data may be obtained corresponding to a gesture from the user to change the formatting for text output in the future, and at a later time, speech data corresponding to a word from the user may obtained and formatted accordingly. Optionally, process 40200 proceeds to act 40204, where the plurality of neuromuscular signals from sensors 40110, or signals derived from the plurality of neuromuscular signals, are provided as input to one or more trained statistical models and a musculo-skeletal representation of the user is determined based, at least in part, on an output of the one or more trained statistical models.

In some embodiments, signals are recorded from a plurality of autonomous sensors arranged on or near the surface of a user's body to record activity associated with movements or activations of the body during performance of a task. In one example, the autonomous sensors comprise an IMU sensor and a plurality of EMG sensors arranged circumferentially (or otherwise oriented) on a wearable device configured to be worn on or around a part of the user's body, such as the user's arm. In some embodiments, the plurality of EMG signals are recorded continuously as a user wears the wearable device including the plurality of autonomous sensors.

In some embodiments, the signals recorded by the autonomous sensors are optionally processed. For example, the signals may be processed using amplification, filtering, rectification, or other types of signal processing. In some embodiments, filtering includes temporal filtering implemented using convolution operations and/or equivalent operations in the frequency domain (e.g., after the application of a discrete Fourier transform). In some embodiments, the signals are processed and used as training data to train the statistical model.

In some embodiments, the autonomous sensor signals are provided as input to a statistical model (e.g., a neural network) trained using any suitable number of layers and any suitable number of nodes in each layer. In some embodiments that continuously record autonomous signals, the continuously recorded autonomous signals (raw or processed) may be continuously or periodically provided as input to the trained statistical model for prediction of a musculo-skeletal representation for the given set of input sensor data. In some embodiments, the trained statistical model is a user-independent model trained based on autonomous sensor and position information measurements from a plurality of users. In other embodiments, the trained model is a user-dependent model trained on data recorded from the individual user from which the data recorded in act 40204 is also acquired.

In some embodiments, after the trained statistical model receives the sensor data as a set of input parameters, a predicted musculo-skeletal representation is output from the trained statistical model. In some embodiments, the predicted musculo-skeletal representation may comprise a set of body position information values (e.g., a set of joint angles) for a multi-segment articulated rigid body model representing at least a portion of the user's body. In other embodiments, the musculo-skeletal representation may comprise a set of probabilities that the user is performing one or more movements or activations from a set of possible movements or activations.

Next, process 40200 proceeds to act 40206, where an instruction for modifying an operation of a speech recognizer is determined, and the instruction is provided to the speech recognizer. In embodiments where process 40200 does not include act 40204, the instruction for modifying the operation of the speech recognizer is determined based, at least in part, on an output of the one or more trained statistical models. For example, the one or more trained statistical models may directly map sensor data, e.g., EMG signal data, to the instruction for modifying the operation of the speech recognizer. In embodiments where process 40200 includes act 40204, the instruction for modifying the operation of the speech recognizer is determined based on the musculo-skeletal representation determined in act 40204. In some embodiments, process 40200 modifies the speech recognition process. For example, process 40200 may modify at least a portion of text output from the speech recognizer, where the modification may relate to punctuation, spelling, formatting, or another suitable modification of the text. In another example, process 40200 may change a caps lock mode of the speech recognizer. In yet another example, process 40200 may change a language mode of the speech recognizer. For example, the speech recognizer may be instructed to change from recognizing English to recognizing French. Some embodiments include a communications interface configured to provide the instruction from a processor, e.g., processor(s) 40112, to the speech recognizer. In some embodiments, a processor, e.g., processor(s) 40112, is programmed to execute the speech recognizer. Process 40200 proceeds to step 40208, where speech recognition is resumed, e.g., for speech data recorded at act 40202 or other suitable audio input.

FIG. 40C describes a process 40300 for using neuromuscular information to improve speech recognition. Process 40300 may be executed by any suitable computing device (s), as aspects of the technology described herein are not limited in this respect. For example, process 40300 may be executed by processor(s) 40112 described with reference to FIG. 40A. As another example, one or more acts of process 40300 may be executed using one or more servers (e.g., servers included as a part of a cloud computing environment). For example, at least a portion of act 40314 relating to determining an edit and/or correct operation based on sensor data may be performed using a cloud computing environment. Although process 40300 is described herein with respect to IMU and EMG signals, it should be appreciated that process 40300 may be used to predict neuromuscular information based on any recorded autonomous signals including, but not limited to, IMU signals, EMG signals, MMG signals, SMG signals, or any suitable combination thereof and a trained statistical model trained on such autonomous signals.

Process 40300 begins at act 40310, where speech recognition results are obtained, e.g., from speech data received from voice interface 40120. In some embodiments, processor(s) 40112 may perform ASR based on the speech data to generate the speech recognition results. In some embodiments, audio input including speech data may be processed by an ASR system, which produces speech recognition results by converting audio input to recognized text. The received speech data may be stored in a datastore (e.g., local or remote storage) associated with system 40100 to facilitate the ASR processing.

Next, at act 40312, sensor data is received, for example, from sensors 40110. The sensor data may be recorded and processed as described with respect to the process of FIG. 40B. The sensor data may include a plurality of neuromuscular signals and/or signals derived from the plurality of neuromuscular signals. The sensor data may be provided as input to one or more trained statistical models and the musculo-skeletal representation of the user may be determined based, at least in part, on an output of the one or more trained statistical models. Process 40300 then proceeds to act 40314, where an edit and/or correct operation is determined based on the sensor data. An instruction relating to the edit and/or correct operation of the speech recognizer is determined based on the determined musculo-skeletal representation, and the instruction is provided to the speech recognizer.

Next, process 40300 proceeds to act 40316 where the edit and/or correct operation is performed on the speech recognition results. For example, the edit and/or correct operation may be performed on the speech recognition results by allowing a user to edit and correct speech recognition results by selecting possibilities from a list. In another example, the edit and/or correct operation may be performed on the speech recognition results by allowing the user to initiate a spelling mode and correct spellings for one or more words in the speech recognition results. In yet another example, the edit and/or correct operation may be performed on the speech recognition results by allowing the user to delete one or more words in the speech recognition results. In another example, the edit and/or correct operation on the speech recognition results may be performed by allowing the user to scroll through the speech recognition results and insert one or more words at a desired insertion point in the speech recognition results. In another example, the edit and/or correct operation may be performed on the speech recognition results by allowing the user to select and replace one or more words in the speech recognition results. In another example, the edit and/or correct operation may be performed on the speech recognition results by auto-completing a frequently used phrase in the speech recognition results or allowing the user to select from a list of suggested completions for a phrase in the speech recognition results.

FIG. 40D describes a process 40400 for using neuromuscular information to improve speech recognition. Process 40400 may be executed by any suitable computing device (s), as aspects of the technology described herein are not limited in this respect. For example, process 40400 may be executed by processor(s) 40112 described with reference to FIG. 40A. As another example, one or more acts of process 40400 may be executed using one or more servers (e.g., servers included as a part of a cloud computing environment). For example, at least a portion of act 40412 relating to detecting EMG-based control information may be performed using a cloud computing environment. Although process 40400 is described herein with respect to IMU and EMG signals, it should be appreciated that process 40400 may determine neuromuscular information based on any recorded autonomous signals including, but not limited to, IMU signals, EMG signals, MMG signals, SMG signals, or any suitable combination thereof and a trained statistical model trained on such autonomous signals.

Process 40400 begins at act 40410, where control information is monitored, e.g., for one or more movements or activations performed by the user. For example, process 40400 may monitor one or more EMG signals relating to neuromuscular information while speech data is obtained for one or multiple users from voice interface 40120. Voice interface 40120 may include a microphone that samples audio input at a particular sampling rate (e.g., 16 kHz). Sensor data relating to the control information may be received from sensors 40110. The sensor data may include a plurality of neuromuscular signals and/or signals derived from the plurality of neuromuscular signals.

Next, process 40400 proceeds to act 40412, where it is determined whether control information relating to a particular movement or activation is detected. The sensor data may be provided as input to one or more trained statistical models and control information of the user may be determined based, at least in part, on an output of the one or more trained statistical models. The sensor data may be provided as input to a trained statistical model to determine control information as described with respect to FIG. 40B.

If it is determined that control information for a particular movement or activation is detected, process 40400 proceeds to act 40414, where an action associated with speech recognition, and determined based on the detected control information, is performed. Otherwise, process 40400 returns to act 40410 to continue monitoring for control information. Performing an action with speech recognition may include, but is not limited to, altering a mode of the speech recognizer, starting or stopping the speech recognizer, or another suitable action associated with the speech recognizer. In another example, the user may perform a specific gesture to toggle the speech recognizer on and off, hold the gesture to keep the speech recognizer on, or hold a mute gesture to mute the speech recognizer. Determining an instruction for performing an action for the speech recognizer may be based on the determined control information, and the instruction may be provided to the speech recognizer. For example, the action associated with speech recognition may be performed by allowing a user to start or stop speech recognition, e.g., by making a gesture imitating a press of a button on a tape recorder. In another example, the action associated with speech recognition may be performed by allowing a user to initiate a spell check mode. In yet another example, the action associated with speech recognition may be performed by allowing a user to change the language of input by making a related gesture.

FIG. 40E describes a process 40500 for using neuromuscular information to improve speech recognition. Process 40500 may be executed by any suitable computing device (s), as aspects of the technology described herein are not limited in this respect. For example, process 40500 may be executed by processor(s) 40112 described with reference to FIG. 40A. As another example, one or more acts of process 40500 may be executed using one or more servers (e.g., servers included as a part of a cloud computing environment). For example, at least a portion of act 40580 relating to determining model estimates may be performed using a cloud computing environment. Although process 40500 is described herein with respect to IMU and EMG signals, it should be appreciated that process 40500 may determine neuromuscular information based on any recorded autonomous signals including, but not limited to, IMU signals, EMG signals, MMG signals, SMG signals, or any suitable combination thereof and a trained statistical model trained on such autonomous signals.

In some embodiments, process 40500 provides for a hybrid neuromuscular and speech input interface where a user may fluidly transition between using speech input, using neuromuscular input or using both speech input and neuromuscular input to perform speech recognition. The neuromuscular input may track body position information, movement, hand state, gestures, activations (e.g., from muscle fibers too weak to cause noticeable movement) or other suitable information relating to the plurality of recorded neuromuscular signals. In some embodiments, the speech input and neuromuscular input are used to provide for lower error rates in speech recognition. In other embodiments, the speech input and the neuromuscular input may be used selectively where one mode of input is preferable over the other. For example, in situations where it is not possible to speak aloud, only the neuromuscular input may be used to perform recognition.

At act 40552 of process 40500, sensor data is recorded, e.g., from sensors 40110, and at act 40554, the recorded sensor data is optionally processed. The sensor data may include a plurality of neuromuscular signals and/or signals derived from the plurality of neuromuscular signals. At act 40562 of process 40500, speech data is recorded, e.g., from one or multiple users from voice interface 40120, and at act 40564, the recorded speech data is optionally processed. Voice interface 40120 may include a microphone that samples audio input at a particular sampling rate (e.g., 16 kHz), and the speech data may be recorded by sampling audio input received by the microphone.

At act 40570 of process 40500, one or both of the processed or unprocessed sensor data and speech data is provided as input to one or more trained statistical models. In some embodiments, both sensor data and speech data are input to the trained statistical model(s) to provide for lower speech recognition error rates. The statistical model(s) may be trained on both inputs used in parallel. In some embodiments, only one of the sensor data or the speech data may be provided as input to the trained statistical models. The statistical models trained on both inputs may be configured to gracefully transition between speech-only mode, sensor-mode, and combined speech+sensor data mode based on particular conditions of the system use, for example, when only one input is available. In some embodiments, both the speech data, e.g., audio input, and the sensor data, e.g., a plurality of neuromuscular signals, are provided as input to the one or more trained statistical models. The audio input may be provided as input to the one or more trained statistical models at a first time and the plurality of neuromuscular signals is provided as input to the one or more trained statistical models at a second time different from the first time. Alternatively, the speech data and the sensor data may be provided as input to the one or more trained statistical models simultaneously.

At act 40580 of process 40500, a speech recognition result (e.g., text) for the input sensor and/or speech data is determined based, at least in part, on an output of the one or more trained statistical models. In some embodiments, the speech recognition result is determined by processing the audio input to determine a first portion of the text, and by processing the plurality of neuromuscular signals to determine a second portion of the text. In some embodiments, the one or more trained statistical models include a first trained statistical model for determining the text based on the audio input and a second trained statistical model for determining the text based on the plurality of neuromuscular signals.

The speech recognition result may be determined for at least a first portion of the text based on a first output of the first trained statistical model. In some embodiments, the text is further determined for at least a second portion of the text based on a second output of the second trained statistical model. In some embodiments, the first portion and the second portion are overlapping. For example, the first three-quarters of the text may be determined using speech input whereas the second three-quarters of the text may be determined using neuromuscular input, with the middle of the text being determined using both speech and neuromuscular input. In this example, the user may have provided both speech input and neuromuscular input from the one-quarter mark to the three-quarter mark, while only providing speech input or neuromuscular input otherwise. In some embodiments, the first portion and the second portion are non-overlapping. For example, the first half of the text may be determined using speech input whereas the second half of the text may be determined using neuromuscular input.

In some embodiments, one or more statistical models for a hybrid neuromuscular and speech input interface are provided such that a first statistical model is trained for determining the text based on the audio input and a second statistical model is trained for determining the text based on the plurality of neuromuscular signals. Such a model implementation may be advantageous for faster training of new movements or activations because only the second statistical model need be updated in the training process. It is noted that the model implementation for the hybrid neuromuscular and speech input interface need not be limited to the described implementation. For example, such systems may employ one model for processing both neuromuscular and speech inputs or multiple models for processing each of the neuromuscular and speech inputs. Further details on how to combine the outputs of such models are provided below.

In some embodiments, an ASR model is provided and subsequently trained to personalize the ASR model according to EMG-based sensor data received for the user. For example, the ASR model may be provided as an artificial neural network with one or more layers, each layer including nodes with assigned weights. A layer of the artificial neural network may receive input in the form of EMG-based sensor data to learn the movements or activations from the user and corresponding output, e.g., text. Alternatively or additionally, the weights in one or more layers of the artificial neural network may be adapted to learn the movements or activations from the user and corresponding output. In some embodiments, a single model receives both speech data and EMG-based sensor data as inputs and the model is trained to generate output corresponding to these inputs. For example, the model may be provided with data collected as the user speaks, e.g., a phrase, and performs a corresponding movement or activation. In some embodiments, an engineered combination of models is provided where EMG-based sensor data relating to neuromuscular information is used to switch between one or more trained statistical models trained on speech data. For example, the EMG-based sensor data may be used to determine when a user makes a movement or activation to switch a language mode of the speech recognizer. Accordingly, if it is determined that the user desires a different language mode, the trained statistical model corresponding to the desired language mode is selected.

In some embodiments, the output predictions of a first statistical model (trained for determining text based on speech data, also referred to as a language model) and a second statistical model (trained for determining text based on sensor data, such as EMG signals) are combined as described below.

For notation, P (A|B) is defined as the conditional probability of A given B. The language model may give a prior distribution P (text) over the possible text utterances. Bayes rule may be applied to calculate the probability of the text given the observed speech and EMG sensor data, according to the following formula:

$$P(\text{text} \mid \text{speech}, EMG) = P(\text{speech}, EMG \mid \text{text}) * P(\text{text}) / P(\text{speech}, EMG)$$

For optimizing the output predictions, i.e., text, the term P (speech, EMG) may be ignored and the combination may focus on the proportionality relationship, according to the following formula:

$$P(\text{text} \mid \text{speech}, EMG) \sim P(\text{speech}, EMG \mid \text{text}) * P(\text{text})$$

The speech data and the EMG data may be assumed to be conditionally independent given the output text, according to the following formula:

$$P(\text{speech}, EMG \mid \text{text}) = P(\text{speech} \mid \text{text}) * P(EMG \mid \text{text})$$

This assumption yields following formula:

$$P(\text{text} \mid \text{speech}, EMG) \sim P(\text{speech} \mid \text{text}) * P(EMG \mid \text{text}) * P(\text{text})$$

In embodiments where the individual models have a stage at which they output these conditional probabilities, the above formula may be applied directly.

In embodiments where the models output the P (text-|speech) and P (text|EMG), Bayes rule may be applied, according to the following formulas:

$$P(\text{speech} \mid \text{text}) = P(\text{text} \mid \text{speech}) * P(\text{speech}) / P(\text{text}), \text{ and}$$

$$P(EMG \mid \text{text}) = P(\text{text} \mid EMG) * P(EMG) / P(\text{text})$$

These two equations may be substituted into the formula derived above, according to the following formula:

$$P(\text{text} \mid \text{speech}, EMG) \sim P(\text{text} \mid \text{speech}) *$$
$$P(\text{speech}) * P(\text{text} \mid EMG) * P(EMG) / P(\text{text})$$

Finally, the terms with just speech and EMG may be dropped because output predictions are being optimized over text, according to the following formula:

$$P(\text{text} \mid \text{speech}, EMG) \sim P(\text{text} \mid \text{speech}) * P(\text{text} \mid EMG) / P(\text{text})$$

This formula combines a speech model that gives P (text|speech) with an EMG model that gives P (text|EMG).

In some embodiments, only one of the substitutions may be applied if a model gives P(EMG|text), according to the following formula:

$$P(\text{text}\,|\,\text{speech}, \textit{EMG}) \sim P(\text{text}\,|\,\text{speech}) * P(\text{EMG}\,|\,\text{text})$$

In some embodiments, the prior distribution of words/phrases in the language model is altered, e.g., when the gesture provides context for interpreting the speech. For example, the gesture may be a natural gesture a user makes in a given context to switch modes, such as a making a first gesture to switch to a proper noun mode. In proper noun mode, the language model output is biased such that proper nouns have a higher prior probability. If the language model is made aware of the upcoming input of a proper noun, the output of the model is more likely to be text for a proper noun. For example, the prior probability of proper nouns may be multiplied by a number greater than one to increase the bias for proper nouns. The language model may function in the same manner as before the switch to proper noun mode, except for applying a higher prior probability to proper nouns.

In some embodiments, the described systems and methods allow for obtaining one or more neuromuscular signals (e.g., EMG signals) in parallel with or substantially at the same time as obtaining speech data for one or multiple users. The neuromuscular information derived from the signals may be used to modify the behavior of the speech recognizer, e.g., switch to another mode of the speech recognizer. For example, neuromuscular information derived from neuromuscular signals from a user may indicate that the user wishes to activate a "spell mode" of the speech recognizer. Accordingly, the neuromuscular information may be used to switch the mode of the speech recognizer to character-based text entry. The user may make movements or activations and the corresponding neuromuscular information may be used to interpret the characters the user wishes to enter. Subsequently, neuromuscular information derived from neuromuscular signals from the user may indicate that the user wishes to deactivate the "spell mode" of the speech recognizer. In this manner, the user may alternate between speech input (e.g., to enter words) and neuromuscular input (e.g., to enter characters) in order to enter the desired text. In some embodiments, when switching to "spell mode," the speech recognizer swaps a language model suitable for speech input (e.g., to enter words) with another language model suitable for neuromuscular input (e.g., to enter characters). In some embodiments, when switching to "spell mode," the language model output is biased towards character-based text entry. For example, a prior distribution in the language model is selected to better recognize character-based entry. If the language model is made aware of the upcoming input of character-based text entry, the output of the model is more likely to recognize the characters as spelling out one or more words.

Some embodiments of the systems and methods described herein provide for determining text input with model(s) that use a linguistic token, such as phonemes, characters, syllables, words, sentences, or another suitable linguistic token, as the basic unit of recognition. An advantage of using phonemes as the linguistic token may be that using a phoneme-based representation is more similar to the natural speech language processing than character-based typing. Additionally, using a phoneme-based model may provide faster recognition performance than a character-based model approach because the phoneme-based approach uses a denser encoding compared to using characters.

For the implementation using phonemes as the linguistic token, the inventors have recognized that creating a phoneme-based vocabulary that is easy to learn and recognize may be challenging in part because the number of phonemes in a language (e.g., 36 phonemes for English) may be larger than the number of characters in the language (e.g., 26 characters). In some embodiments, the text input may be performed using an adaptive movement or activation information recognizer instead of a fixed phoneme vocabulary. In some embodiments, a speech synthesizer provides audio feedback to the user while the user trains the adaptive system to create a mapping between body position information (e.g., movement, hand states, and/or gestures) and phonemes. In some embodiments, the training system may be presented to the user as a game, e.g. a mimicry game. Language models may be applied to the input, similar to a speech recognizer, to decode EMG signals through soft phoneme predictions into text.

In some embodiments, the described systems and methods allow for the user to "speak" with their hands by providing hand states that correspond to different linguistic tokens, such as phonemes. For example, some gesture-based language techniques, such as American Sign Language, map gestures to individual characters (e.g., letters) or entire words. Some embodiments are directed to allowing the user to "speak" with their hands using an intermediate level of representation between characters and entire words, that more closely represents speech production. For example, a phoneme representation may be used and a model may map the user's hand states to particular phonemes. A phoneme-based system may provide a measure of privacy because a user may perform the movement or activation, such as the gesture, without moving or with little motion. It is noted that such movement-free or limited-movement systems need not be limited to using phonemes as their linguistic token. For example, such systems may use another linguistic token, such as characters. Such a system may also enable the user to provide input faster than they could using individual characters, but without having to learn movements or activations for a large vocabulary of words. For example, a phoneme-based system may provide for a speed of 200 words per minute, which is faster than a typical character typing rate. It is noted that such systems may additionally or alternatively use another linguistic token, such as common letter combinations found on a stenographer's keyboard.

In some embodiments, the described systems and methods allow for the user to "speak" with their hands by providing movement or activation that correspond to different linguistic tokens, such as characters. In using such a character representation, a model may map EMG signals for the user's hand states to particular characters. For example, the user may type on a flat surface as if it were a keyboard and perform hand states for keys corresponding to the characters the user wishes to enter. Such a character-based text entry (e.g., via detection of EMG signals) may be combined with speech-based text entry. The user may use speech-based text entry for initial text but, for example at a later point in time, switch modes to character-based text entry (e.g. enter "spell mode") and input hand states corresponding to the characters the user wishes to enter. In other embodiments, speech-based entry may be processed in parallel with text entry, such as using a speech command to change entry mode while typing (e.g., changing to all capitals, executing a control key operation, etc.) or modify a current input from or output to another device (e.g., a keyboard, a heads-up display, etc.). Any combination of entry using speech-based recognition and EMG signal processing may be performed to derive one or more multidimensional input/output mode(s) according to various embodiments.

In some embodiments, the described systems and methods allow for adaptive training of one or more statistical models to map neuromuscular information to linguistic tokens, such as phonemes. For example, the user may be asked to produce one or more simple words using hand states corresponding to phonemes. In some embodiments, the training may not be directed to explicitly generating neuromuscular information, e.g., for a gesture, to phoneme mappings for the user. Instead, the user may be asked to produce hand states for one or more words and the statistical models may be adapted based on the information learned from this process. For example, the user may be presented with a user interface that displays a training "game," where the user earns points for every correct hand state made to produce one or more target words. In some embodiments, a speech synthesizer may provide audio feedback to the user based on the phonemes produced by the user's hand states. The feedback may provide the user understanding on how to improve his or her hand states to produce the correct phonemes for the target words.

In some embodiments, the described systems and methods allow for the user to define an individualized mapping from neuromuscular information to linguistic tokens such as phonemes, by selecting what hand state, gesture, movement, or activation to use for each phoneme. For example, the user may train the one or more statistical models using small finger movements or muscle activations detectable by sensors 40110. If two movements are close to each other, the user may be asked to make the movement slightly differently to distinguish between the two movements. In some embodiments, feedback may be provided by the system to the user to encourage the user to produce movements or activations that are distinct from each other to enable the system to learn a better mapping from movement or activation to phoneme.

In some embodiments, a pre-trained fixed mapping, analogous to typing on a regular keyboard may be provided and the pre-trained mapping may be adapted or individualized to the user's movement or activation characteristics as the user uses the system. In such an adaptive system, the user may be able to minimize their movement over time to achieve the same system performance, such that smaller and smaller movements may be sufficient to produce neuromuscular signals mapped to different phonemes recognizable by the system. The system may be configured to adapt to the user's movements or activations in the background as the user is performing typical everyday tasks. For example, the system may be configured to track keys pressed by a user (e.g., using a key logger) as the user wears the wearable device of the system while typing on a keyboard, and the system may be configured to determine mappings between neuromuscular information, as the user types, and recorded keystrokes.

Moreover, the system may not be limited to training in a phase separate from use of the system. In some embodiments, the system is configured to adapt a pre-trained mapping or another suitable mapping based on information from tracking a signal from the user indicating an erroneous text entry. For example, the signal may include a voice command (e.g., "backspace," "undo," "delete word," or another suitable voice command indicating an error was made), one or more neuromuscular signals (e.g., a gesture relating to a command, such as "backspace," "undo," "delete word," or another suitable command indicating an error was made), a signal from the user accepting an auto-correction of an erroneous text entry, or another suitable user signal indicating an erroneous text entry. The system may adapt a pre-trained mapping or another suitable mapping to the user based on this tracked information.

In some embodiments, the system is configured to adapt a pre-trained mapping or another suitable mapping based on consistency with a language model. For example, in absence of the adaptation to the language model, the system may determine output text to be "she yikes to eat ice cream," instead of "she likes to eat ice cream." The language model may include prior probabilities of certain combinations of words, phrases, sentences, or another suitable linguistic token, and the system may select the output text corresponding to a higher probability in the language model. For example, the language model may indicate that the phrase "likes to eat" has a higher probability than the phrase "yikes to eat." Accordingly, to be consistent with the language model, the system may adapt the pre-trained mapping or another suitable mapping and select output text having the higher probability, e.g., "she likes to eat ice cream."

In some embodiments, the system is configured to map neuromuscular information (derived from one or more neuromuscular signals, e.g., EMG signals) to an error indication from the user. For example, the user may tense one or more muscles after the system erroneously interprets a word the user spoke correctly. The neuromuscular signals relating to that movement or activation from the user may be mapped as an error indication from the user. In this manner, the user is not required to provide a training signal particularly relating to an error indication. In some embodiments, when the system detects neuromuscular information relating to the error indication, the system automatically corrects the error. For example, the system may automatically delete the last interpreted word. In another example, the system may provide the user with one or more options to correct the last interpreted word. In yet another example, the system may automatically replace the last interpreted word with another interpretation based on a language model. In some embodiments, the system may further adapt the pre-trained mapping or another suitable mapping based on the detected error indication. For example, the system may modify a language model associated with the speech recognizer to implement the correct interpretation. The system having been configured to detect the error indication may be able to differentiate between a case when the user made an error (e.g., the user spoke the wrong word) and a case when the speech recognizer made an error (e.g., the user spoke the correct word, but the speech recognizer interpreted it incorrectly). For example, the user may speak the word "yike" instead of "like," and the speech recognizer may interpret the word correctly as "yike." In this case, the system may detect the error to be a user error. In another example, the user may speak the word "like," but the speech recognizer may interpret the word incorrectly as "yike." The system may leverage the capability to separately detect these two types of errors to improve further adaptation of the pre-trained mapping or another suitable mapping to the user.

The above-described embodiments can be implemented in any of numerous ways. For example, the embodiments may be implemented using hardware, software or a combination thereof. When implemented using software, code comprising the software can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware or with one or more processors programmed using microcode or software to perform the functions recited above.

In this respect, it should be appreciated that one implementation of the embodiments of the present invention comprises at least one non-transitory computer-readable storage medium (e.g., a computer memory, a portable memory, a compact disk, etc.) encoded with a computer program (i.e., a plurality of instructions), which, when executed on a processor, performs the above-discussed functions of the embodiments of the technologies described herein. The computer-readable storage medium can be transportable such that the program stored thereon can be loaded onto any computer resource to implement the aspects of the present invention discussed herein. In addition, it should be appreciated that reference to a computer program that, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the present invention.

Various aspects of the technology presented herein may be used alone, in combination, or in a variety of arrangements not specifically discussed in the embodiments described above and therefore are not limited in their application to the details and arrangements of components set forth in the foregoing description and/or in the drawings.

Also, some of the embodiments described above may be implemented as one or more method(s), of which some examples have been provided. The acts performed as part of the method(s) may be ordered in any suitable way. Accordingly, embodiments may be constructed in which acts are performed in an order different than illustrated or described herein, which may include performing some acts simultaneously, even though shown as sequential acts in illustrative embodiments. The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The invention is limited only as defined by the following claims and the equivalents thereto.

The foregoing features may be used, separately or together in any combination, in any of the embodiments discussed herein.

Further, although advantages of the present invention may be indicated, it should be appreciated that not every embodiment of the invention will include every described advantage. Some embodiments may not implement any features described as advantageous herein. Accordingly, the foregoing description and attached drawings are by way of example only.

Variations on the disclosed embodiment are possible. For example, various aspects of the present technology may be used alone, in combination, or in a variety of arrangements not specifically discussed in the embodiments described in the foregoing, and therefore they are not limited in application to the details and arrangements of components set forth in the foregoing description or illustrated in the drawings. Aspects described in one embodiment may be combined in any manner with aspects described in other embodiments.

Use of ordinal terms such as "first," "second," "third," etc., in the description and/or the claims to modify an element does not by itself connote any priority, precedence, or order of one element over another, or the temporal order in which acts of a method are performed, but are used merely as labels to distinguish one element or act having a certain name from another element or act having a same name (but for use of the ordinal term) to distinguish the elements or acts.

The indefinite articles "a" and "an," as used herein in the specification and in the claims, unless clearly indicated to the contrary, should be understood to mean "at least one."

Any use of the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Any use of the phrase "equal" or "the same" in reference to two values (e.g., distances, widths, etc.) means that two values are the same within manufacturing tolerances. Thus, two values being equal, or the same, may mean that the two values are different from one another by +5%.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

"Consisting essentially of," when used in the claims, shall have its ordinary meaning as used in the field of patent law.

Also, the phraseology and terminology used herein is for the purpose of description and should not be regarded as limiting. Use of terms such as "including," "comprising," "comprised of," "having," "containing," and "involving," and variations thereof herein, is meant to encompass the items listed thereafter and equivalents thereof as well as additional items.

The terms "approximately" and "about" if used herein may be construed to mean within +20% of a target value in some embodiments, within +10% of a target value in some embodiments, within +5% of a target value in some embodiments, and within +2% of a target value in some embodiments. The terms "approximately" and "about" may equal the target value.

The term "substantially" if used herein may be construed to mean within 95% of a target value in some embodiments, within 98% of a target value in some embodiments, within 99% of a target value in some embodiments, and within 99.5% of a target value in some embodiments. In some embodiments, the term "substantially" may equal 100% of the target value.

As detailed above, the computing devices and systems described and/or illustrated herein broadly represent any type or form of computing device or system capable of executing computer-readable instructions, such as those contained within the modules described herein. In their most basic configuration, these computing device(s) may each include at least one memory device and at least one physical processor.

In some examples, the term "memory device" generally refers to any type or form of volatile or non-volatile storage device or medium capable of storing data and/or computer-readable instructions. In one example, a memory device may store, load, and/or maintain one or more of the modules described herein. Examples of memory devices include, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In some examples, the term "physical processor" generally refers to any type or form of hardware-implemented processing unit capable of interpreting and/or executing computer-readable instructions. In one example, a physical processor may access and/or modify one or more modules stored in the above-described memory device. Examples of physical processors include, without limitation, micropro-cessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the modules described and/or illustrated herein may represent portions of a single module or application. In addition, in certain embodiments one or more of these modules may represent one or more software applications or programs that, when executed by a computing device, may cause the computing device to perform one or more tasks. For example, one or more of the modules described and/or illustrated herein may represent modules stored and configured to run on one or more of the computing devices or systems described and/or illustrated herein. One or more of these modules may also represent all or portions of one or more special-purpose computers configured to perform one or more tasks.

In addition, one or more of the modules described herein may transform data, physical devices, and/or representations of physical devices from one form to another. For example, one or more of the modules recited herein may receive data to be transformed, transform the data, output a result of the transformation to perform a function, use the result of the transformation to perform a function, and store the result of the transformation to perform a function. Additionally or alternatively, one or more of the modules recited herein may transform a processor, volatile memory, non-volatile memory, and/or any other portion of a physical computing device from one form to another by executing on the computing device, storing data on the computing device, and/or otherwise interacting with the computing device.

In some embodiments, the term "computer-readable medium" generally refers to any form of device, carrier, or medium capable of storing or carrying computer-readable instructions. Examples of computer-readable media include, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), elec-tronic-storage media (e.g., solid-state drives and flash media), and other distribution systems.

The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or include additional steps in addition to those disclosed.

The preceding description has been provided to enable others skilled in the art to best utilize various aspects of the exemplary embodiments disclosed herein. This exemplary description is not intended to be exhaustive or to be limited to any precise form disclosed. Many modifications and variations are possible without departing from the spirit and scope of the present disclosure. The embodiments disclosed herein should be considered in all respects illustrative and not restrictive. Reference should be made to the appended claims and their equivalents in determining the scope of the present disclosure.

Unless otherwise noted, the terms "connected to" and "coupled to" (and their derivatives), as used in the specifi-cation and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specifi-cation and claims, are interchangeable with and have the same meaning as the word "comprising."

What is claimed is:

1. A non-transitory, computer-readable storage medium including executable instructions that, when executed by one or more processors, cause the one or more processors to:
  while a head-wearable device and a wrist-wearable device are communicatively coupled and worn by a user:
    obtain speech data, based on a speech input from the user, at a microphone of the head-wearable device;
    determine text based on the speech data;

obtain neuromuscular data, based on a neuromuscular input from the user, at a neuromuscular sensor of the wrist-wearable device;

cause the text to be modified based on the neuromuscular data to produce modified text; and cause the modified text to be presented to the user.

2. The non-transitory, computer-readable storage medium of claim 1, wherein the executable instructions further cause the one or more processors to:

while the head-wearable device and the wrist-wearable device are communicatively coupled and worn by the user:

obtain additional neuromuscular data, based on an additional neuromuscular input from the user, at the neuromuscular sensor of the wrist-wearable device;

cause the text to be modified based on the additional neuromuscular data to produce additional modified text; and cause the additional modified text to be presented to the user.

3. The non-transitory, computer-readable storage medium of claim 1, wherein the executable instructions further cause the one or more processors to:

while the head-wearable device and the wrist-wearable device are communicatively coupled and worn by the user:

obtain second speech data, based on a second speech input from the user, at the microphone of the head-wearable device;

determine second text based on the second speech data;

obtain second neuromuscular data, based on a second neuromuscular input from the user, at the neuromuscular sensor of the wrist-wearable device;

cause the second text to be modified based on the second neuromuscular data to produce second modified text; and cause the second modified text to be presented to the user.

4. The non-transitory, computer-readable storage medium of claim 1, wherein the executable instructions further cause the one or more processors to:

while the head-wearable device and the wrist-wearable device are communicatively coupled and worn by the user:

in response to obtaining fourth neuromuscular data, based on fourth neuromuscular input from the user, at the neuromuscular sensor of the wrist-wearable device, cause the modified text to be sent to another user.

5. The non-transitory, computer-readable storage medium of claim 1, wherein the executable instructions further cause the one or more processors to:

while the head-wearable device, the wrist-wearable device, and another wrist-wearable device are communicatively coupled and worn by the user:

obtain other neuromuscular data, based on another neuromuscular input from the user, at a neuromuscular sensor of the other wrist-wearable device;

cause the text to be modified based on the other neuromuscular data to produce other modified text; and cause the other modified text to be presented to the user, wherein the wrist-wearable device is worn on a first wrist of the user and the other wrist-wearable device is worn on a second wrist of the user.

6. The non-transitory, computer-readable storage medium of claim 1, wherein the executable instructions further cause the one or more processors to:

while the head-wearable device, the wrist-wearable device, and another wrist-wearable device are communicatively coupled and worn by the user:

in response to determining the text based on the speech data, predict an error in the text, based on one or more trained statistical models; and present a suggested correction, based on one or more trained statistical models, to the user, wherein:

the neuromuscular data, based on the neuromuscular input from the user, indicates that the user accepts the suggested correction; and causing the text to be modified based on the neuromuscular data to produce the modified text includes making the suggested correction to the text.

7. The non-transitory, computer-readable storage medium of claim 1, wherein:

the speech input from the user is a plurality of words spoken by the user; and determining the text based on the speech data includes converting the plurality of words spoken by the user to a textual representation of the plurality of words.

8. The non-transitory, computer-readable storage medium of claim 1, wherein:

the neuromuscular sensor of the wrist-wearable device is an electromyography (EMG) sensor; and the neuromuscular data is EMG data.

9. The non-transitory, computer-readable storage medium of claim 1, wherein the neuromuscular input from the user is one or more of one or more typing actions, one or more tapping gestures, one or more writing gestures, one or more drawing gestures, one or more finger gestures, and one or more one-handed gestures.

10. The non-transitory, computer-readable storage medium of claim 1, wherein causing the text to be modified based on the neuromuscular data includes at least one of adding one or more characters to the text, removing one or more characters from the text, changing one or more characters of the text, and moving one or more characters of the text.

11. The non-transitory, computer-readable storage medium of claim 1, wherein causing the text to be presented to the user includes at least one of:

presenting a visual representation of the text at a display of one or more of the head-wearable device, the wrist-wearable device, and another device communicatively coupled to the head-wearable device and the wrist-wearable device; and presenting an audio representation of the text at a speaker of one or more of the head-wearable device, the wrist-wearable device, and the other device.

12. The non-transitory, computer-readable storage medium of claim 1, wherein:

the head-wearable device is at least one of a pair of smart glasses and an extended-reality (XR) headset; and the wrist-wearable device is a smart watch.

13. A method, the method comprising:

while a head-wearable device and a wrist-wearable device are communicatively coupled and worn by a user:

obtaining speech data, based on a speech input from the user, at a microphone of the head-wearable device;

determining text based on the speech data;

obtaining neuromuscular data, based on a neuromuscular input from the user, at a neuromuscular sensor of the wrist-wearable device;

causing the text to be modified based on the neuromuscular data; and causing the text to be presented to the user.

14. The method of claim 13, the method further comprising:

while the head-wearable device and the wrist-wearable device are communicatively coupled and worn by the user:

obtaining additional neuromuscular data, based on an additional neuromuscular input from the user, at the neuromuscular sensor of the wrist-wearable device;

causing the text to be modified based on the additional neuromuscular data to produce additional modified text; and causing the additional modified text to be presented to the user.

15. The method of claim 13, the method further comprising:

while the head-wearable device and the wrist-wearable device are communicatively coupled and worn by the user:

obtaining second speech data, based on a second speech input from the user, at the microphone of the head-wearable device;

determining second text based on the second speech data;

obtaining second neuromuscular data, based on a second neuromuscular input from the user, at the neuromuscular sensor of the wrist-wearable device;

causing the second text to be modified based on the second neuromuscular data to produce second modified text; and causing the second modified text to be presented to the user.

16. The method of claim 13, the method further comprising:

while the head-wearable device, the wrist-wearable device, and another wrist-wearable device are communicatively coupled and worn by the user:

obtaining other neuromuscular data, based on another neuromuscular input from the user, at a neuromuscular sensor of the other wrist-wearable device;

causing the text to be modified based on the other neuromuscular data to produce other modified text; and causing the other modified text to be presented to the user, wherein the wrist-wearable device is worn on a first wrist of the user and the other wrist-wearable device is worn on a second wrist of the user.

17. An extended-reality (XR) system including:

a head-wearable device;

a wrist-wearable device communicatively coupled to the head-wearable device;

one or more processors;

one or more memory devices including medium including executable instructions that, when executed by the one or more processors, cause the one or more processors to:

while the head-wearable device and the wrist-wearable device are worn by a user:

obtain speech data, based on a speech input from the user, at a microphone of the head-wearable device;

determine text based on the speech data;

obtain neuromuscular data, based on a neuromuscular input from the user, at a neuromuscular sensor of the wrist-wearable device;

cause the text to be modified based on the neuromuscular data; and cause the text to be presented to the user.

18. The XR system of claim 17, wherein the executable instructions further cause the one or more processors to:

while the head-wearable device and the wrist-wearable device are communicatively coupled and worn by the user:

obtain additional neuromuscular data, based on an additional neuromuscular input from the user, at the neuromuscular sensor of the wrist-wearable device;

cause the text to be modified based on the additional neuromuscular data to produce additional modified text; and cause the additional modified text to be presented to the user.

19. The XR system of claim 17, wherein the executable instructions further cause the one or more processors to:

while the head-wearable device and the wrist-wearable device are communicatively coupled and worn by the user:

obtain second speech data, based on a second speech input from the user, at the microphone of the head-wearable device;

determine second text based on the second speech data;

obtain second neuromuscular data, based on a second neuromuscular input from the user, at the neuromuscular sensor of the wrist-wearable device;

cause the second text to be modified based on the second neuromuscular data to produce second modified text; and cause the second modified text to be presented to the user.

20. The XR system of claim 17, wherein the executable instructions further cause the one or more processors to:

while the head-wearable device, the wrist-wearable device, and another wrist-wearable device are communicatively coupled and worn by the user:

obtain other neuromuscular data, based on another neuromuscular input from the user, at a neuromuscular sensor of the other wrist-wearable device;

cause the text to be modified based on the other neuromuscular data to produce other modified text; and cause the other modified text to be presented to the user, wherein the wrist-wearable device is worn on a first wrist of the user and the other wrist-wearable device is worn on a second wrist of the user.

* * * * *